US012275795B2

(12) United States Patent
Abujoub et al.

(10) Patent No.: US 12,275,795 B2
(45) Date of Patent: Apr. 15, 2025

(54) BINDING MOLECULES AGAINST BCMA AND USES THEREOF

(71) Applicant: NOVARTIS AG, Basel (CH)

(72) Inventors: Aida Abujoub, Winchester, MA (US); John Blankenship, Acton, MA (US); Tony Fleming, Stow, MA (US); Brian Holmberg, Somerville, MA (US); Connie Hong, Somerville, MA (US); Lu Huang, Cambridge, MA (US); Haihui Lu, Cambridge, MA (US)

(73) Assignee: NOVARTIS AG, Basel (CH)

( * ) Notice: Subject to any disclaimer, the term of this patent is extended or adjusted under 35 U.S.C. 154(b) by 158 days.

(21) Appl. No.: 17/934,064

(22) Filed: Sep. 21, 2022

(65) Prior Publication Data

US 2023/0295322 A1 Sep. 21, 2023

Related U.S. Application Data

(62) Division of application No. 16/426,914, filed on May 30, 2019, now Pat. No. 11,492,409.

(60) Provisional application No. 62/679,611, filed on Jun. 1, 2018, provisional application No. 62/684,046, filed on Jun. 12, 2018.

(51) Int. Cl.
| | |
|---|---|
| *C07K 16/28* | (2006.01) |
| *A61K 39/395* | (2006.01) |
| *A61K 47/68* | (2017.01) |
| *A61P 35/00* | (2006.01) |
| *C07K 14/715* | (2006.01) |
| *C07K 14/725* | (2006.01) |
| *C07K 14/735* | (2006.01) |
| *C07K 16/30* | (2006.01) |
| *C07K 16/46* | (2006.01) |
| *C12N 5/10* | (2006.01) |
| *C12N 15/63* | (2006.01) |
| *A61K 39/00* | (2006.01) |

(52) U.S. Cl.
CPC ...... *C07K 16/2878* (2013.01); *A61K 39/3955* (2013.01); *A61K 47/6849* (2017.08); *A61P 35/00* (2018.01); *C07K 16/2809* (2013.01); *C07K 16/283* (2013.01); *C07K 16/2866* (2013.01); *C07K 16/2896* (2013.01); *C07K 16/468* (2013.01); *C12N 5/10* (2013.01); *C12N 15/63* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/76* (2013.01)

(58) Field of Classification Search
CPC ............ C07K 16/2809; C07K 16/2878; C07K 16/2896; C07K 16/468; C07K 2317/565; C07K 2317/569; C07K 2317/22; C07K 2317/24; C07K 2317/31; C07K 2317/73; C07K 2317/76; C07K 14/7051; C07K 14/70596; C07K 14/70578; C12N 5/10; C12N 2510/00; C12N 15/63
See application file for complete search history.

(56) References Cited

U.S. PATENT DOCUMENTS

| | | | |
|---|---|---|---|
| 5,169,938 | A | 12/1992 | Yoshida et al. |
| 5,766,947 | A | 6/1998 | Ritterhaus et al. |
| 8,340,621 | B1 | 12/2012 | Husted et al. |
| 9,150,664 | B2 | 10/2015 | Kufer et al. |
| 9,273,141 | B2 | 3/2016 | Algate et al. |
| 9,650,446 | B2 | 5/2017 | Moore et al. |
| 11,492,409 | B2 | 11/2022 | Abujoub et al. |
| 2005/0175606 | A1 | 8/2005 | Huang et al. |
| 2005/0244416 | A1 | 11/2005 | Jung |
| 2007/0212733 | A1 | 9/2007 | Martin |
| 2007/0274998 | A1 | 11/2007 | Utku |
| 2011/0054151 | A1 | 3/2011 | Lazar et al. |
| 2013/0156769 | A1 | 6/2013 | Kufer et al. |
| 2013/0156770 | A1 | 6/2013 | Kufer et al. |
| 2016/0137730 | A1 | 5/2016 | Abrams et al. |
| 2016/0297885 | A1 | 10/2016 | Kuo et al. |
| 2016/0355608 | A1 | 12/2016 | Bernett et al. |

(Continued)

FOREIGN PATENT DOCUMENTS

| | | | |
|---|---|---|---|
| CA | 2785907 | A1 | 7/2011 |
| CA | 2925329 | A1 | 10/2016 |

(Continued)

OTHER PUBLICATIONS

Office Action issued Oct. 6, 2023 in RU application No. 2021133487 (English translation).

(Continued)

*Primary Examiner* — Bridget E Bunner
(74) *Attorney, Agent, or Firm* — Biospark Intellectual Property Law

(57) ABSTRACT

The present disclosure provides BCMA binding molecules that specifically bind to human BCMA, conjugates comprising the BCMA binding molecules, and pharmaceutical compositions comprising the BCMA binding molecules and the conjugates. The disclosure further provides methods of using the BCMA binding molecules to treat cancers that express cell surface BCMA. The disclosure yet further provides recombinant host cells engineered to express the BCMA binding molecules and methods of producing the BCMA binding molecules by culturing the host cells under conditions in which the BCMA binding molecules are expressed.

23 Claims, 62 Drawing Sheets

Figure 1A:
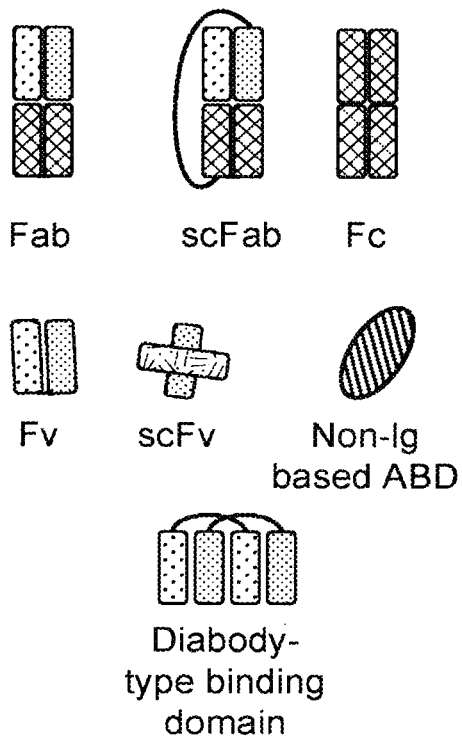

Specification includes a Sequence Listing.

(56) References Cited

U.S. PATENT DOCUMENTS

| | | | |
|---|---|---|---|
| 2017/0209571 A1 | 7/2017 | Kanapuram et al. |
| 2017/0218077 A1 | 8/2017 | Raum et al. |
| 2018/0118836 A1 | 5/2018 | Bernett et al. |
| 2019/0111079 A1 | 4/2019 | Mills |
| 2019/0112381 A1 | 4/2019 | Wesche et al. |
| 2019/0367628 A1 | 12/2019 | Abujoub et al. |
| 2022/0396631 A1 | 12/2022 | Granda et al. |

FOREIGN PATENT DOCUMENTS

| | | | |
|---|---|---|---|
| CN | 108064244 A | 5/2018 |
| CN | 109310755 A | 2/2019 |
| EA | 004635 B1 | 6/2004 |
| EP | 0276497 B1 | 10/1991 |
| EP | 0276496 B1 | 3/1992 |
| EP | 1210425 B1 | 4/2007 |
| EP | 1223964 B1 | 4/2007 |
| EP | 2762497 A1 | 8/2014 |
| EP | 3023437 A1 | 5/2016 |
| EP | 1806143 B1 | 6/2016 |
| EP | 2982694 B1 | 6/2016 |
| EP | 3029068 A1 | 6/2016 |
| EP | 2780374 B1 | 8/2019 |
| EP | 2780375 B1 | 9/2019 |
| RU | 2355705 C2 | 5/2009 |
| WO | 2000040716 A2 | 7/2000 |
| WO | 2001012812 A2 | 2/2001 |
| WO | 2001024811 A1 | 4/2001 |
| WO | 2001087977 A2 | 11/2001 |
| WO | 2002066516 A1 | 8/2002 |
| WO | 2004106383 A1 | 12/2004 |
| WO | 2005040220 A1 | 5/2005 |
| WO | 2005061547 A2 | 7/2005 |
| WO | 2005075511 A1 | 8/2005 |
| WO | 2005108986 A1 | 11/2005 |
| WO | 06053301 A2 | 5/2006 |
| WO | 2006067210 A1 | 6/2006 |
| WO | 2007042261 A2 | 4/2007 |
| WO | 2008119565 A2 | 10/2008 |
| WO | 2008119566 A2 | 10/2008 |
| WO | 2008119567 A2 | 10/2008 |
| WO | 2009132058 A2 | 10/2009 |
| WO | 2010037835 A2 | 4/2010 |
| WO | 2010037836 A2 | 4/2010 |
| WO | 2010037837 A2 | 4/2010 |
| WO | 2010037838 A2 | 4/2010 |
| WO | 2010104949 A2 | 9/2010 |
| WO | 2012055058 A1 | 5/2012 |
| WO | 2012118622 A1 | 9/2012 |
| WO | 2012143498 A1 | 10/2012 |
| WO | 2012163805 A1 | 12/2012 |
| WO | 2013072406 A1 | 5/2013 |
| WO | 2013072415 A1 | 5/2013 |
| WO | 2013154760 A1 | 10/2013 |
| WO | 2014068079 A1 | 5/2014 |
| WO | 2014089335 A1 | 6/2014 |
| WO | 14110601 A1 | 7/2014 |
| WO | 2014122143 A1 | 8/2014 |
| WO | 2014122144 A1 | 8/2014 |
| WO | 2014124280 A1 | 8/2014 |
| WO | 2014140248 A1 | 9/2014 |
| WO | 2015052538 A1 | 4/2015 |
| WO | 2015166073 A1 | 11/2015 |
| WO | 2016014565 A2 | 1/2016 |
| WO | 2016014789 A2 | 1/2016 |
| WO | 2016020322 A1 | 2/2016 |
| WO | 2016075670 A1 | 5/2016 |
| WO | 2016079177 A1 | 5/2016 |
| WO | 2016/086196 A2 | 6/2016 |
| WO | 16086196 A2 | 6/2016 |
| WO | 16090327 A2 | 6/2016 |
| WO | 16105450 A2 | 6/2016 |
| WO | 2016094304 A2 | 6/2016 |
| WO | 2016130598 A1 | 8/2016 |
| WO | 2016166629 A1 | 10/2016 |
| WO | 2016166630 A1 | 10/2016 |
| WO | 2017/031104 A1 | 2/2017 |
| WO | 17021450 A1 | 2/2017 |
| WO | 17031104 A1 | 2/2017 |
| WO | 17134134 A1 | 8/2017 |
| WO | 2017136562 A2 | 8/2017 |
| WO | 2017165464 A1 | 9/2017 |
| WO | 028162 B1 | 10/2017 |
| WO | 2017186928 A1 | 11/2017 |
| WO | 17223111 A1 | 12/2017 |
| WO | 18083204 A1 | 5/2018 |
| WO | 18119215 A1 | 6/2018 |
| WO | 18133877 A1 | 7/2018 |
| WO | 18151836 A1 | 8/2018 |
| WO | 18201051 A1 | 11/2018 |
| WO | 18204907 A1 | 11/2018 |
| WO | 2018201047 A1 | 11/2018 |
| WO | 18237006 A1 | 12/2018 |
| WO | 18237037 A2 | 12/2018 |
| WO | 19001474 A1 | 1/2019 |
| WO | 19035938 A1 | 2/2019 |
| WO | 19075359 A1 | 4/2019 |
| WO | 19075378 A1 | 4/2019 |
| WO | 19077062 A1 | 4/2019 |
| WO | 2019089969 A2 | 5/2019 |
| WO | 2019104075 A1 | 5/2019 |
| WO | 2019229701 A2 | 12/2019 |
| WO | 2020236795 A2 | 11/2020 |

OTHER PUBLICATIONS

International Search Report and Written Opinion issued in PCT/IB2020/055872 on Sep. 24, 2020.
International Search Report and Written Opnion issued in PCT/US2020/033563 on Jul. 29, 2020.
Ansari et al., 2017, "Decreased expression of B cell maturation antigen in patients with common variable immunodeficiency," Ped Allergy Immunol Pulm 30(1): 7-13 (abstract only).
Biorad mini review, "Overview of T cell Receptors", 2016, (www.bio-rad-antibodies.com/t-cell-receptor-minireview.html; accessed Aug. 6, 2021).
Cho, et al., 2018, "Anti-BCMA BiTE® AMG 701 Potently Induces Specific T Cell Lysis of Human Multiple Myeloma (MM) Cells and Immunomodulation in the Bone Marrow Microenvironment," Blood, vol. 132, Supplement 1, p. 592.
Definition of "Component", www.merriam-webster.com/dictionary/component (accessed Aug. 6, 2021).
Definition of "Medicament", www.merriam-webster.com/dictionary/medicament (accessed Aug. 5, 2021).
Diamond et al., 1984, "Somatic mutation of the T15 heavy chain gives rise to an antibody with autoantibody specificity," Proc. Natl. Acad. Sci. 81:5841-5844.
Dogan et al., 2020, "B-cell maturation antigen expression across hematologic cancers: a systemic literature review," Blood Cancer J 10: 73.
Gantke et al., 2017, "Trispecific antibodies for CD16A-directed NK cell engagement and dual-targeting of tumor cells," Protein Engineering, Design and Selection 30(9): 673-684.
Geis et al., 2018, "Hemibodies: Novel trivalent T-cell activating antibody derivatives for personalized Multiple Myeloma therapy," Oncology Research and Treatment 41(4):161.
Law et al., 2018, "Preclinical and nonclincal characterization of HPN217: a tri-specific T cell activating construct (TriTAC) targeting B cell maturation antigen (BCMA) for the treatment of multiple myeloma" Blood 132:3225.
Lee et al., 2016, "Evaluation of B cell maturation antigen as a target for antibody drug conjugate mediated cytotoxicity in multiple myeloma," Brit J Haematol 17 4: 911-922.
Leiba et al., 2007, "Activation of B-cell maturation antigen (BCMA) on human multiple myeloma cells by a proliferation-inducing-ligand (APRIL) promotes myeloma cell function in the bone marrow microenvironment," Blood, 110(11):1503.
Ohno et al., 1985, "Antigen binding specificities of antibodies are primarily determined by seven residues of VH," Proc. Natl. Acad. Sci. 82.

(56) References Cited

OTHER PUBLICATIONS

Rossi et al., 2018, "Antibody-drug conjugates for the treatment of hematalogical malignancies: a comprehensive review," Targeted Oneal 13 : 287-308.
Solopova et al., 2019, "Bispecific antibodies in clinical practice and clinical trials (literature review)" Clinical Oncohematology 12(2):125-144.
Tai et al., 2014, "Novel anti-B cell maturation antigen antibody-drug conjugate (GSK2857916) selectively induces killing of multiple myeloma," Blood 123(20): 3128-3138.
Tai et al., 2016, "APRIL and BCMA promote human multiple myeloma growth and immunosuppression in the bone marrow microenvironment," Blood 127(25): 3225-3236.
Unofficial English translation of Apr. 19, 2024 Office Action issued in connection with RU application No. 2021133487.
Viardot et al., 2018, "Bispecific antibodies in haematological malignancies," Cancer Treatment Rev 65: 87-95.
Yarilin, 1999, "Fundamentals of Immunology," M. Medicine 172-174.
Hipp et al., 2016 "A novel BCMA/CD3 bispecific T-cell engager for the treatment of multiple myeloma induces selective lysis in vitro and in vivo", Leukemia, 31 (8): 1743-1751.
Buelow et al., 2017 "T Cell Engagement without Cytokine Storm: A Novel Bcma x CD3 Antibody Killing Myeloma Cells with Minimal Cytokine Secretion", Blood 30 (1): 501.
Buelow et al., 2017 "Development of a fully human T cell engaging bispecific antibody for the treatment of multiple myeloma", The Patent Office p. 2 of 8 3 Jun. 2, 2017 (Jun. 2, 2017), p. 1, XP055476656, Retrieved from the Internet: URL:http://www.teneobio.com/wpcontent/uploads/2018/01/Poster_I.pdf.
Girgis et al., 2016 "Exploratory Pharmacokinetic/Pharmacodynamic and Tolerability Study of BCMAxCD3 in Cynomolgus Monkeys", Blood, 128 (22): 5668.
Rudikoff et al., 1982 "Single amino acid substitution altering antigen-binding specificity", Proceedings of the National Academy of Sciences (PNAS), US, 79 (6): 1979-1983.
Ryan et al., 2007 Antibody targeting of B-cell maturation antigen on malignant plasma cells, Mal Cancer Ther, 6(11):3009-3018.
Konterman 2005 "Invited review—Recombinant bispecific antibodies for cancer therapy" Acta Pharmacologica Sinica 26(1): 1-9.
Novak et al., 2004 "Expression of BCMA, TACI, and BAFF-R in multiple myeloma: a mechanism for growth and survival", Blood, 103(2):689-694.
Genbank accession No. AB052772 "*Homo sapiens* gene for BCMA, complete cds" Sep. 25, 2022.
Fitzgerald et al., 2001 "The Cytokine FactsBook", 2nd ed., Academic Press, pp. 151-152.
Bossen et al., 2006 "Review—BAFF, APRIL and their receptors: Structure, function and signaling", Seminars in Immunology, 8:263-275.
Bodmer et al., 2002 "Review—The molecular architecture of the TNF superfamily", Trends in Biochemical Sciences, 27(1):19-26.
Hymowitz et al., 2005 "Structures of APRIL—Receptor Complexes", Journal of Biological Chemistry, 280(8): 7218-7227.
Liu et al., 2003 "Ligand-receptor binding revealed by the TNF family member TALL-1", Nature, 423:49-56.
Wallweber et al., 2004 "The Crystal Structure of A Proliferation-inducing Ligand, APRIL", 343:283-290.
Patel et al., 2004 "Engineering an APRIL-specific B-Cell Maturation Antigen", Journal of Biological Chemistry, 279(16):16727-16735.
Vidal-Laliena et al., 2005 "Characterization of antibodies submitted to the B-cell section of the 8th human leukocyte differentiation antigens workshop by flow cytometry and immunohistochemistry" 236:6-16.
Moreaux et al., 2009 "APRIL and TACI interact with syndecan-1 on the surface of multiple myeloma cells to form an essential survival loop", Eur J Heamatol, 83:119-129.
Bellucci et al., 2005 "Graft-versus-tumor response in patients with multiple myeloma is associated with antibody response to BCMA, a plasma-cell membrane receptor", Blood, 105(10):3945-3950.
Bellucci et al., 2004 "complete response to donor lymphocyte infusion in patients with multiple myeloma is associated with antibody response to BCMA, a plasma cell membrane receptor", Blood, 102(11):192a-193a.
Tarte et al., 2002 "BAFF is a survival factor for multiple myeloma cells", Myeloma Biology II, p. 811a (#3203).
Dillon et al., 2006 "an APRIL to remember: Novel TNF ligands as therapeutic targets", Nat ev, 5:235-246.
Betts et al., 2003 "Amino Acid Properties and Consequences of Substitutions", Bioinformatics for Geneticists, pp. 289-316.
Choi et al., 2011 "Bispecific antibodies engage T-cells for antitumor immunotherapy", Expert Opinion on Biological Therapy, 1(7):843-853.
Muller et al., 2010 "Bispecific antibodies for cancer immunotherapy", Biodrugs, 24(2):89-98.
Thakur et al., 2010 "Cancer therapy with bispecific antibodies: Clinical experience", Current Opinion in Molecular Therapeutics, 12(3):340-349.
Chames et al., 2009 "Bispecific antibodies for cancer therapy", Current Opinion in Drug Discovery & Development, 12 (2):276-283.
Baeuerle et al., 2009 "Bispecific T-cell engaging antibodies for cancer therapy", Cancer Research, 69(12):4941-4944.
Baeuerle et al., 2009 "BITE: Teaching antibodies to engage T-cells for cancer therapy", Current Opinion in Molecular Therapeutics, 11(1):22-30.
Baeuerle et al., 2008 "BITE: A new class of antibodies that recruit T-cells", Drugs of the Future, 33(2):137-147.
Muller et al., 2006 "Recombinant bispecific antibodies for cellular cancer immunotherapy", Current Opinion in Molecular Therapeutics, 9(4):319326.
Kufer et al., 2004 "Review—A revival of bispecific antibodies", Trends in Biotechnology, 22(5):238-244.
Frank 2002 "specificity and Cross-Reactivity", Immunology and evolution of infectious diseases textbook, Chapter 4, pp. B3-56.
GenBank accession No. NM_000733, "*Homo sapiens* CD3e molecule (CD3E), mRNA" Jun. 8, 2019.
Panowski et al., 2019 "Preclinical efficacy and safety comparison of CD3 bispecific and ADC modalities targeting BCMA for the treatment of multiple myeloma", AACR, pp. OF1-OF13.
Hager-Braun et al., 2005 Expert Rev. Proteomics, 2(5):745-756.
Rennert et al., 2000 J. Exp. Med., 192(11):1677-1683.
Kuhns et al., 2006, Immunity, 24:133-139.
Koarada et al., 2010, Rheumatology, 49: 662-670.
Pelekanou et al., 2008, BMC Cancer, 8(76): 1-9.
Guy and Vignali 2009, Immunol Rev., 232(1): 1-22.
Kjer-Nielsen et al., 2004, Proceedings of the National Academy of Sciences, 11:7675-7680.
Chames et al., 2009, mAbs, 1:539-547.
Clayton et al., 1991, Proceedings of the National Academy of Sciences USA, 88:5202-5206.
Neisig et al., 1993, Journal of Immunology, 151:870-879.
Bargou et al., 2008, Science, 321:974-977.
Honemann et al., 2004, Leukemia, 18:636-644.
Derksen et al., 2004, "Illegitimate WNT signaling promotes proliferation of multiple myeloma cells" PNAS 101(16):6125.
Dirks et al., 2008, "Brain Tumor Stem Cells: Bringing Order to the Chaos of Brain Cancer" Journal of Clinical Oncology, 26:2916-2924.
Lopez-Lazaro 2015 "The migration ability of stem cells can explain the existence of cancer unknown primary site. Rethinking metastasis" Oncoscience 2(5):467-475.
Mabey 2014 "Epidemiology of sexually transmitted infections: worldwide" Epidemiology and Sexual Behavior, 1-4.
Tran et al., 2010, "Survival comparsion between glioblastoma multiforme and other incurable cancers" Journal of Clinical Neuroscience, 17:417-421.
Vu et al., 2015, "A New Class of T-Cell Bispecific Antibodies for the Treatment of Multiple Myeloma Binding to B Cell Maturation

(56) References Cited

OTHER PUBLICATIONS

Antigen and CD3 and Showing Potent, Specific Antitumor Activity in Myeloma Cells and Long Duration of Action in Cynomolgus Monkeys" Blood, 126(23):2998.

Unofficial English translation of Office Action issued Aug. 8, 2023 in Russian application. 2020143237.

Definition of "plurality" accessed Aug. 8, 2023 from dic.academic.ru/dic.nsf/ushakov/1033406.

Singer et al., 1998, Genes and Genomes, Moscow "Mir" 1:33-37.

H2/L2 Library CDRH2

| IMGT numbering | 55 | 56 | 57 | 58 | 59 | 62 | 63 | 64 | 65 | 66 | 67 | 68 | 69 | 70 | 71 | 72 | 74 |
|---|---|---|---|---|---|---|---|---|---|---|---|---|---|---|---|---|---|
| H2/L2-22 | V | I | S | Y | H | G | S | N | K | Y | Y | A | D | S | V | K | G |
| H2/L2-88 | V | I | S | Y | K | G | S | N | K | Y | Y | A | D | S | V | K | G |
| H2/L2-36 | V | I | S | Y | K | G | S | N | K | Y | Y | A | D | S | V | K | G |
| H2/L2-34 | V | I | S | Y | T | G | T | K | K | Y | Y | A | D | S | V | K | G |
| H2/L2-68 | V | I | S | Y | R | G | F | N | K | Y | Y | A | D | S | V | K | G |
| H2/L2-18 | V | I | S | Y | K | G | S | H | K | Y | Y | A | D | S | V | K | G |
| H2/L2-47 | V | I | S | Y | K | G | S | N | K | Y | Y | A | D | S | V | K | G |
| H2/L2-20 | V | I | S | Y | T | G | S | N | K | Y | Y | A | D | S | V | K | G |
| H2/L2-80 | V | I | S | Y | T | G | S | N | K | Y | Y | A | D | S | V | K | G |
| H2/L2-83 | V | I | S | Y | K | G | S | N | K | Y | Y | A | D | S | V | K | G |
| P1-61 | V | I | S | Y | D | G | S | N | K | Y | Y | A | D | S | V | K | G |

FIG. 4

H2/L2 Library CDRL2

| IMGT numbering | 56 | 57 | 58 | 59 | 60 | 61 | 62 |
|---|---|---|---|---|---|---|---|
| H2/L2-22 | E | V | S | N | R | L | S |
| H2/L2-88 | E | V | S | N | R | L | R |
| H2/L2-36 | E | V | S | N | R | L | R |
| H2/L2-34 | D | V | S | N | R | P | W |
| H2/L2-68 | D | V | S | N | R | L | S |
| H2/L2-18 | D | V | S | N | R | P | W |
| H2/L2-47 | D | V | S | N | R | P | W |
| H2/L2-20 | D | V | S | N | R | L | R |
| H2/L2-80 | D | V | S | N | R | A | W |
| H2/L2-83 | E | V | S | N | R | L | R |
| P1-61 | D | V | S | N | R | P | S |

FIG. 5

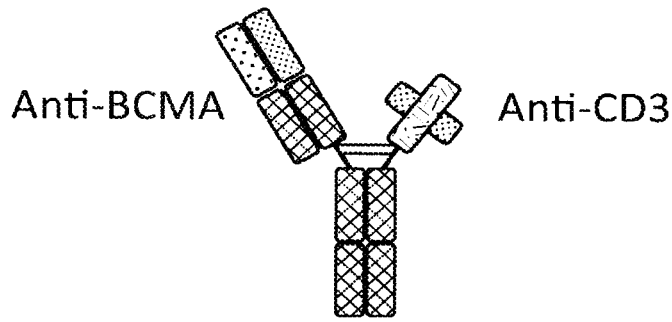

FIG. 6

H3.1 & H3.2 Library CDRH2

| IMGT numbering | 55 | 56 | 57 | 58 | 59 | 62 | 63 | 64 | 65 | 66 | 67 | 68 | 69 | 70 | 71 | 72 | 74 |
|---|---|---|---|---|---|---|---|---|---|---|---|---|---|---|---|---|---|
| H3-1  | V | I | S | Y | D | D | A | H | K | Y | Y | A | D | S | V | K | G |
| H3-2  | V | I | S | Y | N | D | L | N | K | Y | Y | A | D | S | V | K | G |
| H3-3  | V | I | S | Y | S | G | S | N | K | Y | Y | A | D | S | V | K | G |
| H3-4  | V | I | S | Y | D | D | A | H | K | Y | Y | A | D | S | V | K | G |
| H3-5  | V | I | S | Y | T | G | A | N | K | Y | Y | A | D | S | V | K | G |
| H3-6  | V | I | S | Y | D | D | A | H | K | Y | Y | A | D | S | V | K | G |
| H3-7  | V | I | S | Y | T | G | S | N | K | Y | Y | A | D | S | V | K | G |
| H3-8  | V | I | S | Y | D | D | A | H | K | Y | Y | A | D | S | V | K | G |
| H3-9  | V | I | S | Y | D | D | A | H | K | Y | Y | A | D | S | V | K | G |
| H3-10 | V | I | S | Y | N | D | L | N | K | Y | Y | A | D | S | V | K | G |
| H3-11 | V | I | S | Y | N | D | A | N | K | Y | Y | A | D | S | V | K | G |
| H3-12 | V | I | S | Y | D | E | S | N | K | Y | Y | A | D | S | V | K | G |
| H3-13 | V | I | S | Y | D | D | A | H | K | Y | Y | A | D | S | V | K | G |
| H3-14 | V | I | S | Y | D | D | A | H | K | Y | Y | A | D | S | V | K | G |
| H3-15 | V | I | S | Y | D | D | A | N | K | Y | Y | A | D | S | V | K | G |
| P1-61 | V | I | S | Y | D | G | S | N | K | Y | Y | A | D | S | V | K | G |

FIG. 7

H3.1 & H3.2 Library CDRL2

| IMGT numbering | 56 | 57 | 58 | 59 | 60 | 61 | 62 | 63 | 64 | 65 |
|---|---|---|---|---|---|---|---|---|---|---|
| H3-1 | E | V | S | N | R | L | R | G | V | S |
| H3-2 | E | V | S | N | R | L | R | G | V | S |
| H3-3 | E | V | S | N | R | L | R | G | V | S |
| H3-4 | E | V | S | N | R | L | S | G | V | S |
| H3-5 | E | V | S | N | R | L | R | G | V | S |
| H3-6 | E | V | S | N | R | L | R | G | V | S |
| H3-7 | E | V | S | N | R | L | R | G | V | S |
| H3-8 | E | V | S | N | R | L | R | G | V | S |
| H3-9 | E | V | S | N | R | L | R | G | V | S |
| H3-10 | E | V | S | N | R | L | R | G | V | S |
| H3-11 | E | V | S | N | R | L | R | G | V | S |
| H3-12 | E | V | S | N | R | L | R | G | V | S |
| H3-13 | E | V | S | N | R | L | S | G | V | S |
| H3-14 | E | V | S | N | R | L | G | G | V | S |
| H3-15 | E | V | S | N | R | L | S | G | V | S |
| P1-61 | D | V | S | N | R | P | S | G | V | S |

FIG. 8

H3.1 & H3.2 Library CDRH3

| IMGT numbering | 107 | 108 | 109 | 110 | 111 | 111a | 111b | 111c | 112 | 113 | 114 | 115 | 116 | 117 |
|---|---|---|---|---|---|---|---|---|---|---|---|---|---|---|
| H3-1  | S | G | Y | A | L | H | D | Q | Y | K | P | V | D | V |
| H3-2  | S | G | Y | A | L | H | D | F | Q | D | P | T | D | V |
| H3-3  | S | G | Y | A | L | H | D | Q | Y | K | P | V | D | V |
| H3-4  | S | G | Y | A | L | H | D | Q | Y | K | P | V | D | V |
| H3-5  | S | G | Y | N | L | H | D | D | Y | Y | G | L | D | V |
| H3-6  | S | G | Y | A | L | H | D | Q | Y | K | P | V | D | V |
| H3-7  | S | G | Y | E | F | H | E | D | Y | Y | G | L | D | V |
| H3-8  | S | G | Y | A | L | H | D | Q | Y | K | P | V | D | V |
| H3-9  | S | G | Y | A | L | H | D | Q | Y | K | P | V | D | V |
| H3-10 | S | G | Y | E | F | Q | G | D | Y | Y | G | L | D | V |
| H3-11 | S | G | Y | E | L | R | D | D | Y | Y | G | L | D | V |
| H3-12 | S | G | Y | E | V | D | Q | D | Y | Y | G | L | D | V |
| H3-13 | S | G | Y | A | L | H | D | Q | Y | K | P | V | D | V |
| H3-14 | S | G | Y | A | L | H | D | Q | Y | K | P | V | D | V |
| H3-15 | S | G | Y | A | Y | D | G | D | Y | Y | G | L | D | V |
| P1-61 | S | G | Y | A | L | H | D | D | Y | Y | G | L | D | V |

FIG. 9

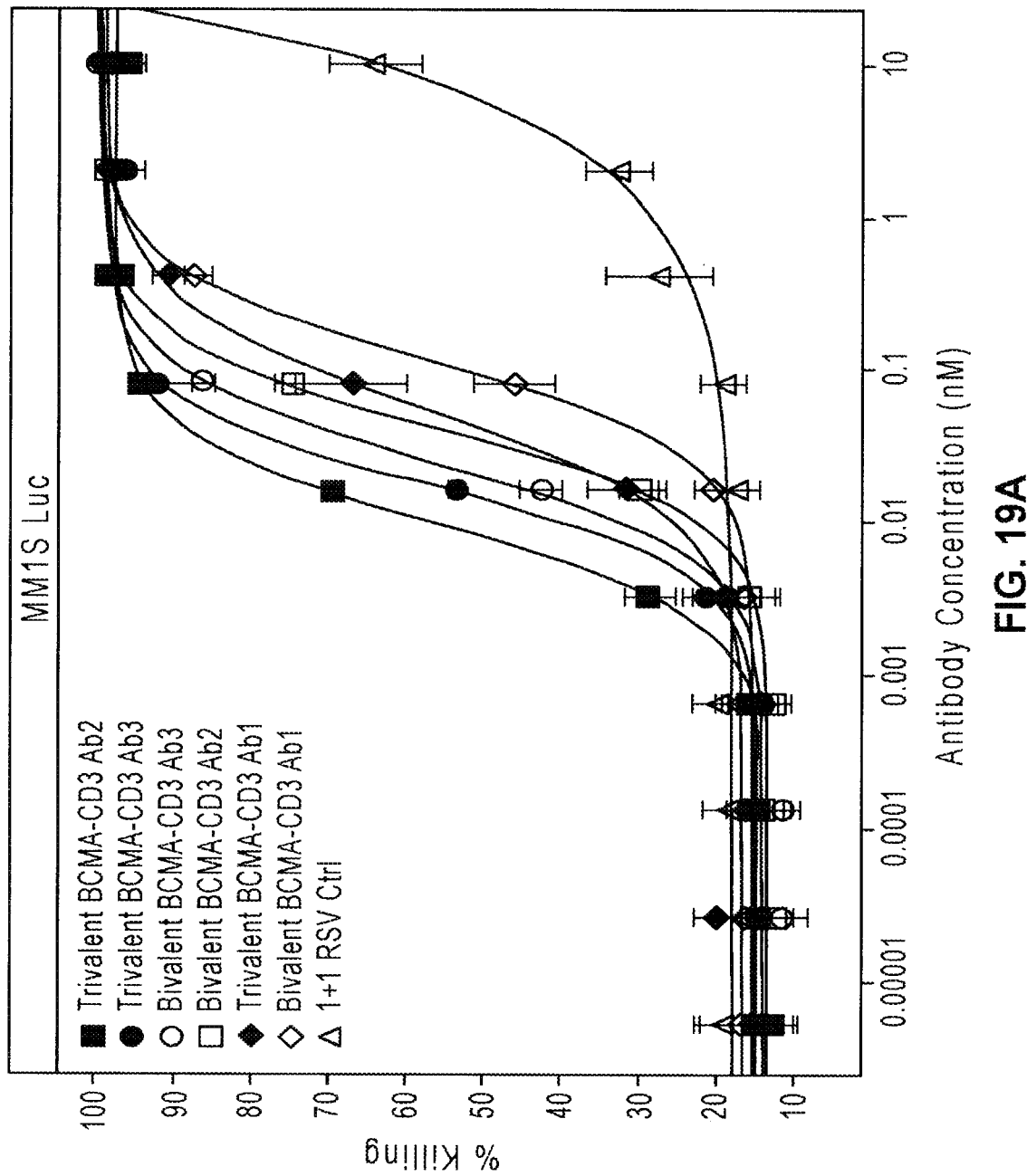

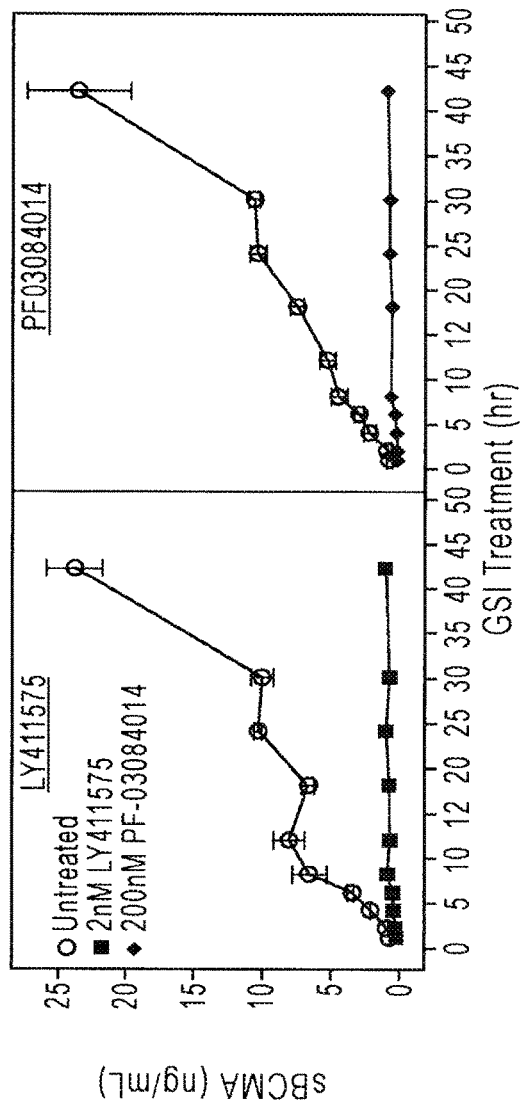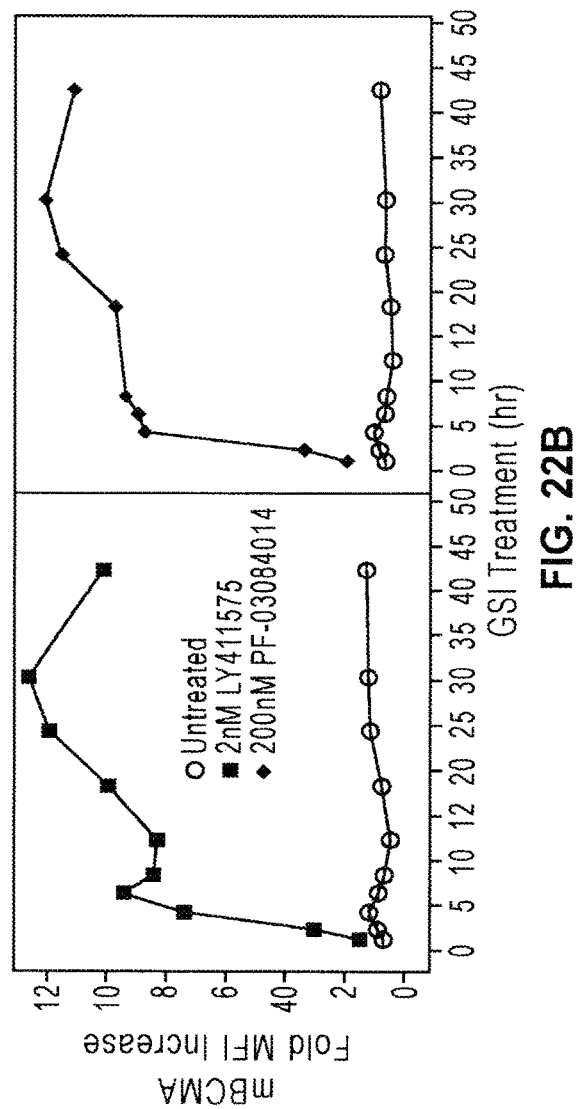
FIG. 22A
FIG. 22B

BINDING MOLECULES AGAINST BCMA AND USES THEREOF

1. CROSS-REFERENCE TO RELATED APPLICATIONS

This application is a division of U.S. application Ser. No. 16/426,914, filed May 30, 2019, which claims the priority benefit of U.S. provisional application No. 62/679,611, filed Jun. 1, 2018, and U.S. provisional application No. 62/684,046, filed Jun. 12, 2018, the contents of all of which are incorporated herein by reference in their entireties.

2. SEQUENCE LISTING

The instant application contains a Sequence Listing which has been submitted electronically in XML file format and is hereby incorporated by reference in its entirety. The XML copy, created on Nov. 11, 2022, is named NOV-003D1_SL.xml and is 738,754 bytes in size.

3. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there are any inconsistencies between the teachings of one or more of the references incorporated herein and the present disclosure, the teachings of the present specification are intended.

4. BACKGROUND

BCMA is a tumor necrosis family receptor (TNFR) member expressed on cells of the B-cell lineage. BCMA expression is the highest on terminally differentiated B cells that assume the long lived plasma cell fate, including plasma cells, plasmablasts and a subpopulation of activated B cells and memory B cells. BCMA is involved in mediating the survival of plasma cells for maintaining long-term humoral immunity. The expression of BCMA has been linked to a number of cancers, autoimmune disorders, and infectious diseases. Cancers with increased expression of BCMA include some hematological cancers, such as multiple myeloma, Hodgkin's and non-Hodgkin's lymphoma, various leukemias, and glioblastoma.

Various BCMA binding molecules are in clinical development, including BCMA antibody-drug conjugates such as GSK2857916 (GlaxoSmithkline) and bispecific BCMA binding molecules targeting BMCA and CD3 such as PF06863135 (Pfizer), EM 901 (EngMab), JNJ-64007957 (Janssen), and AMG 420 (Amgen). See, Cho et al., 2018, Front Immunol. 9:1821; WO 2016/0166629.

One of the primary safety concerns of any antibody-based drugs, including CD3 bispecific molecules, is its potential to induce life-threatening side effects such as cytokine release syndrome ("CRS"). See, Shimabukuro-Vornhagen, A. et al., 2018, J. Immunother Cancer. 6:56.

Thus, there is an unmet medical need for polypeptides, e.g., antibodies and multispecific binding molecules, which bind BCMA, and which have an improved safety profile (e.g., decreasing cytokine release) while still retaining a high efficacy.

5. SUMMARY

The disclosure provides BCMA binding molecules that specifically bind to human BCMA, e.g., antibodies, antigen-binding fragments thereof, and multispecific molecules that specifically bind to human BCMA.

In one aspect, the disclosure provides monospecific BCMA binding molecules (e.g., antibodies and antigen-binding fragments thereof) comprising a BCMA antigen-binding domain ("ABD"). Exemplary BCMA binding molecules, which can be monospecific, are described in Section 7.2 and specific embodiments 1 to 142, infra.

In another aspect, the disclosure provides multispecific binding molecules ("MBMs") (e.g., bispecific binding molecules ("BBMs")) comprising a first ABD that specifically binds to human BCMA ("ABD1" or "BCMA ABD") and a second ABD that specifically binds to a second antigen ("ABD2"), e.g., human CD3 or other component of a TCR complex (sometimes referred to herein as a "TCR ABD"). The terms ABD1, ABD2, BCMA ABD, and TCR ABD are used merely for convenience and are not intended to convey any particular configuration of a BBM. In some embodiments, a TCR ABD binds to CD3 (referred to herein a "CD3 ABD" or the like). Accordingly, disclosures relating to ABD2 and TCR ABDs are also applicable to CD3 ABDs. Such multispecific molecules can be used to direct CD3+ effector T cells to BCMA+ sites, thereby allowing the CD3+ effector T cells to attack and lyse the BCMA+ cells and tumors. Features of exemplary MBMs are described in Sections 7.2 to 7.6 and specific embodiments 143 to 716, infra.

ABDs can be immunoglobulin- or non-immunoglobulin-based, and the MBMs can include immunoglobulin-based ABDs or any combination of immunoglobulin-based ABDs and non-immunoglobulin-based ABDs. Immunoglobulin-based ABDs that can be used in the BCMA binding molecules are described in Sections 7.2 and 7.3.1 and specific embodiments 147 to 329, infra. Non-immunoglobulin-based ABDs that can be used in the MBMs are described in Section 7.3.2 and specific embodiments 330 to 331, infra. Further features of exemplary ABDs that bind to BCMA are described in Section 7.2 and specific embodiments 147 to 155, infra. Further features of exemplary ABDs that bind to a component of a TCR complex are described in Section 7.3.3 and specific embodiments 156 to 331, infra.

The ABDs of a BCMA binding molecule (or portions thereof) can be connected to each other, for example, by short peptide linkers or by an Fc domain. Methods and components for connecting ABDs and portions thereof to form a BCMA binding molecule are described in Section 7.4 and specific embodiments 332 to 620, infra.

In some embodiments, a MBM of the disclosure is a BBM. BBMs have at least two ABDs (i.e., a BBM is at least bivalent), but can also have more than two ABDs. For example, a BBM can have three ABDs (i.e., is trivalent) or four ABDs (i.e., is tetravalent), provided that the BBM has at least one ABD that can bind BCMA and at least one ABD that can bind a target antigen other than BCMA. Exemplary bivalent, trivalent, and tetravalent BBM configurations are shown in FIG. 1 and described in Section 7.5 and specific embodiments 621 to 681, infra.

The disclosure further provides nucleic acids encoding the BCMA binding molecules (either in a single nucleic acid or a plurality of nucleic acids) and recombinant host cells and cell lines engineered to express the nucleic acids and BCMA binding molecules. Exemplary nucleic acids, host cells, and cell lines are described in Section 7.7 and specific embodiments 1051 to 1057, infra.

The present disclosure further provides BCMA binding molecules with extended in vivo half life. Examples of such BCMA binding molecules are described in Section 7.8 and specific embodiments 836-845, infra.

The present disclosure further provides drug conjugates comprising the BCMA binding molecules. Such conjugates are referred to herein as "antibody-drug conjugates" or "ADCs" for convenience, notwithstanding that some of the ABDs can be non-immunoglobulin domains. Examples of ADCs are described in Section 7.9 and specific embodiments 851 to 889, infra.

The present disclosure further provides conjugates comprising the BCMA binding molecules and a polypeptide, marker, diagnostic or detectable agent, or a solid support. Examples of such conjugates are described in Sections 7.10 and 7.11 and specific embodiments 846-850 and 890-891, infra.

Pharmaceutical compositions comprising the BCMA binding molecules and ADCs are also provided. Examples of pharmaceutical compositions are described in Section 7.12 and specific embodiment 892, infra.

Further provided herein are methods of using the BCMA binding molecules, the ADCs, and the pharmaceutical compositions, for example for treating proliferative conditions (e.g., cancers), on which BCMA is expressed, for treating autoimmune disorders, and for treating other diseases and conditions associated with expression of BCMA. Exemplary methods are described in Section 7.13 and specific embodiments 893 to 971 and 1012 to 1050, infra.

The disclosure further provides methods of using the BCMA binding molecules, the ADCs, and the pharmaceutical compositions in combination with other agents and therapies. Exemplary agents, therapies, and methods of combination therapy are described in Section 7.14 and specific embodiments 972 to 1011, infra.

6. BRIEF DESCRIPTION OF THE FIGURES

Figure 1B:
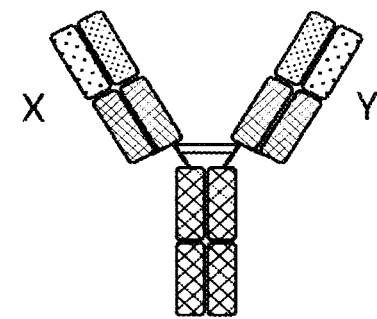

FIGS. 1A-1AG: Exemplary BBM configurations. FIG. 1A illustrates components of the exemplary BBM configurations illustrated in FIGS. 1B-1AG. Not all regions connecting the different domains of each chain are illustrated (e.g., the linker connecting the VH and VL domains of an scFv, the hinge connecting the CH2 and CH3 domains of an Fc domain, etc., are omitted). FIGS. 1B-1F illustrate bivalent BBMs; FIGS. 1G-1Z illustrate trivalent BBMs; FIGS. 1AA-1AG illustrate tetravalent BBMs.

Figure 2A:
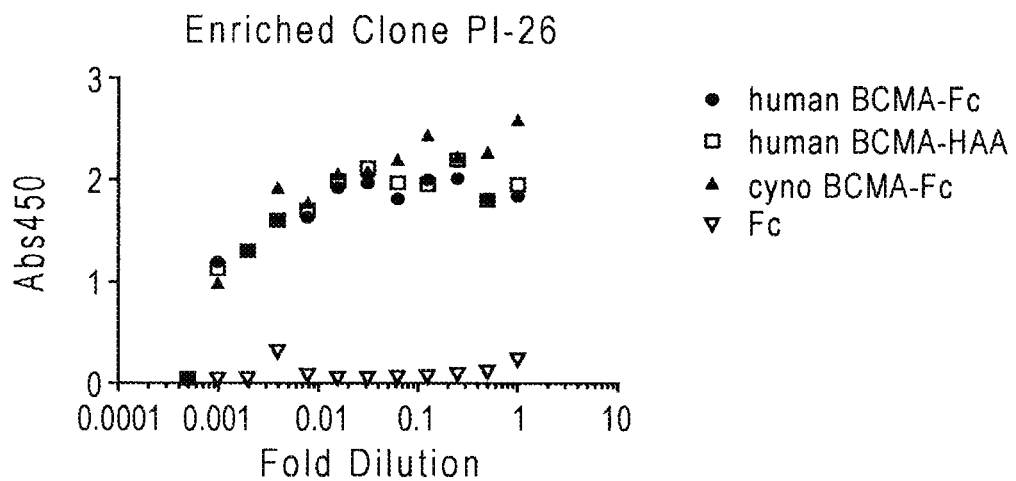
Figure 2B:
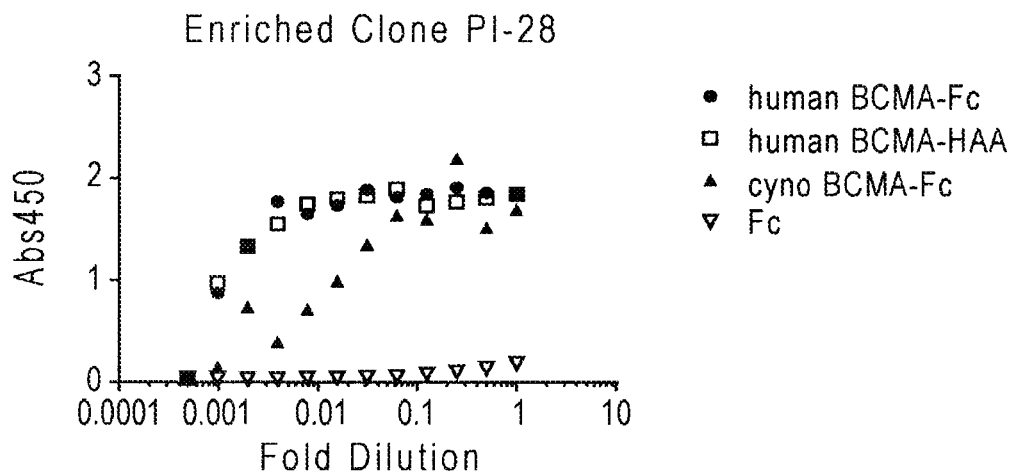
Figure 2C:
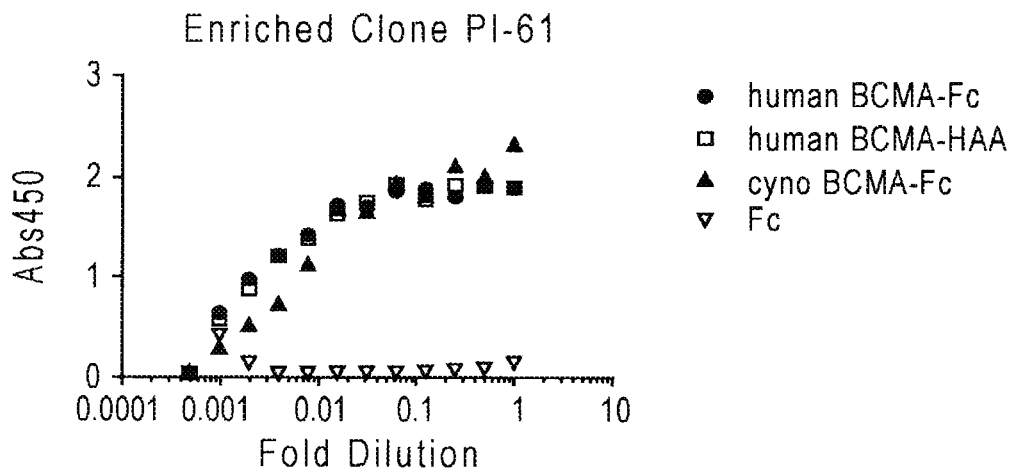
Figure 2D:
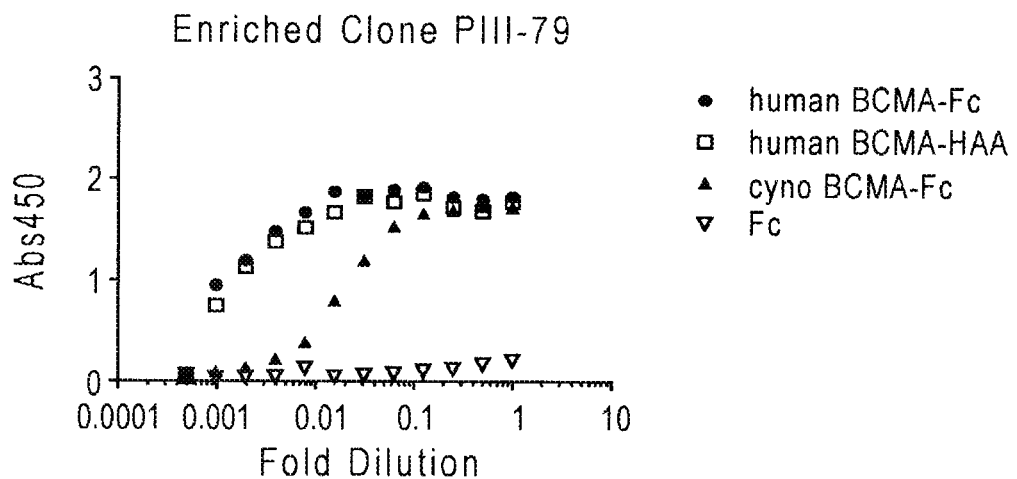
Figure 2E:
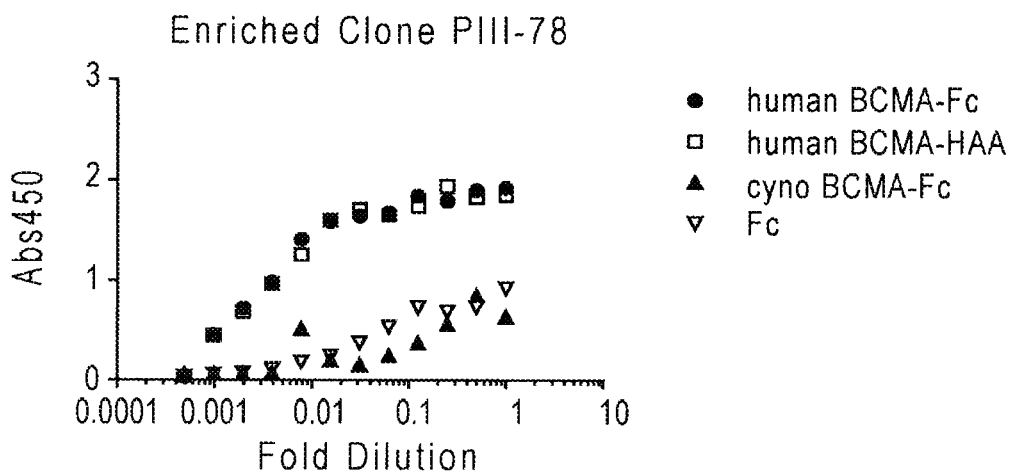
Figure 2F:
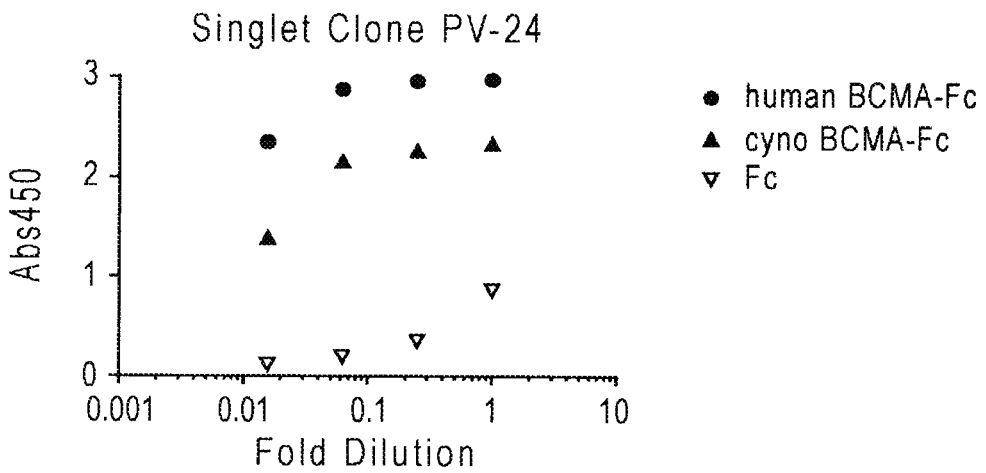
Figure 2G:
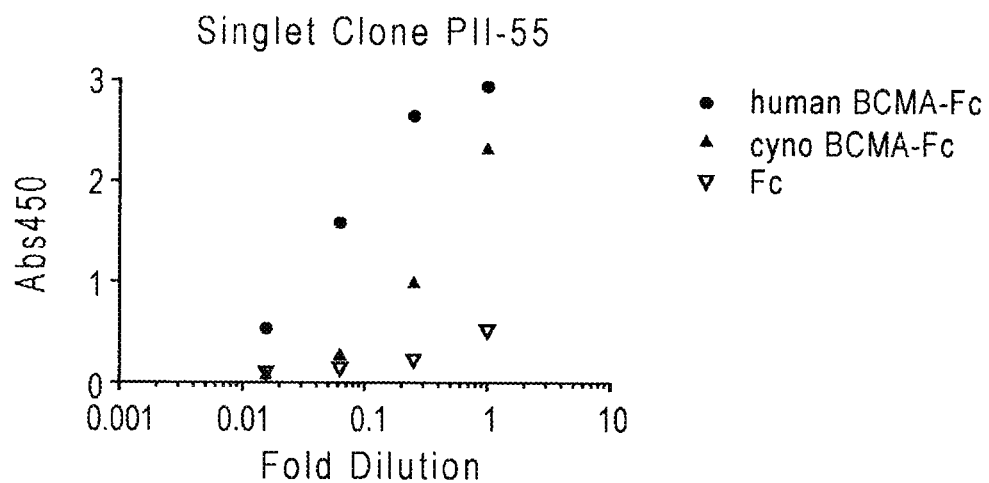
Figure 2H:
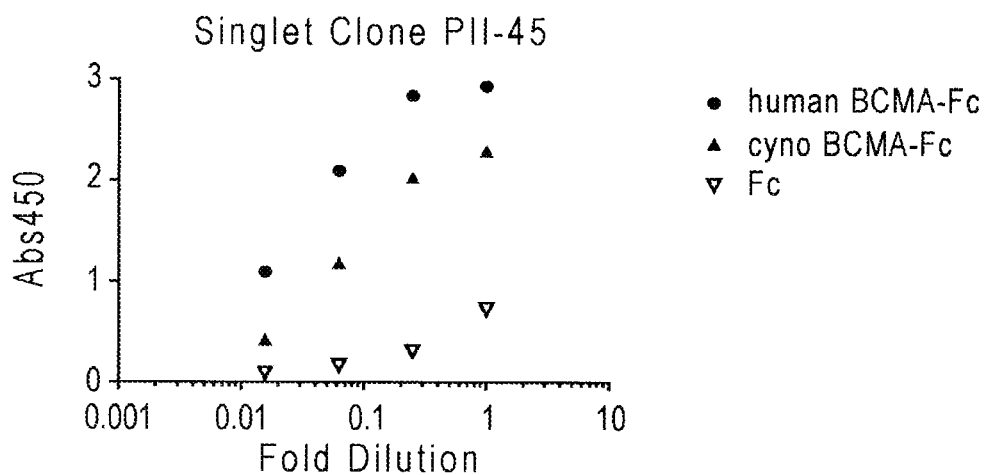
Figure 2I:
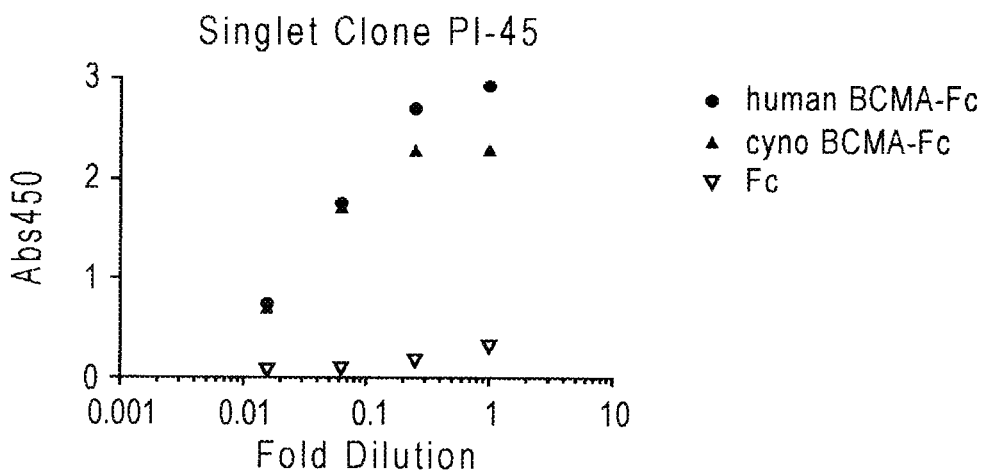

FIGS. 2A-2I: Monoclonal phage ELISA with BCMA-reactive clones (Example 1). FIG. 2A: PI-26; FIG. 2B: PI-28; FIG. 2C: PI-61; FIG. 2D: PIII-79; FIG. 2E: PIII-78; FIG. 2F: PIV-24; FIG. 2G: PII-55; FIG. 2H: PII-45; FIG. 2I: PI-45.

Figure 3A:
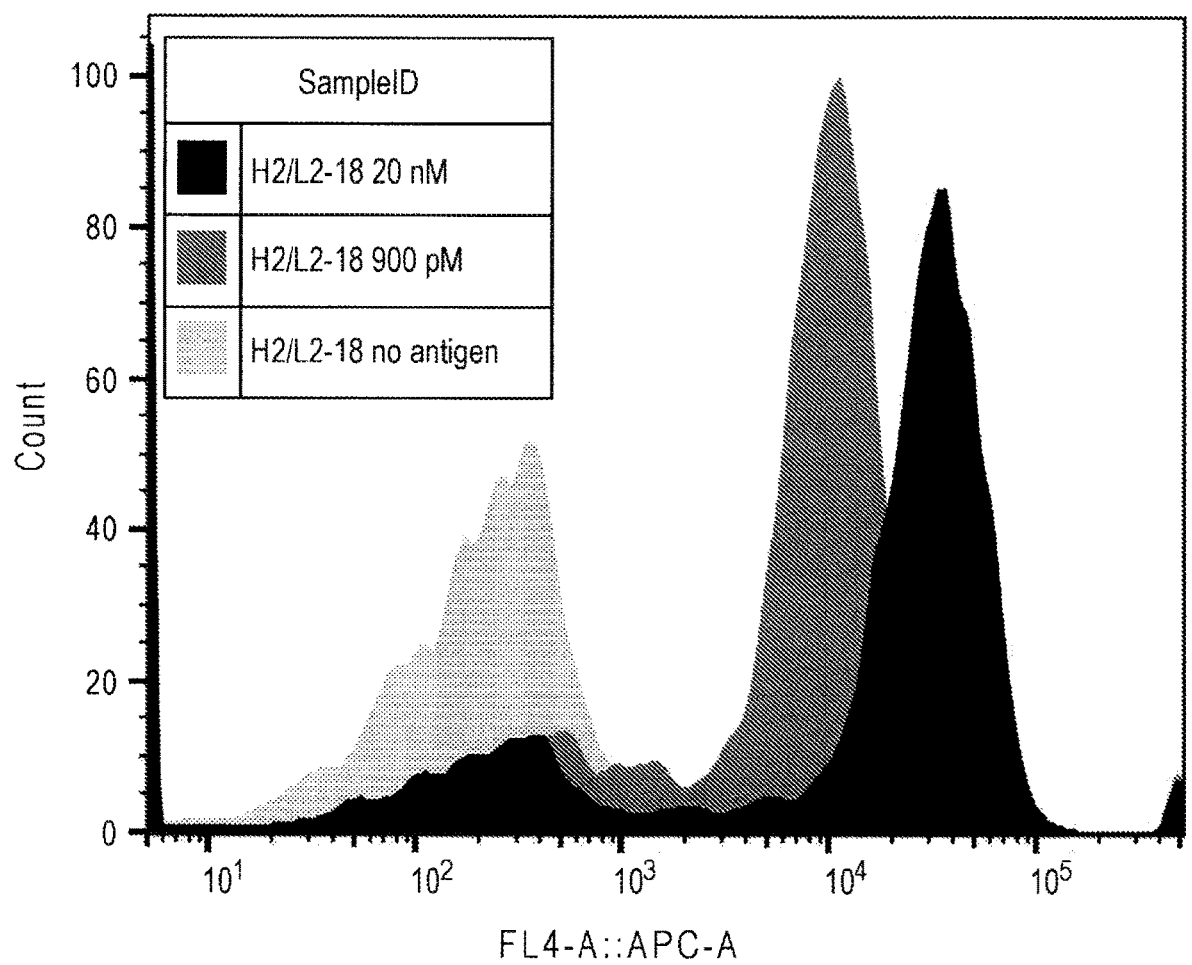
Figure 3B:
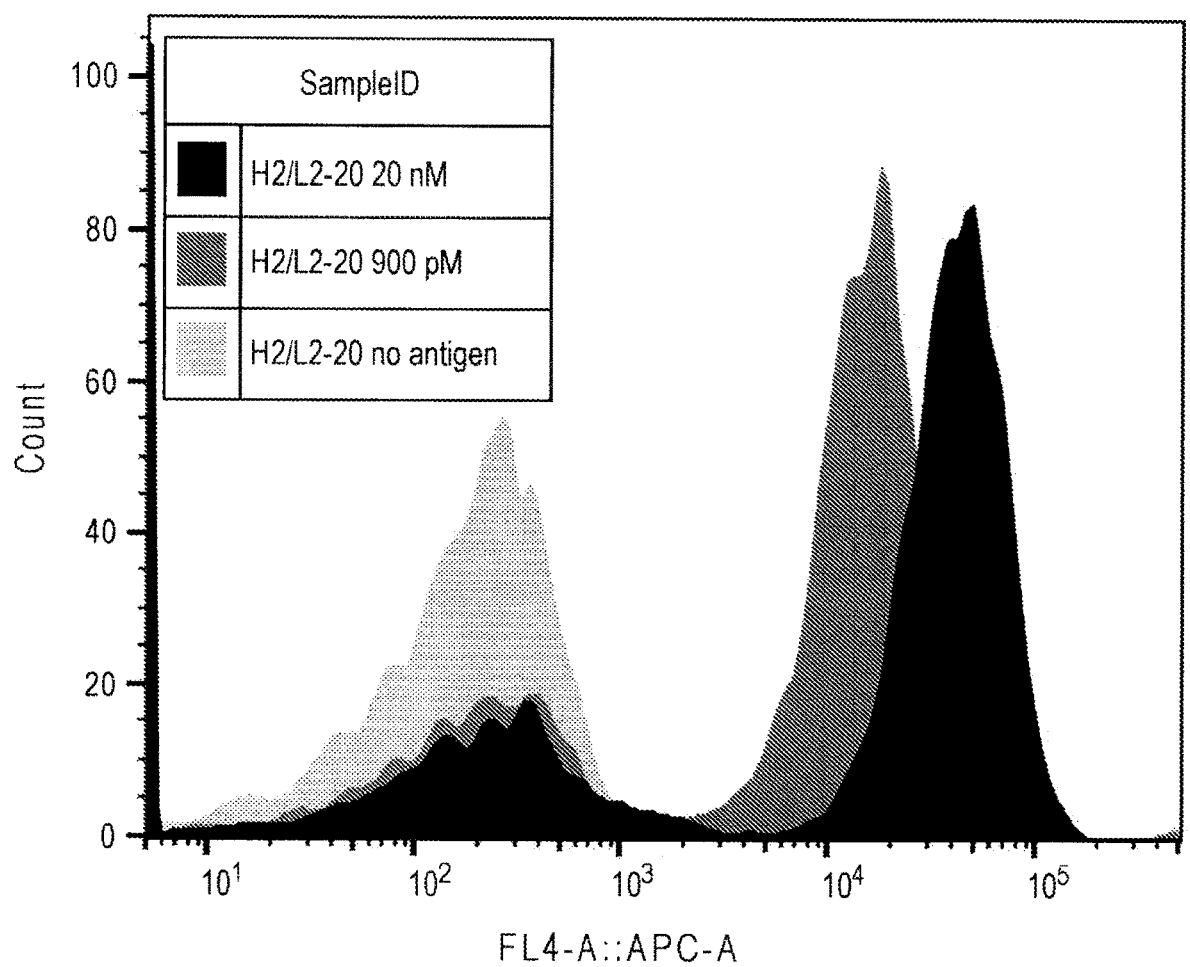
Figure 3C:
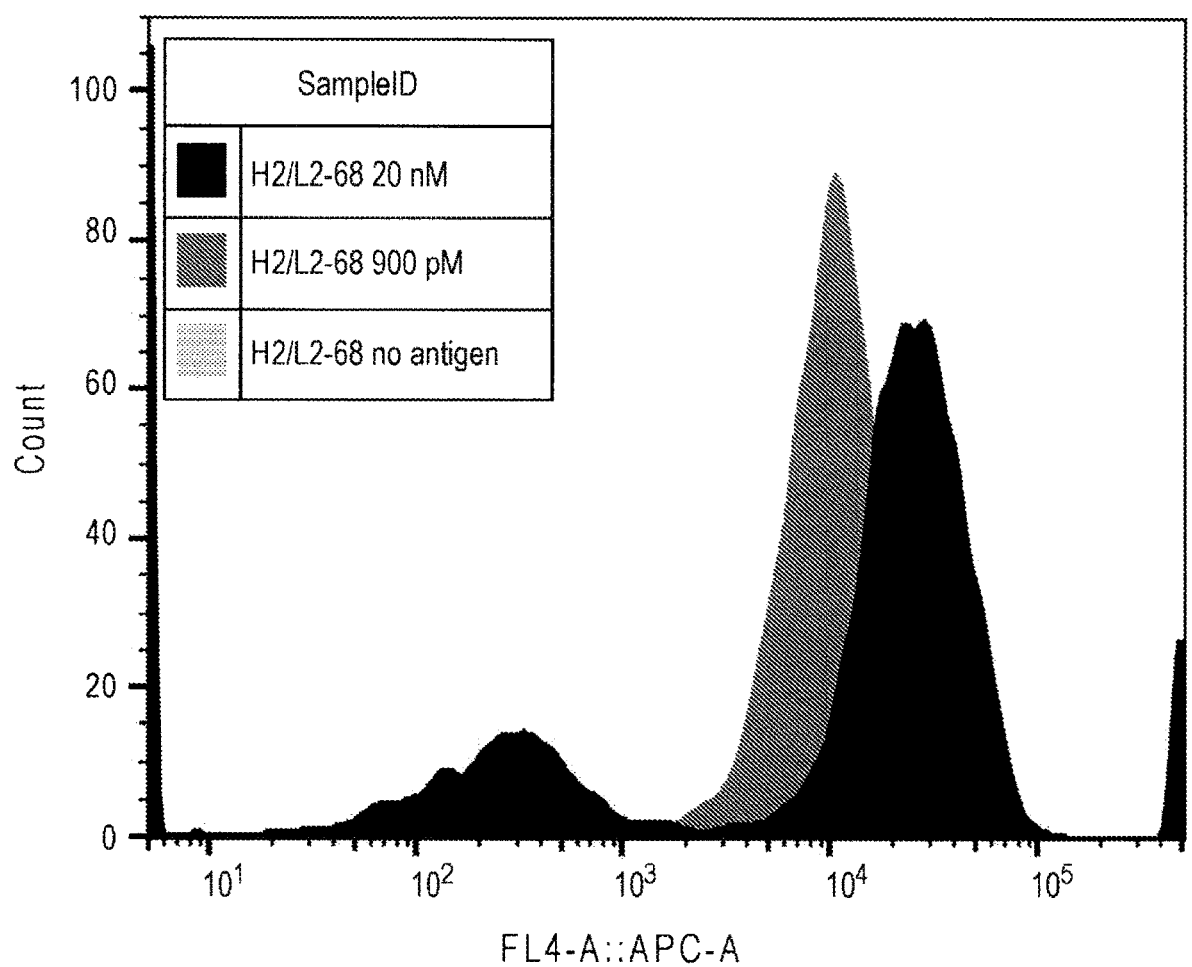
Figure 3D:
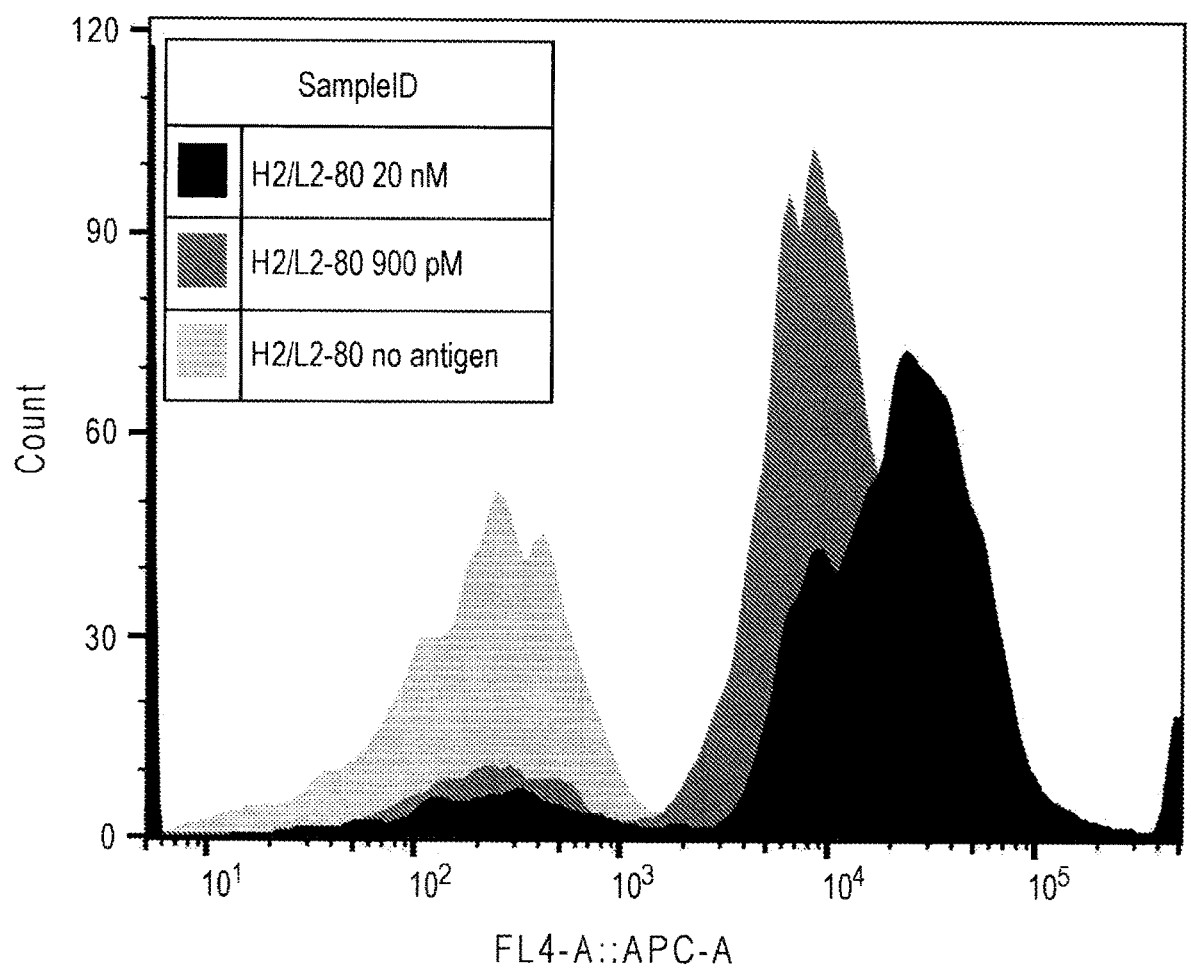
Figure 3E:
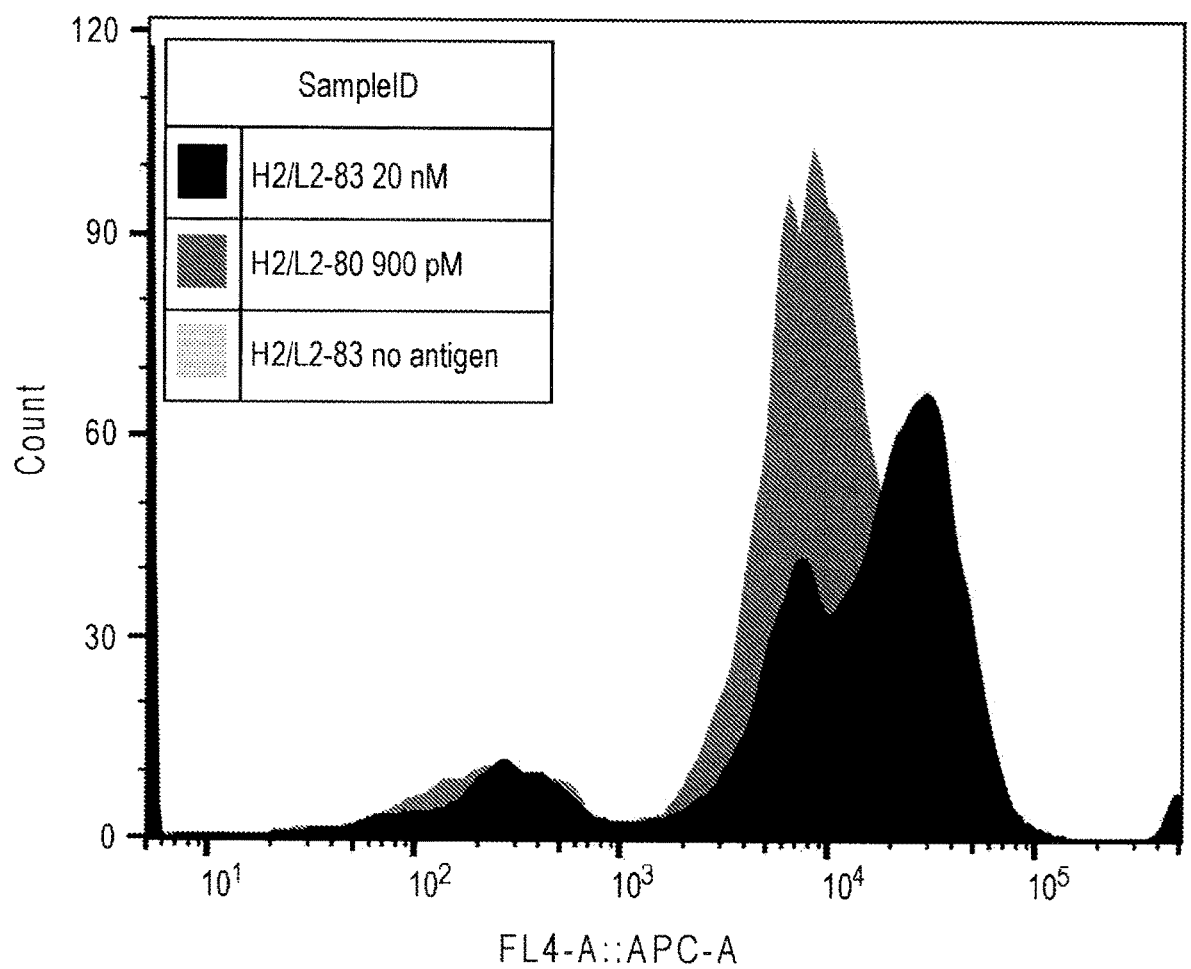
Figure 3F:
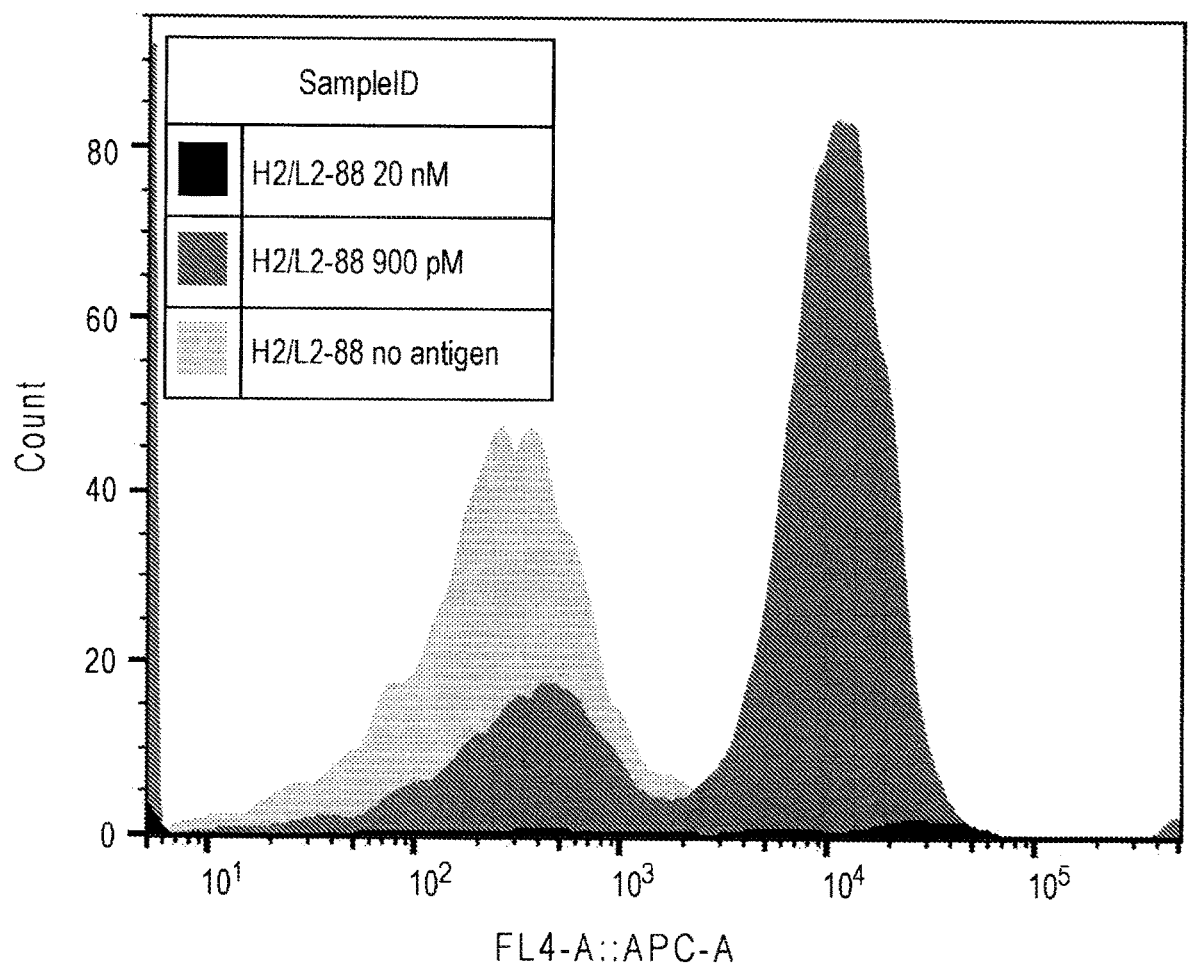
Figure 3G:
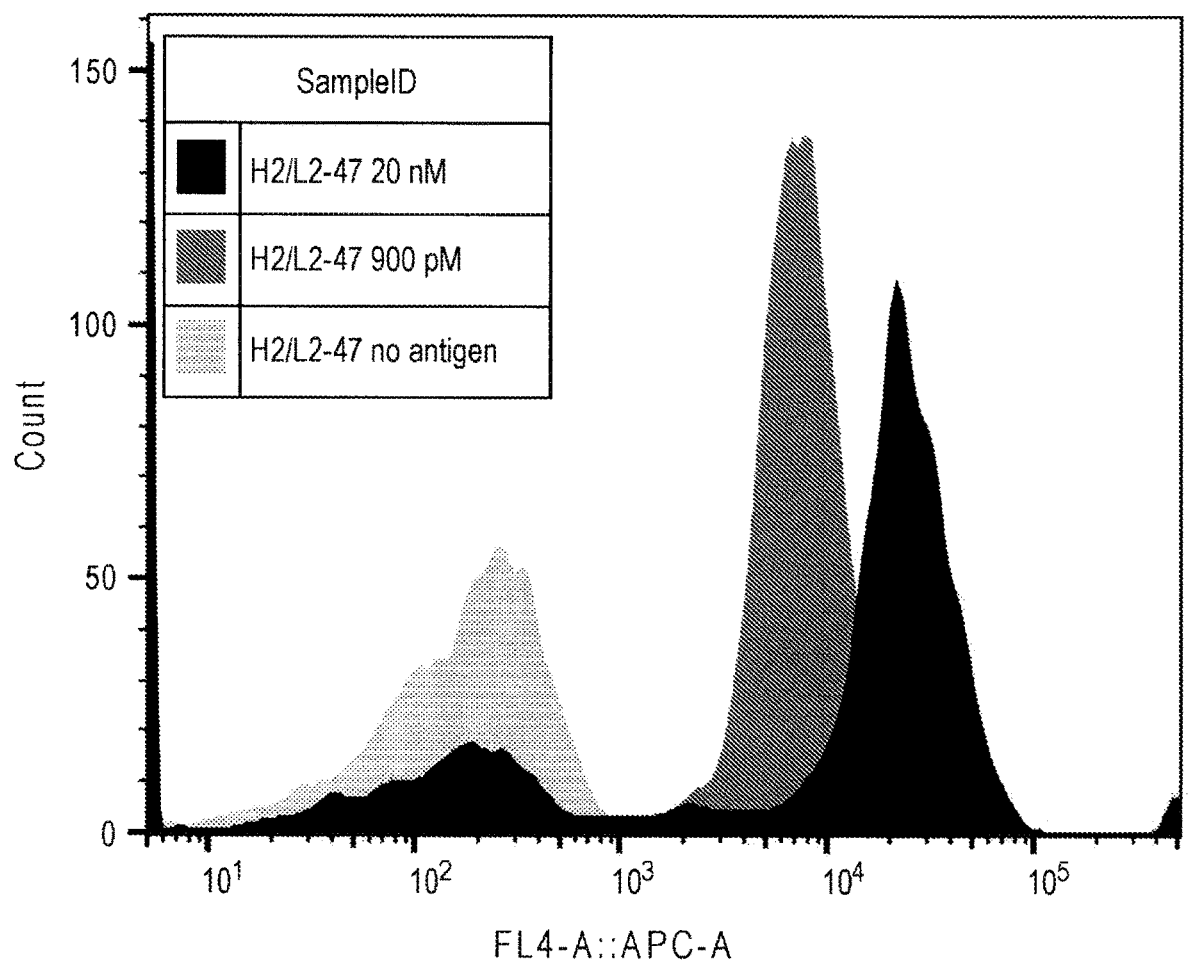
Figure 3H:
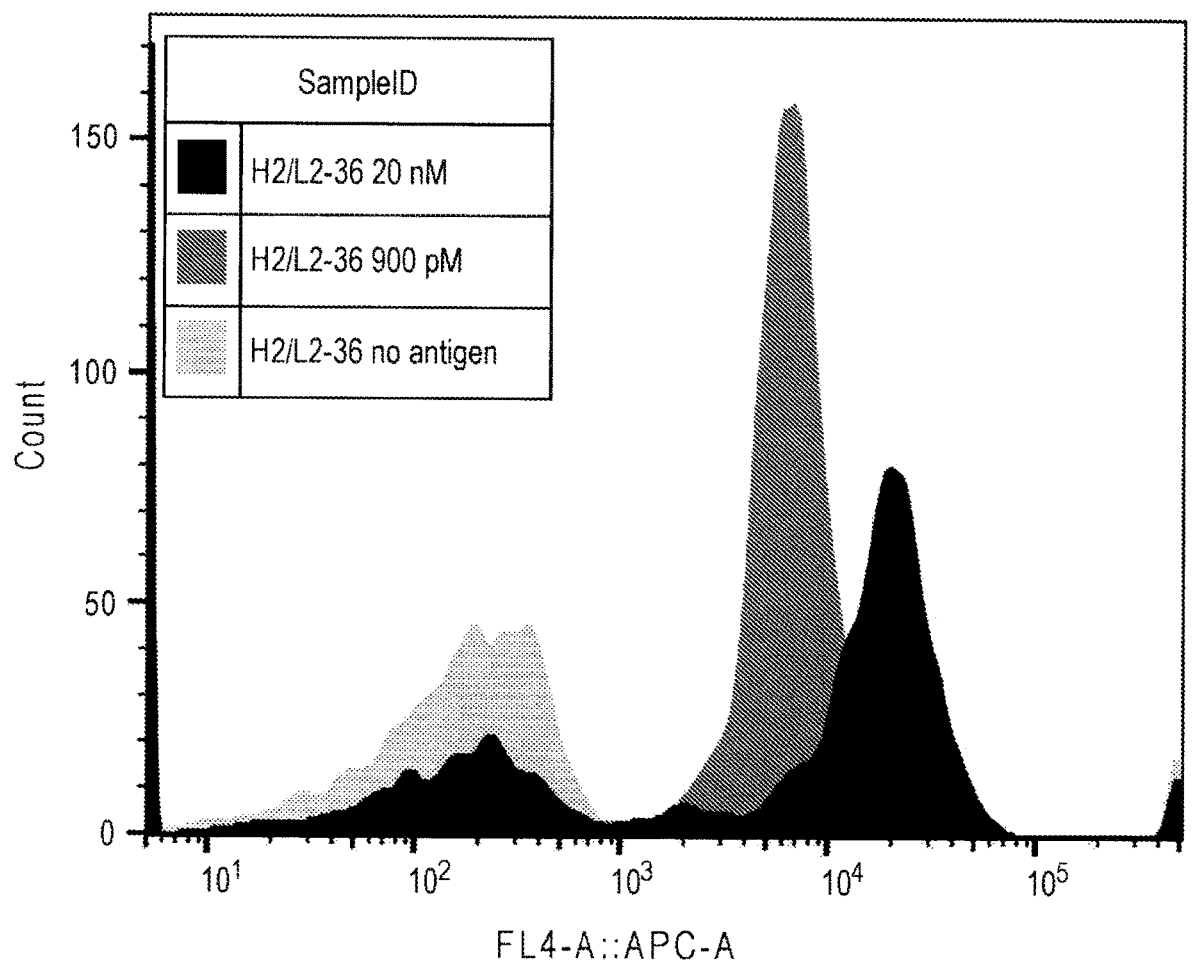
Figure 3I:
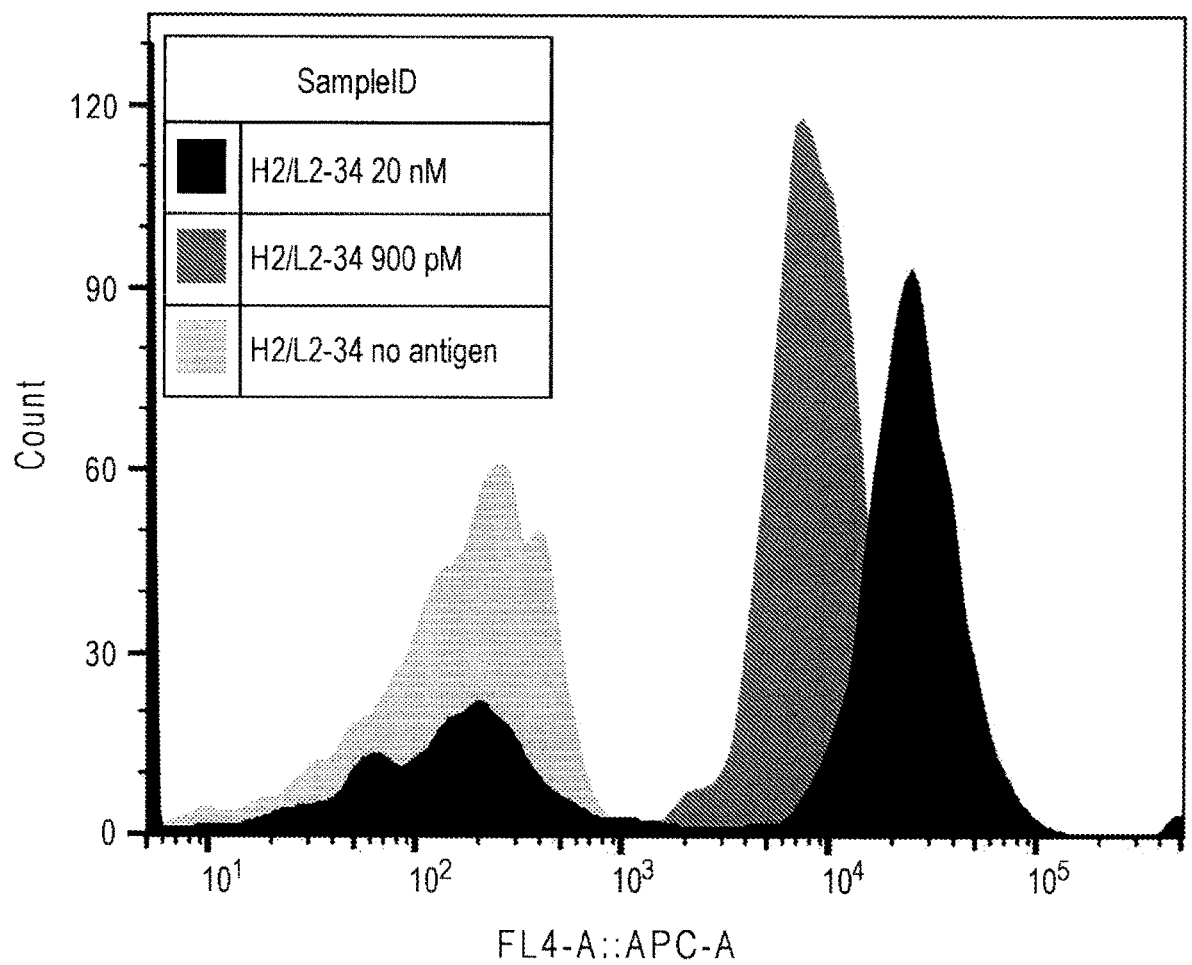

FIGS. 3A-3I: Titration of soluble BCMA onto the surface of individual yeast clones (Example 2). FIG. 3A: clone H2/L2-18; FIG. 3B: clone H2/L2-2; FIG. 3C: clone H2/L2-68; FIG. 3D: clone H2/L2-80; FIG. 3E: clone H2/L2-83; FIG. 3F: clone H2/L2-88; FIG. 3G: clone H2/L2-47; FIG. 3H: clone H2/L2-36; FIG. 3I: clone H2/L2-34.

FIG. 4: CDR-H2 sequences of parental PI-61 (SEQ ID NO:113) and selected clones H2/L2-22 (SEQ ID NO:114), H2/L2-88 (SEQ ID NO:115), H2/L2-36 (SEQ ID NO:115), H2/L2-34 (SEQ ID NO:116), H2/L2-68 (SEQ ID NO:117), H2/L2-18 (SEQ ID NO:118), H2/L2-47 (SEQ ID NO:115), H2/L2-20 (SEQ ID NO:112), H2/L2-80 (SEQ ID NO:112), and H2/L2-83 (SEQ ID NO:115).

FIG. 5: CDR-L2 sequences of parental PI-61 (SEQ ID NO:103) and selected clones H2/L2-22 (SEQ ID NO:104), H2/L2-88 (SEQ ID NO:105), H2/L2-36 (SEQ ID NO:105), H2/L2-34 (SEQ ID NO:106), H2/L2-68 (SEQ ID NO:107), H2/L2-18 (SEQ ID NO:106), H2/L2-47 (SEQ ID NO:106), H2/L2-20 (SEQ ID NO:102), H2/L2-80 (SEQ ID NO:108), and H2/L2-83 (SEQ ID NO:105).

FIG. 6: Heterodimeric bispecific antibody format of the bispecific antibodies of Example 3.

FIG. 7: CDR-H2 sequences of parental PI-61 (SEQ ID NO:113) and selected clones H3-1 (SEQ ID NO:119), H3-2 (SEQ ID NO:120), H3-3 (SEQ ID NO:121), H3-4 (SEQ ID NO:119), H3-5 (SEQ ID NO:122), H3-6 (SEQ ID NO:119), H3-7 (SEQ ID NO:112), H3-8 (SEQ ID NO:119), H3-9 (SEQ ID NO:119), H3-10 (SEQ ID NO:120), H3-11 (SEQ ID NO:123), H3-12 (SEQ ID NO:124), H3-13 (SEQ ID NO:119), H3-14 (SEQ ID NO:119), and H3-15 (SEQ ID NO:125).

FIG. 8: CDR-L2 sequences of parental PI-61 (SEQ ID NO:155) and selected clones H3-1 (SEQ ID NO:157), H3-2 (SEQ ID NO:157), H3-3 (SEQ ID NO:157), H3-4 (SEQ ID NO:156), H3-5 (SEQ ID NO:157), H3-6 (SEQ ID NO:157), H3-7 (SEQ ID NO:157), H3-8 (SEQ ID NO:157), H3-9 (SEQ ID NO:157), H3-10 (SEQ ID NO:157), H3-11 (SEQ ID NO:157), H3-12 (SEQ ID NO:157), H3-13 (SEQ ID NO:156), H3-14 (SEQ ID NO:161), and H3-15 (SEQ ID NO:156).

FIG. 9: CDR-H3 sequences of parental PI-61 (SEQ ID NO:49) and selected clones H3-1 (SEQ ID NO:127), H3-2 (SEQ ID NO:128), H3-3 (SEQ ID NO:127), H3-4 (SEQ ID NO:127), H3-5 (SEQ ID NO:129), H3-6 (SEQ ID NO:127), H3-7 (SEQ ID NO:130), H3-8 (SEQ ID NO:127), H3-9 (SEQ ID NO:127), H3-10 (SEQ ID NO:131), H3-11 (SEQ ID NO:132), H3-12 (SEQ ID NO:133), H3-13 (SEQ ID NO:127), H3-14 (SEQ ID NO:127), and H3-15 (SEQ ID NO:134).

Figure 10:
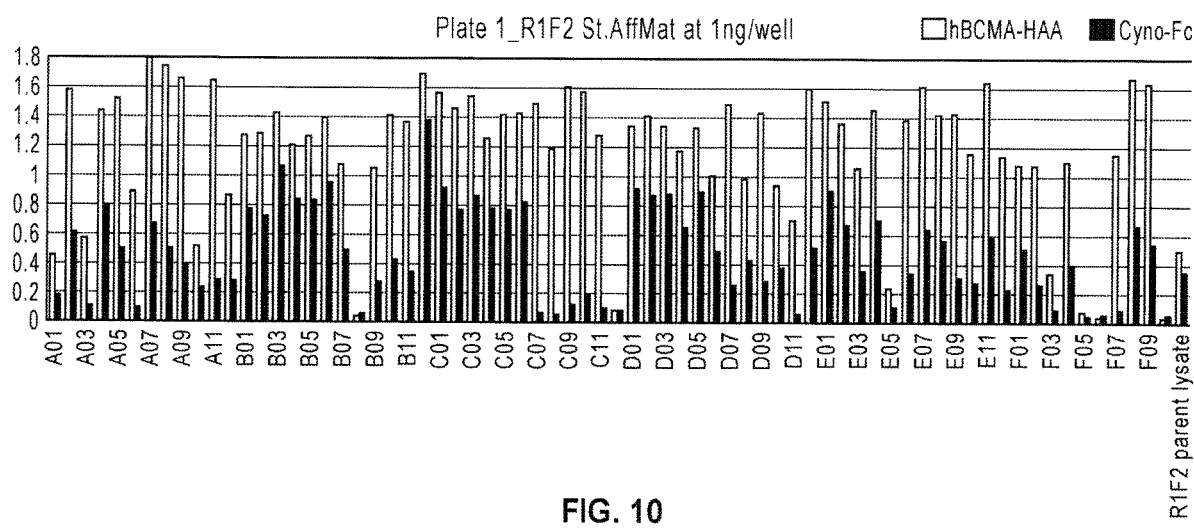

FIG. 10: ELISA screening of clones generated in Example 4 to test binding to recombinant full-length hBCMA and cynoBCMA.

Figure 11A:
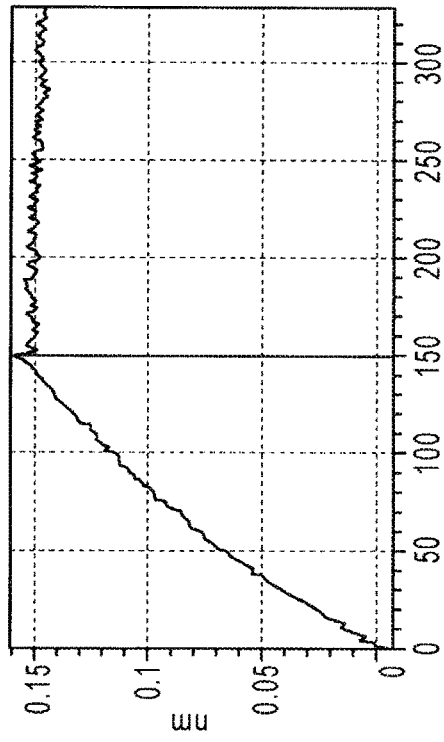
Figure 11B:
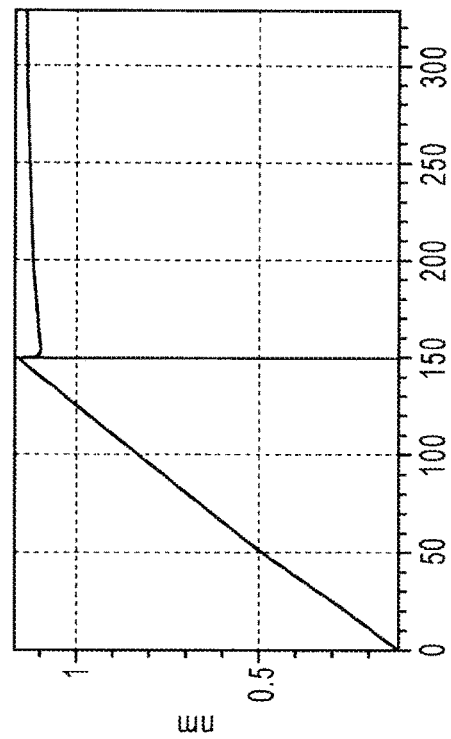
Figure 11C:
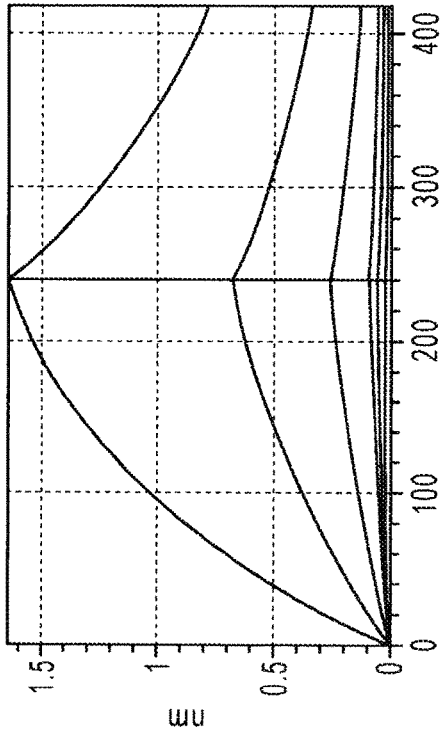
Figure 11D:
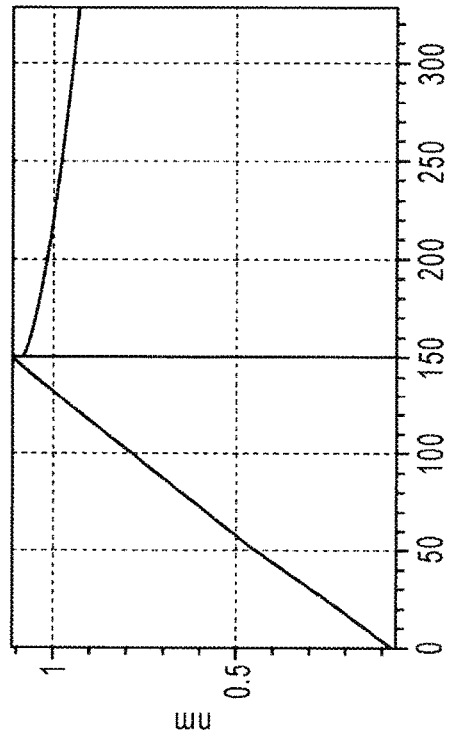
Figure 11E:
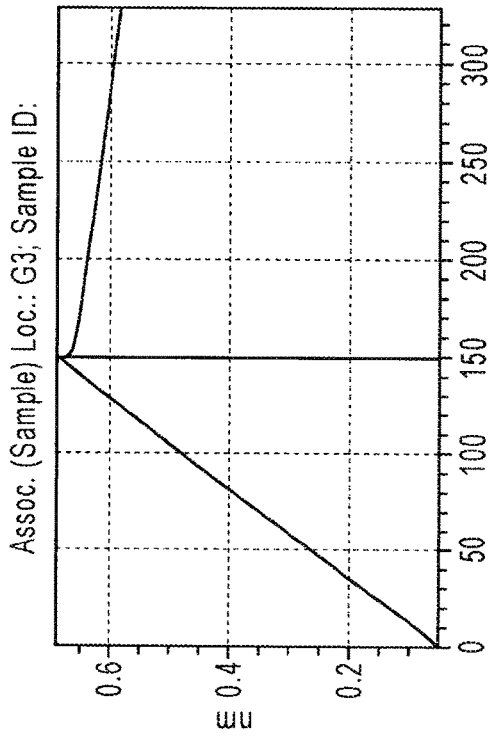
Figure 11F:
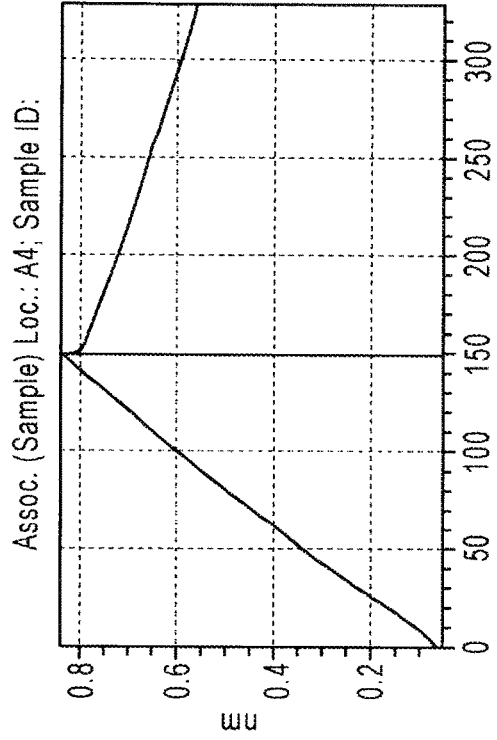
Figure 11G:
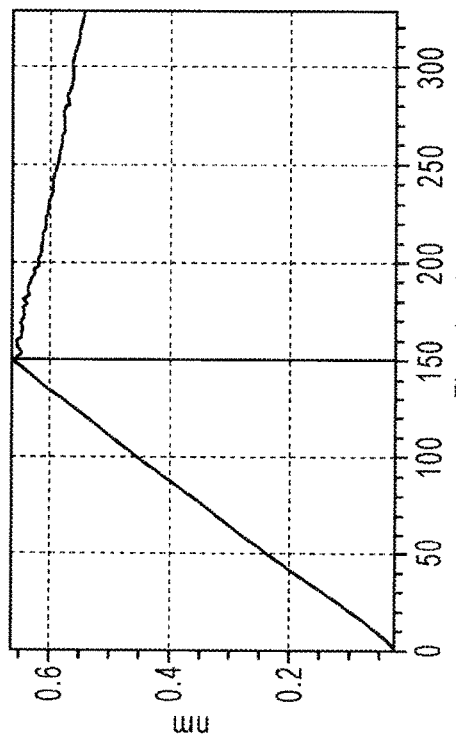
Figure 11H:
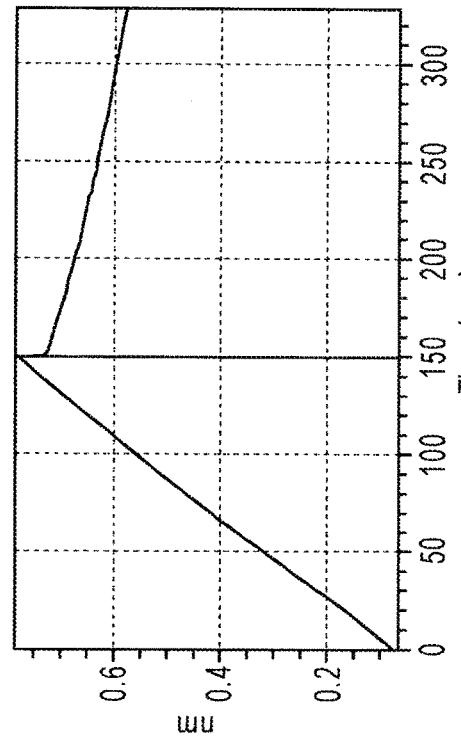
Figure 11I:
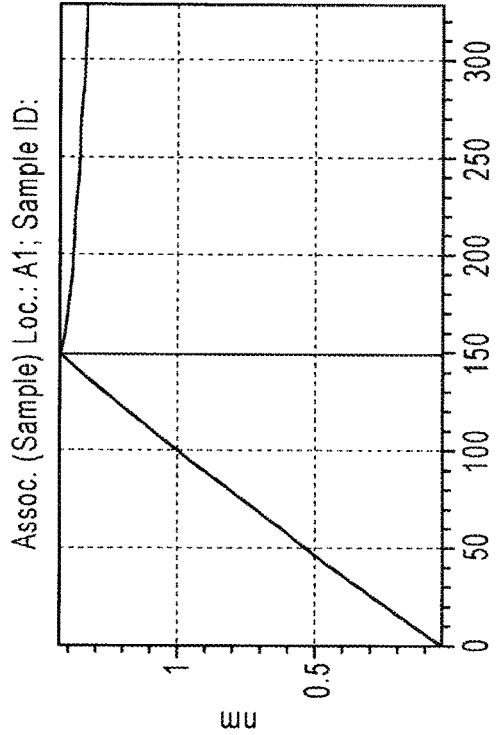
Figure 11J:
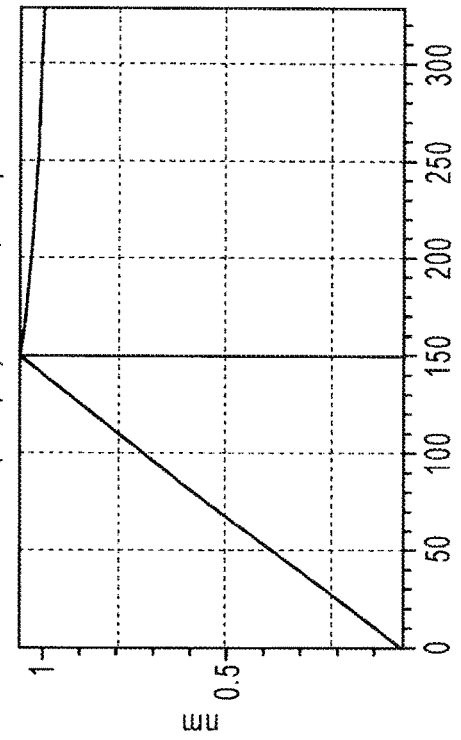
Figure 11K:
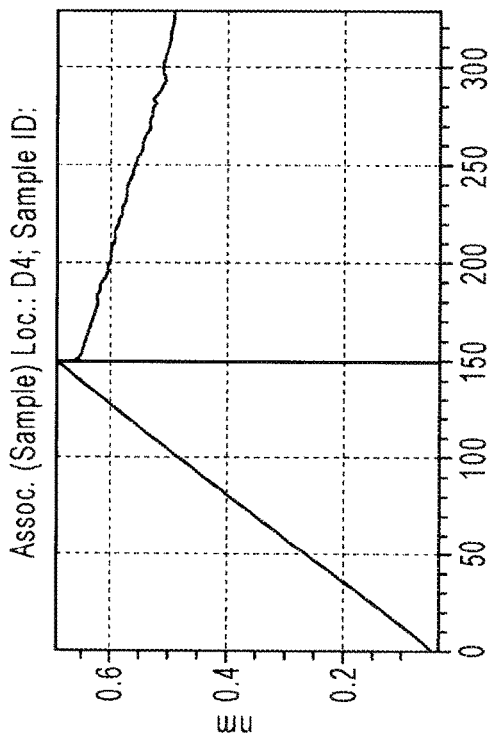
Figure 11L:
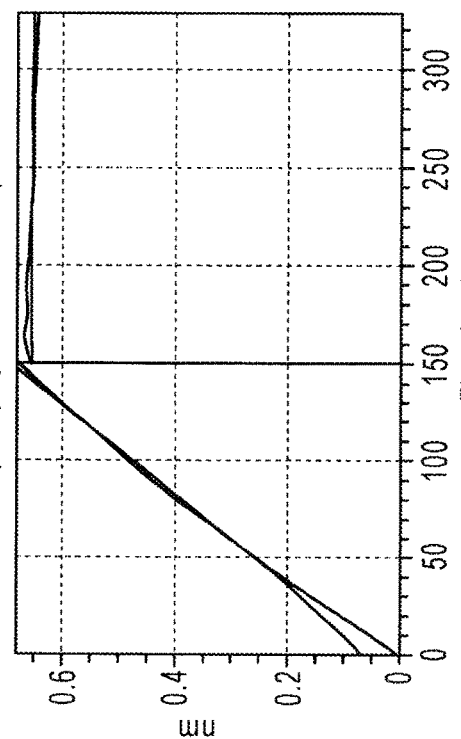
Figure 11M:
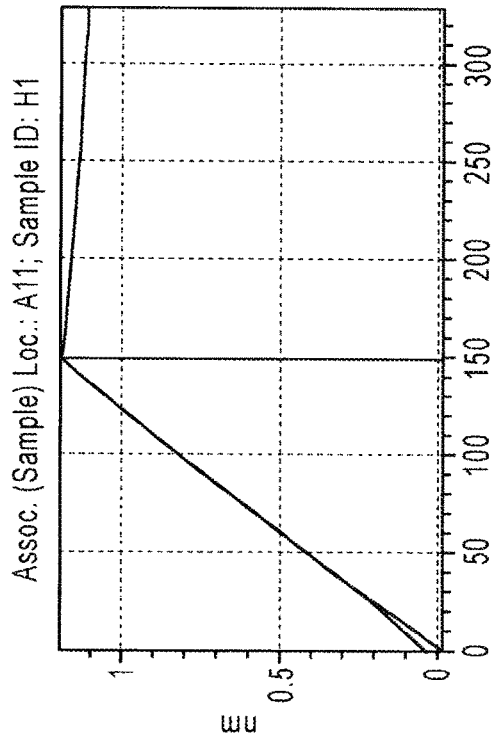
Figure 11N:
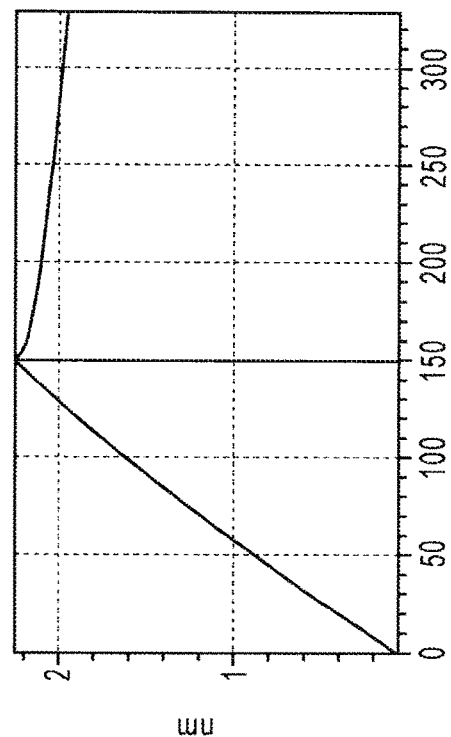
Figure 11O:
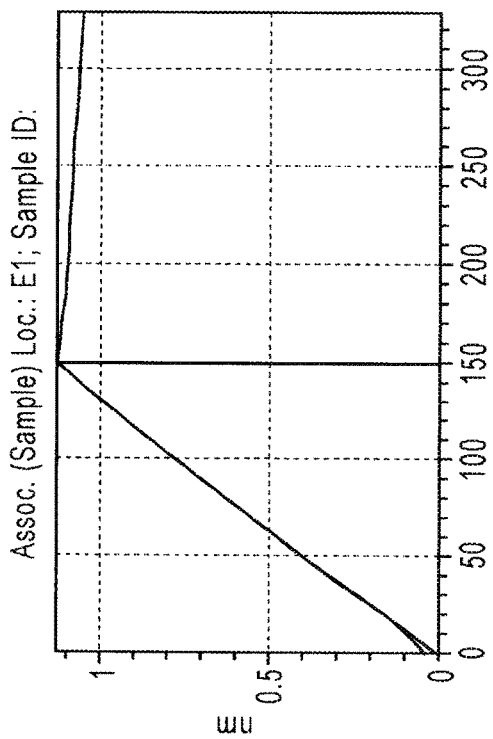
Figure 11P:
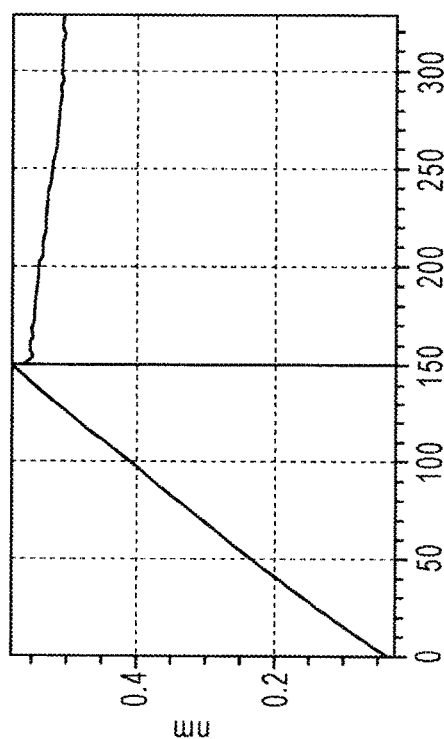
Figure 11Q:
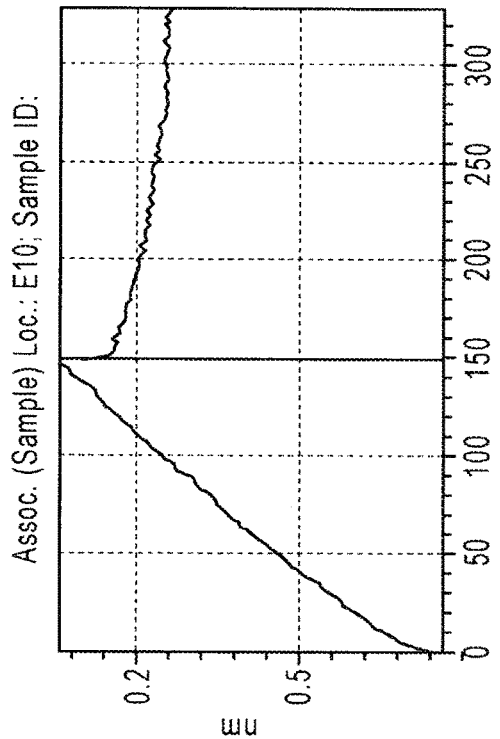
Figure 11S:
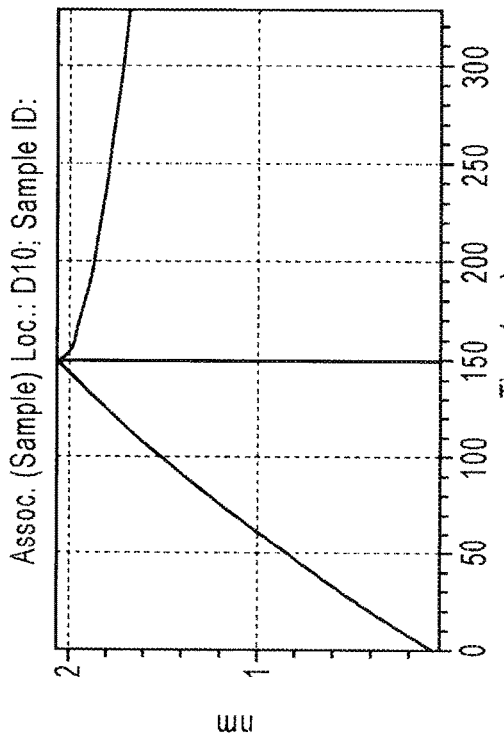
Figure 11R:
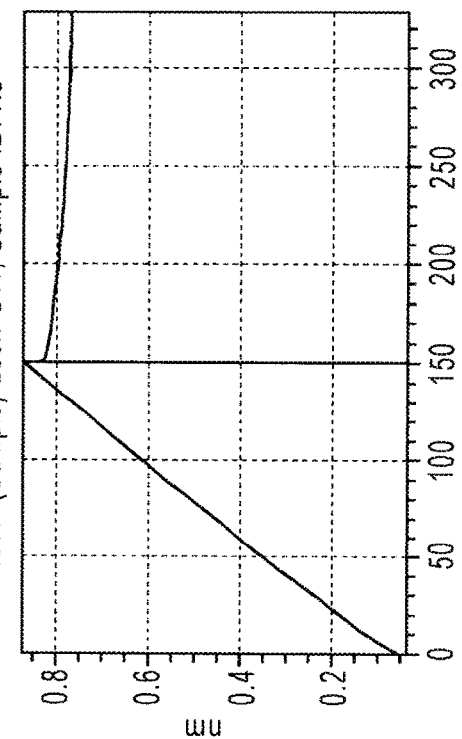

FIGS. 11A-11S: Biolayer Interferometry (BLI) plots showing binding of selected human anti-BCMA antibodies to hBCMA (Example 4). FIG. 11A: R1F2; FIG. 11B: PALF01; FIG. 11C: PALF03; FIG. 11D: PALF04; FIG. 11E: PALF05; FIG. 11F: PALF06; FIG. 11G: PALF07; FIG. 11H: PALF08; FIG. 11I: PALF09; FIG. 11J: PALF11; FIG. 11K: PALF12; FIG. 11L: PALF13; FIG. 11M: PALF14; FIG. 11N: PALF15; FIG. 11O: PALF16; FIG. 11P: PALF17; FIG. 11Q: PALF18; FIG. 11R: PALF19; FIG. 11S: PALF20.

Figure 12A:
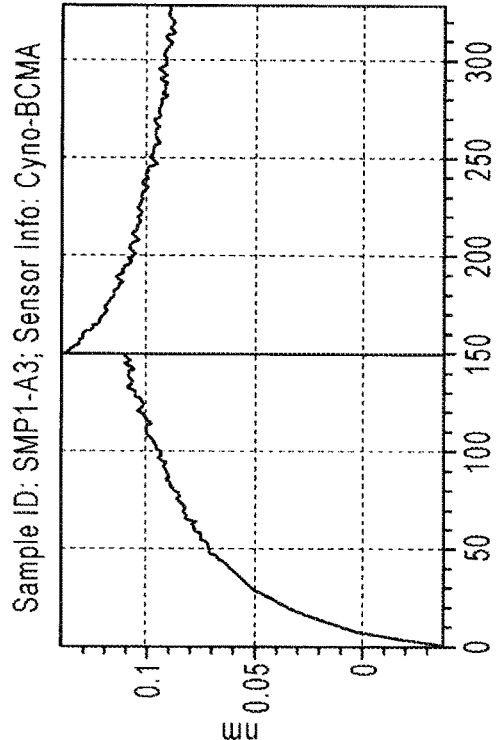
Figure 12B:
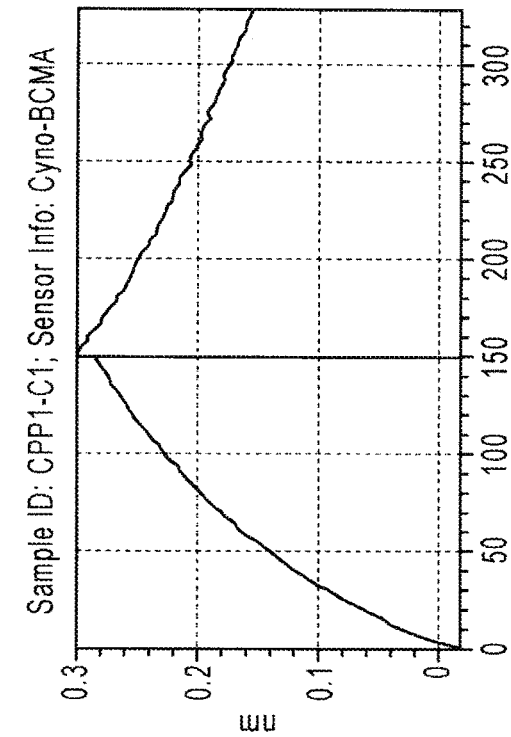
Figure 12C:
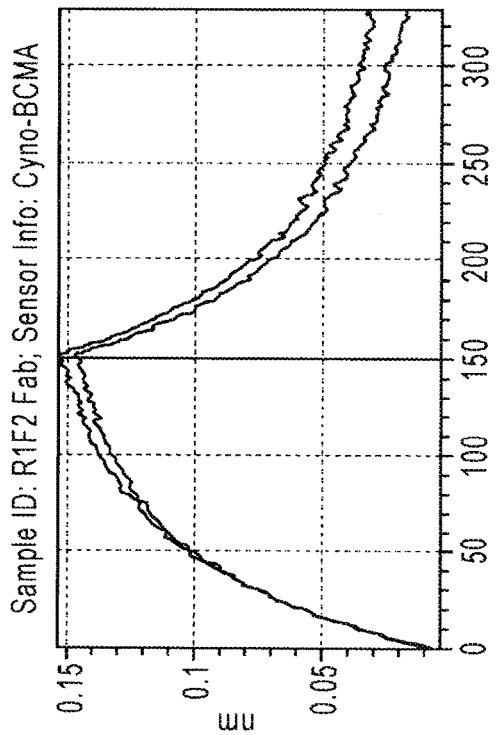
Figure 12D:
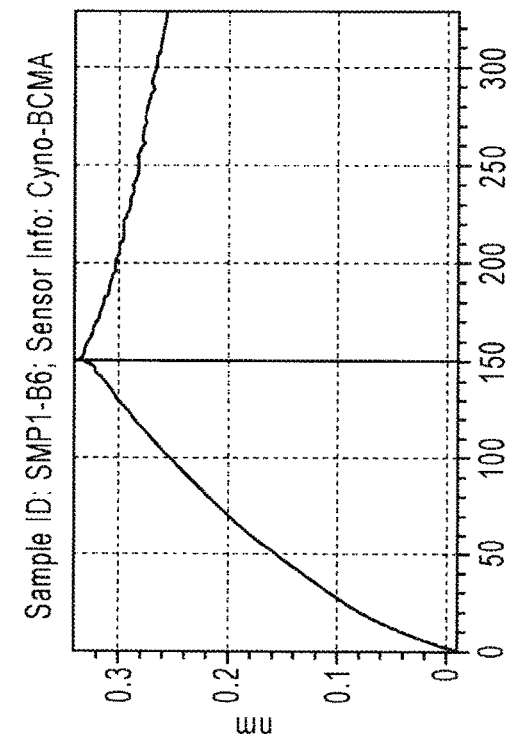
Figure 12E:
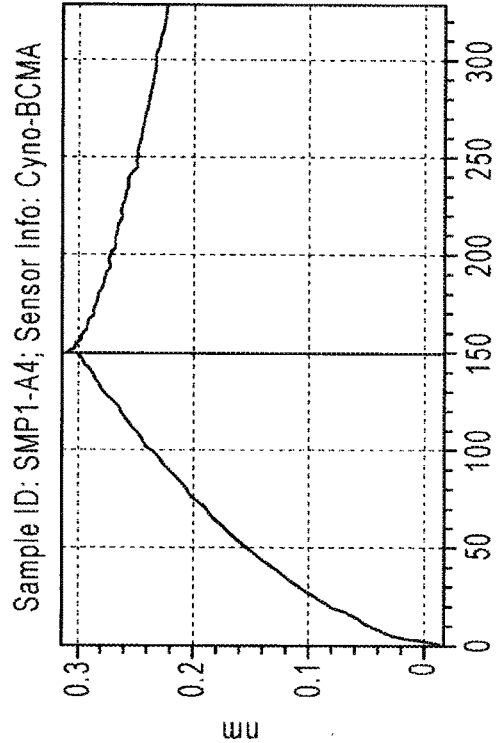
Figure 12F:
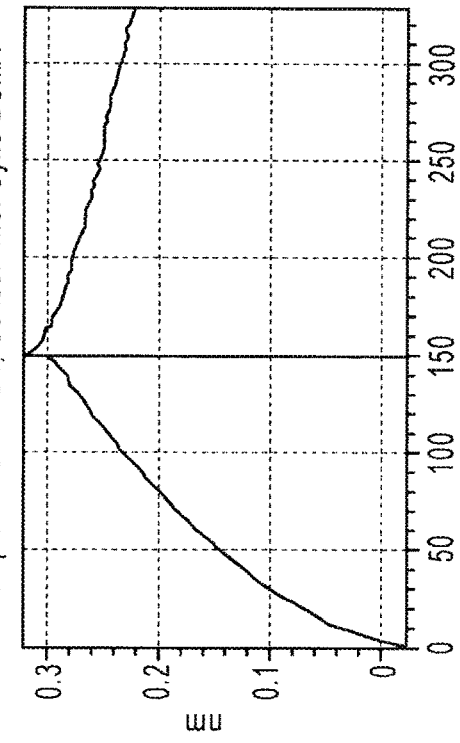
Figure 12G:
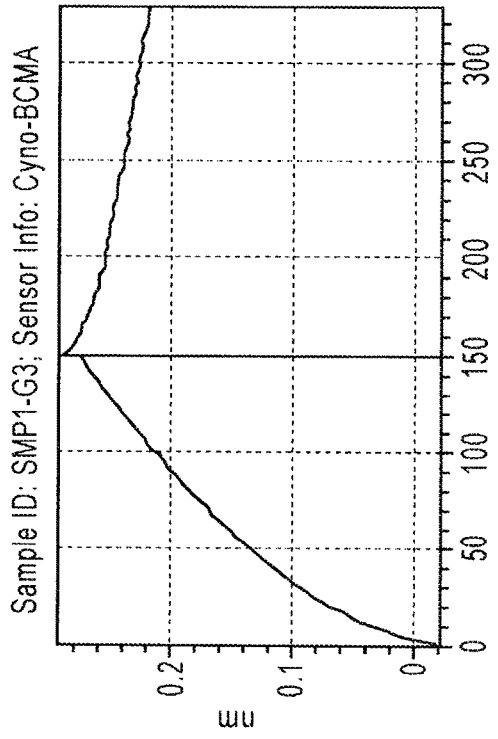
Figure 12H:
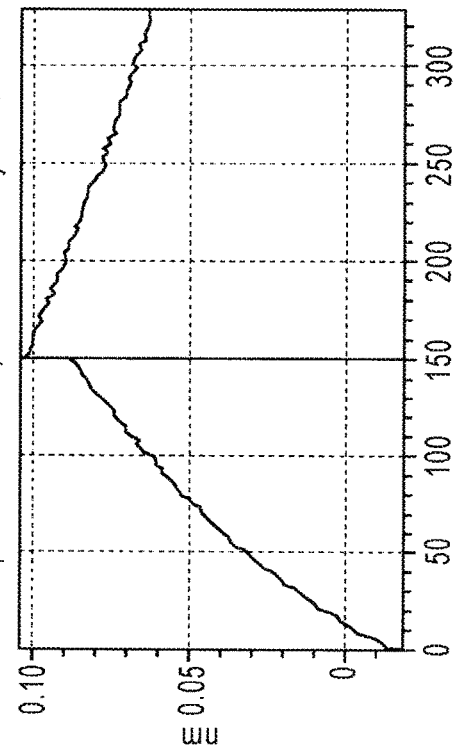
Figure 12I:
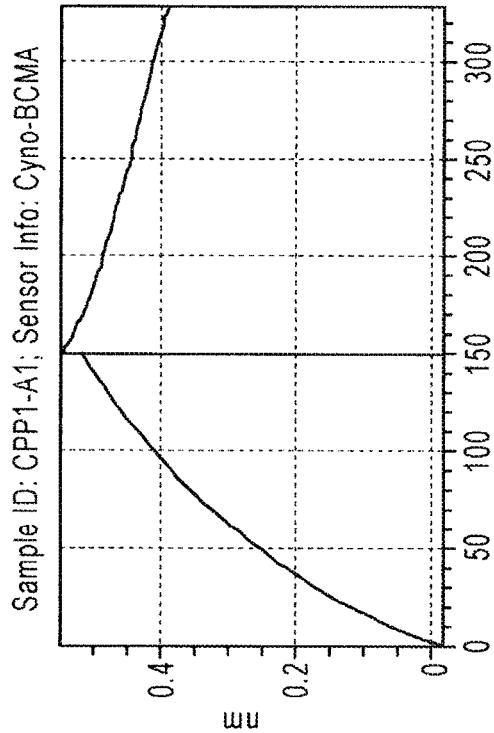
Figure 12J:
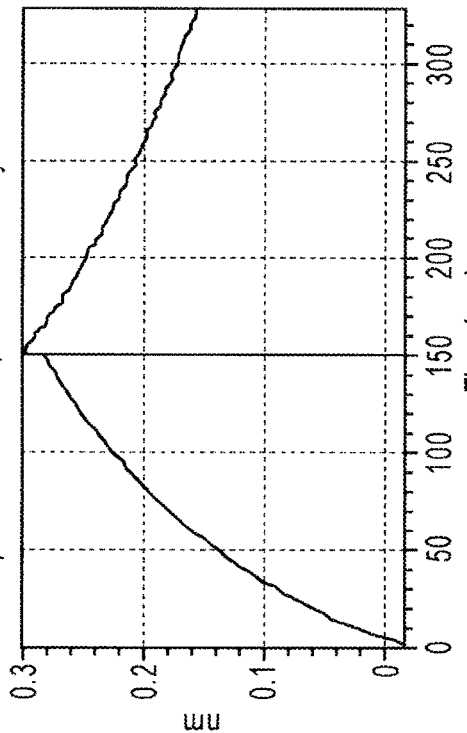
Figure 12K:
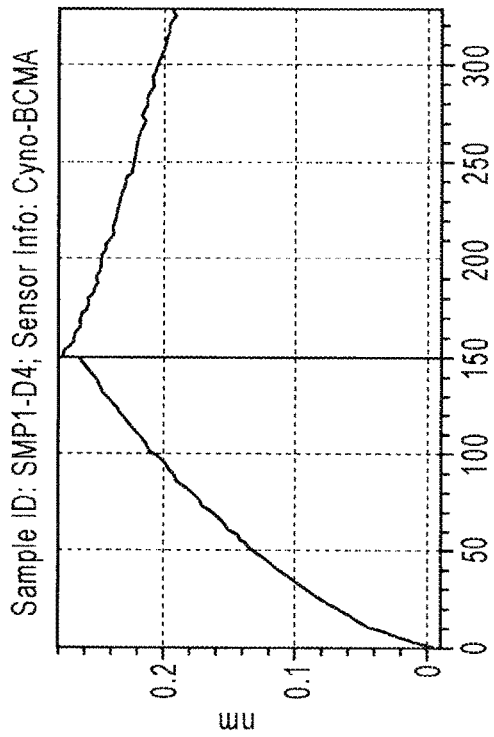
Figure 12L:
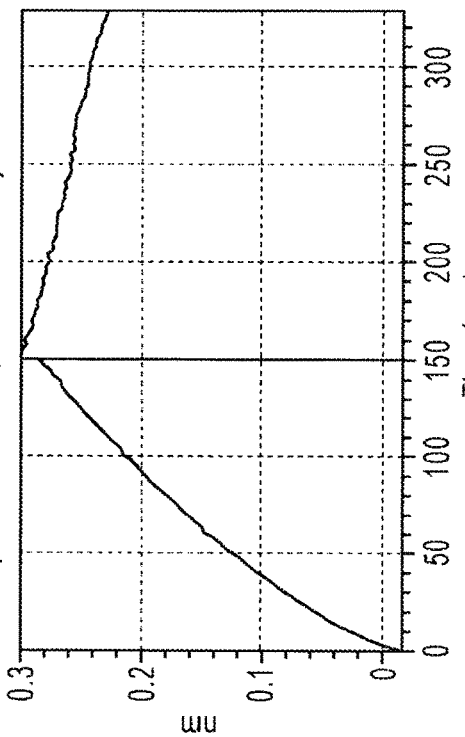
Figure 12M:
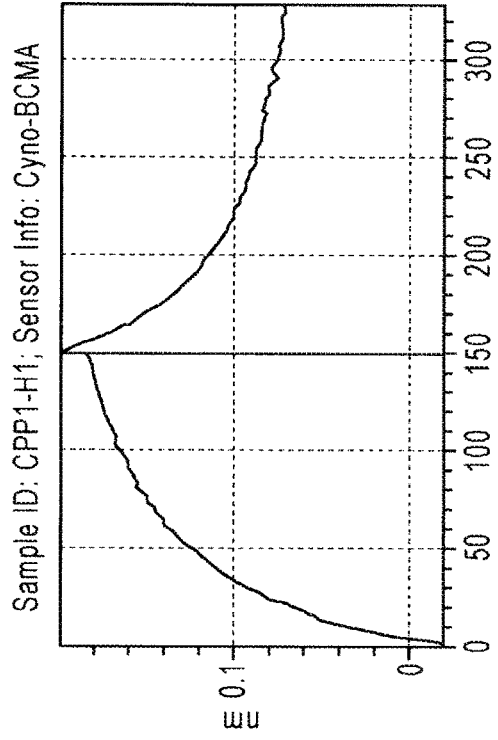
Figure 12N:
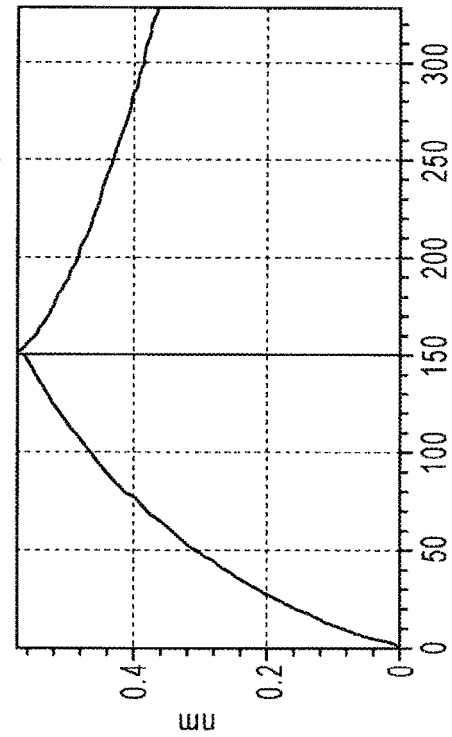
Figure 12O:
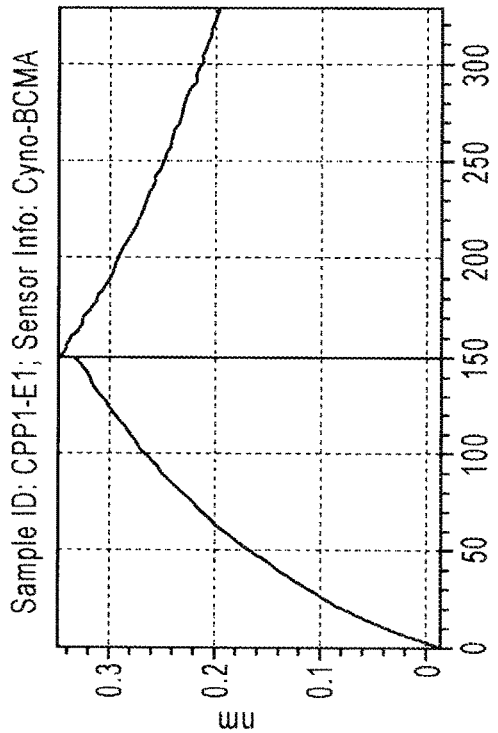
Figure 12P:
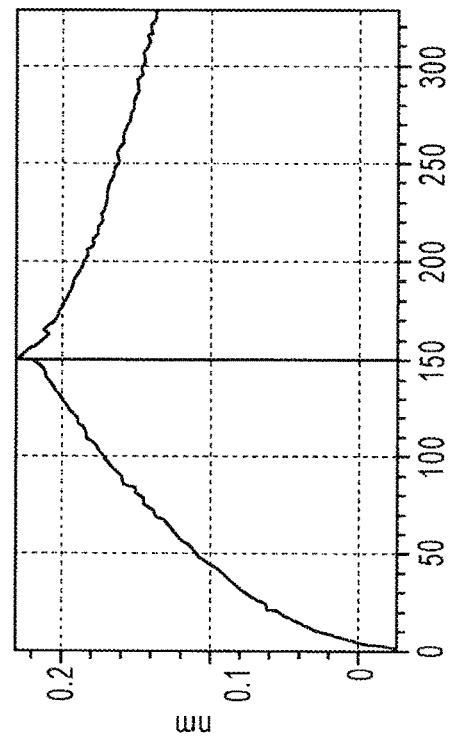
Figure 12R:
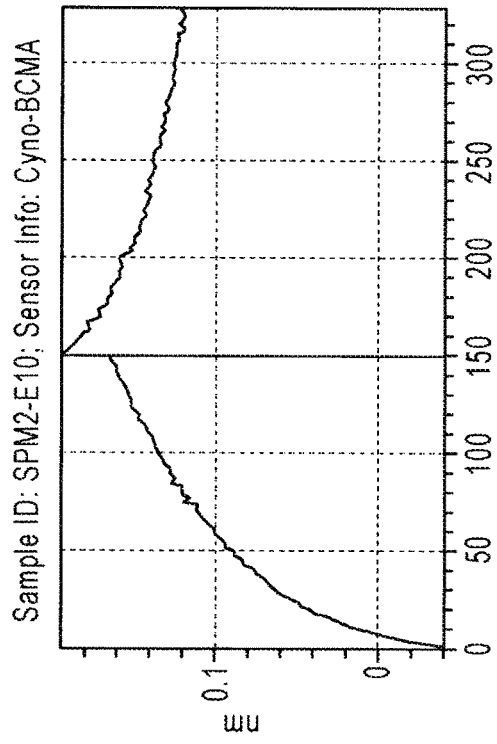
Figure 12Q:
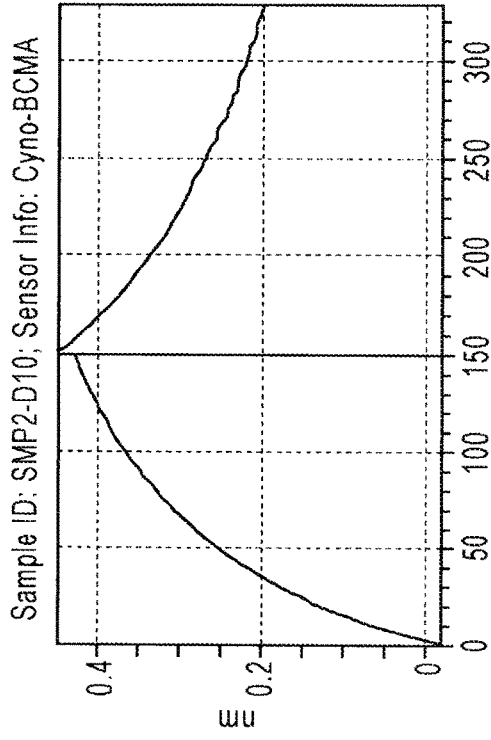
Figure 12S:
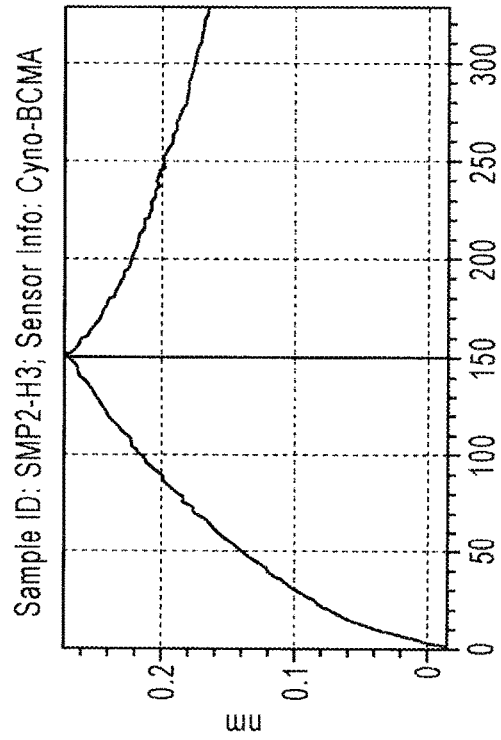
Figure 13A:
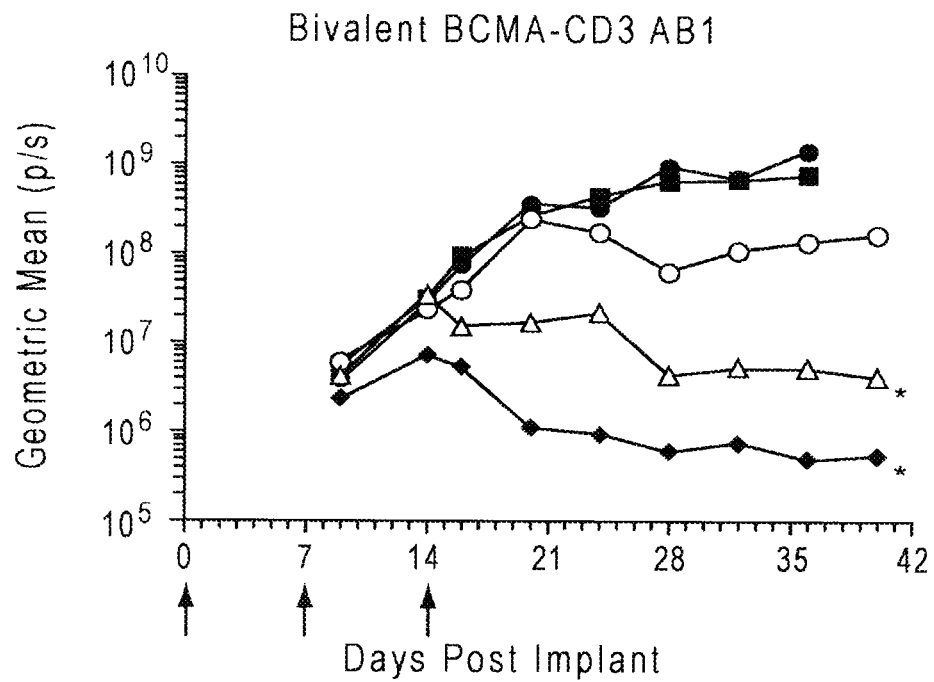
Figure 13B:
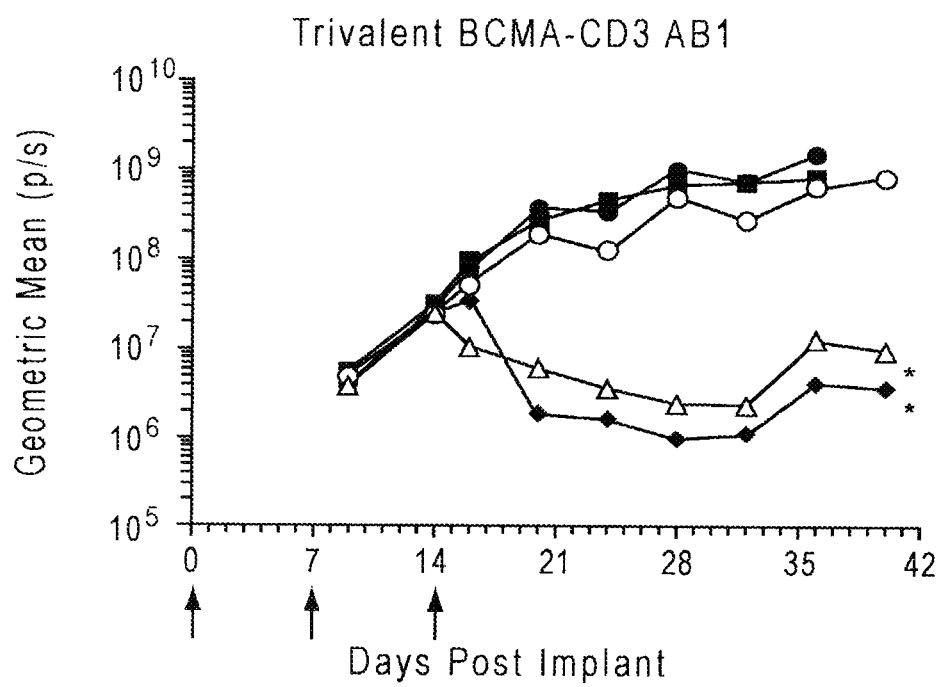
Figure 13C:
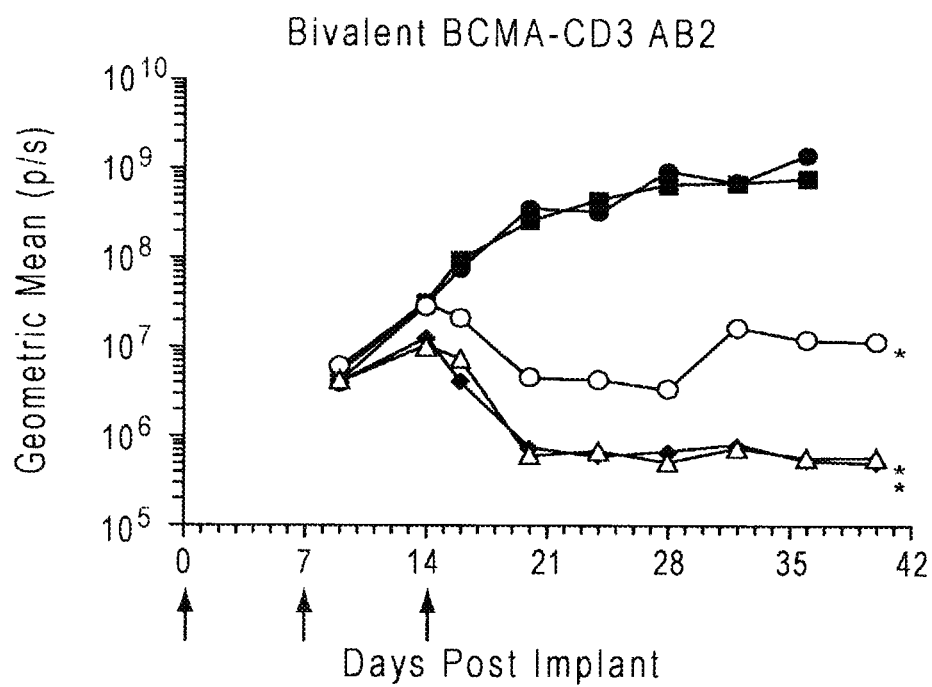
Figure 13D:
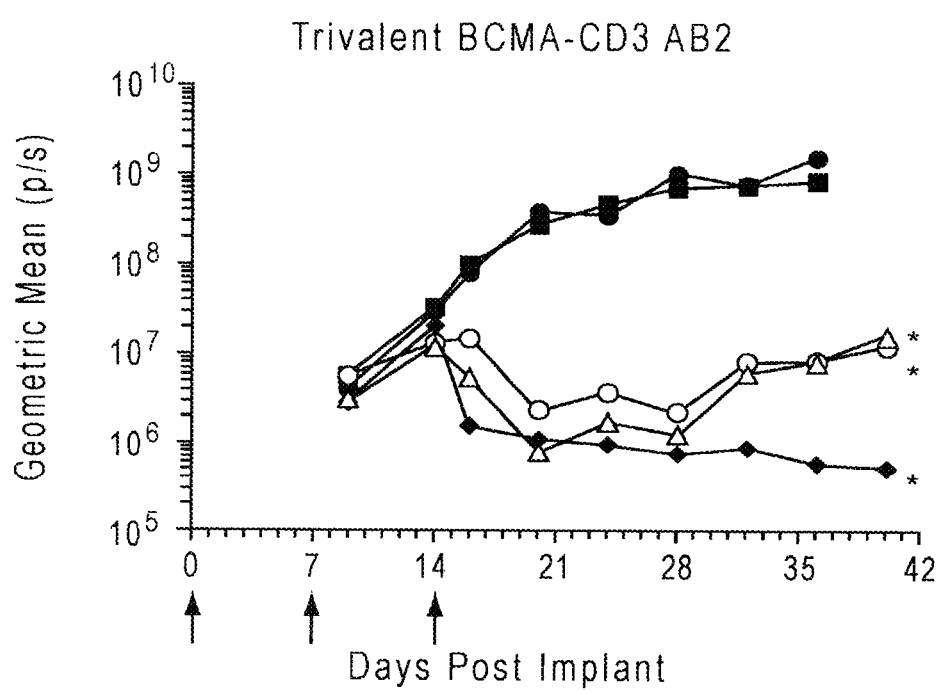
Figure 14A:
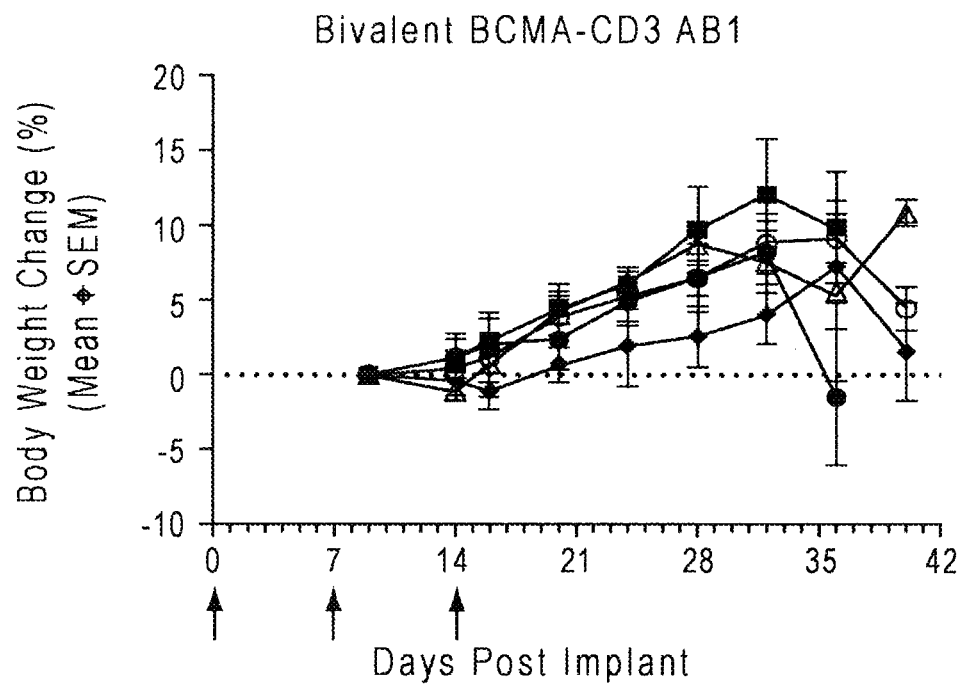
Figure 14B:
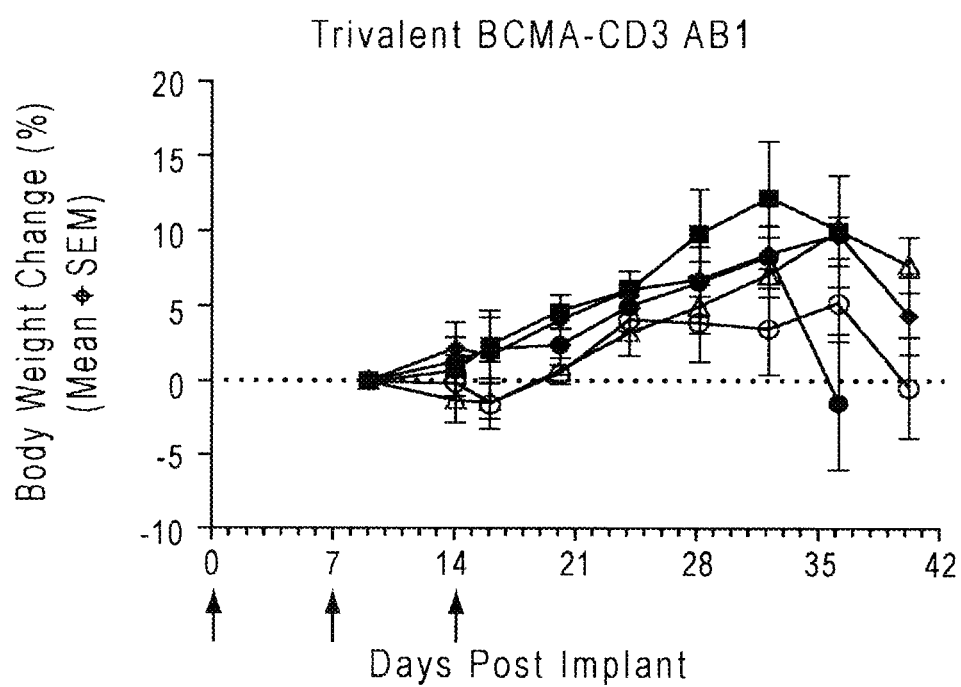
Figure 14C:
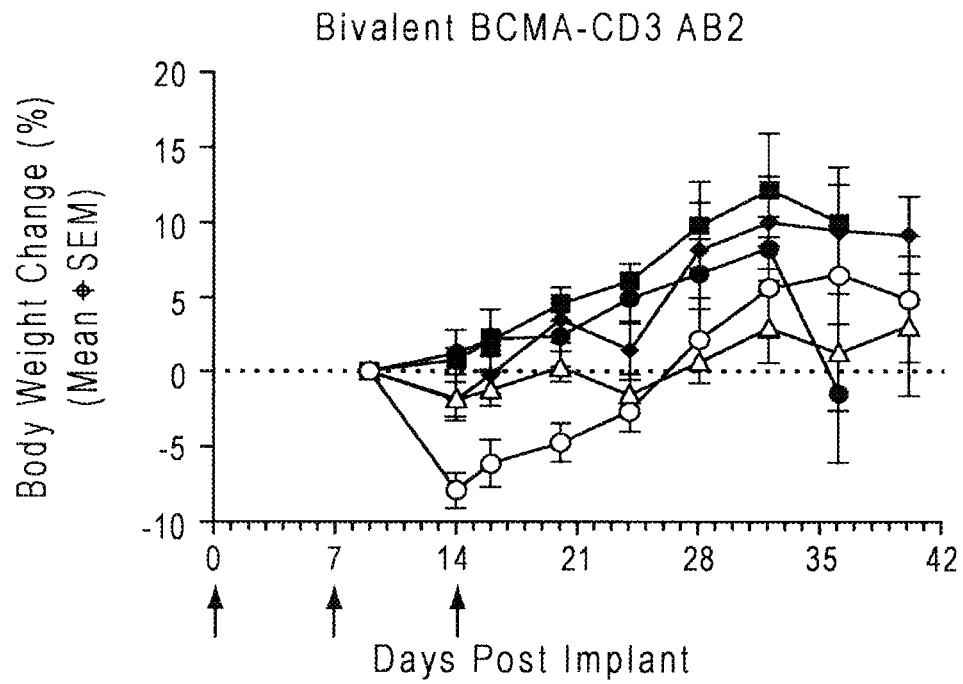
Figure 14D:
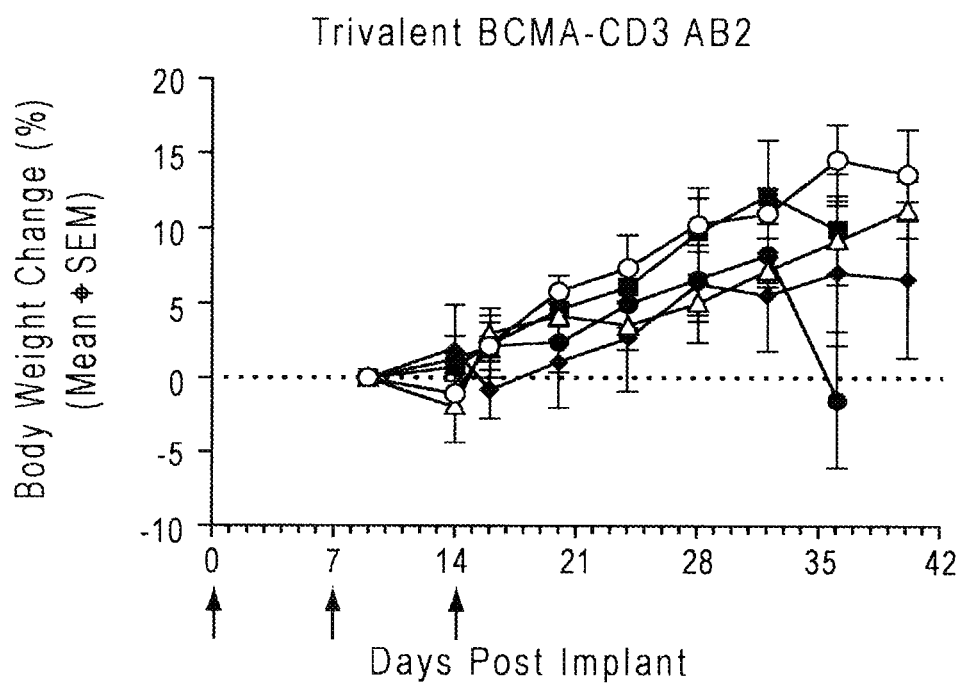
Figure 15A:
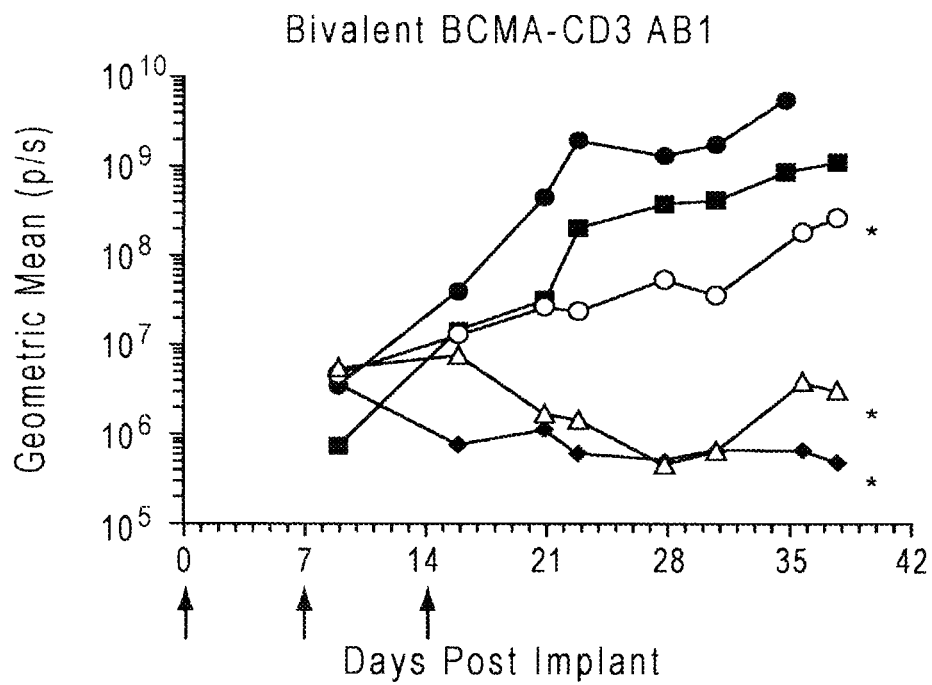
Figure 15B:
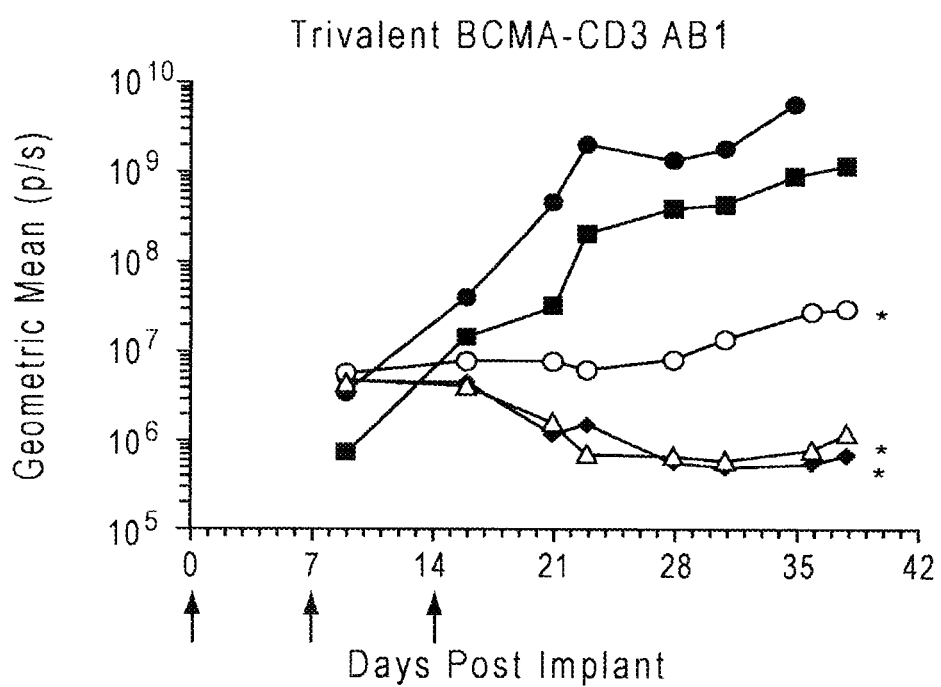
Figure 15C:
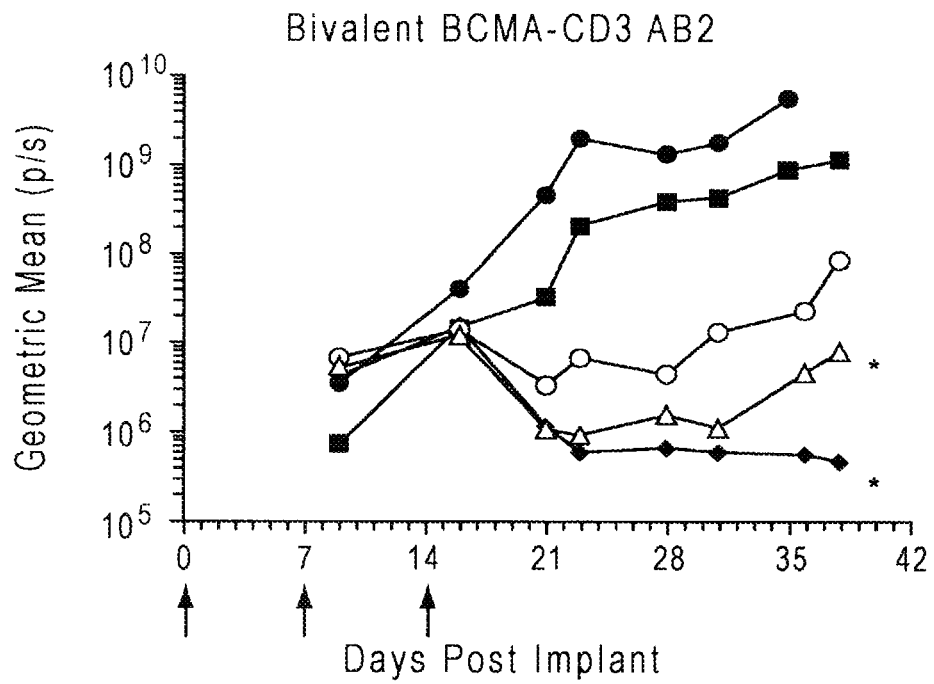
Figure 15D:
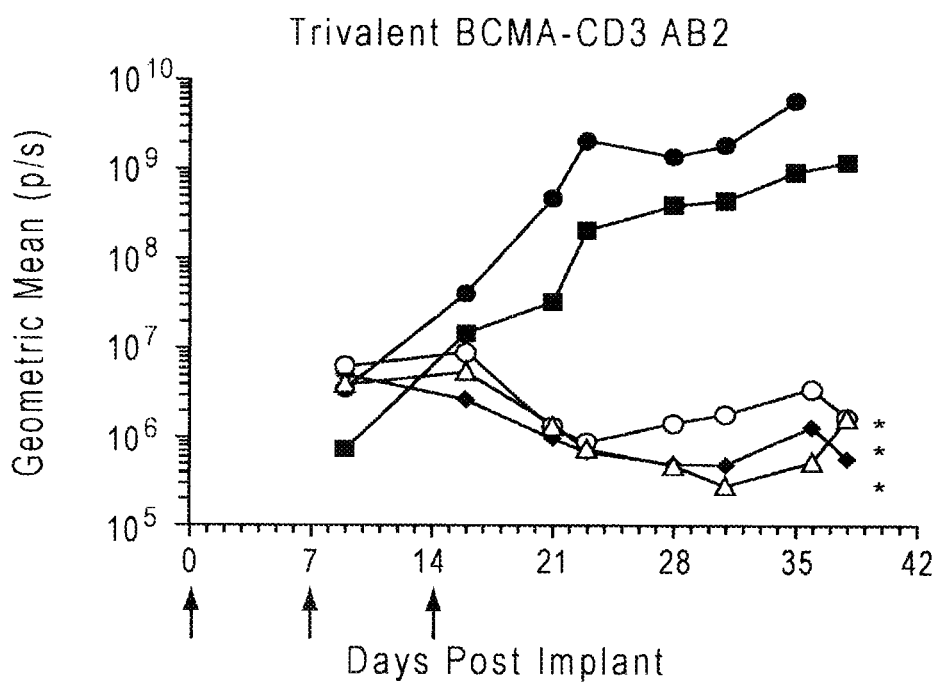
Figure 15E:
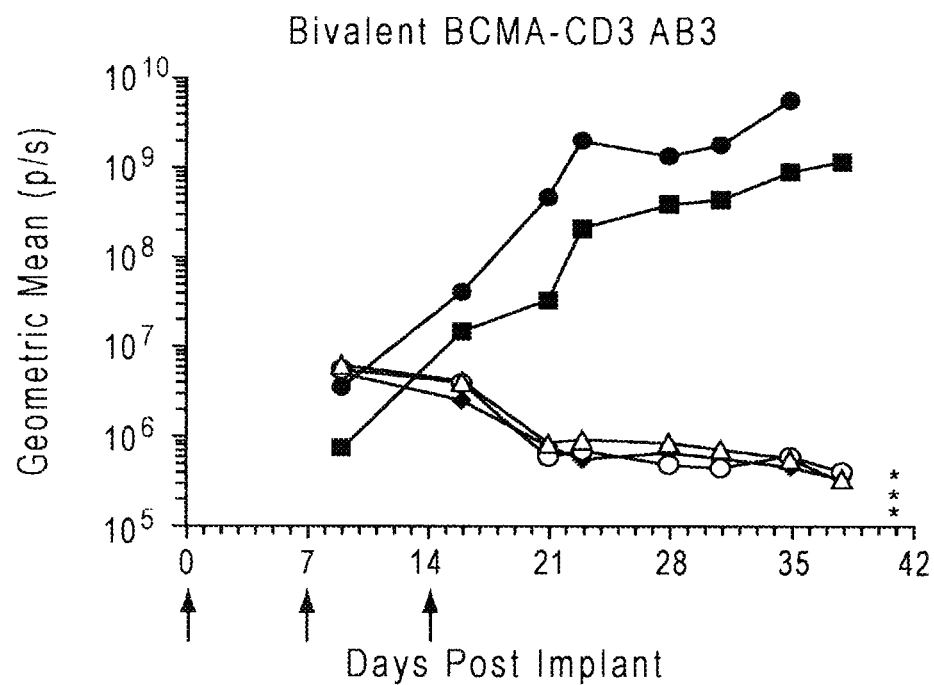
Figure 15F:
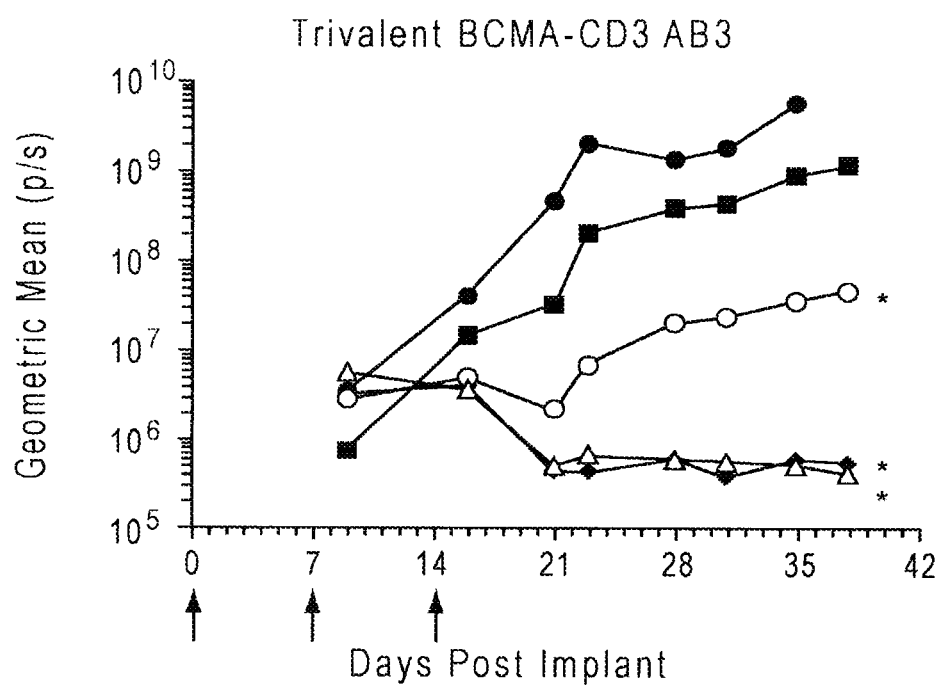
Figure 16A:
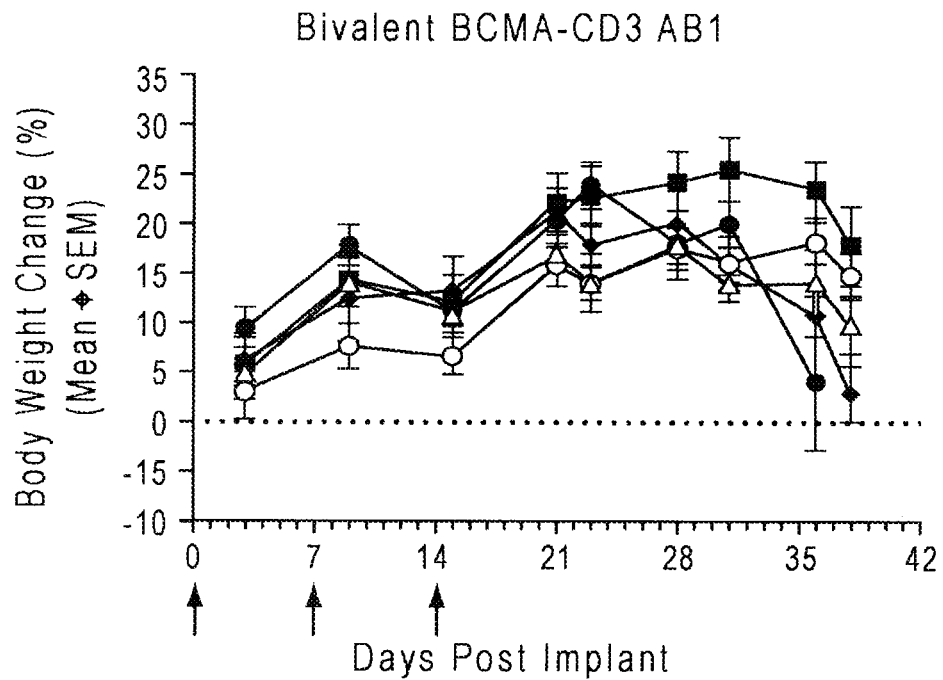
Figure 16B:
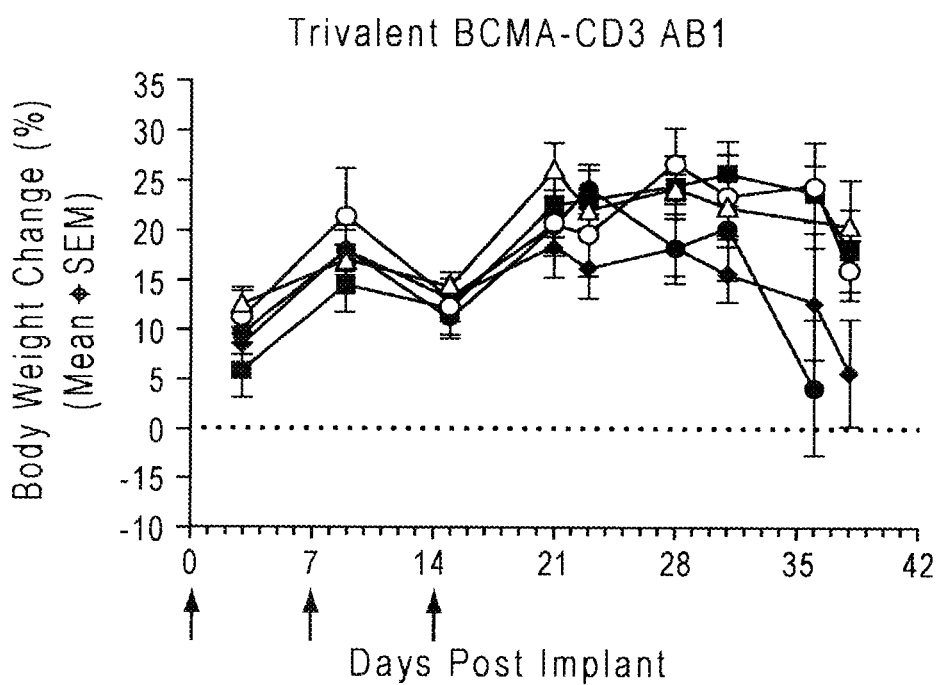
Figure 16C:
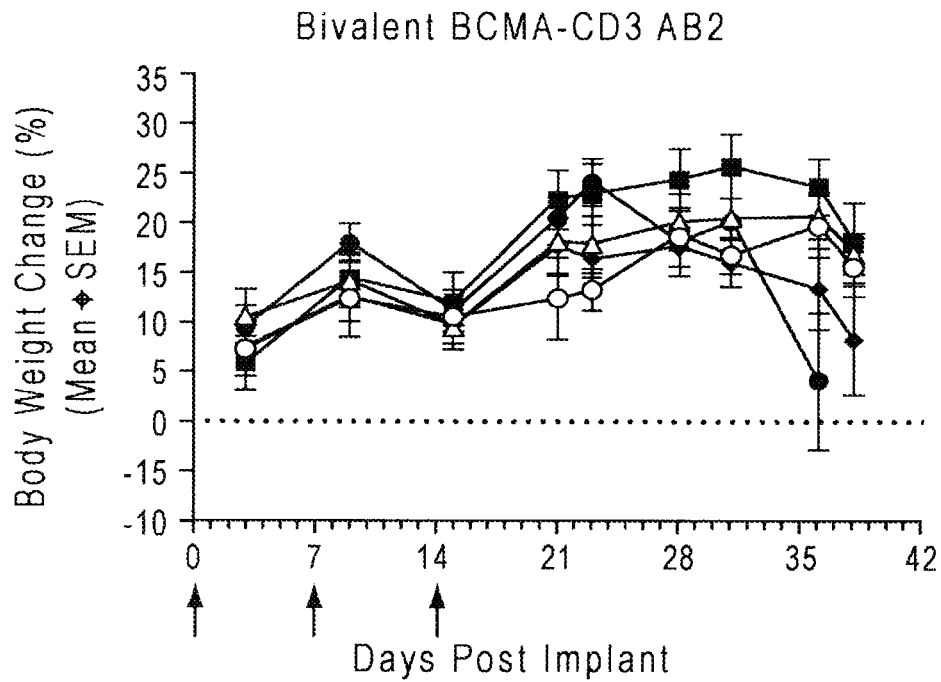
Figure 16D:
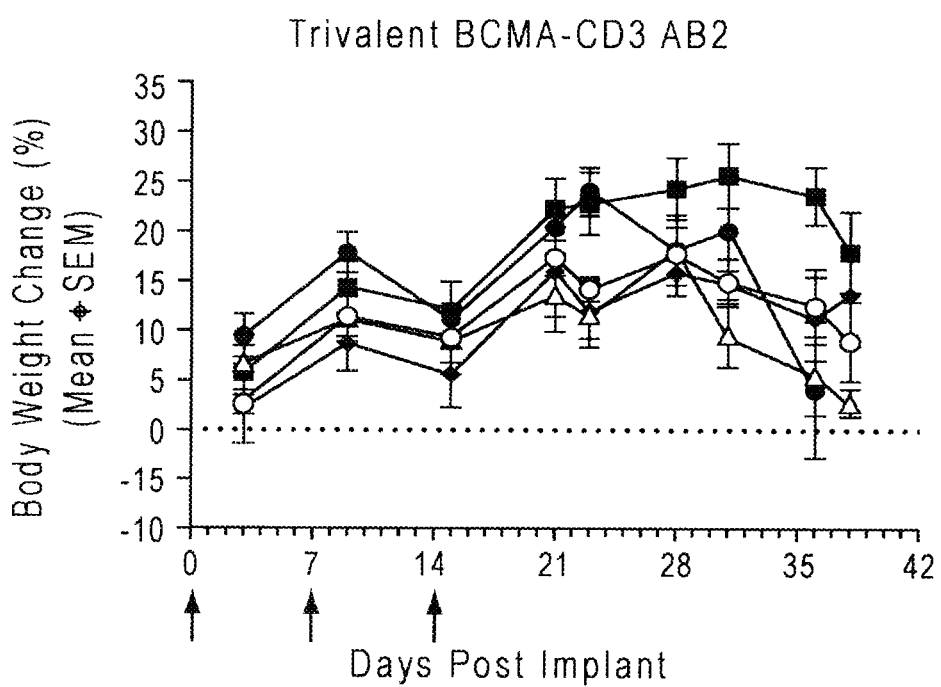
Figure 16E:
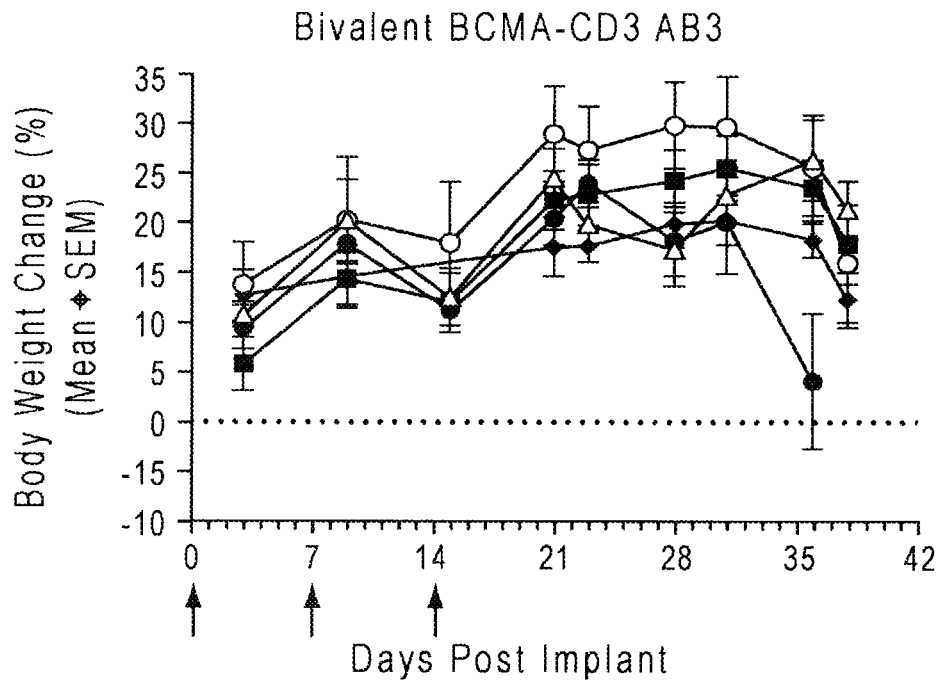
Figure 16F:
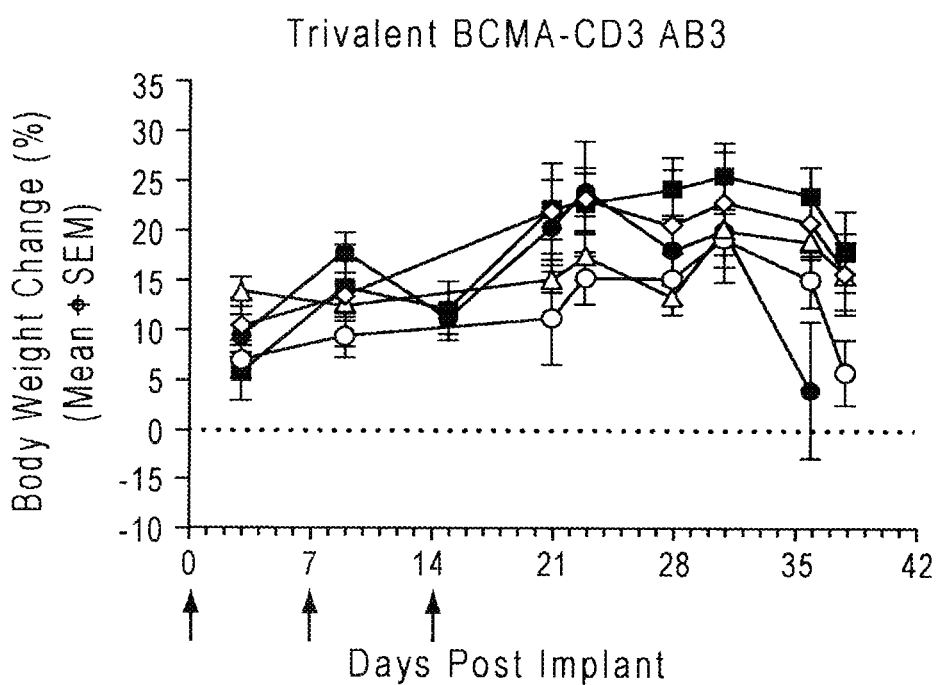

FIGS. 12A-12S: Biolayer Interferometry (BLI) plots showing binding of selected human anti-BCMA antibodies to cynoBCMA (Example 4). FIG. 12A: R1F2; FIG. 12B: PALF01; FIG. 12C: PALF03; FIG. 12D: PALF04; FIG. 12E: PALF05; FIG. 12F: PALF06; FIG. 12G: PALF07; FIG. 12H: PALF08; FIG. 12I: PALF09; FIG. 12J: PALF11; FIG. 12K: PALF12; FIG. 12L: PALF13; FIG. 12M: PALF14; FIG. 12N: PALF15; FIG. 12O: PALF16; FIG. 12P: PALF17; FIG. 12Q: PALF18; FIG. 12R: PALF19; FIG. 12S: PALF20.

FIGS. 13A-13D: Anti-tumor activity of the bivalent or trivalent BCMA-CD3 AB1 (FIG. 13A and FIG. 13B) and AB2 (FIG. 13C and FIG. 13D) in a human PBMC adoptive transfer adaptation of the KMS11Luc orthotopic tumor model (Example 6). Gray circle: 0.03 mg/kg dose; grey triangle: 0.3 mg/kg dose; grey diamond: 3.0 mg/kg dose; black circle: tumor only; black square: untreated control. *$p<0.05$, Dunnett's multiple comparison test.

FIGS. 14A-14D: Body weight change following treatment with bivalent or trivalent BCMA-CD3 AB1 (FIG. 14A and FIG. 14B) or AB2 (FIG. 14C and FIG. 14D) in a human PBMC adoptive transfer adaptation of the KMS11Luc orthotopic tumor model (Example 6). Gray circle: 0.03 mg/kg dose; grey triangle: 0.3 mg/kg dose; grey diamond: 3.0 mg/kg dose; black circle: tumor only; black square: untreated control.

FIGS. 15A-15F: Anti-tumor activity of the bivalent or trivalent BCMA-CD3 AB1 (FIG. 15A and FIG. 15B), AB2 (FIG. 15C and FIG. 15D), and AB3 (FIG. 15E and FIG. 15F) in a human PBMC adoptive transfer adaptation of the KMS11Luc orthotopic tumor model (Example 7). Gray circle: 0.03 mg/kg dose; grey triangle: 0.3 mg/kg dose; grey diamond: 3.0 mg/kg dose; black circle: tumor only; black square: untreated control. *$p<0.05$, Dunnett's multiple comparison test.

FIGS. 16A-16F: Body weight change following treatment with bivalent or trivalent BCMA-CD3 AB1 (FIG. 16A and FIG. 16B), AB2 (FIG. 16C and FIG. 16D), and AB3 (FIG. 16E and FIG. 16F) in a human PBMC adoptive transfer adaptation of the KMS11Luc orthotopic tumor model (Example 7). Gray circle: 0.03 mg/kg dose; grey triangle: 0.3 mg/kg dose; grey diamond: 3.0 mg/kg dose; black circle: tumor only; black square: untreated control.

Figure 17:
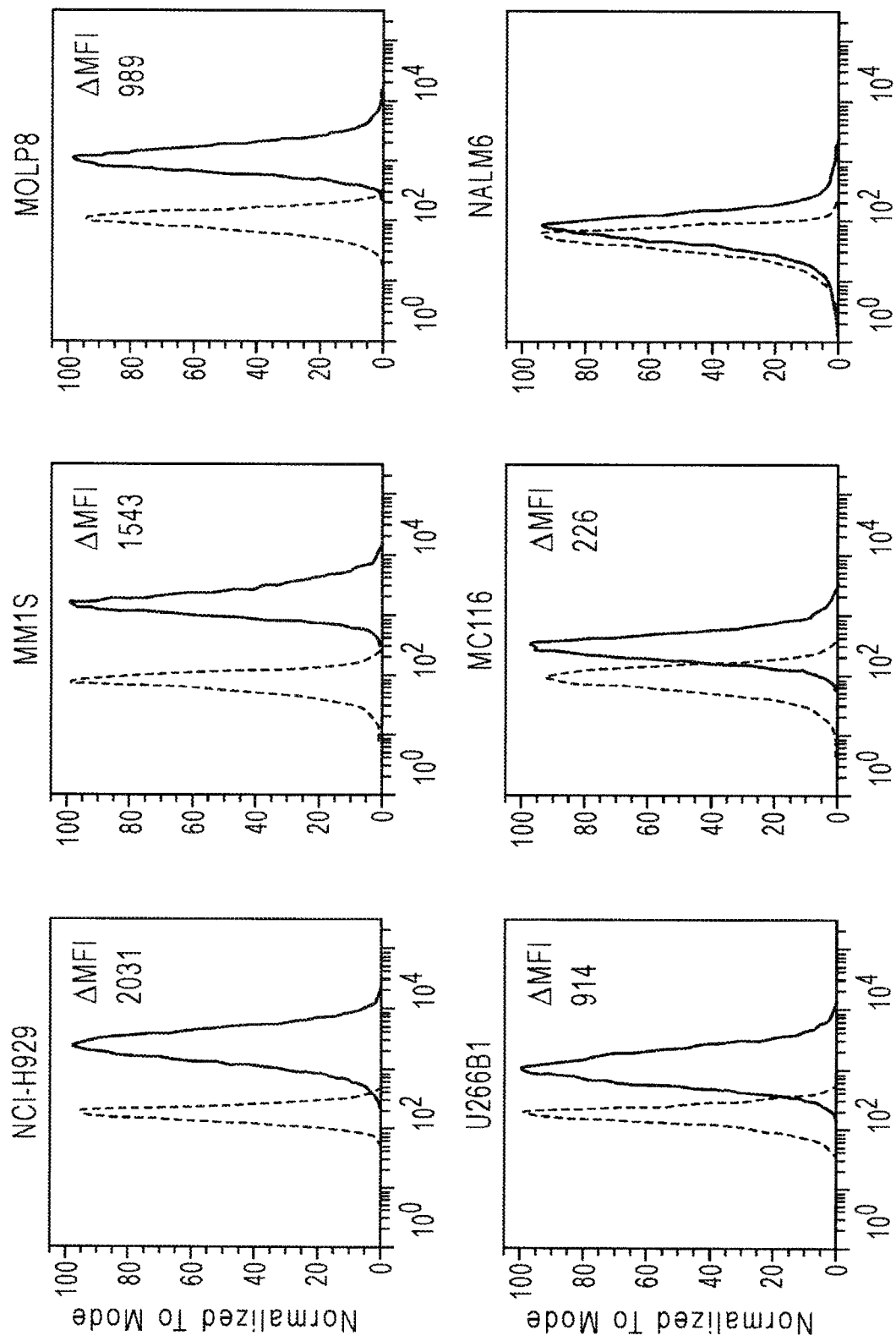

FIG. 17: Cell surface expression of BCMA in multiple myeloma cell lines evaluated by flow cytometry (Example 8). Delta mean fluorescence intensity (MFI) was determined by subtracting the MFI of unstained cells to that of anti-BCMA-BV421 stained cells.

Figure 18:
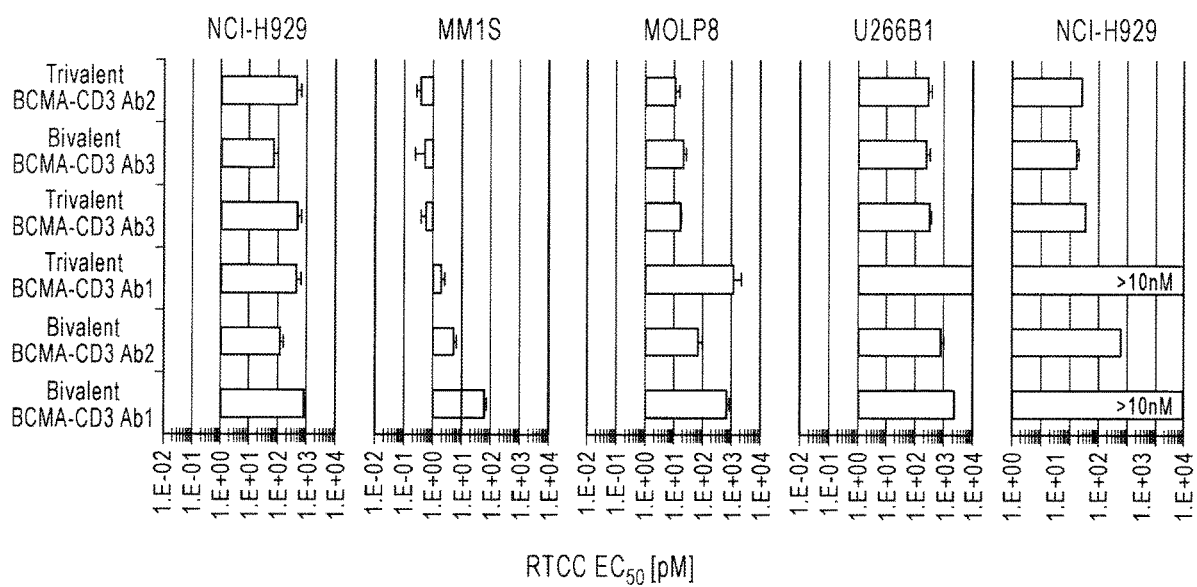

FIG. 18: EC50 results for BCMA-CD3 bispecific antibody-induced RTCC on BCMA$^+$ MM cell lines using expanded T cells (Example 8).

Figure 19B:
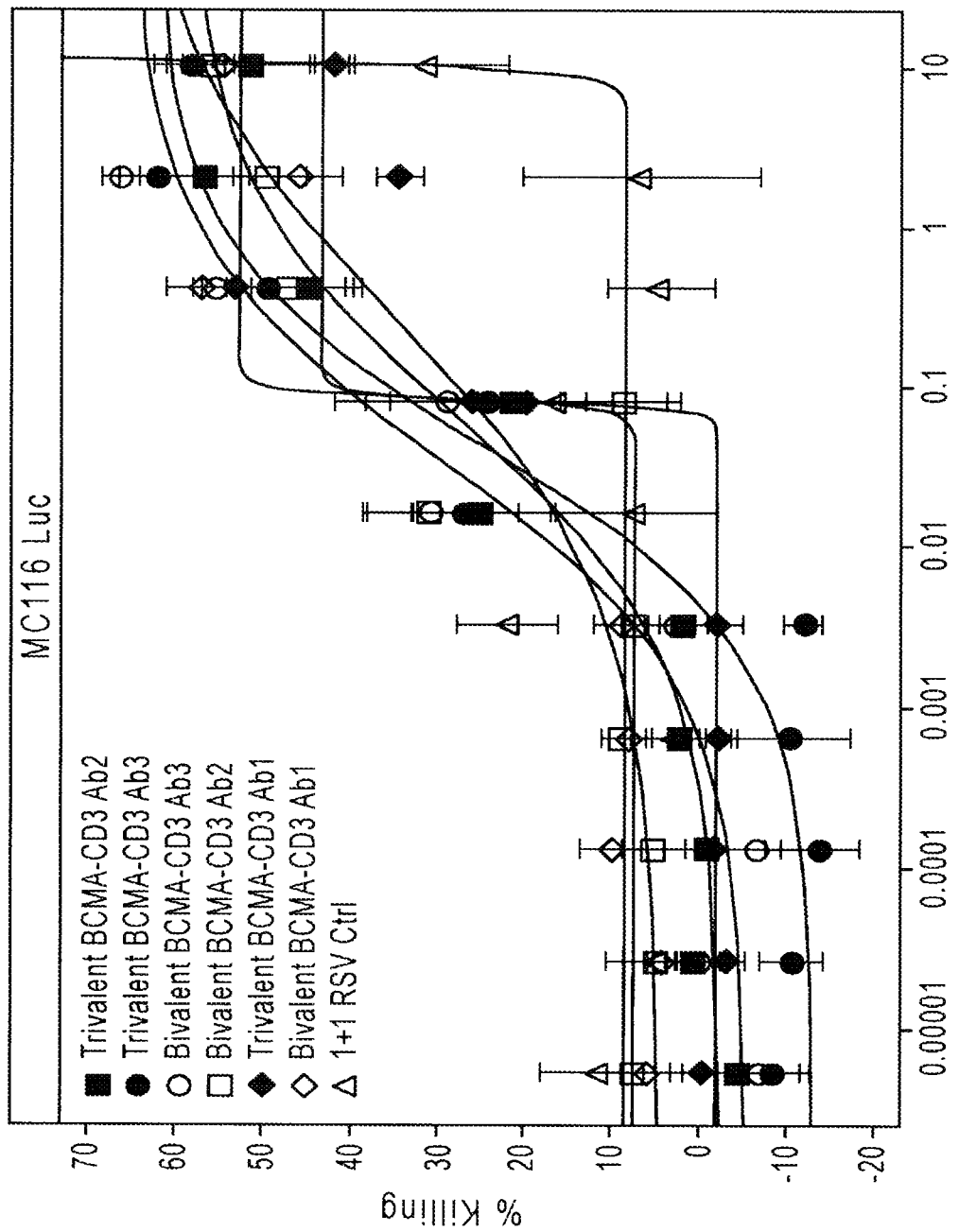

FIGS. 19A-19B: BCMA-CD3 antibody mediated RTCC on BCMA$^+$ MM cell lines MM1S (FIG. 19A) and MC116 (FIG. 19B) using freshly isolated T cells (Example 8).

Figure 20A:
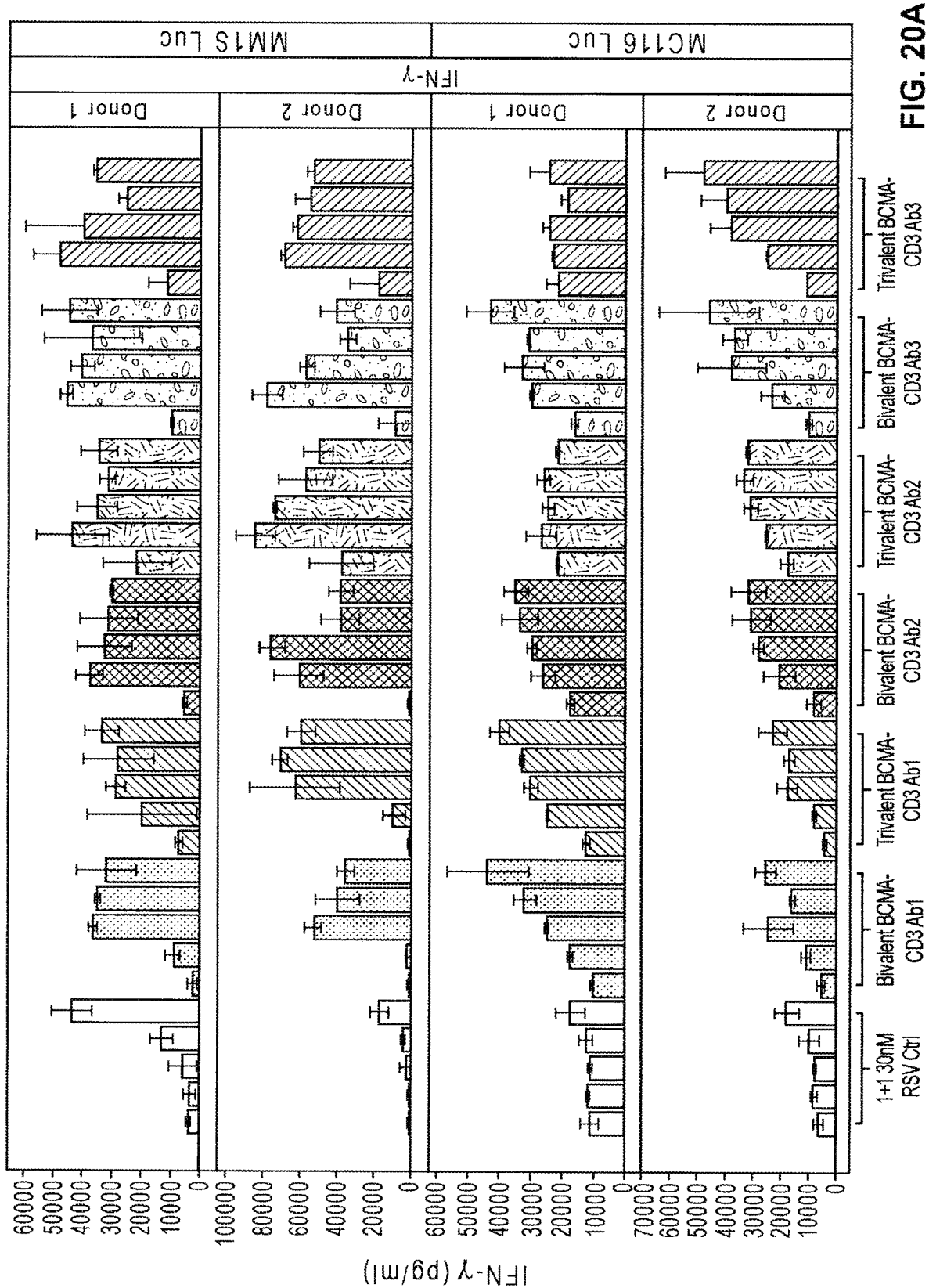
Figure 20B:
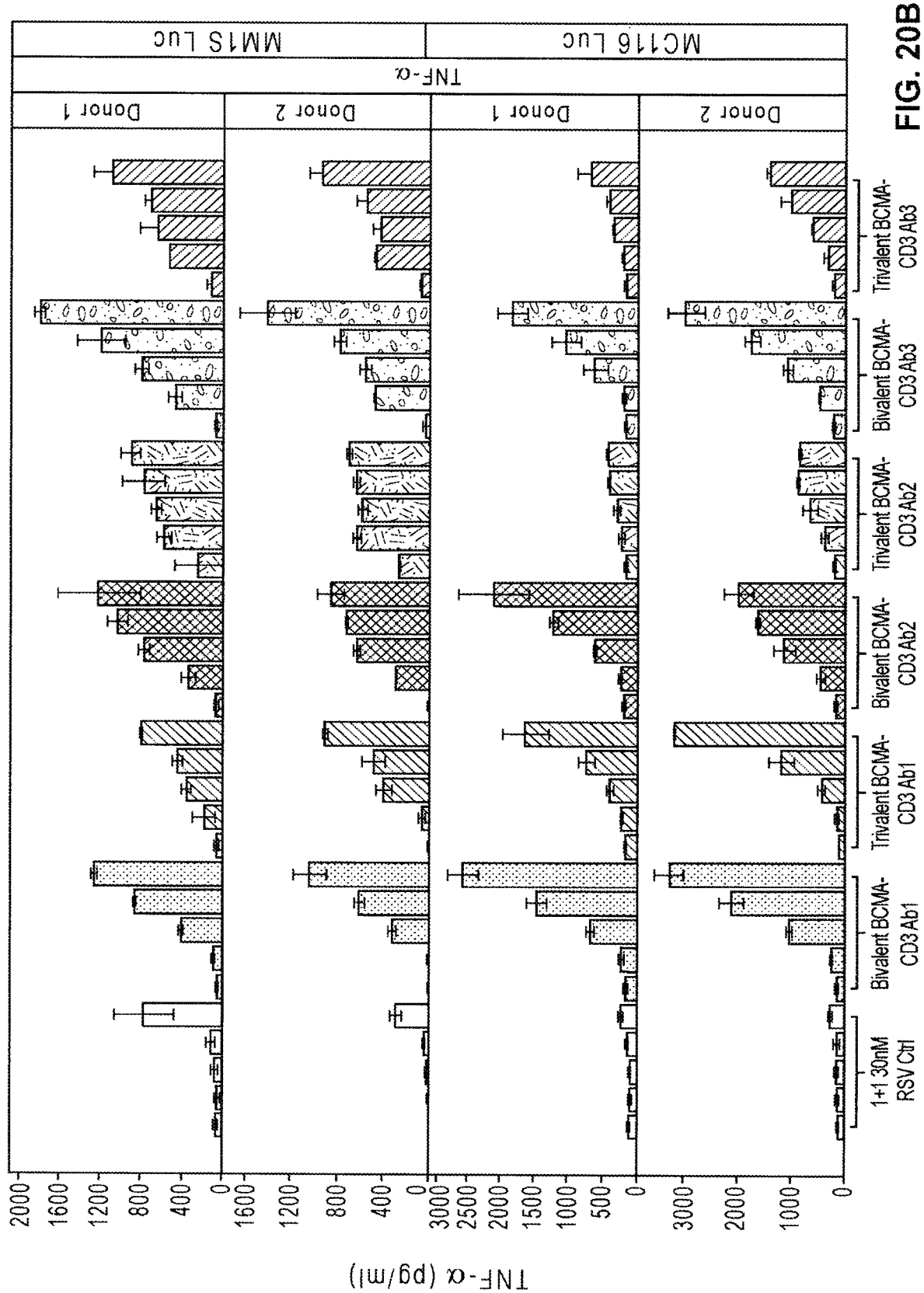

FIGS. 20A-B: Cytokine secretion induced by BCMA-CD3 bispecific antibodies (Example 9). FIG. 20A: IFN-γ; FIG. 20B: TNF-α.

Figure 21A:
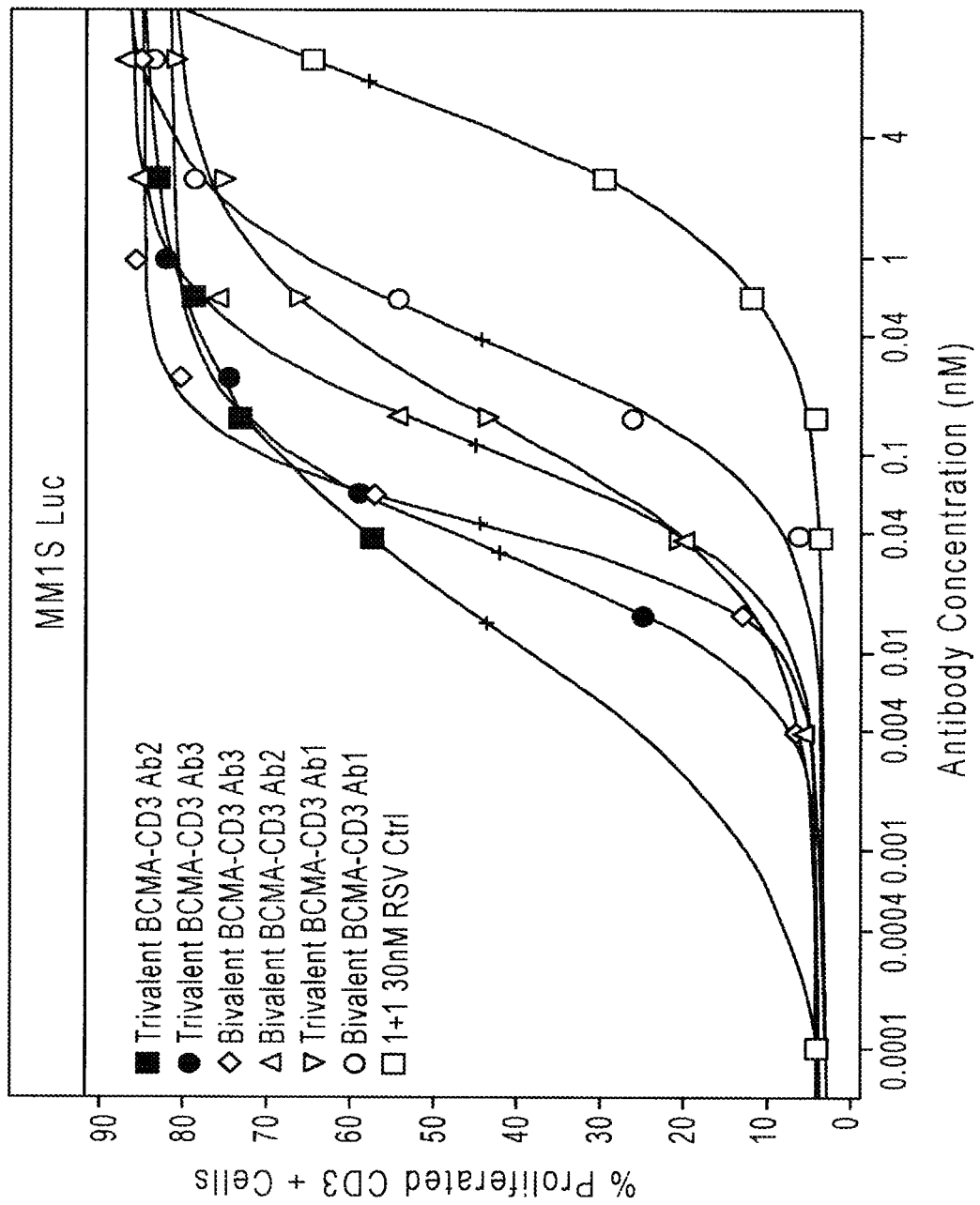
Figure 21B:
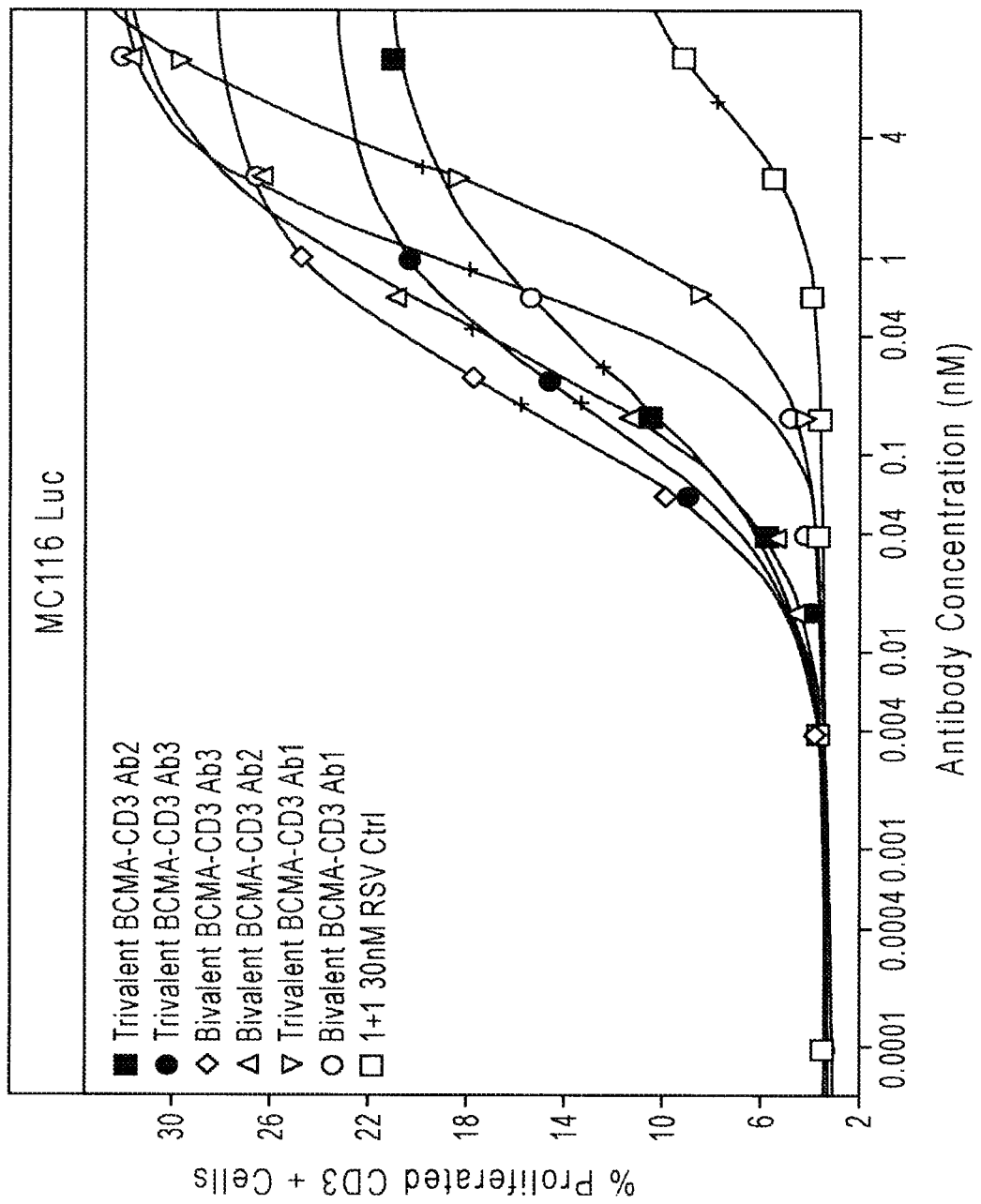

FIGS. 21A-21B: BCMA-CD3 bispecific antibody mediated T cell proliferation in the presence of BCMA+ MM cell lines MM1S (FIG. 21A) and MC116 (FIG. 21B) (Example 9).

FIGS. 22A-22B: Time course of soluble BCMA (sBCMA) concentration (FIG. 22A) and membrane bound (mBCMA) expression (FIG. 22B) from KMS11 cells treated with gamma secretase inhibitors LY411575 and PF03084014 (Example 10). Data for untreated cells are shown with open circles, data for cells treated with LY415575 are shown with solid squares, and data for cells treated with PF03084014 are shown with solid diamonds.

Figure 23A:
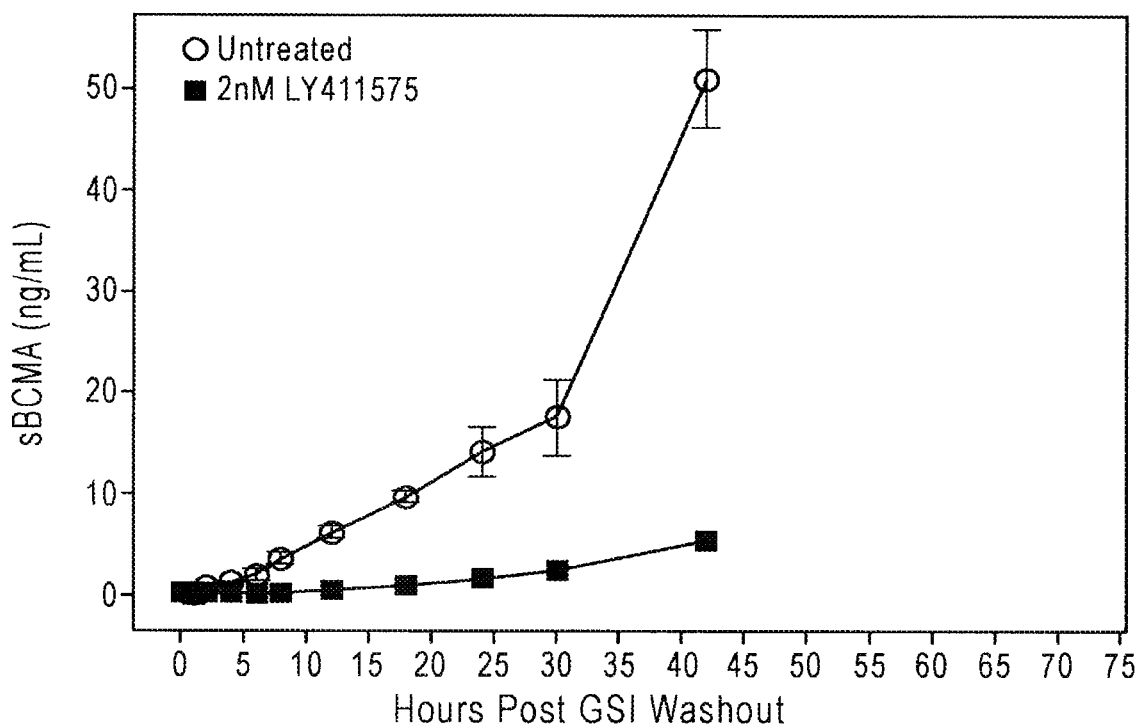
Figure 23B:
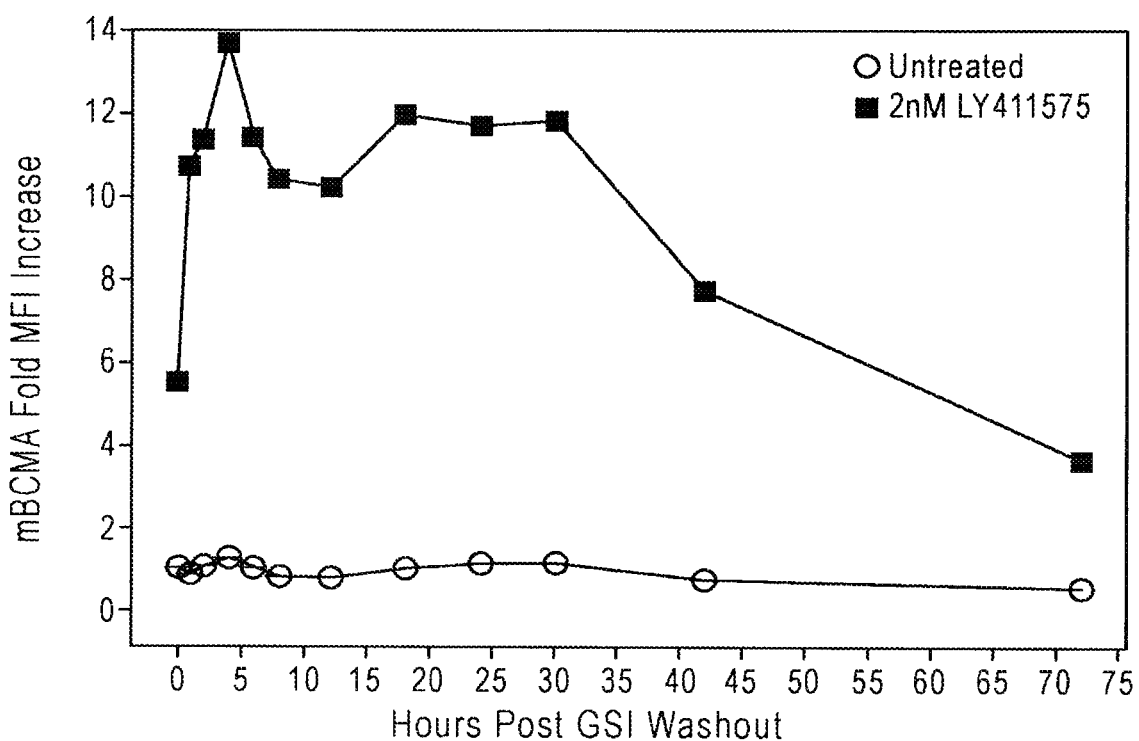

FIGS. 23A-23B: Time course of sBCMA concentration (FIG. 23A) and mBCMA expression (FIG. 23B) from KMS11 cells pre-treated with gamma secretase inhibitor LY411575 for 22 hours prior to the time course (Example 10). Data for untreated cells are shown with open circles and data for cells treated with LY415575 are shown with solid squares.

Figure 24A:
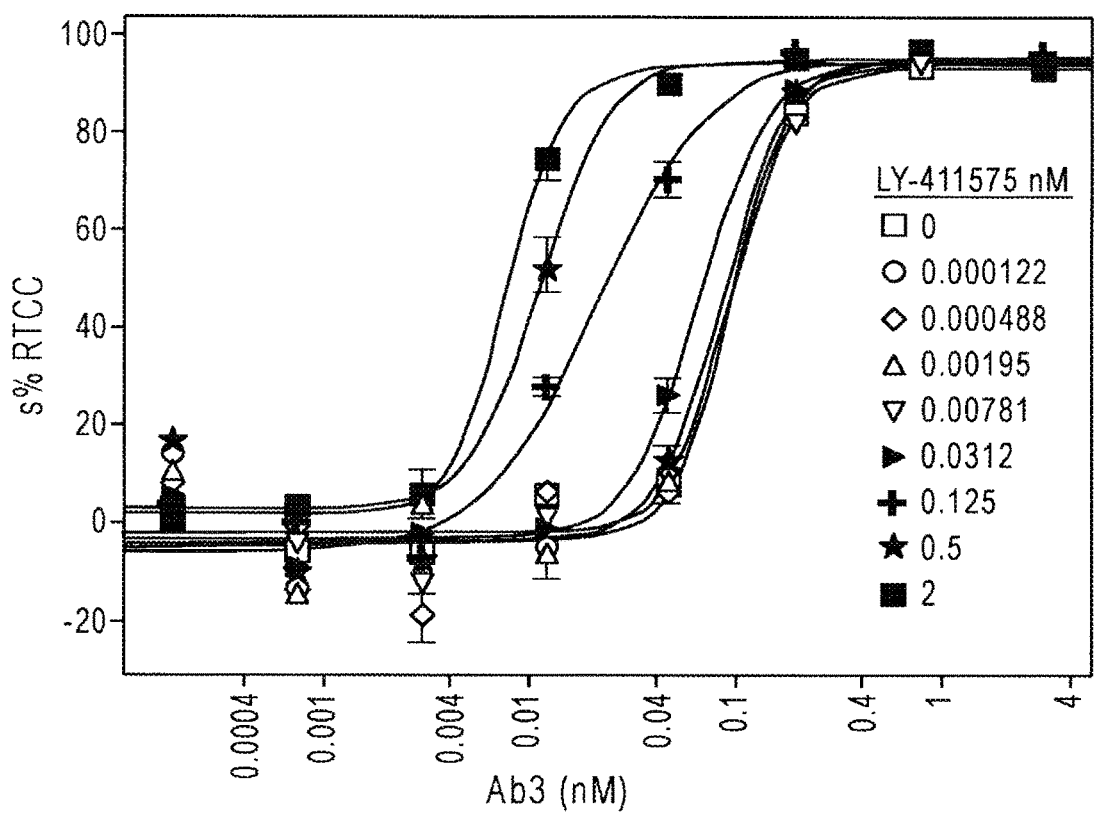
Figure 24B:
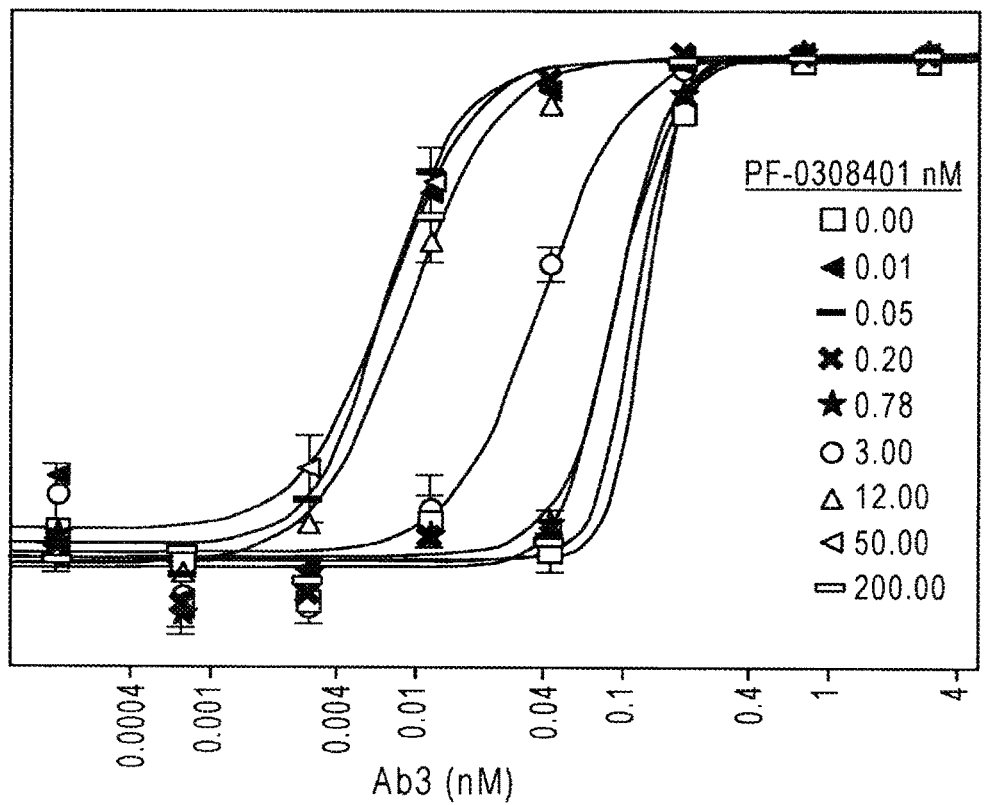
Figure 24C:
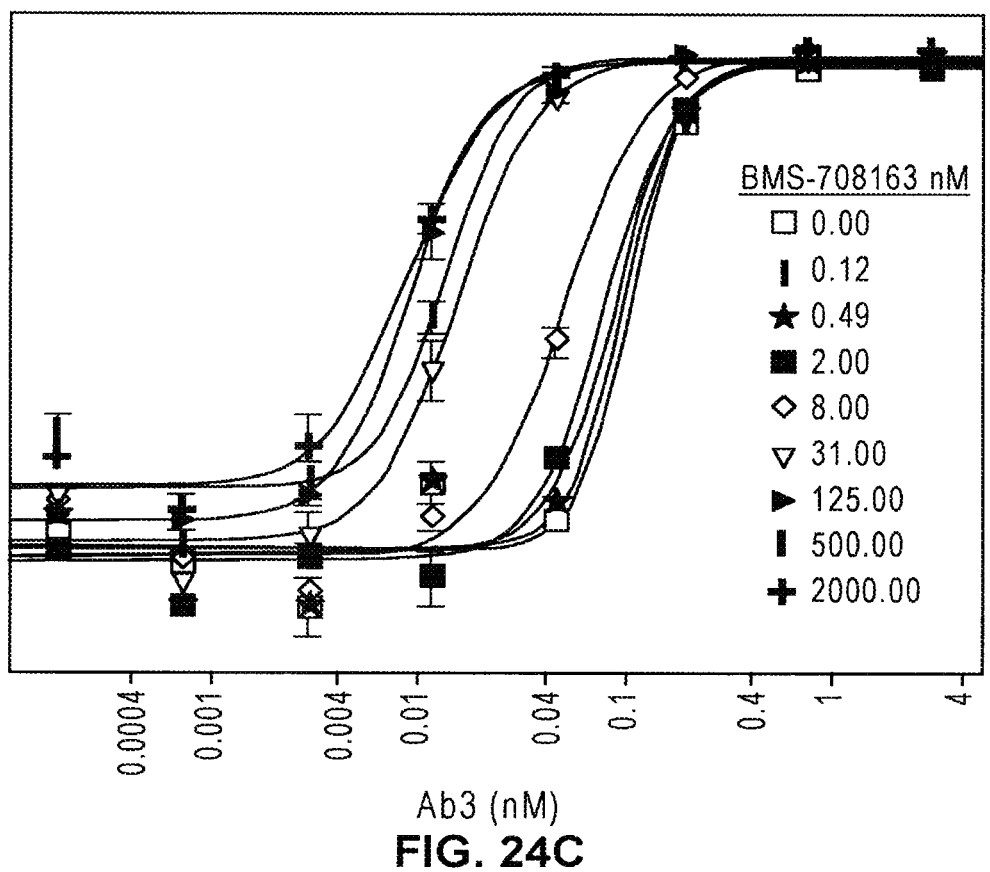

FIGS. 24A-24C: RTCC assay results of combinations of bivalent AB3 and the gamma secretase inhibitors LY411575 (FIG. 24A), PR03084014 (FIG. 24B) and BMS0708163 (FIG. 24C) (Example 11). Concentration of bivalent AB3 (nM) is shown on the X-axis.

Figure 25A:
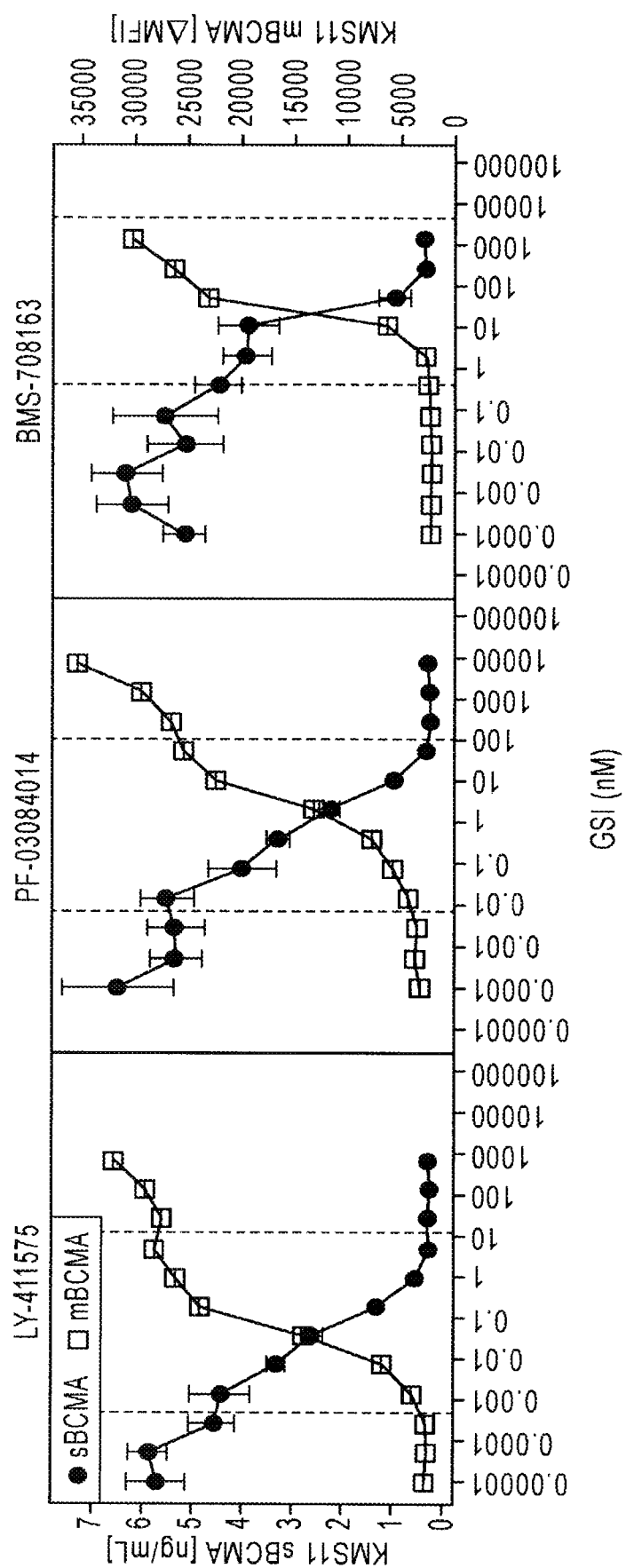
Figure 25B:
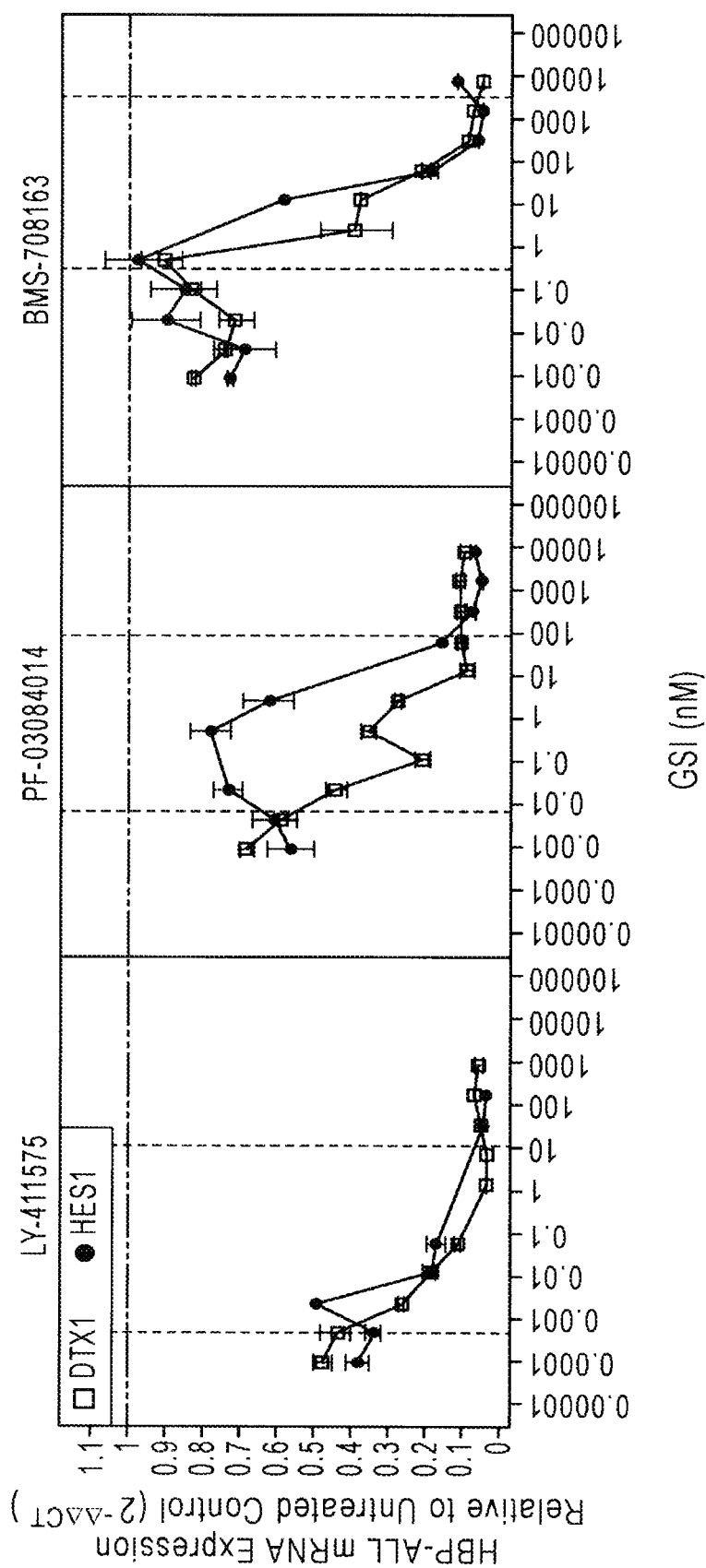
Figure 25C:
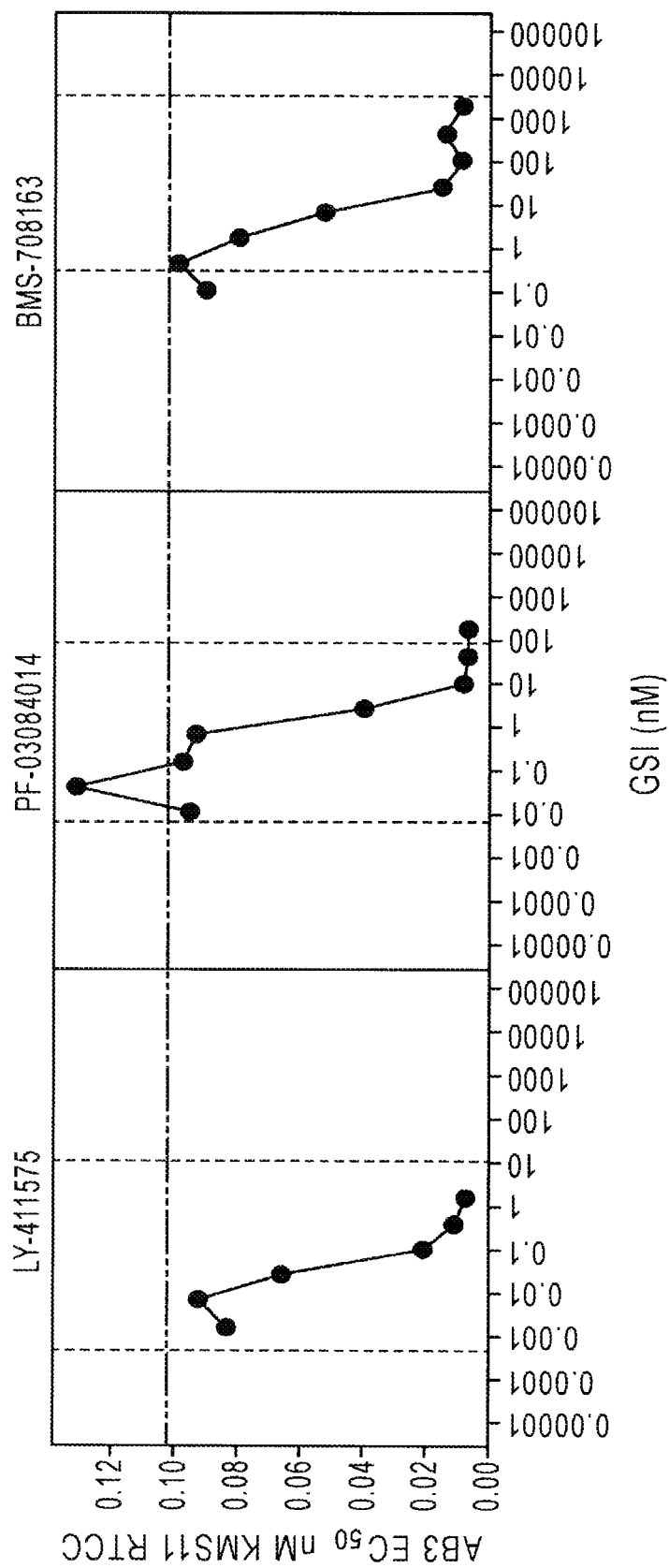

FIGS. 25A-C: Results of assays showing effect of GSIs on BCMA localization (FIG. 25A), NOTCH signaling (FIG. 25B), and bivalent AB3 potency (FIG. 25C) (Example 12).

Figure 26:
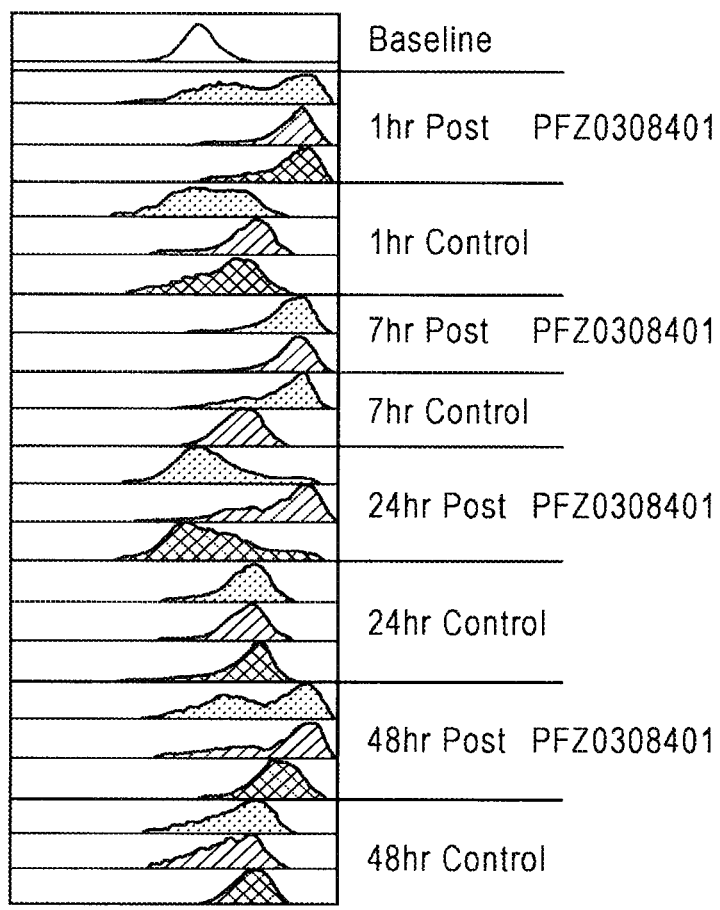

FIG. 26: mBCMA levels in a KMS11 xenograft model following treatment with PFZ03084014, evaluated by flow cytometry (Example 13).

Figure 27:
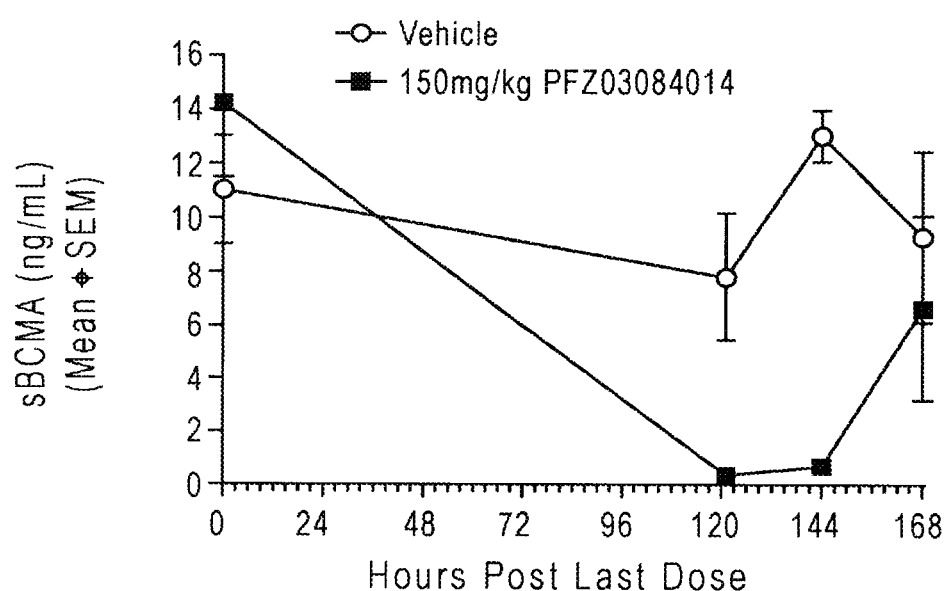

FIG. 27: sBCMA levels in a KMS11 xenograft model following treatment with PFZ03084014, evaluated by ELISA (Example 13).

Figure 28A:
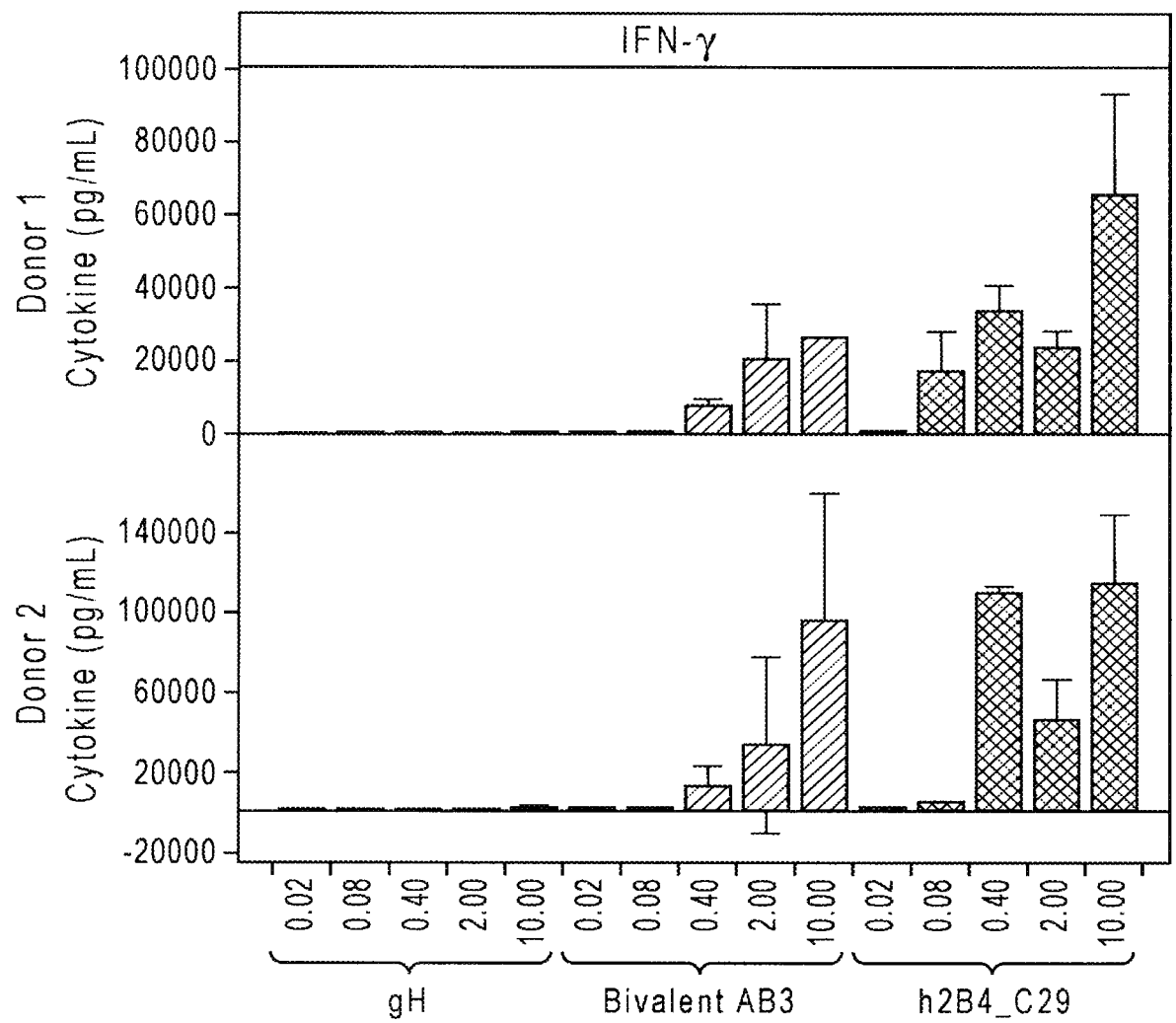
Figure 28B:
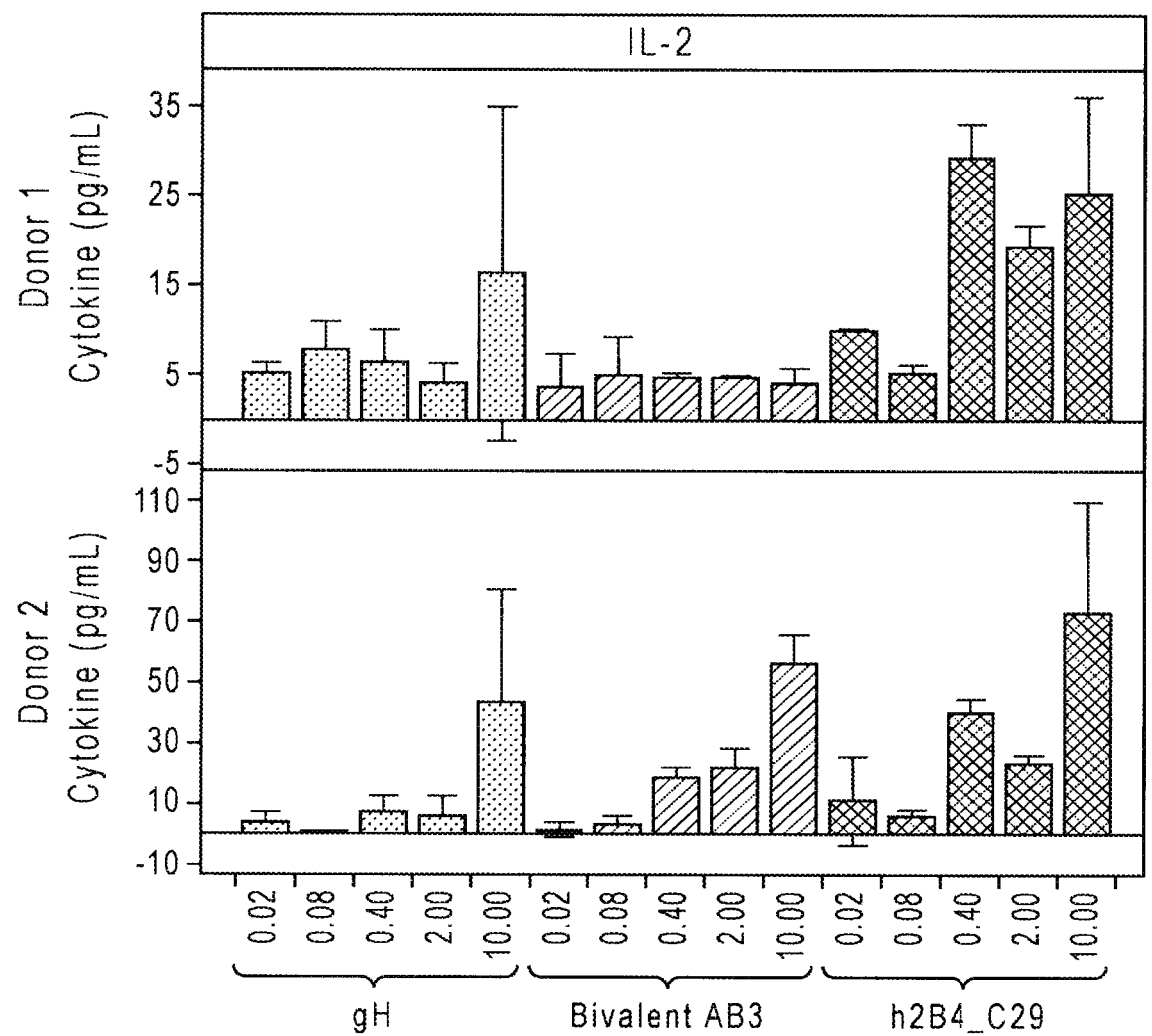
Figure 28C:
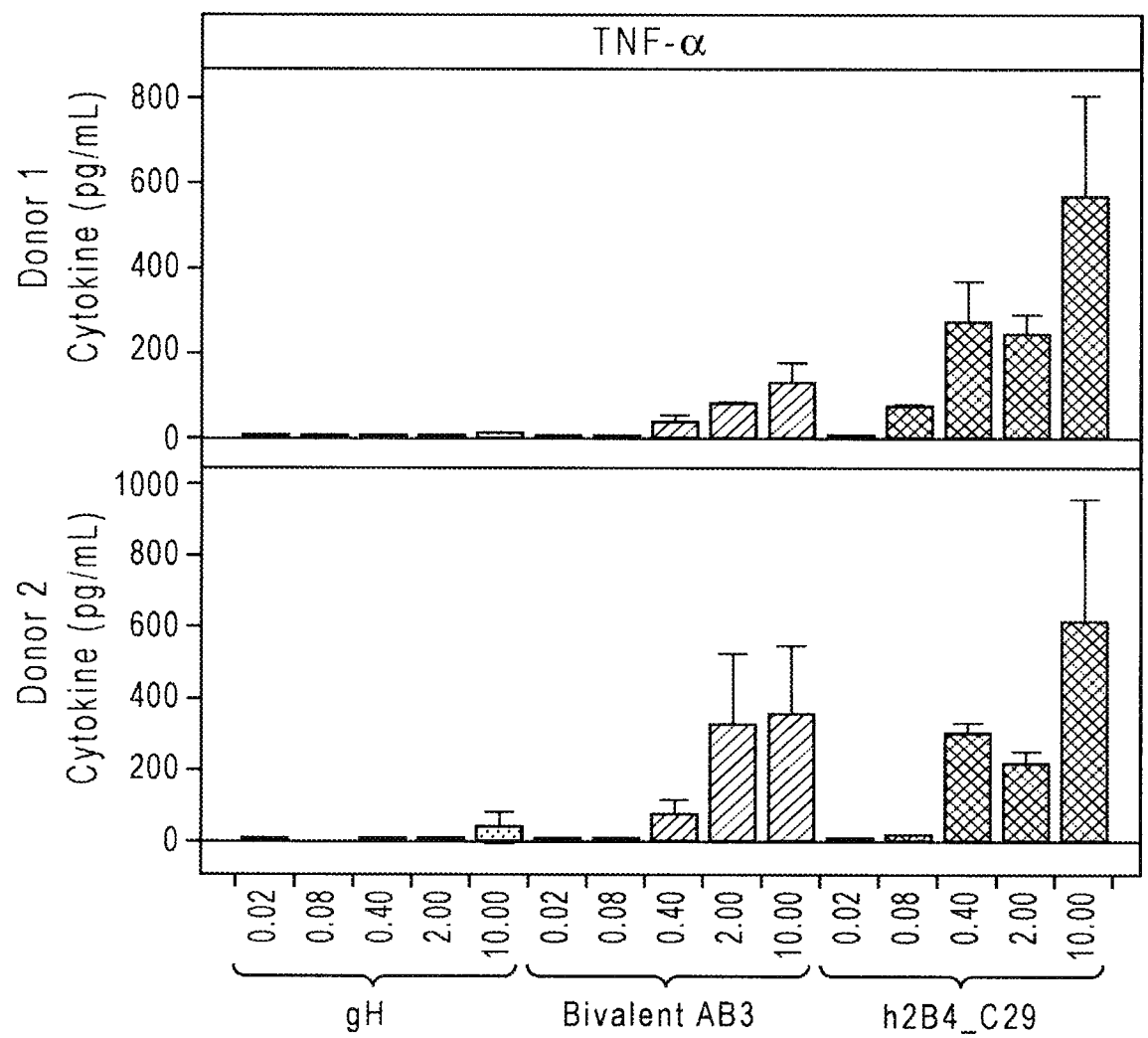

FIGS. 28A-C: Cytokine levels in cell culture supernatants after a 48 hour co-culture of KMS11 cells and T cells (1:3 ratio) in the presence of gH (control), bivalent AB3, and h2B4_C29 (Example 14). FIG. 28A: IFN-γ levels; FIG. 28B: IL-2 levels; FIG. 28C: TNF-α levels.

7. DETAILED DESCRIPTION

7.1. Definitions

As used herein, the following terms are intended to have the following meanings:

ADCC: By "ADCC" or "antibody dependent cell-mediated cytotoxicity" as used herein is meant the cell-mediated reaction where nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

ADCP: By "ADCP" or antibody dependent cell-mediated phagocytosis as used herein is meant the cell-mediated reaction where nonspecific phagocytic cells that express FcγRs recognize bound antibody on a target cell and subsequently cause phagocytosis of the target cell.

Additional Agent: For convenience, an agent that is used in combination with an antigen-binding molecule of the disclosure is referred to herein as an "additional" agent.

Antibody: The term "antibody" as used herein refers to a polypeptide (or set of polypeptides) of the immunoglobulin family that is capable of binding an antigen non-covalently, reversibly and specifically. For example, a naturally occurring "antibody" of the IgG type is a tetramer comprising at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term "antibody" includes, but is not limited to, monoclonal antibodies, human antibodies, humanized antibodies, camelised antibodies, chimeric antibodies, bispecific or multispecific antibodies and anti-idiotypic (anti-Id) antibodies (including, e.g., anti-Id antibodies to antibodies of the disclosure). The antibodies can be of any isotype/class (e.g., IgG, IgE, IgM, IgD, IgA and IgY) or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. In a wild-type antibody, at the N-terminus is a variable region and at the C-terminus is a constant region; the CH3 and CL domains actually comprise the carboxy-terminus of the heavy and light chain, respectively.

Antibody fragment: The term "antibody fragment" of an antibody as used herein refers to one or more portions of an antibody. In some embodiments, these portions are part of the contact domain(s) of an antibody. In some other embodiments, these portion(s) are antigen-binding fragments that retain the ability of binding an antigen non-covalently, reversibly and specifically, sometimes referred to herein as the "antigen-binding fragment", "antigen-binding fragment thereof," "antigen-binding portion", and the like. Examples of binding fragments include, but are not limited to, single-chain Fvs (scFv), a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Thus, the term "antibody fragment" encompasses both proteolytic fragments of antibodies (e.g., Fab and F(ab)2 fragments) and engineered proteins comprising one or more portions of an antibody (e.g., an scFv).

Antibody fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology 23: 1126-1136). Antibody fragments can be grafted into scaffolds based on polypeptides such as Fibronectin type III (Fn3) (see U.S. Pat. No. 6,703,199, which describes fibronectin polypeptide monobodies).

Antibody fragments can be incorporated into single chain molecules comprising a pair of tandem Fv segments (for example, VH-CH1-VH-CH1) which, together with complementary light chain polypeptides (for example, VL-VC-VL-VC), form a pair of antigen-binding regions (Zapata et al., 1995, Protein Eng. 8:1057-1062; and U.S. Pat. No. 5,641, 870).

Antibody Numbering System: In the present specification, the references to numbered amino acid residues in antibody domains are based on the EU numbering system unless otherwise specified (for example, in Tables 1C-1N). This system was originally devised by Edelman et al., 1969, Proc. Nat'l Acad. Sci. USA 63:78-85 and is described in detail in Kabat et al., 1991, in Sequences of Proteins of Immunological Interest, US Department of Health and Human Services, NIH, USA.

Antigen-binding domain: The term "antigen-binding domain" or "ABD" refers to a portion of an antigen-binding molecule that has the ability to bind to an antigen non-covalently, reversibly and specifically. Exemplary ABDs include antigen-binding fragments and portions of both immunoglobulin and non-immunoglobulin based scaffolds that retain the ability of binding an antigen non-covalently, reversibly and specifically. As used herein, the term "antigen-binding domain" encompasses antibody fragments that retain the ability of binding an antigen non-covalently, reversibly and specifically.

Antigen-binding domain chain or ABD chain: Individual ABDs can exist as one (e.g., in the case of an scFv) polypeptide chain or form through the association of more than one polypeptide chains (e.g., in the case of a Fab). As used herein, the term "ABD chain" refers to all or a portion of an ABD that exists on a single polypeptide chain. The use of the term "ABD chain" is intended for convenience and descriptive purposes only and does not connote a particular configuration or method of production.

Antigen-binding fragment: The term "antigen-binding fragment" of an antibody refers to a portion of an antibody that retains has the ability to bind to an antigen non-covalently, reversibly and specifically.

Antigen-binding molecule: The term "antigen-binding molecule" refers to a molecule comprising one or more antigen-binding domains, for example an antibody. The antigen-binding molecule can comprise one or more polypeptide chains, e.g., one, two, three, four or more polypeptide chains. The polypeptide chains in an antigen-binding molecule can be associated with one another directly or indirectly (for example a first polypeptide chain can be associated with a second polypeptide chain which in turn can be associated with a third polypeptide chain to form an antigen-binding molecule in which the first and second polypeptide chains are directly associated with one another, the second and third polypeptide chains are directly associated with one another, and the first and third polypeptide chains are indirectly associated with one another through the second polypeptide chain).

Associated: The term "associated" in the context of domains or regions within an antigen-binding molecule refers to a functional relationship between two or more polypeptide chains and/or two or more portions of a single polypeptide chain. In particular, the term "associated" means that two or more polypeptides (or portions of a single polypeptide) are associated with one another, e.g., non-covalently through molecular interactions and/or covalently through one or more disulfide bridges or chemical cross-linkages, so as to produce a functional antigen-binding domain. Examples of associations that might be present in an antigen-binding molecule include (but are not limited to) associations between Fc regions in an Fc domain, associations between VH and VL regions in a Fab or Fv, and associations between CH1 and CL in a Fab.

B cell: As used herein, the term "B cell" refers to a cell of B cell lineage, which is a type of white blood cell of the lymphocyte subtype. Examples of B cells include plasmablasts, plasma cells, lymphoplasmacytoid cells, memory B cells, follicular B cells, marginal zone B cells, B-1 cells, B-2 cells, and regulatory B cells.

B cell malignancy: As used herein, a B cell malignancy refers to an uncontrolled proliferation of B cells. Examples of B cell malignancy include non-Hodgkin's lymphomas (NHL), Hodgkin's lymphomas, leukemia, and myeloma. For example, a B cell malignancy can be, but is not limited to, multiple myeloma, chronic lymphocytic leukemia (CLL)/small lymphocytic lymphoma (SLL), follicular lymphoma, mantle cell lymphoma (MCL), diffuse large B-cell lymphoma (DLBCL), marginal zone lymphomas, Burkitt lymphoma, lymphoplasmacytic lymphoma (Waldenstrom macroglobulinemia), hairy cell leukemia, primary central nervous system (CNS) lymphoma, primary mediastinal large B-cell lymphoma, mediastinal grey-zone lymphoma (MGZL), splenic marginal zone B-cell lymphoma, extranodal marginal zone B-cell lymphoma of MALT, nodal marginal zone B-cell lymphoma, and primary effusion lymphoma, and plasmacytic dendritic cell neoplasms.

BCMA: As used herein, the term "BCMA" refers to B-cell maturation antigen. BCMA (also known as TNFRSF17, BCM or CD269) is a member of the tumor necrosis receptor (TNFR) family and is predominantly expressed on terminally differentiated B cells, e.g., memory B cells and plasma cells. Its ligands include B-cell activating factor (BAFF) and a proliferation-inducing ligand (APRIL). The protein BCMA is encoded by the gene TNFRSF17. Exemplary BCMA sequences are available at the Uniprot database under accession number Q02223.

Binding Sequences: In reference to Table 1 (including subparts thereof), the term "binding sequences" means an ABD having a full set of CDRs, a VH-VL pair, or an scFv set forth in that table.

Bispecific binding molecule: The term "bispecific binding molecule" or "BBM" refers to a molecule that specifically binds to two antigens and comprises two or more ABDs. The BBMs of the disclosure comprise at least one antigen-binding domain which is specific for BCMA and at least one antigen-binding domain which is specific for a different antigen, e.g., component of a TCR complex. Representative BBMs are illustrated in FIG. 1B-1AG. BBMs can comprise one, two, three, four or even more polypeptide chains.

Bivalent: The term "bivalent" as used herein in the context of an antigen-binding molecule refers to an antigen-binding molecule that has two ABDs. The domains can be the same or different. Accordingly, a bivalent antigen-binding molecule can be monospecific or bispecific. Bivalent BBMs comprise an ABD that specifically binds to BCMA and another ABD that binds to another antigen, e.g., a component of the TCR complex.

Cancer: The term "cancer" refers to a disease characterized by the uncontrolled (and often rapid) growth of aberrant cells. Cancer cells can spread locally or through the bloodstream and lymphatic system to other parts of the body. Examples of various cancers are described herein and include but are not limited to, leukemia, multiple myeloma, asymptomatic myeloma, Hodgkin's lymphoma and non-Hodgkin's lymphoma, e.g., any BCMA-positive cancers of any of the foregoing types. The term "cancerous B cell" refers to a B cell that is undergoing or has undergone uncontrolled proliferation.

CD3: The term "CD3" or "cluster of differentiation 3" refers to the cluster of differentiation 3 co-receptor of the T cell receptor. CD3 helps in activation of both cytotoxic T-cell (e.g., CD8+ naïve T cells) and T helper cells (e.g., CD4+ naïve T cells) and is composed of four distinct chains: one CD3γ chain (e.g., Genbank Accession Numbers NM_000073 and MP_000064 (human)), one CD3δ chain (e.g., Genbank Accession Numbers NM_000732, NM_001040651, NP_00732 and NP_001035741 (human)), and two CD3ε chains (e.g., Genbank Accession Numbers NM_000733 and NP_00724 (human)). The chains of CD3 are highly related cell-surface proteins of the immunoglobulin superfamily containing a single extracellular immunoglobulin domain. The CD3 molecule associates with the T-cell receptor (TCR) and ζ-chain to form the T-cell receptor (TCR) complex, which functions in generating activation signals in T lymphocytes.

Unless expressly indicated otherwise, the reference to CD3 in the application can refer to the CD3 co-receptor, the CD3 co-receptor complex, or any polypeptide chain of the CD3 co-receptor complex.

Chimeric Antibody: The term "chimeric antibody" (or antigen-binding fragment thereof) is an antibody molecule (or antigen-binding fragment thereof) in which (a) the constant region, or a portion thereof, is altered, replaced or exchanged so that the antigen-binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

Complementarity Determining Region: The terms "complementarity determining region" or "CDR," as used herein, refer to the sequences of amino acids within antibody variable regions which confer antigen specificity and binding affinity. For example, in general, there are three CDRs in each heavy chain variable region (e.g., CDR-H1, CDR-H2, and CDR-H3) and three CDRs in each light chain variable region (CDR-L1, CDR-L2, and CDR-L3). The precise amino acid sequence boundaries of a given CDR can be determined using any one of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof, and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). In a combined Kabat and Chothia numbering scheme for a given CDR region (for example, HC CDR1, HC CDR2, HC CDR3, LC CDR1, LC CDR2 or LC CDR3), in some embodiments, the CDRs correspond to the amino acid residues that are defined as part of the Kabat CDR, together with the amino acid residues that are defined as part of the Chothia CDR. As used herein, the CDRs defined according to the "Chothia" number scheme are also sometimes referred to as "hypervariable loops."

For example, under Kabat, the CDR amino acid residues in the heavy chain variable domain (VH) are numbered 31-35 (CDR-H1) (e.g., insertion(s) after position 35), 50-65 (CDR-H2), and 95-102 (CDR-H3); and the CDR amino acid residues in the light chain variable domain (VL) are numbered 24-34 (CDR-L1) (e.g., insertion(s) after position 27), 50-56 (CDR-L2), and 89-97 (CDR-L3). As another example, under Chothia, the CDR amino acids in the VH are numbered 26-32 (CDR-H1) (e.g., insertion(s) after position 31), 52-56 (CDR-H2), and 95-102 (CDR-H3); and the amino acid residues in VL are numbered 26-32 (CDR-L1) (e.g., insertion(s) after position 30), 50-52 (CDR-L2), and 91-96 (CDR-L3). By combining the CDR definitions of both Kabat and Chothia, the CDRs comprise or consist of, e.g., amino acid residues 26-35 (CDR-H1), 50-65 (CDR-H2), and 95-102 (CDR-H3) in human VH and amino acid residues 24-34 (CDR-L1), 50-56 (CDR-L2), and 89-97 (CDR-L3) in human VL. Under IMGT, the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align. Generally, unless specifically indicated, the antibody molecules can include any combination of one or more Kabat CDRs and/or Chothia CDRs.

Concurrently: The term "concurrently" is not limited to the administration of therapies (e.g., prophylactic or therapeutic agents) at exactly the same time, but rather it is meant that a pharmaceutical composition comprising an antigen-binding molecule is administered to a subject in a sequence and within a time interval such that the molecules can act together with the additional therapy(ies) to provide an increased benefit than if they were administered otherwise.

Conservative Sequence Modifications: The term "conservative sequence modifications" refers to amino acid modifications that do not significantly affect or alter the binding characteristics of a BCMA binding molecule or a component thereof (e.g., an ABD or an Fc region). Such conservative modifications include amino acid substitutions, additions and deletions. Modifications can be introduced into a BBM by standard techniques, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a BBM can be replaced with other amino acid residues from the same side chain family and the altered BBM can be tested for, e.g., binding to target molecules and/or effective heterodimerization and/or effector function.

Diabody: The term "diabody" as used herein refers to small antibody fragments with two antigen-binding sites, typically formed by pairing of scFv chains. Each scFv comprises a heavy chain variable domain (VH) connected to a light chain variable domain (VL) in the same polypeptide chain (VH-VL, where the VH is either N-terminal or C-terminal to the VL). Unlike a typical scFv in which the VH and VL are separated by a linker that allows the VH and VL on the same polypeptide chain to pair and form an antigen-binding domain, diabodies typically comprise a linker that is too short to allow pairing between the VH and VL domains on the same chain, forcing the VH and VL domains to pair with the complementary domains of another chain and create two antigen-binding sites. Diabodies are described more fully in, for example, EP 404,097; WO 93/11161; and Hollinger et al., 1993, Proc. Natl. Acad. Sci. USA 90:6444-6448.

dsFv: The term "dsFv" refers to disulfide-stabilized Fv fragments. In a dsFv, a VH and VL are connected by an interdomain disulfide bond. To generate such molecules, one amino acid each in the framework region of in VH and VL are mutated to a cysteine, which in turn form a stable interchain disulfide bond. Typically, position 44 in the VH and position 100 in the VL are mutated to cysteines. See Brinkmann, 2010, Antibody Engineering 181-189, DOI: 10.1007/978-3-642-01147-4_14. The term dsFv encompasses both what is known as a dsFv (a molecule in which the VH and VL are connected by an interchain disulfide bond but not a linker peptide) or scdsFv (a molecule in which the VH and VL are connected by a linker as well as an interchain disulfide bond).

Epitope: An epitope, or antigenic determinant, is a portion of an antigen recognized by an antibody or other antigen-binding moiety as described herein. An epitope can be linear or conformational.

Effector Function: The term "effector function" refers to an activity of an antibody molecule that is mediated by binding through a domain of the antibody other than the antigen-binding domain, usually mediated by binding of effector molecules. Effector function includes complement-mediated effector function, which is mediated by, for example, binding of the C1 component of the complement to the antibody. Activation of complement is important in the opsonization and lysis of cell pathogens. The activation of complement also stimulates the inflammatory response and may also be involved in autoimmune hypersensitivity. Effector function also includes Fc receptor (FcR)-mediated effector function, which can be triggered upon binding of the constant domain of an antibody to an Fc receptor (FcR). Binding of antibody to Fc receptors on cell surfaces triggers a number of important and diverse biological responses including engulfment and destruction of antibody-coated particles, clearance of immune complexes, ADCC, ADCP, release of inflammatory mediators, placental transfer and control of immunoglobulin production. An effector function of an antibody can be altered by altering, e.g., enhancing or reducing, the affinity of the antibody for an effector molecule such as an Fc receptor or a complement component. Binding affinity will generally be varied by modifying the effector molecule binding site, and in this case it is appropriate to locate the site of interest and modify at least part of the site in a suitable way. It is also envisaged that an alteration in the binding site on the antibody for the effector molecule need not alter significantly the overall binding affinity but can alter the geometry of the interaction rendering the effector mechanism ineffective as in non-productive binding. It is further envisaged that an effector function can also be altered by modifying a site not directly involved in effector molecule binding, but otherwise involved in performance of the effector function.

Fab: By "Fab" or "Fab region" as used herein is meant a polypeptide region that comprises the VH, CH1, VL, and CL immunoglobulin domain. These terms can refer to this region in isolation, or this region in the context of an antigen-binding molecule.

Fab domains are formed by association of a CH1 domain attached to a VH domain with a CL domain attached to a VL domain. The VH domain is paired with the VL domain to constitute the Fv region, and the CH1 domain is paired with the CL domain to further stabilize the binding module. A disulfide bond between the two constant domains can further stabilize the Fab domain.

Fab regions can be produced by proteolytic cleavage of immunoglobulin molecules (e.g., using enzymes such as papain) or through recombinant expression. In native immunoglobulin molecules, Fabs are formed by association of two different polypeptide chains (e.g., VH-CH1 on one chain associates with VL-CL on the other chain). The Fab regions are typically expressed recombinantly, typically on two polypeptide chains, although single chain Fabs are also contemplated herein.

Fc region: The term "Fc region" or "Fc chain" as used herein is meant the polypeptide comprising the CH2-CH3 domains of an IgG molecule, and in some cases, inclusive of the hinge. In EU numbering for human IgG1, the CH2-CH3 domain comprises amino acids 231 to 447, and the hinge is 216 to 230. Thus the definition of "Fc region" includes both amino acids 231-447 (CH2-CH3) or 216-447 (hinge-CH2-CH3), or fragments thereof. An "Fc fragment" in this context can contain fewer amino acids from either or both of the N- and C-termini but still retains the ability to form a dimer with another Fc region as can be detected using standard methods, generally based on size (e.g., non-denaturing chromatography, size exclusion chromatography). Human IgG Fc regions are of particular use in the present disclosure, and can be the Fc region from human IgG1, IgG2 or IgG4.

Fc domain: The term "Fc domain" refers to a pair of associated Fc regions. The two Fc regions dimerize to create the Fc domain. The two Fc regions within the Fc domain can be the same (such an Fc domain being referred to herein as an "Fc homodimer") or different from one another (such an Fc domain being referred to herein as an "Fc heterodimer").

Fv: The term "Fv", "Fv fragment" or "Fv region" refer to a region that comprises the VL and VH domains of an antibody fragment in a tight, noncovalent association (a VH-VL dimer). It is in this configuration that the three CDRs of each variable domain interact to define a target binding site. Often, the six CDRs confer target binding specificity to an antigen-binding molecule. However, in some instances even a single variable domain (or half of an Fv comprising only three CDRs specific for a target) can have the ability to recognize and bind target. In a native immunoglobulin molecule, the VH and VL of an Fv are on separate polypeptide chains but can be engineered as a single chain Fv (scFv). The terms also include Fvs that are engineered by the introduction of disulfide bonds for further stability.

The reference to a VH-VL dimer herein is not intended to convey any particular configuration. For example, in scFvs, the VH can be N-terminal or C-terminal to the VL (with the VH and VL typically connected by a linker as discussed herein).

Half Antibody: The term "half antibody" refers to a molecule that comprises at least one ABD or ABD chain and can associate with another molecule comprising an ABD or ABD chain through, e.g., a disulfide bridge or molecular interactions (e.g., knob-in-hole interactions between Fc heterodimers). A half antibody can be composed of one polypeptide chain or more than one polypeptide chains (e.g., the two polypeptide chains of a Fab). In an embodiment, a half-antibody comprises an Fc region.

An example of a half antibody is a molecule comprising a heavy and light chain of an antibody (e.g., an IgG antibody). Another example of a half antibody is a molecule comprising a first polypeptide comprising a VL domain and a CL domain, and a second polypeptide comprising a VH domain, a CH1 domain, a hinge domain, a CH2 domain, and a CH3 domain, where the VL and VH domains form an ABD. Yet another example of a half antibody is a polypeptide comprising an scFv domain, a CH2 domain and a CH3 domain.

A half antibody might include more than one ABD, for example a half-antibody comprising (in N- to C-terminal order) an scFv domain, a CH2 domain, a CH3 domain, and another scFv domain.

Half antibodies might also include an ABD chain that when associated with another ABD chain in another half antibody forms a complete ABD.

Thus, a BBM can comprise one, more typically two, or even more than two half antibodies, and a half antibody can comprise one or more ABDs or ABD chains.

In some BBMs, a first half antibody will associate, e.g., heterodimerize, with a second half antibody. In other BBMs, a first half antibody will be covalently linked to a second half antibody, for example through disulfide bridges or chemical crosslinking. In yet other BBMs, a first half antibody will associate with a second half antibody through both covalent attachments and non-covalent interactions, for example disulfide bridges and knob-in-hole interactions.

The term "half antibody" is intended for descriptive purposes only and does not connote a particular configuration or method of production. Descriptions of a half antibody as a "first" half antibody, a "second" half antibody, a "left" half antibody, a "right" half antibody or the like are merely for convenience and descriptive purposes.

Hole: In the context of a knob-into-hole, a "hole" refers to at least one amino acid side chain which is recessed from the interface of a first Fc chain and is therefore positionable in a compensatory "knob" on the adjacent interfacing surface of a second Fc chain so as to stabilize the Fc heterodimer, and thereby favor Fc heterodimer formation over Fc homodimer formation, for example.

Host cell or recombinant host cell: The terms "host cell" or "recombinant host cell" refer to a cell that has been genetically-engineered, e.g., through introduction of a heterologous nucleic acid. It should be understood that such terms are intended to refer not only to the particular subject cell but to the progeny of such a cell. Because certain modifications can occur in succeeding generations due to either mutation or environmental influences, such progeny may not, in fact, be identical to the parent cell, but are still included within the scope of the term "host cell" as used herein. A host cell can carry the heterologous nucleic acid transiently, e.g., on an extrachromosomal heterologous expression vector, or stably, e.g., through integration of the heterologous nucleic acid into the host cell genome. For purposes of expressing an antigen-binding molecule, a host cell can be a cell line of mammalian origin or mammalian-like characteristics, such as monkey kidney cells (COS, e.g., COS-1, COS-7), HEK293, baby hamster kidney (BHK, e.g., BHK21), Chinese hamster ovary (CHO), NSO, PerC6, BSC-1, human hepatocellular carcinoma cells (e.g., Hep G2), SP2/0, HeLa, Madin-Darby bovine kidney (MDBK), myeloma and lymphoma cells, or derivatives and/or engineered variants thereof. The engineered variants include, e.g., glycan profile modified and/or site-specific integration site derivatives.

Humanized: The term "humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin Io sequence. The humanized antibody optionally will also comprise at least a portion of an immunoglobulin constant region (Fc), typically that of a human immunoglobulin. Humanized antibodies are typically less immunogenic to humans, relative to non-humanized antibodies, and thus offer therapeutic benefits in certain situations. Humanized antibodies can be generated using known methods. See for example, Hwang et al., 2005, Methods 36:35; Queen et al., 1989, Proc. Natl. Acad. Sci. U.S.A. 86:10029-10033; Jones et al., 1986, Nature 321:522-25, 1986; Riechmann et al., 1988, Nature 332:323-27; Verhoeyen et al., 1988, Science 239:1534-36; Orlandi et al., 1989, Proc. Natl. Acad. Sci. U.S.A. 86:3833-3837; U.S. Pat. Nos. 5,225,539; 5,530,101; 5,585,089; 5,693,761; 5,693,762; and 6,180,370; and WO 90/07861. See also the following review articles and references cited therein: Presta, 1992, Curr. Op. Struct. Biol. 2:593-596; Vaswani and Hamilton, 1998, Ann. Allergy, Asthma & Immunol. 1:105-115; Harris, 1995, Biochem. Soc. Transactions 23:1035-1038; Hurle and Gross, 1994, Curr. Op. Biotech. 5:428-433.

Human Antibody: The term "human antibody" as used herein includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., 2000, J Mol Biol 296, 57-86. The structures and locations of immunoglobulin variable domains, e.g., CDRs, can be defined using well known numbering schemes, e.g., the Kabat numbering scheme, the Chothia numbering scheme, or any combination of Kabat and Chothia (see, e.g., Lazikani et al., 1997, J. Mol. Bio. 273:927 948; Kabat et al., 1991, Sequences of Proteins of Immunological Interest, 5th edit., NIH Publication no. 91-3242 U.S. Department of Health and Human Services; Chothia et al., 1987, J. Mol. Biol. 196:901-917; Chothia et al., 1989, Nature 342:877-883).

Human antibodies can include amino acid residues not encoded by human sequences (e.g., mutations introduced by random or site-specific mutagenesis in vitro or by somatic mutation in vivo, or a conservative substitution to promote stability or manufacturing). However, the term "human antibody", as used herein, is not intended to include antibodies in which CDR sequences derived from the germline of another mammalian species, such as a mouse, have been grafted onto human framework sequences.

In combination: Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons.

Knob: In the context of a knob-into-hole, a "knob" refers to at least one amino acid side chain which projects from the interface of a first Fc chain and is therefore positionable in a compensatory "hole" in the interface with a second Fc chain so as to stabilize the Fc heterodimer, and thereby favor Fc heterodimer formation over Fc homodimer formation, for example.

Knobs and holes (or knobs-into-holes): One mechanism for Fc heterodimerization is generally referred to in the art as "knobs and holes", or "knob-in-holes", or "knobs-into-holes". These terms refer to amino acid mutations that create steric influences to favor formation of Fc heterodimers over Fc homodimers, as described in, e.g., Ridgway et al., 1996, Protein Engineering 9(7):617; Atwell et al., 1997, J. Mol. Biol. 270:26; and U.S. Pat. No. 8,216,805. Knob-in-hole mutations can be combined with other strategies to improve heterodimerization, for example as described in Section 7.4.1.6.

Monoclonal Antibody: The term "monoclonal antibody" as used herein refers to polypeptides, including antibodies, antibody fragments, molecules (including BBMs), etc. that are derived from the same genetic source.

Monovalent: The term "monovalent" as used herein in the context of an antigen-binding molecule refers to an antigen-binding molecule that has a single antigen-binding domain.

Multispecific binding molecule: The term "multispecific binding molecule" or "MBM" refers to an antigen-binding molecule that specifically binds to at least two antigens and comprises two or more ABDs. The ABDs can each independently be an antibody fragment (e.g., scFv, Fab, nanobody), a ligand, or a non-antibody derived binder (e.g., fibronectin, Fynomer, DARPin).

Mutation or modification: In the context of the primary amino acid sequence of a polypeptide, the terms "modification" and "mutation" refer to an amino acid substitution, insertion, and/or deletion in the polypeptide sequence relative to a reference polypeptide. Additionally, the term "modification" further encompasses an alteration to an amino acid residue, for example by chemical conjugation (e.g., of a drug or polyethylene glycol moiety) or post-translational modification (e.g., glycosylation).

Nucleic Acid: The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions can be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

Operably linked: The term "operably linked" refers to a functional relationship between two or more peptide or polypeptide domains or nucleic acid (e.g., DNA) segments. In the context of a fusion protein or other polypeptide, the term "operably linked" means that two or more amino acid segments are linked so as to produce a functional polypeptide. For example, in the context of an antigen-binding molecule, separate ABMs (or chains of an ABM) can be operably linked through peptide linker sequences. In the context of a nucleic acid encoding a fusion protein, such as a polypeptide chain of an antigen-binding molecule, "operably linked" means that the two nucleic acids are joined such that the amino acid sequences encoded by the two nucleic acids remain in-frame. In the context of transcriptional regulation, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system.

Polypeptide and Protein: The terms "polypeptide" and "protein" are used interchangeably herein to refer to a polymer of amino acid residues. The terms encompass amino acid polymers in which one or more amino acid residue is an artificial chemical mimetic of a corresponding naturally occurring amino acid, as well as to naturally occurring amino acid polymers and non-naturally occurring amino acid polymer. Additionally, the terms encompass amino acid polymers that are derivatized, for example, by synthetic derivatization of one or more side chains or termini, glycosylation, PEGylation, circular permutation, cyclization, linkers to other molecules, fusion to proteins or protein domains, and addition of peptide tags or labels.

Recognize: The term "recognize" as used herein refers to an ABD that finds and interacts (e.g., binds) with its epitope.

Sequence identity: Sequence identity between two similar sequences (e.g., antibody variable domains) can be measured by algorithms such as that of Smith, T. F. & Waterman, M. S. (1981) "Comparison Of Biosequences," Adv. Appl. Math. 2:482 [local homology algorithm]; Needleman, S. B. & Wunsch, C D. (1970) "A General Method Applicable To The Search For Similarities In The Amino Acid Sequence Of Two Proteins," J. Mol. Biol. 48:443 [homology alignment algorithm], Pearson, W. R. & Lipman, D. J. (1988) "Improved Tools For Biological Sequence Comparison," Proc. Natl. Acad. Sci. (U.S.A.) 85:2444 [search for similarity method]; or Altschul, S. F. et al, (1990) "Basic Local Alignment Search Tool," J. Mol. Biol. 215:403-10, the "BLAST" algorithm, see blast.ncbi.nlm.nih.gov/Blast.cgi. When using any of the aforementioned algorithms, the default parameters (for Window length, gap penalty, etc.) are used. In one embodiment, sequence identity is done using the BLAST algorithm, using default parameters.

Optionally, the identity is determined over a region that is at least about 50 nucleotides (or, in the case of a peptide or polypeptide, at least about 10 amino acids) in length, or in some cases over a region that is 100 to 500 or 1000 or more nucleotides (or 20, 50, 200 or more amino acids) in length. In some embodiments, the identity is determined over a defined domain, e.g., the VH or VL of an antibody. Unless specified otherwise, the sequence identity between two sequences is determined over the entire length of the shorter of the two sequences.

Single Chain Fab or scFab: The terms "single chain Fab" and "scFab" mean a polypeptide comprising an antibody heavy chain variable domain (VH), an antibody constant domain 1 (CH1), an antibody light chain variable domain (VL), an antibody light chain constant domain (CL) and a linker, such that the VH and VL are in association with one another and the CH1 and CL are in association with one another. In some embodiments, the antibody domains and the linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. The linker can be a polypeptide of at least 30 amino acids, e.g., between 32 and 50 amino acids. The single chain Fabs are stabilized via the natural disulfide bond between the CL domain and the CH1 domain.

Simultaneous or concurrent delivery: In some embodiments, the delivery of one treatment is still occurring when the delivery of a second begins, so that there is overlap in terms of administration. This is sometimes referred to herein as "simultaneous" or "concurrent delivery". In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Single Chain Fv or scFv: By "single chain Fv" or "scFv" herein is meant a variable heavy domain covalently attached to a variable light domain, generally using an ABD linker as discussed herein, to form a scFv or scFv domain. A scFv domain can be in either orientation from N- to C-terminus (VH-linker-VL or VL-linker-VH). For a review of scFv see Plückthun in The Pharmacology of Monoclonal Antibodies, vol. 113, Rosenburg and Moore eds., (1994) Springer-Verlag, New York, pp. 269-315.

Specifically (or selectively) binds: The term "specifically (or selectively) binds" to an antigen or an epitope refers to a binding reaction that is determinative of the presence of a cognate antigen or an epitope in a heterogeneous population of proteins and other biologics. An antigen-binding molecule or ABD of the disclosure typically has a dissociation rate constant (KD) (koff/kon) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, or less than $10^{-9}$M, and binds to the target antigen with an affinity that is at least two-fold greater (and more typically at least 20-fold, at least 50-fold or at least 100-fold) than its affinity for binding to a non-specific antigen (e.g., HSA). Binding affinity can be measured using a Biacore, SPR or BLI assay.

The term "specifically binds" does not exclude cross-species reactivity. For example, an antigen-binding module (e.g., an antigen-binding fragment of an antibody) that "specifically binds" to an antigen from one species can also "specifically bind" to that antigen in one or more other species. Thus, such cross-species reactivity does not itself alter the classification of an antigen-binding module as a "specific" binder. In certain embodiments, an antigen-binding domain that specifically binds to a human antigen has cross-species reactivity with one or more non-human mammalian species, e.g., a primate species (including but not limited to one or more of *Macaca fascicularis, Macaca*

*mulatta*, and *Macaca nemestrina*) or a rodent species, e.g., *Mus musculus*. In other embodiments, the antigen-binding domain does not have cross-species reactivity.

Subject: The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

Tandem of VH Domains: The term "a tandem of VH domains (or VHs)" as used herein refers to a string of VH domains, consisting of multiple numbers of identical VH domains of an antibody. Each of the VH domains, except the last one at the end of the tandem, has its C-terminus connected to the N-terminus of another VH domain with or without a linker. A tandem has at least 2 VH domains, and in some embodiments a BBM has 3, 4, 5, 6, 7, 8, 9, or 10 VH domains. The tandem of VH can be produced by joining the encoding nucleic acids of each VH domain in a desired order using recombinant methods with or without a linker (e.g., as described in Section 7.4.3) that enables them to be made as a single polypeptide chain. The N-terminus of the first VH domain in the tandem is defined as the N-terminus of the tandem, while the C-terminus of the last VH domain in the tandem is defined as the C-terminus of the tandem.

Tandem of VL Domains: The term "a tandem of VL domains (or VLs)" as used herein refers to a string of VL domains, consisting of multiple numbers of identical VL domains of an antibody. Each of the VL domains, except the last one at the end of the tandem, has its C-terminus connected to the N-terminus of another VL with or without a linker. A tandem has at least 2 VL domains, and in some embodiments a BBM has 3, 4, 5, 6, 7, 8, 9, or 10 VL domains. The tandem of VL can be produced by joining the encoding nucleic acids of each VL domain in a desired order using recombinant methods with or without a linker (e.g., as described in Section 7.4.3) that enables them to be made as a single polypeptide chain. The N-terminus of the first VL domain in the tandem is defined as the N-terminus of the tandem, while the C-terminus of the last VL domain in the tandem is defined as the C-terminus of the tandem.

Target Antigen: By "target antigen" as used herein is meant the molecule that is bound non-covalently, reversibly and specifically by an antigen binding domain.

Tetravalent: The term "tetravalent" as used herein in the context of an antigen-binding molecule (e.g., a BBM) refers to an antigen-binding molecule that has four ABDs. Antigen-binding molecules of the disclosure that are BBMs are bispecific and specifically bind to BCMA and a second antigen, e.g., a component of a TCR complex. In certain embodiments, the tetravalent BBMs generally have two ABDs that each specifically bind to BCMA and two ABDs that each specifically bind to the second antigen, e.g., the component of a TCR complex, although other configurations are contemplated whereby three ABDs specifically bind to one antigen (e.g., BCMA) and one ABD specifically binds to a different antigen (e.g., a component of the TCR complex). Examples of tetravalent configurations are shown schematically in FIGS. 1AA-1AG.

Therapeutically effective amount: A "therapeutically effective amount" refers to an amount effective, at dosages and for periods of time necessary, to achieve a desired therapeutic result.

Treat, Treatment, Treating: As used herein, the terms "treat", "treatment" and "treating" refer to the reduction or amelioration of the progression, severity and/or duration of a proliferative disorder, or the amelioration of one or more symptoms (e.g., one or more discernible symptoms) of a proliferative disorder resulting from the administration of one or more antigen-binding molecules. In some embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

Tumor: The term "tumor" is used interchangeably with the term "cancer" herein, e.g., both terms encompass solid and liquid, e.g., diffuse or circulating, tumors. As used herein, the term "cancer" or "tumor" includes premalignant, as well as malignant cancers and tumors.

Trivalent: The term "trivalent" as used herein in the context of an antigen-binding molecule (e.g., a BBM) refers to an antigen-binding molecule that has three ABDs. Antigen-binding molecules of the disclosure that are BBMs are bispecific and specifically bind to BCMA and a second antigen, e.g., a component of a TCR complex. Accordingly, the trivalent BBMs have two ABDs that bind to one antigen (e.g., BCMA) and one ABD that binds to a different antigen (e.g., a component of the TCR complex). Examples of trivalent configurations are shown schematically in FIGS. 1G-1Z.

Variable region: By "variable region" or "variable domain" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively, and contains the CDRs that confer antigen specificity. A "variable heavy domain" can pair with a "variable light domain" to form an antigen binding domain ("ABD"). In addition, each variable domain comprises three hypervariable regions ("complementary determining regions," "CDRs") (CDR-H1, CDR-H2, CDR-H3 for the variable heavy domain and CDR-L1, CDR-L2, CDR-L3 for the variable light domain) and four framework (FR) regions, arranged from amino-terminus to carboxy-terminus in the following order: FR1-CDR1-FR2-CDR2-FR3-CDR3-FR4.

Vector: The term "vector" is intended to refer to a polynucleotide molecule capable of transporting another polynucleotide to which it has been linked. One type of vector is a "plasmid", which refers to a circular double stranded DNA loop into which additional DNA segments can be ligated. Another type of vector is a viral vector, where additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

VH: The term "VH" refers to the variable region of an immunoglobulin heavy chain of an antibody, including the heavy chain of an Fv, scFv, dsFv or Fab.

VL: The term "VL" refers to the variable region of an immunoglobulin light chain, including the light chain of an Fv, scFv, dsFv or Fab.

VH-VL or VH-VL Pair: In reference to a VH-VL pair, whether on the same polypeptide chain or on different polypeptide chains, the terms "VH-VL" and "VH-VL pair" are used for convenience and are not intended to convey any particular orientation, unless the context dictates otherwise. Thus, a scFv comprising a "VH-VL" or "VH-VL pair" can have the VH and VL domains in any orientation, for example the VH N-terminal to the VL or the VL N-terminal to the VH.

7.2. BCMA Binding Molecules

In one aspect, the disclosure provides BCMA binding molecules, including monospecific and multispecific molecules that bind to human BCMA. In some embodiments, the BCMA binding molecule is a monospecific binding molecule. For example, the monospecific binding molecule can be an antibody or an antigen-binding fragment thereof (e.g., an antibody fragment, an scFv, a dsFv, a Fv, a Fab, an scFab, a (Fab')2, or a single domain antibody (SDAB). In other embodiments, the BCMA binding molecule is a multispecific (e.g., bispecific) BCMA binding molecule (e.g., a bispecific antibody).

In some embodiments, the BCMA binding molecules are chimeric or humanized monoclonal antibodies. Chimeric and/or humanized antibodies, can be engineered to minimize the immune response by a human patient to antibodies produced in non-human subjects or derived from the expression of non-human antibody genes. Chimeric antibodies comprise a non-human animal antibody variable region and a human antibody constant region. Such antibodies retain the epitope binding specificity of the original monoclonal antibody, but can be less immunogenic when administered to humans, and therefore more likely to be tolerated by the patient. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region. Chimeric monoclonal antibodies can be produced by known recombinant DNA techniques. For example, a gene encoding the constant region of a non-human antibody molecule can be substituted with a gene encoding a human constant region (see Robinson et al., PCT Patent Publication PCT/US86/02269; Akira, et al., European Patent Application 184,187; or Taniguchi, M., European Patent Application 171,496). In addition, other suitable techniques that can be used to generate chimeric antibodies are described, for example, in U.S. Pat. Nos. 4,816,567; 4,978,775; 4,975,369; and 4,816,397.

Chimeric or humanized antibodies and antigen binding fragments thereof of the present disclosure can be prepared based on the sequence of a murine monoclonal antibody. DNA encoding the heavy and light chain immunoglobulins can be obtained from a murine hybridoma of interest and engineered to contain non-murine (e.g., human) immunoglobulin sequences using standard molecular biology techniques. For example, to create a chimeric antibody, the murine variable regions can be linked to human constant regions using known methods (see e.g., U.S. Pat. No. 4,816,567 to Cabilly et al.). To create a humanized antibody, the murine CDR regions can be inserted into a human framework using known methods. See e.g., U.S. Pat. No. 5,225,539 to Winter, and U.S. Pat. Nos. 5,530,101; 5,585,089; 5,693,762 and 6,180,370 to Queen et al.

A humanized antibody can be produced using a variety of known techniques, including but not limited to, CDR-grafting (see, e.g., European Patent No. EP 239,400; International Publication No. WO 91/09967; and U.S. Pat. Nos. 5,225,539, 5,530,101, and 5,585,089), veneering or resurfacing (see, e.g., European Patent Nos. EP 592,106 and EP 519,596; Padlan, 1991, Molecular Immunology, 28(4/5): 489-498; Studnicka et al., 1994, Protein Engineering, 7(6): 805-814; and Roguska et al., 1994, PNAS, 91:969-973), chain shuffling (see, e.g., U.S. Pat. No. 5,565,332), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994). Often, framework residues in the framework regions will be substituted with the corresponding residue from the CDR donor antibody to alter, for example improve, antigen binding. These framework substitutions, e.g., conservative substitutions are identified by well-known methods, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323).

As provided herein, humanized antibodies or antibody fragments can comprise one or more CDRs from nonhuman immunoglobulin molecules and framework regions where the amino acid residues comprising the framework are derived completely or mostly from human germline. Multiple techniques for humanization of antibodies or antibody fragments are well-known and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332).

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework can be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993). In some embodiments, the framework region, e.g., all four framework regions, of the heavy chain variable region are derived from a VH4_4-59 germline sequence. In one embodiment, the framework region can comprise, one, two, three, four or five modifications, e.g., substitutions, e.g., conservative substitutions, e.g., from the amino acid at the corresponding murine sequence. In one embodiment, the framework region, e.g., all four framework regions of the light chain variable region are derived from a VK3_1.25 germline sequence. In one embodiment, the framework region can comprise, one, two, three, four or five modifications, e.g., substitutions, e.g., conservative substitutions, e.g., from the amino acid at the corresponding murine sequence.

In certain embodiments, the BCMA binding molecules comprise a heavy chain variable region from a particular germline heavy chain immunoglobulin gene and/or a light chain variable region from a particular germline light chain immunoglobulin gene. For example, such antibodies can comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody (using the methods outlined herein). A human antibody that is "the product of" or "derived from" a particular human germline immunoglobulin sequence can contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody can be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the disclosure). In certain cases, the humanized antibody can display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the disclosure).

In one embodiment, the parent antibody has been affinity matured. Structure-based methods can be employed for humanization and affinity maturation, for example as described in U.S. Ser. No. 11/004,590. Selection based methods can be employed to humanize and/or affinity mature antibody variable regions, including but not limited to methods described in Wu et al., 1999, J. Mol. Biol. 294:151-162; Baca et al., 1997, J. Biol. Chem. 272(16): 10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods can involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084.

In some embodiments, the BCMA binding molecule comprises an ABD which is a Fab. Fab domains can be produced by proteolytic cleavage of immunoglobulin molecules, using enzymes such as papain, or through recombinant expression. Fab domains typically comprise a CH1 domain attached to a VH domain which pairs with a CL domain attached to a VL domain. In a wild-type immunoglobulin, the VH domain is paired with the VL domain to constitute the Fv region, and the CH1 domain is paired with the CL domain to further stabilize the binding module. A disulfide bond between the two constant domains can further stabilize the Fab domain.

In some embodiments, the BCMA binding molecule comprises an ABD which is a scFab. In an embodiment, the antibody domains and the linker in the scFab fragment have one of the following orders in N-terminal to C-terminal direction: a) VH-CH1-linker-VL-CL, or b) VL-CL-linker-VH-CH1. In some cases, VL-CL-linker-VH-CH1 is used.

In another embodiment, the antibody domains and the linker in the scFab fragment have one of the following orders in N-terminal to C-terminal direction: a) VH-CL-linker-VL-CH1 or b) VL-CH1-linker-VH-CL.

Optionally in the scFab fragment, additionally to the natural disulfide bond between the CL-domain and the CH1 domain, also the antibody heavy chain variable domain (VH) and the antibody light chain variable domain (VL) are disulfide stabilized by introduction of a disulfide bond between the following positions: i) heavy chain variable domain position 44 to light chain variable domain position 100, ii) heavy chain variable domain position 105 to light chain variable domain position 43, or iii) heavy chain variable domain position 101 to light chain variable domain position 100 (numbering according to EU index of Kabat).

Such further disulfide stabilization of scFab fragments is achieved by the introduction of a disulfide bond between the variable domains VH and VL of the single chain Fab fragments. Techniques to introduce unnatural disulfide bridges for stabilization for a single chain Fv are described e.g. in WO 94/029350, Rajagopal et al., 1997, Prot. Engin. 10:1453-59; Kobayashi et al., 1998, Nuclear Medicine & Biology, 25:387-393; and Schmidt, et al., 1999, Oncogene 18:1711-1721. In one embodiment, the optional disulfide bond between the variable domains of the scFab fragments is between heavy chain variable domain position 44 and light chain variable domain position 100. In one embodiment, the optional disulfide bond between the variable domains of the scFab fragments is between heavy chain variable domain position 105 and light chain variable domain position 43 (numbering according to EU index of Kabat).

In some embodiments, the BCMA binding molecule comprises an ABD which is a scFv. Single chain Fv antibody fragments comprise the VH and VL domains of an antibody in a single polypeptide chain, are capable of being expressed as a single chain polypeptide, and retain the specificity of the intact antibody from which it is derived. Generally, the scFv polypeptide further comprises a polypeptide linker between the VH and VL domain that enables the scFv to form the desired structure for target binding. Examples of linkers suitable for connecting the VH and VL chains of an scFV are the ABD linkers identified in Section 7.4.3, for example any of the linkers designated L1 through L58.

Unless specified, as used herein an scFv can have the VL and VH variable regions in either order, e.g., with respect to the N-terminal and C-terminal ends of the polypeptide, the scFv can comprise VL-linker-VH or can comprise VH-linker-VL.

To create an scFv-encoding nucleic acid, the VH and VL-encoding DNA fragments are operably linked to another fragment encoding a linker, e.g., encoding any of the linkers described in Section 7.4.3 (such as the amino acid sequence (Gly4⁻Ser)3 (SEQ ID NO:1)), such that the VH and VL sequences can be expressed as a contiguous single-chain protein, with the VL and VH regions joined by the flexible linker (see e.g., Bird et al., 1988, Science 242:423-426; Huston et al., 1988, Proc. Natl. Acad. Sci. USA 85:5879-5883; McCafferty et al., 1990, Nature 348:552-554).

BCMA binding molecules can also comprise an ABD which is a Fv, a dsFv, a (Fab')2, a single domain antibody (SDAB), a VH or VL domain, or a camelid VHH domain (also called a nanobody).

BCMA binding molecules can comprise a single domain antibody composed of a single VH or VL domain which exhibits sufficient affinity to BCMA. In an embodiment, the single domain antibody is a camelid VHH domain (see, e.g., Riechmann, 1999, Journal of Immunological Methods 231: 25-38; WO 94/04678).

Tables 1A-1 to 1P (collectively "Table 1") list the sequences of exemplary BCMA binding sequences that can be included in BCMA binding molecules.

TABLE 1A-1

AB1/AB2 Family Light Chain CDR Consensus sequences

| Binder | CDR-L1 | SEQ ID NO: | CDR-L2: | SEQ ID NO: | CDR-L3 | SEQ ID NO: |
|---|---|---|---|---|---|---|
| C1 (AB1/AB2 consensus - Kabat) | RASQSISSYLN | 2 | AASSLQS | 5 | QQSYSXPLT (X = S or T) | 7 |
| C2 (AB1/AB2 family consensus - Kabat) | RASQSISSYLN | 2 | AASSLQS | 5 | QQSYX$_1$X$_2$PX$_3$T (X$_1$ = S, G, D, Y, or A; X$_2$ = S, T, or A; X$_3$ = P or L) | 8 |
| C3 (AB1/AB2 consensus - Chothia) | SQSISSY | 3 | AAS | | SYSXPL (X = S or T) | 9 |
| C4 (AB1/AB2 family consensus - Chothia) | SQSISSY | 3 | AAS | | SYX$_1$X$_2$PX$_3$ (X$_1$ = S, G, D, Y, or A; X$_2$ = S, T, or A; X$_3$ = P or L) | |
| C5 (AB1/AB2 consensus - IMGT) | QSISSY | 4 | AAS | | QQSYSXPLT (X = S or T) | 7 |
| C6 (AB1/AB2 family consensus - IMGT) | QSISSY | 4 | AAS | | QQSYX$_1$X$_2$PX$_3$T (X$_1$ = S, G, D, Y, or A; X$_2$ = S, T, or A; X$_3$ = P or L) | 8 |
| C7 (AB1/AB2 consensus - Kabat + Chothia) | RASQSISSYLN | 2 | AASSLQS | 5 | QQSYSXPLT (X = S or T) | 7 |
| C8 (AB1/AB2 family | RASQSISSYLN | 2 | AASSLQS | 5 | QQSYX$_1$X$_2$PX$_3$T (X$_1$ = S, G, D, Y, or A; X$_2$ = S, T, or A; X$_3$ = | 8 |

TABLE 1A-1-continued

AB1/AB2 Family Light Chain CDR Consensus sequences

| Binder | CDR-L1 | SEQ ID NO: | CDR-L2: | SEQ ID NO: | CDR-L3 | SEQ ID NO: |
|---|---|---|---|---|---|---|
| consensus - Kabat + Chothia) | | | | | P or L) | |
| C9 (AB1/AB2 consensus - Kabat + IMGT) | RASQSISSYLN | 2 | AASSLQS | 5 | QQSYSXPLT (X = S or T) | 7 |
| C10 (AB1/AB2 family consensus - Kabat + IMGT) | RASQSISSYLN | 2 | AASSLQS | 5 | QQSYX$_1$X$_2$PX$_3$T (X$_1$ = S, G, D, Y, or A; X$_2$ = S, T, or A; X$_3$ = P or L) | 8 |
| C11 (AB1/AB2 consensus - Chothia + IMGT) | SQSISSY | 3 | AAS | | QQSYSXPLT (X = S or T) | 7 |
| C12 (AB1/AB2 family consensus - Chothia + IMGT) | SQSISSY | 3 | AAS | | QQSYX$_1$X$_2$PX$_3$T (X$_1$ = S, G, D, Y, or A; X$_2$ = S, T, or A; X$_3$ = P or L) | 8 |

TABLE 1A-2

AB1/AB2 Family Heavy Chain CDR Consensus sequences

| Binder | CDR-H1 | SEQ ID NO: | CDR-H2: | SEQ ID NO: | CDR-H3 | SEQ ID NO: |
|---|---|---|---|---|---|---|
| C1 (AB1/AB2 consensus - Kabat) | SYAMS | 11 | AISX$_1$SGGX$_2$X$_3$X$_4$YADSVKG (X$_1$ = G or E; X$_2$ = S or R; X$_3$ = T or A; X$_4$ = Y or A) | 15 | REWWYDDWYLDY | 24 |
| C2 (AB1/AB2 family consensus - Kabat) | SYAMS | 11 | AISX$_1$X$_2$GX$_3$X$_4$X$_5$X$_6$YADSVKG (X$_1$ = G, E, or A; X$_2$ = S, A, H, or E; X$_3$ = G, D, E, H, R, or A; X$_4$ = S, R, V, T, Y; X$_5$ = T, A, E, H, or R; X$_6$ = Y, A, or S) | 16 | REWWYDDWYLDY | 24 |
| C3 (AB1/AB2 consensus - Chothia) | GFTFSSY | 12 | SX$_1$SGGX$_2$ (X$_1$ = G or E; X$_2$ = S or R) | 17 | REWWYDDWYLDY | 24 |
| C4 (AB1/AB2 family consensus - Chothia) | GFTFSSY | 12 | SX$_1$X$_2$GX$_3$X$_4$ (X$_1$ = G, E, or A; X$_2$ = S, A, H, or E; X$_3$ = G, D, E, H, R, or A; X$_4$ = S, R, V, T, Y) | 18 | REWWYDDWYLDY | 24 |
| C5 (AB1/AB2 consensus - IMGT) | GFTFSSYA | 13 | ISX$_1$SGGX$_2$X$_3$ (X$_1$ = G or E; X$_2$ = S or R; X$_3$ = T or A) | 19 | ARREWWYDDWYLDY | 25 |
| C6 (AB1/AB2 family consensus - | GFTFSSYA | 13 | ISX$_1$X$_2$GX$_3$X$_4$X$_5$ (X$_1$ = G, E, or A; X$_2$ = S, A, H, or E; X$_3$ = G, D, E, H, R, or A; X$_4$ = S, R, | 20 | ARREWWYDDWYLDY | 25 |

TABLE 1A-2-continued

AB1/AB2 Family Heavy Chain CDR Consensus sequences

| Binder | CDR-H1 | SEQ ID NO: | CDR-H2: | SEQ ID NO: | CDR-H3 | SEQ ID NO: |
|---|---|---|---|---|---|---|
| IMGT) | | | V, T, Y; $X_5$ = T, A, E, H, or R) | | | |
| C7 (AB1/AB2 consensus - Kabat + Chothia) | GFTFSSYAMS | 14 | AISX$_1$SGGX$_2$X$_3$X$_4$YADSVKG ($X_1$ = G or E; $X_2$ = S or R; $X_3$ = T or A; $X_4$ = Y or A) | 15 | REWWYDDWYLDY | 24 |
| C8 (AB1/AB2 family consensus - Kabat + Chothia) | GFTFSSYAMS | 14 | AISX$_1$X$_2$GX$_3$X$_4$X$_5$X$_6$YADSVKG ($X_1$ = G, E, or A; $X_2$ = S, A, H, or E; $X_3$ = G, D, E, H, R, or A; $X_4$ = S, R, V, T, Y; $X_5$ = T, A, E, H, or R; $X_6$ = Y, A, or S) | 16 | REWWYDDWYLDY | 24 |
| C9 (AB1/AB2 consensus - Kabat + IMGT) | GFTFSSYAMS | 14 | AISX$_1$SGGX$_2$X$_3$X$_4$YADSVKG ($X_1$ = G or E; $X_2$ = S or R; $X_3$ = T or A; $X_4$ = Y or A) | 15 | ARREWWYDDWYLDY | 25 |
| C10 (AB1/AB2 family consensus - Kabat + IMGT) | GFTFSSYAMS | 14 | AISX$_1$X$_2$GX$_3$X$_4$X$_5$X$_6$YADSVKG ($X_1$ = G, E, or A; $X_2$ = S, A, H, or E; $X_3$ = G, D, E, H, R, or A; $X_4$ = S, R, V, T, Y; $X_5$ = T, A, E, H, or R; $X_6$ = Y, A, or S) | 21 | ARREWWYDDWYLDY | 25 |
| C11 (AB1/AB2 consensus - Chothia + IMGT) | GFTFSSYA | 13 | ISX$_1$SGGX$_2$X$_3$ ($X_1$ = G or E, $X_2$ = S or R; $X_3$ = T or A) | 22 | ARREWWYDDWYLDY | 25 |
| C12 (AB1/AB2 family consensus - Chothia + IMGT) | GFTFSSYA | 13 | ISX$_1$X$_2$GX$_3$X$_4$X$_5$ ($X_1$ = G, E, or A; $X_2$ = S, A, H, or E; $X_3$ = G, D, E, H, R, or A; $X_4$ = S, R, V, T, Y; $X_6$ = T, A, E, H, or R) | 23 | ARREWWYDDWYLDY | 25 |

TABLE 1B-1

AB3 Family Light Chain CDR Consensus sequences

| Binder | CDR-L1 | SEQ ID NO: | CDR-L2: | SEQ ID NO: | CDR-L3 | SEQ ID NO: |
|---|---|---|---|---|---|---|
| C13 (AB3/PI-61 consensus - Kabat) | TGTSSDVGGYNYVS | 26 | DVSNRX$_1$X$_2$ ($X_1$ = L or P; $X_2$ = R or S) | 29 | SSYTSSSXLYV (X = A or T) | 37 |
| C14 (AB3 family consensus - Kabat) | TGTSSDVGGYNYVS | 26 | X$_1$VSNRX$_2$X$_3$ ($X_1$ = D or E; $X_2$ = L, P, or A; $X_3$ = R, S, G, or W) | 30 | SSYTSSSXLYV (X = A or T) | 37 |
| C15 (AB3/PI-61 consensus - Chothia) | TSSDVGGYNY | 27 | DVS | 31 | YTSSSXLY (X = A or T) | 38 |
| C16 (AB3 family consensus - Chothia) | TSSDVGGYNY | 27 | XVS (X = D or E) | 32 | YTSSSXLY (X = A or T) | 38 |

TABLE 1B-1-continued

AB3 Family Light Chain CDR Consensus sequences

| Binder | CDR-L1 | SEQ ID NO: | CDR-L2: | SEQ ID NO: | CDR-L3 | SEQ ID NO: |
|---|---|---|---|---|---|---|
| C17 (AB3/PI-61 consensus - IMGT with expanded CDR-L2) | SSDVGGYNY | 28 | DVSNRX$_1$X$_2$GVS (X$_1$ = L OR P; X$_2$ = R OR S) | 33 | SSYTSSSXLYV (X = A or T) | 37 |
| C18 (AB3 family consensus - IMGT with expanded CDR-L2) | SSDVGGYNY | 28 | X$_1$VSNRX$_2$X$_3$GVS (X$_1$ = D or E; X$_2$ = L, P, or A; X$_3$ = R, S, G, or W) | 34 | SSYTSSSXLYV (X = A or T) | 37 |
| C19 (AB3/PI-61 consensus - Kabat + Chothia) | TGTSSDVGGYNYVS | 26 | DVSNRX$_1$X$_2$ (X$_1$ = L OR P; X$_2$ = R OR S) | 29 | SSYTSSSXLYV (X = A or T) | 37 |
| C20 (AB3 family consensus - Kabat + Chothia) | TGTSSDVGGYNYVS | 26 | X$_1$VSNRX$_2$X$_3$ (X$_1$ = D or E; X$_2$ = L, P, or A; X$_3$ = R, S, G, or W) | 30 | SSYTSSSXLYV (X = A or T) | 37 |
| C21 (AB3/PI-61 consensus - Kabat + IMGT) | TGTSSDVGGYNYVS | 26 | DVSNRX$_1$X$_2$ (X$_1$ = L OR P; X$_2$ = R OR S) | 29 | SSYTSSSXLYV (X = A or T) | 37 |
| C22 (AB3 family consensus - Kabat + IMGT) | TGTSSDVGGYNYVS | 26 | X$_1$VSNRX$_2$X$_3$ (X$_1$ = D or E; X$_2$ = L, P, or A; X$_3$ = R, S, G, or W) | 30 | SSYTSSSXLYV (X = A or T) | 37 |
| C23 (AB3/PI-61 consensus - Chothia + IMGT with expanded CDR-L2) | TSSDVGGYNY | 27 | DVSNRXX$_2$GVS (X$_1$ = L or P; X$_2$ = R or S) | 35 | SSYTSSSXLYV (X = A or T) | 37 |
| C24 (AB3 family consensus - Chothia + IMGT with expanded CDR-L2) | TSSDVGGYNY | 27 | X$_1$VSNRX$_2$X$_3$GVS (X$_1$ = D or E; X$_2$ = L, P, or A; X$_3$ = R, S, G, or W) | 34 | SSYTSSSXLYV (X = A or T) | 37 |
| C25 (AB3/PI-61 consensus - IMGT) | SSDVGGYNY | 28 | DVS | 31 | SSYTSSSXLYV (X = A or T) | 37 |
| C26 (AB3 family consensus - IMGT) | SSDVGGYNY | 28 | X$_1$VS (X$_1$ = D or E) | 36 | SSYTSSSXLYV (X = A or T) | 37 |
| C27 (AB3/PI-61 consensus - Chothia + IMGT) | TSSDVGGYNY | 27 | DVS | 31 | SSYTSSSXLYV (X = A or T) | 37 |

TABLE 1B-1-continued

AB3 Family Light Chain CDR Consensus sequences

| Binder | CDR-L1 | SEQ ID NO: | CDR-L2: | SEQ ID NO: | CDR-L3 | SEQ ID NO: |
|---|---|---|---|---|---|---|
| C28 (AB3 family consensus - Chothia + IMGT) | TSSDVGGYNY | 27 | $X_1$VS ($X_1$ = D or E) | 36 | SSYTSSSXLYV (X = A or T) | 37 |

TABLE 1B-2

AB3 Family Heavy Chain CDR Consensus sequences

| Binder | CDR-H1 | SEQ ID NO: | CDR-H2: | SEQ ID NO: | CDR-H3 | SEQ ID NO: |
|---|---|---|---|---|---|---|
| C13 (AB3/PI-61 consensus - Kabat) | SYGMH | 39 | VISYXGSNKYYADSVKG (X = T or D) | 43 | SGYALHDDYYGLDV | 49 |
| C14 (AB3 family consensus - Kabat) | SYGMH | 39 | VISYX$_1$X$_2$X$_3$X$_4$KYYADSVKG (X$_1$ = H, K, T, R, D, N, S; X$_2$ = G, D, or E; X$_3$ = S, T, F, A, L; X$_4$ = H, N or K) | 44 | SGYX$_1$X$_2$X$_3$X$_4$X$_5$X$_6$X$_7$X$_8$X$_9$DV (X$_1$ = A, N, E; X$_2$ = L, F, V, or Y; X$_3$ = H, Q, R, or D; X$_4$ = D, E, G, or Q; X$_5$ = D, Q, or F; X$_6$ = Y or Q; X$_7$ = Y, K, or D; X$_8$ = G or P; X$_9$ = L, Q, V, or T) | 50 |
| C15 (AB3/PI-61 consensus - Chothia) | GFTXSSY (X = V or F) | 40 | SYXGSN (X = T or D) | 45 | SGYALHDDYYGLDV | 49 |
| C16 (AB3 family consensus - Chothia) | GFTXSSY (X = V or F) | 40 | SYX$_1$X$_2$X$_3$X$_4$KG (X$_1$ = H, K, T, R, D, N, S; X$_2$ = G, D, or E; X$_3$ = S, T, F, A, L; X$_4$ = H, N or K) | 46 | SGYX$_1$X$_2$X$_3$X$_4$X$_5$X$_6$X$_7$X$_8$X$_9$DV (X$_1$ = A, N, E; X$_2$ = L, F, V, or Y; X$_3$ = H, Q, R, or D; X$_4$ = D, E, G, or Q; X$_5$ = D, Q, or F; X$_6$ = Y or Q; X$_7$ = Y, K, or D; X$_8$ = G or P; X$_9$ = L, Q, V, or T) | 50 |
| C17 (AB3/PI-61 consensus - IMGT) | GFTXSSYG (X = V or F) | 41 | ISYXGSNK (X = T or D) | 47 | GGSGYALHDDYYGLDV | 51 |
| C18 (AB3 family consensus - IMGT) | GFTXSSYG (X = V or F) | 41 | ISYX$_1$X$_2$X$_3$X$_4$K (X$_1$ = H, K, T, R, D, N, S; X$_2$ = G, D, or E; X$_3$ = S, T, F, A, L; X$_4$ = H, N or K) | 48 | GGSGYX$_1$X$_2$X$_3$X$_4$X$_5$X$_6$X$_7$X$_8$X$_9$DV (X$_1$ = A, N, E; X$_2$ = L, F, V, or Y; X$_3$ = H, Q, R, or D; X$_4$ = D, E, G, or Q; X$_5$ = D, Q, or F; X$_6$ = Y or Q; X$_7$ = Y, K, or D; X$_8$ = G or P; X$_9$ = L, Q, V, or T) | 52 |
| C19 (AB3/PI-61 consensus - Kabat + Chothia) | GFTXSSYGMH (X = V or F) | 42 | VISYXGSNKYYADSVKG (X = T or D) | 43 | SGYALHDDYYGLDV | 49 |
| C20 (AB3 family consensus - Kabat + Chothia) | GFTXSSYGMH (X = V or F) | 42 | VISYX$_1$X$_2$X$_3$X$_4$KYYADSVKG (X$_1$ = H, K, T, R, D, N, S; X$_2$ = G, D, or E; X$_3$ = S, T, F, A, L; X$_4$ = H, N or K) | 44 | SGYX$_1$X$_2$X$_3$X$_4$X$_5$X$_6$X$_7$X$_8$X$_9$DV (X$_1$ = A, N, E; X$_2$ = L, F, V, or Y; X$_3$ = H, Q, R, or D; X$_4$ = D, E, G, or Q; X$_5$ = D, Q, or F; X$_6$ = Y or Q; X$_7$ = Y, K, or D; X$_8$ = G or P; | 50 |

TABLE 1B-2-continued

AB3 Family Heavy Chain CDR Consensus sequences

| Binder | CDR-H1 | SEQ ID NO: | CDR-H2 | SEQ ID NO: | CDR-H3 | SEQ ID NO: |
|---|---|---|---|---|---|---|
| | | | | | $X_9$ = L, Q, V, or T) | |
| C21 (AB3/PI-61 consensus - Kabat + IMGT) | GFTXSSYGM H (X = V or F) | 42 | VISYXGSNKYYADSV KG (X = T or D) | 43 | GGSGYALHDDYYG LDV | 51 |
| C22 (AB3 family consensus - Kabat + IMGT) | GFTXSSYGM H (X = V or F) | 42 | VISYX$_1$X$_2$X$_3$X$_4$KYYAD SVKG ($X_1$ = H, K, T, R, D, N, S; $X_2$ = G, D, or E; $X_3$ = S, T, F, A, L; $X_4$ = H, N or K) | 44 | GGSGYX$_1$X$_2$X$_3$X$_4$X$_5$X$_6$ X$_7$X$_8$X$_9$DV ($X_1$ = A, N, E; $X_2$ = L, F, V, or Y; $X_3$ = H, Q, R, or D; $X_4$ = D, E, G, or Q; $X_5$ = D, Q, or F; $X_6$ = Y or Q; $X_7$ = Y, K, or D; $X_8$ = G or P; $X_9$ = L, Q, V, or T) | 52 |
| C23 (AB3/PI-61 consensus - Chothia + IMGT) | GFTXSSYG (X = V or F) | 41 | ISYXGSNK (X = T or D) | 47 | GGSGYALHDDYYG LDV | 51 |
| C24 (AB3 family consensus - Chothia + IMGT) | GFTXSSYG (X = V or F) | 41 | ISYX$_1$X$_2$X$_3$X$_4$K ($X_1$ = H, K, T, R, D, N, S; $X_2$ = G, D, or E; $X_3$ = S, T, F, A, L; $X_4$ = H, N or K) | 48 | GGSGYX$_1$X$_2$X$_3$X$_4$X$_5$X$_6$ X$_7$X$_8$X$_9$DV ($X_1$ = A, N, E; $X_2$ = L, F, V, or Y; $X_3$ = H, Q, R, or D; $X_4$ = D, E, G, or Q; $X_5$ = D, Q, or F; $X_6$ = Y or Q; $X_7$ = Y, K, or D; $X_8$ = G or P; $X_9$ = L, Q, V, or T) | 52 |
| C25 (AB3/PI-61 consensus - IMGT) | GFTXSSYG (X = V or F) | 41 | ISYXGSNK (X = T or D) | 47 | GGSGYALHDDYYG LDV | 51 |
| C26 (AB3 family consensus - IMGT) | GFTXSSYG (X = V or F) | 41 | ISYX$_1$X$_2$X$_3$X$_4$K ($X_1$ = H, K, T, R, D, N, S; $X_2$ = G, D, or E; $X_3$ = S, T, F, A, L; $X_4$ = H, N or K) | 48 | GGSGYX$_1$X$_2$X$_3$X$_4$X$_5$X$_6$ X$_7$X$_8$X$_9$DV ($X_1$ = A, N, E; $X_2$ = L, F, V, or Y; $X_3$ = H, Q, R, or D; $X_4$ = D, E, G, or Q; $X_5$ = D, Q, or F; $X_6$ = Y or Q; $X_7$ = Y, K, or D; $X_8$ = G or P; $X_9$ = L, Q, V, or T) | 52 |
| C27 (AB3/PI-61 consensus - Chothia + IMGT) | GFTXSSYG (X = V or F) | 41 | ISYXGSNK (X = T or D) | 47 | GGSGYALHDDYYG LDV | 51 |
| C28 (AB3 family consensus - Chothia + IMGT) | GFTXSSYG (X = V or F) | 41 | ISYX$_1$X$_2$X$_3$X$_4$K ($X_1$ = H, K, T, R, D, N, S; $X_2$ = G, D, or E; $X_3$ = S, T, F, A, L; $X_4$ = H, N or K) | 48 | GGSGYX$_1$X$_2$X$_3$X$_4$X$_5$X$_6$ X$_7$X$_8$X$_9$DV ($X_1$ = A, N, E; $X_2$ = L, F, V, or Y; $X_3$ = H, Q, R, or D; $X_4$ = D, E, G, or Q; $X_5$ = D, Q, or F; $X_6$ = Y or Q; $X_7$ = Y, K, or D; $X_8$ = G or P; $X_9$ = L, Q, V, or T) | 52 |

TABLE 1C-1

AB1/AB2 family BCMA Binders - Light Chain CDR sequences according to Kabat numbering scheme

| Binder | CDR-L1 | SEQ ID NO: | CDR-L2 | SEQ ID NO: | CDR-L3 | SEQ ID NO: |
|---|---|---|---|---|---|---|
| AB1 | RASQSISSYLN | 2 | AASSLQS | 5 | QQSYSSPLT | 53 |
| AB2 | RASQSISSYLN | 2 | AASSLQS | 5 | QQSYSTPLT | 54 |
| R1F2 | RASQSISSYLN | 2 | AASSLQS | 5 | QQSYSTPLT | 54 |
| PALF03 | RASQSISSYLN | 2 | AASSLQS | 5 | QQSYGSPPT | 55 |
| PALF04 | RASQSISSYLN | 2 | AASSLQS | 5 | QQSYDSPLT | 56 |
| PALF05 | RASQSISSYLN | 2 | AASSLQS | 5 | QQSYYSPLT | 57 |
| PALF06 | RASQSISSYLN | 2 | AASSLQS | 5 | QQSYYAPLT | 58 |
| PALF07 | RASQSISSYLN | 2 | AASSLQS | 5 | QQSYASPLT | 59 |
| PALF08 | RASQSISSYLN | 2 | AASSLQS | 5 | QQSYGSPLT | 60 |
| PALF09 | RASQSISSYLN | 2 | AASSLQS | 5 | QQSYDAPLT | 61 |
| PALF12 | RASQSISSYLN | 2 | AASSLQS | 5 | QQSYSTPLT | 54 |
| PALF13 | RASQSISSYLN | 2 | AASSLQS | 5 | QQSYSTPLT | 54 |
| PALF14 | RASQSISSYLN | 2 | AASSLQS | 5 | QQSYSTPLT | 54 |
| PALF15 | RASQSISSYLN | 2 | AASSLQS | 5 | QQSYSTPLT | 54 |
| PALF16 | RASQSISSYLN | 2 | AASSLQS | 5 | QQSYSTPLT | 54 |
| PALF17 | RASQSISSYLN | 2 | AASSLQS | 5 | QQSYSTPLT | 54 |
| PALF18 | RASQSISSYLN | 2 | AASSLQS | 5 | QQSYSTPLT | 54 |
| PALF19 | RASQSISSYLN | 2 | AASSLQS | 5 | QQSYSTPLT | 54 |
| PALF20 | RASQSISSYLN | 2 | AASSLQS | 5 | QQSYSTPLT | 54 |

TABLE 1C-2

AB1/AB2 family BCMA Binders - Heavy Chain CDR sequences according to Kabat numbering scheme

| Binder | CDR-H1 | SEQ ID NO: | CDR-H2 | SEQ ID NO: | CDR-H3 | SEQ ID NO: |
|---|---|---|---|---|---|---|
| AB1 | SYAMS | 11 | AISGSGGSTYYADSVKG | 62 | REWWYDDWYLDY | 24 |
| AB2 | SYAMS | 11 | AISESGGRAAYADSVKG | 63 | REWWYDDWYLDY | 24 |
| R1F2 | SYAMS | 11 | AISGSGGSTYYADSVKG | 62 | REWWYDDWYLDY | 24 |
| PALF03 | SYAMS | 11 | AISGSGGSTYYADSVKG | 62 | REWWYDDWYLDY | 24 |
| PALF04 | SYAMS | 11 | AISGSGGSTYYADSVKG | 62 | REWWYDDWYLDY | 24 |
| PALF05 | SYAMS | 11 | AISGSGGSTYYADSVKG | 62 | REWWYDDWYLDY | 24 |
| PALF06 | SYAMS | 11 | AISGSGGSTYYADSVKG | 62 | REWWYDDWYLDY | 24 |
| PALF07 | SYAMS | 11 | AISGSGGSTYYADSVKG | 62 | REWWYDDWYLDY | 24 |
| PALF08 | SYAMS | 11 | AISGSGGSTYYADSVKG | 62 | REWWYDDWYLDY | 24 |
| PALF09 | SYAMS | 11 | AISGSGGSTYYADSVKG | 62 | REWWYDDWYLDY | 24 |
| PALF12 | SYAMS | 11 | AISGSGGRAAYADSVKG | 64 | REWWYDDWYLDY | 24 |
| PALF13 | SYAMS | 11 | AISESGDVEAYADSVKG | 65 | REWWYDDWYLDY | 24 |
| PALF14 | SYAMS | 11 | AISEAGETTSYADSVKG | 66 | REWWYDDWYLDY | 24 |
| PALF15 | SYAMS | 11 | AISEHGHYTSYADSVKG | 67 | REWWYDDWYLDY | 24 |
| PALF16 | SYAMS | 11 | AISGSGHTAAYADSVKG | 68 | REWWYDDWYLDY | 24 |
| PALF17 | SYAMS | 11 | AISGSGRTHAYADSVKG | 69 | REWWYDDWYLDY | 24 |
| PALF18 | SYAMS | 11 | AISAEGGVRAYADSVKG | 70 | REWWYDDWYLDY | 24 |
| PALF19 | SYAMS | 11 | AISGSGGTTAYADSVKG | 71 | REWWYDDWYLDY | 24 |
| PALF20 | SYAMS | 11 | AISGSGATTAYADSVKG | 72 | REWWYDDWYLDY | 24 |

TABLE 1D-1

AB1/AB2 family BCMA Binders - Light Chain CDR sequences according to Chothia numbering scheme

| Binder | CDR-L1 | SEQ ID NO: | CDR-L2 | SEQ ID NO: | CDR-L3 | SEQ ID NO: |
|---|---|---|---|---|---|---|
| AB1 | SQSISSY | 3 | AAS | 6 | SYSSPL | 73 |
| AB2 | SQSISSY | 3 | AAS | 6 | SYSTPL | 74 |
| R1F2 | SQSISSY | 3 | AAS | 6 | SYSTPL | 74 |
| PALF03 | SQSISSY | 3 | AAS | 6 | SYGSPP | 75 |
| PALF04 | SQSISSY | 3 | AAS | 6 | SYDSPL | 76 |
| PALF05 | SQSISSY | 3 | AAS | 6 | SYYSPL | 77 |
| PALF06 | SQSISSY | 3 | AAS | 6 | SYYAPL | 78 |
| PALF07 | SQSISSY | 3 | AAS | 6 | SYASPL | 79 |
| PALF08 | SQSISSY | 3 | AAS | 6 | SYGSPL | 80 |
| PALF09 | SQSISSY | 3 | AAS | 6 | SYDAPL | 81 |
| PALF12 | SQSISSY | 3 | AAS | 6 | SYSTPL | 74 |
| PALF13 | SQSISSY | 3 | AAS | 6 | SYSTPL | 74 |
| PALF14 | SQSISSY | 3 | AAS | 6 | SYSTPL | 74 |
| PALF15 | SQSISSY | 3 | AAS | 6 | SYSTPL | 74 |
| PALF16 | SQSISSY | 3 | AAS | 6 | SYSTPL | 74 |
| PALF17 | SQSISSY | 3 | AAS | 6 | SYSTPL | 74 |
| PALF18 | SQSISSY | 3 | AAS | 6 | SYSTPL | 74 |
| PALF19 | SQSISSY | 3 | AAS | 6 | SYSTPL | 74 |
| PALF20 | SQSISSY | 3 | AAS | 6 | SYSTPL | 74 |

TABLE 1D-2

AB1/AB2 family BCMA Binders - Heavy Chain CDR sequences according to Chothia numbering scheme

| Binder | CDR-H1 | SEQ ID NO: | CDR-H2 | SEQ ID NO: | CDR-H3 | SEQ ID NO: |
|---|---|---|---|---|---|---|
| AB1 | GFTFSSY | 12 | SGSGGS | 82 | REWWYDDWYLDY | 24 |
| AB2 | GFTFSSY | 12 | SESGGR | 83 | REWWYDDWYLDY | 24 |
| R1F2 | GFTFSSY | 12 | SGSGGS | 82 | REWWYDDWYLDY | 24 |
| PALF03 | GFTFSSY | 12 | SGSGGS | 82 | REWWYDDWYLDY | 24 |
| PALF04 | GFTFSSY | 12 | SGSGGS | 82 | REWWYDDWYLDY | 24 |
| PALF05 | GFTFSSY | 12 | SGSGGS | 82 | REWWYDDWYLDY | 24 |
| PALF06 | GFTFSSY | 12 | SGSGGS | 82 | REWWYDDWYLDY | 24 |
| PALF07 | GFTFSSY | 12 | SGSGGS | 82 | REWWYDDWYLDY | 24 |
| PALF08 | GFTFSSY | 12 | SGSGGS | 82 | REWWYDDWYLDY | 24 |
| PALF09 | GFTFSSY | 12 | SGSGGS | 82 | REWWYDDWYLDY | 24 |
| PALF12 | GFTFSSY | 12 | SGSGGR | 84 | REWWYDDWYLDY | 24 |
| PALF13 | GFTFSSY | 12 | SESGDV | 85 | REWWYDDWYLDY | 24 |
| PALF14 | GFTFSSY | 12 | SESGDV | 85 | REWWYDDWYLDY | 24 |
| PALF15 | GFTFSSY | 12 | SEHGHY | 86 | REWWYDDWYLDY | 24 |
| PALF16 | GFTFSSY | 12 | SGSGHT | 87 | REWWYDDWYLDY | 24 |
| PALF17 | GFTFSSY | 12 | SGSGRT | 88 | REWWYDDWYLDY | 24 |
| PALF18 | GFTFSSY | 12 | SAEGGV | 89 | REWWYDDWYLDY | 24 |
| PALF19 | GFTFSSY | 12 | SGSGGT | 90 | REWWYDDWYLDY | 24 |
| PALF20 | GFTFSSY | 12 | SGSGAT | 91 | REWWYDDWYLDY | 24 |

TABLE 1E-1

AB1/AB2 family BCMA Binders - Light Chain CDR sequences according to IMGT numbering scheme

| Binder | CDR-L1 | SEQ ID NO: | CDR-L2 | SEQ ID NO: | CDR-L3 | SEQ ID NO: |
|---|---|---|---|---|---|---|
| AB1 | QSISSY | 4 | AAS | 6 | QQSYSSPLT | 53 |
| AB2 | QSISSY | 4 | AAS | 6 | QQSYSTPLT | 54 |
| R1F2 | QSISSY | 4 | AAS | 6 | QQSYSTPLT | 54 |
| PALF03 | QSISSY | 4 | AAS | 6 | QQSYGSPPT | 55 |
| PALF04 | QSISSY | 4 | AAS | 6 | QQSYDSPLT | 56 |
| PALF05 | QSISSY | 4 | AAS | 6 | QQSYYSPLT | 57 |
| PALF06 | QSISSY | 4 | AAS | 6 | QQSYYAPLT | 58 |
| PALF07 | QSISSY | 4 | AAS | 6 | QQSYASPLT | 59 |
| PALF08 | QSISSY | 4 | AAS | 6 | QQSYGSPLT | 60 |
| PALF09 | QSISSY | 4 | AAS | 6 | QQSYDAPLT | 61 |
| PALF12 | QSISSY | 4 | AAS | 6 | QQSYSTPLT | 54 |
| PALF13 | QSISSY | 4 | AAS | 6 | QQSYSTPLT | 54 |
| PALF14 | QSISSY | 4 | AAS | 6 | QQSYSTPLT | 54 |
| PALF15 | QSISSY | 4 | AAS | 6 | QQSYSTPLT | 54 |
| PALF16 | QSISSY | 4 | AAS | 6 | QQSYSTPLT | 54 |
| PALF17 | QSISSY | 4 | AAS | 6 | QQSYSTPLT | 54 |
| PALF18 | QSISSY | 4 | AAS | 6 | QQSYSTPLT | 54 |
| PALF19 | QSISSY | 4 | AAS | 6 | QQSYSTPLT | 54 |
| PALF20 | QSISSY | 4 | AAS | 6 | QQSYSTPLT | 54 |

TABLE 1E-2

AB1/AB2 family BCMA Binders - Heavy Chain CDR sequences according to IMGT numbering scheme

| Binder | CDR-H1 | SEQ ID NO: | CDR-H2 | SEQ ID NO: | CDR-H3 | SEQ ID NO: |
|---|---|---|---|---|---|---|
| AB1 | GFTFSSYA | 13 | ISGSGGST | 92 | ARREWWYDDWYLDY | 25 |
| AB2 | GFTFSSYA | 13 | ISESGGRA | 93 | ARREWWYDDWYLDY | 25 |
| R1F2 | GFTFSSYA | 13 | ISGSGGST | 92 | ARREWWYDDWYLDY | 25 |
| PALF03 | GFTFSSYA | 13 | ISGSGGST | 92 | ARREWWYDDWYLDY | 25 |
| PALF04 | GFTFSSYA | 13 | ISGSGGST | 92 | ARREWWYDDWYLDY | 25 |
| PALF05 | GFTFSSYA | 13 | ISGSGGST | 92 | ARREWWYDDWYLDY | 25 |
| PALF06 | GFTFSSYA | 13 | ISGSGGST | 92 | ARREWWYDDWYLDY | 25 |
| PALF07 | GFTFSSYA | 13 | ISGSGGST | 92 | ARREWWYDDWYLDY | 25 |
| PALF08 | GFTFSSYA | 13 | ISGSGGST | 92 | ARREWWYDDWYLDY | 25 |
| PALF09 | GFTFSSYA | 13 | ISGSGGST | 92 | ARREWWYDDWYLDY | 25 |
| PALF12 | GFTFSSYA | 13 | ISGSGGRA | 94 | ARREWWYDDWYLDY | 25 |
| PALF13 | GFTFSSYA | 13 | ISESGDVE | 95 | ARREWWYDDWYLDY | 25 |
| PALF14 | GFTFSSYA | 13 | ISESGDVE | 95 | ARREWWYDDWYLDY | 25 |
| PALF15 | GFTFSSYA | 13 | ISEHGHYT | 96 | ARREWWYDDWYLDY | 25 |
| PALF16 | GFTFSSYA | 13 | ISGSGHTA | 97 | ARREWWYDDWYLDY | 25 |
| PALF17 | GFTFSSYA | 13 | ISGSGRTH | 98 | ARREWWYDDWYLDY | 25 |
| PALF18 | GFTFSSYA | 13 | ISAEGGVR | 99 | ARREWWYDDWYLDY | 25 |
| PALF19 | GFTFSSYA | 13 | ISGSGGTT | 100 | ARREWWYDDWYLDY | 25 |
| PALF20 | GFTFSSYA | 13 | ISGSGATT | 101 | ARREWWYDDWYLDY | 25 |

TABLE 1F-1

AB1/AB2 family BCMA Binders - Light Chain CDR sequences according to combination of Kabat and Chothia numbering schemes

| Binder | CDR-L1 | SEQ ID NO: | CDR-L2 | SEQ ID NO: | CDR-L3 | SEQ ID NO: |
|---|---|---|---|---|---|---|
| AB1 | RASQSISSYLN | 2 | AASSLQS | 5 | QQSYSSPLT | 53 |
| AB2 | RASQSISSYLN | 2 | AASSLQS | 5 | QQSYSTPLT | 54 |
| R1F2 | RASQSISSYLN | 2 | AASSLQS | 5 | QQSYSTPLT | 54 |
| PALF03 | RASQSISSYLN | 2 | AASSLQS | 5 | QQSYGSPPT | 55 |
| PALF04 | RASQSISSYLN | 2 | AASSLQS | 5 | QQSYDSPLT | 56 |
| PALF05 | RASQSISSYLN | 2 | AASSLQS | 5 | QQSYYSPLT | 57 |
| PALF06 | RASQSISSYLN | 2 | AASSLQS | 5 | QQSYYAPLT | 58 |
| PALF07 | RASQSISSYLN | 2 | AASSLQS | 5 | QQSYASPLT | 59 |
| PALF08 | RASQSISSYLN | 2 | AASSLQS | 5 | QQSYGSPLT | 60 |
| PALF09 | RASQSISSYLN | 2 | AASSLQS | 5 | QQSYDAPLT | 61 |
| PALF12 | RASQSISSYLN | 2 | AASSLQS | 5 | QQSYSTPLT | 54 |
| PALF13 | RASQSISSYLN | 2 | AASSLQS | 5 | QQSYSTPLT | 54 |
| PALF14 | RASQSISSYLN | 2 | AASSLQS | 5 | QQSYSTPLT | 54 |
| PALF15 | RASQSISSYLN | 2 | AASSLQS | 5 | QQSYSTPLT | 54 |
| PALF16 | RASQSISSYLN | 2 | AASSLQS | 5 | QQSYSTPLT | 54 |
| PALF17 | RASQSISSYLN | 2 | AASSLQS | 5 | QQSYSTPLT | 54 |
| PALF18 | RASQSISSYLN | 2 | AASSLQS | 5 | QQSYSTPLT | 54 |
| PALF19 | RASQSISSYLN | 2 | AASSLQS | 5 | QQSYSTPLT | 54 |
| PALF20 | RASQSISSYLN | 2 | AASSLQS | 5 | QQSYSTPLT | 54 |

TABLE 1F-2

AB1/AB2 family BCMA Binders - Heavy Chain CDR sequences according to combination of Kabat and Chothia numbering schemes

| Binder | CDR-H1 | SEQ ID NO: | CDR-H2 | SEQ ID NO: | CDR-H3 | SEQ ID NO: |
|---|---|---|---|---|---|---|
| AB1 | GFTFSSYAMS | 14 | AISGSGGSTYYADSVKG | 62 | REWWYDDWYLDY | 24 |
| AB2 | GFTFSSYAMS | 14 | AISESGGRAAYADSVKG | 63 | REWWYDDWYLDY | 24 |

TABLE 1F-2-continued

AB1/AB2 family BCMA Binders - Heavy Chain CDR sequences according to combination of Kabat and Chothia numbering schemes

| Binder | CDR-H1 | SEQ ID NO: | CDR-H2 | SEQ ID NO: | CDR-H3 | SEQ ID NO: |
|---|---|---|---|---|---|---|
| R1F2 | GFTFSSYAMS | 14 | AISGSGGSTYYADSVKG | 62 | REWWYDDWYLDY | 24 |
| PALF03 | GFTFSSYAMS | 14 | AISGSGGSTYYADSVKG | 62 | REWWYDDWYLDY | 24 |
| PALF04 | GFTFSSYAMS | 14 | AISGSGGSTYYADSVKG | 62 | REWWYDDWYLDY | 24 |
| PALF05 | GFTFSSYAMS | 14 | AISGSGGSTYYADSVKG | 62 | REWWYDDWYLDY | 24 |
| PALF06 | GFTFSSYAMS | 14 | AISGSGGSTYYADSVKG | 62 | REWWYDDWYLDY | 24 |
| PALF07 | GFTFSSYAMS | 14 | AISGSGGSTYYADSVKG | 62 | REWWYDDWYLDY | 24 |
| PALF08 | GFTFSSYAMS | 14 | AISGSGGSTYYADSVKG | 62 | REWWYDDWYLDY | 24 |
| PALF09 | GFTFSSYAMS | 14 | AISGSGGSTYYADSVKG | 62 | REWWYDDWYLDY | 24 |
| PALF12 | GFTFSSYAMS | 14 | AISGSGGRAAYADSVKG | 64 | REWWYDDWYLDY | 24 |
| PALF13 | GFTFSSYAMS | 14 | AISESGDVEAYADSVKG | 65 | REWWYDDWYLDY | 24 |
| PALF14 | GFTFSSYAMS | 14 | AISEAGETTSYADSVKG | 66 | REWWYDDWYLDY | 24 |
| PALF15 | GFTFSSYAMS | 14 | AISEHGHYTSYADSVKG | 67 | REWWYDDWYLDY | 24 |
| PALF16 | GFTFSSYAMS | 14 | AISGSGHTAAYADSVKG | 68 | REWWYDDWYLDY | 24 |
| PALF17 | GFTFSSYAMS | 14 | AISGSGRTHAYADSVKG | 69 | REWWYDDWYLDY | 24 |
| PALF18 | GFTFSSYAMS | 14 | AISAEGGVRAYADSVKG | 70 | REWWYDDWYLDY | 24 |
| PALF19 | GFTFSSYAMS | 14 | AISGSGGTTAYADSVKG | 71 | REWWYDDWYLDY | 24 |
| PALF20 | GFTFSSYAMS | 14 | AISGSGATTAYADSVKG | 72 | REWWYDDWYLDY | 24 |

TABLE 1G-1

AB1/AB2 family BCMA Binders - Light Chain CDR sequences according to combination of Kabat and IMGT numbering schemes

| Binder | CDR-L1 | SEQ ID NO: | CDR-L2 | SEQ ID NO: | CDR-L3 | SEQ ID NO: |
|---|---|---|---|---|---|---|
| AB1 | RASQSISSYLN | 2 | AASSLQS | 5 | QQSYSSPLT | 53 |
| AB2 | RASQSISSYLN | 2 | AASSLQS | 5 | QQSYSTPLT | 54 |
| R1F2 | RASQSISSYLN | 2 | AASSLQS | 5 | QQSYSTPLT | 54 |
| PALF03 | RASQSISSYLN | 2 | AASSLQS | 5 | QQSYGSPPT | 55 |
| PALF04 | RASQSISSYLN | 2 | AASSLQS | 5 | QQSYDSPLT | 56 |
| PALF05 | RASQSISSYLN | 2 | AASSLQS | 5 | QQSYYSPLT | 57 |
| PALF06 | RASQSISSYLN | 2 | AASSLQS | 5 | QQSYYAPLT | 58 |
| PALF07 | RASQSISSYLN | 2 | AASSLQS | 5 | QQSYASPLT | 59 |
| PALF08 | RASQSISSYLN | 2 | AASSLQS | 5 | QQSYGSPLT | 60 |
| PALF09 | RASQSISSYLN | 2 | AASSLQS | 5 | QQSYDAPLT | 61 |

TABLE 1G-1-continued

AB1/AB2 family BCMA Binders - Light Chain CDR sequences according to combination of Kabat and IMGT numbering schemes

| Binder | CDR-L1 | SEQ ID NO: | CDR-L2: | SEQ ID NO: | CDR-L3 | SEQ ID NO: |
|---|---|---|---|---|---|---|
| PALF12 | RASQSISSYLN | 2 | AASSLQS | 5 | QQSYSTPLT | 54 |
| PALF13 | RASQSISSYLN | 2 | AASSLQS | 5 | QQSYSTPLT | 54 |
| PALF14 | RASQSISSYLN | 2 | AASSLQS | 5 | QQSYSTPLT | 54 |
| PALF15 | RASQSISSYLN | 2 | AASSLQS | 5 | QQSYSTPLT | 54 |
| PALF16 | RASQSISSYLN | 2 | AASSLQS | 5 | QQSYSTPLT | 54 |
| PALF17 | RASQSISSYLN | 2 | AASSLQS | 5 | QQSYSTPLT | 54 |
| PALF18 | RASQSISSYLN | 2 | AASSLQS | 5 | QQSYSTPLT | 54 |
| PALF19 | RASQSISSYLN | 2 | AASSLQS | 5 | QQSYSTPLT | 54 |
| PALF20 | RASQSISSYLN | 2 | AASSLQS | 5 | QQSYSTPLT | 54 |

TABLE 1G-2

AB1/AB2 family BCMA Binders - Heavy Chain CDR sequences according to combination of Kabat and IMGT numbering schemes

| Binder | CDR-H1 | SEQ ID NO: | CDR-H2: | SEQ ID NO: | CDR-H3 | SEQ ID NO: |
|---|---|---|---|---|---|---|
| AB1 | GFTFSSYAMS | 14 | AISGSGGSTYYADSVKG | 62 | ARREWWYDDWYLDY | 25 |
| AB2 | GFTFSSYAMS | 14 | AISESGGRAAYADSVKG | 63 | ARREWWYDDWYLDY | 25 |
| R1F2 | GFTFSSYAMS | 14 | AISGSGGSTYYADSVKG | 62 | ARREWWYDDWYLDY | 25 |
| PALF03 | GFTFSSYAMS | 14 | AISGSGGSTYYADSVKG | 62 | ARREWWYDDWYLDY | 25 |
| PALF04 | GFTFSSYAMS | 14 | AISGSGGSTYYADSVKG | 62 | ARREWWYDDWYLDY | 25 |
| PALF05 | GFTFSSYAMS | 14 | AISGSGGSTYYADSVKG | 62 | ARREWWYDDWYLDY | 25 |
| PALF06 | GFTFSSYAMS | 14 | AISGSGGSTYYADSVKG | 62 | ARREWWYDDWYLDY | 25 |
| PALF07 | GFTFSSYAMS | 14 | AISGSGGSTYYADSVKG | 62 | ARREWWYDDWYLDY | 25 |
| PALF08 | GFTFSSYAMS | 14 | AISGSGGSTYYADSVKG | 62 | ARREWWYDDWYLDY | 25 |
| PALF09 | GFTFSSYAMS | 14 | AISGSGGSTYYADSVKG | 62 | ARREWWYDDWYLDY | 25 |
| PALF12 | GFTFSSYAMS | 14 | AISGSGGRAAYADSVKG | 64 | ARREWWYDDWYLDY | 25 |
| PALF13 | GFTFSSYAMS | 14 | AISESGDVEAYADSVKG | 65 | ARREWWYDDWYLDY | 25 |
| PALF14 | GFTFSSYAMS | 14 | AISEAGETTSYADSVKG | 66 | ARREWWYDDWYLDY | 25 |
| PALF15 | GFTFSSYAMS | 14 | AISEHGHYTSYADSVKG | 67 | ARREWWYDDWYLDY | 25 |
| PALF16 | GFTFSSYAMS | 14 | AISGSGHTAAYADSVKG | 68 | ARREWWYDDWYLDY | 25 |
| PALF17 | GFTFSSYAMS | 14 | AISGSGRTHAYADSVKG | 69 | ARREWWYDDWYLDY | 25 |
| PALF18 | GFTFSSYAMS | 14 | AISAEGGVRAYADSVKG | 70 | ARREWWYDDWYLDY | 25 |

TABLE 1G-2-continued

AB1/AB2 family BCMA Binders - Heavy Chain CDR sequences according to combination of Kabat and IMGT numbering schemes

| Binder | CDR-H1 | SEQ ID NO: | CDR-H2: | SEQ ID NO: | CDR-H3 | SEQ ID NO: |
|---|---|---|---|---|---|---|
| PALF19 | GFTFSSYAMS | 14 | AISGSGGTTAYADSVKG | 71 | ARREWWYDDWYLDY | 25 |
| PALF20 | GFTFSSYAMS | 14 | AISGSGATTAYADSVKG | 72 | ARREWWYDDWYLDY | 25 |

TABLE 1H-1

AB1/AB2 family BCMA Binders - Light Chain CDR sequences according to combination of Chothia and IMGT numbering schemes

| Binder | CDR-L1 | SEQ ID NO: | CDR-L2: | SEQ ID NO: | CDR-L3 | SEQ ID NO: |
|---|---|---|---|---|---|---|
| AB1 | SQSISSY | 3 | AAS | 6 | QQSYSSPLT | 53 |
| AB2 | SQSISSY | 3 | AAS | 6 | QQSYSTPLT | 54 |
| R1F2 | SQSISSY | 3 | AAS | 6 | QQSYSTPLT | 54 |
| PALF03 | SQSISSY | 3 | AAS | 6 | QQSYGSPPT | 55 |
| PALF04 | SQSISSY | 3 | AAS | 6 | QQSYDSPLT | 56 |
| PALF05 | SQSISSY | 3 | AAS | 6 | QQSYYSPLT | 57 |
| PALF06 | SQSISSY | 3 | AAS | 6 | QQSYYAPLT | 58 |
| PALF07 | SQSISSY | 3 | AAS | 6 | QQSYASPLT | 59 |
| PALF08 | SQSISSY | 3 | AAS | 6 | QQSYGSPLT | 60 |
| PALF09 | SQSISSY | 3 | AAS | 6 | QQSYDAPLT | 61 |
| PALF12 | SQSISSY | 3 | AAS | 6 | QQSYSTPLT | 54 |
| PALF13 | SQSISSY | 3 | AAS | 6 | QQSYSTPLT | 54 |
| PALF14 | SQSISSY | 3 | AAS | 6 | QQSYSTPLT | 54 |
| PALF15 | SQSISSY | 3 | AAS | 6 | QQSYSTPLT | 54 |
| PALF16 | SQSISSY | 3 | AAS | 6 | QQSYSTPLT | 54 |
| PALF17 | SQSISSY | 3 | AAS | 6 | QQSYSTPLT | 54 |
| PALF18 | SQSISSY | 3 | AAS | 6 | QQSYSTPLT | 54 |
| PALF19 | SQSISSY | 3 | AAS | 6 | QQSYSTPLT | 54 |
| PALF20 | SQSISSY | 3 | AAS | 6 | QQSYSTPLT | 54 |

TABLE 1H-2

AB1/AB2 family BCMA Binders - Heavy Chain CDR sequences according to combination of Chothia and IMGT numbering schemes

| Binder | CDR-H1 | SEQ ID NO: | CDR-H2 | SEQ ID NO: | CDR-H3 | SEQ ID NO: |
|---|---|---|---|---|---|---|
| AB1 | GFTFSSYA | 13 | ISGSGGST | 92 | ARREWWYDDWYLDY | 25 |
| AB2 | GFTFSSYA | 13 | ISESGGRA | 93 | ARREWWYDDWYLDY | 25 |
| R1F2 | GFTFSSYA | 13 | ISGSGGST | 92 | ARREWWYDDWYLDY | 25 |
| PALF03 | GFTFSSYA | 13 | ISGSGGST | 92 | ARREWWYDDWYLDY | 25 |
| PALF04 | GFTFSSYA | 13 | ISGSGGST | 92 | ARREWWYDDWYLDY | 25 |
| PALF05 | GFTFSSYA | 13 | ISGSGGST | 92 | ARREWWYDDWYLDY | 25 |
| PALF06 | GFTFSSYA | 13 | ISGSGGST | 92 | ARREWWYDDWYLDY | 25 |
| PALF07 | GFTFSSYA | 13 | ISGSGGST | 92 | ARREWWYDDWYLDY | 25 |
| PALF08 | GFTFSSYA | 13 | ISGSGGST | 92 | ARREWWYDDWYLDY | 25 |
| PALF09 | GFTFSSYA | 13 | ISGSGGST | 92 | ARREWWYDDWYLDY | 25 |
| PALF12 | GFTFSSYA | 13 | ISGSGGRA | 94 | ARREWWYDDWYLDY | 25 |
| PALF13 | GFTFSSYA | 13 | ISESGDVE | 95 | ARREWWYDDWYLDY | 25 |
| PALF14 | GFTFSSYA | 13 | ISESGDVE | 95 | ARREWWYDDWYLDY | 25 |
| PALF15 | GFTFSSYA | 13 | ISEHGHYT | 96 | ARREWWYDDWYLDY | 25 |
| PALF16 | GFTFSSYA | 13 | ISGSGHTA | 97 | ARREWWYDDWYLDY | 25 |
| PALF17 | GFTFSSYA | 13 | ISGSGRTH | 98 | ARREWWYDDWYLDY | 25 |
| PALF18 | GFTFSSYA | 13 | ISAEGGVR | 99 | ARREWWYDDWYLDY | 25 |
| PALF19 | GFTFSSYA | 13 | ISGSGGTT | 100 | ARREWWYDDWYLDY | 25 |

TABLE 1H-2-continued

AB1/AB2 family BCMA Binders - Heavy Chain CDR sequences according to combination of Chothia and IMGT numbering schemes

| Binder | CDR-H1 | SEQ ID NO: | CDR-H2 | SEQ ID NO: | CDR-H3 | SEQ ID NO: |
|---|---|---|---|---|---|---|
| PALF20 | GFTFSSYA | 13 | ISGSGATT | 101 | ARREWWYDDWYLDY | 25 |

TABLE 1I-1

AB3 family BCMA Binders - Light Chain CDR sequences according to Kabat numbering scheme

| Binder | CDR-L1 | SEQ ID NO: | CDR-L2 | SEQ ID NO: | CDR-L3 | SEQ ID NO: |
|---|---|---|---|---|---|---|
| AB3 | TGTSSDVGGYNYVS | 26 | DVSNRLR | 102 | SSYTSSSALYV | 110 |
| PI-61 | TGTSSDVGGYNYVS | 26 | DVSNRPS | 103 | SSYTSSSTLYV | 111 |
| H2/L2-22 | TGTSSDVGGYNYVS | 26 | EVSNRLS | 104 | SSYTSSSTLYV | 111 |
| H2/L2-88 | TGTSSDVGGYNYVS | 26 | EVSNRLR | 105 | SSYTSSSALYV | 110 |
| H2/L2-36 | TGTSSDVGGYNYVS | 26 | EVSNRLR | 105 | SSYTSSSTLYV | 111 |
| H2/L2-34 | TGTSSDVGGYNYVS | 26 | DVSNRPW | 106 | SSYTSSSALYV | 110 |
| H2/L2-68 | TGTSSDVGGYNYVS | 26 | DVSNRLS | 107 | SSYTSSSTLYV | 111 |
| H2/L2-18 | TGTSSDVGGYNYVS | 26 | DVSNRPW | 106 | SSYTSSSTLYV | 111 |
| H2/L2-47 | TGTSSDVGGYNYVS | 26 | DVSNRPW | 106 | SSYTSSSTLYV | 111 |
| H2/L2-20 | TGTSSDVGGYNYVS | 26 | DVSNRLR | 102 | SSYTSSSALYV | 110 |
| H2/L2-80 | TGTSSDVGGYNYVS | 26 | DVSNRAW | 108 | SSYTSSSALYV | 110 |
| H2/L2-83 | TGTSSDVGGYNYVS | 26 | EVSNRLR | 105 | SSYTSSSTLYV | 111 |
| H3-1 | TGTSSDVGGYNYVS | 26 | EVSNRLR | 105 | SSYTSSSTLYV | 111 |
| H3-2 | TGTSSDVGGYNYVS | 26 | EVSNRLR | 105 | SSYTSSSTLYV | 111 |
| H3-3 | TGTSSDVGGYNYVS | 26 | EVSNRLR | 105 | SSYTSSSTLYV | 111 |
| H3-4 | TGTSSDVGGYNYVS | 26 | EVSNRLR | 105 | SSYTSSSALYV | 110 |
| H3-5 | TGTSSDVGGYNYVS | 26 | EVSNRLS | 104 | SSYTSSSTLYV | 111 |
| H3-6 | TGTSSDVGGYNYVS | 26 | EVSNRLR | 105 | SSYTSSSALYV | 110 |
| H3-7 | TGTSSDVGGYNYVS | 26 | EVSNRLR | 105 | SSYTSSSTLYV | 111 |
| H3-8 | TGTSSDVGGYNYVS | 26 | EVSNRLR | 105 | SSYTSSSTLYV | 111 |
| H3-9 | TGTSSDVGGYNYVS | 26 | EVSNRLR | 105 | SSYTSSSTLYV | 111 |
| H3-10 | TGTSSDVGGYNYVS | 26 | EVSNRLR | 105 | SSYTSSSTLYV | 111 |
| H3-11 | TGTSSDVGGYNYVS | 26 | EVSNRLR | 105 | SSYTSSSTLYV | 111 |
| H3-12 | TGTSSDVGGYNYVS | 26 | EVSNRLR | 105 | SSYTSSSTLYV | 111 |
| H3-13 | TGTSSDVGGYNYVS | 26 | EVSNRLR | 105 | SSYTSSSTLYV | 111 |
| H3-14 | TGTSSDVGGYNYVS | 26 | EVSNRLS | 104 | SSYTSSSALYV | 110 |
| H3-15 | TGTSSDVGGYNYVS | 26 | EVSNRLG | 109 | SSYTSSSALYV | 110 |

TABLE 1I-2

AB3 family BCMA Binders - Heavy Chain CDR sequences according to Kabat numbering scheme

| Binder | CDR-H1 | SEQ ID NO: | CDR-H2 | SEQ ID NO: | CDR-H3 | SEQ ID NO: |
|---|---|---|---|---|---|---|
| AB3 | SYGMH | 39 | VISYTGSNKYYADSVKG | 112 | SGYALHDDYYGLDV | 49 |
| PI-61 | SYGMH | 39 | VISYDGSNKYYADSVKG | 113 | SGYALHDDYYGLDV | 49 |
| H2/L2-22 | SYGMH | 39 | VISYHGSNKYYADSVKG | 114 | SGYALHDDYYGLDV | 49 |
| H2/L2-88 | SYGMH | 39 | VISYKGSNKYYADSVKG | 115 | SGYALHDDYYGLDV | 49 |
| H2/L2-36 | SYGMH | 39 | VISYKGSNKYYADSVKG | 115 | SGYALHDDYYGLDV | 49 |
| H2/L2-34 | SYGMH | 39 | VISYTGTKKYYADSVKG | 116 | SGYALHDDYYGLDV | 49 |
| H2/L2-68 | SYGMH | 39 | VISYRGFNKYYADSVKG | 117 | SGYALHDDYYGQD | 126 |
| H2/L2-18 | SYGMH | 39 | VISYKGSHKYYADSVKG | 118 | SGYALHDDYYGLDV | 49 |
| H2/L2-47 | SYGMH | 39 | VISYKGSNKYYADSVKG | 115 | SGYALHDDYYGLDV | 49 |
| H2/L2-20 | SYGMH | 39 | VISYTGSNKYYADSVKG | 112 | SGYALHDDYYGLDV | 49 |
| H2/L2-80 | SYGMH | 39 | VISYTGSNKYYADSVKG | 112 | SGYALHDDYYGLDV | 49 |
| H2/L2-83 | SYGMH | 39 | VISYKGSNKYYADSVKG | 115 | SGYALHDDYYGLDV | 49 |

TABLE 1I-2-continued

AB3 family BCMA Binders - Heavy Chain CDR sequences according to Kabat numbering scheme

| Binder | CDR-H1 | SEQ ID NO: | CDR-H2 | SEQ ID NO: | CDR-H3 | SEQ ID NO: |
|---|---|---|---|---|---|---|
| H3-1 | SYGMH | 39 | VISYDDAHKYYADSVKG | 119 | SGYALHDQYKPVDV | 127 |
| H3-2 | SYGMH | 39 | VISYNDLNKYYADSVKG | 120 | SGYALHDFQDPTDV | 128 |
| H3-3 | SYGMH | 39 | VISYSGSNKYYADSVKG | 121 | SGYALHDQYKPVDV | 127 |
| H3-4 | SYGMH | 39 | VISYDDAHKYYADSVKG | 119 | SGYALHDQYKPVDV | 127 |
| H3-5 | SYGMH | 39 | VISYTGANKYYADSVKG | 122 | SGYNLHDDYYGLDV | 129 |
| H3-6 | SYGMH | 39 | VISYDDAHKYYADSVKG | 119 | SGYALHDQYKPVDV | 127 |
| H3-7 | SYGMH | 39 | VISYTGSNKYYADSVKG | 112 | SGYEFHEDYYGLDV | 130 |
| H3-8 | SYGMH | 39 | VISYDDAHKYYADSVKG | 119 | SGYALHDQYKPVDV | 127 |
| H3-9 | SYGMH | 39 | VISYDDAHKYYADSVKG | 119 | SGYALHDQYKPVDV | 127 |
| H3-10 | SYGMH | 39 | VISYNDLNKYYADSVKG | 120 | SGYEFQGDYYGLDV | 131 |
| H3-11 | SYGMH | 39 | VISYNDANKYYADSVKG | 123 | SGYELRDDYYGLDV | 132 |
| H3-12 | SYGMH | 39 | VISYDESNKYYADSVKG | 124 | SGYEVDQDYYGLDV | 133 |
| H3-13 | SYGMH | 39 | VISYDDAHKYYADSVKG | 119 | SGYALHDQYKPVDV | 127 |
| H3-14 | SYGMH | 39 | VISYDDAHKYYADSVKG | 119 | SGYALHDQYKPVDV | 127 |
| H3-15 | SYGMH | 39 | VISYDDANKYYADSVKG | 125 | SGYAYDGDYYGLDV | 134 |

TABLE 1J-1

AB3 family BCMA Binders - Light Chain CDR sequences according to Chothia numbering scheme

| Binder | CDR-L1 | SEQ ID NO: | CDR-L2 | SEQ ID NO: | CDR-L3 | SEQ ID NO: |
|---|---|---|---|---|---|---|
| AB3 | TSSDVGGYNY | 27 | DVS | | YTSSSALY | 136 |
| PI-61 | TSSDVGGYNY | 27 | DVS | | YTSSSTLY | 137 |
| H2/L2-22 | TSSDVGGYNY | 27 | EVS | | YTSSSTLY | 137 |
| H2/L2-88 | TSSDVGGYNY | 27 | EVS | | YTSSSALY | 136 |
| H2/L2-36 | TSSDVGGYNY | 27 | EVS | | YTSSSTLY | 137 |
| H2/L2-34 | TSSDVGGYNY | 27 | EVS | | YTSSSALY | 136 |
| H2/L2-68 | TSSDVGGYNY | 27 | DVS | | YTSSSTLY | 137 |
| H2/L2-18 | TSSDVGGYNY | 27 | DVS | | YTSSSTLY | 137 |
| H2/L2-47 | TSSDVGGYNY | 27 | DVS | | YTSSSTLY | 137 |
| H2/L2-20 | TSSDVGGYNY | 27 | DVS | | YTSSSALY | 136 |
| H2/L2-80 | TSSDVGGYNY | 27 | DVS | | YTSSSALY | 136 |
| H2/L2-83 | TSSDVGGYNY | 27 | EVS | | YTSSSTLY | 137 |
| H3-1 | TSSDVGGYNY | 27 | EVS | | YTSSSTLY | 137 |
| H3-2 | TSSDVGGYNY | 27 | EVS | | YTSSSTLY | 137 |
| H3-3 | TSSDVGGYNY | 27 | EVS | | YTSSSTLY | 137 |
| H3-4 | TSSDVGGYNY | 27 | EVS | | YTSSSALY | 136 |
| H3-5 | TSSDVGGYNY | 27 | EVS | | YTSSSTLY | 137 |
| H3-6 | TSSDVGGYNY | 27 | EVS | | YTSSSALY | 136 |
| H3-7 | TSSDVGGYNY | 27 | EVS | | YTSSSTLY | 137 |
| H3-8 | TSSDVGGYNY | 27 | EVS | | YTSSSTLY | 137 |
| H3-9 | TSSDVGGYNY | 27 | EVS | | YTSSSTLY | 137 |
| H3-10 | TSSDVGGYNY | 27 | EVS | | YTSSSTLY | 137 |
| H3-11 | TSSDVGGYNY | 27 | EVS | | YTSSSTLY | 137 |
| H3-12 | TSSDVGGYNY | 27 | EVS | | YTSSSTLY | 137 |
| H3-13 | TSSDVGGYNY | 27 | EVS | | YTSSSTLY | 137 |
| H3-14 | TSSDVGGYNY | 27 | EVS | | YTSSSALY | 136 |
| H3-15 | TSSDVGGYNY | 27 | EVS | | YTSSSALY | 136 |

TABLE 1J-2

AB3 family BCMA Binders - Heavy Chain CDR sequences according to Chothia numbering scheme

| Binder | CDR-H1 | SEQ ID NO: | CDR-H2 | SEQ ID NO: | CDR-H3 | SEQ ID NO: |
|---|---|---|---|---|---|---|
| AB3 | GFTVSSY | 138 | SYTGSN | 140 | SGYALHDDYYGLDV | 49 |
| PI-61 | GFTFSSY | 12 | SYDGSN | 141 | SGYALHDDYYGLDV | 49 |
| H2/L2-22 | GFTFSSY | 12 | SYHGSN | 142 | SGYALHDDYYGLDV | 49 |
| H2/L2-88 | GFTFSSY | 12 | SYKGSN | 143 | SGYALHDDYYGLDV | 49 |
| H2/L2-36 | GFTFSSY | 12 | SYKGSN | 143 | SGYALHDDYYGLDV | 49 |
| H2/L2-34 | GFTFSSY | 12 | SYTGTK | 144 | SGYALHDDYYGLDV | 49 |
| H2/L2-68 | GFTFSSY | 12 | SYRGFN | 145 | SGYALHDDYYGQDV | 126 |

TABLE 1J-2-continued

AB3 family BCMA Binders - Heavy Chain CDR sequences according to Chothia numbering scheme

| Binder | CDR-H1 | SEQ ID NO: | CDR-H2 | SEQ ID NO: | CDR-H3 | SEQ ID NO: |
|---|---|---|---|---|---|---|
| H2/L2-18 | GFTFSSY | 12 | SYKGSH | 146 | SGYALHDDYYGLDV | 49 |
| H2/L2-47 | GFTFSSY | 12 | SYKGSN | 143 | SGYALHDDYYGLDV | 49 |
| H2/L2-20 | GFTVSSY | 138 | SYTGSN | 140 | SGYALHDDYYGLDV | 49 |
| H2/L2-80 | GFTFSSY | 12 | SYTGSN | 140 | SGYALHDDYYGLDV | 49 |
| H2/L2-83 | GFTFSSY | 12 | SYKGSN | 143 | SGYALHDDYYGLDV | 49 |
| H3-1 | GFTFSSY | 12 | SYDDAH | 147 | SGYALHDQYKPVDV | 127 |
| H3-2 | GFTFSSY | 12 | SYNDLN | 148 | SGYALHDFQDPTDV | 128 |
| H3-3 | GFTVSSY | 138 | SYSGSN | 149 | SGYALHDQYKPVDV | 127 |
| H3-4 | GFTFSSY | 12 | SYDDAH | 147 | SGYALHDQYKPVDV | 127 |
| H3-5 | GFTFSSY | 12 | SYTGAN | 150 | SGYNLHDDYYGLDV | 129 |
| H3-6 | GFTFSSY | 12 | SYDDAH | 147 | SGYALHDQYKPVDV | 127 |
| H3-7 | GFTLSSY | 139 | SYTGSN | 140 | SGYEFHEDYYGLDV | 130 |
| H3-8 | GFTFSSY | 12 | SYDDAH | 147 | SGYALHDQYKPVDV | 127 |
| H3-9 | GFTFSSY | 12 | SYDDAH | 147 | SGYALHDQYKPVDV | 127 |
| H3-10 | GFTFSSY | 12 | SYNDLN | 148 | SGYEFQGDYYGLDV | 131 |
| H3-11 | GFTFSSY | 12 | SYNDAN | 151 | SGYELRDDYYGLDV | 132 |
| H3-12 | GFTFSSY | 12 | SYDESN | 152 | SGYEVQDYYGLDV | 133 |
| H3-13 | GFTFSSY | 12 | SYDDAH | 147 | SGYALHDQYKPVDV | 127 |
| H3-14 | GFTFSSY | 12 | SYDDAH | 147 | SGYALHDQYKPVDV | 127 |
| H3-15 | GFTVSSY | 138 | SYDDAN | 153 | SGYAYDGDYYGLDV | 134 |

TABLE 1K-1(a)

AB3 family BCMA Binders - CDR-L1 and CDR-L3 sequences according to IMGT numbering scheme and CDR-L2 expanded sequences

| Binder | CDR-L1 | SEQ ID NO: | CDR-L2 | SEQ ID NO: | CDR-L3 | SEQ ID NO: |
|---|---|---|---|---|---|---|
| AB3 | SSDVGGYNY | 28 | DVSNRLRGVS | 154 | SSYTSSSALYV | 110 |
| PI-61 | SSDVGGYNY | 28 | DVSNRPSGVS | 155 | SSYTSSSTLYV | 111 |
| H2/L2-22 | SSDVGGYNY | 28 | EVSNRLSGVS | 156 | SSYTSSSTLYV | 111 |
| H2/L2-88 | SSDVGGYNY | 28 | EVSNRLRGVS | 157 | SSYTSSSALYV | 110 |
| H2/L2-36 | SSDVGGYNY | 28 | EVSNRLRGVS | 157 | SSYTSSSTLYV | 111 |
| H2/L2-34 | SSDVGGYNY | 28 | DVSNRPWGVS | 158 | SSYTSSSALYV | 110 |
| H2/L2-68 | SSDVGGYNY | 28 | DVSNRLSGVS | 159 | SSYTSSSTLYV | 111 |
| H2/L2-18 | SSDVGGYNY | 28 | DVSNRPWGVS | 158 | SSYTSSSTLYV | 111 |
| H2/L2-47 | SSDVGGYNY | 28 | DVSNRPWGVS | 158 | SSYTSSSTLYV | 111 |
| H2/L2-20 | SSDVGGYNY | 28 | DVSNRLRGVS | 154 | SSYTSSSALYV | 110 |
| H2/L2-80 | SSDVGGYNY | 28 | DVSNRAWGVS | 160 | SSYTSSSALYV | 110 |
| H2/L2-83 | SSDVGGYNY | 28 | EVSNRLRGVS | 157 | SSYTSSSTLYV | 111 |
| H3-1 | SSDVGGYNY | 28 | EVSNRLRGVS | 157 | SSYTSSSTLYV | 111 |
| H3-2 | SSDVGGYNY | 28 | EVSNRLRGVS | 157 | SSYTSSSTLYV | 111 |
| H3-3 | SSDVGGYNY | 28 | EVSNRLRGVS | 157 | SSYTSSSTLYV | 111 |
| H3-4 | SSDVGGYNY | 28 | EVSNRLRGVS | 157 | SSYTSSSALYV | 110 |
| H3-5 | SSDVGGYNY | 28 | EVSNRLSGVS | 156 | SSYTSSSTLYV | 111 |
| H3-6 | SSDVGGYNY | 28 | EVSNRLRGVS | 157 | SSYTSSSALYV | 110 |
| H3-7 | SSDVGGYNY | 28 | EVSNRLRGVS | 157 | SSYTSSSTLYV | 111 |
| H3-8 | SSDVGGYNY | 28 | EVSNRLRGVS | 157 | SSYTSSSTLYV | 111 |
| H3-9 | SSDVGGYNY | 28 | EVSNRLRGVS | 157 | SSYTSSSTLYV | 111 |
| H3-10 | SSDVGGYNY | 28 | EVSNRLRGVS | 157 | SSYTSSSTLYV | 111 |
| H3-11 | SSDVGGYNY | 28 | EVSNRLRGVS | 157 | SSYTSSSTLYV | 111 |
| H3-12 | SSDVGGYNY | 28 | EVSNRLRGVS | 157 | SSYTSSSTLYV | 111 |
| H3-13 | SSDVGGYNY | 28 | EVSNRLRGVS | 157 | SSYTSSSTLYV | 111 |
| H3-14 | SSDVGGYNY | 28 | EVSNRLSGVS | 156 | SSYTSSSALYV | 110 |
| H3-15 | SSDVGGYNY | 28 | EVSNRLGGVS | 161 | SSYTSSSALYV | 110 |

TABLE 1K-1(b)

AB3 family BCMA Binders - Light Chain CDR sequences according to IMGT numbering scheme

| Binder | CDR-L1 | SEQ ID NO: | CDR-L2 | SEQ ID NO: | CDR-L3 | SEQ ID NO: |
|---|---|---|---|---|---|---|
| AB3 | SSDVGGYNY | 28 | DVS | | SSYTSSSALYV | 110 |
| PI-61 | SSDVGGYNY | 28 | DVS | | SSYTSSSTLYV | 111 |
| H2/L2-22 | SSDVGGYNY | 28 | EVS | | SSYTSSSTLYV | 111 |

TABLE 1K-1(b)-continued

AB3 family BCMA Binders - Light Chain CDR sequences according to IMGT numbering scheme

| Binder | CDR-L1 | SEQ ID NO: | CDR-L2: | SEQ ID NO: | CDR-L3 | SEQ ID NO: |
|---|---|---|---|---|---|---|
| H2/L2-88 | SSDVGGYNY | 28 | EVS | | SSYTSSSALYV | 110 |
| H2/L2-36 | SSDVGGYNY | 28 | EVS | | SSYTSSSTLYV | 111 |
| H2/L2-34 | SSDVGGYNY | 28 | DVS | | SSYTSSSALYV | 110 |
| H2/L2-68 | SSDVGGYNY | 28 | DVS | | SSYTSSSTLYV | 111 |
| H2/L2-18 | SSDVGGYNY | 28 | DVS | | SSYTSSSTLYV | 111 |
| H2/L2-47 | SSDVGGYNY | 28 | DVS | | SSYTSSSTLYV | 111 |
| H2/L2-20 | SSDVGGYNY | 28 | DVS | | SSYTSSSALYV | 110 |
| H2/L2-80 | SSDVGGYNY | 28 | DVS | | SSYTSSSALYV | 110 |
| H2/L2-83 | SSDVGGYNY | 28 | DVS | | SSYTSSSTLYV | 111 |
| H3-1 | SSDVGGYNY | 28 | EVS | | SSYTSSSTLYV | 111 |
| H3-2 | SSDVGGYNY | 28 | EVS | | SSYTSSSTLYV | 111 |
| H3-3 | SSDVGGYNY | 28 | EVS | | SSYTSSSTLYV | 111 |
| H3-4 | SSDVGGYNY | 28 | EVS | | SSYTSSSALYV | 110 |
| H3-5 | SSDVGGYNY | 28 | EVS | | SSYTSSSTLYV | 111 |
| H3-6 | SSDVGGYNY | 28 | EVS | | SSYTSSSALYV | 110 |
| H3-7 | SSDVGGYNY | 28 | EVS | | SSYTSSSTLYV | 111 |
| H3-8 | SSDVGGYNY | 28 | EVS | | SSYTSSSTLYV | 111 |
| H3-9 | SSDVGGYNY | 28 | EVS | | SSYTSSSTLYV | 111 |
| H3-10 | SSDVGGYNY | 28 | EVS | | SSYTSSSTLYV | 111 |
| H3-11 | SSDVGGYNY | 28 | EVS | | SSYTSSSTLYV | 111 |
| H3-12 | SSDVGGYNY | 28 | EVS | | SSYTSSSTLYV | 111 |
| H3-13 | SSDVGGYNY | 28 | EVS | | SSYTSSSTLYV | 111 |
| H3-14 | SSDVGGYNY | 28 | EVS | | SSYTSSSALYV | 110 |
| H3-15 | SSDVGGYNY | 28 | EVS | | SSYTSSSALYV | 110 |

TABLE 1K-2

AB3 family BCMA Binders - Heavy Chain CDR sequences according to IMGT numbering scheme

| Binder | CDR-H1 | SEQ ID NO: | CDR-H2: | SEQ ID NO: | CDR-H3 | SEQ ID NO: |
|---|---|---|---|---|---|---|
| AB3 | GFTVSSYG | 162 | ISYTGSNK | 165 | GGSGYALHDDYYGLDV | 51 |
| PI-61 | GFTFSSYG | 163 | ISYDGSNK | 166 | GGSGYALHDDYYGLDV | 51 |
| H2/L2-22 | GFTFSSYG | 163 | ISYHGSNK | 167 | GGSGYALHDDYYGLDV | 51 |
| H2/L2-88 | GFTFSSYG | 163 | ISYKGSNK | 168 | GGSGYALHDDYYGLDV | 51 |
| H2/L2-36 | GFTFSSYG | 163 | ISYKGSNK | 168 | GGSGYALHDDYYGLDV | 51 |
| H2/L2-34 | GFTFSSYG | 163 | ISYTGTKK | 169 | GGSGYALHDDYYGLDV | 51 |
| H2/L2-68 | GFTFSSYG | 163 | ISYRGFNK | 170 | GGSGYALHDDYYGQDV | 179 |
| H2/L2-18 | GFTFSSYG | 163 | ISYKGSHK | 171 | GGSGYALHDDYYGLDV | 51 |
| H2/L2-47 | GFTFSSYG | 163 | ISYKGSNK | 168 | GGSGYALHDDYYGLDV | 51 |
| H2/L2-20 | GFTVSSYG | 162 | ISYTGSNK | 165 | GGSGYALHDDYYGLDV | 51 |
| H2/L2-80 | GFTFSSYG | 163 | ISYTGSNK | 165 | GGSGYALHDDYYGLDV | 51 |
| H2/L2-83 | GFTFSSYG | 163 | ISYKGSNK | 168 | GGSGYALHDDYYGLDV | 51 |
| H3-1 | GFTFSSYG | 163 | ISYDDAHK | 172 | GGSGYALHDQYKPVDV | 180 |
| H3-2 | GFTFSSYG | 163 | ISYNDLNK | 173 | GGSGYALHDFQDPTDV | 181 |
| H3-3 | GFTVSSYG | 162 | ISYSGSNK | 174 | GGSGYALHDQYKPVDV | 180 |
| H3-4 | GFTFSSYG | 163 | ISYDDAHK | 172 | GGSGYALHDQYKPVDV | 180 |
| H3-5 | GFTFSSYG | 163 | ISYTGANK | 175 | GGSGYNLHDDYYGLDV | 182 |
| H3-6 | GFTFSSYG | 163 | ISYDDAHK | 172 | GGSGYALHDQYKPVDV | 180 |
| H3-7 | GFTLSSYG | 164 | ISYTGSNK | 165 | GGSGYEFHEDYYGLDV | 183 |
| H3-8 | GFTFSSYG | 163 | ISYDDAHK | 172 | GGSGYALHDQYKPVDV | 180 |
| H3-9 | GFTFSSYG | 163 | ISYDDAHK | 172 | GGSGYALHDQYKPVDV | 180 |
| H3-10 | GFTFSSYG | 163 | ISYNDLNK | 173 | GGSGYEFQGDYYGLDV | 184 |
| H3-11 | GFTFSSYG | 163 | ISYNDANK | 176 | GGSGYELRDDYYGLDV | 185 |
| H3-12 | GFTFSSYG | 163 | ISYDESNK | 177 | GGSGYEVDQDYYGLDV | 186 |
| H3-13 | GFTFSSYG | 163 | ISYDDAHK | 172 | GGSGYALHDQYKPVDV | 180 |
| H3-14 | GFTFSSYG | 163 | ISYDDAHK | 172 | GGSGYALHDQYKPVDV | 180 |
| H3-15 | GFTVSSYG | 162 | ISYDDANK | 178 | GGSGYAYDGDYYGLDV | 187 |

TABLE 1L-1

AB3 family BCMA Binders - Light Chain CDR sequences according to combination of Kabat and Chothia numbering schemes

| Binder | CDR-L1 | SEQ ID NO: | CDR-L2 | SEQ ID NO: | CDR-L3 | SEQ ID NO: |
|---|---|---|---|---|---|---|
| AB3 | TGTSSDVGGYNYVS | 26 | DVSNRLR | 102 | SSYTSSSALYV | 110 |
| PI-61 | TGTSSDVGGYNYVS | 26 | DVSNRPS | 103 | SSYTSSSTLYV | 111 |
| H2/L2-22 | TGTSSDVGGYNYVS | 26 | EVSNRLS | 104 | SSYTSSSTLYV | 111 |
| H2/L2-88 | TGTSSDVGGYNYVS | 26 | EVSNRLR | 105 | SSYTSSSALYV | 110 |
| H2/L2-36 | TGTSSDVGGYNYVS | 26 | EVSNRLR | 105 | SSYTSSSTLYV | 111 |
| H2/L2-34 | TGTSSDVGGYNYVS | 26 | DVSNRPW | 106 | SSYTSSSALYV | 110 |
| H2/L2-68 | TGTSSDVGGYNYVS | 26 | DVSNRLS | 107 | SSYTSSSTLYV | 111 |
| H2/L2-18 | TGTSSDVGGYNYVS | 26 | DVSNRPW | 106 | SSYTSSSTLYV | 111 |
| H2/L2-47 | TGTSSDVGGYNYVS | 26 | DVSNRPW | 106 | SSYTSSSTLYV | 111 |
| H2/L2-20 | TGTSSDVGGYNYVS | 26 | DVSNRLR | 102 | SSYTSSSALYV | 110 |
| H2/L2-80 | TGTSSDVGGYNYVS | 26 | DVSNRAW | 108 | SSYTSSSALYV | 110 |
| H2/L2-83 | TGTSSDVGGYNYVS | 26 | EVSNRLR | 105 | SSYTSSSTLYV | 111 |
| H3-1 | TGTSSDVGGYNYVS | 26 | EVSNRLR | 105 | SSYTSSSTLYV | 111 |
| H3-2 | TGTSSDVGGYNYVS | 26 | EVSNRLR | 105 | SSYTSSSTLYV | 111 |
| H3-3 | TGTSSDVGGYNYVS | 26 | EVSNRLR | 105 | SSYTSSSTLYV | 111 |
| H3-4 | TGTSSDVGGYNYVS | 26 | EVSNRLR | 105 | SSYTSSSALYV | 110 |
| H3-5 | TGTSSDVGGYNYVS | 26 | EVSNRLS | 104 | SSYTSSSTLYV | 111 |
| H3-6 | TGTSSDVGGYNYVS | 26 | EVSNRLR | 105 | SSYTSSSALYV | 110 |
| H3-7 | TGTSSDVGGYNYVS | 26 | EVSNRLR | 105 | SSYTSSSTLYV | 111 |
| H3-8 | TGTSSDVGGYNYVS | 26 | EVSNRLR | 105 | SSYTSSSTLYV | 111 |
| H3-9 | TGTSSDVGGYNYVS | 26 | EVSNRLR | 105 | SSYTSSSTLYV | 111 |
| H3-10 | TGTSSDVGGYNYVS | 26 | EVSNRLR | 105 | SSYTSSSTLYV | 111 |
| H3-11 | TGTSSDVGGYNYVS | 26 | EVSNRLR | 105 | SSYTSSSTLYV | 111 |
| H3-12 | TGTSSDVGGYNYVS | 26 | EVSNRLR | 105 | SSYTSSSTLYV | 111 |
| H3-13 | TGTSSDVGGYNYVS | 26 | EVSNRLR | 105 | SSYTSSSTLYV | 111 |
| H3-14 | TGTSSDVGGYNYVS | 26 | EVSNRLS | 104 | SSYTSSSALYV | 110 |
| H3-15 | TGTSSDVGGYNYVS | 26 | EVSNRLG | 109 | SSYTSSSALYV | 110 |

TABLE 1L-2

AB3 family BCMA Binders - Heavy Chain CDR sequences according to combination of Kabat and Chothia numbering schemes

| Binder | CDR-H1 | SEQ ID NO: | CDR-H2 | SEQ ID NO: | CDR-H3 | SEQ ID NO: |
|---|---|---|---|---|---|---|
| AB3 | GFTVSSYGMH | 188 | VISYTGSNKYYADSVKG | 112 | SGYALHDDYYGLDV | 49 |
| PI-61 | GFTFSSYGMH | 189 | VISYDGSNKYYADSVKG | 113 | SGYALHDDYYGLDV | 49 |
| H2/L2-22 | GFTFSSYGMH | 189 | VISYHGSNKYYADSVKG | 114 | SGYALHDDYYGLDV | 49 |
| H2/L2-88 | GFTFSSYGMH | 189 | VISYKGSNKYYADSVKG | 115 | SGYALHDDYYGLDV | 49 |
| H2/L2-36 | GFTFSSYGMH | 189 | VISYKGSNKYYADSVKG | 115 | SGYALHDDYYGLDV | 49 |
| H2/L2-34 | GFTFSSYGMH | 189 | VISYTGTKKYYADSVKG | 116 | SGYALHDDYYGLDV | 49 |
| H2/L2-68 | GFTFSSYGMH | 189 | VISYRGFNKYYADSVKG | 117 | SGYALHDDYYGQDV | 126 |

TABLE 1L-2-continued

AB3 family BCMA Binders - Heavy Chain CDR sequences according to combination of Kabat and Chothia numbering schemes

| Binder | CDR-H1 | SEQ ID NO: | CDR-H2 | SEQ ID NO: | CDR-H3 | SEQ ID NO: |
|---|---|---|---|---|---|---|
| H2/L2-18 | GFTFSSYGMH | 189 | VISYKGSHKYYADSVKG | 118 | SGYALHDDYYGLDV | 49 |
| H2/L2-47 | GFTFSSYGMH | 189 | VISYKGSNKYYADSVKG | 115 | SGYALHDDYYGLDV | 49 |
| H2/L2-20 | GFTVSSYGMH | 188 | VISYTGSNKYYADSVKG | 112 | SGYALHDDYYGLDV | 49 |
| H2/L2-80 | GFTFSSYGMH | 189 | VISYTGSNKYYADSVKG | 112 | SGYALHDDYYGLDV | 49 |
| H2/L2-83 | GFTFSSYGMH | 189 | VISYKGSNKYYADSVKG | 115 | SGYALHDDYYGLDV | 49 |
| H3-1 | GFTFSSYGMH | 189 | VISYDDAHKYYADSVKG | 119 | SGYALHDQYKPVDV | 127 |
| H3-2 | GFTFSSYGMH | 189 | VISYNDLNKYYADSVKG | 120 | SGYALHDFQDPTDV | 128 |
| H3-3 | GFTVSSYGMH | 188 | VISYSGSNKYYADSVKG | 121 | SGYALHDQYKPVDV | 127 |
| H3-4 | GFTFSSYGMH | 189 | VISYDDAHKYYADSVKG | 119 | SGYALHDQYKPVDV | 127 |
| H3-5 | GFTFSSYGMH | 189 | VISYTGANKYYADSVKG | 122 | SGYNLHDDYYGLDV | 129 |
| H3-6 | GFTFSSYGMH | 189 | VISYDDAHKYYADSVKG | 119 | SGYALHDQYKPVDV | 127 |
| H3-7 | GFTLSSYGMH | 190 | VISYTGSNKYYADSVKG | 112 | SGYEFHEDYYGLDV | 130 |
| H3-8 | GFTFSSYGMH | 189 | VISYDDAHKYYADSVKG | 119 | SGYALHDQYKPVDV | 127 |
| H3-9 | GFTFSSYGMH | 189 | VISYDDAHKYYADSVKG | 119 | SGYALHDQYKPVDV | 127 |
| H3-10 | GFTFSSYGMH | 189 | VISYNDLNKYYADSVKG | 120 | SGYEFQGDYYGLDV | 131 |
| H3-11 | GFTFSSYGMH | 189 | VISYNDANKYYADSVKG | 123 | SGYELRDDYYGLDV | 132 |
| H3-12 | GFTFSSYGMH | 189 | VISYDESNKYYADSVKG | 124 | SGYEVDQDYYGLDV | 133 |
| H3-13 | GFTFSSYGMH | 189 | VISYDDAHKYYADSVKG | 119 | SGYALHDQYKPVDV | 127 |
| H3-14 | GFTFSSYGMH | 189 | VISYDDAHKYYADSVKG | 119 | SGYALHDQYKPVDV | 127 |
| H3-15 | GFTVSSYGMH | 188 | VISYDDANKYYADSVKG | 125 | SGYAYDGDYYGLDV | 134 |

TABLE 1M-1

AB3 family BCMA Binders - Light Chain CDR sequences according to combination of Kabat and IMGT numbering schemes

| Binder | CDR-L1 | SEQ ID NO: | CDR-L2 | SEQ ID NO: | CDR-L3 | SEQ ID NO: |
|---|---|---|---|---|---|---|
| AB3 | TGTSSDVGGYNYVS | 26 | DVSNRLR | 102 | SSYTSSSALYV | 110 |

TABLE 1M-1-continued

AB3 family BCMA Binders - Light Chain CDR sequences
according to combination of Kabat and IMGT numbering schemes

| Binder | CDR-L1 | SEQ ID NO: | CDR-L2: | SEQ ID NO: | CDR-L3 | SEQ ID NO: |
|---|---|---|---|---|---|---|
| PI-61 | TGTSSDVGGYNYVS | 26 | DVSNRPS | 103 | SSYTSSSTLYV | 111 |
| H2/L2-22 | TGTSSDVGGYNYVS | 26 | EVSNRLS | 104 | SSYTSSSTLYV | 111 |
| H2/L2-88 | TGTSSDVGGYNYVS | 26 | EVSNRLR | 105 | SSYTSSSALYV | 110 |
| H2/L2-36 | TGTSSDVGGYNYVS | 26 | EVSNRLR | 105 | SSYTSSSTLYV | 111 |
| H2/L2-34 | TGTSSDVGGYNYVS | 26 | DVSNRPW | 106 | SSYTSSSALYV | 110 |
| H2/L2-68 | TGTSSDVGGYNYVS | 26 | DVSNRLS | 107 | SSYTSSSTLYV | 111 |
| H2/L2-18 | TGTSSDVGGYNYVS | 26 | DVSNRPW | 106 | SSYTSSSTLYV | 111 |
| H2/L2-47 | TGTSSDVGGYNYVS | 26 | DVSNRPW | 106 | SSYTSSSTLYV | 111 |
| H2/L2-20 | TGTSSDVGGYNYVS | 26 | DVSNRLR | 102 | SSYTSSSALYV | 110 |
| H2/L2-80 | TGTSSDVGGYNYVS | 26 | DVSNRAW | 108 | SSYTSSSALYV | 110 |
| H2/L2-83 | TGTSSDVGGYNYVS | 26 | EVSNRLR | 105 | SSYTSSSTLYV | 111 |
| H3-1 | TGTSSDVGGYNYVS | 26 | EVSNRLR | 105 | SSYTSSSTLYV | 111 |
| H3-2 | TGTSSDVGGYNYVS | 26 | EVSNRLR | 105 | SSYTSSSTLYV | 111 |
| H3-3 | TGTSSDVGGYNYVS | 26 | EVSNRLR | 105 | SSYTSSSTLYV | 111 |
| H3-4 | TGTSSDVGGYNYVS | 26 | EVSNRLR | 105 | SSYTSSSALYV | 110 |
| H3-5 | TGTSSDVGGYNYVS | 26 | EVSNRLS | 104 | SSYTSSSTLYV | 111 |
| H3-6 | TGTSSDVGGYNYVS | 26 | EVSNRLR | 105 | SSYTSSSALYV | 110 |
| H3-7 | TGTSSDVGGYNYVS | 26 | EVSNRLR | 105 | SSYTSSSTLYV | 111 |
| H3-8 | TGTSSDVGGYNYVS | 26 | EVSNRLR | 105 | SSYTSSSTLYV | 111 |
| H3-9 | TGTSSDVGGYNYVS | 26 | EVSNRLR | 105 | SSYTSSSTLYV | 111 |
| H3-10 | TGTSSDVGGYNYVS | 26 | EVSNRLR | 105 | SSYTSSSTLYV | 111 |
| H3-11 | TGTSSDVGGYNYVS | 26 | EVSNRLR | 105 | SSYTSSSTLYV | 111 |
| H3-12 | TGTSSDVGGYNYVS | 26 | EVSNRLR | 105 | SSYTSSSTLYV | 111 |
| H3-13 | TGTSSDVGGYNYVS | 26 | EVSNRLR | 105 | SSYTSSSTLYV | 111 |

TABLE 1M-1-continued

AB3 family BCMA Binders - Light Chain CDR sequences according to combination of Kabat and IMGT numbering schemes

| Binder | CDR-L1 | SEQ ID NO: | CDR-L2: | SEQ ID NO: | CDR-L3 | SEQ ID NO: |
|---|---|---|---|---|---|---|
| H3-14 | TGTSSDVGGYNYVS | 26 | EVSNRLS | 104 | SSYTSSSALYV | 110 |
| H3-15 | TGTSSDVGGYNYVS | 26 | EVSNRLG | 109 | SSYTSSSALYV | 110 |

TABLE 1M-2

AB3 family BCMA Binders - Heavy Chain CDR sequences according to combination of Kabat and IMGT numbering schemes

| Binder | CDR-H1 | SEQ ID NO: | CDR-H2: | SEQ ID NO: | CDR-H3 | SEQ ID NO: |
|---|---|---|---|---|---|---|
| AB3 | GFTVSSYGMH | 188 | VISYTGSNKYYADSVKG | 112 | GGSGYALHDDYYGLDV | 51 |
| PI-61 | GFTFSSYGMH | 189 | VISYDGSNKYYADSVKG | 113 | GGSGYALHDDYYGLDV | 51 |
| H2/L2-22 | GFTFSSYGMH | 189 | VISYHGSNKYYADSVKG | 114 | GGSGYALHDDYYGLDV | 51 |
| H2/L2-88 | GFTFSSYGMH | 189 | VISYKGSNKYYADSVKG | 115 | GGSGYALHDDYYGLDV | 51 |
| H2/L2-36 | GFTFSSYGMH | 189 | VISYKGSNKYYADSVKG | 115 | GGSGYALHDDYYGLDV | 51 |
| H2/L2-34 | GFTFSSYGMH | 189 | VISYTGTKKYYADSVKG | 116 | GGSGYALHDDYYGLDV | 51 |
| H2/L2-68 | GFTFSSYGMH | 189 | VISYRGFNKYYADSVKG | 117 | GGSGYALHDDYYGQDV | 179 |
| H2/L2-18 | GFTFSSYGMH | 189 | VISYKGSHKYYADSVKG | 118 | GGSGYALHDDYYGLDV | 51 |
| H2/L2-47 | GFTFSSYGMH | 189 | VISYKGSNKYYADSVKG | 115 | GGSGYALHDDYYGLDV | 51 |
| H2/L2-20 | GFTVSSYGMH | 188 | VISYTGSNKYYADSVKG | 112 | GGSGYALHDDYYGLDV | 51 |
| H2/L2-80 | GFTFSSYGMH | 189 | VISYTGSNKYYADSVKG | 112 | GGSGYALHDDYYGLDV | 51 |
| H2/L2-83 | GFTFSSYGMH | 189 | VISYKGSNKYYADSVKG | 115 | GGSGYALHDDYYGLDV | 51 |
| H3-1 | GFTFSSYGMH | 189 | VISYDDAHKYYADSVKG | 119 | GGSGYALHDQYKPVDV | 180 |
| H3-2 | GFTFSSYGMH | 189 | VISYNDLNKYYADSVKG | 120 | GGSGYALHDFQDPTDV | 181 |
| H3-3 | GFTVSSYGMH | 188 | VISYSGSNKYYADSVKG | 121 | GGSGYALHDQYKPVDV | 180 |
| H3-4 | GFTFSSYGMH | 189 | VISYDDAHKYYADSVKG | 119 | GGSGYALHDQYKPVDV | 180 |
| H3-5 | GFTFSSYGMH | 189 | VISYTGANKYYADSVKG | 122 | GGSGYNLHDDYYGLDV | 182 |
| H3-6 | GFTFSSYGMH | 189 | VISYDDAHKYYADSVKG | 119 | GGSGYALHDQYKPLDV | 180 |
| H3-7 | GFTLSSYGMH | 190 | VISYTGSNKYYADSVKG | 112 | GGSGYEFHEDYYGLDV | 183 |

TABLE 1M-2-continued

AB3 family BCMA Binders - Heavy Chain CDR sequences according to combination of Kabat and IMGT numbering schemes

| Binder | CDR-H1 | SEQ ID NO: | CDR-H2: | SEQ ID NO: | CDR-H3 | SEQ ID NO: |
|---|---|---|---|---|---|---|
| H3-8 | GFTFSSYGMH | 189 | VISYDDAHKYYADSVKG | 119 | GGSGYALHDQYKPVDV | 180 |
| H3-9 | GFTFSSYGMH | 189 | VISYDDAHKYYADSVKG | 119 | GGSGYALHDQYKPVDV | 180 |
| H3-10 | GFTFSSYGMH | 189 | VISYNDLNKYYADSVKG | 120 | GGSGYEFQGDYYGLDV | 184 |
| H3-11 | GFTFSSYGMH | 189 | VISYNDANKYYADSVKG | 123 | GGSGYELRDDYYGLDV | 185 |
| H3-12 | GFTFSSYGMH | 189 | VISYDESNKYYADSVKG | 124 | GGSGYEVDQDYYGLDV | 186 |
| H3-13 | GFTFSSYGMH | 189 | VISYDDAHKYYADSVKG | 119 | GGSGYALHDQYKPVDV | 180 |
| H3-14 | GFTFSSYGMH | 189 | VISYDDAHKYYADSVKG | 119 | GGSGYALHDQYKPVDV | 180 |
| H3-15 | GFTVSSYGMH | 188 | VISYDDANKYYADSVKG | 125 | GGSGYAYDGDYYGLDV | 187 |

TABLE 1N-1(a)

AB3 family BCMA Binders - CDR-L1 and CDR-L3 sequences according to combination of Chothia and IMGT numbering schemes and CDR-L2 expanded sequences

| Binder | CDR-L1 | SEQ ID NO: | CDR-L2: | SEQ ID NO: | CDR-L3 | SEQ ID NO: |
|---|---|---|---|---|---|---|
| AB3 | TSSDVGGYNY | 27 | DVSNRLRGVS | 154 | SSYTSSSALYV | 110 |
| PI-61 | TSSDVGGYNY | 27 | DVSNRPSGVS | 155 | SSYTSSSTLYV | 111 |
| H2/L2-22 | TSSDVGGYNY | 27 | EVSNRLSGVS | 156 | SSYTSSSTLYV | 111 |
| H2/L2-88 | TSSDVGGYNY | 27 | EVSNRLRGVS | 157 | SSYTSSSALYV | 110 |
| H2/L2-36 | TSSDVGGYNY | 27 | EVSNRLRGVS | 157 | SSYTSSSTLYV | 111 |
| H2/L2-34 | TSSDVGGYNY | 27 | DVSNRPWGVS | 158 | SSYTSSSALYV | 110 |
| H2/L2-68 | TSSDVGGYNY | 27 | DVSNRLSGVS | 159 | SSYTSSSTLYV | 111 |
| H2/L2-18 | TSSDVGGYNY | 27 | DVSNRPWGVS | 158 | SSYTSSSTLYV | 111 |
| H2/L2-47 | TSSDVGGYNY | 27 | DVSNRPWGVS | 158 | SSYTSSSTLYV | 111 |
| H2/L2-20 | TSSDVGGYNY | 27 | DVSNRLRGVS | 154 | SSYTSSSALYV | 110 |
| H2/L2-80 | TSSDVGGYNY | 27 | DVSNRAWGVS | 160 | SSYTSSSALYV | 110 |
| H2/L2-83 | TSSDVGGYNY | 27 | EVSNRLRGVS | 157 | SSYTSSSTLYV | 111 |
| H3-1 | TSSDVGGYNY | 27 | EVSNRLRGVS | 157 | SSYTSSSTLYV | 111 |
| H3-2 | TSSDVGGYNY | 27 | EVSNRLRGVS | 157 | SSYTSSSTLYV | 111 |
| H3-3 | TSSDVGGYNY | 27 | EVSNRLRGVS | 157 | SSYTSSSTLYV | 111 |
| H3-4 | TSSDVGGYNY | 27 | EVSNRLRGVS | 157 | SSYTSSSALYV | 110 |
| H3-5 | TSSDVGGYNY | 27 | EVSNRLSGVS | 156 | SSYTSSSTLYV | 111 |
| H3-6 | TSSDVGGYNY | 27 | EVSNRLRGVS | 157 | SSYTSSSALYV | 110 |
| H3-7 | TSSDVGGYNY | 27 | EVSNRLRGVS | 157 | SSYTSSSTLYV | 111 |

TABLE 1N-1(a)-continued

AB3 family BCMA Binders - CDR-L1 and CDR-L3 sequences according to combination of Chothia and IMGT numbering schemes and CDR-L2 expanded sequences

| Binder | CDR-L1 | SEQ ID NO: | CDR-L2: | SEQ ID NO: | CDR-L3 | SEQ ID NO: |
|---|---|---|---|---|---|---|
| H3-8 | TSSDVGGYNY | 27 | EVSNRLRGVS | 157 | SSYTSSSTLYV | 111 |
| H3-9 | TSSDVGGYNY | 27 | EVSNRLRGVS | 157 | SSYTSSSTLYV | 111 |
| H3-10 | TSSDVGGYNY | 27 | EVSNRLRGVS | 157 | SSYTSSSTLYV | 111 |
| H3-11 | TSSDVGGYNY | 27 | EVSNRLRGVS | 157 | SSYTSSSTLYV | 111 |
| H3-12 | TSSDVGGYNY | 27 | EVSNRLRGVS | 157 | SSYTSSSTLYV | 111 |
| H3-13 | TSSDVGGYNY | 27 | EVSNRLRGVS | 157 | SSYTSSSTLYV | 111 |
| H3-14 | TSSDVGGYNY | 27 | EVSNRLSGVS | 156 | SSYTSSSALYV | 110 |
| H3-15 | TSSDVGGYNY | 27 | EVSNRLGGVS | 161 | SSYTSSSALYV | 110 |

TABLE 1N-1(b)

AB3 family BCMA Binders - Light Chain CDR sequences according to combination of Chothia and IMGT numbering schemes

| Binder | CDR-L1 | SEQ ID NO: | CDR-L2: | SEQ ID NO: | CDR-L3 | SEQ ID NO: |
|---|---|---|---|---|---|---|
| AB3 | TSSDVGGYNY | 27 | DVS | | SSYTSSSALYV | 110 |
| PI-61 | TSSDVGGYNY | 27 | DVS | | SSYTSSSTLYV | 111 |
| H2/L2-22 | TSSDVGGYNY | 27 | EVS | | SSYTSSSTLYV | 111 |
| H2/L2-88 | TSSDVGGYNY | 27 | EVS | | SSYTSSSALYV | 110 |
| H2/L2-36 | TSSDVGGYNY | 27 | EVS | | SSYTSSSTLYV | 111 |
| H2/L2-34 | TSSDVGGYNY | 27 | DVS | | SSYTSSSALYV | 110 |
| H2/L2-68 | TSSDVGGYNY | 27 | DVS | | SSYTSSSTLYV | 111 |
| H2/L2-18 | TSSDVGGYNY | 27 | DVS | | SSYTSSSTLYV | 111 |
| H2/L2-47 | TSSDVGGYNY | 27 | DVS | | SSYTSSSTLYV | 111 |
| H2/L2-20 | TSSDVGGYNY | 27 | DVS | | SSYTSSSALYV | 110 |
| H2/L2-80 | TSSDVGGYNY | 27 | DVS | | SSYTSSSALYV | 110 |
| H2/L2-83 | TSSDVGGYNY | 27 | EVS | | SSYTSSSTLYV | 111 |
| H3-1 | TSSDVGGYNY | 27 | EVS | | SSYTSSSTLYV | 111 |
| H3-2 | TSSDVGGYNY | 27 | EVS | | SSYTSSSTLYV | 111 |
| H3-3 | TSSDVGGYNY | 27 | EVS | | SSYTSSSTLYV | 111 |
| H3-4 | TSSDVGGYNY | 27 | EVS | | SSYTSSSALYV | 110 |
| H3-5 | TSSDVGGYNY | 27 | EVS | | SSYTSSSTLYV | 111 |
| H3-6 | TSSDVGGYNY | 27 | EVS | | SSYTSSSALYV | 110 |
| H3-7 | TSSDVGGYNY | 27 | EVS | | SSYTSSSTLYV | 111 |
| H3-8 | TSSDVGGYNY | 27 | EVS | | SSYTSSSTLYV | 111 |
| H3-9 | TSSDVGGYNY | 27 | EVS | | SSYTSSSTLYV | 111 |
| H3-10 | TSSDVGGYNY | 27 | EVS | | SSYTSSSTLYV | 111 |
| H3-11 | TSSDVGGYNY | 27 | EVS | | SSYTSSSTLYV | 111 |

TABLE 1N-1(b)-continued

AB3 family BCMA Binders - Light Chain CDR sequences
according to combination of Chothia and IMGT numbering schemes

| Binder | CDR-L1 | SEQ ID NO: | CDR-L2: | SEQ ID NO: | CDR-L3 | SEQ ID NO: |
|---|---|---|---|---|---|---|
| H3-12 | TSSDVGGYNY | 27 | EVS | | SSYTSSSTLYV | 111 |
| H3-13 | TSSDVGGYNY | 27 | EVS | | SSYTSSSTLYV | 111 |
| H3-14 | TSSDVGGYNY | 27 | EVS | | SSYTSSSALYV | 110 |
| H3-15 | TSSDVGGYNY | 27 | EVS | | SSYTSSSALYV | 110 |

TABLE 1N-2

AB3 family BCMA Binders - Heavy Chain CDR sequences
according to combination of Chothia and IMGT numbering schemes

| Binder | CDR-H1 | SEQ ID NO: | CDR-H2: | SEQ ID NO: | CDR-H3 | SEQ ID NO: |
|---|---|---|---|---|---|---|
| AB3 | GFTVSSYG | 162 | ISYTGSNK | 165 | GGSGYALHDDYYGLDV | 51 |
| PI-61 | GFTFSSYG | 163 | ISYDGSNK | 166 | GGSGYALHDDYYGLDV | 51 |
| H2/L2-22 | GFTFSSYG | 163 | ISYHGSNK | 167 | GGSGYALHDDYYGLDV | 51 |
| H2/L2-88 | GFTFSSYG | 163 | ISYKGSNK | 168 | GGSGYALHDDYYGLDV | 51 |
| H2/L2-36 | GFTFSSYG | 163 | ISYKGSNK | 168 | GGSGYALHDDYYGLDV | 51 |
| H2/L2-34 | GFTFSSYG | 163 | ISYTGTKK | 169 | GGSGYALHDDYYGLDV | 51 |
| H2/L2-68 | GFTFSSYG | 163 | ISYRGFNK | 170 | GGSGYALHDDYYGQDV | 179 |
| H2/L2-18 | GFTFSSYG | 163 | ISYKGSHK | 171 | GGSGYALHDDYYGLDV | 51 |
| H2/L2-47 | GFTFSSYG | 163 | ISYKGSNK | 168 | GGSGYALHDDYYGLDV | 51 |
| H2/L2-20 | GFTVSSYG | 162 | ISYTGSNK | 165 | GGSGYALHDDYYGLDV | 51 |
| H2/L2-80 | GFTFSSYG | 163 | ISYTGSNK | 165 | GGSGYALHDDYYGLDV | 51 |
| H2/L2-83 | GFTFSSYG | 163 | ISYKGSNK | 168 | GGSGYALHDDYYGLDV | 51 |
| H3-1 | GFTFSSYG | 163 | ISYDDAHK | 172 | GGSGYALHDQYKPVDV | 180 |
| H3-2 | GFTFSSYG | 163 | ISYNDLNK | 173 | GGSGYALHDFQDPTDV | 181 |
| H3-3 | GFTVSSYG | 162 | ISYSGSNK | 174 | GGSGYALHDQYKPVDV | 180 |
| H3-4 | GFTFSSYG | 163 | ISYDDAHK | 172 | GGSGYALHDQYKPVDV | 180 |
| H3-5 | GFTFSSYG | 163 | ISYTGANK | 175 | GGSGYNLHDDYYGLDV | 182 |
| H3-6 | GFTFSSYG | 163 | ISYDDAHK | 172 | GGSGYALHDQYKPVDV | 180 |

TABLE 1N-2-continued

AB3 family BCMA Binders - Heavy Chain CDR sequences according to combination of Chothia and IMGT numbering schemes

| Binder | CDR-H1 | SEQ ID NO: | CDR-H2 | SEQ ID NO: | CDR-H3 | SEQ ID NO: |
|---|---|---|---|---|---|---|
| H3-7 | GFTLSSYG | 164 | ISYTGSNK | 165 | GGSGYEFHEDYYGLDV | 183 |
| H3-8 | GFTFSSYG | 163 | ISYDDAHK | 172 | GGSGYALHDQYKPVDV | 180 |
| H3-9 | GFTFSSYG | 163 | ISYDDAHK | 172 | GGSGYALHDQYKPVDV | 180 |
| H3-10 | GFTFSSYG | 163 | ISYNDLNK | 173 | GGSGYEFQGDYYGLDV | 184 |
| H3-11 | GFTFSSYG | 163 | ISYNDANK | 176 | GGSGYELRDDYYGLDV | 185 |
| H3-12 | GFTFSSYG | 163 | ISYDESNK | 177 | GGSGYEVDQDYYGLDV | 186 |
| H3-13 | GFTFSSYG | 163 | ISYDDAHK | 172 | GGSGYALHDQYKPVDV | 180 |
| H3-14 | GFTFSSYG | 163 | ISYDDAHK | 172 | GGSGYALHDQYKPVDV | 180 |
| H3-15 | GFTVSSYG | 162 | ISYDDANK | 178 | GGSGYAYDGDYYGLDV | 187 |

TABLE 1O-1

BCMA Binders - Light chain variable sequences

| Binder | Sequence | SEQ ID NO: |
|---|---|---|
| AB1 | DIQMTQSPSSLSASVGDRVTITCRASQSISSYLNWYQQKPGKAPKLLIYAASSLQSGVPSRFSGSGSGTDFTLTISSLQPEDFATYYCQQSYSSPLTFGQGTKVEIK | 191 |
| AB2 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| R1F2 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF03 | DIQMTQSPSSLSASVGDRVTITCRASQSISSYLNWYQQKPGKAPKLLIYAASSLQSGVPSRFSGSGSGTDFTLTISSLQPEDFATYYCQQSYGSPPTFGQGTKVEIK | 193 |
| PALF04 | DIQMTQSPSSLSASVGDRVTITCRASQSISSYLNWYQQKPGKAPKLLIYAASSLQSGVPSRFSGSGSGTDFTLTISSLQPEDFATYYCQQSYDSPLTFGQGTKVEIK | 194 |
| PALF05 | DIQMTQSPSSLSASVGDRVTITCRASQSISSYLNWYQQKPGKAPKLLIYAASSLQSGVPSRFSGSGSGTDFTLTISSLQPEDFATYYCQQSYYSPLTFGQGTKVEIK | 195 |
| PALF06 | DIQMTQSPSSLSASVGDRVTITCRASQSISSYLNWYQQKPGKAPKLLIYAASSLQSGVPSRFSGSGSGTDFTLTISSLQPEDFATYYCQQSYYAPLTFGQGTKVEIK | 196 |
| PALF07 | DIQMTQSPSSLSASVGDRVTITCRASQSISSYLNWYQQKPGKAPKLLIYAASSLQSGVPSRFSGSGSGTDFTLTISSLQPEDFATYYCQQSYASPLTFGQGTKVEIK | 197 |
| PALF08 | DIQMTQSPSSLSASVGDRVTITCRASQSISSYLNWYQQKPGKAPKLLIYAASSLQSGVPSRFSGSGSGTDFTLTISSLQPEDFATYYCQQSYGSPLTFGQGTKVEIK | 198 |
| PALF09 | DIQMTQSPSSLSASVGDRVTITCRASQSISSYLNWYQQKPGKAPKLLIYAASSLQSGVPSRFSGSGSGTDFTLTISSLQPEDFATYYCQQSYDAPLTFGQGTKVEIK | 199 |
| PALF12 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF13 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |

TABLE 10-1-continued

BCMA Binders - Light chain variable sequences

| Binder | Sequence | SEQ ID NO: |
|---|---|---|
| PALF14 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF15 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF16 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF17 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF18 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF19 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF20 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| AB3 | QSALTQPASVSGSPGQSITISCTGTSSDVGGYNYVSWYQQHPGKAPKLMIYDVSNRLRGVSNRFSGSKSGNTASLTISGLQAEDEADYYCSSYTSSSALYVFGSGTKVTVL | 200 |
| PI-61 | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTLYVFGSGTKVTVL | 201 |
| H2/L2-22 | QSALTQPASVSGSPGQSITISCTGTSSDVGGYNYVSWYQQHPGKAPKLMIYEVSNRLSGVSNRFSGSKFGNTASLTISGLQAEDEADYYCSSYTSSSTLYVFGSGTKVTVL | 202 |
| H2/L2-88 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSALYVFGSGTKVTVL | 203 |
| H2/L2-36 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H2/L2-34 | QSALTQPASVSGSPGQSITISCTGTSSDVGGYNYVSWYQQHPGKAPKLMIYDVSNRPWGVSNRFSGSKFGNTASLTISGLQAEDEADYYCSSYTSSSALYVFGSGTKVTVM | 205 |
| H2/L2-68 | QSALTQPASVSGSPGQSITISCTGTSSDVGGYNYVSWYQQHPGKAPKLMIYDVSNRLSGVSNRFSGSKFGNTASLTISGLQAEDEADYYCSSYTSSSTLYVFGSGTKVTVL | 206 |
| H2/L2-18 | QSALTQPASVSGSPGQSITISCTGTSSDVGGYNYVSWYQQHPGKAPKLMIYDVSNRPWGVSNRFSGSKFGNTASLTISGLQAEDEADYYCSSYTSSSTLYVFGSGTKVTVL | 207 |
| H2/L2-47 | QSALTQPASVSGSPGQSITISCTGTSSDVGGYNYVSWYQQHPGKAPKLMIYDVSNRPWGVSNRFSGSKFGNTASLTISGLQAEDEADYYCSSYTSSSTLYVFGSGTKVTVL | 207 |
| H2/L2-20 | QSALTQPASVSGSPGQSITISCTGTSSDVGGYNYVSWYQQHPGKAPKLMIYDVSNRLRGVSNRFSGSKFGNTASLTISGLQAEDEADYYCSSYTSSSALYVFGSGTKVTVL | 208 |
| H2/L2-80 | QSALTQPASVSGSPGQSITISCTGTSSDVGGYNYVSWYQQHPGKAPKLMIYDVSNRAWGVSNRFSGSKFGNTASLTISGLQAEDEADYYCSSYTSSSALYVFGSGTKVTVL | 209 |
| H2/L2-83 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-1 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |

TABLE 10-1-continued

BCMA Binders - Light chain variable sequences

| Binder | Sequence | SEQ ID NO: |
|---|---|---|
| H3-2 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-3 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-4 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSALYVFGSGTKVTVL | 203 |
| H3-5 | QSALTQPASVSGSPGQSITISCTGTSSDVGGYNYVSWYQQHPGKAPKLMIYEVSNRLSGVSNRFSGSKFGNTASLTISGLQAEDEADYYCSSYTSSSTLYVFGSGTKVTVL | 202 |
| H3-6 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSALYVFGSGTKVTVL | 203 |
| H3-7 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-8 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-9 | QSALTQPASVSGSPGQSITISCTGTSSDVGGYNYVSWYQQHPGKAPKLMIYEVSNRLRGVSNRFSGSKFGNTASLTISGLQAEDEAYYYCSSYTSSSTLYVFGSGTKVTVL | 210 |
| H3-10 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-11 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-12 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-13 | QSALTQPASVSGSPGQSITISCTGTSSDVGGYNYVSWYQQHPGKAPKLMIYEVSNRLRGVSNRFSGSKFGNTASLTISGLQAEDEADYYCSSYTSSSTLYVFGSGTKVTVL | 204 |
| H3-14 | QSALTQPASVSGSPGQSITISCTGTSSDVGGYNYVSWYQQHPGKAPKLMIYEVSNRLSGVSNRFSGSKFGNTASLTISGLQAEDEADYYCSSYTSSSALYVFGSGTKVTVL | 211 |
| H3-15 | QSALTQPASVSGSPGQSITISCTGTSSDVGGYNYVSWYQQHPGKAPKLMIYEVSNRLGGVSNRFSGSKFGNTASLTISGLQAEDEADYYCSSYTSSSALYVFGSGTKVTVL | 212 |

TABLE 10-2

BCMA Binders - Heavy chain variable sequences

| Binder | Sequence | SEQ ID NO: |
|---|---|---|
| AB1 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
| AB2 | EVQLLESGGGLVQPGGSLRLSCAASGFTFSSYAMSWVRQAPGKGLEWVSAISESGGRAAYADSVKGRFTISRDNSKNTLYLQMNSLRAEDTAVYYCARREWWYDDWYLDYWGQGTLVTVSS | 214 |

TABLE 10-2-continued

BCMA Binders - Heavy chain variable sequences

| Binder | Sequence | SEQ ID NO: |
|---|---|---|
| R1F2 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF03 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF04 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF05 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF06 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF07 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF08 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF09 | EVQLLESGGGLVQPGGSLRLSCAASGFTFSSYAMSWVRQAPGKGLEWVSAISG SGGSTYYADSVKGRFTISRDNSKNTLYLQMNSLRAEDTAVYYCARREWWYDDW YLDYWGQGTLVTVSS | 213 |
| PALF12 | EVQLLESGGGLVQPGGSLRLSCAASGFTFSSYAMSWVRQAPGKGLEWVSAISG SGGRAAYADSVKGRFTISRDNSKNTLYLQMNSLRAEDTAVYYCARREWWYDD WYLDYWGQGTLVTVSS | 215 |
| PALF13 | EVQLLESGGGLVQPGGSLRLSCAASGFTFSSYAMSWVRQAPGKGLEWVSAISE SGDVEAYADSVKGRFTISRDNSKNTLYLQMNSLRAEDTAVYYCARREWWYDDW YLDYWGQGTLVTVSS | 216 |
| PALF14 | EVQLLESGGGLVQPGGSLRLSCAASGFTFSSYAMSWVRQAPGKGLEWVSAISE AGETTSYADSVKGRFTISRDNSKNTLYLQMNSLRAEDTAVYYCARREWWYDDW YLDYWGQGTLVTVSS | 217 |
| PALF15 | EVQLLESGGGLVQPGGSLRLSCAASGFTFSSYAMSWVRQAPGKGLEWVSAISE HGHYTSYADSVKGRFTISRDNSKNTLYLQMNSLRAEDTAVYYCARREWWYDDW YLDYWGQGTLVTVSS | 218 |
| PALF16 | EVQLLESGGGLVQPGGSLRLSCAASGFTFSSYAMSWVRQAPGKGLEWVSAISG SGHTAAYADSVKGRFTISRDNSKNTLYLQMNSLRAEDTAVYYCARREWWYDDW YLDYWGQGTLVTVSS | 219 |
| PALF17 | EVQLLESGGGLVQPGGSLRLSCAASGFTFSSYAMSWVRQAPGKGLEWVSAISG SGRTHAYADSVKGRFTISRDNSKNTLYLQMNSLRAEDTAVYYCARREWWYDDW YLDYWGQGTLVTVSS | 220 |
| PALF18 | EVQLLESGGGLVQPGGSLRLSCAASGFTFSSYAMSWVRQAPGKGLEWVSAISA EGGVRAYADSVKGRFTISRDNSKNTLYLQMNSLRAEDTAVYYCARREWWYDD WYLDYWGQGTLVTVSS | 221 |
| PALF19 | EVQLLESGGGLVQPGGSLRLSCAASGFTFSSYAMSWVRQAPGKGLEWVSAISG SGGTTAYADSVKGRFTISRDNSKNTLYLQMNSLRAEDTAVYYCARREWWYDDW YLDYWGQGTLVTVSS | 222 |
| PALF20 | EVQLLESGGGLVQPGGSLRLSCAASGFTFSSYAMSWVRQAPGKGLEWVSAISG SGATTAYADSVKGRFTISRDNSKNTLYLQMNSLRAEDTAVYYCARREWWYDDW YLDYWGQGTLVTVSS | 223 |
| AB3 | QVQLVESGGGVVQPGRSLRLSCAASGFTVSSYGMHWVRQAPGKGLEWVAVIS YTGSNKYYADSVKGRFTISRDNSKNTLYLQMNSLRAEDTAVYYCGGSGYALHDD YYGLDVWGQGTLVTVSS | 224 |
| PI-61 | QVQLQESGGGVVQPGRSLRLSCAASGFTFSSYGMHWVRQAPGKGLEWVAVIS YDGSNKYYADSVKGRFTISRDNSKNTLYLQMNSLRAEDTAVYYCGGSGYALHDD YYGLDVWGQGTLVTVSS | 225 |

TABLE 10-2-continued

BCMA Binders - Heavy chain variable sequences

| Binder | Sequence | SEQ ID NO: |
|---|---|---|
| H2/L2-22 | QAQLQSSEGGVVQPGRSLRLSCAASGFTFSSYGMHWVRQAPGKGLEWVAVIS YHGSNKYYADSVKGRFTISRDNSKNTLYLQMNSLRAEDTAVYYCGGSGYALHDD YYGLDVWGQGTLVTVSSS | 226 |
| H2/L2-88 | QVQLQSSEGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSS | 227 |
| H2/L2-36 | QAQLQSSGGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSS | 228 |
| H2/L2-34 | QVQLQDSEGGVVQPGRSLRLSCAASGFTFSSYGMHWVRQAPGKGLEWVAVIS YTGTKKYYADSVKGRFTISRDNSKNTLYLQMNSLRAEDTAVYYCGGSGYALHDD YYGLDVWGQGTLVTVSS | 229 |
| H2/L2-68 | QAQLQSSEGGVVQPGRSLRLSCAASGFTFSSYGMHWVRQAPGKGLEWVAVIS YRGFNKYYADSVKGRFTISRDNSKNTLYLQMNSLRAEDTAVYYCGGSGYALHDD YYGQDVWGQGTLVTVSS | 230 |
| H2/L2-18 | QAQLQGSGGGVVQPGRSLRLSCAASGFTFSSYGMHWVRQAPGKGLEWVAVIS YKGSHKYYADSVKGRFTISRDNSKNTLYLQMNSLRAEDTAVYYCGGSGYALHDD YYGLDVWGQGTLVTVSS | 231 |
| H2/L2-47 | QVQLQSSEGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSS | 227 |
| H2/L2-20 | QAQLQSSGGGVVQPGRSLRLSCAASGFTVSSYGMHWVRQAPGKGLEWVAVIS YTGSNKYYADSVKGRFTISRDNSKNTLYLQMNSLRAEDTAVYYCGGSGYALHDD YYGLDVWGQGTLVTVSS | 232 |
| H2/L2-80 | QVQLQSSGGGVVQPGRSLRLSCAASGFTFSSYGMHWVRQAPGKGLEWVAVIS YTGSNKYYADSVKGRFTISRDNSKNTLYLQMNSLRAEDTAVYYCGGSGYALHDD YYGLDVWGQGTLVTVSS | 233 |
| H2/L2-83 | QAQLQGSGGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSS | 234 |
| H3-1 | QVQLQGSGGGVVQPGRSLRLSCAASGFTFSSYGMHWVRQAPGKGLEWVAVIS YDDAHKYYADSVKGRFTISRDNSKNTLYLQMNSLRAEDTAVYYCGGSGYALHDQ YKPVDVWGQGTLVTVSS | 235 |
| H3-2 | QAQLQESEGGVVQPGGSLRLSCAASGFTFSSYGMHWVRQAPGKGLEWVAVIS YNDLNKYYADSVKGRFTISRDNSKNTLYLQMNSLRAEDTAVYYCGGSGYALHDF QDPTDVWGQGTLVTVSS | 236 |
| H3-3 | QVQLQSSGGGVVQPGRSLRLSCAASGFTVSSYGMHWVRQAPGKGLEWVAVIS YSGSNKYYADSVKGRFTISRDNSKNTLYLQMNSLRAEDTAVYYCGGSGYALHDQ YKPVDVWGQGTLVTVSS | 237 |
| H3-4 | QVQLQGSGGGVVQPGRSLRLSCAASGFTFSSYGMHWVRQAPGKGLEWVAVIS YDDAHKYYADSVKGRFTISRDNSKNTLYLQMNSLRAEDTAVYYCGGSGYALHDQ YKPVDVWGQGTLVTVSS | 235 |
| H3-5 | QVQLQGSGGGVVQPGRSLRLSCAASGFTFSSYGMHWVRQAPGKGLEWVAVIS YTGANKYYADSVKGRFTISRDNSKNTLYLQMNSLRAEDTAVYYCGGSGYNLHDD YYGLDVWGQGTLVTVSS | 238 |
| H3-6 | QAQLQRSGGGVVQPGRSLRLSCAASGFTFSSYGMHWVRQAPGKGLEWVAVIS YDDAHKYYADSVKGRFTISRDNSKNTLYLQMNSLRAEDTAVYYCGGSGYALHDQ YKPVDVWGQGTLVTVSS | 239 |
| H3-7 | QVQLQSSEGGVVQPGRSLRLSCAASGFTLSSYGMHWVRQAPGKGLEWVAVIS YTGSNKYYADSVKGRFTISRDNSKNTLYLQMNSLRAEDTAVYYCGGSGYEFHED YYGLDVWGQGTLVTVSS | 240 |
| H3-8 | QAQLQGSEGGVVQPGRSLRLSCAASGFTFSSYGMHWVRQAPGKGLEWVAVIS YDDAHKYYADSVKGRFTISRDNSKNTLYLQMNSLRAEDTAVYYCGGSGYALHDQ YKPVDVWGQGTLVTVSS | 241 |

TABLE 10-2-continued

BCMA Binders - Heavy chain variable sequences

| Binder | Sequence | SEQ ID NO: |
|---|---|---|
| H3-9 | QVQLQGSGGGVVQPGRSLRLSCAASGFTFSSYGMHWVRQAPGKGLEWVAVIS YDDAHKYYADSVKGRFTISRDNSKNTLYLQMNSLRAEDTAVYYCGGSGYALHDQ YKPVDVWGQGTLVTVSS | 235 |
| H3-10 | QVQLQSSGGGVVQPGRSLRLSCAASGFTFSSYGMHWVRQAPGKGLEWVAVIS YNDLNKYYADSVKGRFTISRDNSKNTLYLQMNSLRAEDTAVYYCGGSGYEFQGD YYGLDVWGQGTLVTVSS | 242 |
| H3-11 | QVQLQSSEGGVVQPGRSLRLSCAASGFTFSSYGMHWVRQAPGKGLEWVAVIS YNDANKYYADSVKGRFTISRDNSKNTLYLQMNSLRAEDTAVYYCGGSGYELRDD YYGLDVWGQGTLVTVSS | 243 |
| H3-12 | QAQLQSSEGGVVQPGRSLRLSCAASGFTFSSYGMHWVRQAPGKGLEWVAVIS YDESNKYYADSVKGRFTISRDNSKNTLYLQMNSLRAEDTAVYYCGGSGYEVDQ DYYGLDVWGQGTLVTVSS | 244 |
| H3-13 | QVQLQESGGGVVQPGRSLRLSCAASGFTFSSYGMHWVRQAPGKGLEWVAVIS YDDAHKYYADSVKGRFTISRDNSKNTLYLQMNSLRAEDTAVYYCGGSGYALHDQ YKPVDVWGQGTLVTVSS | 245 |
| H3-14 | QVQLQGSGGGVVQPGRSLRLSCAASGFTFSSYGMHWVRQAPGKGLEWVAVIS YDDAHKYYADSVKGRFTISRDNSKNTLYLQMNSLRAEDTAVYYCGGSGYALHDQ YKPVDVWGQGTLVTVSS | 235 |
| H3-15 | QVQLQGSGGGVVQPGRSLRLSCAASGFTVSSYGMHWVRQAPGKGLEWVAVIS YDDANKYYADSVKGRFTISRDSSKNTLYLQMNSLRAEDTAVYYCGGSGYAYDG DYYGLDVWGQGTLVTVSS | 246 |

TABLE 1P

BCMA Binders - scFv sequences

| Binder | Sequence | SEQ ID NO: |
|---|---|---|
| H2/L2-88 | QVQLQSSEGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSSGGGGSGGGGSGGGGSGGGGSQSALTQPASVSGS PGQSITISCTGTSSDVGGYNYVSWYQQHPGKAPKLMIYEVSNRLRGVSNRFSGS KFGNTASLTISGLQAEDEADYYCSSYTSSSALYVFGSGTKVTVL | 247 |
| H2/L2-36 | QAQLQSSGGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSSGGGGSGGGGSGGGGSGGGGSQSALTQPASVSGS PGQSITISCTGTSSDVGGYNYVSWYQQHPGKAPKLMIYEVSNRLRGVSNRFSGS KFGNTASLTISGLQAEDEADYYCSSYTSSSTLYVFGSGTKVTVL | 248 |
| H2/L2-34 | QVQLQDSEGGVVQPGRSLRLSCAASGFTFSSYGMHWVRQAPGKGLEWVAVIS YTGTKKYYADSVKGRFTISRDNSKNTLYLQMNSLRAEDTAVYYCGGSGYALHDD YYGLDVWGQGTLVTVSSGGGGSGGGGSGGGGSGGGGSQSALTQPASVSGS PGQSITISCTGTSSDVGGYNYVSWYQQHPGKAPKLMIYDVSNRPWGVSNRFSG SKFGNTASLTISGLQAEDEADYYCSSYTSSSALYVFGSGTKVTVM | 249 |
| H2/L2-68 | QAQLQSSEGGVVQPGRSLRLSCAASGFTFSSYGMHWVRQAPGKGLEWVAVIS YRGFNKYYADSVKGRFTISRDNSKNTLYLQMNSLRAEDTAVYYCGGSGYALHDD YYGQDVWGQGTLVTVSSGGGGSGGGGSGGGGSGGGGSQSALTQPASVSGS PGQSITISCTGTSSDVGGYNYVSWYQQHPGKAPKLMIYDVSNRLSGVSNRFSGS KFGNTASLTISGLQAEDEADYYCSSYTSSSTLYVFGSGTKVTVL | 250 |
| H2/L2-18 | QAQLQGSGGGVVQPGRSLRLSCAASGFTFSSYGMHWVRQAPGKGLEWVAVIS YKGSHKYYADSVKGRFTISRDNSKNTLYLQMNSLRAEDTAVYYCGGSGYALHDD YYGLDVWGQGTLVTVSSGGGGSGGGGSGGGGSGGGGSQSALTQPASVSGS PGQSITISCTGTSSDVGGYNYVSWYQQHPGKAPKLMIYDVSNRPWGVSNRFSG SKFGNTASLTISGLQAEDEADYYCSSYTSSSTLYVFGSGTKVTVL | 251 |
| H2/L2-47 | QVQLQSSEGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSSGGGGSGGGGSGGGGSGGGGSQSALTQPASVSGS PGQSITISCTGTSSDVGGYNYVSWYQQHPGKAPKLMIYDVSNRPWGVSNRFSG SKFGNTASLTISGLQAEDEADYYCSSYTSSSTLYVFGSGTKVTVL | 252 |

TABLE 1P-continued

BCMA Binders - scFv sequences

| Binder | Sequence | SEQ ID NO: |
|---|---|---|
| H2/L2-20 | QAQLQSSGGGVVQPGRSLRLSCAASGFTVSSYGMHWVRQAPGKGLEWVAVIS YTGSNKYYADSVKGRFTISRDNSKNTLYLQMNSLRAEDTAVYYCGGSGYALHDD YYGLDVWGQGTLVTVSSSGGGGSGGGGSGGGGSGGGGSQSALTQPASVSGS PGQSITISCTGTSSDVGGYNYVSWYQQHPGKAPKLMIYDVSNRLRGVSNRFSGS KFGNTASLTISGLQAEDEADYYCSSYTSSSALYVFGSGTKVTVL | 253 |
| H2/L2-80 | QVQLQSSGGGVVQPGRSLRLSCAASGFTFSSYGMHWVRQAPGKGLEWVAVIS YTGSNKYYADSVKGRFTISRDNSKNTLYLQMNSLRAEDTAVYYCGGSGYALHDD YYGLDVWGQGTLVTVSSSGGGGSGGGGSGGGGSGGGGSQSALTQPASVSGS PGQSITISCTGTSSDVGGYNYVSWYQQHPGKAPKLMIYDVSNRAWGVSNRFSG SKFGNTASLTISGLQAEDEADYYCSSYTSSSALYVFGSGTKVTVL | 254 |
| H2/L2-83 | QAQLQGSGGGVVQPGRSLRLSCAASGFTFSSYGMHWVRQAPGKGLEWVAVIS YKGSNKYYADSVKGRFTISRDNSKNTLYLQMNSLRAEDTAVYYCGGSGYALHDD YYGLDVWGQGTLVTVSSSGGGGSGGGGSGGGGSGGGGSQSALTQPASVSGS PGQSITISCTGTSSDVGGYNYVSWYQQHPGKAPKLMIYEVSNRLRGVSNRFSGS KFGNTASLTISGLQAEDEADYYCSSYTSSSTLYVFGSGTKVTVL | 255 |

Tables 1A-1 to 1B-2 list CDR consensus sequences derived from the CDR sequences of the exemplary BCMA binding molecules described in the Examples. The CDR consensus sequences include sequences based upon the Kabat CDR sequences of the exemplary BCMA binding molecules, the Chothia CDR sequences of the exemplary BCMA binding molecules, the IMGT CDR sequences of the exemplary BCMA binding molecules, a combination of the Kabat and Chothia CDR sequences of the exemplary BCMA binding molecules, a combination of the Kabat and IMGT CDR sequences of the exemplary BCMA binding molecules, and a combination of the Chothia and IMGT CDR sequences of the exemplary BCMA binding molecules. The specific CDR sequences of the exemplary BCMA binding molecules described in the Examples are listed in Tables 1C1-1N-2. Exemplary VL and VH sequences are listed in Tables 1O-1 and 1O-2, respectively. Exemplary scFv sequences are listed in Table 1P.

In some embodiments, the BCMA binding molecules comprise a light chain CDR having an amino acid sequence of any one of the CDR consensus sequences listed in Table 1A-1 or Table 1B-1. In particular embodiments, the present disclosure provides BCMA binding molecules, comprising (or alternatively, consisting of) one, two, three, or more light chain CDRs selected the light chain CDRs described in Table 1A-1 or Table 1B-1.

In some embodiments, the BCMA binding molecules comprise a heavy chain CDR having an amino acid sequence of any one of the heavy chain CDRs listed in Table 1A-2 or Table 1B-2. In particular embodiments, the present disclosure provides BCMA binding molecules, comprising (or alternatively, consisting of) one, two, three, or more heavy chain CDRs selected the heavy chain CDRs described in Table 1A-2 or Table 1B-2.

In some embodiments, a BCMA binding molecule comprises CDR-L1, CDR-L2, CDR-L3, CDR-H1, CDR-H2 and CDR-H3 sequences of C1 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C2 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C3 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C4 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C5 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C6 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C7 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C8 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C9 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C10 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C11 as set forth in Tables 1A-1 and 1A-2. In some embodiments, a BCMA binding molecule comprises CDR-L1, CDR-L2, CDR-L3, CDR-H1, CDR-H2 and CDR-H3 sequences of C12 as set forth in Tables 1A-1 and 1A-2.

In some embodiments, a BCMA binding molecule comprises CDR-L1, CDR-L2, CDR-L3, CDR-H1, CDR-H2 and CDR-H3 sequences of C13 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C14 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C15 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C16 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C17 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C18 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C19 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C20 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C21 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C22 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C23 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C24 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C25 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C26 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C27 as set forth in Tables 1B-1 and 1B-2. In some embodiments, a BCMA binding molecule comprises CDR-L1, CDR-L2, CDR-L3, CDR-H1, CDR-H2 and CDR-H3 sequences of C28 as set forth in Tables 1B-1 and 1B-2.

In some embodiments, the BCMA binding molecules comprise a light chain CDR having an amino acid sequence of any one of the CDRs listed in Table 1C-1, Table 1D-1, Table 1E-1, Table 1F-1, Table 1G-1, Table 1H-1, Table 1I-1, Table 1J-1, Table 1K-1(a), Table 1K-1(b), Table 1L-1, Table 1M-1, Table 1N-1(a) or Table 1N-1(b). In particular embodiments, the present disclosure provides BCMA binding molecules, comprising (or alternatively, consisting of) one, two, three, or more light chain CDRs selected the light chain CDRs described in Table 1C-1, Table 1D-1, Table 1E-1, Table 1F-1, Table 1G-1, Table 1H-1, Table 1I-1, Table 1J-1, Table 1K-1(a), Table 1K-1(b), Table 1L-1, Table 1M-1, Table 1N-1(a) and Table 1N-1(b).

In some embodiments, the BCMA binding molecules comprise a heavy chain CDR having an amino acid sequence of any one of the heavy chain CDRs listed in Table 1C-2, Table 1D-2, Table 1E-2, Table 1F-2, Table 1G-2, Table 1H-2, Table 1I-2, Table 1J-2, Table 1K-2, Table 1L-2, Table 1M-2, or Table 1N-2. In particular embodiments, the present disclosure provides BCMA binding molecules, comprising (or alternatively, consisting of) one, two, three, or more heavy chain CDRs selected the heavy chain CDRs described in Table 1C-2, Table 1D-2, Table 1E-2, Table 1F-2, Table 1G-2, Table 1H-2, Table 1I-2, Table 1J-2, Table 1K-2, Table 1L-2, Table 1M-2, and Table 1N-2.

In some embodiments, the BCMA binding molecules comprise a VL domain having an amino acid sequence of any VL domain described in Table 1O-1. Other BCMA binding molecules can include amino acids that have been mutated, yet have at least 80, 85, 90, 95, 96, 97, 98, or 99 percent identity in the VL domain with the VL domains depicted in the sequences described in Table 1O-1.

In some embodiments, the BCMA binding molecules comprise a VH domain having an amino acid sequence of any VH domain described in Table 1O-2. Other BCMA binding molecules can include amino acids that have been mutated, yet have at least 80, 85, 90, 95, 96, 97, 98, or 99 percent identity in the VH domain with the VH domains depicted in the sequences described in Table 1O-2.

Other BCMA binding molecules include amino acids that have been mutated, yet have at least 80, 85, 90, 95, 96, 97, 98, or 99 percent identity in the CDR regions with the CDR sequences described in Table 1. In some embodiments, such BCMA binding molecules include mutant amino acid sequences where no more than 1, 2, 3, 4 or 5 amino acids have been mutated in the CDR regions when compared with the CDR sequences described in Table 1.

Other BCMA binding molecules include VH and/or VL domains comprising amino acid sequences having at least 80, 85, 90, 95, 96, 97, 98, or 99 percent identity to the VH and/or VL sequences described in Table 1. In some embodiments, BCMA binding molecules include VH and/or VL domains where no more than 1, 2, 3, 4 or 5 amino acids have been mutated when compared with the VH and/or VL domains depicted in the sequences described in Table 1, while retaining substantially the same therapeutic activity.

VH and VL sequences (amino acid sequences and the nucleotide sequences encoding the amino acid sequences) can be "mixed and matched" to create other BCMA binding molecules. Such "mixed and matched" BCMA binding molecules can be tested using known binding assays (e.g., ELISAs, assays described in the Examples). When chains are mixed and matched, a VH sequence from a particular VH/VL pairing should be replaced with a structurally similar VH sequence. A VL sequence from a particular VH/VL pairing should be replaced with a structurally similar VL sequence.

Accordingly, in one embodiment, the present disclosure provides BCMA binding molecules having: a heavy chain variable region (VH) comprising an amino acid sequence selected from any one of the VH sequences described in Table 1-O2; and a light chain variable region (VL) comprising an amino acid sequence described in Table 1-O1.

In another embodiment, the present disclosure provides BCMA binding molecules that comprise the CDR-H1, CDR-H2, CDR-H3, CDR-L1, CDR-L2, and CDR-L3 as described in Table 1, or any combination thereof.

In some embodiments, a BCMA binding molecule comprises CDR-L1, CDR-L2, CDR-L3, CDR-H1, CDR-H2 and CDR-H3 sequences of AB1 as set forth in Tables 1C-1 and 1C-2. In some embodiments, a BCMA binding molecule comprises CDR-L1, CDR-L2, CDR-L3, CDR-H1, CDR-H2 and CDR-H3 sequences of AB1 as set forth in Tables 1D-1 and 1D-2. In some embodiments, a BCMA binding molecule comprises CDR-L1, CDR-L2, CDR-L3, CDR-H1, CDR-H2 and CDR-H3 sequences of AB1 as set forth in Tables 1E-1 and 1E-2. In some embodiments, a BCMA binding molecule comprises CDR-L1, CDR-L2, CDR-L3, CDR-H1, CDR-H2 and CDR-H3 sequences of AB1 as set forth in Tables 1F-1 and 1F-2. In some embodiments, a BCMA binding molecule comprises CDR-L1, CDR-L2, CDR-L3, CDR-H1, CDR-H2 and CDR-H3 sequences of AB1 as set forth in Tables 1G-1 and 1G-2. In some embodiments, a BCMA binding molecule comprises CDR-L1, CDR-L2, CDR-L3, CDR-H1, CDR-H2 and CDR-H3 sequences of AB1 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of AB2 as set forth in Tables 1C-1 and 1C-2. In some embodiments, a BCMA binding molecule comprises CDR-L1, CDR-L2, CDR-L3, CDR-H1, CDR-H2 and CDR-H3 sequences of AB2 as set forth in Tables 1D-1 and 1D-2. In some embodiments, a BCMA binding molecule comprises CDR-L1, CDR-L2, CDR-L3, CDR-H1, CDR-H2 and CDR-H3 sequences of AB2 as set forth in Tables 1E-1 and 1E-2. In some embodiments, a BCMA binding molecule comprises CDR-L1, CDR-L2, CDR-L3, CDR-H1, CDR-H2 and CDR-H3 sequences of AB2 as set forth in Tables 1F-1 and 1F-2. In some embodiments, a BCMA binding molecule comprises CDR-L1, CDR-L2, CDR-L3, CDR-H1, CDR-H2 and CDR-H3 sequences of AB2 as set forth in Tables 1G-1 and 1G-2. In some embodiments, a BCMA binding molecule comprises CDR-L1, CDR-L2, CDR-L3, CDR-H1, CDR-H2 and CDR-H3 sequences of AB2 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of R1F2 as set forth in Tables 1C-1 and 1C-2. In some embodiments, a BCMA binding molecule comprises CDR-L1, CDR-L2, CDR-L3, CDR-H1, CDR-H2 and CDR-H3 sequences of R1F2 as set forth in Tables 1D-1 and 1D-2. In some embodiments, a BCMA binding molecule comprises CDR-L1, CDR-L2, CDR-L3, CDR-H1, CDR-H2 and CDR-H3 sequences of R1F2 as set forth in Tables 1E-1 and 1E-2. In some embodiments, a BCMA binding molecule comprises CDR-L1, CDR-L2, CDR-L3, CDR-H1, CDR-H2 and CDR-H3 sequences of R1F2 as set forth in Tables 1F-1 and 1F-2. In some embodiments, a BCMA binding molecule comprises CDR-L1, CDR-L2, CDR-L3, CDR-H1, CDR-H2 and CDR-H3 sequences of R1F2 as set forth in Tables 1G-1 and 1G-2. In some embodiments, a BCMA binding molecule comprises CDR-L1, CDR-L2, CDR-L3, CDR-H1, CDR-H2 and CDR-H3 sequences of R1F2 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF03 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF03 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF03 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF03 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF03 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF03 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF04 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF04 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF04 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF04 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF04 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF04 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF05 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF05 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF05 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF05 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF05 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF05 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF06 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF06 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF06 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF06 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF06 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF06 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF07 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF07 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF07 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF07 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF07 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF07 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF08 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF08 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF08 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF08 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF08 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF08 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF09 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF09 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF09 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF09 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF09 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF09 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF12 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF12 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF12 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF12 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF12 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF12 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF13 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF13 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF13 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF13 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF13 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF13 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF14 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF14 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF14 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF14 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF14 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF14 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF15 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF15 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF15 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF15 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF15 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF15 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF16 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF16 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF16 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF16 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF16 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF16 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF17 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF17 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF17 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF17 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF17 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF17 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF18 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF18 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF18 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF18 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF18 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF18 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF19 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF19 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF19 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF19 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF19 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF19 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of PALF20 as set forth in Tables 1C-1 and 1C-2. In some embodiments, a BCMA binding molecule comprises CDR-L1, CDR-L2, CDR-L3, CDR-H1, CDR-H2 and CDR-H3 sequences of PALF20 as set forth in Tables 1D-1 and 1D-2. In some embodiments, a BCMA binding molecule comprises CDR-L1, CDR-L2, CDR-L3, CDR-H1, CDR-H2 and CDR-H3 sequences of PALF20 as set forth in Tables 1E-1 and 1E-2. In some embodiments, a BCMA binding molecule comprises CDR-L1, CDR-L2, CDR-L3, CDR-H1, CDR-H2 and CDR-H3 sequences of PALF20 as set forth in Tables 1F-1 and 1F-2. In some embodiments, a BCMA binding molecule comprises CDR-L1, CDR-L2, CDR-L3, CDR-H1, CDR-H2 and CDR-H3 sequences of PALF20 as set forth in Tables 1G-1 and 1G-2. In some embodiments, a BCMA binding molecule comprises CDR-L1, CDR-L2, CDR-L3, CDR-H1, CDR-H2 and CDR-H3 sequences of PALF20 as set forth in Tables 1H-1 and 1H-2.

In some embodiments, a BCMA binding molecule comprises CDR-L1, CDR-L2, CDR-L3, CDR-H1, CDR-H2 and CDR-H3 sequences of AB3 as set forth in Tables 1I-1 and 1I-2. In some embodiments, a BCMA binding molecule comprises CDR-L1, CDR-L2, CDR-L3, CDR-H1, CDR-H2 and CDR-H3 sequences of AB3 as set forth in Tables 1J-1 and 1J-2. In some embodiments, a BCMA binding molecule comprises CDR-L1, CDR-L2, CDR-L3, CDR-H1, CDR-H2 and CDR-H3 sequences of AB3 as set forth in Tables 1K-1 and 1K-2. In some embodiments, a BCMA binding molecule comprises CDR-L1, CDR-L2, CDR-L3, CDR-H1, CDR-H2 and CDR-H3 sequences of AB3 as set forth in Tables 1L-1 and 1L-2. In some embodiments, a BCMA binding molecule comprises CDR-L1, CDR-L2, CDR-L3, CDR-H1, CDR-H2 and CDR-H3 sequences of AB3 as set forth in Tables 1M-1 and 1M-2. In some embodiments, a BCMA binding molecule comprises CDR-L1, CDR-L2, CDR-L3, CDR-H1, CDR-H2 and CDR-H3 sequences of AB3 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of PI-61 as set forth in Tables 1I-1 and 1I-2. In some embodiments, a BCMA binding molecule comprises CDR-L1, CDR-L2, CDR-L3, CDR-H1, CDR-H2 and CDR-H3 sequences of PI-61 as set forth in Tables 1J-1 and 1J-2. In some embodiments, a BCMA binding molecule comprises CDR-L1, CDR-L2, CDR-L3, CDR-H1, CDR-H2 and CDR-H3 sequences of PI-61 as set forth in Tables 1K-1 and 1K-2. In some embodiments, a BCMA binding molecule comprises CDR-L1, CDR-L2, CDR-L3, CDR-H1, CDR-H2 and CDR-H3 sequences of PI-61 as set forth in Tables 1L-1 and 1L-2. In some embodiments, a BCMA binding molecule comprises CDR-L1, CDR-L2, CDR-L3, CDR-H1, CDR-H2 and CDR-H3 sequences of PI-61 as set forth in Tables 1M-1 and 1M-2. In some embodiments, a BCMA binding molecule comprises CDR-L1, CDR-L2, CDR-L3, CDR-H1, CDR-H2 and CDR-H3 sequences of PI-61 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-22 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-22 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-22 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-22 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-22 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-22 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-88 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-88 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-88 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-88 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-88 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-88 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-36 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-36 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-36 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-36 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-36 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-36 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-34 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-34 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-34 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-34 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-34 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-34 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-68 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-68 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-68 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-68 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-68 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-68 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-18 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-18 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-18 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-18 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-18 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-18 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-47 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-47 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-47 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-47 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-47 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-47 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-20 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-20 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-20 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-20 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-20 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-20 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-80 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-80 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-80 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-80 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-80 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-80 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H2/L2-83 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H2/L2-83 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H2/L2-83 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H2/L2-83 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H2/L2-83 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H2/L2-83 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-1 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-1 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-1 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-1 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-1 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-1 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-2 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-2 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-2 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-2 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-2 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-2 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-3 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-3 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-3 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-3 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-3 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-3 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-4 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-4 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-4 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-4 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-4 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-4 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-5 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-5 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-5 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-5 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-5 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-5 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-6 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-6 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-6 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-6 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-6 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-6 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-7 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-7 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-7 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-7 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-7 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-7 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-8 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-8 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-8 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-8 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-8 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-8 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-9 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-9 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-9 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-9 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-9 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-9 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-10 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-10 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-10 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-10 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-10 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-10 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-11 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-11 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-11 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-11 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-11 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-11 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-12 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-12 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-12 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-12 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-12 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-12 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-13 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-13 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-13 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-13 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-13 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-13 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-14 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-14 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-14 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-14 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-14 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-14 as set forth in Tables 1N-1 and 1N-2.

In some embodiments, a BCMA binding molecule comprises CDR-L1, CDR-L2, CDR-L3, CDR-H1, CDR-H2 and CDR-H3 sequences of H3-15 as set forth in Tables 1I-1 and 1I-2. In some embodiments, a BCMA binding molecule comprises CDR-L1, CDR-L2, CDR-L3, CDR-H1, CDR-H2 and CDR-H3 sequences of H3-15 as set forth in Tables 1J-1 and 1J-2. In some embodiments, a BCMA binding molecule comprises CDR-L1, CDR-L2, CDR-L3, CDR-H1, CDR-H2 and CDR-H3 sequences of H3-15 as set forth in Tables 1K-1 and 1K-2. In some embodiments, a BCMA binding molecule comprises CDR-L1, CDR-L2, CDR-L3, CDR-H1, CDR-H2 and CDR-H3 sequences of H3-15 as set forth in Tables 1L-1 and 1L-2. In some embodiments, a BCMA binding molecule comprises CDR-L1, CDR-L2, CDR-L3, CDR-H1, CDR-H2 and CDR-H3 sequences of H3-15 as set forth in Tables 1M-1 and 1M-2. In some embodiments, a BCMA binding molecule comprises CDR-L1, CDR-L2, CDR-L3, CDR-H1, CDR-H2 and CDR-H3 sequences of H3-15 as set forth in Tables 1N-1 and 1N-2.

In some embodiments, a BCMA binding molecule comprises a light chain variable sequence and/or heavy chain variable sequence of AB1 as set forth in Table 1O-1 and Table 1O-2. In some embodiments, a BCMA binding molecule comprises a light chain variable sequence and/or heavy chain variable sequence of AB2 as set forth in Table 1O-1 and Table 1O-2. In some embodiments, a BCMA binding molecule comprises a light chain variable sequence and/or heavy chain variable sequence of R1F2 as set forth in Table 1O-1 and Table 1O-2. In some embodiments, a BCMA binding molecule comprises a light chain variable sequence and/or heavy chain variable sequence of PALF03 as set forth in Table 1O-1 and Table 1O-2. In some embodiments, a BCMA binding molecule comprises a light chain variable sequence and/or heavy chain variable sequence of PALF04 as set forth in Table 1O-1 and Table 1O-2. In some embodiments, a BCMA binding molecule comprises a light chain variable sequence and/or heavy chain variable sequence of PALF05 as set forth in Table 1O-1 and Table 1O-2. In some embodiments, a BCMA binding molecule comprises a light chain variable sequence and/or heavy chain variable sequence of PALF06 as set forth in Table 1O-1 and Table 1O-2. In some embodiments, a BCMA binding molecule comprises a light chain variable sequence and/or heavy chain variable sequence of PALF07 as set forth in Table 1O-1 and Table 1O-2. In some embodiments, a BCMA binding molecule comprises a light chain variable sequence and/or heavy chain variable sequence of PALF08 as set forth in Table 1O-1 and Table 1O-2. In some embodiments, a BCMA binding molecule comprises a light chain variable sequence and/or heavy chain variable sequence of PALF09 as set forth in Table 1O-1 and Table 1O-2. In some embodiments, a BCMA binding molecule comprises a light chain variable sequence and/or heavy chain variable sequence of PALF12 as set forth in Table 1O-1 and Table 1O-2. In some embodiments, a BCMA binding molecule comprises a light chain variable sequence and/or heavy chain variable sequence of PALF13 as set forth in Table 1O-1 and Table 1O-2. In some embodiments, a BCMA binding molecule comprises a light chain variable sequence and/or heavy chain variable sequence of PALF14 as set forth in Table 1O-1 and Table 1O-2. In some embodiments, a BCMA binding molecule comprises a light chain variable sequence and/or heavy chain variable sequence of PALF15 as set forth in Table 1O-1 and Table 1O-2. In some embodiments, a BCMA binding molecule comprises a light chain variable sequence and/or heavy chain variable sequence of PALF16 as set forth in Table 1O-1 and Table 1O-2. In some embodiments, a BCMA binding molecule comprises a light chain variable sequence and/or heavy chain variable sequence of PALF17 as set forth in Table 1O-1 and Table 1O-2. In some embodiments, a BCMA binding molecule comprises a light chain variable sequence and/or heavy chain variable sequence of PALF18 as set forth in Table 1O-1 and Table 1O-2. In some embodiments, a BCMA binding molecule comprises a light chain variable sequence and/or heavy chain variable sequence of PALF19 as set forth in Table 1O-1 and Table 1O-2. In some embodiments, a BCMA binding molecule comprises a light chain variable sequence and/or heavy chain variable sequence of PALF20 as set forth in Table 1O-1 and Table 1O-2. In some embodiments, a BCMA binding molecule comprises a light chain variable sequence and/or heavy chain variable sequence of AB3 as set forth in Table 1O-1 and Table 1O-2. In some embodiments, a BCMA binding molecule comprises a light chain variable sequence and/or heavy chain variable sequence of PI-61 as set forth in Table 1O-1 and Table 1O-2. In some embodiments, a BCMA binding molecule comprises a light chain variable sequence and/or heavy chain variable sequence of H3-1 as set forth in Table 1O-1 and Table 1O-2. In some embodiments, a BCMA binding molecule comprises a light chain variable sequence and/or heavy chain variable sequence of H3-2 as set forth in Table 1O-1 and Table 1O-2. In some embodiments, a BCMA binding molecule comprises a light chain variable sequence and/or heavy chain variable sequence of H3-3 as set forth in Table 1O-1 and Table 1O-2. In some embodiments, a BCMA binding molecule comprises a light chain variable sequence and/or heavy chain variable sequence of H3-4 as set forth in Table 1O-1 and Table 1O-2. In some embodiments, a BCMA binding molecule comprises a light chain variable sequence and/or heavy chain variable sequence of H3-5 as set forth in Table 1O-1 and Table 1O-2. In some embodiments, a BCMA binding molecule comprises a light chain variable sequence and/or heavy chain variable sequence of H3-6 as set forth in Table 1O-1 and Table 1O-2. In some embodiments, a BCMA binding molecule comprises a light chain variable sequence and/or heavy chain variable sequence of H3-7 as set forth in Table 1O-1 and Table 1O-2. In some embodiments, a BCMA binding molecule comprises a light chain variable sequence and/or heavy chain variable sequence of H3-8 as set forth in Table 1O-1 and Table 1O-2. In some embodiments, a BCMA binding molecule comprises a light chain variable sequence and/or heavy chain variable sequence of H3-9 as set forth in Table 1O-1 and Table 1O-2. In some embodiments, a BCMA binding molecule comprises a light chain variable sequence and/or heavy chain variable sequence of H3-10 as set forth in Table 1O-1 and Table 1O-2. In some embodiments, a BCMA binding molecule comprises a light chain variable sequence and/or heavy chain variable sequence of H3-11 as set forth in Table 1O-1 and Table 1O-2. In some embodiments, a BCMA binding molecule comprises a light chain variable sequence and/or heavy chain variable sequence of H3-12 as set forth in Table 1O-1 and Table 1O-2. In some embodiments, a BCMA binding molecule comprises a light chain variable sequence and/or heavy chain variable sequence of H3-13 as set forth in Table 1O-1 and Table 1O-2. In some embodiments, a BCMA binding molecule comprises a light chain variable sequence and/or heavy chain variable sequence of H3-14 as set forth in Table 1O-1 and Table 1O-2. In some embodiments, a BCMA binding molecule comprises a light chain variable sequence and/or heavy chain variable sequence of H3-15 as set forth in Table 1O-1 and Table 1O-2.

In some embodiments, a BCMA binding molecule comprises a scFv sequence of H2/L2-88 as set forth in Table 1P. In some embodiments, a BCMA binding molecule comprises a scFv sequence of H2/L2-36 as set forth in Table 1P. In some embodiments, a BCMA binding molecule comprises a scFv sequence of H2/L2-34 as set forth in Table 1P. In some embodiments, a BCMA binding molecule comprises a scFv sequence of H2/L2-68 as set forth in Table 1P. In some embodiments, a BCMA binding molecule comprises a scFv sequence of H2/L2-18 as set forth in Table 1P. In some embodiments, a BCMA binding molecule comprises a scFv sequence of H2/L2-47 as set forth in Table 1P. In some embodiments, a BCMA binding molecule comprises a scFv sequence of H2/L2-20 as set forth in Table 1P. In some embodiments, a BCMA binding molecule comprises a scFv sequence of H2/L2-80 as set forth in Table 1P. In some embodiments, a BCMA binding molecule comprises a scFv sequence of H2/L2-83 as set forth in Table 1P.

Given that each BCMA binding molecule binds BCMA, and that antigen binding specificity is provided primarily by the CDR-H1, CDR-H2, CDR-H3, CDR-L1, CDR-L2, and CDR-L3 regions, the CDR-H1, CDR-H2, CDR-H3, CDR-L1, CDR-L2, and CDR-L3 sequences can be "mixed and matched". Such "mixed and matched" BCMA binding molecules can be tested using known binding assays and those described in the Examples (e.g., ELISAs). When VH CDR sequences are mixed and matched, the CDR-H1, CDR-H2 and/or CDR-H3 sequence from a particular VH sequence should be replaced with a structurally similar CDR sequence(s). Likewise, when VL CDR sequences are mixed and matched, the CDR-L1, CDR-L2 and/or CDR-L3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from CDR sequences shown herein for monoclonal antibodies or other BCMA binding molecules of the present disclosure.

In some embodiments, a BCMA binding molecule comprises a VL sequence selected from the VL sequences set forth in Table 1O-1 and a VH sequence selected the VH sequences set forth in Table 1O-2. In some embodiments, a BCMA binding molecule comprises a CDR-H1 sequence selected from the CDR-H1 sequences set forth in Table 1A-2, Table 1B-2, Table 1C-2, Table 1D-2, Table 1E-2, Table 1F-2, Table 1G-2, Table 1H-2, Table 1I-2, Table 1J-2, Table 1K-2, Table 1L-2, Table 1M-2, and Table 1N-2; a CDR-H2 sequence selected from the CDR-H2 sequences set forth in Table 1A-2, Table 1B-2, Table 1C-2, Table 1D-2, Table 1E-2, Table 1F-2, Table 1G-2, Table 1H-2, Table 1I-2, Table 1J-2, Table 1K-2, Table 1L-2, Table 1M-2, and Table 1N-2; a CDR-H3 sequence selected from the CDR-H3 sequences set forth in Table 1A-2, Table 1B-2, Table 1C-2, Table 1D-2, Table 1E-2, Table 1F-2, Table 1G-2, Table 1H-2, Table 1I-2, Table 1J-2, Table 1K-2, Table 1L-2, Table 1M-2, and Table 1N-2; a CDR-L1 sequence selected from the CDR-L1 sequences set forth in Table 1A-1, Table 1B-1, Table 1C-1, Table 1D-1, Table 1E-1, Table 1F-1, Table 1G-1, Table 1H-1, Table 1I-1, Table 1J-1, Table 1K-1(a), Table 1K-1(b), Table 1L-1, Table 1M-1, Table 1N-1(a), and Table 1N-1(b); a CDR-L2 sequence selected from the CDR-L2 sequences set forth in Table 1A-1, Table 1B-1, Table 1C-1, Table 1D-1, Table 1E-1, Table 1F-1, Table 1G-1, Table 1H-1, Table 1I-1, Table 1J-1, Table 1K-1(a), Table 1K-1(b), Table 1L-1, Table 1M-1, Table 1N-1(a), and Table 1N-1(b); and a CDR-L3 sequence selected from the CDR-L3 sequences set forth in Table 1A-1, Table 1B-1, Table 1C-1, Table 1D-1, Table 1E-1, Table 1F-1, Table 1G-1, Table 1H-1, Table 1I-1, Table 1J-1, Table 1K-1(a), Table 1K-1(b), Table 1L-1, Table 1M-1, Table 1N-1(a), and Table 1N-1(b).

The BCMA binding molecules can be fused or chemically conjugated (including both covalent and non-covalent conjugations) to a heterologous protein or polypeptide (or fragment thereof, for example to a polypeptide of at least 10, at least 20, at least 30, at least 40, at least 50, at least 60, at least 70, at least 80, at least 90 or at least 100 amino acids). For example, a BCMA binding molecule can be fused directly or indirectly to a detectable protein, e.g., an enzyme or a fluorescent protein such as those described in Section 7.10. Methods for fusing or conjugating proteins, polypeptides, or peptides to an antibody or an antibody fragment are known and can be used to fuse or conjugate a protein or polypeptide to a BCMA binding molecule of the disclosure. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., (1991) Proc. Natl. Acad. Sci. USA 88:10535-10539; Zheng et al., (1995) J. Immunol. 154:5590-5600; and Vil et al., (1992) Proc. Natl. Acad. Sci. USA 89:11337-11341.

Additional BCMA binding molecules can be generated through the techniques of gene-shuffling, motif-shuffling, exon-shuffling, and/or codon-shuffling (collectively referred to as "DNA shuffling"). DNA shuffling can be employed to alter the activities of molecules of the disclosure or fragments thereof (e.g., molecules or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313.

The BCMA binding molecules described herein or fragments thereof can be altered by being subjected to random mutagenesis by error-prone PCR, random nucleotide insertion or other methods prior to recombination. A polynucleotide encoding a fragment of a BCMA binding molecule described herein can be recombined with one or more components, motifs, sections, parts, domains, fragments, etc. of one or more heterologous molecules.

Moreover, BCMA binding molecules can be fused to marker sequences, such as a peptide to facilitate purification. In some embodiments, the marker amino acid sequence is a hexa-histidine peptide (SEQ ID NO:603), such as the tag provided in a pQE vector (QIAGEN, Inc., 9259 Eton Avenue, Chatsworth, CA, 91311), among others, many of which are commercially available. As described in Gentz et al., (1989) Proc. Natl. Acad. Sci. USA 86:821-824, for instance, hexa-histidine (SEQ ID NO:603) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "flag" tag.

7.3. Antigen Binding Domains of Multispecific Binding Molecules

Typically, one or more ABDs of the MBMs comprise immunoglobulin-based antigen-binding domains, for example the sequences of antibody fragments or derivatives as described in Section 7.2. These antibody fragments and derivatives typically include the CDRs of an antibody and can include larger fragments and derivatives thereof, e.g., Fabs, scFabs, Fvs, and scFvs.

7.3.1. Immunoglobulin Based ABDs
7.3.1.1. Fabs

In certain aspects, MBMs comprise one or more ABDs that are Fab domains, e.g., as described in Section 7.2.

For the MBMs of the disclosure, it is advantageous to use Fab heterodimerization strategies to permit the correct association of Fab domains belonging to the same ABD and minimize aberrant pairing of Fab domains belonging to different ABDs. For example, the Fab heterodimerization strategies shown in Table 2 below can be used:

Accordingly, in certain embodiments, correct association between the two polypeptides of a Fab is promoted by exchanging the VL and VH domains of the Fab for each other or exchanging the CH1 and CL domains for each other, e.g., as described in WO 2009/080251.

Correct Fab pairing can also be promoted by introducing one or more amino acid modifications in the CH1 domain and one or more amino acid modifications in the CL domain of the Fab and/or one or more amino acid modifications in the VH domain and one or more amino acid modifications in the VL domain. The amino acids that are modified are typically part of the VH:VL and CH1:CL interface such that the Fab components preferentially pair with each other rather than with components of other Fabs.

In one embodiment, the one or amino acid modifications are limited to the conserved framework residues of the variable (VH, VL) and constant (CH1, CL) domains as indicated by the Kabat numbering of residues. Almagro, 2008, Frontiers In Bioscience 13:1619-1633 provides a definition of the framework residues on the basis of Kabat, Chothia, and IMGT numbering schemes.

In one embodiment, the modifications introduced in the VH and CH1 and/or VL and CL domains are complementary to each other. Complementarity at the heavy and light chain interface can be achieved on the basis of steric and hydrophobic contacts, electrostatic/charge interactions or any combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces.

In one embodiment, the one or more introduced modifications introduce a new hydrogen bond across the interface of the Fab components. In one embodiment, the one or more introduced modifications introduce a new salt bridge across the interface of the Fab components. Exemplary substitutions are described in WO 2014/150973 and WO 2014/082179.

In some embodiments, the Fab domain comprises a 192E substitution in the CH1 domain and 114A and 137K substi-

TABLE 2

Fab Heterodimerization Strategies

| Name | STRATEGY | VH | CH1 | VL | CL | REFERENCE |
|------|----------|-----|-----|-----|-----|-----------|
| F1 | CrossMabCH1-CL | WT | CL domain | WT | CH1 domain | Schaefer et al., 2011, Cancer Cell 2011; 20: 472-86; PMID: 22014573. |
| F2 | orthogonal Fab VHVRD1CH1CRD2-VLVRD1CλCRD2 | 39K, 62E | H172A, F174G | 1R, 38D, (36F) | L135Y, S176W | Lewis et al., 2014, Nat Biotechnol 32: 191-8 |
| F3 | orthogonal Fab VHVRD2CH1wt-VLVRD2Cλwt | 39Y | WT | 38R | WT | Lewis et al., 2014, Nat Biotechnol 32: 191-8 |
| F4 | TCR CαCβ | 39K | TCR Cα | 38D | TCR Cβ | Wu et al., 2015, MAbs 7: 364-76 |
| F5 | CR3 | WT | T192E | WT | N137K, S114A | Golay at al., 2016, J Immunol 196: 3199-211. |
| F6 | MUT4 | WT | L143Q, S188V | WT | V133T, S176V | Golay at al., 2016, J Immunol 196: 3199-211. |
| F7 | DuetMab | WT | F126C | WT | S121C | Mazor et al., 2015, MAbs 7: 377-89; Mazor et al., 2015, MAbs 7: 461-669. | tutions in the CL domain, which introduces a salt-bridge between the CH1 and CL domains (see, Golay et al., 2016, J Immunol 196:3199-211).

In some embodiments, the Fab domain comprises a 143Q and 188V substitutions in the CH1 domain and 113T and 176V substitutions in the CL domain, which serves to swap hydrophobic and polar regions of contact between the CH1 and CL domain (see, Golay et al., 2016, J Immunol 196: 3199-211).

In some embodiments, the Fab domain can comprise modifications in some or all of the VH, CH1, VL, CL domains to introduce orthogonal Fab interfaces which promote correct assembly of Fab domains (Lewis et al., 2014 Nature Biotechnology 32:191-198). In an embodiment, 39K, 62E modifications are introduced in the VH domain, H172A, F174G modifications are introduced in the CH1 domain, 1R, 38D, (36F) modifications are introduced in the VL domain, and L135Y, S176W modifications are introduced in the CL domain. In another embodiment, a 39Y modification is introduced in the VH domain and a 38R modification is introduced in the VL domain.

Fab domains can also be modified to replace the native CH1:CL disulfide bond with an engineered disulfide bond, thereby increasing the efficiency of Fab component pairing. For example, an engineered disulfide bond can be introduced by introducing a 126C in the CH1 domain and a 121C in the CL domain (see, Mazor et al., 2015, MAbs 7:377-89).

Fab domains can also be modified by replacing the CH1 domain and CL domain with alternative domains that promote correct assembly. For example, Wu et al., 2015, MAbs 7:364-76, describes substituting the CH1 domain with the constant domain of the α T cell receptor and substituting the CL domain with the β domain of the T cell receptor, and pairing these domain replacements with an additional charge-charge interaction between the VL and VH domains by introducing a 38D modification in the VL domain and a 39K modification in the VH domain.

MBMs can comprise one or more ABDs that are single chain Fab fragments, e.g., as described in Section 7.2.

7.3.1.2. scFvs

In certain aspects, MBMs comprise one or more ABDs that are scFvs, e.g., as described in Section 7.2.

7.3.1.3. Other Immunoglobulin-Based ABDs

MBMs can also comprise ABDs having an immunoglobulin format which is other than Fab or scFv, for example Fv, dsFv, (Fab')2, a single domain antibody (SDAB), a VH or VL domain, or a camelid VHH domain (also called a nanobody).

An ABD can be a single domain antibody composed of a single VH or VL domain which exhibits sufficient affinity to the target. In an embodiment, the single domain antibody is a camelid VHH domain (see, e.g., Riechmann, 1999, Journal of Immunological Methods 231:25-38; WO 94/04678).

7.3.2. Non-Immunoglobulin Based ABDs

In certain embodiments, MBMs comprise one or more of the ABDs that are derived from non-antibody scaffold proteins (including, but not limited to, designed ankyrin repeat proteins (DARPins), Avimers (short for avidity multimers), Anticalin/Lipocalins, Centyrins, Kunitz domains, Adnexins, Affilins, Affitins (also known as Nonfitins), Knottins, Pronectins, Versabodies, Duocalins, and Fynomers), ligands, receptors, cytokines or chemokines.

Non-immunoglobulin scaffolds that can be used in the MBMs include those listed in Tables 3 and 4 of Mintz and Crea, 2013, Bioprocess International 11(2):40-48; in FIG. 1, Table 1 and Figure I of Vazquez-Lombardi et al., 2015, Drug Discovery Today 20(10):1271-83; in Table 1 and Box 2 of Skrlec et al., 2015, Trends in Biotechnology 33(7):408-18. The contents of Tables 3 and 4 of Mintz and Crea, 2013, Bioprocess International 11(2):40-48; in FIG. 1, Table 1 and Figure I of Vazquez-Lombardi et al., 2015, Drug Discovery Today 20(10):1271-83; in Table 1 and Box 2 of Skrlec et al., 2015, Trends in Biotechnology 33(7):408-18 (collectively, "Scaffold Disclosures") are incorporated by reference herein. In a particular embodiment, the Scaffold Disclosures are incorporated by reference for what they disclose relating to Adnexins. In another embodiment, the Scaffold Disclosures are incorporated by reference for what they disclose relating to Avimers. In another embodiment, the Scaffold Disclosures are incorporated by reference for what they disclose relating to Affibodies. In yet another embodiment, the Scaffold Disclosures are incorporated by reference for what they disclose relating to Anticalins. In yet another embodiment, the Scaffold Disclosures are incorporated by reference for what they disclose relating to DARPins. In yet another embodiment, the Scaffold Disclosures are incorporated by reference for what they disclose relating to Kunitz domains. In yet another embodiment, the Scaffold Disclosures are incorporated by reference for what they disclose relating to Knottins. In yet another embodiment, the Scaffold Disclosures are incorporated by reference for what they disclose relating to Pronectins. In yet another embodiment, the Scaffold Disclosures are incorporated by reference for what they disclose relating to Nanofitins. In yet another embodiment, the Scaffold Disclosures are incorporated by reference for what they disclose relating to Affilins. In yet another embodiment, the Scaffold Disclosures are incorporated by reference for what they disclose relating to Adnectins. In yet another embodiment, the Scaffold Disclosures are incorporated by reference for what they disclose relating to ABDs. In yet another embodiment, the Scaffold Disclosures are incorporated by reference for what they disclose relating to Adhirons. In yet another embodiment, the Scaffold Disclosures are incorporated by reference for what they disclose relating to Affimers. In yet another embodiment, the Scaffold Disclosures are incorporated by reference for what they disclose relating to Alphabodies. In yet another embodiment, the Scaffold Disclosures are incorporated by reference for what they disclose relating to Armadillo Repeat Proteins. In yet another embodiment, the Scaffold Disclosures are incorporated by reference for what they disclose relating to Atrimers/Tetranectins. In yet another embodiment, the Scaffold Disclosures are incorporated by reference for what they disclose relating to Obodies/OB-folds. In yet another embodiment, the Scaffold Disclosures are incorporated by reference for what they disclose relating to Centyrins. In yet another embodiment, the Scaffold Disclosures are incorporated by reference for what they disclose relating to Repebodies. In yet another embodiment, the Scaffold Disclosures are incorporated by reference for what they disclose relating to Anticalins. In yet another embodiment, the Scaffold Disclosures are incorporated by reference for what they disclose relating to Atrimers. In yet another embodiment, the Scaffold Disclosures are incorporated by reference for what they disclose relating to bicyclic peptides. In yet another embodiment, the Scaffold Disclosures are incorporated by reference for what they disclose relating to cys-knots. In yet another embodiment, the Scaffold Disclosures are incorporated by reference for what they disclose relating to Fn3 scaffolds (including Adnectins, Centryrins, Pronectins, and Tn3).

In an embodiment, an ABD can be a designed ankyrin repeat protein ("DARPin"). DARPins are antibody mimetic proteins that typically exhibit highly specific and high-affinity target protein binding. They are typically genetically engineered and derived from natural ankyrin proteins and consist of at least three, usually four or five repeat motifs of these proteins. Their molecular mass is about 14 or 18 kDa (kilodaltons) for four- or five-repeat DARPins, respectively. Examples of DARPins can be found, for example in U.S. Pat. No. 7,417,130. Multispecific binding molecules comprising DARPin binding modules and immunoglobulin-based binding modules are disclosed in, for example, U.S. Publication No. 2015/0030596 A1.

In another embodiment, an ABD can be an Affibody. An Affibody is well known and refers to affinity proteins based on a 58 amino acid residue protein domain, derived from one of the IgG binding domain of staphylococcal protein A.

In another embodiment, an ABD can be an Anticalin. Anticalins are well known and refer to another antibody mimetic technology, where the binding specificity is derived from Lipocalins. Anticalins may also be formatted as dual targeting protein, called Duocalins.

In another embodiment, an ABD can be a Versabody. Versabodies are well known and refer to another antibody mimetic technology. They are small proteins of 3-5 kDa with >15% cysteines, which form a high disulfide density scaffold, replacing the hydrophobic core of typical proteins.

Other non-immunoglobulin ABDs include "A" domain oligomers (also known as Avimers) (see for example, U.S. Patent Application Publication Nos. 2005/0164301, 2005/0048512, and 2004/017576), Fn3 based protein scaffolds (see for example, U.S. Patent Application Publication 2003/0170753), VASP polypeptides, Avian pancreatic polypeptide (aPP), Tetranectin (based on CTLD3), Affililin (based on γB-crystallin/ubiquitin), Knottins, SH3 domains, PDZ domains, Tendamistat, Neocarzinostatin, Protein A domains, Lipocalins, Transferrin, and Kunitz domains. In one aspect, ABDs useful in the construction of the MBMs comprise fibronectin-based scaffolds as exemplified in WO 2011/130324.

Moreover, in certain aspects, an ABD comprises a ligand binding domain of a receptor or a receptor binding domain of a ligand.

7.3.3. TCR ABDs

The MBMs contain an ABD that specifically binds to BCMA and at least one ABD which is specific for a different antigen, e.g., a component of a TCR complex. The TCR is a disulfide-linked membrane-anchored heterodimeric protein normally consisting of the highly variable alpha (α) and beta (β) chains expressed as part of a complex with the invariant CD3 chain molecules. T cells expressing this receptor are referred to as α:β (or αβ) T cells, though a minority of T cells express an alternate receptor, formed by variable gamma (γ) and delta (δ) chains, referred as γδ T cells.

In an embodiment, MBMs contain an ABD that specifically binds to CD3.

7.3.3.1. CD3 ABDs

The MBMs can contain an ABD that specifically binds to CD3. The term "CD3" refers to the cluster of differentiation 3 co-receptor (or co-receptor complex, or polypeptide chain of the co-receptor complex) of the T cell receptor. The amino acid sequence of the polypeptide chains of human CD3 are provided in NCBI Accession P04234, P07766 and P09693. CD3 proteins can also include variants. CD3 proteins can also include fragments. CD3 proteins also include post-translational modifications of the CD3 amino acid sequences. Post-translational modifications include, but are not limited to, N- and O-linked glycosylation.

In some embodiments, a MBM can comprise an ABD which is an anti-CD3 antibody (e.g., as described in US 2016/0355600, WO 2014/110601, and WO 2014/145806) or an antigen-binding domain thereof. Exemplary anti-CD3 VH, VL, and scFV sequences that can be used in a MBM are provided in Table 3A.

TABLE 3A

| Binding Domain | Chain | Sequence | SEQ ID NO: |
|---|---|---|---|
| CD3-1 | VH | QVQLQQSGAELARPGASVKMSCKASGYTFTRYTMHWVKQRPGQGLEWIGYINPSRGYTNYNQKFKDKATLTTDKSSSTAYMQLSSLTSEDSAVYYCARYYDDHYCLDYWGQGTTLTVSS | 256 |
|  | VL | QIVLTQSPAIMSASPGEKVTMTCSASSSVSYMNWYQQKSGTSPKRWIYDTSKLASGVPAHFRGSGSGTSYSLTISGMEAEDAATYYCQQWSSNPFTFGSGTKLEIN | 257 |
| CD3-2 | VH | EVQLVESGGGLVQPKGSLKLSCAASGFTFNTYAMNWVRQAPGKGLEWVARIRSKYNNYATYYADSVKDRFTISRDDSQSILYLQMNNLKTEDTAMYYCVRHGNFGNSYVSWFAYWGQGTLVTVSA | 258 |
|  | VL | QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWVFGGGTKLTVL | 259 |
| CD3-3 | VH | QVQLQQSGAELARPGASVKMSCKASGYTFTSYTMHWVKQRPGQGLEWIGYINPSSGYTKYNQKFKDKATLTADKSSSTAYMQLSSLTSEDSAVYYCARWQDYDVYFDYWGQGTTLTVSS | 260 |
|  | VL | QIVLSQSPAILSASPGEKVTMTCRASSSVSYMHWYQQKPGSSPKPWIYATSNLASGVPARFSGSGSGTSYSLTISRVEAEDAATYYCQQWSSNPPTFGGGTKLETK | 261 |
| CD3-4 | VH | QVQLQQSGAELARPGASVKMSCKASGYTFTRYTMHWVKQRPGQGLEWIGYINPSRGYTNYNQKFKDKATLTTDKSSSTAYMQLSSLTSEDSAVYYCARYYDDHYCLDYWGQGTTLTVSS | 256 |
|  | VL | QIVLTQSPAIMSASPGEKVTMTCRASSSVSYMNWYQQKSGTSPKRWIYDTSKVASGVPYRFSGSGSGTSYSLTISSMEAEDAATYYCQQWSSNPLTFGSGTKLEIN | 262 |

TABLE 3A-continued

CD3 Binders - Variable domain sequences

| Binding Domain | Chain | Sequence | SEQ ID NO: |
|---|---|---|---|
| CD3-5 | VH | QVQLVQSGGGVVQPGRSLRLSCKASGYTFTRYTMHWVRQAPGKG LEWIGYINPSRGYTNYNQKVKDRFTISRDNSKNTAFLQMDSLRPEDT GVYFCARYYDDHYCLDYWGQGTPVTSS | 263 |
|  | VL | DIQMTQSPSSLSASVGDRVTITCSASSSVSYMNWYQQTPGKAPKR WIYDTSKLASGVPSRFSGSGSGTDYTFTISSLQPEDIATYYCQQWS SNPFTFGQGTKLQIT | 264 |
| CD3-6 | VH | QVQLVESGGGVVQPGRSLRLSCAASGFKFSGYGMHWVRQAPGKG LEWVAVIWYDGSKKYYVDSVKGRFTISRDNSKNTLYLQMNSLRAED TAVYYCARQMGYWHFDLWGRGTLVTVSS | 265 |
|  | VL | EIVLTQSPATLSLSPGERATLSCRASQSVSSYLAWYQQKPGQAPRL LIYDASNRATGIPARFSGSGSGTDFTLTISSLEPEDFAVYYCQQRSN WPPLTFGGGTKVEIK | 266 |
| CD3-7 | VH | EVQLVESGGGLVQPGGSLRLSCAASGFTFSTYAMNWVRQAPGKGL EWVGRIRSKYNNYATYYADSVKDRFISRDDSKNSLYLQMNSLKTED TAVYYCVRHGNFGNSYVSWFAYWGQGTLVTVSS | 267 |
|  | VL | QAVVTQEPSLTVSPGGTVTLTCRSSTGAVTTSNYANWVQQKPGQA PRGLIGGTNKRAPWTPARFSGSLLGGKAALIGAQAEDEADYYCALW YSNLWVFGGGTKLTVL | 268 |
| CD3-8 | VH | DIKLQQSGAELARPGASVKMSCKTSGYTFTRYTMHWVKQRPGQGL EWIGYINPSRGYTNYNQKFKDKATLTTDKSSSTAYMQLSSLTSEDSA VYYCARYYDDHYCLDYWGQGTTLTVSS | 269 |
|  | VL | DIQLTQSPAIMSASPGEKVTMTCRASSSVSYMNWYQQKSGTSPKR WIYDTSKVASGVPYRFSGSGSGTSYSLISSMEAEDAATYYCQQWS SNPLTFGAGTKLELK | 270 |
| CD3-9 | VH | EVQLVESGGGLVQPGGSLRLSCAASGFTFNTYAMNWVRQAPGKG LEWVARIRSKYNNYATYYADSVKDRFISRDDSKNSLYLQMNSLKTE DTAVYYCVRHGNFGNSYVSWFAYWGQGTLVTVSS | 271 |
|  | VL | QAVVTQEPSLTVSPGGTVTLTCRSSTGAVTTSNYANWVQQKPGQA PRGLIGGTNKRAPWTPARFSGSLLGGKAALIGAQAEDEADYYCALW YSNLWVFGGGTKLTVL | 268 |
| CD3-10 | VH | EVKLLESGGGLVQPGKGSLKLSCAASGFTFNTYAMNWVRQAPGKGL EWVARIRSKYNNYATYYADSVKDRFTISRDDSQSILYLQMNNLKTED TAMYYCVRHGNFGNSYVSWFAYWGQGTLVTVSA | 272 |
|  | VL | QAVVTQESALTTSPGETVTLTCRSSTGAVTTSNYANWVQEKPDHLF TGLIGGTNKRAPGVPARFSGSLIGDKAALTITGAQTEDEAIYFCALWY SNLWVFGGGTKLTVL | 259 |
| CD3-11 | VH | EVQLVESGGGLVQPGGSLKLSCAASGFTFNSYAMNWVRQAPGKG LEWVARIRSKYNNYATYYADSVKGRFTISRDDSKNTAYLQMNNLKT EDTAVYYCVRHGNFGNSYVSWWAYWGQGTLVTVSS | 273 |
|  | VL | QTVVTQEPSLTVSPGGTVTLTCGSSTGAVTSGNYPNWVQQKPGQA PRGLIGGTKFLAPGTPQRFSGSLLGGKAALTLSGVQPEDEAEYYCV LWYSNRWVFGGGTKLTVL | 274 |
| CD3-12 | VH | EVQLVESGGGLVQPGGSLKLSCAASGFTFNKYAMNWVRQAPGKG LEWVARIRSKYNNYATYYADSVKDRFTISRDDSKNTAYLQMNNLKT EDTAVYYCVRHGNFGNSYISYWAYWGQGTLVTVSS | 275 |
|  | VL | QTVVTQEPSLTVSPGGTVTLTCGSSTGAVTSGNYPNWVQQKPGQA PRGLIGGTKFLAPGTPARFSGSLLGGKAALTLSGVQPEDEAEYYCVL WYSNRWVFGGGTKLTVL | 276 |
| CD3-13 | VH | QVQLVQSGAEVKKPGASVKVSCKASGYTFTRYTMHWVRQAPGQG LEWMGYINPSRGYTNYNQKFKDRVTMTTDTSISTAYMELSRLRSDD TAVYYCARYYDDHYCLDYWGQGTLVTVSS | 277 |
|  | VL | EIVLTQSPATLSLSPGERATLSCSASSSVSYMNWYQQKPGQAPRLLI YDTSKLASGVPAHFRGSGSGTDFTLTISSLEPEDFAVYYCQQWSSN PFTFGQGTKVEIK | 278 |
| CD3-14 | VH | EVQLVESGGGLVQPGGSLRLSCAASGFTFSTYAMNWVRQAPGKGL EWVSRIRSKYNNYATYYADSVKDRFTISRDDSKNTLYLQMNSLRAE DTAVYYCARHGNFGNSYVSWFAYWGQGTMVTVSS | 279 |
|  | VL | QAVVTQEPSLTVSPGGTVTLTCRSSTGAVTTSNYANVVQQKPGQA PRGLIGGTNKRAPGTPARFSGSLLGGKAALTLSGVQPEDEAEYYCA LWYSNLWVFGGGTKLTVL | 280 |
| CD3-15 | VH | EVQLVESGGGLVQPGGSLRLSCAASGFTFNTYAMNWVRQAPGKG LEWVGRIRSKYNNYATYYADSVKDRFTISRDDSKNSLYLQMNSLKT EDTAVYYCVRHGNFGNSYVSWFAYWGQGTLVTVSS | 281 |

TABLE 3A-continued

CD3 Binders - Variable domain sequences

| Binding Domain | Chain | Sequence | SEQ ID NO: |
|---|---|---|---|
| | VL | QAVVTQEPSLTVSPGGTVTLTCRSSTGAVTTSNYANWVQEKPGQA PRGLIGGTNKRAPVVTPARFSGSLLGGKAALTITGAQAEDEADYYCA LWYSNLWVFGGGTKLTVL | 282 |
| CD3-16 | VH | EVQLVESGGGLVQPGGSLRLSCAASGFTFNTYAMNWVRQAPGKG LEWVGRIRSKYNNYATYYADSVKGRFTISRDDSKNTLYLQMNSLRA EDTAVYYCVRHGNFGNSYVSWFAYWGQGTLVTVSS | 283 |
| | VL | QAVVTQEPSLTVSPGGTVTLTCGSSTGAVTTSNYANWVQQKPGQA PRGLIGGTNKRAPGVPARFSGSLLGGKAALTLSGAQPEDEAEYYCA LWYSNLWVFGGGTKLTVL | 284 |
| CD3-17 | VH | EVQLVESGGGLVQPGGSLRLSCAASGFTFSTYAMNWVRQAPGKGL EWVGRIRSKYNNYATYYADSVKGRFTISRDDSKNTLYLQMNSLRAE DTAVYYCVRHGNFGDSYVSWFAYWGQGTLVTVSS | 285 |
| | VL | QAVVTQEPSLTVSPGGTVTLTCGSSTGAVTTSNYANWVQQKPGKS PRGLIGGTNKRAPGVPARFSGSLLGGKAALTISGAQPEDEADYYCA LWYSNHWVFGGGTKLTVL | 286 |
| CD3-18 | VH | QVQLVQSGGGVVQPGRSLRLSCKASGYTFTRYTMHWVRQAPGKG LEWIGYINPSRGYTNYNQKVKDRFTISRDNSKNTAFLQMDSLRPEDT GVYFCARYYDDHYCLDYWGQGTPVTVSS | 263 |
| | VL | DIQMTQSPSSLSASVGDRVTITCSASSSVSYMNWYQQTPGKAPKR WIYDTSKLASGVPSRFSGSGSGTDYTFTISSLQPEDIATYYCQQWS SNPFTFGQGT | 287 |
| CD3-19 | VH | QVQLVQSGGGVVQPGRSLRLSCKASGYTFTRYTMHWVRQAPGKG LEWIGYINPSRGYTNYNQKVKDRFTISRDNSKNTAFLQMDSLRPEDT GVYFCARYYDDHYSLDYWGQGTPVTVSS | 288 |
| | VL | DIQMTQSPSSLSASVGDRVTITCSASSSVSYMNWYQQTPGKAPKR WIYDTSKLASGVPSRFSGSGSGTDYTFTISSLQPEDIATYYCQQWS SNPFTFGQGT | 287 |
| CD3-20 | VH | EVQLQQSGPELVKPGASMKISCKASGYSFTGYTMNWVKQSHGKNL EWMGLINPYKGVSTYNQKFKDKATLTVDKSSSTAYMELLSLTSEDS AVYYCARSGYYGDSDWYFDVWGQGTTLTVFS | 289 |
| | VL | DIQMTQTTSSLSASLGDRVTISCRASQDIRNYLNWYQQKPDGTVKLL IYYTSRLHSGVPSKFSGSGSGTDYSLTISNLEQEDIATYFCQQGNTL PVVTFAGGTKLEIK | 290 |
| CD3-21 | VH | EVQLVESGGGLVQPGGSLRLSCAASGFTFNTYAMNWVRQAPGKG LEWVGRIRSKYNNYATYYADSVKGRFTISRDDSKNTLYLQMNSLRA EDTAVYYCVRHGNFGNSYVSWFAYWGQGTLVTVSS | 283 |
| | VL | QAVVTQEPSLTVSPGGTVTLTCGSSTGAVTTSNYANWVQQKPGQA PRGLIGGTNKRAPGVPARFSGSLLGGKAALTLSGAQPEDEAEYYCA LWYSNLWVFGGGTKLTVL | 284 |
| | scFv | EVQLVESGGGLVQPGGSLRLSCAASGFTFNTYAMNWVRQAPGKG LEWVGRIRSKYNNYATYYADSVKGRFTISRDDSKNTLYLQMNSLRA EDTAVYYCVRHGNFGNSYVSWFAYWGQGTLVTVSSGGGGSGGG GSGGGGSQAVVTQEPSLTVSPGGTVTLTCGSSTGAVTTSNYANWV QQKPGQAPRGLIGGTNKRAPGVPARFSGSLLGGKAALTLSGAQPE DEAEYYCALWYSNLWVFGGGTKLTVLGSHHHHHH | 291 |
| CD3-22 | VH | EVQLVESGGGLVQPGGSLRLSCAASGFTFSTYAMNWVRQAPGKGL EWVGRIRSKYNNYATYYADSVKGRFTISRDDSKNTLYLQMNSLRAE DTAVYYCVRHGNFGDSYVSWFAYWGQGTLVTVSS | 285 |
| | VL | QAVVTQEPSLTVSPGGTVTLTCGSSTGAVTTSNYANWVQQKPGKS PRGLIGGTNKRAPGVPARFSGSLLGGKAALTISGAQPEDEADYYCA LWYSNHWVFGGGTKLTVL | 286 |
| | scFv | EVQLVESGGGLVQPGGSLRLSCAASGFTFSTYAMNWVRQAPGKGL EWVGRIRSKYNNYATYYADSVKGRFTISRDDSKNTLYLQMNSLRAE DTAVYYCVRHGNFGDSYVSWFAYWGQGTLVTVSSGKPGSGKPGS GKPGSGKPGSQAVVTQEPSLTVSPGGTVTLTCGSSTGAVTTSNYA NWVQQKPGKSPRGLIGGTNKRAPGVPARFSGSLLGGKAALTISGA QPEDEADYYCALWYSNHWVFGGGTKLTVL | 292 |
| CD3-23 | VH | EVQLVESGGGLVQPGGSLRLSCAASGFTFSTYAMNWVRQAPGKGL EWVGRIRSKANNYATYYADSVKGRFTISRDDSKNTLYLQMNSLRAE DTAVYYCVRHGNFGDSYVSWFAYWGQGTLVTVSS | 293 |
| | VL | QAVVTQEPSLTVSPGGTVTLTCGSSTGAVTTSNYANWVQQKPGKS PRGLIGGTNKRAPGVPARFSGSLLGGKAALTISGAQPEDEADYYCA LWYSNHWVFGGGTKLTVL | 286 |

TABLE 3A-continued

CD3 Binders - Variable domain sequences

| Binding Domain | Chain | Sequence | SEQ ID NO: |
|---|---|---|---|
| | scFv | EVQLVESGGGLVQPGGSLRLSCAASGFTFSTYAMNWVRQAPGKGL EWVGRIRSKANNYATYYADSVKGRFTISRDDSKNTLYLQMNSLRAE DTAVYYCVRHGNFGDSYVSWFAYWGQGTLVTVSSGKPGSGKPGS GKPGSGKPGSQAVVTQEPSLTVSPGGTVTLTCGSSTGAVTTSNYA NWVQQKPGKSPRGLIGGTNKRAPGVPARFSGSLLGGKAALTISGA QPEDEADYYCALWYSNHWVFGGGTKLTVL | 294 |
| CD3-24 | VH | EVQLVESGGGLVQPGGSLRLSCAASGFTFSTYAMNWVRQAPGKGL EWVGRIRSKYNNYATYYADSVKGRFTISRDDSKNTLYLQMNSLRAE DTAVYYCVRHGNFGDEYVSWFAYWGQGTLVTVSS | 295 |
| | VL | QAVVTQEPSLTVSPGGTVTLTCGSSTGAVTTSNYANWVQQKPGKS PRGLIGGTNKRAPGVPARFSGSLLGGKAALTISGAQPEDEADYYCA LWYSNHWVFGGGTKLTVL | 286 |
| | scFv | EVQLVESGGGLVQPGGSLRLSCAASGFTFSTYAMNWVRQAPGKGL EWVGRIRSKYNNYATYYADSVKGRFTISRDDSKNTLYLQMNSLRAE DTAVYYCVRHGNFGDEYVSWFAYWGQGTLVTVSSGKPGSGKPGS GKPGSGKPGSQAVVTQEPSLTVSPGGTVTLTCGSSTGAVTTSNYA NWVQQKPGKSPRGLIGGTNKRAPGVPARFSGSLLGGKAALTISGA QPEDEADYYCALWYSNHWVFGGGTKLTVL | 296 |
| CD3-25 | VH | EVQLVESGGGLVQPGGSLRLSCAASGFTFSTYAMNWVRQAPGKGL EWVGRIRSKYNNYATYYADSVKGRFTISRDDSKNTLYLQMNSLRAE DTAVYYCVRHGNFGDPYVSWFAYWGQGTLVTVSS | 297 |
| | VL | QAVVTQEPSLTVSPGGTVTLTCGSSTGAVTTSNYANWVQQKPGKS PRGLIGGTNKRAPGVPARFSGSLLGGKAALTISGAQPEDEADYYCA LWYSNHWVFGGGTKLTVL | 286 |
| | scFv | EVQLVESGGGLVQPGGSLRLSCAASGFTFSTYAMNWVRQAPGKGL EVWGRIRSKYNNYATYYADSVKGRFTISRDDSKNTLYLQMNSLRAE DTAVYYCVRHGNFGDPYVSWFAYWGQGTLVTVSSGKPGSGKPGS GKPGSGKPGSQAVVTQEPSLTVSPGGTVTLTCGSSTGAVTTSNYA NWVQQKPGKSPRGLIGGTNKRAPGVPARFSGSLLGGKAALTISGA QPEDEADYYCALWYSNHWVFGGGTKLTVL | 298 |
| CD3-26 | VH | EVQLVESGGGLVQPGGSLRLSCAASGFTFSTYAMNWVRQAPGKGL EVWGRIRSKYNNYATYYADSVKGRFTISRDDSKNTLYLQMNSLRAE DTAVYYCVRHGNFGDSYVSWFDYWGQGTLVTVSS | 299 |
| | VL | QAVVTQEPSLTVSPGGTVTLTCGSSTGAVTTSNYANWVQQKPGKS PRGLIGGTNKRAPGVPARFSGSLLGGKAALTISGAQPEDEADYYCA LWYSNHWVFGGGTKLTVL | 286 |
| | scFv | EVQLVESGGGLVQPGGSLRLSCAASGFTFSTYAMNWVRQAPGKGL EWVGRIRSKYNNYATYYADSVKGRFTISRDDSKNTLYLQMNSLRAE DTAVYYCVRHGNFGDSYVSWFDYWGQGTLVTVSSGKPGSGKPGS GKPGSGKPGSQAVVTQEPSLTVSPGGTVTLTCGSSTGAVTTSNYA NWVQQKPGKSPRGLIGGTNKRAPGVPARFSGSLLGGKAALTISGA QPEDEADYYCALWYSNHWVFGGGTKLTVL | 300 |
| CD3-27 | VH | EVQLVESGGGLVQPGGSLRLSCAASGFTFSTYAMSWVRQAPGKGL EWVGRIRSKYNNYATYYADSVKGRFTISRDDSKNTLYLQMNSLRAE DTAVYYCVRHGNFGDSYVSWFAYWGQGTLVTVSS | 301 |
| | VL | QAVVTQEPSLTVSPGGTVTLTCGSSTGAVTTSNYANWVQQKPGKS PRGLIGGTNKRAPGVPARFSGSLLGGKAALTISGAQPEDEADYYCA LWYSNHWVFGGGTKLTVL | 286 |
| | scFv | EVQLVESGGGLVQPGGSLRLSCAASGFTFSTYAMSWVRQAPGKGL EWVGRIRSKYNNYATYYADSVKGRFTISRDDSKNTLYLQMNSLRAE DTAVYYCVRHGNFGDSYVSWFAYWGQGTLVTVSSGKPGSGKPGS GKPGSGKPGSQAVVTQEPSLTVSPGGTVTLTCGSSTGAVTTSNYA NWVQQKPGKSPRGLIGGTNKRAPGVPARFSGSLLGGKAALTISGA QPEDEADYYCALWYSNHWVFGGGTKLTVL | 302 |

CDR sequences for a number of CD3 binders as defined by the Kabat numbering scheme (Kabat et al, 1991, Sequences of Proteins of Immunological Interest, 5th Ed. Public Health Service, National Institutes of Health, Bethesda, Md.), Chothia numbering scheme (Al-Lazikani et al., 1997, J. Mol. Biol 273:927-948), and a combination of Kabat and Chothia numbering are provided in Tables 3B-3D, respectively.

TABLE 3B

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-1 | VH | RYTMH | 303 | YINPSRGYTNYNQKFKD | 323 | YYDDHYCLDY | 347 |
|  | VL | SASSSVSYMN | 304 | DTSKLAS | 324 | QQWSSNPFT | 348 |
| CD3-2 | VH | TYAMN | 305 | RIRSKYNNYATYYADSVKD | 325 | HGNFGNSYVSWFAY | 349 |
|  | VL | RSSTGAVTTSNYAN | 306 | GTNKRAP | 326 | ALWYSNLWV | 350 |
| CD3-3 | VH | SYTMH | 307 | YINPSSGYTKYNQKFKD | 327 | WQDYDVYFDY | 351 |
|  | VL | RASSSVSYMH | 308 | ATSNLAS | 328 | QQWSSNPPT | 352 |
| CD3-4 | VH | RYTMH | 303 | YINPSRGYTNYNQKFKD | 323 | YYDDHYCLDY | 347 |
|  | VL | RASSSVSYMN | 309 | DTSKVAS | 329 | QQWSSNPLT | 353 |
| CD3-5 | VH | RYTMH | 303 | YINPSRGYTNYNQKVKD | 330 | YYDDHYCLDY | 347 |
|  | VL | SASSSVSYMN | 304 | DTSKLAS | 324 | QQWSSNPFT | 348 |
| CD3-6 | VH | GYGMH | 310 | VIWYDGSKKYYVDSVKG | 331 | QMGYWHFDL | 354 |
|  | VL | RASQSVSSYLA | 311 | DASNRAT | 332 | QQRSNWPPLT | 355 |
| CD3-7 | VH | TYAMN | 305 | RIRSKYNNYATYYAD | 333 | VRHGNFGNSYVSWFAY | 356 |
|  | VL | RSSTGAVTTSNYAN | 306 | GTNKRAP | 326 | ALWYSNLWV | 350 |
| CD3-8 | VH | RYTMH | 303 | YINPSRGYTNYNQKFKD | 323 | YYDDHYCLDY | 347 |
|  | VL | RASSSVSYMN | 309 | DTSKVAS | 329 | QQWSSNPLT | 353 |
| CD3-9 | VH | TYAMN | 305 | RIRSKYNNYATYYAD | 333 | VRHGNFGNSYVSWFAY | 356 |
|  | VL | RSSTGAVTTSNYAN | 306 | GTNKRAP | 326 | ALWYSNLWV | 350 |
| CD3-10 | VH | TYAMN | 305 | RIRSKYNNYATYYADSVKD | 325 | HGNFGNSYVSWFAY | 349 |
|  | VL | RSSTGAVTTSNYAN | 306 | GTNKRAP | 326 | ALWYSNLWV | 350 |
| CD3-11 | VH | SYAMN | 312 | RIRSKYNNYATYYADSVKG | 334 | HGNFGNSYVSWWAY | 357 |
|  | VL | GSSTGAVTSGNYPN | 313 | GTKFLAP | 335 | VLWYSNRWV | 358 |
| CD3-12 | VH | KYAMN | 314 | RIRSKYNNYATYYADSVKD | 325 | HGNFGNSYISYWAY | 359 |
|  | VL | GSSTGAVTSGNYPN | 313 | GTKFLAP | 335 | VLWYSNRWV | 358 |
| CD3-13 | VH | RYTMH | 303 | YINPSRGYTNYNQKFKD | 323 | YYDDHYCLDY | 347 |
|  | VL | SASSSVSYMN | 304 | DTSKLAS | 324 | QQWSSNPFT | 348 |
| CD3-14 | VH | TYAMN | 305 | RIRSKYNNYATYYADSVKD | 325 | HGNFGNSYVSWFAY | 349 |
|  | VL | RSSTGAVTTSNYAN | 306 | GTNKRAP | 326 | ALWYSNLWV | 350 |
| CD3-15 | VH | TYAMN | 305 | RIRSKYNNYATYYADSVKD | 325 | HGNFGNSYVSWFAY | 349 |
|  | VL | RSSTGAVTTSNYAN | 306 | GTNKRAP | 326 | ALWYSNLWV | 350 |
| CD3-16 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-17 | VH | TYAMN | 305 | RIRSKYNNYATYYADSVKG | 334 | HGNFGDSYVSWFAY | 360 |
| | VL | GSSTGAVTTSNYAN | 315 | GTNKRAP | 326 | ALWYSNHWV | 361 |
| CD3-18 | VH | RYTMH | 303 | YINPSRGYTNYNQKVKD | 330 | YYDDHYCLDY | 347 |
| | VL | SASSSVSYMN | 304 | DTSKLAS | 324 | QQWSSNPFT | 348 |
| CD3-19 | VH | RYTMH | 303 | YINPSRGYTNYNQKVKD | 330 | YYDDHYSLDY | 362 |
| | VL | SASSSVSYMN | 304 | DTSKLAS | 324 | QQWSSNPFT | 348 |
| CD3-20 | VH | GYTMN | 316 | LINPYKGVSTYNQKFKD | 336 | SGYYGDSDWYFDV | 363 |
| CD3-21 | VH | TYAMN | 305 | RIRSKYNNYATYYADSVKG | 334 | HGNFGNSYVSWFAY | 349 |
| | VL | GSSTGAVTTSNYAN | 315 | GTNKRAP | 326 | ALWYSNLWV | 350 |
| | VL | RASQDIRNYLN | 317 | YTSRLH | 337 | QQGNTLPWT | 364 |
| CD3-22 | VH | TYAMN | 305 | RIRSKYNNYATYYADSVKG | 334 | HGNFGDSYVSWFAY | 360 |
| | VL | GSSTGAVTTSNYAN | 315 | GTNKRAP | 326 | ALWYSNHWV | 361 |
| CD3-23 | VH | TYAMN | 305 | RIRSKANNYATYYADSVKG | 338 | HGNFGDSYVSWFAY | 360 |
| | VL | GSSTGAVTTSNYAN | 315 | GTNKRAP | 326 | ALWYSNHWV | 361 |
| CD3-24 | VH | TYAMN | 305 | RIRSKYNNYATYYADSVKG | 334 | HGNFGDEYVSWFAY | 365 |
| | VL | GSSTGAVTTSNYAN | 315 | GTNKRAP | 326 | ALWYSNHWV | 361 |
| CD3-25 | VH | TYAMN | 305 | RIRSKYNNYATYYADSVKG | 334 | HGNFGDPYVSWFAY | 366 |
| | VL | GSSTGAVTTSNYAN | 315 | GTNKRAP | 326 | ALWYSNHWV | 361 |
| CD3-26 | VH | TYAMN | 305 | RIRSKYNNYATYYADSVKG | 334 | HGNFGDSYVSWFDY | 367 |
| | VL | GSSTGAVTTSNYAN | 315 | GTNKRAP | 326 | ALWYSNHWV | 361 |
| CD3-27 | VH | TYAMS | 318 | RIRSKYNNYATYYADSVKG | 334 | HGNFGDSYVSWFAY | 360 |
| | VL | GSSTGAVTTSNYAN | 315 | GTNKRAP | 326 | ALWYSNHWV | 361 |
| CD3-28 | VH | TYAMN | 305 | RIRSKYNNYATYYADSVKG | 334 | HGNFGDSYVSWFAY | 360 |
| | VL | GSSTGAVTTSNYAN | 315 | GTNKRAP | 326 | ALWYSNHWV | 361 |
| CD3-29 | VH | TYAMN | 305 | RIRSKYNNYATYYADSVKG | 334 | HGNFGNSYVSWFAY | 349 |
| | VL | GSSTGAVTTSNYAN | 315 | GTNKRAP | 326 | ALWYSNLWV | 350 |
| CD3-30 | VH | TYAMN | 305 | RIRSKYNNYATYYADSVKG | 334 | HGNFGNSYVSWFAY | 349 |
| | VL | GSSTGAVTTSNYAN | 315 | GTNKRAP | 326 | ALWYSNLWV | 350 |
| CD3-31 | VH | TYAMN | 305 | RIRSKYNNYATYYADSVKG | 334 | HGNFGNSYVSWFAY | 349 |
| | VL | GSSTGAVTTSNYAN | 315 | GTNKRAP | 326 | ALWYSNLWV | 350 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-32 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-33 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-34 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-35 | VH | TYAMH | 319 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-36 | VH | TYAMS | 318 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-37 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-38 | VH | TYAMN | 305 | RIRSKANNYYATYYADSVKG | 339 | HGNFGNSYVSWFAY | 349 |
|  | VL | GSSTGAVTTSNYAN | 315 | GTNKRAP | 326 | ALWYSNLWV | 350 |
| CD3-39 | VH | TYAMN | 305 | RIRSKANSYATYYADSVKG | 340 | HGNFGNSYVSWFAY | 349 |
|  | VL | GSSTGAVTTSNYAN | 315 | GTNKRAP | 326 | ALWYSNLWV | 350 |
| CD3-40 | VH | TYAMN | 305 | RIRSKYNNYATAYADSVKG | 341 | HGNFGNSYVSWFAY | 349 |
|  | VL | GSSTGAVTTSNYAN | 315 | GTNKRAP | 326 | ALWYSNLWV | 350 |
| CD3-41 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-42 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-43 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-44 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-45 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-46 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-47 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-48 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-49 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-50 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNLWV | 350 |
| CD3-51 | VH | TYAMN | 305 | RIRSKYNNYATYYADSVKG | 334 | HGNFGQSYVSWFAY | 368 |
|  | VL | GSSTGAVTTSNYAN | 315 | GTNKRAP | 326 | ALWYSNLWV | 350 |
| CD3-52 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-53 | VH | TYAMN | 305 | RIRSKYNNYATYYADSVKG | 334 | HGNFGNSYVSWFDY | 369 |
|  | VL | GSSTGAVTTSNYAN | 315 | GTNKRAP | 326 | ALWYSNLWV | 350 |
| CD3-54 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-55 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-56 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-57 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-58 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-59 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-60 | VH | TYAMN | 305 | RIRSKYNNYATYYADSVKG | 334 | HGNFGNSYVSWFAY | 349 |
|  | VL | GSSTGAVTSSNYAN | 320 | GTNKRAP | 326 | ALWYSNLWV | 350 |
| CD3-61 | VH | TYAMN | 305 | RIRSKYNNYATYYADSVKG | 334 | HGNFGNSYVSWFAY | 349 |
|  | VL | GSSTGAVTSGHYAN | 321 | GTNKRAP | 326 | ALWYSNLWV | 350 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-62 | VH | TYAMN | 305 | RIRSKYNNYATYYADSVKG | 334 | HGNFGNSYVSWFAY | 349 |
|  | VL | GSSTGAVTTSNYAN | 315 | DTNKRAP | 342 | ALWYSNLWV | 350 |
| CD3-63 | VH | TYAMN | 305 | RIRSKYNNYATYYADSVKG | 334 | HGNFGNSYVSWFAY | 349 |
|  | VL | GSSTGAVTTSNYAN | 315 | GTNNRAP | 343 | ALWYSNLWV | 350 |
| CD3-64 | VH | TYAMN | 305 | RIRSKYNNYATYYADSVKG | 334 | HGNFGNSYVSWFAY | 349 |
|  | VL | GSSTGAVTTSNYAN | 315 | GTNKRAS | 344 | ALWYSNLWV | 350 |
| CD3-65 | VH | TYAMN | 305 | RIRSKYNNYATYYADSVKG | 334 | HGNFGNSYVSWFAY | 349 |
|  | VL | GSSTGAVTTSNYAN | 315 | GTSNKHS | 345 | ALWYSNLWV | 350 |
| CD3-66 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-67 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-68 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-69 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-70 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-71 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-72 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-73 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | LLWYSNLWV | 370 |
| CD3-74 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-75 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-76 | VH | TYAMN | 305 | RIRSKYNNYATYYADSVKG | 334 | HGNFGNSYVSWFAY | 349 |
|  | VL | RSSTGAVTTSNYAN | 306 | GTNKRAP | 326 | ALWYSNLWV | 350 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-77 | VH | TYAMN | 305 | RIRSKYNNYATYYADSVKG | 334 | HGNFGNSYVSWFAY | 349 |
|  | VL | KSSTGAVTTSNYAN | 322 | GTNKRAP | 326 | ALWYSNLWV | 350 |
| CD3-78 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-79 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-80 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-81 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-82 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-83 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-84 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-85 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-86 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-87 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNLWV | 350 |
| CD3-88 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNLWV | 350 |
| CD3-89 | VH | TYAMN | 305 | RIRSKANNYATYYADSVKG | 338 | HGNFGDSYVSWFAY | 360 |
|  | VL | GSSTGAVTTSNYAN | 315 | GTNKRAP | 326 | ALWYSNLWV | 350 |
| CD3-90 | VH | TYAMN | 305 | RIRSKYNNYATYYADSVKG | 334 | HGNFGDSYVSWFDY | 367 |
|  | VL | GSSTGAVTTSNYAN | 315 | GTNKRAP | 326 | ALWYSNLWV | 350 |
| CD3-91 | VH | TYAMS | 318 | RIRSKANNYATYYADSVKG | 338 | HGNFGDSYVSWFDY | 367 |
|  | VL | GSSTGAVTTSNYAN | 315 | GTNKRAP | 326 | ALWYSNLWV | 350 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-92 | VH | TYAMN | 305 | RIRSNGGYSTYYADSVKG | 346 | HGNFGNSYVSWFAY | 349 |
|  | VL | GSSTGAVTTSNYAN | 315 | GTNKRAP | 326 | ALWYSNLWV | 350 |
| CD3-93 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-94 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-95 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNLWV | 350 |
| CD3-96 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-97 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-98 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-99 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-100 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-101 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-102 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-103 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-104 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-105 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-106 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-107 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-108 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-109 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-110 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-111 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-112 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-113 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-114 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-115 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-116 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-117 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-118 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-119 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-120 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-121 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |

TABLE 3B-continued

CD3 Binders - CDR sequences according to Kabat numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-122 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-123 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-124 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-125 | VH | TYAMN | 305 | RIRSKYNNYATYYADSVKG | 334 | HGNFGDSYVSWFAY | 360 |
|  | VL | GSSTGAVTTSNYAN | 315 | GTNKRAP | 326 | ALWYSNHWV | 361 |
| CD3-126 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |
| CD3-127 | VH | TYAMN | 305 | RIRSKYNNYATYYADSVKG | 334 | HGNFGNSYVSWFAY | 349 |
|  | VL | GSSTGAVTTSNYAN | 315 | GTNKRAP | 326 | ALWYSNHWV | 361 |

TABLE 3C

CD3 Binders - CDR sequences according to Chothia numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-1 | VH | GYTFTRY | 371 | NPSRGY | 384 | YYDDHYCLDY | 347 |
|  | VL | SSSVSY | 372 | DTS | 385 | WSSNPF | 396 |
| CD3-2 | VH | GFTFNTY | 373 | RSKYNNYA | 386 | HGNFGNSYVSWFAY | 349 |
|  | VL | STGAVTTSNY | 374 | GTN | 387 | WYSNLW | 397 |
| CD3-3 | VH | GYTFTSY | 375 | NPSSGY | 388 | WQDYDVYFDY | 351 |
|  | VL | SSSVSY | 372 | ATS | 389 | WSSNPP | 398 |
| CD3-4 | VH | GYTFTRY | 371 | NPSRGY | 384 | YYDDHYCLDY | 347 |
|  | VL | SSSVSY | 372 | DTS | 385 | WSSNPL | 399 |
| CD3-5 | VH | GYTFTRY | 371 | NPSRGY | 384 | YYDDHYCLDY | 347 |
|  | VL | SSSVSY | 372 | DTS | 385 | WSSNPF | 396 |
| CD3-6 | VH | GFKFSGY | 376 | WYDGSK | 390 | QMGYWHFDL | 354 |
|  | VL | SQSVSSY | 377 | DAS | 391 | RSNWPPL | 400 |
| CD3-7 | VH | GFTFSTY | 378 | RSKYNNYAT | 392 | HGNFGNSYVSWFA | 401 |
|  | VL | STGAVTTSNY | 374 | GTN | 387 | WYSNLW | 397 |
| CD3-8 | VH | GYTFTRY | 371 | NPSRGY | 384 | YYDDHYCLDY | 347 |
|  | VL | SSSVSY | 372 | DTS | 385 | WSSNPL | 399 |
| CD3-9 | VH | GFTFNTY | 373 | RSKYNNYAT | 392 | HGNFGNSYVSWFA | 401 |
|  | VL | STGAVTTSNY | 374 | GTN | 387 | WYSNLW | 397 |

TABLE 3C-continued

CD3 Binders - CDR sequences according to Chothia numbering scheme

| Binding Domain | Chain | CDR1 | SEQ ID NO: | CDR2 | SEQ ID NO: | CDR3 | SEQ ID NO: |
|---|---|---|---|---|---|---|---|
| CD3-10 | VH | GFTFNTY | 373 | RSKYNNYA | 386 | HGNFGNSYVSWFAY | 349 |
|  | VL | STGAVTTSNY | 374 | GTN | 387 | WYSNLW | 397 |
| CD3-11 | VH | GFTFNSY | 379 | RSKYNNYA | 386 | HGNFGNSYVSWWAY | 357 |
|  | VL | STGAVTSGNY | 380 | GTK | 393 | WYSNRW | 402 |
| CD3-12 | VH | GFTFNKY | 381 | RSKYNNYA | 386 | HGNFGNSYISYWAY | 359 |
|  | VL | STGAVTSGNY | 380 | GTK | 393 | WYSNRW | 402 |
| CD3-13 | VH | GYTFTRY | 371 | NPSRGY | 384 | YYDDHYCLDY | 347 |
|  | VL | SSSVSY | 372 | DTS | 385 | WSSNPF | 396 |
| CD3-14 | VH | GFTFSTY | 378 | RSKYNNYA | 386 | HGNFGNSYVSWFAY | 349 |
|  | VL | STGAVTTSNY | 374 | GTN | 387 | WYSNLW | 397 |
| CD3-15 | VH | GFTFNTY | 373 | RSKYNNYA | 386 | HGNFGNSYVSWFAY | 349 |
|  | VL | STGAVTTSNY | 374 | GTN | 387 | WYSNLW | 397 |
| CD3-16 | VH | GFTFNTY | 373 | RSKYNNYA | 386 | HGNFGNSYVSWFAY | 349 |
|  | VL | STGAVTTSNY | 374 | GTN | 387 | WYSNLW | 397 |
| CD3-17 | VH | GFTFSTY | 378 | RSKYNNYA | 386 | HGNFGDSYVSWFAY | 360 |
|  | VL | STGAVTTSNY | 374 | GTN | 387 | WYSNHW | 403 |
| CD3-18 | VH | GYTFTRY | 371 | NPSRGY | 384 | YYDDHYCLDY | 347 |
|  | VL | SSSVSY | 372 | DTS | 385 | WSSNPF | 396 |
| CD3-19 | VH | GYTFTRY | 371 | NPSRGY | 384 | YYDDHYSLDY | 362 |
|  | VL | SSSVSY | 372 | DTS | 385 | WSSNPF | 396 |
| CD3-20 | VH | GYSFTGY | 382 | NPYKGV | 394 | SGYYGDSDWYFDV | 363 |
|  | VL | SQDIRNY | 383 | YTS | 395 | GNTLPW | 404 |

TABLE 3D

CD3 Binders - CDR sequences according to combination of Kabat and Chothia numbering schemes

| Binding Domain | Chain | CDR1 | SEQ ID NO: | CDR2 | SEQ ID NO: | CDR3 | SEQ ID NO: |
|---|---|---|---|---|---|---|---|
| CD3-1 | VH | GYTFTRYTMH | 405 | YINPSRGYTNYNQKFKD | 323 | YYDDHYCLDY | 347 |
|  | VL | SASSSVSYMN | 304 | DTSKLAS | 324 | QQWSSNPFT | 348 |
| CD3-2 | VH | GFTFNTYAMN | 406 | RIRSKYNNYATYYADSVKD | 325 | HGNFGNSYVSWFAY | 349 |
|  | VL | RSSTGAVTTSNYAN | 306 | GTNKRAP | 326 | ALWYSNLWV | 350 |
| CD3-3 | VH | GYTFSYTMH | 407 | YINPSSGYTKYNQKFKD | 327 | WQDYDVYFDY | 351 |
|  | VL | RASSSVSYMH | 308 | ATSNLAS | 328 | QQWSSNPPT | 352 |

TABLE 3D-continued

CD3 Binders - CDR sequences according to combination of Kabat and Chothia numbering schemes

| Binding Domain | Chain | CDR1 | SEQ ID NO: | CDR2 | SEQ ID NO: | CDR3 | SEQ ID NO: |
|---|---|---|---|---|---|---|---|
| CD3-4 | VH | GYTFTRYTMH | 405 | YINPSRGYTNYNQKFKD | 323 | YYDDHYCLDY | 347 |
| | VL | RASSSVSYMN | 309 | DTSKVAS | 329 | QQWSSNPLT | 353 |
| CD3-5 | VH | GYTFTRYTMH | 405 | YINPSRGYTNYNQKVKD | 330 | YYDDHYCLDY | 347 |
| | VL | SASSSVSYMN | 304 | DTSKLAS | 324 | QQWSSNPFT | 348 |
| CD3-6 | VH | GFKFSGYGMH | 408 | VIWYDGSKKYYVDSVKG | 331 | QMGYWHFDL | 354 |
| | VL | RASQSVSSYLA | 311 | DASNRAT | 332 | QQRSNWPPLT | 355 |
| CD3-7 | VH | GFTFSTYAMN | 409 | RIRSKYNNYATYYADSVK | 413 | HGNFGNSYVSWFAY | 349 |
| | VL | RSSTGAVTTSNYAN | 306 | GTNKRAP | 326 | ALWYSNLWV | 350 |
| CD3-8 | VH | GYTFTRYTMH | 405 | YINPSRGYTNYNQKFKD | 323 | YYDDHYCLDY | 347 |
| | VL | RASSSVSYMN | 309 | DTSKVAS | 329 | QQWSSNPLT | 353 |
| CD3-9 | VH | GFTFNTYAMN | 406 | RIRSKYNNYATYYADSVK | 413 | HGNFGNSYVSWFAY | 349 |
| | VL | RSSTGAVTTSNYAN | 306 | GTNKRAP | 326 | ALWYSNLWV | 350 |
| CD3-10 | VH | GFTFNTYAMN | 406 | RIRSKYNNYATYYADSVKD | 325 | HGNFGNSYVSWFAY | 349 |
| | VL | RSSTGAVTTSNYAN | 306 | GTNKRAP | 326 | ALWYSNLWV | 350 |
| CD3-11 | VH | GFTFNSYAMN | 410 | RIRSKYNNYATYYADSVKG | 334 | HGNFGNSYVSVWVAY | 357 |
| | VL | GSSTGAVTSGNYPN | 313 | GTKFLAP | 335 | VLWYSNRWV | 358 |
| CD3-12 | VH | GFTFNKYAMN | 411 | RIRSKYNNYATYYADSVKD | 325 | HGNFGNSYISYWAY | 359 |
| | VL | GSSTGAVTSGNYPN | 313 | GTKFLAP | 335 | VLWYSNRWV | 358 |
| CD3-13 | VH | GYTFTRYTMH | 405 | YINPSRGYTNYNQKFKD | 323 | YYDDHYCLDY | 347 |
| | VL | SASSSVSYMN | 304 | DTSKLAS | 324 | QQWSSNPFT | 348 |
| CD3-14 | VH | GFTFSTYAMN | 409 | RIRSKYNNYATYYADSVKD | 325 | HGNFGNSYVSWFAY | 349 |
| | VL | RSSTGAVTTSNYAN | 306 | GTNKRAP | 326 | ALWYSNLWV | 350 |
| CD3-15 | VH | GFTFNTYAMN | 406 | RIRSKYNNYATYYADSVKD | 325 | HGNFGNSYVSWFAY | 349 |
| | VL | RSSTGAVTTSNYAN | 306 | GTNKRAP | 326 | ALWYSNLWV | 350 |
| CD3-16 | VH | GFTFNTYAMN | 406 | RIRSKYNNYATYYADSVKG | 334 | HGNFGNSYVSWFAY | 349 |
| | VL | GSSTGAVTTSNYAN | 315 | GTNKRAP | 326 | ALWYSNLWV | 350 |
| CD3-17 | VH | GFTFSTYAMN | 409 | RIRSKYNNYATYYADSVKG | 334 | HGNFGDSYVSWFAY | 360 |
| | VL | GSSTGAVTTSNYAN | 315 | GTNKRAP | 326 | ALWYSNHWV | 361 |
| CD3-18 | VH | GYTFTRYTMH | 405 | YINPSRGYTNYNQKVKD | 330 | YYDDHYCLDY | 347 |
| | VL | SASSSVSYMN | 304 | DTSKLAS | 324 | QQWSSNPFT | 348 |
| CD3-19 | VH | GYTFTRYTMH | 405 | YINPSRGYTNYNQKVKD | 330 | YYDDHYSLDY | 362 |
| | VL | SASSSVSYMN | 304 | DTSKLAS | 324 | QQWSSNPFT | 348 |

TABLE 3D-continued

CD3 Binders - CDR sequences according to
combination of Kabat and Chothia numbering schemes

| Binding Domain | Chain | CDR1 | SEQ ID NO: | CDR2 | SEQ ID NO: | CDR3 | SEQ ID NO: |
|---|---|---|---|---|---|---|---|
| CD3-20 | VH | GYSFTGYTMN | 412 | LINPYKGVSTYNQKFKD | 336 | SGYYGDSDWYFDV | 363 |
| | VL | RASQDIRNYLN | 317 | YTSRLHS | 414 | QQGNTLPWT | 364 |

In some embodiments, a MBM can comprise a CD3 ABD which comprises the CDRs of any of CD3-1 to CD3-127 as defined by Kabat numbering (e.g., as set forth in Table 3B). In other embodiments, a MBM can comprise a CD3 ABD which comprises the CDRs of any of CD3-1 to CD3-127 as defined by Chothia numbering (e.g., as set forth in Table 3C). In yet other embodiments, a MBM can comprise a CD3 ABD which comprises the CDRs of any of CD3-1 to CD3-127 as defined by a combination of Kabat and Chothia numbering (e.g., as set forth in Table 3D).

In some embodiments, a CD3 ABD comprises the CDR sequences of CD3-1. In some embodiments, a CD3 ABD comprises the CDR sequences of CD3-2. In some embodiments, a CD3 ABD comprises the CDR sequences of CD3-3. In some embodiments, a CD3 ABD comprises the CDR sequences of CD3-4. In some embodiments, a CD3 ABD comprises the CDR sequences of CD3-5. In some embodiments a CD3 ABD comprises the CDR sequences of CD3-6. In some embodiments, a CD3 ABD comprises the CDR sequences of CD3-7. In some embodiments, a CD3 ABD comprises the CDR sequences of CD3-8. In some embodiments, a CD3 ABD comprises the CDR sequences of CD3-9. In some embodiments, a CD3 ABD comprises the CDR sequences of CD3-10. In some embodiments, a CD3 ABD comprises the CDR sequences of CD3-11. In some embodiments, a CD3 ABD comprises the CDR sequences of CD3-12. In some embodiments, a CD3 ABD comprises the CDR sequences of CD3-13. In some embodiments, a CD3 ABD comprises the CDR sequences of CD3-14. In some embodiments, a CD3 ABD comprises the CDR sequences of CD3-15. In some embodiments, a CD3 ABD comprises the CDR sequences of CD3-16. In some embodiments, a CD3 ABD comprises the CDR sequences of CD3-17. In some embodiments, a CD3 ABD comprises the CDR sequences of CD3-18. In some embodiments, a CD3 ABD comprises the CDR sequences of CD3-19. In some embodiments, a CD3 ABD comprises the CDR sequences of CD3-20. In some embodiments, a CD3 ABD comprises the CDR sequences of CD3-21. In some embodiments, a CD3 ABD comprises the CDR sequences of CD3-22. In some embodiments, a CD3 ABD comprises the CDR sequences of CD3-23. In some embodiments, a CD3 ABD comprises the CDR sequences of CD3-24. In some embodiments, a CD3 ABD comprises the CDR sequences of CD3-25. In some embodiments, a CD3 ABD comprises the CDR sequences of CD3-26. In some embodiments, a CD3 ABD comprises the CDR sequences of CD3-27. In some embodiments, a CD3 ABD comprises the CDR sequences of CD3-28. In some embodiments, a CD3 ABD comprises the CDR sequences of CD3-29. In some embodiments, a CD3 ABD comprises the CDR sequences of CD3-30. In some embodiments, a CD3 ABD comprises the CDR sequences of CD3-31. In some embodiments, a CD3 ABD comprises the CDR sequences of CD3-32. In some embodiments, a CD3 ABD comprises the CDR sequences of CD3-33. In some embodiments, a CD3 ABD comprises the CDR sequences of CD3-34. In some embodiments, a CD3 ABD comprises the CDR sequences of CD3-35. In some embodiments, a CD3 ABD comprises the CDR sequences of CD3-36. In some embodiments, a CD3 ABD comprises the CDR sequences of CD3-37. In some embodiments, a CD3 ABD comprises the CDR sequences of CD3-38. In some embodiments, a CD3 ABD comprises the CDR sequences of CD3-39. In some embodiments, a CD3 ABD comprises the CDR sequences of CD3-40. In some embodiments, a CD3 ABD comprises the CDR sequences of CD3-41. In some embodiments, a CD3 ABD comprises the CDR sequences of CD3-42. In some embodiments, a CD3 ABD comprises the CDR sequences of CD3-43. In some embodiments, a CD3 ABD comprises the CDR sequences of CD3-44. In some embodiments, a CD3 ABD comprises the CDR sequences of CD3-45. In some embodiments, a CD3 ABD comprises the CDR sequences of CD3-46. In some embodiments, a CD3 ABD comprises the CDR sequences of CD3-47. In some embodiments, a CD3 ABD comprises the CDR sequences of CD3-48. In some embodiments, a CD3 ABD comprises the CDR sequences of CD3-49. In some embodiments, a CD3 ABD comprises the CDR sequences of CD3-50. In some embodiments, a CD3 ABD comprises the CDR sequences of CD3-51. In some embodiments, a CD3 ABD comprises the CDR sequences of CD3-52. In some embodiments, a CD3 ABD comprises the CDR sequences of CD3-53. In some embodiments, a CD3 ABD comprises the CDR sequences of CD3-54. In some embodiments, a CD3 ABD comprises the CDR sequences of CD3-55. In some embodiments, a CD3 ABD comprises the CDR sequences of CD3-56. In some embodiments, a CD3 ABD comprises the CDR sequences of CD3-57. In some embodiments, a CD3 ABD comprises the CDR sequences of CD3-58. In some embodiments, a CD3 ABD comprises the CDR sequences of CD3-59. In some embodiments, a CD3 ABD comprises the CDR sequences of CD3-60. In some embodiments, a CD3 ABD comprises the CDR sequences of CD3-61. In some embodiments, a CD3 ABD comprises the CDR sequences of CD3-62. In some embodiments, a CD3 ABD comprises the CDR sequences of CD3-63. In some embodiments, a CD3 ABD comprises the CDR sequences of CD3-64. In some embodiments, a CD3 ABD comprises the CDR sequences of CD3-65. In some embodiments, a CD3 ABD comprises the CDR sequences of CD3-66. In some embodiments, a CD3 ABD comprises the CDR sequences of CD3-67. In some embodiments, a CD3 ABD comprises the CDR sequences of CD3-68. In some embodiments, a CD3 ABD comprises the CDR sequences of CD3-69. In some embodiments, a CD3 ABD comprises the CDR sequences of CD3-70. In some embodiments, a CD3 ABD comprises the CDR sequences of CD3-71. In some embodiments, a CD3 ABD comprises the CDR sequences of CD3-72. In some embodiments, a CD3 ABD comprises the CDR sequences of CD3-73. In some embodiments, a CD3 ABD comprises the CDR sequences of CD3-74. In some embodiments, a CD3 ABD comprises the CDR sequences of CD3-75. In some embodiments, a CD3 ABD comprises the CDR sequences of CD3-76. In some embodiments, a CD3 ABD comprises the CDR sequences of CD3-77. In some embodiments, a CD3 ABD comprises the CDR sequences of CD3-78. In some embodiments, a CD3 ABD comprises the CDR sequences of CD3-79. In some embodiments, a CD3 ABD comprises the CDR sequences of CD3-80. In some embodiments, a CD3 ABD comprises the CDR sequences of CD3-81. In some embodiments, a CD3 ABD comprises the CDR sequences of CD3-82. In some embodiments, a CD3 ABD comprises the CDR sequences of CD3-83. In some embodiments, a CD3 ABD comprises the CDR sequences of CD3-84. In some embodiments, a CD3 ABD comprises the CDR sequences of CD3-85. In some embodiments, a CD3 ABD comprises the CDR sequences of CD3-86. In some embodiments, a CD3 ABD comprises the CDR sequences of CD3-87. In some embodiments, a CD3 ABD comprises the CDR sequences of CD3-88. In some embodiments, a CD3 ABD comprises the CDR sequences of CD3-89. In some embodiments, a CD3 ABD comprises the CDR sequences of CD3-90. In some embodiments, a CD3 ABD comprises the CDR sequences of CD3-91. In some embodiments, a CD3 ABD comprises the CDR sequences of CD3-92. In some embodiments, a CD3 ABD comprises the CDR sequences of CD3-93. In some embodiments, a CD3 ABD comprises the CDR sequences of CD3-94. In some embodiments, a CD3 ABD comprises the CDR sequences of CD3-95. In some embodiments, a CD3 ABD comprises the CDR sequences of CD3-96. In some embodiments, a CD3 ABD comprises the CDR sequences of CD3-97. In some embodiments, a CD3 ABD comprises the CDR sequences of CD3-98. In some embodiments, a CD3 ABD comprises the CDR sequences of CD3-99. In some embodiments, a CD3 ABD comprises the CDR sequences of CD3-100. In some embodiments, a CD3 ABD comprises the CDR sequences of CD3-101. In some embodiments, a CD3 ABD comprises the CDR sequences of CD3-102. In some embodiments, a CD3 ABD comprises the CDR sequences of CD3-103. In some embodiments, a CD3 ABD comprises the CDR sequences of CD3-104. In some embodiments, a CD3 ABD comprises the CDR sequences of CD3-105. In some embodiments, a CD3 ABD comprises the CDR sequences of CD3-106. In some embodiments, a CD3 ABD comprises the CDR sequences of CD3-107. In some embodiments, a CD3 ABD comprises the CDR sequences of CD3-108. In some embodiments, a CD3 ABD comprises the CDR sequences of CD3-109. In some embodiments, a CD3 ABD comprises the CDR sequences of CD3-110. In some embodiments, a CD3 ABD comprises the CDR sequences of CD3-111. In some embodiments, a CD3 ABD comprises the CDR sequences of CD3-112. In some embodiments, a CD3 ABD comprises the CDR sequences of CD3-113. In some embodiments, a CD3 ABD comprises the CDR sequences of CD3-114. In some embodiments, a CD3 ABD comprises the CDR sequences of CD3-115. In some embodiments, a CD3 ABD comprises the CDR sequences of CD3-116. In some embodiments, a CD3 ABD comprises the CDR sequences of CD3-117. In some embodiments, a CD3 ABD comprises the CDR sequences of CD3-118. In some embodiments, a CD3 ABD comprises the CDR sequences of CD3-119. In some embodiments, a CD3 ABD comprises the CDR sequences of CD3-120. In some embodiments, a CD3 ABD comprises the CDR sequences of CD3-121. In some embodiments, a CD3 ABD comprises the CDR sequences of CD3-122. In some embodiments, a CD3 ABD comprises the CDR sequences of CD3-123. In some embodiments, a CD3 ABD comprises the CDR sequences of CD3-124. In some embodiments, a CD3 ABD comprises the CDR sequences of CD3-125. In some embodiments, a CD3 ABD comprises the CDR sequences of CD3-126. In some embodiments, a CD3 ABD comprises the CDR sequences of CD3-127.

A MBM can comprise the complete heavy and light variable sequences of any one of CD3-1 to CD3-127. In some embodiments, a MBM comprises a CD3 ABD which comprises the VH and VL sequences of CD3-1. In some embodiments, a MBM comprises a CD3 ABD which comprises the VH and VL sequences of CD3-1. In some embodiments, a MBM comprises a CD3 ABD which comprises the VH and VL sequences of CD3-2. In some embodiments, a MBM comprises a CD3 ABD which comprises the VH and VL sequences of CD3-3. In some embodiments, a MBM comprises a CD3 ABD which comprises the VH and VL sequences of CD3-4. In some embodiments, a MBM comprises a CD3 ABD which comprises the VH and VL sequences of CD3-5. In some embodiments, a MBM comprises a CD3 ABD which comprises the VH and VL sequences of CD3-6. In some embodiments, a MBM comprises a CD3 ABD which comprises the VH and VL sequences of CD3-7. In some embodiments, a MBM comprises a CD3 ABD which comprises the VH and VL sequences of CD3-8. In some embodiments, a MBM comprises a CD3 ABD which comprises the VH and VL sequences of CD3-9. In some embodiments, a MBM comprises a CD3 ABD which comprises the VH and VL sequences of CD3-10. In some embodiments, a MBM comprises a CD3 ABD which comprises the VH and VL sequences of CD3-11. In some embodiments, a MBM comprises a CD3 ABD which comprises the VH and VL sequences of CD3-12. In some embodiments, a MBM comprises a CD3 ABD which comprises the VH and VL sequences of CD3-13. In some embodiments, a MBM comprises a CD3 ABD which comprises the VH and VL sequences of CD3-14. In some embodiments, a MBM comprises a CD3 ABD which comprises the VH and VL sequences of CD3-15. In some embodiments, a MBM comprises a CD3 ABD which comprises the VH and VL sequences of CD3-16. In some embodiments, a MBM comprises a CD3 ABD which comprises the VH and VL sequences of CD3-17. In some embodiments, a MBM comprises a CD3 ABD which comprises the VH and VL sequences of CD3-18. In some embodiments, a MBM comprises a CD3 ABD which comprises the VH and VL sequences of CD3-19. In some embodiments, a MBM comprises a CD3 ABD which comprises the VH and VL sequences of CD3-20. In some embodiments, a MBM comprises a CD3 ABD which comprises the VH and VL sequences of CD3-21. In some embodiments, a MBM comprises a CD3 ABD which comprises the VH and VL sequences of CD3-22. In some embodiments, a MBM comprises a CD3 ABD which comprises the VH and VL sequences of CD3-23. In some embodiments, a MBM comprises a CD3 ABD which comprises the VH and VL sequences of CD3-24. In some embodiments, a MBM comprises a CD3 ABD which comprises the VH and VL sequences of CD3-25. In some embodiments, a MBM comprises a CD3 ABD which comprises the VH and VL sequences of CD3-26. In some embodiments, a MBM comprises a CD3 ABD which comprises the VH and VL sequences of CD3-27.

In addition to the CDR sets described in Tables 3B-3D (i.e., the set of six CDRs for each of CD3-1 to CD3-127), the present disclosure provides variant CDR sets. In one embodiment, a set of 6 CDRs can have 1, 2, 3, 4 or 5 amino acid changes from a CDR set described in Tables 3B-3D, as long as the CD3 ABD is still able to bind to the target antigen, as measured by at least one of a Biacore, surface plasmon resonance (SPR) and/or BLI (biolayer interferometry, e.g., Octet assay) assay.

In addition to the variable heavy and variable light domains disclosed in Table 3A that form an ABD to CD3, the present disclosure provides variant VH and VL domains. In one embodiment, the variant VH and VL domains each 7.3.3.2. TCR-α/β ABDs The MBMs can contain an ABD that specifically binds to the TCR-α chain, the TCR-β chain, or the TCR-αβ dimer. Exemplary anti-TCR-α/β antibodies are known (see, e.g., US 2012/0034221; Borst et al., 1990, Hum Immunol. 29(3): 175-88 (describing antibody BMA031)). The VH, VL, and Kabat CDR sequences of antibody BMA031 are provided in Table 4.

TABLE 4

BMA031 sequences

| Domain | Sequence | SEQ ID NO: |
|---|---|---|
| BMA031 CDR-H1 | KASGYKFTSYVMH | 416 |
| BMA031 CDR-H2 | YINPYNDVTKYNEKFK | 417 |
| BMA031 CDR-H3 | GSYYDYDGFVY | 418 |
| BMA031 CDR-L1 | SATSSVSYMH | 419 |
| BMA031 CDR-L2 | DTSKLAS | 324 |
| BMA031 CDR-L3 | QQWSSNPLT | 353 |
| BMA031 VH | EVQLQQSGPELVKPGASVKMSCKASGYKFTSYVMHWVKQKPGQGLE WIGYINPYNDVTKYNEKFKGKATLTSDKSSSTAYMELSSLTSEDSAVH YCARGSYYDYDGFVYWGQGTLVTVSA | 420 |
| BMA031 VL | QIVLTQSPAIMSASPGEKVTMTCSATSSVSYMHWYQQKSGTSPKRWI YDTSKLASGVPARFSGSGSGTSYSLTISSMEAEDAATYYCQQWSSNP LTFGAGTKLELK | 421 | can have from 1, 2, 3, 4, 5, 6, 7, 8, 9 or 10 amino acid changes from the VH and VL domain set forth in Table 3A, as long as the ABD is still able to bind to the target antigen, as measured at least one of a Biacore, surface plasmon resonance (SPR) and/or BLI (biolayer interferometry, e.g., Octet assay) assay. In another embodiment, the variant VH and VL are at least 90, 95, 97, 98 or 99% identical to the respective VH or VL disclosed in Table 3A, as long as the ABD is still able to bind to the target antigen, as measured by at least one of a Biacore, surface plasmon resonance (SPR) and/or BLI (biolayer interferometry, e.g., Octet assay) assay.

In some embodiments, the antigen-binding domain that specifically binds to human CD3 is non-immunoglobulin based and is instead derived from a non-antibody scaffold protein, for example one of the non-antibody scaffold proteins described in Section 7.3.2. In an embodiment, the antigen-binding domain that specifically binds to human CD3 comprises Affilin-144160, which is described in WO 2017/013136. Affilin-144160 has the following amino acid sequence:

(SEQ ID NO: 415)
MQIFVKTLTGKTITLEVEPSDTIENVKAKIQDKEGIPPDQQWLWFAGKQL

EDGRTLSDYNIQKESTLKLWLVDKAAMQIFVYTRTGKTITLEVEPSDTIE

NVKAKIQDKEGIPPDQQRLIWAGKQLEDGRTLSDYNIALESGLHLVLRLR

AA

In an embodiment, a TCR ABD can comprise the CDR sequences of antibody BMA031. In other embodiments, a TCR ABD can comprise the VH and VL sequences of antibody BMA031.

7.3.3.3. TCR-γ/δ ABDs

The MBMs can contain an ABD that specifically binds to the TCR-γ chain, the TCR-δ chain, or the TCR-γδ dimer. Exemplary anti-TCR-γ/δ antibodies are known (see, e.g., U.S. Pat. No. 5,980,892 (describing δTCS1, produced by the hybridoma deposited with the ATCC as accession number HB 9578)).

7.4. Connectors

It is contemplated that the BCMA binding molecules can in some instances include pairs of ABDs or ABD chains (e.g., the VH-CH1 or VL-CL component of a Fab) connected directly to one another, e.g., as a fusion protein without a linker. For example, the BCMA binding molecules comprise connector moieties linking individual ABDs or ABD chains. The use of connector moieties can improve target binding, for example by increasing flexibility of the ABDs within a BCMA binding molecule and thus reducing steric hindrance. The ABDs or ABD chains can be connected to one another through, for example, Fc domains (each Fc domain representing a pair of associated Fc regions) and/or ABD linkers. The use of Fc domains will typically require the use of hinge regions as connectors of the ABDs or ABD chains for optimal antigen binding. Thus, the term "connector" encompasses, but is not limited to, Fc regions, Fc domains, and hinge regions.

Connectors can be selected or modified to, for example, increase or decrease the biological half-life of a BCMA binding molecule. For example, to decrease biological half-life, one or more amino acid mutations can be introduced into a CH2-CH3 domain interface region of an Fc-hinge fragment such that a BCMA binding molecule comprising the fragment has impaired Staphylococcyl Protein A (SpA) binding relative to native Fc-hinge domain SpA binding. This approach is described in further detail in U.S. Pat. No. 6,165,745 by Ward et al. Alternatively, a BCMA binding molecule can be modified to increase its biological half-life. For example, one or more of the following mutations can be introduced: T252L, T254S, T256F, as described in U.S. Pat. No. 6,277,375 to Ward. Alternatively, to increase the biological half-life, a BCMA binding molecule can be altered within a CH1 or CL region to contain a salvage receptor binding epitope taken from two loops of a CH2 domain of an Fc region of an IgG, as described in U.S. Pat. Nos. 5,869,046 and 6,121,022 by Presta et al.

Examples of Fc domains (formed by the pairing of two Fc regions), hinge regions and ABD linkers are described in Sections 7.4.1, 7.4.2, and 7.4.3, respectively.

7.4.1. Fc Domains

The BCMA binding molecules can include an Fc domain derived from any suitable species. In one embodiment, the Fc domain is derived from a human Fc domain.

The Fc domain can be derived from any suitable class of antibody, including IgA (including subclasses IgA1 and IgA2), IgD, IgE, IgG (including subclasses IgG1, IgG2, IgG3 and IgG4), and IgM. In one embodiment, the Fc domain is derived from IgG1, IgG2, IgG3 or IgG4. In one embodiment, the Fc domain is derived from IgG1. In one embodiment, the Fc domain is derived from IgG4.

In a native antibody the Fc regions are typically identical, but for the purpose of producing multispecific binding molecules, e.g., the MBMs of the disclosure, the Fc regions might advantageously be different to allow for heterodimerization, as described in Section 7.4.1.5 below.

Typically each Fc region comprises or consists of two or three heavy chain constant domains.

In native antibodies, the Fc region of IgA, IgD and IgG is composed of two heavy chain constant domains (CH2 and CH3) and that of IgE and IgM is composed of three heavy chain constant domains (CH2, CH3 and CH4). These dimerize to create an Fc domain.

In the present disclosure, the Fc region can comprise heavy chain constant domains from one or more different classes of antibody, for example one, two or three different classes.

In one embodiment, the Fc region comprises CH2 and CH3 domains derived from IgG1.

In one embodiment, the Fc region comprises CH2 and CH3 domains derived from IgG2.

In one embodiment, the Fc region comprises CH2 and CH3 domains derived from IgG3.

In one embodiment, the Fc region comprises CH2 and CH3 domains derived from IgG4.

In one embodiment, the Fc region comprises a CH4 domain from IgM. The IgM CH4 domain is typically located at the C-terminus of the CH3 domain.

In one embodiment, the Fc region comprises CH2 and CH3 domains derived from IgG and a CH4 domain derived from IgM.

It will be appreciated that the heavy chain constant domains for use in producing an Fc region for the BCMA binding molecules of the present disclosure can include variants of the naturally occurring constant domains described above. Such variants can comprise one or more amino acid variations compared to wild type constant domains. In one example the Fc region of the present disclosure comprises at least one constant domain that varies in sequence from the wild type constant domain. It will be appreciated that the variant constant domains can be longer or shorter than the wild type constant domain. For example, the variant constant domains are at least 60% identical or similar to a wild type constant domain. In another example the variant constant domains are at least 70% identical or similar. In another example the variant constant domains are at least 75% identical or similar. In another example the variant constant domains are at least 80% identical or similar. In another example the variant constant domains are at least 85% identical or similar. In another example the variant constant domains are at least 90% identical or similar. In another example the variant constant domains are at least 95% identical or similar. In another example the variant constant domains are at least 99% identical or similar. Exemplary Fc variants are described in Sections 7.4.1.1 through 7.4.1.5, infra.

IgM and IgA occur naturally in humans as covalent multimers of the common H2L2 antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. The tailpiece includes a cysteine residue that forms a disulfide bond between heavy chains in the polymer, and is believed to have an important role in polymerization. The tailpiece also contains a glycosylation site. In certain embodiments, the BCMA binding molecules of the present disclosure do not comprise a tailpiece.

The Fc domains that are incorporated into the BCMA binding molecules of the present disclosure can comprise one or more modifications that alter one or more functional properties of the proteins, such as serum half-life, complement fixation, Fc receptor binding, and/or antigen-dependent cellular cytotoxicity. Furthermore, a BCMA binding molecule can be chemically modified (e.g., one or more chemical moieties can be attached to the BCMA binding molecule) or be modified to alter its glycosylation, again to alter one or more functional properties of the BCMA binding molecule.

Effector function of an antibody molecule includes complement-mediated effector function, which is mediated by, for example, binding of the C1 component of the complement to the antibody. Activation of complement is important in the opsonization and direct lysis of pathogens. In addition, it stimulates the inflammatory response by recruiting and activating phagocytes to the site of complement activation. Effector function includes Fc receptor (FcR)-mediated effector function, which can be triggered upon binding of the constant domains of an antibody to an Fc receptor (FcR). Antigen-antibody complex-mediated crosslinking of Fc receptors on effector cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Fc regions can be altered by replacing at least one amino acid residue with a different amino acid residue to alter the effector functions. For example, one or more amino acids can be replaced with a different amino acid residue such that the Fc region has an altered affinity for an effector ligand.

The effector ligand to which affinity is altered can be, for example, an Fc receptor or the C1 component of complement. This approach is described in, e.g., U.S. Pat. Nos. 5,624,821 and 5,648,260, both by Winter et al. Modified Fc regions can also alter C1q binding and/or reduce or abolish complement dependent cytotoxicity (CDC). This approach is described in, e.g., U.S. Pat. No. 6,194,551 by Idusogie et al. Modified Fc regions can also alter the ability of an Fc region to fix complement. This approach is described in, e.g., the PCT Publication WO 94/29351 by Bodmer et al. Allotypic amino acid residues include, but are not limited to, constant region of a heavy chain of the IgG1, IgG2, and IgG3 subclasses as well as constant region of a light chain of the kappa isotype as described by Jefferis et al., 2009, MAbs, 1:332-338.

Fc regions can also be modified to "silence" the effector function, for example, to reduce or eliminate the ability of a BCMA binding molecule to mediate antibody dependent cellular cytotoxicity (ADCC) and/or antibody dependent cellular phagocytosis (ADCP). This can be achieved, for example, by introducing a mutation in an Fc region. Such mutations have been described in the art: LALA and N297A (Strohl, 2009, Curr. Opin. Biotechnol. 20(6):685-691); and D265A (Baudino et al., 2008, J. Immunol. 181: 6664-69; Strohl, supra). Examples of silent Fc IgG1 antibodies comprise the so-called LALA mutant comprising L234A and L235A mutation in the IgG1 Fc amino acid sequence. Another example of a silent IgG1 antibody comprises the D265A mutation. Another silent IgG1 antibody comprises the so-called DAPA mutant comprising D265A and P329A mutations in the IgG1 Fc amino acid sequence. Another silent IgG1 antibody comprises the N297A mutation, which results in aglycosylated/non-glycosylated antibodies.

Fc regions can be modified to increase the ability of a BCMA binding molecule containing the Fc region to mediate antibody dependent cellular cytotoxicity (ADCC) and/or antibody dependent cellular phagocytosis (ADCP), for example, by modifying one or more amino acid residues to increase the affinity of the BCMA binding molecule for an activating Fcγ receptor, or to decrease the affinity of the BCMA binding molecule for an inhibitory Fcγ receptor. Human activating Fcγ receptors include FcγRIa, FcγRIIa, FcγRIIIa, and FcγRIIIb, and human inhibitory Fcγ receptor includes FcγRIIb. This approach is described in, e.g., the PCT Publication WO 00/42072 by Presta. Moreover, binding sites on human IgG1 for FcγRI, FcγRII, FcγRIII and FcRn have been mapped and variants with improved binding have been described (see Shields et al., J. Biol. Chem. 276:6591-6604, 2001). Optimization of Fc-mediated effector functions of monoclonal antibodies such as increased ADCC/ADCP function has been described (see Stroh), 2009, Current Opinion in Biotechnology 20:685-691). Mutations that can enhance ADCC/ADCP function include one or more mutations selected from G236A, S239D, F243L, P247I, D280H, K290S, R292P, S298A, S298D, S298V, Y300L, V305I, A330L, I332E, E333A, K334A, A339D, A339Q, A339T, and P396L (all positions by EU numbering).

Fc regions can also be modified to increase the ability of a BCMA binding molecule to mediate ADCC and/or ADCP, for example, by modifying one or more amino acids to increase the affinity of the BCMA binding molecule for an activating receptor that would typically not recognize the parent BCMA binding molecule, such as FcαRI. This approach is described in, e.g., Borrok et al., 2015, mAbs. 7(4):743-751.

Accordingly, in certain aspects, the BCMA binding molecules of the present disclosure can include Fc domains with altered effector function such as, but not limited to, binding to Fc-receptors such as FcRn or leukocyte receptors (for example, as described above or in Section 7.4.1.1), binding to complement (for example as described above or in Section 7.4.1.2), modified disulfide bond architecture (for example as described above or in Section 7.4.1.3), or altered glycosylation patterns (for example as described above or in Section 7.4.1.4). The Fc domains can also be altered to include modifications that improve manufacturability of asymmetric BCMA binding molecules, for example by allowing heterodimerization, which is the preferential pairing of non-identical Fc regions over identical Fc regions. Heterodimerization permits the production of BCMA binding molecules in which different ABDs are connected to one another by an Fc domain containing Fc regions that differ in sequence. Examples of heterodimerization strategies are exemplified in Section 7.4.1.5 (and subsections thereof).

It will be appreciated that any of the modifications described in Sections 7.4.1.1 through 7.4.1.5 can be combined in any suitable manner to achieve the desired functional properties and/or combined with other modifications to alter the properties of the BCMA binding molecules.

7.4.1.1. Fc Domains with Altered FcR Binding

The Fc domains of the BCMA binding molecules may show altered binding to one or more Fc-receptors (FcRs) in comparison with the corresponding native immunoglobulin. The binding to any particular Fc-receptor can be increased or decreased. In one embodiment, the Fc domain comprises one or more modifications which alter its Fc-receptor binding profile.

Human cells can express a number of membrane bound FcRs selected from FcαR, FcεR, FcγR, FcRn and glycan receptors. Some cells are also capable of expressing soluble (ectodomain) FcR (Fridman et al., 1993, J Leukocyte Biology 54: 504-512). FcγR can be further divided by affinity of IgG binding (high/low) and biological effect (activating/inhibiting). Human FcγRI is widely considered to be the sole 'high affinity' receptor whilst all of the others are considered as medium to low. FcγRIIb is the sole receptor with 'inhibitory' functionality by virtue of its intracellular ITIM motif whilst all of the others are considered as 'activating' by virtue of ITAM motifs or pairing with the common FcγR-γchain. FcγRIIIb is also unique in that although activatory it associates with the cell via a GPI anchor. In total, humans express six "standard" FcγRs: FcγRI, FcγRIIa, FcγRIIb, FcγRIIc, FcγRIIIa, and FcγRIIIb. In addition to these sequences there are a large number of sequence or allotypic variants spread across these families. Some of these have been found to have important functional consequence and so are sometimes considered to be receptor sub-types of their own. Examples include FcγRIIa$^{H134R}$, FcγRIIb$^{I190T}$, FcγRIIIa$^{F158V}$, FcγRIIIb$^{NA1}$, FcγRIIIb$^{NA2}$, and FcγRIII$^{SH}$. Each receptor sequence has been shown to have different affinities for the 4 sub-classes of IgG: IgG1, IgG2, IgG3 and IgG4 (Bruhns, 1993, Blood 113:3716-3725). Other species have somewhat different numbers and functionality of FcγR, with the mouse system being the best studied to date and comprising of 4 FcγR, FcγRI FcγRIIb FcγRIII FcγRIV (Bruhns, 2012, Blood 119:5640-5649). Human FcγRI on cells is normally considered to be "occupied" by monomeric IgG in normal serum conditions due to its affinity for IgG1/IgG3/IgG4 (about $10^{-8}$ M) and the concentration of these IgG in serum (about 10 mg/ml). Hence cells bearing FcγRI on their surface are considered to be capable for "screening" or "sampling" of their antigenic environment vicariously through the bound polyspecific IgG. The other receptors having lower affinities for IgG sub-classes (in the range of about $10^{-5}$-$10^{-7}$ M) are normally considered to be "unoccupied." The low affinity receptors are hence inherently sensitive to the detection of and activation by antibody involved immune complexes. The increased Fc density in an antibody immune complex results in increased functional affinity of binding avidity to low affinity FcγR. This has been demonstrated in vitro using a number of methods (Shields et al., 2001, J Biol Chem 276(9):6591-6604; Lux et al., 2013, J Immunol 190:4315-4323). It has also been implicated as being one of the primary modes of action in the use of anti-RhD to treat ITP in humans (Crow, 2008, Transfusion Medicine Reviews 22:103-116).

Many cell types express multiple types of FcγR and so binding of IgG or antibody immune complex to cells bearing FcγR can have multiple and complex outcomes depending upon the biological context. Most simply, cells can either receive an activatory, inhibitory or mixed signal. This can result in events such as phagocytosis (e.g., macrophages and neutrophils), antigen processing (e.g., dendritic cells), reduced IgG production (e.g., B-cells) or degranulation (e.g., neutrophils, mast cells). There are data to support that the inhibitory signal from FcγRIIb can dominate that of activatory signals (Proulx, 2010, Clinical Immunology 135:422-429).

There are a number of useful Fc substitutions that can be made to alter binding to one or more of the FcγR receptors. Substitutions that result in increased binding as well as decreased binding can be useful. For example, it is known that increased binding to FcγRIIIa generally results in increased ADCC (antibody dependent cell-mediated cytotoxicity; the cell-mediated reaction where nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present disclosure include those listed in US 2006/0024298 (particularly FIG. 41), US 2006/0121032, US 2006/0235208, and US 2007/0148170. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T.

FcRn has a crucial role in maintaining the long half-life of IgG in the serum of adults and children. The receptor binds IgG in acidified vesicles (pH<6.5) protecting the IgG molecule from degradation, and then releasing it at the higher pH of 7.4 in blood.

FcRn is unlike leukocyte Fc receptors, and instead, has structural similarity to MHC class I molecules. It is a heterodimer composed of a β$_2$-microglobulin chain, non-covalently attached to a membrane-bound chain that includes three extracellular domains. One of these domains, including a carbohydrate chain, together with β$_2$-microglobulin interacts with a site between the CH2 and CH3 domains of Fc. The interaction includes salt bridges made to histidine residues on IgG that are positively charged at pH<6.5. At higher pH, the His residues lose their positive charges, the FcRn-IgG interaction is weakened and IgG dissociates.

In one embodiment, a BCMA binding molecule comprises an Fc domain that binds to human FcRn.

In one embodiment, the Fc domain has an Fc region(s) (e.g., one or two) comprising a histidine residue at position 310, and in some cases also at position 435. These histidine residues are important for human FcRn binding. In one embodiment, the histidine residues at positions 310 and 435 are native residues, i.e., positions 310 and 435 are not modified. Alternatively, one or both of these histidine residues can be present as a result of a modification.

The BCMA binding molecules can comprise one or more Fc regions that alter Fc binding to FcRn. The altered binding can be increased binding or decreased binding.

In one embodiment, the BCMA binding molecule comprises an Fc domain in which at least one (and optionally both) Fc regions comprises one or more modifications such that it binds to FcRn with greater affinity and avidity than the corresponding native immunoglobulin.

Fc substitutions that increase binding to the FcRn receptor and increase serum half life are described in US 2009/0163699, including, but not limited to, 434S, 434A, 428L, 308F, 259I, 428L/434S, 259I/308F, 436I/428L, 436I or V/434S, 436V/428L and 259I/308F/428L.

In one embodiment, the Fc region is modified by substituting the threonine residue at position 250 with a glutamine residue (T250Q).

In one embodiment, the Fc region is modified by substituting the methionine residue at position 252 with a tyrosine residue (M252Y).

In one embodiment, the Fc region is modified by substituting the serine residue at position 254 with a threonine residue (S254T).

In one embodiment, the Fc region is modified by substituting the threonine residue at position 256 with a glutamic acid residue (T256E).

In one embodiment, the Fc region is modified by substituting the threonine residue at position 307 with an alanine residue (T307A).

In one embodiment, the Fc region is modified by substituting the threonine residue at position 307 with a proline residue (T307P).

In one embodiment, the Fc region is modified by substituting the valine residue at position 308 with a cysteine residue (V308C).

In one embodiment, the Fc region is modified by substituting the valine residue at position 308 with a phenylalanine residue (V308F).

In one embodiment, the Fc region is modified by substituting the valine residue at position 308 with a proline residue (V308P).

In one embodiment, the Fc region is modified by substituting the glutamine residue at position 311 with an alanine residue (Q311A).

In one embodiment, the Fc region is modified by substituting the glutamine residue at position 311 with an arginine residue (Q311R).

In one embodiment, the Fc region is modified by substituting the methionine residue at position 428 with a leucine residue (M428L).

In one embodiment, the Fc region is modified by substituting the histidine residue at position 433 with a lysine residue (H433K).

In one embodiment, the Fc region is modified by substituting the asparagine residue at position 434 with a phenylalanine residue (N434F).

In one embodiment, the Fc region is modified by substituting the asparagine residue at position 434 with a tyrosine residue (N434Y).

In one embodiment, the Fc region is modified by substituting the methionine residue at position 252 with a tyrosine residue, the serine residue at position 254 with a threonine residue, and the threonine residue at position 256 with a glutamic acid residue (M252Y/S254T/T256E).

In one embodiment, the Fc region is modified by substituting the valine residue at position 308 with a proline residue and the asparagine residue at position 434 with a tyrosine residue (V308P/N434Y).

In one embodiment, the Fc region is modified by substituting the methionine residue at position 252 with a tyrosine residue, the serine residue at position 254 with a threonine residue, the threonine residue at position 256 with a glutamic acid residue, the histidine residue at position 433 with a lysine residue and the asparagine residue at position 434 with a phenylalanine residue (M252Y/S254T/T256E/H433K/N434F).

It will be appreciated that any of the modifications listed above can be combined to alter FcRn binding.

In one embodiment, the BCMA binding molecule comprises an Fc domain in which one or both Fc regions comprise one or more modifications such that the Fc domain binds to FcRn with lower affinity and avidity than the corresponding native immunoglobulin.

In one embodiment, the Fc region comprises any amino acid residue other than histidine at position 310 and/or position 435.

The BCMA binding molecule can comprise an Fc domain in which one or both Fc regions comprise one or more modifications which increase its binding to FcγRIIb. FcγRIIb is the only inhibitory receptor in humans and the only Fc receptor found on B cells.

In one embodiment, the Fc region is modified by substituting the proline residue at position 238 with an aspartic acid residue (P238D).

In one embodiment, the Fc region is modified by substituting the glutamic acid residue at position 258 with an alanine residue (E258A).

In one embodiment, the Fc region is modified by substituting the serine residue at position 267 with an alanine residue (S267A).

In one embodiment, the Fc region is modified by substituting the serine residue at position 267 with a glutamic acid residue (S267E).

In one embodiment, the Fc region is modified by substituting the leucine residue at position 328 with a phenylalanine residue (L328F).

In one embodiment, the Fc region is modified by substituting the glutamic acid residue at position 258 with an alanine residue and the serine residue at position 267 with an alanine residue (E258A/S267A).

In one embodiment, the Fc region is modified by substituting the serine residue at position 267 with a glutamic acid residue and the leucine residue at position 328 with a phenylalanine residue (S267E/L328F).

It will be appreciated that any of the modifications listed above can be combined to increase FcγRIIb binding.

In one embodiment, BCMA binding molecules are provided comprising Fc domains which display decreased binding to FcγR.

In one embodiment, the BCMA binding molecule comprises an Fc domain in which one or both Fc regions comprise one or more modifications that decrease Fc binding to FcγR.

The Fc domain can be derived from IgG1.

In one embodiment, the Fc region is modified by substituting the leucine residue at position 234 with an alanine residue (L234A).

In one embodiment, the Fc region is modified by substituting the leucine residue at position 235 with an alanine residue (L235A).

In one embodiment, the Fc region is modified by substituting the glycine residue at position 236 with an arginine residue (G236R).

In one embodiment, the Fc region is modified by substituting the asparagine residue at position 297 with an alanine residue (N297A) or a glutamine residue (N297Q).

In one embodiment, the Fc region is modified by substituting the serine residue at position 298 with an alanine residue (S298A).

In one embodiment, the Fc region is modified by substituting the leucine residue at position 328 with an arginine residue (L328R).

In one embodiment, the Fc region is modified by substituting the leucine residue at position 234 with an alanine residue and the leucine residue at position 235 with an alanine residue (L234A/L235A).

In one embodiment, the Fc region is modified by substituting the phenylalanine residue at position 234 with an alanine residue and the leucine residue at position 235 with an alanine residue (F234A/L235A).

In one embodiment, the Fc region is modified by substituting the glycine residue at position 236 with an arginine residue and the leucine residue at position 328 with an arginine residue (G236R/L328R).

It will be appreciated that any of the modifications listed above can be combined to decrease FcγR binding.

In one embodiment, a BCMA binding molecule comprises an Fc domain in which one or both Fc regions comprise one or more modifications that decrease Fc binding to FcγRIIIa without affecting the Fc's binding to FcγRII.

In one embodiment, the Fc region is modified by substituting the serine residue at position 239 with an alanine residue (S239A).

In one embodiment, the Fc region is modified by substituting the glutamic acid residue at position 269 with an alanine residue (E269A).

In one embodiment, the Fc region is modified by substituting the glutamic acid residue at position 293 with an alanine residue (E293A).

In one embodiment, the Fc region is modified by substituting the tyrosine residue at position 296 with a phenylalanine residue (Y296F).

In one embodiment, the Fc region is modified by substituting the valine residue at position 303 with an alanine residue (V303A).

In one embodiment, the Fc region is modified by substituting the alanine residue at position 327 with a glycine residue (A327G).

In one embodiment, the Fc region is modified by substituting the lysine residue at position 338 with an alanine residue (K338A).

In one embodiment, the Fc region is modified by substituting the aspartic acid residue at position 376 with an alanine residue (D376A).

It will be appreciated that any of the modifications listed above can be combined to decrease FcγRIIIa binding.

Fc region variants with decreased FcR binding can be referred to as "FcγR ablation variants," "FcγR silencing variants" or "Fc knock out (FcKO or KO)" variants. For some therapeutic applications, it is desirable to reduce or remove the normal binding of an Fc domain to one or more or all of the Fcγ receptors (e.g., FcγR1, FcγRIIa, FcγRIIb, FcγRIIIa) to avoid additional mechanisms of action. That is, for example, in many embodiments, particularly in the use of BBMs that bind CD3 monovalently, it is generally desirable to ablate FcγRIIIa binding to eliminate or significantly reduce ADCC activity. In some embodiments, at least one of the Fc regions of the BCMA binding molecules described herein comprises one or more Fcγ receptor ablation variants. In some embodiments, both of the Fc regions comprise one or more Fcγ receptor ablation variants. These ablation variants are depicted in Table 5, and each can be independently and optionally included or excluded, with some aspects utilizing ablation variants selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del ("del" connotes a deletion, e.g., G236del refers to a deletion of the glycine at position 236). It should be noted that the ablation variants referenced herein ablate FcγR binding but generally not FcRn binding.

TABLE 5

Ablation Variants

| Variant | Variant(s), cont. |
|---------|-------------------|
| G236R | P329K |
| S239G | A330L |
| S239K | A330S/P331S |
| S239Q | I332K |
| S239R | I332R |
| V266D | V266D/A327Q |
| S267K | V266D/P329K |
| S267R | S267R/A327Q |
| H268K | S267R/P329K |
| E269R | G236R/L328R |
| 299R | E233P/L234V/L235A/G236del/S239K |
| 299K | E233P/L234V/L235A/G236del/S267K |
| K322A | E233P/L234V/L235A/G236del/S239K/A327G |
| A327G | E233P/L234V/L235A/G236del/S267K/A327G |
| A327L | E233P/L234V/L235A/G236del |
| A327N | S239K/S267K |
| A327Q | 267K/P329K |
| L328E | |
| L328R | |
| P329A | |
| P329H | |

In some embodiments, the multispecific BCMA binding molecule of the present disclosure comprises a first Fc region and a second Fc region. In some embodiments, the first Fc region and/or the second Fc region can comprise the following mutations: E233P, L234V, L235A, G236del, and S267K.

The Fc domain of human IgG1 has the highest binding to the Fcγ receptors, and thus ablation variants can be used when the constant domain (or Fc domain) in the backbone of the heterodimeric antibody is IgG1.

Alternatively, or in addition to ablation variants in an IgG1 background, mutations at the glycosylation position 297, e.g., substituting the asparagine residue at position 297 with an alanine residue (N297A) or a glutamine residue (N297Q), can significantly ablate binding to FcγRIIIa, for example. Human IgG2 and IgG4 have naturally reduced binding to the Fcγ receptors, and thus those backbones can be used with or without the ablation variants.

7.4.1.2. Fc Domains with Altered Complement Binding

The BCMA binding molecules can comprise an Fc domain in which one or both Fc regions comprises one or more modifications that alter Fc binding to complement. Altered complement binding can be increased binding or decreased binding.

In one embodiment, the Fc region comprises one or more modifications which decrease its binding to C1q. Initiation of the classical complement pathway starts with binding of hexameric C1q protein to the CH2 domain of antigen bound IgG and IgM.

In one embodiment, the BCMA binding molecule comprises an Fc domain in which one or both Fc regions comprises one or more modifications to decrease Fc binding to C1q.

In one embodiment, the Fc region is modified by substituting the leucine residue at position 234 with an alanine residue (L234A).

In one embodiment, the Fc region is modified by substituting the leucine residue at position 235 with an alanine residue (L235A).

In one embodiment, the Fc region is modified by substituting the leucine residue at position 235 with a glutamic acid residue (L235E).

In one embodiment, the Fc region is modified by substituting the glycine residue at position 237 with an alanine residue (G237A).

In one embodiment, the Fc region is modified by substituting the lysine residue at position 322 with an alanine residue (K322A).

In one embodiment, the Fc region is modified by substituting the proline residue at position 331 with an alanine residue (P331A).

In one embodiment, the Fc region is modified by substituting the proline residue at position 331 with a serine residue (P331S).

In one embodiment, a BCMA binding molecule comprises an Fc domain derived from IgG4. IgG4 has a naturally lower complement activation profile than IgG1, but also weaker binding of FcγR. Thus, in one embodiment, the BCMA binding molecule comprises an IgG4 Fc domain and also comprises one or more modifications that increase FcγR binding.

It will be appreciated that any of the modifications listed above can be combined to reduce C1q binding.

7.4.1.3. Fc Domains with Altered Disulfide Architecture

The BCMA binding molecule can include an Fc domain comprising one or more modifications to create and/or remove a cysteine residue. Cysteine residues have an important role in the spontaneous assembly of Fc-based multispecific binding molecules, by forming disulfide bridges between individual pairs of polypeptide monomers. Thus, by altering the number and/or position of cysteine residues, it is possible to modify the structure of the BCMA binding molecule to produce a protein with improved therapeutic properties.

A BCMA binding molecule of the present disclosure can comprise an Fc domain in which one or both Fc regions, e.g., both Fc regions, comprise a cysteine residue at position 309. In one embodiment, the cysteine residue at position 309 is created by a modification, e.g., for an Fc domain derived from IgG1, the leucine residue at position 309 is substituted with a cysteine residue (L309C), for an Fc domain derived from IgG2, the valine residue at position 309 is substituted with a cysteine residue (V309C).

In one embodiment, the Fc region is modified by substituting the valine residue at position 308 with a cysteine residue (V308C).

In one embodiment, two disulfide bonds in the hinge region are removed by mutating a core hinge sequence CPPC (SEQ ID NO:422) to SPPS (SEQ ID NO:423).

7.4.1.4. Fc Domains with Altered Glycosylation

In certain aspects, BCMA binding molecules with improved manufacturability are provided that comprise fewer glycosylation sites than a corresponding immunoglobulin. These proteins have less complex post translational glycosylation patterns and are thus simpler and less expensive to manufacture.

In one embodiment, a glycosylation site in the CH2 domain is removed by substituting the asparagine residue at position 297 with an alanine residue (N297A) or a glutamine residue (N297Q). In addition to improved manufacturability, these aglycosyl mutants also reduce FcγR binding as described herein above.

In some embodiments, a BCMA binding molecule can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing a BCMA binding molecule in a host cell with altered glycosylation machinery. Cells with altered glycosylation machinery have been described in the art and can be used as host cells in which to express BCMA binding molecules to thereby produce BCMA binding molecules with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields et al., 2002, J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

7.4.1.5. Fc Heterodimerization

Many multispecific molecule formats entail dimerization between two Fc regions that, unlike a native immunoglobulin, are operably linked to non-identical antigen-binding domains (or portions thereof, e.g., a VH or VH-CH1 of a Fab). Inadequate heterodimerization of two Fc regions to form an Fc domain has always been an obstacle for increasing the yield of desired multispecific molecules and represents challenges for purification. A variety of approaches available in the art can be used in for enhancing dimerization of Fc regions that might be present in the BCMA binding molecules (and particularly in the MBMs of the disclosure), for example as disclosed in EP 1870459A1; U.S. Pat. Nos. 5,582,996; 5,731,168; 5,910,573; 5,932,448; 6,833,441; 7,183,076; U.S. Patent Application Publication No. 2006204493A1; and PCT Publication No. WO2009/089004A1.

The present disclosure provides BCMA binding molecules comprising Fc heterodimers. Heterodimerization strategies are used to enhance dimerization of Fc regions operably linked to different ABDs (or portions thereof, e.g., a VH or VH-CH1 of a Fab) and reduce dimerization of Fc regions operably linked to the same ABD or portion thereof. Typically, each Fc region in the Fc heterodimer comprises a CH3 domain of an antibody. The CH3 domains are derived from the constant region of an antibody of any isotype, class or subclass, and in some cases of IgG (IgG1, IgG2, IgG3 and IgG4) class, as described in the preceding section.

Typically, the BCMA binding molecules comprise other antibody fragments in addition to CH3 domains, such as, CH1 domains, CH2 domains, hinge domain, VH domain(s), VL domain(s), CDR(s), and/or antigen-binding fragments described herein. In some embodiments, the two hetero-polypeptides are two heavy chains forming a bispecific or multispecific molecules. Heterodimerization of the two different heavy chains at CH3 domains give rise to the desired antibody or antibody-like molecule, while homodimerization of identical heavy chains will reduce yield of the desired antibody or molecule. In an exemplary embodiment, the two or more hetero-polypeptide chains comprise two chains comprising CH3 domains and forming the molecules of any of the multispecific molecule formats described above of the present disclosure. In an embodiment, the two hetero-polypeptide chains comprising CH3 domains comprise modifications that favor heterodimeric association of the polypeptides, relative to unmodified chains. Various examples of modification strategies are provided below in Table 6 and Sections 7.4.1.5.1 to 7.4.1.5.7.

TABLE 6

Fc Heterodimerization Strategies

| NO. | STRATEGY | CH3 DOMAIN 1 | CH3 DOMAIN 2 | REFERENCES |
|---|---|---|---|---|
| Fc 1 | knobs-into-holes (Y-T) | T366Y | Y407T | Ridgway et al., 1996, Protein Eng 9: 617-21 |
| Fc 2 | knobs-into-holes (CW-CSAV) | S354C, T366W | Y349C, T366S, L368A, Y407V | Atwell et al., 1997, J Mol Biol. 270(1): 26-35; Merchant et al., 1998, Nat Biotechnol 16: 677-681 |
| Fc 3 | HA-TF | S364H, F405A | Y349T, T394F | Moore et al., 2011, MAbs 3(6): 546-57 |
| Fc 4 | ZW1 (VYAV-VLLW) | T350V, L351Y, F405A, Y407V | T350V, T366L, K392L, T394W | Von Kreudenstein et al., 2013, MAbs 5: 646-54 |
| Fc 5 | CH3 charge pairs (DD-KK) | K392D, K409D | E356K, D399K | Gunasekaran et al., 2010, J Biol Chem 285: 19637-46 |
| Fc 6 | IgG1 hingE, CH3 charge pairs (EEE-RRR) | IgG1: D221E, P228E, L368E | IgG1: D221R, P228R, K409R | Strop et al., 2012, J Mol Biol 420: 204-19 |

TABLE 6-continued

| | Fc Heterodimerization Strategies | | | |
|---|---|---|---|---|
| NO. | STRATEGY | CH3 DOMAIN 1 | CH3 DOMAIN 2 | REFERENCES |
| Fc 7 | IgG2 hingE, CH3 charge pairs (EEE-RRRR) | IgG2: C223E, P228E, L368E | IgG2: C223R, E225R, P228R, K409R | Strop et al., 2012, J Mol Biol 420: 204-19 |
| Fc 8 | EW-RVT | K360E, K409W | Q347R, D399V, F405T | Choi et al., 2013, Mol Cancer Ther 12: 2748-59 |
| Fc 9 | EW-RVTS-S | K360E, K409W, Y349C | Q347R, D399V, F405T, S354C | Choi et al., 2015, Mol Immunol 65: 377-83 |
| Fc 10 | Biclonic | 366K (+351K) | 351D or E or D at 349, 368, 349, or 349 + 355 | Geuijen et al., 2014, Journal of Clinical Oncology 32: suppl: 560 |
| Fc 11 | DuoBody (L-R) | F405L | K409R | Labrijn et al., 2013, Proc Natl Acad Sci USA 110: 5145-50 |
| Fc 12 | SEEDbody | IgG/A chimera | IgG/A chimera | Davis et al., 2010, Protein Eng Des Sel 23: 195-202 |
| Fc 13 | BEAT | residues from TCRα interface | residues from TCRβ interface | Moretti et al., 2013, BMC Proceedings 7(Suppl 6): O9 |
| Fc 14 | 7.8.60 (DMA-RRVV) | K360D, D399M, Y407A | E345R, Q347R, T366V, K409V | Leaver-Fey et al., Structure 24: 641-51 |
| Fc 15 | 20.8.34 (SYMV-GDQA) | Y349S, K370Y, T366M, K409V | E356G, E357D, S364Q, Y407A | Leaver-Fey et al., Structure 24: 641-51 |
| Fc 16 | Skew variant 12757 | None | None | FIG. 34 of US 2016/0355600 |
| Fc 17 | Skew variant 12758 | L368D, K370S | S364K | FIG. 34 of US 2016/0355600 |
| Fc 18 | Skew variant 12759 | L368D, K370S | S364K, E357L | FIG. 34 of US 2016/0355600 |
| Fc 19 | Skew variant 12760 | L368D, K370S | S364K, E357Q | FIG. 34 of US 2016/0355600 |
| Fc 20 | Skew variant 12761 | T411E, K360E, Q362E | D401K | FIG. 34 of US 2016/0355600 |
| Fc 21 | Skew variant 12496 | L368E, K370S | S364K | FIG. 34 of US 2016/0355600 |
| Fc 22 | Skew variant 12511 | K370S | S364K | FIG. 34 of US 2016/0355600 |
| Fc 23 | Skew variant 12840 | L368E, K370S | S364K, E357Q | FIG. 34 of US 2016/0355600 |
| Fc 24 | Skew variant 12841 | K370S | S364K, E357Q | FIG. 34 of US 2016/0355600 |
| Fc 25 | Skew variant 12894 | L368E, K370S | S364K | FIG. 34 of US 2016/0355600 |
| Fc 26 | Skew variant 12895 | K370S | S364K | FIG. 34 of US 2016/0355600 |
| Fc 27 | Skew variant 12896 | L368E, K370S | S364K, E357Q | FIG. 34 of US 2016/0355600 |
| Fc 28 | Skew variant 12901 | K370S | S364K, E357Q | FIG. 34 of US 2016/0355600 |
| Fc 29 | pI_ISO(−) | I199T, N203D, K274Q, R355Q, N384S, K392N, V397M, Q419E, DEL447 | | FIG. 31 of US 2016/0355600 |
| Fc 30 | pI_(−)_Isosteric_A | N208D, Q295E, N384D, Q418E, N421D | | FIG. 31 of US 2016/0355600 |
| Fc 31 | pI_(−)_isosteric_B | N208D, Q295E, Q418E, N421D | | FIG. 31 of US 2016/0355600 |
| Fc 32 | pI_ISO(+RR) | Q196K, I199T, P217R, P228R, N276K | | FIG. 31 of US 2016/0355600 |
| Fc 33 | pI_ISO(+) | Q196K, I199T, N276K | | FIG. 31 of US 2016/0355600 |
| Fc 34 | pI_(+)_isosteric_A | E269Q, E272Q, E283Q, E357Q | | FIG. 31 of US 2016/0355600 |
| Fc 35 | pI_(+)_isosteric_B | E269Q, E272Q, E283Q | | FIG. 31 of US 2016/0355600 |
| Fc 36 | pI_(+) isosteric_E269Q E272Q | E269Q, E272Q | | FIG. 31 of US 2016/0355600 |
| Fc 37 | pI_(+)_isosteric_ E269Q, E283Q | E269Q, E283Q | | FIG. 31 of US 2016/0355600 |

TABLE 6-continued

Fc Heterodimerization Strategies

| NO. | STRATEGY | CH3 DOMAIN 1 | CH3 DOMAIN 2 | REFERENCES |
|---|---|---|---|---|
| Fc 38 | pI_(+)_isosteric_E2720, E283Q | E272Q, E283Q | | FIG. 31 of US 2016/0355600 |
| Fc 39 | pI_(+)_isosteric_E269Q | E269Q | | FIG. 31 of US 2016/0355600 |
| Fc 40 | Heterodimerization | F405A | T394F | FIG. 30A of US 2016/0355600 |
| Fc 41 | Heterodimerization | S364D | Y349K | FIG. 30A of US 2016/0355600 |
| Fc 42 | Heterodimerization | S364E | L368K | FIG. 30A of US 2016/0355600 |
| Fc 43 | Heterodimerization | S364E | Y349K | FIG. 30A of US 2016/0355600 |
| Fc 44 | Heterodimerization | S364F | K370G | FIG. 30A of US 2016/0355600 |
| Fc 45 | Heterodimerization | S364H | Y349K | FIG. 30A of US 2016/0355600 |
| Fc 46 | Heterodimerization | S364H | Y349T | FIG. 30A of US 2016/0355600 |
| Fc 47 | Heterodimerization | S364Y | K370G | FIG. 30A of US 2016/0355600 |
| Fc 48 | Heterodimerization | T411K | K370E | FIG. 30A of US 2016/0355600 |
| Fc 49 | Heterodimerization | V397S, F405A | T394F | FIG. 30A of US 2016/0355600 |
| Fc 50 | Heterodimerization | K370R, T411K | K370E, T411E | FIG. 30A of US 2016/0355600 |
| Fc 51 | Heterodimerization | L351E, S364D | Y349K, L351K | FIG. 30A of US 2016/0355600 |
| Fc 52 | Heterodimerization | L351E, S364E | Y349K, L351K | FIG. 30A of US 2016/0355600 |
| Fc 53 | Heterodimerization | L351E, T366D | L351K, T366K | FIG. 30A of US 2016/0355600 |
| Fc 54 | Heterodimerization | P395T, V397S, F405A | T394F | FIG. 30A of US 2016/0355600 |
| Fc 55 | Heterodimerization | S364D, K370G | S364Y, K370R | FIG. 30A of US 2016/0355600 |
| Fc 56 | Heterodimerization | S364D, T394F | Y349K, F405A | FIG. 30A of US 2016/0355600 |
| Fc 57 | Heterodimerization | S364E, F405A | Y349K, T394F | FIG. 30A of US 2016/0355600 |
| Fc 58 | Heterodimerization | S364E, F405S | Y349K, T394Y | FIG. 30A of US 2016/0355600 |
| Fc 59 | Heterodimerization | S364E, T411E | Y349K, D401K | FIG. 30A of US 2016/0355600 |
| Fc 60 | Heterodimerization | S364H, D401K | Y349T, T411E | FIG. 30A of US 2016/0355600 |
| Fc 61 | Heterodimerization | S364H, F405A | Y349T, T394F | FIG. 30A of US 2016/0355600 |
| Fc 62 | Heterodimerization | S364H, T394F | Y349T, F405A | FIG. 30A of US 2016/0355600 |
| Fc 63 | Heterodimerization | Y349C, S364E | Y349K, S354C | FIG. 30A of US 2016/0355600 |
| Fc 64 | Heterodimerization | L351E, S364D, F405A | Y349K, L351K, T394F | FIG. 30A of US 2016/0355600 |
| Fc 65 | Heterodimerization | L351K, S364H, D401K | Y349T, L351E, T411E | FIG. 30A of US 2016/0355600 |
| Fc 66 | Heterodimerization | S364E, T411E, F405A | Y349K, T394F, D401K | FIG. 30A of US 2016/0355600 |
| Fc 67 | Heterodimerization | S364H, D401K, F405A | Y349T, T394F, T411E | FIG. 30A of US 2016/0355600 |
| Fc 68 | Heterodimerization | S364H, F405A, T411E | Y349T, T394F, D401K | FIG. 30A of US 2016/0355600 |
| Fc 69 | Heterodimerization | T411E, K360E, N390D | D401K | FIG. 30C of US 2016/0355600 |
| Fc 70 | Heterodimerization | T411E, Q362E, N390D | D401K | FIG. 30C of US 2016/0355600 |
| Fc 71 | Heterodimerization | T411E, Q347R | D401K, K360D | FIG. 30C of US 2016/0355600 |
| Fc 72 | Heterodimerization | T411E, Q347R | D401K, K360E | FIG. 30C of US 2016/0355600 |
| Fc 73 | Heterodimerization | T411E, K360 | D401K, Q347K | FIG. 30C of US 2016/0355600 |
| Fc 74 | Heterodimerization | T411E, K360D | D401K, Q347R | FIG. 30C of US 2016/0355600 |

TABLE 6-continued

Fc Heterodimerization Strategies

| NO. | STRATEGY | CH3 DOMAIN 1 | CH3 DOMAIN 2 | REFERENCES |
|---|---|---|---|---|
| Fc 75 | Heterodimerization | T411E, K360E | D401K, Q347K | FIG. 30C of US 2016/0355600 |
| Fc 76 | Heterodimerization | T411E, K360E | D401K, Q347R | FIG. 30C of US 2016/0355600 |
| Fc 77 | Heterodimerization | T411E, S364K | D401K, K370S | FIG. 30C of US 2016/0355600 |
| Fc 78 | Heterodimerization | T411E, K370S | D401K, S364K | FIG. 30C of US 2016/0355600 |
| Fc 79 | Heterodimerization | Q347E | E357Q | FIG. 30C of US 2016/0355600 |
| Fc 80 | Heterodimerization | Q347E | E357Q, Q362K | FIG. 30C of US 2016/0355600 |
| Fc 81 | Heterodimerization | K360D, Q362E | Q347R | FIG. 30C of US 2016/0355600 |
| Fc 82 | Heterodimerization | K360D, Q362E | D401K | FIG. 30C of US 2016/0355600 |
| Fc 83 | Heterodimerization | K360D, Q362E | Q347R, D401K | FIG. 30C of US 2016/0355600 |
| Fc 84 | Heterodimerization | K360E, Q362E | Q347R | FIG. 30C of US 2016/0355600 |
| Fc 85 | Heterodimerization | K360E, Q362E | D401K | FIG. 30C of US 2016/0355600 |
| Fc 86 | Heterodimerization | K360E, Q362E | Q347R, D401K | FIG. 30C of US 2016/0355600 |
| Fc 87 | Heterodimerization | Q362E, N390D | D401K | FIG. 30C of US 2016/0355600 |
| Fc 88 | Heterodimerization | Q347E, K360D | D401N | FIG. 30C of US 2016/0355600 |
| Fc 89 | Heterodimerization | K360D | Q347R, N390K | FIG. 30C of US 2016/0355600 |
| Fc 90 | Heterodimerization | K360D | N390K, D401N | FIG. 30C of US 2016/0355600 |
| Fc 91 | Heterodimerization | K360E | Y349H | FIG. 30C of US 2016/0355600 |
| Fc 92 | Heterodimerization | K370S, Q347E | S364K | FIG. 30C of US 2016/0355600 |
| Fc 93 | Heterodimerization | K370S, E357L | S364K | FIG. 30C of US 2016/0355600 |
| Fc 94 | Heterodimerization | K370S, E357Q | S364K | FIG. 30C of US 2016/0355600 |
| Fc 95 | Heterodimerization | K370S, Q347E, E357L | S364K | FIG. 30C of US 2016/0355600 |
| Fc 96 | Heterodimerization | K370S, Q347E, E357Q | S364K | FIG. 30C of US 2016/0355600 |
| Fc 97 | Heterodimerization | L368D, K370S, Q347E | S364K | FIG. 30D of US 2016/0355600 |
| Fc 98 | Heterodimerization | L368D, K370S, E357L | S364K | FIG. 30D of US 2016/0355600 |
| Fc 99 | Heterodimerization | L368D, K370S, E357Q | S364K | FIG. 30D of US 2016/0355600 |
| Fc 100 | Heterodimerization | L368D, K370S, Q347E, E357L | S364K | FIG. 30D of US 2016/0355600 |
| Fc 101 | Heterodimerization | L368D, K370S, Q347E, E357Q | S364K | FIG. 30D of US 2016/0355600 |
| Fc 102 | Heterodimerization | L368E, K370S, Q347E | S364K | FIG. 30D of US 2016/0355600 |
| Fc 103 | Heterodimerization | L368E, K370S, E357L | S364K | FIG. 30D of US 2016/0355600 |
| Fc 104 | Heterodimerization | L368E, K370S, E357Q | S364K | FIG. 30D of US 2016/0355600 |
| Fc 105 | Heterodimerization | L368E, K370S, Q347E, E357L | S364K | FIG. 30D of US 2016/0355600 |
| Fc 106 | Heterodimerization | L368E, K370S, Q347E, E357Q | S364K | FIG. 30D of US 2016/0355600 |
| Fc 107 | Heterodimerization | L368D, K370T, Q347E | S364K | FIG. 30D of US 2016/0355600 |
| Fc 108 | Heterodimerization | L368D, K370T, E357L | S364K | FIG. 30D of US 2016/0355600 |
| Fc 109 | Heterodimerization | L368D, K370T, E357Q | S364K | FIG. 30D of US 2016/0355600 |
| Fc 110 | Heterodimerization | L368D, K370T, Q347E, E357L | S364K | FIG. 30D of US 2016/0355600 |
| Fc 111 | Heterodimerization | L368D, K370T, Q347E, E357Q | S364K | FIG. 30D of US 2016/0355600 |
| Fc 112 | Heterodimerization | L368E, K370T, Q347E | S364K | FIG. 30D of US 2016/0355600 |

TABLE 6-continued

Fc Heterodimerization Strategies

| NO. | STRATEGY | CH3 DOMAIN 1 | CH3 DOMAIN 2 | REFERENCES |
|---|---|---|---|---|
| Fc 113 | Heterodimerization | L368E, K370T, E357L | S364K | FIG. 30D of US 2016/0355600 |
| Fc 114 | Heterodimerization | L368E, K370T, E357Q | S364K | FIG. 30D of US 2016/0355600 |
| Fc 115 | Heterodimerization | L368E, K370T, Q347E, E357L | S364K | FIG. 30D of US 2016/0355600 |
| Fc 116 | Heterodimerization | L368E, K370T, Q347E, E357Q | S364K | FIG. 30D of US 2016/0355600 |
| Fc 117 | Heterodimerization | T411E, Q362E | D401K, T411K | FIG. 30D of US 2016/0355600 |
| Fc 118 | Heterodimerization | T411E, N390D | D401K, T411K | FIG. 30D of US 2016/0355600 |
| Fc 119 | Heterodimerization | T411E, Q362E | D401R, T411R | FIG. 30D of US 2016/0355600 |
| Fc 120 | Heterodimerization | T411E, N390D | D401R, T411R | FIG. 30D of US 2016/0355600 |
| Fc 121 | Heterodimerization | Y407T | T366Y | FIG. 30D of US 2016/0355600 |
| Fc 122 | Heterodimerization | F405A | T394W | FIG. 30D of US 2016/0355600 |
| Fc 123 | Heterodimerization | T366Y, F405A | T394W, Y407T | FIG. 30D of US 2016/0355600 |
| Fc 124 | Heterodimerization | T366S, L368A, Y407V | T366W | FIG. 30D of US 2016/0355600 |
| Fc 125 | Heterodimerization | T366S, L368A, | T366W, S354C | FIG. 30D of US 2016/0355600 |
| Fc 126 | Heterodimerization | K392D, K409D E356K, D399K | Y407V, Y349C | FIG. 30E of US 2016/0355600 |
| Fc 127 | Heterodimerization | K370D, K392D, K409D | E356K, E357K, D399K | FIG. 30E of US 2016/0355600 |
| Fc 128 | Heterodimerization | I199T, N203D, K247Q, R355Q, N384S, K392N, V397M, Q419E, K447 | Q196K, L99T, P217R, P228R, N276K | FIG. 30E of US 2016/0355600 |
| Fc 129 | Heterodimerization | I199T, N203D, K247Q, R355Q, N384S, K392N, V397M, Q419E, K447 | Q196K, L99T, N276K | FIG. 30E of US 2016/0355600 |
| Fc 130 | Heterodimerization | N384S, K392N, V397M, Q419E | N276K | FIG. 30E of US 2016/0355600 |
| Fc 131 | Heterodimerization | D221E, P228E, L368E | D221R, P228R, K409R | FIG. 30E of US 2016/0355600 |
| Fc 132 | Heterodimerization | C220E, P228E, L368E | C220R, E224R, P228R, K409R | FIG. 30E of US 2016/0355600 |
| Fc 133 | Heterodimerization | F405L | K409R | FIG. 30E of US 2016/0355600 |
| Fc 134 | Heterodimerization | T366I, K392M, T394W | F405A, Y407V | FIG. 30E of US 2016/0355600 |
| Fc 135 | Heterodimerization | T366V, K409F | L351Y, Y407A | FIG. 30E of US 2016/0355600 |
| Fc 136 | Heterodimerization | T366A, K392E, K409F, T411E | D399R, S400R, Y407A | FIG. 30E of US 2016/0355600 |
| Fc 137 | Heterodimerization | L351K | L351E | FIG. 30E of US 2016/0355600 |
| Fc 138 | Heterodimerization | I199T, N203D, K247Q, R355Q, Q419E, K447 | Q196K, L199T, P217R, P228R, N276K | FIG. 30E of US 2016/0355600 |
| Fc 139 | Heterodimerization | I199T, N203D, K247Q, R355Q, Q419E, K447 | Q196K, I199T, N276K | FIG. 30E of US 2016/0355600 |
| Fc 140 | Heterodimerization | I199T, N203D, K274Q, R355Q, N384S, K392N, V397M, Q419E DEL447 | | FIG. 30E of US 2016/0355600 |
| Fc 141 | Heterodimerization | N208D, Q295E N384D, Q418E N421D | | FIG. 30E of US 2016/0355600 |
| Fc 142 | Heterodimerization | N208D, Q295E Q418E, N421D | | FIG. 30E of US 2016/0355600 |
| Fc 143 | Heterodimerization | Q196K, I199T P217R, P228R N276K | | FIG. 30E of US 2016/0355600 |

TABLE 6-continued

Fc Heterodimerization Strategies

| NO. | STRATEGY | CH3 DOMAIN 1 | CH3 DOMAIN 2 | REFERENCES |
|---|---|---|---|---|
| Fc 144 | Heterodimerization | Q196K, I199T | N276K | FIG. 30E of US 2016/0355600 |
| Fc 145 | Heterodimerization | E269Q, E272Q E283Q, E357Q | | FIG. 30E of US 2016/0355600 |
| Fc 146 | Heterodimerization | E269Q, E272Q E283Q, | | FIG. 30E of US 2016/0355600 |
| Fc 147 | Heterodimerization | E269Q, E272Q | | FIG. 30E of US 2016/0355600 |
| Fc 148 | Heterodimerization | E269Q, E283Q | | FIG. 30E of US 2016/0355600 |
| Fc 149 | Heterodimerization | E272Q, E283Q | | FIG. 30E of US 2016/0355600 |
| Fc 150 | Heterodimerization | E269Q | | FIG. 30E of US 2016/0355600 |

7.4.1.5.1. Steric Variants

BCMA binding molecules can comprise one or more, e.g., a plurality, of modifications to one or more of the constant domains of an Fc domain, e.g., to the CH3 domains. In one example, a BCMA binding molecule of the present disclosure comprises two polypeptides that each comprise a heavy chain constant domain of an antibody, e.g., a CH2 or CH3 domain. In an example, the two heavy chain constant domains, e.g., the CH2 or CH3 domains of the BCMA binding molecule comprise one or more modifications that allow for a heterodimeric association between the two chains. In one aspect, the one or more modifications are disposed on CH2 domains of the two heavy chains. In one aspect, the one or more modifications are disposed on CH3 domains of at least two polypeptides of the BCMA binding molecule.

One mechanism for Fc heterodimerization is generally referred to in the art as "knobs and holes", or "knob-in-holes", or "knobs-into-holes". These terms refer to amino acid mutations that create steric influences to favor formation of Fc heterodimers over Fc homodimers, as described in, e.g., Ridgway et al., 1996, Protein Engineering 9(7):617; Atwell et al., 1997, J. Mol. Biol. 270:26; U.S. Pat. No. 8,216,805. Knob-in-hole mutations can be combined with other strategies to improve heterodimerization.

In one aspect, the one or more modifications to a first polypeptide of the BCMA binding molecule comprising a heavy chain constant domain can create a "knob" and the one or more modifications to a second polypeptide of the BCMA binding molecule creates a "hole," such that heterodimerization of the polypeptide of the BCMA binding molecule comprising a heavy chain constant domain causes the "knob" to interface (e.g., interact, e.g., a CH2 domain of a first polypeptide interacting with a CH2 domain of a second polypeptide, or a CH3 domain of a first polypeptide interacting with a CH3 domain of a second polypeptide) with the "hole." The knob projects from the interface of a first polypeptide of the BCMA binding molecule comprising a heavy chain constant domain and is therefore positionable in a compensatory "hole" in the interface with a second polypeptide of the BCMA binding molecule comprising a heavy chain constant domain so as to stabilize the heteromultimer, and thereby favor heteromultimer formation over homomultimer formation, for example. The knob can exist in the original interface or can be introduced synthetically (e.g. by altering nucleic acid encoding the interface). The import residues for the formation of a knob are generally naturally occurring amino acid residues and can be selected from arginine (R), phenylalanine (F), tyrosine (Y) and tryptophan (W). In some cases, tryptophan and tyrosine are selected. In an embodiment, the original residue for the formation of the protuberance has a small side chain volume, such as alanine, asparagine, aspartic acid, glycine, serine, threonine or valine.

A "hole" comprises at least one amino acid side chain which is recessed from the interface of a second polypeptide of the BCMA binding molecule comprising a heavy chain constant domain and therefore accommodates a corresponding knob on the adjacent interfacing surface of a first polypeptide of the BCMA binding molecule comprising a heavy chain constant domain. The hole can exist in the original interface or can be introduced synthetically (e.g. by altering nucleic acid encoding the interface). The import residues for the formation of a hole are usually naturally occurring amino acid residues and are in some cases selected from alanine (A), serine (S), threonine (T) and valine (V). In one embodiment, the amino acid residue is serine, alanine or threonine. In another embodiment, the original residue for the formation of the hole has a large side chain volume, such as tyrosine, arginine, phenylalanine or tryptophan.

In an embodiment, a first CH3 domain is modified at residue 366, 405 or 407 to create either a "knob" or a "hole" (as described above), and the second CH3 domain that heterodimerizes with the first CH3 domain is modified at: residue 407 if residue 366 is modified in the first CH3 domain, residue 394 if residue 405 is modified in the first CH3 domain, or residue 366 if residue 407 is modified in the first CH3 domain to create a "hole" or "knob" complementary to the "knob" or "hole" of the first CH3 domain.

In another embodiment, a first CH3 domain is modified at residue 366, and the second CH3 domain that heterodimerizes with the first CH3 domain is modified at residues 366, 368 and/or 407, to create a "hole" or "knob" complementary to the "knob" or "hole" of the first CH3 domain. In one embodiment, the modification to the first CH3 domain introduces a tyrosine (Y) residue at position 366. In an embodiment, the modification to the first CH3 is T366Y. In one embodiment, the modification to the first CH3 domain introduces a tryptophan (W) residue at position 366. In an embodiment, the modification to the first CH3 is T366W. In some embodiments, the modification to the second CH3 domain that heterodimerizes with the first CH3 domain modified at position 366 (e.g., has a tyrosine (Y) or tryptophan (W) introduced at position 366, e.g., comprises the modification T366Y or T366W), comprises a modification at position 366, a modification at position 368 and a modification at position 407. In some embodiments, the modification at position 366 introduces a serine (S) residue, the modification at position 368 introduces an alanine (A), and the modification at position 407 introduces a valine (V). In some embodiments, the modifications comprise T366S, L368A and Y407V. In one embodiment, the first CH3 domain of the multispecific molecule comprises the modification T366Y, and the second CH3 domain that heterodimerizes with the first CH3 domain comprises the modifications T366S, L368A and Y407V, or vice versa. In one embodiment, the first CH3 domain of the multispecific molecule comprises the modification T366W, and the second CH3 domain that heterodimerizes with the first CH3 domain comprises the modifications T366S, L368A and Y407V, or vice versa.

Additional steric or "skew" (e.g., knob-in-hole) modifications are described in PCT publication no. WO2014/145806 (for example, FIG. 3, FIG. 4 and FIG. 12 of WO2014/145806), PCT publication no. WO2014/110601, and PCT publication no. WO 2016/086186, WO 2016/086189, WO 2016/086196 and WO 2016/182751. An example of a KIH variant comprises a first constant chain comprising a L368D and a K370S modification, paired with a second constant chain comprising a S364K and E357Q modification.

Additional knob-in-hole modification pairs suitable for use in the BCMA binding molecules of the present disclosure are further described in, for example, WO1996/027011, and Merchant et al., 1998, Nat. Biotechnol., 16:677-681.

In further embodiments, the CH3 domains can be additionally modified to introduce a pair of cysteine residues. Without being bound by theory, it is believed that the introduction of a pair of cysteine residues capable of forming a disulfide bond provide stability to heterodimerized BCMA binding molecules comprising paired CH3 domains. In some embodiments, the first CH3 domain comprises a cysteine at position 354, and the second CH3 domain that heterodimerizes with the first CH3 domain comprises a cysteine at position 349. In some embodiments, the first CH3 domain comprises a cysteine at position 354 (e.g., comprises the modification S354C) and a tyrosine (Y) at position 366 (e.g., comprises the modification T366Y), and the second CH3 domain that heterodimerizes with the first CH3 domain comprises a cysteine at position 349 (e.g., comprises the modification Y349C), a serine at position 366 (e.g., comprises the modification T366S), an alanine at position 368 (e.g., comprises the modification L368A), and a valine at position 407 (e.g., comprises the modification Y407V). In some embodiments, the first CH3 domain comprises a cysteine at position 354 (e.g., comprises the modification S354C) and a tryptophan (W) at position 366 (e.g., comprises the modification T366W), and the second CH3 domain that heterodimerizes with the first CH3 domain comprises a cysteine at position 349 (e.g., comprises the modification Y349C), a serine at position 366 (e.g., comprises the modification T366S), an alanine at position 368 (e.g., comprises the modification L368A), and a valine at position 407 (e.g., comprises the modification Y407V).

An additional mechanism that finds use in the generation of heterodimers is sometimes referred to as "electrostatic steering" as described in Gunasekaran et al., 2010, J. Biol. Chem. 285(25):19637. This is sometimes referred to herein as "charge pairs". In this embodiment, electrostatics are used to skew the formation towards heterodimerization. As a skilled artisan will appreciate, these can also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R and C220E/P228E/368E paired with C220R/E224R/P228R/K409R.

Additional variants that can be combined with other variants, optionally and independently in any amount, such as pI variants outlined herein or other steric variants that are shown in FIG. 37 of US 2012/0149876.

In some embodiments, the steric variants outlined herein can be optionally and independently incorporated with any pI variant (or other variants such as Fc variants, FcRn variants) into one or both Fc regions, and can be independently and optionally included or excluded from the BCMA binding molecules of the disclosure.

A list of suitable skew variants is found in Table 7 showing some pairs of particular utility in many embodiments. Of particular use in many embodiments are the pairs of sets including, but not limited to, S364K/E357Q:L368D/K370S; L368D/K370S:S364K; L368E/K370S:S364K; T411T/E360E/Q362E:D401K; L368D/K370S:S364K/E357L; and K370S:S364K/E357Q. In terms of nomenclature, the pair "S364K/E357Q:L368D/K370S" means that one of the Fc regions has the double variant set S364K/E357Q and the other has the double variant set L368D/K370S.

TABLE 7

Exemplary skew variants

| Fc region 1 | Fc region 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |

TABLE 7-continued

Exemplary skew variants

| Fc region 1 | Fc region 2 |
|---|---|
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| N208D Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| Q295E N384D Q418E N421D | |
| N208D Q295E Q418E N421D | |
| Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

In some embodiments, a BCMA binding molecule comprises a first Fc region and a second Fc region. In some embodiments, the first Fc region comprises the following mutations: L368D and K370S, and the second Fc region comprises the following mutations: S364K and E357Q. In some embodiments, the first Fc region comprises the following mutations: S364K and E357Q, and the second Fc region comprises the following mutations: L368D and K370S.

7.4.1.5.2. Alternative Knob and Hole: IgG Heterodimerization

Heterodimerization of polypeptide chains of a BCMA binding molecule comprising paired CH3 domains can be increased by introducing one or more modifications in a CH3 domain which is derived from the IgG1 antibody class. In an embodiment, the modifications comprise a K409R modification to one CH3 domain paired with F405L modification in the second CH3 domain. Additional modifications can also, or alternatively, be at positions 366, 368, 370, 399, 405, 407, and 409. In some cases, heterodimerization of polypeptides comprising such modifications is achieved under reducing conditions, e.g., 10-100 mM 2-MEA (e.g., 25, 50, or 100 mM 2-MEA) for 1-10, e.g., 1.5-5, e.g., 5, hours at 25-37 C, e.g., 25 C or 37 C.

The amino acid replacements described herein can be introduced into the CH3 domains using techniques which are well known (see, e.g., McPherson, ed., 1991, Directed Mutagenesis: a Practical Approach; Adelman et al., 1983, DNA, 2:183).

The IgG heterodimerization strategy is further described in, for example, WO2008/119353, WO2011/131746, and WO2013/060867.

In any of the embodiments described in this Section, the CH3 domains can be additionally modified to introduce a pair of cysteine residues as described in Section 7.4.1.3.

7.4.1.5.3. pI (Isoelectric Point) Variants

In general, as will be appreciated by a skilled artisan, there are two general categories of pI variants: those that increase the pI of the protein (basic changes) and those that decrease the pI of the protein (acidic changes). As described herein, all combinations of these variants can be done: one Fc region can be wild type, or a variant that does not display a significantly different pI from wild-type, and the other can be either more basic or more acidic. Alternatively, each Fc region is changed, one to more basic and one to more acidic.

Exemplary combinations of pI variants are shown in Table 8. As outlined herein and shown in Table 8, these changes are shown relative to IgG1, but all isotypes can be altered this way, as well as isotype hybrids. In the case where the heavy chain constant domain is from IgG2-4, R133E and R133Q can also be used.

TABLE 8

Exemplary pI Variant Combinations

| Variant constant region | Substitutions |
| --- | --- |
| pI_ISO(−) | I199T N203D K274Q R355Q N384S K392N V397M Q419E DEL447 |
| pI_(−)_isosteric_A | N208D Q295E N384D Q418E N421D |
| pI_(−)_isosteric A-Fc only | Q295E N384D Q418E N421D |
| pI_(−)_isosteric_B | N208D Q295E Q418E N421D |
| pI_(−)_isosteric_B-Fc only | Q295E Q418E N421D |
| pI_ISO(+RR) | Q196K I199T P217R P228R N276K |
| pI_ISO(+) | Q196K I199T N276K |
| pI_(+)_isosteric_A | E269Q E272Q E283Q E357Q |
| pI_(+)_isosteric_B | E269Q E272Q E283Q |
| pI_(+)_isosteric_E269Q/E272Q | E269Q E272Q |
| pI_(+)_isosteric_E269Q/E283Q | E269Q E283Q |
| pI_(+)_isosteric_E272Q/E283Q | E272Q E283Q |
| pI_(+)_isosteric_E269Q | E269Q |

Figure 1C:
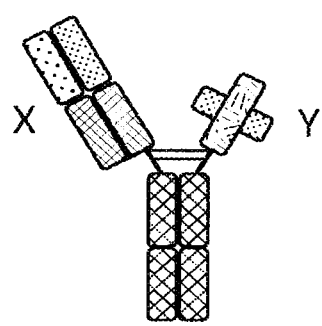

In one embodiment, for example in the FIGS. 1C, G, H, O, P, and Q formats, a combination of pI variants has one Fc region (the negative Fab side) comprising 208D/295E/384D/418E/421D variants (N208D/Q295E/N384D/Q418E/N421D when relative to human IgG1) and a second Fc region (the positive scFv side) comprising a positively charged scFv linker, e.g., L36 (described in Section 7.4.3). However, as will be appreciated by a skilled artisan, the first Fc region includes a CH1 domain, including position 208. Accordingly, in constructs that do not include a CH1 domain (for example for antibodies that do not utilize a CH1 domain as one of the domains, for example in a dual scFv format or a "one armed" format such as those depicted in FIG. 1D, E or F), an exemplary negative pI variant Fc set includes 295E/384D/418E/421D variants (Q295E/N384D/Q418E/N421D when relative to human IgG1).

In some embodiments, a first Fc region has a set of substitutions from Table B and a second Fc region is connected to a charged linker (e.g., selected from those described in Section 7.4.3).

In some embodiments, the BCMA binding molecule of the present disclosure comprises a first Fc region and a second Fc region. In some embodiments, the first Fc region comprises the following mutations: N208D, Q295E, N384D, Q418E, and N421D. In some embodiments, the second Fc region comprises the following mutations: N208D, Q295E, N384D, Q418E, and N421D.

7.4.1.5.4. Isotopic Variants

In addition, many embodiments of the disclosure rely on the "importation" of pI amino acids at particular positions from one IgG isotype into another, thus reducing or eliminating the possibility of unwanted immunogenicity being introduced into the variants. A number of these are shown in FIG. 21 of US Publ. 2014/0370013. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting Fc region is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significantly affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g., by changing a higher pI amino acid to a lower pI amino acid), or to allow accommodations in structure for stability, as is further described below.

In addition, by pI engineering both the heavy and light constant domains of a BCMA binding molecule comprising two half antibodies, significant changes in each half antibody can be seen. Having the pIs of the two half antibodies differ by at least 0.5 can allow separation by ion exchange chromatography or isoelectric focusing, or other methods sensitive to isoelectric point.

7.4.1.5.5. Calculating pI

The pI of a half antibody comprising an Fc region and an ABD or ABD chain can depend on the pI of the variant heavy chain constant domain and the pI of the total half antibody, including the variant heavy chain constant domain and ABD or ABD chain. Thus, in some embodiments, the change in pI is calculated on the basis of the variant heavy chain constant domain, using the chart in the FIG. 19 of US Pub. 2014/0370013. As discussed herein, which half antibody to engineer is generally decided by the inherent pI of the half antibodies. Alternatively, the pI of each half antibody can be compared.

7.4.1.5.6. pI Variants that Also Confer Better FcRn In Vivo Binding

In the case where a pI variant decreases the pI of an Fc region, it can have the added benefit of improving serum retention in vivo.

pI variant Fc regions are believed to provide longer half-lives to antigen binding molecules in vivo, because binding to FcRn at pH 6 in an endosome sequesters the Fc (Ghetie and Ward, 1997, Immunol Today. 18(12): 592-598). The endosomal compartment then recycles the Fc to the cell surface. Once the compartment opens to the extracellular space, the higher pH ~7.4, induces the release of Fc back into the blood. In mice, Dall' Acqua et al. showed that Fc mutants with increased FcRn binding at pH 6 and pH 7.4 actually had reduced serum concentrations and the same half life as wild-type Fc (Dall' Acqua et al. 2002, J. Immunol. 169:5171-5180). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

It has been suggested that antibodies with variable regions that have lower isoelectric points can also have longer serum half-lives (Igawa et al., 2010, PEDS. 23(5): 385-392). However, the mechanism of this is still poorly understood. Moreover, variable regions differ from antibody to antibody. Constant region variants with reduced pI and extended half-life would provide a more modular approach to improving the pharmacokinetic properties of BCMA binding molecules, as described herein.

7.4.1.5.7. Polar Bridge

Heterodimerization of polypeptide chains of BCMA binding molecules comprising an Fc domain can be increased by introducing modifications based on the "polar-bridging" rationale, which is to make residues at the binding interface of the two polypeptide chains to interact with residues of similar (or complimentary) physical property in the heterodimer configuration, while with residues of different physical property in the homodimer configuration. In particular, these modifications are designed so that, in the heterodimer formation, polar residues interact with polar residues, while hydrophobic residues interact with hydrophobic residues. In contrast, in the homodimer formation, residues are modified so that polar residues interact with hydrophobic residues. The favorable interactions in the heterodimer configuration and the unfavorable interactions in the homodimer configuration work together to make it more likely for Fc regions to form heterodimers than to form homodimers.

In an exemplary embodiment, the above modifications are generated at one or more positions of residues 364, 368, 399, 405, 409, and 411 of a CH3 domain.

In some embodiments, one or more modifications selected from the group consisting of S364L, T366V, L368Q, N399K, F405S, K409F and R411K are introduced into one of the two CH3 domains. One or more modifications selected from the group consisting of Y407F, K409Q and T411N can be introduced into the second CH3 domain.

In another embodiment, one or more modifications selected from the group consisting of S364L, T366V, L368Q, D399K, F405S, K409F and T411K are introduced into one CH3 domain, while one or more modifications selected from the group consisting of Y407F, K409Q and T411D are introduced into the second CH3 domain.

In one exemplary embodiment, the original residue of threonine at position 366 of one CH3 domain is replaced by valine, while the original residue of tyrosine at position 407 of the other CH3 domain is replaced by phenylalanine.

In another exemplary embodiment, the original residue of serine at position 364 of one CH3 domain is replaced by leucine, while the original residue of leucine at position 368 of the same CH3 domain is replaced by glutamine.

In yet another exemplary embodiment, the original residue of phenylalanine at position 405 of one CH3 domain is replaced by serine and the original residue of lysine at position 409 of this CH3 domain is replaced by phenylalanine, while the original residue of lysine at position 409 of the other CH3 domain is replaced by glutamine.

In yet another exemplary embodiment, the original residue of aspartic acid at position 399 of one CH3 domain is replaced by lysine, and the original residue of threonine at position 411 of the same CH3 domain is replaced by lysine, while the original residue of threonine at position 411 of the other CH3 domain is replaced by aspartic acid.

The amino acid replacements described herein can be introduced into the CH3 domains using techniques which are well known (see, e.g., McPherson, ed., 1991, Directed Mutagenesis: a Practical Approach; Adelman et al., 1983, DNA, 2:183). The polar bridge strategy is described in, for example, WO2006/106905, WO2009/089004 and K. Gunasekaran, et al. (2010) JBC, 285:19637-19646.

Additional polar bridge modifications are described in, for example, PCT publication no. WO2014/145806 (for example, FIG. 6 of WO2014/145806), PCT publication no. WO2014/110601, and PCT publication no. WO 2016/086186, WO 2016/086189, WO 2016/086196 and WO 2016/182751. An example of a polar bridge variant comprises a constant chain comprising a N208D, Q295E, N384D, Q418E and N421D modification.

In any of the embodiments described herein, the CH3 domains can be additionally modified to introduce a pair of cysteine residues as described in Section 7.4.1.3.

Additional strategies for enhancing heterodimerization are described in, for example, WO2016/105450, WO2016/086186, WO2016/086189, WO2016/086196, WO2016/141378, and WO2014/145806, and WO2014/110601. Any of the strategies can be employed in a BCMA binding molecule described herein.

7.4.1.6. Combination of Heterodimerization Variants and Other Fc Variants

As will be appreciated by a skilled artisan, all of the recited heterodimerization variants (including skew and/or pI variants) can be optionally and independently combined in any way, as long as the Fc regions of an Fc domain retain their ability to dimerize. In addition, all of these variants can be combined into any of the heterodimerization formats.

In the case of pI variants, while embodiments finding particular use are shown in the Table 8, other combinations can be generated, following the basic rule of altering the pI difference between two Fc regions in an Fc heterodimer to facilitate purification.

In addition, any of the heterodimerization variants, skew and pI, are also independently and optionally combined with Fc ablation variants, Fc variants, FcRn variants, as generally outlined herein.

In some embodiments, a particular combination of skew and pI variants that finds use in the present disclosure is T366S/L368A/Y407V: T366W (optionally including a bridging disulfide, T366S/L368A/Y407V/Y349C: T366W/S354C) with one Fc region comprising Q295E/N384D/Q418E/N481D and the other a positively charged scFv linker (when the format includes an scFv domain). As will be appreciated by a skilled artisan, the "knobs-in-holes" variants do not change pI, and thus can be used on either one of the Fc regions in an Fc heterodimer.

In some embodiments, first and second Fc regions that find use the present disclosure include the amino acid substitutions S364K/E357Q:L368D/K370S, where the first and/or second Fc region includes the ablation variant substitutions 233P/L234V/L235A/G236del/S267K, and the first and/or second Fc region comprises the pI variant substitutions N208D/Q295E/N384D/Q418E/N421D (pI_(−)_isosteric_A).

7.4.2. Hinge Regions

The BCMA binding molecules can also comprise hinge regions, e.g., connecting an antigen-binding domain to an Fc region. The hinge region can be a native or a modified hinge region. Hinge regions are typically found at the N-termini of Fc regions.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions can comprise a complete hinge region derived from an antibody of a different class or subclass from that of the Fc region. Alternatively, the modified hinge region can comprise part of a natural hinge or a repeating unit in which each unit in the repeat is derived from a natural hinge region. In a further alternative, the natural hinge region can be altered by converting one or more cysteine or other residues into neutral residues, such as serine or alanine, or by converting suitably placed residues into cysteine residues. By such means the number of cysteine residues in the hinge region can be increased or decreased. This approach is described further in U.S. Pat. No. 5,677,425 by Bodmer et al . . . Altering the number of cysteine residues in a hinge region can, for example, facilitate assembly of light and heavy chains, or increase or decrease the stability of a BCMA binding molecule. Other modified hinge regions can be entirely synthetic and can be designed to possess desired properties such as length, cysteine composition and flexibility.

A number of modified hinge regions have been described for example, in U.S. Pat. No. 5,677,425, WO9915549, WO2005003170, WO2005003169, WO2005003170, WO9825971 and WO2005003171.

Examples of suitable hinge sequences are shown in Table 9.

TABLE 9

Hinge Sequences

| Hinge Name | Hinge Description | Hinge Sequence | SEQ ID NO: |
|---|---|---|---|
| H1 | Human IgA1 | VPSTPPTPSPSTPPTPSPS | 424 |
| H2 | Human IgA2 | VPPPPP | 425 |
| H3 | Human IgD | ESPKAQASSVPTAQPQAEGSLAKATTAPATTRN TGRGGEEKKKEKEKEEQEERETKTP | 426 |
| H4 | Human IgG1 | EPKSCDKTHTCPPCP | 427 |
| H5 | Human IgG2 | ERKCCVECPPCP | 428 |
| H6 | Human IgG3 | ELKTPLGDTTHTCPRCPEPKSCDTPPPCPRCPE PKSCDTPPPCPRCPEPKSCDTPPPCPRCP | 429 |
| H7 | Human IgG4 | ESKYGPPCPSCP | 430 |
| H8 | Human IgG4(P) | ESKYGPPCPPCP | 431 |
| H9 | Engineered v1 | CPPC | 422 |
| H10 | Engineered v2 | CPSC | 432 |
| H11 | Engineered v3 | CPRC | 433 |
| H12 | Engineered v4 | SPPC | 434 |
| H13 | Engineered v5 | CPPS | 435 |
| H14 | Engineered v6 | SPPS | 423 |
| H15 | Engineered v7 | DKTHTCAA | 436 |
| H16 | Engineered v8 | DKTHTCPPCPA | 437 |
| H17 | Engineered v9 | DKTHTCPPCPATCPPCPA | 438 |
| H18 | Engineered v10 | DKTHTCPPCPATCPPCPATCPPCPA | 439 |
| H19 | Engineered v11 | DKTHTCPPCPAGKPTLYNSLVMSDTAGTCY | 440 |
| H20 | Engineered v12 | DKTHTCPPCPAGKPTHVNVSVVMAEVDGTCY | 441 |
| H21 | Engineered v13 | DKTHTCCVECPPCPA | 442 |

TABLE 9-continued

Hinge Sequences

| Hinge Name | Hinge Description | Hinge Sequence | SEQ ID NO: |
|---|---|---|---|
| H22 | Engineered v14 | DKTHTCPRCPEPKSCDTPPPCPRCPA | 443 |
| H23 | Engineered v15 | DKTHTCPSCPA | 444 |

In one embodiment, the Fc region possesses an intact hinge region at its N-terminus.

In one embodiment, the Fc region and hinge region are derived from IgG4 and the hinge region comprises the modified sequence CPPC (SEQ ID NO:422). The core hinge region of human IgG4 contains the sequence CPSC (SEQ ID NO:432) compared to IgG1 which contains the sequence CPPC (SEQ ID NO:422). The serine residue present in the IgG4 sequence leads to increased flexibility in this region, and therefore a proportion of molecules form disulfide bonds within the same protein chain (an intrachain disulfide) rather than bridging to the other heavy chain in the IgG molecule to form the interchain disulfide. (Angel et al., 1993, Mol Immunol 30(1):105-108). Changing the serine residue to a proline to give the same core sequence as IgG1 allows complete formation of inter-chain disulfides in the IgG4 hinge region, thus reducing heterogeneity in the purified product. This altered isotype is termed IgG4P.

7.4.3. ABD Linkers

In certain aspects, the present disclosure provides BCMA binding molecules where two or more components of an ABD (e.g., a VH and a VL of an scFv), two or more ABDs, or an ABD and a non-ABD domain (e.g., a dimerization domain such as an Fc region) are connected to one another by a peptide linker. Such linkers are referred to herein an "ABD linkers", as opposed to the ADC linkers used to attach drugs to BCMA binding molecules as described, for example, in Section 7.9.2.

A peptide linker can range from 2 amino acids to 60 or more amino acids, and in certain aspects a peptide linker ranges from 3 amino acids to 50 amino acids, from 4 to 30 amino acids, from 5 to 25 amino acids, from 10 to 25 amino acids or from 12 to 20 amino acids. In particular embodiments, a peptide linker is 2 amino acids, 3 amino acids, 4 amino acid, 5 amino acids, 6 amino acids, 7 amino acids, 8 amino acids, 9 amino acids, 10 amino acids, 11 amino acids, 12 amino acids, 13 amino acids, 14 amino acid, 15 amino acids, 16 amino acids, 17 amino acids, 18 amino acids, 19 amino acids, 20 amino acids, 21 amino acids, 22 amino acids, 23 amino acids, 24 amino acid, 25 amino acids, 26 amino acids, 27 amino acids, 28 amino acids, 29 amino acids, 30 amino acids, 31 amino acids, 32 amino acids, 33 amino acids, 34 amino acid, 35 amino acids, 36 amino acids, 37 amino acids, 38 amino acids, 39 amino acids, 40 amino acids, 41 amino acids, 42 amino acids, 43 amino acids, 44 amino acid, 45 amino acids, 46 amino acids, 47 amino acids, 48 amino acids, 49 amino acids, or 50 amino acids in length.

Charged and/or flexible linkers can be used.

Examples of flexible ABD linkers that can be used in the BCMA binding molecules include those disclosed by Chen et al., 2013, Adv Drug Deliv Rev. 65(10):1357-1369 and Klein et al., 2014, Protein Engineering, Design & Selection 27(10):325-330. A particularly useful flexible linker is (GGGGS)n (also referred to as (G4S)n) (SEQ ID NO:445). In some embodiments, n is any number between 1 and 10, i.e., 1, 2, 3, 4, 5, 6, 7, 8, 9, and 10, or any range bounded by any two of the foregoing numbers, e.g., 1 to 5, 2 to 5, 3 to 6, 2 to 4, 1 to 4, and so on and so forth.

Other examples of suitable ABD linkers for use in the BCMA binding molecules of the present disclosure are shown in Table 10 below:

TABLE 10

ABD Linker Sequences

| Linker Name | Linker Sequence | SEQ ID NO: |
|---|---|---|
| L1 | ADAAP | 446 |
| L2 | ADAAPTVSIFP | 447 |
| L3 | ADAAPTVSIFPP | 448 |
| L4 | AKTTAP | 449 |
| L5 | AKTTAPSVYPLAP | 450 |
| L6 | AKTTPKLEEGEFSEARV | 451 |
| L7 | AKTTPKLGG | 452 |
| L8 | AKTTPP | 453 |
| L9 | AKTTPPSVTPLAP | 454 |
| L10 | ASTKGP | 455 |
| L11 | ASTKGPSVFPLAP | 456 |
| L12 | ASTKGPSVFPLAPASTKGPSVFPLAP | 457 |
| L13 | EGKSSGSGSESKST | 458 |
| L14 | GEGESGEGESGEGES | 459 |
| L15 | GEGESGEGESGEGESGEGES | 460 |
| L16 | GEGGSGEGGSGEGGS | 461 |
| L17 | GENKVEYAPALMALS | 462 |
| L18 | GGEGSGGEGSGGEGS | 463 |
| L19 | GGGESGGEGSGEGGS | 464 |
| L20 | GGGESGGGESGGGES | 465 |
| L21 | (GGGGS)$_n$ (also referred to as (G4S)$_n$), where n can be 1-10. | 445 |
| L22 | GGGGSGGGS | 466 |
| L23 | GGGGSGGGGSGGGGS | 1 |
| L24 | GGGGSGGGGSGGGGSGGGGS | 467 |
| L25 | GGGKSGGGKSGGGKS | 468 |
| L26 | GGGKSGGKGSGKGGS | 469 |

TABLE 10-continued

ABD Linker Sequences

| Linker Name | Linker Sequence | SEQ ID NO: |
|---|---|---|
| L27 | GGKGSGGKGSGGKGS | 470 |
| L28 | GGSGG | 471 |
| L29 | GGSGGGGSG | 472 |
| L30 | GGSGGGSGGGGS | 473 |
| L31 | GHEAAAVMQVQYPAS | 474 |
| L32 | GKGGSGKGGSGKGGS | 475 |
| L33 | GKGKSGKGKSGKGKS | 476 |
| L34 | GKGKSGKGKSGKGKSGKGKS | 477 |
| L35 | GKPGSGKPGSGKPGS | 478 |
| L36 | GKPGSGKPGSGKPGSGKPGS | 479 |
| L37 | GPAKELTPLKEAKVS | 480 |
| L38 | GSAGSAAGSGEF | 481 |
| L39 | IRPRAIGGSKPRVA | 482 |
| L40 | KESGSVSSEQLAQFRSLD | 483 |
| L41 | KTTPKLEEGEFSEAR | 484 |
| L42 | QPKAAP | 485 |
| L43 | QPKAAPSVTLFPP | 486 |
| L44 | RADAAAA(G4S)4 | 487 |
| L45 | RADAAAAGGPGS | 488 |
| L46 | RADAAP | 489 |
| L47 | RADAAPTVS | 490 |
| L48 | SAKTTP | 491 |
| L49 | SAKTTPKLEEGEFSEARV | 492 |
| L50 | SAKTTPKLGG | 493 |
| L51 | STAGDTHLGGEDFD | 494 |
| L52 | TVAAP | 495 |
| L53 | TVAAPSVFIFPP | 496 |
| L54 | TVAAPSVFIFPPTVAAPSVFIFPP | 497 |
| L55 | GSTSGSGKPGSGEGSTKG | 498 |
| L56 | PRGASKSGSASQTGSAPGS | 499 |
| L57 | GTAAAGAGAAGGAAAGAAG | 500 |
| L58 | GTSGSSGSGSGGSGSGGG | 501 |

In various aspects, the disclosure provides a BCMA binding molecule which comprises one or more ABD linkers. Each of the ABD linkers can be range from 2 amino acids to 60 amino acids in length, e.g., 4 to 30 amino acids, from 5 to 25 amino acids, from 10 to 25 amino acids or from 12 to 20 amino acids in length, optionally selected from Table 10 above. In particular embodiments, the BCMA binding molecule comprises two, three, four, five or six ABD linkers. The ABD linkers can be on one, two, three, four or even more polypeptide chains of the BCMA binding molecule.

7.5. Bispecific Binding Molecule Configurations

Exemplary BBM configurations are shown in FIG. 1. FIG. 1A shows the components of the BBM configurations shown in FIGS. 1B-1AG. The scFv, Fab, scFab, non-immunoglobulin based ABD, and Fc domains each can have the characteristics described for these components in Sections 7.2 and 7.3. The components of the BBM configurations shown in FIG. 1 can be associated with each other by any of the means described in Sections 7.4 (e.g., by direct bonds, ABD linkers, disulfide bonds, Fc domains with modified with knob-in-hole interactions, etc.). The orientations and associations of the various components shown in FIG. 1 are merely exemplary; as will be appreciated by a skilled artisan, other orientations and associations can be suitable (e.g., as described in Sections 7.2 and 7.3).

BBMs are not limited to the configurations shown in FIG. 1. Other configurations that can be used are known to those skilled in the art. See, e.g., WO 2014/145806; WO 2017/124002; Liu et al., 2017, Front Immunol. 8:38; Brinkmann & Kontermann, 2017, mAbs 9:2, 182-212; US 2016/0355600; Klein et al., 2016, MAbs 8(6):1010-20; and US 2017/0145116.

7.5.1. Exemplary Bivalent BBMs

The BBMs can be bivalent, i.e., they have two antigen-binding domains, one or two of which binds BCMA (ABD1) and one of which binds a second target antigen (ABD2), e.g., a component of a TCR complex.

Exemplary bivalent BBM configurations are shown in FIGS. 1B-1F.

Figure 1D:
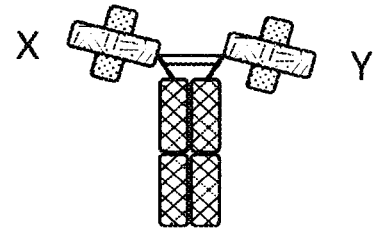

As depicted in FIGS. 1B-1D, a BBM can comprise two half antibodies, one comprising one ABD and the other comprising one ABD, the two halves paired through an Fc domain.

In the embodiment of FIG. 1B, the first (or left) half antibody comprises a Fab and an Fc region, and the second (or right) half antibody comprises a Fab and an Fc region. The first and second half antibodies are associated through the Fc regions forming an Fc domain.

In the embodiment of FIG. 1C, the first (or left) half antibody comprises a Fab and an Fc region, and the second (or right) half antibody comprises a scFv and an Fc region. The first and second half antibodies are associated through the Fc regions forming an Fc domain.

In the embodiment of FIG. 1D, the first (or left) half antibody comprises an scFv and an Fc region, and the second (or right) half antibody comprises an scFv and an Fc region. The first and second half antibodies are associated through the Fc regions forming an Fc domain.

Figure 1E:
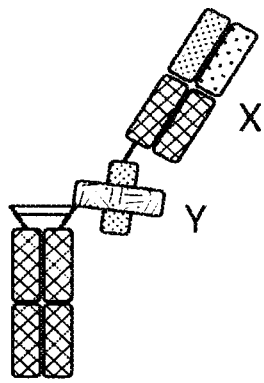
Figure 1F:
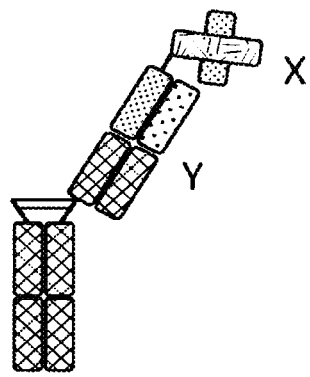
Figure 1G:
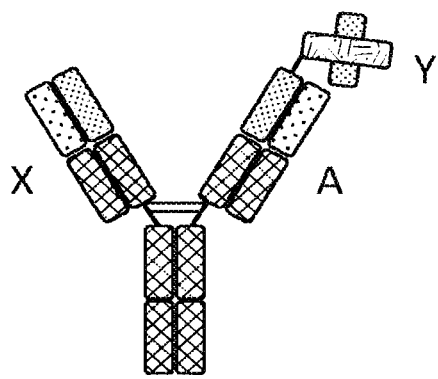

As depicted in FIGS. 1E-1F, a bivalent BBM can comprise two ABDs attached to one Fc region of an Fc domain.

In the embodiment of FIG. 1E, the BBM comprises a Fab, a scFv and an Fc domain, where the scFv is located between the Fab and the Fc domain.

In the embodiment of FIG. 1F, (the "one-arm scFv-mAb" configuration) BBM comprises a Fab, a scFv and an Fc domain, where the Fab is located between the scFv and the Fc domain.

In the configuration shown in FIGS. 1B-1F, each of X and Y represent either ABD1 or ABD2, provided that the BBM comprises one ABD1 and one ABD2. Accordingly, the present disclosure provides a bivalent BBM as shown in any one of FIGS. 1B through 1F, where X is an ABD1 and Y is an ABD2 (this configuration of ABDs designated as "B1" for convenience). The present disclosure also provides a bivalent BBM as shown in any one of FIGS. 1B through 1F, where X is an ABD2 and Y is an ABD1 (this configuration of ABDs designated as "B2" for convenience).

7.5.2. Exemplary Trivalent BBMs

The BBMs can be trivalent, i.e., they have three antigen-binding domains, one or two of which binds BCMA (ABD1) and one or two of which binds a second target antigen (ABD2), e.g., a component of a TCR complex.

Exemplary trivalent BBM configurations are shown in FIGS. 1G-1Z.

As depicted in FIGS. 1G-1N, 1Q-1W, 1Y-1Z a BBM can comprise two half antibodies, one comprising two ABDs and the other comprising one ABD, the two halves paired through an Fc domain.

In the embodiment of FIG. 1G, the first (or left) half antibody comprises Fab and an Fc region, and the second (or right) half antibody comprises a scFv, a Fab, and an Fc region. The first and second half antibodies are associated through the Fc regions forming an Fc domain.

Figure 1H:
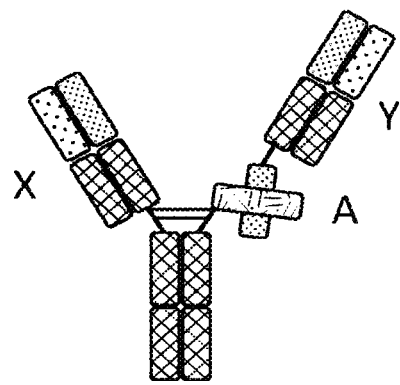

In the embodiment of FIG. 1H, the first (or left) half antibody comprises a Fab and an Fc region, and the second (or right) half antibody comprises a Fab, an scFv, and an Fc region. The first and second half antibodies are associated through the Fc regions forming an Fc domain.

Figure 1I:
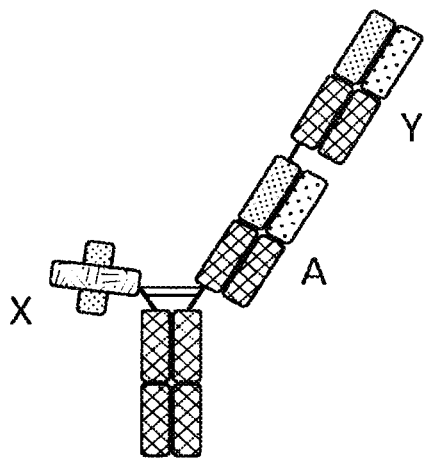

In the embodiment of FIG. 1I, the first (or left) half antibody comprises an scFv and an Fc region, and the second (or right) half antibody comprises two Fabs and an Fc region. The first and second half antibodies are associated through the Fc regions forming an Fc domain.

Figure 1J:
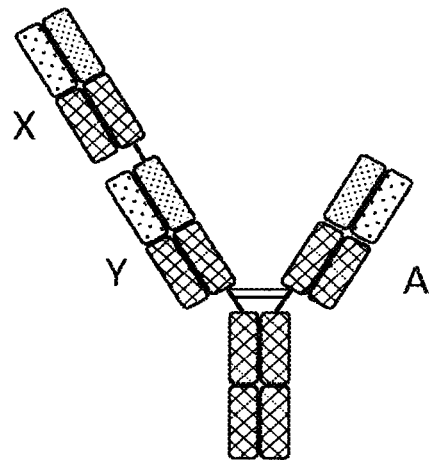

In the embodiment of FIG. 1J, the first (or left) half antibody comprises two Fav and an Fc region, and the second (or right) half antibody comprises a Fab and an Fc region. The first and second half antibodies are associated through the Fc regions forming an Fc domain.

Figure 1K:
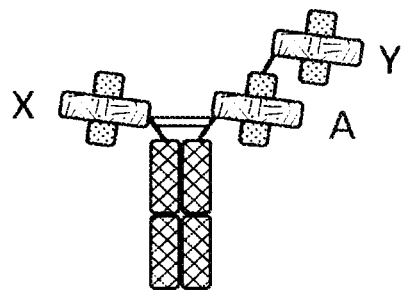

In the embodiment of FIG. 1K, the first (or left) half antibody comprises an scFv and an Fc region, and the second (or right) half antibody comprises two scFvs and an Fc region. The first and second half antibodies are associated through the Fc regions forming an Fc domain.

Figure 1L:
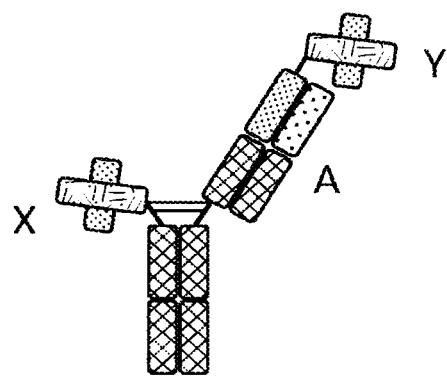

In the embodiment of FIG. 1L, the first (or left) half antibody comprises an scFv and an Fc region, and the second (or right) half antibody comprises an scFv, a Fab, and an Fc region. The first and second half antibodies are associated through the Fc regions forming an Fc domain.

Figure 1M:
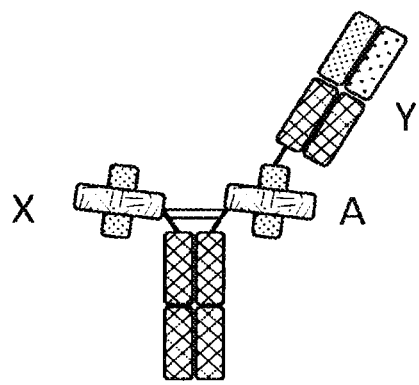

In the embodiment of FIG. 1M, the first (or left) half antibody comprises a scFv and an Fc region, and the second (or right) half antibody comprises a Fab, a scFv and an Fc region. The first and second half antibodies are associated through the Fc regions forming an Fc domain.

Figure 1N:
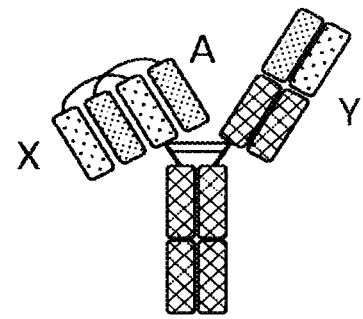
Figure 1O:
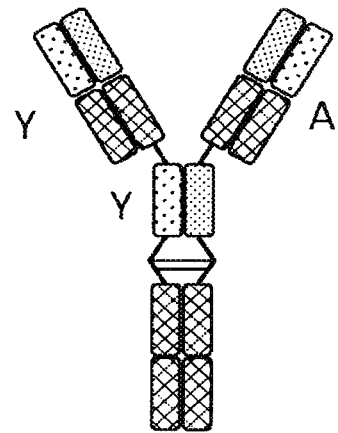
Figure 1P:
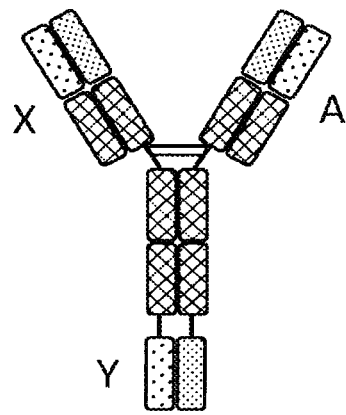

In the embodiment of FIG. 1N, the first (or left) half antibody comprises a diabody-type binding domain and an Fc region, and the second (or right) half antibody comprises a Fab and an Fc region. The first and second half antibodies are associated through the Fc regions forming an Fc domain.

Figure 1Q:
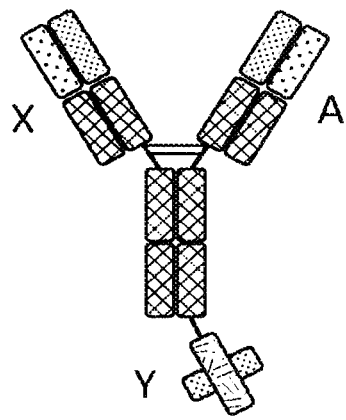

In the embodiment of FIG. 1Q, the first (or left) half antibody comprises a Fab and an Fc region, and the second (or right) half antibody comprises a Fab, an Fc region, and an scFv. The first and second half antibodies are associated through the Fc regions forming an Fc domain.

Figure 1R:
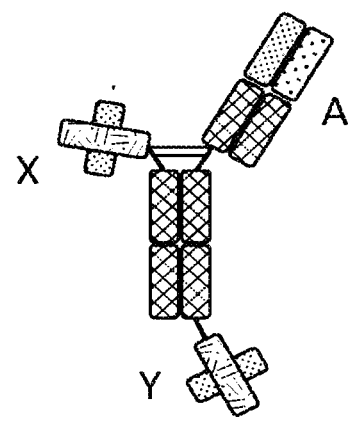

In the embodiment of FIG. 1R, the first (or left) half antibody comprises a scFv and an Fc region, and the second (or right) half antibody comprises a Fab, an Fc region, and an scFv. The first and second half antibodies are associated through the Fc regions forming an Fc domain.

Figure 1S:
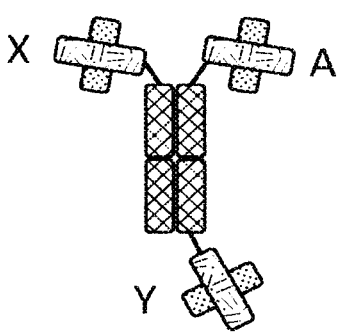

In the embodiment of FIG. 1S, the first (or left) half antibody comprises an scFv and an Fc region, and the second (or right) half antibody comprises an scFv, an Fc region, and a second scFv. The first and second half antibodies are associated through the Fc regions forming an Fc domain.

Figure 1T:
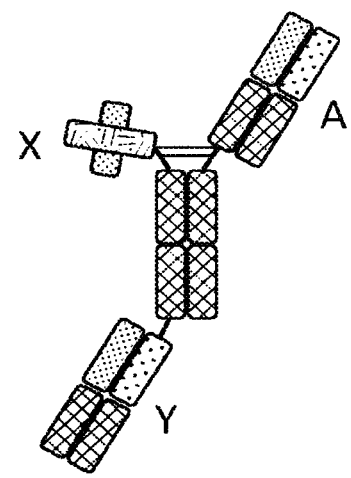

In the embodiment of FIG. 1T, the first (or left) half antibody comprises an scFv, an Fc region, and a Fab, and the second (or right) half antibody comprises a Fab and an Fc region. The first and second half antibodies are associated through the Fc regions forming an Fc domain.

Figure 1U:
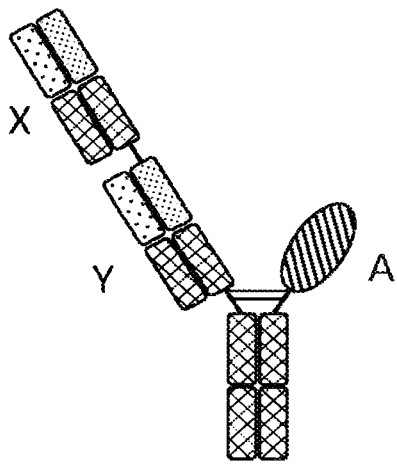

In the embodiment of FIG. 1U, the first (or left) half antibody comprises two Fab and an Fc region, and the second (or right) half antibody comprises a non-immunoglobulin based ABD and an Fc region. The first and second half antibodies are associated through the Fc regions forming an Fc domain.

Figure 1V:
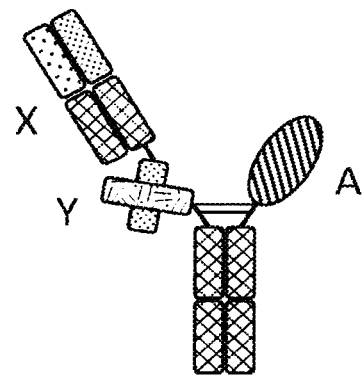

In the embodiment of FIG. 1V, the first (or left) half antibody comprises a Fab, an scFv, and an Fc region, and the second (or right) half antibody comprises a non-immunoglobulin based ABD and an Fc region. The first and second half antibodies are associated through the Fc regions forming an Fc domain.

Figure 1W:
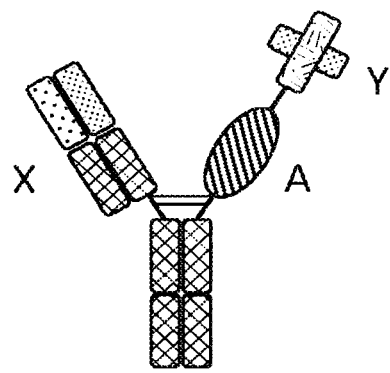
Figure 1X:

In the embodiment of FIG. 1W, the first (or left) half antibody comprises a Fab and an Fc region, and the second (or right) half antibody comprises a scFv, a non-immunoglobulin based ABD, and an Fc region. The first and second half antibodies are associated through the Fc regions forming an Fc domain.

Figure 1Y:
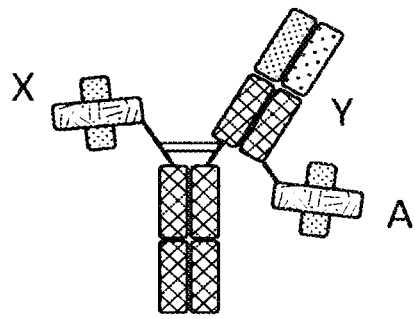
Figure 1Z:
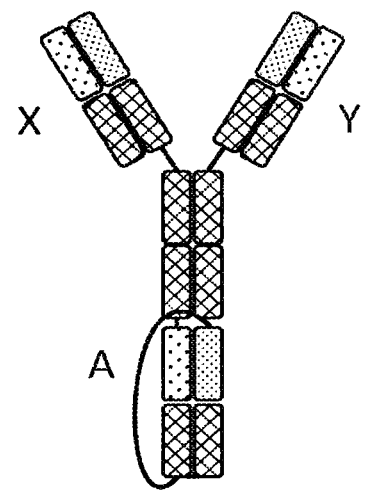
Figure 1A:
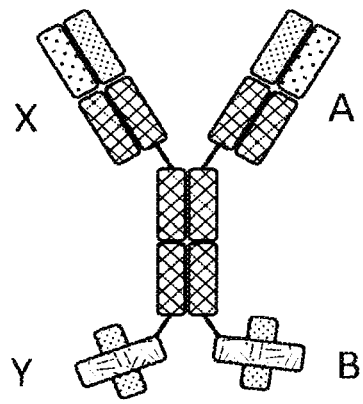
Figure 1A:
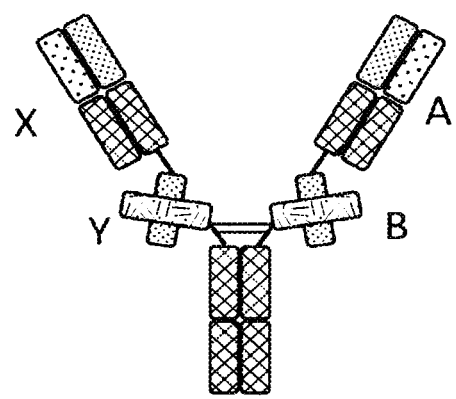
Figure 1A:
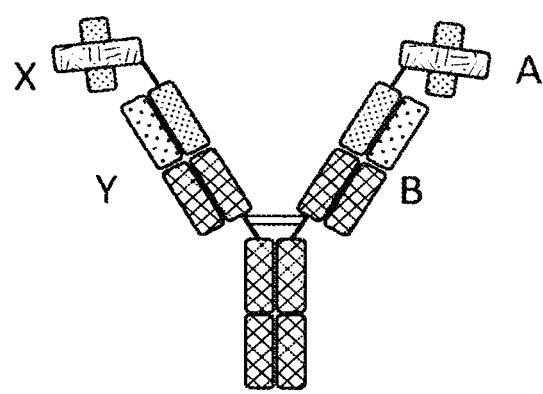
Figure 1A:
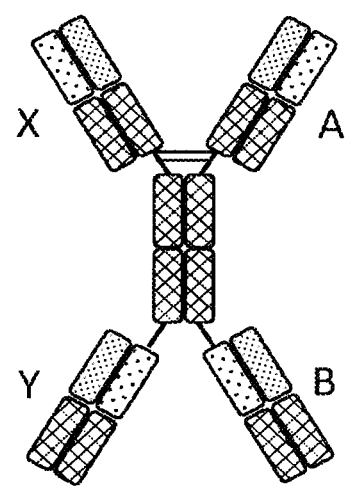
Figure 1A:
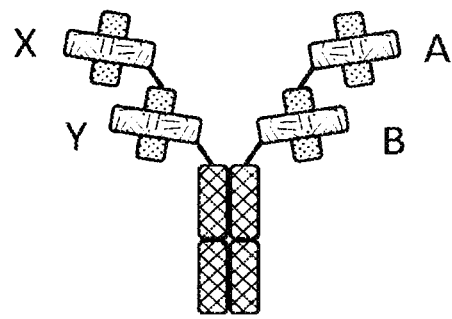
Figure 1A:
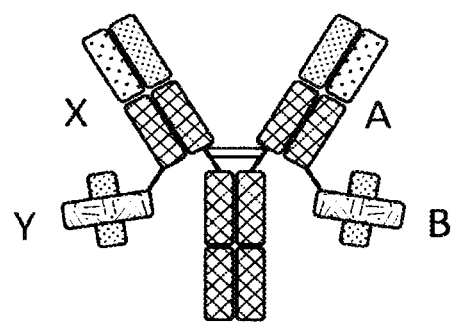
Figure 1A:
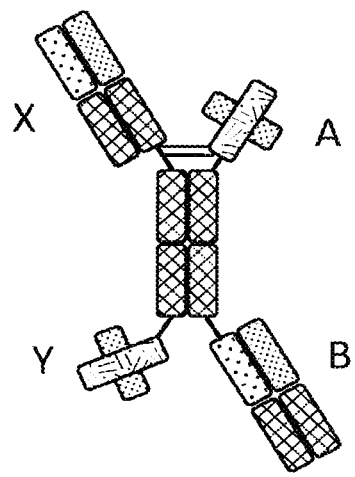

In the embodiment of FIG. 1Y, the first (or left) half antibody comprises an scFv and an Fc region, and the second (or right) half antibody comprises a Fab, an scFv and an Fc region. The first and second half antibodies are associated through the Fc regions forming an Fc domain.

In the embodiment of FIG. 1Z, the first (or left) half antibody comprises a Fab, an Fc region, and a scFab, and the second (or right) half antibody comprises a Fab and an Fc region. The first and second half antibodies are associated through the Fc regions forming an Fc domain.

Alternatively, as depicted in FIGS. 1O and 1P, trivalent a BBM can comprise two half antibodies, each comprising one complete ABD (a Fab in FIGS. 1O and 1P) and a portion of another ABD (one a VH, the other a VL). The two half antibodies are paired through an Fc domain, whereupon the VH and the VL associate to form a complete antigen-binding Fv domain.

The BBM can be a single chain, as shown in FIG. 1X. The BBM of FIG. 1X comprises three scFv domains connected through linkers.

In the configuration shown in FIGS. 1G-1Z, each of X, Y and A represent either an ABD1 or ABD2, provided that the BBM comprises at least ABD1 and at least one ABD2. Thus, the trivalent MBMs will include one or two ABD1s and one or two ABD2s. In some embodiments, a trivalent BBM comprises two ABD1s and one ABD2. In other embodiments, a trivalent BBM of the disclosure comprises one ABD1 and two ABD2s.

Accordingly, in the present disclosure provides a trivalent BBM as shown in any one of FIGS. 1G through 1Z, where X is an ABD1, Y is an ABD1 and A is an ABD2 (this configuration of ABDs designated as "T1" for convenience).

The disclosure further provides a trivalent BBM as shown in any one of FIGS. 1G through 1Z, where X is an ABD1, Y is an ABD2 and A is an ABD1 (this configuration of ABDs designated as "T2" for convenience).

The disclosure further provides a trivalent BBM as shown in any one of FIGS. 1G through 1Z, where X is an ABD2, Y is an ABD1 and A is an ABD1 (this configuration of ABDs designated as "T3" for convenience).

The disclosure further provides a trivalent BBM as shown in any one of FIGS. 1G through 1Z, where X is an ABD1, Y is an ABD2 and A is an ABD2 (this configuration of ABDs designated as "T4" for convenience).

The disclosure further provides a trivalent BBM as shown in any one of FIGS. 1G through 1Z, where X is an ABD2, Y is an ABD1 and A is an ABD2 (this configuration of ABDs designated as "T5" for convenience).

The disclosure further provides a trivalent BBM as shown in any one of FIGS. 1G through 1Z, where X is an ABD2, Y is an ABD2 and A is an ABD1 (this configuration of ABDs designated as "T6" for convenience).

7.5.3. Exemplary Tetravalent BBMs

The BBMs can be tetravalent, i.e., they have four antigen-binding domains, one, two, or three of which binds BCMA (ABD1) and one, two, or three of which binds a second target antigen (ABD2), e.g., a component of a TCR complex.

Exemplary tetravalent BBM configurations are shown in FIGS. 1AA-1AG.

As depicted in FIGS. 1AA-1AG, a tetravalent BBM can comprise two half antibodies, each comprising two complete ABDs, the two halves paired through an Fc domain.

In the embodiment of FIG. 1AA, the first (or left) half antibody comprises a Fab, an Fc region, and an scFv, and the second (or right) half antibody comprises a Fab, an Fc region, and an scFv. The first and second half antibodies are associated through the Fc regions forming an Fc domain.

In the embodiment of FIG. 1AB, the first (or left) half antibody comprises a Fab, an scFv, and an Fc region, and the second (or right) half antibody comprises a Fab, an scFv, and an Fc region. The first and second half antibodies are associated through the Fc regions forming an Fc domain.

In the embodiment of FIG. 1AC, the first (or left) half antibody comprises an scFv, a Fab, and an Fc region, and the second (or right) half antibody comprises an scFv, a Fab, and an Fc region. The first and second half antibodies are associated through the Fc regions forming an Fc domain.

In the embodiment of FIG. 1AD, the first (or left) half antibody comprises a Fab, an Fc region, and a second Fab, and the second (or right) half antibody comprises a Fab, an Fc region, and a second Fab. The first and second half antibodies are associated through the Fc regions forming an Fc domain.

In the embodiment of FIG. 1AE, the first (or left) half antibody comprises an scFv, a second scFv, and an Fc region, and the second (or right) half antibody comprises an scFv, a second scFv, and an Fc region. The first and second half antibodies are associated through the Fc regions forming an Fc domain.

In the embodiment of FIG. 1AF, the first (or left) half antibody comprises a Fab, an scFv, and an Fc region, and the second (or right) half antibody comprises a Fab, an scFv, and an Fc region. The first and second half antibodies are associated through the Fc regions forming an Fc domain.

In the embodiment of FIG. 1AG, the first (or left) half antibody comprises a Fab, an Fc region, and an scFv, and the second (or right) half antibody comprises a scFv, an Fc region, and a Fab. The first and second half antibodies are associated through the Fc regions forming an Fc domain.

In the configuration shown in FIGS. 1AA-1AG, each of X, Y, A, and B represent ABD1 or ABD2, although not necessarily in that order, and provided that the BBM comprises at least one ABD1 and at least one ABD2. Thus, the tetravalent ABDs will include one, two, or three ABD1s and one, two, or ABD2s. In some embodiments, a tetravalent BBM comprises three ABD1s and one ABD2. In other embodiments, a tetravalent BBM comprises two ABD1s two ABD2s. In yet other embodiments, a tetravalent BBM comprises one ABD1 and three ABD2s.

Accordingly, in the present disclosure provides a tetravalent BBM as shown in any one of FIGS. 1AA-1AG, where X is an ABD1 and each of Y, A, and B are ABD2s (this configuration of ABDs designated as "Tv 1" for convenience).

The disclosure further provides a tetravalent BBM as shown in any one of FIGS. 1AA-1AG, where Y is an ABD1 and each of X, A, and B are ABD2s (this configuration of ABDs designated as "Tv 2" for convenience).

The disclosure further provides a tetravalent BBM as shown in any one of FIGS. 1AA-1AG, where A is an ABD1 and each of X, Y, and B are ABD2s (this configuration of ABDs designated as "Tv 3" for convenience).

The disclosure further provides a tetravalent BBM as shown in any one of FIGS. 1AA-1AG, where B is an ABD1 and each of X, Y, and A are ABD2s (this configuration of ABDs designated as "Tv 4" for convenience).

The disclosure further provides a tetravalent BBM as shown in any one of FIGS. 1AA-1AG, where X and Y are both ABD1s and both of A and B are ABD2s (this configuration of ABDs designated as "Tv 5" for convenience).

The disclosure further provides a tetravalent BBM as shown in any one of FIGS. 1AA-1AG, where X and A are both ABD1s and both of Y and B are ABD2s (this configuration of ABDs designated as "Tv 6" for convenience).

The disclosure further provides a tetravalent BBM as shown in any one of FIGS. 1AA-1AG, where X and B are both ABD1s and both of Y and A are ABD2s (this configuration of ABDs designated as "Tv 7" for convenience).

The disclosure further provides a tetravalent BBM as shown in any one of FIGS. 1AA-1AG, where Y and A are both ABD1s and both of X and B are ABD2s (this configuration of ABDs designated as "Tv 8" for convenience).

The disclosure further provides a tetravalent BBM as shown in any one of FIGS. 1AA-1AG, where Y and B are both ABD1s and both of X and A are ABD2s (this configuration of ABDs designated as "Tv 9" for convenience).

The disclosure further provides a tetravalent BBM as shown in any one of FIGS. 1AA-1AG, where A and B are both ABD1s and both of X and Y are ABD2s (this configuration of ABDs designated as "Tv 10" for convenience).

The disclosure further provides a tetravalent BBM as shown in any one of FIGS. 1AA-1AG, where each of X, Y, and A is an ABD1 and B is an ABD2 (this configuration of ABDs designated as "Tv 11" for convenience).

The disclosure further provides a tetravalent BBM as shown in any one of FIGS. 1AA-1AG, where each of X, Y, and B is an ABD1 and A is an ABD2 (this configuration of ABDs designated as "Tv 12" for convenience).

The disclosure further provides a tetravalent BBM as shown in any one of FIGS. 1AA-1AG, where each of X, A, and B is an ABD1 and Y is an ABD2 (this configuration of ABDs designated as "Tv 13" for convenience).

The disclosure further provides a tetravalent BBM as shown in any one of FIGS. 1AA-1AG, where each of Y, A, and B is an ABD1 and X is an ABD2 (this configuration of ABDs designated as "Tv 14" for convenience).

7.6. Exemplary BBMs

The BBMs of the disclosure comprise at least one ABD that binds specifically to BCMA and at least one ABD that binds to a second target antigen such as CD3. Exemplary anti-BCMAxanti-CD3 BBMs are set forth in Table 11A-11F.

BBMs can comprise, for example, the CDR sequences of an exemplary BBM set forth in Table 11A-11F. In some embodiments, a BBM comprises the heavy and light chain variable region sequences of an exemplary BBM set forth in Table 11A-F.

TABLE 11A

Bivalent AB1
(hBCMA Fab/hCD3 scFv 1x1 format)

| | SEQ ID NO | Sequence |
|---|---|---|
| HC BCMA arm | 502 | EVQLLESGGGLVQPGGSLRLSCAASGFTFSSYAM SWVRQAPGKGLEWVSAISGSGGSTYYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSDTKVDKKVEPKSCDKTHTCPPCPAPP VAGPSVFLFPPKPKDTLMISRTPEVTCVVVDVKHE DPEVKFNWYVDGVEVHNAKTKPREEEYNSTYRV VSVLTVLHQDWLNGKEYKCKVSNKALPAPIEKTIS KAKGQPREPQVYTLPPSREEMTKNQVSLTCDVS GFYPSDIAVEWESDGQPENNYKTTPPVLDSDGSF FLYSKLTVDKSRWEQGDVFSCSVMHEALHNHYT QKSLSLSPGK |
| LC BCMA arm | 503 | DIQMTQSPSSLSASVGDRVTITCRASQSISSYLNW YQQKPGKAPKLLIYAASSLQSGVPSRFSGSGSGT DFTLTISSLQPEDFATYYCQQSYSSPLTFGQGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC |
| CD3 arm | 504 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVLEPKSSDKTHTC PPCPAPPVAGPSVFLFPPKPKDTLMISRTPEVTCV VVDVKHEDPEVKFNWYVDGVEVHNAKTKPREEQ YNSTYRVVSVLTVLHQDWLNGKEYKCKVSNKALP APIEKTISKAKGQPREPQVYTLPPSREQMTKNQV KLTCLVKGFYPSDIAVEWESNGQPENNYKTTPPV LDSDGSFFLYSKLTVDKSRWQQGNVFSCSVMHE ALHNHYTQKSLSLSPGK |

TABLE 11B

Trivalent AB1
(BCMA Fab/hCD3 scFv 2x1 format)

| | SEQ ID NO | Sequence |
|---|---|---|
| HC BCMA arm | 502 | EVQLLESGGGLVQPGGSLRLSCAASGFTFSSYAM SWVRQAPGKGLEWVSAISGSGGSTYYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSDTKVDKKVEPKSCDKTHTCPPCPAPP VAGPSVFLFPPKPKDTLMISRTPEVTCVVVDVKHE DPEVKFNWYVDGVEVHNAKTKPREEEYNSTYRV VSVLTVLHQDWLNGKEYKCKVSNKALPAPIEKTIS KAKGQPREPQVYTLPPSREEMTKNQVSLTCDVS GFYPSDIAVEWESDGQPENNYKTTPPVLDSDGSF FLYSKLTVDKSRWEQGDVFSCSVMHEALHNHYT QKSLSLSPGK |
| LC BCMA arm | 503 | DIQMTQSPSSLSASVGDRVTITCRASQSISSYLNW YQQKPGKAPKLLIYAASSLQSGVPSRFSGSGSGT DFTLTISSLQPEDFATYYCQQSYSSPLTFGQGTKV |

TABLE 11B-continued

Trivalent AB1
(BCMA Fab/hCD3 scFv 2x1 format)

| | SEQ ID NO | Sequence |
|---|---|---|
| | | EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC |
| CD3 arm | 505 | EVQLLESGGGLVQPGGSLRLSCAASGFTFSSYAM SWVRQAPGKGLEWVSAISGSGGSTYYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSNTKVDKKVEPKSCGGGSGGGGSE VQLVESGGGLVQPGGSLRLSCAASGFTFSTYAM NWVRQAPGKGLEWVGRIRSKANNYATYYADSVK GRFTISRDDSKNTLYLQMNSLRAEDTAVYYCVRH GNFGDSYVSWFAYWGQGTLVTVSSGKPGSGKP GSGKPGSGKPGSQAVVTQEPSLTVSPGGTVTLT CGSSTGAVTTSNYANVVVQQKPGKSPRGLIGGTN KRAPGVPARFSGSLLGGKAALTISGAQPEDEADY YCALWYSNHWVFGGGTKLTVLGGGGSGGGGSK THTCPPCPAPPVAGPSVFLFPPKPKDTLMISRTPE VTCVVVDVKHEDPEVKFNWYVDGVEVHNAKTKP REEQYNSTYRVVSVLTVLHQDWLNGKEYKCKVS NKALPAPIEKTISKAKGQPREPQVYTLPPSREQMT KNQVKLTCLVKGFYPSDIAVEWESNGQPENNYKT TPPVLDSDGSFFLYSKLTVDKSRWQQGNVFSCSV MHEALHNHYTQKSLSLSPGK |

TABLE 11C

Bivalent AB2
(BCMA Fab/hCD3 scFv 1x1 format)

| | SEQ ID NO | Sequence |
|---|---|---|
| HC BCMA arm | 506 | EVQLLESGGGLVQPGGSLRLSCAASGFTFSSYAM SWVRQAPGKGLEWVSAISESGGRAAYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSDTKVDKKVEPKSCDKTHTCPPCPAPP VAGPSVFLFPPKPKDTLMISRTPEVTCVVVDVKHE DPEVKFNWYVDGVEVHNAKTKPREEEYNSTYRV VSVLTVLHQDWLNGKEYKCKVSNKALPAPIEKTIS KAKGQPREPQVYTLPPSREEMTKNQVSLTCDVS GFYPSDIAVEWESDGQPENNYKTTPPVLDSDGSF FLYSKLTVDKSRWEQGDVFSCSVMHEALHNHYT QKSLSLSPGK |
| LC BCMA arm | 507 | DIQMTQSPSSLSASVGDRVTITCRASQSISSYLNW YQQKPGKAPKLLIYAASSLQSGVPSRFSGSGSGT DFTLTISSLQPEDFATYYCQQSYSTPLTFGQGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC |
| CD3 arm | 504 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVLEPKSSDKTHTC PPCPAPPVAGPSVFLFPPKPKDTLMISRTPEVTCV VVDVKHEDPEVKFNWYVDGVEVHNAKTKPREEQ |

TABLE 11C-continued

Bivalent AB2
(BCMA Fab/hCD3 scFv 1x1 format)

| SEQ ID NO | Sequence |
|---|---|
| | YNSTYRVVSVLTVLHQDWLNGKEYKCKVSNKALP APIEKTISKAKGQPREPQVYTLPPSREQMTKNQV KLTCLVKGFYPSDIAVEWESNGQPENNYKTTPPV LDSDGSFFLYSKLTVDKSRWQQGNVFSCSVMHE ALHNHYTQKSLSLSPGK |

TABLE 11D

Trivalent AB2
(BCMA Fab/hCD3 scFv 2x1 format)

| | SEQ ID NO | Sequence |
|---|---|---|
| HC BCMA arm | 506 | EVQLLESGGGLVQPGGSLRLSCAASGFTFSSYAM SWVRQAPGKGLEWVSAISESGGRAAYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSDTKVDKKVEPKSCDKTHTCPPCPAPP VAGPSVFLFPPKPKDTLMISRTPEVTCVVVDVKHE DPEVKFNWYVDGVEVHNAKTKPREEEYNSTYRV VSVLTVLHQDWLNGKEYKCKVSNKALPAPIEKTIS KAKGQPREPQVYTLPPSREEMTKNQVSLTCDVS GFYPSDIAVEWESDGQPENNYKTTPPVLDSDGSF FLYSKLTVDKSRWEQGDVFSCSVMHEALHNHYT QKSLSLSPGK |
| LC BCMA arm | 507 | DIQMTQSPSSLSASVGDRVTITCRASQSISSYLNW YQQKPGKAPKLLIYAASSLQSGVPSRFSGSGSGT DFTLTISSLQPEDFATYYCQQSYSTPLTFGQGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC |
| CD3 arm | 508 | EVQLLESGGGLVQPGGSLRLSCAASGFTFSSYAM SWVRQAPGKGLEWVSAISESGGRAAYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSNTKVDKKVEPKSCGGGSGGGGSE VQLVESGGGLVQPGGSLRLSCAASGFTFSTYAM NWVRQAPGKGLEWVGRIRSKANNYATYYADSVK GRFTISRDDSKNTLYLQMNSLRAEDTAVYYCVRH GNFGDSYVSWFAYWGQGTLVTVSSGKPGSGKP GSGKPGSGKPGSQAVVTQEPSLTVSPGGTVTLT CGSSTGAVTTSNYANWVQQKPGKSPRGLIGGTN KRAPGVPARFSGSLLGGKAALTISGAQPEDEADY YCALWYSNHWVFGGGTKLTVLGGGGSGGGGSK THTCPPCPAPPVAGPSVFLFPPKPKDTLMISRTPE VTCVVVDVKHEDPEVKFNWYVDGVEVHNAKTKP REEQYNSTYRVVSVLTVLHQDWLNGKEYKCKVS NKALPAPIEKTISKAKGQPREPQVYTLPPSREQMT KNQVKLTCLVKGFYPSDIAVEWESNGQPENNYKT TPPVLDSDGSFFLYSKLTVDKSRWQQGNVFSCSV MHEALHNHYTQKSLSLSPGK |

TABLE 11E

Bivalent AB3
(hBCMA Fab/hCD3 scFv 1x1 format)

| | SEQ ID NO | Sequence |
|---|---|---|
| HC BCMA arm | 509 | QVQLVESGGGVVQPGRSLRLSCAASGFTVSSYG MHWVRQAPGKGLEWVAVISYTGSNKYYADSVKG RFTISRDNSKNTLYLQMNSLRAEDTAVYYCGGSG YALHDDYYGLDVWGQGTLVTVSSASTKGPSVFPL APSSKSTSGGTAALGCLVKDYFPEPVTVSWNSGA LTSGVHTFPAVLQSSGLYSLSSVVTVPSSSLGTQT YICNVNHKPSDTKVDKKVEPKSCDKTHTCPPCPA PPVAGPSVFLFPPKPKDTLMISRTPEVTCVVVDVK HEDPEVKFNWYVDGVEVHNAKTKPREEEYNSTY RVVSVLTVLHQDWLNGKEYKCKVSNKALPAPIEK TISKAKGQPREPQVYTLPPSREEMTKNQVSLTCD VSGFYPSDIAVEWESDGQPENNYKTTPPVLDSDG SFFLYSKLTVDKSRWEQGDVFSCSVMHEALHNH YTQKSLSLSPGK |
| LC BCMA arm | 510 | QSALTQPASVSGSPGQSITISCTGTSSDVGGYNY VSWYQQHPGKAPKLMIYDVSNRLRGVSNRFSGS KSGNTASLTISGLQAEDEADYYCSSYTSSSALYVF GSGTKVTVLGQPKAAPSVTLFPPSSEELQANKAT LVCLISDFYPGAVTVAWKADSSPVKAGVETTTPSK QSNNKYAASSYLSLTPEQWKSHRSYSCQVTHEG STVEKTVAPTECS |
| CD3 arm | 504 | EVQLVESGGGLVQPGGSLRLSCAASGFTFSTYA MNVVVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVLEPKSSDKTHTC PPCPAPPVAGPSVFLFPPKPKDTLMISRTPEVTCV VVDVKHEDPEVKFNWYVDGVEVHNAKTKPREEQ YNSTYRVVSVLTVLHQDWLNGKEYKCKVSNKALP APIEKTISKAKGQPREPQVYTLPPSREQMTKNQV KLTCLVKGFYPSDIAVEWESNGQPENNYKTTPPV LDSDGSFFLYSKLTVDKSRWQQGNVFSCSVMHE ALHNHYTQKSLSLSPGK |

TABLE 11F

Trivalent AB3
(BCMA Fab/hCD3 scFv 2x1 format)

| | SEQ ID NO | Sequence |
|---|---|---|
| HC BCMA arm | 509 | QVQLVESGGGVVQPGRSLRLSCAASGFTVSSYG MHWVRQAPGKGLEWVAVISYTGSNKYYADSVKG RFTISRDNSKNTLYLQMNSLRAEDTAVYYCGGSG YALHDDYYGLDVWGQGTLVTVSSASTKGPSVFPL APSSKSTSGGTAALGCLVKDYFPEPVTVSWNSGA LTSGVHTFPAVLQSSGLYSLSSVVTVPSSSLGTQT YICNVNHKPSDTKVDKKVEPKSCDKTHTCPPCPA PPVAGPSVFLFPPKPKDTLMISRTPEVTCVVVDVK HEDPEVKFNWYVDGVEVHNAKTKPREEEYNSTY RVVSVLTVLHQDWLNGKEYKCKVSNKALPAPIEK TISKAKGQPREPQVYTLPPSREEMTKNQVSLTCD VSGFYPSDIAVEWESDGQPENNYKTTPPVLDSDG SFFLYSKLTVDKSRWEQGDVFSCSVMHEALHNH YTQKSLSLSPGK |
| LC BCMA arm | 510 | QSALTQPASVSGSPGQSITISCTGTSSDVGGYNY VSWYQQHPGKAPKLMIYDVSNRLRGVSNRFSGS KSGNTASLTISGLQAEDEADYYCSSYTSSSALYVF GSGTKVTVLGQPKAAPSVTLFPPSSEELQANKAT LVCLISDFYPGAVTVAWKADSSPVKAGVETTTPSK QSNNKYAASSYLSLTPEQWKSHRSYSCQVTHEG STVEKTVAPTECS |

TABLE 11F-continued

Trivalent AB3
(BCMA_Fab/hCD3_scFv 2x1 format)

| | SEQ ID NO | Sequence |
|---|---|---|
| CD3 arm | 511 | QVQLVESGGGVVQPGRSLRLSCAASGFTVSSYG MHWVRQAPGKGLEWVAVISYTGSNKYYADSVKG RFTISRDNSKNTLYLQMNSLRAEDTAVYYCGGSG YALHDDYYGLDVWGQGTLVTVSSASTKGPSVFPL APSSKSTSGGTAALGCLVKDYFPEPVTVSWNSGA LTSGVHTFPAVLQSSGLYSLSSVVTVPSSSLGTQT YICNVNHKPSNTKVDKKVEPKSCGGGGSGGGGS EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVLGGGGSGGGGS KTHTCPPCPAPPVAGPSVFLFPPKPKDTLMISRTP EVTCVVVDVKHEDPEVKFNWYVDGVEVHNAKTK PREEQYNSTYRVVSVLTVLHQDWLNGKEYKCKV SNKALPAPIEKTISKAKGQPREPQVYTLPPSREQM TKNQVKLTCLVKGFYPSDIAVEWESNGQPENNYK TTPPVLDSDGSFFLYSKLTVDKSRWQQGNVFSCS VMHEALHNHYTQKSLSLSPGK |

7.7. Nucleic Acids and Host Cells

In another aspect, the disclosure provides nucleic acids (i.e., polynucleotides) encoding the BCMA binding molecules of the disclosure. In some embodiments, the BCMA binding molecules are encoded by a single nucleic acid. In other embodiments, the BCMA binding molecules are encoded by a plurality of (e.g., two, three, four or more) nucleic acids.

A single nucleic acid can encode a BCMA binding molecule that comprises a single polypeptide chain, a BCMA binding molecule that comprises two or more polypeptide chains, or a portion of a BCMA binding molecule that comprises more than two polypeptide chains (for example, a single nucleic acid can encode two polypeptide chains of a BCMA binding molecule comprising three, four or more polypeptide chains, or three polypeptide chains of a BCMA binding molecule comprising four or more polypeptide chains). For separate control of expression, the open reading frames encoding two or more polypeptide chains can be under the control of separate transcriptional regulatory elements (e.g., promoters and/or enhancers). The open reading frames encoding two or more polypeptides can also be controlled by the same transcriptional regulatory elements, and separated by internal ribosome entry site (IRES) sequences allowing for translation into separate polypeptides.

In some embodiments, a BCMA binding molecule comprising two or more polypeptide chains is encoded by two or more nucleic acids. The number of nucleic acids encoding a BCMA binding molecule can be equal to or less than the number of polypeptide chains in the BCMA binding molecule (for example, when more than one polypeptide chains are encoded by a single nucleic acid).

The nucleic acids can be DNA or RNA (e.g., mRNA).

In another aspect, the disclosure provides host cells and vectors containing the nucleic acids of the disclosure. The nucleic acids can be present in a single vector or separate vectors present in the same host cell or separate host cell, as described in more detail herein below.

7.7.1. Vectors

The disclosure provides vectors comprising nucleotide sequences encoding a BCMA binding molecule or a BCMA binding molecule component described herein. In one embodiment, the vectors comprise nucleotides encoding an immunoglobulin-based ABD described herein. In one embodiment, the vectors comprise nucleotides encoding an Fc domain described herein. In one embodiment, the vectors comprise nucleotides encoding a recombinant non-immunoglobulin based ABD described herein. A vector can encode one or more ABDs, one or more Fc domains, one or more non-immunoglobulin based ABD, or any combination thereof (e.g., when multiple components or sub-components are encoded as a single polypeptide chain). In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes can be selected by introducing one or more markers which allow for the selection of transfected host cells. The marker can provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements can include splice signals, as well as transcriptional promoters, enhancers, and termination signals.

Once the expression vector or DNA sequence containing the constructs has been prepared for expression, the expression vectors can be transfected or introduced into an appropriate host cell. Various techniques can be employed to achieve this, such as, for example, protoplast fusion, calcium phosphate precipitation, electroporation, retroviral transduction, viral transfection, gene gun, lipid based transfection or other conventional techniques. Methods and conditions for culturing the resulting transfected cells and for recovering the expressed polypeptides are known to those skilled in the art, and can be varied or optimized depending upon the specific expression vector and mammalian host cell employed, based upon the present description.

7.7.2. Cells

The disclosure also provides host cells comprising a nucleic acid of the disclosure.

In one embodiment, the host cells are genetically engineered to comprise one or more nucleic acids described herein.

In one embodiment, the host cells are genetically engineered by using an expression cassette. The phrase "expression cassette," refers to nucleotide sequences, which are capable of affecting expression of a gene in hosts compatible with such sequences. Such cassettes can include a promoter, an open reading frame with or without introns, and a termination signal. Additional factors necessary or helpful in effecting expression can also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

7.8. BCMA Binding Molecules with Extended In Vivo Half-Life

The BCMA binding molecules of the disclosure can be modified to have an extended half-life in vivo.

A variety of strategies can be used to extend the half life of BCMA binding molecules of the disclosure. For example, by chemical linkage to polyethylene glycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of BCMA binding molecules in vivo, inert polymer molecules such as high molecular weight PEG can be attached to the BCMA binding molecules with or without a multifunctional linker either through site-specific conjugation of the PEG to the N- or C-terminus of a polypeptide comprising the BCMA binding molecule or via epsilon-amino groups present on lysine residues. To pegylate a BCMA binding molecule, the molecule can be reacted with polyethylene glycol (PEG), such as a reactive ester or aldehyde derivative of PEG, under conditions in which one or more PEG groups become attached to the BCMA binding molecules. The pegylation can be carried out by an acylation reaction or an alkylation reaction with a reactive PEG molecule (or an analogous reactive water-soluble polymer). As used herein, the term "polyethylene glycol" is intended to encompass any one of the forms of PEG that have been used to derivatize other proteins, such as mono (C1-C10)alkoxy- or aryloxy-polyethylene glycol or polyethylene glycol-maleimide. In one embodiment, the BCMA binding molecule to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known and can be applied to BCMA binding molecules of the disclosure. See for example, EP 0154316 by Nishimura et al. and EP 0401384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum half life extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum half life of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to BCMA binding molecules. HES is a modified natural polymer derived from waxy maize starch and can be metabolized by the body's enzymes. HES solutions are usually administered to substitute deficient blood volume and to improve the rheological properties of the blood. Hesylation of a BCMA binding molecule enables the prolongation of the circulation half-life by increasing the stability of the molecule, as well as by reducing renal clearance, resulting in an increased biological activity. By varying different parameters, such as the molecular weight of HES, a wide range of HES BCMA binding molecule conjugates can be customized.

BCMA binding molecules having an increased half-life in vivo can also be generated introducing one or more amino acid modifications (i.e., substitutions, insertions or deletions) into an IgG constant domain, or FcRn binding fragment thereof (e.g., an Fc or hinge Fc domain fragment). See, e.g., International Publication No. WO 98/23289; International Publication No. WO 97/34631; and U.S. Pat. No. 6,277,375.

Furthermore, the BCMA binding molecules can be conjugated to albumin, a domain of albumin, an albumin-binding protein, or an albumin-binding antibody or antibody fragments thereof, in order to make the molecules more stable in vivo or have a longer half life in vivo. The techniques are well-known, see, e.g., International Publication Nos. WO 93/15199, WO 93/15200, and WO 01/77137; and European Patent No. EP 413,622.

The BCMA binding molecules of the present disclosure can also be fused to one or more human serum albumin (HSA) polypeptides, or a portion thereof. The use of albumin as a component of an albumin fusion protein as a carrier for various proteins has been suggested in WO 93/15199, WO 93/15200, and EP 413 622. The use of N-terminal fragments of HSA for fusions to polypeptides has also been proposed (EP 399 666). Accordingly, by genetically or chemically fusing or conjugating the molecules to albumin, can stabilize or extend the shelf-life, and/or to retain the molecule's activity for extended periods of time in solution, in vitro and/or in vivo. Additional methods pertaining to HSA fusions can be found, for example, in WO 2001077137 and WO 200306007. In an embodiment, the expression of the fusion protein is performed in mammalian cell lines, for example, CHO cell lines.

The BCMA binding molecules of the present disclosure can also be fused to an antibody or antibody fragment thereof that binds to albumin, e.g., human serum albumin (HSA). The albumin-binding antibody or antibody fragment thereof can be a Fab, a scFv, a Fv, an scFab, a (Fab')2, a single domain antibody, a camelid VHH domain, a VH or VL domain, or a full-length monoclonal antibody (mAb).

The BCMA binding molecules of the present disclosure can also be fused to a fatty acid to extend their half-life. Fatty acids suitable for linking to a biomolecule have been described in the art, e.g., WO2015/200078, WO2015/191781, US2013/0040884. Suitable half-life extending fatty acids include those defined as a C6-70alkyl, a C6-70alkenyl or a C6-70alkynyl chain, each of which is substituted with at least one carboxylic acid (for example 1, 2, 3 or 4 CO2H) and optionally further substituted with hydroxyl group. For example, the BCMA binding molecules described herein can be linked to a fatty acid having any of the following Formulae A1, A2 or A3:

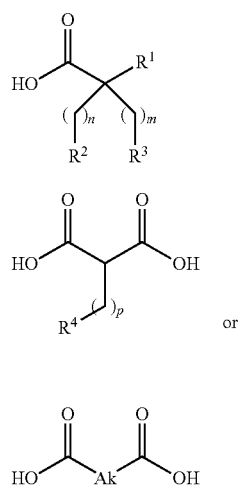

$R^1$ is $CO_2H$ or H;

$R^2$, $R^3$ and $R^4$ are independently of each other H, OH, $CO_2H$, —CH═$CH_2$ or —C≡CH;

Ak is a branched $C_6$-$C_{30}$ alkylene;

n, m and p are independently of each other an integer between 6 and 30; or an amide, ester or pharmaceutically acceptable salt thereof.

In some embodiments, the fatty acid is of Formula A1, e.g., a fatty acid of Formula A1 where n and m are independently 8 to 20, e.g., 10 to 16. In another embodiment, the fatty acid moiety is of Formula A1 and where at least one of $R^2$ and $R^3$ is $CO_2H$.

In some embodiments, the fatty acid is selected from the following Formulae:

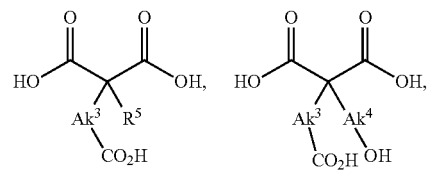

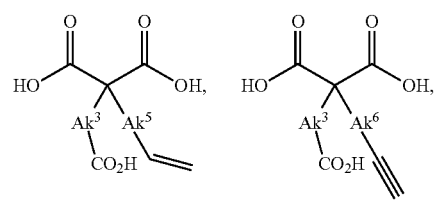

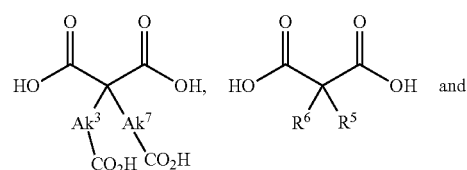 and

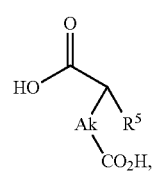

where $Ak^3$, $Ak^4$, $Ak^5$, $Ak^6$ and $Ak^7$ are independently a $(C_{8-20})$alkylene, $R^5$ and $R^6$ are independently $(C_{8-20})$alkyl.

In some embodiments, the fatty acid is selected from the following Formulae:

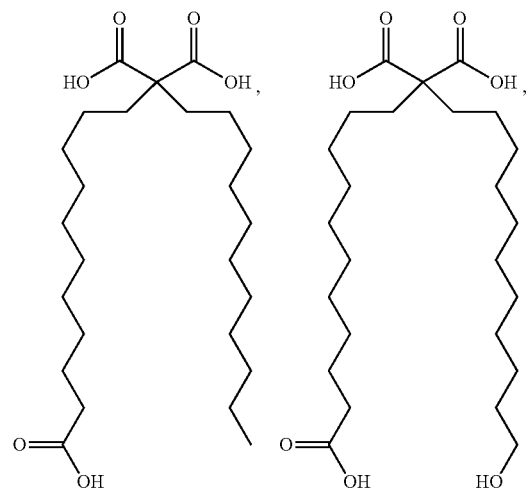

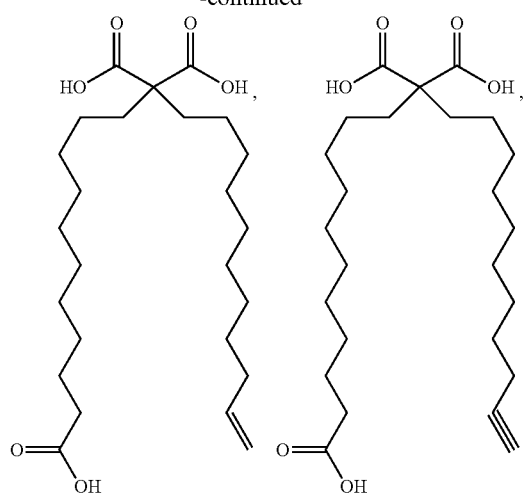
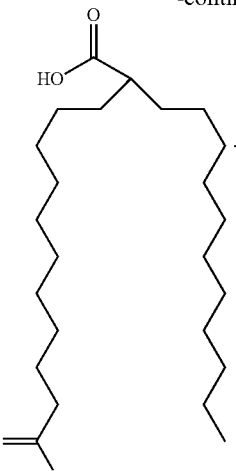
In some embodiments, the fatty acid is selected from the following Formulae:
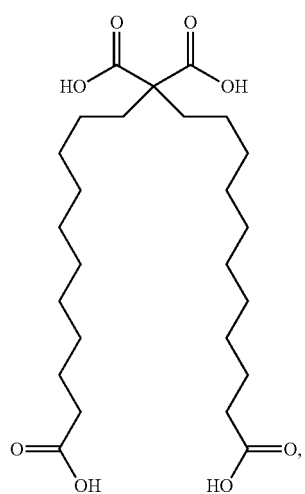 [SMILES: O=C(O)CCCCCCCCCCC(CCCCCCCCCCC(=O)O)(C(=O)O)C(=O)O]
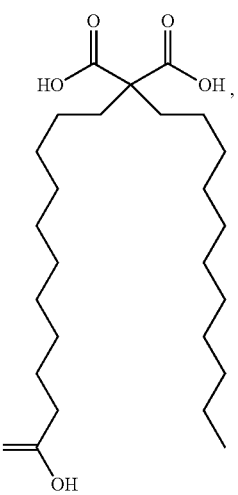
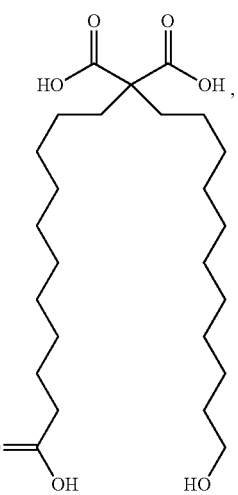
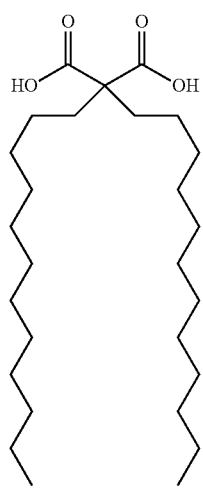
and
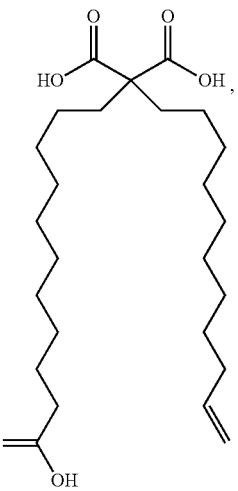

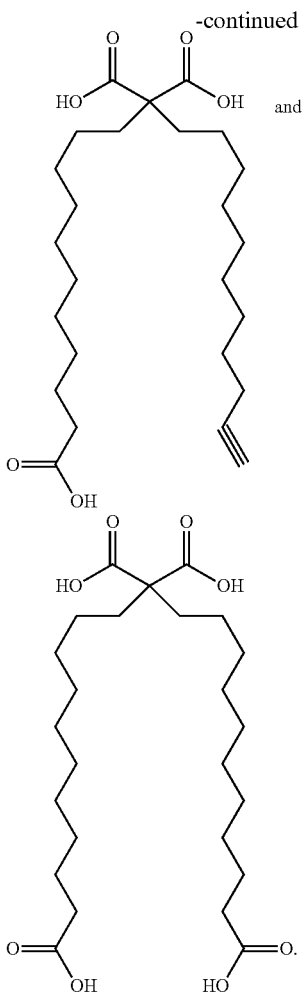

In some embodiments, the fatty acid is of Formula A2 or A3. In a particular embodiment, the conjugate comprises a fatty acid moiety of Formula A2 where p is 8 to 20, or a fatty acid moiety of Formula A3 where Ak is $C_{8-20}$ alkylene.

7.9. Antibody-Drug Conjugates

The BCMA binding molecules of the disclosure can be conjugated, e.g., via a linker, to a drug moiety. Such conjugates are referred to herein as antibody-drug conjugates (or "ADCs") for convenience, notwithstanding the fact that one or more of the ABDs might be based on non-immunoglobulin scaffolds, e.g., a MBM comprising one or more non-immunoglobulin based ABDs, such as a TCR ABD comprising Affilin-144160).

In certain aspects, the drug moiety exerts a cytotoxic or cytostatic activity. In one embodiment, the drug moiety is chosen from a maytansinoid, a kinesin-like protein KIF11 inhibitor, a V-ATPase (vacuolar-type H+-ATPase) inhibitor, a pro-apoptotic agent, a Bcl2 (B-cell lymphoma 2) inhibitor, an MCL1 (myeloid cell leukemia 1) inhibitor, a HSP90 (heat shock protein 90) inhibitor, an IAP (inhibitor of apoptosis) inhibitor, an mTOR (mechanistic target of rapamycin) inhibitor, a microtubule stabilizer, a microtubule destabilizer, an auristatin, a dolastatin, a MetAP (methionine aminopeptidase), a CRM1 (chromosomal maintenance 1) inhibitor, a DPPIV (dipeptidyl peptidase IV) inhibitor, a proteasome inhibitor, an inhibitor of a phosphoryl transfer reaction in mitochondria, a protein synthesis inhibitor, a kinase inhibitor, a CDK2 (cyclin-dependent kinase 2) inhibitor, a CDK9 (cyclin-dependent kinase 9) inhibitor, a kinesin inhibitor, an HDAC (histone deacetylase) inhibitor, a DNA damaging agent, a DNA alkylating agent, a DNA intercalator, a DNA minor groove binder, a RNA polymerase inhibitor, a topoisomerase inhibitor, or a DHFR (dihydrofolate reductase) inhibitor. In some embodiments, the drug moiety is a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In one embodiment, the macrocyclic chelator is 1,4,7,10-tetraazacyclododecane-N,N',N",N'"-tetraacetic acid (DOTA).

In one embodiment, the linker is chosen from a cleavable linker, a non-cleavable linker, a hydrophilic linker, a procharged linker, or a dicarboxylic acid based linker.

In some embodiments, the ADCs are compounds according to structural formula (I):

[D-L-XY]$_n$-Ab or salts thereof, where each "D" represents, independently of the others, a cytotoxic and/or cytostatic agent ("drug"); each "L" represents, independently of the others, a linker; "Ab" represents a BCMA binding molecule described herein; each "XY" represents a linkage formed between a functional group $R^x$ on the linker and a "complementary" functional group $R^y$ on the antibody, and n represents the number of drugs linked to, or drug-to-antibody ratio (DAR), of the ADC.

Some embodiments of the various antibodies (Ab) that can comprise the ADCs include the various embodiments of BCMA binding molecules described above.

In some embodiments of the ADCs and/or salts of structural formula (I), each D is the same and/or each L is the same.

Some embodiments of cytotoxic and/or cytostatic agents (D) and linkers (L) that can comprise the ADCs of the disclosure, as well as the number of cytotoxic and/or cytostatic agents linked to the ADCs, are described in more detail below.

7.9.1. Cytotoxic and/or Cytostatic Agents

The cytotoxic and/or cytostatic agents can be any agents known to inhibit the growth and/or replication of and/or kill cells, and in particular cancer and/or tumor cells. Numerous agents having cytotoxic and/or cytostatic properties are known in the literature. Non-limiting examples of classes of cytotoxic and/or cytostatic agents include, by way of example and not limitation, radionuclides, alkylating agents, topoisomerase I inhibitors, topoisomerase II inhibitors, DNA intercalating agents (e.g., groove binding agents such as minor groove binders), RNA/DNA antimetabolites, cell cycle modulators, kinase inhibitors, protein synthesis inhibitors, histone deacetylase inhibitors, mitochondria inhibitors, and antimitotic agents.

Specific non-limiting examples of agents within certain of these various classes are provided below.

Alkylating Agents: asaley ((L-Leucine, N—[N-acetyl-4-[bis-(2-chloroethyl)amino]-DL-phenylalanyl]-, ethylester; NSC 167780; CAS Registry No. 3577897)); AZQ ((1,4-cyclohexadiene-1,4-dicarbamic acid, 2,5-bis(1-aziridinyl)-3,6-dioxo-, diethyl ester; NSC 182986; CAS Registry No. 57998682)); BCNU ((N,N'-Bis(2-chloroethyl)-N-nitrosourea; NSC 409962; CAS Registry No. 154938)); busulfan (1,4-butanediol dimethanesulfonate; NSC 750; CAS Registry No. 55981); (carboxyphthalato)platinum (NSC 27164; CAS Registry No. 65296813); CBDCA ((cis-(1,1-cyclobutanedicarboxylato)diammineplatinum(II)); NSC 241240; CAS Registry No. 41575944)); CCNU ((N-(2- chloroethyl)-N'-cyclohexyl-N-nitrosourea; NSC 79037; CAS Registry No. 13010474)); CHIP (iproplatin; NSC 256927); chlorambucil (NSC 3088; CAS Registry No. 305033); chlorozotocin ((2-[[[(2-chloroethyl) nitrosoamino] carbonyl]amino]-2-deoxy-D-glucopyranose; NSC 178248; CAS Registry No. 54749905)); cis-platinum (cisplatin; NSC 119875; CAS Registry No. 15663271); clomesone (NSC 338947; CAS Registry No. 88343720); cyanomorpholino-doxorubicin (NCS 357704; CAS Registry No. 88254073); cyclodisone (NSC 348948; CAS Registry No. 99591738); dianhydrogalactitol (5,6-diepoxydulcitol; NSC 132313; CAS Registry No. 23261203); fluorodopan ((5-[(2-chloroethyl)-(2-fluoroethyl)amino]-6-methyl-uracil; NSC 73754; CAS Registry No. 834913); hepsulfam (NSC 329680; CAS Registry No. 96892578); hycanthone (NSC 142982; CAS Registry No. 23255938); melphalan (NSC 8806; CAS Registry No. 3223072); methyl CCNU ((1-(2-chloroethyl)-3-(trans-4-methylcyclohexane)-1-nitrosourea; NSC 95441; 13909096); mitomycin C (NSC 26980; CAS Registry No. 50077); mitozolamide (NSC 353451; CAS Registry No. 85622953); nitrogen mustard ((bis(2-chloroethyl)methylamine hydrochloride; NSC 762; CAS Registry No. 55867); PCNU ((1-(2-chloroethyl)-3-(2,6-dioxo-3-piperidyl)-1-nitrosourea; NSC 95466; CAS Registry No. 13909029)); piperazine alkylator ((1-(2-chloroethyl)-4-(3-chloropropyl)-piperazine dihydrochloride; NSC 344007)); piperazinedione (NSC 135758; CAS Registry No. 41109802); pipobroman ((N,N-bis(3-bromopropionyl) piperazine; NSC 25154; CAS Registry No. 54911)); porfiromycin (N-methylmitomycin C; NSC 56410; CAS Registry No. 801525); spirohydantoin mustard (NSC 172112; CAS Registry No. 56605164); teroxirone (triglycidylisocyanurate; NSC 296934; CAS Registry No. 2451629); tetraplatin (NSC 363812; CAS Registry No. 62816982); thio-tepa (N,N',N''-tri-1,2-ethanediylthio phosphoramide; NSC 6396; CAS Registry No. 52244); triethylenemelamine (NSC 9706; CAS Registry No. 51183); uracil nitrogen mustard (desmethyldopan; NSC 34462; CAS Registry No. 66751); Yoshi-864 ((bis(3-mesyloxy propyl)amine hydrochloride; NSC 102627; CAS Registry No. 3458228).

Topoisomerase I Inhibitors: camptothecin (NSC 94600; CAS Registry No. 7689-03-4); various camptothecin derivatives and analogs (for example, NSC 100880, NSC 603071, NSC 107124, NSC 643833, NSC 629971, NSC 295500, NSC 249910, NSC 606985, NSC 74028, NSC 176323, NSC 295501, NSC 606172, NSC 606173, NSC 610458, NSC 618939, NSC 610457, NSC 610459, NSC 606499, NSC 610456, NSC 364830, and NSC 606497); morpholinisoxorubicin (NSC 354646; CAS Registry No. 89196043); SN-38 (NSC 673596; CAS Registry No. 86639-52-3).

Topoisomerase II Inhibitors: doxorubicin (NSC 123127; CAS Registry No. 25316409); amonafide (benzisoquinolinedione; NSC 308847; CAS Registry No. 69408817); m-AMSA ((4'-(9-acridinylamino)-3'-methoxymethanesulfonanilide; NSC 249992; CAS Registry No. 51264143)); anthrapyrazole derivative ((NSC 355644); etoposide (VP-16; NSC 141540; CAS Registry No. 33419420); pyrazoloacridine ((pyrazolo[3,4,5-kl]acridine-2(6H)-propanamine, 9-methoxy-N, N-dimethyl-5-nitro-, monomethanesulfonate; NSC 366140; CAS Registry No. 99009219); bisantrene hydrochloride (NSC 337766; CAS Registry No. 71439684); daunorubicin (NSC 821151; CAS Registry No. 23541506); deoxydoxorubicin (NSC 267469; CAS Registry No. 63950061); mitoxantrone (NSC 301739; CAS Registry No. 70476823); menogaril (NSC 269148; CAS Registry No. 71628961); N,N-dibenzyl daunomycin (NSC 268242; CAS Registry No. 70878512); oxanthrazole (NSC 349174; CAS Registry No. 105118125); rubidazone (NSC 164011; CAS Registry No. 36508711); teniposide (VM-26; NSC 122819; CAS Registry No. 29767202).

DNA Intercalating Agents: anthramycin (CAS Registry No. 4803274); chicamycin A (CAS Registry No. 89675376); tomaymycin (CAS Registry No. 35050556); DC-81 (CAS Registry No. 81307246); sibiromycin (CAS Registry No. 12684332); pyrrolobenzodiazepine derivative (CAS Registry No. 945490095); SGD-1882 ((S)-2-(4-aminophenyl)-7-methoxy-8-(3-4(S)-7-methoxy-2-(4-methoxyphenyl)-5-oxo-5,11a-dihydro-1H-benzo[e]pyrrolo[1,2-a][1,4] diazepin-8-yl)oxy)propox-y)-1H-benzo[e]pyrrolo[1,2-a][1, 4]diazepin-5(11aH)-one); SG2000 (SJG-136; (11aS,11a'S)-8,8'-(propane-1,3-diylbis(oxy))bis(7-methoxy-2-methylene-2,3-dihydro-1H-benzo[e]pyrrolo[1,2-a][1,4]diazepin-5 (11aH)-one); NSC 694501; CAS Registry No. 232931576).

RNA/DNA Antimetabolites: L-alanosine (NSC 153353; CAS Registry No. 59163416); 5-azacytidine (NSC 102816; CAS Registry No. 320672); 5-fluorouracil (NSC 19893; CAS Registry No. 51218); acivicin (NSC 163501; CAS Registry No. 42228922); aminopterin derivative N-[2-chloro-5-[[(2,4-diamino-5-methyl-6-quinazolinyl)methyl] amino]benzoyl-]L-aspartic acid (NSC 132483); aminopterin derivative N-[4-[[(2,4-diamino-5-ethyl-6-quinazolinyl) methyl]amino]benzoyl]L-asparti-c acid (NSC 184692); aminopterin derivative N-[2-chloro-4-[[(2,4-diamino-6-pteridinylhmethyl]amino]benzoyl]L-aspartic acid monohydrate (NSC 134033); an antifo ((N$^\alpha$-(4-amino-4-deoxypteroyl)-N$^7$-hemiphthaloyl-L-ornithin-e; NSC 623017)); Bakers soluble antifol (NSC 139105; CAS Registry No. 41191042); dichlorallyl lawsone ((2-(3,3-dichloroallyl)-3-hydroxy-1,4-naphthoquinone; NSC 126771; CAS Registry No. 36417160); brequinar (NSC 368390; CAS Registry No. 96201886); ftorafur ((pro-drug; 5-fluoro-1-(tetrahydro-2-furyl)-uracil; NSC 148958; CAS Registry No. 37076689); 5,6-dihydro-5-azacytidine (NSC 264880; CAS Registry No. 62402317); methotrexate (NSC 740; CAS Registry No. 59052); methotrexate derivative (N-[[4-[[(2,4-diamino-6-pteridinylhmethyl]methylamino]-1-naphthalenyl]car-bonyl] L-glutamic acid; NSC 174121); PALA ((N-(phosphonoacetyl)-L-aspartate; NSC 224131; CAS Registry No. 603425565); pyrazofurin (NSC 143095; CAS Registry No. 30868305); trimetrexate (NSC 352122; CAS Registry No. 82952645).

DNA Antimetabolites: 3-HP (NSC 95678; CAS Registry No. 3814797); 2'-deoxy-5-fluorouridine (NSC 27640; CAS Registry No. 50919); 5-HP (NSC 107392; CAS Registry No. 19494894); α-TGDR (α-2'-deoxy-6-thioguanosine; NSC 71851 CAS Registry No. 2133815); aphidicolin glycinate (NSC 303812; CAS Registry No. 92802822); ara C (cytosine arabinoside; NSC 63878; CAS Registry No. 69749); 5-aza-2'-deoxycytidine (NSC 127716; CAS Registry No. 2353335); β-TGDR (β-2'-deoxy-6-thioguanosine; NSC 71261; CAS Registry No. 789617); cyclocytidine (NSC 145668; CAS Registry No. 10212256); guanazole (NSC 1895; CAS Registry No. 1455772); hydroxyurea (NSC 32065; CAS Registry No. 127071); inosine glycodialdehyde (NSC 118994; CAS Registry No. 23590990); macbecin II (NSC 330500; CAS Registry No. 73341738); pyrazoloimidazole (NSC 51143; CAS Registry No. 6714290); thioguanine (NSC 752; CAS Registry No. 154427); thiopurine (NSC 755; CAS Registry No. 50442).

Cell Cycle Modulators: silibinin (CAS Registry No. 22888-70-6); epigallocatechin gallate (EGCG; CAS Registry No. 989515); procyanidin derivatives (e.g., procyanidin A1 [CAS Registry No. 103883030], procyanidin B1 [CAS Registry No. 20315257], procyanidin B4 [CAS Registry No. 29106512], arecatannin B1 [CAS Registry No. 79763283]);

isoflavones (e.g., genistein [4',5,7-trihydroxyisoflavone; CAS Registry No. 446720], daidzein [4',7-dihydroxyisoflavone, CAS Registry No. 486668]; indole-3-carbinol (CAS Registry No. 700061); quercetin (NSC 9219; CAS Registry No. 117395); estramustine (NSC 89201; CAS Registry No. 2998574); nocodazole (CAS Registry No. 31430189); podophyllotoxin (CAS Registry No. 518285); vinorelbine tartrate (NSC 608210; CAS Registry No. 125317397); cryptophycin (NSC 667642; CAS Registry No. 124689652).

Kinase Inhibitors: afatinib (CAS Registry No. 850140726); axitinib (CAS Registry No. 319460850); ARRY-438162 (binimetinib) (CAS Registry No. 606143899); bosutinib (CAS Registry No. 380843754); cabozantinib (CAS Registry No. 1140909483); ceritinib (CAS Registry No. 1032900256); crizotinib (CAS Registry No. 877399525); dabrafenib (CAS Registry No. 1195765457); dasatinib (NSC 732517; CAS Registry No. 302962498); erlotinib (NSC 718781; CAS Registry No. 183319699); everolimus (NSC 733504; CAS Registry No. 159351696); fostamatinib (NSC 745942; CAS Registry No. 901119355); gefitinib (NSC 715055; CAS Registry No. 184475352); ibrutinib (CAS Registry No. 936563961); imatinib (NSC 716051; CAS Registry No. 220127571); lapatinib (CAS Registry No. 388082788); lenvatinib (CAS Registry No. 857890392); mubritinib (CAS Registry No. 366017096); nilotinib (CAS Registry No. 923288953); nintedanib (CAS Registry No. 656247175); palbociclib (CAS Registry No. 571190302); pazopanib (NSC 737754; CAS Registry No. 635702646); pegaptanib (CAS Registry No. 222716861); ponatinib (CAS Registry No. 1114544318); rapamycin (NSC 226080; CAS Registry No. 53123889); regorafenib (CAS Registry No. 755037037); AP 23573 (ridaforolimus) (CAS Registry No. 572924540); INCB018424 (ruxolitinib) (CAS Registry No. 1092939177); ARRY-142886 (selumetinib) (NSC 741078; CAS Registry No. 606143-52-6); sirolimus (NSC 226080; CAS Registry No. 53123889); sorafenib (NSC 724772; CAS Registry No. 475207591); sunitinib (NSC 736511; CAS Registry No. 341031547); tofacitinib (CAS Registry No. 477600752); temsirolimus (NSC 683864; CAS Registry No. 163635043); trametinib (CAS Registry No. 871700173); vandetanib (CAS Registry No. 443913733); vemurafenib (CAS Registry No. 918504651); SU6656 (CAS Registry No. 330161870); CEP-701 (lesaurtinib) (CAS Registry No. 111358884); XL019 (CAS Registry No. 945755566); PD-325901 (CAS Registry No. 391210109); PD-98059 (CAS Registry No. 167869218); ATP-competitive TORC1/TORC2 inhibitors including PI-103 (CAS Registry No. 371935749), PP242 (CAS Registry No. 1092351671), PP30 (CAS Registry No. 1092788094), Torin 1 (CAS Registry No. 1222998368), LY294002 (CAS Registry No. 154447366), XL-147 (CAS Registry No. 934526893), CAL-120 (CAS Registry No. 870281348), ETP-45658 (CAS Registry No. 1198357797), PX 866 (CAS Registry No. 502632668), GDC-0941 (CAS Registry No. 957054307), BGT226 (CAS Registry No. 1245537681), BEZ235 (CAS Registry No. 915019657), XL-765 (CAS Registry No. 934493762).

Protein Synthesis Inhibitors: acriflavine (CAS Registry No. 65589700); amikacin (NSC 177001; CAS Registry No. 39831555); arbekacin (CAS Registry No. 51025855); astromicin (CAS Registry No. 55779061); azithromycin (NSC 643732; CAS Registry No. 83905015); bekanamycin (CAS Registry No. 4696768); chlortetracycline (NSC 13252; CAS Registry No. 64722); clarithromycin (NSC 643733; CAS Registry No. 81103119); clindamycin (CAS Registry No. 18323449); clomocycline (CAS Registry No. 1181540); cycloheximide (CAS Registry No. 66819); dactinomycin (NSC 3053; CAS Registry No. 50760); dalfopristin (CAS Registry No. 112362502); demeclocycline (CAS Registry No. 127333); dibekacin (CAS Registry No. 34493986); dihydrostreptomycin (CAS Registry No. 128461); dirithromycin (CAS Registry No. 62013041); doxycycline (CAS Registry No. 17086281); emetine (NSC 33669; CAS Registry No. 483181); erythromycin (NSC 55929; CAS Registry No. 114078); flurithromycin (CAS Registry No. 83664208); framycetin (neomycin B; CAS Registry No. 119040); gentamycin (NSC 82261; CAS Registry No. 1403663); glycylcyclines, such as tigecycline (CAS Registry No. 220620097); hygromycin B (CAS Registry No. 31282049); isepamicin (CAS Registry No. 67814760); josamycin (NSC 122223; CAS Registry No. 16846245); kanamycin (CAS Registry No. 8063078); ketolides such as telithromycin (CAS Registry No. 191114484), cethromycin (CAS Registry No. 205110481), and solithromycin (CAS Registry No. 760981837); lincomycin (CAS Registry No. 154212); lymecycline (CAS Registry No. 992212); meclocycline (NSC 78502; CAS Registry No. 2013583); metacycline (rondomycin; NSC 356463; CAS Registry No. 914001); midecamycin (CAS Registry No. 35457808); minocycline (NSC 141993; CAS Registry No. 10118908); miocamycin (CAS Registry No. 55881077); neomycin (CAS Registry No. 119040); netilmicin (CAS Registry No. 56391561); oleandomycin (CAS Registry No. 3922905); oxazolidinones, such as eperezolid (CAS Registry No. 165800044), linezolid (CAS Registry No. 165800033), posizolid (CAS Registry No. 252260029), radezolid (CAS Registry No. 869884786), ranbezolid (CAS Registry No. 392659380), sutezolid (CAS Registry No. 168828588), tedizolid (CAS Registry No. 856867555); oxytetracycline (NSC 9169; CAS Registry No. 2058460); paromomycin (CAS Registry No. 7542372); penimepicycline (CAS Registry No. 4599604); peptidyl transferase inhibitors, e.g., chloramphenicol (NSC 3069; CAS Registry No. 56757) and derivatives such as azidamfenicol (CAS Registry No. 13838089), florfenicol (CAS Registry No. 73231342), and thiamphenicol (CAS Registry No. 15318453), and pleuromutilins such as retapamulin (CAS Registry No. 224452668), tiamulin (CAS Registry No. 55297955), valnemulin (CAS Registry No. 101312929); pirlimycin (CAS Registry No. 79548735); puromycin (NSC 3055; CAS Registry No. 53792); quinupristin (CAS Registry No. 120138503); ribostamycin (CAS Registry No. 53797356); rokitamycin (CAS Registry No. 74014510); rolitetracycline (CAS Registry No. 751973); roxithromycin (CAS Registry No. 80214831); sisomicin (CAS Registry No. 32385118); spectinomycin (CAS Registry No. 1695778); spiramycin (CAS Registry No. 8025818); streptogramins such as pristinamycin (CAS Registry No. 270076603), quinupristin/dalfopristin (CAS Registry No. 126602899), and virginiamycin (CAS Registry No. 11006761); streptomycin (CAS Registry No. 57921); tetracycline (NSC 108579; CAS Registry No. 60548); tobramycin (CAS Registry No. 32986564); troleandomycin (CAS Registry No. 2751099); tylosin (CAS Registry No. 1401690); verdamicin (CAS Registry No. 49863481).

Histone Deacetylase Inhibitors: abexinostat (CAS Registry No. 783355602); belinostat (NSC 726630; CAS Registry No. 414864009); chidamide (CAS Registry No. 743420022); entinostat (CAS Registry No. 209783802); givinostat (CAS Registry No. 732302997); mocetinostat (CAS Registry No. 726169739); panobinostat (CAS Registry No. 404950807); quisinostat (CAS Registry No. 875320299); resminostat (CAS Registry No. 864814880); romidepsin (CAS Registry No. 128517077); sulforaphane (CAS Registry No. 4478937); thioureidobutyronitrile (Kevetrin™; CAS Registry No. 6659890); valproic acid (NSC 93819; CAS Registry No. 99661); vorinostat (NSC 701852; CAS Registry No. 149647789); ACY-1215 (rocilinostat; CAS Registry No. 1316214524); CUDC-101 (CAS Registry No. 1012054599); CHR-2845 (tefinostat; CAS Registry No. 914382608); CHR-3996 (CAS Registry No. 1235859138); 4SC-202 (CAS Registry No. 910462430); CG200745 (CAS Registry No. 936221339); SB939 (pracinostat; CAS Registry No. 929016966).

Mitochondria Inhibitors: pancratistatin (NSC 349156; CAS Registry No. 96281311); rhodamine-123 (CAS Registry No. 63669709); edelfosine (NSC 324368; CAS Registry No. 70641519); d-alpha-tocopherol succinate (NSC 173849; CAS Registry No. 4345033); compound 11β (CAS Registry No. 865070377); aspirin (NSC 406186; CAS Registry No. 50782); ellipticine (CAS Registry No. 519233); berberine (CAS Registry No. 633658); cerulenin (CAS Registry No. 17397896); GX015-070 (Obatoclax®; 1H-Indole, 2-(2-((3,5-dimethyl-1H-pyrrol-2-yl)methylene)-3-methoxy-2H-pyrrol-5-yl)-; NSC 729280; CAS Registry No. 803712676); celastrol (tripterine; CAS Registry No. 34157830); metformin (NSC 91485; CAS Registry No. 1115704); Brilliant green (NSC 5011; CAS Registry No. 633034); ME-344 (CAS Registry No. 1374524556).

Antimitotic Agents: allocolchicine (NSC 406042); auristatins, such as MMAE (monomethyl auristatin E; CAS Registry No. 474645-27-7) and MMAF (monomethyl auristatin F; CAS Registry No. 745017-94-1; halichondrin B (NSC 609395); colchicine (NSC 757; CAS Registry No. 64868); cholchicine derivative (N-benzoyl-deacetyl benzamide; NSC 33410; CAS Registry No. 63989753); dolastatin 10 (NSC 376128; CAS Registry No 110417-88-4); maytansine (NSC 153858; CAS Registry No. 35846-53-8); rhozoxin (NSC 332598; CAS Registry No. 90996546); taxol (NSC 125973; CAS Registry No. 33069624); taxol derivative ((2'-N-[3-(dimethylamino)propyl]glutaramate taxol; NSC 608832); thiocolchicine (3-demethylthiocolchicine; NSC 361792); trityl cysteine (NSC 49842; CAS Registry No. 2799077); vinblastine sulfate (NSC 49842; CAS Registry No. 143679); vincristine sulfate (NSC 67574; CAS Registry No. 2068782).

Any of these agents that include or that can be modified to include a site of attachment to a BCMA binding molecule can be included in the ADCs disclosed herein.

In an embodiment, the cytotoxic and/or cytostatic agent is an antimitotic agent.

In another embodiment, the cytotoxic and/or cytostatic agent is an auristatin, for example, monomethyl auristatin E ("MMAE) or monomethyl auristatin F ("MMAF").

7.9.2. ADC Linkers

In the ADCs of the disclosure, the cytotoxic and/or cytostatic agents are linked to the BCMA binding molecule by way of ADC linkers. The ADC linker linking a cytotoxic and/or cytostatic agent to the BCMA binding molecule of an ADC can be short, long, hydrophobic, hydrophilic, flexible or rigid, or can be composed of segments that each independently have one or more of the above-mentioned properties such that the linker can include segments having different properties. The linkers can be polyvalent such that they covalently link more than one agent to a single site on the BCMA binding molecule, or monovalent such that covalently they link a single agent to a single site on the BCMA binding molecule.

As will be appreciated by a skilled artisan, the ADC linkers link cytotoxic and/or cytostatic agents to the BCMA binding molecule by forming a covalent linkage to the cytotoxic and/or cytostatic agent at one location and a covalent linkage to the BCMA binding molecule at another. The covalent linkages are formed by reaction between functional groups on the ADC linker and functional groups on the agents and BCMA binding molecule. As used herein, the expression "ADC linker" is intended to include (i) unconjugated forms of the ADC linker that include a functional group capable of covalently linking the ADC linker to a cytotoxic and/or cytostatic agent and a functional group capable of covalently linking the ADC linker to a BCMA binding molecule; (ii) partially conjugated forms of the ADC linker that include a functional group capable of covalently linking the ADC linker to a BCMA binding molecule and that is covalently linked to a cytotoxic and/or cytostatic agent, or vice versa; and (iii) fully conjugated forms of the ADC linker that are covalently linked to both a cytotoxic and/or cytostatic agent and a BCMA binding molecule. In some embodiments of ADC linkers and ADCs of the disclosure, as well as synthons used to conjugate linker-agents to BCMA binding molecules, moieties comprising the functional groups on the ADC linker and covalent linkages formed between the ADC linker and BCMA binding molecule are specifically illustrated as $R_x$ and XY, respectively.

The ADC linkers can, but need not be, chemically stable to conditions outside the cell, and can be designed to cleave, immolate and/or otherwise specifically degrade inside the cell. Alternatively, ADC linkers that are not designed to specifically cleave or degrade inside the cell can be used. Choice of stable versus unstable ADC linker can depend upon the toxicity of the cytotoxic and/or cytostatic agent. For agents that are toxic to normal cells, stable linkers can be used. Agents that are selective or targeted and have lower toxicity to normal cells can be utilized, as chemical stability of the ADC linker to the extracellular milieu is less important. A wide variety of ADC linkers useful for linking drugs to BCMA binding molecules in the context of ADCs are known. Any of these ADC linkers, as well as other ADC linkers, can be used to link the cytotoxic and/or cytostatic agents to the BCMA binding molecule of the ADCs of the disclosure.

Exemplary polyvalent ADC linkers that can be used to link many cytotoxic and/or cytostatic agents to a single BCMA binding molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640. For example, the Fleximer linker technology developed by Mersana et al. has the potential to enable high-DAR ADCs with good physicochemical properties. As shown below, the Mersana technology is based on incorporating drug molecules into a solubilizing poly-acetal backbone via a sequence of ester bonds. The methodology renders highly-loaded ADCs (DAR up to 20) while maintaining good physicochemical properties.

Additional examples of dendritic type linkers can be found in US 2006/116422; US 2005/271615; de Groot et al., 2003, Angew. Chem. Int. Ed. 42:4490-4494; Amir et al., 2003, Angew. Chem. Int. Ed. 42:4494-4499; Shamis et al., 2004, J. Am. Chem. Soc. 126:1726-1731; Sun et al., 2002, Bioorganic & Medicinal Chemistry Letters 12:2213-2215; Sun et al., 2003, Bioorganic & Medicinal Chemistry 11:1761-1768; King et al., 2002, Tetrahedron Letters 43:1987-1990.

Exemplary monovalent ADC linkers that can be used are described, for example, in Nolting, 2013, Antibody-Drug Conjugates, Methods in Molecular Biology 1045:71-100; Kitson et al., 2013, CROs-MOs—Chemica-ggi—Chemistry Today 31(4):30-38; Ducry et al., 2010, Bioconjugate Chem. 21:5-13; Zhao et al., 2011, J. Med. Chem. 54:3606-3623; U.S. Pat. Nos. 7,223,837; 8,568,728; 8,535,678; and WO2004010957.

By way of example and not limitation, some cleavable and noncleavable ADC linkers that can be included in the ADCs are described below.

7.9.2.1. Cleavable ADC Linkers

In certain embodiments, the ADC linker selected is cleavable in vivo. Cleavable ADC linkers can include chemically or enzymatically unstable or degradable linkages. Cleavable ADC linkers generally rely on processes inside the cell to liberate the drug, such as reduction in the cytoplasm, exposure to acidic conditions in the lysosome, or cleavage by specific proteases or other enzymes within the cell. Cleavable ADC linkers generally incorporate one or more chemical bonds that are either chemically or enzymatically cleavable while the remainder of the ADC linker is noncleavable. In certain embodiments, an ADC linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing ADC linkers are the acidic environment of endosomes and lysosomes, while the disulfide containing ADC linkers are reduced in the cytosol, which contains high thiol concentrations, e.g., glutathione. In certain embodiments, the plasma stability of an ADC linker comprising a chemically labile group can be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the ADC linker, the ADC linker can be varied by chemical modification, e.g., substitution, allowing tuning to achieve more efficient release in the lysosome with a minimized loss in circulation.

Hydrazone-containing ADC linkers can contain additional cleavage sites, such as additional acid-labile cleavage sites and/or enzymatically labile cleavage sites. ADCs including exemplary hydrazone-containing ADC linkers include the following structures:

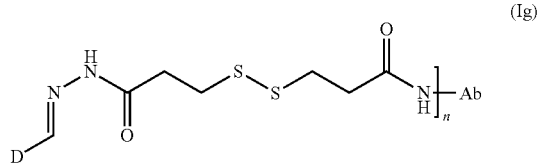

(Ig)

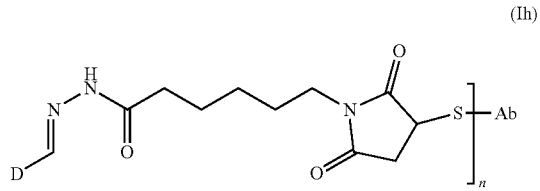

(Ih)

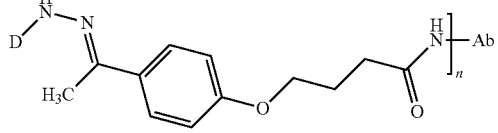

(Ii)

where D and Ab represent the cytotoxic and/or cytostatic agent (drug) and Ab, respectively, and n represents the number of drug-ADC linkers linked to the BCMA binding molecule. In certain ADC linkers such as linker (Ig), the ADC linker comprises two cleavable groups—a disulfide and a hydrazone moiety. For such ADC linkers, effective release of the unmodified free drug requires acidic pH or disulfide reduction and acidic pH. Linkers such as (Ih) and (Ii) have been shown to be effective with a single hydrazone cleavage site.

Additional ADC linkers which remain intact during systemic circulation and undergo hydrolysis and release the drug when the ADC is internalized into acidic cellular compartments include carbonates. Such ADC linkers can be useful in cases where the cytotoxic and/or cytostatic agent can be covalently attached through an oxygen.

Other acid-labile groups that can be included in ADC linkers include cis-aconityl-containing ADC linkers. cis-Aconityl chemistry uses a carboxylic acid juxtaposed to an amide bond to accelerate amide hydrolysis under acidic conditions.

Cleavable ADC linkers can also include a disulfide group. Disulfides are thermodynamically stable at physiological pH and are designed to release the drug upon internalization inside cells, where the cytosol provides a significantly more reducing environment compared to the extracellular environment. Scission of disulfide bonds generally requires the presence of a cytoplasmic thiol cofactor, such as (reduced) glutathione (GSH), such that disulfide-containing ADC linkers are reasonably stable in circulation, selectively releasing the drug in the cytosol. The intracellular enzyme protein disulfide isomerase, or similar enzymes capable of cleaving disulfide bonds, can also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 Tumor cells, where irregular blood flow leads to a hypoxic state, result in enhanced activity of reductive enzymes and therefore even higher glutathione concentrations. In certain embodiments, the in vivo stability of a disulfide-containing ADC linker can be enhanced by chemical modification of the ADC linker, e.g., use of steric hindrance adjacent to the disulfide bond.

ADCs including exemplary disulfide-containing ADC linkers include the following structures:

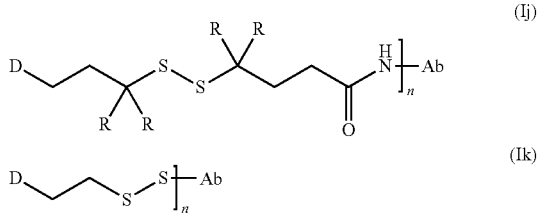

(Ij)

(Ik)

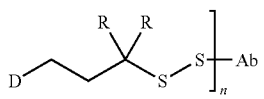
(II)

where D and Ab represent the drug and BCMA binding molecule, respectively, n represents the number of drug-ADC linkers linked to the BCMA binding molecule and R is independently selected at each occurrence from hydrogen or alkyl, for example. In certain embodiments, increasing steric hindrance adjacent to the disulfide bond increases the stability of the ADC linker. Structures such as (Ij) and (II) show increased in vivo stability when one or more R groups is selected from a lower alkyl such as methyl.

Another type of cleavable ADC linker that can be used is an ADC linker that is specifically cleaved by an enzyme. Such ADC linkers are typically peptide-based or include peptidic regions that act as substrates for enzymes. Peptide based ADC linkers tend to be more stable in plasma and extracellular milieu than chemically labile ADC linkers. Peptide bonds generally have good serum stability, as lysosomal proteolytic enzymes have very low activity in blood due to endogenous inhibitors and the unfavorably high pH value of blood compared to lysosomes. Release of a drug from a BCMA binding molecule occurs specifically due to the action of lysosomal proteases, e.g., cathepsin and plasmin. These proteases can be present at elevated levels in certain tumor cells.

In exemplary embodiments, the cleavable peptide is selected from tetrapeptides such as Gly-Phe-Leu-Gly (SEQ ID NO:512), Ala-Leu-Ala-Leu (SEQ ID NO:513) or dipeptides such as Val-Cit, Val-Ala, Met-(D)Lys, Asn-(D)Lys, Val-(D)Asp, Phe-Lys, Ile-Val, Asp-Val, His-Val, NorVal-(D) Asp, Ala-(D)Asp 5, Met-Lys, Asn-Lys, Ile-Pro, Me3Lys-Pro, PhenylGly-(D)Lys, Met-(D)Lys, Asn-(D)Lys, Pro-(D) Lys, Met-(D)Lys, Asn-(D)Lys, AM Met-(D)Lys, Asn-(D) Lys, AW Met-(D)Lys, and Asn-(D)Lys. In certain embodiments, dipeptides can be selected over longer polypeptides due to hydrophobicity of the longer peptides.

A variety of dipeptide-based cleavable ADC linkers useful for linking drugs such as doxorubicin, mitomycin, camptothecin, tallysomycin, pyrrolobenzodiazepine, and auristatin/auristatin family members to BCMA binding molecules have been described (see, Dubowchik et al., 1998, J. Org. Chem. 67:1866-1872; Dubowchik et al., 1998, Bioorg. Med. Chem. Lett. 8(21):3341-3346; Walker et al., 2002, Bioorg. Med. Chem. Lett. 12:217-219; Walker et al., 2004, Bioorg. Med. Chem. Lett. 14:4323-4327; Sutherland et al., 2013, Blood 122: 1455-1463; and Francisco et al., 2003, Blood 102:1458-1465). All of these dipeptide ADC linkers, or modified versions of these dipeptide ADC linkers, can be used in the ADCs of the disclosure. Other dipeptide ADC linkers that can be used include those found in ADCs such as Seattle Genetics' Brentuximab Vendotin SGN-35 (Adcetris™), Seattle Genetics SGN-75 (anti-CD-70, Val-Cit-monomethyl auristatin F (MMAF), Seattle Genetics SGN-CD33A (anti-CD-33, Val-Ala-(SGD-1882)), Celldex Therapeutics glembatumumab (CDX-011) (anti-NMB, Val-Cit-monomethyl auristatin E (MMAE), and Cytogen PSMA-ADC (PSMA-ADC-1301) (anti-PSMA, Val-Cit-MMAE).

Enzymatically cleavable ADC linkers can include a self-immolative spacer to spatially separate the drug from the site of enzymatic cleavage. The direct attachment of a drug to a peptide ADC linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs can be attached through carbamate functionalities to the benzylic hydroxyl group of the ADC linker (PABC). The resulting prodrugs are activated upon protease-mediated cleavage, leading to a 1,6-elimination reaction releasing the unmodified drug, carbon dioxide, and remnants of the ADC linker group. The following scheme depicts the fragmentation of p-amidobenzyl ether and release of the drug:

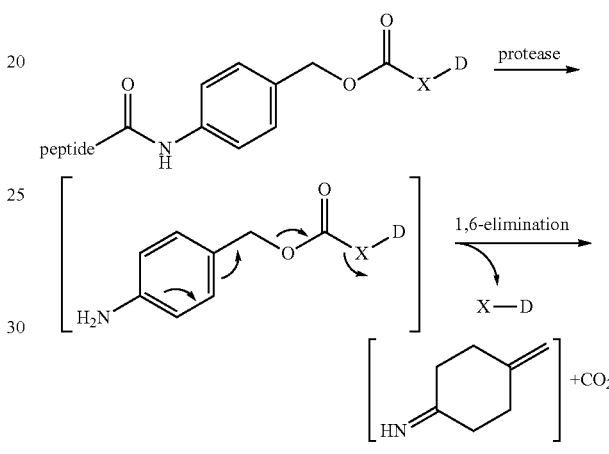

where X-D represents the unmodified drug.

Heterocyclic variants of this self-immolative group have also been described. See for example, U.S. Pat. No. 7,989,434.

In some embodiments, the enzymatically cleavable ADC linker is a β-glucuronic acid-based ADC linker. Facile release of the drug can be realized through cleavage of the β-glucuronide glycosidic bond by the lysosomal enzyme β-glucuronidase. This enzyme is present abundantly within lysosomes and is overexpressed in some tumor types, while the enzyme activity outside cells is low. β-Glucuronic acid-based ADC linkers can be used to circumvent the tendency of an ADC to undergo aggregation due to the hydrophilic nature of β-glucuron ides. In some embodiments, β-glucuronic acid-based ADC linkers can be used as ADC linkers for ADCs linked to hydrophobic drugs. The following scheme depicts the release of the drug from and ADC containing a β-glucuronic acid-based ADC linker:

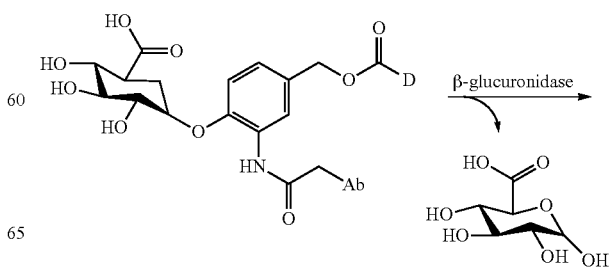

207

-continued

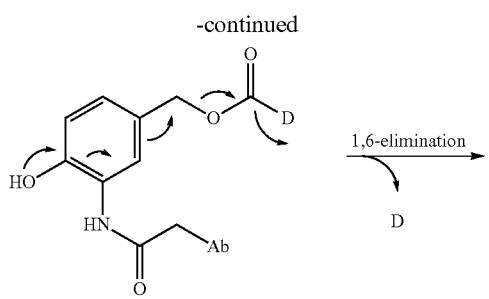

1,6-elimination →

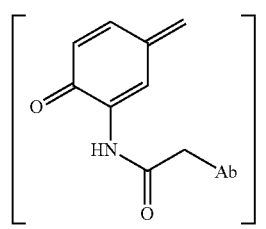

+CO₂

A variety of cleavable β-glucuronic acid-based ADC linkers useful for linking drugs such as auristatins, camptothecin and doxorubicin analogues, CBI minor-groove binders, and psymberin to BCMA binding molecules have been described (see, Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013; Jeffrey et al., 2006, Bioconjug. Chem. 17:831-840; Jeffrey et al., 2007, Bioorg. Med. Chem. Lett. 17:2278-2280; and Jiang et al., 2005, J. Am. Chem. Soc. 127:11254-11255). All of these β-glucuronic acid-based ADC linkers can be used in the ADCs of the disclosure.

Additionally, cytotoxic and/or cytostatic agents containing a phenol group can be covalently bonded to an ADC linker through the phenolic oxygen. One such ADC linker, described in WO 2007/089149, relies on a methodology in which a diamino-ethane "SpaceLink" is used in conjunction with traditional "PABO"-based self-immolative groups to deliver phenols. The cleavage of the ADC linker is depicted schematically below, where D represents a cytotoxic and/or cytostatic agent having a phenolic hydroxyl group.

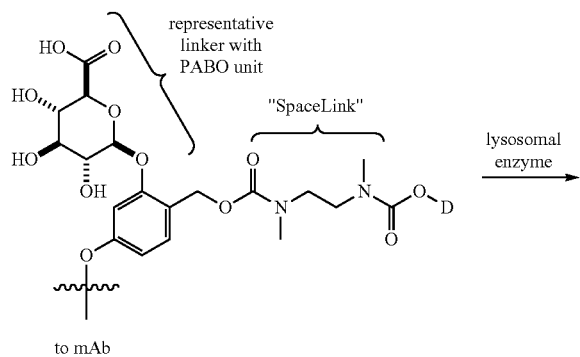

208

-continued

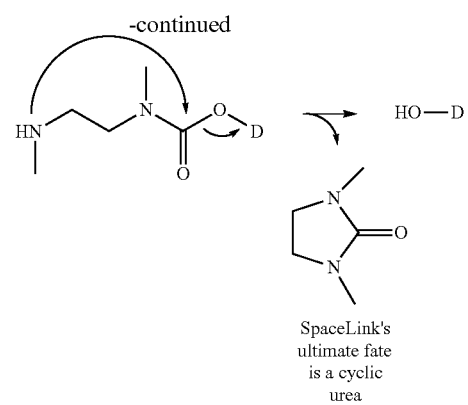

SpaceLink's ultimate fate is a cyclic urea

Cleavable ADC linkers can include noncleavable portions or segments, and/or cleavable segments or portions can be included in an otherwise non-cleavable ADC linker to render it cleavable. By way of example only, polyethylene glycol (PEG) and related polymers can include cleavable groups in the polymer backbone. For example, a polyethylene glycol or polymer ADC linker can include one or more cleavable groups such as a disulfide, a hydrazone or a dipeptide.

Other degradable linkages that can be included in ADC linkers include ester linkages formed by the reaction of PEG carboxylic acids or activated PEG carboxylic acids with alcohol groups on a biologically active agent, where such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

In certain embodiments, the ADC linker comprises an enzymatically cleavable peptide moiety, for example, an ADC linker comprising structural formula (IVa) or (IVb):

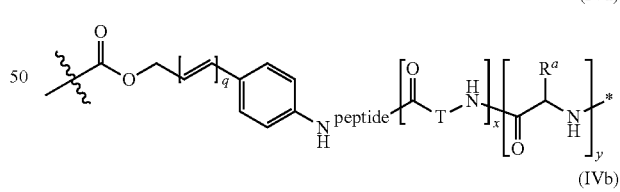
(IVa)

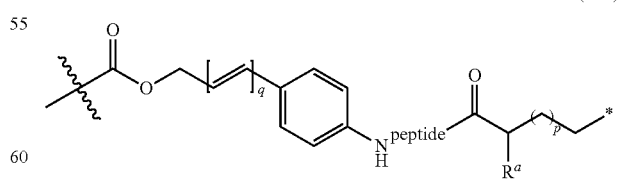
(IVb)

or a salt thereof, where: peptide represents a peptide (illustrated C→N and not showing the carboxy and amino "termini") cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; p is an integer ranging from 0 to 5; q is 0 or 1; x is 0 or 1; y is 0 or 1; ⌇ represents the point of attachment of the ADC linker to a cytotoxic and/or cytostatic agent; and * represents the point of attachment to the remainder of the ADC linker.

In certain embodiments, the peptide is selected from a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit. In certain embodiments, the dipeptide is selected from: Cit-Val; and Ala-Val.

Specific exemplary embodiments of ADC linkers according to structural formula (IVa) that can be included in the ADCs include the ADC linkers illustrated below (as illustrated, the ADC linkers include a group suitable for covalently linking the ADC linker to a BCMA binding molecule):

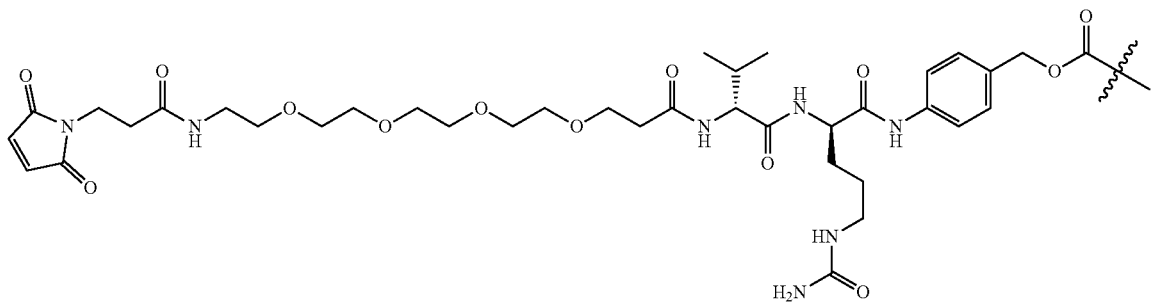
(IVa.1)

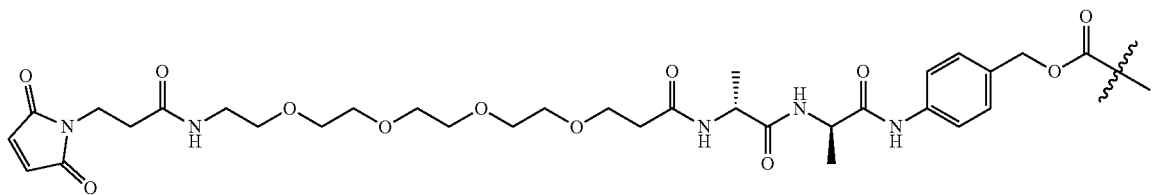
(IVa.2)

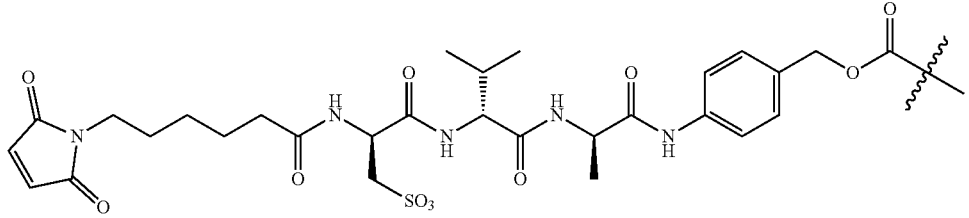
(IVa.3)

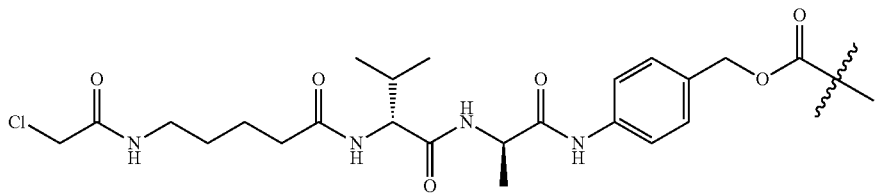
(IVa.4)

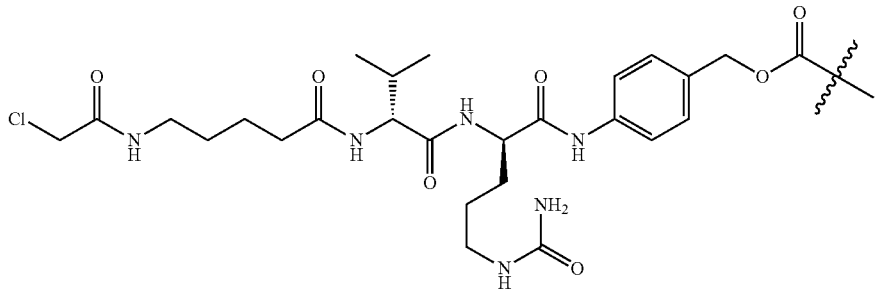
(IVa.5)

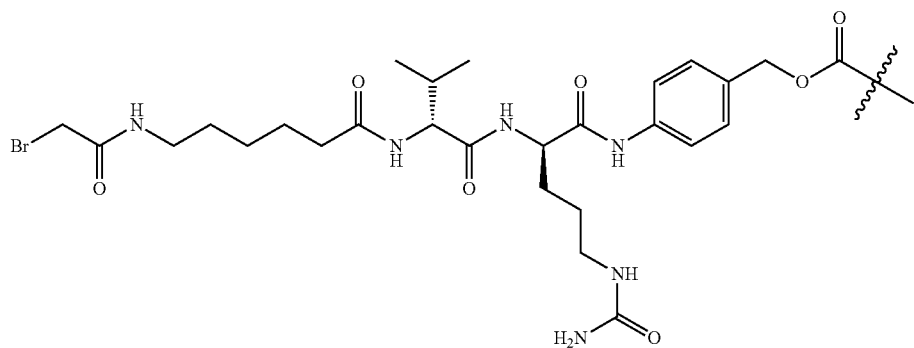
(IVa.6)
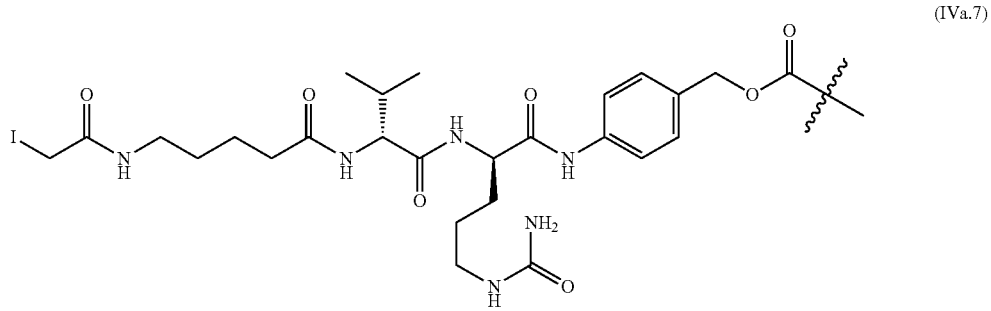
(IVa.7)
Specific exemplary embodiments of ADC linkers according to structural formula (IVb) that can be included in the ADCs include the ADC linkers illustrated below (as illustrated, the ADC linkers include a group suitable for covalently linking the ADC linker to a BCMA binding molecule):
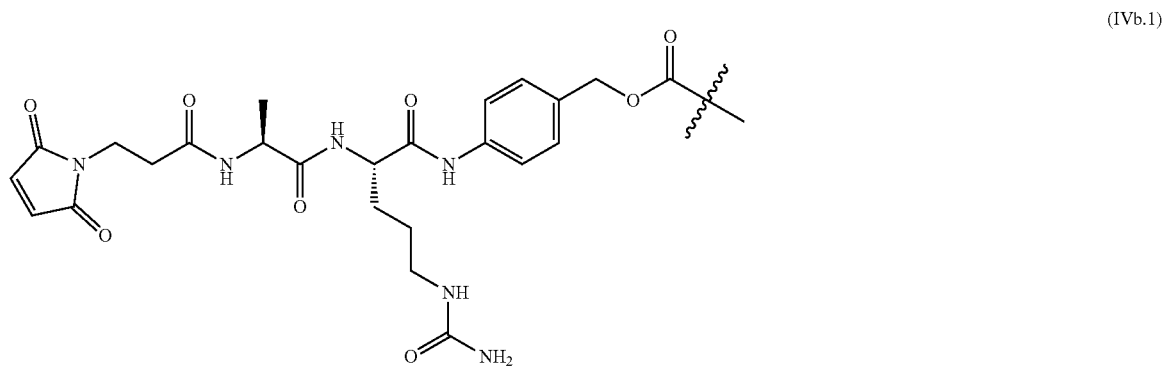
(IVb.1)
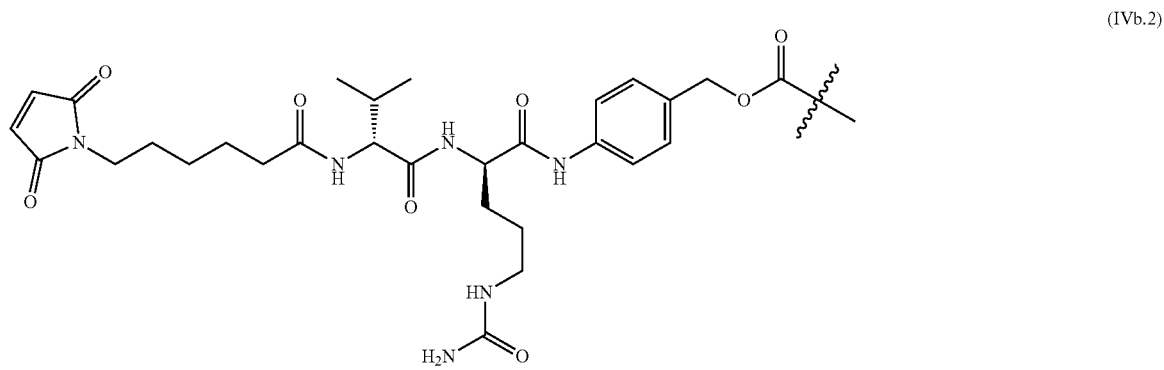
(IVb.2)

(IVb.3)
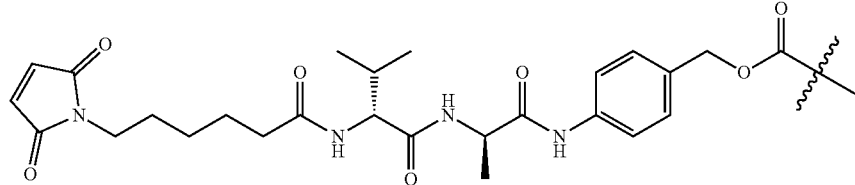
(IVb.4)
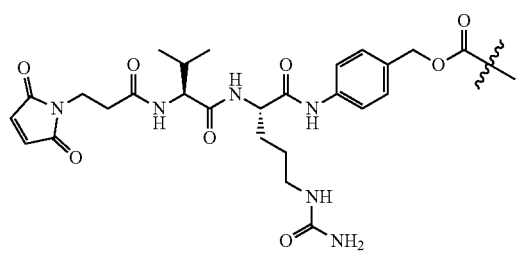
(IVb.5)
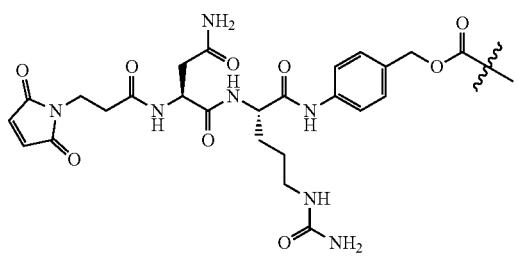
(IVb.6)
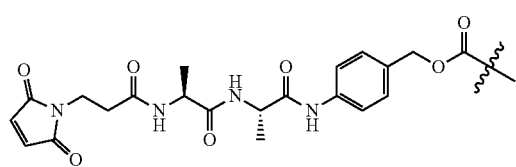
(IVb.7)
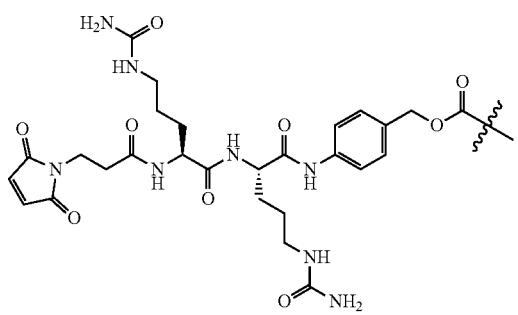
(IVb.8)
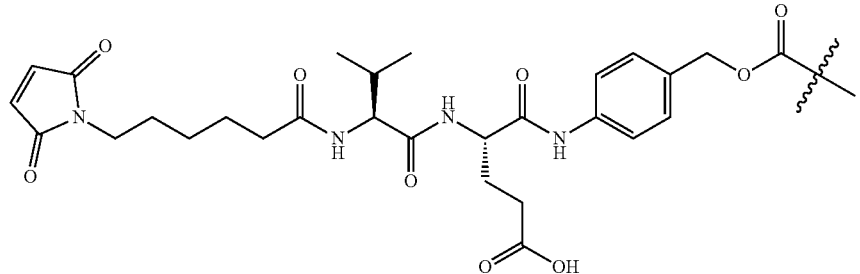
(IVb.9)
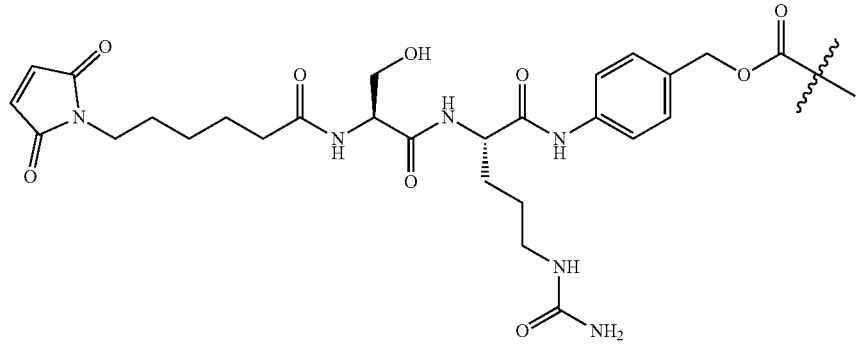

-continued
(IVb.10)
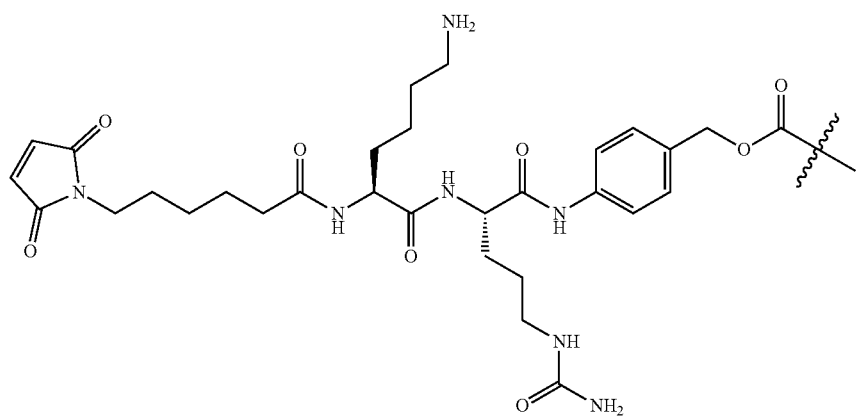
(IVb.11) (IVb.12)
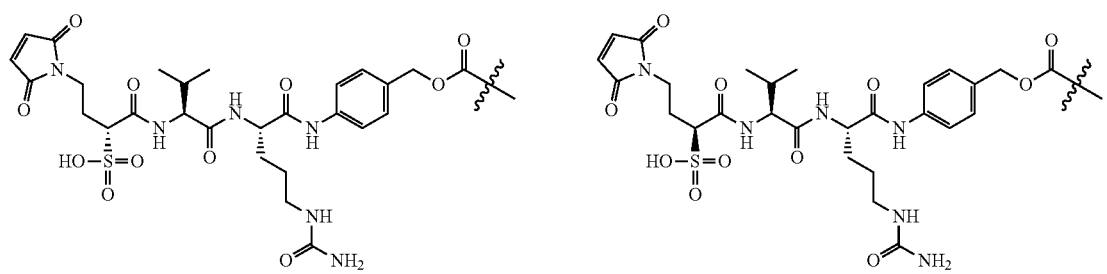
(IVb.13)
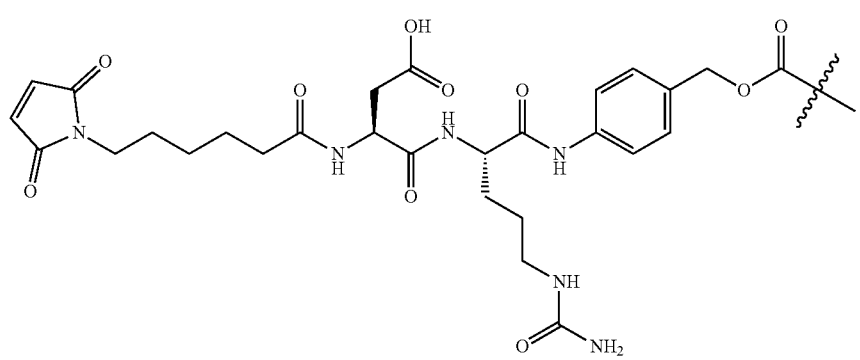
(IVb.14)
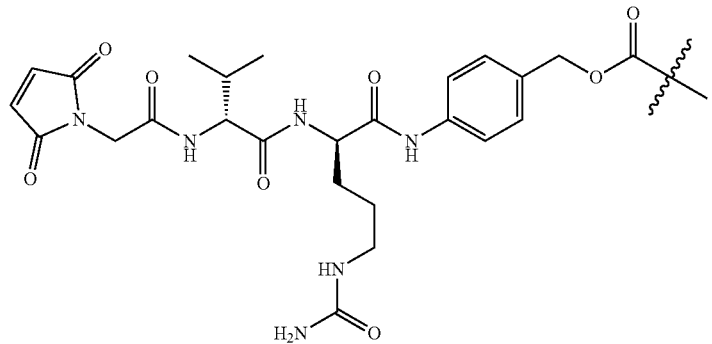

-continued
(IVb.15)
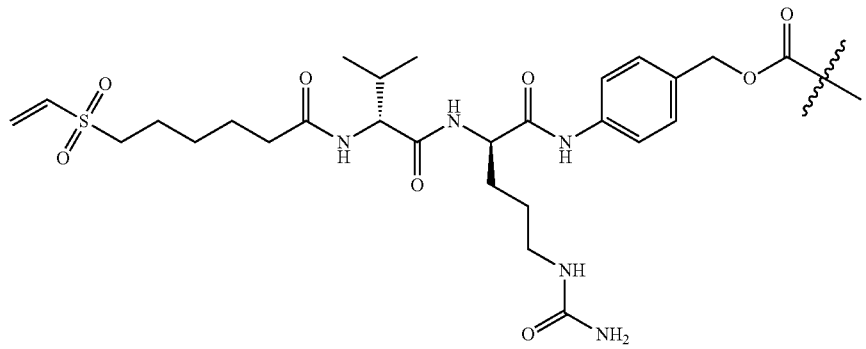
(IVb.16)
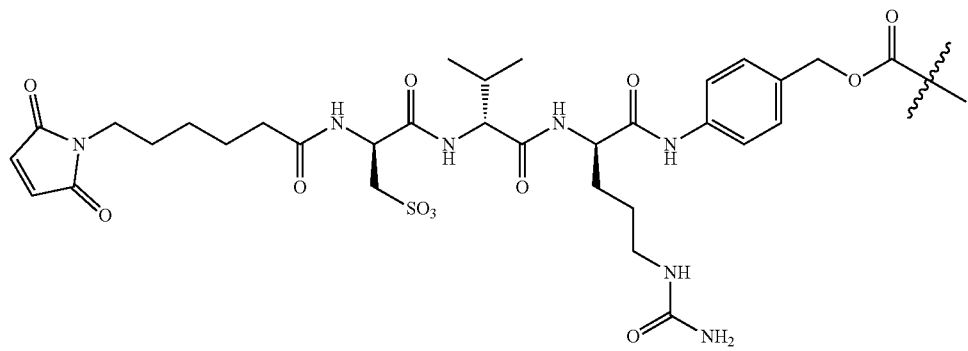
(IVb.17)
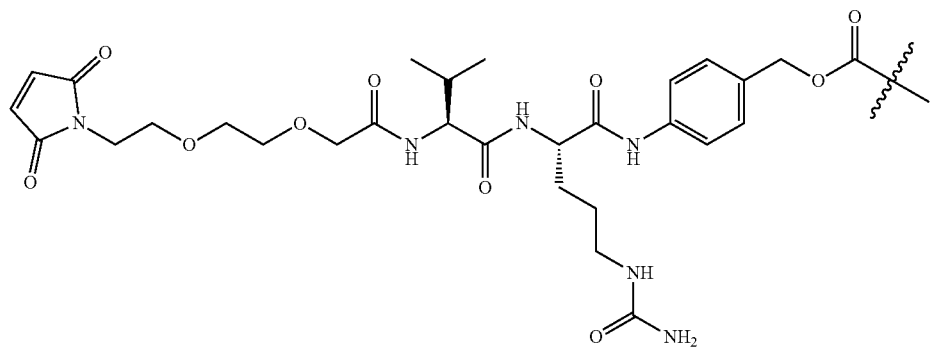
(IVb.18)
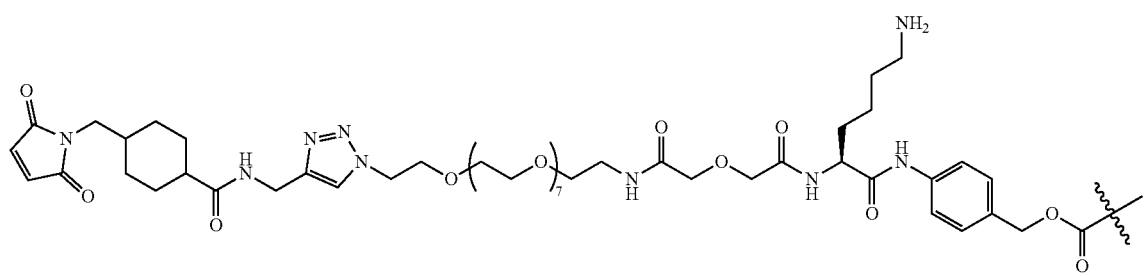
(IVb.19)
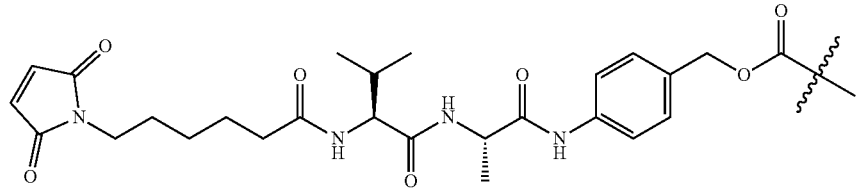

In certain embodiments, the ADC linker comprises an enzymatically cleavable peptide moiety, for example, an ADC linker comprising structural formula (IVc) or (IVd):

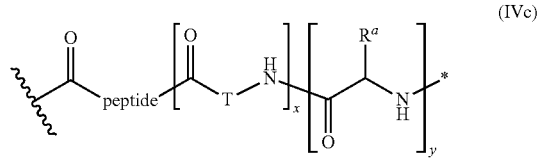
(IVc)

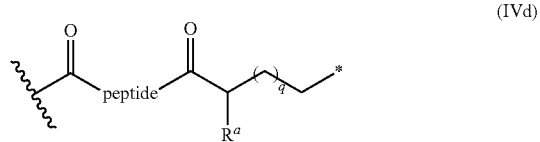
(IVd)

or a salt thereof, where: peptide represents a peptide (illustrated C→N and not showing the carboxy and amino "termini") cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; p is an integer ranging from 0 to 5; q is 0 or 1; x is 0 or 1; y is 0 or 1; ·x ∫ represents the point of attachment of the ADC linker to a cytotoxic and/or cytostatic agent; and * represents the point of attachment to the remainder of the ADC linker.

Specific exemplary embodiments of ADC linkers according to structural formula (IVc) that can be included in the ADCs include the ADC linkers illustrated below (as illustrated, the ADC linkers include a group suitable for covalently linking the ADC linker to a BCMA binding molecule):

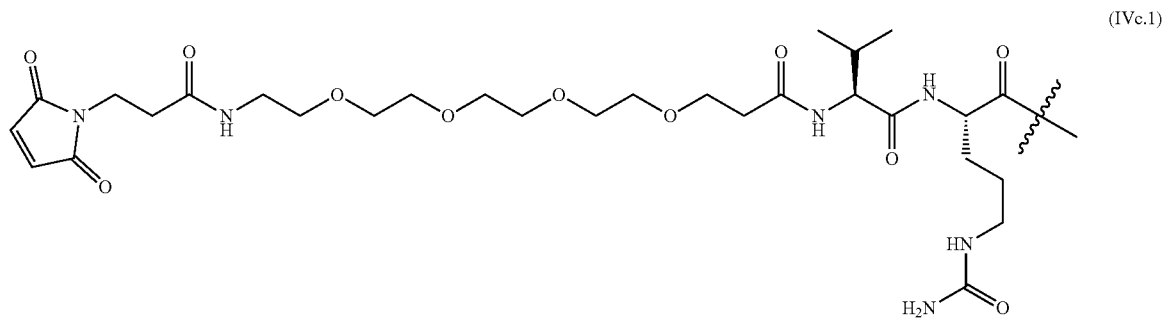
(IVc.1)

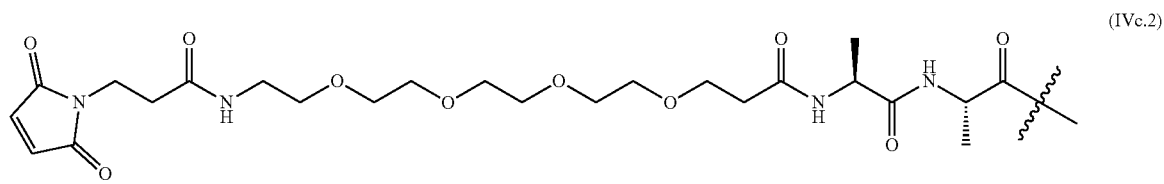
(IVc.2)

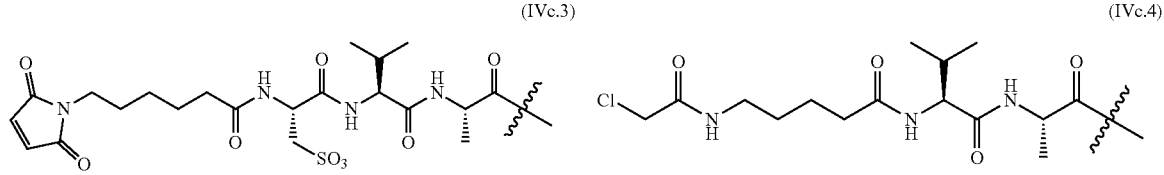
(IVc.3)  (IVc.4)

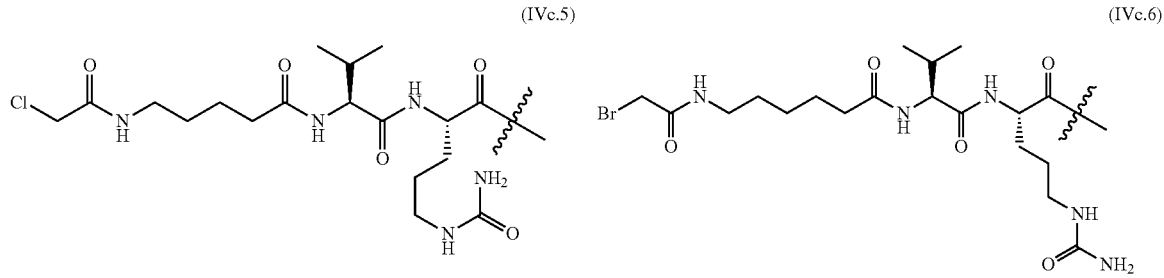
(IVc.5)  (IVc.6)

(IVc.7)
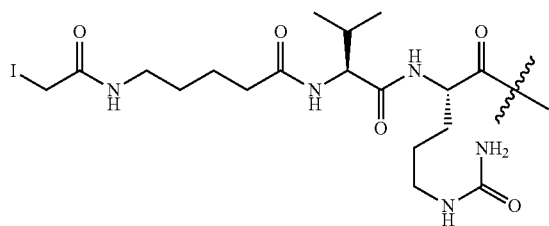
Specific exemplary embodiments of ADC linkers according to structural formula (IVd) that can be included in the ADCs include the ADC linkers illustrated below (as illustrated, the ADC linkers include a group suitable for covalently linking the ADC linker to a BCMA binding molecule):
-continued
(IVd.1)
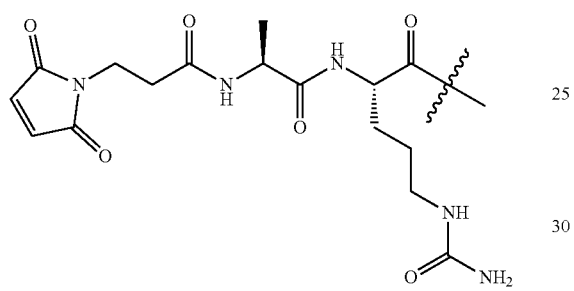
(IVd.2)
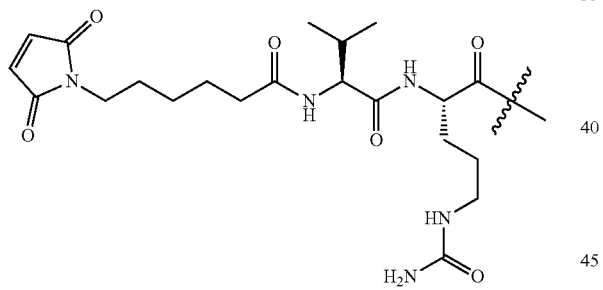
(IVd.3)
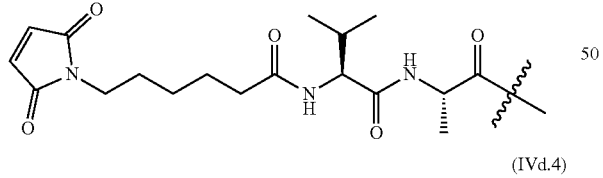
(IVd.4)
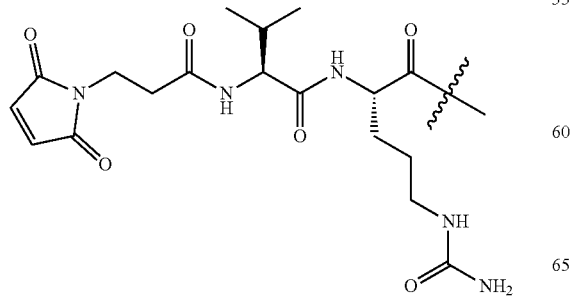
(IVd.5)
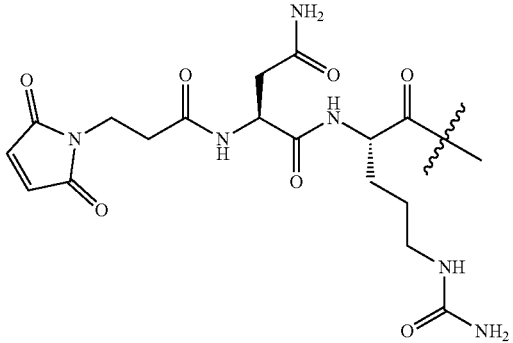
(IVd.6)
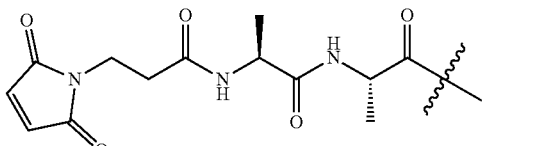
(IVd.7)
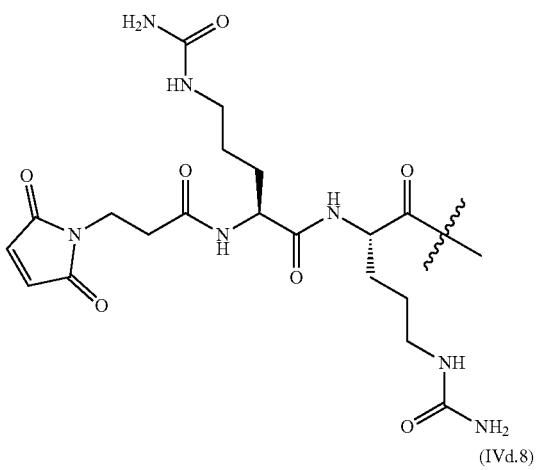
(IVd.8)
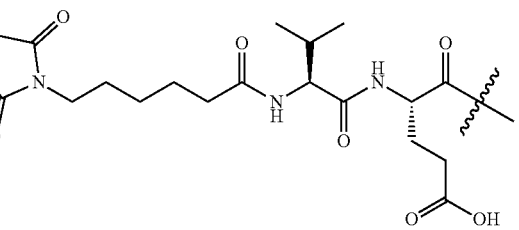

(IVd.9)
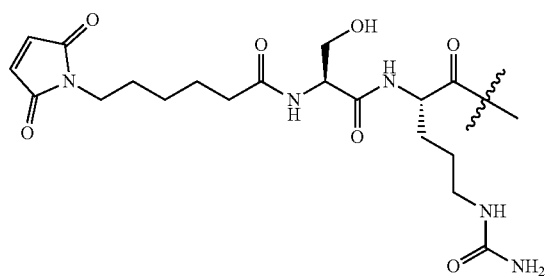
(IVd.10)
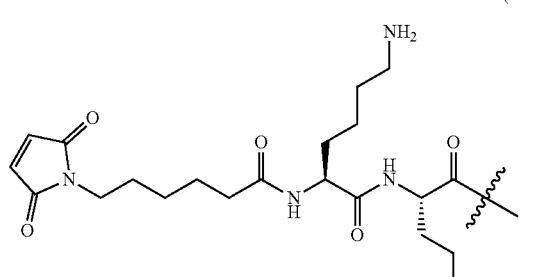
(IVd.11)
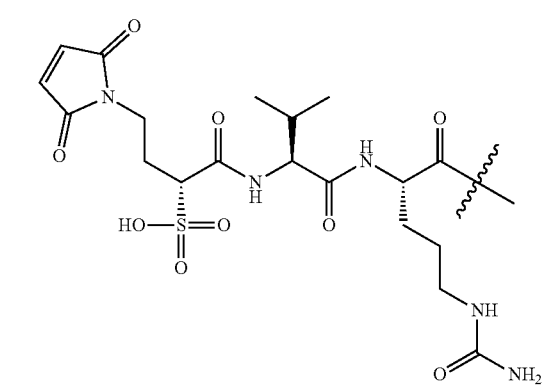
(IVd.12)
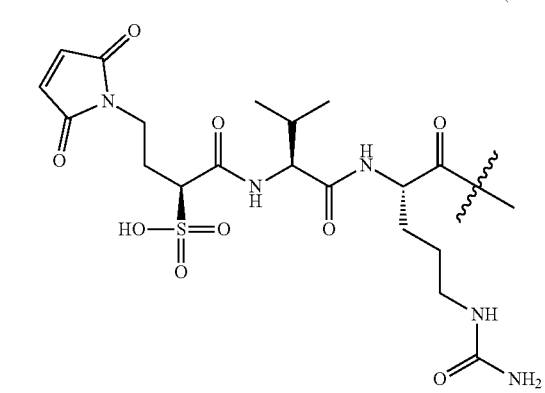
(IVd.13)
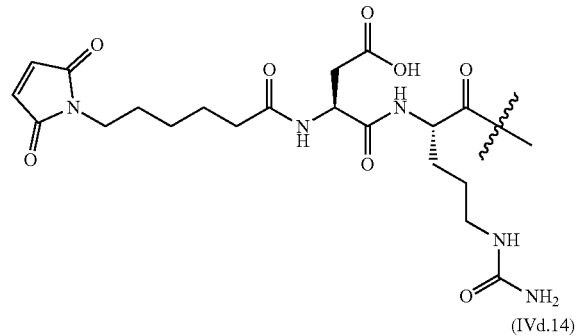
(IVd.14)
(IVd.15)
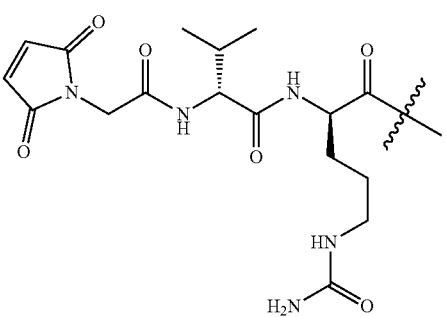
(IVd.16)
(IVd.17)
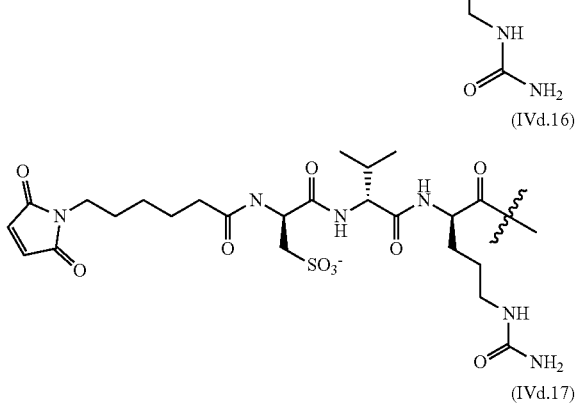
In certain embodiments, the ADC linker comprising structural formula (IVa), (IVb), (IVc), or (IVd) further comprises a carbonate moiety cleavable by exposure to an acidic medium. In particular embodiments, the ADC linker is attached through an oxygen to a cytotoxic and/or cytostatic agent.

7.9.2.2. Non-Cleavable Linkers

Although cleavable ADC linkers can provide certain advantages, the ADC linkers comprising the ADCs need not be cleavable. For noncleavable ADC linkers, the release of drug does not depend on the differential properties between the plasma and some cytoplasmic compartments. The release of the drug is postulated to occur after internalization of the ADC via antigen-mediated endocytosis and delivery to lysosomal compartment, where the BCMA binding molecule is degraded to the level of amino acids through intracellular proteolytic degradation. This process releases a drug derivative, which is formed by the drug, the ADC linker, and the amino acid residue to which the ADC linker was covalently attached. The amino acid drug metabolites from conjugates with noncleavable ADC linkers are more hydrophilic and generally less membrane permeable, which leads to less bystander effects and less nonspecific toxicities compared to conjugates with a cleavable ADC linker. In general, ADCs with noncleavable ADC linkers have greater stability in circulation than ADCs with cleavable ADC linkers. Non-cleavable ADC linkers can be alkylene chains, or can be polymeric in nature, such as, for example, based upon polyalkylene glycol polymers, amide polymers, or can include segments of alkylene chains, polyalkylene glycols and/or amide polymers.

A variety of non-cleavable ADC linkers used to link drugs to BCMA binding molecules have been described. See, Jeffrey et al., 2006, Bioconjug. Chem. 17; 831-840; Jeffrey et al., 2007, Bioorg. Med. Chem. Lett. 17:2278-2280; and Jiang et al., 2005, J. Am. Chem. Soc. 127:11254-11255. All of these ADC linkers can be included in the ADCs of the disclosure.

In certain embodiments, the ADC linker is non-cleavable in vivo, for example an ADC linker according to structural formula (VIa), (VIb), (VIc) or (VId) (as illustrated, the ADC linkers include a group suitable for covalently linking the ADC linker to a BCMA binding molecule:

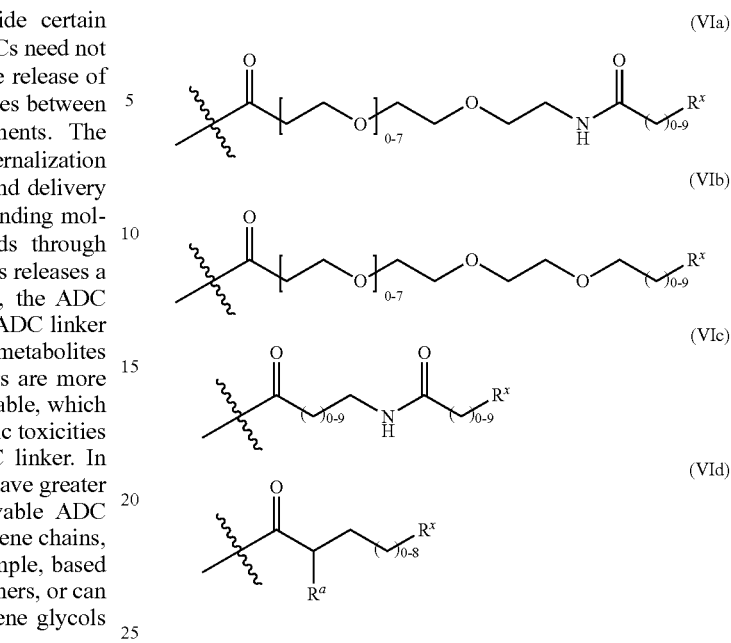

or salts thereof, where: $R^a$ is selected from hydrogen, alkyl, sulfonate and methyl sulfonate; $R^x$ is a moiety including a functional group capable of covalently linking the ADC linker to a BCMA binding molecule; and ⌇ represents the point of attachment of the ADC linker to a cytotoxic and/or cytostatic agent.

Specific exemplary embodiments of ADC linkers according to structural formula (VIa)-(VId) that can be included in the ADCs include the ADC linkers illustrated below (as illustrated, the ADC linkers include a group suitable for covalently linking the ADC linker to a BCMA binding molecule, and ⌇ represents the point of attachment to a cytotoxic and/or cytostatic agent):

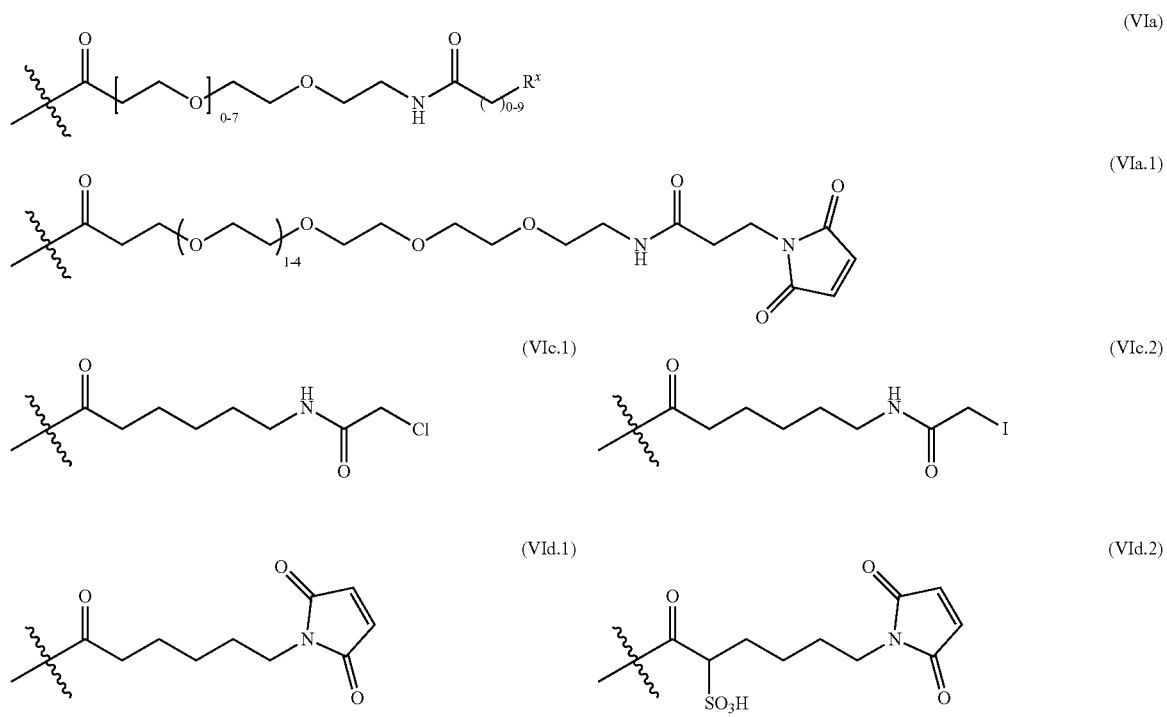

(VId.3)

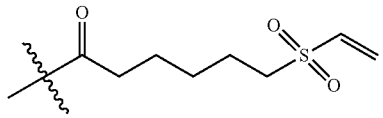

7.9.2.3. Groups Used to Attach Linkers to BCMA Binding Molecules

A variety of groups can be used to attach ADC linker-drug synthons to BCMA binding molecules to yield ADCs. Attachment groups can be electrophilic in nature and include: maleimide groups, activated disulfides, active esters such as NHS esters and HOBt esters, haloformates, acid halides, alkyl and benzyl halides such as haloacetamides. As discussed below, there are also emerging technologies related to "self-stabilizing" maleimides and "bridging disulfides" that can be used in accordance with the disclosure. The specific group used will depend, in part, on the site of attachment to the BCMA binding molecule.

One example of a "self-stabilizing" maleimide group that hydrolyzes spontaneously under BCMA binding molecule conjugation conditions to give an ADC species with improved stability is depicted in the schematic below. See US20130309256 A1; also Lyon et al., Nature Biotech published online, doi:10.1038/nbt.2968.

Normal System:

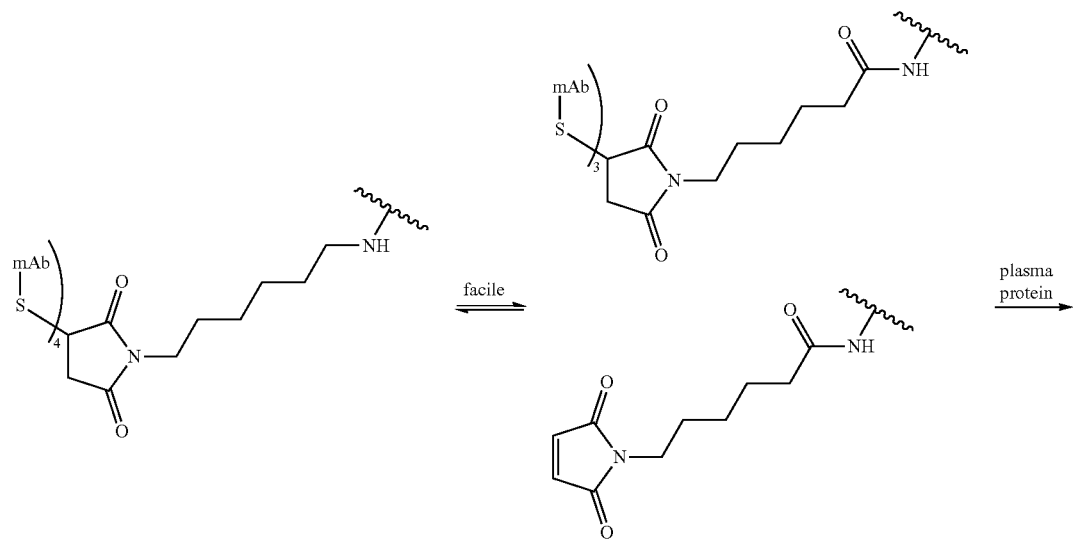

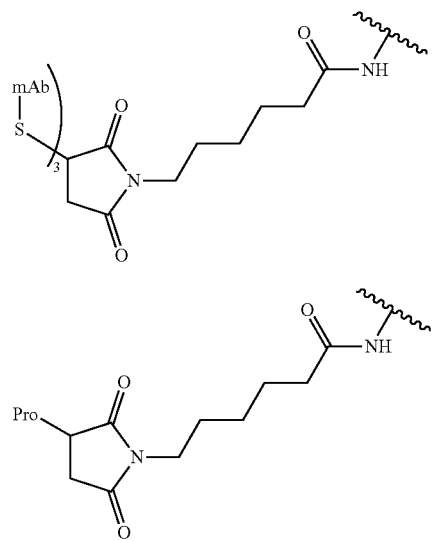

Leads to "DAR loss" over time
SGN MalDPR (Maleimido Dipropylamino) System:

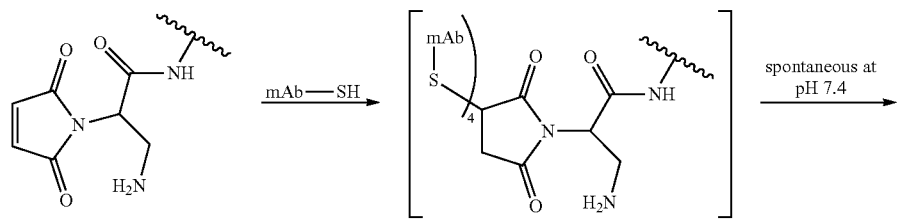

US20130309256A1

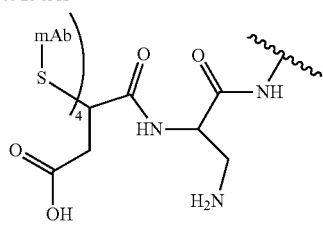

stable in plasma
(retro hetero-Michael
reaction shown above slow)

Polytherics has disclosed a method for bridging a pair of sulfhydryl groups derived from reduction of a native hinge disulfide bond. See, Badescu et al., 2014, Bioconjugate Chem. 25:1124-1136. The reaction is depicted in the schematic below. An advantage of this methodology is the ability to synthesize enriched DAR4 ADCs by full reduction of IgGs (to give 4 pairs of sulfhydryls) followed by reaction with 4 equivalents of the alkylating agent. ADCs containing "bridged disulfides" have increased stability.

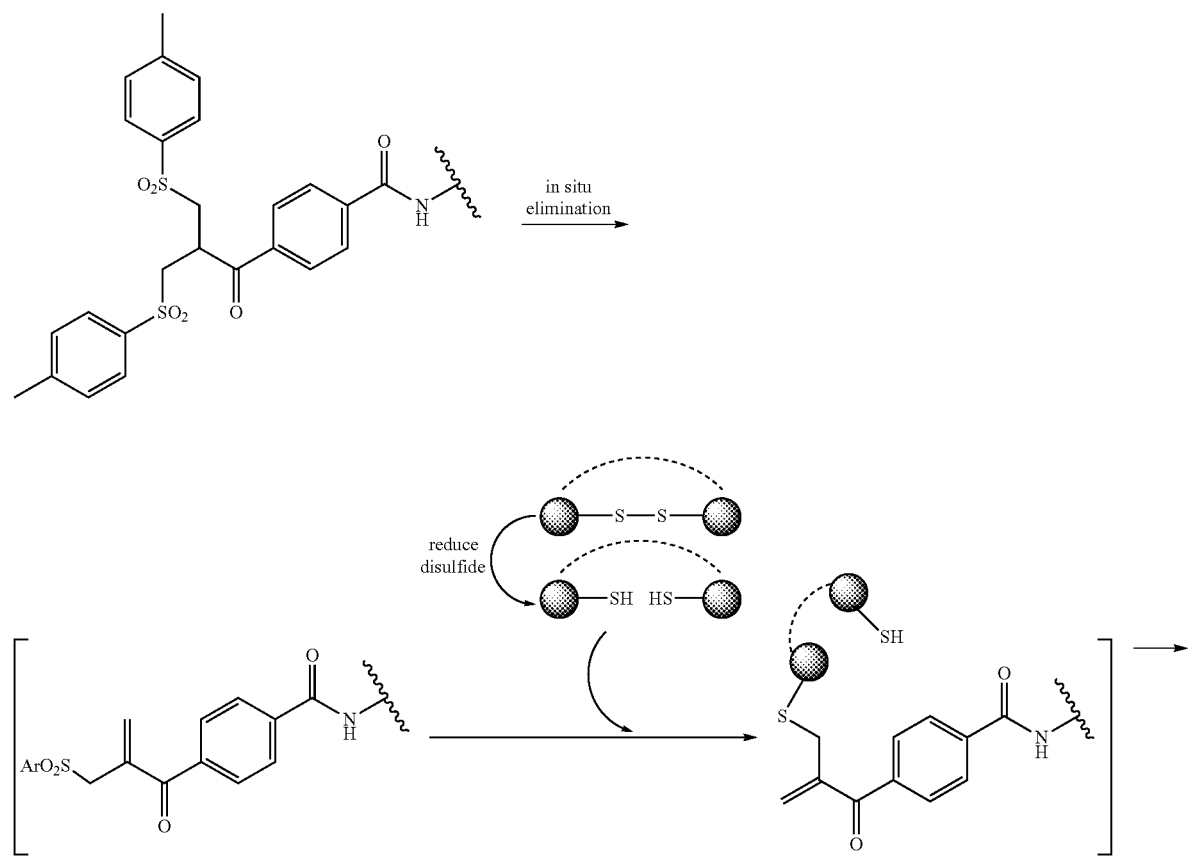

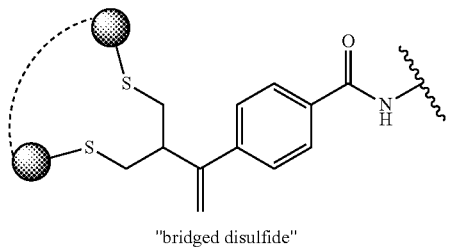

"bridged disulfide"

Similarly, as depicted below, a maleimide derivative (1, below) that is capable of bridging a pair of sulfhydryl groups has been developed. See WO2013/085925.

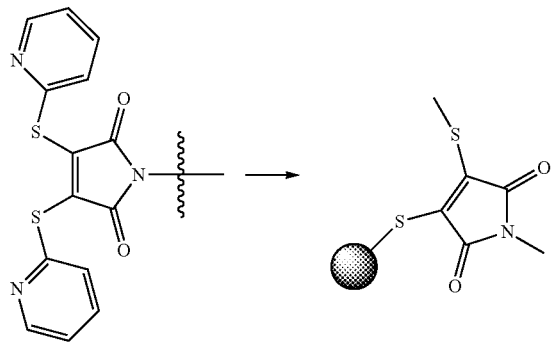

7.9.2.4. ADC Linker Selection Considerations

As is known by skilled artisans, the ADC linker selected for a particular ADC can be influenced by a variety of factors, including but not limited to, the site of attachment to the BCMA binding molecule (e.g., lys, cys or other amino acid residues), structural constraints of the drug pharmacophore and the lipophilicity of the drug. The specific ADC linker selected for an ADC should seek to balance these different factors for the specific BCMA binding molecule/drug combination. For a review of the factors that are influenced by choice of ADC linkers in ADCs, see Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013.

For example, ADCs have been observed to effect killing of bystander antigen-negative cells present in the vicinity of the antigen-positive tumor cells. The mechanism of bystander cell killing by ADCs has indicated that metabolic products formed during intracellular processing of the ADCs can play a role. Neutral cytotoxic metabolites generated by metabolism of the ADCs in antigen-positive cells appear to play a role in bystander cell killing while charged metabolites can be prevented from diffusing across the membrane into the medium and therefore cannot affect bystander killing. In certain embodiments, the ADC linker is selected to attenuate the bystander killing effect caused by cellular metabolites of the ADC. In certain embodiments, the ADC linker is selected to increase the bystander killing effect.

The properties of the ADC linker can also impact aggregation of the ADC under conditions of use and/or storage. Typically, ADCs reported in the literature contain no more than 3-4 drug molecules per antibody molecule (see, e.g., Chari, 2008, Acc Chem Res 41:98-107). Attempts to obtain higher drug-to-antibody ratios ("DAR") often failed, particularly if both the drug and the ADC linker were hydrophobic, due to aggregation of the ADC (King et al., 2002, J Med Chem 45:4336-4343; Hollander et al., 2008, Bioconjugate Chem 19:358-361; Burke et al., 2009 Bioconjugate Chem 20:1242-1250). In many instances, DARs higher than 3-4 could be beneficial as a means of increasing potency. In instances where the cytotoxic and/or cytostatic agent is hydrophobic in nature, it can be desirable to select ADC linkers that are relatively hydrophilic as a means of reducing ADC aggregation, especially in instances where DARS greater than 3-4 are desired. Thus, in certain embodiments, the ADC linker incorporates chemical moieties that reduce aggregation of the ADCs during storage and/or use. An ADC linker can incorporate polar or hydrophilic groups such as charged groups or groups that become charged under physiological pH to reduce the aggregation of the ADCs. For example, an ADC linker can incorporate charged groups such as salts or groups that deprotonate, e.g., carboxylates, or protonate, e.g., amines, at physiological pH.

Exemplary polyvalent ADC linkers that have been reported to yield DARs as high as 20 that can be used to link numerous cytotoxic and/or cytostatic agents to a BCMA binding molecule are described in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640.

In particular embodiments, the aggregation of the ADCs during storage or use is less than about 10% as determined by size-exclusion chromatography (SEC). In particular embodiments, the aggregation of the ADCs during storage or use is less than 10%, such as less than about 5%, less than about 4%, less than about 3%, less than about 2%, less than about 1%, less than about 0.5%, less than about 0.1%, or even lower, as determined by size-exclusion chromatography (SEC).

7.9.3. Methods of Making ADCs

The ADCs can be synthesized using chemistries that are well-known. The chemistries selected will depend upon, among other things, the identity of the cytotoxic and/or cytostatic agent(s), the ADC linker and the groups used to attach ADC linker to the BCMA binding molecule. Generally, ADCs according to formula (I) can be prepared according to the following scheme:

$$D\text{-}L\text{-}R^x + Ab\text{-}R^y \rightarrow [D\text{-}L\text{-}XY]_n\text{-}Ab \qquad (I)$$

where D, L, Ab, XY and n are as previously defined, and $R^x$ and $R^y$ represent complementary groups capable of forming a covalent linkages with one another, as discussed above.

The identities of groups $R^x$ and $R^y$ will depend upon the chemistry used to link synthon D-L-$R^x$ to the BCMA binding molecule. Generally, the chemistry used should not alter the integrity of the BCMA binding molecule, for example its ability to bind its target. In some cases, the binding properties of the conjugated antibody will closely resemble those of the unconjugated BCMA binding molecule. A variety of chemistries and techniques for conjugating molecules to biological molecules and in particular to immunoglobulins, whose components are typically building blocks of the BCMA binding molecules of the disclosure, are well-known. See, e.g., Amon et al., "Monoclonal Antibodies For Immunotargeting Of Drugs In Cancer Therapy," in: Monoclonal Antibodies And Cancer Therapy, Reisfeld et al. Eds., Alan R. Liss, Inc., 1985; Hellstrom et al., "Antibodies For Drug Delivery," in: Controlled Drug Delivery, Robinson et al. Eds., Marcel Dekker, Inc., 2nd Ed. 1987; Thorpe, "Antibody Carriers Of Cytotoxic Agents In Cancer Therapy: A Review," in: Monoclonal Antibodies '84: Biological And Clinical Applications, Pinchera et al., Eds., 1985; "Analysis, Results, and Future Prospective of the Therapeutic Use of Radiolabeled Antibody In Cancer Therapy," in: Monoclonal Antibodies For Cancer Detection And Therapy, Baldwin et al., Eds., Academic Press, 1985; Thorpe et al., 1982, Immunol. Rev. 62:119-58; PCT publication WO 89/12624. Any of these chemistries can be used to link the synthons to a BCMA binding molecule.

A number of functional groups $R^x$ and chemistries useful for linking synthons to accessible lysine residues are known, and include by way of example and not limitation NHS-esters and isothiocyanates.

A number of functional groups $R^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines can be converted to other useful groups, such as hydroxyls, by linking an appropriate small molecule to the amine. This strategy can be used to increase the number of available linking sites on the antibody by conjugating multifunctional small molecules to side chains of accessible amino acid residues of the BCMA binding molecule. Functional groups $R^x$ suitable for covalently linking the synthons to these "converted" functional groups are then included in the synthons.

The BCMA binding molecule can also be engineered to include amino acid residues for conjugation. An approach for engineering BBMs to include non-genetically encoded amino acid residues useful for conjugating drugs in the context of ADCs is described by Axup et al., 2012, Proc Natl Acad Sci USA. 109(40):16101-16106, as are chemistries and functional group useful for linking synthons to the non-encoded amino acids.

Typically, the synthons are linked to the side chains of amino acid residues of the BCMA binding molecule, including, for example, the primary amino group of accessible lysine residues or the sulfhydryl group of accessible cysteine residues. Free sulfhydryl groups can be obtained by reducing interchain disulfide bonds.

For linkages where $R^y$ is a sulfhydryl group (for example, when $R^x$ is a maleimide), the BCMA binding molecule is generally first fully or partially reduced to disrupt interchain disulfide bridges between cysteine residues.

Cysteine residues that do not participate in disulfide bridges can engineered into a BCMA binding molecule by modification of one or more codons. Reducing these unpaired cysteines yields a sulfhydryl group suitable for conjugation. In some embodiments, BCMA binding molecule are engineered to introduce one or more cysteine residues as sites for conjugation to a drug moiety (see, Junutula, et al, 2008, Nat Biotechnol, 26:925-932).

Sites for cysteine substitution can be selected in a constant region to provide stable and homogeneous conjugates. A BCMA binding molecule can have, for example, two or more cysteine substitutions, and these substitutions can be used in combination with other modification and conjugation methods as described herein. Methods for inserting cysteine at specific locations of an antibody are known, see, e.g., Lyons et al., 1990, Protein Eng., 3:703-708, WO 2011/005481, WO2014/124316, WO 2015/138615. In certain embodiments, a BCMA binding molecule comprises a substitution of one or more amino acids with cysteine on a constant region selected from positions 117, 119, 121, 124, 139, 152, 153, 155, 157, 164, 169, 171, 174, 189, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain, where the positions are numbered according to the EU system. In some embodiments, a BCMA binding molecule comprises a substitution of one or more amino acids with cysteine on a constant region selected from positions 107, 108, 109, 114, 129, 142, 143, 145, 152, 154, 156, 159, 161, 165, 168, 169, 170, 182, 183, 197, 199, and 203 of a light chain, where the positions are numbered according to the EU system, and where the light chain is a human kappa light chain. In certain embodiments a BCMA binding molecule comprises a combination of substitution of two or more amino acids with cysteine on a constant region, where the combinations comprise substitutions at positions 375 of a heavy chain, position 152 of a heavy chain, position 360 of a heavy chain, or position 107 of a light chain and where the positions are numbered according to the EU system. In certain embodiments a BCMA binding molecule comprises a substitution of one amino acid with cysteine on a constant region where the substitution is position 375 of a heavy chain, position 152 of a heavy chain, position 360 of a heavy chain, position 107 of a light chain, position 165 of a light chain or position 159 of a light chain and where the positions are numbered according to the EU system, and where the light chain is a kappa chain.

In particular embodiments, a BCMA binding molecule comprises a combination of substitution of two amino acids with cysteine on a constant regions, where the BCMA binding molecule comprises cysteines at positions 152 and 375 of a heavy chain, where the positions are numbered according to the EU system.

In other particular embodiments, a BCMA binding molecule comprises a substitution of one amino acid with cysteine at position 360 of a heavy chain, where the positions are numbered according to the EU system.

In other particular embodiments, a BCMA binding molecule comprises a substitution of one amino acid with cysteine at position 107 of a light chain, where the positions are numbered according to the EU system, and where the light chain is a kappa chain.

Other positions for incorporating engineered cysteines can include, by way of example and not limitation, positions S112C, S113C, A114C, S115C, A176C, S180C, S252C, V286C, V292C, S357C, A359C, S398C, S428C (Kabat numbering) on the human IgG₁ heavy chain and positions V110C, S114C, S121C, S127C, S168C, V205C (Kabat numbering) on the human Ig kappa light chain (see, e.g., U.S. Pat. Nos. 7,521,541, 7,855,275 and 8,455,622).

BCMA binding molecules useful in ADCs disclosed herein can additionally or alternatively be modified to introduce one or more other reactive amino acids (other than cysteine), including Pcl, pyrrolysine, peptide tags (such as S6, A1 and ybbR tags), and non-natural amino acids, in place of at least one amino acid of the native sequence, thus providing a reactive site on the BCMA binding molecule for conjugation to a drug moiety. For example, BCMA binding molecules can be modified to incorporate Pcl or pyrrolysine (W. Ou et al., 2011, PNAS, 108(26):10437-10442; WO2014124258) or unnatural amino acids (Axup, et al., 2012, PNAS, 109:16101-16106; for review, see C. C. Liu and P. G. Schultz, 2010, Annu Rev Biochem 79:413-444; Kim, et al., 2013, Curr Opin Chem Biol. 17:412-419) as sites for conjugation to a drug. Similarly, peptide tags for enzymatic conjugation methods can be introduced into a BCMA binding molecule (see, Strop et al. 2013, Chem Biol. 20(2): 161-7; Rabuka, 2010, Curr Opin Chem Biol. 14(6):790-6; Rabuka, et al., 2012, Nat Protoc. 7(6):1052-67). One other example is the use of 4'-phosphopantetheinyl transferases (PPTase) for the conjugation of Coenzyme A analogs (WO2013184514). Such modified or engineered MBMs can be conjugated with payloads or linker-payload combinations according to known methods.

As will appreciated by skilled artisans, the number of agents (e.g., cytotoxic and/or cytostatic agents) linked to a BCMA binding molecule can vary, such that a collection of ADCs can be heterogeneous in nature, where some BCMA binding molecules contain one linked agent, some two, some three, etc. (and some none). The degree of heterogeneity will depend upon, among other things, the chemistries used for linking the cytotoxic and/or cytostatic agents. For example, where the BCMA binding molecules are reduced to yield sulfhydryl groups for attachment, heterogeneous mixtures of BCMA binding molecules having zero, 2, 4, 6 or 8 linked agents per molecule are often produced. Furthermore, by limiting the molar ratio of attachment compound, BCMA binding molecules having zero, 1, 2, 3, 4, 5, 6, 7 or 8 linked agents per molecule are often produced. Thus, it will be understood that depending upon context, stated drug BCMA binding molecule ratios (DTRs) can be averages for a collection of BCMA binding molecules. For example, "DTR4" can refer to an ADC preparation that has not been subjected to purification to isolate specific DTR peaks and can comprise a heterogeneous mixture of ADC molecules having different numbers of cytostatic and/or cytotoxic agents attached per BCMA binding molecule (e.g., 0, 2, 4, 6, 8 agents per BCMA binding molecule), but has an average drug-to-BCMA binding molecule ratio of 4. Similarly, in some embodiments, "DTR2" refers to a heterogeneous ADC preparation in which the average drug-to-BCMA binding molecule ratio is 2.

When enriched preparations are desired, BCMA binding molecules having defined numbers of linked cytotoxic and/or cytostatic agents can be obtained via purification of heterogeneous mixtures, for example, via column chromatography, e.g., hydrophobic interaction chromatography.

Purity can be assessed by a variety of methods. As a specific example, an ADC preparation can be analyzed via HPLC or other chromatography and the purity assessed by analyzing areas under the curves of the resultant peaks.

7.10. BCMA Binding Molecules Conjugated to Detectable Agents

BCMA binding molecules of the disclosure can be conjugated to a diagnostic or detectable agent. Such molecules can be useful for monitoring or prognosing the onset, development, progression and/or severity of a disease or disorder as part of a clinical testing procedure, such as determining the efficacy of a particular therapy. Such diagnosis and detection can accomplished by coupling the BCMA binding molecules to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, 47Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; and positron emitting metals using various positron emission tomographies, and nonradioactive paramagnetic metal ions.

7.11. BCMA Binding Molecules Attached to Solid Supports

The BCMA binding molecules can also be attached to solid supports, which are particularly useful for immunoassays or purification of the target antigen(s). Such solid supports include, but are not limited to, glass, cellulose, polyacrylamide, nylon, polystyrene, polyvinyl chloride or polypropylene.

7.12. Pharmaceutical Compositions

The BCMA binding molecules of the disclosure (as well as their conjugates; references to BCMA binding molecules in this disclosure also refers to conjugates comprising the BCMA binding molecules, such as ADCs, unless the context dictates otherwise) can be formulated as pharmaceutical compositions comprising the BCMA binding molecules, for example containing one or more pharmaceutically acceptable excipients or carriers. To prepare pharmaceutical or sterile compositions comprising the BCMA binding molecules of the present disclosure a BCMA binding molecule preparation can be combined with one or more pharmaceutically acceptable excipient or carrier.

For example, formulations of BCMA binding molecules can be prepared by mixing BCMA binding molecules with physiologically acceptable carriers, excipients, or stabilizers in the form of, e.g., lyophilized powders, slurries, aqueous solutions, lotions, or suspensions (see, e.g., Hardman et al., 2001, Goodman and Gilman's The Pharmacological Basis of Therapeutics, McGraw-Hill, New York, N.Y.; Gennaro, 2000, Remington: The Science and Practice of Pharmacy, Lippincott, Williams, and Wilkins, New York, N.Y.; Avis, et al. (eds.), 1993, Pharmaceutical Dosage Forms: General Medications, Marcel Dekker, NY; Lieberman, et al. (eds.), 1990, Pharmaceutical Dosage Forms: Tablets, Marcel Dekker, NY; Lieberman, et al. (eds.), 1990, Pharmaceutical Dosage Forms: Disperse Systems, Marcel Dekker, NY; Weiner and Kotkoskie, 2000, Excipient Toxicity and Safety, Marcel Dekker, Inc., New York, N.Y.).

Selecting an administration regimen for a BCMA binding molecule depends on several factors, including the serum or tissue turnover rate of the BCMA binding molecule, the level of symptoms, the immunogenicity of the BCMA binding molecule, and the accessibility of the target cells. In certain embodiments, an administration regimen maximizes the amount of BCMA binding molecule delivered to the subject consistent with an acceptable level of side effects. Accordingly, the amount of BCMA binding molecule delivered depends in part on the particular BCMA binding molecule and the severity of the condition being treated. Guidance in selecting appropriate doses of antibodies and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert et al., 2003, New Engl. J. Med. 348:601-608; Milgrom et al., 1999, New Engl. J. Med. 341:1966-1973; Slamon et al., 2001, New Engl. J. Med. 344:783-792; Beniaminovitz et al., 2000, New Engl. J. Med. 342:613-619; Ghosh et al., 2003, New Engl. J. Med. 348:24-32; Lipsky et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the BCMA binding molecules in the pharmaceutical compositions of the present disclosure can be varied so as to obtain an amount of the BCMA binding molecule which is effective to achieve the desired therapeutic response for a particular subject, composition, and mode of administration, without being toxic to the subject. The selected dosage level will depend upon a variety of pharmacokinetic factors including the activity of the particular BCMA binding molecule, the route of administration, the time of administration, the rate of excretion of the particular BCMA binding molecule being employed, the duration of the treatment, other agents (e.g., active agents such as therapeutic drugs or compounds and/or inert materials used as carriers) in combination with the particular BCMA binding molecule employed, the age, sex, weight, condition, general health and prior medical history of the subject being treated, and like factors known in the medical arts.

Compositions comprising the BCMA binding molecules can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

An effective amount for a particular subject can vary depending on factors such as the condition being treated, the overall health of the subject, the method route and dose of administration and the severity of side effects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The route of administration can be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer et al., 1981, J. Biomed. Mater. Res. 15:167-277; Langer, 1982, Chem. Tech. 12:98-105; Epstein et al., 1985, Proc. Natl. Acad. Sci. USA 82:3688-3692; Hwang et al., 1980, Proc. Natl. Acad. Sci. USA 77:4030-4034; U.S. Pat. Nos. 6,350,466 and 6,316,024). Where necessary, the composition can also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903.

A composition of the present disclosure can also be administered via one or more routes of administration using one or more of a variety of known methods. As will be appreciated by a skilled artisan, the route and/or mode of administration will vary depending upon the desired results. Selected routes of administration for BCMA binding molecules include intravenous, intramuscular, intradermal, intraperitoneal, subcutaneous, spinal or other general routes of administration, for example by injection or infusion. General administration can represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-general route, such as a topical, epidermal or mucosal route of administration, for example, intranasally, orally, vaginally, rectally, sublingually or topically. In one embodiment, the BCMA binding molecule is administered by infusion. In another embodiment, the BCMA binding molecule is administered subcutaneously.

If the BCMA binding molecules are administered in a controlled release or sustained release system, a pump can be used to achieve controlled or sustained release (see Langer, supra; Sefton, 1987, CRC Crit. Ref Biomed. Eng. 14:20; Buchwald et al., 1980, Surgery 88:507; Saudek et al., 1989, N. Engl. J. Med. 321:574). Polymeric materials can be used to achieve controlled or sustained release of the therapies of the disclosure (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more BCMA binding molecules of the disclosure. See, e.g., U.S. Pat. No. 4,526,938, PCT publication WO 91/05548, PCT publication WO 96/20698, Ning et al., 1996, Radiotherapy & Oncology 39:179-189, Song et al., 1995, PDA Journal of Pharmaceutical Science & Technology 50:372-397, Cleek et al., 1997, Pro. Int'l. Symp. Control. Rel. Bioact. Mater. 24:853-854, and Lam et al., 1997, Proc. Intl Symp. Control Rel. Bioact. Mater. 24:759-760.

If the BCMA binding molecules are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations where the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known.

If the compositions comprising the BCMA binding molecules are administered intranasally, the BCMA binding molecules can be formulated in an aerosol form, spray, mist or in the form of drops. In particular, prophylactic or therapeutic agents for use according to the present disclosure can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit can be determined by providing a valve to deliver a metered amount. Capsules and cartridges (composed of, e.g., gelatin) for use in an inhaler or insufflator can be formulated containing a powder mix of the BCMA binding molecule and a suitable powder base such as lactose or starch.

The BCMA binding molecules of the disclosure can be administered in combination therapy regimens, as described in Section 7.14, infra.

In certain embodiments, the BCMA binding molecules can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes can comprise one or more moieties which are selectively transported into specific cells or organs, thus enhance targeted drug delivery (see, e.g., Ranade, 1989, J. Clin. Pharmacol. 29:685). Exemplary targeting moieties include folate or biotin (see, e.g., U.S. Pat. No. 5,416,016 to Low et al.); mannosides (Umezawa et al., 1988, Biochem. Biophys. Res. Commun. 153:1038); antibodies (Bloeman et al., 1995, FEBS Lett. 357:140; Owais et al., 1995, Antimicrob. Agents Chemother. 39:180); surfactant protein A receptor (Briscoe et al., 1995, Am. J. Physiol. 1233:134); p 120 (Schreier et al., 1994, J. Biol. Chem. 269:9090); see also Keinanen and Laukkanen, 1994, FEBS Lett. 346:123; Killion and Fidler, 1994, Immunomethods 4:273.

When used in combination therapy, e.g., as described in Section 7.14, infra, a BCMA binding molecule and one or more additional agents can be administered to a subject in the same pharmaceutical composition. Alternatively, the BCMA binding molecule and the additional agent(s) of the combination therapies can be administered concurrently to a subject in separate pharmaceutical compositions.

The therapeutic methods described herein can further comprise carrying a "companion diagnostic" test whereby a sample from a subject who is a candidate for therapy with a BCMA binding molecule is tested for the expression of BCMA. The companion diagnostic test can be performed prior to initiating therapy with a BCMA binding molecule and/or during a therapeutic regimen with a BCMA binding molecule to monitor the subject's continued suitability for BCMA binding molecule therapy. The agent used in the companion diagnostic can be the BCMA binding molecule itself or another diagnostic agent, for example a labeled monospecific antibody against BCMA or a nucleic acid probe to detect BCMA RNA. The sample that can be tested in a companion diagnostic assay can be any sample in which the cells targeted by the BCMA binding molecule can be present, from example a tumor (e.g., a solid tumor) biopsy, lymph, stool, urine, blood or any other bodily fluid that might contain circulating tumor cells.

7.13. Therapeutic Indications

The BCMA binding molecules of the disclosure can be used in the treatment of any disease associated with BCMA expression. For example, a BCMA binding molecule can be used to treat a subject who has undergone treatment for a disease associated with elevated expression of BCMA, where the subject who has undergone treatment for elevated levels of BCMA exhibits a disease associated with elevated levels of BCMA.

In one aspect, the disclosure provides a method of inhibiting growth of a BCMA-expressing tumor cell, comprising contacting the tumor cell with a BCMA binding molecule such that the growth of the tumor cell is inhibited.

In one aspect, the disclosure provides a method of treating and/or preventing a disease that arises in individuals who are immunocompromised, comprising administering a BCMA binding molecule. In particular, disclosed herein is a method of treating diseases, disorders and conditions associated with expression of BCMA, comprising administering a BCMA binding molecule.

In certain aspects, disclosed herein is a method of treating patients at risk for developing diseases, disorders and conditions associated with expression of BCMA, comprising administering a BCMA binding molecule.

Thus, the present disclosure provides methods for the treatment or prevention of diseases, disorders and conditions associated with expression of BCMA comprising administering to a subject in need thereof, a therapeutically effective amount of a BCMA binding molecule.

The present disclosure also provides methods for preventing, treating and/or managing a disease associated with BCMA-expressing cells (e.g., a hematologic cancer or atypical cancer expressing BCMA), the methods comprising administering to a subject in need a BCMA binding molecule. In one aspect, the subject is a human. Non-limiting examples of disorders associated with BCMA-expressing cells include viral or fungal infections, and disorders related to mucosal immunity.

7.13.1. Cancer and Cancer-Related Diseases and Disorders

In one aspect, the disclosure provides a method of treating cancer in a subject. The method comprises administering to the subject a BCMA binding molecule such that the cancer is treated in the subject. An example of a cancer that is treatable by the BCMA-targeting agent is a cancer associated with expression of BCMA.

In one aspect, the disclosure provides methods for treating a cancer where part of the tumor is negative for BCMA and part of the tumor is positive for BCMA.

In one aspect, the disclosure provides methods for treating a cancer where BCMA is expressed on both normal cells and cancers cells, but is expressed at lower levels on normal cells, using a BCMA binding molecule of the disclosure. In one embodiment, the method further comprises selecting a BCMA binding molecule that binds with an affinity that allows the BCMA binding molecule to bind and kill the cancer cells expressing BCMA but kill less than 30%, 25%, 20%, 15%, 10%, 5% or less of the normal cells expressing BCMA, e.g., as determined by an assay described herein. For example, a killing assay such as flow cytometry based on Cr51 CTL can be used. In one embodiment, the BCMA binding molecule has an antigen binding domain that has a binding affinity $K_D$ of $10^{-4}$ M to $10^{-8}$ M, e.g., $10^{-5}$ M to $10^{-7}$ M, e.g., $10^{-6}$ M or $10^{-7}$ M, for BCMA.

In one aspect, disclosed herein is a method of treating a proliferative disease such as a cancer or malignancy or a precancerous condition such as a myelodysplasia, a myelodysplastic syndrome or a preleukemia, comprising administering BCMA binding molecule. In one aspect, the cancer is a hematological cancer. Hematological cancer conditions are the types of cancer such as leukemia and malignant lymphoproliferative conditions that affect blood, bone marrow and the lymphatic system. In one aspect, the hematological cancer is a leukemia. An example of a disease or disorder associated with BCMA is multiple myeloma (also known as MM) (See Claudio et al., *Blood.* 2002, 100(6): 2175-86; and Novak et al., *Blood.* 2004, 103(2):689-94). Multiple myeloma, also known as plasma cell myeloma or Kahler's disease, is a cancer characterized by an accumulation of abnormal or malignant plasma B-cells in the bone marrow. Frequently, the cancer cells invade adjacent bone, destroying skeletal structures and resulting in bone pain and fractures. Most cases of myeloma also feature the production of a paraprotein (also known as M proteins or myeloma proteins), which is an abnormal immunoglobulin produced in excess by the clonal proliferation of the malignant plasma cells. Blood serum paraprotein levels of more than 30 g/L is diagnostic of multiple myeloma, according to the diagnostic criteria of the International Myeloma Working Group (IMWG) (See Kyle et al. (2009), Leukemia. 23:3-9). Other symptoms or signs of multiple myeloma include reduced kidney function or renal failure, bone lesions, anemia, hypercalcemia, and neurological symptoms.

Other plasma cell proliferative disorders that can be treated by the compositions and methods described herein include, but are not limited to, asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

Another example of a disease or disorder associated with BCMA is Hodgkin's lymphoma and non-Hodgkin's lymphoma (See Chiu et al., *Blood.* 2007, 109(2):729-39; He et al., *J Immunol.* 2004, 172(5):3268-79).

Hodgkin's lymphoma (HL), also known as Hodgkin's disease, is a cancer of the lymphatic system that originates from white blood cells, or lymphocytes. The abnormal cells that comprise the lymphoma are called Reed-Sternberg cells. In Hodgkin's lymphoma, the cancer spreads from one lymph node group to another. Hodgkin's lymphoma can be subclassified into four pathologic subtypes based upon Reed-Sternberg cell morphology and the cell composition around the Reed-Sternberg cells (as determined through lymph node biopsy): nodular sclerosing HL, mixed-cellularity subtype, lymphocyte-rich or lymphocytic predominance, lymphocyte depleted. Some Hodgkin's lymphoma can also be nodular lymphocyte predominant Hodgkin's lymphoma, or can be unspecified. Symptoms and signs of Hodgkin's lymphoma include painless swelling in the lymph nodes in the neck, armpits, or groin, fever, night sweats, weight loss, fatigue, itching, or abdominal pain.

Non-Hodgkin's lymphoma (NHL) comprises a diverse group of blood cancers that include any kind of lymphoma other than Hodgkin's lymphoma. Subtypes of non-Hodgkin's lymphoma are classified primarily by cell morphology, chromosomal aberrations, and surface markers. NHL subtypes (or NHL-associated cancers) include B cell lymphomas such as, but not limited to, Burkitt's lymphoma, B-cell chronic lymphocytic leukemia (B-CLL), B-cell prolymphocytic leukemia (B-PLL), chronic lymphocytic leukemia (CLL), diffuse large B-cell lymphoma (DLBCL) (e.g., intravascular large B-cell lymphoma and primary mediastinal B-cell lymphoma), follicular lymphoma (e.g., follicle center lymphoma, follicular small cleaved cell), hair cell leukemia, high grade B-cell lymphoma (Burkitt's like), lymphoplasmacytic lymphoma (Waldenstrom's macroglublinemia), mantle cell lymphoma, marginal zone B-cell lymphomas (e.g., extranodal marginal zone B-cell lymphoma or mucosa-associated lymphoid tissue (MALT) lymphoma, nodal marginal zone B-cell lymphoma, and splenic marginal zone B-cell lymphoma), plasmacytoma/myeloma, precursor B-lymphoblastic leukemia/lymphoma (PB-LBL/L), primary central nervous system (CNS) lymphoma, primary intraocular lymphoma, small lymphocytic lymphoma (SLL); and T cell lymphomas, such as, but not limited to, anaplastic large cell lymphoma (ALCL), adult T-cell lymphoma/leukemia (e.g., smoldering, chronic, acute and lymphomatous), angiocentric lymphoma, angioimmunoblastic T-cell lymphoma, cutaneous T-cell lymphomas (e.g., mycosis fungoides, Sezary syndrome, etc.), extranodal natural killer/T-cell lymphoma (nasal-type), enteropathy type intestinal T-cell lymphoma, large granular lymphocyte leukemia, precursor T-lymphoblastic lymphoma/leukemia (T-LBL/L), T-cell chronic lymphocytic leukemia/prolymphocytic leukemia (T-CLL/PLL), and unspecified peripheral T-cell lymphoma. Symptoms and signs of Hodgkin's lymphoma include painless swelling in the lymph nodes in the neck, armpits, or groin, fever, night sweats, weight loss, fatigue, itching, abdominal pain, coughing, or chest pain.

BCMA expression has also been associated with Waldenstrom's macroglobulinemia (WM), also known as lymphoplasmacytic lymphoma (LPL). (See Elsawa et al., *Blood.* 2006, 107(7):2882-8). Waldenstrom's macroglobulinemia was previously considered to be related to multiple myeloma, but has more recently been classified as a subtype of non-Hodgkin's lymphoma. WM is characterized by uncontrolled B-cell lymphocyte proliferation, resulting in anemia and production of excess amounts of paraprotein, or immunoglobulin M (IgM), which thickens the blood and results in hyperviscosity syndrome. Other symptoms or signs of WM include fever, night sweats, fatigue, anemia, weight loss, lymphadenopathy or splenomegaly, blurred vision, dizziness, nose bleeds, bleeding gums, unusual bruises, renal impairment or failure, amyloidosis, or peripheral neuropathy.

Another example of a disease or disorder associated with BCMA expression is brain cancer. Specifically, expression of BCMA has been associated with astrocytoma or glioblastoma (See Deshayes et al, *Oncogene.* 2004, 23(17):3005-12, Pelekanou et al., *PLoS One.* 2013, 8(12):e83250). Astrocytomas are tumors that arise from astrocytes, which are a type of glial cell in the brain. Glioblastoma (also known as glioblastoma multiforme or GBM) is the most malignant form of astrocytoma, and is considered the most advanced stage of brain cancer (stage IV). There are two variants of glioblastoma: giant cell glioblastoma and gliosarcoma. Other astrocytomas include juvenile pilocytic astrocytoma (JPA), fibrillary astrocytoma, pleomorphic xantroastrocytoma (PXA), desembryoplastic neuroepithelial tumor (DNET), and anaplastic astrocytoma (AA).

Symptoms or signs associated with glioblastoma or astrocytoma include increased pressure in the brain, headaches, seizures, memory loss, changes in behavior, loss in movement or sensation on one side of the body, language dysfunction, cognitive impairments, visual impairment, nausea, vomiting, and weakness in the arms or legs.

Surgical removal of the tumor (or resection) is the standard treatment for removal of as much of the glioma as possible without damaging or with minimal damage to the normal, surrounding brain. Radiation therapy and/or chemotherapy are often used after surgery to suppress and slow recurrent disease from any remaining cancer cells or satellite lesions. Radiation therapy includes whole brain radiotherapy (conventional external beam radiation), targeted three-dimensional conformal radiotherapy, and targeted radionuclides. Chemotherapeutic agents commonly used to treat glioblastoma include temozolomide, gefitinib or erlotinib, and cisplatin. Angiogenesis inhibitors, such as Bevacizumab (Avastin®), are also commonly used in combination with chemotherapy and/or radiotherapy.

Supportive treatment is also frequently used to relieve neurological symptoms and improve neurologic function, and is administered in combination any of the cancer therapies described herein. The primary supportive agents include anticonvulsants and corticosteroids. Thus, the compositions and methods of the present disclosure can be used in combination with any of the standard or supportive treatments to treat a glioblastoma or astrocytoma.

The present disclosure provides for compositions and methods for treating cancer. In one aspect, the cancer is a hematologic cancer including but not limited to a leukemia or a lymphoma. In one aspect, disclosed herein are methods of treating cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further diseases associated with BCMA expression include, but are not limited to, e.g., atypical and/or non-classical cancers, malignancies, precancerous conditions or proliferative diseases expressing BCMA.

In some embodiments, a BCMA binding molecule can be used to treat a disease including but not limited to a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

In some embodiments, a BCMA binding molecule can be used to treat a disease including but not limited to a cancer, e.g., a cancer described herein, e.g., a prostate cancer (e.g., castrate-resistant or therapy-resistant prostate cancer, or metastatic prostate cancer), pancreatic cancer, or lung cancer.

The present disclosure also provides methods for inhibiting the proliferation or reducing a BCMA-expressing cell population, the methods comprising contacting a population of cells comprising a BMCA-expressing cell with a BCMA binding molecule. In a specific aspect, the present disclosure provides methods for inhibiting the proliferation or reducing the population of cancer cells expressing BCMA, the methods comprising contacting the BCMA-expressing cancer cell population with a BCMA binding molecule. In one aspect, the disclosure provides methods for inhibiting the proliferation or reducing the population of cancer cells expressing BCMA, the methods comprising contacting the BMCA-expressing cancer cell population with a BCMA binding molecule. In certain aspects, the methods reduce the quantity, number, amount or percentage of cells and/or cancer cells by at least 25%, at least 30%, at least 40%, at least 50%, at least 65%, at least 75%, at least 85%, at least 95%, or at least 99% in a subject with or an animal model for myeloid leukemia or another cancer associated with BCMA-expressing cells relative to a negative control. In one aspect, the subject is a human.

The present disclosure provides methods for preventing relapse of cancer associated with BCMA-expressing cells, the methods comprising administering to a subject in need thereof a BCMA binding molecule.

7.13.2. Non-Cancer Related Diseases and Disorders

Non-cancer related diseases and disorders associated with BCMA expression can also be treated by the compositions and methods disclosed herein. Examples of non-cancer related diseases and disorders associated with BCMA expression include, but are not limited to: viral infections; e.g., HIV, fungal infections, e.g., *C. neoformans*; and autoimmune diseases.

Autoimmune disorders that can be treated with the BCMA binding molecules of the disclosure include systemic lupus erythematosus (SLE), Sjögren's syndrome, scleroderma, rheumatoid arthritis (RA), juvenile idiopathic arthritis, graft versus host disease, dermatomyositis, type I diabetes mellitus, Hashimoto's thyroiditis, Graves's disease, Addison's disease, celiac disease, disorders related to mucosal immunity, irritable bowel diseases (e.g., Crohn's Disease, ulcerative colitis), pernicious anaemia, pemphigus vulgaris, vitiligo, autoimmune haemolytic anaemia, idiopathic thrombocytopenic purpura, giant cell arteritis, myasthenia gravis, multiple sclerosis (MS) (e.g., relapsing-remitting MS (RRMS)), glomerulonephritis, Goodpasture's syndrome, bullous pemphigoid, colitis ulcerosa, Guillain-Barré syndrome, chronic inflammatory demyelinating polyneuropathy, anti-phospholipid syndrome, narcolepsy, sarcoidosis, and Wegener's granulomatosis.

In some embodiments, the BCMA binding molecules are used to treat systemic lupus erythematosus (SLE).

In some embodiments, the BCMA binding molecules are used to treat Sjögren's syndrome.

In some embodiments, the BCMA binding molecules are used to treat scleroderma.

In some embodiments, the BCMA binding molecules are used to treat rheumatoid arthritis (RA).

In some embodiments, the BCMA binding molecules are used to treat juvenile idiopathic arthritis.

In some embodiments, the BCMA binding molecules are used to treat graft versus host disease.

In some embodiments, the BCMA binding molecules are used to treat dermatomyositis.

In some embodiments, the BCMA binding molecules are used to treat type I diabetes mellitus.

In some embodiments, the BCMA binding molecules are used to treat Hashimoto's thyroiditis.

In some embodiments, the BCMA binding molecules are used to treat Graves's disease.

In some embodiments, the BCMA binding molecules are used to treat Addison's disease.

In some embodiments, the BCMA binding molecules are used to treat celiac disease.

In some embodiments, the BCMA binding molecules are used to treat Crohn's Disease.

In some embodiments, the BCMA binding molecules are used to treat pernicious anaemia.

In some embodiments, the BCMA binding molecules are used to treat pemphigus vulgaris.

In some embodiments, the BCMA binding molecules are used to treat vitiligo.

In some embodiments, the BCMA binding molecules are used to treat autoimmune haemolytic anaemia.

In some embodiments, the BCMA binding molecules are used to treat idiopathic thrombocytopenic purpura.

In some embodiments, the BCMA binding molecules are used to treat giant cell arteritis.

In some embodiments, the BCMA binding molecules are used to treat myasthenia gravis.

In some embodiments, the BCMA binding molecules are used to treat multiple sclerosis (MS). In some embodiments, the MS is relapsing-remitting MS (RRMS).

In some embodiments, the BCMA binding molecules are used to treat glomerulonephritis.

In some embodiments, the BCMA binding molecules are used to treat Goodpasture's syndrome.

In some embodiments, the BCMA binding molecules are used to treat bullous pemphigoid.

In some embodiments, the BCMA binding molecules are used to treat colitis ulcerosa.

In some embodiments, the BCMA binding molecules are used to treat Guillain-Barré syndrome.

In some embodiments, the BCMA binding molecules are used to treat chronic inflammatory demyelinating polyneuropathy.

In some embodiments, the BCMA binding molecules are used to treat anti-phospholipid syndrome.

In some embodiments, the BCMA binding molecules are used to treat narcolepsy.

In some embodiments, the BCMA binding molecules are used to treat sarcoidosis.

In some embodiments, the BCMA binding molecules are used to treat Wegener's granulomatosis.

7.14. Combination Therapy

A BCMA binding molecule of the disclosure can be used in combination other known agents and therapies. For example, the BCMA binding molecules can be used in treatment regimens in combination with surgery, chemotherapy, antibodies, radiation, peptide vaccines, steroids, cytoxins, proteasome inhibitors, immunomodulatory drugs (e.g., IMiDs), BH3 mimetics, cytokine therapies, stem cell transplant or any combination thereof.

For convenience, an agent that is used in combination with a BCMA binding molecule is referred to herein as an "additional" agent.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". The term "concurrently" is not limited to the administration of therapies (e.g., a BCMA binding molecule and an additional agent) at exactly the same time, but rather it is meant that a pharmaceutical composition comprising a BCMA binding molecule is administered to a subject in a sequence and within a time interval such that the BCMA binding molecules can act together with the additional therapy(ies) to provide an increased benefit than if they were administered otherwise. For example, each therapy can be administered to a subject at the same time or sequentially in any order at different points in time; however, if not administered at the same time, they should be administered sufficiently close in time so as to provide the desired therapeutic effect.

A BCMA binding molecule and one or more additional agents can be administered simultaneously, in the same or in separate compositions, or sequentially. For sequential administration, the BCMA binding molecule can be administered first, and the additional agent can be administered second, or the order of administration can be reversed.

The BCMA binding molecule and the additional agent(s) can be administered to a subject in any appropriate form and by any suitable route. In some embodiments, the routes of administration are the same. In other embodiments the routes of administration are different.

In other embodiments, the delivery of one treatment ends before the delivery of the other treatment begins.

In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The BCMA binding molecules and/or additional agents can be administered during periods of active disorder, or during a period of remission or less active disease. A BCMA binding molecule can be administered before the treatment with the additional agent(s), concurrently with the treatment with the additional agent(s), post-treatment with the additional agent(s), or during remission of the disorder.

When administered in combination, the BCMA binding molecule and/or the additional agent(s) can be administered in an amount or dose that is higher, lower or the same than the amount or dosage of each agent used individually, e.g., as a monotherapy.

The additional agent(s) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising a BCMA binding molecule is administered to a subject in a sequence and within a time interval such that the molecules of the disclosure can act together with the additional therapy(ies) to provide an increased benefit than if they were administered otherwise. For example, each therapy can be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route.

The BCMA binding molecule and the additional agent(s) can be administered to a subject by the same or different routes of administration.

The BCMA binding molecules and the additional agent(s) can be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain instances, the one or more additional agents, are other anti-cancer agents, anti-allergic agents, anti-nausea agents (or anti-emetics), pain relievers, cytoprotective agents, and combinations thereof.

In one embodiment, a BCMA binding molecule can be used in combination with an anti-cancer agent (e.g., a chemotherapeutic agent). Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab, obinutuzumab, ofatumumab, daratumumab, elotuzumab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the BCMA binding molecules of the present disclosure include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; vinca alkaloids; proteasome inhibitors; GITR agonists (e.g., GWN323); protein tyrosine phosphatase inhibitors; a CDK4 kinase inhibitor; a BTK inhibitor; a MKN kinase inhibitor; a DGK kinase inhibitor; an oncolytic virus; a BH3 mimetic; and cytokine therapies.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amadei®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.04,9] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502, CAS 1013101-36-4); and N2-[1,4-dioxo-4-[[4-(4-oxo-8-phenyl-4H-1-benzopyran-2-yl) morpholinium-4-yl]methoxy]butyl]-L-arginylglycyl-L-α-aspartylL-serine- (SEQ ID NO:514), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); IMIDs (such as thalidomide (Thalomid®), lenalidomide, pomalidomide, and apremilast), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteasome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

Exemplary BH3 mimetics include venetoclax, ABT-737 (4-{4-[(4'-Chloro-2-biphenylyl)methyl]-1-piperazinyl}-N-[(4-{[(2R)-4-(dimethylamino)-1-(phenylsulfanyl)-2-butanyl]amino}-3-nitrophenyl)sulfonyl]benzamide and navitoclax (formerly ABT-263).

Exemplary cytokine therapies include interleukin 2 (IL-2) and interferon-alpha (IFN-alpha).

In certain aspects, "cocktails" of different chemotherapeutic agents are administered as the additional agent(s).

In one aspect, the disclosure provides a method for treating subjects that have a disease associated with expression of BCMA, comprising administering to the subject an effective amount of: (i) a BCMA binding molecule, and (ii) a gamma secretase inhibitor (GSI).

In one aspect, the disclosure provides a method for treating subjects that have undergone treatment for a disease associated with expression of BCMA, comprising administering to the subject an effective amount of: (i) a BCMA binding molecule, and (ii) a GSI.

In one embodiment, the BCMA binding molecule and the GSI are administered simultaneously or sequentially. In one embodiment, the BCMA binding molecule is administered prior to the administration of the GSI. In one embodiment, the GSI is administered prior to the administration of the BCMA binding molecule. In one embodiment, the BCMA binding molecule and the GSI are administered simultaneously.

In one embodiment, the GSI is administered prior to the administration of the BCMA binding molecule (e.g., GSI is administered 1, 2, 3, 4, or 5 days prior to the administration of the BCMA binding molecule), optionally where after the administration of the GSI and prior to the administration of the BCMA binding molecule, the subject shows an increase in cell surface BCMA expression levels and/or a decrease in soluble BCMA levels.

In some embodiments, the GSI is a small molecule that reduces the expression and/or function of gamma secretase, e.g., a small-molecule GSI disclosed herein. In one embodiment, the GSI is chosen from LY-450139, PF-5212362, BMS-708163, MK-0752, ELN-318463, BMS-299897, LY-411575, DAPT, AL-101 (also known as BMS-906024), AL-102 (also known as BMS-986115), PF-3084014, RO4929097, and LY3039478. In one embodiment, the GSI is chosen from PF-5212362, ELN-318463, BMS-906024, and LY3039478. Exemplary GSIs are disclosed in Takebe et al., Pharmacol Ther. 2014 February; 141(2):140-9; and Ran et al., EMBO Mol Med. 2017 July; 9(7):950-966. In some embodiments, the GSI is AL-101. In some embodiments, the GSI is AL-102.

In some embodiments, MK-0752 is administered in combination with docetaxel. In some embodiments, MK-0752 is administered in combination with gemcitabine. In some embodiments, BMS-906024 is administered in combination with chemotherapy.

In some embodiments, the GSI can be a compound of formula (I) or a pharmaceutically acceptable salt thereof;

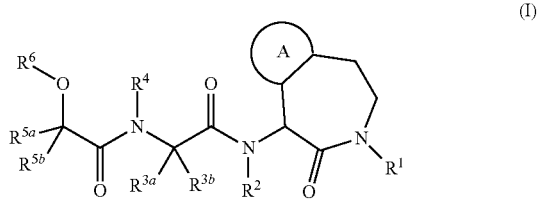

(I)

where ring A is aryl or heteroaryl; each of $R^1$, $R^2$, and $R^4$ is independently hydrogen, $C_1$-$C_6$ alkyl, cycloalkyl, heterocyclyl, cycloalkylalkyl, heterocyclylalkyl, aryl, heteroaryl, aralkyl, or heteroaralkyl, where each $C_1$-$C_6$ alkyl, cycloalkyl, heterocyclyl, cycloalkylalkyl, heterocyclylalkyl, aryl, heteroaryl, aralkyl, or heteroaralkyl is substituted with 0-6 independent occurrences of halogen, —$OR^A$, —$SR^A$, —$C(O)OR^A$, —$C(O)N(R^A)(R^B)$, —$N(R^A)(R^B)$, or —$C(NR^C)N(R^A)(R^B)$; each $R^{3a}$, $R^{3b}$, $R^{5a}$, and $R^{5b}$ is independently hydrogen, halogen, —OH, $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl, where each $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl is substituted with 0-6 independent occurrences of halogen, —OH, —$OR^A$, —$SR^A$, —$C(O)OR^A$, —$C(O)N(R^A)(R^B)$, —$N(R^A)(R^B)$, or —$C(NR^C)N(R^A)(R^B)$; $R^6$ is hydrogen, $C_1$-$C_6$ alkyl, cycloalkyl, heterocyclyl, cycloalkylalkyl, heterocyclylalkyl, aryl, heteroaryl, aralkyl, or heteroaralkyl, where each $C_1$-$C_6$ alkyl, cycloalkyl, heterocyclyl, cycloalkylalkyl, heterocyclylalkyl, aryl, heteroaryl, aralkyl, or heteroaralkyl is substituted with 0-6 independent occurrences of halogen, —OH, or $C_1$-$C_6$ alkoxy; and each $R^A$, $R^B$, and $R^C$ is independently hydrogen, $C_1$-$C_6$ alkyl, cycloalkyl, heterocyclyl, cycloalkylalkyl, heterocyclylalkyl, aryl, heteroaryl, aralkyl, or heteroaralkyl, where each $C_1$-$C_6$ alkyl, cycloalkyl, heterocyclyl, cycloalkylalkyl, heterocyclylalkyl, aryl, heteroaryl, aralkyl, or heteroaralkyl is substituted with 0-6 independent occurrences of halogen, —OH, or $C_1$-$C_6$ alkoxy.

In some embodiments, ring A is aryl (e.g., phenyl). In some embodiments, $R^1$ is —$CH_3$. In some embodiments, each of $R^2$ and $R^4$ is independently hydrogen. In some embodiments, $R^{3a}$ is —$CH_3$ and $R^{3b}$ is hydrogen. In some embodiments, $R^{5a}$ is hydrogen and $R^{5b}$ is —$CH(CH_3)_2$. In some embodiments, $R^6$ is hydrogen.

In a further embodiment, the GSI is a compound described in U.S. Pat. No. 7,468,365. In one embodiment, the GSI is LY-450139, i.e., semagacestat, (S)-2-hydroxy-3-methyl-N—((S)-1-(((S)-3-methyl-2-oxo-2,3,4,5-tetrahydro-1H-benzo[d]azepin-1-yl)amino)-1-oxopropan-2-yl)butanamide, or a pharmaceutically acceptable salt thereof. In one embodiment the GSI is

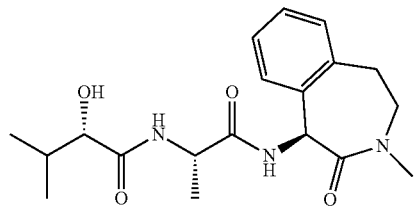 [SMILES: CC(C)[C@H](O)C(=O)N[C@@H](C)C(=O)N[C@@H]1C(=O)N(C)CCc2ccccc21]

or a pharmaceutically acceptable salt thereof.

In some embodiments, the GSI is a compound of formula (II) or a pharmaceutically acceptable salt thereof;

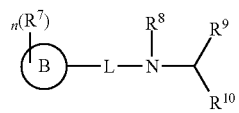

(II)

where ring B is aryl or heteroaryl; L is a bond, $C_1$-$C_6$ alkylene, —$S(O)_2$—, —$C(O)$—, —$N(R^E)(O)C$—, or —$OC(O)$—; each $R^7$ is independently halogen, —OH, $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl, where each $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl is independently substituted with 0-6 occurrences of halogen, —$OR^D$, —$SR^D$, —$C(O)OR^D$, —$C(O)N(R^D)(R^E)$, —$N(R^D)(R^E)$, or —$C(NR^F)N(R^D)(R^E)$; $R^8$ is hydrogen, $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl, where each $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl is substituted with 0-6 independent occurrences of halogen, —$OR^D$, —$SR^D$, —$C(O)OR^D$, —$C(O)N(R^D)(R^E)$, —$N(R^D)(R^E)$, or —$C(NR^F)N(R^D)(R^E)$; each of $R^9$ and $R^{10}$ is independently hydrogen, halogen, —OH, $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl, where each $C_1$-$C_6$ alkyl, $C_1$-$C_6$ alkoxy, cycloalkyl, heterocyclyl, aryl, heteroaryl, aralkyl, or heteroaralkyl is substituted with 0-6 independent occurrences of halogen, —$OR^D$, —$SR^D$, —$C(O)OR^D$, —$C(O)N(R^D)(R^E)$, —$N(R^D)(R^E)$, or —$C(NR^I)N(R^G)(R^H)$; each $R^D$, $R^E$, and $R^F$ is independently hydrogen, $C_1$-$C_6$ alkyl, cycloalkyl, heterocyclyl, cycloalkylalkyl, heterocyclylalkyl, aryl, heteroaryl, aralkyl, or heteroaralkyl, where each C $C_1$-$C_6$ alkyl, cycloalkyl, heterocyclyl, cycloalkylalkyl, heterocyclylalkyl, aryl, heteroaryl, aralkyl, or heteroaralkyl is substituted with 0-6 independent occurrences of halogen, —OH, or $C_1$-$C_6$ alkoxy; and n is 0, 1, 2, 3, 4, or 5.

In some embodiments, ring B is heteroaryl (e.g., thiofuranyl). In some embodiments, L is —$S(O)_2$. In some embodiments, $R^7$ is chloro and n is 1. In some embodiments, $R^8$ is —$CH_2OH$. In some embodiments, each of $R^9$ and $R^{10}$ is independently —$CF_3$.

In a further embodiment, the GSI is a compound described in U.S. Pat. No. 7,687,666. In one embodiment, the GSI is PF-5212362, i.e., begacestat, GSI-953, or (R)-5-chloro-N-(4,4,4-trifluoro-1-hydroxy-3-(trifluoromethyl)butan-2-yl)thiophene-2-sulfonamide, a pharmaceutically acceptable salt thereof. In one embodiment, the GSI is

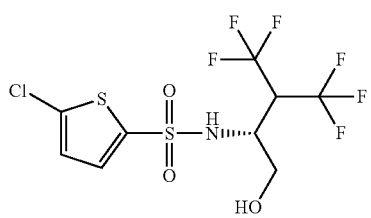 [SMILES: O=S(=O)(N[C@@H](CO)C(C(F)(F)F)C(F)(F)F)c1ccc(Cl)s1]

or a pharmaceutically acceptable salt thereof.

In some embodiments, the GSI is a compound is a compound of formula (III) or a pharmaceutically acceptable salt thereof:

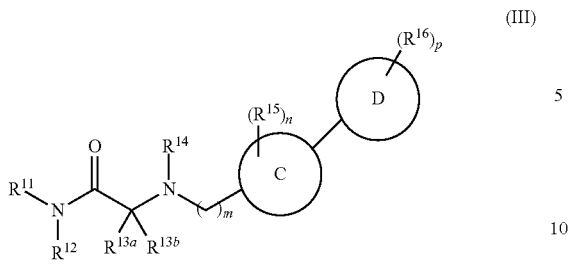

(III)

where each of rings C and D is independently aryl or heteroaryl;

each of $R^{11}$, $R^{12}$, and $R^{14}$ is independently hydrogen, $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl, where each $C_1$-$C_6$ alkyl, $C_1$-$C_6$ alkoxy, —S(O)$R^G$—, —S(O)$_2R^G$—, cycloalkyl, heterocyclyl, cycloalkylalkyl, heterocyclylalkyl, aryl, heteroaryl, aralkyl, or heteroaralkyl is substituted with 0-6 independent occurrences of halogen, —O$R^G$, —S$R^G$, —C(O)O$R^G$, —C(O)N($R^G$)($R^H$), —N($R^G$)($R^H$), or —C(N$R^I$)N($R^G$)($R^H$); each of $R^{13a}$ and $R^{13b}$ is hydrogen, halogen, —OH, $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl, where each $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl is substituted with 0-6 independent occurrences of halogen, —O$R^G$, —S$R^G$, —C(O)O$R^G$, —C(O)N($R^G$)($R^H$), —N($R^G$)($R^H$), or —C(N$R^I$)N($R^G$)($R^H$); each $R^{15}$ and $R^{16}$ is independently halogen, —OH, $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl, where each $C_1$-$C_6$ alkyl, $C_1$-$C_6$ alkoxy, cycloalkyl, heterocyclyl, cycloalkylalkyl, heterocyclylalkyl, aryl, heteroaryl, aralkyl, or heteroaralkyl is substituted with 0-6 independent occurrences of halogen, —O$R^G$, —S$R^G$, —C(O)O$R^G$, —C(O)N($R^G$)($R^H$), —N($R^G$)($R^H$), or —C(N$R^I$)N($R^G$)($R^H$); each $R^G$, $R^H$, and $R^I$ is independently hydrogen, $C_1$-$C_6$ alkyl, cycloalkyl, heterocyclyl, cycloalkylalkyl, heterocyclylalkyl, aryl, heteroaryl, aralkyl, or heteroaralkyl, where each $C_1$-$C_6$ alkyl, cycloalkyl, heterocyclyl, cycloalkylalkyl, heterocyclylalkyl, aryl, heteroaryl, aralkyl, or heteroaralkyl is substituted with 0-6 independent occurrences of halogen, —OH, or $C_1$-$C_6$ alkoxy; and each of m, n, and p is independently 0, 1, 2, 3, 4, or 5.

In some embodiments, ring C is aryl (e.g., phenyl). In some embodiments, ring D is heteroaryl (e.g., 1,2,4-oxadiazole). In some embodiments, $R^{15}$ is fluoro and n is 1. In some embodiments, p is 0. In some embodiments, m is 1. In some embodiments, $R^{14}$ is —S(O)$_2R^G$ and $R^G$ is chlorophenyl. In some embodiments, $R^{13a}$ is —CH$_2$CH$_2$CF$_3$ and $R^{13b}$ is hydrogen. In some embodiments, each $R^{11}$ and $R^{12}$ is independently hydrogen.

In a further embodiment, the GSI is a compound described in U.S. Pat. No. 8,084,477. In one embodiment, the GSI is BMS-708163, i.e., avagacestat, or (R)-2-((4-chloro-N-(2-fluoro-4-(1,2,4-oxadiazol-3-yl)benzyl)phenyl)sulfonamido)-5,5,5-trifluoropentanamide, or a pharmaceutically acceptable salt thereof. In one embodiment, the GSI is

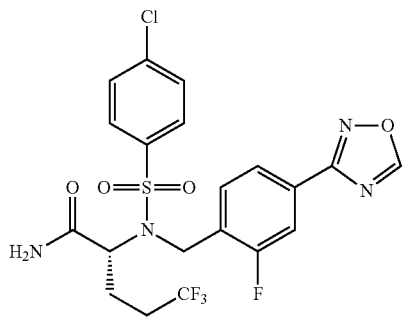 [SMILES: NC(=O)[C@@H](CCC(F)(F)F)N(Cc1ccc(-c2ncon2)cc1F)S(=O)(=O)c1ccc(Cl)cc1]

or a pharmaceutically acceptable salt thereof.

In some embodiments, the gamma secretase inhibitor is a compound of formula (IV) or a pharmaceutically acceptable salt thereof:

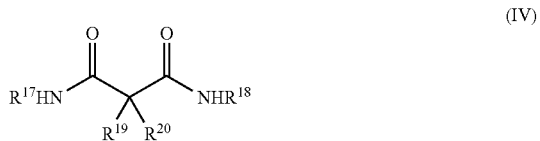

(IV)

where $R^{17}$ is selected from a.

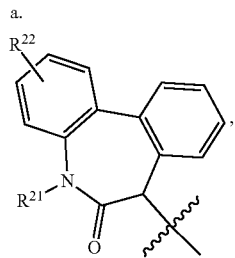

b.

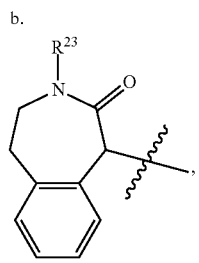

c.

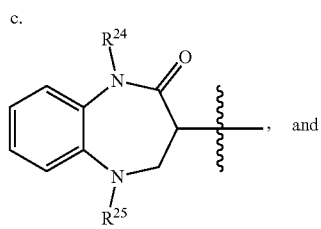

, and

-continued d.

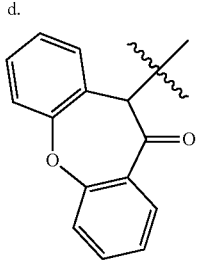

$R^{18}$ is lower alkyl, lower alkinyl, —(CH$_2$)$_n$—O-lower alkyl, —(CH$_2$)$_n$—S-lower alkyl, —(CH$_2$)$_n$—CN, —(CR'R")$_n$—CF$_3$, —(CR'R")$_n$—CHF$_2$, —(CR'R")$_n$—CH$_2$F, —(CH$_2$)$_n$, —C(O)O-lower alkyl, —(CH$_2$)$_n$-halogen, or is —(CH2)$_n$-cycloalkyl optionally substituted by one or more substituents selected from the group consisting of phenyl, halogen and CF$_3$; R', R" are each independently hydrogen, lower alkyl, lower alkoxy, halogen or hydroxy; $R^{19}$, $R^{20}$ are each independently hydrogen, lower alkyl, lower alkoxy, phenyl or halogen; $R^{21}$ is hydrogen, lower alkyl, —(CH2)$_n$—CF$_3$ or —(CH$_2$)$_n$-cycloalkyl; $R^{22}$ is hydrogen or halogen; $R^{23}$ is hydrogen or lower alkyl; $R^{24}$ is hydrogen, lower alkyl, lower alkinyl, —(CH2)$_n$—CF$_3$, —(CH$_2$)$_n$-cycloalkyl or —(CH2)$_n$-phenyl optionally substituted by halogen; $R^{25}$ is hydrogen, lower alkyl, —C(O)H, —C(O)-lower alkyl, —C(O)—CF$_3$, —C(O)—CH$_2$F, —C(O)—CHF$_2$, —C(O)— cycloalkyl, —C(O)—(CH$_2$)$_n$—O-lower alkyl, —C(O)O—(CH$_2$)$_n$-cycloalkyl, —C(O)-phenyl optionally substituted by one or more substituents selected from the group consisting of halogen and —C(O)O-lower alkyl, or is —S(O)2-lower alkyl, —S(O)$_2$—CF$_3$, —(CH2)$_n$-cycloalkyl or is —(CH$_2$)$_n$-phenyl optionally substituted by halogen; n is 0, 1, 2, 3 or 4.

In some embodiments, $R^{17}$ is 5,7-dihydro-6H-dibenzo[b,d]azepin-6-onyl. In some embodiments, each $R^{19}$ and $R^{20}$ is independently —CH$_3$. In some embodiments, $R^{18}$ is CH$_2$CF$_2$CF$_3$.

In some embodiments, the GSI is a compound described in U.S. Pat. No. 7,160,875. In one embodiment, the GSI is RO4929097, i.e., (S)-2,2-dimethyl-N1-(6-oxo-6,7-dihydro-5H-dibenzo[b,d]azepin-7-yl)-N3-(2,2,3,3,3-pentafluoropropyl)malonamide, or a pharmaceutically acceptable salt thereof. In one embodiment, the GSI is

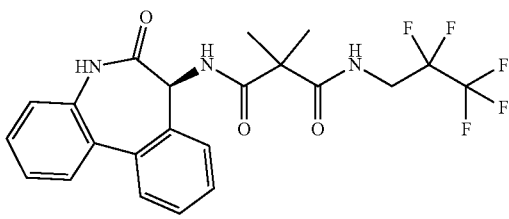 [SMILES: CC(C)(C(=O)NCC(F)(F)C(F)(F)F)C(=O)N[C@@H]1C(=O)Nc2ccccc2-c2ccccc21]

or a pharmaceutically acceptable salt thereof.

In some embodiments, the GSI is

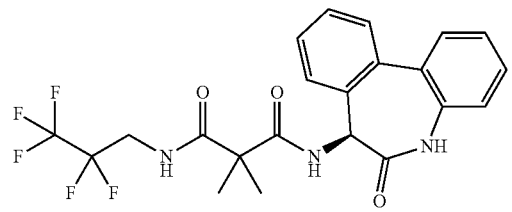 [SMILES: CC(C)(C(=O)NCC(F)(F)C(F)(F)F)C(=O)N[C@@H]1C(=O)Nc2ccccc2-c2ccccc21]

or a pharmaceutically acceptable salt thereof.

In some embodiments, the GSI is a compound of Formula (V) or a pharmaceutically acceptable salt thereof:

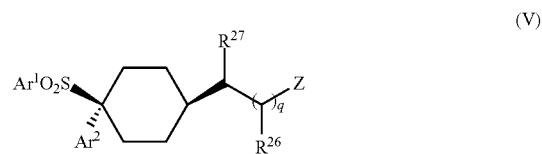

(V)

where
q is 0 or 1; Z represents halogen, —CN, —NO$_2$, —N$_3$, —CF$_3$, —OR$^{2a}$, —N(R$^{2a}$)$_2$, —CO$_2$R$^{2a}$, —OCOR$^{2a}$, —COR$^{2a}$, —CON(R$^{2a}$)$_2$, —OCON(R$^{2a}$)$_2$, —CONR$^{2a}$(OR$^{2a}$), —CON(R$^{2a}$)N(R$^{2a}$)$_2$, —CONHC(=NOH)R$^{2a}$, heterocyclyl, phenyl or heteroaryl, the heterocyclyl, phenyl or heteroaryl bearing 0-3 substituents selected from halogen, —CN, —NO$_2$, —CF$_3$, —OR$^{2a}$, —N(R$^{2a}$)$_2$, —CO$_2$R$^{2a}$, —COR$^{2a}$, —CON(R$^{2a}$)$_2$ and C$_{1-4}$ alkyl; R$^{27}$ represents H, C$_{1-4}$ alkyl, or OH; R$^{26}$ represents H or C$_{1-4}$ alkyl; with the proviso that when m is 1, R$^{26}$ and R$^{27}$ do not both represent C$_{1-4}$ alkyl; Ar$^1$ represents C$_{6-10}$ aryl or heteroaryl, either of which bears 0-3 substituents independently selected from halogen, —CN, —NO$_2$, —CF$_3$, —OH, —OCF$_3$, C$_{1-4}$ alkoxy or C$_{1-4}$ alkyl which optionally bears a substituent selected from halogen, CN, NO$_2$, CF$_3$, OH and C$_{1-4}$ alkoxy; Ar$^2$ represents C$_{6-10}$ aryl or heteroaryl, either of which bears 0-3 substituents independently selected from halogen, —CN, —NO$_2$, —CF$_3$, —OH, —OCF$_3$, C$_{1-4}$ alkoxy or C$_{1-4}$ alkyl which optionally bears a substituent selected from halogen, —CN, —NO$_2$, —CF$_3$, —OH and C$_{1-4}$ alkoxy; R$^{2a}$ represents H, C$_{1-6}$ alkyl, C$_{3-6}$ cycloalkyl, C3_6cycloalkyl, C$_{1-6}$ alkyl, C$_{2-6}$ alkenyl, any of which optionally bears a substituent selected from halogen, —CN, —NO$_2$, —CF$_3$, —OR$^{2b}$, —CO$_2$R$^{2b}$, —N(R$^{2b}$)$_2$, —CON(R$^{2b}$)$_2$, Ar and COAr; or R$^{2a}$ represents Ar; or two R$^{2a}$ groups together with a nitrogen atom to which they are mutually attached can complete an N-heterocyclyl group bearing 0-4 substituents independently selected from =O, =S, halogen, C$_{1-4}$ alkyl, —CN, —NO$_2$, —CF$_3$, —OH, C$_{1-4}$ alkoxy, C$_{1-4}$ alkoxycarbonyl, CO$_2$H, amino, C$_{1-4}$ alkylamino, di(C$_{1-4}$ alkyl)amino, carbamoyl, Ar and COAr; R$^{2b}$ represents H, C$_{1-6}$ alkyl, C$_{3-6}$ cycloalkyl, C$_{3-6}$ cycloalkylC$_{1-6}$ alkyl, C$_{2-6}$ alkenyl, any of which optionally bears a substituent selected from halogen, —CN, —NO$_2$, —CF$_3$, —OH, C$_{1-4}$ alkoxy, C$_{1-4}$ alkoxycarbonyl, —CO$_2$H, amino, C$_{1-4}$ alkylamino, di(C$_{1-4}$ alkyl)amino, carbamoyl, Ar and COAr; or R$^{2b}$ represents Ar; or two R$^{2b}$ groups together with a nitrogen atom to which they are mutually attached can complete an N-heterocyclyl group bearing 0-4 substituents independently selected from =O, =S, halogen, C$_{1-4}$ alkyl, —CN, —NO$_2$, CF$_3$, —OH, C$_{1-4}$ alkoxy, C$_{1-4}$ alkoxycarbonyl, —CO$_2$H, amino, C$_{1-4}$ alkylamino, di(C$_{1-4}$ alkyl)amino, carbamoyl, Ar and COAr; Ar represents phenyl or heteroaryl bearing 0-3 substituents selected from halogen, C$_{1-4}$ alkyl, —CN, —NO$_2$, —CF$_3$, —OH, C$_{1-4}$ alkoxy, C$_{1-4}$ alkoxycarbonyl, amino, C$_{1-4}$ alkylamino, di(C$_{1-4}$ alkyl)amino, carbamoyl, C$_{1-4}$ alkylcarbamoyl and di(C$_{1-4}$ alkyl)carbamoyl.

In some embodiments, q is 1. In some embodiments, Z is CO$_2$H. In some embodiments, each of R$^{27}$ and R$^{26}$ is independently hydrogen. In some embodiments, Ar$^1$ is chlorophenyl. In some embodiments, Ar$^2$ is difluorophenyl.

In some embodiments, the GSI is a compound described in U.S. Pat. No. 6,984,663. In one embodiment, the GSI is MK-0752, i.e., 3-((1S,4R)-4-((4-chlorophenyl)sulfonyl)-4-(2,5-difluorophenyl)cyclohexyl)propanoic acid, or a pharmaceutically acceptable salt thereof. In some embodiments, the GSI is

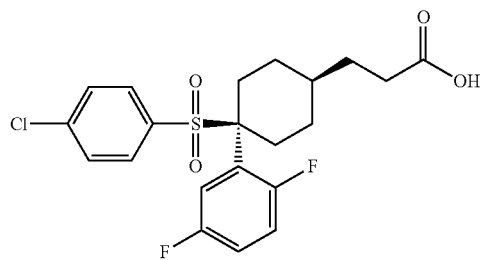 [SMILES: O=C(O)CC[C@H]1CC[C@@](c2cc(F)ccc2F)(S(=O)(=O)c2ccc(Cl)cc2)CC1]

or a pharmaceutically acceptable salt thereof.

In some embodiments, the GSI is a compound of formula (VI) or a pharmaceutically acceptable salt thereof.

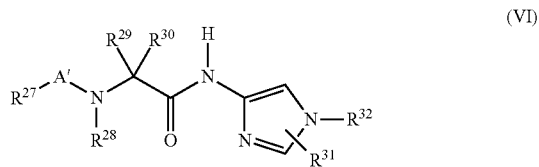

(VI)

where A' is absent or selected from

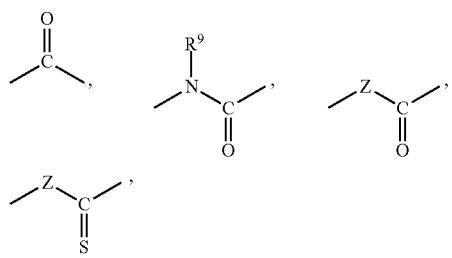

and —S(O)$_2$—;

Z is selected from —CH$_2$, —CH(OH), —CH(C$_1$-C$_6$ alkyl), —CH(C$_1$-C$_6$ alkoxy), —CH(NR$^{33}$R$^{34}$), —CH(CH$_2$(OH)), —CH(CH(C$_1$-C$_4$ alkyl)(OH)) and —CH(C(C$_1$-C$_4$ alkyl)(C$_1$-C$_4$ alkyl)(OH)), for example —CH(C(CH$_3$)(CH$_3$)(OH)) or —CH(C(CH$_3$)(CH$_2$CH$_3$)(OH)); R$^{27}$ is selected from C$_1$-C$_{20}$ alkyl, C$_2$-C$_{20}$ alkenyl, C$_2$-C$_{20}$ alkynyl, C$_1$-C$_{20}$ alkoxy, C$_2$-C$_{20}$ alkenoxy, C$_1$-C$_{20}$ hydroxyalkyl, C$_3$-C$_8$ cycloalkyl, benzo (C$_3$-C$_8$ cycloalkyl), benzo(C$_3$-C$_8$ heterocycloalkyl), C$_4$-C$_8$ cycloalkenyl, (C$_5$-C$_{11}$)bi- or tricycloalkyl, benzo (C$_5$-C$_{11}$)bi- or tricycloalkyl, C$_7$-C$_{11}$tricycloalkenyl, (3-8 membered) heterocycloalkyl, C$_6$-C$_{14}$ aryl and (5-14 membered) heteroaryl, where each hydrogen atom of the alkyl, alkenyl, alkynyl, alkoxy and alkenoxy is optionally independently replaced with halo, and where the cycloalkyl, benzo(C$_3$-C$_8$ cycloalkyl), cycloalkenyl, (3-8 membered) heterocycloalkyl, C$_6$-C$_{14}$ aryl and (5-14 membered) heteroaryl is optionally independently substituted with from one to four substituents independently selected from C$_1$-C$_{10}$ alkyl optionally substituted with from one to three halo atoms, C$_1$-C$_{10}$ alkoxy optionally substituted with from one to three halo atoms, C$_1$-C$_{10}$ hydroxyalkyl, halo, e.g., fluorine, —OH, —CN, —NR$^{33}$R$^{34}$, —C(=O) NR$^{33}$R$^{34}$, —C(=O)R$^{35}$, C$_3$-C$_8$ cycloalkyl and (3-8 membered) heterocycloalkyl; R$^{28}$ is selected from hydrogen, C$_1$-C$_6$ alkyl, C$_2$-C$_6$ alkenyl, C$_3$-C$_8$ cycloalkyl and C$_5$-C$_8$ cycloalkenyl, where R$^{28}$ is optionally independently substituted with from one to three substituents independently selected from C$_1$-C$_4$ alkyl optionally substituted with from one to three halo atoms, C$_1$-C$_4$ alkoxy optionally substituted with from one to three halo atoms, halo and —OH; or R$^{27}$ and R$^{28}$ together with the A' group when present and the nitrogen atom to which R$^{28}$ is attached, or R$^{27}$ and R$^{28}$ together with the nitrogen atom to which R$^{27}$ and R$^{28}$ are attached when A' is absent, can optionally form a four to eight membered ring; R$^{29}$ is selected from hydrogen, C$_1$-C$_6$ alkyl, C$_2$-C$_6$ alkenyl, C$_2$-C$_6$ alkynyl, C$_3$-C$_6$ cycloalkyl, C$_5$-C$_6$ cycloalkenyl and (3-8 membered) heterocycloalkyl, where the alkyl, alkenyl, alkynyl, cycloalkyl, cycloalkenyl and heterocycloalkyl are each optionally independently substituted with from one to three substituents independently selected from C$_1$-C$_4$alkoxy, halo, —OH—S(C$_1$-C$_4$)alkyl and (3-8 membered) heterocycloalkyl; R$^{30}$ is hydrogen, C$_1$-C$_6$ alkyl or halo; or R$^{29}$ and R$^{30}$ can together with the carbon atom to which they are attached optionally form a moiety selected from cyclopropyl, cyclobutyl, cyclopentyl, cyclohexyl, morpholino, piperidino, pyrrolidino, tetrahydrofuranyl and perhydro-2H-pyran, where the moiety formed by R$^{29}$ and R$^{30}$ is optionally substituted with from one to three substituents independently selected from C$_1$-C$_6$ alkyl optionally substituted with from one to three halo atoms, C$_1$-C$_6$ alkoxy optionally substituted with from one to three halo atoms, halo, —OH, —CN and allyl; R$^{31}$ is selected from hydrogen, C$_1$-C$_6$ alkyl, C$_2$-C$_6$ alkylene, C$_1$-C$_6$ alkoxy, halo, —CN, C$_3$-C$_{12}$ cycloalkyl, C$_4$-C$_{12}$ cycloalkenyl and C$_6$-C$_{10}$ aryl, (5-10 membered) heteroaryl, where the alkyl, alkylene and alkoxy of R$^{31}$ are each optionally independently substituted with from one to three substituents independently selected from halo and —CN, and where the cycloalkyl, cycloalkenyl and aryl and heteroaryl of R$^{31}$ are each optionally independently substituted with from one to three substituents independently selected from C$_1$-C$_4$ alkyl optionally substituted with from one to three halo atoms, C$_1$-C$_4$ alkoxy optionally substituted with from one to three halo atoms, halo and —CN; R$^{32}$ is selected from hydrogen, C$_1$-C$_{20}$ alkyl, C$_1$-C$_{20}$ alkoxy, C$_1$-C$_{20}$ hydroxyalkyl, C$_3$-C$_{12}$ cycloalkyl, C$_4$-C$_{12}$ cycloalkenyl, (C$_5$-C$_{20}$) bi- or tricycloalkyl, (C$_7$-C$_{20}$)bi- or tricycloalkenyl, (3-12 membered) heterocycloalkyl, (7-20 membered) hetero bi- or heterotricycloalkyl, C$_6$-C$_{14}$ aryl and (5-15 membered) heteroaryl, where $R^{32}$ is optionally independently substituted with from one to four substituents independently selected from $C_1$-$C_{20}$ alkyl optionally substituted with from one to three halo atoms, $C_1$-$C_{20}$ alkoxy, —OH, —CN, —NO$_2$, —NR$^{33}$R$^{34}$, —C(=O) NR$^{33}$R$^{34}$, —C(=O)R$^{35}$, —C(=O)OR$^{35}$, —S(O)$_n$ NR$^{33}$R$^{34}$, —S(O)$_n$R$^{35}$, $C_3$-$C_{12}$ cycloalkyl, (4-12 membered) heterocycloalkyl optionally substituted with from one to three OH or halo groups, (4-12 membered) heterocycloalkoxy, $C_6$-$C_{14}$ aryl, (5-15 membered) heteroaryl, $C_6$-$C_{12}$ aryloxy and (5-12 membered) heteroaryloxy; or $R^{33}$ and $R^{34}$ can together with the carbon and nitrogen atoms to which they are respectively attached optionally form a (5-8 membered) heterocycloalkyl ring, a (5-8 membered) heterocycloalkenyl ring or a (6-10 membered) heteroaryl ring, where the heterocycloalkyl, heterocycloalkenyl and heteroaryl rings are each optionally independently substituted with from one to three substituents independently selected from halo, $C_1$-$C_6$ alkyl, optionally substituted with from one to three halo atoms, $C_1$-$C_6$ alkoxy optionally substituted with from one to three halo atoms, $C_1$-$C_6$ hydroxyalkyl, —OH, —(CH$_2$)$_{zero-10}$NR$^{33}$R$^{34}$, —(CH$_2$)$_{zero-10}$C(=O)NR$^{33}$R$^{34}$, —S(O)$_2$ NR$^{33}$R$^{34}$ and $C_3$-$C_{12}$ cycloalkyl; $R^{33}$ and $R^{34}$ are each independently selected from hydrogen, $C_1$-$C_{10}$ alkyl where each hydrogen atom of the $C_1$-$C_{10}$ alkyl is optionally independently replaced with a halo atom, e.g., a fluorine atom, $C_2$-$C_{10}$ alkenyl, $C_2$-$C_{10}$ alkynyl, $C_1$-$C_6$ alkoxy where each hydrogen atom of the $C_1$-$C_6$ alkoxy is optionally independently replaced with a halo atom, $C_2$-$C_6$ alkenoxy, $C_2$-$C_6$ alkynoxy, —C(=O)R11, —S(O)$_n$R11, $C_3$-$C_8$ cycloalkyl, $C_4$-$C_8$ cycloalkenyl, ($C_5$-$C_{11}$)bi- or tricycloalkyl, ($C_7$-$C_{11}$)bi- or tricycloalkenyl, (3-8 membered) heterocycloalkyl, $C_6$-$C_{14}$ aryl and (5-14 membered) heteroaryl, where the alkyl and alkoxy are each optionally independently substituted with from one to three substituents independently selected from halo and —OH, and where the cycloalkyl, cycloalkenyl, bi- or tricycloalkyl, bi- or tricycloalkenyl, heterocycloalkyl, aryl and heteroaryl are each optionally independently substituted with from one to three substituents independently selected from halo, —OH, $C_1$-$C_6$ alkyl optionally independently substituted with from one to six halo atoms, $C_2$-$C_6$ alkenyl, $C_2$-$C_6$ alkynyl, $C_1$-$C_6$ alkoxy, $C_2$-$C_6$ alkenoxy, $C_2$-$C_6$ alkynoxy and $C_1$-$C_6$ hydroxyalkyl; or NR$^{33}$R$^{34}$ can form a (4-7 membered) heterocycloalkyl, where the heterocycloalkyl optionally comprises from one to two further heteroatoms independently selected from N, O, and S, and where the heterocycloalkyl optionally contains from one to three double bonds, and where the heterocycloalkyl is optionally independently substituted with from one to three substituents independently selected from $C_1$-$C_6$ alkyl optionally substituted with from one to six halo atoms, $C_2$-$C_6$ alkenyl, $C_2$-$C_6$ alkynyl, $C_1$-$C_6$ alkoxy, $C_2$-$C_6$ alkenoxy, $C_2$-$C_6$ alkynoxy, $C_1$-$C_6$ hydroxyalkyl, $C_2$-$C_6$hydroxyalkenyl, $C_2$-$C_6$hydroxyalkynyl, halo, —OH, —CN, —NO$_2$, —C(=O)R$^{35}$, —C(=O)OR$^{35}$, —S(O)$_n$R$^{35}$ and —S(O)$_n$NR$^{33}$R$^{34}$; R$^{35}$ is selected from hydrogen, $C_1$-$C_8$ alkyl, $C_3$-$C_8$ cycloalkyl, $C_4$-$C_8$ cycloalkenyl, ($C_5$-$C_{11}$)bi- or tricycloalkyl, —($C_7$-$C_{11}$)bi- or tricycloalkenyl, (3-8 membered) heterocycloalkyl, $C_6$-$C_{10}$ aryl and (5-14 membered) heteroaryl, where the alkyl of R$^{35}$ is optionally independently substituted with from one to three substituents independently selected from —OH, —CN and $C_3$-$C_8$ cycloalkyl, and where each hydrogen atom of the alkyl is optionally independently replaced with a halo atom, e.g., a fluorine atom, and where the cycloalkyl, cycloalkenyl, heterocycloalkyl, aryl and heteroaryl of R$^{35}$ are each optionally independently substituted with from one to three substituents independently selected from halo, $C_1$-$C_8$ alkyl optionally substituted with from one to three halo atoms, —OH, —CN and $C_3$-$C_8$cycloalkyl; n is in each instance an integer independently selected from zero, 1, 2 and 3; and the pharmaceutically acceptable salts of such compounds.

In some embodiments, the GSI is a compound described in U.S. Pat. No. 7,795,447. In one embodiment, the GSI is PF-3084014, i.e., nirogacestat or (S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide, or a pharmaceutically acceptable salt thereof.

In some embodiments, the GSI is

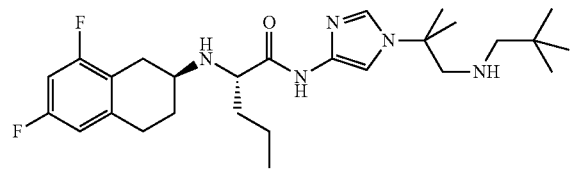 [SMILES: CCC[C@H](N[C@H]1CCc2cc(F)cc(F)c2C1)C(=O)Nc1cn(C(C)(C)CNCC(C)(C)C)cn1]

or a pharmaceutically acceptable salt thereof.

In some embodiments, the GSI is a compound of formula (VII):

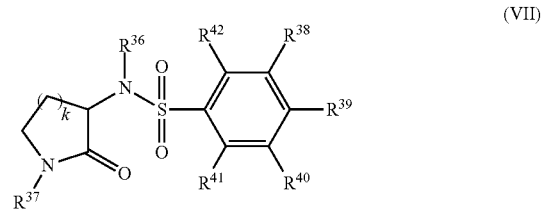

(VII)

or a pharmaceutically acceptable salt thereof where k is 1, 2, or 3; R$^{36}$ is aryl $C_1$-$C_8$ alkyl, aryl $C_2$-$C_6$ alkenyl, or arylalkynyl, where the aryl group is substituted with 0-5 occurrences of $C_1$-$C_6$ alkyl, $C_1$-$C_6$ alkoxy, halogen, haloalkyl, haloalkoxy, heteroaryl, heteroaryl($C_1$-$C_6$) alkoxy, arylalkoxy, aryloxy, $C_1$-$C_6$ alkoxycarbonyl, —OCH$_2$CH$_2$O—, —OCH$_2$O—, —C(O)NR$^{43}$R$^{44}$, —NHR', —NR'R", —N(R$^{16}$)C(O)R$^{17}$, heterocycloalkyl, phenyl, aryl $C_1$-$C_6$ alkanoyl, phenylalkoxy, phenyloxy, CN, —SO$_2$-aryl, —S(O)$_n$R$^{25}$, —($C_1$-$C_4$ alkyl)-S(O)$_x$R$^{25}$, —($C_1$-$C_4$ alkyl)-SO$_2$-aryl, OH, $C_1$-$C_6$ thioalkoxy, $C_2$-$C_6$ alkenyl, —OSO$_2$-aryl, or CO$_2$H, where each heteroaryl is independently substituted with 0-3 occurrences of $C_1$-$C_6$ alkyl, heteroaryl substituted with 0-2 occurrences of halogen, alkyl, alkoxy, haloalkyl, haloalkoxy, alkoxyalkyl or CN, $C_1$-$C_6$ alkoxy, $C_1$-$C_4$ alkoxy $C_1$-$C_4$ alkyl, $C_3$-$C_6$ cycloalkyl, halogen, or phenyl substituted with 0-5 occurrences of halogen, OH, $C_1$-$C_6$ alkyl, $C_1$-$C_4$ alkoxy, CF$_3$, OCF$_3$, CN, or $C_1$-$C_6$ thioalkoxy, where each heterocycloalkyl and aryl are independently substituted with 0-2 occurrences of halogen, alkyl, alkoxy, haloalkyl, haloalkoxy, alkoxyalkyl or CN, $C_1$-$C_6$ alkyl, $C_1$-$C_6$ alkoxy, $C_1$-$C_4$ alkoxy $C_1$-$C_4$ alkyl, $C_3$-$C_6$ cycloalkyl, halogen, or phenyl substituted with 0-5 occurrences of halogen, OH, $C_1$-$C_6$ alkyl, $C_1$-$C_4$ alkoxy, $CF_3$, $OCF_3$, CN, or $C_1$-$C_6$ thioalkoxy; $R^{16}$ is hydrogen or $C_1$-$C_6$ alkyl; $R^{17}$ is $C_1$-$C_6$ alkyl, aryl, heteroaryl, $C_1$-$C_6$ alkoxy, OH, aryloxy, heteroaryloxy, aryl($C_1$-$C_6$)alkoxy, —$NR^{18}R^{19}$, cycloalkyl, or arylalkyl, where the cyclic portions of each are independently substituted with 0-5 occurrences of alkyl, alkoxy, halo, haloalkyl, haloalkoxy, CN, $NH_2$, NH(alkyl), N(alkyl)(alkyl), $CO_2H$, or $C_1$-$C_6$ alkoxycarbonyl; $R^{18}$ and $R^{19}$ are independently hydrogen, $C_1$-$C_6$ alkyl, aryl, heteroaryl, heterocycloalkyl or aryl($C_1$-$C_6$)alkyl, where the cyclic portions of each are substituted with 0-3 occurrences of alkyl, alkoxy, halogen, hydroxyl, $CF_3$, or $OCF_3$; each R' is independently hydrogen, $C_1$-$C_6$ alkyl, aryl, aryl($C_1$-$C_4$)alkyl, $C_1$-$C_6$ alkanoyl, $C_3$-$C_8$ cycloalkyl, aryl($C_1$-$C_6$)alkanoyl, heterocycloalkyl, heteroaryl($C_1$-$C_4$)alkyl, —$SO_2$-alkyl, —$SO_2$-aryl, —$SO_2$-heteroaryl, heterocycloalkyl($C_1$-$C_6$)alkanoyl, or heteroaryl($C_1$-$C_6$)alkanoyl, where the alkyl portion of the alkyl and alkanoyl groups are optionally substituted with halogen or $C_1$-$C_6$ alkoxy and the aryl and heteroaryl groups are optionally substituted with alkyl, alkoxy, halogen, haloalkyl, haloalkoxy; each R" is independently hydrogen or $C_1$-$C_6$ alkyl, where the alkyl group is optionally substituted with halogen;

$R^{36}$ is $C_3$-$C_7$ cycloalkyl($C_1$-$C_6$ alkyl) where the cyclic portion is substituted with 0-5 occurrences of halogen, $C_1$-$C_6$ alkyl, OH, alkoxycarbonyl, or $C_1$-$C_6$ alkoxy; or $R^{36}$ is $C_1$-$C_{14}$ alkyl, $C_2$-$C_{16}$ alkenyl, or $C_2$-$C_8$ alkynyl, each of which is substituted 0-5 occurrences of OH, halogen, $C_1$-$C_6$ alkoxy, aryl, arylalkoxy, aryloxy, heteroaryl, heterocycloalkyl, aryl($C_1$-$C_6$)alkyl, —$CO_2$($C_1$-$C_6$ alkyl), —NR'R", $C_1$-$C_6$ thioalkoxy, —$NHS(O)_x$ $R^{25}$, —N($C_1$-$C_6$ alkyl)-$S(O)_xR^{25}$, —$S(O)_xR^{25}$, —$C(O)NR^{43}R^{44}$, —$N(R^{16})C(O)NR^{16}R^{17}$, or —$N(R_{16})C(O)R^{17}$; where the above aryl groups are substituted with 0-3 occurrences of OH, $C_1$-$C_6$ alkoxy, $C_1$-$C_6$ alkyl, or halogen; $R^{43}$ and $R^{44}$ are independently hydrogen, $C_1$-$C_6$ alkyl, aryl, arylalkyl, heteroaryl, heteroarylalkyl, heterocycloalkyl, heterocycloalkylalkyl, arylalkanoyl, alkenyl, cycloalkyl, alkynyl, cycloalkenyl, pyridyl, imidazolyl, thiazolyl, oxazolyl, or indolyl, where each alkyl is substituted with 0-3 occurrences of $NH_2$, NH($C_1$-$C_6$ alkyl), N($C_1$-$C_6$ alkyl) ($C_1$-$C_6$ alkyl), OH, $C_1$-$C_6$ thioalkoxy, heterocycloalkyl, aryl, heteroaryl, CN, halogen, or alkoxy optionally substituted with OH or phenyl, where the aryl, heteroaryl and heterocycloalkyl groups are substituted with 0-3 occurrences of $C_1$-$C_4$ alkyl, $C_1$-$C_4$alkoxy, $CF_3$, $OCF_3$, OH, halogen, thioalkoxy, phenyl or heteroaryl; or $R^{43}$, $R^{44}$, and the nitrogen to which they are attached form a heterocycloalkyl ring containing from 3 to 7 ring members, where the cyclic portions of $R^{43}$ and $R^{44}$ or the heterocyclic ring formed from $R^{43}$, $R^{44}$, and the nitrogen to which they are attached are substituted with 0-3 occurrences of alkyl, alkoxy, halo, OH, thioalkoxy, $NH_2$, NH($C_1$-$C_6$ alkyl), N($C_1$-$C_6$ alkyl) ($C_1$-$C_6$ alkyl), $CF_3$, $OCF_3$, phenyl optionally substituted with a halogen, —($C_1$-$C_4$ alkyl)-N(H or $C_1$-$C_4$ alkyl)-phenyl, $C_1$-$C_4$ hydroxyalkyl, arylalkoxy, arylalkyl, arylalkanoyl, C(O)$NH_2$, C(O)NH($C_1$-$C_6$ alkyl), C(O)N($C_1$-$C_6$ alkyl) ($C_1$-$C_6$ alkyl), heterocycloalkylalkyl, $C_1$-$C_6$ alkoxycarbonyl, $C_2$-$C_6$ alkanoyl, heteroaryl, or —$SO_2$($C_1$-$C_6$ alkyl); x is 0, 1, or 2; $R^{25}$ is $C_1$-$C_6$ alkyl, OH, $NR^{26}R^{27}$; $R^{26}$ and $R^{27}$ are independently hydrogen, $C_1$-$C_6$ alkyl, phenyl($C_1$-$C_4$ alkyl), aryl, or heteroaryl; or $R^{26}$, $R^{27}$ and the nitrogen to which they are attached form a heterocycloalkyl ring;

$R^{36}$ is heteroaryl($C_1$-$C_6$)alkyl where the cyclic portion is substituted 0-5 occurrences of halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —$S(O)_xR^{25}$, ($C_1$-$C_4$ alkyl)-$S(O)_xR^{25}$, CN, $C_1$-$C_6$ thioalkoxy, $C_1$-$C_6$ alkoxycarbonyl, —NR'R", —C(O)NR'R", heterocycloalkyl, where the above aryl groups are substituted with 0-4 occurrences of halogen, $C_1$-$C_6$ alkyl, $C_1$-$C_6$ alkoxy, $C_1$-$C_4$ haloalkyl, $C_1$-$C_4$ haloalkoxy, or CN; where the above heteroaryl and heterocycloalkyl groups are substituted with 0-3 occurrences of halogen, $CF_3$, ($C_1$-$C_4$)alkyl, $C_1$-$C_6$ thioalkoxy, OH, $C_1$-$C_4$ hydroxyalkyl, or $C_1$-$C_4$ alkoxy; or $R^{36}$ is heterocycloalkyl($C_1$-$C_6$ alkyl) where the cyclic portion is substituted with 0-3 occurrences of halogen, $C_1$-$C_6$ alkyl, $C_1$-$C_6$ alkoxy, $C_1$-$C_4$ haloalkyl, $C_1$-$C_4$ haloalkoxy, aryl, arylalkyl, aryloxy, heteroaryl, —$SO_2$-aryl, —$S(O)_xR^{25}$, ($C_1$-$C_4$ alkyl)-$S(O)_xR^{25}$, CN, $C_1$-$C_6$ thioalkoxy, $C_1$-$C_6$ alkoxycarbonyl, —NR'R", —C(O)NR'R", heterocycloalkyl;

$R^{37}$ is hydrogen, $C_1$-$C_6$ alkyl, or phenyl($C_1$-$C_4$)alkyl; $R^{38}$ is hydrogen, halogen, $C_1$-$C_6$ alkyl, $C_1$-$C_6$ alkoxy, $C_1$-$C_6$ haloalkyl, CN; $R^{39}$ is hydrogen, halogen, $C_1$-$C_6$ alkyl optionally substituted with —$CO_2$—($C_1$-$C_6$ alkyl), $C_1$-$C_6$ alkoxy, $C_1$-$C_6$ haloalkyl, $C_1$-$C_6$ haloalkoxy, CN, aryloxy, isocyanato, —$SO_2$($C_1$-$C_6$ alkyl), —NHR', —NR'R", $C_1$-$C_6$ alkanoyl, heteroaryl, aryl; or $R^{38}$ and $R^{39}$ and the carbons to which they are attached form a heterocycloalkyl ring which is substituted with 0-3 occurrences of $C_1$-$C_4$ alkyl, $C_1$-$C_4$ alkoxy, halogen, or $C_1$-$C_4$ alkanoyl where the alkanoyl group is substituted with 0-3 halogen atoms; $R^{40}$ is hydrogen, —$SO_2NR'R"$, halogen; or $R^{39}$ and $R^{40}$ and the carbons to which they are attached form a benzo ring; or $R^{39}$ and $R^{40}$ and the carbons to which they are attached form a 1-oxa-2,3-diazacyclopentyl ring; $R^{40}$ and $R^{41}$ are independently hydrogen or F; or $R^{40}$, $R^{41}$, and the carbons to which they are attached for a 1,2,5-oxadiazolyl ring; or $R^{40}$, $R^{41}$, and the carbons to which they are attached form a naphthyl ring.

In some embodiments, $R^{36}$ is 4-bromobenzyl. In some embodiments, $R^{37}$ is hydrogen. In some embodiments, k is 2. In some embodiments, each of $R^{38}$, $R^{40}$, $R^{41}$, and $R^{42}$ is independently hydrogen. In some embodiments, $R^{39}$ is chloro.

In some embodiments, the GSI is a compound described in U.S. Pat. No. 7,939,657. In one embodiment, the GSI is ELN-318463, i.e., HY-50882 or (R)—N-(4-bromobenzyl)-4-chloro-N-(2-oxoazepan-3-yl)benzenesulfonamide, or a pharmaceutically acceptable salt thereof. In some embodiments, the GSI is

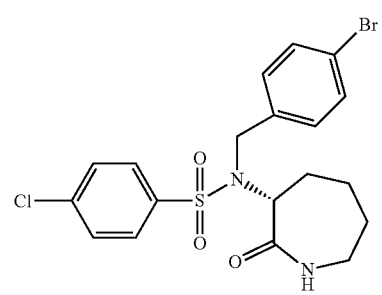 [SMILES: O=C1NCCCC[C@H]1N(Cc1ccc(Br)cc1)S(=O)(=O)c1ccc(Cl)cc1]

or a pharmaceutically acceptable salt thereof.

In some embodiments, the GSI is a compound of formula (VIII):

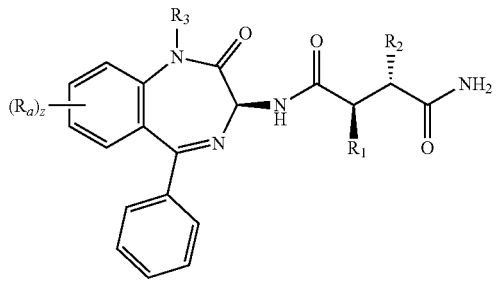

(VIII)

or a pharmaceutically acceptable salt thereof, where $R_1$ is —$CH_2CF_3$ or —$CH_2CH_2CF_3$; $R_2$ is —$CH_2CF_3$, —$CH_2CH_2CF_3$, or —$CH_2CH_2CH_2CF_3$; $R_3$ is hydrogen or —$CH_3$; each $R_a$ is independently F, Cl, —CN, —$OCH_3$, and/or —$NHCH_2CH_2OCH_3$; and z is 0, 1, or 2.

In some embodiments, $R_1$ is —$CH_2CH_2CF_3CH_2CH_2CF_3$. In some embodiments, $R_2$—$CH_2CH_2CF_3$. In some embodiments, $R_3$ is —$CH_3$. In some embodiments, z is 0.

In some embodiments, the GSI is a compound described in U.S. Pat. No. 8,629,136. In one embodiment, the GSI is BMS-906024, i.e., (2R,3S)—N-[(3S)-1-methyl-2-oxo-5-phenyl-2,3-dihydro-1H-1,4-benzodiazepin-3-yl]-2,3-bis(3,3,3-trifluoropropyl)succinamide, or a pharmaceutically acceptable salt thereof. In one embodiment, the GSI is

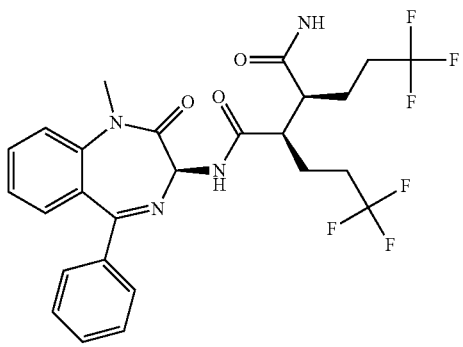 [SMILES: CN1C(=O)[C@@H](NC(=O)[C@H](CCC(F)(F)F)[C@H](CCC(F)(F)F)C(N)=O)N=C(c2ccccc2)c2ccccc21]

or a pharmaceutically acceptable salt thereof.

In some embodiments, the GSI is a compound described in U.S. Pat. No. 8,629,136. In one embodiment, the GSI is LY3039478, i.e., crenigacestat or 4,4,4-trifluoro-N—((R)-1-(((S)-5-(2-hydroxyethyl)-6-oxo-6,7-dihydro-5H-benzo[d]pyrido[2,3-b]azepin-7-yl)amino)-1-oxopropan-2-yl)butanamide, or a pharmaceutically acceptable salt thereof. In some embodiments, the GSI is:

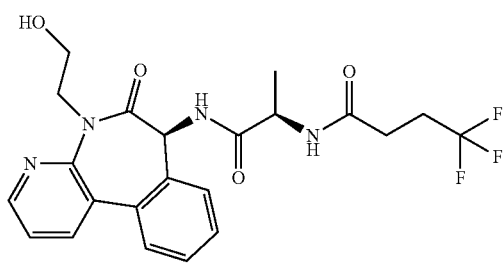 [SMILES: C[C@@H](NC(=O)CCC(F)(F)F)C(=O)N[C@@H]1C(=O)N(CCO)c2ncccc2-c2ccccc21]

or a pharmaceutically acceptable salt thereof.

In some embodiments, the GSI is BMS-299897, i.e., 2-[(1R)-1-[[(4-chlorophenyl)sulfonyl](2,5-difluorophenyl)amino]ethyl-5-fluorobenzenebutanoic acid or a pharmaceutically acceptable salt thereof. In some embodiments, the GSI is

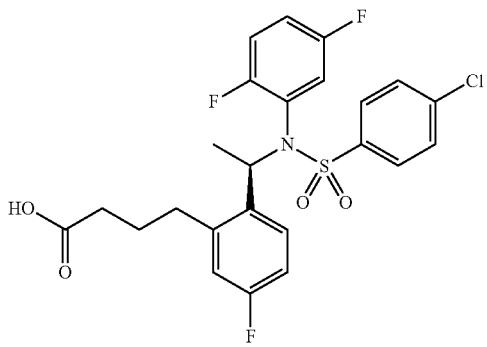 [SMILES: C[C@H](c1ccc(F)cc1CCCC(=O)O)N(c1cc(F)ccc1F)S(=O)(=O)c1ccc(Cl)cc1]

or a pharmaceutically acceptable salt thereof.

In some embodiments, the GSI is LY-411575, i.e., LSN-411575, (S)-2-((S)-2-(3,5-difluorophenyl)-2-hydroxyacetamido)-N—((S)-5-methyl-6-oxo-6,7-dihydro-5H-dibenzo[b,d]azepin-7-yl)propanamide, or a pharmaceutically acceptable salt thereof. In some embodiments, the GSI is

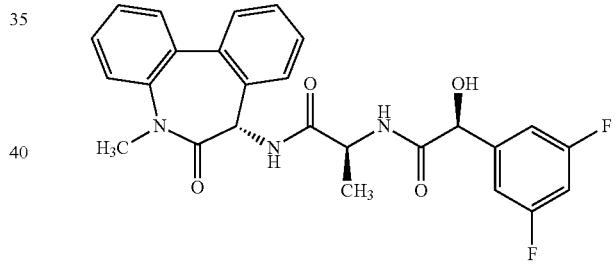

or a pharmaceutically acceptable salt thereof.

In some embodiments, the GSI is DAPT, i.e., N-[(3,5-difluorophenyl)acetyl]-L-alanyl-2-phenyl]glycine-1,1-dimethylethyl ester or a pharmaceutically acceptable salt thereof. In some embodiments, the GSI is

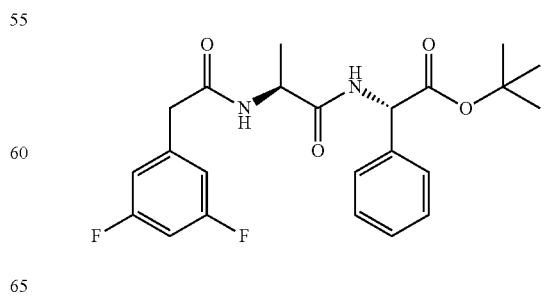

or a pharmaceutically acceptable salt thereof.

In some embodiments, the GSI is a compound of the following formulae:

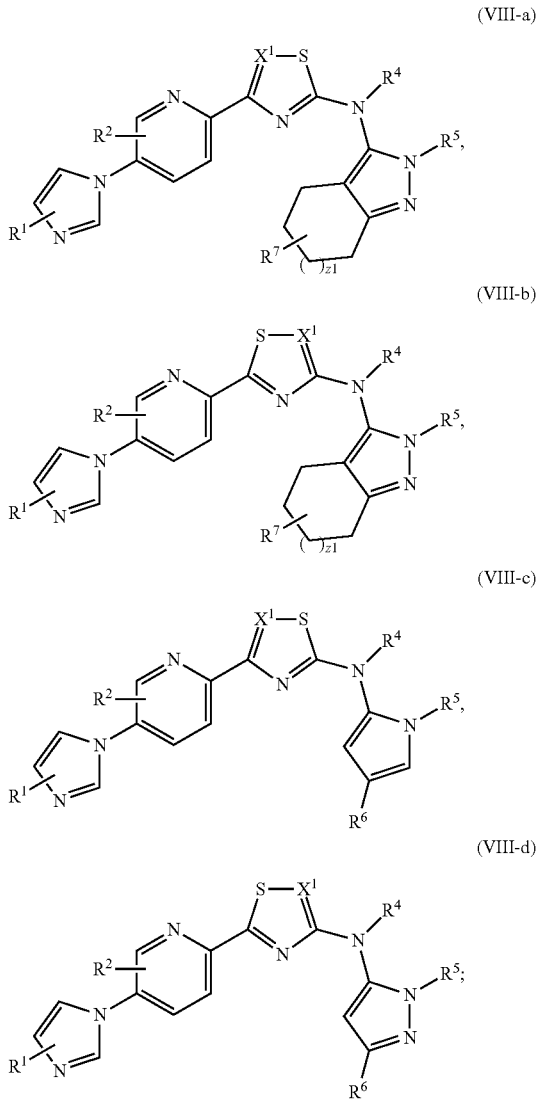

(VIII-a)

(VIII-b)

(VIII-c)

(VIII-d)

where, z1 is 0, 1 or 2; $X^1$ is $C(R^3)$ or N; $R^1$ is hydrogen, halogen, —$N_3$, —$CF_3$, —$CCl_3$, —$CBr_3$, —$Cl_3$, —CN, —CHO, —$OR^{1A}$, —$NR^{1A}R^{1B}$, —$COOR^{1A}$, —$C(O)NR^{1A}R^{1B}$, —$NO_2$, —$SR^{1A}$, —$S(O)_{n1}OR^{1A}$, —$S(O)_{n1}NR^{1A}R^{1B}$, —$NHNR^{1A}R^{1B}$, —$ONR^{1A}R^{1B}$, —$NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$N_3$, —$CF_3$, —$CCl_3$, —$CBr_3$, —$Cl_3$, —CN, —CHO, —$OR^{2A}$, —$NR^{2A}R^{2B}$, —$OOR^{2A}$, —$C(O)NR^{2A}R^{2B}$, —$NO_2$, —$SR^{2A}$, —$S(O)_{n2}R^{2A}$, —$S(O)_{n2}OR^{2A}$, —$S(O)_{n2}NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$N_3$, —$CF_3$, —$CCl_3$, —$CBr_3$, —$Cl_3$, —CN, —CHO, —$OR^{3A}$, —$NR^{3A}R^{3B}$, —$COOR^{3A}$, —$C(O)NR^{3A}R^{3B}$, —$NO_2$, —$SR^{3A}$, —$S(O)_{n3}R^{3A}$, —$S(O)_{n3}OR^{3A}$, —$S(O)_{n3}ONR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$N_3$, —$CF_3$, —$CCl_3$, —$CBr_3$, —$Cl_3$, —CN, —CHO, —$OR^{4A}$, —$NR^{4A}R^{4B}$, —$COOR^{4A}$, —$C(O)NR^{4A}R^{4B}$, —$NO_2$, —$SR^{4A}$, —$S(O)_{n4}R^{4A}$, —$S(O)_{n4}OR^{4A}$, —$S(O)_{n4}NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, —$N_3$, —$CF_3$, —$CCl_3$, —$CBr_3$, —$Cl_3$, —CN, —CHO, —$OR^{5A}$, —$NR^{5A}R^{5B}$, —$COOR^{5A}$, —$C(O)NR^{5A}R^{5B}$, —$NO_2$, —$SR^{5A}$, —$S(O)_{n5}R^{5A}$, —$S(O)_{n5}OR^{5A}$, —$S(O)_{n5}NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, where $R^4$ and $R^5$ are optionally joined together to form a substituted or unsubstituted heterocycloalkyl, or substituted or unsubstituted heteroaryl; $R^6$ is —$CF_3$, substituted or unsubstituted cyclopropyl, or substituted or unsubstituted cyclobutyl; $R^7$ is independently hydrogen, halogen, —$N_3$, —$CF_3$, —$CCl_3$, —$CBr_3$, —$Cl_3$, —CN, —CHO, —$OR^{7A}$, —$NR^{7A}R^{7B}$, —$COOR^{7A}$, —$C(O)NR^{7A}R^{7B}$, —$NO_2$, —$SR^{7A}$, —$S(O)_{n7}R^{7A}$, —$S(O)_{n7}OR^{7A}$, —$S(O)_{n7}NR^{7A}R^{7B}$, —$NHNR^{7A}R^{7B}$, —$ONR^{7A}R^{7B}$, —$NHC(O)NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{7A}$ and $R^{7B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5 and n7 are independently 1 or 2.

In some embodiments, the GSI of formulae (VIII-a), (VIII-b), (VIII-c), or (VIII-d) is described in International Patent Publication No. WO 2014/165263 (e.g., in embodiments P1-P12). In some embodiments, the GSI of formulae (VIII-a), (VIII-b), (VIII-c), or (VIII-d) is selected from:

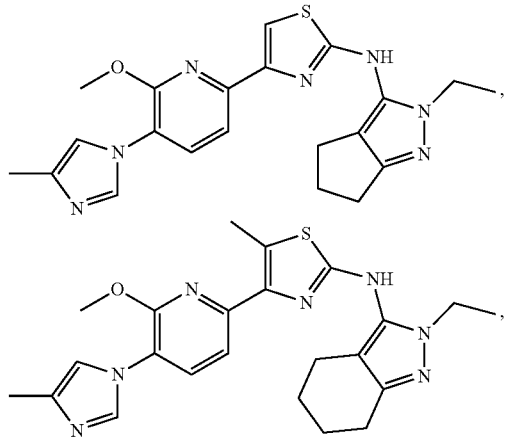

-continued

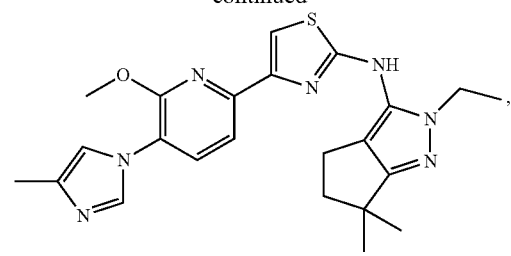

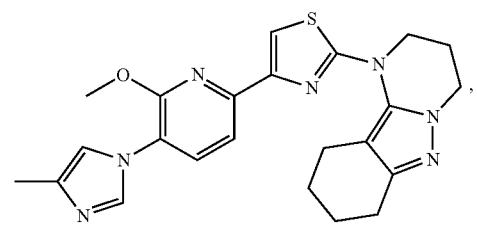

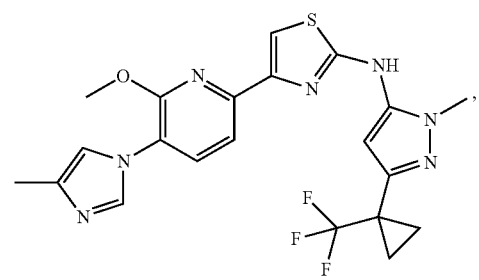

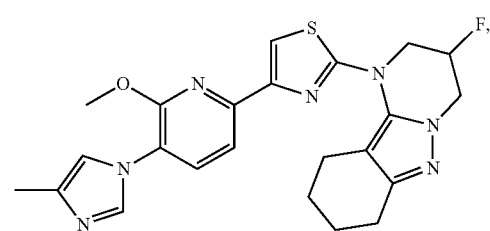

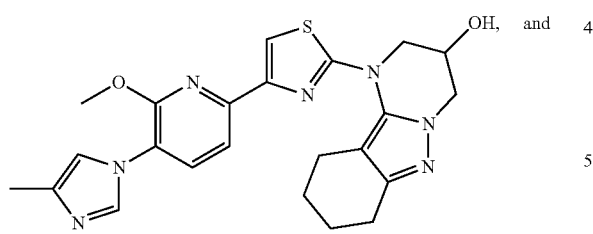

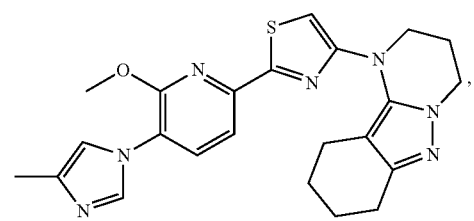

or a pharmaceutically acceptable salt thereof.

In some embodiments, the GSI is a compound of formula (IX):

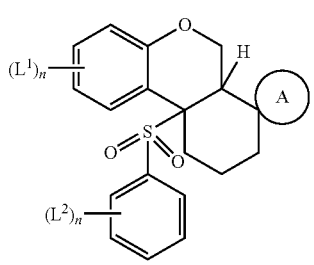

(XIV)

or a pharmaceutically acceptable salt thereof, where A is a 4 to 7 membered spirocyclic ring comprising at least one heteroatom selected from the group consisting of N, O, S, $S(O)_2$, $P(O)R^1$, and $N—S(O)_2—R^1$, where the spirocyclic ring is optionally substituted with 1 to 3 substituents selected from the group consisting of C1-3alkyl and =O; $R^1$ is C1-6alkyl optionally substituted with halo; each $L^1$ is independently selected from the group consisting of 1) C1-3alkyl optionally substituted with halo, and 2) halo; each $L^2$ is independently selected from the group consisting of 1) C1-3alkyl optionally substituted with halo, and 2) halo; and n is 0 to 3.

In some embodiments, the GSI is a compound described in U.S. Patent Publication No. US-2015-307533 (e.g., in the Table on pages 13-16). In some embodiments, the GSI of formula (IX) is selected from:

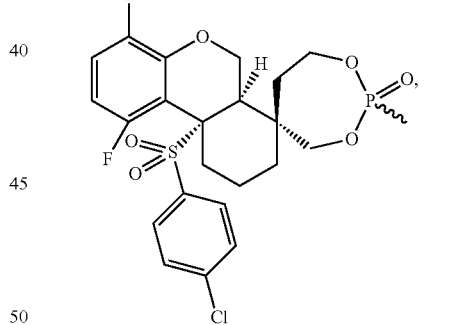

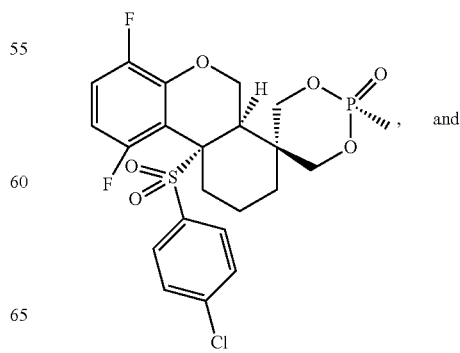

-continued

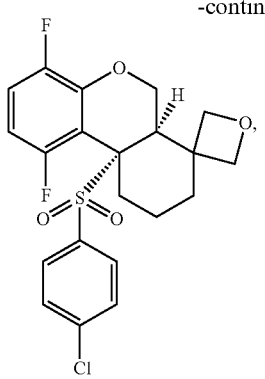

or a pharmaceutically acceptable salt thereof.

In some embodiments, the GSI is a compound of formula (X):

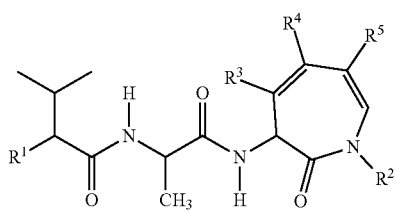

(X)

or a pharmaceutically acceptable salt thereof, where $R^1$ is hydroxy or fluoro; $R^2$ is $C_1$-$C_4$ alkyl; $R^3$ is hydrogen or phenyl; $R^4$ is hydrogen, phenyl, or $C_1$-$C_4$ alkyl; $R^5$ is hydrogen or phenyl; provided that one of $R^3$, $R^4$, and $R^5$ is other than hydrogen and the other two are hydrogen.

In some embodiments, the GSI is a compound in U.S. Pat. No. 8,188,069. In one embodiment, the GSI is

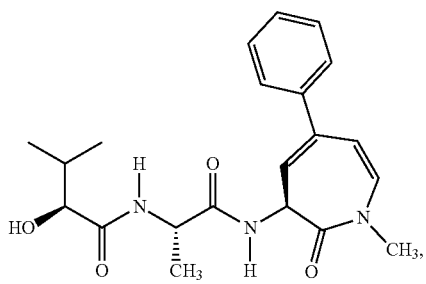 [SMILES: CC(C)[C@H](O)C(=O)N[C@@H](C)C(=O)N[C@H]1C=C(c2ccccc2)C=CN(C)C1=O]

or a pharmaceutically acceptable salt thereof.

In some embodiments, the GSI is a compound of formula (XI):

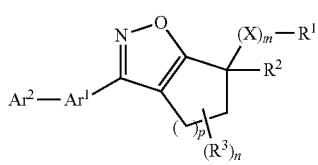

(XI)

or a pharmaceutically acceptable salt thereof, where: $R^1$ is 1) hydrogen, 2) (C1-C6)alkyl optionally substituted with 1 to 5 halogens or phenyl, where the phenyl is optionally substituted with 1 to 3 halogens, 3) phenyl optionally substituted with 1 to 3 (C1-C6)alkyls or 1 to 5 halogens, or 4) (C4-C6)cycloalkyl optionally substituted with 1 to 3 (C1-C6)alkyls or 1 to 5 halogens; $R^2$ is 1) hydrogen, 2) (C1-C6)alkyl optionally substituted with 1 to 5 halogens or phenyl, where the phenyl is optionally substituted with 1 to 3 halogens, or 3) phenyl optionally substituted with 1 to 3 halogens; $R^3$ is (C1-C6)alkyl, —OH or halogen;

X is —$NR^4$—, —O—, —S—, or —$SO_2$—; $R^4$ is hydrogen or (C1-C3)alkyl;

p is 1 to 3; m is 0 or 1; n is 0 to 3; and $Ar^2$-$Ar^1$ is selected from the group consisting of:

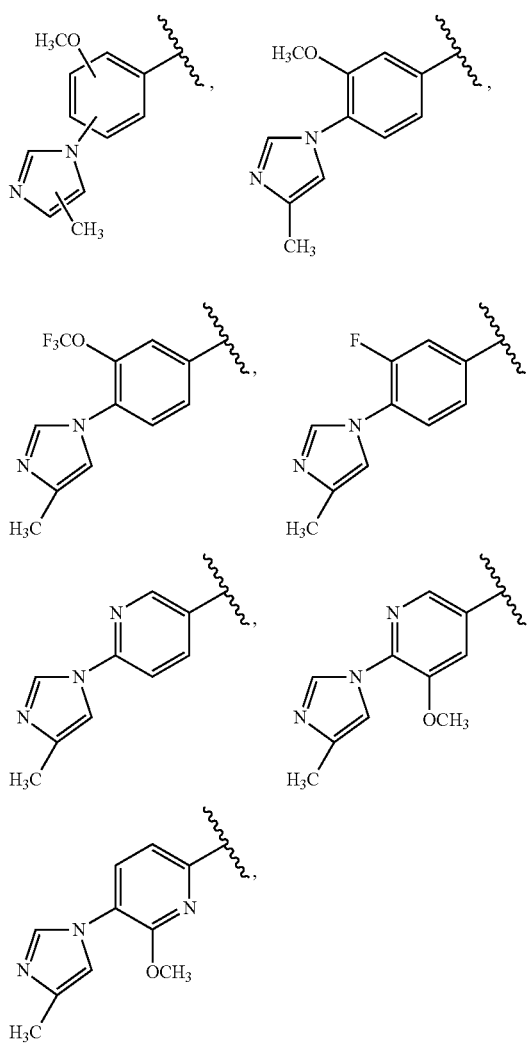

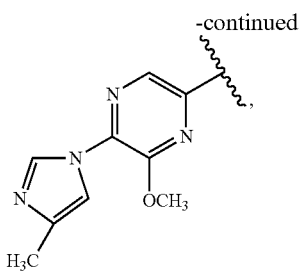

or a pharmaceutically acceptable salt thereof.

In some embodiments, the GSI is a compound described in U.S. Pat. No. 9,096,582 (e.g., in the Table on pages 13-17). In some embodiments, the GSI is selected from:

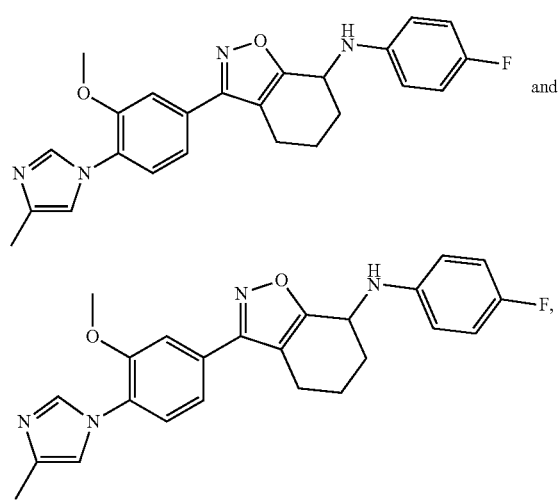

or a pharmaceutically acceptable salt thereof.

In some embodiments, the GSI is a compound of formula (XII):

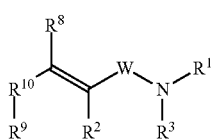

(XII)

or a pharmaceutically acceptable salt thereof, where or the pharmaceutically acceptable salts thereof, where: $R^1$, $R^2$, $R^3$, $R^8$, $R^9$, $R^{10}$, and W are independently selected; W is selected from the group consisting of; —S(O)—, and —S(O)$_2$—; $R^1$ is selected from the group consisting of H, alkyl-, alkenyl-, alkynyl-, aryl-, arylalkyl-, alkylaryl-, cycloalkyl-, cycloalkenyl-, cycloalkylalkyl-, fused benzocycloalkyl (i.e., benzo-fusedcycloalkyl), fused benzoheterocycloalkyl (i.e., benzo-fusedheterocycloalkyl), fused heteroarylcycloalkyl (i.e., heteroarylfusedcycloalkyl), fused heteroarylheterocycloalkyl (i.e., heteroarylfused-heterocycloalkyl), heteroaryl-, heteroarylalkyl-, heterocyclyl-, heterocyclenyl, -and heterocyclyalkyl-; where each of the alkyl-, alkenyl- and alkynyl-, aryl-, arylalkyl-, alkylaryl-, cycloalkyl-, cycloalkenyl-, cycloalkylalkyl-, fused benzocycloalkyl, fused benzohetero- cycloalkyl, fused heteroarylcycloalkyl, fused heteroarylheterocycloalkyl, heteroaryl-, heteroarylalkyl-, heterocyclyl-, heterocyclenyl and heterocyclyalkyl-$R^1$ groups is optionally substituted with 1-5 independently selected $R^{21}$ groups; $R^2$ and $R^3$ are each independently selected from the group consisting of H, alkyl-, alkenyl-, alkynyl-, aryl-, arylalkyl-, alkylaryl-, cycloalkyl-, cycloalkenyl-, cycloalkylalkyl-, heteroaryl-, heteroarylalkyl-, heterocyclyl-, heterocyclenyl-, and heterocyclyalkyl-; where each of the alkyl-, alkenyl- and alkynyl-, aryl-, arylalkyl-, alkylaryl-, cycloalkyl-, cycloalkenyl, cycloalkylalkyl-, cycloalkenyl-, heteroaryl-, heteroarylalkyl-, heterocyclyl-, heterocyclenyl- and heterocyclyalkyl-$R^1$ groups is optionally substituted with 1-5 independently selected $R^{21}$ groups; or $R^2$ and $R^3$ taken together, along with the atoms to which they are bound, form a ring selected from the group consisting of: (a) a 5 to 6 membered heterocycloalkyl ring, the heterocycloalkyl ring optionally comprising, in addition to W and in addition to the N adjacent to W, at least one other heteroatom independently selected from the group consisting of: —O—, —S(O)—, —S(O)$_2$, and —C(O)—, and (b) a 5 to 6 membered heterocycloalkenyl ring, the heterocycloalkenyl ring optionally comprising, in addition to W and in addition to the N adjacent to W, at least one other heteroatom independently selected from the group consisting of: —O—, —S(O)—, —S(O)$_2$, and —C(O)—; where the ring is optionally substituted with 1-5 independently selected $R^{21}$ groups; or $R^2$ and $R^3$ taken together along with the atoms to which they are bound, and $R^1$ and $R^3$ are taken together along with the atoms to which they are bound, form the fused ring moiety:

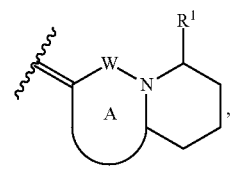

where Ring A is a ring selected from the group consisting of:
(a) a 5 to 6 membered heterocycloalkyl ring, the heterocycloalkyl ring optionally comprising, in addition to W and in addition to the N adjacent to W, at least one other heteroatom independently selected from the group consisting of: —O—, —NR$^{14}$—, —S(O)—, —S(O)$_2$, and —C(O)—, and (b) a 5 to 6 membered heterocycloalkenyl ring, the heterocycloalkenyl ring optionally comprising, in addition to W and in addition to the N adjacent to W, at least one other heteroatom independently selected from the group consisting of: —O—, —NR$^{14}$—, —S(O)—, —S(O)$_2$, and —C(O)—, and where the fused ring moiety is optionally substituted with 1-5 independently selected $R^{21}$ groups; or $R^1$ and $R^3$ taken together with the atoms to which they are bound form a fused benzoheterocycloalkyl ring, and where the fused ring is optionally substituted with 1-5 independently selected $R^{21}$ groups, $R^8$ is selected from the group consisting of H, alkyl-, alkenyl-, alkynyl-, aryl-, arylalkyl-, alkylaryl-, cycloalkyl-, cycloalkenyl, cycloalkylalkyl-, heteroaryl-, heteroarylalkyl-, heterocyclyl-, heterocyclenyl- and heterocyclyalkyl-; where each of the $R^8$ alkyl-, alkenyl- and alkynyl-, aryl-, arylalkyl-, alkylaryl-, cycloalkyl-, cycloalkenyl, cycloalkylalkyl-, heteroaryl-, heteroarylalkyl-, heterocyclyl, heterocyclenyl- and heterocyclyalkyl- is optionally substituted with 1-3 independently selected $R^{21}$ groups; $R^9$ is selected from the group consisting of: alkyl-, alkenyl-, alkynyl-, aryl-, arylalkyl-, alkylaryl-, cycloalkyl-, cycloalkenyl, cycloalkylalkyl, heteroaryl-, heteroarylalkyl-, heterocyclyl-, heterocyclenyl-, and heterocyclyalkyl-, where each of the $R^9$ alkyl-, alkenyl- and alkynyl-, aryl-, arylalkyl-, alkylaryl-, cycloalkyl-, cycloalkenyl, cycloalkyl alkyl-, heteroaryl-, heteroarylalkyl-, heterocyclyl-, heterocyclenyl-, heterocyclyalkyl- and heterocyclyalkyl- is optionally substituted with 1-3 independently selected $R^{21}$ groups;

$R^{10}$ is selected from the group consisting of: a bond, alkyl-, alkenyl-, alkynyl-, aryl-, arylalkyl-, alkylaryl-, cycloalkyl-, cycloalkenyl, cycloalkylalkyl-, heteroaryl-, heteroarylalkyl-, heterocyclyl-, heterocyclenyl-, heterocyclyalkyl-, heterocyclyalkenyl-,

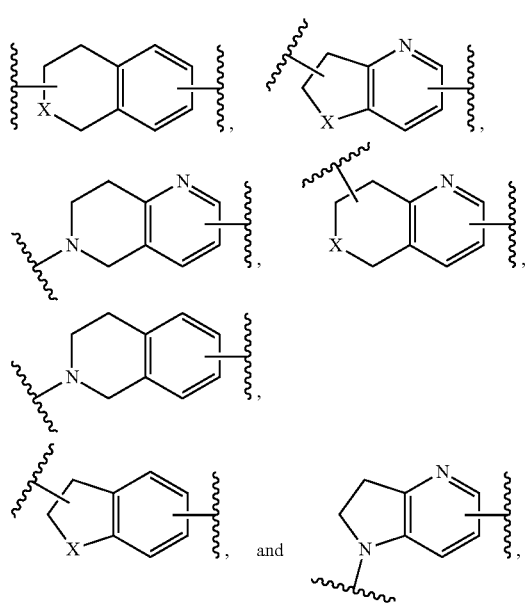

where X is selected from the group consisting of: O, —N($R^{14}$)— or —S—; and where each of the $R^{10}$ moieties is optionally substituted with 1-3 independently selected $R^{21}$ groups; $R^{14}$ is selected from the group consisting of H, alkyl, alkenyl, alkynyl, cycloalkyl, cycloalkylalkyl, cycloalkenyl, heterocyclyl, heterocyclenyl, heterocyclylalkyl, heterocyclyalkenyl-, aryl, arylalkyl, heteroaryl, heteroarylalkyl, —ON, —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$); $R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, ($R^{18}$)$_n$-alkyl, ($R^{18}$)$_n$-cycloalkyl, ($R^{18}$)$_n$-cycloalkylalkyl, ($R^{18}$)$_n$-heterocyclyl, ($R^{18}$)$_n$-heterocyclylalkyl, ($R^{18}$)$_n$-aryl, ($R^{18}$)$_n$-arylalkyl, ($R^{18}$)$_n$-heteroaryl and ($R^{18}$)$_n$-heteroarylalkyl; each $R^{18}$ is independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)$R^{19}$, —C(O)OH, —C(O)O$R^{19}$, —C(O)NH$R^{20}$, —C(O)NH$_2$, —C(O)NH$_2$—C(O)N(alkyl)$_2$, —C(O)N(alkyl)(aryl), —C(O)N(alkyl)(heteroaryl), —S$R^{19}$, —S(O)$_2$$R^{20}$, —S(O)NH$_2$, —S(O)NH(alkyl), —S(O)N(alkyl)(alkyl), —S(O)NH(aryl), —S(O)$_2$NH$_2$, —S(O)$_2$NH$R^{19}$, —S(O)$_2$NH(het-erocyclyl), —S(O)$_2$N(alkyl)$_2$, —S(O)$_2$N(alkyl)(aryl), —OCF$_3$, —OH, —O$R^{20}$, —O— heterocyclyl, —O-cycloalkylalkyl, —O-heterocyclylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$$R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl); or two $R^{18}$ moieties on adjacent carbons can be linked together to form a

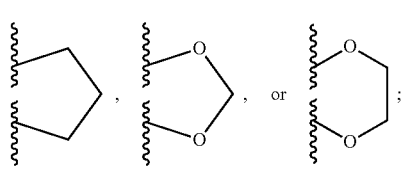

$R^{19}$ is selected from the group consisting of: alkyl, cycloalkyl, aryl, arylalkyl and heteroarylalkyl; $R^{20}$ is selected from the group consisting of: alkyl, cycloalkyl, aryl, halo substituted aryl, arylalkyl, heteroaryl and heteroarylalkyl; each $R^{21}$ is independently selected from the group consisting of: alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —ON, —O$R^{15}$, —C(O)$R^{15}$, —C(O)O$R^{15}$, —C(O)N($R^{15}$)($R^{16}$), —S$R^{15}$, —S(O)N($R^{16}$)($R^{16}$), —CH($R^{15}$)($R^{16}$), —S(O)$_2$N($R^{16}$)($R^{16}$), —C(=NO$R^{16}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —CH$_2$—N($R^{15}$)C(O)N($R^{16}$)($R^{17}$), —OH$_2$—$R^{15}$; —CH$_2$N($R^{15}$)($R^{16}$), —N($R^{15}$)S(O)$R^{16}$, —N($R^{15}$)S(O)$_2$$R^{16}$, —CH$_2$—N($R^{15}$)S(O)$_2$$R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —S(O)$R^{15}$, =NO$R^{15}$, —N$_3$, —NO$_2$ and —S(O)$_2$$R^{15}$; where each of the alkyl, alkenyl, alkynyl, cycloalkyl, cycloalkylalkyl, cycloalkenyl, heterocycloalkyl, heterocycloalkylalkyl, aryl, arylalkyl, heteroaryl, and heteroarylalkyl $R^{21}$ groups is optionally substituted with 1 to 5 independently selected $R^{22}$ groups; and each $R^{22}$ group is independently selected from the group consisting of alkyl, cycloalkyl, cycloalkenyl, heterocycloalkyl, aryl, heteroaryl, halo, —CF$_3$, —CN, —O$R^{15}$, —C(O)$R^{15}$, —C(O)O$R^{15}$, -alkyl-C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —N($R^{15}$)S(O)$R^{16}$, —N($R^{15}$)S(O)$_2$$R^{16}$, —CH$_2$—N($R^{15}$)S(O)$_2$$R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$); —N($R^{15}$)C(O)O$R^{16}$, —CH$_2$—N($R^{15}$)C(O)O$R^{16}$, —N$_3$, =NO$R^{15}$, —NO$_2$, —S(O)$R^{15}$ and —S(O)$_2$$R^{15}$.

In some embodiments, the GSI is a compound described in U.S. Patent Publication No. US-2011-0257163 (e.g., in paragraphs [0506] to [0553]) In some embodiments, the GSI of formula (XII) is a pharmaceutically acceptable ester. In some embodiments, the GSI of formula (XII) is selected from:

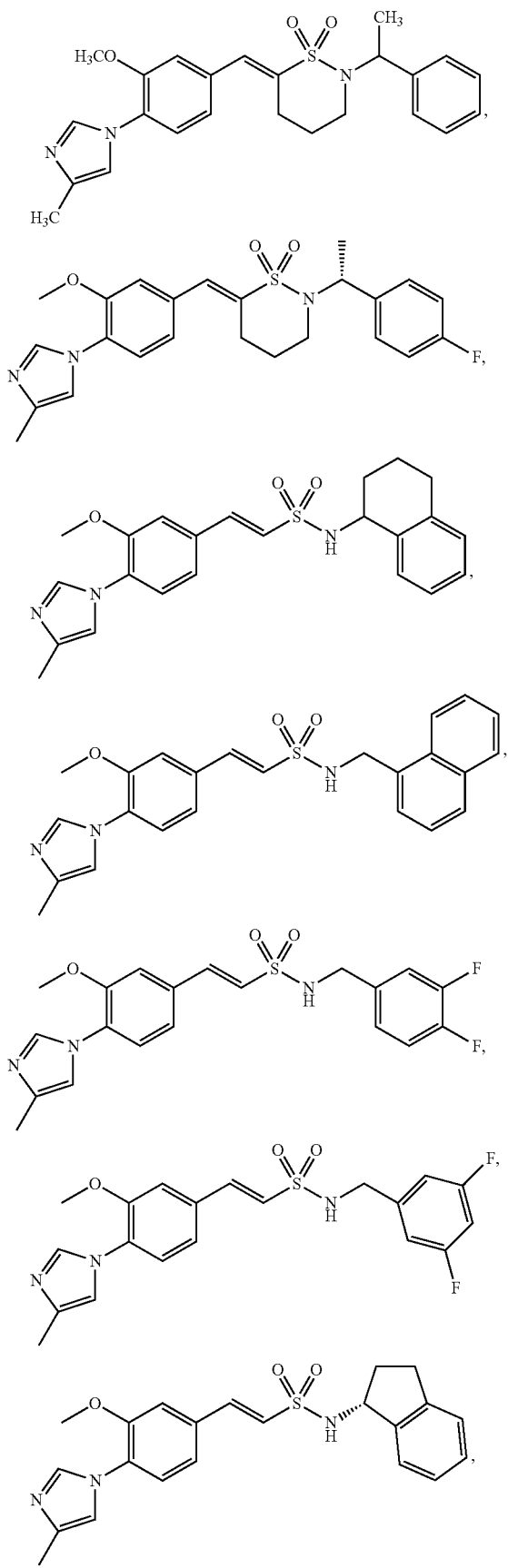

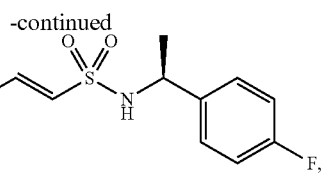

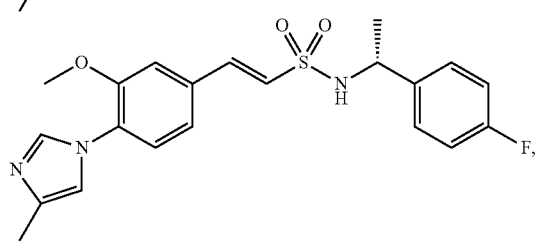

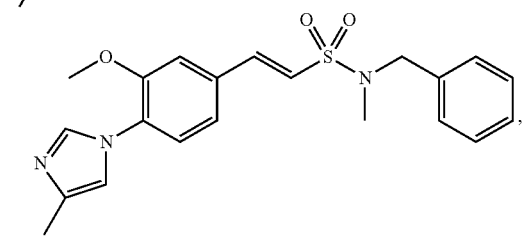

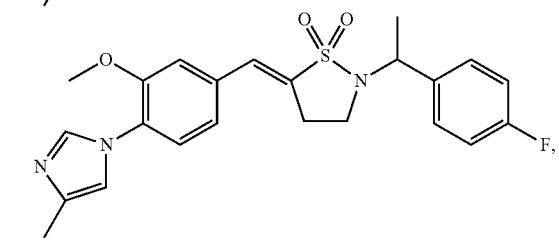

and pharmaceutically acceptable salts thereof.

In some embodiments, the GSI is a compound of formula (XIII):

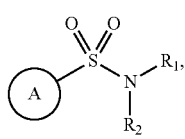

(XIII)

or a pharmaceutically acceptable salt thereof, where the A-ring is aryl, cycloalkyl, heteroaryl or heterocycloalkyl, where each ring is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenoxy, —S(O)$_{0-2}$—($C_1$-$C_6$ alkyl), —NR$_{10}$R$_{11}$, $C_1$-$C_6$ alkanoyl, $C_0$-$C_3$alkylCO$_2$R', heteroaryl, heterocycloalkyl, aryl, aralkyl, or —SO$_2$NR$_{10}$R$_{11}$; $R_1$ and $R_2$ combine to form a [3.3.1] or a [3.2.1] ring system, where 0 or 1 of the carbons in the ring system is optionally replaced with an —O—, —S(O)$_x$—, or —NR$_{15}$— group; and where the [3.3.1] or [3.2.1] ring system is optionally substituted with 1, 2, 3, or 4 groups that are independently oxo, halogen, $C_1$-$C_6$ alkyl, —O($C_1$-$C_2$ alkyl)O—, —S($C_1$-$C_2$ alkyl)S—, $C_2$-$C_6$ alkenyl, $C_1$-$C_6$ haloalkyl, $C_2$-$C_6$ alkynyl, hydroxy, hydroxyalkyl, $C_1$-$C_6$ alkoxy, haloalkoxy, —C(O)OR$_{13}$, —($C_1$-$C_4$ alkyl)-C(O)OR$_{16}$, —CONR$_{10}$R$_{11}$, —OC(O)NR$_{10}$R$_{11}$, —NR'C(O)OR", —NR'S(O)$_2$R", —OS(O)$_2$R', —NR-'COR", CN, =N—NR$_{12}$, or =N—O—R$_{13}$; where x is 0, 1, or 2; R$_{10}$ and R$_{11}$ at each occurrence are independently hydrogen or C$_1$-C$_6$ alkyl, where the alkyl is optionally substituted with an aryl, where the aryl is optionally substituted with 1 to 5 groups that are independently halogen, hydroxyl, alkyl, alkoxy, haloalkyl, haloalkoxy, CN or NO$_2$; or R$_{10}$ and R$_{11}$ together can form a 3-8 membered ring optionally including an additional heteroatom such as N, O or S; R$_{12}$ is hydrogen, C$_1$-C$_6$ alkyl or —SO$_2$-aryl, where the aryl is optionally substituted with 1 to 5 groups that are independently halogen, hydroxyl, alkyl, alkoxy, haloalkyl, haloalkoxy, CN or NO$_2$; R$_{13}$ is hydrogen or C$_1$-C$_6$ alkyl optionally substituted with aryl, hydroxyl, or halogen, where the aryl is optionally substituted with 1 to 5 groups that are independently halogen, hydroxyl, alkyl, alkoxy, haloalkyl, haloalkoxy, CN or NO$_2$;

R$_{15}$ is hydrogen, aryl, heteroaryl, —SO$_2$R', —C(O)R', —C(O)OR', or C$_1$-C$_6$ alkyl optionally substituted with aryl, hydroxyl, or halogen, where the aryl groups are optionally substituted with 1 to 5 groups that are independently halogen, hydroxyl, alkyl, alkoxy, haloalkyl, haloalkoxy, CN or NO$_2$; and R' and R" are independently hydrogen, C$_1$-C$_6$ alkyl, haloalkyl, C$_2$-C$_6$ alkenyl or phenyl optionally substituted with 1 to 5 groups that are independently halogen, C$_1$-C$_6$ alkyl, —C(O)OR', C$_1$-C$_6$ alkoxy, haloalkyl, haloalkoxy, hydroxyl, CN, phenoxy, —SO$_2$—(C$_1$-C$_6$ alkyl), —NR$_{10}$R$_{11}$, C$_1$-C$_6$ alkanoyl, pyridyl, phenyl, NO$_2$, or —SO$_2$NR$_{10}$R$_{11}$.

In some embodiments, the GSI of formula (XIII) is described in U.S. Patent Publication No. US-2011-178199 (e.g., in paragraphs [0798] to [0799] and Tables 1-4). In some embodiments, the GSI of formula (XIII) comprises a bridged n-bicyclic sulfonamide or a pharmaceutically acceptable salt thereof. In some embodiments, the GSI of formula (XIII) is selected from:

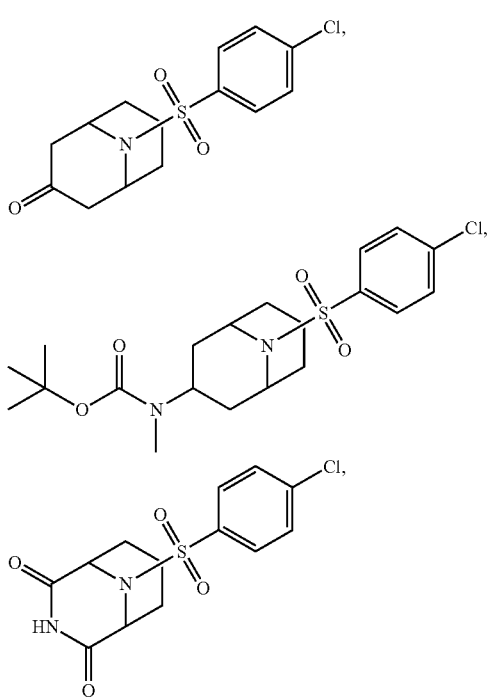

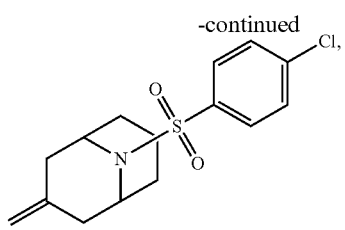

and pharmaceutically acceptable salts thereof.

In some embodiments, the GSI is a compound of formula (XIV):

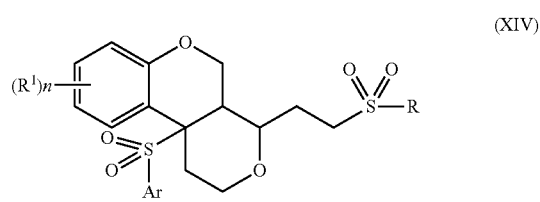

or a pharmaceutically acceptable salt thereof, where R is selected from the group consisting of: (1) -pyridinyl, (2) -pyrazolinyl, (3) -1,2,4-oxadiazolyl, (4) —(C1-C2) alkyl-pyridinyl, (5) —(C1-C2)alkyl-pyrazolinyl, and (6) —(C1-C2)alkyl-1,2,4-oxadiazolyl, where the pyridinyl, pyrazolinyl, and -1,2,4-oxadiazolyl, is unsubstituted or substituted with one L$^1$ group; R$^1$ is independently selected from the group consisting halogen, (C1-C6)alkyl, —CN, —CF$_3$, —O—(C1-C6)alkyl, —O-(halo(C1-C6)alkyl), —C(O)—O—(C1-C6)-OH-substituted (C1-C4)alkyl, halo(C1-C6)alkyl, —(C1-C4)alkoxy-OH, —(C1-C4)alkoxy(C1-C4)alkoxy and —S(O)$_2$(C1-C6)alkyl; n is 0, 1, 2, or 3; Ar is selected from the group consisting of phenyl optionally substituted with 1 or 2 L$^2$ groups, and pyridyl optionally substituted with 1 or 2 L$^2$ groups;

L$^1$ is independently selected from the group consisting of —OCH$_3$, —NH$_2$, =O, and (C1-C5)alkyl; and L$^2$ is independently selected from the group consisting of halogen, (C1-C6)alkyl, —CN, —CF$_3$, —O—(C1-C6) alkyl, —O-(halo(C1-C6)alkyl), —C(O)—O—(C1-C6) alkyl, —OH-substituted (C1-C6)alkyl, halo(C1-C6)alkyl, —OH-substituted (C1-C4)alkoxy, —(C1-C4) alkoxy(C1-C4)alkoxy and —S(O)$_2$(C1-C6)alkyl.

In some embodiments, the GSI is a compound described in U.S. Pat. No. 9,226,927 (e.g., compound 4, 8a, 8b, 11, 14, 25a, 25b, 25c, 25d, 25e, 25f, 25g, 25h, 27a, or 27b). In some embodiments, the GSI of formula (XIV) comprises a bridged n-bicyclic sulfonamide or a pharmaceutically acceptable salt thereof. In some embodiments, the GSI of formula (XIV) is selected from:

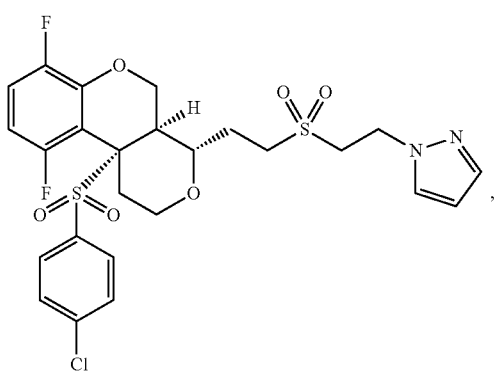

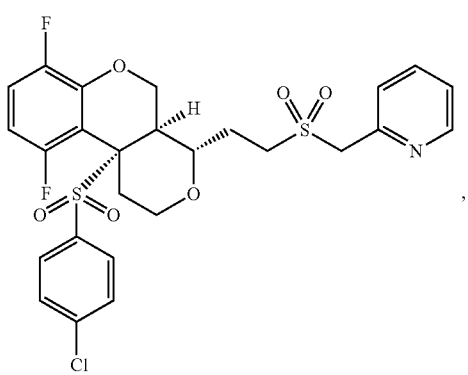

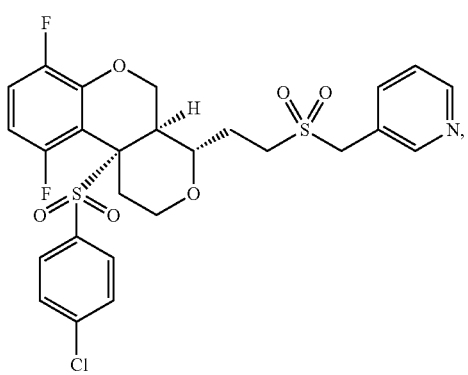

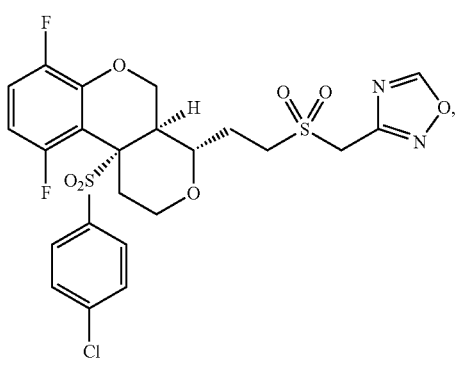

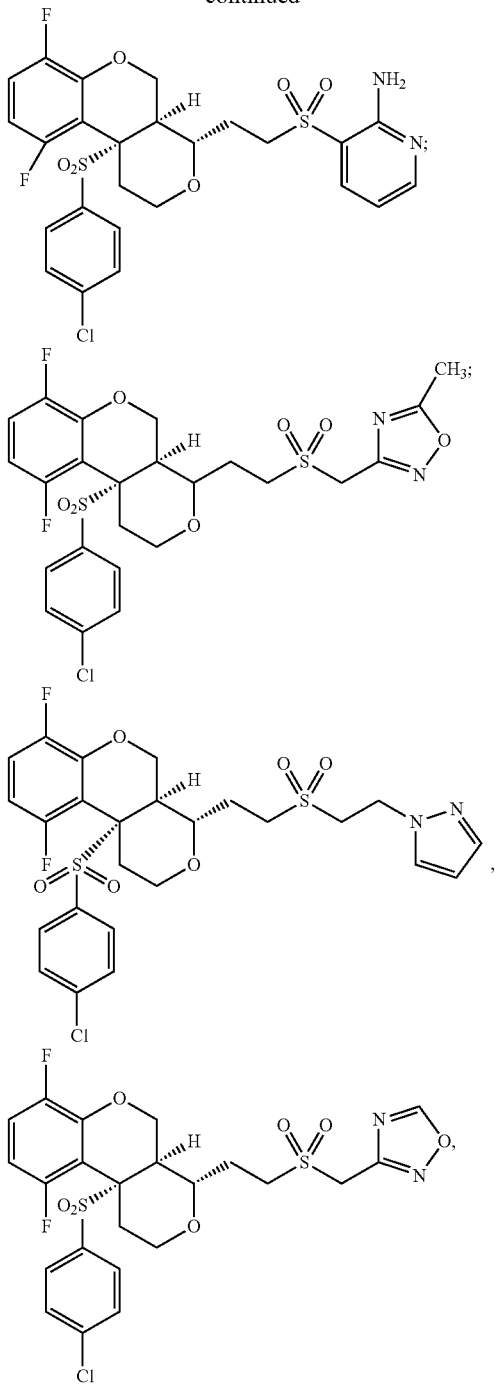

and pharmaceutically acceptable salts thereof.

In some embodiments, the GSI is an antibody molecule that reduces the expression and/or function of gamma secretase. In some embodiments, the GSI is an antibody molecule targeting a subunit of gamma secretase. In some embodiments, the GSI is chosen from an anti-presenilin antibody molecule, an anti-nicastrin antibody molecule, an anti-APH-1 antibody molecule, or an anti-PEN-2 antibody molecule.

Exemplary antibody molecules that target a subunit of gamma secretase (e.g., e.g., presenilin, nicastrin, APH-1, or PEN-2) are described in U.S. Pat. Nos. 8,394,376, 8,637,274, and 5,942,400.

In one aspect, the disclosure provides a method for treating subjects having a B cell condition or disorder, comprising administering to the subject an effective amount of: (i) a BCMA binding molecule, and (ii) a gamma secretase modulator (e.g., a GSI). Exemplary B cell conditions or disorders that can be treated with the combination of a BCMA binding molecule and a gamma secretase modulator include multiple myeloma, Waldenstrom's macroglobulinemia, chronic lymphocytic leukemia, B cell non-Hodgkin's lymphoma, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, rapidly progressive glomerulonephritis, heavy-chain disease, primary or immunocyte-associated amyloidosis, and monoclonal gammopathy of undetermined significance.

In some embodiments, the gamma secretase modulator is a gamma secretase modulator described in WO 2017/019496. In some embodiments, the gamma secretase modulator is γ-secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor IV (GSI IV); γ-secretase inhibitor V (GSI V), N-Benzyloxycarbonyl-Leu-phenylalaninal; γ-secretase inhibitor VI (GSI VI), 1-(S)-endo-N-(1,3,3)-Trimethylbicyclo[2.2.1]hept-2-yl)-4-fluorophenyl Sulfonamide; γ-secretase inhibitor VII (GSI VII), Menthyloxycarbonyl-LL-CHO; γ-secretase inhibitor IX (GSI IX), (DAPT), N—[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N—[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal; Isovaleryl-V V-Sta-A-Sta-OCH$_3$; MK-0752 (Merck); MRK-003 (Merck); semagacestat/LY450139 (Eli Lilly); RO4929097; PF-03084014; BMS-708163; MPC-7869 (γ-secretase modifier), YO-01027 (Dibenzazepine); LY411575 (Eli Lilly and Co.); L-685458 (Sigma-Aldrich); BMS-289948 (4-chloro-N-(2,5-difluorophenyl)-N—((IR)-{4-fluoro-2-[3-(1H-imidazol-1-yl)propyl]phenyl}ethyl)benzenesulfonamide hydrochloride); or BMS-299897 (4-[2-((IR)-1-{[(4-chlorophenyl)sulfonyl]-2,5-difluoroanilino}ethyl)-5-fluorophenyl]butanoic acid) (Bristol Myers Squibb).

In some embodiments, a BCMA binding molecule can be used in combination with a member of the thalidomide class of compounds. Members of the thalidomide class of compounds include, but are not limited to, lenalidomide (CC-5013), pomalidomide (CC-4047 or ACTIMID), thalidomide, and salts and derivatives thereof. In some embodiments, the BCMA binding molecule is used in combination with a mixture of one, two, three, or more members of the thalidomide class of compounds. Thalidomide analogs and immunomodulatory properties of thalidomide analogs are described in Bodera and Stankiewicz, Recent Pat Endocr Metab Immune Drug Discov. 2011 September; 5(3): 192-6. The structural complex of thalidomide analogs and the E3 ubiquitin is described in Gandhi et al., Br J Haematol. 2014 March; 164(6):811-21. The modulation of the E3 ubiquitin ligase by thalidomide analogs is described in Fischer et al., Nature. 2014 Aug. 7; 512(7512):49-53.

In some embodiments, the member of the thalidomide class of compounds comprises a compound of Formula I:

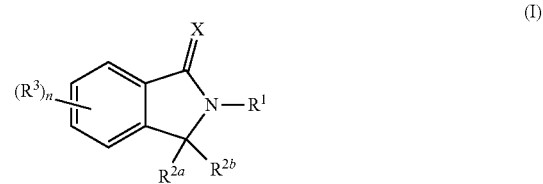

(I)

or a pharmaceutically acceptable salt, ester, hydrate, solvate, or tautomer thereof, where:

X is O or S;

$R^1$ is $C_1$-$C_6$ alkyl, $C_2$-$C_6$ alkenyl, $C_2$-$C_6$ alkynyl, $C_1$-$C_6$ heteroalkyl, carbocyclyl, heterocyclyl, aryl, or heteroaryl, each of which is optionally substituted by one or more $R^4$;

each of $R^{2a}$ and $R^{2b}$ is independently hydrogen or $C_1$-$C_6$ alkyl; or $R^{2a}$ and $R^{2b}$ together with the carbon atom to which they are attached form a carbonyl group or a thiocarbonyl group;

each of $R^3$ is independently $C_1$-$C_6$ alkyl, $C_2$-$C_6$ alkenyl, $C_2$-$C_6$ alkynyl, $C_1$-$C_6$ heteroalkyl, halo, cyano, —C(O)$R^A$, —(O)O$R^B$, —O$R^B$, —N($R^C$)($R^D$), —C(O)N($R^C$)($R^D$), —N($R^C$)C(O)$R^A$, —S(O)$_x$$R^E$, —S(O)$_x$N($R^C$)($R^D$), or —N($R^C$)S(O)$_x$$R^E$, where each alkyl, alkenyl, alkynyl, and heteroalkyl is independently and optionally substituted with one or more $R^6$;

each $R^4$ is independently $C_1$-$C_6$ alkyl, $C_2$-$C_6$ alkenyl, $C_2$-$C_6$ alkynyl, $C_1$-$C_6$ heteroalkyl, halo, cyano, oxo, —C(O)$R^A$, —(O)O$R^B$, —O$R^B$, —N($R^C$)($R^D$), —C(O)N($R^C$)($R^D$), —N($R^C$)C(O)$R^A$, —S(O)$_x$$R^E$, —S(O)$_x$N($R^C$)($R^D$), —N($R^C$)S(O)$_x$$R^E$, carbocyclyl, heterocyclyl, aryl, or heteroaryl, where each alkyl, alkenyl, alkynyl, heteroalkyl, carbocyclyl, heterocyclyl, aryl, and heteroaryl is independently and optionally substituted with one or more $R^7$;

each of $R^A$, $R^B$, $R^C$, $R^D$, and $R^E$ is independently hydrogen or $C_1$-$C_6$ alkyl;

each $R^6$ is independently $C_1$-$C_6$ alkyl, oxo, cyano, —$OR^B$, —$N(R^C)(R^D)$, —$C(O)N(R^C)(R^D)$, —$N(R^C)C(O)R^A$, aryl, or heteroaryl, where each aryl and heteroaryl is independently and optionally substituted with one or more $R^8$;

each $R^7$ is independently halo, oxo, cyano, —$OR^B$, —$N(R^C)(R^D)$, —$C(O)N(R^C)(R^D)$, or —$N(R^C)C(O)R^A$;

each $R^8$ is independently $C_1$-$C_6$ alkyl, cyano, —$OR^B$, —$N(R^C)(R^D)$, —$C(O)N(R^C)(R^D)$, or —$N(R^C)C(O)R^A$;

n is 0, 1, 2, 3 or 4; and x is 0, 1, or 2.

In some embodiments, X is O.

In some embodiments, $R^1$ is heterocyclyl. In some embodiments, $R^1$ is a 6-membered heterocyclyl or a 5-membered heterocyclyl. In some embodiments, $R^1$ is a nitrogen-containing heterocyclyl. In some embodiments, $R^1$ is piperidinyl (e.g., piperidine-2,6-dionyl).

In some embodiments, each of $R^{2a}$ and $R^{2b}$ is independently hydrogen. In some embodiments, $R^{2a}$ and $R^{2b}$ together with the carbon to which they are attached form a carbonyl group.

In some embodiments, $R^3$ is $C_1$-$C_6$ heteroalkyl, —$N(R^C)(R^D)$ or —$N(R^C)C(O)R^A$. In some embodiments, $R^3$ is $C_1$-$C_6$ heteroalkyl (e.g., $CH_2NHC(O)CH_2$-phenyl-t-butyl), —$N(R^C)(R^D)$ (e.g., —$NH_2$), or —$N(R^C)C(O)R^A$ (e.g., NHC(O)$CH_3$).

In an embodiment, X is O. In an embodiment, $R^1$ is heterocyclyl (e.g., piperidine-2,6-dionyl). In an embodiment, each of $R^{2a}$ and $R^{2b}$ is independently hydrogen. In an embodiment, n is 1. In an embodiment, $R^3$ is —$N(R^C)(R^D)$ (e.g., —$NH_2$). In an embodiment, the compound comprises lenalidomide, e.g., 3-(4-amino-1-oxoisoindolin-2-yl)piperidine-2,6-dione, or a pharmaceutically acceptable salt thereof. In an embodiment, the compound is lenalidomide, e.g., according to the following formula:

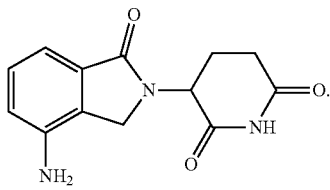 [SMILES: Nc1cccc2c1CN(C1CCC(=O)NC1=O)C2=O]

In an embodiment, X is O. In an embodiment, $R^1$ is heterocyclyl (e.g., piperidinyl-2,6-dionyl). In some embodiments, $R^{2a}$ and $R^{2b}$ together with the carbon to which they are attached form a carbonyl group. In an embodiment, n is 1. In an embodiment, $R^3$ is —$N(R^C)(R^D)$ (e.g., —$NH_2$). In an embodiment, the compound comprises pomalidomide, e.g., 4-amino-2-(2,6-dioxopiperidin-3-yl)isoindoline-1,3-dione, or a pharmaceutically acceptable salt thereof. In an embodiment, the compound is pomalidomide, e.g., according to the following formula:

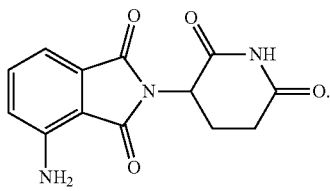 [SMILES: Nc1cccc2c1C(=O)N(C1CCC(=O)NC1=O)C2=O]

In an embodiment, X is O. In an embodiment, $R^1$ is heterocyclyl (e.g., piperidinyl-2,6-dionyl). In an embodiment, $R^{2a}$ and $R^{2b}$ together with the carbon to which they are attached form a carbonyl group. In an embodiment, n is 0. In an embodiment, the compound comprises thalidomide, e.g., 2-(2,6-dioxopiperidin-3-yl)isoindoline-1,3-dione, or a pharmaceutically acceptable salt thereof. In an embodiment, the product is thalidomide, e.g., according to the following formula:

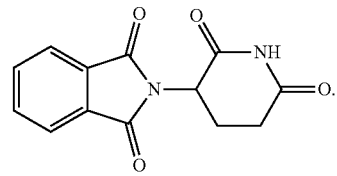 [SMILES: O=C1CCC(N2C(=O)c3ccccc3C2=O)C(=O)N1]

In an embodiment, X is O. In an embodiment, $R^1$ is heterocyclyl (e.g., piperidine-2,6-dionyl). In an embodiment, each of $R^{2a}$ and $R^{2b}$ is independently hydrogen. In an embodiment, n is 1. In an embodiment, $R^3$ is $C_1$-$C_6$ heteroalkyl (e.g., $CH_2NHC(O)CH_2$-phenyl-t-butyl) In an embodiment, the compound comprises 2-(4-(tert-butyl)phenyl)-N-((2-(2,6-dioxopiperidin-3-yl)-1-oxoisoindolin-5-yl)methyl)acetamide, or a pharmaceutically acceptable salt thereof. In an embodiment, the compound has the structure as shown in the following formula:

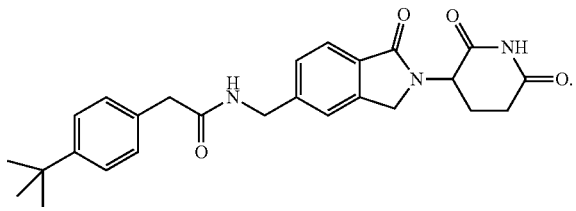 [SMILES: CC(C)(C)c1ccc(CC(=O)NCc2ccc3c(c2)CN(C2CCC(=O)NC2=O)C3=O)cc1]

In some embodiments, the compound is a compound of Formula (I-a):

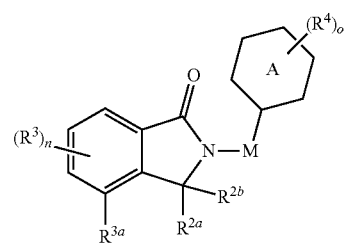

(I-a)

or a pharmaceutically acceptable salt, ester, hydrate, or tautomer thereof, where:

Ring A is carbocyclyl, heterocyclyl, aryl, or heteroaryl, each of which optionally substituted with one or more $R^4$;

M is absent, $C_1$-$C_6$ alkyl, $C_2$-$C_6$ alkenyl, $C_2$-$C_6$ alkynyl, or $C_1$-$C_6$ heteroalkyl, where each alkyl, alkenyl, alkynyl, and heteroalkyl is optionally substituted with one or more $R^4$;

each of $R^{2a}$ and $R^{2b}$ is independently hydrogen or $C_1$-$C_6$ alkyl; or $R^{2a}$ and $R^{2b}$ together with the carbon atom to which they are attached to form a carbonyl group or thiocarbonyl group;

$R^{3a}$ is hydrogen, $C_1$-$C_6$ alkyl, $C_2$-$C_6$ alkenyl, $C_2$-$C_6$ alkynyl, $C_1$-$C_6$ heteroalkyl, halo, cyano, —C(O)$R^A$, —(O)O$R^B$, —O$R^B$, —N($R^C$)($R^D$), —C(O)N($R^C$)($R^D$), —N($R^C$)C(O)$R^A$, —S(O)$_x R^E$, —S(O)$_x$N($R^C$)($R^D$), or —N($R^C$)S(O)$_x R^E$, where each alkyl, alkenyl, alkynyl, and heteroalkyl is optionally substituted with one or more $R^6$;

each of $R^3$ is independently $C_1$-$C_6$ alkyl, $C_2$-$C_6$ alkenyl, $C_2$-$C_6$ alkynyl, $C_1$-$C_6$ heteroalkyl, halo, cyano, —C(O)$R^A$, —(O)O$R^B$, —O$R^B$, —N($R^C$)($R^D$), —C(O)N($R^C$)($R^D$), —N($R^C$)C(O)$R^A$, —S(O)$_x R^E$, —S(O)$_x$N($R^C$)($R^D$), or —N($R^C$)S(O)$_x R^E$, where each alkyl, alkenyl, alkynyl, and heteroalkyl is independently and optionally substituted with one or more $R^6$;

each $R^4$ is independently $C_1$-$C_6$ alkyl, $C_2$-$C_6$ alkenyl, $C_2$-$C_6$ alkynyl, $C_1$-$C_6$ heteroalkyl, halo, cyano, oxo, —C(O)$R^A$, —(O)O$R^B$, —O$R^B$, —N($R^C$)($R^D$), —C(O)N($R^C$)($R^D$), —N($R^C$)C(O)$R^A$, S(O)$_x R^E$, —S(O)$_x$N($R^C$)($R^D$), —N($R^C$)S(O)$_x R^E$, carbocyclyl, heterocyclyl, aryl, or heteroaryl, where each alkyl, alkenyl, alkynyl, carbocyclyl, heterocyclyl, aryl, or heteroaryl is independently and optionally substituted with one or more $R^7$;

each of $R^A$, $R^B$, $R^C$, $R^D$, and $R^E$ is independently hydrogen or $C_1$-$C_6$ alkyl;

each $R^6$ is independently $C_1$-$C_6$ alkyl, oxo, cyano, —O$R^B$, —N($R^C$)($R^D$), —C(O)N($R^C$)($R^D$), —N($R^C$)C(O)$R^A$, aryl, or heteroaryl, where each aryl or heteroaryl is independently and optionally substituted with one or more $R^8$;

each $R^7$ is independently halo, oxo, cyano, —O$R^B$, —N($R^C$)($R^D$), —C(O)N($R^C$)($R^D$), or —N($R^C$)C(O)$R^A$;

each $R^8$ is independently $C_1$-$C_6$ alkyl, cyano, —O$R^B$, —N($R^C$)($R^D$), —C(O)N($R^C$)($R^D$), or —N($R^C$)C(O)$R^A$;

n is 0, 1, 2, or 3;

o is 0, 1, 2, 3, 4, or 5; and x is 0, 1, or 2.

In some embodiments, X is O.

In some embodiments, M is absent.

In some embodiments, Ring A is heterocyclyl. In some embodiments, Ring A is heterocyclyl, e.g., a 6-membered heterocyclyl or a 5-membered heterocyclyl. In some embodiments, Ring A is a nitrogen-containing heterocyclyl. In some embodiments, Ring A is piperidinyl (e.g., piperidine-2,6-dionyl).

In some embodiments, M is absent and Ring A is heterocyclyl (e.g., piperidinyl, e.g., piperidine-2,6-dionyl).

In some embodiments, each of $R^{2a}$ and $R^{2b}$ is independently hydrogen. In some embodiments, $R^{2a}$ and $R^{2b}$ together with the carbon to which they are attached form a carbonyl group.

In some embodiments, $R^{3a}$ is hydrogen, —N($R^C$)($R^D$) or —N($R^C$)C(O)$R^A$. In some embodiments, $R^{3a}$ is hydrogen. In some embodiments, $R^{3a}$ is —N($R^C$)($R^D$) (e.g., —NH$_2$). In some embodiments, $R^{3a}$ is —N($R^C$)C(O)$R^A$ (e.g., NHC(O)CH$_3$).

In some embodiments, $R^3$ is $C_1$-$C_6$ heteroalkyl (e.g., CH$_2$NHC(O)CH$_2$-phenyl-t-butyl). In some embodiments, n is 0 or 1. In some embodiments, n is 0. In some embodiments, n is 1.

The compound can comprise one or more chiral centers or exist as one or more stereoisomers. In some embodiments, the compound comprises a single chiral center and is a mixture of stereoisomers, e.g., an R stereoisomer and an S stereoisomer. In some embodiments, the mixture comprises a ratio of R stereoisomers to S stereoisomers, for example, about a 1:1 ratio of R stereoisomers to S stereoisomers (i.e., a racemic mixture). In some embodiments, the mixture comprises a ratio of R stereoisomers to S stereoisomers of about 51:49, about 52:48, about 53:47, about 54:46, about 55:45, about 60:40, about 65:35, about 70:30, about 75:25, about 80:20, about 85:15, about 90:10, about 95:5, or about 99:1. In some embodiments, the mixture comprises a ratio of S stereoisomers to R stereoisomers of about 51:49, about 52:48, about 53:47, about 54:46, about 55:45, about 60:40, about 65:35, about 70:30, about 75:25, about 80:20, about 85:15, about 90:10, about 95:5, or about 99:1. In some embodiments, the compound is a single stereoisomer of Formula (I) or Formula (I-a), e.g., a single R stereoisomer or a single S stereoisomer.

In some embodiments, the BCMA binding molecule is administered in combination with a kinase inhibitor. In one embodiment, the kinase inhibitor is a PI3-kinase inhibitor, e.g., CLR457, BGT226, or BYL719. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102. In one embodiment, the kinase inhibitor is a DGK inhibitor, e.g., a DGK inhibitor described herein, such as, e.g., DGKinh1 (D5919) or DGKinh2 (D5794).

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In an embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In some embodiments, a BCMA binding molecule is administered to a subject in combination with a BTK inhibitor (e.g., ibrutinib). In embodiments, a BCMA binding molecule is administered to a subject in combination with ibrutinib (also called PCI-32765) (e.g., to a subject having CLL, mantle cell lymphoma (MCL), or small lymphocytic lymphoma (SLL). For example, the subject can have a deletion in the short arm of chromosome 17 (del(17p), e.g., in a leukemic cell). In other examples, the subject does not have a del(17p). In some embodiments, the subject has relapsed CLL or SLL, e.g., the subject has previously been administered a cancer therapy (e.g., previously been administered one, two, three, or four prior cancer therapies). In some embodiments, the subject has refractory CLL or SLL. In other embodiments, the subject has follicular lymphoma, e.g., relapse or refractory follicular lymphoma. In some embodiments, ibrutinib is administered at a dosage of about 300-600 mg/day (e.g., about 300-350, 350-400, 400-450, 450-500, 500-550, or 550-600 mg/day, e.g., about 420 mg/day or about 560 mg/day), e.g., orally. In some embodiments, the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered. In some embodiments, ibrutinib is administered in combination with rituximab. See, e.g., Burger et al. (2013) Ibrutinib In Combination With Rituximab (iR) Is Well Tolerated and Induces a High Rate Of Durable Remissions In Patients With High-Risk Chronic Lymphocytic Leukemia (CLL): New, Updated Results Of a Phase II Trial In 40 Patients, Abstract 675 presented at 55th ASH Annual Meeting and Exposition, New Orleans, LA 7-10 December. Without being bound by theory, it is thought that the addition of ibrutinib enhances the T cell proliferative response and can shift T cells from a T-helper-2 (Th2) to T-helper-1 (Th1) phenotype. Th1 and Th2 are phenotypes of helper T cells, with Th1 versus Th2 directing different immune response pathways. A Th1 phenotype is associated with proinflammatory responses, e.g., for killing cells, such as intracellular pathogens/viruses or cancerous cells, or perpetuating autoimmune responses. A Th2 phenotype is associated with eosinophil accumulation and anti-inflammatory responses.

In some embodiments, the BCMA binding molecule is administered in combination with an inhibitor of Epidermal Growth Factor Receptor (EGFR).

In some embodiments, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757.

In some embodiments, the EGFR inhibitor, e.g., (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of 150-250 mg, e.g., per day. In some embodiments, the EGFR inhibitor, e.g., (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of about 150, 200, or 250 mg, or about 150-200 or 200-250 mg.

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is a covalent, irreversible tyrosine kinase inhibitor. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 inhibits activating EGFR mutations (L858R, ex19del). In other embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 does not inhibit, or does not substantially inhibit, wild-type (wt) EGFR. Compound A40 has shown efficacy in EGFR mutant NSCLC patients. In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 also inhibits one or more kinases in the TEC family of kinases. The Tec family kinases include, e.g., ITK, BMX, TEC, RLK, and BTK, and are central in the propagation of T-cell receptor and chemokine receptor signaling (Schwartzberg et al. (2005) Nat. Rev. Immunol. p. 284-95). For example, Compound A40 can inhibit ITK with a biochemical IC50 of 1.3 nM. ITK is a critical enzyme for the survival of Th2 cells and its inhibition results in a shift in the balance between Th2 and Th1 cells.

In some embodiments, the EGFR inhibitor is chosen from one of more of erlotinib, gefitinib, cetuximab, panitumumab, necitumumab, PF-00299804, nimotuzumab, or RO5083945.

In some embodiments, the BCMA binding molecule is administered in combination with an adenosine A2A receptor (A2AR) antagonist. Exemplary A2AR antagonists include, e.g., PBF509 (Palobiofarma/Novartis), CPI444/V81444 (Corvus/Genentech), AZD4635/HTL-1071 (AstraZeneca/Heptares), Vipadenant (Redox/Juno), GBV-2034 (Globavir), AB928 (Arcus Biosciences), Theophylline, Istradefylline (Kyowa Hakko Kogyo), Tozadenant/SYN-115 (Acorda), KW-6356 (Kyowa Hakko Kogyo), ST-4206 (Leadiant Biosciences), Preladenant/SCH 420814 (Merck/Schering), and NIR178 (Novartis).

In certain embodiments, the A2AR antagonist is PBF509. PBF509 and other A2AR antagonists are disclosed in U.S. Pat. No. 8,796,284 and WO 2017/025918. In certain embodiments, the A2AR antagonist is 5-bromo-2,6-di-(1H-pyrazol-1-yl)pyrimidine-4-amine. In certain embodiments, the A2AR antagonist has the following structure:

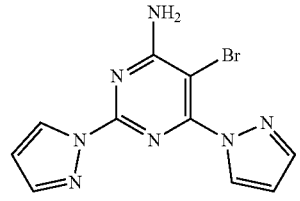 [SMILES: Nc1nc(-n2cccn2)nc(-n2cccn2)c1Br]

In certain embodiments, the A2AR antagonist is CPI444/V81444. CPI-444 and other A2AR antagonists are disclosed in WO 2009/156737. In certain embodiments, the A2AR antagonist is (S)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine. In certain embodiments, the A2AR antagonist is (R)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine, or racemate thereof. In certain embodiments, the A2AR antagonist is 7-(5-methylfuran-2-yl)-3-((6-(((tetrahydrofuran-3-yl)oxy)methyl) pyridin-2-yl)methyl)-3H-[1,2,3]triazolo[4,5-d]pyrimidin-5-amine. In certain embodiments, the A2AR antagonist has the following structure:

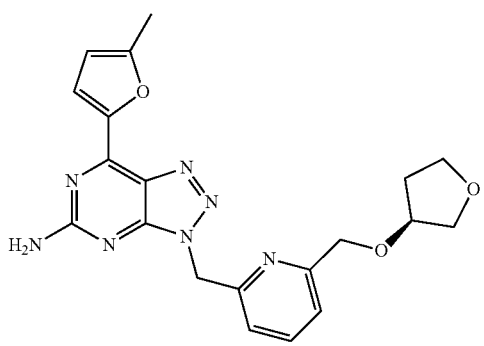 [SMILES: Cc1ccc(-c2nc(N)nc3c2nnn3Cc2cccc(CO[C@H]3CCOC3)n2)o1]

In certain embodiments, the A2AR antagonist is AZD4635/HTL-1071. A2AR antagonists are disclosed in WO 2011/095625. In certain embodiments, the A2AR antagonist is 6-(2-chloro-6-methylpyridin-4-yl)-5-(4-fluorophenyl)-1,2,4-triazin-3-amine. In certain embodiments, the A2AR antagonist has the following structure:

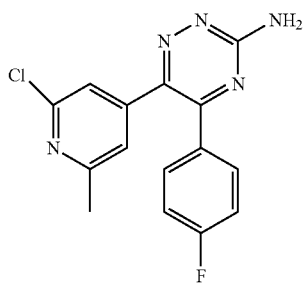 [SMILES: Cc1cc(-c2nnc(N)nc2-c2ccc(F)cc2)cc(Cl)n1]

In certain embodiments, the A2AR antagonist is ST-4206 (Leadiant Biosciences). In certain embodiments, the A2AR antagonist is an A2AR antagonist described in U.S. Pat. No. 9,133,197. In certain embodiments, the A2AR antagonist has the following structure:

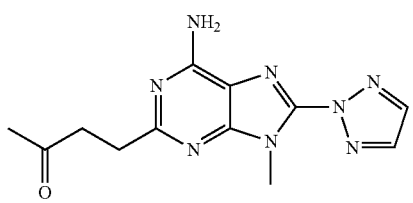 [SMILES: CC(=O)CCc1nc(N)c2nc(-n3nccn3)n(C)c2n1]

In certain embodiments, the A2AR antagonist is an A2AR antagonist described in U.S. Pat. Nos. 8,114,845, 9,029,393, US20170015758, or US20160129108.

In certain embodiments, the A2AR antagonist is istradefylline (CAS Registry Number: 155270-99-8). Istradefylline is also known as KW-6002 or 8-[(E)-2-(3,4-dimethoxyphenyl)vinyl]-1,3-diethyl-7-methyl-3,7-dihydro-1H-purine-2,6-dione. Istradefylline is disclosed, e.g., in LeWitt et al. (2008) *Annals of Neurology* 63 (3): 295-302).

In certain embodiments, the A2aR antagonist is tozadenant (Biotie). Tozadenant is also known as SYN115 or 4-hydroxy-N-(4-methoxy-7-morpholin-4-yl-1,3-benzothiazol-2-yl)-4-methylpiperidine-1-carboxamide. Tozadenant blocks the effect of endogenous adenosine at the A2a receptors, resulting in the potentiation of the effect of dopamine at the D2 receptor and inhibition of the effect of glutamate at the mGluR5 receptor. In some embodiments, the A2aR antagonist is preladenant (CAS Registry Number: 377727-87-2). Preladenant is also known as SCH 420814 or 2-(2-Furanyl)-7-[2-[4-[4-(2-methoxyethoxy)phenyl]-1-piperazinyl]ethyl]7H-pyrazolo[4,3-e][1,2,4]triazolo[1,5-c]pyrimidine-5-amine. Preladenant was developed as a drug that acted as a potent and selective antagonist at the adenosine A2A receptor.

In certain embodiments, the A2aR antagonist is vipadenan. Vipadenan is also known as BIIB014, V2006, or 3-[(4-amino-3-methylphenyl)methyl]-7-(furan-2-yl)triazolo[4,5-d]pyrimidin-5-amine.

Other exemplary A2aR antagonists include, e.g., ATL-444, MSX-3, SCH-58261, SCH-412,348, SCH-442,416, VER-6623, VER-6947, VER-7835, CGS-15943, or ZM-241,385.

In some embodiments, the A2aR antagonist is an A2aR pathway antagonist (e.g., a CD-73 inhibitor, e.g., an anti-CD73 antibody) is MEDI9447. MEDI9447 is a monoclonal antibody specific for CD73. Targeting the extracellular production of adenosine by CD73 can reduce the immunosuppressive effects of adenosine. MEDI9447 was reported to have a range of activities, e.g., inhibition of CD73 ecto-nucleotidase activity, relief from AMP-mediated lymphocyte suppression, and inhibition of syngeneic tumor growth. MEDI9447 can drive changes in both myeloid and lymphoid infiltrating leukocyte populations within the tumor microenvironment. These changes include, e.g., increases in CD8 effector cells and activated macrophages, as well as a reduction in the proportions of myeloid-derived suppressor cells (MDSC) and regulatory T lymphocytes.

In some embodiments, the BCMA binding molecule is administered in combination with a CAR-expressing cell therapy such as a CD19 CAR-expressing cell therapy.

In one embodiment, the antigen binding domain of the CD19 CAR has the same or a similar binding specificity as the FMC63 scFv fragment described in Nicholson et al. Mol. Immun. 34 (16-17): 1157-1165 (1997). In one embodiment, the antigen binding domain of the CD19 CAR includes the scFv fragment described in Nicholson et al. *Mol. Immun.* 34 (16-17): 1157-1165 (1997).

In some embodiments, the CD19 CAR includes an antigen binding domain (e.g., a humanized antigen binding domain) according to Table 3 of WO2014/153270. WO2014/153270 also describes methods of assaying the binding and efficacy of various CAR constructs.

In one aspect, the parental murine scFv sequence is the CAR19 construct provided in PCT publication WO2012/079000. In one embodiment, the anti-CD19 binding domain is a scFv described in WO2012/079000.

In one embodiment, the CAR molecule comprises the fusion polypeptide sequence provided as SEQ ID NO:12 in PCT publication WO2012/079000, which provides an scFv fragment of murine origin that specifically binds to human CD19.

In one embodiment, the CD19 CAR comprises an amino acid sequence provided as SEQ ID NO:12 in PCT publication WO2012/079000.

In one embodiment, the CD19 CAR has the USAN designation TISAGENLECLEUCEL-T. In embodiments, CTL019 is made by a gene modification of T cells is mediated by stable insertion via transduction with a self-inactivating, replication deficient Lentiviral (LV) vector containing the CTL019 transgene under the control of the EF-1 alpha promoter. CTL019 can be a mixture of transgene positive and negative T cells that are delivered to the subject on the basis of percent transgene positive T cells.

In other embodiments, the CD19 CAR comprises an antigen binding domain (e.g., a humanized antigen binding domain) according to Table 3 of WO2014/153270.

Humanization of murine CD19 antibody is desired for the clinical setting, where the mouse-specific residues can induce a human-anti-mouse antigen (HAMA) response in patients who receive CART19 treatment, i.e., treatment with T cells transduced with the CAR19 construct. The production, characterization, and efficacy of humanized CD19 CAR sequences is described in International Application WO2014/153270, including Examples 1-5 (p. 115-159).

In some embodiments, CD19 CAR constructs are described in PCT publication WO 2012/079000.

CD19 CAR constructs containing humanized anti-CD19 scFv domains are described in PCT publication WO 2014/153270.

Any known CD19 CAR, e.g., the CD19 antigen binding domain of any known CD19 CAR, in the art can be used in accordance with the present disclosure. For example, LG-740; CD19 CAR described in the U.S. Pat. Nos. 8,399,645; 7,446,190; Xu et al., Leuk Lymphoma. 2013 54(2): 255-260(2012); Cruz et al., Blood 122(17):2965-2973 (2013); Brentjens et al., Blood, 118(18):4817-4828 (2011); Kochenderfer et al., Blood 116(20):4099-102 (2010); Kochenderfer et al., Blood 122 (25):4129-39(2013); and 16th Annu Meet Am Soc Gen Cell Ther (ASGCT) (May 15-18, Salt Lake City) 2013, Abst 10.

Exemplary CD19 CARs include CD19 CARs described herein, or an anti-CD19 CAR described in Xu et al. Blood 123.24(2014):3750-9; Kochenderfer et al. Blood 122.25 (2013):4129-39, Cruz et al. Blood 122.17(2013):2965-73, NCT00586391, NCT01087294, NCT02456350, NCT00840853, NCT02659943, NCT02650999, NCT02640209, NCT01747486, NCT02546739, NCT02656147, NCT02772198, NCT00709033, NCT02081937, NCT00924326, NCT02735083, NCT02794246, NCT02746952, NCT01593696, NCT02134262, NCT01853631, NCT02443831, NCT02277522, NCT02348216, NCT02614066, NCT02030834, NCT02624258, NCT02625480, NCT02030847, NCT02644655, NCT02349698, NCT02813837, NCT02050347, NCT01683279, NCT02529813, NCT02537977, NCT02799550, NCT02672501, NCT02819583, NCT02028455, NCT01840566, NCT01318317, NCT01864889, NCT02706405, NCT01475058, NCT01430390, NCT02146924, NCT02051257, NCT02431988, NCT01815749, NCT02153580, NCT01865617, NCT02208362, NCT02685670, NCT02535364, NCT02631044, NCT02728882, NCT02735291, NCT01860937, NCT02822326, NCT02737085, NCT02465983, NCT02132624, NCT02782351, NCT01493453, NCT02652910, NCT02247609, NCT01029366, NCT01626495, NCT02721407, NCT01044069, NCT00422383, NCT01680991, NCT02794961, or NCT02456207.

In some embodiments, the BCMA binding molecule is administered in combination with a CD20 inhibitor.

In one embodiment, the CD20 inhibitor is an anti-CD20 antibody or fragment thereof. In an embodiment, the antibody is a monospecific antibody and in another embodiment, the antibody is a bispecific antibody. In an embodiment, the CD20 inhibitor is a chimeric mouse/human monoclonal antibody, e.g., rituximab. In an embodiment, the CD20 inhibitor is a human monoclonal antibody such as ofatumumab. In an embodiment, the CD20 inhibitor is a humanized antibody such as ocrelizumab, veltuzumab, obinutuzumab, ocaratuzumab, or PRO131921 (Genentech). In an embodiment, the CD20 inhibitor is a fusion protein comprising a portion of an anti-CD20 antibody, such as TRU-015 (Trubion Pharmaceuticals).

In some embodiments, the BCMA binding molecule is administered in combination with a CD22 CAR-expressing cell therapy (e.g., cells expressing a CAR that binds to human CD22).

In some embodiments, the BCMA binding molecule is administered in combination with a CD22 inhibitor. In some embodiments, the CD22 inhibitor is a small molecule or an anti-CD22 antibody molecule. In some embodiments, the antibody is a monospecific antibody, optionally conjugated to a second agent such as a chemotherapeutic agent. For instance, in an embodiment, the antibody is an anti-CD22 monoclonal antibody-MMAE conjugate (e.g., DCDT2980S). In an embodiment, the antibody is an scFv of an anti-CD22 antibody, e.g., an scFv of antibody RFB4. This scFv can be fused to all of or a fragment of Pseudomonas exotoxin-A (e.g., BL22). In an embodiment, the antibody is a humanized anti-CD22 monoclonal antibody (e.g., epratuzumab). In an embodiment, the antibody or fragment thereof comprises the Fv portion of an anti-CD22 antibody, which is optionally covalently fused to all or a fragment or (e.g., a 38 KDa fragment of) Pseudomonas exotoxin-A (e.g., moxetumomab pasudotox). In an embodiment, the anti-CD22 antibody is an anti-CD19/CD22 bispecific antibody, optionally conjugated to a toxin. For instance, in one embodiment, the anti-CD22 antibody comprises an anti-CD19/CD22 bispecific portion, (e.g., two scFv ligands, recognizing human CD19 and CD22) optionally linked to all of or a portion of diphtheria toxin (DT), e.g., first 389 amino acids of diphtheria toxin (DT), DT 390, e.g., a ligand-directed toxin such as DT2219ARL). In another embodiment, the bispecific portion (e.g., anti-CD19/anti-CD22) is linked to a toxin such as deglycosylated ricin A chain (e.g., Combotox).

In some embodiments, the CD22 inhibitor is a multispecific antibody molecule, e.g., a bispecific antibody molecule, e.g., a bispecific antibody molecule that binds to CD20 and CD3. Exemplary bispecific antibody molecules that bind to CD20 and CD3 are disclosed in WO2016086189 and WO2016182751. In some embodiments, the bispecific antibody molecule that binds to CD20 and CD3 is XENP13676 as disclosed in FIG. 74, SEQ ID NOs: 323, 324, and 325 of WO2016086189.

In some embodiments, the CD22 CAR-expressing cell therapy includes an antigen binding domain according to WO2016/164731.

In some embodiments, the BCMA binding molecule is administered in combination with a FCRL2 or FCRL5 inhibitor. In some embodiments, the FCRL2 or FCRL5 inhibitor is an anti-FCRL2 antibody molecule, e.g., a bispecific antibody molecule, e.g., a bispecific antibody that binds to FCRL2 and CD3. In some embodiments, the FCRL2 or FCRL5 inhibitor is an anti-FCRL5 antibody molecule, e.g., a bispecific antibody molecule, e.g., a bispecific antibody that binds to FCRL5 and CD3. In some embodiments, the FCRL2 or FCRL5 inhibitor is a FCRL2 CAR-expressing cell therapy. In some embodiments, the FCRL2 or FCRL5 inhibitor is a FCRL5 CAR-expressing cell therapy.

Exemplary anti-FCRL5 antibody molecules are disclosed in US20150098900, US20160368985, WO2017096120 (e.g., antibodies ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 disclosed in WO2017096120).

Exemplary FCRL5 CAR molecules are disclosed in WO2016090337.

In some embodiments, the BCMA binding molecule is administered in combination with an IL15/IL-15Ra complex. In some embodiments, the IL-15/IL-15Ra complex is chosen from NIZ985 (Novartis), ATL-803 (Altor) or CYP0150 (Cytune).

In some embodiments, the IL-15/IL-15Ra complex comprises human IL-15 complexed with a soluble form of human IL-15Ra. The complex can comprise IL-15 covalently or noncovalently bound to a soluble form of IL-15Ra. In a particular embodiment, the human IL-15 is noncovalently bonded to a soluble form of IL-15Ra. In a particular embodiment, the human IL-15 of the composition comprises an amino acid sequence as described in WO 2014/066527 and the soluble form of human IL-15Ra comprises an amino acid sequence as described in WO 2014/066527. The molecules described herein can be made by vectors, host cells, and methods described in WO 2007/084342.

In some embodiments, the IL-15/IL-15Ra complex is ALT-803, an IL-15/IL-15Ra Fc fusion protein (IL-15N72D: IL-15RaSu/Fc soluble complex). ALT-803 is disclosed in WO 2008/143794.

In some embodiments, the IL-15/IL-15Ra complex comprises IL-15 fused to the sushi domain of IL-15Ra (CYP0150, Cytune). The sushi domain of IL-15Ra refers to a domain beginning at the first cysteine residue after the signal peptide of IL-15Ra, and ending at the fourth cysteine residue after the signal peptide. The complex of IL-15 fused to the sushi domain of IL-15Ra is disclosed in WO 2007/04606 and WO 2012/175222.

In some embodiments, the BCMA binding molecule is administered in combination with a PD-1 inhibitor. In some embodiments, the PD-1 inhibitor is chosen from PDR001 (Novartis), Nivolumab (Bristol-Myers Squibb), Pembrolizumab (Merck & Co), Pidilizumab (CureTech), MEDI0680 (Medimmune), REGN2810 (Regeneron), TSR-042 (Tesaro), PF-06801591 (Pfizer), BGB-A317 (Beigene), BGB-108 (Beigene), INCSHR1210 (Incyte), or AMP-224 (Amplimmune). In one embodiment, the PD-1 inhibitor is an anti-PD-1 antibody molecule. In one embodiment, the PD-1 inhibitor is an anti-PD-1 antibody molecule as described in US 2015/0210769.

In one embodiment, the anti-PD-1 antibody molecule is Nivolumab (Bristol-Myers Squibb), also known as MDX-1106, MDX-1106-04, ONO-4538, BMS-936558, or OPDIVO®. Nivolumab (clone 5C4) and other anti-PD-1 antibodies are disclosed in U.S. Pat. No. 8,008,449 and WO 2006/121168. In one embodiment, the anti-PD-1 antibody molecule comprises one or more of the CDR sequences (or collectively all of the CDR sequences), the heavy chain or light chain variable region sequence, or the heavy chain or light chain sequence of Nivolumab.

In one embodiment, the anti-PD-1 antibody molecule is Pembrolizumab (Merck & Co), also known as Lambrolizumab, MK-3475, MK03475, SCH-900475, or KEYTRUDA®. Pembrolizumab and other anti-PD-1 antibodies are disclosed in Hamid, O. et al. (2013) *New England Journal of Medicine* 369 (2): 134-44, U.S. Pat. No. 8,354,509, and WO 2009/114335. In one embodiment, the anti-PD-1 antibody molecule comprises one or more of the CDR sequences (or collectively all of the CDR sequences), the heavy chain or light chain variable region sequence, or the heavy chain or light chain sequence of Pembrolizumab.

In one embodiment, the anti-PD-1 antibody molecule is Pidilizumab (CureTech), also known as CT-011. Pidilizumab and other anti-PD-1 antibodies are disclosed in Rosenblatt, J. et al. (2011) *J Immunotherapy* 34(5): 409-18, U.S. Pat. Nos. 7,695,715, 7,332,582, and 8,686,119. In one embodiment, the anti-PD-1 antibody molecule comprises one or more of the CDR sequences (or collectively all of the CDR sequences), the heavy chain or light chain variable region sequence, or the heavy chain or light chain sequence of Pidilizumab.

In one embodiment, the anti-PD-1 antibody molecule is MEDI0680 (Medimmune), also known as AMP-514. MEDI0680 and other anti-PD-1 antibodies are disclosed in U.S. Pat. No. 9,205,148 and WO 2012/145493. In one embodiment, the anti-PD-1 antibody molecule comprises one or more of the CDR sequences (or collectively all of the CDR sequences), the heavy chain or light chain variable region sequence, or the heavy chain or light chain sequence of MEDI0680.

In one embodiment, the anti-PD-1 antibody molecule is REGN2810 (Regeneron). In one embodiment, the anti-PD-1 antibody molecule comprises one or more of the CDR sequences (or collectively all of the CDR sequences), the heavy chain or light chain variable region sequence, or the heavy chain or light chain sequence of REGN2810.

In one embodiment, the anti-PD-1 antibody molecule is PF-06801591 (Pfizer). In one embodiment, the anti-PD-1 antibody molecule comprises one or more of the CDR sequences (or collectively all of the CDR sequences), the heavy chain or light chain variable region sequence, or the heavy chain or light chain sequence of PF-06801591.

In one embodiment, the anti-PD-1 antibody molecule is BGB-A317 or BGB-108 (Beigene). In one embodiment, the anti-PD-1 antibody molecule comprises one or more of the CDR sequences (or collectively all of the CDR sequences), the heavy chain or light chain variable region sequence, or the heavy chain or light chain sequence of BGB-A317 or BGB-108.

In one embodiment, the anti-PD-1 antibody molecule is INCSHR1210 (Incyte), also known as INCSHR01210 or SHR-1210. In one embodiment, the anti-PD-1 antibody molecule comprises one or more of the CDR sequences (or collectively all of the CDR sequences), the heavy chain or light chain variable region sequence, or the heavy chain or light chain sequence of INCSHR1210.

In one embodiment, the anti-PD-1 antibody molecule is TSR-042 (Tesaro), also known as ANB011. In one embodiment, the anti-PD-1 antibody molecule comprises one or more of the CDR sequences (or collectively all of the CDR sequences), the heavy chain or light chain variable region sequence, or the heavy chain or light chain sequence of TSR-042.

Further known anti-PD-1 antibodies include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727.

In one embodiment, the anti-PD-1 antibody is an antibody that competes for binding with, and/or binds to the same epitope on PD-1 as, one of the anti-PD-1 antibodies described herein.

In one embodiment, the PD-1 inhibitor is a peptide that inhibits the PD-1 signaling pathway, e.g., as described in U.S. Pat. No. 8,907,053. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342).

In some embodiments, the BCMA binding molecule is administered in combination with a PD-L1 inhibitor. In some embodiments, the PD-L1 inhibitor is chosen from FAZ053 (Novartis), Atezolizumab (Genentech/Roche), Avelumab (Merck Serono and Pfizer), Durvalumab (MedImmune/AstraZeneca), or BMS-936559 (Bristol-Myers Squibb).

In one embodiment, the PD-L1 inhibitor is an anti-PD-L1 antibody molecule. In one embodiment, the PD-L1 inhibitor is an anti-PD-L1 antibody molecule as disclosed in US 2016/0108123.

In one embodiment, the anti-PD-L1 antibody molecule is Atezolizumab (Genentech/Roche), also known as MPDL3280A, RG7446, RO5541267, YW243.55.S70, or TECENTRIQ™. Atezolizumab and other anti-PD-L1 antibodies are disclosed in U.S. Pat. No. 8,217,149. In one embodiment, the anti-PD-L1 antibody molecule comprises one or more of the CDR sequences (or collectively all of the CDR sequences), the heavy chain or light chain variable region sequence, or the heavy chain or light chain sequence of Atezolizumab.

In one embodiment, the anti-PD-L1 antibody molecule is Avelumab (Merck Serono and Pfizer), also known as MSB0010718C. Avelumab and other anti-PD-L1 antibodies are disclosed in WO 2013/079174. In one embodiment, the anti-PD-L1 antibody molecule comprises one or more of the CDR sequences (or collectively all of the CDR sequences), the heavy chain or light chain variable region sequence, or the heavy chain or light chain sequence of Avelumab.

In one embodiment, the anti-PD-L1 antibody molecule is Durvalumab (MedImmune/AstraZeneca), also known as MEDI4736. Durvalumab and other anti-PD-L1 antibodies are disclosed in U.S. Pat. No. 8,779,108. In one embodiment, the anti-PD-L1 antibody molecule comprises one or more of the CDR sequences (or collectively all of the CDR sequences), the heavy chain or light chain variable region sequence, or the heavy chain or light chain sequence of Durvalumab.

In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158. In one embodiment, the anti-PD-L1 antibody molecule comprises one or more of the CDR sequences (or collectively all of the CDR sequences), the heavy chain or light chain variable region sequence, or the heavy chain or light chain sequence of BMS-936559.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082.

In some embodiments, the BCMA binding molecule is administered in combination with a LAG-3 inhibitor. In some embodiments, the LAG-3 inhibitor is chosen from LAG525 (Novartis), BMS-986016 (Bristol-Myers Squibb), or TSR-033 (Tesaro).

In one embodiment, the LAG-3 inhibitor is an anti-LAG-3 antibody molecule. In one embodiment, the LAG-3 inhibitor is an anti-LAG-3 antibody molecule as disclosed in US 2015/0259420.

In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839. In one embodiment, the anti-LAG-3 antibody molecule comprises one or more of the CDR sequences (or collectively all of the CDR sequences), the heavy chain or light chain variable region sequence, or the heavy chain or light chain sequence of BMS-986016.

In one embodiment, the anti-LAG-3 antibody molecule is TSR-033 (Tesaro). In one embodiment, the anti-LAG-3 antibody molecule comprises one or more of the CDR sequences (or collectively all of the CDR sequences), the heavy chain or light chain variable region sequence, or the heavy chain or light chain sequence of TSR-033.

In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059. In one embodiment, the anti-LAG-3 antibody molecule comprises one or more of the CDR sequences (or collectively all of the CDR sequences), the heavy chain or light chain variable region sequence, or the heavy chain or light chain sequence of IMP731. In one embodiment, the anti-LAG-3 antibody molecule comprises one or more of the CDR sequences (or collectively all of the CDR sequences), the heavy chain or light chain variable region sequence, or the heavy chain or light chain sequence of GSK2831781.

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839.

In one embodiment, the anti-LAG-3 inhibitor is a soluble LAG-3 protein, e.g., IMP321 (Prima BioMed), e.g., as disclosed in WO 2009/044273.

In some embodiments, the BCMA binding molecule is administered in combination with a TIM-3 inhibitor. In some embodiments, the TIM-3 inhibitor is MGB453 (Novartis) or TSR-022 (Tesaro).

In one embodiment, the TIM-3 inhibitor is an anti-TIM-3 antibody molecule. In one embodiment, the TIM-3 inhibitor is an anti-TIM-3 antibody molecule as disclosed in US 2015/0218274.

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of TSR-022. In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270.

In one embodiment, the anti-TIM-3 antibody molecule is the antibody clone F38-2E2. In one embodiment, the anti-TIM-3 antibody molecule comprises one or more of the CDR sequences (or collectively all of the CDR sequences), the heavy chain or light chain variable region sequence, or the heavy chain or light chain sequence of F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087.

In one embodiment, the anti-TIM-3 antibody is an antibody that competes for binding with, and/or binds to the same epitope on TIM-3 as, one of the anti-TIM-3 antibodies described herein.

In some embodiments, the BCMA binding molecule is administered in combination with a transforming growth factor beta (TGF-β) inhibitor. In some embodiments, the TGF-β inhibitor is fresolimumab (CAS Registry Number: 948564-73-6). Fresolimumab is also known as GC1008. Fresolimumab is a human monoclonal antibody that binds to and inhibits TGF-beta isoforms 1, 2 and 3. Fresolimumab is disclosed, e.g., in WO 2006/086469, U.S. Pat. Nos. 8,383,780, and 8,591,901.

In some embodiments, the TGF-β inhibitor is XOMA 089. XOMA 089 is also known as XPA.42.089. XOMA 089 is a fully human monoclonal antibody that binds and neutralizes TGF-beta 1 and 2 ligands, and is disclosed in PCT Publication No. WO 2012/167143.

In some embodiments, the BCMA binding molecule is administered in combination with an anti-CD73 antibody molecule. In one embodiment, an anti-CD73 antibody molecule is a full antibody molecule or an antigen-binding fragment thereof. In certain embodiments, the anti-CD73 antibody molecule binds to a CD73 protein and reduces, e.g., inhibits or antagonizes, an activity of CD73, e.g., human CD73.

In one embodiment, the anti-CD73 antibody molecule is an anti-CD73 antibody disclosed in WO2016/075099. In one embodiment, the anti-CD73 antibody molecule is MEDI 9447, e.g., as disclosed in WO2016/075099. Alternative names for MEDI 9447 include clone 10.3 or 73combo3. MEDI 9447 is an IgG1 antibody that inhibits, e.g., antagonizes, an activity of CD73. MEDI 9447 and other anti-CD73 antibody molecules are also disclosed in WO2016/075176 and US2016/0129108.

In one embodiment, the anti-CD73 antibody molecule comprises a heavy chain variable domain, a light chain variable domain, or both, of MEDI 9477.

In one embodiment, the anti-CD73 antibody molecule is an anti-CD73 antibody disclosed in WO2016/081748. In one embodiment, the anti-CD73 antibody molecule is 11F11, e.g., as disclosed in WO2016/081748. 11F11 is an IgG2 antibody that inhibits, e.g., antagonizes, an activity of CD73. Antibodies derived from 11F11, e.g., CD73.4, and CD73.10; clones of 11F11, e.g., 11F11-1 and 11F11-2; and other anti-CD73 antibody molecules are disclosed in WO2016/081748 and U.S. Pat. No. 9,605,080.

In one embodiment, the anti-CD73 antibody molecule comprises a heavy chain variable domain, a light chain variable domain, or both, of 11F11-1 or 11F11-2.

In one embodiment, the anti-CD73 antibody molecule is an anti-CD73 antibody disclosed in e.g., U.S. Pat. No. 9,605,080.

In one embodiment, the anti-CD73 antibody molecule is CD73.4, e.g., as disclosed in U.S. Pat. No. 9,605,080. In one embodiment, the anti-CD73 antibody molecule comprises a heavy chain variable domain, a light chain variable domain, or both, of CD73.4.

In one embodiment, the anti-CD73 antibody molecule is CD73.10, e.g., as disclosed in U.S. Pat. No. 9,605,080. In one embodiment, the anti-CD73 antibody molecule comprises a heavy chain variable domain, a light chain variable domain, or both, of CD73.10.

In one embodiment, the anti-CD73 antibody molecule is an anti-CD73 antibody disclosed in WO2009/0203538. In one embodiment, the anti-CD73 antibody molecule is 067-213, e.g., as disclosed in WO2009/0203538.

In one embodiment, the anti-CD73 antibody molecule comprises a heavy chain variable domain, a light chain variable domain, or both, of 067-213.

In one embodiment, the anti-CD73 antibody molecule is an anti-CD73 antibody disclosed in U.S. Pat. No. 9,090,697. In one embodiment, the anti-CD73 antibody molecule is TY/23, e.g., as disclosed in U.S. Pat. No. 9,090,697. In one embodiment, the anti-CD73 antibody molecule comprises a heavy chain variable domain, a light chain variable domain, or both, of TY/23.

In one embodiment, the anti-CD73 antibody molecule is an anti-CD73 antibody disclosed in WO2016/055609. In one embodiment, the anti-CD73 antibody molecule comprises a heavy chain variable domain, a light chain variable domain, or both, of an anti-CD73 antibody disclosed in WO2016/055609.

In one embodiment, the anti-CD73 antibody molecule is an anti-CD73 antibody disclosed in WO2016/146818. In one embodiment, the anti-CD73 antibody molecule comprises a heavy chain variable domain, a light chain variable domain, or both, of an anti-CD73 antibody disclosed in WO2016/146818.

In one embodiment, the anti-CD73 antibody molecule is an anti-CD73 antibody disclosed in WO2004/079013. In one embodiment, the anti-CD73 antibody molecule comprises a heavy chain variable domain, a light chain variable domain, or both, of an anti-CD73 antibody disclosed in WO2004/079013.

In one embodiment, the anti-CD73 antibody molecule is an anti-CD73 antibody disclosed in WO2012/125850. In one embodiment, the anti-CD73 antibody molecule comprises a heavy chain variable domain, a light chain variable domain, or both, of an anti-CD73 antibody disclosed in WO2012/125850.

In one embodiment, the anti-CD73 antibody molecule is an anti-CD73 antibody disclosed in WO2015/004400. In one embodiment, the anti-CD73 antibody molecule comprises a heavy chain variable domain, a light chain variable domain, or both, of an anti-CD73 antibody disclosed in WO2015/004400.

In one embodiment, the anti-CD73 antibody molecule is an anti-CD73 antibody disclosed in WO2007/146968. In one embodiment, the anti-CD73 antibody molecule comprises a heavy chain variable domain, a light chain variable domain, or both, of an anti-CD73 antibody disclosed in WO2007146968.

In one embodiment, the anti-CD73 antibody molecule is an anti-CD73 antibody disclosed in US2007/0042392. In one embodiment, the anti-CD73 antibody molecule comprises a heavy chain variable domain, a light chain variable domain, or both, of an anti-CD73 antibody disclosed in US2007/0042392.

In one embodiment, the anti-CD73 antibody molecule is an anti-CD73 antibody disclosed in US2009/0138977. In one embodiment, the anti-CD73 antibody molecule comprises a heavy chain variable domain, a light chain variable domain, or both, of an anti-CD73 antibody disclosed in US2009/0138977.

In one embodiment, the anti-CD73 antibody molecule is an anti-CD73 antibody disclosed in Flocke et al., Eur J Cell Biol. 1992 June; 58(1):62-70. In one embodiment, the anti-CD73 antibody molecule comprises a heavy chain variable domain, a light chain variable domain, or both, of an anti-CD73 antibody disclosed in Flocke et al., Eur J Cell Biol. 1992 June; 58(1):62-70.

In one embodiment, the anti-CD73 antibody molecule is an anti-CD73 antibody disclosed in Stagg et al., PNAS. 2010 January 107(4): 1547-1552. In some embodiments, the anti-CD73 antibody molecule is TY/23 or TY11.8, as disclosed in Stagg et al. In one embodiment, the anti-CD73 antibody molecule comprises a heavy chain variable domain, a light chain variable domain, or both, of an anti-CD73 antibody disclosed in Stagg et al.

In some embodiments, the BCMA binding molecule is administered in combination with an interleukine-17 (IL-17) inhibitor.

In some embodiments, the IL-17 inhibitor is secukinumab (CAS Registry Numbers: 875356-43-7 (heavy chain) and 875356-44-8 (light chain)). Secukinumab is also known as AIN457 and COSENTYX®. Secukinumab is a recombinant human monoclonal IgG1/κ antibody that binds specifically to IL-17A. It is expressed in a recombinant Chinese Hamster Ovary (CHO) cell line. Secukinumab is described, e.g., in WO 2006/013107, U.S. Pat. Nos. 7,807,155, 8,119,131, 8,617,552, and EP 1776142.

In some embodiments, the IL-17 inhibitor is CJM112. CJM112 is also known as XAB4. CJM112 is a fully human monoclonal antibody (e.g., of the IgG1/K isotype) that targets IL-17A. CJM112 is disclosed, e.g., in WO 2014/122613.

CJM112 can bind to human, cynomolgus, mouse and rat IL-17A and neutralize the bioactivity of these cytokines in vitro and in vivo. IL-17A, a member of the IL-17 family, is a major proinflammatory cytokine that has been indicated to play important roles in many immune mediated conditions, such as psoriasis and cancers (Witowski et al. (2004) Cell Mol. Life Sci. p. 567-79; Miossec and Kolls (2012) Nat. Rev. Drug Discov. p. 763-76).

In some embodiments, the IL-17 inhibitor is ixekizumab (CAS Registry Number: 1143503-69-8). Ixekizumab is also known as LY2439821. Ixekizumab is a humanized IgG4 monoclonal antibody that targets IL-17A. Ixekizumab is described, e.g., in WO 2007/070750, U.S. Pat. Nos. 7,838,638, and 8,110,191.

In some embodiments, the IL-17 inhibitor is brodalumab (CAS Registry Number: 1174395-19-7). Brodalumab is also known as AMG 827 or AM-14. Brodalumab binds to the interleukin-17 receptor A (IL-17RA) and prevents IL-17 from activating the receptor. Brodalumab is disclosed, e.g., in WO 2008/054603, U.S. Pat. Nos. 7,767,206, 7,786,284, 7,833,527, 7,939,070, 8,435,518, 8,545,842, 8,790,648, and 9,073,999.

In some embodiments, the BCMA binding molecule is administered in combination with an interleukine-1 beta (IL-1β) inhibitor.

In some embodiments, the IL-1β inhibitor is canakinumab. Canakinumab is also known as ACZ885 or ILARIS®. Canakinumab is a human monoclonal IgG1/K antibody that neutralizes the bioactivity of human IL-1β. Canakinumab is disclosed, e.g., in WO 2002/16436, U.S. Pat. No. 7,446,175, and EP 1313769.

In some embodiments, the BCMA binding molecule is administered in combination with a CD32B inhibitor. In some embodiments, the CD32B inhibitor is an anti-CD32B antibody molecule. Exemplary anti-CD32B antibody molecules are disclosed in U.S. Pat. Nos. 8,187,593, 8,778,339, 8,802,089, US20060073142, US20170198040, and US20130251706.

In some embodiments, the BCMA binding molecule is administered in combination with one of the compounds listed in Table A.

TABLE A

| Compound Designation | Generic Name Tradename | Compound Structure | Patents/Patent Application Publications |
|---|---|---|---|
| A1 | Sotrastaurin | 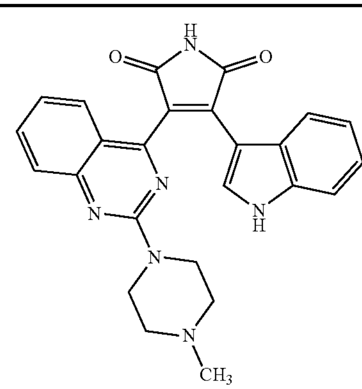 | EP 1682103<br>US 2007/142401<br>WO 2005/039549 |

TABLE A-continued

| Compound Designation | Generic Name Tradename | Compound Structure | Patents/Patent Application Publications |
|---|---|---|---|
| A2 | Nilotinib HCl monohydrate TASIGNA ® | HCl·H₂O | WO 2004/005281 U.S. Pat. No. 7,169,791 |
| A3 | | 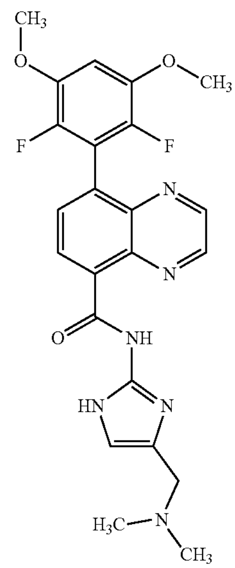 [SMILES: COc1cc(OC)c(F)c(-c2ccc(C(=O)Nc3nc(CN(C)C)c[nH]3)c3nccnc23)c1F] | WO 2009/141386 US 2010/0105667 |
| A4 | | 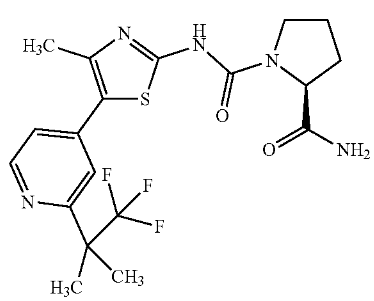 [SMILES: Cc1nc(NC(=O)N2CCC[C@H]2C(N)=O)sc1-c1ccnc(C(C)(C)C(F)(F)F)c1] | WO 2010/029082 |

TABLE A-continued

| Compound Designation | Generic Name Tradename | Compound Structure | Patents/Patent Application Publications |
|---|---|---|---|
| A5 | | 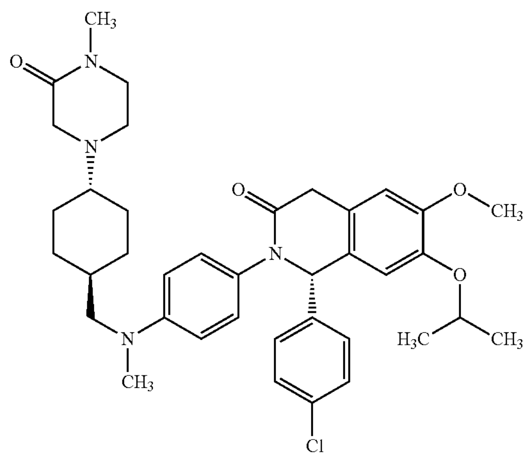 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] | WO 2011/076786 |
| A6 | Deferasirox EXJADE ® | 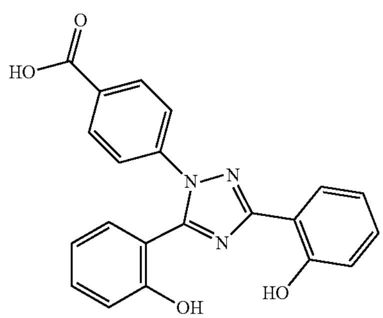 [SMILES: O=C(O)c1ccc(-n2nc(-c3ccccc3O)nc2-c2ccccc2O)cc1] | WO 1997/049395 |
| A7 | Letrozole FEMARA ® | 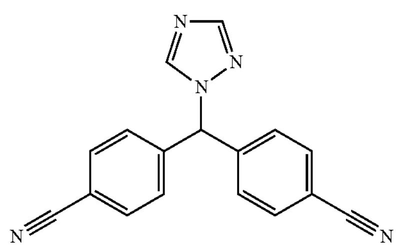 [SMILES: N#Cc1ccc(C(c2ccc(C#N)cc2)n2cncn2)cc1] | U.S. Pat. No. 4,978,672 |
| A8 | | 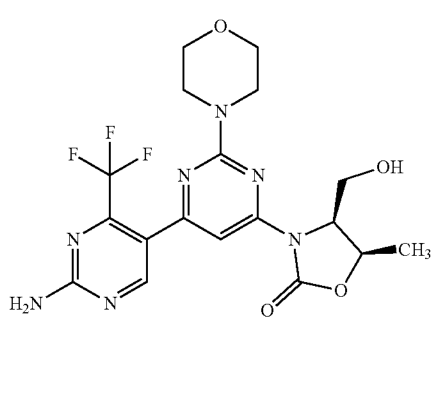 [SMILES: C[C@H]1OC(=O)N(c2cc(-c3cnc(N)nc3C(F)(F)F)nc(N3CCOCC3)n2)[C@H]1CO] | WO 2013/124826 US 2013/0225574 |

TABLE A-continued
| Compound Designation | Generic Name Tradename | Compound Structure | Patents/Patent Application Publications |
|---|---|---|---|
| A9 | | 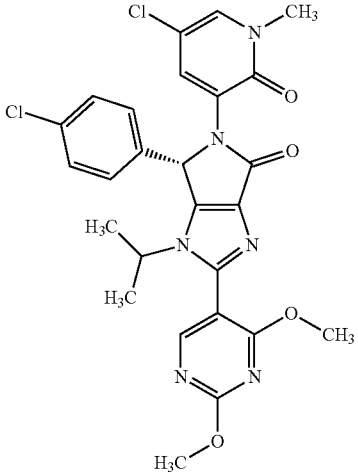 [SMILES: COc1ncc(-c2nc3c(n2C(C)C)[C@H](c2ccc(Cl)cc2)N(c2cc(Cl)cn(C)c2=O)C3=O)c(OC)n1] | WO 2013/111105 |
| A10 | BLZ945 | 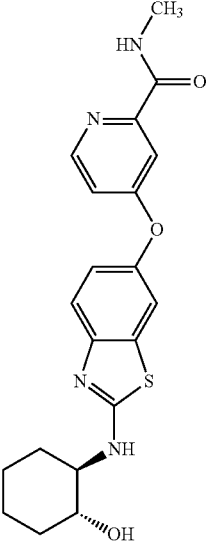 [SMILES: CNC(=O)c1cc(Oc2ccc3nc(N[C@@H]4CCCC[C@H]4O)sc3c2)ccn1] | WO 2007/121484 |

TABLE A-continued
| Compound Designation | Generic Name Tradename | Compound Structure | Patents/Patent Application Publications |
|---|---|---|---|
| A11 | Imatinib mesylate GLEEVEC ® | 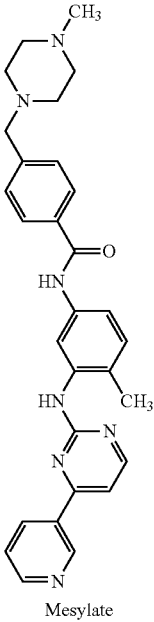 [SMILES: Cc1ccc(NC(=O)c2ccc(CN3CCN(C)CC3)cc2)cc1Nc1nccc(-c2cccnc2)n1]<br>Mesylate | WO 1999/003854 |
| A12 | Capmatinib | 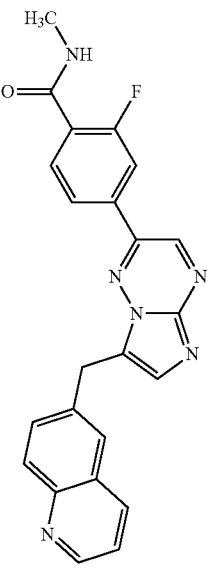<br>Dihydrochloric salt | EP 2099447<br>U.S. Pat. No. 7,767,675<br>U.S. Pat. No. 8,420,645 |

TABLE A-continued

| Compound Designation | Generic Name Tradename | Compound Structure | Patents/Patent Application Publications |
|---|---|---|---|
| A13 | Ruxolitinib Phosphate JAKAFI ® | 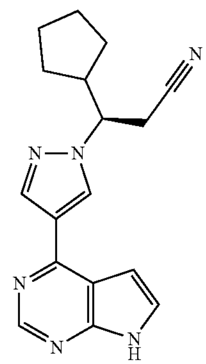 | WO 2007/070514<br>EP 2474545<br>U.S. Pat. No. 7,598,257<br>WO 2014/018632 |
| A14 | Panobinostat | 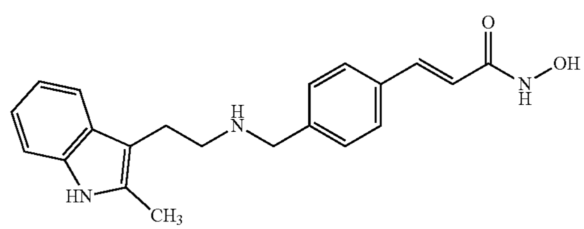 [SMILES: Cc1[nH]c2ccccc2c1CCNCc1ccc(/C=C/C(=O)NO)cc1] | WO 2014/072493<br>WO 2002/022577<br>EP 1870399 |
| A15 | Osilodrostat | 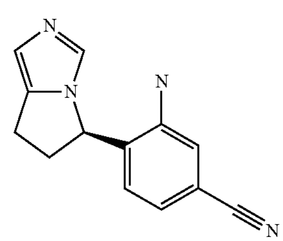 [SMILES: N#Cc1ccc([C@H]2CCc3cncn32)c(N)c1] | WO 2007/024945 |
| A16 | | 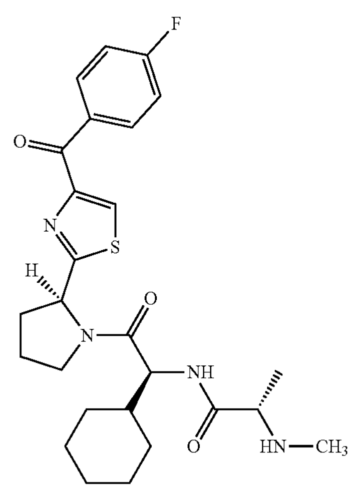 [SMILES: CN[C@@H](C)C(=O)N[C@H](C(=O)N1CCC[C@H]1c1nc(C(=O)c2ccc(F)cc2)cs1)C1CCCCC1] | WO 2008/016893<br>EP 2051990<br>U.S. Pat. No. 8,546,336 |

TABLE A-continued
| Compound Designation | Generic Name Tradename | Compound Structure | Patents/Patent Application Publications |
|---|---|---|---|
| A17 | ceritinib ZYKADIA™ | 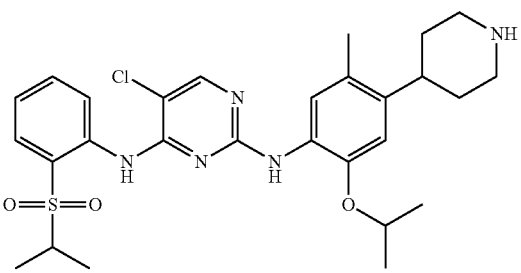 [SMILES: Cc1cc(Nc2ncc(Cl)c(Nc3ccccc3S(=O)(=O)C(C)C)n2)c(OC(C)C)cc1C1CCNCC1] | WO 2008/073687 U.S. Pat. No. 8,039,479 |
| A18 | Ribociclib KISQALI® | 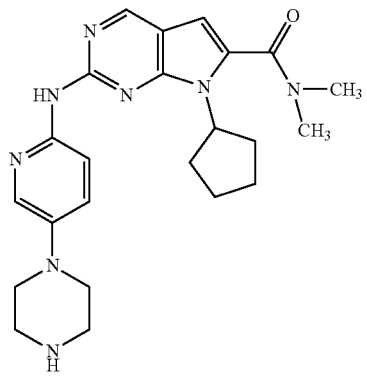 [SMILES: CN(C)C(=O)c1cc2cnc(Nc3ccc(N4CCNCC4)cn3)nc2n1C1CCCC1] | U.S. Pat. No. 8,415,355 U.S. Pat. No. 8,685,980 |
| A19 | | 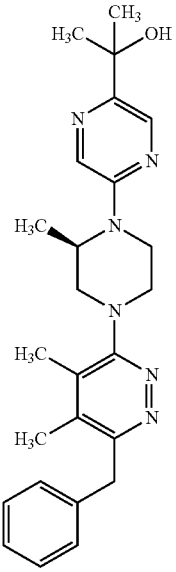 [SMILES: Cc1c(Cc2ccccc2)nnc(N2CCN(c3cnc(C(C)(C)O)cn3)[C@H](C)C2)c1C] | WO 2010/007120 |

TABLE A-continued
| Compound Designation | Generic Name Tradename | Compound Structure | Patents/Patent Application Publications |
|---|---|---|---|
| A20 | | Human monoclonal antibody to PRLR | U.S. Pat. No. 7,867,493 |
| A21 | | 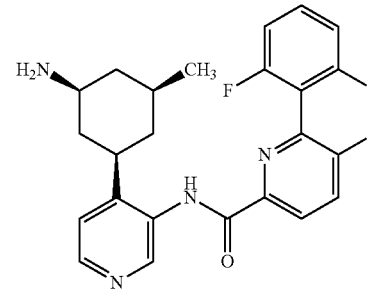 | WO 2010/026124<br>EP 2344474<br>US 2010/0056576<br>WO2008/106692 |
| A22 | WNT974 | 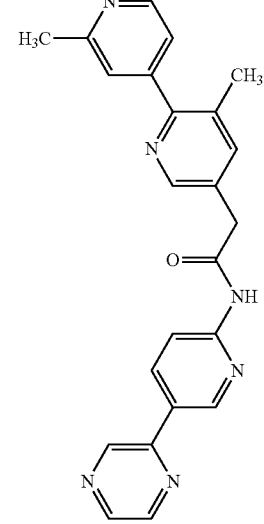 | WO 2010/101849 |
| A23 | | 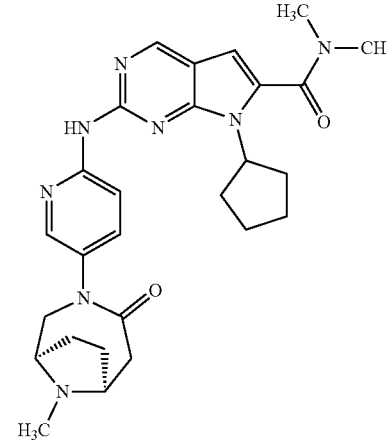 | WO 2011/101409 |
| A24 | | Human monoclonal antibody to HER3,, e.g., LJM716 | WO 2012/022814<br>EP 2606070<br>U.S. Pat. No. 8,735,551 |
| A25 | | Antibody Drug Conjugate (ADC) | WO 2014/160160, e.g., Ab: 12425 (see Table 1, paragraph [00191]) Linker: SMCC (see |

TABLE A-continued

| Compound Designation | Generic Name Tradename | Compound Structure | Patents/Patent Application Publications |
|---|---|---|---|
| A26 | | Monoclonal antibody or Fab to M-CSF, e.g., MCS110 | paragraph [00117] Payload: DM1 (see paragraph [00111] See also Claim 29 WO 2004/045532 |
| A27 | Midostaurin | 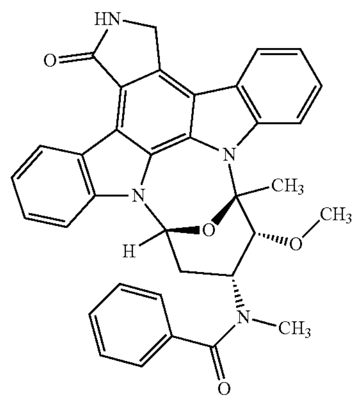 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] | WO 2003/037347 EP 1441737 US 2012/252785 |
| A28 | Everolimus AFINITOR ® | 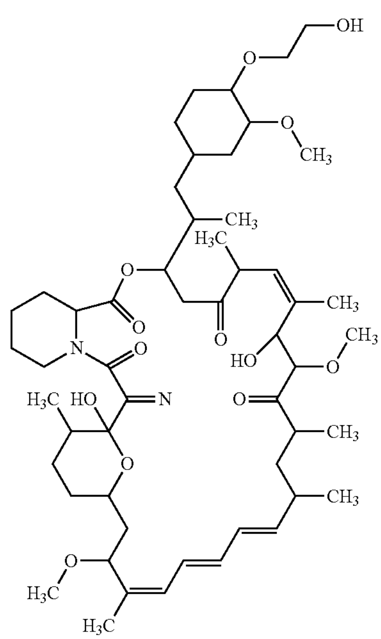 [SMILES: COC1CC2CCC(C)C(O)(O2)C(=N)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] | WO 2014/085318 |

TABLE A-continued
| Compound Designation | Generic Name Tradename | Compound Structure | Patents/Patent Application Publications |
|---|---|---|---|
| A29 | | 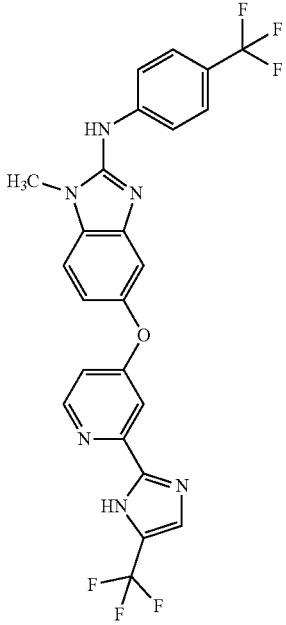 [SMILES: Cn1c(Nc2ccc(C(F)(F)F)cc2)nc2cc(Oc3ccnc(-c4ncc(C(F)(F)F)[nH]4)c3)ccc21] | WO 2007/030377 U.S. Pat. No. 7,482,367 |
| A30 | Pasireotide diaspartate SIGNIFOR ® | 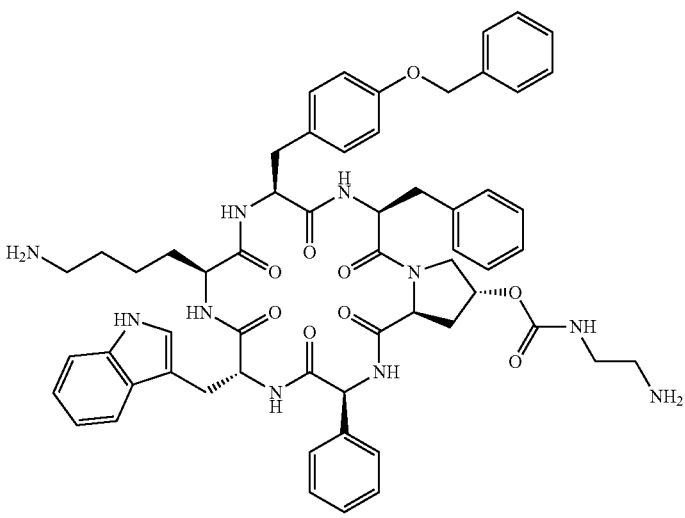 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] | U.S. Pat. No. 7,473,761 |
| A31 | | 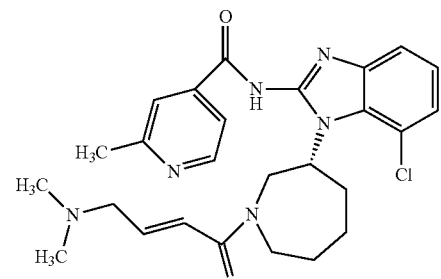 | WO 2013/184757 |

TABLE A-continued

| Compound Designation | Generic Name Tradename | Compound Structure | Patents/Patent Application Publications |
|---|---|---|---|
| A32 | | 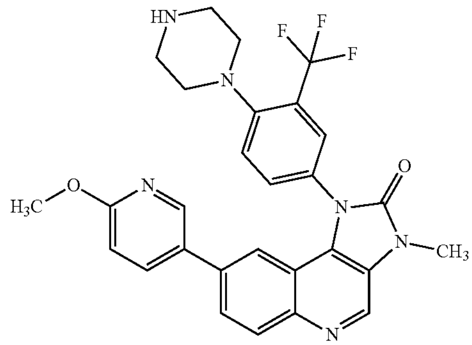 | WO 2006/122806 |
| A33 | | 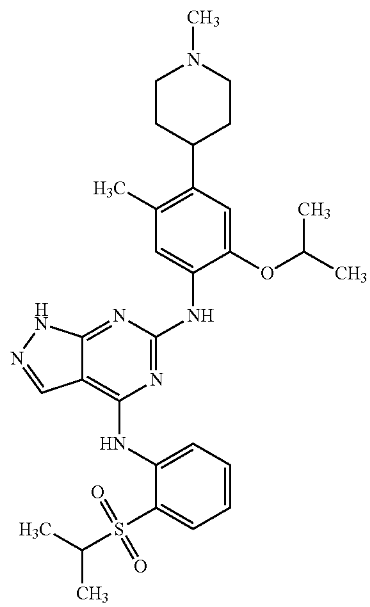 [SMILES: Cc1cc(Nc2nc(Nc3ccccc3S(=O)(=O)C(C)C)c3cn[nH]c3n2)c(OC(C)C)cc1C1CCN(C)CC1] | WO 2008/073687 U.S. Pat. No. 8,372,858 |
| A34 | | 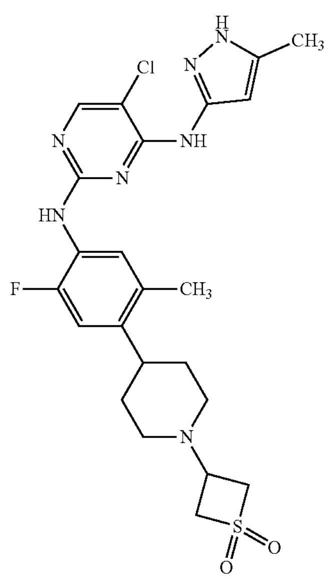 [SMILES: Cc1cc(Nc2nc(Nc3cc(C)c(C4CCN(C5CS(=O)(=O)C5)CC4)cc3F)ncc2Cl)n[nH]1] | WO 2010/002655 U.S. Pat. No. 8,519,129 |

TABLE A-continued
| Compound Designation | Generic Name Tradename | Compound Structure | Patents/Patent Application Publications |
|---|---|---|---|
| A35 | | 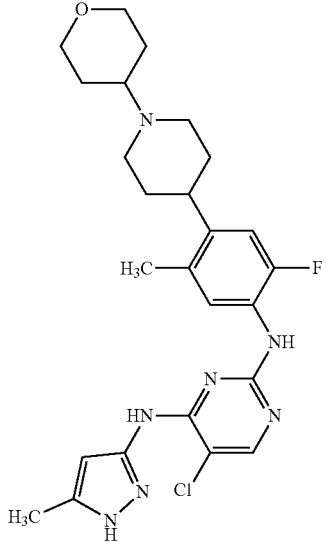 [SMILES: Cc1cc(Nc2nc(Nc3cc(C)c(C4CCN(C5CCOCC5)CC4)cc3F)ncc2Cl)n[nH]1] | WO 2010/002655<br>U.S. Pat. No. 8,519,129 |
| A36 | | 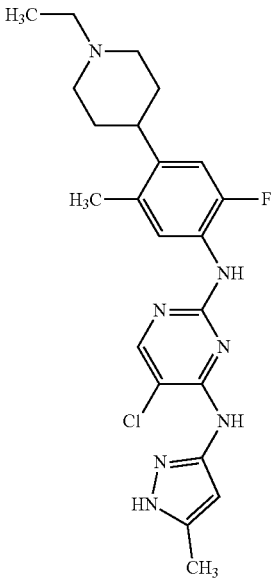 [SMILES: CCN1CCC(c2cc(F)c(Nc3ncc(Cl)c(Nc4cc(C)[nH]n4)n3)cc2C)CC1] | WO 2010/002655 |

TABLE A-continued
| Compound Designation | Generic Name Tradename | Compound Structure | Patents/Patent Application Publications |
|---|---|---|---|
| A37 | Valspodar AMDRAY ™ | 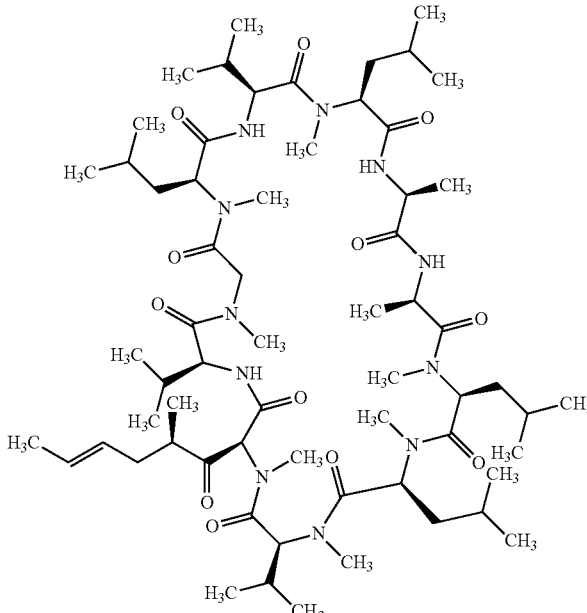 | EP 296122 |
| A38 | Vatalanib succinate | 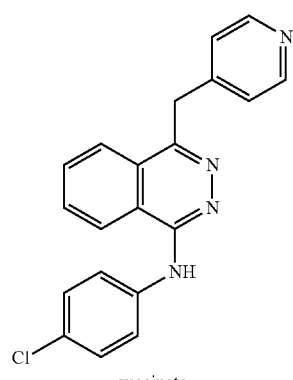<br>succinate | WO 98/35958 |
| A39 | | IDH inhibitor, e.g., IDH305 | WO2014/141104 |
| A40 | Asciminib | BCR-ABL inhibitor<br>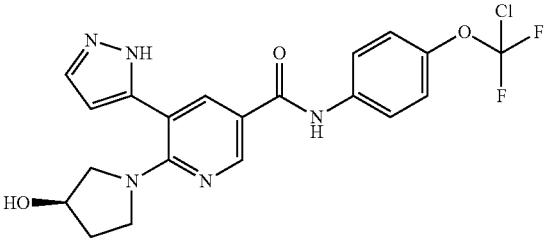 | WO2013/171639<br>WO2013/171640<br>WO2013/171641<br>WO2013/171642 |
| A41 | | cRAF inhibitor | WO2014/151616 |
| A42 | | ERK1/2 ATP competitive inhibitor | WO2015/066188 |

TABLE A-continued

| Compound Designation | Generic Name Tradename | Compound Structure | Patents/Patent Application Publications |
|---|---|---|---|
| A43 | | 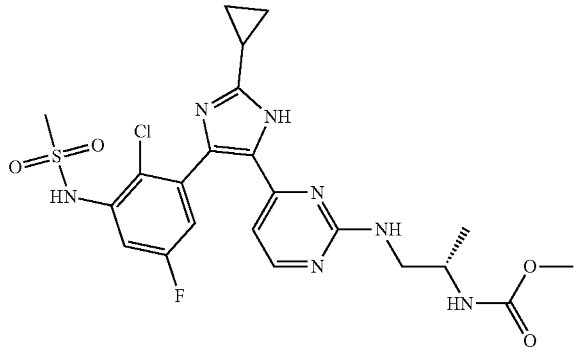 [SMILES: COC(=O)N[C@@H](C)CNc1nccc(-c2[nH]c(C3CC3)nc2-c2cc(F)cc(NS(C)(=O)=O)c2Cl)n1] | WO2011/023773 |
| A44 | | 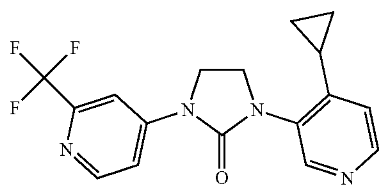 [SMILES: O=C1N(c2ccnc(C(F)(F)F)c2)CCN1c1cnccc1C1CC1] | WO2012/149413 |
| A45 | SHP099 | 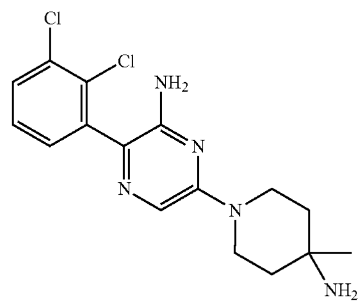 [SMILES: CC1(N)CCN(c2cnc(-c3cccc(Cl)c3Cl)c(N)n2)CC1] | WO2015/107493 |
| A46 | | SHP2 inhibitor of Formula I | WO2015/107495 |
| A47 | | 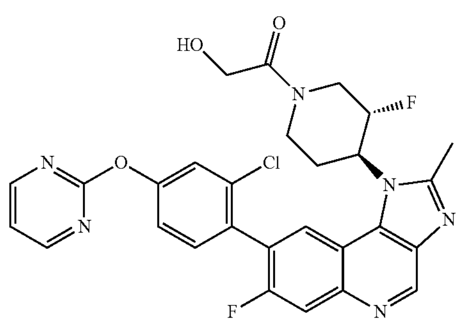 [SMILES: Cc1nc2cnc3cc(F)c(-c4ccc(Oc5ncccn5)cc4Cl)cc3c2n1[C@H]1CCN(C(=O)CO)C[C@@H]1F] | WO2015/022662 |
| A48 | | 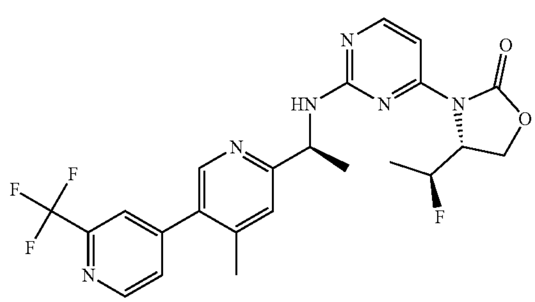 [SMILES: Cc1cc([C@H](C)Nc2nccc(N3C(=O)OC[C@@H]3[C@H](C)F)n2)ncc1-c1ccnc(C(F)(F)F)c1] | WO2014/141104 |

TABLE A-continued
| Compound Designation | Generic Name Tradename | Compound Structure | Patents/Patent Application Publications |
|---|---|---|---|
| A49 | | 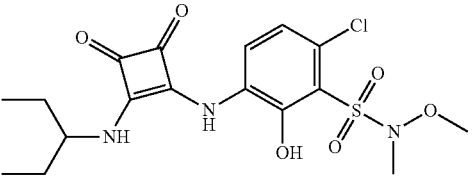<br>or a choline salt thereof | WO2010/015613<br>WO2013030803<br>U.S. Pat. No. 7,989,497, |
| A50 | | A2A receptor antagonist of Formula (I) | WO 2017/025918<br>WO2011/121418<br>U.S. Pat. No. 8,796,284 |
| A51 | | 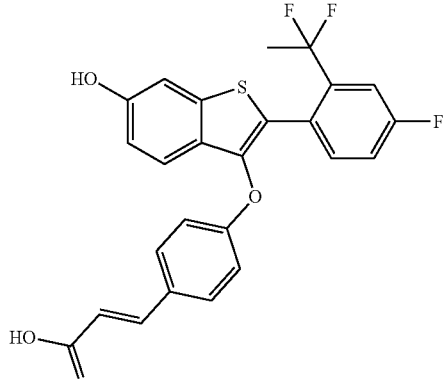 | WO2014/130310 |
| A52 | trametinib | 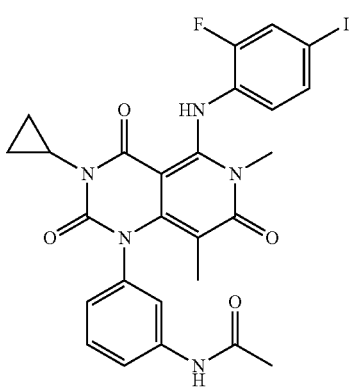 [SMILES: CC(=O)Nc1cccc(-n2c(=O)n(C3CC3)c(=O)c3c(Nc4ccc(I)cc4F)n(C)c(=O)c(C)c32)c1] | WO2005/121142<br>U.S. Pat. No. 7,378,423 |
| A53 | dabrafenib | 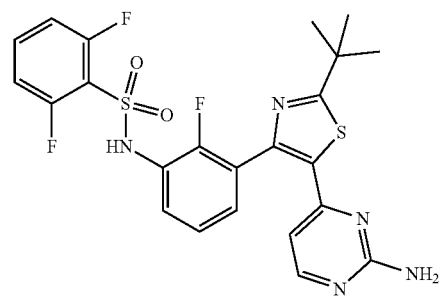 [SMILES: CC(C)(C)c1nc(-c2cccc(NS(=O)(=O)c3c(F)cccc3F)c2F)c(-c2ccnc(N)n2)s1] | WO 2009/137391<br>U.S. Pat. No. 7,994,185 |

TABLE A-continued

| Compound Designation | Generic Name Tradename | Compound Structure | Patents/Patent Application Publications |
|---|---|---|---|
| A54 | octreotide | 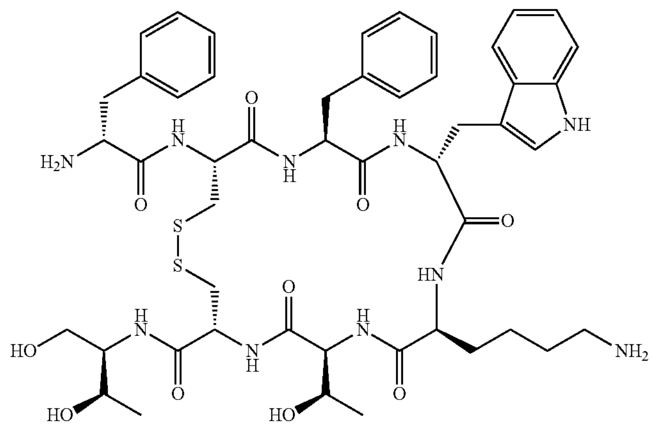 [SMILES: C[C@@H](O)[C@@H]1NC(=O)[C@H](CCCCN)NC(=O)[C@@H](Cc2c[nH]c3ccccc23)NC(=O)[C@H](Cc2ccccc2)NC(=O)[C@@H](NC(=O)[C@H](N)Cc2ccccc2)CSSC[C@@H](C(=O)N[C@H](CO)[C@@H](C)O)NC1=O] | U.S. Pat. No. 4,395,403 EP 0 029 579 |
| A55 | | 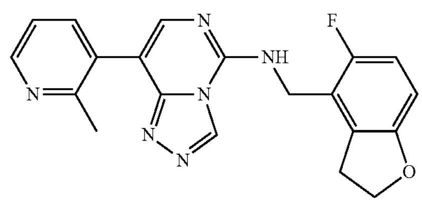 [SMILES: Cc1ncccc1-c1cnc(NCc2c(F)ccc3c2CCO3)n2cnnc12] | WO 2016/103155 U.S. Pat. No. 9,580,437 EP 3237418 |
| A56 | | 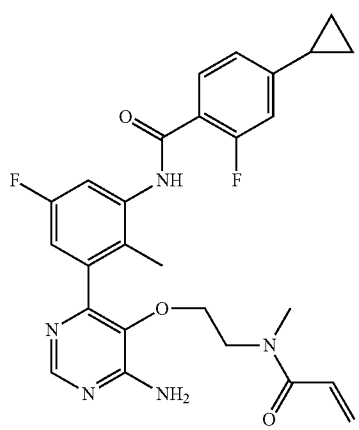 [SMILES: C=CC(=O)N(C)CCOc1c(N)ncnc1-c1cc(F)cc(NC(=O)c2ccc(C3CC3)cc2F)c1C] | U.S. Pat. No. 9,512,084 WO/2015/079417 |
| A57 | | 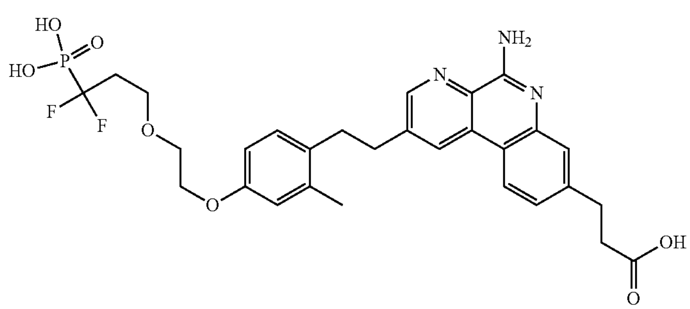 [SMILES: Cc1cc(OCCOCCC(F)(F)P(=O)(O)O)ccc1CCc1cnc2c(N)nc3cc(CCC(=O)O)ccc3c2c1] | WO2011/049677 |

In some embodiments, a BCMA binding molecule is administered in combination with one or more of a CAR-T therapy, NIZ985, a GITR agonist such as GWN323, PTK787, MBG453, mAb12425, CLR457, BGT226, BYL719, AMN107, ABL001, IDH305/LQS305, LJM716, MCS110, WNT974/LGK974, BLZ945, NIR178, QBM076, MBG453, CGS-20267, LHS534, LKG960, LDM099/SHP099, TNO155, LCL161, MAP855/LQN716, RAD001, LEJ511, LDK378, LOU064, LSZ102, LEQ506, RAF265/CHIR265, canakinumab, gevokizumab, Anakinra, Rilonacept, CGS-20267, PSC833, GGP-57148B, CGM097, HDM201, LBH589, PKC412, LHC165, MAK683, INC280, INC424, LJE704, LAG525, and NIS793.

In some embodiments, the BCMA binding molecule is administered in combination with a standard treatment.

Standard treatment for multiple myeloma and associated diseases includes chemotherapy, stem cell transplant (autologous or allogeneic), radiation therapy, and other drug therapies. Frequently used anti-myeloma drugs include alkylating agents (e.g., bendamustine, cyclophosphamide and melphalan), proteasome inhibitors (e.g., bortezomib), corticosteroids (e.g., dexamethasone and prednisone), and immunomodulators (e.g., thalidomide and lenalidomide or Revlimid®), or any combination thereof. Biphosphonate drugs are also frequently administered in combination with the standard anti-MM treatments to prevent bone loss. Patients older than 65-70 years of age are unlikely candidates for stem cell transplant. In some cases, double-autologous stem cell transplants are options for patients less than 60 years of age with suboptimal response to the first transplant. The compositions and methods of the present disclosure can be administered in combination with any one of the currently prescribed treatments for multiple myeloma.

Hodgkin's lymphoma is commonly treated with radiation therapy, chemotherapy, or hematopoietic stem cell transplantation. The most common therapy for non-Hodgkin's lymphoma is R-CHOP, which consists of four different chemotherapies (cyclophosphamide, doxorubicin, vincristine, and prenisolone) and rituximab (Rituxan®). Other therapies commonly used to treat NHL include other chemotherapeutic agents, radiation therapy, stem cell transplantation (autologous or allogeneic bone marrow transplantation), or biological therapy, such as immunotherapy. Other examples of biological therapeutic agents include, but are not limited to, rituximab (Rituxan®), tositumomab (Bexxar®), epratuzumab (LymphoCide®), and alemtuzumab (MabCampath®). The compositions and methods of the present disclosure can be administered in combination with any one of the currently prescribed treatments for Hodgkin's lymphoma or non-Hodgkin's lymphoma.

Standard treatment for WM consists of chemotherapy, specifically with rituximab (Rituxan®). Other chemotherapeutic drugs can be used in combination, such as chlorambucil (Leukeran®), cyclophosphamide (Neosar®), fludarabine (Fludara®), cladribine (Leustatin®), vincristine, and/or thalidomide. Corticosteriods, such as prednisone, can also be administered in combination with the chemotherapy. Plasmapheresis, or plasma exchange, is commonly used throughout treatment of the patient to alleviate some symptoms by removing the paraprotein from the blood. In some cases, stem cell transplantation is an option for some patients.

BCMA binding molecules that are bispecific for BCMA and CD3 can be administered in combination with an agent which reduces or ameliorates a side effect associated with the administration of a BCMA binding molecule that is bispecific for BCMA and CD3. Side effects associated with the administration of a bispecific BCMA binding molecule can include, but are not limited to, cytokine release syndrome ("CRS") and hemophagocytic lymphohistiocytosis (HLH), also termed Macrophage Activation Syndrome (MAS). Symptoms of CRS can include high fevers, nausea, transient hypotension, hypoxia, and the like. CRS can include clinical constitutional signs and symptoms such as fever, fatigue, anorexia, myalgias, arthalgias, nausea, vomiting, and headache. CRS can include clinical skin signs and symptoms such as rash. CRS can include clinical gastrointestinal signs and symptoms such as nausea, vomiting and diarrhea. CRS can include clinical respiratory signs and symptoms such as tachypnea and hypoxemia. CRS can include clinical cardiovascular signs and symptoms such as tachycardia, widened pulse pressure, hypotension, increased cardiac output (early) and potentially diminished cardiac output (late). CRS can include clinical coagulation signs and symptoms such as elevated d-dimer, hypofibrinogenemia with or without bleeding. CRS can include clinical renal signs and symptoms such as azotemia. CRS can include clinical hepatic signs and symptoms such as transaminitis and hyperbilirubinemia. CRS can include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a BCMA binding molecule that is bispecific for BCMA and CD3 described herein to a subject and further administering one or more agents to manage elevated levels of a soluble factor resulting from treatment with a BCMA binding molecule that is bispecific for BCMA and CD3. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and inhibitor of IL-1R, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others. In some embodiments, the subject is administered a corticosteroid, e.g., methylprednisolone, hydrocortisone, in combination with Benadryl and Tylenol prior to the administration of a BCMA binding molecule that is bispecific for BCMA and CD3 to mitigate the CRS risk.

In some embodiments, the subject is administered a vasopressor, such as, e.g., norepinephrine, dopamine, phenylephrine, epinephrine, vasopressin, or any combination thereof.

In an embodiment, the subject can be administered an antipyretic agent. In an embodiment, the subject can be administered an analgesic agent.

In some cases, however, it is known that antibody based therapies, including bispecific antibodies, can induce massive cytokine release leading to CRS even with coadministration or treatment with agents that can manage CRS. In some cases, the CRS can be so severe that it is life-threatening and/or cause death. See, Shimabukuro-Vornhagen, A. et al., 2018, J. Immunother Cancer. 6:56. Therefore, there is a need to development antibody-based therapies that induce less cytokine release, but at the same time retain and/or improve its efficacy.

8. EXAMPLES

8.1. Example 1: Isolation of Anti-BCMA Antibodies Using Phage Display 8.1.1. Overview BCMA is a cell surface receptor expressed on plasma cells, as well as other B-cell malignancies, particularly multiple myeloma. For effective pharmaceutical development, it is highly desirable to have an antibody that is cross-reactive with both human antigens as well as the corresponding antigen in a model non-human primate species, such as cynomolgus macaque, for the purpose of non-clinical pharmacokinetic and toxicology studies.
8.1.2. Materials and Methods
8.1.2.1. Panning To find antibodies that were cross-reactive with both human and cynomolgus BCMA, a naïve phage library containing human antibody fragments was panned against recombinant human and cynomolgus BCMA antigens using standard procedures. Briefly, Fc-tagged human BCMA (cat #BC7-H5254) and cynomolgus BCMA (cat #BCA-05253) proteins were purchased from ACRO Biosystems (Newark, DE), and biotinylated in-house.

In the first round of panning, the naïve phage pool was resuspended and depleted three times with biotinylated human Fc (cat #009-060-008, Jackson ImmunoResearch, West Grove, PA) captured on streptavidin Dynabeads (cat #M-280, Thermo Fisher Scientific, Waltham, MA). The phage pool was then split in two and panned against 40 µg of either biotinylated human or cyno BCMA-Fc captured on Dynabeads in the presence of a 5-fold excess of non-biotinylated human Fc (cat #009-000-008, Jackson ImmunoResearch, West Grove, PA). Captured phage were incubated for 60 minutes, washed 10 times with wash buffer (PBS+2% milk+1% BSA+0.05% Tween 20), and eluted from the beads by treatment with 200 µL of elution buffer (Pierce IgG Elution Buffer, cat #21004, Thermo Fisher Scientific, Waltham, MA). Eluted phage were then neutralized by treatment with 20 µL of neutralization buffer (1M Tris pH 9, cat #T1090, Teknova, Hollister, CA). Elution and neutralization step was repeated once, elutates were combined and used to infect 10 mL of ER2738 cells (cat #60522, Lucigen, Middleton, WI) cultured in 2YT media (cat #Y0167, Teknova, Hollister, CA). Separate cultures were maintained for phage pools screened against human or cyno BCMA. Infected ER2738 cells were incubated at 37° C. for 30 min, then added to 25 mL of 2YT buffer containing 100 µg/mL of carbencillin (cat #C2112, Teknova, Hollister, CA). An excess of M13K07 helper phage (cat #N0315S, New England Biolabs, Ipswich, MA) was then added to the media, and the resulting culture was grown overnight at 37° C. The culture supernatant was harvested by centrifugation, decanted, and amplified phage were recovered from the supernatant by precipitation with PEG/NaCl (PEG 6000/2.5M NaCl, cat #P4168, Teknova, Hollister, CA), centrifugation, and resuspension in PBS.

In the second round of panning, approximately $1 \times 10^{13}$ phage from each of the first round output pools were panned against alternate antigens (phage panned against human BCMA in the first round were used to pan against cyno BCMA in the second round, and vice versa), using a lower concentration of captured antigen (15 µg of either biotinylated human or cyno BCMA-Fc captured on Dynabeads). The remaining protocol matched that followed in the first round of panning, including Fc depletion steps.

In the third round of panning, output phage from both pools of panning were combined, and panned against 1 µg of human BCMA-His-APP-Avi (Table 12) captured on Sera-Mag SpeedBead Neutravidin (cat #7815-2104-011150, Thermo Fisher Scientific, Waltham, MA). The remaining protocol matched that followed in the first and second rounds of panning, including Fc depletion steps, as well as an additional depletion step with unlabeled Sera-Mag SpeedBead Neutravidin beads.

In the fourth round of panning, the output phage from the third round was panned against 1 µg of cyno BCMA-Fc (cat #90103-C02H-50, Sino Biological, Beijing, China) captured on Protein A Dynabeads (cat #10001D, Thermo Fisher Scientific, Waltham, MA). The remaining protocol matched that followed in the first, second, and third rounds of panning, including Fc depletion steps, as well as an additional depletion step with unlabeled Protein A Dynabeads.
8.1.2.2. Sequence Enrichment and Phage ELISA Based Screening Approximately 400 single phage colonies were picked from the fourth round panning output and sequenced using an M13 reverse primer. The top five enriched clones and a few singlet clones (PI-26, PI-28, PI-61, PIII-78, PIII-79, PIV-24, PI-45, PII-45, PII-55) were chosen to be amplified and rescued as phage for phage ELISA. The singlet clones were chosen based on enriched doublets (highest degree of enrichment) after the third round of panning and singlets after the fourth round of panning.

Three Streptavidin coated NUNC clear-flat-bottomed 96-well plates (cat #436014, Thermo Fisher Scientific, Waltham, MA) were each coated with in-house biotinylated Fc-tagged human BCMA (cat #BC7-H5254, ACRO Biosystems, Newark, DE), human BCMA-His-APP-Avi, and biotinylated human IgG1 Fc (cat #009-060-008, Jackson Immunoresearch, West Grove, PA) at 1 µg/mL in dPBS. A NUNC Maxisorp clear-flat-bottomed 96-well plate (cat #442404, Thermo Fisher Scientific, Waltham, MA) was coated with Fc-tagged cynomolgus BCMA (cat #BCA-05253, ACRO Biosystems, Newark, DE) at 1 µg/mL in dPBS. Plates were incubated overnight at 2-8° C.

Antigen coated plates were washed on a BioTek plate washer (EL406, BioTek, Winooski, VT) with PBS, Tween20 and blocked with 300 µL/well of Blocking Buffer (dPBS, 5% BSA, 0.05% Polysorbate 20, 0.01% d-Biotin) for 2 hours. Plates were washed again and 100 µL/well of the titrated phage samples were added and incubated for 2 hours at room temperature. The plates were washed after the phage sample incubation and 50 µL/well of 1:5000 diluted HRP conjugated anti-M13 detection antibody (cat #27-9421-01, GE, Pistacaway, NJ) was incubated for 30 minutes at room temperature. Plates were washed and the ELISA was developed by dispensing 100 µL/well of 1-Component Peroxidase Substrate (cat #50-77-04, SeraCare, Milford, MA) and quenching the reaction with 50 µL/well of 1 N HCl. 450 nm absorbance was read on the EnVision Plate Reader (2105-0010, Perkin Elmer, Waltham, MA).

8.1.3. Results

ELISA data for each monoclonal phage titration is shown in FIG. 2. All five enriched clones showed robust binding to human BCMA in either the Fc-tagged or His-APP-Avi-tagged formats. Clones PI-26 and PI-61 showed comparable levels of binding between Fc-tagged cyno BCMA and Fc-tagged human BCMA. Clones PI-28 and PIII-79 showed binding to Fc-tagged cyno BCMA as well as human BCMA, but the signal for binding to cyno BCMA titered down before human BCMA, suggestive of a lower binding affinity. Clone PIII-78 showed residual levels of binding to Fc-tagged cyno BCMA as well as Fc tag alone, suggesting a degree of non-specific binding and minimal cross-reactivity to cyno. All four singlet clones demonstrated strong binding to Fc-tagged human BCMA but weaker binding to Fc-tagged cyno BCMA in terms of affinity for Clones PII-55 and PII-45 and signal amplitude for clones PI-45 and PIV-24. Non-specific Fc binding was minimal for all four. Owing to their comparable binding to human and cyno BCMA, only clone PIII-78 was eliminated from this screen and the remaining eight clones, PI-26, PI-61, PI-28, PIII-79, PI-45, PII-45, PII-55, PIV-24, were identified as potential lead candidates and converted into bispecific antibodies.

TABLE 12

| Name | Library DNA sequence | SEQ ID NO: | Mature protein sequence | SEQ ID NO: |
|---|---|---|---|---|
| Human BCMA-His-APP-Avi | ATGTTGCAAATGGCTGGGCAAT GTAGTCAGAATGAGTACTTCGA TTCTCTTCTCCATGCTTGTATCC CCTGCCAGCTGAGGTGTTCAA GCAATACTCCGCCCCTTACCTG TCAACGATATTGTAATGCCTCC GTGACCAATTCCGTGAAGGGAA CCAATGCTGGATCCCATCACCA TCACCATCACGAATTTAGACAT GATAGCGGCCTGAACGACATTT TCGAGGCTCAAAAGATCGAGTG GCACGAG | 515 | MLQMAGQCSQNEYF DSLLHACIPCQLRCSS NTPPLTCQRYCNASV TNSVKGTNAGSHHHH HHEFRHDSGLNDIFEA QKIEWHE | 518 |
| PI-61 VH | CAGGTGCAGCTGCAGGAGTCG GGGGGAGGCGTGGTCCAGCCT GGGAGGTCCCTGAGACTCTCC TGTGCAGCCTCTGGATTCACCT TCAGTAGCTATGGCATGCACTG GGTCCGCCAGGCTCCAGGCAA GGGGCTGGAGTGGGTGGCAGT TATATCATATGATGGAAGTAATA AATACTATGCAGACTCCGTGAA GGGCCGATTCACCATCTCCAGA GACAATTCCAAGAACACGCTGT ATCTGCAAATGAACAGCCTGAG AGCCGAGGACACGGCCGTATA TTACTGTGGGGGGAGTGGTTA CGCCCTTCACGATGACTACTAC GGCTTGGACGTCTGGGGCCAA GGCACCCTGGTCACCGTCTCC TCA | 516 | QVQLQESGGGVVQP GRSLRLSCAASGFTFS SYGMHWVRQAPGKG LEWVAVISYDGSNKYY ADSVKGRFTISRDNSK NTLYLQMNSLRAEDTA VYYCGGSGYALHDDY YGLDVWGQGTLVTVSS | 225 |
| PI-61 VL | CAGTCTGCCCTGACTCAGCCTG CCTCCGTGTCTGGGTCTCCTG GACAGTCGATCACCATCTCCTG CACTGGAACCAGCAGTGACGTT GGTGGTTATAACTATGTCTCCT GGTACCAACAGCACCCAGGCA AAGCCCCCAAACTCATGATTTA TGATGTCAGTAATCGGCCCTCA GGGGTTTCTAATCGCTTCTCTG GCTCCAAGTCTGGCAACACGG CCTCCCTGACCATCTCTGGGCT CCAGGCTGAGGACGAGGCTGA TTATTACTGCAGCTCATATACAA GCAGCAGCACCCTTTATGTCTT CGGAAGTGGGACCAAGGTCAC CGTCCTA | 517 | QSALTQPASVSGSPG QSITISCTGTSSDVGG YNYVSWYQQHPGKAP KLMIYDVSNRPSGVSN RFSGSKSGNTASLTIS GLQAEDEADYYCSSY TSSSTLYVFGSGTKVT VL | 201 |

8.2. Example 2: Affinity Maturation of PI-61 Using Yeast Display 8.2.1. Overview As detailed in Example 1, the PI-61 antibody had a lower affinity for cynomolgus BCMA ($K_D$~240 nM) compared to human BCMA ($K_D$~34 nM) as determined by surface plasmon resonance. For pharmaceutical development, it would be desirable to have equivalent affinities for both human and cynomolgus antigens, as well as a higher overall binding affinity. To improve the affinity, three variant libraries were synthesized featuring mutations in 4 CDR regions, displayed on the surface of yeast, and screened to isolate variants of PI-61 with higher binding affinities to human and cynomolgus BCMA.

8.2.2. Library 1 Construction and Screening: CDR H2/CDR L2 Variants

The CDR H2 and CDR L2 regions of PI-61 (shown in Table 13) were selected for mutagenesis as they contained regions of variance from human germline and a putative aspartic acid isomerization site (DG), which would be undesirable for pharmaceutical development. DNA libraries were designed with mutations at positions 57-64 (SYDGSN, (SEQ ID NO:141)) (IMGT numbering) of CDR H2 and positions 56-57 (DV) and 68-69 (PS) of CDR L2.

The first library to be created was CDR L2. Synthetic DNA corresponding to the PI-61 scFv modified with the L2 library was combined with vector DNA from the pYUNBC4 yeast expression vector and electroporated into a yeast strain overexpressing the Aga1 protein under control of the Gal1 promoter to enable homologous recombination and assembly of the final library.

For the first round of screening, the L2 yeast library was grown 20° C. for 3 days in 400 mL of SD-ura broth (Clontech, Mountain View, CA), then pelleted by centrifuging for 5 minutes at 5000×g. Supernatant was removed, and the yeast pellet was resuspended in 400 mL of SD-ura broth with 1% raffinose and 2% galactose (Clontech, Mountain View, CA) and grown at 20° C. for 22 hours to induce expression. The culture was pelleted, supernatant removed, the pellet washed once with PBSM (PBS (Invitrogen) with 1% BSA (bovine serum albumin) and 2 mM EDTA), then resuspended in 15 mL of PBSM. The L2 library was heat treated at 37° C. for 10 min, cooled to 4 C, then depleted with streptavidin and anti-biotin magnetic beads (Miltenyi) for 15 min, beads removed using a MACS LS column (Miltenyi) and washed. The yeast library was then resuspended in 35 mL PBSM containing 10 nM biotinylated human BCMA (sequence shown in Table 12), and incubated for 1 hr at room temperature. Yeast were pelleted, washed twice with PBSM, and resuspended in 10 mL of PBSM with 100 µL of streptavidin magnetic beads, incubated for 5 min at 4° C., pelleted, resuspended in 15 mL PBSM and separated on a MACS LS column. Captured cells were washed with PBSM, eluted and added to 10 mL SD-ura broth with 2% glucose and grown at 30 C with shaking overnight.

The L2 library output from the first round of selection was used as a template for construction of the H2 library. Synthetic DNA with increased CDR H2 diversity in the VH domain was combined with vector DNA from the L2 library output and electroporated into yeast. This resulting library combining diversity in CDR L2 and CDR H2 shall be referred to as library L2/H2 hereafter.

For the second round of screening, the L2/H2 library was cultured and expression induced as described for the first round of screening, and similarly depleted against streptavidin and anti-biotin magnetic beads. The L2/H2 library was heat treated at 34° C. for 10 min, cooled to 4 C, resuspended in PBSM, and incubated with 25 nM biotinylated human BCMA for 1 hr at room temperature. Yeast were pelleted, washed twice with PBSM, and resuspended in 10 mL of PBSM with 200 uL of streptavidin magnetic beads, incubated for 5 min at 4° C., pelleted, resuspended in 15 mL PBSM and separated on a MACS LS column. Captured cells were washed with PBSM, eluted and added to 50 mL SD-ura broth with 1% raffinose, 2% galactose and incubated for 24 hours at 23° C.

For the third round of screening, yeast from the second round output were pelleted, washed, and resuspended in PBSM and incubated with 1 nM cyno BCMA-APP-Avi (Table 13) for 1 hour at room temperature. Yeast were pelleted, washed twice with PBSM, and resuspended in 5 mL of PBSM with 50 uL of streptavidin magnetic beads, incubated for 5 min at 4° C., pelleted, resuspended in 15 mL PBSM and separated on a MACS LS column. Captured cells were washed with PBSM, eluted and added to 200 mL SD-ura broth with 2% glucose and grown for 3 days at 18° C.

For the fourth round of screening, yeast from the third round output were pelleted, washed, and resuspended in 200 mL SD-ura broth with 1% raffinose, 2% galactose, and incubated for 22 hours at 20° C. to induce expression. Two 2.5 mL samples were taken of the resulting culture, pelleted, resuspended in PBSM and each incubated with 250 pM biotinylated human BCMA. The first sample was incubated with human BCMA for 45 min at room temperature, pelleted, washed twice with PBSF, and then resuspended in 1 mL PBSF (PBS with 0.1% BSA). The second sample was incubated with human BCMA for 45 minutes at room temperature. Both samples were pelleted, washed twice with PBSF, and resuspended in 200 uL of PBSF+a 1:30 dilution of rabbit anti-cMyc-FITC (Abcam)+a 1:100 dilution of neutravidin-dylight 633 (Invitrogen). Samples were incubated at 4 C for 30 min, pelleted, washed twice with PBSF, resuspended in 3 mL PBSF, filtered through 40 um filters, then sorted using flow cytometry on a FACS Aria cell sorter (Becton Dickinson Biosciences, San Jose, CA). Approximately $5\times10^5$ yeast were isolated and resuspended in 4 mL SD-ura broth with 2% glucose and grown overnight at 30° C.

For the fifth round of screening, the overnight culture resulting from the fourth round output was diluted to 20 mL in SD-ura broth. 10 mL was taken, pelleted, resuspended in 20 mL of SD-ura broth with 1% raffinose, 2% galactose, and incubated for 22 hours at 20° C. to induce expression. The next day, the resulting library was then heat treated at 40° C. for 10 min, cooled to 4 C, resuspended in PBSM, split into two samples and incubated with 100 pM biotinylated cyno BCMA following a similar protocol as the fourth round of screening, as listed above. However, chicken anti-cMyc-FITC (Abcam) and streptavidin-dylight 633 (Invitrogen) were used for labeling the yeast prior to cell sorting. Again, yeast showing a high intensity of staining were gated and sorted. Approximately $1.5\times10^5$ yeast were isolated and resuspended in 4 mL SD-ura broth with 2% glucose and grown overnight at 30° C.

For the sixth round of screening, the overnight culture resulting from the fifth round output was used to inoculate 100 mL of SD-ura broth with 2% glucose and grown for 6 hours at 30° C. The culture was then pelleted, resuspended in 50 mL of SD-ura broth with 1% raffinose, 2% galactose, and incubated for 20 hours at 20° C. to induce expression. Culture was then pelleted, washed twice with PBSM, resuspended in 10 mL of PBSM with 2.5 nM of biotinylated human BCMA, and mixed for 2 min, pelleted, washed twice with PBSM, then resuspended in 1 mL of PBSM with 100 nM of unlabeled human BCMA and incubated for 2 hours. The samples were then pelleted, resuspended in 100 uL of PBSF+a 1:30 dilution of goat anti-cMyc-FITC (Abcam)+a 1:100 dilution of neutravidin-dylight 633 (Invitrogen) and incubated for 25 minutes. The samples were then pelleted, washed twice with PBSF, resuspended in 1 mL PBSF and sorted on a FACS Aria cell sorter. Approximately $1.6\times10^5$ yeast were isolated and resuspended in 3 mL SD-ura broth with 2% glucose and grown overnight at 30° C.

The resulting pool was diluted in to SD-URA 2% glucose and plated on CM-URA glucose agar plates (Teknova) in order to obtain well-spaced colonies. Agar plates were grown at 30° C. for three days, then 384 colonies were picked in to 4×96 well deep-well plates containing 500 μl/well SD-URA 1% raffinose, 2% galactose. These plates were incubated at 20° C. with shaking for 2 days to induce expression.

Each sample plate was used to create three test plates for flow cytometric analysis. Approximately 100,000 yeast cells from each sample well were transferred to the corresponding well on each of three 96 well test plates, which containing 20 nM, 900 pM, or no biotinylated cyno BCMA. Labeling was essentially as above for sorting, except using 1:200 each streptavidin-dylight 633 (Invitrogen) and neutravidin-dylight 633 (Invitrogen) in PBSF as secondary reagent and excluding any anti-cMyc antibody. The test plates were analyzed on a Cytoflex flow cytometer (Beckman Coulter, Brea, CA)

The top 94 hits as ranked by the ratio of median fluorescence above background at 900 pM BCMA to median fluorescence above background at 20 nM were patched from the original agar plate on to fresh CM-URA glucose agar plates (Teknova) and grown at 30° C. for 2 days. The scFv portion of the 94 hits were amplified by colony PCR, purified using HT ExoSap-IT (Thermo Fisher Scientific, Waltham, MA), and submitted to Genewiz (South Plainfield, NJ) for sanger sequencing.

The top nine clones which did not contain any undesirable mutations (additional cysteines, putative post-translational modification sites, etc.) (sequences shown in Table 13) were selected for conversion from scFv to a CD3 bispecific format. These clones should be the highest affinity binders to BCMA, which should result in more potent molecules when formatted as bispecific antibodies. FIG. 3 shows a titration of soluble BCMA onto the surface of individual yeast clones. MFI values for each clone are shown in Table 14.

TABLE 13

| Name | DNA sequence | SEQ ID NO: | Mature protein sequence | SEQ ID NO: |
|---|---|---|---|---|
| PI-61 CDR H1 | | | GFTFSSYGMH | 189 |
| PI-61 CDR H2 | | | VISYDGSNKYYADSVKG | 113 |
| PI-61 CDR H3 | | | GGSGYALHDDYYGLDV | 51 |
| PI-61 CDR L1 | | | TGTSSDVGGYNYVS | 26 |
| PI-61 CDR L2 | | | DVSNRPS | 103 |
| PI-61 CDR L3 | | | SSYTSSSTLYV | 111 |
| Cyno BCMA APP-Avi | ATGCTCCAGATGGCACGGCAATGTAG TCAGAACGAGTATTTTGATAGCCTGCT CCACGATTGCAAGCCCTGTCAGCTGC GGTGTAGCTCCACTCCGCCATTGACG TGTCAGCGGTACTGCAACGCAAGTAT GACAAACTCAGTCAAGGGCATGAACG CAGGATCCCATCACCATCACCATCACG AATTTAGACATGATAGCGGCCTGAACG ACATTTTCGAGGCTCAAAAGATCGAGT GGCACGAG | 519 | MLQMARQCSQNEYFDSLLH DCKPCQLRCSSTPPLTCQR YCNASMTNSVKGMNAGSH HHHHHEFRHDSGLNDIFEA QKIEWHE | 529 |
| H2/L2-88 scFv | CAAGTGCAGCTCCAGAGTTCCGAAGG CGGAGTGGTGCAGCCTGGAAGGAGCC TGCGCCTGTCATGCGCAGCGTCCGGG TTCACCTTCTCATCCTACGGCATGCAC TGGGTCAGACAGGCCCCGGGAAAAGG ATTGGAATGGGTGGCCGTGATTTCATA CAAGGGTTCCAACAAGTACTACGCCG ATTCCGTGAAGGGACGGTTTACCATCT CGCGGGACAACTCGAAGAACACCCTG TACCTCCAAATGAACAGCCTGCGCGC CGAAGATACTGCCGTGTACTACTGCG GCGGTTCCGGTTACGCGCTCCACGAC GACTATTACGGGCTGGACGTCTGGGG ACAGGGCACCCTGGTCACTGTGTCCT CGTCAGGTGGTGGTGGTTCTGGTGGT GGCGGCTCAGGCGGCGGCGGCTCAG GTGGTGGAGGATCCCAGTCCGCTCTG ACCCAACCGGCTTCCGTGAGCGGAAG CCCCGGACAGTCCATTACTATCAGCTG TACCGGCACCTCCTCCGACGTCGGTG GATACAACTACGTGTCCTGGTATCAGC AGCATCCTGGAAAGGCTCCAAAGCTC ATGATCTACGAGGTGTCGAACAGACTG AGGGGTGTGTCCAATCGCTTTCGGG CTCCAAGTTCGGAAACACGGCCTCACT GACTATCTCGGGACTGCAGGCCGAAG | 520 | QVQLQSSEGGVVQPGRSL RLSCAASGFTFSSYGMHWV RQAPGKGLEWVAVISYKGS NKYYADSVKGRFTISRDNSK NTLYLQMNSLRAEDTAVYY CGGSGYALHDDYYGLDVW GQGTLVTVSSSGGGGSGG GGSGGGGSGGGGSQSALT QPASVSGSPGQSITISCTGT SSDVGGYNYVSWYQQHPG KAPKLMIYEVSNRLRGVSNR FSGSKFGNTASLTISGLQAE DEADYYCSSYTSSSALYVF GSGTKVTVL | 247 |

TABLE 13-continued

| Name | DNA sequence | SEQ ID NO: | Mature protein sequence | SEQ ID NO: |
|---|---|---|---|---|
| | ATGAAGCCGACTACTACTGCTCCTCCT ACACCTCGTCCTCCGCTCTGTACGTGT TCGGGTCCGGCACCAAAGTCACTGTG CTG | | | |
| H2/L2-36 scFv | CAAGCGCAGCTCCAGAGTTCCGGAGG CGGAGTGGTGCAGCCTGGAAGGAGCC TGCGCCTGTCATGCGCAGCGTCCGGG TTCACCTTCTCATCCTACGGCATGCAC TGGGTCAGACAGGCCCCGGGAAAAGG ATTGGAATGGGTGGCCGTGATTTCCTA CAAGGGGTCCAACAAGTACTACGCCG ATTCCGTGAAGGGACGGTTTACCATCT CGCGGGACAACTCGAAGAACACCCTG TACCTCCAAATGAACAGCCTGCGCGC CGAAGATACTGCCGTGTACTACTGCG GCGGTTCCGGTTACGCGCTCCACGAC GACTATTACGGGCTGGACGTCTGGGG ACAGGGCACCCTGGTCACTGTGTCCT CGTCAGGTGGTGGTGGTTCTGGTGGT GGCGGCTCAGGCGGCGGCGGCTCAG GTGGTGGAGGATCCCAGTCCGCTCTG ACCCAACCGGCTTCCGTGAGCGGAAG CCCCGGACAGTCCATTACTATCAGCTG TACCGGCACCTCCTCCGACGTCGGTG GATACAACTACGTGTCCTGGTATCAGC AGCATCCTGGAAAGGCTCCAAAGCTC ATGATCTACGAAGTGTCGAACAGACTG AGAGGTGTGTCCAATCGCTTTTCGGG CTCCAAGTTCGGAAACACGGCCTCACT GACTATCTCGGGACTGCAGGCCGAAG ATGAAGCCGACTACTACTGCTCCTCCT ACACCTCGTCCTCCACTCTGTACGTGT TCGGGTCCGGCACCAAAGTCACTGTG CTG | 521 | QAQLQSSGGGVVQPGRSL RLSCAASGFTFSSYGMHWV RQAPGKGLEWVAVISYKGS NKYYADSVKGRFTISRDNSK NTLYLQMNSLRAEDTAVYY CGGSGYALHDDYYGLDVW GQGTLVTVSSSGGGGSGG GGSGGGGSGGGGSQSALT QPASVSGSPGQSITISCTGT SSDVGGYNYVSWYQQHPG KAPKLMIYEVSNRLRGVSNR FSGSKFGNTASLTISGLQAE DEADYYCSSYTSSSTLYVF GSGTKVTVL | 248 |
| H2/L2-34 scFv | CAAGTGCAGCTCCAGGATTCCGAAGG CGGAGTGGTGCAGCCTGGAAGGAGCC TGCGCCTGTCATGCGCAGCGTCCGGG TTCACCTTCTCATCCTACGGCATGCAC TGGGTCAGACAGGCCCCGGGAAAAGG ATTGGAATGGGTGGCCGTGATTTCCTA CACTGGTACCAAAAGTACTACGCCGA TTCCGTGAAGGGACGGTTTACCATCTC GCGGGACAACTCGAAGAACACCCTGT ACCTCCAAATGAACAGCCTGCGCGCC GAAGATACTGCCGTGTACTACTGCGG CGGTTCCGGTTACGCGCTCCACGACG ACTATTACGGGCTGGACGTCTGGGGA CAGGGCACCCTGGTCACTGTGTCCTC GTCAGGTGGTGGTGGTTCTGGTGGTG GCGGCTCAGGCGGCGGCGGCTCAGG TGGTGGAGGATCCCAGTCCGCTCTGA CCCAACCGGCTTCCGTGAGCGGAAGC CCCGGACAGTCCATTACTATCAGCTGT ACCGGCACCTCCTCCGACGTCGGTGG ATACAACTACGTGTCCTGGTATCAGCA GCATCCTGGAAAGGCTCCAAAGCTCAT GATCTACGACGTGTCGAACAGACCGT GGGGTGTGTCCAATCGCTTTTCGGGC TCCAAGTTCGGAAACACGGCCTCACT GACTATCTCGGGACTGCAGGCCGAAG ATGAAGCCGACTACTACTGCTCCTCCT ACACCTCGTCCTCCGCTCTGTACGTGT TCGGGTCCGGCACCAAAGTCACTGTG ATG | 522 | QVQLQDSEGGVVQPGRSL RLSCAASGFTFSSYGMHWV RQAPGKGLEWVAVISYTGT KKYYADSVKGRFTISRDNSK NTLYLQMNSLRAEDTAVYY CGGSGYALHDDYYGLDVW GQGTLVTVSSSGGGGSGG GGSGGGGSGGGGSQSALT QPASVSGSPGQSITISCTGT SSDVGGYNYVSWYQQHPG KAPKLMIYDVSNRPWGVSN RFSGSKFGNTASLTISGLQA EDEADYYCSSYTSSSALYVF GSGTKVTVM | 249 |
| H2/L2-68 scFv | CAAGCGCAGCTCCAGAGTTCCGAAGG CGGAGTGGTGCAGCCTGGAAGGAGCC TGCGCCTGTCATGCGCAGCGTCCGGG TTCACCTTCTCATCCTACGGCATGCAC TGGGTCAGACAGGCCCCGGGAAAAGG ATTGGAATGGGTGGCCGTGATTTCCTA CCGGGGTTTTAACAAGTACTACGCCGA TTCCGTGAAGGGACGGTTTACCATCTC GCGGGACAACTCGAAGAACACCCTGT ACCTCCAAATGAACAGCCTGCGCGCC | 523 | QAQLQSSEGGVVQPGRSL RLSCAASGFTFSSYGMHWV RQAPGKGLEWVAVISYRGF NKYYADSVKGRFTISRDNSK NTLYLQMNSLRAEDTAVYY CGGSGYALHDDYYGQDVW GQGTLVTVSSSGGGGSGG GGSGGGGSGGGGSQSALT QPASVSGSPGQSITISCTGT SSDVGGYNYVSWYQQHPG | 250 |

TABLE 13-continued

| Name | DNA sequence | SEQ ID NO: | Mature protein sequence | SEQ ID NO: |
|---|---|---|---|---|
| | GAAGATACTGCCGTGTACTACTGCGG CGGTTCCGGTTACGCGCTCCACGACG ACTATTACGGGCAGGACGTCTGGGGA CAGGGCACCCTGGTCACTGTGTCCTC GTCAGGTGGTGGTGGTTCTGGTGGTG GCGGCTCAGGCGGCGGCGGCTCAGG TGGTGGAGGATCCCAGTCCGCTCTGA CCCAACCGGCTTCCGTGAGCGGAAGC CCCGGACAGTCCATTACTATCAGCTGT ACCGGCACCTCCTCCGACGTCGGTGG ATACAACTACGTGTCCTGGTATCAGCA GCATCCTGGAAAGGCTCCAAAGCTCAT GATCTACGACGTGTCGAACAGACTGA GCGGTGTGTCCAATCGCTTTTCGGGC TCCAAGTTCGGAAACACGGCCTCACT GACTATCTCGGGACTGCAGGCCAAG ATGAAGCCGACTACTACTGCTCCTCCT ACACATCGTCCTCCACTCTGTACGTGT TCGGGTCCGGCACCAAAGTCACTGTG CTG | | KAPKLMIYDVSNRLSGVSNR FSGSKFGNTASLTISGLQAE DEADYYCSSYTSSSTLYVF GSGTKVTVL | |
| H2/L2-18 scFv | CAAGCGCAGCTCCAGGGGTCCGGAG GCGGAGTGGTGCAGCCTGGAAGGAG CCTGCGCCTGTCATGCGCAGCGTCCG GGTTCACCTTCTCATCCTACGGCATGC ACTGGGTCAGACAGGCCCCGGGAAAA GGATTGGAATGGGTGGCCGTGATTTC CTACAAGGGGTCCCACAAGTACTACG CCGATTCCGTGAAGGGACGGTTTACC ATCTCGCGGGACAACTCGAAGAACAC CCTGTACCTCCAAATGAACAGCCTGCG CGCCGAAGATACTGCCGTGTACTACT GCGGCGGTTCCGGTTACGCGCTCCAC GACGACTATTACGGGCTGGACGTCTG GGGACAGGGCACCCTGGTCACTGTGT CCTCGTCAGGTGGTGGTGGTTCTGGT GGTGGCGGCTCAGGCGGCGGCGGCT CAGGTGGTGGAGGATCCCAGTCCGCT CTGACCCAACCGGCTTCCGTGAGCGG AAGCCCCGGACAGTCCATTACTATCAG CTGTACCGGCACCTCCTCCGACGTCG GTGGATACAACTACGTGTCCTGGTATC AGCAGCATCCTGGAAAGGCTCCAAAG CTCATGATCTACGACGTGTCGAACAGA CCGTGGGGTGTGTCCAATCGCTTTTC GGGCTCCAAGTTCGGAAACACGGCCT CACTGACTATCTCGGGACTGCAGGCC GAAGATGAAGCCGACTACTACTGCTCC TCCTACACCTCGTCCTCCACTCTGTAC GTGTTCGGGTCCGGCACCAAAGTCAC TGTGCTG | 524 | QAQLQGSGGGVVQPGRSL RLSCAASGFTFSSYGMHWV RQAPGKGLEWVAVISYKGS HKYYADSVKGRFTISRDNSK NTLYLQMNSLRAEDTAVYY CGGSGYALHDDYYGLDVW GQGTLVTVSSSGGGGSGG GGSGGGGSGGGGSQSALT QPASVSGSPGQSITISCTGT SSDVGGYNYVSWYQQHPG KAPKLMIYDVSNRPWGVSN RFSGSKFGNTASLTISGLQA EDEADYYCSSYTSSSTLYVF GSGTKVTVL | 251 |
| H2/L2-47 scFv | CAAGTGCAGCTCCAGAGTTCCGAAGG CGGAGTGGTGCAGCCTGGAAGGAGCC TGCGCCTGTCATGCGCAGCGTCCGGG TTCACCTTCTCATCCTACGGCATGCAC TGGGTCAGACAGGCCCCGGGAAAAGG ATTGGAATGGGTGGCCGTGATTTCCTA CAAGGGGTCGAACAAGTACTACGCCG ATTCCGTGAAGGGACGGTTTACCATCT CGCGGGACAACTCGAAGAACACCCTG TACCTCCAAATGAACAGCCTGCGCGC CGAAGATACTGCCGTGTACTACTGCGG CGGTTCCGGTTACGCGCTCCACGAC GACTATTACGGGCTGGACGTCTGGGG ACAGGGCACCCTGGTCACTGTGTCCT CGTCAGGTGGTGGTGGTTCTGGTGGT GGCGGCTCAGGCGGCGGCGGCTCAG GTGGTGGAGGATCCCAGTCCGCTCTG ACCCAACCGGCTTCCGTGAGCGGAAG CCCCGGACAGTCCATTACTATCAGCTG TACCGGCACCTCCTCCGACGTCGGTG GATACAACTACGTGTCCTGGTATCAGC AGCATCCTGGAAAGGCTCCAAAGCTC ATGATCTACGACGTGTCGAACAGACC GTGGGGTGTGTCCAATCGCTTTTCGG GCTCCAAGTTCGGAAACACGGCCTCA | 525 | QVQLQSSEGGVVQPGRSL RLSCAASGFTFSSYGMHWV RQAPGKGLEWVAVISYKGS NKYYADSVKGRFTISRDNSK NTLYLQMNSLRAEDTAVYY CGGSGYALHDDYYGLDVW GQGTLVTVSSSGGGGSGG GGSGGGGSGGGGSQSALT QPASVSGSPGQSITISCTGT SSDVGGYNYVSWYQQHPG KAPKLMIYDVSNRPWGVSN RFSGSKFGNTASLTISGLQA EDEADYYCSSYTSSSTLYVF GSGTKVTVL | 252 |

TABLE 13-continued

| Name | DNA sequence | SEQ ID NO: | Mature protein sequence | SEQ ID NO: |
|---|---|---|---|---|
| | CTGACTATCTCGGGACTGCAGGCCGA AGATGAAGCCGACTACTACTGCTCCTC CTACACCTCGTCCTCCACTCTGTACGT GTTCGGGTCCGGCACCAAAGTCACTG TGCTG | | | |
| H2/L2-20 scFv | CAAGCGCAGCTCCAGAGTTCCGGAGG TGGAGTGGTGCAGCCTGGAAGGAGCC TGCGCCTGTCATGCGCAGCGTCCGGG TTCACCGTCTCATCCTACGGCATGCAC TGGGTCAGACAGGCCCCGGGAAAAGG ATTGGAATGGGTGGCCGTGATTTCCTA CACTGGGTCCAACAAGTACTACGCCG ATTCCGTGAAGGGACGGTTTACCATCT CGCGGGACAACTCGAAGAACACCCTG TACCTCCAAATGAACAGCCTGCGCGC CGAAGATACTGCCGTGTACTACTGCG GCGGTTCCGGTTACGCGCTCCACGAC GACTATTACGGGCTGGACGTCTGGGG ACAGGGCACCCTGGTCACTGTGTCCT CGTCAGGTGGTGGTGGTTCTGGTGGT GGCGGCTCAGGCGGCGGCGGCTCAG GTGGTGGAGGATCCCAGTCCGCTCTG ACCCAACCGGCTTCCGTGAGCGGAAG CCCCGGACAGTCCATTACTATCAGCTG TACCGGCACCTCCTCCGACGTCGGTG GATACAACTACGTGTCCTGGTATCAGC AGCATCCTGGAAAGGCTCCAAAGCTC ATGATCTACGACGTGTCGAACAGACTG AGGGGTGTGTCCAATCGCTTTTCGGG CTCCAAGTTCGGAAACACGGCCTCACT GACTATCTCGGGATTGCAGGCCGAAG ATGAAGCCGACTACTACTGCTCCTCCT ACACCTCGTCATCCGCTCTGTACGTGT TCGGGTCCGGCACCAAAGTCACTGTG CTG | 526 | QAQLQSSGGGVVQPGRSL RLSCAASGFTVSSYGMHWV RQAPGKGLEWVAVISYTGS NKYYADSVKGRFTISRDNSK NTLYLQMNSLRAEDTAVYY CGGSGYALHDDYYGLDVW GQGTLVTVSSSGGGSGG GGSGGGGSGGGGSQSALT QPASVSGSPGQSITISCTGT SSDVGGYNYVSWYQQHPG KAPKLMIYDVSNRLRGVSN RFSGSKFGNTASLTISGLQA EDEADYYCSSYTSSSALYVF GSGTKVTVL | 253 |
| H2/L2-80 scFv | CAAGTGCAGCTCCAGAGTTCCGGAGG CGGAGTGGTGCAGCCTGGAAGGAGCC TGCGCCTGTCATGCGCAGCGTCCGGG TTCACCTTCTCATCCTACGGCATGCAC TGGGTCAGACAGGCCCCGGGAAAAGG ATTGGAATGGGTGGCCGTGATTTCATA CACTGGTTCTAACAAGTACTACGCCGA TTCCGTGAAGGGACGGTTTACCATCTC GCGGGACAACTCGAAGAACACCCTGT ACCTCCAAATGAACAGCCTGCGCGCC GAAGATACTGCCGTGTACTACTGCGG CGGTTCCGGTTACGCGCTCCACGACG ACTATTACGGGCTGGACGTCTGGGA CAGGGCACCCTGGTCACTGTGTCCTC GTCAGGTGGTGGTGGTTCTGGTGGTG GCGGCTCAGGCGGCGGCGGCTCAGG TGGTGGAGGATCCCAGTCCGCTCTGA CCCAACCGGCTTCCGTGAGCGGAAGC CCCGGACAGTCCATTACTATCAGCTGT ACCGGCACCTCCTCCGACGTCGGTGG ATACAACTACGTGTCCTGGTATCAGCA GCATCCTGGAAAGGCTCCAAAGCTCAT GATCTACGACGTGTCGAACAGAGCGT GGGGTGTGTCCAATCGCTTTTCGGGC TCCAAGTTCGGAAACACGGCCTCACT GACTATCTCGGGACTGCAGGCCGAAG ATGAAGCCGACTACTACTGCTCCTCCT ACACCTCGTCCTCCGCTCTGTACGTGT TCGGGTCCGGTACCAAAGTCACTGTG CTG | 527 | QVQLQSSGGGVVQPGRSL RLSCAASGFTFSSYGMHWV RQAPGKGLEWVAVISYTGS NKYYADSVKGRFTISRDNSK NTLYLQMNSLRAEDTAVYY CGGSGYALHDDYYGLDVW GQGTLVTVSSSGGGSGG GGSGGGGSGGGGSQSALT QPASVSGSPGQSITISCTGT SSDVGGYNYVSWYQQHPG KAPKLMIYDVSNRAWGVSN RFSGSKFGNTASLTISGLQA EDEADYYCSSYTSSSALYVF GSGTKVTVL | 254 |
| H2/L2-83 scFv | CAAGCGCAGCTCCAGGGGTCCGGAG GCGGAGTGGTGCAGCTGGAAGGAGC CCTGCGCCTGTCATGCGCAGCGTCCG GGTTCACCTTCTCATCCTACGGCATGC ACTGGGTCAGACAGGCCCCGGGAAAA GGATTGGAATGGGTGGCCGTGATTTC CTATAAGGGTTCCAACAAGTACTACGC CGATTCCGTGAAGGGACGGTTTACCAT CTCGCGGGACAACTCGAAGAACACCC | 528 | QAQLQGSGGGVVQPGRSL RLSCAASGFTFSSYGMHWV RQAPGKGLEWVAVISYKGS NKYYADSVKGRFTISRDNSK NTLYLQMNSLRAEDTAVYY CGGSGYALHDDYYGLDVW GQGTLVTVSSSGGGSGG GGSGGGGSGGGGSQSALT QPASVSGSPGQSITISCTGT | 255 |

TABLE 13-continued

| Name | DNA sequence | SEQ ID NO: | Mature protein sequence | SEQ ID NO: |
|------|--------------|------------|-------------------------|------------|
|      | TGTACCTCCAAATGAACAGCCTGCGC<br>GCCGAAGATACTGCCGTGTACTACTG<br>CGGCGGTTCCGGTTACGCGCTCCACG<br>ACGACTATTACGGGCTGGACGTCTGG<br>GGACAGGGCACCCTGGTCACTGTGTC<br>CTCGTCAGGTGGTGGTGGTTCTGGTG<br>GTGGCGGCTCAGGCGGCGGCGGCTC<br>AGGTGGTGGAGGATCCCAGTCCGCTC<br>TGACCCAACCGGCTTCCGTGAGCGGA<br>AGCCCCGGACAGTCCATTACTATCAGC<br>TGTACCGGCACCTCCTCCGACGTCGG<br>TGGATACAACTACGTGTCCTGGTATCA<br>GCAGCATCCTGGAAAGGCTCCAAAGC<br>TCATGATCTACGAAGTGTCGAACAGAT<br>TGAGAGGTGTGTCCAATCGCTTTTCGG<br>GCTCCAAGTTCGGAAACACGGCCTCA<br>CTGACTATCTCGGGACTGCAGGCCGA<br>AGATGAAGCCGACTACTACTGCTCCTC<br>CTACACCTCGTCCTCCACTCTGTACGT<br>GTTCGGGTCCGGCACCAAAGTCACTG<br>TGCTG |            | SSDVGGYNYVSWYQQHPG<br>KAPKLMIYEVSNRLRGVSNR<br>FSGSKFGNTASLTISGLQAE<br>DEADYYCSSYTSSSTLYVF<br>GSGTKVTVL |            |

TABLE 14

Summary of MFI values from single clone flow cytometry analysis

| Clone | 20 nM BCMA | 900 pM BCMA | no antigen |
|-------|------------|-------------|------------|
| H2/L2-88 | 4481.8 | 6441.1 | 129.5 |
| H2/L2-36 | 6428.4 | 5589.8 | 44.8 |
| H2/L2-34 | 10368.2 | 6053.3 | 68.1 |
| H2/L2-68 | 16176.2 | 7375.8 | 207 |
| H2/L2-18 | 19873.6 | 7184.8 | 73.3 |
| H2/L2-47 | 14182.2 | 5931.1 | 43.2 |
| H2/L2-20 | 20664.5 | 7034.2 | 37.2 |
| H2/L2-80 | 17949.9 | 6535.9 | 71.1 |
| H2/L2-83 | 10670.6 | 4880.2 | 123.6 |

FIG. 4 highlights the CDRH2 differences between the parental PI-61 and the selected clones. Of interest is position 59 (IMGT numbering) which, as an aspartate in the parental sequence, formed part of a potential aspartate isomerization site. This has been mutated in the identified sequences, mostly to either arginine or threonine.

FIG. 5 shows additional mutations in CDRL2 between the parental PI-61 and the identified clones. Position 56 (IMGT numbering) has been mutated from aspartate to glutamate in several of the sequences. Most of the sequences have a proline to leucine mutation at position 61. Additionally, position 62 has been mutated from serine to either arginine or tryptophan in a majority of the identified sequences.

Screening conditions for all six rounds are summarized in Table 15.

TABLE 15

Screening of CDR L2 and CDR L2/H2 yeast libraries

| Round | Method | Library | # input cells | Target | Antigen concentration | Labeling time (min) | Dissociation time (min) |
|-------|--------|---------|---------------|--------|----------------------|---------------------|-------------------------|
| 1 | MACS | L2 | 5.00E+09 | Human BCMA | 10 nM | | |
| 2 | MACS | L2/H2 | 5.00E+09 | Human BCMA | 25 nM | | |
| 3 | MACS | L2/H2 | 1.00E+09 | Cyno BCMA | 1 nM | | |
| 4 | FACS | L2/H2 | 7.50E+07 | Human BCMA | 250 pM | | |
| 5 | FACS | L2/H2 | 2.50E+07 | Cyno BCMA | 100 pM | | |
| 6 | FACS | L2/H2 | 2.50E+07 | Human BCMA | 2.5 nM | 2 | 120 |

8.2.3. Library 2 Construction and Screening: CDR H3.1 Variants

The N-terminal half of CDR H3 of PI-61 was selected for mutagenesis as it contained regions of variance from human germline, and CDR H3 regions are typically important for contacts with antigen. A DNA library (termed H3.1 hereafter) was designed with mutations at positions 107-112.2 (SGYALHD (SEQ ID NO:530)) (IMGT numbering) of CDR-H3. The output from library 1 was used as input for creation of this library in order to ensure that all identified sequences had mutations to remove the potential aspartate isomerization site which was present in the parental PI-61 CDRH2.

The H2/L2 output scFv DNA was amplified, modified with the H3.1 library, combined with vector DNA from the pYUNBC4 yeast expression vector, and electroporated into yeast to enable homologous recombination and assembly of the final library.

Screening of Library 2 was performed substantially similarly to screening with Library 1 (see above). The sorting procedure and secondary reagents were essentially the same, with the exception of number of rounds and the order of antigen alternation between rounds. The antigen concentrations used, association time, and dissociation time also differed and are listed in Table 16.

TABLE 16

Screening of CDR H3.1 yeast library

| Round | Method | # input cells | Target | Antigen concentration | Labeling time (min) | Dissociation time (min) |
|---|---|---|---|---|---|---|
| 1 | MACS | 2.00E+09 | Cyno BCMA | 4 nM | 2 | 90 |
| 2 | FACS | 5.00E+07 | Human BCMA | 250 pM | 2 | 105 |
| 3 | FACS | 2.00E+07 | Cyno BCMA | 100 pM | 1 | 180 |
| 4 | FACS | 2.00E+07 | Human BCMA | 400 pM | 30 | 900 |

8.2.4. Library 3 Construction and Screening: CDR H3.2 Variants

The C-terminal half of CDR H3 of PI-61 was also selected for mutagenesis as it contained regions of variance from human germline, and CDR H3 regions are typically important for contacts with antigen. A DNA library (termed H3.2 hereafter) was designed with mutations at positions 112.1-117 (DYYGLDV (SEQ ID NO:531)) (IMGT numbering) of CDR H3. The output from Library 1 was used as input for creation of this library in order to ensure that all identified sequences had mutations to remove the potential aspartate isomerization site which was present in the parental PI-61 CDRH2.

The H2/L2 output scFv DNA was amplified, modified with the H3.2 library, combined with vector DNA from the pYUNBC4 yeast expression vector, and electroporated into yeast to enable homologous recombination and assembly of the final library.

Screening of Library 3 was performed substantially similarly to screening with Library 1 (see above). The sorting procedure and secondary reagents were essentially the same, with the exception of number of rounds and the order of antigen alternation between rounds. The antigen concentrations used, association time, and dissociation time also differed and are listed in Table 17.

TABLE 17

Screening of CDR H3.1 yeast library

| Round | Method | # input cells | Target | Antigen concentration | Labeling time (min) | Dissociation time (min) |
|---|---|---|---|---|---|---|
| 1 | MACS | 2.00E+09 | Human BCMA | 9 nM | 5 | 120 |
| 2 | FACS | 5.00E+07 | Cyno BCMA | 200 pM | 2 | 105 |
| 3 | FACS | 2.00E+07 | Human BCMA | 200 pM | 1.5 | 90 |
| 4 | FACS | 2.00E+07 | Cyno BCMA | 100 pM | 2 | 120 |
| 5 | FACS | 2.00E+07 | Human BCMA | 100 nM | 30 | 900 |

8.3. Example 3: Screening of Affinity Matured Libraries Using Activation Assays

8.3.1. Overview

Affinity matured anti-BCMA pools were identified in Example 2, but these antibodies were displayed on the yeast surface as scFvs. One therapeutic application of these antibody sequences would be as bispecific antibodies to redirect T-cell cytotoxicity against BCMA-expressing tumor cells. To evaluate the utility of these antibody sequences as bispecific antibodies, the variable domain sequences were cloned into a heterodimeric bispecific antibody format (FIG. 6), expressed in HEK 293 cells and tested for the ability to bind BCMA on tumor cells and the ability to activate T-cells in a target-dependent fashion using a Jurkat NFAT luciferase (JNL) reporter assay.

8.3.2. CD3 Cotransfection and Expression

The H3.1 and H3.2 Library pools of Example 2 were converted to Fab format and subcloned in to a bicistronic IgG vector with a heterodimeric Fc (FIG. 6). When cotransfected along with a similar vector containing an anti CD3 scFv fused to a heterodimeric Fc, expression of these clones yields heterodimeric bispecific antibodies with an anti-BCMA Fab on the first heavy chain and an anti-CD3 scFv on the second heavy chain (FIG. 6). A 1:1 mixture of the two vectors at 1 µg/ml total DNA was mixed with 3 µg/ml PEI (40K linear, Polysciences, Warrington, PA), added to Expi293 cells (Invitrogen), and grown for five days at 37° C./8% carbon dioxide with shaking in order to produce bispecific antibodies. After expression, the cells were pelleted by centrifugation and then the conditioned medium was clarified by 0.45 µm filtration. This clarified conditioned medium was used directly in JNL activation assays.

8.3.3. JNL Activation Assays

The target cells used were an engineered 300-19 cell line (Tufts University, Boston, MA) overexpressing a cynomolgus BCMA construct. They were premixed with JNL reporter cells in RPMI (Invitrogen)+10% Fetal Bovine Serum (VWR Seradigm, Radnor, PA)+2 mM L-glutamine and added to every well of 384 well white tissue culture plates. One 384 well test plate was set up for each 96 well sample plate. The conditioned medium containing the test antibodies were diluted in RPMI and each sample was added to four wells in the corresponding cell-containing test plate at final dilutions of 1:10, 1:100, 1:1000, and 1:10000. The test plates were incubated for five hours at 37° C./5% carbon dioxide in order for NFAT driven luciferase expression to occur. The test plates were equilibrated to room temperature, and then One-Glo (Promega, Madison, WI) was added to each well at a 1:1 dilution. The plates were incubated for 10 minutes at room temperature, then read on an Envision Plate reader (Perkin Elmer) using a Luminescence 700 filter. Average antibody concentrations were used and the data were fit using GraphPad Prism and the equation $Y=\text{Bottom}+(\text{Top}-\text{Bottom})/(1+10^{\wedge}((\text{Log EC50}-X)))$ to obtain approximate EC50 values for each sample. The top 94 clones as ranked by approximate EC50 were sequenced, and after discarding undesirable CDR sequences (cysteines, putative modification sites, etc.), 72 clones were selected for retesting. The second assay was similar to the first, except each clone was tested separately against both human and cynomolgus BCMA overexpressing cell lines. Additionally, for each sample antibody, an eight point three-fold dilution series was used, with a highest approximate concentration of 4000 pM and a lowest of 1.83 pM. These data were again fitted with the same equation, and the top clones which showed high potency activation with both human and cynomolgus BCMA (Table 18) were selected for scale up and additional testing. VH and VL nucleotide and amino acid sequences for the clones are shown in Table 19.

TABLE 18

Potency of selected hits in JNL activation assays against Human and Cynomolgus BCMA-expressing cell lines

| clone | Human EC50 (M) | Cynomolgus EC50 (M) |
|---|---|---|
| H3-1 | 4.1E−10 | 8.4E−11 |
| H3-2 | 2.7E−10 | 1.2E−10 |
| H3-3 | 3.8E−10 | 1.5E−10 |
| H3-4 | 3.6E−10 | 1.7E−10 |
| H3-5 | 3.3E−10 | 2.6E−10 |
| H3-6 | 4.8E−10 | 3.0E−10 |
| H3-7 | 2.0E−10 | 3.2E−10 |
| H3-8 | 3.3E−10 | 3.9E−10 |
| H3-9 | 4.1E−10 | 4.1E−10 |
| H3-10 | 3.5E−10 | 4.1E−10 |
| H3-11 | 3.1E−10 | 4.1E−10 |
| H3-12 | 4.9E−10 | 4.2E−10 |
| H3-13 | 3.0E−10 | 4.7E−10 |
| H3-14 | 3.0E−10 | 4.7E−10 |
| H3-15 | 4.0E−10 | 4.8E−10 |
| H3-16 | 3.7E−10 | 4.9E−10 |
| H3-17 | 3.4E−10 | 5.0E−10 |

TABLE 19

| Name | DNA sequence | SEQ ID NO: | Mature protein Sequence | SEQ ID NO: |
|---|---|---|---|---|
| H3-1 VH | CAAGTGCAGCTCCAGGGGTCCGGAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACGATGATGCCCACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCCGGTTACGCGCTCCACGACCAGTATA AGCCAGTCGATGTCTGGGGACAGGGCACC CTGGTCACTGTGTCCTCG | 532 | QVQLQGSGGGVVQPGRSL RLSCAASGFTFSSYGMHW VRQAPGKGLEWVAVISYDD AHKYYADSVKGRFTISRDN SKNTLYLQMNSLRAEDTAV YYCGGSGYALHDQYKPVD VWGQGTLVTVSS | 235 |
| H3-1 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTAAGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCGC TCTGTACGTGTTCGGGTCCGGCACCAAAG TCACTGTGCTG | 533 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |

TABLE 19-continued

| Name | DNA sequence | SEQ ID NO: | Mature protein Sequence | SEQ ID NO: |
|---|---|---|---|---|
| H3-2 VH | CAAGCGCAGCTCCAGGAGTCCGAAGGCGG AGTGGTGCAGCCTGGAGGGAGCCTGCGC CTGTCATGCGCAGCGTCCGGGTTCACCTT CTCATCCTACGGCATGCACTGGGTCAGAC AGGCCCCGGGAAAAGGATTGGAATGGGTG GCCGTGATTTCCTACAATGATTTGAACAAG TACTACGCCGATTCCGTGAAGGGACGGTTT ACCATCTCGCGGGACAACTCGAAGAACAC CCTGTACCTCCAAATGAACAGCCTGCGCG CCGAAGATACTGCCGTGTACTACTGCGGC GGTTCCGGTTACGCGCTCCACGACTTCCA GGATCCAACAGATGTCTGGGGACAGGGCA CCCTGGTCACTGTGTCCTCG | 534 | QAQLQESEGGVVQPGGSL RLSCAASGFTFSSYGMHW VRQAPGKGLEWVAVISYND LNKYYADSVKGRFTISRDN SKNTLYLQMNSLRAEDTAV YYCGGSGYALHDFQDPTD VWGQGTLVTVSS | 236 |
| H3-2 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTAAGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCGC TCTGTACGTGTTCGGGTCCGGCACCAAAG TCACTGTGCTG | 533 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |
| H3-3 VH | CAAGTGCAGCTCCAGAGTTCCGGAGGTGG AGTGGTGCAGCCTGGAAGGAGCCTGCGCC TGTCATGCGCAGCGTCCGGGTTCACCGTC TCATCCTACGGCATGCACTGGGTCAGACA GGCCCCGGGAAAAGGATTGGAATGGGTGG CCGTGATTTCCTACAGTGGGTCCAACAAGT ACTACGCCGATTCCGTGAAGGGACGGTTT ACCATCTCGCGGGACAACTCGAAGAACAC CCTGTACCTCCAAATGAACAGCCTGCGCG CCGAAGATACTGCCGTGTACTACTGCGGC GGTTCCGGTTACGCGCTCCACGACCAGTA TAAGCCAGTCGATGTCTGGGGACAGGGCA CCCTGGTCACTGTGTCCTCG | 535 | QVQLQSSGGGVVQPGRSL RLSCAASGFTVSSYGMHW VRQAPGKGLEWVAVISYSG SNKYYADSVKGRFTISRDN SKNTLYLQMNSLRAEDTAV YYCGGSGYALHDQYKPVD VWGQGTLVTVSS | 237 |
| H3-3 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAGGTGTCGAACAGACTGAGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCGC TCTGTACGTGTTCGGGTCCGGCACCAAAG TCACTGTGCTG | 536 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |
| H3-4 VH | CAAGTGCAGCTCCAGGGGTCCGGAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACGATGATGCCCACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCCGGTTACGCGCTCCACGACCAGTATA AGCCAGTCGATGTCTGGGGACAGGGCACC CTGGTCACTGTGTCCTCG | 532 | QVQLQGSGGGVVQPGRSL RLSCAASGFTFSSYGMHW VRQAPGKGLEWVAVISYDD AHKYYADSVKGRFTISRDN SKNTLYLQMNSLRAEDTAV YYCGGSGYALHDQYKPVD VWGQGTLVTVSS | 235 |
| H3-4 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTGAGAG GTGTGTCCAATCGCTTTTCGGGCTCCAAGT TCGGAAACACGGCATCACTGACTATCTCGG GACTGCAGGCCGAAGATGAAGCCTACTAC | 537 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSALYVFGSGTKVTVL | 203 |

TABLE 19-continued

| Name | DNA sequence | SEQ ID NO: | Mature protein Sequence | SEQ ID NO: |
|---|---|---|---|---|
| | TACTGCTCCTCCTACACCTCGTCCTCCACT CTGTACGTGTTCGGGTCCGGCACCAAAGT CACTGTGCTG | | | |
| H3-5 VH | CAAGTGCAGCTCCAGGGTTCCGGAGGCGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACACTGGGGCCAACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCTGGTTATAACTTGCACGATGACTATTA CGGGCTGGACGTCTGGGGACAGGGCACC CTGGTCACTGTGTCCTCG | 538 | QVQLQGSGGGVVQPGRSL RLSCAASGFTFSSYGMHW VRQAPGKGLEWVAVISYTG ANKYYADSVKGRFTISRDN SKNTLYLQMNSLRAEDTAV YYCGGSGYNLHDDYYGLD VWGQGTLVTVSS | 238 |
| H3-5 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAGGTGTCGAACAGACTGAGGG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCAC TCTGTACGTGTTCGGGTCCGGCACCAAAG TCACTGTGCTG | 539 | QSALTQPASVSGSPGQSITI SCTGTSSDVGGYNYVSWY QQHPGKAPKLMIYEVSNRL SGVSNRFSGSKFGNTASLT ISGLQAEDEADYYCSSYTS SSTLYVFGSGTKVTVL | 202 |
| H3-6 VH | CAAGCGCAGCTCCAGAGGTCCGGAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACGATATGCCCACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCCGGTTACGCGCTCCACGACCAGTATA AGCCAGTCGATGTCTGGGGACAGGGCACC CTGGTCACTGTGTCCTCG | 540 | QAQLQRSGGGVVQPGRSL RLSCAASGFTFSSYGMHW VRQAPGKGLEWVAVISYDD AHKYYADSVKGRFTISRDN SKNTLYLQMNSLRAEDTAV YYCGGSGYALHDQYKPVD VWGQGTLVTVSS | 239 |
| H3-6 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTAAGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCGC TCTGTACGTGTTCGGGTCCGGCACCAAAG TCACTGTGCTG | 533 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSALYVFGSGTKVTVL | 203 |
| H3-7 VH | CAAGTGCAGCTCCAGAGTTCCGAAGGTGG AGTGGTGCAGCCTGGAAGGAGCCTGCGCC TGTCATGCGCAGCGTCCGGGTTCACCTTAT CATCCTACGGCATGCACTGGGTCAGACAG GCCCCGGGAAAAGGATTGGAATGGGTGGC CGTGATTTCCTACACTGGGTCCAATAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCTGGTTATGAATTCCACGAAGACTATT ACGGGCTGGACGTCTGGGGACAGGGCAC CCTGGTCACTGTGTCCTCG | 541 | QVQLQSSEGGVVQPGRSL RLSCAASGFTLSSYGMHW VRQAPGKGLEWVAVISYTG SNKYYADSVKGRFTISRDN SKNTLYLQMNSLRAEDTAV YYCGGSGYEFHEDYYGLD VWGQGTLVTVSS | 240 |
| H3-7 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT | 542 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS | 204 |

TABLE 19-continued

| Name | DNA sequence | SEQ ID NO: | Mature protein Sequence | SEQ ID NO: |
|---|---|---|---|---|
| | GATCTACGAAGTGTCGAACAGACTGAGGG GTGTGTCCAATCGCTTTTCGGGCTCCAAGT TCGGAAACACGGCCTCACTGACTATCTCTG GACTGCAGGCCGAAGATGAAGCCGACTAC TACTGCTCCTCCTACACCACGTCCTCCACT CTGTACGTGTTCGGGTCCGGCACCAAAGT CACTGTGCTG | | SSTLYVFGSGTKVTVL | |
| H3-8 VH | CAAGCGCAGCTCCAGGGGTCCGAAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACGATGATGCCCACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCCGGTTACGCGCTCCACGACCAGTATA AGCCAGTCGATGTCTGGGGACAGGGCACC CTGGTCACTGTGTCCTCG | 543 | QAQLQGSEGGVVQPGRSL RLSCAASGFTFSSYGMHW VRQAPGKGLEWVAVISYDD AHKYYADSVKGRFTISRDN SKNTLYLQMNSLRAEDTAV YYCGGSGYALHDQYKPVD VWGQGTLVTVSS | 241 |
| H3-8 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAGGTGTCGAACAGACTGAGCG GTGTGTCCAATCGCTTTTCGGGCTCCAAGT TCGGAAACACGGCCTCACTGACTATCTCG GACTGCAGGCCGAAGATGAAGCCGACTA CTACTGCTCCTCCTACACCTCGTCCTCCAC TCTGTACGTGTTCGGGTCCGGCACCAAAG TCACTGTGCTG | 544 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |
| H3-9 VH | CAAGTGCAGCTCCAGGGGTCCGGAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACGATGATGCCCACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCCGGTTACGCGCTCCACGACCAGTATA AGCCAGTCGATGTCTGGGGACAGGGCACC CTGGTCACTGTGTCCTCG | 532 | QVQLQGSGGGVVQPGRSL RLSCAASGFTFSSYGMHW VRQAPGKGLEWVAVISYDD AHKYYADSVKGRFTISRDN SKNTLYLQMNSLRAEDTAV YYCGGSGYALHDQYKPVD VWGQGTLVTVSS | 235 |
| H3-9 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTAAGCG GTGTGTCCAATCGCTTTTCGGGCTCCAAGT TCGGAAACACGGCCTCACTGACTATCTCG GACTGCAGGCCGAAGATGAAGCCGACTA CTACTGCTCCTCCTACACCTCGTCCTCCGC TCTGTACGTGTTCGGGTCCGGCACCAAAG TCACTGTGCTG | 533 | QSALTQPASVSGSPGQSITI SCTGTSSDVGGYNYVSWY QQHPGKAPKLMIYEVSNRL RGVSNRFSGSKFGNTASLT ISGLQAEDEAYYYCSSYTS SSTLYVFGSGTKVTVL | 210 |
| H3-10 VH | CAAGTGCAGCTCCAGAGTTCCGGAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACAATGATTTGAACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCTGGTTATGAATTCCAGGGTGACTATT ACGGGCTGGACGTCTGGGGACAGGGCAC CCTGGTCACTGTGTCCTCG | 545 | QVQLQSSGGGVVQPGRSL RLSCAASGFTFSSYGMHW VRQAPGKGLEWVAVISYND LNKYYADSVKGRFTISRDN SKNTLYLQMNSLRAEDTAV YYCGGSGYEFQGDYYGLD VWGQGTLVTVSS | 242 |

TABLE 19-continued

| Name | DNA sequence | SEQ ID NO: | Mature protein Sequence | SEQ ID NO: |
|---|---|---|---|---|
| H3-10 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTGAGGG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCAC TCTGTACGTGTTCGGGTCCGGCACCAAAG TCACTGTGCTG | 546 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |
| H3-11 VH | CAAGTGCAGCTCCAGAGTTCCGAAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCCGGGAAAAGGATTGGAATGGGTGGC CGTGATTTCCTACAATGATGCCAACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCTGGTTATGAATTGAGAGATGACTATT ACGGGCTGGACGTCTGGGGACAGGGCAC CCTGGTCACTGTGTCCTCG | 547 | QVQLQSSEGGVVQPGRSL RLSCAASGFTFSSYGMHW VRQAPGKGLEWVAVISYND ANKYYADSVKGRFTISRDN SKNTLYLQMNSLRAEDTAV YYCGGSGYELRDDYYGLD VWGQGTLVTVSS | 243 |
| H3-11 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAGGTGTCGAACAGACTGAGAG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCAC TCTGTACGTGTTCGGGTCCGGCACCAAAG TCACTGTGCTG | 548 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |
| H3-12 VH | CAAGCGCAGCTCCAGAGTTCCGAAGGCGG AGTGGTGCAGCCTGGAAGGAGCCTGCGTC TGTCATGCGCAGCGTCCGGGTTCACCTTCT CATCCTACGGCATGCACTGGGTCAGACAG GCCCCCGGGAAAAGGATTGGAATGGGTGGC CGTGATTTCCTACGATGAGTCCAACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCTGGTTATGAAGTCGATCAGGACTATT ACGGGCTGGACGTCTGGGGACAGGGCAC CCTGGTCACTGTGTCCTCG | 549 | QAQLQSSEGGVVQPGRSL RLSCAASGFTFSSYGMHW VRQAPGKGLEWVAVISYDE SNKYYADSVKGRFTISRDN SKNTLYLQMNSLRAEDTAV YYCGGSGYEVDQDYYGLD VWGQGTLVTVSS | 244 |
| H3-12 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAGGTGTCGAACAGACTGCGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCAC ACTGTACGTGTTCGGGTCCGGCACCAAAG TCACTGTGCTG | 550 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |
| H3-13 VH | CAAGTGCAGCTCCAGGAGTCCGGAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCCGGGAAAAGGATTGGAATGGGTGGC CGTGATTTCCTACGATGATGCCCACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG | 551 | QVQLQESGGVVQPGRSL RLSCAASGFTFSSYGMHW VRQAPGKGLEWVAVISYDD AHKYYADSVKGRFTISRDN SKNTLYLQMNSLRAEDTAV YYCGGSGYALHDQYKPVD VWGQGTLVTVSS | 245 |

TABLE 19-continued

| Name | DNA sequence | SEQ ID NO: | Mature protein Sequence | SEQ ID NO: |
|---|---|---|---|---|
| | GTTCCGGTTACGCGCTCCACGACCAGTATA AGCCAGTCGATGTCTGGGGACAGGGCACC CTGGTCACTGTGTCCTCG | | | |
| H3-13 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTAAGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCGC TCTGTACGTGTTCGGGTCCGGCACCAAAG TCACTGTGCTG | 533 | QSALTQPASVSGSPGQSITI SCTGTSSDVGGYNYVSWY QQHPGKAPKLMIYEVSNRL RGVSNRFSGSKFGNTASLT ISGLQAEDEADYYCSSYTS SSTLYVFGSGTKVTVL | 204 |
| H3-14 VH | CAAGTGCAGCTCCAGGGGTCCGGAGGTGG AGTGGTGCAGCCTGGAAGGAGCCTGCGCC TGTCATGCGCAGCGTCCGGGTTCACCTTCT CATCCTACGGCATGCACTGGGTCAGACAG GCCCCGGGAAAAGGATTGGAATGGGTGGC CGTGATTTCCTACGATGATGCCCACAAGTA CTACGCCGATTCCGTGAAGGGACGGTTTA CCATCTCGCGGGACAACTCGAAGAACACC CTGTACCTCCAAATGAACAGCCTGCGCGC CGAAGATACTGCCGTGTACTACTGCGGCG GTTCCGGTTACGCGCTCCACGACCAGTATA AGCCAGTCGATGTCTGGGGACAGGGCACC CTGGTCACTGTGTCCTCG | 532 | QVQLQGSGGGVVQPGRSL RLSCAASGFTFSSYGMHW VRQAPGKGLEWVAVISYDD AHKYYADSVKGRFTISRDN SKNTLYLQMNSLRAEDTAV YYCGGSGYALHDQYKPVD VWGQGTLVTVSS | 235 |
| H3-14 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAAGTGTCGAACAGACTAAGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCGC TCTGTACGTGTTCGGGTCCGGCACCAAAG TCACTGTGCTG | 533 | QSALTQPASVSGSPGQSITI SCTGTSSDVGGYNYVSWY QQHPGKAPKLMIYEVSNRL SGVSNRFSGSKFGNTASLT ISGLQAEDEADYYCSSYTS SSALYVFGSGTKVTVL | 211 |
| H3-15 VH | CAAGTGCAGCTCCAGGGTTCCGGAGGTGG AGTGGTGCAGCCTGGAAGGAGCCTGCGCC TGTCATGCGCAGCGTCCGGGTTCACCGTC TCATCCTACGGCATGCACTGGGTCAGACA GGCCCCGGGAAAAGGATTGGAATGGGTGG CCGTGATTTCATACGATGATGCCAACAAGT ACTACGCCGATTCCGTGAAGGGACGGTTT ACCATCTCGCGGGACAGCTCGAAGAACAC CCTGTACCTCCAAATGAACAGCCTGCGCG CCGAAGATACTGCCGTGTACTACTGCGGC GGTTCTGGTTATGCTTATGATGGTGACTAT TACGGGCTGGACGTCTGGGGACAGGGCAC CCTGGTCACTGTGTCCTCG | 552 | QVQLQGSGGGVVQPGRSL RLSCAASGFTVSSYGMHW VRQAPGKGLEWVAVISYDD ANKYYADSVKGRFTISRDS SKNTLYLQMNSLRAEDTAV YYCGGSGYAYDGDYYGLD VWGQGTLVTVSS | 246 |
| H3-15 VL | CAGTCCGCTCTGACCCAACCGGCTTCCGT GAGCGGAAGCCCCGGACAGTCCATTACTA TCAGCTGTACCGGCACCTCCTCCGACGTC GGTGGATACAACTACGTGTCCTGGTATCAG CAGCATCCTGGAAAGGCTCCAAAGCTCAT GATCTACGAGGTGTCGAACAGACTGCGCG GTGTGTCCAATCGCTTTTCGGGCTCCAAGT TCGGAAACACGGCCTCACTGACTATCTCG GGACTGCAGGCCGAAGATGAAGCCGACTA CTACTGCTCCTCCTACACCTCGTCCTCCGC TCTGTACGTTTCGGGTCCGGCACCAAAG TCACTGTGCTG | 553 | QSALTQPASVSGSPGQSITI SCTGTSSDVGGYNYVSWY QQHPGKAPKLMIYEVSNRL GGVSNRFSGSKFGNTASLT ISGLQAEDEADYYCSSYTS SSALYVFGSGTKVTVL | 212 |

These identified clones, which have an EC50 value of 500 pM or lower in the JNL activation assay against both human and cynomolgus BCMA, represent a noted improvement over the initially identified clone, PI-61. This parental clone had approximate affinities of 34 nM toward human BCMA and 240 nM toward cynomolgus BCMA.

FIG. 7 shows the CDR H2 regions of the identified and parental clones. Of particular note, the high probability aspartate-glycine isomerization site at positions 59 and 62 (IMGT numbering) of CDRH2 has been replaced by several amino acid pairs, most commonly aspartate-aspartate. Additionally, position 63 has been mutated from serine to alanine in most of the matured hits.

FIG. 8 shows the CDR L2 regions of the identified and parental clones. All identified clones show an aspartate to glutamate mutation at position 56 and a proline to leucine mutation at position 61. Additionally, a serine to arginine mutation at position 62 was present in most clones.

FIG. 9 shows the CDR H3 regions of the identified and parental clones. Several mutations are enriched in the improved clones, including alanine to glutamate as position 110, aspartate to glutamine at position 111c, and tyrosine-glycine-leucine mutated to lysine-proline-valine at positions 113 through 115.

8.4. Example 4: Isolation of Anti-BCMA Antibodies Using Phage Display

8.4.1. Generation of Parental Clone R1F2

Panning was done by coating streptavidin beads with biotinylated BCMA proteins (human BCMA and Cyno BCMA (Ags)). Ags-coated beads were washed with Phosphate Buffered Saline (PBS) with 0.05% Tween 20 (PBST), and blocked with 2% Bovine Serum Albumins (BSA). Phage libraries were blocked with 2% BSA and were pre-adsorbed on blank streptavidin beads to eliminate phages that bind to streptavidin. Blocked and pre-adsorbed phage libraries were added to Ag coated beads and incubated for 1 hour at room temperature with mixing. Unspecifically bound phages were washed off by several washing steps. Specifically bound phages were eluted from Streptavidin beads by addition of Glycine pH 2. The eluate was transferred to an E. coli TG1 culture for phage infection. Following incubation at 37° C. for 45 minutes, cultures were centrifuged; the bacterial pellets were re suspended in fresh medium and plated on agar plates with Ampicillin, and incubated at 37° C. overnight. Colonies from each pool were scraped off the plates and were used to make glycerol stocks or directly used for phage rescue, polyclonal amplification of phage, and for phage precipitation.

New phage particles presenting Fab fragments on their surface were produced for each selection round. For each phage preparation, 12 ml 2×YT/Ampicillin/Glucose medium were inoculated with bacteria from the corresponding library (as described the preceding paragraph) or its glycerol stock, resulting in an $OD_{600}$ of 0.1-0.2. Cultures were shaken for 60-90 minutes at 120 rpm at 37° C. until an $OD_{600}$ of 0.45-0.55 was reached. Then, helper phage was added at a multiplicity of infection of 20 to the bacterial culture followed by an incubation for 30 minutes at 37° C. without shaking and then for 30 minutes at 37° C. with shaking at 160 rpm. Bacteria were spun down and helper phage containing supernatant was discarded. Phage-infected bacteria were re-suspended in 20 ml 2× YT/Amp/Kan/IPTG medium and incubated overnight at 25° C. with shaking at 120 rpm. The next day bacteria from the overnight culture were pelleted and the supernatant containing the Fab-presenting phage was collected. Phage precipitation was performed by adding ⅕ total volume of pre-cooled PEG/NaCl to the phage-containing supernatant. The sample was incubated for at least 30 minutes on ice until clouds of precipitating phage became visible. Precipitated phages were spun down and re-suspended in PBS. Purified phages were used for subsequent round of panning.

Panning pools of the last round were sub cloned into a bacterial expression vector and the generated culture was plated on agar plates for single colony picking. Single clones were picked from agar plates into the wells of 2 microtiter plates (duplicates), a master plate and a daughter plate. The master plate wells were pre-filled with 2×YT containing Ampicillin, and low glucose. Upon outgrowth, glycerol was added to these plates and they were stored at −80° C. The daughter plates were pre-filled with induction medium (2×YT containing Ampicillin, and IPTG). Plates were incubated at 30° C. and shaken overnight for Fab expression. The next day expression cultures were lysed by addition of Lysozyme buffer.

Enzyme Linked Immunosorbent Assay (ELISA) was used to test binding of the Fabs (in crude bacterial lysates) to recombinant full-length BCMA Ags. Biotinylated Ags were captured via neutravidin coated plates. Plates were washed with PBST and blocked with 2% BSA. Bacterial lysates (containing Fabs) were added to plates, after incubation and washing to remove nonspecific binding, bound Fabs were detected with anti-Fab-HRP (Horseradish Perroxidase). After incubation and several washes, a substrate was added and color development was stopped by adding 0.5N HCl. Signal (absorbance) was measured at 450 nm.

Affinity of a Fab to its antigen can be increased by an iterative CDR optimization approach introducing pre-built CDR maturation cassette libraries while the framework regions remain unaffected. The cloning of the maturation libraries was performed in the vector encoding for the parental Fab fragments. Three libraries were made for clone R1F2; 2 libraries for Light chain CDR3 (CDR-L3) representing 2 different lengths of CDR-L3, and one heavy chain CDR-H2 library. The corresponding CDR was removed from the parental clone by restriction digest and swapped with irrelevant sequence to reduce background of the parental clone. In a second step, the irrelevant sequence was removed and replaced with a repertoire of DNA fragments containing the desired diversified CDR by ligation reaction. The ligation mixture was electroporated into bacterial cells (TGIF') for library amplification.

Panning of matured libraries was carried out as described above with increased stringency during washing steps. Screening was performed by ELISA as described above using low antigen concentrations to differentiate improved clones' profile from the parental profile (FIG. 10). Selected clones were re-arrayed onto compression plates and sequenced to determine uniqueness and for follow up assays.

8.4.2. Characterization of Matured Human Anti-BCMA Antibodies

Biolayer Interferometry (BLI) was used to determine the affinity of unique clones to BCMA proteins. Streptavidin tips (ForteBio) were coated with biotinylated antigen, bacterial lysates-containing Fabs were diluted in binding buffer, and antigen coated tips were dipped into lysates for binding/association measurement (On-Rate). After that, tips were dipped into buffer to monitor dissociation (Off-Rate). Calculations of apparent KD were done using Fortebio's proprietary Analysis Software. Many clones with improved affinities over parental R1F2 were identified (FIG. 11 and FIG. 12; Table 20) and subsequently sub-cloned into bi-specific format for production and functional assays.

TABLE 20

| Clone | Description | Mature protein sequence | SEQ ID |
|---|---|---|---|
| R1F2 | CDR H1 (IMGT) | GFTFSSYA | 13 |
|  | CDR H2 (IMGT) | ISGSGGST | 92 |
|  | CDR H3 (IMGT) | ARREWWYDDWYLDY | 25 |
|  | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
|  | CDR L1 (IMGT) | QSISSY | 4 |
|  | CDR L2 (IMGT) | AAS | 6 |
|  | CDR L3 (IMGT) | QQSYSTPLT | 54 |
|  | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF01 | CDR H1 (IMGT) | GFTFSSYA | 13 |
|  | CDR H2 (IMGT) | ISGSGGST | 92 |
|  | CDR H3 (IMGT) | ARREWWYDDWYLDY | 25 |
|  | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
|  | CDR L1 (IMGT) | QSISSY | 4 |
|  | CDR L2 (IMGT) | AAS | 6 |
|  | CDR L3 (IMGT) | QQSYSSPLT | 53 |
|  | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSSPLTFGQGTKVEIK | 191 |
| PALF03 | CDR H1 (IMGT) | GFTFSSYA | 13 |
|  | CDR H2 (IMGT) | ISGSGGST | 92 |
|  | CDR H3 (IMGT) | ARREWWYDDWYLDY | 25 |
|  | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
|  | CDR L1 (IMGT) | QSISSY | 4 |
|  | CDR L2 (IMGT) | AAS | 6 |
|  | CDR L3 (IMGT) | QQSYGSPPT | 55 |
|  | VL | DIQMTQSPSSLSASVGDRVTITCRASQSISSYLNWYQQKPGKAPKLLIYAASSLQSGVPSRFSGSGSGTDFTLTISSLQPEDFATYYCQQSYGSPPTFGQGTKVEIK | 193 |
| PALF04 | CDR H1 (IMGT) | GFTFSSYA | 13 |
|  | CDR H2 (IMGT) | ISGSGGST | 92 |
|  | CDR H3 (IMGT) | ARREWWYDDWYLDY | 25 |
|  | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
|  | CDR L1 (IMGT) | QSISSY | 4 |
|  | CDR L2 (IMGT) | AAS | 6 |
|  | CDR L3 (IMGT) |  |  |
|  | VL | DIQMTQSPSSLSASVGDRVTITCRASQSISSYLNWYQQKPGKAPKLLIYAASSLQSGVPSRFSGSGSGTDFTLTISSLQPEDFATYYCQQSYDSPLTFGQGTKVEIK | 194 |

TABLE 20-continued

| Clone | Description | Mature protein sequence | SEQ ID |
|---|---|---|---|
| PALF05 | CDR H1 (IMGT) | GFTFSSYA | 13 |
| | CDR H2 (IMGT) | ISGSGGST | 92 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
| | CDR L1 (IMGT) | QSISSY | 4 |
| | CDR L2 (IMGT) | AAS | 6 |
| | CDR L3 (IMGT) | QQSYYSPLT | 57 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYYSPLTFGQGTKVEIK | 195 |
| PALF06 | CDR H1 (IMGT) | GFTFSSYA | 13 |
| | CDR H2 (IMGT) | ISGSGGST | 92 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
| | CDR L1 (IMGT) | QSISSY | 4 |
| | CDR L2 (IMGT) | AAS | 6 |
| | CDR L3 (IMGT) | QQSYYAPLT | 58 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYYAPLTFGQGTKVEIK | 196 |
| PALF07 | CDR H1 (IMGT) | GFTFSSYA | 13 |
| | CDR H2 (IMGT) | ISGSGGST | 92 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
| | CDR L1 (IMGT) | QSISSY | 4 |
| | CDR L2 (IMGT) | AAS | 6 |
| | CDR L3 (IMGT) | QQSYASPLT | 59 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYASPLTFGQGTKVEIK | 197 |
| PALF08 | CDR H1 (IMGT) | GFTFSSYA | 13 |
| | CDR H2 (IMGT) | ISGSGGST | 92 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWYDDWYLDYWGQGTLVTVSS | 213 |
| | CDR L1 (IMGT) | QSISSY | 4 |
| | CDR L2 (IMGT) | AAS | 6 |
| | CDR L3 (IMGT) | QQSYGSPLT | 60 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYGSPLTFGQGTKVEIK | 198 |

TABLE 20-continued

| Clone | Description | Mature protein sequence | SEQ ID |
|---|---|---|---|
| PALF09 | CDR H1 (IMGT) | GFTFSSYA | 13 |
| | CDR H2 (IMGT) | ISGSGGST | 92 |
| | CDR H3 (IMGT) | ARREWWYDDWYLDY | 25 |
| | VH | EVQLLESGGGLVQPGGSLRLSCAASGFTFSSYAMSWVRQAPGKGLE WVSAISGSGGSTYYADSVKGRFTISRDNSKNTLYLQMNSLRAEDTAV YYCARREWWYDDWYLDYWGQGTLVTVSS | 213 |
| | CDR L1 (IMGT) | QSISSY | 4 |
| | CDR L2 (IMGT) | AAS | 6 |
| | CDR L3 (IMGT) | QQSYDAPLT | 61 |
| | VL | DIQMTQSPSSLSASVGDRVTITCRASQSISSYLNWYQQKPGKAPKLLI YAASSLQSGVPSRFSGSGSGTDFTLTISSLQPEDFATYYCQQSYDAP LTFGQGTKVEIK | 199 |
| PALF11 | CDR H1 (IMGT) | GFTFSSYA | 13 |
| | CDR H2 (IMGT) | ISESGGRA | 93 |
| | CDR H3 (IMGT) | ARREWWYDDWYLDY | 25 |
| | VH | EVQLLESGGGLVQPGGSLRLSCAASGFTFSSYAMSWVRQAPGKGLE WVSAISESGGRAAYADSVKGRFTISRDNSKNTLYLQMNSLRAEDTAV YYCARREWWYDDWYLDYWGQGTLVTVSS | 214 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLI YAASSLQSGVPSRFSGSGSGTDFTLTISSLQPEDFATYYCQQSYSTP LTFGQGTKVEIK | 192 |
| PALF12 | CDR H1 (IMGT) | GFTFSSYA | 13 |
| | CDR H2 (IMGT) | ISGSGGRA | 94 |
| | CDR H3 (IMGT) | ARREWWYDDWYLDY | 25 |
| | VH | EVQLLESGGGLVQPGGSLRLSCAASGFTFSSYAMSWVRQAPGKGLE WVSAISGSGGRAAYADSVKGRFTISRDNSKNTLYLQMNSLRAEDTAV YYCARREWWYDDWYLDYWGQGTLVTVSS | 215 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLI YAASSLQSGVPSRFSGSGSGTDFTLTISSLQPEDFATYYCQQSYSTP LTFGQGTKVEIK | 192 |
| PALF13 | CDR H1 (IMGT) | GFTFSSYA | 13 |
| | CDR H2 (IMGT) | | |
| | CDR H3 (IMGT) | ARREWWYDDWYLDY | 25 |
| | VH | EVQLLESGGGLVQPGGSLRLSCAASGFTFSSYAMSWVRQAPGKGLE WVSAISESGDVEAYADSVKGRFTISRDNSKNTLYLQMNSLRAEDTAV YYCARREWWYDDWYLDYWGQGTLVTVSS | 216 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLI YAASSLQSGVPSRFSGSGSGTDFTLTISSLQPEDFATYYCQQSYSTP LTFGQGTKVEIK | 192 |

TABLE 20-continued

| Clone | Description | Mature protein sequence | SEQ ID |
|---|---|---|---|
| PALF14 | CDR H1 (IMGT) | GFTFSSYA | 13 |
| | CDR H2 (IMGT) | ISESGDVE | 95 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISEAGETTSYADSVKGRFTISRDNSKNTLYLQMNSLRAEDTAVYYCARREWWYDDWYLDYWGQGTLVTVSS | 217 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF15 | CDR H1 (IMGT) | GFTFSSYA | 13 |
| | CDR H2 (IMGT) | ISEHGHYT | 96 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISEHGHYTSYADSVKGRFTISRDNSKNTLYLQMNSLRAEDTAVYYCARREWWYDDWYLDYWGQGTLVTVSS | 218 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF16 | CDR H1 (IMGT) | GFTFSSYA | 13 |
| | CDR H2 (IMGT) | ISGSGHTA | 97 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISGSGHTAAYADSVKGRFTISRDNSKNTLYLQMNSLRAEDTAVYYCARREWWYDDWYLDYWGQGTLVTVSS | 219 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |
| PALF17 | CDR H1 (IMGT) | GFTFSSYA | 13 |
| | CDR H2 (IMGT) | ISGSGRTH | 98 |
| | CDR H3 (IMGT) | ARREWWYDDWYLDY | 25 |
| | VH | EVQLLESGGGLVQPGGSLRLSCAASGFTFSSYAMSWVRQAPGKGLEWVSAISGSGRTHAYADSVKGRFTISRDNSKNTLYLQMNSLRAEDTAVYYCARREWWYDDWYLDYWGQGTLVTVSS | 220 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 192 |

TABLE 20-continued

| Clone | Description | Mature protein sequence | SEQ ID |
|---|---|---|---|
| PALF18 | CDR H1 (IMGT) | GFTFSSYA | 13 |
| | CDR H2 (IMGT) | ISAEGGVR | 99 |
| | CDR H3 (IMGT) | ARREWWYDDWYLDY | 25 |
| | VH | EVQLLESGGGLVQPGGSLRLSCAASGFTFSSYAMSWVRQAPGKGLE WVSAISAEGGVRAYADSVKGRFTISRDNSKNTLYLQMNSLRAEDTAV YYCARREWWYDDWYLDYWGQGTLVTVSS | 221 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLI YAASSLQSGVPSRFSGSGSGTDFTLTISSLQPEDFATYYCQQSYSTP LTFGQGTKVEIK | 192 |
| PALF19 | CDR H1 (IMGT) | GFTFSSYA | 13 |
| | CDR H2 (IMGT) | ISGSGGTT | 100 |
| | CDR H3 (IMGT) | ARREWWYDDWYLDY | 25 |
| | VH | EVQLLESGGGLVQPGGSLRLSCAASGFTFSSYAMSWVRQAPGKGLE WVSAISGSGGTTAYADSVKGRFTISRDNSKNTLYLQMNSLRAEDTAV YYCARREWWYDDWYLDYWGQGTLVTVSS | 222 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLI YAASSLQSGVPSRFSGSGSGTDFTLTISSLQPEDFATYYCQQSYSTP LTFGQGTKVEIK | 192 |
| PALF20 | CDR H1 (IMGT) | GFTFSSYA | 13 |
| | CDR H2 (IMGT) | ISGSGATT | 101 |
| | CDR H3 (IMGT) | ARREWWYDDWYLDY | 25 |
| | VH | EVQLLESGGGLVQPGGSLRLSCAASGFTFSSYAMSWVRQAPGKGLE WVSAISGSGATTAYADSVKGRFTISRDNSKNTLYLQMNSLRAEDTAV YYCARREWWYDDWYLDYWGQGTLVTVSS | 223 |
| | CDR L1 (IMGT) | QSISSY | 4 |
| | CDR L2 (IMGT) | AAS | 6 |
| | CDR L3 (IMGT) | QQSYSTPLT | 54 |
| | VL | DIQMTQSPSSLSASVGDRVTITCRASQSISSYLNWYQQKPGKAPKLLI YAASSLQSGVPSRFSGSGSGTDFTLTISSLQPEDFATYYCQQSYSTP LTFGQGTKVEIK | 192 |

8.5. Example 5: Production and Characterization of Anti-BCMA×Anti-CD3 Bispecific Binding Molecules Antibodies PALF01 and PALF11 (Example 4) and H2/L2-20 (Example 2) were converted to an anti-BCMA× anti-CD3 bispecific format, with the resulting bispecific antibodies being named AB1, AB2, and AB3, respectively.

8.5.1. Materials and Methods

8.5.1.1. Germlining of H2/L2-20 Candidate to Produce AB3

All candidate clone sequences for subsequent characterization were aligned to their nearest human germlines to ensure the frameworks were as close to the natural framework represented in the human antibody repertoire. Clones from Example 4 were 100% identical to the human germline sequences outside of the CDRs and were thus produced with no further changes to their primary amino acid sequence. Clone H2/L2-20 had mutations outside the CDRs in both the variable light and variable heavy chain regions, and these were mutated to the residues to the closest human germline to produce the final AB3 sequence as part of the gene synthesis of the final constructs.

8.5.1.2. Production of Anti-BCMA×Anti-CD3 IgG1 Bispecific Antibodies in Knob-Into-Holes Format Gene synthesis was performed by ATUM (Newark, CA, USA). Anti-BCMA heavy chains were synthesized as fusions of the variable domains to constant hIgG1 domains containing mutations for the hole to facilitate heterodimerization as well as a N297A silencing mutation. Light chain plasmids was synthesized as described above. The anti-CD3 arms were produced as single chain fragment variable fused to constant hIgG1 domains containing mutations for the knob to facilitate heterodimerization as well as the N297A silencing mutation. Bispecific antibodies were co-expressed transiently in HEK293 cells. Briefly, transfection was performed using PEI Max as the transfection reagent. For small scale (<5L) transfections, cells were grown in shake flasks on an orbital shaker (115 rpm) in a humidified incubator (85%) at 5% CO2). Anti-BCMA light and heavy chain plasmids were combined with anti-CD3 plasmids at 2:2:3 ratio with PEI at a final ratio of 1 DNA: 3 PEI. 1 mg/L culture of plasmid was used for transfection at 0.5 million cells/mL serum media. After 5 days of expression, the antibody was harvested by clarification of the media via centrifugation and filtration. Purification was performed via either anti-CH1 affinity batch chromatography (CaptureSelect IgG-CH1 Affinity Matrix, Thermo-Fisher Scientific, Waltham, MA, USA) or Protein A affinity batch chromatography (MabSelect®SuRe, GE Healthcare Life Sciences, Uppsala, Sweden). Resin was added at a ratio of 1 mL resin for every 100 mL supernatant and allowed to batch bind for up to 4 hours. Disposable columns were loaded with supernatant allowed to drain via gravity and washed with 20 CV of PBS. Antibody was eluted with 20 CV of 20 mM citrate, 125 mM NaCl, 50 mM sucrose pH 3.2. The eluted IgG protein was adjusted to pH 5.5 with 1 M sodium citrate. If the antibody contained aggregates, preparative size exclusion chromatography was performed using Hi Load 16/60 Superdex 200 grade column (GE Healthcare Life Sciences, Uppsala, Sweden) as a final polishing step.

8.5.1.3. Production of Anti-BCMA-Anti-CD3 Bivalent and Trivalent Binding Molecules Bivalent binding molecules in the format shown in FIG. 1C and trivalent binding molecules in the format shown in FIG. 1H were made.

Gene synthesis was performed as described above. Anti-BCMA heavy chains were synthesized as fusions of the variable domains to constant hIgG1 domains containing mutations L368D/K370S to facilitate heterodimerization as well as E233P/L234V/L235A/G236del/S267K silencing mutations. Light chain plasmids were synthesized as described above. The anti-CD3 arm for the bivalent BBMs was produced as single chain fragment variable fused to constant hIgG1 domains containing mutations S364K/E357Q to facilitate heterodimerization as well as E233P/L234V/L235A/G236del/S267K silencing mutations. The anti-CD3 arm for the trivalent BBMs was produced as anti-BCMA heavy chain Fab fusion to the single chain fragment variable CD3 fused to constant hIgG1 domains containing mutations S364K/E357Q to facilitate heterodimerization as well as E233P/L234V/L235A/G236del/S267K silencing mutations. BBMs were co-expressed transiently in HEK293 cells. Briefly, transfection was performed using PEI Max as transfection reagent. For small scale (<5L) transfections, cells were grown in shake flasks on an orbital shaker (115 rpm) in a humidified incubator (85%) at 5% CO2). Anti-BCMA light and heavy chain plasmids were combined with anti-CD3 plasmids with PEI at a final ratio of 1 DNA:3 PEI. 1 mg/L culture of plasmid was used for transfection at 0.5 million cells/mL serum media. After 5 days of expression, the BBM was harvested by clarification of the media via centrifugation and filtration. Purification was performed via either anti-CH1 affinity batch chromatography (CaptureSelect IgG-CH1 Affinity Matrix, Thermo-Fisher Scientific, Waltham, MA, USA) or Protein A affinity batch chromatography (MabSelect®SuRe, GE Healthcare Life Sciences, Uppsala, Sweden). Resin was added at a ratio of 1 mL resin for every 100 mL supernatant and allowed to batch bind for up to 4 hours. Disposable columns were loaded with supernatant allowed to drain via gravity and washed with 20 CV of PBS. BBM was eluted with 20 CV of 20 mM citrate, 125 mM NaCl, 50 mM sucrose pH 3.2. The eluted IgG protein was adjusted to pH 5.5 with 1 M sodium citrate. If the BBM contained aggregates, preparative size exclusion chromatography was performed using Hi Load 16/60 Superdex 200 grade column (GE Healthcare Life Sciences, Uppsala, Sweden) as a final polishing step. Samples which contained homodimers were purified via preparative cation exchange chromatography.

8.5.1.4. BCMAxCD3 BBM Sequences

Amino acid and DNA sequences for the constructs made in Example 5 are shown in Table 21.

TABLE 21A

Bivalent AB1
(hBCMA Fab/hCD3 scFv 1x1 format)

| | SEQ ID NO | Sequence |
|---|---|---|
| Anti-BCMA Fab (PALF01) | | |
| CDR-H1 (Kabat) | 11 | SYAMS |
| CDR-H2 (Kabat) | 62 | AISGSGGSTYYADSVKG |
| CDR-H3 (Kabat) | 24 | REWWYDDWYLDY |
| CDR-H1 (Chothia) | 12 | GFTFSSY |
| CDR-H2 (Chothia) | 82 | SGSGGS |
| CDR-H3 (Chothia) | 24 | REWWYDDWYLDY |
| CDR-H1 (IMGT) | 13 | GFTFSSYA |
| CDR-H2 (IMGT) | 92 | ISGSGGST |
| CDR-H3 (IMGT) | 25 | ARREWWYDDWYLDY |

TABLE 21A-continued

Bivalent AB1
(hBCMA Fab/hCD3 scFv 1x1 format)

| | SEQ ID NO | Sequence |
|---|---|---|
| VH | 213 | EVQLLESGGGLVQPGGSLRLSCAASGFTFSSYAM SWVRQAPGKGLEWVSAISGSGGSTYYADSVKGR FTISRDNSKNTLYLQMNSLRAEDTAVYYCARREW WYDDWYLDYWGQGTLVTVSS |
| DNA VH | 554 | GAGGTGCAGCTGCTGGAGAGCGGGGGTGGAC TGGTGCAGCCGGGAGGTTCCCTCCGGTTGTCA TGTGCCGCATCCGGCTTTACTTTCTCTTCCTAC GCCATGTCGTGGGTCAGACAGGCCCCGGGAAA GGGACTTGAGTGGGTGTCGGCCATCTCCGGTT CCGGGGGATCCACCTACTACGCGGACTCCGTG AAGGGCCGCTTCACTATTTCACGGGACAACAGC AAGAACACCCTGTACCTCCAAATGAACTCGCTG CGCGCCGAAGATACCGCCGTCTACTACTGCGC GCGGAGGGAATGGTGGTACGACGATTGGTATC TGGACTACTGGGGCCAGGGCACTCTCGTGACC GTGTCCAGC |
| Fab Heavy Chain | 555 | EVQLLESGGGLVQPGGSLRLSCAASGFTFSSYAM SWVRQAPGKGLEWVSAISGSGGSTYYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSDTKVDKKVEPKSC |
| DNA Heavy Chain | 556 | GAGGTGCAGCTGCTGGAGAGCGGGGGTGGAC TGGTGCAGCCGGGAGGTTCCCTCCGGTTGTCA TGTGCCGCATCCGGCTTTACTTTCTCTTCCTAC GCCATGTCGTGGGTCAGACAGGCCCCGGGAAA GGGACTTGAGTGGGTGTCGGCCATCTCCGGTT CCGGGGGATCCACCTACTACGCGGACTCCGTG AAGGGCCGCTTCACTATTTCACGGGACAACAGC AAGAACACCCTGTACCTCCAAATGAACTCGCTG CGCGCCGAAGATACCGCCGTCTACTACTGCGC GCGGAGGGAATGGTGGTACGACGATTGGTATC TGGACTACTGGGGCCAGGGCACTCTCGTGACC GTGTCCAGCGCTAGCACCAAGGGCCCGTCAGT GTTTCCTCTGGCCCCAAGCTCCAAGTCCACCTC CGGTGGTACAGCCGCGTTGGGATGCTTGGTCA AGGACTACTTTCCGGAACCCGTGACCGTGTCCT GGAACTCCGGCGCCCTGACTAGCGGAGTGCAC ACCTTCCCCGCTGTGCTGCAGTCTAGCGGGCT GTATTCCCTCTCGTCCGTGGTCACCGTGCCGTC CTCATCCCTGGGAACCCAGACCTACATTTGCAA CGTGAACCACAAGCCGTCAGACACCAAGGTGG ACAAGAAGGTGGAGCCGAAGTCCTGC |
| CDR-L1 (Kabat) | 2 | RASQSISSYLN |
| CDR-L2 (Kabat) | 5 | AASSLQS |
| CDR-L3 (Kabat) | 53 | QQSYSSPLT |
| CDR-L1 (Chothia) | 3 | SQSISSY |
| CDR-L2 (Chothia) | 6 | AAS |
| CDR-L3 (Chothia) | 73 | SYSSPL |
| CDR-L1 (IMGT) | 4 | QSISSY |
| CDR-L2 (IMGT) | 6 | AAS |
| CDR-L3 (IMGT) | 53 | QQSYSSPLT |
| VL | 191 | DIQMTQSPSSLSASVGDRVTITCRASQSISSYLNW YQQKPGKAPKLLIYAASSLQSGVPSRFSGSGSGT DFTLTISSLQPEDFATYYCQQSYSSPLTFGQGTKV EIK |
| DNA VL | 557 | GACATTCAGATGACTCAGTCCCCGTCCTCCTTG TCCGCCTCCGTGGGAGACAGAGTCACCATCAC TTGCCGGGCATCGCAGAGCATCTCTTCATACCT |

TABLE 21A-continued

Bivalent AB1
(hBCMA Fab/hCD3 scFv 1x1 format)

| | SEQ ID NO | Sequence |
|---|---|---|
| | | GAACTGGTATCAGCAGAAGCCCGGAAAGGCCC CTAAGCTGCTGATCTACGCGGCCAGCAGCCTTC AGTCCGGCGTGCCATCAAGGTTCAGCGGATCG GGTTCGGGCACCGATTTTACTCTGACCATTAGC TCCCTGCAACCCGAGGACTTCGCTACCTACTAC TGTCAGCAGTCCTACTCCTCCCCGCTGACCTTC GGACAAGGGACCAAAGTCGAAATCAAG |
| Fab Light Chain | 503 | DIQMTQSPSSLSASVGDRVTITCRASQSISSYLNW YQQKPGKAPKLLIYAASSLQSGVPSRFSGSGSGT DFTLTISSLQPEDFATYYCQQSYSSPLTFGQGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC |
| DNA Light Chain | 558 | GACATTCAGATGACTCAGTCCCCGTCCTCCTTG TCCGCCTCCGTGGGAGACAGAGTCACCATCAC TTGCCGGGCATCGCAGAGCATCTCTTCATACCT GAACTGGTATCAGCAGAAGCCCGGAAAGGCCC CTAAGCTGCTGATCTACGCGGCCAGCAGCCTTC AGTCCGGCGTGCCATCAAGGTTCAGCGGATCG GGTTCGGGCACCGATTTTACTCTGACCATTAGC TCCCTGCAACCCGAGGACTTCGCTACCTACTAC TGTCAGCAGTCCTACTCCTCCCCGCTGACCTTC GGACAAGGGACCAAAGTCGAAATCAAGCGTAC GGTGGCCGCTCCCAGCGTGTTCATCTTCCCCC CCAGCGACGAGCAGCTGAAGAGCGGCACCGCC AGCGTGGTGTGCCTGCTGAACAACTTCTACCCC CGGGAGGCCAAGGTGCAGTGGAAGGTGGACAA CGCCCTGCAGAGCGGCAACAGCCAGGAGAGC GTCACCGAGCAGGACAGCAAGGACTCCACCTA CAGCCTGAGCAGCACCCTGACCCTGAGCAAGG CCGACTACGAGAAGCATAAGGTGTACGCCTGC GAGGTGACCCACCAGGGCCTGTCCAGCCCCGT GACCAAGAGCTTCAACAGGGGCGAGTGC |
| Anti-CD3 scFv (~30 nM) (CD3-23) | | |
| CDR-H1 (Kabat) | 305 | TYAMN |
| CDR-H2 (Kabat) | 338 | RIRSKANNYATYYADSVKG |
| CDR-H3 (Kabat) | 360 | HGNFGDSYVSWFAY |
| CDR-H1 (Chothia) | 378 | GFTFSTY |
| CDR-H2 (Chothia) | 559 | RSKANNYA |
| CDR-H3 (Chothia) | 360 | HGNFGDSYVSWFAY |
| CDR-H1 (IMGT) | 560 | GFTFSTYA |
| CDR-H2 (IMGT) | 561 | IRSKANNYAT |
| CDR-H3 (IMGT) | 562 | VRHGNFGDSYVSWFAY |
| VH | 293 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSS |
| DNA VH | 563 | GAAGTGCAGCTTGTGGAGTCCGGGGGAGGATT GGTCCAACCCGGTGGCTCGCTGAGGCTGAGTT GCGCCGCTTCGGGGTTTACCTTCAGCACCTAC GCTATGAACTGGGTCAGACAGGCGCCTGGAAA GGGTTTGGAGTGGGTCGGACGCATCCGGTCCA AGGCCAACAACTACGCGACTTACTATGCCGACT CCGTCAAGGGACGGTTCACCATCTCCCGGGAC GACAGCAAGAACACCCTGTACCTCCAAATGAAC TCCCTTCGGGCCGAAGATACCGCCGTGTACTAC |

TABLE 21A-continued

Bivalent AB1
(hBCMA Fab/hCD3 scFv 1x1 format)

| | SEQ ID NO | Sequence |
|---|---|---|
| | | TGCGTGAGACACGGCAACTTCGGCGACTCCTA CGTGTCCTGGTTTGCCTACTGGGGCCAGGGTA CTCTCGTGACCGTGTCATCA |
| CDR-L1 (Kabat) | 315 | GSSTGAVTTSNYAN |
| CDR-L2 (Kabat) | 326 | GTNKRAP |
| CDR-L3 (Kabat) | 361 | ALWYSNHWV |
| CDR-L1 (Chothia) | 374 | STGAVTTSNY |
| CDR-L2 (Chothia) | 387 | GTN |
| CDR-L3 (Chothia) | 403 | WYSNHW |
| CDR-L1 (IMGT) | 564 | TGAVTTSNY |
| CDR-L2 (IMGT) | 565 | GTNKRAPGVP |
| CDR-L3 (IMGT) | 361 | ALWYSNHWV |
| VL | 286 | QAVVTQEPSLTVSPGGTVTLTCGSSTGAVTTSNY ANWVQQKPGKSPRGLIGGTNKRAPGVPARFSGS LLGGKAALTISGAQPEDEADYYCALWYSNHWVFG GGTKLTVL |
| DNA VL | 566 | CAGGCTGTGGTCACCCAGGAACCCTCCCTGAC TGTGTCCCCGGGAGGAACCGTGACACTGACTT GTGGCAGCTCCACCGGAGCCGTGACCACCTCC AACTACGCCAACTGGGTGCAGCAAAAGCCAGG AAAGTCCCCTAGGGGGCTGATCGGTGGCACGA ACAAGCGGGCACCTGGAGTGCCTGCCCGATTC TCGGGTAGCCTGCTGGGGGGAAAAGCCGCCCT GACCATTTCGGGCGCTCAGCCAGAGGACGAAG CCGACTATTACTGCGCACTCTGGTACTCCAACC ACTGGGTGTTCGGTGGAGGCACCAAGCTGACC GTGCTG |
| Linker | 479 | GKPGSGKPGSGKPGSGKPGS |
| scFv (VH-linker-VL) | 294 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVL |
| DNa scFv | 567 | GAAGTGCAGCTTGTGGAGTCCGGGGGAGGATT GGTCCAACCCGGTGGCTCGCTGAGGCTGAGTT GCGCCGCTTCGGGGTTTACCTTCAGCACCTAC GCTATGAACTGGGTCAGACAGGCGCCTGGAAA GGGTTTGGAGTGGGTCGGACGCATCCGGTCCA AGGCCAACAACTACGCGACTTACTATGCCGACT CCGTCAAGGGACGGTTCACCATCTCCCGGGAC GACAGCAAGAACACCCTGTACCTCCAAATGAAC TCCCTTCGGGCCGAAGATACCGCCGTGTACTAC TGCGTGAGACACGGCAACTTCGGCGACTCCTA CGTGTCCTGGTTTGCCTACTGGGGCCAGGGTA CTCTCGTGACCGTGTCATCAGGAAAGCCAGGCT CGGGGAAGCCTGGCTCCGGAAAGCCTGGGAG CGGAAAGCCGGGATCGCAGGCTGTGGTCACCC AGGAACCCTCCCTGACTGTGTCCCCGGGAGGA ACCGTGACACTGACTTGTGGCAGCTCCACCGG AGCCGTGACCACCTCCAACTACGCCAACTGGG TGCAGCAAAAGCCAGGAAAGTCCCCTAGGGGG CTGATCGGTGGCACGAACAAGCGGGCACCTGG AGTGCCTGCCCGATTCTCGGGTAGCCTGCTGG GGGGAAAAGCCGCCCTGACCATTTCGGGCGCT |

TABLE 21A-continued

Bivalent AB1
(hBCMA Fab/hCD3 scFv 1x1 format)

| SEQ ID NO | Sequence |
|---|---|
| | CAGCCAGAGGACGAAGCCGACTATTACTGCGC<br>ACTCTGGTACTCCAACCACTGGGTGTTCGGTGG<br>AGGCACCAAGCTGACCGTGCTG |

Full Ab region

| | SEQ ID NO | Sequence |
|---|---|---|
| HC BCMA arm | 502 | EVQLLESGGGLVQPGGSLRLSCAASGFTFSSYAM<br>SWVRQAPGKGLEWVSAISGSGGSTYYADSVKGR<br>FTISRDNSKNTLYLQMNSLRAEDTAVYYCARREW<br>WYDDWYLDYWGQGTLVTVSSASTKGPSVFPLAP<br>SSKSTSGGTAALGCLVKDYFPEPVTVSWNSGALT<br>SGVHTFPAVLQSSGLYSLSSVVTVPSSSLGTQTYI<br>CNVNHKPSDTKVDKKVEPKSCDKTHTCPPCPAPP<br>VAGPSVFLFPPKPKDTLMISRTPEVTCVVVDVKHE<br>DPEVKFNWYVDGVEVHNAKTKPREEEYNSTYRV<br>VSVLTVLHQDWLNGKEYKCKVSNKALPAPIEKTIS<br>KAKGQPREPQVYTLPPSREEMTKNQVSLTCDVS<br>GFYPSDIAVEWESDGQPENNYKTTPPVLDSDGSF<br>FLYSKLTVDKSRWEQGDVFSCSVMHEALHNHYT<br>QKSLSLSPGK |
| DNA HC | 568 | GAGGTGCAGCTGCTGGAGAGCGGGGGTGGAC<br>TGGTGCAGCCGGGAGGTTCCCTCCGGTTGTCA<br>TGTGCCGCATCCGGCTTTACTTTCTCTTCCTAC<br>GCCATGTCGTGGGTCAGACAGGCCCCGGGAAA<br>GGGACTTGAGTGGGTGTCGGCCATCTCCGGTT<br>CCGGGGGATCCACCTACTACGCGGACTCCGTG<br>AAGGGCCGCTTCACTATTTCACGGGACAACAGC<br>AAGAACACCCTGTACCTCCAAATGAACTCGCTG<br>CGCGCCGAAGATACCGCCGTCTACTACTGCGC<br>GCGGAGGGAATGGTGGTACGACGATTGGTATC<br>TGGACTACTGGGGCCAGGGCACTCTCGTGACC<br>GTGTCCAGCGCTAGCACCAAGGGCCCGTCAGT<br>GTTTCCTCTGGCCCCAAGCTCCAAGTCCACCTC<br>CGGTGGTACAGCCGCGTTGGGATGCTTGGTCA<br>AGGACTACTTTCCGGAACCCGTGACCGTGTCCT<br>GGAACTCCGGCGCCCTGACTAGCGGAGTGCAC<br>ACCTTCCCCGCTGTGCTGCAGTCTAGCGGGCT<br>GTATTCCCTCTCGTCCGTGGTCACCGTGCCGTC<br>CTCATCCCTGGGAACCCAGACCTACATTTGCAA<br>CGTGAACCACAAGCCGTCAGACACCAAGGTGG<br>ACAAGAAGGTGGAGCCGAAGTCCTGCGACAAG<br>ACCCATACTTGTCCTCCTTGCCCCGCTCCACCT<br>GTGGCGGGACCTTCCGTGTTCCTTTTCCCGCC<br>GAAGCCGAAGGACACTCTGATGATCTCGCGGA<br>CTCCCGAAGTCACTTGCGTGGTGGTGGACGTC<br>AAACACGAAGATCCCGAGGTCAAGTTCAATTGG<br>TACGTGGACGGGGTGGAAGTCCACAACGCCAA<br>GACTAAGCCGCGCGAGGAAGAGTACAATTCCA<br>CTTACCGGGTCGTGTCGGTGCTGACTGTGCTG<br>CATCAGGACTGGCTGAACGGAAAGGAGTACAA<br>GTGCAAAGTGTCGAACAAGGCCCTGCCTGCAC<br>CAATCGAAAAGACCATTAGCAAAGCCAAGGGCC<br>AGCCGAGAGAACCCCAAGTCTACACTCTGCCAC<br>CATCCCGCGAAGAAATGACCAAGAACCAAGTGT<br>CGCTGACGTGCGACGTGTCGGGATTCTACCCG<br>TCCGATATTGCCGTGGAATGGGAGAGCGACGG<br>CCAACCCGAGAACAACTACAAGACTACCCCCCC<br>CGTCTTGGATTCCGATGGTTCCTTCTTCCTGTA<br>CTCCAAGCTGACCGTGGATAAGTCCCGATGGG<br>AGCAGGGCGATGTGTTCTCGTGCTCCGTGATG<br>CATGAAGCCCTGCACAACCACTATACCCAGAAG<br>TCACTGTCGCTGAGCCCTGGGAAG |
| LC BCMA arm | 503 | DIQMTQSPSSLSASVGDRVTITCRASQSISSYLNW<br>YQQKPGKAPKLLIYAASSLQSGVPSRFSGSGSGT<br>DFTLTISSLQPEDFATYYCQQSYSSPLTFGQGTKV<br>EIKRTVAAPSVFIFPPSDEQLKSGTASVVCLLNNFY<br>PREAKVQWKVDNALQSGNSQESVTEQDSKDSTY<br>SLSSTLTLSKADYEKHKVYACEVTHQGLSSPVTKS<br>FNRGEC |

TABLE 21A-continued

Bivalent AB1
(hBCMA Fab/hCD3 scFv 1x1 format)

| | SEQ ID NO | Sequence |
|---|---|---|
| DNA LC | 558 | GACATTCAGATGACTCAGTCCCCGTCCTCCTTG<br>TCCGCCTCCGTGGGAGACAGAGTCACCATCAC<br>TTGCCGGGCATCGCAGAGCATCTCTTCATACCT<br>GAACTGGTATCAGCAGAAGCCCGGAAAGGCCC<br>CTAAGCTGCTGATCTACGCGGCCAGCAGCCTTC<br>AGTCCGGCGTGCCATCAAGGTTCAGCGGATCG<br>GGTTCGGGCACCGATTTTACTCTGACCATTAGC<br>TCCCTGCAACCCGAGGACTTCGCTACCTACTAC<br>TGTCAGCAGTCCTACTCCTCCCCGCTGACCTTC<br>GGACAAGGGACCAAAGTCGAAATCAAGCGTAC<br>GGTGGCCGCTCCCAGCGTGTTCATCTTCCCCC<br>CCAGCGACGAGCAGCTGAAGAGCGGCACCGCC<br>AGCGTGGTGTGCCTGCTGAACAACTTCTACCCC<br>CGGGAGGCCAAGGTGCAGTGGAAGGTGGACAA<br>CGCCCTGCAGAGCGGCAACAGCCAGGAGAGC<br>GTCACCGAGCAGGACAGCAAGGACTCCACCTA<br>CAGCCTGAGCAGCACCCTGACCCTGAGCAAGG<br>CCGACTACGAGAAGCATAAGGTGTACGCCTGC<br>GAGGTGACCCACCAGGGCCTGTCCAGCCCCGT<br>GACCAAGAGCTTCAACAGGGGCGAGTGC |
| CD3 arm | 504 | EVQLVESGGGLVQPGGSLRLSCAASGFTFSTYA<br>MNWVRQAPGKGLEWVGRIRSKANNYATYYADSV<br>KGRFTISRDDSKNTLYLQMNSLRAEDTAVYYCVR<br>HGNFGDSYVSWFAYWGQGTLVTVSSGKPGSGK<br>PGSGKPGSGKPGSQAVVTQEPSLTVSPGGTVTL<br>TCGSSTGAVTTSNYANWVQQKPGKSPRGLIGGT<br>NKRAPGVPARFSGSLLGGKAALTISGAQPEDEAD<br>YYCALWYSNHWVFGGGTKLTVLEPKSSDKTHTC<br>PPCPAPPVAGPSVFLFPPKPKDTLMISRTPEVTCV<br>VVDVKHEDPEVKFNWYVDGVEVHNAKTKPREEQ<br>YNSTYRVVSVLTVLHQDWLNGKEYKCKVSNKALP<br>APIEKTISKAKGQPREPQVYTLPPSREQMTKNQV<br>KLTCLVKGFYPSDIAVEWESNGQPENNYKTTPPV<br>LDSDGSFFLYSKLTVDKSRWQQGNVFSCSVMHE<br>ALHNHYTQKSLSLSPGK |
| DNA CD3 | 569 | GAAGTGCAGCTTGTGGAGTCCGGGGGAGGATT<br>GGTCCAACCCGGTGGCTCGCTGAGGCTGAGTT<br>GCGCCGCTTCGGGGTTTACCTTCAGCACCTAC<br>GCTATGAACTGGGTCAGACAGGCGCCTGGAAA<br>GGGTTTGGAGTGGGTCGGACGCATCCGGTCCA<br>AGGCCAACAACTACGCGACTTACTATGCCGACT<br>CCGTCAAGGGACGGTTCACCATCTCCCGGGAC<br>GACAGCAAGAACACCCTGTACCTCCAAATGAAC<br>TCCCTTCGGGCCGAAGATACCGCCGTGTACTAC<br>TGCGTGAGACACGGCAACTTCGGCGACTCCTA<br>CGTGTCCTGGTTTGCCTACTGGGGCCAGGGTA<br>CTCTCGTGACCGTGTCATCAGGAAAGCCAGGCT<br>CGGGGAAGCCTGGCTCCGGAAAGCCTGGGAG<br>CGGAAAGCCGGGATCGCAGGCTGTGGTCACCC<br>AGGAACCCTCCCTGACTGTGTCCCCGGGAGGA<br>ACCGTGACACTGACTTGTGGCAGCTCCACCGG<br>AGCCGTGACCACCTCCAACTACGCCAACTGGG<br>TGCAGCAAAAGCCAGGAAAGTCCCCTAGGGGG<br>CTGATCGGTGGCACGAACAAGCGGGCACCTGG<br>AGTGCCTGCCCGATTCTCGGGTAGCCTGCTGG<br>GGGGAAAAGCCGCCCTGACCATTTCGGGCGCT<br>CAGCCAGAGGACGAAGCCGACTATTACTGCGC<br>ACTCTGGTACTCCAACCACTGGGTGTTCGGTGG<br>AGGCACCAAGCTGACCGTGCTGGAGCCAAAGT<br>CAAGCGACAAAACTCACACTTGCCCTCCTTGTC<br>CGGCTCCTCCTGTGGCTGGTCCCTCCGTGTTC<br>CTCTTCCCGCCGAAGCCGAAGGACACCCTCAT<br>GATTTCCCGGACGCCCGAAGTCACTTGTGTGGT<br>GGTCGATGTGAAGCATGAGGACCCCGAAGTGA<br>AGTTCAATTGGTACGTGGATGGCGTGGAGGTC<br>CACAACGCCAAGACCAAGCCGCGCGAAGAACA<br>GTACAACAGCACCTACCGCGTCGTGAGCGTGC<br>TCACCGTGCTCCACCAAGATTGGCTGAACGGAA<br>AGGAGTACAAGTGCAAAGTGTCCAACAAGGCC<br>CTTCCTGCACCTATTGAAAAGACTATTAGCAAG<br>GCCAAGGGACAGCCCCGCGAACCTCAAGTGTA<br>CACTCTGCCGCCGTCCAGAGAGCAGATGACCA |

TABLE 21A-continued

Bivalent AB1
(hBCMA Fab/hCD3 scFv 1x1 format)

| SEQ ID NO | Sequence |
|---|---|
| | AAAACCAGGTCAAGCTCACTTGTCTCGTGAAGG<br>GCTTCTACCCGTCCGATATCGCGGTCGAATGG<br>GAGTCAAACGGCCAGCCCGAGAACAACTACAA<br>GACTACCCCACCGGTGCTTGACTCCGACGGTT<br>CGTTCTTTCTGTACTCCAAGCTGACCGTGGACA<br>AGTCCCGGTGGCAGCAAGGGAATGTGTTCAGC<br>TGCTCCGTGATGCACGAAGCCCTGCATAACCAC<br>TACACCCAGAAGTCGCTCAGCCTGTCCCCTGGA<br>AAA |

TABLE 21B

Trivalent AB1
(hBCMA Fab/hCD3 scfv 2x1 format)

| | SEQ ID NO | Sequence |
|---|---|---|
| Anti-BCMA Fab (PALF01) | | |
| CDR-H1 (Kabat) | 11 | SYAMS |
| CDR-H2 (Kabat) | 62 | AISGSGGSTYYADSVKG |
| CDR-H3 (Kabat) | 24 | REWWYDDWYLDY |
| CDR-H1 (Chothia) | 12 | GFTFSSY |
| CDR-H2 (Chothia) | 82 | SGSGGS |
| CDR-H3 (Chothia) | 24 | REWWYDDWYLDY |
| CDR-H1 (IMGT) | 13 | GFTFSSYA |
| CDR-H2 (IMGT) | 92 | ISGSGGST |
| CDR-H3 (IMGT) | 25 | ARREWWYDDWYLDY |
| VH | 213 | EVQLLESGGGLVQPGGSLRLSCAASGFTFSSYAM<br>SWVRQAPGKGLEWVSAISGSGGSTYYADSVKGR<br>FTISRDNSKNTLYLQMNSLRAEDTAVYYCARREW<br>WYDDWYLDYWGQGTLVTVSS |
| DNA VH | 570 | GAAGTGCAACTTTTGGAAAGCGGAGGCGGATT<br>GGTGCAACCTGGCGGCTCACTGAGACTGAGCT<br>GCGCCGCCTCCGGATTCACTTTCTCCTCCTACG<br>CCATGTCCTGGGTCCGACAGGCGCCCGGGAAG<br>GGCCTCGAATGGGTGTCGGCCATTTCCGGATC<br>TGGTGGAAGCACCTACTACGCTGATAGCGTGAA<br>GGGTCGCTTCACCATTTCGCGCGACAATTCGAA<br>GAACACCCTGTATCTGCAAATGAATAGCTTGAG<br>AGCCGAAGATACCGCCGTGTACTACTGCGCAC<br>GGCGGGAGTGGTGGTACGACGATTGGTACCTG<br>GACTACTGGGGCAGGGGACACTCGTGACCGT<br>GTCGAGC |
| Fab Heavy Chain | 555 | EVQLLESGGGLVQPGGSLRLSCAASGFTFSSYAM<br>SWVRQAPGKGLEWVSAISGSGGSTYYADSVKGR<br>FTISRDNSKNTLYLQMNSLRAEDTAVYYCARREW<br>WYDDWYLDYWGQGTLVTVSSASTKGPSVFPLAP<br>SSKSTSGGTAALGCLVKDYFPEPVTVSWNSGALT<br>SGVHTFPAVLQSSGLYSLSSVVTVPSSSLGTQTYI<br>CNVNHKPSDTKVDKKVEPKSC |
| DNA Heavy Chain | 571 | GAAGTGCAACTTTTGGAAAGCGGAGGCGGATT<br>GGTGCAACCTGGCGGCTCACTGAGACTGAGCT<br>GCGCCGCCTCCGGATTCACTTTCTCCTCCTACG<br>CCATGTCCTGGGTCCGACAGGCGCCCGGGAAG<br>GGCCTCGAATGGGTGTCGGCCATTTCCGGATC<br>TGGTGGAAGCACCTACTACGCTGATAGCGTGAA |

TABLE 21B-continued

Trivalent AB1
(hBCMA_Fab/hCD3_scfv 2x1 format)

| | SEQ ID NO | Sequence |
|---|---|---|
| | | GGGTCGCTTCACCATTTCGCGCGACAATTCGAA<br>GAACACCCTGTATCTGCAAATGAATAGCTTGAG<br>AGCCGAAGATACCGCCGTGTACTACTGCGCAC<br>GGCGGGAGTGGTGGTACGACGATTGGTACCTG<br>GACTACTGGGGCAGGGGACACTCGTGACCGT<br>GTCGAGCGCTTCCACCAAGGGACCGAGCGTGT<br>TCCCGCTGGCGCCGAGCAGCAAATCGACTTCT<br>GGGGGAACCGCAGCCCTGGGTTGCCTGGTCAA<br>GGACTACTTCCCGGAACCAGTCACTGTGTCCTG<br>GAACAGCGGTGCCCTCACCTCGGGCGTGCACA<br>CCTTCCCGGCCGTGCTGCAGTCTAGCGGACTC<br>TACTCGCTCTCCTCCGTGGTCACCGTGCCCTCC<br>TCATCACTGGGAACCCAGACATACATTTGCAAC<br>GTGAACCACAAGCCCTCGGACACTAAGGTGGA<br>CAAAAAAGTGGAACCAAAGTCCTGC |
| CDR-L1 (Kabat) | 2 | RASQSISSYLN |
| CDR-L2 (Kabat) | 5 | AASSLQS |
| CDR-L3 (Kabat) | 53 | QQSYSSPLT |
| CDR-L1 (Chothia) | 3 | SQSISSY |
| CDR-L2 (Chothia) | 6 | AAS |
| CDR-L3 (Chothia) | 73 | SYSSPL |
| CDR-L1 (IMGT) | 4 | QSISSY |
| CDR-L2 (IMGT) | 6 | AAS |
| CDR-L3 (IMGT) | 53 | QQSYSSPLT |
| VL | 191 | DIQMTQSPSSLSASVGDRVTITCRASQSISSYLNW<br>YQQKPGKAPKLLIYAASSLQSGVPSRFSGSGSGT<br>DFTLTISSLQPEDFATYYCQQSYSSPLTFGQGTKV<br>EIK |
| DNA VL | 572 | GACATTCAGATGACCCAGTCCCCGAGCTCCCTG<br>TCGGCTTCCGTGGGCGACAGAGTGACGATTAC<br>TTGCCGCGCGTCCCAAAGCATCTCCTCCTACCT<br>GAACTGGTACCAGCAGAAGCCGGGAAAGGCCC<br>CAAAGCTGTTGATCTACGCCGCCTCATCGCTCC<br>AATCTGGAGTGCCTTCCCGGTTTTCGGGGTCG<br>GGCAGCGGGACTGATTTCACCCTGACCATCAG<br>CAGCCTGCAGCCTGAAGATTTCGCCACCTACTA<br>CTGCCAGCAGTCCTATTCCTCACCCCTGACTTT<br>CGGACAAGGCACCAAGGTCGAGATCAAG |
| Fab Light Chain | 503 | DIQMTQSPSSLSASVGDRVTITCRASQSISSYLNW<br>YQQKPGKAPKLLIYAASSLQSGVPSRFSGSGSGT<br>DFTLTISSLQPEDFATYYCQQSYSSPLTFGQGTKV<br>EIKRTVAAPSVFIFPPSDEQLKSGTASVVCLLNNFY<br>PREAKVQWKVDNALQSGNSQESVTEQDSKDSTY<br>SLSSTLTLSKADYEKHKVYACEVTHQGLSSPVTKS<br>FNRGEC |
| DNA Light Chain | 573 | GACATTCAGATGACCCAGTCCCCGAGCTCCCTG<br>TCGGCTTCCGTGGGCGACAGAGTGACGATTAC<br>TTGCCGCGCGTCCCAAAGCATCTCCTCCTACCT<br>GAACTGGTACCAGCAGAAGCCGGGAAAGGCCC<br>CAAAGCTGTTGATCTACGCCGCCTCATCGCTCC<br>AATCTGGAGTGCCTTCCCGGTTTTCGGGGTCG<br>GGCAGCGGGACTGATTTCACCCTGACCATCAG<br>CAGCCTGCAGCCTGAAGATTTCGCCACCTACTA<br>CTGCCAGCAGTCCTATTCCTCACCCCTGACTTT<br>CGGACAAGGCACCAAGGTCGAGATCAAGCGTA<br>CGGTGGCTGCACCATCTGTCTTCATCTTCCCGC<br>CATCTGATGAGCAGTTGAAATCTGGAACTGCCT<br>CTGTTGTGTGCCTGCTGAATAACTTCTATCCCA<br>GAGAGGCCAAAGTACAGTGGAAGGTGGATAAC<br>GCCCTCCAATCGGGTAACTCCCAGGAGAGTGT<br>CACAGAGCAGGACAGCAAGGACAGCACCTACA |

TABLE 21B-continued

Trivalent AB1
(hBCMA_Fab/hCD3_scfv 2x1 format)

| | SEQ ID NO | Sequence |
|---|---|---|
| | | GCCTCAGCAGCACCCTGACGCTGAGCAAAGCA GACTACGAGAAACACAAAGTCTACGCCTGCGAA GTCACCCATCAGGGCCTGAGCTCGCCCGTCAC AAAGAGCTTCAACAGGGGAGAGTGT |
| Anti-CD3 scFv (~30 nM) (CD3-23) | | |
| CDR-H1 (Kabat) | 305 | TYAMN |
| CDR-H2 (Kabat) | 338 | RIRSKANNYATYYADSVKG |
| CDR-H3 (Kabat) | 360 | HGNFGDSYVSWFAY |
| CDR-H1 (Chothia) | 378 | GFTFSTY |
| CDR-H2 (Chothia) | 559 | RSKANNYA |
| CDR-H3 (Chothia) | 360 | HGNFGDSYVSWFAY |
| CDR-H1 (IMGT) | 560 | GFTFSTYA |
| CDR-H2 (IMGT) | 561 | IRSKANNYAT |
| CDR-H3 (IMGT) | 562 | VRHGNFGDSYVSWFAY |
| VH | 293 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSS |
| DNA VH | 574 | GAGGTGCAGCTCGTCGAATCCGGTGGAGGGCT GGTGCAACCGGGGGGCTCGCTTAGGCTTAGCT GCGCTGCGTCAGGGTTCACCTTCTCAACTTACG CGATGAATTGGGTCAGACAGGCACCCGGAAAG GGACTGGAATGGGTCGGAAGAATCAGATCGAA GGCCAACAACTACGCCACTTACTACGCCGACTC CGTGAAGGGAAGGTTCACTATCTCGCGGGACG ACTCCAAGAACACTCTGTATCTCCAAATGAACTC ACTCCGGGCCGAGGATACTGCGGTGTACTATT GCGTGCGGCATGGAAACTTCGGGGACAGCTAC GTCAGCTGGTTCGCCTACTGGGGCCAAGGCAC TCTCGTCACCGTGTCATCC |
| CDR-L1 (Kabat) | 315 | GSSTGAVTTSNYAN |
| CDR-L2 (Kabat) | 326 | GTNKRAP |
| CDR-L3 (Kabat) | 361 | ALWYSNHWV |
| CDR-L1 (Chothia) | 374 | STGAVTTSNY |
| CDR-L2 (Chothia) | 387 | GTN |
| CDR-L3 (Chothia) | 403 | WYSNHW |
| CDR-L1 (IMGT) | 564 | TGAVTTSNY |
| CDR-L2 (IMGT) | 565 | GTNKRAPGVP |
| CDR-L3 (IMGT) | 361 | ALWYSNHWV |
| VL | 286 | QAVVTQEPSLTVSPGGTVTLTCGSSTGAVTTSNY ANWVQQKPGKSPRGLIGGTNKRAPGVPARFSGS LLGGKAALTISGAQPEDEADYYCALWYSNHWVFG GGTKLTVL |
| DNA VL | 575 | CAGGCCGTCGTGACCCAGGAACCGAGCCTGAC CGTGTCCCCCGGCGGTACCGTGACCTTGACTT GCGGTTCCTCCACTGGAGCCGTGACTACCTCG AACTACGCCAACTGGGTGCAGCAGAAGCCGGG AAAGTCGCCTCGCGGACTGATCGGTGGAACTA ACAAACGCGCCCCGGGCGTGCCAGCCAGATTC AGCGGTAGCCTGCTCGGCGGAAAGGCCGCGCT |

TABLE 21B-continued

Trivalent AB1
(hBCMA_Fab/hCD3_scfv 2x1 format)

| | SEQ ID NO | Sequence |
|---|---|---|
| | | GACCATCTCCGGGGCCCAGCCCGAGGATGAGG<br>CCGACTATTACTGCGCTCTGTGGTACTCCAACC<br>ACTGGGTGTTTGGCGGGGGCACTAAGCTGACT<br>GTGCTG |
| Linker | 479 | GKPGSGKPGSGKPGSGKPGS |
| scFv (VH-linker-VL) | 294 | EVQLVESGGGLVQPGGSLRLSCAASGFTFSTYA<br>MNWVRQAPGKGLEWVGRIRSKANNYATYYADSV<br>KGRFTISRDDSKNTLYLQMNSLRAEDTAVYYCVR<br>HGNFGDSYVSWFAYWGQGTLVTVSSGKPGSGK<br>PGSGKPGSGKPGSQAVVTQEPSLTVSPGGTVTL<br>TCGSSTGAVTTSNYANWVQQKPGKSPRGLIGGT<br>NKRAPGVPARFSGSLLGGKAALTISGAQPEDAD<br>YYCALWYSNHWVFGGGTKLTVL |
| DNA scFv | 576 | GAGGTGCAGCTCGTCGAATCCGGTGGAGGGCT<br>GGTGCAACCGGGGGGCTCGCTTAGGCTTAGCT<br>GCGCTGCGTCAGGGTTCACCTTCTCAACTTACG<br>CGATGAATTGGGTCAGACAGGCACCCGGAAAG<br>GGACTGGAATGGGTCGGAAGAATCAGATCGAA<br>GGCCAACAACTACGCCACTTACTACGCCGACTC<br>CGTGAAGGGAAGGTTCACTATCTCGCGGGACG<br>ACTCCAAGAACACTCTGTATCTCCAAATGAACTC<br>ACTCCGGGCCGAGGATACTGCGGTGTACTATT<br>GCGTGCGGCATGGAAACTTCGGGGACAGCTAC<br>GTCAGCTGGTTCGCCTACTGGGGCAAGGCAC<br>TCTCGTCACCGTGTCATCCGGGAAGCCGGGTT<br>CCGGAAAGCCTGGATCGGGCAAACCGGGATCG<br>GGAAAACCCGGAAGCCAGGCCGTCGTGACCCA<br>GGAACCGAGCCTGACCGTGTCCCCCGGCGGTA<br>CCGTGACCTTGACTTGCGGTTCCTCCACTGGAG<br>CCGTGACTACCTCGAACTACGCCAACTGGGTG<br>CAGCAGAAGCCGGGAAAGTCGCCTCGCGGACT<br>GATCGGTGGAACTAACAAACGCGCCCCGGGCG<br>TGCCAGCCAGATTCAGCGGTAGCCTGCTCGGC<br>GGGAAAGGCCGCGCTGACCATCTCCGGGGCCCA<br>GCCCGAGGATGAGGCCGACTATTACTGCGCTC<br>TGTGGTACTCCAACCACTGGGTGTTTGGCGGG<br>GGCACTAAGCTGACTGTGCTG |

Fc region

| HC BCMA arm | 502 | EVQLLESGGGLVQPGGSLRLSCAASGFTFSSYAM<br>SWVRQAPGKGLEWVSAISGSGGSTYYADSVKGR<br>FTISRDNSKNTLYLQMNSLRAEDTAVYYCARREW<br>WYDDWYLDYWGQGTLVTVSSASTKGPSVFPLAP<br>SSKSTSGGTAALGCLVKDYFPEPVTVSWNSGALT<br>SGVHTFPAVLQSSGLYSLSSVVTVPSSSLGTQTYI<br>CNVNHKPSDTKVDKKVEPKSCDKTHTCPPCPAPP<br>VAGPSVFLFPPKPKDTLMISRTPEVTCVVVDVKHE<br>DPEVKFNWYVDGVEVHNAKTKPREEEYNSTYRV<br>VSVLTVLHQDWLNGKEYKCKVSNKALPAPIEKTIS<br>KAKGQPREPQVYTLPPSREEMTKNQVSLTCDVS<br>GFYPSDIAVEWESDGQPENNYKTTPPVLDSDGSF<br>FLYSKLTVDKSRWEQGDVFSCSVMHEALHNHYT<br>QKSLSLSPGK |
| --- | --- | --- |
| DNA HC | 577 | GAAGTGCAACTTTTGGAAAGCGGAGGCGGATT<br>GGTGCAACCTGGCGGCTCACTGAGACTGAGCT<br>GCGCCGCCTCCGGATTCACTTTCTCCTCCTACG<br>CCATGTCCTGGGTCCGACAGGCGCCCGGGAAG<br>GGCCTCGAATGGGTGTCGGCCATTTCCGGATC<br>TGGTGGAAGCACCTACTACGCTGATAGCGTGAA<br>GGGTCGCTTCACCATTTCGCGCGACAATTCGAA<br>GAACACCCTGTATCTGCAAATGAATAGCTTGAG<br>AGCCGAAGATACCGCCGTGTACTACTGCGCAC<br>GGCGGGAGTGGTGGTACGACGATTGGTACCTG<br>GACTACTGGGGCAGGGGACACTCGTGACCGT<br>GTCGAGCGCTTCCACCAAGGGACCGAGCGTGT<br>TCCCGCTGGCGCCAGCAGCAAATCGACTTCT<br>GGGGGAACCGCAGCCCTGGGTTGCCTGGTCAA<br>GGACTACTTCCCGGAACCAGTCACTGTGTCCTG<br>GAACAGCGGTGCCCTCACCTCGGGCGTGCACA |

TABLE 21B-continued

Trivalent AB1
(hBCMA_Fab/hCD3_scfv 2x1 format)

| | SEQ ID NO | Sequence |
|---|---|---|
| | | CCTTCCCGGCCGTGCTGCAGTCTAGCGGACTC<br>TACTCGCTCTCCTCCGTGGTCACCGTGCCCTCC<br>TCATCACTGGGAACCCAGACATACATTTGCAAC<br>GTGAACCACAAGCCCTCGGACACTAAGGTGGA<br>CAAAAAAGTGGAACCAAAGTCCTGCGACAAGAC<br>CCACACTTGTCCGCCCTGCCCTGCCCCTCCCG<br>TGGCGGGCCCGTCAGTGTTTCTGTTTCCGCCAA<br>AGCCTAAGGATACCCTCATGATCAGCCGCACTC<br>CTGAAGTGACCTGTGTCGTGGTGGACGTGAAA<br>CACGAGGACCCGGAGGTCAAGTTTAATTGGTAC<br>GTGGATGGGGTGGAGGTGCACAACGCCAAAAC<br>TAAGCCCCGGGAAGAAGAGTACAATTCCACCTA<br>CCGCGTCGTGTCAGTGTTGACGGTCCTGCACC<br>AAGACTGGCTGAACGGAAAGGAGTACAAGTGC<br>AAGGTGTCCAACAAGGCACTGCCCGCCCCCAT<br>CGAAAAGACCATTTCAAAAGCTAAGGGCCAGCC<br>GCGGGAACCACAGGTCTACACCCTGCCTCCCT<br>CCCGGGAAGAGATGACCAAGAACCAAGTCTCC<br>CTCACGTGTGACGTGTCCGGCTTCTACCCTTCG<br>GACATTGCTGTGGAATGGGAGTCCGACGGGCA<br>GCCCGAAAACAACTACAAGACCACTCCCCCTGT<br>GCTGGACTCCGACGGCTCATTCTTTCTGTACTC<br>CAAGCTCACCGTCGATAAGTCGAGATGGGAGC<br>AGGGAGATGTGTTCTCCTGCTCCGTGATGCACG<br>AGGCCCTGCATAACCATTACACTCAGAAGTCCC<br>TCTCCCTGTCCCTGGGAAG |
| LC BCMA arm | 503 | DIQMTQSPSSLSASVGDRVTITCRASQSISSYLNW<br>YQQKPGKAPKLLIYAASSLQSGVPSRFSGSGSGT<br>DFTLTISSLQPEDFATYYCQQSYSSPLTFGQGTKV<br>EIKRTVAAPSVFIFPPSDEQLKSGTASVVCLLNNFY<br>PREAKVQWKVDNALQSGNSQESVTEQDSKDSTY<br>SLSSTLTLSKADYEKHKVYACEVTHQGLSSPVTKS<br>FNRGEC |
| DNA LC | 573 | GACATTCAGATGACCCAGTCCCCGAGCTCCCTG<br>TCGGCTTCCGTGGGCGACAGAGTGACGATTAC<br>TTGCCGCGCGTCCCAAAGCATCTCCTCCTACCT<br>GAACTGGTACCAGCAGAAGCCGGGAAAGGCCC<br>CAAAGCTGTTGATCTACGCCGCCTCATCGCTCC<br>AATCTGGAGTGCCTTCCCGGTTTTCGGGGTCG<br>GGCAGCGGGACTGATTTCACCCTGACCATCAG<br>CAGCCTGCAGCCTGAAGATTTCGCCACCTACTA<br>CTGCCAGCAGTCCTATTCCTCACCCCTGACTTT<br>CGGACAAGGCACCAAGGTCGAGATCAAGCGTA<br>CGGTGGCTGCACCATCTGTCTTCATCTTCCCGC<br>CATCTGATGAGCAGTTGAAATCTGGAACTGCCT<br>CTGTTGTGTGCCTGCTGAATAACTTCTATCCCA<br>GAGAGGCCAAAGTACAGTGGAAGGTGGATAAC<br>GCCCTCCAATCGGGTAACTCCCAGGAGAGTGT<br>CACAGAGCAGGACAGCAAGGACAGCACCTACA<br>GCCTCAGCAGCACCCTGACGCTGAGCAAAGCA<br>GACTACGAGAAACACAAAGTCTACGCCTGCGAA<br>GTCACCCATCAGGGCCTGAGCTCGCCCGTCAC<br>AAAGAGCTTCAACAGGGGAGAGTGT |
| CD3 arm | 505 | EVQLLESGGGLVQPGGSLRLSCAASGFTFSSYAM<br>SWVRQAPGKGLEWVSAISGSGGSTYYADSVKGR<br>FTISRDNSKNTLYLQMNSLRAEDTAVYYCARREW<br>WYDDWYLDYWGQGTLVTVSSASTKGPSVFPLAP<br>SSKSTSGGTAALGCLVKDYFPEPVTVSWNSGALT<br>SGVHTFPAVLQSSGLYSLSSVVTVPSSSLGTQTYI<br>CNVNHKPSNTKVDKKVEPKSCGGGGSGGGGSE<br>VQLVESGGGLVQPGGSLRLSCAASGFTFSTYAM<br>NWVRQAPGKGLEWVGRIRSKANNYATYYADSVK<br>GRFTISRDDSKNTLYLQMNSLRAEDTAVYYCVRH<br>GNFGDSYVSWFAYWGQGTLVTVSSGKPGSGKP<br>GSGKPGSGKPGSQAVVTQEPSLTVSPGGTVTLT<br>CGSSTGAVTTSNYANWVQQKPGKSPRGLIGGTN<br>KRAPGVPARFSGSLLGGKAALTISGAQPEDEADY<br>YCALWYSNHWVFGGGTKLTVLGGGGSGGGGSK<br>THTCPPCPAPPVAGPSVFLFPPKPKDTLMISRTPE<br>VTCVVVDVKHEDPEVKFNWYVDGVEVHNAKTKP<br>REEQYNSTYRVVSVLTVLHQDWLNGKEYKCKVS |

TABLE 21B-continued

Trivalent AB1
(hBCMA_Fab/hCD3_scfv 2x1 format)

| | SEQ ID NO | Sequence |
|---|---|---|
| | | NKALPAPIEKTISKAKGQPREPQVYTLPPSREQMT<br>KNQVKLTCLVKGFYPSDIAVEWESNGQPENNYKT<br>TPPVLDSDGSFFLYSKLTVDKSRWQQGNVFSCSV<br>MHEALHNHYTQKSLSLSPGK |
| DNA CD3 | 578 | GAAGTGCAACTTTTGGAAAGCGGAGGCGGATT<br>GGTGCAACCTGGCGGCTCACTGAGACTGAGCT<br>GCGCCGCCTCCGGATTCACTTTCTCCTCCTACG<br>CCATGTCCTGGGTCCGACAGGCGCCCGGGAAG<br>GGCCTCGAATGGGTGTCGGCCATTTCCGGATC<br>TGGTGGAAGCACCTACTACGCTGATAGCGTGAA<br>GGGTCGCTTCACCATTTCGCGCGACAATTCGAA<br>GAACACCCTGTATCTGCAAATGAATAGCTTGAG<br>AGCCGAAGATACCGCCGTGTACTACTGCGCAC<br>GGCGGGAGTGGTGGTACGACGATTGGTACCTG<br>GACTACTGGGGCAGGGGACACTCGTGACCGT<br>GTCGAGCGCTTCCACCAAGGGACCGAGCGTGT<br>TCCCGCTGGCGCCGAGCAGCAAATCGACTTCT<br>GGGGGAACCGCAGCCCTGGGTTGCCTGGTCAA<br>GGACTACTTCCCGGAACCAGTCACTGTGTCCTG<br>GAACAGCGGTGCCCTCACCTCGGGCGTGCACA<br>CCTTCCCGGCCGTGCTGCAGTCTAGCGGACTC<br>TACTCGCTCTCCTCCGTGGTCACCGTGCCCTCC<br>TCATCACTGGGAACCCAGACATACATTTGCAAC<br>GTGAACCACAAGCCGTCCAACACCAAGGTCGA<br>CAAGAAAGTGGAGCCTAAGTCCTGTGGTGGCG<br>GAGGCTCCGGCGGAGGAGGATCGGAGGTGCA<br>GCTCGTCGAATCCGGTGGAGGGCTGGTGCAAC<br>CGGGGGGCTCGCTTAGGCTTAGCTGCGCTGCG<br>TCAGGGTTCACCTTCTCAACTTACGCGATGAAT<br>TGGGTCAGACAGGCACCCGGAAAGGGACTGGA<br>ATGGGTCGGAAGAATCAGATCGAAGGCCAACA<br>ACTACGCCACTTACTACGCCGACTCCGTGAAGG<br>GAAGGTTCACTATCTCGCGGGACGACTCCAAGA<br>ACACTCTGTATCTCCAAATGAACTCACTCCGGG<br>CCGAGGATACTGCGGTGTACTATTGCGTGCGG<br>CATGGAAACTTCGGGGACAGCTACGTCAGCTG<br>GTTCGCCTACTGGGGCCAAGGCACTCTCGTCA<br>CCGTGTCATCCGGGAAGCCGGGTTCCGGAAAG<br>CCTGGATCGGGCAAACCGGGATCGGGAAAACC<br>CGGAAGCCAGGCCGTCGTGACCCAGGAACCGA<br>GCCTGACCGTGTCCCCCGGCGGTACCGTGACC<br>TTGACTTGCGGTTCCTCCACTGGAGCCGTGACT<br>ACCTCGAACTACGCCAACTGGGTGCAGCAGAA<br>GCCGGGAAAGTCGCCTCGCGGACTGATCGGTG<br>GAACTAACAAACGCGCCCGGGCGTGCCAGCC<br>AGATTCAGCGGTAGCCTGCTCGGCGGAAAGGC<br>CGCGCTGACCATCTCCGGGGCCCAGCCCGAGG<br>ATGAGGCCGACTATTACTGCGCTCTGTGGTACT<br>CCAACCACTGGGTGTTTGGCGGGGGCACTAAG<br>CTGACTGTGCTGGGCGGCGGCGGCTCCGGGG<br>GGGGGGGCTCCAAGACCCACACTTGTCCGCCC<br>TGCCCTGCCCCTCCCGTGGCGGGCCCGTCAGT<br>GTTTCTGTTTCCGCCAAAGCCTAAGGATACCCT<br>CATGATCAGCCGCACTCCTGAAGTGACCTGTGT<br>CGTGGTGGACGTGAAACACGAGGACCCGGAGG<br>TCAAGTTTAATTGGTACGTGGATGGGGTGGAGG<br>TGCACAACGCCAAAACTAAGCCCCGGGAAGAA<br>CAGTACAATTCCACCTACCGCGTCGTGTCAGTG<br>TTGACGGTCCTGCACCAAGACTGGCTGAACGG<br>AAAGGAGTACAAGTGCAAGGTGTCCAACAAGG<br>CACTGCCCGCCCCCATCGAAAAGACCATTTCAA<br>AAGCTAAGGGCCAGCCGCGGGAACCACAGGTC<br>TACACCCTGCCTCCCTCCCGGGAACAGATGAC<br>CAAGAACCAAGTCAAGCTCACGTGTCTCGTGAA<br>GGGCTTCTACCCTTCGGACATTGCTGTGGAATG<br>GGAGTCCAACGGGCAGCCCGAAACAACTACA<br>AGACCACTCCCCCTGTGCTGGACTCCGACGGC<br>TCATTCTTTCTGTACTCCAAGCTCACCGTCGATA<br>AGTCGAGATGGCAGCAGGGAAACGTGTTCTCC<br>TGCTCCGTGATGCACGAGGCCCTGCATAACCAT<br>TACACTCAGAAGTCCCTCTCCCTGTCCCCTGGG<br>AAG |

TABLE 21C

Bivalent BCMA-CD3 AB2
(BCMA Fab/hCD3 scFv 1x1 format)

| | SEQ ID NO | Sequence |
|---|---|---|
| Anti-BCMA Fab (PALF11) | | |
| CDR-H1 (Kabat) | 11 | SYAMS |
| CDR-H2 (Kabat) | 63 | AISESGGRAAYADSVKG |
| CDR-H3 (Kabat) | 24 | REWWYDDWYLDY |
| CDR-H1 (Chothia) | 12 | GFTFSSY |
| CDR-H2 (Chothia) | 83 | SESGGR |
| CDR-H3 (Chothia) | 24 | REWWYDDWYLDY |
| CDR-H1 (IMGT) | 13 | GFTFSSYA |
| CDR-H2 (IMGT) | 93 | ISESGGRA |
| CDR-H3 (IMGT) | 25 | ARREWWYDDWYLDY |
| VH | 214 | EVQLLESGGGLVQPGGSLRLSCAASGFTFSSYAM SWVRQAPGKGLEWVSAISESGGRAAYADSVKGR FTISRDNSKNTLYLQMNSLRAEDTAVYYCARREW WYDDWYLDYWGQGTLVTVSS |
| DNA VH | 579 | GAAGTGCAGCTGCTGGAGAGCGGCGGAGGTCT GGTGCAGCCAGGCGGATCCTTGCGCCTCAGTT GTGCCGCGTCCGGATTCACTTTCTCGTCTTACG CCATGTCCTGGGTCAGACAGGCCCCTGGGAAG GGTCTGGAGTGGGTGTCCGCGATCAGCGAGTC AGGAGGGAGAGCCGCCTACGCCGACTCCGTGA AGGGCCGCTTTACCATTTCGCGGGACAACTCCA AGAACACCCTGTACCTTCAAATGAACAGCCTGC GGGCAGAGGACACCGCCGTCTACTACTGCGCC CGGAGGGAATGGTGGTACGATGATTGGTATCT GGACTACTGGGGCCAGGGAACTCTCGTGACCG TGTCCTCG |
| Fab Heavy Chain | 580 | EVQLLESGGGLVQPGGSLRLSCAASGFTFSSYAM SWVRQAPGKGLEWVSAISESGGRAAYADSVKGR FTISRDNSKNTLYLQMNSLRAEDTAVYYCARREW WYDDWYLDYWGQGTLVTVSSASTKGPSVFPLAP SSKSTSGGTAALGCLVKDYFPEPVTVSWNSGALT SGVHTFPAVLQSSGLYSLSSVVTVPSSSLGTQTYI CNVNHKPSDTKVDKKVEPKSC |
| DNA Heavy Chain | 581 | GAAGTGCAGCTGCTGGAGAGCGGCGGAGGTCT GGTGCAGCCAGGCGGATCCTTGCGCCTCAGTT GTGCCGCGTCCGGATTCACTTTCTCGTCTTACG CCATGTCCTGGGTCAGACAGGCCCCTGGGAAG GGTCTGGAGTGGGTGTCCGCGATCAGCGAGTC AGGAGGGAGAGCCGCCTACGCCGACTCCGTGA AGGGCCGCTTTACCATTTCGCGGGACAACTCCA AGAACACCCTGTACCTTCAAATGAACAGCCTGC GGGCAGAGGACACCGCCGTCTACTACTGCGCC CGGAGGGAATGGTGGTACGATGATTGGTATCT GGACTACTGGGGCCAGGGAACTCTCGTGACCG TGTCCTCGGCTAGCACCAAGGGCCCGTCAGTG TTTCCTCTGGCCCCAAGCTCCAAGTCCACCTCC GGTGGTACAGCCGCGTTGGGATGCTTGGTCAA GGACTACTTTCCGGAACCCGTGACCGTGTCCTG GAACTCCGGCGCCCTGACTAGCGGAGTGCACA CCTTCCCCGCTGTGCTGCAGTCTAGCGGGCTG TATTCCCTCTCGTCCGTGGTCACCGTGCCGTCC TCATCCCTGGGAACCCAGACCTACATTTGCAAC GTGAACCACAAGCCGTCAGACACCAAGGTGGA CAAGAAGGTGGAGCCGAAGTCCTGC |
| CDR-L1 (Kabat) | 2 | RASQSISSYLN |
| CDR-L2 (Kabat) | 5 | AASSLQS |
| CDR-L3 (Kabat) | 54 | QQSYSTPLT |

TABLE 21C-continued

Bivalent BCMA-CD3 AB2
(BCMA Fab/hCD3 scFv 1x1 format)

| | SEQ ID NO | Sequence |
|---|---|---|
| CDR-L1 (Chothia) | 3 | SQSISSY |
| CDR2 (Chothia) | 6 | AAS |
| CDR-L3 (Chothia) | 74 | SYSTPL |
| CDR-L1 (IMGT) | 4 | QSISSY |
| CDR-L2 (IMGT) | 6 | AAS |
| CDR-L3 (IMGT) | 54 | QQSYSTPLT |
| VL | 192 | DIQMTQSPSSLSASVGDRVTITCRASQSISSYLNW YQQKPGKAPKLLIYAASSLQSGVPSRFSGSGSGT DFTLTISSLQPEDFATYYCQQSYSTPLTFGQGTKV EIK |
| DNA VL | 582 | GACATTCAGATGACCCAGTCCCCGTCCTCGCTG AGCGCATCAGTCGGCGATCGCGTGACTATTACT TGTCGGGCGTCCCAGTCGATCTCCTCGTACTTG AACTGGTATCAGCAGAAGCCCGGAAAAGCCCC GAAGTTACTGATCTACGCTGCCTCATCCCTCCA ATCTGGGGTGCCTTCGCGGTTCTCCGGTTCCG GAAGCGGAACCGACTTCACCCTGACCATCAGC AGCCTGCAGCCAGAGGACTTTGCCACCTACTAC TGCCAGCAGTCCTACTCCACACCCCTCACTTTC GGACAAGGCACCAAGGTCGAAATCAAG |
| Fab Light Chain | 507 | DIQMTQSPSSLSASVGDRVTITCRASQSISSYLNW YQQKPGKAPKLLIYAASSLQSGVPSRFSGSGSGT DFTLTISSLQPEDFATYYCQQSYSTPLTFGQGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC |
| DNA Light Chain | 583 | GACATTCAGATGACCCAGTCCCCGTCCTCGCTG AGCGCATCAGTCGGCGATCGCGTGACTATTACT TGTCGGGCGTCCCAGTCGATCTCCTCGTACTTG AACTGGTATCAGCAGAAGCCCGGAAAAGCCCC GAAGTTACTGATCTACGCTGCCTCATCCCTCCA ATCTGGGGTGCCTTCGCGGTTCTCCGGTTCCG GAAGCGGAACCGACTTCACCCTGACCATCAGC AGCCTGCAGCCAGAGGACTTTGCCACCTACTAC TGCCAGCAGTCCTACTCCACACCCCTCACTTTC GGACAAGGCACCAAGGTCGAAATCAAGCGTAC GGTGGCCGCTCCCAGCGTGTTCATCTTCCCCC CCAGCGACGAGCAGCTGAAGAGCGGCACCGCC AGCGTGGTGTGCCTGCTGAACAACTTCTACCCG CGGGAGGCCAAGGTGCAGTGGAAGGTGGACAA CGCCCTGCAGAGCGGCAACAGCCAGGAGAGC GTCACCGAGCAGGACAGCAAGGACTCCACCTA CAGCCTGAGCAGCACCCTGACCCTGAGCAAGG CCGACTACGAGAAGCATAAGGTGTACGCCTGC GAGGTGACCCACCAGGGCCTGTCCAGCCCCGT GACCAAGAGCTTCAACAGGGGCGAGTGC |

Anti-CD3 scFv (~30 nM)
(CD3-23)

| | SEQ ID NO | Sequence |
|---|---|---|
| CDR-H1 (Kabat) | 305 | TYAMN |
| CDR-H2 (Kabat) | 338 | RIRSKANNYATYYADSVKG |
| CDR-H3 (Kabat) | 360 | HGNFGDSYVSWFAY |
| CDR-H1 (Chothia) | 378 | GFTFSTY |
| CDR-H2 (Chothia) | 559 | RSKANNYA |
| CDR-H3 (Chothia) | 360 | HGNFGDSYVSWFAY |
| CDR-H1 (IMGT) | 560 | GFTFSTYA |

TABLE 21C-continued

Bivalent BCMA-CD3 AB2
(BCMA Fab/hCD3 scFv 1x1 format)

| | SEQ ID NO | Sequence |
|---|---|---|
| CDR-H2 (IMGT) | 561 | IRSKANNYAT |
| CDR-H3 (IMGT) | 562 | VRHGNFGDSYVSWFAY |
| VH | 293 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSS |
| DNA VH | 563 | GAAGTGCAGCTTGTGGAGTCCGGGGGAGGATT GGTCCAACCCGGTGGCTCGCTGAGGCTGAGTT GCGCCGCTTCGGGGTTTACCTTCAGCACCTAC GCTATGAACTGGGTCAGACAGGCGCCTGGAAA GGGTTTGGAGTGGGTCGGACGCATCCGGTCCA AGGCCAACAACTACGCGACTTACTATGCCGACT CCGTCAAGGGACGGTTCACCATCTCCCGGGAC GACAGCAAGAACACCCTGTACCTCCAAATGAAC TCCCTTCGGGCCGAAGATACCGCCGTGTACTAC TGCGTGAGACACGGCAACTTCGGCGACTCCTA CGTGTCCTGGTTTGCCTACTGGGGCCAGGGTA CTCTCGTGACCGTGTCATCA |
| CDR-L1 (Kabat) | 315 | GSSTGAVTTSNYAN |
| CDR-L2 (Kabat) | 326 | GTNKRAP |
| CDR-L3 (Kabat) | 361 | ALWYSNHWV |
| CDR-L1 (Chothia) | 374 | STGAVTTSNY |
| CDR-L2 (Chothia) | 387 | GTN |
| CDR-L3 (Chothia) | 403 | WYSNHW |
| CDR-L1 (IMGT) | 564 | TGAVTTSNY |
| CDR-L2 (IMGT) | 565 | GTNKRAPGVP |
| CDR-L3 (IMGT) | 361 | ALWYSNHWV |
| VL | 286 | QAVVTQEPSLTVSPGGTVTLTCGSSTGAVTTSNY ANWVQQKPGKSPRGLIGGTNKRAPGVPARFSGS LLGGKAALTISGAQPEDEADYYCALWYSNHWVFG GGTKLTVL |
| DNA VL | 566 | CAGGCTGTGGTCACCCAGGAACCCTCCCTGAC TGTGTCCCCGGGAGGAACCGTGACACTGACTT GTGGCAGCTCCACCGGAGCCGTGACCACCTCC AACTACGCCAACTGGGTGCAGCAAAAGCCAGG AAAGTCCCCTAGGGGGCTGATCGGTGGCACGA ACAAGCGGGCACCTGGAGTGCCTGCCCGATTC TCGGGTAGCCTGCTGGGGGGAAAAGCCGCCCT GACCATTTCGGGCGCTCAGCCAGAGGACGAAG CCGACTATTACTGCGCACTCTGGTACTCCAACC ACTGGGTGTTCGGTGGAGGCACCAAGCTGACC GTGCTG |
| Linker | 479 | GKPGSGKPGSGKPGSGKPGS |
| scFv (VH-linker-VL) | 294 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVL |
| DNA scFv | 567 | GAAGTGCAGCTTGTGGAGTCCGGGGGAGGATT GGTCCAACCCGGTGGCTCGCTGAGGCTGAGTT GCGCCGCTTCGGGGTTTACCTTCAGCACCTAC GCTATGAACTGGGTCAGACAGGCGCCTGGAAA GGGTTTGGAGTGGGTCGGACGCATCCGGTCCA AGGCCAACAACTACGCGACTTACTATGCCGACT CCGTCAAGGGACGGTTCACCATCTCCCGGGAC |

TABLE 21C-continued

Bivalent BCMA-CD3 AB2
(BCMA Fab/hCD3 scFv 1x1 format)

| | SEQ ID NO | Sequence |
|---|---|---|
| | | GACAGCAAGAACACCCTGTACCTCCAAATGAAC<br>TCCCTTCGGGCCGAAGATACCGCCGTGTACTAC<br>TGCGTGAGACACGGCAACTTCGGCGACTCCTA<br>CGTGTCCTGGTTTGCCTACTGGGGCCAGGGTA<br>CTCTCGTGACCGTGTCATCAGGAAAGCCAGGCT<br>CGGGGAAGCCTGGCTCCGGAAAGCCTGGGAG<br>CGGAAAGCCGGGATCGCAGGCTGTGGTCACCC<br>AGGAACCCTCCCTGACTGTGTCCCCGGGAGGA<br>ACCGTGACACTGACTTGTGGCAGCTCCACCGG<br>AGCCGTGACCACCTCCAACTACGCCAACTGGG<br>TGCAGCAAAAGCCAGGAAAGTCCCCTAGGGGG<br>CTGATCGGTGGCACGAACAAGCGGGCACCTGG<br>AGTGCCTGCCCGATTCTCGGGTAGCCTGCTGG<br>GGGGAAAAGCCGCCCTGACCATTTCGGGCGCT<br>CAGCCAGAGGACGAAGCCGACTATTACTGCGC<br>ACTCTGGTACTCCAACCACTGGGTGTTCGGTGG<br>AGGCACCAAGCTGACCGTGCTG |

Full Ab region

| HC BCMA arm | 506 | EVQLLESGGGLVQPGGSLRLSCAASGFTFSSYAM<br>SWVRQAPGKGLEWVSAISESGGRAAYADSVKGR<br>FTISRDNSKNTLYLQMNSLRAEDTAVYYCARREW<br>WYDDWYLDYWGQGTLVTVSSASTKGPSVFPLAP<br>SSKSTSGGTAALGCLVKDYFPEPVTVSWNSGALT<br>SGVHTFPAVLQSSGLYSLSSVVTVPSSSLGTQTYI<br>CNVNHKPSDTKVDKKVEPKSCDKTHTCPPCPAPP<br>VAGPSVFLFPPKPKDTLMISRTPEVTCVVVDVKHE<br>DPEVKFNWYVDGVEVHNAKTKPREEEYNSTYRV<br>VSVLTVLHQDWLNGKEYKCKVSNKALPAPIEKTIS<br>KAKGQPREPQVYTLPPSREEMTKNQVSLTCDVS<br>GFYPSDIAVEWESDGQPENNYKTTPPVLDSDGSF<br>FLYSKLTVDKSRWEQGDVFSCSVMHEALHNHYT<br>QKSLSLSPGK |
|---|---|---|
| DNA HC | 584 | GAAGTGCAGCTGCTGGAGAGCGGCGGAGGTCT<br>GGTGCAGCCAGGCGGATCCTTGCGCCTCAGTT<br>GTGCCGCGTCCGGATTCACTTTCTCGTCTTACG<br>CCATGTCCTGGGTCAGACAGGCCCCTGGGAAG<br>GGTCTGGAGTGGGTGTCCGCGATCAGCGAGTC<br>AGGAGGGAGAGCCGCCTACGCCGACTCCGTGA<br>AGGGCCGCTTTACCATTTCGCGGGACAACTCCA<br>AGAACACCCTGTACCTTCAAATGAACAGCCTGC<br>GGGCAGAGGACACCGCCGTCTACTACTGCGCC<br>CGGAGGGAATGGTGGTACGATGATTGGTATCT<br>GGACTACTGGGGCCAGGGAACTCTCGTGACCG<br>TGTCCTCGGCTAGCACCAAGGGCCCGTCAGTG<br>TTTCCTCTGGCCCCAAGCTCCAAGTCCACCTCC<br>GGTGGTACAGCCGCGTTGGGATGCTTGGTCAA<br>GGACTACTTTCCGGAACCCGTGACCGTGTCCTG<br>GAACTCCGGCGCCCTGACTAGCGGAGTGCACA<br>CCTTCCCCGCTGTGCTGCAGTCTAGCGGGCTG<br>TATTCCCTCTCGTCCGTGGTCACCGTGCCGTCC<br>TCATCCCTGGGAACCCAGACCTACATTTGCAAC<br>GTGAACCACAAGCCGTCAGACACCAAGGTGGA<br>CAAGAAGGTGGAGCCGAAGTCCTGCGACAAGA<br>CCCATACTTGTCCTCCTTGCCCCGCTCCACCTG<br>TGGCGGGACCTTCCGTGTTCCTTTTCCCGCCGA<br>AGCCGAAGGACACTCTGATGATCTCGCGGACT<br>CCCGAAGTCACTTGCGTGGTGGTGGACGTCAA<br>ACACGAAGATCCCGAGGTCAAGTTCAATTGGTA<br>CGTGGACGGGGTGGAAGTCCACAACGCCAAGA<br>CTAAGCCGCGCGAGGAAGAGTACAATTCCACTT<br>ACCGGGTCGTGTCGGTGCTGACTGTGCTGCAT<br>CAGGACTGGCTGAACGGAAAGGAGTACAAGTG<br>CAAAGTGTCGAACAAGGCCCTGCCTGCACCAAT<br>CGAAAAGACCATTAGCAAAGCCAAGGGCCAGC<br>CGAGAGAACCCCAAGTCTACACTCTGCCACCAT<br>CCCGCGAAGAAATGACCAAGAACCAAGTGTCG<br>CTGACGTGCGACGTGTCGGGATTCTACCCGTC<br>CGATATTGCCGTGGAATGGGAGAGCGACGGCC<br>AACCCGAGAACAACTACAAGACTACCCCCCCCG<br>TCTTGGATTCCGATGGTTCCTTCTTCCTGTACTC<br>CAAGCTGACCGTGGATAAGTCCCGATGGGAGC<br>AGGGCGATGTGTTCTCGTGCTCCGTGATGCATG |

TABLE 21C-continued

Bivalent BCMA-CD3 AB2
(BCMA Fab/hCD3 scFv 1x1 format)

| | SEQ ID NO | Sequence |
|---|---|---|
| | | AAGCCCTGCACAACCACTATACCCAGAAGTCAC<br>TGTCGCTGAGCCCTGGGAAG |
| LC BCMA arm | 507 | DIQMTQSPSSLSASVGDRVTITCRASQSISSYLNW<br>YQQKPGKAPKLLIYAASSLQSGVPSRFSGSGSGT<br>DFTLTISSLQPEDFATYYCQQSYSTPLTFGQGTKV<br>EIKRTVAAPSVFIFPPSDEQLKSGTASVVCLLNNFY<br>PREAKVQWKVDNALQSGNSQESVTEQDSKDSTY<br>SLSSTLTLSKADYEKHKVYACEVTHQGLSSPVTKS<br>FNRGEC |
| DNA LC | 583 | GACATTCAGATGACCCAGTCCCCGTCCTCGCTG<br>AGCGCATCAGTCGGCGATCGCGTGACTATTACT<br>TGTCGGGCGTCCCAGTCGATCTCCTCGTACTTG<br>AACTGGTATCAGCAGAAGCCCGGAAAAGCCCC<br>GAAGTTACTGATCTACGCTGCCTCATCCCTCCA<br>ATCGGGGTGCCTTCGCGGTTCTCCGGTTCCG<br>GAAGCGGAACCGACTTCACCCTGACCATCAGC<br>AGCCTGCAGCCAGAGGACTTTGCCACCTACTAC<br>TGCCAGCAGTCCTACTCCACACCCCTCACTTTC<br>GGACAAGGCACCAAGGTCGAAATCAAGCGTAC<br>GGTGGCCGCTCCCAGCGTGTTCATCTTCCCCC<br>CCAGCGACGAGCAGCTGAAGAGCGGCACCGCC<br>AGCGTGGTGTGCCTGCTGAACAACTTCTACCCC<br>CGGGAGGCCAAGGTGCAGTGGAAGGTGGACAA<br>CGCCCTGCAGAGCGGCAACAGCCAGGAGAGC<br>GTCACCGAGCAGGACAGCAAGGACTCCACCTA<br>CAGCCTGAGCAGCACCCTGACCCTGAGCAAGG<br>CCGACTACGAGAAGCATAAGGTGTACGCCTGC<br>GAGGTGACCCACCAGGGCCTGTCCAGCCCCGT<br>GACCAAGAGCTTCAACAGGGGCGAGTGC |
| CD3 arm | 504 | EVQLVESGGGLVQPGGSLRLSCAASGFTFSTYA<br>MNWVRQAPGKGLEWVGRIRSKANNYATYYADSV<br>KGRFTISRDDSKNTLYLQMNSLRAEDTAVYYCVR<br>HGNFGDSYVSWFAYWGQGTLVTVSSGKPGSGK<br>PGSGKPGSGKPGSQAVVTQEPSLTVSPGGTVTL<br>TCGSSTGAVTTSNYANWVQQKPGKSPRGLIGGT<br>NKRAPGVPARFSGSLLGGKAALTISGAQPEDEAD<br>YYCALWYSNHWVFGGGTKLTVLEPKSSDKTHTC<br>PPCPAPPVAGPSVFLFPPKPKDTLMISRTPEVTCV<br>VVDVKHEDPEVKFNWYVDGVEVHNAKTKPREEQ<br>YNSTYRVVSVLTVLHQDWLNGKEYKCKVSNKALP<br>APIEKTISKAKGQPREPQVYTLPPSREQMTKNQV<br>KLTCLVKGFYPSDIAVEWESNGQPENNYKTTPPV<br>LDSDGSFFLYSKLTVDKSRWQQGNVFSCSVMHE<br>ALHNHYTQKSLSLSPGK |
| DNA CD3 | 569 | GAAGTGCAGCTTGTGGAGTCCGGGGGAGGATT<br>GGTCCAACCCGGTGGCTCGCTGAGGCTGAGTT<br>GCGCCGCTTCGGGGTTTACCTTCAGCACCTAC<br>GCTATGAACTGGGTCAGACAGGCGCCTGGAAA<br>GGGGTTTGGAGTGGGTCGGACGCATCCGGTCCA<br>AGGCCAACAACTACGCGACTTACTATGCCGACT<br>CCGTCAAGGGACGGTTCACCATCTCCCGGGAC<br>GACAGCAAGAACACCCTGTACCTCCAAATGAAC<br>TCCCTTCGGGCCGAAGATACCGCCGTGTACTAC<br>TGCGTGAGACACGGCAACTTCGGCGACTCCTA<br>CGTGTCCTGGTTTGCCTACTGGGGCCAGGGTA<br>CTCTCGTGACCGTGTCATCAGGAAAGCCAGGCT<br>CGGGGAAGCCTGGCTCCGGAAAGCCTGGGAG<br>CGGAAAGCCGGGATCGCAGGCTGTGGTCACCC<br>AGGAACCCTCCCTGACTGTGTCCCCGGGAGGA<br>ACCGTGACACTGACTTGTGGCAGCTCCACCGG<br>AGCCGTGACCACCTCCAACTACGCCAACTGGG<br>TGCAGCAAAAGCCAGGAAAGTCCCCTAGGGGG<br>CTGATCGGTGGCACGAACAAGCGGGCACCTGG<br>AGTGCCTGCCCGATTCTCGGGTAGCCTGCTGG<br>GGGGAAAAGCCGCCCTGACCATTTCGGGCGCT<br>CAGCCAGAGGACGAAGCCGACTATTACTGCGC<br>ACTCTGGTACTCCAACCACTGGGTGTTCGGTGG<br>AGGCACCAAGCTGACCGTGCTGGAGCCAAAGT<br>CAAGCGACAAAACTCACACTTGCCCTCCTTGTC<br>CGGCTCCTCCTGTGGCTGGTCCCTCCGTGTTC<br>CTCTTCCCGCCGAAGCCGAAGGACACCCTCAT |

TABLE 21C-continued

Bivalent BCMA-CD3 AB2
(BCMA Fab/hCD3 scFv 1x1 format)

| SEQ ID NO | Sequence |
|---|---|
| | GATTTCCCGGACGCCCGAAGTCACTTGTGTGGT
GGTCGATGTGAAGCATGAGGACCCCGAAGTGA
AGTTCAATTGGTACGTGGATGGCGTGGAGGTC
CACAACGCCAAGACCAAGCCGCGCGAAGAACA
GTACAACAGCACCTACCGCGTCGTGAGCGTGC
TCACCGTGCTCCACCAAGATTGGCTGAACGGAA
AGGAGTACAAGTGCAAAGTGTCCAACAAGGCC
CTTCCTGCACCTATTGAAAAGACTATTAGCAAG
GCCAAGGGACAGCCCCGCGAACCTCAAGTGTA
CACTCTGCCGCCGTCCAGAGAGCAGATGACCA
AAAACCAGGTCAAGCTCACTTGTCTCGTGAAGG
GCTTCTACCCGTCCGATATCGCGGTCGAATGG
GAGTCAAACGGCCAGCCCGAGAACAACTACAA
GACTACCCCACCGGTGCTTGACTCCGACGGTT
CGTTCTTTCTGTACTCCAAGCTGACCGTGGACA
AGTCCCGGTGGCAGCAAGGGAATGTGTTCAGC
TGCTCCGTGATGCACGAAGCCCTGCATAACCAC
TACACCCAGAAGTCGCTCAGCCTGTCCCCTGGA
AAA |

TABLE 21D

Trivalent BCMA-CD3 AB2
(BCMA Fab/hCD3 scFv 2x1 format)

| | SEQ ID NO | Sequence |
|---|---|---|
| Anti-BCMA Fab (PALF11) | | |
| CDR-H1 (Kabat) | 11 | SYAMS |
| CDR-H2 (Kabat) | 63 | AISESGGRAAYADSVKG |
| CDR-H3 (Kabat) | 24 | REWWYDDWYLDY |
| CDR-H1 (Chothia) | 12 | GFTFSSY |
| CDR-H2 (Chothia) | 83 | SESGGR |
| CDR-H3 (Chothia) | 24 | REWWYDDWYLDY |
| CDR-H1 (IMGT) | 13 | GFTFSSYA |
| CDR-H2 (IMGT) | 93 | ISESGGRA |
| CDR-H3 (IMGT) | 25 | ARREWWYDDWYLDY |
| VH | 214 | EVQLLESGGGLVQPGGSLRLSCAASGFTFSSYAM
SWVRQAPGKGLEWVSAISESGGRAAYADSVKGR
FTISRDNSKNTLYLQMNSLRAEDTAVYYCARREW
WYDDWYLDYWGQGTLVTVSS |
| DNA VH | 579 | GAAGTGCAGCTGCTGGAGAGCGGCGGAGGTCT
GGTGCAGCCAGGCGGATCCTTGCGCCTCAGTT
GTGCCGCGTCCGGATTCACTTTCTCGTCTTACG
CCATGTCCTGGGTCAGACAGGCCCCTGGGAAG
GGTCTGGAGTGGGTGTCCGCGATCAGCGAGTC
AGGAGGGAGAGCCGCCTACGCCGACTCCGTGA
AGGGCCGCTTTACCATTTCGCGGGACAACTCCA
AGAACACCCTGTACCTTCAAATGAACAGCCTGC
GGGCAGAGGACACCGCCGTCTACTACTGCGCC
CGGAGGGAATGGTGGTACGATGATTGGTATCT
GGACTACTGGGGCCAGGGAACTCTCGTGACCG
TGTCCTCG |
| Fab Heavy Chain | 580 | EVQLLESGGGLVQPGGSLRLSCAASGFTFSSYAM
SWVRQAPGKGLEWVSAISESGGRAAYADSVKGR
FTISRDNSKNTLYLQMNSLRAEDTAVYYCARREW
WYDDWYLDYWGQGTLVTVSSASTKGPSVFPLAP |

TABLE 21D-continued

Trivalent BCMA-CD3 AB2
(BCMA Fab/hCD3 scFv 2x1 format)

| | SEQ ID NO | Sequence |
|---|---|---|
| | | SSKSTSGGTAALGCLVKDYFPEPVTVSWNSGALT SGVHTFPAVLQSSGLYSLSSVVTVPSSSLGTQTYI CNVNHKPSDTKVDKKVEPKSC |
| DNA Heavy Chain | 585 | GAAGTGCAGCTGCTGGAGAGCGGCGGAGGTCT GGTGCAGCCAGGCGGATCCTTGCGCCTCAGTT GTGCCGCGTCCGGATTCACTTTCTCGTCTTACG CCATGTCCTGGGTCAGACAGGCCCCTGGGAAG GGTCTGGAGTGGGTGTCCGCGATCAGCGAGTC AGGAGGGAGAGCCGCCTACGCCGACTCCGTGA AGGGCCGCTTTACCATTTCGCGGGACAACTCCA AGAACACCCTGTACCTTCAAATGAACAGCCTGC GGGCAGAGGACACCGCCGTCTACTACTGCGCC CGGAGGGAATGGTGGTACGATGATTGGTATCT GGACTACTGGGGCCAGGGAACTCTCGTGACCG TGTCCTCGGCTAGCACCAAGGGTCCGTCAGTG TTTCCTCTGGCCCCAAGCTCCAAGTCCACCTCC GGTGGTACAGCCGCGTTGGGATGCTTGGTCAA GGACTACTTTCCGGAACCCGTGACCGTGTCCTG GAACTCCGGCGCCCTGACTAGCGGAGTGCACA CCTTCCCCGCTGTGCTGCAGTCTAGCGGGCTG TATTCCCTCTCGTCCGTGGTCACCGTGCCGTCC TCATCCCTGGGAACCCAGACCTACATTTGCAAC GTGAACCACAAGCCGTCAGACACCAAGGTGGA CAAGAAGGTGGAGCCGAAGTCCTGC |
| CDR-L1 (Kabat) | 2 | RASQSISSYLN |
| CDR-L2 (Kabat) | 5 | AASSLQS |
| CDR-L3 (Kabat) | 54 | QQSYSTPLT |
| CDR-L1 (Chothia) | 3 | SQSISSY |
| CDR-L2 (Chothia) | 6 | AAS |
| CDR-L3 (Chothia) | 74 | SYSTPL |
| CDR-L1 (IMGT) | 4 | QSISSY |
| CDR-L2 (IMGT) | 6 | AAS |
| CDR-L3 (IMGT) | 54 | QQSYSTPLT |
| VL | 192 | DIQMTQSPSSLSASVGDRVTITCRASQSISSYLNW YQQKPGKAPKLLIYAASSLQSGVPSRFSGSGSGT DFTLTISSLQPEDFATYYCQQSYSTPLTFGQGTKV EIK |
| DNA VL | 582 | GACATTCAGATGACCCAGTCCCCGTCCTCGCTG AGCGCATCAGTCGGCGATCGCGTGACTATTACT TGTCGGGCGTCCCAGTCGATCTCCTCGTACTTG AACTGGTATCAGCAGAAGCCCGGAAAAGCCCC GAAGTTACTGATCTACGCTGCCTCATCCCTCCA ATCTGGGGTGCCTTCGCGGTTCTCCGGTTCCG GAAGCGGAACCGACTTCACCCTGACCATCAGC AGCCTGCAGCCAGAGGACTTTGCCACCTACTAC TGCCAGCAGTCCTACTCCACACCCCTCACTTTC GGACAAGGCACCAAGGTCGAAATCAAG |
| Fab Light Chain | 507 | DIQMTQSPSSLSASVGDRVTITCRASQSISSYLNW YQQKPGKAPKLLIYAASSLQSGVPSRFSGSGSGT DFTLTISSLQPEDFATYYCQQSYSTPLTFGQGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTKS FNRGEC |
| DNA Light Chain | 583 | GACATTCAGATGACCCAGTCCCCGTCCTCGCTG AGCGCATCAGTCGGCGATCGCGTGACTATTACT TGTCGGGCGTCCCAGTCGATCTCCTCGTACTTG AACTGGTATCAGCAGAAGCCCGGAAAAGCCCC GAAGTTACTGATCTACGCTGCCTCATCCCTCCA ATCTGGGGTGCCTTCGCGGTTCTCCGGTTCCG GAAGCGGAACCGACTTCACCCTGACCATCAGC |

TABLE 21D-continued

Trivalent BCMA-CD3 AB2
(BCMA Fab/hCD3 scFv 2x1 format)

| SEQ ID NO | Sequence |
|---|---|

| | | AGCCTGCAGCCAGAGGACTTTGCCACCTACTAC<br>TGCCAGCAGTCCTACTCCACACCCCTCACTTTC<br>GGACAAGGCACCAAGGTCGAAATCAAGCGTAC<br>GGTGGCCGCTCCCAGCGTGTTCATCTTCCCCC<br>CCAGCGACGAGCAGCTGAAGAGCGGCACCGCC<br>AGCGTGGTGTGCCTGCTGAACAACTTCTACCCC<br>CGGGAGGCCAAGGTGCAGTGGAAGGTGGACAA<br>CGCCCTGCAGAGCGGCAACAGCCAGGAGAGC<br>GTCACCGAGCAGGACAGCAAGGACTCCACCTA<br>CAGCCTGAGCAGCACCCTGACCCTGAGCAAGG<br>CCGACTACGAGAAGCATAAGGTGTACGCCTGC<br>GAGGTGACCCACCAGGGCCTGTCCAGCCCCGT<br>GACCAAGAGCTTCAACAGGGGCGAGTGC |

Anti-CD3 scFv (~30 nM)
(CD3-23)

| | | |
|---|---|---|
| CDR-H1 (Kabat) | 305 | TYAMN |
| CDR-H2 (Kabat) | 338 | RIRSKANNYATYYADSVKG |
| CDR-H3 (Kabat) | 360 | HGNFGDSYVSWFAY |
| CDR-H1 (Chothia) | 378 | GFTFSTY |
| CDR-H2 (Chothia) | 559 | RSKANNYA |
| CDR-H3 (Chothia) | 360 | HGNFGDSYVSWFAY |
| CDR-H1 (IMGT) | 560 | GFTFSTYA |
| CDR-H2 (IMGT) | 561 | IRSKANNYAT |
| CDR-H3 (IMGT) | 562 | VRHGNFGDSYVSWFAY |
| VH | 293 | EVQLVESGGGLVQPGGSLRLSCAASGFTFSTYA<br>MNWVRQAPGKGLEWVGRIRSKANNYATYYADSV<br>KGRFTISRDDSKNTLYLQMNSLRAEDTAVYYCVR<br>HGNFGDSYVSWFAYWGQGTLVTVSS |
| DNA VH | 586 | GAAGTCCAACTGGTCGAGTCAGGCGGCGGACT<br>TGTCCAGCCCGGAGGTAGCCTGCGCCTCTCCT<br>GTGCTGCCTCCGGTTTTACCTTCTCGACCTATG<br>CCATGAACTGGGTGCGCCAAGCACCTGGGAAG<br>GGACTCGAATGGGTCGGCAGGATTCGGTCCAA<br>GGCCAACAACTACGCTACCTACTACGCCGACTC<br>GGTCAAGGGGCGGTTCACTATTTCCCGCGACG<br>ACTCCAAGAACACTCTGTATCTTCAGATGAATAG<br>CTTGAGAGCCGAGGATACCGCCGTGTACTATTG<br>CGTGCGCCACGGGAACTTCGGCGATTCCTACG<br>TGTCCTGGTTCGCTTACTGGGGACAGGGCACC<br>CTGGTCACCGTGTCAAGC |
| CDR-L1 (Kabat) | 315 | GSSTGAVTTSNYAN |
| CDR-L2 (Kabat) | 326 | GTNKRAP |
| CDR-L3 (Kabat) | 361 | ALWYSNHWV |
| CDR-L1 (Chothia) | 374 | STGAVTTSNY |
| CDR-L2 (Chothia) | 387 | GTN |
| CDR-L3 (Chothia) | 403 | WYSNHW |
| CDR-L1 (IMGT) | 564 | TGAVTTSNY |
| CDR-L2 (IMGT) | 565 | GTNKRAPGVP |
| CDR-L3 (IMGT) | 361 | ALWYSNHWV |
| VL | 286 | QAVVTQEPSLTVSPGGTVTLTCGSSTGAVTTSNY<br>ANWVQQKPGKSPRGLIGGTNKRAPGVPARFSGS<br>LLGGKAALTISGAQPEDEADYYCALWYSNHWVFG<br>GGTKLTVL |

TABLE 21D-continued

Trivalent BCMA-CD3 AB2
(BCMA Fab/hCD3 scFv 2x1 format)

| | SEQ ID NO | Sequence |
|---|---|---|
| DNA VL | 587 | AGGCGGTGGTGACCCAAGAACCCTCCCTGACC<br>GTGTCACCGGGAGGCACCGTGACCCTGACTTG<br>CGGGAGCTCCACTGGCGCAGTGACTACATCCA<br>ACTACGCCAACTGGGTGCAGCAGAAGCCTGGA<br>AAGTCCCCGAGAGGACTCATTGGAGGAACCAA<br>CAAGAGAGCCCCTGGTGTCCCTGCCCGCTTTA<br>GCGGTTCGCTGTTGGGAGGAAAGGCCGCTCTG<br>ACTATTTCCGGCGCTCAGCCAGAGGACGAGGC<br>TGACTACTACTGCGCATTGTGGTACTCCAATCA<br>CTGGGTGTTCGGAGGGGGCACTAAGCTGACCG<br>TGCTG |
| Linker | 479 | GKPGSGKPGSGKPGSGKPGS |
| scFv (VH-linker-VL) | 294 | EVQLVESGGGLVQPGGSLRLSCAASGFTFSTYA<br>MNWVRQAPGKGLEWVGRIRSKANNYATYYADSV<br>KGRFTISRDDSKNTLYLQMNSLRAEDTAVYYCVR<br>HGNFGDSYVSWFAYWGQGTLVTVSSGKPGSGK<br>PGSGKPGSGKPGSQAVVTQEPSLTVSPGGTVTL<br>TCGSSTGAVTTSNYANWVQQKPGKSPRGLIGGT<br>NKRAPGVPARFSGSLLGGKAALTISGAQPEDEAD<br>YYCALWYSNHWVFGGGTKLTVL |
| DNA scFv | 588 | GAAGTCCAACTGGTCGAGTCAGGCGGCGGACT<br>TGTCCAGCCCGGAGGTAGCCTGCGCCTCTCCT<br>GTGCTGCCTCCGGTTTTACCTTCTCGACCTATG<br>CCATGAACTGGGTGCGCCAAGCACCTGGGAAG<br>GGACTCGAATGGGTCGGCAGGATTCGGTCCAA<br>GGCCAACAACTACGCTACCTACTACGCCGACTC<br>GGTCAAGGGGCGGTTCACTATTTCCCGCGACG<br>ACTCCAAGAACACTCTGTATCTTCAGATGAATAG<br>CTTGAGAGCCGAGGATACCGCCGTGTACTATTG<br>CGTGCGCCACGGGAACTTCGGCGATTCCTACG<br>TGTCCTGGTTCGCTTACTGGGGACAGGGCACC<br>CTGGTCACCGTGTCAAGCGGAAAGCCCGGGTC<br>CGGAAAACCCGGGTCGGGAAAGCCGGGGAGC<br>GGAAAGCCCGGTTCACAGGCGGTGGTGACCCA<br>AGAACCCTCCCTGACCGTGTCACCGGGAGGCA<br>CCGTGACCCTGACTTGCGGGAGCTCCACTGGC<br>GCAGTGACTACATCCAACTACGCCAACTGGGTG<br>CAGCAGAAGCCTGGAAAGTCCCCGAGAGGACT<br>CATTGGAGGAACCAACAAGAGAGCCCCTGGTG<br>TCCCTGCCCGCTTTAGCGGTTCGCTGTTGGGA<br>GGAAAGGCCGCTCTGACTATTTCCGGCGCTCA<br>GCCAGAGGACGAGGCTGACTACTACTGCGCAT<br>TGTGGTACTCCAATCACTGGGTGTTCGGAGGG<br>GGCACTAAGCTGACCGTGCTG |

Fc region

| | | |
|---|---|---|
| HC BCMA arm | 506 | EVQLLESGGGLVQPGGSLRLSCAASGFTFSSYAM<br>SWVRQAPGKGLEWVSAISESGGRAAYADSVKGR<br>FTISRDNSKNTLYLQMNSLRAEDTAVYYCARREW<br>WYDDWYLDYWGQGTLVTVSSASTKGPSVFPLAP<br>SSKSTSGGTAALGCLVKDYFPEPVTVSWNSGALT<br>SGVHTFPAVLQSSGLYSLSSVVTVPSSSLGTQTYI<br>CNVNHKPSDTKVDKKVEPKSCDKTHTCPPCPAPP<br>VAGPSVFLFPPKPKDTLMISRTPEVTCVVVDVKHE<br>DPEVKFNWYVDGVEVHNAKTKPREEEYNSTYRV<br>VSVLTVLHQDWLNGKEYKCKVSNKALPAPIEKTIS<br>KAKGQPREPQVYTLPPSREEMTKNQVSLTCDVS<br>GFYPSDIAVEWESDGQPENNYKTTPPVLDSDGSF<br>FLYSKLTVDKSRWEQGDVFSCSVMHEALHNHYT<br>QKSLSLSPGK |
| DNA HC | 589 | GAAGTGCAGCTGCTGGAGAGCGGCGGAGGTCT<br>GGTGCAGCCAGGCGGATCCTTGCGCCTCAGTT<br>GTGCCGCGTCCGGATTCACTTTCTCGTCTTACG<br>CCATGTCCTGGGTCAGACAGGCCCCTGGGAAG<br>GGTCTGGAGTGGGTGTCCGCGATCAGCGAGTC<br>AGGAGGGAGAGCCGCCTACGCCGACTCCGTGA<br>AGGGCCGCTTTACCATTTCGCGGGACAACTCCA<br>AGAACACCCTGTACCTTCAAATGAACAGCCTGC<br>GGGCAGAGGACACCGCCGTCTACTACTGCGCC |

TABLE 21D-continued

Trivalent BCMA-CD3 AB2
(BCMA Fab/hCD3 scFv 2x1 format)

| | SEQ ID NO | Sequence |
|---|---|---|
| | | CGGAGGGAATGGTGGTACGATGATTGGTATCT<br>GGACTACTGGGGCCAGGGAACTCTCGTGACCG<br>TGTCCTCGGCTAGCACCAAGGGTCCGTCAGTG<br>TTTCCTCTGGCCCCAAGCTCCAAGTCCACCTCC<br>GGTGGTACAGCCGCGTTGGGATGCTTGGTCAA<br>GGACTACTTTCCGGAACCCGTGACCGTGTCCTG<br>GAACTCCGGCGCCCTGACTAGCGGAGTGCACA<br>CCTTCCCCGCTGTGCTGCAGTCTAGCGGGCTG<br>TATTCCCTCTCGTCCGTGGTCACCGTGCCGTCC<br>TCATCCCTGGGAACCCAGACCTACATTTGCAAC<br>GTGAACCACAAGCCGTCAGACACCAAGGTGGA<br>CAAGAAGGTGGAGCCGAAGTCCTGCGACAAGA<br>CCCATACTTGTCCTCCTTGCCCCGCTCCACCTG<br>TGGCGGGACCTTCCGTGTTCCTTTTCCCGCCGA<br>AGCCGAAGGACACTCTGATGATCTCGCGGACT<br>CCCGAAGTCACTTGCGTGGTGGTGGACGTCAA<br>ACACGAAGATCCCGAGGTCAAGTTCAATTGGTA<br>CGTGGACGGGGTGGAAGTCCACAACGCCAAGA<br>CTAAGCCGCGCGAGGAAGAGTACAATTCCACTT<br>ACCGGGTCGTGTCGGTGCTGACTGTGCTGCAT<br>CAGGACTGGCTGAACGGAAAGGAGTACAAGTG<br>CAAAGTGTCGAACAAGGCCCTGCCTGCACCAAT<br>CGAAAAGACCATTAGCAAAGCCAAGGGCCAGC<br>CGAGAGAACCCCAAGTCTACACTCTGCCACCAT<br>CCCGCGAAGAAATGACCAAGAACCAAGTGTCG<br>CTGACGTGCGACGTGTCGGGATTCTACCCGTC<br>CGATATTGCCGTGGAATGGGAGAGCGACGGCC<br>AACCCGAGAACAACTACAAGACTACCCCCCCG<br>TCTTGGATTCCGATGGTTCCTTCTTCCTGTACTC<br>CAAGCTGACCGTGGATAAGTCCCGATGGGAGC<br>AGGGCGATGTGTTCTCGTGCTCCGTGATGCATG<br>AAGCCCTGCACAACCACTATACCCAGAAGTCAC<br>TGTCGCTGAGCCCTGGGAAG |
| LC BCMA arm | 507 | DIQMTQSPSSLSASVGDRVTITCRASQSISSYLNW<br>YQQKPGKAPKLLIYAASSLQSGVPSRFSGSGSGT<br>DFTLTISSLQPEDFATYYCQQSYSTPLTFGQGTKV<br>EIKRTVAAPSVFIFPPSDEQLKSGTASVVCLLNNFY<br>PREAKVQWKVDNALQSGNSQESVTEQDSKDSTY<br>SLSSTLTLSKADYEKHKVYACEVTHQGLSSPVTKS<br>FNRGEC |
| DNA LC | 583 | GACATTCAGATGACCCAGTCCCCGTCCTCGCTG<br>AGCGCATCAGTCGGCGATCGCGTGACTATTACT<br>TGTCGGGCGTCCCAGTCGATCTCCTCGTACTTG<br>AACTGGTATCAGCAGAAGCCCGGAAAAGCCCC<br>GAAGTTACTGATCTACGCTGCCTCATCCCTCCA<br>ATCTGGGGTGCCTTCGCGGTTCTCCGGTTCCG<br>GAAGCGGAACCGACTTCACCCTGACCATCAGC<br>AGCCTGCAGCCAGAGGACTTTGCCACCTACTAC<br>TGCCAGCAGTCCTACTCCACACCCCTCACTTTC<br>GGACAAGGCACCAAGGTCGAAATCAAGCGTAC<br>GGTGGCCGCTCCCAGCGTGTTCATCTTCCCCC<br>CCAGCGACGAGCAGCTGAAGAGCGGCACCGCC<br>AGCGTGGTGTGCCTGCTGAACAACTTCTACCCC<br>CGGGAGGCCAAGGTGCAGTGGAAGGTGGACAA<br>CGCCCTGCAGAGCGGCAACAGCCAGGAGAGC<br>GTCACCGAGCAGGACAGCAAGGACTCCACCTA<br>CAGCCTGAGCAGCACCCTGACCCTGAGCAAGG<br>CCGACTACGAGAAGCATAAGGTGTACGCCTGC<br>GAGGTGACCCACCAGGGCCTGTCCAGCCCCGT<br>GACCAAGAGCTTCAACAGGGGCGAGTGC |
| CD3 arm | 508 | EVQLLESGGGLVQPGGSLRLSCAASGFTFSSYAM<br>SWVRQAPGKGLEWVSAISESGGRAAYADSVKGR<br>FTISRDNSKNTLYLQMNSLRAEDTAVYYCARREW<br>WYDDWYLDYWGQGTLVTVSSASTKGPSVFPLAP<br>SSKSTSGGTAALGCLVKDYFPEPVTVSWNSGALT<br>SGVHTFPAVLQSSGLYSLSSVVTVPSSSLGTQTYI<br>CNVNHKPSNTKVDKKVEPKSCGGGGSGGGGSE<br>VQLVESGGGLVQPGGSLRLSCAASGFTFSTYAM<br>NWVRQAPGKGLEWVGRIRSKANNYATYYADSVK<br>GRFTISRDDSKNTLYLQMNSLRAEDTAVYYCVRH<br>GNFGDSYVSWFAYWGQGTLVTVSSGKPGSGKP<br>GSGKPGSGKPGSQAVVTQEPSLTVSPGGTVTLT |

TABLE 21D-continued

Trivalent BCMA-CD3 AB2
(BCMA Fab/hCD3 scFv 2x1 format)

| | SEQ ID NO | Sequence |
|---|---|---|
| | | CGSSTGAVTTSNYANWVQQKPGKSPRGLIGGTN
KRAPGVPARFSGSLLGGKAALTISGAQPEDEADY
YCALWYSNHWVFGGGTKLTVLGGGGSGGGGSK
THTCPPCPAPPVAGPSVFLFPPKPKDTLMISRTPE
VTCVVVDVKHEDPEVKFNWYVDGVEVHNAKTKP
REEQYNSTYRVVSVLTVLHQDWLNGKEYKCKVS
NKALPAPIEKTISKAKGQPREPQVYTLPPSREQMT
KNQVKLTCLVKGFYPSDIAVEWESNGQPENNYKT
TPPVLDSDGSFFLYSKLTVDKSRWQQGNVFSCSV
MHEALHNHYTQKSLSLSPGK |
| DNA CD3 | 590 | GAAGTGCAGCTGCTGGAGAGCGGCGGAGGTCT
GGTGCAGCCAGGCGGATCCTTGCGCCTCAGTT
GTGCCGCGTCCGGATTCACTTTCTCGTCTTACG
CCATGTCCTGGGTCAGACAGGCCCCTGGGAAG
GGTCTGGAGTGGGTGTCCGCGATCAGCGAGTC
AGGAGGGAGAGCCGCCTACGCCGACTCCGTGA
AGGGCCGCTTTACCATTTCGCGGGACAACTCCA
AGAACACCCTGTACCTTCAAATGAACAGCCTGC
GGGCAGAGGACACCGCCGTCTACTACTGCGCC
CGGAGGGAATGGTGGTACGATGATTGGTATCT
GGACTACTGGGGCCAGGGAACTCTCGTGACCG
TGTCCTCGGCTAGCACCAAGGGCCCTTCGGTG
TTCCCCCTCGCCCCTTCATCAAAGTCCACTTCA
GGAGGAACCGCCGCCTTGGGTTGCCTCGTGAA
GGATTACTTCCCCGAACCAGTGACCGTGTCCTG
GAACTCCGGAGCCCTGACCAGCGGAGTGCACA
CTTTCCCTGCGGTGTTGCAGAGCTCCGGCCTCT
ACAGCCTGAGCAGCGTGGTGACCGTGCCGAGC
TCCTCCCTGGGCACTCAGACCTACATCTGCAAC
GTCAACCACAAGCCCTCGAATACCAAGGTCGAC
AAGAAGGTGGAGCCGAAGTCCTGTGGCGGAGG
AGGATCGGGAGGGGGTGGATCGGAAGTCCAAC
TGGTCGAGTCAGGCGGCGGACTTGTCCAGCCC
GGAGGTAGCCTGCGCCTCTCCTGTGCTGCCTC
CGGTTTTACCTTCTCGACCTATGCCATGAACTG
GGTGCGCCAAGCACCTGGGAAGGGACTCGAAT
GGGTCGGCAGGATTCGGTCCAAGGCCAACAAC
TACGCTACCTACTACGCCGACTCGGTCAAGGG
GCGGTTCACTATTTCCCGCGACGACTCCAAGAA
CACTCTGTATCTTCAGATGAATAGCTTGAGAGC
CGAGGATACCGCCGTGTACTATTGCGTGCGCC
ACGGGAACTTCGGCGATTCCTACGTGTCCTGGT
TCGCTTACTGGGGACAGGGCACCCTGGTCACC
GTGTCAAGCGGAAAGCCCGGGTCGGAAAACC
CGGGTCGGAAAGCCGGGGAGCGGAAAGCCC
GGTTCACAGGCGGTGGTGACCCAAGAACCCTC
CCTGACCGTGTCACCGGGAGGCACCGTGACCC
TGACTTGCGGGAGCTCCACTGGCGCAGTGACT
ACATCCAACTACGCCAACTGGGTGCAGCAGAA
GCCTGGAAAGTCCCCGAGAGGACTCATTGGAG
GAACCAACAAGAGAGCCCCTGGTGTCCCTGCC
CGCTTTAGCGGTTCGCTGTTGGGAGGAAAGGC
CGCTCTGACTATTTCCGGCGCTCAGCCAGAGG
ACGAGGCTGACTACTACTGCGCATTGTGGTACT
CCAATCACTGGGTGTTCGGAGGGGGCACTAAG
CTGACCGTGCTGGGTGGTGGCGGATCTGGTGG
TGGCGGCTCGAAAACCCACACCTGTCCACCTTG
TCCGGCGCCTCCTGTCGCTGGACCCTCCGTGT
TCCTCTTCCCTCCCAAGCCGAAGGATACGCTGA
TGATCAGCCGGACCCCGAAGTGACTTGTGTG
GTGGTGGATGTGAAGCACGAAGATCCCGAAGT
CAAGTTCAACTGGTACGTGGACGGAGTGGAGG
TCCACAATGCCAAGACCAAGCCGCGGGAAGAA
CAGTACAACTCGACCTACCGGGTGGTCAGCGT
GCTGACTGTGCTCCACCAAGACTGGCTGAACG
GGAAGGAGTACAAGTGCAAAGTGTCGAACAAG
GCCCTTCCTGCACCTATCGAAAAGACCATCTCC
AAGGCGAAAGGACAGCCGAGAGAGCCCCAGGT
CTACACTCTGCCGCCATCCAGAGAGCAAATGAC
CAAGAACCAAGTCAAGCTGACCTGTCTTGTCAA
GGGTTTCTACCCGTCCGATATCGCGGTCGAATG
GGAGTCAAACGGCCAGCCCGAGAACAACTACA
AGACTACCCCACCGGTGCTTGACTCCGACGGTT
CGTTCTTTCTGTACTCCAAGCTGACCGTGGACA |

TABLE 21D-continued

Trivalent BCMA-CD3 AB2
(BCMA Fab/hCD3 scFv 2x1 format)

| SEQ ID NO | Sequence |
|---|---|
| | AGTCCCGGTGGCAGCAAGGGAATGTGTTCAGC |
| | TGCTCCGTGATGCACGAAGCCCTGCATAACCAC |
| | TACACCCAGAAGTCGCTCAGCCTGTCCCTGGA |
| | AAA |

TABLE 21E

Bivalent BCMA-CD3 AB3
(hBCMA Fab/hCD3 scFv 1x1 format)

| | SEQ ID NO | Sequence |
|---|---|---|
| Anti-BCMA Fab (B61-11) | | |
| CDR-H1 (Kabat) | 39 | SYGMH |
| CDR-H2 (Kabat) | 112 | VISYTGSNKYYADSVKG |
| CDR-H3 (Kabat) | 49 | SGYALHDDYYGLDV |
| CDR-H1 (Chothia) | 138 | GFTVSSY |
| CDR-H2 (Chothia) | 140 | SYTGSN |
| CDR-H3 (Chothia) | 49 | SGYALHDDYYGLDV |
| CDR-H1 (IMGT) | 162 | GFTVSSYG |
| CDR-H2 (IMGT) | 165 | ISYTGSNK |
| CDR-H3 (IMGT) | 51 | GGSGYALHDDYYGLDV |
| VH | 224 | QVQLVESGGGVVQPGRSLRLSCAASGFTVSSYG MHWVRQAPGKGLEWVAVISYTGSNKYYADSVKG RFTISRDNSKNTLYLQMNSLRAEDTAVYYCGGSG YALHDDYYGLDVWGQGTLVTVSS |
| DNA VH | 591 | CAAGTGCAGCTCGTGGAGTCTGGAGGGGGAGT CGTGCAGCCTGGACGCTCCCTGAGACTGTCCT GTGCGGCTTCGGGATTCACTGTGTCCAGCTAC GGCATGCATTGGGTCCGCCAAGCACCGGGAAA AGGCCTGGAGTGGGTGGCCGTGATCTCCTACA CCGGCTCAAACAAGTACTACGCCGACAGCGTG AAGGGCCGGTTCACCATTTCAAGGGACAACTCC AAGAATACCCTGTATCTGCAAATGAACTCGCTG CGGGCAGAGGACACCGCCGTGTACTACTGCGG TGGCTCCGGTTACGCCCTGCACGATGACTACTA CGGGCTCGATGTCTGGGGACAGGGGACGCTCG TGACTGTGTCCTCG |
| Fab Heavy Chain | 592 | QVQLVESGGGVVQPGRSLRLSCAASGFTVSSYG MHWVRQAPGKGLEWVAVISYTGSNKYYADSVKG RFTISRDNSKNTLYLQMNSLRAEDTAVYYCGGSG YALHDDYYGLDVWGQGTLVTVSSASTKGPSVFPL APSSKSTSGGTAALGCLVKDYFPEPVTVSWNSGA LTSGVHTFPAVLQSSGLYSLSSVVTVPSSSLGTQT YICNVNHKPSDTKVDKKVEPKSC |
| DNA Heavy Chain | 593 | CAAGTGCAGCTCGTGGAGTCTGGAGGGGGAGT CGTGCAGCCTGGACGCTCCCTGAGACTGTCCT GTGCGGCTTCGGGATTCACTGTGTCCAGCTAC GGCATGCATTGGGTCCGCCAAGCACCGGGAAA AGGCCTGGAGTGGGTGGCCGTGATCTCCTACA CCGGCTCAAACAAGTACTACGCCGACAGCGTG AAGGGCCGGTTCACCATTTCAAGGGACAACTCC AAGAATACCCTGTATCTGCAAATGAACTCGCTG CGGGCAGAGGACACCGCCGTGTACTACTGCGG TGGCTCCGGTTACGCCCTGCACGATGACTACTA CGGGCTCGATGTCTGGGGACAGGGGACGCTCG TGACTGTGTCCTCGGCTAGCACCAAGGGCCCG TCAGTGTTTCCTCTGGCCCCAAGCTCCAAGTCC ACCTCCGGTGGTACAGCCGCGTTGGGATGCTT |

TABLE 21E-continued

Bivalent BCMA-CD3 AB3
(hBCMA Fab/hCD3 scFv 1x1 format)

| | SEQ ID NO | Sequence |
|---|---|---|
| | | GGTCAAGGACTACTTTCCGGAACCCGTGACCGT<br>GTCCTGGAACTCCGGCGCCCTGACTAGCGGAG<br>TGCACACCTTCCCCGCTGTGCTGCAGTCTAGCG<br>GCTGTATTCCCTCTCGTCCGTGGTCACCGTGC<br>CGTCCTCATCCCTGGGAACCCAGACCTACATTT<br>GCAACGTGAACCACAAGCCGTCAGACACCAAG<br>GTGGACAAGAAGGTGGAGCCGAAGTCCTGC |
| CDR-L1 (Kabat) | 26 | TGTSSDVGGYNYVS |
| CDR-L2 (Kabat) | 102 | DVSNRLR |
| CDR-L3 (Kabat) | 110 | SSYTSSSALYV |
| CDR-L1 (Chothia) | 27 | TSSDVGGYNY |
| CDR-L2 (Chothia) | 31 | DVS |
| CDR-L3 (Chothia) | 136 | YTSSSALY |
| CDR-L1 (IMGT) | 28 | SSDVGGYNY |
| CDR-L2 (IMGT) | 31 | DVS |
| CDR-L3 (IMGT) | 110 | SSYTSSSALYV |
| VL | 200 | QSALTQPASVSGSPGQSITISCTGTSSDVGGYNY<br>VSWYQQHPGKAPKLMIYDVSNRLRGVSNRFSGS<br>KSGNTASLTISGLQAEDEADYYCSSYTSSSALYVF<br>GSGTKVTVL |
| DNA VL | 594 | CAGTCGGCGCTGACTCAGCCCGCATCCGTGAG<br>CGGTTCACCGGGACAGAGCATCACCATTTCCTG<br>CACCGGAACCTCAAGCGACGTGGGCGGCTACA<br>ACTACGTGTCCTGGTATCAGCAGCACCCGGGA<br>AAGGCCCCAAAGCTCATGATCTACGACGTGTCC<br>AATAGACTGCGGGGAGTGTCCAACCGGTTCTC<br>GGGAAGCAAATCCGGCAACACTGCTTCCCTGA<br>CCATCAGCGGACTCCAGGCCGAAGATGAGGCC<br>GACTACTACTGCTCATCCTACACGTCCTCTTCG<br>GCGCTTTACGTGTTCGGGTCGGGGACCAAGGT<br>CACCGTCCTG |
| Fab Light Chain | 510 | QSALTQPASVSGSPGQSITISCTGTSSDVGGYNY<br>VSWYQQHPGKAPKLMIYDVSNRLRGVSNRFSGS<br>KSGNTASLTISGLQAEDEADYYCSSYTSSSALYVF<br>GSGTKVTVLGQPKAAPSVTLFPPSSEELQANKAT<br>LVCLISDFYPGAVTVAWKADSSPVKAGVETTTPSK<br>QSNNKYAASSYLSLTPEQWKSHRSYSCQVTHEG<br>STVEKTVAPTECS |
| DNA Light Chain | 595 | CAGTCGGCGCTGACTCAGCCCGCATCCGTGAG<br>CGGTTCACCGGGACAGAGCATCACCATTTCCTG<br>CACCGGAACCTCAAGCGACGTGGGCGGCTACA<br>ACTACGTGTCCTGGTATCAGCAGCACCCGGGA<br>AAGGCCCCAAAGCTCATGATCTACGACGTGTCC<br>AATAGACTGCGGGGAGTGTCCAACCGGTTCTC<br>GGGAAGCAAATCCGGCAACACTGCTTCCCTGA<br>CCATCAGCGGACTCCAGGCCGAAGATGAGGCC<br>GACTACTACTGCTCATCCTACACGTCCTCTTCG<br>GCGCTTTACGTGTTCGGGTCGGGGACCAAGGT<br>CACCGTCCTGGGCCAACCTAAGGCGGCGCCCT<br>CAGTGACCCTGTTCCCTCCGTCGTCTGAAGAAC<br>TCCAGGCCAACAAGGCCACCCTCGTGTGCCTG<br>ATTTCGGACTTCTACCCGGGAGCCGTCACTGTG<br>GCCTGGAAGGCCGACAGCAGCCCAGTGAAGGC<br>CGGCGTGGAAACTACCACCCCGTCCAAGCAGT<br>CCAACAATAAGTACGCAGCCAGCTCCTACCTGT<br>CCCTGACCCCCGAACAATGGAAGTCACACAGAT<br>CCTACTCCTGTCAAGTCACCCACGAGGGCAGC<br>ACTGTCGAAAAGACCGTGGCACCGACTGAGTG<br>CTCG |

TABLE 21E-continued

Bivalent BCMA-CD3 AB3
(hBCMA Fab/hCD3 scFv 1x1 format)

| | SEQ ID NO | Sequence |
|---|---|---|
| Anti-CD3 scFv (~30 nM) (CD3-23) | | |
| CDR-H1 (Kabat) | 305 | TYAMN |
| CDR-H2 (Kabat) | 338 | RIRSKANNYATYYADSVKG |
| CDR-H3 (Kabat) | 360 | HGNFGDSYVSWFAY |
| CDR-H1 (Chothia) | 378 | GFTFSTY |
| CDR-H2 (Chothia) | 559 | RSKANNYA |
| CDR-H3 (Chothia) | 360 | HGNFGDSYVSWFAY |
| CDR-H1 (IMGT) | 560 | GFTFSTYA |
| CDR-H2 (IMGT) | 561 | IRSKANNYAT |
| CDR-H3 (IMGT) | 562 | VRHGNFGDSYVSWFAY |
| VH | 293 | EVQLVESGGGLVQPGGSLRLSCAASGFTFSTYAMNWVRQAPGKGLEWVGRIRSKANNYATYYADSVKGRFTISRDDSKNTLYLQMNSLRAEDTAVYYCVRHGNFGDSYVSWFAYWGQGTLVTVSS |
| DNA VH | 563 | GAAGTGCAGCTTGTGGAGTCCGGGGGAGGATTGGTCCAACCCGGTGGCTCGCTGAGGCTGAGTTGCGCCGCTTCGGGGTTTACCTTCAGCACCTACGCTATGAACTGGGTCAGACAGGCGCCTGGAAAGGGGTTTGGAGTGGGTCGGACGCATCCGGTCCAAGGCCAACAACTACGCGACTTACTATGCCGACTCCGTCAAGGGACGGTTCACCATCTCCCGGGACGACAGCAAGAACACCCTGTACCTCCAAATGAACTCCCTTCGGGCCGAAGATACCGCCGTGTACTACTGCGTGAGACACGGCAACTTCGGCGACTCCTACGTGTCCTGGTTTGCCTACTGGGGCCAGGGTACTCTCGTGACCGTGTCATCA |
| CDR-L1 (Kabat) | 315 | GSSTGAVTTSNYAN |
| CDR-L2 (Kabat) | 326 | GTNKRAP |
| CDR-L3 (Kabat) | 361 | ALWYSNHWV |
| CDR-L1 (Chothia) | 374 | STGAVTTSNY |
| CDR-L2 (Chothia) | 387 | GTN |
| CDR-L3 (Chothia) | 403 | WYSNHW |
| CDR-L1 (IMGT) | 564 | TGAVTTSNY |
| CDR-L2 (IMGT) | 565 | GTNKRAPGVP |
| CDR-L3 (IMGT) | 361 | ALWYSNHWV |
| VL | 286 | QAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLTVL |
| DNA VL | 566 | CAGGCTGTGGTCACCCAGGAACCCTCCCTGACTGTGTCCCGGGAGGAACCGTGACACTGACTTGTGGCAGCTCCACCGGAGCCGTGACCACCTCCAACTACGCCAACTGGGTGCAGCAAAAGCCAGGAAAGTCCCCTAGGGGGCTGATCGGTGGCACGAACAAGCGGGCACCTGGAGTGCCTGCCCGATTCTCGGGTAGCCTGCTGGGGGGAAAAGCCGCCCTGACCATTTCGGGCGCTCAGCCAGAGGACGAAGCCGACTATTACTGCGCACTCTGGTACTCCAACCACTGGGTGTTCGGTGGAGGCACCAAGCTGACCGTGCTG |

TABLE 21E-continued

Bivalent BCMA-CD3 AB3
(hBCMA Fab/hCD3 scFv 1x1 format)

| | SEQ ID NO | Sequence |
|---|---|---|
| Linker | 479 | GKPGSGKPGSGKPGSGKPGS |
| scFv (VH-linker-VL) | 294 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVL |
| DNA scFv | 567 | GAAGTGCAGCTTGTGGAGTCCGGGGGAGGATT GGTCCAACCCGGTGGCTCGCTGAGGCTGAGTT GCGCCGCTTCGGGGTTTACCTTCAGCACCTAC GCTATGAACTGGGTCAGACAGGCGCCTGGAAA GGGTTTGGAGTGGGTCGGACGCATCCGGTCCA AGGCCAACAACTACGCGACTTACTATGCCGACT CCGTCAAGGGACGGTTCACCATCTCCCGGGAC GACAGCAAGAACACCCTGTACCTCCAAATGAAC TCCCTTCGGGCCGAAGATACCGCCGTGTACTAC TGCGTGAGACACGGCAACTTCGGCGACTCCTA CGTGTCCTGGTTTGCCTACTGGGGCCAGGGTA CTCTCGTGACCGTGTCATCAGGAAAGCCAGGCT CGGGGAAGCCTGGCTCCGGAAAGCCTGGGAG CGGAAAGCCGGGATCGCAGGCTGTGGTCACCC AGGAACCCTCCCTGACTGTGTCCCCGGGAGGA ACCGTGACACTGACTTGTGGCAGCTCCACCGG AGCCGTGACCACCTCCAACTACGCCAACTGGG TGCAGCAAAAGCCAGGAAAGTCCCCTAGGGGG CTGATCGGTGGCACGAACAAGCGGGCACCTGG AGTGCCTGCCCGATTCTCGGGTAGCCTGCTGG GGGGAAAAGCCGCCCTGACCATTTCGGGCGCT CAGCCAGAGGACGAAGCCGACTATTACTGCGC ACTCTGGTACTCCAACCACTGGGTGTTCGGTGG AGGCACCAAGCTGACCGTGCTG |

Full Ab region

| | | |
|---|---|---|
| HC BCMA arm | 509 | QVQLVESGGGVVQPGRSLRLSCAASGFTVSSYG MHWVRQAPGKGLEWVAVISYTGSNKYYADSVKG RFTISRDNSKNTLYLQMNSLRAEDTAVYYCGGSG YALHDDYYGLDVWGQGTLVTVSSASTKGPSVFPL APSSKSTSGGTAALGCLVKDYFPEPVTVSWNSGA LTSGVHTFPAVLQSSGLYSLSSVVTVPSSSLGTQT YICNVNHKPSDTKVDKKVEPKSCDKTHTCPPCPA PPVAGPSVFLFPPKPKDTLMISRTPEVTCVVVDVK HEDPEVKFNWYVDGVEVHNAKTKPREEEYNSTY RVVSVLTVLHQDWLNGKEYKCKVSNKALPAPIEK TISKAKGQPREPQVYTLPPSREEMTKNQVSLTCD VSGFYPSDIAVEWESDGQPENNYKTTPPVLDSDG SFFLYSKLTVDKSRWEQGDVFSCSVMHEALHNH YTQKSLSLSPGK |
| DNA HC | 596 | CAAGTGCAGCTCGTGGAGTCTGGAGGGGGAGT CGTGCAGCCTGGACGCTCCCTGAGACTGTCCT GTGCGGCTTCGGGATTCACTGTGTCCAGCTAC GGCATGCATTGGGTCCGCCAAGCACCGGGAAA AGGCCTGGAGTGGGTGGCCGTGATCTCCTACA CCGGCTCAAACAAGTACTACGCCGACAGCGTG AAGGGCCGGTTCACCATTTCAAGGGACAACTCC AAGAATACCCTGTATCTGCAAATGAACTCGCTG CGGGCAGAGGACACCGCCGTGTACTACTGCGG TGGCTCCGGTTACGCCCTGCACGATGACTACTA CGGGCTCGATGTCTGGGGACAGGGGACGCTCG TGACTGTGTCCTCGGCTAGCACCAAGGGCCCG TCAGTGTTTCCTCTGGCCCCAAGCTCCAAGTCC ACCTCCGGTGGTACAGCCGCGTTGGGATGCTT GGTCAAGGACTACTTTCCGGAACCCGTGACCGT GTCCTGGAACTCCGGCGCCCTGACTAGCGGAG TGCACACCTTCCCCGCTGTGCTGCAGTCTAGCG GGCTGTATTCCCTCTCGTCCGTGGTCACCGTGC CGTCCTCATCCCTGGGAACCCAGACCTACATTT GCAACGTGAACCACAAGCCGTCAGACACCAAG GTGGACAAGAAGGTGGAGCCGAAGTCCTGCGA CAAGACCCATACTTGTCCTCCTTGCCCCGCTCC |

TABLE 21E-continued

Bivalent BCMA-CD3 AB3
(hBCMA Fab/hCD3 scFv 1x1 format)

| | SEQ ID NO | Sequence |
|---|---|---|
| | | ACCTGTGGCGGGACCTTCCGTGTTCCTTTTCCC GCCGAAGCCGAAGGACACTCTGATGATCTCGC GGACTCCCGAAGTCACTTGCGTGGTGGTGGAC GTCAAACACGAAGATCCCGAGGTCAAGTTCAAT TGGTACGTGGACGGGGTGGAAGTCCACAACGC CAAGACTAAGCCGCGCGAGGAAGAGTACAATT CCACTTACCGGGTCGTGTCGGTGCTGACTGTG CTGCATCAGGACTGGCTGAACGGAAAGGAGTA CAAGTGCAAAGTGTCGAACAAGGCCCTGCCTG CACCAATCGAAAAGACCATTAGCAAAGCCAAGG GCCAGCCGAGAGAACCCCAAGTCTACACTCTG CCACCATCCCGCGAAGAAATGACCAAGAACCAA GTGTCGCTGACGTGCGACGTGTCGGGATTCTA CCCGTCCGATATTGCCGTGGAATGGGAGAGCG ACGGCCAACCCGAGAACAACTACAAGACTACCC CCCCCGTCTTGGATTCCGATGGTTCCTTCTTCC TGTACTCCAAGCTGACCGTGGATAAGTCCCGAT GGGAGCAGGGCGATGTGTTCTCGTGCTCCGTG ATGCATGAAGCCCTGCACAACCACTATACCCAG AAGTCACTGTCGCTGAGCCCTGGGAAG |
| LC BCMA arm | 510 | QSALTQPASVSGSPGQSITISCTGTSSDVGGYNY VSWYQQHPGKAPKLMIYDVSNRLRGVSNRFSGS KSGNTASLTISGLQAEDEADYYCSSYTSSSALYVF GSGTKVTVLGQPKAAPSVTLFPPSSEELQANKAT LVCLISDFYPGAVTVAWKADSSPVKAGVETTTPSK QSNNKYAASSYLSLTPEQWKSHRSYSCQVTHEG STVEKTVAPTECS |
| DNA LC | 595 | CAGTCGGCGCTGACTCAGCCCGCATCCGTGAG CGGTTCACCGGGACAGAGCATCACCATTTCCTG CACCGGAACCTCAAGCGACGTGGGCGGCTACA ACTACGTGTCCTGGTATCAGCAGCACCCGGGA AAGGCCCCAAAGCTCATGATCTACGACGTGTCC AATAGACTGCGGGGAGTGTCCAACCGGTTCTC GGGAAGCAAATCCGGCAACACTGCTTCCCTGA CCATCAGCGGACTCCAGGCCGAAGATGAGGCC GACTACTACTGCTCATCCTACACGTCCTCTTCG GCGCTTTACGTGTTCGGGTCGGGGACCAAGGT CACCGTCCTGGGCCAACCTAAGGCGGCGCCCT CAGTGACCCTGTTCCCTCCGTCGTCTGAAGAAC TCCAGGCCAACAAGGCCACCCTCGTGTGCCTG ATTTCGGACTTCTACCCGGGAGCCGTCACTGTG GCCTGGAAGGCCGACAGCAGCCCAGTGAAGGC CGGCGTGGAAACTACCACCCCGTCCAAGCAGT CCAACAATAAGTACGCAGCCAGCTCCTACCTGT CCCTGACCCCCGAACAATGGAAGTCACACAGAT CCTACTCCTGTCAAGTCACCCACGAGGGCAGC ACTGTCGAAAAGACCGTGGCACCGACTGAGTG CTCG |
| CD3 arm | 504 | EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVLEPKSSDKTHTC PPCPAPPVAGPSVFLFPPKPKDTLMISRTPEVTCV VVDVKHEDPEVKFNWYVDGVEVHNAKTKPREEQ YNSTYRVVSVLTVLHQDWLNGKEYKCKVSNKALP APIEKTISKAKGQPREPQVYTLPPSREQMTKNQV KLTCLVKGFYPSDIAVEWESNGQPENNYKTTPPV LDSDGSFFLYSKLTVDKSRWQQGNVFSCSVMHE ALHNHYTQKSLSLSPGK |
| DNA CD3 | 569 | GAAGTGCAGCTTGTGGAGTCCGGGGGAGGATT GGTCCAACCCGGTGGCTCGCTGAGGCTGAGTT GCGCCGCTTCGGGGTTTACCTTCAGCACCTAC GCTATGAACTGGGTCAGACAGGCGCCTGGAAA GGGTTTGGAGTGGGTCGGACGCATCCGGTCCA AGGCCAACAACTACGCGACTTACTATGCCGACT CCGTCAAGGGACGGTTCACCATCTCCCGGGAC GACAGCAAGAACACCCTGTACCTCCAAATGAAC |

TABLE 21E-continued

Bivalent BCMA-CD3 AB3
(hBCMA Fab/hCD3 scFv 1x1 format)

| SEQ ID NO | Sequence |
|---|---|
| | TCCCTTCGGGCCGAAGATACCGCCGTGTACTAC
TGCGTGAGACACGGCAACTTCGGCGACTCCTA
CGTGTCCTGGTTTGCCTACTGGGGCCAGGGTA
CTCTCGTGACCGTGTCATCAGGAAAGCCAGGCT
CGGGGAAGCCTGGCTCCGGAAAGCCTGGGAG
CGGAAAGCCGGGATCGCAGGCTGTGGTCACCC
AGGAACCCTCCCTGACTGTGTCCCCGGGAGGA
ACCGTGACACTGACTTGTGGCAGCTCCACCGG
AGCCGTGACCACCTCCAACTACGCCAACTGGG
TGCAGCAAAAGCCAGGAAAGTCCCCTAGGGGG
CTGATCGGTGGCACGAACAAGCGGGCACCTGG
AGTGCCTGCCCGATTCTCGGGTAGCCTGCTGG
GGGGAAAAGCCGCCCTGACCATTTCGGGCGCT
CAGCCAGAGGACGAAGCCGACTATTACTGCGC
ACTCTGGTACTCCAACCACTGGGTGTTCGGTGG
AGGCACCAAGCTGACCGTGCTGGAGCCAAAGT
CAAGCGACAAAACTCACACTTGCCCTCCTTGTC
CGGCTCCTCCTGTGGCTGGTCCCTCCGTGTTC
CTCTTCCCGCCGAAGCCGAAGGACACCCTCAT
GATTTCCCGGACGCCCGAAGTCACTTGTGTGGT
GGTCGATGTGAAGCATGAGGACCCCGAAGTGA
AGTTCAATTGGTACGTGGATGGCGTGGAGGTC
CACAACGCCAAGACCAAGCCGCGCGAAGAACA
GTACAACAGCACCTACCGCGTCGTGAGCGTGC
TCACCGTGCTCCACCAAGATTGGCTGAACGGAA
AGGAGTACAAGTGCAAAGTGTCCAACAAGGCC
CTTCCTGCACCTATTGAAAAGACTATTAGCAAG
GCCAAGGGACAGCCCCGCGAACCTCAAGTGTA
CACTCTGCCGCCGTCCAGAGAGCAGATGACCA
AAAACCAGGTCAAGCTCACTTGTCTCGTGAAGG
GCTTCTACCCGTCCGATATCGCGGTCGAATGG
GAGTCAAACGGCCAGCCCGAGAACAACTACAA
GACTACCCCACCGGTGCTTGACTCCGACGGTT
CGTTCTTTCTGTACTCCAAGCTGACCGTGGACA
AGTCCCGGTGGCAGCAAGGGAATGTGTTCAGC
TGCTCCGTGATGCACGAAGCCCTGCATAACCAC
TACACCCAGAAGTCGCTCAGCCTGTCCCCTGGA
AAA |

TABLE 21F

Trivalent AB3
((hBCMA Fab/hCD3 scFv 2x1 format))

| SEQ ID NO | Sequence |
|---|---|

Anti-BCMA Fab
(B61-11)

| | | |
|---|---|---|
| CDR-H1 (Kabat) | 39 | SYGMH |
| CDR-H2 (Kabat) | 112 | VISYTGSNKYYADSVKG |
| CDR-H3 (Kabat) | 49 | SGYALHDDYYGLDV |
| CDR-H1 (Chothia) | 138 | GFTVSSY |
| CDR-H2 (Chothia) | 140 | SYTGSN |
| CDR-H3 (Chothia) | 49 | SGYALHDDYYGLDV |
| CDR-H1 (IMGT) | 162 | GFTVSSYG |
| CDR-H2 (IMGT) | 165 | ISYTGSNK |
| CDR-H3 (IMGT) | 51 | GGSGYALHDDYYGLDV |
| VH | 224 | QVQLVESGGGVVQPGRSLRLSCAASGFTVSSYG
MHWVRQAPGKGLEWVAVISYTGSNKYYADSVKG
RFTISRDNSKNTLYLQMNSLRAEDTAVYYCGGSG
YALHDDYYGLDVWGQGTLVTVSS |

TABLE 21F-continued

Trivalent AB3
((hBCMA Fab/hCD3 scFv 2x1 format))

| | SEQ ID NO | Sequence |
|---|---|---|
| DNA VH | 597 | CAAGTGCAGCTTGTGGAGTCGGGAGGGGAGT<br>GGTGCAGCCTGGTCGCTCACTGAGGCTGAGCT<br>GTGCTGCCTCCGGCTTTACCGTGTCCTCCTACG<br>GAATGCATTGGGTCAGACAGGCACCGGGAAAA<br>GGCCTGGAATGGGTGGCCGTCATCAGCTACAC<br>CGGCTCCAACAAGTACTACGCCGACTCAGTGAA<br>GGGGCGGTTCACTATTAGCCGCGATAACTCGAA<br>GAATACCCTGTATCTGCAAATGAACTCTTTGCG<br>GGCCGAAGATACCGCCGTGTACTACTGCGGAG<br>GCTCCGGTTACGCGCTCCACGACGACTACTAC<br>GGACTGGACGTGTGGGGACAGGGGACTCTCGT<br>GACCGTGTCGTCC |
| Fab Heavy Chain | 592 | QVQLVESGGGVVQPGRSLRLSCAASGFTVSSYG<br>MHWVRQAPGKGLEWVAVISYTGSNKYYADSVKG<br>RFTISRDNSKNTLYLQMNSLRAEDTAVYYCGGSG<br>YALHDDYYGLDVWGQGTLVTVSSASTKGPSVFPL<br>APSSKSTSGGTAALGCLVKDYFPEPVTVSWNSGA<br>LTSGVHTFPAVLQSSGLYSLSSVVTVPSSSLGTQT<br>YICNVNHKPSDTKVDKKVEPKSC |
| DNA Heavy Chain | 598 | CAAGTGCAGCTTGTGGAGTCGGGAGGGGAGT<br>GGTGCAGCCTGGTCGCTCACTGAGGCTGAGCT<br>GTGCTGCCTCCGGCTTTACCGTGTCCTCCTACG<br>GAATGCATTGGGTCAGACAGGCACCGGGAAAA<br>GGCCTGGAATGGGTGGCCGTCATCAGCTACAC<br>CGGCTCCAACAAGTACTACGCCGACTCAGTGAA<br>GGGGCGGTTCACTATTAGCCGCGATAACTCGAA<br>GAATACCCTGTATCTGCAAATGAACTCTTTGCG<br>GGCCGAAGATACCGCCGTGTACTACTGCGGAG<br>GCTCCGGTTACGCGCTCCACGACGACTACTAC<br>GGACTGGACGTGTGGGGACAGGGGACTCTCGT<br>GACCGTGTCGTCCGCTAGCACCAAGGGACCGA<br>GCGTGTTCCCGCTGGCGCCGAGCAGCAAATCG<br>ACTTCTGGGGGAACCGCAGCCCTGGGTTGCCT<br>GGTCAAGGACTACTTCCCGGAACCAGTCACTGT<br>GTCCTGGAACAGCGGTGCCCTCACCTCGGGCG<br>TGCACACCTTCCCGGCCGTGCTGCAGTCTAGC<br>GGACTCTACTCGCTCTCCTCCGTGGTCACCGTG<br>CCCTCCTCATCACTGGGAACCCAGACATACATT<br>TGCAACGTGAACCACAAGCCCTCGGACACTAAG<br>GTGGACAAAAAAGTGGAACCAAAGTCCTGC |
| CDR-L1 (Kabat) | 26 | TGTSSDVGGYNYVS |
| CDR-L2 (Kabat) | 102 | DVSNRLR |
| CDR-L3 (Kabat) | 110 | SSYTSSSALYV |
| CDR-L1 (Chothia) | 27 | TSSDVGGYNY |
| CDR-L2 (Chothia) | 31 | DVS |
| CDR-L3 (Chothia) | 136 | YTSSSALY |
| CDR-L1 (IMGT) | 28 | SSDVGGYNY |
| CDR-L2 (IMGT) | 31 | DVS |
| CDR-L3 (IMGT) | 110 | SSYTSSSALYV |
| VL | 200 | QSALTQPASVSGSPGQSITISCTGTSSDVGGYNY<br>VSWYQQHPGKAPKLMIYDVSNRLRGVSNRFSGS<br>KSGNTASLTISGLQAEDEADYYCSSYTSSSALYVF<br>GSGTKVTVL |
| DNA VL | 599 | CAATCCGCCCTGACTCAGCCGGCCAGCGTGTC<br>AGGTTCCCCGGGCCAAAGCATTACCATCTCCTG<br>CACTGGGACCTCCTCCGATGTCGGGGGCTACA<br>ACTACGTGTCGTGGTATCAGCAGCACCCTGGAA<br>AGGCGCCCAAGCTGATGATCTACGACGTGTCC<br>AACCGGCTGAGGGGAGTCAGCAACCGCTTCAG<br>CGGCTCCAAGTCCGGAAACACCGCATCACTCA<br>CAATCAGCGGTCTGCAGGCTGAGGATGAAGCG<br>GACTACTACTGTTCCTCCTACACCTCCTCCTCG |

TABLE 21F-continued

Trivalent AB3
((hBCMA Fab/hCD3 scFv 2x1 format))

| | SEQ ID NO | Sequence |
|---|---|---|
| | | GCGCTTTACGTCTTTGGGTCGGGAACCAAAGTCACTGTGCTG |
| Fab Light Chain | 510 | QSALTQPASVSGSPGQSITISCTGTSSDVGGYNYVSWYQQHPGKAPKLMIYDVSNRLRGVSNRFSGSKSGNTASLTISGLQAEDEADYYCSSYTSSSALYVFGSGTKVTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| DNA Light Chain | 600 | CAATCCGCCCTGACTCAGCCGGCCAGCGTGTCAGGTTCCCCGGGCCAAAGCATTACCATCTCCTGCACTGGGACCTCCTCCGATGTCGGGGGCTACAACTACGTGTCGTGGTATCAGCAGCACCCTGGAAAGGCGCCCAAGCTGATGATCTACGACGTGTCCAACCGGCTGAGGGGAGTCAGCAACCGCTTCAGCGGCTCCAAGTCCGGAAACACCGCATCACTCACAATCAGCGGTCTGCAGGCTGAGGATGAAGCGGACTACTACTGTTCCTCCTACACCTCCTCCTCGGCGCTTTACGTCTTTGGGTCGGGAACCAAAGTCACTGTGCTGGGACAGCCGAAGGCAGCCCCATCCGTGACCCTGTTCCCCCCGTCATCCGAGGAACTGCAGGCTAACAAGGCCACCCTCGTGTGCCTGATTAGCGACTTCTACCCTGGAGCCGTGACCGTGGCCTGGAAGGCCGACTCCAGCCCAGTGAAGGCCGGAGTGGAGACTACCACCCCGAGCAAACAGTCGAACAATAAGTACGCCGCGTCATCGTACCTGTCCCTCACGCCCGAACAGTGGAAGTCCCATAGATCGTACTCCTGCCAAGTGACCCACGAGGGCAGCACTGTGGAAAAGACTGTGGCCCCTACCGAGTGCTCT |

Anti-CD3 scFv (~30 nM) (CD3-23)

| | SEQ ID NO | Sequence |
|---|---|---|
| CDR-H1 (Kabat) | 305 | TYAMN |
| CDR-H2 (Kabat) | 338 | RIRSKANNYATYYADSVKG |
| CDR-H3 (Kabat) | 360 | HGNFGDSYVSWFAY |
| CDR-H1 (Chothia) | 378 | GFTFSTY |
| CDR-H2 (Chothia) | 559 | RSKANNYA |
| CDR-H3 (Chothia) | 360 | HGNFGDSYVSWFAY |
| CDR-H1 (IMGT) | 560 | GFTFSTYA |
| CDR-H2 (IMGT) | 561 | IRSKANNYAT |
| CDR-H3 (IMGT) | 562 | VRHGNFGDSYVSWFAY |
| VH | 293 | EVQLVESGGGLVQPGGSLRLSCAASGFTFSTYAMNWVRQAPGKGLEWVGRIRSKANNYATYYADSVKGRFTISRDDSKNTLYLQMNSLRAEDTAVYYCVRHGNFGDSYVSWFAYWGQGTLVTVSS |
| DNA VH | 574 | GAGGTGCAGCTCGTCGAATCCGGTGGAGGGCTGGTGCAACCGGGGGGCTCGCTTAGGCTTAGCTGCGCTGCGTCAGGGTTCACCTTCTCAACTTACGCGATGAATTGGGTCAGACAGGCACCCGGAAAGGGACTGGAATGGGTCGGAAGAATCAGATCGAAGGCCAACAACTACGCCACTTACTACGCCGACTCCGTGAAGGGAAGGTTCACTATCTCGCGGGACGACTCCAAGAACACTCTGTATCTCCAAATGAACTCACTCCGGGCCGAGGATACTGCGGTGTACTATTGCGTGCGGCATGGAAACTTCGGGGACAGCTACGTCAGCTGGTTCGCCTACTGGGGCCAAGGCACTCTCGTCACCGTGTCATCC |
| CDR-L1 (Kabat) | 315 | GSSTGAVTTSNYAN |
| CDR-L2 (Kabat) | 326 | GTNKRAP |

TABLE 21F-continued

Trivalent AB3
((hBCMA Fab/hCD3 scFv 2x1 format))

| | SEQ ID NO | Sequence |
|---|---|---|
| CDR-L3 (Kabat) | 361 | ALWYSNHWV |
| CDR-L1 (Chothia) | 374 | STGAVTTSNY |
| CDR-L2 (Chothia) | 387 | GTN |
| CDR-L3 (Chothia) | 403 | WYSNHW |
| CDR-L1 (IMGT) | 564 | TGAVTTSNY |
| CDR-L2 (IMGT) | 565 | GTNKRAPGVP |
| CDR-L3 (IMGT) | 361 | ALWYSNHWV |
| VL | 286 | QAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLTVL |
| DNA VL | 575 | CAGGCCGTCGTGACCCAGGAACCGAGCCTGACCGTGTCCCCCGGCGGTACCGTGACCTTGACTTGCGGTTCCTCCACTGGAGCCGTGACTACCTCGAACTACGCCAACTGGGTGCAGCAGAAGCCGGGAAAGTCGCCTCGCGGACTGATCGGTGGAACTAACAAACGCGCCCCGGGCGTGCCAGCCAGATTCAGCGGTAGCCTGCTCGGCGGAAAGGCCGCGCTGACCATCTCCGGGGCCCAGCCCGAGGATGAGGCCGACTATTACTGCGCTCTGTGGTACTCCAACCACTGGGTGTTTGGCGGGGGCACTAAGCTGACTGTGCTG |
| Linker | 479 | GKPGSGKPGSGKPGSGKPGS |
| scFv (VH-linker-VL) | 294 | EVQLVESGGGLVQPGGSLRLSCAASGFTFSTYAMNWVRQAPGKGLEWVGRIRSKANNYATYYADSVKGRFTISRDDSKNTLYLQMNSLRAEDTAVYYCVRHGNFGDSYVSWFAYWGQGTLVTVSSGKPGSGKPGSGKPGSGKPGSQAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLTVL |
| DNA scFv | 576 | GAGGTGCAGCTCGTCGAATCCGGTGGAGGGCTGGTGCAACCGGGGGGCTCGCTTAGGCTTAGCTGCGCTGCGTCAGGGTTCACCTTCTCAACTTACGCGATGAATTGGGTCAGACAGGCACCCGGAAAGGGACTGGAATGGGTCGGAAGAATCAGATCGAAGGCCAACAACTACGCCACTTACTACGCCGACTCCGTGAAGGGAAGGTTCACTATCTCGCGGGACGACTCCAAGAACACTCTGTATCTCCAAATGAACTCACTCCGGGCCGAGGATACTGCGGTGTACTATTGCGTGCGGCATGGAAACTTCGGGGACAGCTACGTCAGCTGGTTCGCCTACTGGGGCCAAGGCACTCTCGTCACCGTGTCATCCGGGAAGCCGGGTTCCGGAAAGCCTGGATCGGGCAAACCGGGATCGGGAAAACCCGGAAGCCAGGCCGTCGTGACCCAGGAACCGAGCCTGACCGTGTCCCCCGGCGGTACCGTGACCTTGACTTGCGGTTCCTCCACTGGAGCCGTGACTACCTCGAACTACGCCAACTGGGTGCAGCAGAAGCCGGGAAAGTCGCCTCGCGGACTGATCGGTGGAACTAACAAACGCGCCCCGGGCGTGCCAGCCAGATTCAGCGGTAGCCTGCTCGGCGGAAAGGCCGCGCTGACCATCTCCGGGGCCCAGCCCGAGGATGAGGCCGACTATTACTGCGCTCTGTGGTACTCCAACCACTGGGTGTTTGGCGGGGGCACTAAGCTGACTGTGCTG |
| Fc region | | |
| HC BCMA arm | 509 | QVQLVESGGGVVQPGRSLRLSCAASGFTVSSYGMHWVRQAPGKGLEWVAVISYTGSNKYYADSVKGRFTISRDNSKNTLYLQMNSLRAEDTAVYYCGGSGYALHDDYYGLDVWGQGTLVTVSSASTKGPSVFPLAPSSKSTSGGTAALGCLVKDYFPEPVTVSWNSGA |

TABLE 21F-continued

Trivalent AB3 ((hBCMA Fab/hCD3 scFv 2x1 format))

| | SEQ ID NO | Sequence |
|---|---|---|
| | | LTSGVHTFPAVLQSSGLYSLSSVVTVPSSSLGTQT YICNVNHKPSDTKVDKKVEPKSCDKTHTCPPCPA PPVAGPSVFLFPPKPKDTLMISRTPEVTCVVVDVK HEDPEVKFNWYVDGVEVHNAKTKPREEEYNSTY RWSVLTVLHQDWLNGKEYKCKVSNKALPAPIEK TISKAKGQPREPQVYTLPPSREEMTKNQVSLTCD VSGFYPSDIAVEWESDGQPENNYKTTPPVLDSDG SFFLYSKLTVDKSRWEQGDVFSCSVMHEALHNH YTQKSLSLSPGK |
| DNA HC | 601 | CAAGTGCAGCTTGTGGAGTCGGGAGGGGGAGT GGTGCAGCCTGGTCGCTCACTGAGGCTGAGCT GTGCTGCCTCCGGCTTTACCGTGTCCTCCTACG GAATGCATTGGGTCAGACAGGCACCGGGAAAA GGCCTGGAATGGGTGGCCGTCATCAGCTACAC CGGCTCCAACAAGTACTACGCCGACTCAGTGAA GGGGCGGTTCACTATTAGCCGCGATAACTCGAA GAATACCCTGTATCTGCAAATGAACTCTTTGCG GGCCGAAGATACCGCCGTGTACTACTGCGGAG GCTCCGGTTACGCGCTCCACGACGACTACTAC GGACTGGACGTGTGGGGACAGGGGACTCTCGT GACCGTGTCGTCCGCTAGCACCAAGGGACCGA GCGTGTTCCCGCTGGCGCCGAGCAGCAAATCG ACTTCTGGGGGAACCGCAGCCCTGGGTTGCCT GGTCAAGGACTACTTCCCGGAACCAGTCACTGT GTCCTGGAACAGCGGTGCCCTCACCTCGGGCG TGCACACCTTCCCGGCCGTGCTGCAGTCTAGC GGACTCTACTCGCTCTCCTCCGTGGTCACCGTG CCCTCCTCATCACTGGGAACCCAGACATACATT TGCAACGTGAACCACAAGCCCTCGGACACTAAG GTGGACAAAAAAGTGGAACCAAAGTCCTGCGAC AAGACCCACACTTGTCCGCCCTGCCCTGCCCCT CCCGTGGCGGGCCCGTCAGTGTTTCTGTTTCC GCCAAAGCCTAAGGATACCCTCATGATCAGCCG CACTCCTGAAGTGACCTGTGTCGTGGTGGACGT GAAACACGAGGACCCGGAGGTCAAGTTTAATTG GTACGTGGATGGGGTGGAGGTGCACAACGCCA AAACTAAGCCCCGGGAAGAAGAGTACAATTCCA CCTACCGCGTCGTGTCAGTGTTGACGGTCCTG CACCAAGACTGGCTGAACGGAAAGGAGTACAA GTGCAAGGTGTCCAACAAGGCACTGCCCGCCC CCATCGAAAAGACCATTTCAAAAGCTAAGGGCC AGCCGCGGGAACCACAGGTCTACACCCTGCCT CCCTCCCGGGAAGAGATGACCAAGAACCAAGT CTCCCTCACGTGTGACGTGTCCGGCTTCTACCC TTCGGACATTGCTGTGGAATGGGAGTCCGACG GGCAGCCCGAAAACAACTACAAGACCACTCCC CCTGTGCTGGACTCCGACGGCTCATTCTTTCTG TACTCCAAGCTCACCGTCGATAAGTCGAGATGG GAGCAGGGAGATGTGTTCTCCTGCTCCGTGAT GCACGAGGCCCTGCATAACCATTACACTCAGAA GTCCCTCTCCCTGTCCCCTGGGAAG |
| LC BCMA arm | 510 | QSALTQPASVSGSPGQSITISCTGTSSDVGGYNY VSWYQQHPGKAPKLMIYDVSNRLRGVSNRFSGS KSGNTASLTISGLQAEDEADYYCSSYTSSSALYVF GSGTKVTVLGQPKAAPSVTLFPPSSEELQANKAT LVCLISDFYPGAVTVAWKADSSPVKAGVETTTPSK QSNNKYAASSYLSLTPEQWKSHRSYSCQVTHEG STVEKTVAPTECS |
| DNA LC | 600 | CAATCCGCCCTGACTCAGCCGGCCAGCGTGTC AGGTTCCCCGGGCCAAAGCATTACCATCTCCTG CACTGGGACCTCCTCCGATGTCGGGGGCTACA ACTACGTGTCGTGGTATCAGCAGCACCCTGGAA AGGCGCCCAAGCTGATGATCTACGACGTGTCC AACCGGCTGAGGGGAGTCAGCAACCGCTTCAG CGGCTCCAAGTCCGGAAACACCGCATCACTCA CAATCAGCGGTCTGCAGGCTGAGGATGAAGCG GACTACTACTGTTCCTCCTACACCTCCTCCTCG GCGCTTTACGTCTTTGGGTCGGGAACCAAAGTC ACTGTGCTGGGACAGCCGAAGGCAGCCCCATC CGTGACCCTGTTCCCCCCGTCATCCGAGGAACT GCAGGCTAACAAGGCCACCCTCGTGTGCCTGA TTAGCGACTTCTACCCTGGAGCCGTGACCGTG |

TABLE 21F-continued

Trivalent AB3 ((hBCMA Fab/hCD3 scFv 2x1 format))

| | SEQ ID NO | Sequence |
|---|---|---|
| | | GCCTGGAAGGCCGACTCCAGCCCAGTGAAGGC CGGAGTGGAGACTACCACCCCGAGCAAACAGT CGAACAATAAGTACGCCGCGTCATCGTACCTGT CCCTCACGCCCGAACAGTGGAAGTCCCATAGAT CGTACTCCTGCCAAGTGACCCACGAGGGCAGC ACTGTGGAAAAGACTGTGGCCCCTACCGAGTG CTCT |
| CD3 arm | 511 | QVQLVESGGGVVQPGRSLRLSCAASGFTVSSYG MHWVRQAPGKGLEWVAVISYTGSNKYYADSVKG RFTISRDNSKNTLYLQMNSLRAEDTAVYYCGGSG YALHDDYYGLDVWGQGTLVTVSSASTKGPSVFPL APSSKSTSGGTAALGCLVKDYFPEPVTVSWNSGA LTSGVHTFPAVLQSSGLYSLSSVVTVPSSSLGTQT YICNVNHKPSNTKVDKKVEPKSCGGGGSGGGGS EVQLVESGGGLVQPGGSLRLSCAASGFTFSTYA MNWVRQAPGKGLEWVGRIRSKANNYATYYADSV KGRFTISRDDSKNTLYLQMNSLRAEDTAVYYCVR HGNFGDSYVSWFAYWGQGTLVTVSSGKPGSGK PGSGKPGSGKPGSQAVVTQEPSLTVSPGGTVTL TCGSSTGAVTTSNYANWVQQKPGKSPRGLIGGT NKRAPGVPARFSGSLLGGKAALTISGAQPEDEAD YYCALWYSNHWVFGGGTKLTVLGGGGSGGGGS KTHTCPPCPAPPVAGPSVFLFPPKPKDTLMISRTP EVTCVVVDVKHEDPEVKFNWYVDGVEVHNAKTK PREEQYNSTYRVVSVLTVLHQDWLNGKEYKCKV SNKALPAPIEKTISKAKGQPREPQVYTLPPSREQM TKNQVKLTCLVKGFYPSDIAVEWESNGQPENNYK TTPPVLDSDGSFFLYSKLTVDKSRWQQGNVFSCS VMHEALHNHYTQKSLSLSPGK |
| DNA CD3 | 602 | CAAGTGCAGCTTGTGGAGTCGGGAGGGGGAGT GGTGCAGCCTGGTCGCTCACTGAGGCTGAGCT GTGCTGCCTCCGGCTTTACCGTGTCCTCCTACG GAATGCATTGGGTCAGACAGGCACCGGGAAAA GGCCTGGAATGGGTGGCCGTCATCAGCTACAC CGGCTCCAACAAGTACTACGCCGACTCAGTGAA GGGGCGGTTCACTATTAGCCGCGATAACTCGAA GAATACCCTGTATCTGCAAATGAACTCTTTGCG GGCCGAAGATACCGCCGTGTACTACTGCGGAG GCTCCGGTTACGCGCTCCACGACGACTACTAC GGACTGGACGTGTGGGGACAGGGGACTCTCGT GACCGTGTCGTCCGCTAGCACCAAGGGACCGA GCGTGTTCCCGCTGGCGCCGAGCAGCAAATCG ACTTCTGGGGGAACCGCAGCCCTGGGTTGCCT GGTCAAGGACTACTTCCCGGAACCAGTCACTGT GTCCTGGAACAGCGGTGCCCTCACCTCGGGCG TGCACACCTTCCCGGCCGTGCTGCAGTCTAGC GGACTCTACTCGCTCTCCTCCGTGGTCACCGTG CCCTCCTCATCACTGGGAACCCAGACATACATT TGCAACGTGAACCACAAGCCGTCCAACACCAAG GTCGACAAGAAAGTGGAGCCTAAGTCCTGTGGT GGCGGAGGCTCCGGCGGAGGAGGATCGGAGG TGCAGCTCGTCGAATCCGGTGGAGGGCTGGTG CAACCGGGGGGCTCGCTTAGGCTTAGCTGCGC TGCGTCAGGGTTCACCTTCTCAACTTACGCGAT GAATTGGGTCAGACAGGCACCCGGAAAGGGAC TGGAATGGGTCGGAAGAATCAGATCGAAGGCC AACAACTACGCCACTTACTACGCCGACTCCGTG AAGGGAAGGTTCACTATCTCGCGGGACGACTC CAAGAACACTCTGTATCTCCAAATGAACTCACTC CGGGCCGAGGATACTGCGGTGTACTATTGCGT GCGGCATGGAAACTTCGGGGACAGCTACGTCA GCTGGTTCGCCTACTGGGGCCAAGGCACTCTC GTCACCGTGTCATCCGGGAAGCCGGGTTCCGG AAAGCCTGGATCGGGCAAACCGGGATCGGGAA AACCCGGAAGCCAGGCCGTCGTGACCCAGGAA CCGAGCCTGACCGTGTCCCCGGCGGTACCGT GACCTTGACTTGCGGTTCCTCCACTGGAGCCGT GACTACCTCGAACTACGCCAACTGGGTGCAGC AGAAGCCGGGAAAGTCGCCTCGCGGACTGATC GGTGGAACTAACAAACGCGCCCCGGGCGTGCC AGCCAGATTCAGCGGTAGCCTGCTCGGCGGAA AGGCCGCGCTGACCATCTCCGGGGCCCAGCCC GAGGATGAGGCCGACTATTACTGCGCTCTGTGT |

TABLE 21F-continued

Trivalent AB3
((hBCMA Fab/hCD3 scFv 2x1 format))

SEQ ID NO Sequence

```
GTACTCCAACCACTGGGTGTTTGGCGGGGGCA
CTAAGCTGACTGTGCTGGGCGGCGGCGGCTCC
GGGGGGGGGGGCTCCAAGACCCACACTTGTCC
GCCCTGCCCTGCCCCTCCCGTGGCGGGCCCGT
CAGTGTTTCTGTTTCCGCCAAAGCCTAAGGATA
CCCTCATGATCAGCCGCACTCCTGAAGTGACCT
GTGTCGTGGTGGACGTGAAACACGAGGACCCG
GAGGTCAAGTTTAATTGGTACGTGGATGGGGTG
GAGGTGCACAACGCCAAAACTAAGCCCCGGGA
AGAACAGTACAATTCCACCTACCGCGTCGTGTC
AGTGTTGACGGTCCTGCACCAAGACTGGCTGAA
CGGAAAGGAGTACAAGTGCAAGGTGTCCAACA
AGGCACTGCCCGCCCCCATCGAAAAGACCATTT
CAAAAGCTAAGGGCCAGCCGCGGGAACCACAG
GTCTACACCCTGCCTCCCTCCCGGGAACAGAT
GACCAAGAACCAAGTCAAGCTCACGTGTCTCGT
GAAGGGCTTCTACCCTTCGGACATTGCTGTGGA
ATGGGAGTCCAACGGGCAGCCCGAAAACAACT
ACAAGACCACTCCCCCTGTGCTGGACTCCGAC
GGCTCATTCTTTCTGTACTCCAAGCTCACCGTC
GATAAGTCGAGATGGCAGCAGGGAAACGTGTT
CTCCTGCTCCGTGATGCACGAGGCCCTGCATAA
CCATTACACTCAGAAGTCCCTCTCCCTGTCCCC
TGGGAAG
```

8.5.1.5. Affinity Determination by Solution Equilibrium Titration

Solution equilibrium titration (SET) was performed to generate apparent KDs for the bispecific BCMA binding molecules. In this format, recombinant human and recombinant cynomolgus monkey BCMA was coated onto MSD plates at a low concentration so that the complex concentrations were ideally below the KDs. The bispecifics were fixed and tested at a few concentrations (1 nM, 0.1 nM, 0.01 nM) and each concentration was pre-incubated with the titrated BCMA in solution. This complex was allowed to pre-incubate overnight. This mixture was then added to the plate for a short incubation in order to capture the free bispecific. The more free bispecific detected, the weaker the interaction and, therefore, the weaker the affinity. Briefly, antigen was coated on standard binding MSD plates (Meso-Scale Discovery, 384-well: MSD cat #L21XA, 96-well: MSD cat #L15XA) at 0.2-0.3 µg/ml in 25 µl PBS and incubated overnight at 4° C.

Bispecific antibodies were diluted to a fixed concentration (e.g., 10 pM) in incubation buffer (PBS with 2% BSA (Sigma cat #A4503) and 1% Tween20 and 1% Triton-X (Sigma cat #234729)), and added to a serial dilution of antigen in incubation buffer. Samples were allowed to reach equilibrium by incubation at room temperature overnight.

Plates were washed 3× in wash buffer (PBS with 0.05% Tween20), and blocked with 100 µl incubation buffer at room temperature for 2 hrs. Plates were then washed 3× in wash buffer. Samples containing bispecific antibodies (fixed concentration) and antigen (titration) were added to the plate (25 µl), and incubated at room temperature for 15 min. Plates were then washed 3× in wash buffer. 25 µl detection antibody was then added (Anti-Human (Goat) Sulfo-TAG, 1:1000 in incubation buffer, MSD cat #R32AJ-1), and incubated at room temperature for 30 min. Plates were washed 3× in wash buffer, and 50 µl of 1×MSD Read buffer T was added (with surfactant, MSD cat #R92TC-1). Plates were then read on a MSD Spector Imager 6000.

Data was analyzed using GraphPad Prism software v4, with background (an average of wells containing no Fab) subtracted from each value. X-axis values (concentration of antigen in solution) were transformed into $\log_{10} x$.

$K_D$ values (KD) were fitted from the following model:

$$Y = (\text{Top} - ((\text{Top}/(2 \times \text{Fab})) \times ((((10\hat{\ }x) + \text{Fab}) + KD) - ((((((10\hat{\ }x) + \text{Fab}) + KD) \times (((10\hat{\ }x) + \text{Fab}) + KD)) - ((4 \times (10\hat{\ }x)) \times \text{Fab}))\hat{\ }0.5))))$$

Top=signal at antigen concentration=0
x=concentration of BCMA in solution
Fab=concentration of applied monovalent analyte (Fab)

8.5.2. Results

Apparent affinities for each of the BCMA binding arms tested are shown in Table 22.

TABLE 22

BCMA binding affinity of BCMA bispecific antibodies

| Bispecific Construct | Human BCMA (pM) | Cyno BCMA (pM) |
|---|---|---|
| AB1 | 4503 | 2526 |
| AB2 | 200 | 1060 |
| AB3 | 61.53 | 104.6 |

8.6. Example 6: Anti-Tumor Activity of Bivalent and Trivalent BCMA-CD3 AB1 and AB2 in an Adoptive Transfer Adaptation of the KMS11-Luc Multiple Myeloma Orthotopic Tumor Model in NSG Mice

8.6.1. Materials and Methods

The anti-tumor activity of bivalent and trivalent BCMA-CD3 AB1 and AB2 was tested in an adoptive transfer adaptation of the KMS11-Luc multiple myeloma orthotopic tumor model in NSG mice.

On Day 0, KMS11-Luc cells were harvested and suspended in Hanks Balanced Salt Solution (HBSS) at a concentration of $10\times10^6$ cells/mL. Female NOD.Cg-Prkdc$^{scid}$ Il2rg$^{tm1Wjl}$/SzJ mice (NSG mice) at ~6 weeks old (Jackson Laboratories, ME), were injected with $1\times10^6$ KMS11-Luc cells (in a volume of 100 μL) intravenously (IV) in the lateral tail vein.

Seven days following tumor inoculation, each mouse received an adoptive transfer (AdT) of $10\times10^6$ of peripheral blood mononuclear cells (PBMCs) (in a volume of 100 μL) via IV injection in the lateral tail vein. The PBMCs were previously isolated from a human leukopak, frozen and stored in Cryostor10 media in vapor phase liquid Nitrogen tank until use. Immediately prior to AdT, PBMCs were thawed and suspended at a concentration of $100\times10^6$ cells/ml in Hanks Balanced Salt Solution (HBSS).

When tumor burden (TB) reached an average of ~$1.0\times10^7$ photons/sec (p/s) measured via bioluminescence, mice (n=5/group) were treated with a single IV administration of bivalent BCMA-CD3 AB1, trivalent BCMA-CD3 AB1, bivalent BCMA-CD3 AB2 or trivalent BCMA-CD3 AB2 at dose levels of 0.03 mg/kg, 0.3 mg/kg or 3.0 mg/kg. Anti-tumor activity of each antibody was compared to an untreated control group that received tumor implant and AdT but no treatment (tumor+AdT). A tumor only group was included to meter the allogeneic response observed with untreated control. All treatments were administered at 10 mL/kg according to individual mouse body weights. Anti-tumor activity was determined by percent change in tumor burden vs. change in untreated control (% ΔT/ΔC) or % regression.

Tumor burden and body weights were recorded twice weekly. Tumor burden was measured by bioluminescence signal intensity in p/s using a bioluminescence imaging system (IVIS200, Perkin Elmer). Anti-tumor activity was determined by percent change in tumor burden versus control (% ΔT/ΔC) using the formula: $100\times\Delta TB_{treatment, time}/\Delta TB_{control\ group,\ time}$ if ΔTB≥0; or percent regression: $(-1\times(100\times(TB_{final}-TB_{initial})/TB_{initial})$ if ΔTV<0, $TB_{initial}$ is the tumor burden on the day of treatment initiation (% ΔT/ΔC values <42% were considered to have anti-tumor activity). Percent body weight change was determined using the formula: $100\times((BW_{time}-BW_{initial})/BW_{initial})$. Statistical analysis using One-way ANOVA with Dunnett's multiple comparison test was performed using Graphpad Prism Software, Version. 7.03.

On day 36 following KMS11-Luc implantation, all animals from the untreated control group were euthanized due to tumor burden.

8.6.2. Results 8.6.2.1. Anti-Tumor Activity of Bivalent and Trivalent BCMA-CD3 AB1

Antibody treatment with bivalent BCMA-CD3 AB1 at 0.3 mg/kg and 3.0 mg/kg resulted in significant tumor regressions of 57.8% and 85.3%, respectively. Antibody treatment with bivalent BCMA-CD3 AB1 at 0.03 mg/kg did not exhibit significant anti-tumor activity (67.4% ΔT/ΔC value). Antibody treatment with trivalent BCMA-CD3 AB1 resulted in significant anti-tumor responses at 0.3 mg/kg (2.4% ΔT/ΔC) and 3.0 mg/kg (73.6% regression). Antibody treatment with trivalent BCMA-CD3 AB1 at 0.03 mg/kg was not active in this model (Table 23, FIG. 13).

TABLE 23

In vivo efficacy of bivalent or trivalent BCMA-CD3 AB1 evaluated in a human PBMC adoptive transfer adaptation of the KMS11-Luc orthotopic tumor model in mice on day 36 post-implantation

| Test agent | Dose (mg/kg) | Schedule | Tumor Response | | Host Response | | |
|---|---|---|---|---|---|---|---|
| | | | ΔT/ΔC (%) | Regression (%) | Δ Tumor burden from initial (p/s) (Geometric mean) Day 36 | Δ Body weight from initial (%) (Mean ± SEM) Day 36 | Survival (survivors/total) |
| Untreated control | N/A | — | — | — | $6.4 \times 10^8$ | 9.9 ± 3.6 | 4/5 |
| Bivalent BCMA-CD3 AB1 | 0.03 | Single dose/IV | 67.4 | — | $4.3 \times 10^8$ | 9.1 ± 1.6 | 5/5 |
| Bivalent BCMA-CD3 AB1 | 0.3 | Single dose/IV | — | 57.8* | $-2.2 \times 10^7$ | 10.9 ± 0.9 | 5/5 |
| Bivalent BCMA-CD3 AB1 | 3.0 | Single dose/IV | — | 85.3* | $-1.2 \times 10^7$ | 1.6 ± 3.4 | 5/5 |
| Trivalent BCMA-CD3 AB1 | 0.03 | Single dose/IV | 100 | — | $1.1 \times 10^9$ | -0.5 ± 3.4 | 5/5 |
| Trivalent BCMA-CD3 AB1 | 0.3 | Single dose/IV | 2.4* | — | $1.53 \times 10^7$ | 7.7 ± 2.0 | 5/5 |
| Trivalent BCMA-CD3 AB1 | 3.0 | Single dose/IV | — | 73.6* | $-1.7 \times 10^7$ | -4.3 ± 2.5 | 5/5 |

*p < 0.05, Dunnett's multiple comparison test

There was no antibody associated body weight loss with bivalent or trivalent BCMA-CD3 AB1. The body weight change observed with the treatment of bivalent and trivalent BCMA-CD3 AB1 was most likely due to the onset of graft-versus host disease (GvHD). Body weight loss is an endpoint parameter for both disease burden and onset of GvHD. At 35-42 days post-PBMC injection (28-35 days post-tumor implant), animals began to exhibit weight loss attributed to GvHD. Animals with high tumor burden also demonstrated disease-burden associated weight loss. Over the course of the study, body weights increased relative the initial measurement taken on the day of tumor implant (Table 23, FIG. 14). However, at the end of study, the body weight loss observed relative to the peak gain is indicative of GvHD and disease-burden induced weight loss. This study had minimal allogeneic response (FIG. 13).

8.6.2.2. Anti-Tumor Activity of Bivalent and Trivalent BCMA-CD3 AB2

Antibody treatment with bivalent BCMA-CD3 AB2 resulted in significant anti-tumor activity. Bivalent BCMA-CD3 AB2 at 0.03 mg/kg resulted in % ΔT/ΔC value of 0.9%, and 0.3 mg/kg and 3.0 mg/kg achieved 90.7% and 91.7% regressions, respectively. Treatment with trivalent BCMA-CD3 AB2 resulted in significant anti-tumor responses with % ΔT/ΔC values of 2.4% and 5.7% for the 0.03 mg/kg and 0.3 mg/kg dose levels, respectively. Trivalent BCMA-CD3 AB2 at 3.0 mg/kg achieved 96.8% regression (Table 24, FIG. 13).

There was no antibody associated body weight loss with bivalent or trivalent BCMA-CD3 AB2. Body weight loss due to the onset of GvHD was not observed for this construct by the end of the study (Table 24, FIG. 14). This study had minimal allogeneic response (FIG. 13).

8.7. Example 7: Anti-Tumor Activity of Bivalent and Trivalent BCMA-CD3 AB1, AB2, and AB3 in an Adoptive Transfer Adaptation of the KMS11-Luc Multiple Myeloma Orthotopic Tumor Model in NSG Mice 8.7.1. Materials and Methods The materials and methods used in Example 7 correspond to those used in Example 6 except that on day 38 following KMS11-Luc implantation, all animals from the untreated control group were euthanized due to tumor burden, and the remaining animals were euthanized on Day 40.

8.7.2. Results 8.7.2.1. Anti-Tumor Activity of Bivalent and Trivalent BCMA-CD3 AB1

Antibody treatments with bivalent BCMA-CD3 AB1 resulted in significant anti-tumor activity. Bivalent BCMA-CD3 AB1 at 0.03 mg/kg resulted in % ΔT/ΔC of 24.7%. Bivalent BCMA-CD3 AB1 at 0.3 mg/kg and 3.0 mg/kg resulted in regressions of 50.7% and 22.7%, respectively. Trivalent BCMA-CD3 AB1 treatment resulted in significant anti-tumor responses at 0.03 mg/kg (2.6% % ΔT/ΔC), 0.3 mg/kg (64.2% regression) and 3.0 mg/kg (89.5% regressions) (Table 25, FIG. 15).

TABLE 24

In vivo efficacy of bivalent or trivalent BCMA-CD3 AB2 evaluated in a human PBMC adoptive transfer adaptation of the KMS11-Luc orthotopic tumor model in mice on day 36 post-implantation

| | | | Tumor Response | | | Host Response | |
| --- | --- | --- | --- | --- | --- | --- | --- |
| | | | | | | Δ Body | |
| Test agent | Dose (mg/kg) | Schedule | ΔT/ΔC (%) | Regression (%) | Δ Tumor burden from initial (P/S) (Geometric mean) Day 36 | weight from initial (%) (Mean ± SEM) Day 36 | Survival (survivors/total) |
| Untreated control | N/A | — | — | — | $6.7 \times 10^8$ | 9.9 ± 3.6 | 4/5 |
| Bivalent BCMA-CD3 AB2 | 0.03 | Single dose/IV | 0.9* | | $5.7 \times 10^6$ | 6.4 ± 3.2 | 5/5 |
| Bivalent BCMA-CD3 AB2 | 0.3 | Single dose/IV | — | 90.7* | $-1.5 \times 10^7$ | 1.3 ± 3.9 | 5/5 |
| Bivalent BCMA-CD3 AB2 | 3.0 | Single dose/IV | — | 91.7* | $-1.70 \times 10^7$ | 9.3 ± 3.0 | 5/5 |
| Trivalent BCMA-CD3 AB2 | 0.03 | Single dose/IV | 2.4* | — | $1.7 \times 10^7$ | 14.5 ± 3.0 | 5/5 |
| Trivalent BCMA-CD3 AB2 | 0.3 | Single dose/IV | 5.7* | — | $3.7 \times 10^7$ | 9.2 ± 2.3 | 5/5 |
| Trivalent BCMA-CD3 AB2 | 3.0 | Single dose/IV | — | 96.8* | $-2.2 \times 10^6$ | 7.0 ± 4.9 | 5/5 |

*p < 0.05, Dunnett's multiple comparison test

TABLE 25

In vivo efficacy of bivalent or trivalent BCMA-CD3 AB1 evaluated in a human PBMC adoptive transfer adaptation of the KMS11-Luc orthotopic tumor model in mice on day 38 post-implantation

| Test agent | Dose (mg/kg) | Schedule | ΔT/ΔC (%) | Regression (%) | Δ Tumor burden from initial (p/s) (Geometric mean) Day 38 | Host Response Δ Body weight from initial (%) (Mean ± SEM) Day 38 | Survival (survivors/total) Day 38 |
|---|---|---|---|---|---|---|---|
| Untreated control | N/A | — | — | — | $2.2 \times 10^9$ | $17.9 \pm 4.0$ | 5/5 |
| Bivalent BCMA-CD3 AB1 | 0.03 | Single dose/IV | 24.7* | — | $5.3 \times 10^8$ | $14.8 \pm 2.4$ | 5/5 |
| Bivalent BCMA-CD3 AB1 | 0.3 | Single dose/IV | — | 50.7* | $-3.9 \times 10^6$ | $9.9 \pm 2.9$ | 5/5 |
| Bivalent BCMA-CD3 AB1 | 3.0 | Single dose/IV | — | 22.7* | $-3.6 \times 10^6$ | $2.9 \pm 2.8$ | 5/5 |
| Trivalent BCMA-CD3 AB1 | 0.03 | Single dose/IV | 2.6* | — | $5.5 \times 10^7$ | $16.0 \pm 3.0$ | 5/5 |
| Trivalent BCMA-CD3 AB1 | 0.3 | Single dose/IV | — | 64.2* | $-4.7 \times 10^7$ | $20.4 \pm 4.5$ | 5/5 |
| Trivalent BCMA-CD3 AB1 | 3.0 | Single dose/IV | — | 89.5* | $-6.4 \times 10^6$ | $5.6 \pm 5.4$ | 5/5 |

*$p < 0.05$, Dunnett's multiple comparison test

There was no antibody associated body weight loss with bivalent or trivalent BCMA-CD3 AB1. The body weight change observed with the treatment of bivalent and trivalent BCMA-CD3 AB1 is most likely due to the onset of GvHD. Body weight loss is an endpoint parameter for both disease burden and onset of GvHD. At 35-42 days post-PBMC injection (28-35 days post-tumor implant), animals began to exhibit weight loss attributed to GvHD. Animals with high tumor burden also demonstrated disease-burden associated weight loss. Over the course of the study, body weights increased relative the initial measurement taken on the day of tumor implant (Table 25, FIG. 16). However, at the end of study, the body weight loss observed relative to the peak gain was indicative of GvHD and disease-burden induced weight loss (Table 25, FIG. 16).

8.7.2.2. Anti-Tumor Activity of Bivalent and Trivalent BCMA-CD3 AB2

The bivalent BCMA-CD3 AB2 antibody treatments at 0.3 mg/kg and 3.0 mg/kg resulted in significant anti-tumor activity, achieving % ΔT/ΔC values of 33.3% and 0.4% at 0.03 mg/kg and 0.3 mg/kg, respectively. Bivalent BCMA-CD3 AB2 at 3.0 mg/kg achieved 96% regression. Trivalent BCMA-CD3 AB2 resulted in significant anti-tumor responses with all treatments, resulting in regressions of 66.1% for the 0.03 mg/kg dose, 80.8% for the 0.3 mg/kg dose and 69.3% for the 3.0 mg/kg dose (Table 26, FIG. 15).

TABLE 26

In vivo efficacy of bivalent or trivalent BCMA-CD3 AB2 evaluated in a human PBMC adoptive transfer adaptation of the KMS11-Luc orthotopic tumor model in mice on day 38 post-implantation

| Test agent | Dose (mg/kg) | Schedule | ΔT/ΔC (%) | Regression (%) | Δ Tumor burden from initial (P/S) (Geometric mean) Day 38 | Host Response Δ Body weight from initial (%) (Mean ± SEM) Day 38 | Survival (survivors/total) Day 38 |
|---|---|---|---|---|---|---|---|
| Untreated control | N/A | — | — | — | $2.2 \times 10^9$ | $17.9 \pm 4.0$ | 5/5 |
| Bivalent BCMA-CD3 AB2 | 0.03 | Single dose/IV | 33.3 | — | $7.2 \times 10^8$ | $15.5 \pm 3.0$ | 5/5 |
| Bivalent BCMA-CD3 AB2 | 0.3 | Single dose/IV | 0.4* | — | $7.9 \times 10^6$ | $16.9 \pm 2.1$ | 5/5 |

TABLE 26-continued

In vivo efficacy of bivalent or trivalent BCMA-CD3 AB2 evaluated in a human PBMC adoptive transfer adaptation of the KMS11-Luc orthotopic tumor model in mice on day 38 post-implantation

| | | | | Tumor Response | | Host Response | |
| --- | --- | --- | --- | --- | --- | --- | --- |
| Test agent | Dose (mg/kg) | Schedule | ΔT/ ΔC (%) | Regression (%) | Δ Tumor burden from initial (P/S) (Geometric mean) Day 38 | Δ Body weight from initial (%) (Mean ± SEM) Day 38 | Survival (survivors/ total) Day 38 |
| Bivalent BCMA-CD3 AB2 | 3.0 | Single dose/IV | — | 96.0* | $-2.9 \times 10^6$ | 8.1 ± 5.5 | 5/5 |
| Trivalent BCMA-CD3 AB2 | 0.03 | Single dose/IV | — | 66.1* | $-5.6 \times 10^6$ | 8.9 ± 3.9 | 5/5 |
| Trivalent BCMA-CD3 AB2 | 0.3 | Single dose/IV | — | 80.8* | $-6.5 \times 10^6$ | 2.8 ± 1.4 | 5/5 |
| Trivalent BCMA-CD3 AB2 | 3.0 | Single dose/IV | — | 69.3* | $-4.9 \times 10^6$ | 13.6 ± 5.2 | 5/5 |

*$p < 0.05$, Dunnett's multiple comparison test

There was no antibody associated body weight loss with bivalent or trivalent BCMA-CD3 AB2. The body weight change observed with the treatment of bivalent and trivalent BCMA-CD3 AB2 is most likely due to the onset of GvHD. Body weight loss is an endpoint parameter for both disease burden and onset of GvHD. At 35-42 days post-PBMC injection (28-35 days post-tumor implant), animals began to exhibit weight loss attributed to GvHD. Animals with high tumor burden also demonstrated disease-burden associated weight loss. Over the course of the study, body weights increase relative the initial measurement taken on the day of tumor implant (Table 26, FIG. 16). However, at the end of study, the body weight loss observed relative to the peak gain is indicative of GvHD and disease-burden induced weight loss (Table 26, FIG. 16).

8.7.2.3. Anti-Tumor Activity of Bivalent and Trivalent BCMA-CD3 AB3

Bivalent BCMA-CD3 AB3 resulted in significant anti-tumor activity, with % regressions of 87.6%, 91.3% and 85.2% at 0.03 mg/kg, 0.3 mg/kg and 3.0 mg/kg, respectively. Treatment with trivalent BCMA-CD3 AB3 resulted in significant anti-tumor responses. Trivalent BCMA-CD3 AB3 at 0.03 mg/kg resulted in % ΔT/ΔC value of 29.0%, and 0.3 mg/kg and 3.0 mg/kg resulted in 85.4% and 90.4% regression, respectively. (Table 27, FIG. 15).

TABLE 27

In vivo efficacy of bivalent or trivalent BCMA-CD3 AB3 evaluated in a human PBMC adoptive transfer adaptation of the KMS11-Luc orthotopic tumor model in mice on day 38 post-implantation

| | | | | Tumor Response | | Host Response | |
| --- | --- | --- | --- | --- | --- | --- | --- |
| Test agent | Dose (mg/kg) | Schedule | ΔT/ ΔC (%) | Regression (%) | Δ Tumor burden from initial (p/s) (Geometric mean) Day 38 | Δ Body weight from initial (%) (Mean ± SEM) Day 38 | Survival (survivors/ total) Day 38 |
| Untreated control | N/A | — | — | — | $2.2 \times 10^9$ | 17.9 ± 4.0 | 5/5 |
| Bivalent BCMA-CD3 AB3 | 0.03 | Single dose/IV | — | 87.6* | $-4 \times 10^6$ | 16.0 ± 5.9 | 5/5 |
| Bivalent BCMA-CD3 AB3 | 0.3 | Single dose/IV | — | 91.3* | $-3.9 \times 10^6$ | 21.4 ± 2.9 | 5/5 |
| Bivalent BCMA-CD3 AB3 | 3.0 | Single dose/IV | — | 85.2* | $-5.60 \times 10^6$ | 12.2 ± 2.7 | 5/5 |
| Trivalent BCMA-CD3 AB3 | 0.03 | Single dose/IV | 29.0* | — | $6.3 \times 10^8$ | 5.8 ± 3.3 | 5/5 |
| Trivalent BCMA-CD3 AB3 | 0.3 | Single dose/IV | — | 85.4* | $-5.1 \times 10^6$ | 15.6 ± 3.3 | 5/5 |

TABLE 27-continued

In vivo efficacy of bivalent or trivalent BCMA-CD3 AB3 evaluated in a human PBMC adoptive transfer adaptation of the KMS11-Luc orthotopic tumor model in mice on day 38 post-implantation

| | | | | Tumor Response | | Host Response | |
|---|---|---|---|---|---|---|---|
| Test agent | Dose (mg/kg) | Schedule | $\Delta T/\Delta C$ (%) | Regression (%) | $\Delta$ Tumor burden from initial (p/s) (Geometric mean) Day 38 | $\Delta$ Body weight from initial (%) (Mean ± SEM) Day 38 | Survival (survivors/total) Day 38 |
| Trivalent BCMA-CD3 AB3 | 3.0 | Single dose/IV | — | 90.4* | $-4.6 \times 10^6$ | 15.7 ± 4.1 | 5/5 |

*p < 0.05, Dunnett's multiple comparison test

There was no antibody associated body weight loss with bivalent or trivalent BCMA-CD3 AB3. The body weight change observed with the treatment of bivalent and trivalent BCMA-CD3 AB3 is most likely due to the onset of GvHD. Body weight loss is an endpoint parameter for both disease burden and onset of GvHD. At 35-42 days post-PBMC injection (28-35 days post-tumor implant), animals began to exhibit weight loss attributed to GvHD. Animals with high tumor burden also demonstrated disease-burden associated weight loss. Over the course of the study, body weights increase relative the initial measurement taken on the day of tumor implant (Table 27, FIG. 16). However, at the end of study, the body weight loss observed relative to the peak gain is indicative of GvHD and disease-burden induced weight loss (Table 27, FIG. 16).

8.8. Example 8: BCMA×CD3 Bispecific Antibody Mediated BCMA$^+$ MM Cell Lysis by T Cells In Vitro

8.8.1. Overview

The potency of BCMA×CD3 bispecific antibodies AB1, AB2, and AB3 in bivalent and trivalent format to mediate multiple myeloma (MM) cell line lysis by human T cells was measured in redirected T cell cytotoxicity (RTCC) assays. Five MM cell lines ((NCI-H929, MM1S, MOLP8, U266B1, MC116) and a BCMA-negative control cell line (NALM6) were used as target cells.

8.8.2. Materials and Methods

BCMA$^+$ MM lines (NCI-H929, MM1S, MOLP8, U266B1, MC116) as well as a BCMA$^-$ control cell line (NALM6) were transduced using lentiviral particles (GenTarget Inc, Cat #LVP435) to constitutively express luciferase. Cell surface expression of BCMA was determined by flow cytometry using BV421 labeled anti-BCMA Ab (clone 19F2, Biolegend 357520, data were acquired on BD LSR-Fortessa, and analyzed using FlowJo, v10).

Human T cells were isolated from peripheral blood of healthy human donors. First, peripheral blood mononuclear cells (PBMCs) were fractionated from donor blood using a Ficoll-Paque PLUS (GE Healthcare #17-1440-02) density gradient. T-cells were then isolated from PBMCs by negative selection according to manufacturer's recommended protocol (Miltenyi #130-096-535). In some studies, freshly isolated T cells were used as effector cells directly in RTCC assays at the effector:target (E:T) cell ratio of 3:1 or 6:1. In other studies, the isolated T-cells were further expanded using Human T-Activator CD3/CD28 Dynabeads (Gibco #11132D) for nine days, then debeaded magnetically and stored as viable frozen aliquots in liquid nitrogen. The expanded T cells were used as effector T cells in RTCC assays where they were thawed from frozen aliquots, counted and used immediately at an Effector:Target (E:T) cell ratio of 3:1.

For RTCC assays using fresh T cells, target cells were plated at 25,000 cells/well together with 75,000 or 150,000 cells/well effector cells (freshly isolated T-cells) in Costar 96-well plates (Corning 3904) in T cell medium (TCM). For RTCC assays using expanded T cells, target cells were plated at 7,500 cells/well together with 22,500 cells/well effector cells (expanded T-cells) in 384-well plates (Costar 3765) in TCM. TCM is RPMI/1640-based with the addition of 10% FBS, 2 mM L-glutamine, 0.1 mM Non-essential amino acids, 1 mM Sodium pyruvate, 10 mM HEPES, 0.055 mM 2-mercaptoethanol (Gibco 22400089, 16140, 25030-081, 11140-050, 11360-070, 15630-080, 21985-023, respectively). The bispecific antibodies were individually diluted in serial dilutions and added to the wells. The assay was incubated at 37° C./5% CO2 for 48 hr (fresh T cells) or 20 hr (expanded T cells), followed by measurements of luciferase activity to indicate target cell viability (BrightGlo, Promega #E2650) following manufacturer's protocols. Target cells only without T cells or antibodies served as control for 100% luciferase activity (100% viability). Data were analyzed using Spotfire, where EC50 values were calculated using logistic regression curve fit.

8.8.3. Results

NCI-H929 expresses high levels of BCMA, MM1S, MOLP8 and U266B1 have medium level of BCMA expression, whereas MC116 showed low level of cell surface BCMA (FIG. 17). Control cell line NALM6 showed no detectable BCMA expression. All bivalent and trivalent antibodies tested were selective for BCMA$^+$ multiple myeloma (MM) cells and mediated potent RTCC activity by expanded T cells (FIG. 18). Among all bivalent antibodies, RTCC activity correlates with anti-BCMA affinity. For the medium affinity anti-BCMA binder, BCMA-CD3 AB2, trivalent AB2 demonstrated superior activity than bivalent AB2 on BCMA$^{med}$ and BCMA$^{low}$ MM cells, but not on BCMA$^{high}$ MM cells. For the high or low affinity anti-BCMA binders, BCMA-CD3 AB3 and AB1, trivalent format did not show a clear advantage over the bivalent format across most of the cell lines tested. Similarly, when freshly isolated T cells were used as effector cells BCMA-CD3 antibodies mediated RTCC on BCMA+ MM cell lines (FIG. 19A and FIG. 19B), indicating that in vitro pre-activation of T cells was not required.

8.9. Example 9: BCMA×CD3 Bispecific Antibodies Induced T Cell Activation in the Presence of BCMA+ MM Cells 8.9.1. Overview Some MM patients have low T cell counts and high tumor burden, and it has been shown that MM cells express checkpoint molecules that suppress T cell cytotoxicity. Therefore, T cell activation and proliferation are desirable outcomes of bispecific Ab administration. The extent of T cell activation was determined by measuring cytokine secretion and T cell proliferation mediated by the bispecific antibodies AB1, AB2, and AB3 in the presence of target cells.

8.9.2. Materials and Methods 8.9.2.1. Cytokine Secretion

Cytokines were measured from the supernatant of the RTCC assays using fresh T cells at 48 hr. The 96-well plates were centrifuged at 500×g for 5 min, and supernatants were harvested and cytokine quantitation was performed using the V-Plex Pro-inflammatory Panel I (human) Kit (MesoScale Discovery, Cat #K15049D-4) as per the manufacturer protocol.

8.9.2.2. T Cell Proliferation

MM1S and MC116 target cells were irradiated on the day of the assay and plated at a density of 60,000 cells per well in Costar 96-well plates (Corning, Cat #3904) in T Cell Media (TCM). T cells were freshly isolated from healthy donor blood as described in Example 8. Isolated T cells were labelled with 2.5 uM Cell Trace Violet following the manufacturer's protocol and then co-cultured with target cells at an E:T ratio of 1:1. A dilution series of BCMA-CD3 antibodies ranging from 0.005 pM-10,000 μm was added to cells and the plates were incubated in a 5% CO2, 37° C. incubator for 96 hrs. Thereafter the cells were harvested, treated with Human TruStain FcX (Fc Block) [Biolegend, Cat #422302] following manufacturer instructions and then stained with Fixable Viability Dye eFlour 780 (ThermoFisher Scientific, Cat #65-0865-14) by incubation at 4C for 30 mins. The cells were then washed and stained with PerCP-Cy5.5 conjugated anti-human CD3 mAb (Biolegend, Cat #317336) by incubation at 4C for 30 mins. The samples were then run on BD LSR Fortessa and analyzed using FlowJo to determine % proliferated CD3+ T cells based on CD3 staining and dilution of Cell Trace Violet dye.

8.9.3. Results

All bivalent and trivalent BCMA-CD3 antibodies are able to induce IFNγ and TNFα cytokine secretion from T cells after co-culture with BCMA+ MM1S or MC116 cells (FIGS. 20A-B). The level of secreted cytokines correlated with the affinity of the bispecific antibodies. It is worth noting that the trivalent antibodies induced lower TNFα secretion than the corresponding bivalent antibodies. A non-targeting RSV-CD3 antibody was used as negative control, and minimal cytokine secretion were detected except at the highest concentration tested. The data indicated that only target specific engagement and activation of T cells as mediated by BCMA-CD3 antibodies induces robust cytokine secretion.

All six BCMA-CD3 antibodies promoted T cell proliferation in a dose-dependent manner in the presence of BCMA+ MM cell lines (FIG. 21). The negative control RSV-CD3 Ab stimulated T cell proliferation only at high concentrations (>1 μM), indicating that simultaneous engagement of BCMA- and CD3-binding arms are required for potent induction of T cell proliferation, consistent with the RTCC activity and cytokine secretion. For the bivalent format the potency of T cell proliferation correlated with affinity of antibody. Furthermore, the extent of proliferation can depend on the density of cell surface BCMA as $BCMA^{low}$ MC116 cells induced less efficient T cell proliferation than $BCMA^{med}$ MM1S cells.

8.10. Example 10: Time Course of Response of Multiple Myeloma Cell Line KMS11 to Treatment with Gamma Secretase Inhibitors 8.10.1. Overview Treatment of MM cells with GSIs inhibits the shedding of BCMA as a circulating soluble factor, resulting in accumulation of BCMA on the cell surface. To determine the kinetics of GSI activity, KMS11 cells were treated with GSIs. Samples were collected over a 42-hr time course to measure sBCMA (shed BCMA) and mBCMA (membrane BCMA). Studies were performed to determine how quickly cells respond to GSI treatment and to determine how long the effect of GSI treatment persists following pre-treatment and removal of the drug.

8.10.2. Materials and Methods 8.10.2.1. GSI Treatment of KMS11 Cells

KMS11 cells were cultured in a 6 well plate at $4 \times 10^6$ cells/well in 4 mL of RPMI1640 supplemented with 20% FBS (Gibco #11875-085, Seradigm #1500-500) per well. GSI stock solutions were prepared in DMSO at 10 mM, and added to the cells at final concentrations of 2 nM for LY411575 (Sigma #SML0506) or 200 nM for PF03084014 (Selleckchem #S8018) respectively. Cells were incubated at 37° C./5% $CO_2$, and samples were collected at the following time points: 0, 1, 2, 4, 6, 8, 12, 18, 24, 30 and 42 hr. Collected samples were evaluated for BCMA expression by ELISA and flow cytometry as outline below.

A pre-treatment study was conducted as above except that KMS11 cells were treated overnight (22 hr) with only LY411575. Cells were washed twice with 3 volumes of growth medium, and re-plated with fresh growth medium without the GSI to the original 4 mL volume. Cells were incubated at 37° C./5% CO2, and samples were collected at the following time points: 0, 1, 2, 4, 6, 8, 12, 18, 24, 30 and 42 hr. 0 hr is the starting point after the overnight treatment and washing.

8.10.2.2. Analysis of BCMA Membrane Expression In Vitro by Flow Cytometry

For each collected sample, cells were pelleted by centrifugation. Supernatants were transferred to a fresh plate and frozen at −20° C. for later analysis by ELISA. Cell pellets were resuspended in 50 μL MACS buffer containing BSA (Miltenyi #130-091-222, 130-091-376) and stained with anti-BCMA-PE (Biolegend #357504, 3:50 dilution) for 30 minutes at 4° C. Cells were washed, fixed for 20 minutes in 10% neutral buffered formalin (VWR #16004-126) and stored at 4° C. until all timepoints were collected. Samples from all timepoints were analyzed together by flow cytometry on a BD LSR Fortessa instrument. FlowJo v10 software was used for analysis. The ratio of mean fluorescent intensity (MFI) of PE (BCMA) for GSI treated wells was divided by the MFI for untreated KMS11 wells. These ratios were plotted in Tibco Spotfire or Graphpad Prism against the concentration of GSI.

Where receptor density of BCMA was provided, the anti-BCMA antibody binding capacity (ABC) on KMS11 cells was determined using Quantum Simply Cellular beads (Bangs Laboratories #815) following vendor supplied protocol. The ABC is an estimate of the quantity of receptors per cell.

8.10.2.3. Measurement of Shed BCMA Levels by ELISA sBCMA levels in supernatants collected and frozen at the various timepoints were determined by ELISA following vendor supplied protocol (R&D Systems #DY193). Briefly, recombinant human BCMA-Fc protein was included in the kit, and used to generate a standard curve. Collected samples were assayed and sBCMA concentrations extrapolated from the standard curve. Quantified values as determined by the kit were divided by 5.5 to correct for a molecular mass difference between BCMA-Fc fusion protein used in the kit as a standard curve (32,554.6 Da) and the mass of endogenously shed BCMA extra-cellular domain (5,899.3 Da). The results were plotted in Tibco Spotfire or Graphpad Prism against the concentration of GSI.

8.10.3. Results sBCMA concentrations from KMS11 cells showed no increase over time when treated with LY411575 or PF03084014 (FIG. 22A black lines), whereas a steady increase of sBCMA was observed over time from the untreated cells (FIG. 22A, gray line). mBCMA levels increased over time for KMS11 cells treated with LY411575 or PF03084014 (FIG. 22B, black lines), but remained constant for untreated KMS11 cells.

The results showed that GSIs act rapidly, with increases in membrane BCMA observed in as little as 1 hour, and with near maximal effect at 6 hours. The GSIs continued to inhibit shed BCMA and enhance membrane BCMA levels for more than 30 hours in the cell culture.

sBCMA concentrations from KMS11 cells following GSI pre-treatment and removal (washout) stayed low with a very slow increase over time, whereas untreated cells exhibited much faster accumulation of sBCMA (FIG. 23A). mBCMA levels in untreated cells remained constant over time (FIG. 23B). In contrast, mBCMA density on GSI treated KMS11 cells reached the maximum level at 4 hr and persisted at a level ~12 fold higher than the untreated cells until the 30 hr time point before decreasing (FIG. 23B).

The data showed that with overnight treatment, the effect of GSI on sBCMA and mBCMA can persist for up to 30 hours following removal of drug (washout).

8.11. Example 11: Activity of Bivalent AB3 in Combination with GSI 8.11.1. Overview A redirected T cell cytotoxicity (RTCC) assay was performed to study the enhancement of bivalent AB3 activity when dosed in combination with a GSI. The assay was performed with various dose range combinations of bivalent AB3 and three different GSIs in an 8×8 matrix fashion.

8.11.2. Materials and Methods 8.11.2.1. Healthy Human T Cell Isolation and Expansion Human T cells were isolated from peripheral blood of healthy human donors. First, peripheral blood mononuclear cells (PBMCs) were fractionated from donor blood using a Ficoll-Paque PLUS (GE Healthcare #17-1440-02) density gradient. T-cells were then isolated from PBMCs by negative selection according to manufacturer's recommended protocol (Miltenyi #130-096-535). The isolated T-cells were further expanded using Human T-Activator CD3/CD28 Dynabeads (Gibco #11132D) for nine days, then debeaded magnetically and stored as viable frozen aliquots in liquid nitrogen. The expanded T cells were used as effector T cells in RTCC assays where they were thawed from frozen aliquots, counted and used immediately at an Effector:Target (E:T) cell ratio of 3:1.

8.11.2.2. RTCC Assay

The target MM cell line KMS11 was transduced to constitutively express luciferase, which was used to measure cell viability/survival. KMS11 cells were pelleted and resuspended in fresh media immediately prior to plating to remove any basal level of shed BCMA that can have been present. 2,500 KMS11-luc target cells in 25 µL TCM were added to wells of 384-well plates. 50 nL of serially diluted bivalent AB3 and GSI solutions (LY411575, PR03084014, and BMS0708163) were acoustically dispensed to corresponding wells of the assay plates. 7,500 expanded T cells, as described above, were added to corresponding wells of assay plate in 20 µL TCM. The assay was incubated at 37° C./5% CO2 for 20 hr, followed by measurement of luciferase activity to indicate target cell viability (BrightGlo, Promega #E2650) following manufacturer's protocols. Target cells only (KMS11) without T cells or antibodies serve as control and represent 100% luciferase activity (100% viability). Data were plotted and analyzed using Spotfire, where EC50 values were calculated using sigmoidal, 4-parameter non-linear regression curve fit.

8.11.3. Results

Bivalent AB3 showed a dose dependent effect on KMS11 cell death in the RTCC assay. As GSI concentrations were increased in the presence of bivalent AB3, the response curves shifted to the left, and occurred with combination of each of the three GSIs: LY411575 (FIG. 24A), PF03084014 (FIG. 24B), and BMS0708163 (FIG. 24C).

LY411575 at 7.8 pM or lower had no effect on bivalent AB3 activity, a small effect at 31.2 pM, and a significant enhancement on bivalent AB3 potency at concentrations of 125 pM or higher. Similarly, PF03084014 showed modest enhancement at 3 nM and significant enhancement at 12 nM or higher. For BMS-708163, modest enhancement was observed at 8 nM and a significant enhancement was observed at 31 nM or higher. The maximal enhancement in the potency of bivalent AB3 by a GSI combination is 10 to 15-fold (EC50 values in FIG. 3C). These results demonstrated that the RTCC potency of bivalent AB3 was synergistically enhanced when dosed in combination with a GSI.

8.12. Example 12: GSI Effective Dose Range for BCMA Shedding Inhibition, Notch Signaling Inhibition, and Synergy with Bivalent AB3

8.12.1. Overview

The same GSI concentrations were used in different assays in order to overlay and compare effective dose ranges of GSIs. The effect of GSIs on sBCMA and mBCMA of KMS11 cells were re-measured to match the same concentrations used in combination with bivalent AB3. To determine the effective dose range of GSIs for NOTCH inhibition, HPB-ALL cells were treated with GSI and mRNA of NOTCH target transcripts were evaluated. GSI effect on the RTCC EC50 values of bivalent AB3 (FIG. 24) were plotted against the concentration of GSIs to overlay and compare effective dose ranges.

8.12.2. Materials and Methods 8.12.2.1. GSI Treatment of KMS11 Cells

KMS11 cells were cultured in a 96-well plate at 50,000 cells per well in a final volume of 100 µL that included a 12-point, 5-fold serial dilution of GSIs in RPMI1640 supplemented with 20% FBS (Gibco #11875-085, Seradigm #1500-500). The starting concentration of LY411575

(Sigma #SML0506) prior to dilution was 1 µM. The starting concentrations of PF03084014 (Selleckchem #S8018) and BMS-708163 (Selleckchem #S1262) prior to dilution were 10 µM. Cells were incubated for 20 hours at 37° C./5% CO2. Cells were pelleted, the supernatant was collected for ELISA determination of shed BCMA levels, and cell pellets were stained for flow cytometry evaluation of BCMA membrane expression levels according to the methods described in Example 10. Results were plotted in Tibco Spotfire.

8.12.2.2. NOTCH Signaling Inhibition Assay

T cell leukemia cell line HBP-ALL (DSMZ #ACC483) was cultured and treated with GSIs in the same way as described above for KMS11 cells. Cells were incubated for 29 hours at 37° C./5% CO2, pelleted and lysed with buffer RLT (Qiagen). RNA was purified using RNeasy mini (Qiagen #74106) following vendor supplied protocol. Resulting RNA was used to synthesize cDNA following vendor supplied protocol (ABI #4322171). Transcript levels of downstream Notch target genes HES1 and DTX1 (ABI #Hs_0017878.m1, Hs_01114113.m1), each multiplexed with human Cyclophilin A endogenous control (ABI 4326316RE) for template normalization, were evaluated by qPCR on the AB17900 instrument using TaqMan universal PCR master mix (ABI 4304437) and following vendor supplied protocols. Resulting Threshold Cycle (CT) values were used to determine relative expression of each gene compared to an untreated control. For each well, the CT of the endogenous control was subtracted from the CT of the target gene (Delta CT, ΔCT). The delta CT of the untreated control well was then subtracted from the delta CT of the treated well (DeltaDelta CT, ΔΔCT). To correct for the logarithmic amplification of PCR, a doubling of product with each cycle, relative expression level is expressed as $2^{-\Delta\Delta CT}$. Untreated wells have a relative expression of 1; decreases in expression upon treatment will have relative expression levels lower than 1. Relative expression levels were plotted in Tibco Spotfire.

8.12.2.3. RTCC EC50 Values

Data from bivalent AB3 and GSI combinations from Example 11 (FIG. 24) were plotted and analyzed using Spotfire, where EC50 values were calculated using sigmoidal, 4-parameter non-linear regression curve fit.

8.12.3. Results

Dose-response curves of GSIs on sBCMA and mBCMA (KMS11 cells), Notch signaling (HBP-ALL cells), and RTCC activity of bivalent AB3 (KMS11 cells) across the same dose ranges were aligned. GSI treatment inhibited sBCMA and increased mBCMA expression on KMS11 cells in a dose dependent manner (FIG. 25A). The minimum concentration of GSIs to enhance the RTCC activity of bivalent AB3 were slightly higher than that required to reduce shedding of BCMA. As expected, the greatest synergy with bivalent AB3 was achieved at the same concentrations where maximal effect on sBCMA and mBCMA were observed (FIG. 25A; FIG. 25C). Within the same effective dose range (delineated by dashed lines) Notch signaling inhibition was observed in a concentration-dependent manner (FIG. 25B).

8.13. Example 13: In Vivo Response to GSI Treatment in a KMS11 Xenograft Model

8.13.1. Overview

Without being bound by theory, it is believed that a GSI administered in combination with a BCMA binding molecule (e.g., a BBM) will increase the effectiveness of the BCMA binding molecule in treating diseases and disorders associated with BCMA expression by decreasing the amount of soluble BCMA and increasing the amount of membrane bound BCMA available for binding to the BCMA binding molecule. Studies were performed to evaluate the effect of GSIs on sBCMA and mBCMA in vivo in a KMS11 xenograft model.

8.13.2. Materials and Methods

8.13.2.1. In Vivo GSI Treatment

On Day 0, KMS11-Luc cells were harvested and suspended in Hanks Balanced Salt Solution (HBSS) and 50% matrigel solution at a concentration of $25 \times 10^6$ cells/mL. Female NOD.Cg-Prkdc$^{scid}$Il2rg$^{tm1Wjl}$/SzJ mice (NSG mice) at ~6 weeks old (Jackson Laboratories, ME, USA), were implanted sub-cutaneously (SQ) with 200 µL of the cell suspension to deliver $5 \times 10^6$ KMS11-Luc cells SQ in the right flank. Seven days following tumor inoculation, each mouse received an adoptive transfer (AdT) of $10 \times 10^6$ of peripheral blood mononuclear cells (PBMCs) in 100 µL via IV injection in the lateral tail vein. The PBMCs were previously isolated from a human leukopak, frozen and stored in Cryostor10 media in vapor phase liquid Nitrogen tank until use. Immediately prior to AdT, PBMCs were thawed and suspended at a concentration of $100 \times 10^6$ cells/ml in Hanks Balanced Salt Solution (HBSS). When tumor burden (TB) reached an average of ~400 m$^3$ (Day 15) animals were randomized and received either vehicle or 150 mg/kg or PF03084014 dosed at 10 mL/kg BID for 5 days. At 1, 7, 24 and 48 hours post last dose, cohorts of animals (n=3) were euthanized and the tumors and serum were extracted to evaluate levels of membrane BCMA (tumor PD) and shed/soluble BCMA (serum).

Tumor burden and body weights were recorded twice weekly. Tumor burden was measured by caliper measurements and recorded in WinWedge. Body weights were captured and recorded in WinWedge.

8.13.2.2. Evaluation of Membrane BCMA by Flow Cytometry

To obtain single cell suspensions from excised tumors, the tissues were minced with scissors followed by mechanical homogenization in dissociation buffer containing RPMI (Gibco, Life Technologies) with Liberase™ research grade collagenase (Roche) and DNase I recombinase (Roche) using the GentleMAX (Miltenyi). Following a 5 minute incubation at 37° C. in a water or bead bath, the homogenates were quenched with 10% FBS and filtered on a 70-µM sieve (352350, Falcon). The concentration of single cell suspensions were measured on the Vi-Cell (Beckman Coulter), and cells were pelleted by centrifugation for 5 minutes at 1200 rpm. The supernatants were discarded and cell pellets were resuspended in 400 µL of RPMI (Gibco, Life Technologies). Tumor cells were plated in a volume of 100 µL/well at a cell density of 500,000 to 2 million/well.

For cell surface staining, live/dead stain was added to plated samples in DPBS and incubated for 30 minutes. Following live/dead staining, cells were incubated with saturating concentrations of mouse Fc block (BD Biosciences) for 30 minutes, followed by a 30 minute incubation with fluorochrome-conjugated antibodies with the flow cytometry panel in Table 28.

TABLE 28

| Marker | Clone | Fluorophore | dilution |
|---|---|---|---|
| BCMA | VICKY | PE | 1:50 |
| mCD45 | 30-F11 | FITC | 1:50 |
| HLA-ABC | DX17 | APC | 1:50 |
| Live dead | — | efluor780 (APC-Cy7) | 1:1000 |

During the blocking and staining procedures, cells were maintained on ice and shielded from light. Following surface staining, cells were fixed in 4% PFA and resuspended in 200 μL 2% FBS+PBS. All samples were analyzed together by flow cytometry at the completion of the study. Data acquisition was performed on an LSR-II flow cytometer (BD biosciences). The machine performances were verified daily using Cytometer Setup program in DIVA (BD Biosciences).

Analysis was performed using FLOWJO v10.0.7 software from Treestar. For each analysis, the population of interest was gated to identify live leukocytes using a combination of morphological parameters (All cells: SSC-A vs FSC-A, single cells: SSC-H vs SSC-W), and dead cell exclusion using eFluor780 (BD Biosciences). Mouse CD45-specific labeling was used to exclude mouse blood cells, human HLA-specific labeling was used to isolate and identify human cells, followed by human BCMA-specific labeled antibody to identify the membrane levels of BCMA on the tumor cells. BCMA expression on treated vs. untreated samples at each time point was reported as mean fluorescent intensity (MFI).

8.13.2.3. Measurement of Shed BCMA Levels by ELISA

Shed BCMA levels in serum were measured by ELISA as described in Example 10.

8.13.3. Results

Membrane BCMA levels, measured as mean florescent intensity (MFI), are shown in FIG. 26. Shed BCMA levels, represented as mean data with the SEM, are shown in FIG. 27. There was a 10-fold increase in mBCMA following PFZ03084014 treatment compared to the vehicle control. This increase was sustained through the 7 hour time point. By 24 hours post last dose, mBCMA levels had dropped back to levels similar to those observed for the vehicle control. Levels of sBCMA were ablated for up to 24 hours post last dose of PFZ03084014. Between 24 and 48 hours post last dose, levels of sBCMA subsequently increased, returning to levels comparable to those observed for the vehicle treated animals. The results of this in vivo study support the use of GSIs in combination with BCMA binding molecules for treating diseases and disorders associated with expression of BCMA, as GSI treatment was found to increase mBCMA levels and decrease sBCMA levels.

8.14. Example 14: Bivalent AB3 Compared with Other BCMA-CD3 Bispecific Molecules h2B4_C29 is a BCMA-CD3 bispecific antibody in development for the treatment of multiple myeloma (see, WO2016/0166629). Preliminary data with bivalent AB3 and h2B4_C29 from KMS11 and PBMC/T cell co-culture studies indicate that bivalent AB3 mediates lower levels of cytokine induction than h2B4_C29 (FIG. 28), suggesting that patients treated with AB3 may have a reduced risk of cytokine release syndrome compared to patients treated with h2B4_C29. Preliminary data also indicates that T cells activated by h2B4_C29 in the presence of KMS11 cells mediate more TCR downregulation than T cells activated by bivalent AB3 (data not shown), suggesting that bivalent AB3 may exhibit more sustained anti-cancer activity than h2B4_C29.

In a KMS11 xenograft model, some preliminary data suggests that bivalent AB3 and h2B4_C29 have greater anti-tumor activity compared to BCMA-CD3 bispecific molecules from EngMab and Janssen (data not shown).

9. SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

1. A BCMA binding molecule that specifically binds to human BCMA and comprises CDR-L1, CDR-L2 and CDR-L3 sequences set forth in Table 1A-1, Table 1B-1, Table 1C-1, Table 1D-1, Table 1E-1, Table 1F-1, Table 1G-1, Table 1H-1, Table 1I-1, Table 1J-1, Table 1K-1(a), Table 1K-1(b), Table 1L-1, Table 1M-1, Table 1N-1(a), or Table 1N-1(b), and the corresponding CDR-H1, CDR-H2 and CDR-H3 sequence set forth in Table 1A-2, Table 1B-2, Table 1C-2, Table 1D-2, Table 1E-2, Table 1F-2, Table 1G-2, Table 1H-2, Table 1I-2, Table 1J-2, Table 1K-2, Table 1K-2, Table 1L-2, Table 1M-2, Table 1N-2, or Table 1N-2, respectively.

2. A BCMA binding molecule that specifically binds to human BCMA and comprises CDR-L1, CDR-L2 and CDR-L3 sequences set forth in Table 1A-1, Table 1B-1, Table 1C-1, Table 1D-1, Table 1E-1, Table 1F-1, Table 1G-1, Table 1H-1, Table 1I-1, Table 1J-1, Table 1K-1(a), Table 1L-1, Table 1M-1, or Table 1N-1(a), and the corresponding CDR-H1, CDR-H2 and CDR-H3 sequence set forth in Table 1A-2, Table 1B-2, Table 1C-2, Table 1D-2, Table 1E-2, Table 1F-2, Table 1G-2, Table 1H-2, Table 1I-2, Table 1J-2, Table 1K-2, Table 1L-2, Table 1M-2, or Table 1N-2, respectively.

3. The BCMA binding molecule of embodiment 1 or embodiment 2, which comprises CDR-L1, CDR-L2 and CDR-L3 sequences set forth in Table 1A-1 and the corresponding CDR-H1, CDR-H2 and CDR-H3 sequence set forth in Table 1A-2.

4. The BCMA binding molecule of embodiment 1 or embodiment 2, which comprises CDR-L1, CDR-L2 and CDR-L3 sequences set forth in Table 1B-1 and the corresponding CDR-H1, CDR-H2 and CDR-H3 sequence set forth in Table 1B-2.

5. The BCMA binding molecule of embodiment 1 or embodiment 2, which comprises CDR-L1, CDR-L2 and CDR-L3 sequences set forth in Table 1C-1 and the corresponding CDR-H1, CDR-H2 and CDR-H3 sequence set forth in Table 1C-2.

6. The BCMA binding molecule of embodiment 1 or embodiment 2, which comprises CDR-L1, CDR-L2 and CDR-L3 sequences set forth in Table 1D-1 and the corresponding CDR-H1, CDR-H2 and CDR-H3 sequence set forth in Table 1D-2.

7. The BCMA binding molecule of embodiment 1 or embodiment 2, which comprises CDR-L1, CDR-L2 and CDR-L3 sequences set forth in Table 1E-1 and the corresponding CDR-H1, CDR-H2 and CDR-H3 sequence set forth in Table 1E-2.

8. The BCMA binding molecule of embodiment 1 or embodiment 2, which comprises CDR-L1, CDR-L2 and CDR-L3 sequences set forth in Table 1F-1 and the corresponding CDR-H1, CDR-H2 and CDR-H3 sequence set forth in Table 1F-2.

9. The BCMA binding molecule of embodiment 1 or embodiment 2, which comprises CDR-L1, CDR-L2 and CDR-L3 sequences set forth in Table 1G-1 and the corresponding CDR-H1, CDR-H2 and CDR-H3 sequence set forth in Table 1G-2.

10. The BCMA binding molecule of embodiment 1 or embodiment 2, which comprises CDR-L1, CDR-L2 and CDR-L3 sequences set forth in Table 1H-1 and the corresponding CDR-H1, CDR-H2 and CDR-H3 sequence set forth in Table 1H-2.

11. The BCMA binding molecule of embodiment 1 or embodiment 2, which comprises CDR-L1, CDR-L2 and CDR-L3 sequences set forth in Table 1I-1 and the corresponding CDR-H1, CDR-H2 and CDR-H3 sequence set forth in Table 1I-2.

12. The BCMA binding molecule of embodiment 1 or embodiment 2, which comprises CDR-L1, CDR-L2 and CDR-L3 sequences set forth in Table 1J-1 and the corresponding CDR-H1, CDR-H2 and CDR-H3 sequence set forth in Table 1J-2.

13. The BCMA binding molecule of embodiment 1 or embodiment 2, which comprises CDR-L1, CDR-L2 and CDR-L3 sequences set forth in Table 1K-1(a) and the corresponding CDR-H1, CDR-H2 and CDR-H3 sequence set forth in Table 1K-2.

14. The BCMA binding molecule of embodiment 1, which comprises CDR-L1, CDR-L2 and CDR-L3 sequences set forth in Table 1K-1(b) and the corresponding CDR-H1, CDR-H2 and CDR-H3 sequence set forth in Table 1K-2.

15. The BCMA binding molecule of embodiment 1 or embodiment 2, which comprises CDR-L1, CDR-L2 and CDR-L3 sequences set forth in Table 1L-1 and the corresponding CDR-H1, CDR-H2 and CDR-H3 sequence set forth in Table 1L-2.

16. The BCMA binding molecule of embodiment 1 or embodiment 2, which comprises CDR-L1, CDR-L2 and CDR-L3 sequences set forth in Table 1M-1 and the corresponding CDR-H1, CDR-H2 and CDR-H3 sequence set forth in Table 1M-2.

17. The BCMA binding molecule of embodiment 1 or embodiment 2, which comprises CDR-L1, CDR-L2 and CDR-L3 sequences set forth in Table 1N-1(a) and the corresponding CDR-H1, CDR-H2 and CDR-H3 sequence set forth in Table 1N-2.

18. The BCMA binding molecule of embodiment 1, which comprises CDR-L1, CDR-L2 and CDR-L3 sequences set forth in Table 1N-1(b) and the corresponding CDR-H1, CDR-H2 and CDR-H3 sequence set forth in Table 1N-2.

19. The BCMA binding molecule of embodiment 3, wherein the CDR-L1, CDR-L2, CDR-L3, CDR-H1, CDR-H2 and CDR-H3 sequences are those of C1.

20. The BCMA binding molecule of embodiment 3, wherein the CDR-L1, CDR-L2, CDR-L3, CDR-H1, CDR-H2 and CDR-H3 sequences are those of C2.

21. The BCMA binding molecule of embodiment 3, wherein the CDR-L1, CDR-L2, CDR-L3, CDR-H1, CDR-H2 and CDR-H3 sequences are those of C3.

22. The BCMA binding molecule of embodiment 3, wherein the CDR-L1, CDR-L2, CDR-L3, CDR-H1, CDR-H2 and CDR-H3 sequences are those of C4.

23. The BCMA binding molecule of embodiment 3, wherein the CDR-L1, CDR-L2, CDR-L3, CDR-H1, CDR-H2 and CDR-H3 sequences are those of C5.

24. The BCMA binding molecule of embodiment 3, wherein the CDR-L1, CDR-L2, CDR-L3, CDR-H1, CDR-H2 and CDR-H3 sequences are those of C6.

25. The BCMA binding molecule of embodiment 3, wherein the CDR-L1, CDR-L2, CDR-L3, CDR-H1, CDR-H2 and CDR-H3 sequences are those of C7.

26. The BCMA binding molecule of embodiment 3, wherein the CDR-L1, CDR-L2, CDR-L3, CDR-H1, CDR-H2 and CDR-H3 sequences are those of C8.

27. The BCMA binding molecule of embodiment 3, wherein the CDR-L1, CDR-L2, CDR-L3, CDR-H1, CDR-H2 and CDR-H3 sequences are those of C9.

28. The BCMA binding molecule of embodiment 3, wherein the CDR-L1, CDR-L2, CDR-L3, CDR-H1, CDR-H2 and CDR-H3 sequences are those of C10.

29. The BCMA binding molecule of embodiment 3, wherein the CDR-L1, CDR-L2, CDR-L3, CDR-H1, CDR-H2 and CDR-H3 sequences are those of C11.

30. The BCMA binding molecule of embodiment 3, wherein the CDR-L1, CDR-L2, CDR-L3, CDR-H1, CDR-H2 and CDR-H3 sequences are those of C12.

31. The BCMA binding molecule of embodiment 4, wherein the CDR-L1, CDR-L2, CDR-L3, CDR-H1, CDR-H2 and CDR-H3 sequences are those of C13.

32. The BCMA binding molecule of embodiment 4, wherein the CDR-L1, CDR-L2, CDR-L3, CDR-H1, CDR-H2 and CDR-H3 sequences are those of C14.

33. The BCMA binding molecule of embodiment 4, wherein the CDR-L1, CDR-L2, CDR-L3, CDR-H1, CDR-H2 and CDR-H3 sequences are those of C15.

34. The BCMA binding molecule of embodiment 4, wherein the CDR-L1, CDR-L2, CDR-L3, CDR-H1, CDR-H2 and CDR-H3 sequences are those of C16.

35. The BCMA binding molecule of embodiment 4, wherein the CDR-L1, CDR-L2, CDR-L3, CDR-H1, CDR-H2 and CDR-H3 sequences are those of C17.

36. The BCMA binding molecule of embodiment 4, wherein the CDR-L1, CDR-L2, CDR-L3, CDR-H1, CDR-H2 and CDR-H3 sequences are those of C18.

37. The BCMA binding molecule of embodiment 4, wherein the CDR-L1, CDR-L2, CDR-L3, CDR-H1, CDR-H2 and CDR-H3 sequences are those of C19.

38. The BCMA binding molecule of embodiment 4, wherein the CDR-L1, CDR-L2, CDR-L3, CDR-H1, CDR-H2 and CDR-H3 sequences are those of C20.

39. The BCMA binding molecule of embodiment 4, wherein the CDR-L1, CDR-L2, CDR-L3, CDR-H1, CDR-H2 and CDR-H3 sequences are those of C21.

40. The BCMA binding molecule of embodiment 4, wherein the CDR-L1, CDR-L2, CDR-L3, CDR-H1, CDR-H2 and CDR-H3 sequences are those of C22.

41. The BCMA binding molecule of embodiment 4, wherein the CDR-L1, CDR-L2, CDR-L3, CDR-H1, CDR-H2 and CDR-H3 sequences are those of C23.

42. The BCMA binding molecule of embodiment 4, wherein the CDR-L1, CDR-L2, CDR-L3, CDR-H1, CDR-H2 and CDR-H3 sequences are those of C24.

43. The BCMA binding molecule of embodiment 4, wherein the CDR-L1, CDR-L2, CDR-L3, CDR-H1, CDR-H2 and CDR-H3 sequences are those of C25.

44. The BCMA binding molecule of embodiment 4, wherein the CDR-L1, CDR-L2, CDR-L3, CDR-H1, CDR-H2 and CDR-H3 sequences are those of C26.

45. The BCMA binding molecule of embodiment 4, wherein the CDR-L1, CDR-L2, CDR-L3, CDR-H1, CDR-H2 and CDR-H3 sequences are those of C27.

46. The BCMA binding molecule of embodiment 4, wherein the CDR-L1, CDR-L2, CDR-L3, CDR-H1, CDR-H2 and CDR-H3 sequences are those of C28.

47. The BCMA binding molecule of any one of embodiments 5 to 10, wherein the CDR-L1, CDR-L2, CDR-L3, CDR-H1, CDR-H2 and CDR-H3 sequences are those of AB1.

48. The BCMA binding molecule of any one of embodiments 5 to 10, wherein the CDR-L1, CDR-L2, CDR-L3, CDR-H1, CDR-H2 and CDR-H3 sequences are those of AB2.

49. The BCMA binding molecule of any one of embodiments 5 to 10, wherein the CDR-L1, CDR-L2, CDR-L3, CDR-H1, CDR-H2 and CDR-H3 sequences are those of R1F2.
50. The BCMA binding molecule of any one of embodiments 5 to 10, wherein the CDR-L1, CDR-L2, CDR-L3, CDR-H1, CDR-H2 and CDR-H3 sequences are those of PALF03.
51. The BCMA binding molecule of any one of embodiments 5 to 10, wherein the CDR-L1, CDR-L2, CDR-L3, CDR-H1, CDR-H2 and CDR-H3 sequences are those of PALF04.
52. The BCMA binding molecule of any one of embodiments 5 to 10, wherein the CDR-L1, CDR-L2, CDR-L3, CDR-H1, CDR-H2 and CDR-H3 sequences are those of PALF05.
53. The BCMA binding molecule of any one of embodiments 5 to 10, wherein the CDR-L1, CDR-L2, CDR-L3, CDR-H1, CDR-H2 and CDR-H3 sequences are those of PALF06.
54. The BCMA binding molecule of any one of embodiments 5 to 10, wherein the CDR-L1, CDR-L2, CDR-L3, CDR-H1, CDR-H2 and CDR-H3 sequences are those of PALF07.
55. The BCMA binding molecule of any one of embodiments 5 to 10, wherein the CDR-L1, CDR-L2, CDR-L3, CDR-H1, CDR-H2 and CDR-H3 sequences are those of PALF08.
56. The BCMA binding molecule of any one of embodiments 5 to 10, wherein the CDR-L1, CDR-L2, CDR-L3, CDR-H1, CDR-H2 and CDR-H3 sequences are those of PALF09.
57. The BCMA binding molecule of any one of embodiments 5 to 10, wherein the CDR-L1, CDR-L2, CDR-L3, CDR-H1, CDR-H2 and CDR-H3 sequences are those of PALF12.
58. The BCMA binding molecule of any one of embodiments 5 to 10, wherein the CDR-L1, CDR-L2, CDR-L3, CDR-H1, CDR-H2 and CDR-H3 sequences are those of PALF13.
59. The BCMA binding molecule of any one of embodiments 5 to 10, wherein the CDR-L1, CDR-L2, CDR-L3, CDR-H1, CDR-H2 and CDR-H3 sequences are those of PALF14.
60. The BCMA binding molecule of any one of embodiments 5 to 10, wherein the CDR-L1, CDR-L2, CDR-L3, CDR-H1, CDR-H2 and CDR-H3 sequences are those of PALF15.
61. The BCMA binding molecule of any one of embodiments 5 to 10, wherein the CDR-L1, CDR-L2, CDR-L3, CDR-H1, CDR-H2 and CDR-H3 sequences are those of PALF16.
62. The BCMA binding molecule of any one of embodiments 5 to 10, wherein the CDR-L1, CDR-L2, CDR-L3, CDR-H1, CDR-H2 and CDR-H3 sequences are those of PALF17.
63. The BCMA binding molecule of any one of embodiments 5 to 10, wherein the CDR-L1, CDR-L2, CDR-L3, CDR-H1, CDR-H2 and CDR-H3 sequences are those of PALF18.
64. The BCMA binding molecule of any one of embodiments 5 to 10, wherein the CDR-L1, CDR-L2, CDR-L3, CDR-H1, CDR-H2 and CDR-H3 sequences are those of PALF19.
65. The BCMA binding molecule of any one of embodiments 5 to 10, wherein the CDR-L1, CDR-L2, CDR-L3, CDR-H1, CDR-H2 and CDR-H3 sequences are those of PALF20.
66. The BCMA binding molecule of any one of embodiments 11 to 18, wherein the CDR-L1, CDR-L2, CDR-L3, CDR-H1, CDR-H2 and CDR-H3 sequences are those of AB3.
67. The BCMA binding molecule of any one of embodiments 11 to 18, wherein the CDR-L1, CDR-L2, CDR-L3, CDR-H1, CDR-H2 and CDR-H3 sequences are those of PI-61.
68. The BCMA binding molecule of any one of embodiments 11 to 18, wherein the CDR-L1, CDR-L2, CDR-L3, CDR-H1, CDR-H2 and CDR-H3 sequences are those of H2/L2-22.
69. The BCMA binding molecule of any one of embodiments 11 to 18, wherein the CDR-L1, CDR-L2, CDR-L3, CDR-H1, CDR-H2 and CDR-H3 sequences are those of H2/L2-88.
70. The BCMA binding molecule of any one of embodiments 11 to 18, wherein the CDR-L1, CDR-L2, CDR-L3, CDR-H1, CDR-H2 and CDR-H3 sequences are those of H2/L2-36.
71. The BCMA binding molecule of any one of embodiments 11 to 18, wherein the CDR-L1, CDR-L2, CDR-L3, CDR-H1, CDR-H2 and CDR-H3 sequences are those of H2/L2-34.
72. The BCMA binding molecule of any one of embodiments 11 to 18, wherein the CDR-L1, CDR-L2, CDR-L3, CDR-H1, CDR-H2 and CDR-H3 sequences are those of H2/L2-68.
73. The BCMA binding molecule of any one of embodiments 11 to 18, wherein the CDR-L1, CDR-L2, CDR-L3, CDR-H1, CDR-H2 and CDR-H3 sequences are those of H2/L2-18.
74. The BCMA binding molecule of any one of embodiments 11 to 18, wherein the CDR-L1, CDR-L2, CDR-L3, CDR-H1, CDR-H2 and CDR-H3 sequences are those of H2/L2-47.
75. The BCMA binding molecule of any one of embodiments 11 to 18, wherein the CDR-L1, CDR-L2, CDR-L3, CDR-H1, CDR-H2 and CDR-H3 sequences are those of H2/L2-20.
76. The BCMA binding molecule of any one of embodiments 11 to 18, wherein the CDR-L1, CDR-L2, CDR-L3, CDR-H1, CDR-H2 and CDR-H3 sequences are those of H2/L2-80.
77. The BCMA binding molecule of any one of embodiments 11 to 18, wherein the CDR-L1, CDR-L2, CDR-L3, CDR-H1, CDR-H2 and CDR-H3 sequences are those of H2/L2-83.
78. The BCMA binding molecule of any one of embodiments 11 to 18, wherein the CDR-L1, CDR-L2, CDR-L3, CDR-H1, CDR-H2 and CDR-H3 sequences are those of H3-1.
79. The BCMA binding molecule of any one of embodiments 11 to 18, wherein the CDR-L1, CDR-L2, CDR-L3, CDR-H1, CDR-H2 and CDR-H3 sequences are those of H3-2.
80. The BCMA binding molecule of any one of embodiments 11 to 18, wherein the CDR-L1, CDR-L2, CDR-L3, CDR-H1, CDR-H2 and CDR-H3 sequences are those of H3-3.

81. The BCMA binding molecule of any one of embodiments 11 to 18, wherein the CDR-L1, CDR-L2, CDR-L3, CDR-H1, CDR-H2 and CDR-H3 sequences are those of H3-4.
82. The BCMA binding molecule of any one of embodiments 11 to 18, wherein the CDR-L1, CDR-L2, CDR-L3, CDR-H1, CDR-H2 and CDR-H3 sequences are those of H3-5.
83. The BCMA binding molecule of any one of embodiments 11 to 18, wherein the CDR-L1, CDR-L2, CDR-L3, CDR-H1, CDR-H2 and CDR-H3 sequences are those of H3-6.
84. The BCMA binding molecule of any one of embodiments 11 to 18, wherein the CDR-L1, CDR-L2, CDR-L3, CDR-H1, CDR-H2 and CDR-H3 sequences are those of H3-7.
85. The BCMA binding molecule of any one of embodiments 11 to 18, wherein the CDR-L1, CDR-L2, CDR-L3, CDR-H1, CDR-H2 and CDR-H3 sequences are those of H3-8.
86. The BCMA binding molecule of any one of embodiments 11 to 18, wherein the CDR-L1, CDR-L2, CDR-L3, CDR-H1, CDR-H2 and CDR-H3 sequences are those of H3-9.
87. The BCMA binding molecule of any one of embodiments 11 to 18, wherein the CDR-L1, CDR-L2, CDR-L3, CDR-H1, CDR-H2 and CDR-H3 sequences are those of H3-10.
88. The BCMA binding molecule of any one of embodiments 11 to 18, wherein the CDR-L1, CDR-L2, CDR-L3, CDR-H1, CDR-H2 and CDR-H3 sequences are those of H3-11.
89. The BCMA binding molecule of any one of embodiments 11 to 18, wherein the CDR-L1, CDR-L2, CDR-L3, CDR-H1, CDR-H2 and CDR-H3 sequences are those of H3-12.
90. The BCMA binding molecule of any one of embodiments 11 to 18, wherein the CDR-L1, CDR-L2, CDR-L3, CDR-H1, CDR-H2 and CDR-H3 sequences are those of H3-13.
91. The BCMA binding molecule of any one of embodiments 11 to 18, wherein the CDR-L1, CDR-L2, CDR-L3, CDR-H1, CDR-H2 and CDR-H3 sequences are those of H3-14.
92. The BCMA binding molecule of any one of embodiments 11 to 18, wherein the CDR-L1, CDR-L2, CDR-L3, CDR-H1, CDR-H2 and CDR-H3 sequences are those of H3-15.
93. The BCMA binding molecule of embodiment 1 or embodiment 2, which comprises a light chain variable sequence set forth in Table 1O-1 and the corresponding heavy chain variable sequence set forth in Table 1O-2.
94. The BCMA binding molecule of embodiment 93, wherein the light chain variable sequence and the corresponding heavy chain variable sequence are those of AB1.
95. The BCMA binding molecule of embodiment 93, wherein the light chain variable sequence and the corresponding heavy chain variable sequence are those of AB2.
96. The BCMA binding molecule of embodiment 93, wherein the light chain variable sequence and the corresponding heavy chain variable sequence are those of AB3.
97. The BCMA binding molecule of embodiment 93, wherein the light chain variable sequence and the corresponding heavy chain variable sequence are those of R1F2.
98. The BCMA binding molecule of embodiment 93, wherein the light chain variable sequence and the corresponding heavy chain variable sequence are those of PALF03.
99. The BCMA binding molecule of embodiment 93, wherein the light chain variable sequence and the corresponding heavy chain variable sequence are those of PALF04.
100. The BCMA binding molecule of embodiment 93, wherein the light chain variable sequence and the corresponding heavy chain variable sequence are those of PALF05.
101. The BCMA binding molecule of embodiment 93, wherein the light chain variable sequence and the corresponding heavy chain variable sequence are those of PALF06.
102. The BCMA binding molecule of embodiment 93, wherein the light chain variable sequence and the corresponding heavy chain variable sequence are those of PALF07.
103. The BCMA binding molecule of embodiment 93, wherein the light chain variable sequence and the corresponding heavy chain variable sequence are those of PALF08.
104. The BCMA binding molecule of embodiment 93, wherein the light chain variable sequence and the corresponding heavy chain variable sequence are those of PALF09.
105. The BCMA binding molecule of embodiment 93, wherein the light chain variable sequence and the corresponding heavy chain variable sequence are those of PALF12.
106. The BCMA binding molecule of embodiment 93, wherein the light chain variable sequence and the corresponding heavy chain variable sequence are those of PALF13.
107. The BCMA binding molecule of embodiment 93, wherein the light chain variable sequence and the corresponding heavy chain variable sequence are those of PALF14.
108. The BCMA binding molecule of embodiment 93, wherein the light chain variable sequence and the corresponding heavy chain variable sequence are those of PALF15.
109. The BCMA binding molecule of embodiment 93, wherein the light chain variable sequence and the corresponding heavy chain variable sequence are those of PALF16.
110. The BCMA binding molecule of embodiment 93, wherein the light chain variable sequence and the corresponding heavy chain variable sequence are those of PALF17.
111. The BCMA binding molecule of embodiment 93, wherein the light chain variable sequence and the corresponding heavy chain variable sequence are those of PALF18.
112. The BCMA binding molecule of embodiment 93, wherein the light chain variable sequence and the corresponding heavy chain variable sequence are those of PALF19.

113. The BCMA binding molecule of embodiment 93, wherein the light chain variable sequence and the corresponding heavy chain variable sequence are those of PALF20.
114. The BCMA binding molecule of embodiment 93, wherein the light chain variable sequence and the corresponding heavy chain variable sequence are those of PI-61.
115. The BCMA binding molecule of embodiment 93, wherein the light chain variable sequence and the corresponding heavy chain variable sequence are those of H2/L2-88.
116. The BCMA binding molecule of embodiment 93, wherein the light chain variable sequence and the corresponding heavy chain variable sequence are those of H2/L2-36.
117. The BCMA binding molecule of embodiment 93, wherein the light chain variable sequence and the corresponding heavy chain variable sequence are those of H2/L2-34.
118. The BCMA binding molecule of embodiment 93, wherein the light chain variable sequence and the corresponding heavy chain variable sequence are those of H2/L2-68.
119. The BCMA binding molecule of embodiment 93, wherein the light chain variable sequence and the corresponding heavy chain variable sequence are those of H2/L2-18.
120. The BCMA binding molecule of embodiment 93, wherein the light chain variable sequence and the corresponding heavy chain variable sequence are those of H2/L2-47.
121. The BCMA binding molecule of embodiment 93, wherein the light chain variable sequence and the corresponding heavy chain variable sequence are those of H2/L2-20.
122. The BCMA binding molecule of embodiment 93, wherein the light chain variable sequence and the corresponding heavy chain variable sequence are those of H2/L2-80.
123. The BCMA binding molecule of embodiment 93, wherein the light chain variable sequence and the corresponding heavy chain variable sequence are those of H2/L2-83.
124. The BCMA binding molecule of embodiment 93, wherein the light chain variable sequence and the corresponding heavy chain variable sequence are those of H3-1.
125. The BCMA binding molecule of embodiment 93, wherein the light chain variable sequence and the corresponding heavy chain variable sequence are those of H3-2.
126. The BCMA binding molecule of embodiment 93, wherein the light chain variable sequence and the corresponding heavy chain variable sequence are those of H3-3.
127. The BCMA binding molecule of embodiment 93, wherein the light chain variable sequence and the corresponding heavy chain variable sequence are those of H3-4.
128. The BCMA binding molecule of embodiment 93, wherein the light chain variable sequence and the corresponding heavy chain variable sequence are those of H3-5.
129. The BCMA binding molecule of embodiment 93, wherein the light chain variable sequence and the corresponding heavy chain variable sequence are those of H3-6.
130. The BCMA binding molecule of embodiment 93, wherein the light chain variable sequence and the corresponding heavy chain variable sequence are those of H3-7.
131. The BCMA binding molecule of embodiment 93, wherein the light chain variable sequence and the corresponding heavy chain variable sequence are those of H3-8.
132. The BCMA binding molecule of embodiment 93, wherein the light chain variable sequence and the corresponding heavy chain variable sequence are those of H3-9.
133. The BCMA binding molecule of embodiment 93, wherein the light chain variable sequence and the corresponding heavy chain variable sequence are those of H3-10.
134. The BCMA binding molecule of embodiment 93, wherein the light chain variable sequence and the corresponding heavy chain variable sequence are those of H3-11.
135. The BCMA binding molecule of embodiment 93, wherein the light chain variable sequence and the corresponding heavy chain variable sequence are those of H3-12.
136. The BCMA binding molecule of embodiment 93, wherein the light chain variable sequence and the corresponding heavy chain variable sequence are those of H3-13.
137. The BCMA binding molecule of embodiment 93, wherein the light chain variable sequence and the corresponding heavy chain variable sequence are those of H3-14.
138. The BCMA binding molecule of embodiment 93, wherein the light chain variable sequence and the corresponding heavy chain variable sequence are those of H3-15.
139. The BCMA binding molecule of any one of embodiments 1 to 138, which comprises an antibody, an antibody fragment, an scFv, a dsFv, a Fv, a Fab, an scFab, a (Fab')2, or a single domain antibody (SDAB).
140. The BCMA binding molecule of embodiment 139, which comprises an antibody or an antibody fragment.
141. The BCMA binding molecule of embodiment 139, which comprises a scFv.
142. The BCMA binding molecule of embodiment 141, wherein the scFv comprises a sequence set forth in Table 1P.
143. The BCMA binding molecule of any one of embodiments 1 to 142, which is a multispecific binding molecule.
144. The BCMA binding molecule of embodiment 143, which is a bispecific binding molecule (BBM).
145. The BCMA binding molecule of embodiment 144, wherein the BBM comprises:
   (a) an antigen-binding domain 1 (ABD1) that binds specifically to BCMA; and
   (b) an antigen-binding domain 2 (ABD2) that binds specifically to a component of a human T-cell receptor (TCR) complex.
146. The BCMA binding molecule of embodiment 145, wherein ABD1 is capable of binding BCMA at the same time as ABD2 is bound to the component of a human TCR complex.

147. The BCMA binding molecule of embodiment 145 or embodiment 146, wherein ABD1 is an antibody, an antibody fragment, an scFv, a dsFv, a Fv, a Fab, an scFab, a (Fab')2, a single domain antibody (SDAB), a VH or VL domain, or a camelid VHH domain.

148. The BCMA binding molecule of embodiment 147, wherein ABD1 is an scFv.

149. The BCMA binding molecule of embodiment 147, wherein ABD1 is a Fab.

150. The BCMA binding molecule of embodiment 147, wherein the Fab is a Fab heterodimer.

151. The BCMA binding molecule of embodiment 147, wherein ABD1 is an anti-BCMA antibody or an antigen-binding domain thereof.

152. The BCMA binding molecule of any one of embodiments 145 to 151, wherein ABD2 is an antibody, an antibody fragment, an scFv, a dsFv, a Fv, a Fab, an scFab, a (Fab')2, a single domain antibody (SDAB), a VH or VL domain, or a camelid VHH domain.

153. The BCMA binding molecule of embodiment 152, wherein ABD2 is an scFv.

154. The BCMA binding molecule of embodiment 152, wherein ABD2 is a Fab.

155. The BCMA binding molecule of embodiment 154, wherein the Fab is a Fab heterodimer.

156. The BCMA binding molecule of any one of embodiments 145 to 155, wherein the component of the TCR complex is CD3.

157. The BCMA binding molecule of embodiment 156, wherein ABD2 is an anti-CD3 antibody or an antigen-binding domain thereof.

158. The BCMA binding molecule of embodiment 157, wherein ABD2 comprises the CDR sequences of any one of CD3-1 to CD3-127.

159. The BCMA binding molecule of embodiment 158, wherein ABD2 comprises the CDR sequences of CD3-1.

160. The BCMA binding molecule of embodiment 158, wherein ABD2 comprises the CDR sequences of CD3-2.

161. The BCMA binding molecule of embodiment 158, wherein ABD2 comprises the CDR sequences of CD3-3.

162. The BCMA binding molecule of embodiment 158, wherein ABD2 comprises the CDR sequences of CD3-4.

163. The BCMA binding molecule of embodiment 158, wherein ABD2 comprises the CDR sequences of CD3-5.

164. The BCMA binding molecule of embodiment 158, wherein ABD2 comprises the CDR sequences of CD3-6.

165. The BCMA binding molecule of embodiment 158, wherein ABD2 comprises the CDR sequences of CD3-7.

166. The BCMA binding molecule of embodiment 158, wherein ABD2 comprises the CDR sequences of CD3-8.

167. The BCMA binding molecule of embodiment 158, wherein ABD2 comprises the CDR sequences of CD3-9.

168. The BCMA binding molecule of embodiment 158, wherein ABD2 comprises the CDR sequences of CD3-10.

169. The BCMA binding molecule of embodiment 158, wherein ABD2 comprises the CDR sequences of CD3-11.

170. The BCMA binding molecule of embodiment 158, wherein ABD2 comprises the CDR sequences of CD3-12.

171. The BCMA binding molecule of embodiment 158, wherein ABD2 comprises the CDR sequences of CD3-13.

172. The BCMA binding molecule of embodiment 158, wherein ABD2 comprises the CDR sequences of CD3-14.

173. The BCMA binding molecule of embodiment 158, wherein ABD2 comprises the CDR sequences of CD3-15.

174. The BCMA binding molecule of embodiment 158, wherein ABD2 comprises the CDR sequences of CD3-16.

175. The BCMA binding molecule of embodiment 158, wherein ABD2 comprises the CDR sequences of CD3-17.

176. The BCMA binding molecule of embodiment 158, wherein ABD2 comprises the CDR sequences of CD3-18.

177. The BCMA binding molecule of embodiment 158, wherein ABD2 comprises the CDR sequences of CD3-19.

178. The BCMA binding molecule of embodiment 158, wherein ABD2 comprises the CDR sequences of CD3-20.

179. The BCMA binding molecule of embodiment 158, wherein ABD2 comprises the CDR sequences of CD3-21.

180. The BCMA binding molecule of embodiment 158, wherein ABD2 comprises the CDR sequences of CD3-22.

181. The BCMA binding molecule of embodiment 158, wherein ABD2 comprises the CDR sequences of CD3-23.

182. The BCMA binding molecule of embodiment 158, wherein ABD2 comprises the CDR sequences of CD3-24.

183. The BCMA binding molecule of embodiment 158, wherein ABD2 comprises the CDR sequences of CD3-25.

184. The BCMA binding molecule of embodiment 158, wherein ABD2 comprises the CDR sequences of CD3-26.

185. The BCMA binding molecule of embodiment 158, wherein ABD2 comprises the CDR sequences of CD3-27.

186. The BCMA binding molecule of embodiment 158, wherein ABD2 comprises the CDR sequences of CD3-28.

187. The BCMA binding molecule of embodiment 158, wherein ABD2 comprises the CDR sequences of CD3-29.

188. The BCMA binding molecule of embodiment 158, wherein ABD2 comprises the CDR sequences of CD3-30.

189. The BCMA binding molecule of embodiment 158, wherein ABD2 comprises the CDR sequences of CD3-31.

190. The BCMA binding molecule of embodiment 158, wherein ABD2 comprises the CDR sequences of CD3-32.

191. The BCMA binding molecule of embodiment 158, wherein ABD2 comprises the CDR sequences of CD3-33.

192. The BCMA binding molecule of embodiment 158, wherein ABD2 comprises the CDR sequences of CD3-34.
193. The BCMA binding molecule of embodiment 158, wherein ABD2 comprises the CDR sequences of CD3-35.
194. The BCMA binding molecule of embodiment 158, wherein ABD2 comprises the CDR sequences of CD3-36.
195. The BCMA binding molecule of embodiment 158, wherein ABD2 comprises the CDR sequences of CD3-37.
196. The BCMA binding molecule of embodiment 158, wherein ABD2 comprises the CDR sequences of CD3-38.
197. The BCMA binding molecule of embodiment 158, wherein ABD2 comprises the CDR sequences of CD3-39.
198. The BCMA binding molecule of embodiment 158, wherein ABD2 comprises the CDR sequences of CD3-40.
199. The BCMA binding molecule of embodiment 158, wherein ABD2 comprises the CDR sequences of CD3-41.
200. The BCMA binding molecule of embodiment 158, wherein ABD2 comprises the CDR sequences of CD3-42.
201. The BCMA binding molecule of embodiment 158, wherein ABD2 comprises the CDR sequences of CD3-43.
202. The BCMA binding molecule of embodiment 158, wherein ABD2 comprises the CDR sequences of CD3-44.
203. The BCMA binding molecule of embodiment 158, wherein ABD2 comprises the CDR sequences of CD3-45.
204. The BCMA binding molecule of embodiment 158, wherein ABD2 comprises the CDR sequences of CD3-46.
205. The BCMA binding molecule of embodiment 158, wherein ABD2 comprises the CDR sequences of CD3-47.
206. The BCMA binding molecule of embodiment 158, wherein ABD2 comprises the CDR sequences of CD3-48.
207. The BCMA binding molecule of embodiment 158, wherein ABD2 comprises the CDR sequences of CD3-49.
208. The BCMA binding molecule of embodiment 158, wherein ABD2 comprises the CDR sequences of CD3-50.
209. The BCMA binding molecule of embodiment 158, wherein ABD2 comprises the CDR sequences of CD3-51.
210. The BCMA binding molecule of embodiment 158, wherein ABD2 comprises the CDR sequences of CD3-52.
211. The BCMA binding molecule of embodiment 158, wherein ABD2 comprises the CDR sequences of CD3-53.
212. The BCMA binding molecule of embodiment 158, wherein ABD2 comprises the CDR sequences of CD3-54.
213. The BCMA binding molecule of embodiment 158, wherein ABD2 comprises the CDR sequences of CD3-55.
214. The BCMA binding molecule of embodiment 158, wherein ABD2 comprises the CDR sequences of CD3-56.
215. The BCMA binding molecule of embodiment 158, wherein ABD2 comprises the CDR sequences of CD3-57.
216. The BCMA binding molecule of embodiment 158, wherein ABD2 comprises the CDR sequences of CD3-58.
217. The BCMA binding molecule of embodiment 158, wherein ABD2 comprises the CDR sequences of CD3-59.
218. The BCMA binding molecule of embodiment 158, wherein ABD2 comprises the CDR sequences of CD3-60.
219. The BCMA binding molecule of embodiment 158, wherein ABD2 comprises the CDR sequences of CD3-61.
220. The BCMA binding molecule of embodiment 158, wherein ABD2 comprises the CDR sequences of CD3-62.
221. The BCMA binding molecule of embodiment 158, wherein ABD2 comprises the CDR sequences of CD3-63.
222. The BCMA binding molecule of embodiment 158, wherein ABD2 comprises the CDR sequences of CD3-64.
223. The BCMA binding molecule of embodiment 158, wherein ABD2 comprises the CDR sequences of CD3-65.
224. The BCMA binding molecule of embodiment 158, wherein ABD2 comprises the CDR sequences of CD3-66.
225. The BCMA binding molecule of embodiment 158, wherein ABD2 comprises the CDR sequences of CD3-67.
226. The BCMA binding molecule of embodiment 158, wherein ABD2 comprises the CDR sequences of CD3-68.
227. The BCMA binding molecule of embodiment 158, wherein ABD2 comprises the CDR sequences of CD3-69.
228. The BCMA binding molecule of embodiment 158, wherein ABD2 comprises the CDR sequences of CD3-70.
229. The BCMA binding molecule of embodiment 158, wherein ABD2 comprises the CDR sequences of CD3-71.
230. The BCMA binding molecule of embodiment 158, wherein ABD2 comprises the CDR sequences of CD3-72.
231. The BCMA binding molecule of embodiment 158, wherein ABD2 comprises the CDR sequences of CD3-73.
232. The BCMA binding molecule of embodiment 158, wherein ABD2 comprises the CDR sequences of CD3-74.
233. The BCMA binding molecule of embodiment 158, wherein ABD2 comprises the CDR sequences of CD3-75.
234. The BCMA binding molecule of embodiment 158, wherein ABD2 comprises the CDR sequences of CD3-76.
235. The BCMA binding molecule of embodiment 158, wherein ABD2 comprises the CDR sequences of CD3-77.

236. The BCMA binding molecule of embodiment 158, wherein ABD2 comprises the CDR sequences of CD3-78.

237. The BCMA binding molecule of embodiment 158, wherein ABD2 comprises the CDR sequences of CD3-79.

238. The BCMA binding molecule of embodiment 158, wherein ABD2 comprises the CDR sequences of CD3-80.

239. The BCMA binding molecule of embodiment 158, wherein ABD2 comprises the CDR sequences of CD3-81.

240. The BCMA binding molecule of embodiment 158, wherein ABD2 comprises the CDR sequences of CD3-82.

241. The BCMA binding molecule of embodiment 158, wherein ABD2 comprises the CDR sequences of CD3-83.

242. The BCMA binding molecule of embodiment 158, wherein ABD2 comprises the CDR sequences of CD3-84.

243. The BCMA binding molecule of embodiment 158, wherein ABD2 comprises the CDR sequences of CD3-85.

244. The BCMA binding molecule of embodiment 158, wherein ABD2 comprises the CDR sequences of CD3-86.

245. The BCMA binding molecule of embodiment 158, wherein ABD2 comprises the CDR sequences of CD3-87.

246. The BCMA binding molecule of embodiment 158, wherein ABD2 comprises the CDR sequences of CD3-88.

247. The BCMA binding molecule of embodiment 158, wherein ABD2 comprises the CDR sequences of CD3-89.

248. The BCMA binding molecule of embodiment 158, wherein ABD2 comprises the CDR sequences of CD3-90.

249. The BCMA binding molecule of embodiment 158, wherein ABD2 comprises the CDR sequences of CD3-91.

250. The BCMA binding molecule of embodiment 158, wherein ABD2 comprises the CDR sequences of CD3-92.

251. The BCMA binding molecule of embodiment 158, wherein ABD2 comprises the CDR sequences of CD3-93.

252. The BCMA binding molecule of embodiment 158, wherein ABD2 comprises the CDR sequences of CD3-94.

253. The BCMA binding molecule of embodiment 158, wherein ABD2 comprises the CDR sequences of CD3-95.

254. The BCMA binding molecule of embodiment 158, wherein ABD2 comprises the CDR sequences of CD3-96.

255. The BCMA binding molecule of embodiment 158, wherein ABD2 comprises the CDR sequences of CD3-97.

256. The BCMA binding molecule of embodiment 158, wherein ABD2 comprises the CDR sequences of CD3-98.

257. The BCMA binding molecule of embodiment 158, wherein ABD2 comprises the CDR sequences of CD3-99.

258. The BCMA binding molecule of embodiment 158, wherein ABD2 comprises the CDR sequences of CD3-100.

259. The BCMA binding molecule of embodiment 158, wherein ABD2 comprises the CDR sequences of CD3-101.

260. The BCMA binding molecule of embodiment 158, wherein ABD2 comprises the CDR sequences of CD3-102.

261. The BCMA binding molecule of embodiment 158, wherein ABD2 comprises the CDR sequences of CD3-103.

262. The BCMA binding molecule of embodiment 158, wherein ABD2 comprises the CDR sequences of CD3-104.

263. The BCMA binding molecule of embodiment 158, wherein ABD2 comprises the CDR sequences of CD3-105.

264. The BCMA binding molecule of embodiment 158, wherein ABD2 comprises the CDR sequences of CD3-106.

265. The BCMA binding molecule of embodiment 158, wherein ABD2 comprises the CDR sequences of CD3-107.

266. The BCMA binding molecule of embodiment 158, wherein ABD2 comprises the CDR sequences of CD3-108.

267. The BCMA binding molecule of embodiment 158, wherein ABD2 comprises the CDR sequences of CD3-109.

268. The BCMA binding molecule of embodiment 158, wherein ABD2 comprises the CDR sequences of CD3-110.

269. The BCMA binding molecule of embodiment 158, wherein ABD2 comprises the CDR sequences of CD3-111.

270. The BCMA binding molecule of embodiment 158, wherein ABD2 comprises the CDR sequences of CD3-112.

271. The BCMA binding molecule of embodiment 158 wherein ABD2 comprises the CDR sequences of CD3-113.

272. The BCMA binding molecule of embodiment 158, wherein ABD2 comprises the CDR sequences of CD3-114.

273. The BCMA binding molecule of embodiment 158, wherein ABD2 comprises the CDR sequences of CD3-115.

274. The BCMA binding molecule of embodiment 158, wherein ABD2 comprises the CDR sequences of CD3-116.

275. The BCMA binding molecule of embodiment 158, wherein ABD2 comprises the CDR sequences of CD3-117.

276. The BCMA binding molecule of embodiment 158, wherein ABD2 comprises the CDR sequences of CD3-118.

277. The BCMA binding molecule of embodiment 158, wherein ABD2 comprises the CDR sequences of CD3-119.

278. The BCMA binding molecule of embodiment 158, wherein ABD2 comprises the CDR sequences of CD3-120.

279. The BCMA binding molecule of embodiment 158, wherein ABD2 comprises the CDR sequences of CD3-121.

280. The BCMA binding molecule of embodiment 158, wherein ABD2 comprises the CDR sequences of CD3-122.

281. The BCMA binding molecule of embodiment 158, wherein ABD2 comprises the CDR sequences of CD3-123.

282. The BCMA binding molecule of embodiment 158, wherein ABD2 comprises the CDR sequences of CD3-124.

283. The BCMA binding molecule of embodiment 158, wherein ABD2 comprises the CDR sequences of CD3-125.

284. The BCMA binding molecule of embodiment 158, wherein ABD2 comprises the CDR sequences of CD3-126.

285. The BCMA binding molecule of embodiment 158, wherein ABD2 comprises the CDR sequences of CD3-127.

286. The BCMA binding molecule of any one of embodiments 159 to 285, wherein the CDRs are defined by Kabat numbering, as set forth in Table 3B.

287. The BCMA binding molecule of any one of embodiments 159 to 178, wherein the CDRs are defined by Chothia numbering, as set forth in Table 3C.

288. BCMA binding molecule of any one of embodiments 159 to 178, wherein the CDRs are defined by a combination of Kabat and Chothia numbering, as set forth in Table 3D.

289. The BCMA binding molecule of embodiment 157, wherein ABD2 comprises the heavy and light chain variable sequences of CD3-1, as set forth in Table 3A.

290. The BCMA binding molecule of embodiment 157, wherein ABD2 comprises the heavy and light chain variable sequences of CD3-2, as set forth in Table 3A.

291. The BCMA binding molecule of embodiment 157, wherein ABD2 comprises the heavy and light chain variable sequences of CD3-3, as set forth in Table 3A.

292. The BCMA binding molecule of embodiment 157, wherein ABD2 comprises the heavy and light chain variable sequences of CD3-4, as set forth in Table 3A.

293. The BCMA binding molecule of embodiment 157, wherein ABD2 comprises the heavy and light chain variable sequences of CD3-5, as set forth in Table 3A.

294. The BCMA binding molecule of embodiment 157, wherein ABD2 comprises the heavy and light chain variable sequences of CD3-6, as set forth in Table 3A.

295. The BCMA binding molecule of embodiment 157, wherein ABD2 comprises the heavy and light chain variable sequences of CD3-7, as set forth in Table 3A.

296. The BCMA binding molecule of embodiment 157, wherein ABD2 comprises the heavy and light chain variable sequences of CD3-8, as set forth in Table 3A.

297. The BCMA binding molecule of embodiment 157, wherein ABD2 comprises the heavy and light chain variable sequences of CD3-9, as set forth in Table 3A.

298. The BCMA binding molecule of embodiment 157, wherein ABD2 comprises the heavy and light chain variable sequences of CD3-10, as set forth in Table 3A.

299. The BCMA binding molecule of embodiment 157, wherein ABD2 comprises the heavy and light chain variable sequences of CD3-11, as set forth in Table 3A.

300. The BCMA binding molecule of embodiment 157, wherein ABD2 comprises the heavy and light chain variable sequences of CD3-12, as set forth in Table 3A.

301. The BCMA binding molecule of embodiment 157, wherein ABD2 comprises the heavy and light chain variable sequences of CD3-13, as set forth in Table 3A.

302. The BCMA binding molecule of embodiment 157, wherein ABD2 comprises the heavy and light chain variable sequences of CD3-14, as set forth in Table 3A.

303. The BCMA binding molecule of embodiment 157, wherein ABD2 comprises the heavy and light chain variable sequences of CD3-15, as set forth in Table 3A.

304. The BCMA binding molecule of embodiment 157, wherein ABD2 comprises the heavy and light chain variable sequences of CD3-16, as set forth in Table 3A.

305. The BCMA binding molecule of embodiment 157, wherein ABD2 comprises the heavy and light chain variable sequences of CD3-17, as set forth in Table 3A.

306. The BCMA binding molecule of embodiment 157, wherein ABD2 comprises the heavy and light chain variable sequences of CD3-18, as set forth in Table 3A.

307. The BCMA binding molecule of embodiment 157, wherein ABD2 comprises the heavy and light chain variable sequences of CD3-19, as set forth in Table 3A.

308. The BCMA binding molecule of embodiment 157, wherein ABD2 comprises the heavy and light chain variable sequences of CD3-20, as set forth in Table 3A.

309. The BCMA binding molecule of embodiment 157, wherein ABD2 comprises the heavy and light chain variable sequences of CD3-21, as set forth in Table 3A.

310. The BCMA binding molecule of embodiment 157, wherein ABD2 comprises the heavy and light chain variable sequences of CD3-22, as set forth in Table 3A.

311. The BCMA binding molecule of embodiment 157, wherein ABD2 comprises the heavy and light chain variable sequences of CD3-23, as set forth in Table 3A.

312. The BCMA binding molecule of embodiment 157, wherein ABD2 comprises the heavy and light chain variable sequences of CD3-24, as set forth in Table 3A.

313. The BCMA binding molecule of embodiment 157, wherein ABD2 comprises the heavy and light chain variable sequences of CD3-25, as set forth in Table 3A.

314. The BCMA binding molecule of embodiment 157, wherein ABD2 comprises the heavy and light chain variable sequences of CD3-26, as set forth in Table 3A.

315. The BCMA binding molecule of embodiment 157, wherein ABD2 comprises the heavy and light chain variable sequences of CD3-27, as set forth in Table 3A.

316. The BCMA binding molecule of any one of embodiments 145 to 155, wherein the component of the TCR complex is TCR-α, TCR-β, or a TCR-α/β dimer.

317. The BCMA binding molecule of embodiment 316, wherein ABD2 is an antibody or an antigen-binding domain thereof.

318. The BCMA binding molecule of embodiment 317, wherein ABD2 comprises the CDR sequences of BMA031.

319. The BCMA binding molecule of embodiment 318, wherein the CDR sequences are defined by Kabat numbering.

320. The BCMA binding molecule of embodiment 318, wherein the CDR sequences are defined by Chothia numbering.

321. The BCMA binding molecule of embodiment 318, wherein the CDR sequences are defined by a combination of Kabat and Chothia numbering.

322. The BCMA binding molecule of embodiment 318, wherein ABD2 comprises the heavy and light chain variable sequences of BMA031.

323. The BCMA binding molecule of any one of embodiments 145 to 155, wherein the component of the TCR complex is TCR-γ, TCR-δ, or a TCR-γ/δ dimer.

324. The BCMA binding molecule of embodiment 323, wherein ABD2 is an antibody or an antigen-binding domain thereof.

325. The BCMA binding molecule of embodiment 324, wherein ABD2 comprises the CDR sequences of δTCS1.

326. The BCMA binding molecule of embodiment 325, wherein the CDR sequences are defined by Kabat numbering.

327. The BCMA binding molecule of embodiment 325, wherein the CDR sequences are defined by Chothia numbering.

328. The BCMA binding molecule of embodiment 325, wherein the CDR sequences are defined by a combination of Kabat and Chothia numbering.

329. The BCMA binding molecule of embodiment 325, wherein ABD2 comprises the heavy and light chain variable sequences of δTCS1.

330. The BCMA binding molecule of any one of embodiments 145 to 151, wherein ABD2 is a non-immunoglobulin scaffold-based ABD.

331. The BCMA binding molecule of embodiment 330, wherein ABD2 is a Kunitz domain, an Adnexin, an Affibody, a DARPin, an Avimer, an Anticalin, a Lipocalin, a Centyrin, a Versabody, a Knottin, an Adnectin, a Pronectin, an Affitin/Nanofitin, an Affilin, an Atrimer/Tetranectin, a bicyclic peptide, a cys-knot, a Fn3 scaffold, an Obody, a Tn3, an Affimer, BD, an Adhiron, a Duocalin, an Alphabody, an Armadillo Repeat Protein, a Repebody, or a Fynomer.

332. The BCMA binding molecule of any one of embodiments 145 to 331, which comprises a first variant Fc region and a second variant Fc region that together form an Fc heterodimer.

333. The BCMA binding molecule of embodiment 332, wherein the first and second variant Fc regions comprise the amino acid substitutions S364K/E357Q: L368D/K370S.

334. The BCMA binding molecule of embodiment 332, wherein the first and second variant Fc regions comprise the amino acid substitutions L368D/K370S:S364.

335. The BCMA binding molecule of embodiment 332, wherein the first and second variant Fc regions comprise the amino acid substitutions L368E/K370S: S364K.

336. The BCMA binding molecule of embodiment 332, wherein the first and second variant Fc regions comprise the amino acid substitutions T411T/E360E/Q362E:D401K.

337. The BCMA binding molecule of embodiment 332, wherein the first and second variant Fc regions comprise the amino acid substitutions L368D 370S:S364/E357L.

338. The BCMA binding molecule of embodiment 332, wherein the first and second variant Fc regions comprise the amino acid substitutions 370S:S364K/E357Q.

339. The BCMA binding molecule of embodiment 332, wherein the first and second variant Fc regions comprise the amino acid substitutions of any one of the steric variants listed in FIG. 4 of WO 2014/110601 (reproduced in Table 6).

340. The BCMA binding molecule of embodiment 332, wherein the first and second variant Fc regions comprise the amino acid substitutions of any one of the variants listed in FIG. 5 of WO 2014/110601 (reproduced in Table 6).

341. The BCMA binding molecule of embodiment 332, wherein the first and second variant Fc regions comprise the amino acid substitutions of any one of the variants listed in FIG. 6 of WO 2014/110601 (reproduced in Table 6).

342. The BCMA binding molecule of any one of embodiments 332 to 341, wherein the first variant Fc region is operably linked to ABD1 and the second variant Fc region is operably linked to ABD2.

343. The BCMA binding molecule of any one of embodiments 332 to 341, wherein the first variant Fc region is operably linked to ABD2 and the second variant Fc region is operably linked to ABD1.

344. The BCMA binding molecule of any one of embodiments 332 to 343, wherein at least one of the Fc regions comprises an ablation variant modification.

345. The BCMA binding molecule of embodiment 342, wherein the ablation variant modifications are selected from Table 5.

346. The BCMA binding molecule of embodiment 345, wherein the ablation variant modification comprises G236R.

347. The BCMA binding molecule of embodiment 345, wherein the ablation variant modification comprises S239G.

348. The BCMA binding molecule of embodiment 345, wherein the ablation variant modification comprises S239K.

349. The BCMA binding molecule of embodiment 345, wherein the ablation variant modification comprises S239Q.

350. The BCMA binding molecule of embodiment 345, wherein the ablation variant modification comprises S239R.

351. The BCMA binding molecule of embodiment 345, wherein the ablation variant modification comprises V266D.

352. The BCMA binding molecule of embodiment 345, wherein the ablation variant modification comprises S267K.

353. The BCMA binding molecule of embodiment 345, wherein the ablation variant modification comprises S267R.

354. The BCMA binding molecule of embodiment 345, wherein the ablation variant modification comprises H268K.

355. The BCMA binding molecule of embodiment 345, wherein the ablation variant modification comprises E269R.

356. The BCMA binding molecule of embodiment 345, wherein the ablation variant modification comprises 299R.

357. The BCMA binding molecule of embodiment 345, wherein the ablation variant modification comprises 299K 358. The BCMA binding molecule of embodiment 345, wherein the ablation variant modification comprises K322A 359. The BCMA binding molecule of embodiment 345, wherein the ablation variant modification comprises A327G 360. The BCMA binding molecule of embodiment 345, wherein the ablation variant modification comprises A327L 361. The BCMA binding molecule of embodiment 345, wherein the ablation variant modification comprises A327N 362. The BCMA binding molecule of embodiment 345, wherein the ablation variant modification comprises A327Q
363. The BCMA binding molecule of embodiment 345, wherein the ablation variant modification comprises L328E
364. The BCMA binding molecule of embodiment 345, wherein the ablation variant modification comprises L328R
365. The BCMA binding molecule of embodiment 345, wherein the ablation variant modification comprises P329A
366. The BCMA binding molecule of embodiment 345, wherein the ablation variant modification comprises P329H
367. The BCMA binding molecule of embodiment 345, wherein the ablation variant modification comprises P329K
368. The BCMA binding molecule of embodiment 345, wherein the ablation variant modification comprises A330L
369. The BCMA binding molecule of embodiment 345, wherein the ablation variant modification comprises A330S/P331S
370. The BCMA binding molecule of embodiment 345, wherein the ablation variant modification comprises I332K
371. The BCMA binding molecule of embodiment 345, wherein the ablation variant modification comprises I332R
372. The BCMA binding molecule of embodiment 345, wherein the ablation variant modification comprises V266D/A327Q
373. The BCMA binding molecule of embodiment 345, wherein the ablation variant modification comprises V266D/P329K
374. The BCMA binding molecule of embodiment 345, wherein the ablation variant modification comprises G236R/L328R
375. The BCMA binding molecule of embodiment 345, wherein the ablation variant modification comprises E233P/L234V/L235A/G236del/S239K.
376. The BCMA binding molecule of embodiment 345, wherein the ablation variant modification comprises E233P/L234V/L235A/G236del/S267K.
377. The BCMA binding molecule of embodiment 345, wherein the ablation variant modification comprises E233P/L234V/L235A/G236del/S239K/A327G.
378. The BCMA binding molecule of embodiment 345, wherein the ablation variant modification comprises E233P/L234V/L235A/G236del/S267K/A327G.
379. The BCMA binding molecule of embodiment 345, wherein the ablation variant modification comprises E233P/L234V/L235A/G236del.
380. The BCMA binding molecule of embodiment 345, wherein the ablation variant modification comprises S239K/S267K.
381. The BCMA binding molecule of embodiment 345, wherein the ablation variant modification comprises 267K/P329K.
382. The BCMA binding molecule of any one of embodiments 344 to 381, wherein the Fc region comprising the ablation variant modification is operably linked to ABD1.
383. The BCMA binding molecule of any one of embodiments 344 to 381, wherein the Fc region comprising the ablation variant modification is operably linked to ABD2.
384. The BCMA binding molecule of any one of embodiments 344 to 381, wherein both Fc regions comprise the ablation variant modification.
385. The BCMA binding molecule of any one of embodiments 332 to 384, wherein at least one of the Fc regions further comprises pI variant substitutions.
386. The BCMA binding molecule of embodiment 342, wherein the pI variant substitutions are selected from Table 8.
387. The BCMA binding molecule of embodiment 386, wherein the pI variant substitutions comprise the substitutions present in pI_ISO(−).
388. The BCMA binding molecule of embodiment 386, wherein the pI variant substitutions comprise the substitutions present in pI_(−)_isosteric_A.
389. The BCMA binding molecule of embodiment 386, wherein the pI variant substitutions comprise the substitutions present in pI_(−)_isosteric_B.
390. The BCMA binding molecule of embodiment 386, wherein the pI variant substitutions comprise the substitutions present in PI_ISO(+RR).
391. The BCMA binding molecule of embodiment 386, wherein the pI variant substitutions comprise the substitutions present in pI_ISO(+).
392. The BCMA binding molecule of embodiment 386, wherein the pI variant substitutions comprise the substitutions present in pI_(+)_isosteric_A.
393. The BCMA binding molecule of embodiment 386, wherein the pI variant substitutions comprise the substitutions present in pI_(+)_isosteric_B.
394. The BCMA binding molecule of embodiment 386, wherein the pI variant substitutions comprise the substitutions present in pI_(+)_isosteric_E269Q/E272Q.
395. The BCMA binding molecule of embodiment 386, wherein the pI variant substitutions comprise the substitutions present in pI_(+)_isosteric_E269Q/E283Q.
396. The BCMA binding molecule of embodiment 386, wherein the pI variant substitutions comprise the substitutions present in pI_(+)_isosteric_E272Q/E283Q.
397. The BCMA binding molecule of embodiment 386, wherein the pI variant substitutions comprise the substitutions present in pI_(+)_isosteric_E269Q.
398. The BCMA binding molecule of any one of embodiments 385 to 397, wherein the Fc region operably linked to AB1 comprises the pI variant substitutions.
399. The BCMA binding molecule of any one of embodiments 385 to 398, wherein the Fc region operably linked to AB1 comprises the pI variant substitutions.
400. The BCMA binding molecule of any one of embodiments 332 to 399, wherein the first and/or second Fc region further comprises one or more amino acid substitution(s) selected from 434A, 434S, 428L, 308F, 259I, 428L/434S, 259I/308F, 436I/428L, 436I or V/434S, 436V/428L, 252Y, 252Y/254T/256E, 259I/308F/428L, 236A, 239D, 239E, 332E, 332D, 239D/332E, 267D, 267E, 328F, 267E/328F, 236A/332E, 239D/332E/330Y, 239D, 332E/330L, 236R, 328R, 236R/328R, 236N/267E, 243L, 298A and 299T.
401. The BCMA binding molecule of any one of embodiments 332 to 399, wherein the first and/or second Fc region further comprises one or more amino acid substitution comprises the amino acid substitution 434A, 434S or 434V.

402. The BCMA binding molecule of embodiment 401, wherein the first and/or second Fc region further comprises one or more amino acid substitution comprises the amino acid substitution 428L.
403. The BCMA binding molecule of any one of embodiments 401 to 402, wherein the first and/or second Fc region further comprises one or more amino acid substitution comprises the amino acid substitution 308F.
404. The BCMA binding molecule of any one of embodiments 401 to 403, wherein the first and/or second Fc region further comprises one or more amino acid substitution comprises the amino acid substitution 259I.
405. The BCMA binding molecule of any one of embodiments 401 to 404, wherein the first and/or second Fc region further comprises one or more amino acid substitution comprises the amino acid substitution 436I.
406. The BCMA binding molecule of any one of embodiments 401 to 405, wherein the first and/or second Fc region further comprises one or more amino acid substitution comprises the amino acid substitution 252Y.
407. The BCMA binding molecule of any one of embodiments 401 to 406, wherein the first and/or second Fc region further comprises one or more amino acid substitution comprises the amino acid substitution 254T.
408. The BCMA binding molecule of any one of embodiments 401 to 407, wherein the first and/or second Fc region further comprises one or more amino acid substitution comprises the amino acid substitution 256E.
409. The BCMA binding molecule of any one of embodiments 401 to 408, wherein the first and/or second Fc region further comprises one or more amino acid substitution comprises the amino acid substitution 239D or 239E.
410. The BCMA binding molecule of any one of embodiments 401 to 409, wherein the first and/or second Fc region further comprises one or more amino acid substitution comprises the amino acid substitution 332E or 332D.
411. The BCMA binding molecule of any one of embodiments 401 to 410, wherein the first and/or second Fc region further comprises one or more amino acid substitution comprises the amino acid substitution 267D or 267E.
412. The BCMA binding molecule of any one of embodiments 401 to 411, wherein the first and/or second Fc region further comprises one or more amino acid substitution comprises the amino acid substitution 330L.
413. The BCMA binding molecule of any one of embodiments 401 to 412, wherein the first and/or second Fc region further comprises one or more amino acid substitution comprises the amino acid substitution 236R or 236N.
414. The BCMA binding molecule of any one of embodiments 401 to 413, wherein the first and/or second Fc region further comprises one or more amino acid substitution comprises the amino acid substitution 328R.
415. The BCMA binding molecule of any one of embodiments 401 to 414, wherein the first and/or second Fc region further comprises one or more amino acid substitution comprises the amino acid substitution 243L.
416. The BCMA binding molecule of any one of embodiments 401 to 415, wherein the first and/or second Fc region further comprises one or more amino acid substitution comprises the amino acid substitution 298A.
417. The BCMA binding molecule of any one of embodiments 401 to 416, wherein the first and/or second Fc region further comprises one or more amino acid substitution comprises the amino acid substitution 299T.
418. The BCMA binding molecule of embodiment 332, wherein:
    (a) the first and second variant Fc regions comprise the amino acid substitutions S364K/E357Q:L368D/K370S;
    (b) the first and/or second variant Fc regions comprises the ablation variant modifications E233P/L234V/L235A/G236del/S267K, and
    (c) the first and/or second variant Fc regions comprises the pI variant substitutions N208D/Q295E/N384D/Q418E/N421D (pI_(-)_isosteric_A).
419. The BCMA binding molecule of embodiment 418, wherein the first variant Fc region is operably linked to ABD1 and the second variant Fc region is operably linked to ABD2.
420. The BCMA binding molecule of embodiment 418, wherein the first variant Fc region is operably linked to ABD2 and the second variant Fc region is operably linked to ABD1.
421. The BCMA binding molecule of any one of embodiments 418 to 420, wherein the first variant Fc region comprises the ablation variant modifications E233P/L234V/L235A/G236del/S267K.
422. The BCMA binding molecule of any one of embodiments 418 to 421, wherein the second variant Fc region comprises the ablation variant modifications E233P/L234V/L235A/G236del/S267K.
423. The BCMA binding molecule of any one of embodiments 418 to 422, wherein the first variant Fc region comprises the pI variant substitutions N208D/Q295E/N384D/Q418E/N421D (pI_(-)_isosteric_A).
424. The BCMA binding molecule of any one of embodiments 418 to 423, wherein the second variant Fc region comprises the pI variant substitutions N208D/Q295E/N384D/Q418E/N421D (pI_(-)_isosteric_A).
425. The BCMA binding molecule of any one of embodiments 145 to 331, which comprises an Fc domain.
426. The BCMA binding molecule of embodiment 425, wherein the Fc domain is an Fc heterodimer.
427. The BCMA binding molecule of embodiment 426, wherein the Fc heterodimer comprises at least one of the Fc modifications set forth in Table 6.
428. The BCMA binding molecule of embodiment 426, wherein the Fc heterodimer comprises knob-in-hole ("KIH") modifications.
429. The BCMA binding molecule of embodiment 428, wherein the KIH modifications are any of the KIH modifications described in Section 7.4.1.5.1 or in Table 6.
430. The BCMA binding molecule of embodiment 428, wherein the KIH modifications are any of the alternative KIH modifications described in Section 7.4.1.5.2 or in Table 6.

431. The BCMA binding molecule of any one of embodiments 426 to 430, which comprises polar bridge modifications.
432. The BCMA binding molecule of embodiment 431, wherein the polar bridge modifications are any of the polar bridge modifications described in Section 7.4.1.5.7 or in Table 6.
433. The BCMA binding molecule of any one of embodiments to 426 to 432, which comprises at least one of the Fc modifications designated as Fc 1 through Fc 150.
434. The BCMA binding molecule of embodiment 433, which comprises at least one of the Fc modifications designated as Fc 1 through Fc 5.
435. The BCMA binding molecule of embodiment 433, which comprises at least one of the Fc modifications designated as Fc 6 through Fc 10.
436. The BCMA binding molecule of embodiment 433, which comprises at least one of the Fc modifications designated as Fc 11 through Fc 15.
437. The BCMA binding molecule of embodiment 433, which comprises at least one of the Fc modifications designated as Fc 16 through Fc 20.
438. The BCMA binding molecule of embodiment 433, which comprises at least one of the Fc modifications designated as Fc 21 through Fc 25.
439. The BCMA binding molecule of embodiment 433, which comprises at least one of the Fc modifications designated as Fc 26 through Fc 30.
440. The BCMA binding molecule of embodiment 433, which comprises at least one of the Fc modifications designated as Fc 31 through Fc 35.
441. The BCMA binding molecule of embodiment 433, which comprises at least one of the Fc modifications designated as Fc 36 through Fc 40.
442. The BCMA binding molecule of embodiment 433, which comprises at least one of the Fc modifications designated as Fc 41 through Fc 45.
443. The BCMA binding molecule of embodiment 433, which comprises at least one of the Fc modifications designated as Fc 46 through Fc 50.
444. The BCMA binding molecule of embodiment 433, which comprises at least one of the Fc modifications designated as Fc 51 through Fc 55.
445. The BCMA binding molecule of embodiment 433, which comprises at least one of the Fc modifications designated as Fc 56 through Fc 60.
446. The BCMA binding molecule of embodiment 433, which comprises at least one of the Fc modifications designated as Fc 61 through Fc 65.
447. The BCMA binding molecule of embodiment 433, which comprises at least one of the Fc modifications designated as Fc 66 through Fc 70.
448. The BCMA binding molecule of embodiment 433, which comprises at least one of the Fc modifications designated as Fc 71 through Fc 75.
449. The BCMA binding molecule of embodiment 433, which comprises at least one of the Fc modifications designated as Fc 76 through Fc 80.
450. The BCMA binding molecule of embodiment 433, which comprises at least one of the Fc modifications designated as Fc 81 through Fc 85.
451. The BCMA binding molecule of embodiment 433, which comprises at least one of the Fc modifications designated as Fc 86 through Fc 90.
452. The BCMA binding molecule of embodiment 433, which comprises at least one of the Fc modifications designated as Fc 91 through Fc 95.
453. The BCMA binding molecule of embodiment 433, which comprises at least one of the Fc modifications designated as Fc 96 through Fc 100.
454. The BCMA binding molecule of embodiment 433, which comprises at least one of the Fc modifications designated as Fc 101 through Fc 105.
455. The BCMA binding molecule of embodiment 433, which comprises at least one of the Fc modifications designated as Fc 106 through Fc 110.
456. The BCMA binding molecule of embodiment 433, which comprises at least one of the Fc modifications designated as Fc 111 through Fc 115.
457. The BCMA binding molecule of embodiment 433, which comprises at least one of the Fc modifications designated as Fc 116 through Fc 120.
458. The BCMA binding molecule of embodiment 433, which comprises at least one of the Fc modifications designated as Fc 121 through Fc 125.
459. The BCMA binding molecule of embodiment 433, which comprises at least one of the Fc modifications designated as Fc 126 through Fc 130.
460. The BCMA binding molecule of embodiment 433, which comprises at least one of the Fc modifications designated as Fc 131 through Fc 135.
461. The BCMA binding molecule of embodiment 433, which comprises at least one of the Fc modifications designated as Fc 136 through Fc 140.
462. The BCMA binding molecule of embodiment 433, which comprises at least one of the Fc modifications designated as Fc 141 through Fc 145.
463. The BCMA binding molecule of embodiment 433, which comprises at least one of the Fc modifications designated as Fc 146 through Fc 150.
464. The BCMA binding molecule of any one of embodiments 425 to 463, wherein the Fc domain has altered effector function.
465. The BCMA binding molecule of embodiment 464, wherein the Fc domain has altered binding to one or more Fc receptors.
466. The BCMA binding molecule of embodiment 465, wherein the one or more Fc receptors comprise FcRN.
467. The BCMA binding molecule of embodiment 465 or embodiment 466, wherein the one or more Fc receptors comprise leukocyte receptors.
468. The BCMA binding molecule of any one of embodiments 425 to 467, wherein the Fc has modified disulfide bond architecture.
469. The BCMA binding molecule of any one of embodiments 425 to 468, wherein the Fc has altered glycosylation patterns.
470. The BCMA binding molecule of any one of embodiments 425 to 469, wherein the Fc comprises a hinge region.
471. The BCMA binding molecule of embodiment 470, wherein the hinge region comprises any one of the hinge regions described in Section 7.4.2.
472. The BCMA binding molecule of embodiment 471, wherein the hinge region comprises the amino acid sequence of the hinge region designated H1.
473. The BCMA binding molecule of embodiment 471, wherein the hinge region comprises the amino acid sequence of the hinge region designated H2.
474. The BCMA binding molecule of embodiment 471, wherein the hinge region comprises the amino acid sequence of the hinge region designated H3.

475. The BCMA binding molecule of embodiment 471, wherein the hinge region comprises the amino acid sequence of the hinge region designated H4.

476. The BCMA binding molecule of embodiment 471, wherein the hinge region comprises the amino acid sequence of the hinge region designated H5.

477. The BCMA binding molecule of embodiment 471, wherein the hinge region comprises the amino acid sequence of the hinge region designated H6.

478. The BCMA binding molecule of embodiment 471, wherein the hinge region comprises the amino acid sequence of the hinge region designated H7.

479. The BCMA binding molecule of embodiment 471, wherein the hinge region comprises the amino acid sequence of the hinge region designated H8.

480. The BCMA binding molecule of embodiment 471, wherein the hinge region comprises the amino acid sequence of the hinge region designated H9.

481. The BCMA binding molecule of embodiment 471, wherein the hinge region comprises the amino acid sequence of the hinge region designated H10.

482. The BCMA binding molecule of embodiment 471, wherein the hinge region comprises the amino acid sequence of the hinge region designated H11.

483. The BCMA binding molecule of embodiment 471, wherein the hinge region comprises the amino acid sequence of the hinge region designated H12.

484. The BCMA binding molecule of embodiment 471, wherein the hinge region comprises the amino acid sequence of the hinge region designated H13.

485. The BCMA binding molecule of embodiment 471, wherein the hinge region comprises the amino acid sequence of the hinge region designated H14.

486. The BCMA binding molecule of embodiment 471, wherein the hinge region comprises the amino acid sequence of the hinge region designated H15.

487. The BCMA binding molecule of embodiment 471, wherein the hinge region comprises the amino acid sequence of the hinge region designated H16.

488. The BCMA binding molecule of embodiment 471, wherein the hinge region comprises the amino acid sequence of the hinge region designated H17.

489. The BCMA binding molecule of embodiment 471, wherein the hinge region comprises the amino acid sequence of the hinge region designated H18.

490. The BCMA binding molecule of embodiment 471, wherein the hinge region comprises the amino acid sequence of the hinge region designated H19.

491. The BCMA binding molecule of embodiment 471, wherein the hinge region comprises the amino acid sequence of the hinge region designated H20.

492. The BCMA binding molecule of embodiment 471, wherein the hinge region comprises the amino acid sequence of the hinge region designated H21.

493. The BCMA binding molecule of any one of embodiments 1 to 492, which comprises at least one scFv domain.

494. The BCMA binding molecule of embodiment 493, wherein at least one scFv comprises a linker connecting the VH and VL domains.

495. The BCMA binding molecule of embodiment 494, wherein the linker is 5 to 25 amino acids in length.

496. The BCMA binding molecule of embodiment 495, wherein the linker is 12 to 20 amino acids in length.

497. The BCMA binding molecule of any one of embodiments 494 to 496, wherein the linker is a charged linker and/or a flexible linker.

498. The BCMA binding molecule of any one of embodiments 494 to 497, wherein the linker is selected from any one of linkers L1 through L54.

499. The BCMA binding molecule of embodiment 498, wherein the linker region comprises the amino acid sequence of the linker designated L1.

500. The BCMA binding molecule of embodiment 498, wherein the linker region comprises the amino acid sequence of the linker designated L2.

501. The BCMA binding molecule of embodiment 498, wherein the linker region comprises the amino acid sequence of the linker designated L3.

502. The BCMA binding molecule of embodiment 498, wherein the linker region comprises the amino acid sequence of the linker designated L4.

503. The BCMA binding molecule of embodiment 498, wherein the linker region comprises the amino acid sequence of the linker designated L5.

504. The BCMA binding molecule of embodiment 498, wherein the linker region comprises the amino acid sequence of the linker designated L6.

505. The BCMA binding molecule of embodiment 498, wherein the linker region comprises the amino acid sequence of the linker designated L7.

506. The BCMA binding molecule of embodiment 498, wherein the linker region comprises the amino acid sequence of the linker designated L8.

507. The BCMA binding molecule of embodiment 498, wherein the linker region comprises the amino acid sequence of the linker designated L9.

508. The BCMA binding molecule of embodiment 498, wherein the linker region comprises the amino acid sequence of the linker designated L10.

509. The BCMA binding molecule of embodiment 498, wherein the linker region comprises the amino acid sequence of the linker designated L11.

510. The BCMA binding molecule of embodiment 498, wherein the linker region comprises the amino acid sequence of the linker designated L12.

511. The BCMA binding molecule of embodiment 498, wherein the linker region comprises the amino acid sequence of the linker designated L13.

512. The BCMA binding molecule of embodiment 498, wherein the linker region comprises the amino acid sequence of the linker designated L14.

513. The BCMA binding molecule of embodiment 498, wherein the linker region comprises the amino acid sequence of the linker designated L15.

514. The BCMA binding molecule of embodiment 498, wherein the linker region comprises the amino acid sequence of the linker designated L16.

515. The BCMA binding molecule of embodiment 498, wherein the linker region comprises the amino acid sequence of the linker designated L17.

516. The BCMA binding molecule of embodiment 498, wherein the linker region comprises the amino acid sequence of the linker designated L18.

517. The BCMA binding molecule of embodiment 498, wherein the linker region comprises the amino acid sequence of the linker designated L19.

518. The BCMA binding molecule of embodiment 498, wherein the linker region comprises the amino acid sequence of the linker designated L20.

519. The BCMA binding molecule of embodiment 498, wherein the linker region comprises the amino acid sequence of the linker designated L21.

520. The BCMA binding molecule of embodiment 498, wherein the linker region comprises the amino acid sequence of the linker designated L22.
521. The BCMA binding molecule of embodiment 498, wherein the linker region comprises the amino acid sequence of the linker designated L23.
522. The BCMA binding molecule of embodiment 498, wherein the linker region comprises the amino acid sequence of the linker designated L24.
523. The BCMA binding molecule of embodiment 498, wherein the linker region comprises the amino acid sequence of the linker designated L25.
524. The BCMA binding molecule of embodiment 498, wherein the linker region comprises the amino acid sequence of the linker designated L26.
525. The BCMA binding molecule of embodiment 498, wherein the linker region comprises the amino acid sequence of the linker designated L27.
526. The BCMA binding molecule of embodiment 498, wherein the linker region comprises the amino acid sequence of the linker designated L28.
527. The BCMA binding molecule of embodiment 498, wherein the linker region comprises the amino acid sequence of the linker designated L29.
528. The BCMA binding molecule of embodiment 498, wherein the linker region comprises the amino acid sequence of the linker designated L30.
529. The BCMA binding molecule of embodiment 498, wherein the linker region comprises the amino acid sequence of the linker designated L31.
530. The BCMA binding molecule of embodiment 498, wherein the linker region comprises the amino acid sequence of the linker designated L32.
531. The BCMA binding molecule of embodiment 498, wherein the linker region comprises the amino acid sequence of the linker designated L33.
532. The BCMA binding molecule of embodiment 498, wherein the linker region comprises the amino acid sequence of the linker designated L34.
533. The BCMA binding molecule of embodiment 498, wherein the linker region comprises the amino acid sequence of the linker designated L35.
534. The BCMA binding molecule of embodiment 498, wherein the linker region comprises the amino acid sequence of the linker designated L36.
535. The BCMA binding molecule of embodiment 498, wherein the linker region comprises the amino acid sequence of the linker designated L37.
536. The BCMA binding molecule of embodiment 498, wherein the linker region comprises the amino acid sequence of the linker designated L38.
537. The BCMA binding molecule of embodiment 498, wherein the linker region comprises the amino acid sequence of the linker designated L39.
538. The BCMA binding molecule of embodiment 498, wherein the linker region comprises the amino acid sequence of the linker designated L40.
539. The BCMA binding molecule of embodiment 498, wherein the linker region comprises the amino acid sequence of the linker designated L41.
540. The BCMA binding molecule of embodiment 498, wherein the linker region comprises the amino acid sequence of the linker designated L42.
541. The BCMA binding molecule of embodiment 498, wherein the linker region comprises the amino acid sequence of the linker designated L43.
542. The BCMA binding molecule of embodiment 498, wherein the linker region comprises the amino acid sequence of the linker designated L44.
543. The BCMA binding molecule of embodiment 498, wherein the linker region comprises the amino acid sequence of the linker designated L45.
544. The BCMA binding molecule of embodiment 498, wherein the linker region comprises the amino acid sequence of the linker designated L46.
545. The BCMA binding molecule of embodiment 498, wherein the linker region comprises the amino acid sequence of the linker designated L47.
546. The BCMA binding molecule of embodiment 498, wherein the linker region comprises the amino acid sequence of the linker designated L48.
547. The BCMA binding molecule of embodiment 498, wherein the linker region comprises the amino acid sequence of the linker designated L49.
548. The BCMA binding molecule of embodiment 498, wherein the linker region comprises the amino acid sequence of the linker designated L50.
549. The BCMA binding molecule of embodiment 498, wherein the linker region comprises the amino acid sequence of the linker designated L51.
550. The BCMA binding molecule of embodiment 498, wherein the linker region comprises the amino acid sequence of the linker designated L52.
551. The BCMA binding molecule of embodiment 498, wherein the linker region comprises the amino acid sequence of the linker designated L53.
552. The BCMA binding molecule of embodiment 498, wherein the linker region comprises the amino acid sequence of the linker designated L54.
553. The BCMA binding molecule of any one of embodiments 1 to 552, which comprises at least one Fab domain.
554. The BCMA binding molecule of embodiment 553, wherein at least one Fab domain comprises any of the Fab heterodimerization modifications set forth in Table 2.
555. The BCMA binding molecule of embodiment 554, wherein at least one Fab domain comprises the Fab heterodimerization modifications designated as F1.
556. The BCMA binding molecule of embodiment 554, wherein at least one Fab domain comprises the Fab heterodimerization modifications designated as F2.
557. The BCMA binding molecule of embodiment 554, wherein at least one Fab domain comprises the Fab heterodimerization modifications designated as F3.
558. The BCMA binding molecule of embodiment 554, wherein at least one Fab domain comprises the Fab heterodimerization modifications designated as F4.
559. The BCMA binding molecule of embodiment 554, wherein at least one Fab domain comprises the Fab heterodimerization modifications designated as F5.
560. The BCMA binding molecule of embodiment 554, wherein at least one Fab domain comprises the Fab heterodimerization modifications designated as F6.
561. The BCMA binding molecule of embodiment 554, wherein at least one Fab domain comprises the Fab heterodimerization modifications designated as F7.
562. The BCMA binding molecule of any one of embodiments 145 to 561, which is a bispecific binding molecule that comprises at least two ABDs, an ABD and an ABD chain, or two ABD chains connected to one another via a linker.

563. The BCMA binding molecule of embodiment 562, wherein the linker is 5 to 25 amino acids in length.

564. The BCMA binding molecule of embodiment 563, wherein the linker is 12 to 20 amino acids in length.

565. The BCMA binding molecule of any one of embodiments 562 to 564, wherein the linker is a charged linker and/or a flexible linker.

566. The BCMA binding molecule of any one of embodiments 562 to 565, wherein the linker is selected from any one of linkers L1 through L54.

567. The BCMA binding molecule of embodiment 566, wherein the linker region comprises the amino acid sequence of the linker designated L1.

568. The BCMA binding molecule of embodiment 566, wherein the linker region comprises the amino acid sequence of the linker designated L2.

569. The BCMA binding molecule of embodiment 566, wherein the linker region comprises the amino acid sequence of the linker designated L3.

570. The BCMA binding molecule of embodiment 566, wherein the linker region comprises the amino acid sequence of the linker designated L4.

571. The BCMA binding molecule of embodiment 566, wherein the linker region comprises the amino acid sequence of the linker designated L5.

572. The BCMA binding molecule of embodiment 566, wherein the linker region comprises the amino acid sequence of the linker designated L6.

573. The BCMA binding molecule of embodiment 566, wherein the linker region comprises the amino acid sequence of the linker designated L7.

574. The BCMA binding molecule of embodiment 566, wherein the linker region comprises the amino acid sequence of the linker designated L8.

575. The BCMA binding molecule of embodiment 566, wherein the linker region comprises the amino acid sequence of the linker designated L9.

576. The BCMA binding molecule of embodiment 566, wherein the linker region comprises the amino acid sequence of the linker designated L10.

577. The BCMA binding molecule of embodiment 566, wherein the linker region comprises the amino acid sequence of the linker designated L11.

578. The BCMA binding molecule of embodiment 566, wherein the linker region comprises the amino acid sequence of the linker designated L12.

579. The BCMA binding molecule of embodiment 566, wherein the linker region comprises the amino acid sequence of the linker designated L13.

580. The BCMA binding molecule of embodiment 566, wherein the linker region comprises the amino acid sequence of the linker designated L14.

581. The BCMA binding molecule of embodiment 566, wherein the linker region comprises the amino acid sequence of the linker designated L15.

582. The BCMA binding molecule of embodiment 566, wherein the linker region comprises the amino acid sequence of the linker designated L16.

583. The BCMA binding molecule of embodiment 566, wherein the linker region comprises the amino acid sequence of the linker designated L17.

584. The BCMA binding molecule of embodiment 566, wherein the linker region comprises the amino acid sequence of the linker designated L18.

585. The BCMA binding molecule of embodiment 566, wherein the linker region comprises the amino acid sequence of the linker designated L19.

586. The BCMA binding molecule of embodiment 566, wherein the linker region comprises the amino acid sequence of the linker designated L20.

587. The BCMA binding molecule of embodiment 566, wherein the linker region comprises the amino acid sequence of the linker designated L21.

588. The BCMA binding molecule of embodiment 566, wherein the linker region comprises the amino acid sequence of the linker designated L22.

589. The BCMA binding molecule of embodiment 566, wherein the linker region comprises the amino acid sequence of the linker designated L23.

590. The BCMA binding molecule of embodiment 566, wherein the linker region comprises the amino acid sequence of the linker designated L24.

591. The BCMA binding molecule of embodiment 566, wherein the linker region comprises the amino acid sequence of the linker designated L25.

592. The BCMA binding molecule of embodiment 566, wherein the linker region comprises the amino acid sequence of the linker designated L26.

593. The BCMA binding molecule of embodiment 566, wherein the linker region comprises the amino acid sequence of the linker designated L27.

594. The BCMA binding molecule of embodiment 566, wherein the linker region comprises the amino acid sequence of the linker designated L28.

595. The BCMA binding molecule of embodiment 566, wherein the linker region comprises the amino acid sequence of the linker designated L29.

596. The BCMA binding molecule of embodiment 566, wherein the linker region comprises the amino acid sequence of the linker designated L30.

597. The BCMA binding molecule of embodiment 566, wherein the linker region comprises the amino acid sequence of the linker designated L31.

598. The BCMA binding molecule of embodiment 566, wherein the linker region comprises the amino acid sequence of the linker designated L32.

599. The BCMA binding molecule of embodiment 566, wherein the linker region comprises the amino acid sequence of the linker designated L33.

600. The BCMA binding molecule of embodiment 566, wherein the linker region comprises the amino acid sequence of the linker designated L34.

601. The BCMA binding molecule of embodiment 566, wherein the linker region comprises the amino acid sequence of the linker designated L35.

602. The BCMA binding molecule of embodiment 566, wherein the linker region comprises the amino acid sequence of the linker designated L36.

603. The BCMA binding molecule of embodiment 566, wherein the linker region comprises the amino acid sequence of the linker designated L37.

604. The BCMA binding molecule of embodiment 566, wherein the linker region comprises the amino acid sequence of the linker designated L38.

605. The BCMA binding molecule of embodiment 566, wherein the linker region comprises the amino acid sequence of the linker designated L39.

606. The BCMA binding molecule of embodiment 566, wherein the linker region comprises the amino acid sequence of the linker designated L40.

607. The BCMA binding molecule of embodiment 566, wherein the linker region comprises the amino acid sequence of the linker designated L41.

608. The BCMA binding molecule of embodiment 566, wherein the linker region comprises the amino acid sequence of the linker designated L42.
609. The BCMA binding molecule of embodiment 566, wherein the linker region comprises the amino acid sequence of the linker designated L43.
610. The BCMA binding molecule of embodiment 566, wherein the linker region comprises the amino acid sequence of the linker designated L44.
611. The BCMA binding molecule of embodiment 566, wherein the linker region comprises the amino acid sequence of the linker designated L45.
612. The BCMA binding molecule of embodiment 566, wherein the linker region comprises the amino acid sequence of the linker designated L46.
613. The BCMA binding molecule of embodiment 566, wherein the linker region comprises the amino acid sequence of the linker designated L47.
614. The BCMA binding molecule of embodiment 566, wherein the linker region comprises the amino acid sequence of the linker designated L48.
615. The BCMA binding molecule of embodiment 566, wherein the linker region comprises the amino acid sequence of the linker designated L49.
616. The BCMA binding molecule of embodiment 498, wherein the linker region comprises the amino acid sequence of the linker designated L50.
617. The BCMA binding molecule of embodiment 498, wherein the linker region comprises the amino acid sequence of the linker designated L51.
618. The BCMA binding molecule of embodiment 498, wherein the linker region comprises the amino acid sequence of the linker designated L52.
619. The BCMA binding molecule of embodiment 498, wherein the linker region comprises the amino acid sequence of the linker designated L53.
620. The BCMA binding molecule of embodiment 566, wherein the linker region comprises the amino acid sequence of the linker designated L54.
621. The BCMA binding molecule of any one of embodiments 145 to 620, which is a bivalent BCMA binding molecule.
622. The BCMA binding molecule of embodiment 621, wherein the bivalent BCMA binding molecule has any one of the configurations depicted in FIGS. 1B-1F.
623. The BCMA binding molecule of embodiment 622, wherein the bivalent BCMA binding molecule has the configuration depicted in FIG. 1B.
624. The BCMA binding molecule of embodiment 622, wherein the bivalent BCMA binding molecule has the configuration depicted in FIG. 1C.
625. The BCMA binding molecule of embodiment 622, wherein the bivalent BCMA binding molecule has the configuration depicted in FIG. 1D.
626. The BCMA binding molecule of embodiment 622, wherein the bivalent BCMA binding molecule has the configuration depicted in FIG. 1E.
627. The BCMA binding molecule of embodiment 622, wherein the bivalent BCMA binding molecule has the configuration depicted in FIG. 1F.
628. The BCMA binding molecule of any one of embodiments 622 to 627, in which the ABDs have the configuration designated as B1.
629. The BCMA binding molecule of any one of embodiments 622 to 627, in which the ABDs have the configuration designated as B2.
630. The BCMA binding molecule of any one of embodiments 145 to 620, which is a trivalent BCMA binding molecule.
631. The BCMA binding molecule of embodiment 630, wherein the trivalent BCMA binding molecule has any one of the configurations depicted in FIGS. 1G-1Z.
632. The BCMA binding molecule of embodiment 631, wherein the trivalent BCMA binding molecule has the configuration depicted in FIG. 1G.
633. The BCMA binding molecule of embodiment 631, wherein the trivalent BCMA binding molecule has the configuration depicted in FIG. 1H.
634. The BCMA binding molecule of embodiment 631, wherein the trivalent BCMA binding molecule has the configuration depicted in FIG. 1I.
635. The BCMA binding molecule of embodiment 631, wherein the trivalent BCMA binding molecule has the configuration depicted in FIG. 1J.
636. The BCMA binding molecule of embodiment 631, wherein the trivalent BCMA binding molecule has the configuration depicted in FIG. 1K.
637. The BCMA binding molecule of embodiment 631, wherein the trivalent BCMA binding molecule has the configuration depicted in FIG. 1L.
638. The BCMA binding molecule of embodiment 631, wherein the trivalent BCMA binding molecule has the configuration depicted in FIG. 1M.
639. The BCMA binding molecule of embodiment 631, wherein the trivalent BCMA binding molecule has the configuration depicted in FIG. 1N.
640. The BCMA binding molecule of embodiment 631, wherein the trivalent BCMA binding molecule has the configuration depicted in FIG. 1O.
641. The BCMA binding molecule of embodiment 631, wherein the trivalent BCMA binding molecule has the configuration depicted in FIG. 1P.
642. The BCMA binding molecule of embodiment 631, wherein the trivalent BCMA binding molecule has the configuration depicted in FIG. 1Q.
643. The BCMA binding molecule of embodiment 631, wherein the trivalent BCMA binding molecule has the configuration depicted in FIG. 1R.
644. The BCMA binding molecule of embodiment 631, wherein the trivalent BCMA binding molecule has the configuration depicted in FIG. 1S.
645. The BCMA binding molecule of embodiment 631, wherein the trivalent BCMA binding molecule has the configuration depicted in FIG. 1T.
646. The BCMA binding molecule of embodiment 631, wherein the trivalent BCMA binding molecule has the configuration depicted in FIG. 1U.
647. The BCMA binding molecule of embodiment 631, wherein the trivalent BCMA binding molecule has the configuration depicted in FIG. 1V.
648. The BCMA binding molecule of embodiment 631, wherein the trivalent BCMA binding molecule has the configuration depicted in FIG. 1W.
649. The BCMA binding molecule of embodiment 631, wherein the trivalent BCMA binding molecule has the configuration depicted in FIG. 1X.
650. The BCMA binding molecule of embodiment 631, wherein the trivalent BCMA binding molecule has the configuration depicted in FIG. 1Y.
651. The BCMA binding molecule of embodiment 631, wherein the trivalent BCMA binding molecule has the configuration depicted in FIG. 1Z.

652. The BCMA binding molecule of any one of embodiments 631 to 651, in which the ABDs have the configuration designated as T1.
653. The BCMA binding molecule of any one of embodiments 631 to 651, in which the ABDs have the configuration designated as T2.
654. The BCMA binding molecule of any one of embodiments 631 to 651, in which the ABDs have the configuration designated as T3.
655. The BCMA binding molecule of any one of embodiments 631 to 651, in which the ABDs have the configuration designated as T4.
656. The BCMA binding molecule of any one of embodiments 631 to 651, in which the ABDs have the configuration designated as T5.
657. The BCMA binding molecule of any one of embodiments 631 to 651, in which the ABDs have the configuration designated as T6.
658. The BCMA binding molecule of any one of embodiments 145 to 620, which is a tetravalent BCMA binding molecule.
659. The BCMA binding molecule of embodiment 658, wherein the tetravalent BCMA binding molecule has any one of the configurations depicted in FIGS. 1AA-1AG.
660. The BCMA binding molecule of embodiment 659, wherein the tetravalent BCMA binding molecule has the configuration depicted in FIG. 1AA.
661. The BCMA binding molecule of embodiment 659, wherein the tetravalent BCMA binding molecule has the configuration depicted in FIG. 1AB.
662. The BCMA binding molecule of embodiment 659, wherein the tetravalent BCMA binding molecule has the configuration depicted in FIG. 1AC.
663. The BCMA binding molecule of embodiment 659, wherein the tetravalent BCMA binding molecule has the configuration depicted in FIG. 1AD.
664. The BCMA binding molecule of embodiment 659, wherein the tetravalent BCMA binding molecule has the configuration depicted in FIG. 1AE.
665. The BCMA binding molecule of embodiment 659, wherein the tetravalent BCMA binding molecule has the configuration depicted in FIG. 1AF.
666. The BCMA binding molecule of embodiment 659, wherein the tetravalent BCMA binding molecule has the configuration depicted in FIG. 1AG.
667. The BCMA binding molecule of any one of embodiments 659 to 666, in which the ABDs have any one of the configurations designated Tv 1 through Tv 24.
668. The BCMA binding molecule of embodiment 667, in which the ABDs have the configuration designated Tv 1.
669. The BCMA binding molecule of embodiment 667, in which the ABDs have the configuration designated Tv 2.
670. The BCMA binding molecule of embodiment 667, in which the ABDs have the configuration designated Tv 3.
671. The BCMA binding molecule of embodiment 667, in which the ABDs have the configuration designated Tv 4.
672. The BCMA binding molecule of embodiment 667, in which the ABDs have the configuration designated Tv 5.
673. The BCMA binding molecule of embodiment 667, in which the ABDs have the configuration designated Tv 6.
674. The BCMA binding molecule of embodiment 667, in which the ABDs have the configuration designated Tv 7.
675. The BCMA binding molecule of embodiment 667, in which the ABDs have the configuration designated Tv 8.
676. The BCMA binding molecule of embodiment 667, in which the ABDs have the configuration designated Tv 9.
677. The BCMA binding molecule of embodiment 667, in which the ABDs have the configuration designated Tv 10.
678. The BCMA binding molecule of embodiment 667, in which the ABDs have the configuration designated Tv 11.
679. The BCMA binding molecule of embodiment 667, in which the ABDs have the configuration designated Tv 12.
680. The BCMA binding molecule of embodiment 667, in which the ABDs have the configuration designated Tv 13.
681. The BCMA binding molecule of embodiment 667, in which the ABDs have the configuration designated Tv 14.
682. The BCMA binding molecule of any one of embodiments 1 to 681, which has cross-species reactivity.
683. The BCMA binding molecule of embodiment 682, wherein the BCMA binding molecule further binds specifically to BCMA in one or more non-human mammalian species.
684. The BCMA binding molecule of embodiment 683, wherein the one or more non-human mammalian species comprises one or more non-human primate species.
685. The BCMA binding molecule of embodiment 684, wherein the one or more non-human primate species comprises *Macaca fascicularis*.
686. The BCMA binding molecule of embodiment 684 or embodiment 685, wherein the one or more non-human primate species comprises *Macaca mulatta*.
687. The BCMA binding molecule of any one of embodiments 684 to 686, wherein the one or more non-human primate species comprises *Macaca nemestrina*.
688. The BCMA binding molecule of any one of embodiments 682 to 687, wherein the one or more non-human mammalian species comprises *Mus musculus*.
689. The BCMA binding molecule of any one of embodiments 1 to 681, wherein the BCMA binding molecule does not have cross-species reactivity.
690. The BCMA binding molecule of any one of embodiments 145 to 681, which is a BBM and wherein ABD1 and/or ABD2 has cross-species reactivity.
691. The BCMA binding molecule of embodiment 690, wherein ABD1 further binds specifically to BCMA in one or more non-human mammalian species.
692. The BCMA binding molecule of embodiment 690 or embodiment 691, wherein ABD2 further binds specifically to the component of the TCR complex in one or more non-human mammalian species.
693. The BCMA binding molecule of any one of embodiments 690 to 692, wherein the one or more non-human mammalian species comprises one or more non-human primate species.
694. The BCMA binding molecule of embodiment 693, wherein the one or more non-human primate species comprises *Macaca fascicularis*.

695. The BCMA binding molecule of embodiment 693 or embodiment 694, wherein the one or more non-human primate species comprises *Macaca mulatta*.
696. The BCMA binding molecule of any one of embodiments 693 to 695, wherein the one or more non-human primate species comprises *Macaca nemestrina*.
697. The BCMA binding molecule of any one of embodiments 692 to 696, wherein the one or more non-human mammalian species comprises *Mus musculus*.
698. The BCMA binding molecule of any one of embodiments 145 to 681, which is a BBM and wherein ABD1 and ABD2 do not have cross-species reactivity.
699. A BCMA binding molecule comprising:
  (a) a first polypeptide comprising:
    (i) a first heavy chain constant domain comprising a first Fc region;
    (ii) a scFv comprising a scFv variable light domain, an scFv linker and a scFv variable heavy domain; wherein the scFv is covalently attached to the N-terminus of the first Fc region by a hinge;
  (b) a second polypeptide comprising:
    (i) a heavy chain variable domain;
    (ii) a second heavy chain constant domain comprising a second Fc region; and
  (c) a third polypeptide comprising a light chain constant domain and a light chain variable domain;
  wherein
  A. the first and second Fc regions form an Fc domain;
  B. the first and second Fc regions have a set of amino acid substitutions comprising S364K/E357Q:L368D/370S, for example wherein the first Fc region comprises S364K/E357Q substitutions and the second Fc region comprises L368D/370S substitutions;
  C. the first and/or second Fc regions comprise amino acid modifications E223P, L234V, L235A, G236del, S267K, for example wherein the first and second Fc regions both comprise amino acid modifications E223P, L234V, L235A, G236del, S267K;
  D. the first and/or second Fc regions comprise amino acid substitutions N208D, Q295E, N384D, Q418E, and N421D, for example wherein the second Fc region but not the first Fc region comprises amino acid substitutions N208D, Q295E, N384D, Q418E, and N421D;
  E. the heavy chain variable domain of the second polypeptide and the light chain variable domain of the third polypeptide comprise the CDR sequences of AB1 as set forth in Table 1C-1 and Table 1C-2, Table 1D-1 and Table 1D-2, Table 1E-1 and Table 1E-2, Table 1F-1 and Table 1F-2, Table 1G-1 and Table 1G-2, or Table 1H-1 and Table 1H-2; and
  F. the scFv binds human CD3.
700. The BCMA binding molecule of embodiment 699, wherein the light chain variable domain of the third polypeptide and the heavy chain domain of the second polypeptide comprise the light chain variable domain and heavy chain variable domain sequences of AB1 as set forth in Table 1O-1 and Table 1O-2.
701. A BCMA binding molecule comprising:
  a first polypeptide comprising:
    (i) a first heavy chain constant domain comprising a first Fc region;
    (ii) a scFv comprising a scFv variable light domain, an scFv linker and a scFv variable heavy domain; wherein the scFv is covalently attached to the N-terminus of the first Fc region by a hinge;
  (b) a second polypeptide comprising a second heavy chain comprising:
    (i) a heavy chain variable domain;
    (ii) a second heavy chain constant domain comprising a second Fc region; and
  (c) a third polypeptide comprising a light chain constant domain and a light chain variable domain;
  wherein
  A. the first and second Fc regions form an Fc domain;
  B. the first and second Fc regions have a set of amino acid substitutions comprising S364K/E357Q:L368D/370S, for example wherein the first Fc region comprises S364K/E357Q substitutions and the second Fc region comprises L368D/370S substitutions;
  C. the first and/or second Fc regions comprise amino acid modifications E223P, L234V, L235A, G236del, S267K, for example wherein the first and second Fc regions both comprise amino acid modifications E223P, L234V, L235A, G236del, S267K;
  D. the first and/or second Fc regions comprise amino acid substitutions N208D, Q295E, N384D, Q418E, and N421D, for example wherein the second Fc region but not the first Fc region comprises amino acid substitutions N208D, Q295E, N384D, Q418E, and N421D;
  E. the heavy chain variable domain of the second polypeptide and the light chain variable domain of the third polypeptide comprise the CDR sequences of AB2 as set forth in Table 1C-1 and Table 1C-2, Table 1D-1 and Table 1D-2, Table 1E-1 and Table 1E-2, Table 1F-1 and Table 1F-2, Table 1G-1 and Table 1G-2, or Table 1H-1 and Table 1H-2; and
  F. the scFv binds human CD3.
702. The BCMA binding molecule of embodiment 701, wherein the light chain variable domain of the third polypeptide and the heavy chain domain of the second polypeptide comprise the light chain variable domain and heavy chain variable domain sequences of AB2 as set forth in Table 1O-1 and Table 1O-2.
703. A BCMA binding molecule comprising:
  (a) a first polypeptide comprising:
    (i) a first heavy chain constant domain comprising a first Fc region;
    (ii) a scFv comprising a scFv variable light domain, an scFv linker and a scFv variable heavy domain; wherein the scFv is covalently attached to the N-terminus of the first Fc region by a hinge;
  (b) a second polypeptide comprising a second heavy chain comprising:
    (i) a heavy chain variable domain;
    (ii) a second heavy chain constant domain comprising a second Fc region; and
  (c) a third polypeptide comprising a light chain constant domain and a light chain variable domain;
  wherein
  A. the first and second Fc regions form an Fc domain;
  B. the first and second Fc regions have a set of amino acid substitutions comprising S364K/E357Q:L368D/370S, for example wherein the first Fc region comprises S364K/E357Q substitutions and the second Fc region comprises L368D/370S substitutions;
  C. the first and/or second Fc regions comprise amino acid modifications E223P, L234V, L235A, G236del, S267K, for example wherein the first and second Fc regions both comprise amino acid modifications E223P, L234V, L235A, G236del, S267K;
  D. the first and/or second Fc regions comprise amino acid substitutions N208D, Q295E, N384D, Q418E, and N421D, for example wherein the second Fc region but not the first Fc region comprises amino acid substitutions N208D, Q295E, N384D, Q418E, and N421D;
E. the heavy chain variable domain of the second polypeptide and the light chain variable domain of the third polypeptide comprise the CDR sequences of AB3 as set forth in Table 1I-1 and Table 1I-2, Table 1J-1 and Table 1J-2, Table 1K-1(a) and Table 1K-2, Table 1K-1(b) and Table 1K-2, Table 1L-1 and Table 1L-2, Table 1M-1 and Table 1M-2, or Table 1N-1 and Table 1N-2; and
F. the scFv binds human CD3.

704. The BCMA binding molecule of embodiment 703, wherein the light chain variable domain of the third polypeptide and the heavy chain domain of the second polypeptide comprise the light chain variable domain and heavy chain variable domain sequences of AB3 as set forth in Table 1O-1 and Table 1O-2.

705. The BCMA binding molecule of any one of embodiments 699 to 704, wherein the scFv variable light domain and the scFv variable heavy domain comprise the variable light domain and the variable heavy domain of CD3-23 as set forth in Table 3A.

706. The BCMA binding molecule of any one of embodiments 699 to 705, wherein the amino acid sequence of the scFv linker is selected from the amino acid sequences set forth in Table 10.

707. The BCMA binding molecule of embodiment 706, wherein the scFv linker comprises the amino acid sequence of the linker designated L36.

708. A BCMA binding molecule comprising:
(a) a first polypeptide comprising:
  (i) a first heavy chain constant domain comprising a first Fc region;
  (ii) a scFv comprising an amino acid sequence of the scFv designated CD3-23 in Table 3A; wherein the scFv is covalently attached to the N-terminus of the first Fc region by a hinge;
(b) a second polypeptide comprising:
  (i) a heavy chain variable domain;
  (ii) a second heavy chain constant domain comprising a second Fc region; and
(c) a third polypeptide comprising a light chain constant domain and a light chain variable domain;
wherein
A. the first and second Fc regions form an Fc domain;
B. the first and second Fc regions have a set of amino acid substitutions comprising S364K/E357Q:L368D/370S, for example wherein the first Fc region comprises S364K/E357Q substitutions and the second Fc region comprises L368D/370S substitutions;
C. the first and/or second Fc regions comprise amino acid modifications E223P, L234V, L235A, G236del, S267K, for example wherein the first and second Fc regions both comprise amino acid modifications E223P, L234V, L235A, G236del, S267K;
D. the first and/or second Fc regions comprise amino acid substitutions N208D, Q295E, N384D, Q418E, and N421D, for example wherein the second Fc region but not the first Fc region comprises amino acid substitutions N208D, Q295E, N384D, Q418E, and N421D;
E. the light chain variable domain and the heavy chain variable domain comprise the light chain variable domain and heavy chain variable domain sequences of AB1 as set forth in Table 1O-1 and Table 1O-2.

709. A BCMA binding molecule comprising:
(a) a first polypeptide comprising:
  (i) a first heavy chain constant domain comprising a first Fc region;
  (ii) a scFv comprising an amino acid sequence of the scFv designated CD3-23 in Table 3A; wherein the scFv is covalently attached to the N-terminus of the first Fc region by a hinge;
(b) a second polypeptide comprising:
  (i) a heavy chain variable domain;
  (ii) a second heavy chain constant domain comprising a second Fc region; and
(c) a third polypeptide comprising a light chain constant domain and a light chain variable domain;
wherein
A. the first and second Fc regions form an Fc domain;
B. the first and second Fc regions have a set of amino acid substitutions comprising S364K/E357Q:L368D/370S, for example wherein the first Fc region comprises S364K/E357Q substitutions and the second Fc region comprises L368D/370S substitutions;
C. the first and/or second Fc regions comprise amino acid modifications E223P, L234V, L235A, G236del, S267K, for example wherein the first and second Fc regions both comprise amino acid modifications E223P, L234V, L235A, G236del, S267K;
D. the first and/or second Fc regions comprise amino acid substitutions N208D, Q295E, N384D, Q418E, and N421D, for example wherein the second Fc region but not the first Fc region comprises amino acid substitutions N208D, Q295E, N384D, Q418E, and N421D;
E. the light chain variable domain and the heavy chain variable domain comprise the light chain variable domain and heavy chain variable domain sequences of AB2 as set forth in Table 1O-1 and Table 1O-2.

710. A BCMA binding molecule comprising:
(a) a first polypeptide comprising:
  (i) a first heavy chain constant domain comprising a first Fc region;
  (ii) a scFv comprising an amino acid sequence of the scFv designated CD3-23 in Table 3A; wherein the scFv is covalently attached to the N-terminus of the first Fc region by a hinge;
(b) a second polypeptide comprising:
  (i) a heavy chain variable domain;
  (ii) a second heavy chain constant domain comprising a second Fc region; and
(c) a third polypeptide comprising a light chain constant domain and a light chain variable domain;
wherein
A. the first and second Fc regions form an Fc domain;
B. the first and second Fc regions have a set of amino acid substitutions comprising S364K/E357Q:L368D/370S, for example wherein the first Fc region comprises S364K/E357Q substitutions and the second Fc region comprises L368D/370S substitutions;
C. the first and/or second Fc regions comprise amino acid modifications E223P, L234V, L235A, G236del, S267K, for example wherein the first and second Fc regions both comprise amino acid modifications E223P, L234V, L235A, G236del, S267K;
D. the first and/or second Fc regions comprise amino acid substitutions N208D, Q295E, N384D, Q418E, and N421D, for example wherein the second Fc region but not the first Fc region comprises amino acid substitutions N208D, Q295E, N384D, Q418E, and N421D;
E. the light chain variable domain and the heavy chain variable domain comprise the light chain variable domain and heavy chain variable domain sequences of AB3 as set forth in Table 1O-1 and Table 1O-2.

711. A BCMA binding molecule comprising or consisting of polypeptides having the amino acid sequences of bivalent AB1, as set forth in Table 11A.

712. A BCMA binding molecule comprising or consisting of polypeptides having the amino acid sequences of trivalent AB1, as set forth in Table 11B.

713. A BCMA binding molecule comprising or consisting of polypeptides having the amino acid sequences of bivalent AB2, as set forth in Table 11C.

714. A BCMA binding molecule comprising or consisting of polypeptides having the amino acid sequences of trivalent AB2, as set forth in Table 11D.

715. A BCMA binding molecule comprising or consisting of polypeptides having the amino acid sequences of bivalent AB3, as set forth in Table 11E.

716. A BCMA binding molecule comprising or consisting of polypeptides having the amino acid sequences of trivalent AB3, as set forth in Table 11F.

717. The BCMA binding molecule of any one of embodiments 1 to 716 for use as a medicament.

718. The BCMA binding molecule of any one of embodiments 1 to 716 for use in treating a disease or disorder associated with expression of BCMA.

719. The BCMA binding molecule of embodiment 718, wherein the disease or disorder comprises a cancer.

720. The BCMA binding molecule of embodiment 719, wherein the cancer comprises a B cell malignancy.

721. The BCMA binding molecule of embodiment 720, wherein the B cell malignancy is Hodgkin's lymphoma, non-Hodgkin's lymphoma or multiple myeloma.

722. The BCMA binding molecule of embodiment 719, wherein the cancer is Hodgkin's lymphoma.

723. The BCMA binding molecule of embodiment 722, wherein the Hodgkin's lymphoma is nodular sclerosing Hodgkin's lymphoma.

724. The BCMA binding molecule of embodiment 722, wherein the Hodgkin's lymphoma is mixed-cellularity subtype Hodgkin's lymphoma.

725. The BCMA binding molecule of embodiment 722, wherein the Hodgkin's lymphoma is lymphocyte-rich or lymphocytic predominance Hodgkin's lymphoma.

726. The BCMA binding molecule of embodiment 722, wherein the Hodgkin's lymphoma is lymphocyte depleted Hodgkin's lymphoma.

727. The BCMA binding molecule of embodiment 719, wherein the cancer is non-Hodgkin's lymphoma.

728. The BCMA binding molecule of embodiment 727, wherein the non-Hodgkin's lymphoma is a B cell lymphoma or a T cell lymphoma.

729. The BCMA binding molecule of embodiment 727, wherein the non-Hodgkin's lymphoma is a B cell lymphoma.

730. The BCMA binding molecule of embodiment 727, wherein the non-Hodgkin's lymphoma is diffuse large B-cell lymphoma (DLBCL), follicular lymphoma, chronic lymphocytic leukemia (CLL)/small lymphocytic lymphoma (SLL), mantle cell lymphoma (MCL), marginal zone lymphoma, Burkitt lymphoma, lymphoplasmacytic lymphoma (Waldenstrom macroglobulinemia), hairy cell leukemia, primary central nervous system (CNS) lymphoma, primary mediastinal large B-cell lymphoma, mediastinal grey-zone lymphoma (MGZL), splenic marginal zone B-cell lymphoma, extranodal marginal zone B-cell lymphoma of MALT, nodal marginal zone B-cell lymphoma, or primary effusion lymphoma.

731. The BCMA binding molecule of embodiment 730, wherein the non-Hodgkin's lymphoma is diffuse large B-cell lymphoma (DLBCL).

732. The BCMA binding molecule of embodiment 730, wherein the non-Hodgkin's lymphoma is follicular lymphoma.

733. The BCMA binding molecule of embodiment 730, wherein the non-Hodgkin's lymphoma is chronic lymphocytic leukemia (CLL)/small lymphocytic lymphoma (SLL).

734. The BCMA binding molecule of embodiment 730, wherein the non-Hodgkin's lymphoma is mantle cell lymphoma (MCL).

735. The BCMA binding molecule of embodiment 730, wherein the non-Hodgkin's lymphoma is marginal zone lymphoma.

736. The BCMA binding molecule of embodiment 730, wherein the non-Hodgkin's lymphoma is Burkitt lymphoma.

737. The BCMA binding molecule of embodiment 730, wherein the non-Hodgkin's lymphoma is lymphoplasmacytic lymphoma (Waldenstrom macroglobulinemia).

738. The BCMA binding molecule of embodiment 730, wherein the non-Hodgkin's lymphoma is hairy cell leukemia.

739. The BCMA binding molecule of embodiment 730, wherein the non-Hodgkin's lymphoma is primary central nervous system (CNS) lymphoma.

740. The BCMA binding molecule of embodiment 730, wherein the non-Hodgkin's lymphoma is primary mediastinal large B-cell lymphoma.

741. The BCMA binding molecule of embodiment 730, wherein the non-Hodgkin's lymphoma is mediastinal grey-zone lymphoma (MGZL).

742. The BCMA binding molecule of embodiment 730, wherein the non-Hodgkin's lymphoma is splenic marginal zone B-cell lymphoma.

743. The BCMA binding molecule of embodiment 730, wherein the non-Hodgkin's lymphoma is extranodal marginal zone B-cell lymphoma of MALT.

744. The BCMA binding molecule of embodiment 730, wherein the non-Hodgkin's lymphoma is nodal marginal zone B-cell lymphoma.

745. The BCMA binding molecule of embodiment 730, wherein the non-Hodgkin's lymphoma is primary effusion lymphoma.

746. The BCMA binding molecule of embodiment 727, wherein the non-Hodgkin's lymphoma is a T cell lymphoma.

747. The BCMA binding molecule of embodiment 746, wherein the non-Hodgkin's lymphoma is anaplastic large cell lymphoma (ALCL), adult T-cell lymphoma/leukemia, angiocentric lymphoma, angioimmunoblastic T-cell lymphoma, cutaneous T-cell lymphoma, extranodal natural killer/T-cell lymphoma, enteropathy type intestinal T-cell lymphoma, precursor T-lymphoblastic lymphoma/leukemia (T-LBL/L), or unspecified peripheral T-cell lymphoma.

748. The BCMA binding molecule of embodiment 747, wherein the non-Hodgkin's lymphoma is anaplastic large cell lymphoma (ALCL).

749. The BCMA binding molecule of embodiment 747, wherein the non-Hodgkin's lymphoma is adult T-cell lymphoma/leukemia.

750. The BCMA binding molecule of embodiment 747, wherein the non-Hodgkin's lymphoma is angiocentric lymphoma.
751. The BCMA binding molecule of embodiment 747, wherein the non-Hodgkin's lymphoma is angioimmunoblastic T-cell lymphoma.
752. The BCMA binding molecule of embodiment 747, wherein the non-Hodgkin's lymphoma is cutaneous T-cell lymphoma.
753. The BCMA binding molecule of embodiment 747, wherein the non-Hodgkin's lymphoma is extranodal natural killer/T-cell lymphoma.
754. The BCMA binding molecule of embodiment 747, wherein the non-Hodgkin's lymphoma is enteropathy type intestinal T-cell lymphoma.
755. The BCMA binding molecule of embodiment 747, wherein the non-Hodgkin's lymphoma is precursor T-lymphoblastic lymphoma/leukemia (T-LBL/L).
756. The BCMA binding molecule of embodiment 747, wherein the non-Hodgkin's lymphoma is unspecified peripheral T-cell lymphoma.
757. The BCMA binding molecule of embodiment 719, wherein the cancer is multiple myeloma.
758. The BCMA binding molecule of embodiment 719, wherein the cancer is a plasmacytic dendritic cell neoplasm.
759. The BCMA binding molecule of embodiment 719, wherein the cancer comprises a leukemia.
760. The BCMA binding molecule of embodiment 759, wherein the leukemia is B-cell acute lymphoid leukemia ("BALL"), T-cell acute lymphoid leukemia ("TALL"), acute lymphoid leukemia (ALL), chronic myelogenous leukemia (CML), chronic lymphocytic leukemia (CLL), B-cell chronic lymphocytic leukemia (B-CLL), B-cell prolymphocytic leukemia (B-PLL), hair cell leukemia, plasmacytoma/myeloma, precursor B-lymphoblastic leukemia/lymphoma (PB-LBL/L), large granular lymphocyte leukemia, precursor T-lymphoblastic lymphoma/leukemia (T-LBL/L), T-cell chronic lymphocytic leukemia/prolymphocytic leukemia (T-CLL/PLL).
761. The BCMA binding molecule of embodiment 760, wherein the leukemia is B-cell acute lymphoid leukemia ("BALL").
762. The BCMA binding molecule of embodiment 760, wherein the leukemia is T-cell acute lymphoid leukemia ("TALL").
763. The BCMA binding molecule of embodiment 760, wherein the leukemia is acute lymphoid leukemia (ALL).
764. The BCMA binding molecule of embodiment 760, wherein the leukemia is chronic myelogenous leukemia (CML).
765. The BCMA binding molecule of embodiment 760, wherein the leukemia is chronic lymphocytic leukemia (CLL).
766. The BCMA binding molecule of embodiment 760, wherein the leukemia is B-cell chronic lymphocytic leukemia (B-CLL).
767. The BCMA binding molecule of embodiment 760, wherein the leukemia is B-cell prolymphocytic leukemia (B-PLL).
768. The BCMA binding molecule of embodiment 760, wherein the leukemia is hair cell leukemia.
769. The BCMA binding molecule of embodiment 760, wherein the leukemia is plasmacytoma/myeloma.
770. The BCMA binding molecule of embodiment 760, wherein the leukemia is precursor B-lymphoblastic leukemia/lymphoma (PB-LBL/L).
771. The BCMA binding molecule of embodiment 760, wherein the leukemia is large granular lymphocyte leukemia.
772. The BCMA binding molecule of embodiment 760, wherein the leukemia is precursor T-lymphoblastic lymphoma/leukemia (T-LBL/L).
773. The BCMA binding molecule of embodiment 760, wherein the leukemia is T-cell chronic lymphocytic leukemia/prolymphocytic leukemia (T-CLL/PLL).
774. The BCMA binding molecule of embodiment 719, wherein the cancer is a brain cancer.
775. The BCMA binding molecule of embodiment 774, wherein the brain cancer is astrocytoma or glioblastoma.
776. The BCMA binding molecule of embodiment 775, wherein the brain cancer is astrocytoma.
777. The BCMA binding molecule of embodiment 775, wherein the brain cancer is glioblastoma.
778. The BCMA binding molecule of embodiment 719, wherein the cancer is prostate cancer.
779. The BCMA binding molecule of embodiment 778, wherein the prostate cancer is castrate-resistant prostate cancer.
780. The BCMA binding molecule of embodiment 778, wherein the prostate cancer is therapy-resistant prostate cancer.
781. The BCMA binding molecule of embodiment 778, wherein the prostate cancer is metastatic prostate cancer.
782. The BCMA binding molecule of embodiment 719, wherein the cancer is pancreatic cancer.
783. The BCMA binding molecule of embodiment 719, wherein the cancer is lung cancer.
784. The BCMA binding molecule of embodiment 718, wherein the disease or disorder comprises a plasma cell neoplasm.
785. The BCMA binding molecule of embodiment 784, wherein plasma cell neoplasm comprises smoldering multiple myeloma (SMM) or monoclonal gammopathy of undetermined significance (MGUS).
786. The BCMA binding molecule of embodiment 785, wherein the plasma cell neoplasm comprises smoldering multiple myeloma (SMM).
787. The BCMA binding molecule of embodiment 785, wherein the plasma cell neoplasm comprises monoclonal gammopathy of undetermined significance (MGUS).
788. The BCMA binding molecule of embodiment 718, wherein the disease or disorder comprises a plasmacytoma.
789. The BCMA binding molecule of embodiment 788, wherein the plasmacytoma is plasma cell dyscrasia, solitary myeloma, solitary plasmacytoma, extramedullary plasmacytoma, or multiple plasmacytoma.
790. The BCMA binding molecule of embodiment 788, wherein the plasmacytoma is plasma cell dyscrasia.
791. The BCMA binding molecule of embodiment 788, wherein the plasmacytoma is solitary myeloma.
792. The BCMA binding molecule of embodiment 788, wherein the plasmacytoma is solitary plasmacytoma.
793. The BCMA binding molecule of embodiment 788, wherein the plasmacytoma is extramedullary plasmacytoma.

794. The BCMA binding molecule of embodiment 788, wherein the plasmacytoma is multiple plasmacytoma.
795. The BCMA binding molecule of embodiment 718, wherein the disease or disorder comprises systemic amyloid light chain amyloidosis.
796. The BCMA binding molecule of embodiment 718, wherein the disease or disorder comprises POEMS syndrome.
797. The BCMA binding molecule of embodiment 718, wherein the disease or disorder is an infection.
798. The BCMA binding molecule of embodiment 797, wherein the infection is a viral infection.
799. The BCMA binding molecule of embodiment 798, wherein the viral infection is an HIV infection.
800. The BCMA binding molecule of embodiment 797, wherein the infection is a fungal infection.
801. The BCMA binding molecule of embodiment 800, wherein the fungal infection is a *C. neoformans* infection.
802. The BCMA binding molecule of embodiment 718, wherein the disease or disorder is an autoimmune disorder.
803. The BCMA binding molecule of embodiment 802, wherein the autoimmune disorder is systemic lupus erythematosus (SLE), Sjögren's syndrome, scleroderma, rheumatoid arthritis (RA), juvenile idiopathic arthritis, graft versus host disease, dermatomyositis, type I diabetes mellitus, Hashimoto's thyroiditis, Graves's disease, Addison's disease, celiac disease, Crohn's Disease, pernicious anaemia, pemphigus vulgaris, vitiligo, autoimmune haemolytic anaemia, idiopathic thrombocytopenic purpura, giant cell arteritis, myasthenia gravis, multiple sclerosis (MS) (e.g., relapsing-remitting MS (RRMS)), glomerulonephritis, Goodpasture's syndrome, bullous pemphigoid, colitis ulcerosa, Guillain-Barré syndrome, chronic inflammatory demyelinating polyneuropathy, anti-phospholipid syndrome, narcolepsy, sarcoidosis, or Wegener's granulomatosis.
804. The BCMA binding molecule of embodiment 802, wherein the autoimmune disorder is systemic lupus erythematosus (SLE).
805. The BCMA binding molecule of embodiment 802, wherein the autoimmune disorder is Sjögren's syndrome.
806. The BCMA binding molecule of embodiment 802, wherein the autoimmune disorder is scleroderma.
807. The BCMA binding molecule of embodiment 802, wherein the autoimmune disorder is rheumatoid arthritis (RA).
808. The BCMA binding molecule of embodiment 802, wherein the autoimmune disorder is juvenile idiopathic arthritis.
809. The BCMA binding molecule of embodiment 802, wherein the autoimmune disorder is graft versus host disease.
810. The BCMA binding molecule of embodiment 802, wherein the autoimmune disorder is dermatomyositis.
811. The BCMA binding molecule of embodiment 802, wherein the autoimmune disorder is type I diabetes mellitus.
812. The BCMA binding molecule of embodiment 802, wherein the autoimmune disorder is Hashimoto's thyroiditis.
813. The BCMA binding molecule of embodiment 802, wherein the autoimmune disorder is Graves's disease.
814. The BCMA binding molecule of embodiment 802, wherein the autoimmune disorder is Addison's disease.
815. The BCMA binding molecule of embodiment 802, wherein the autoimmune disorder is celiac disease.
816. The BCMA binding molecule of embodiment 802, wherein the autoimmune disorder is Crohn's Disease.
817. The BCMA binding molecule of embodiment 802, wherein the autoimmune disorder is pernicious anaemia.
818. The BCMA binding molecule of embodiment 802, wherein the autoimmune disorder is pemphigus vulgaris.
819. The BCMA binding molecule of embodiment 802, wherein the autoimmune disorder is vitiligo.
820. The BCMA binding molecule of embodiment 802, wherein the autoimmune disorder is autoimmune haemolytic anaemia.
821. The BCMA binding molecule of embodiment 802, wherein the autoimmune disorder is idiopathic thrombocytopenic purpura.
822. The BCMA binding molecule of embodiment 802, wherein the autoimmune disorder is giant cell arteritis.
823. The BCMA binding molecule of embodiment 802, wherein the autoimmune disorder is myasthenia gravis.
824. The BCMA binding molecule of embodiment 802, wherein the autoimmune disorder is multiple sclerosis (MS).
825. The BCMA binding molecule of embodiment 802, wherein the MS is relapsing-remitting MS (RRMS).
826. The BCMA binding molecule of embodiment 802, wherein the autoimmune disorder is glomerulonephritis.
827. The BCMA binding molecule of embodiment 802, wherein the autoimmune disorder is Goodpasture's syndrome.
828. The BCMA binding molecule of embodiment 802, wherein the autoimmune disorder is bullous pemphigoid.
829. The BCMA binding molecule of embodiment 802, wherein the autoimmune disorder is colitis ulcerosa.
830. The BCMA binding molecule of embodiment 802, wherein the autoimmune disorder is Guillain-Barré syndrome.
831. The BCMA binding molecule of embodiment 802, wherein the autoimmune disorder is chronic inflammatory demyelinating polyneuropathy.
832. The BCMA binding molecule of embodiment 802, wherein the autoimmune disorder is anti-phospholipid syndrome.
833. The BCMA binding molecule of embodiment 802, wherein the autoimmune disorder is narcolepsy.
834. The BCMA binding molecule of embodiment 802, wherein the autoimmune disorder is sarcoidosis.
835. The BCMA binding molecule of embodiment 802, wherein the autoimmune disorder is Wegener's granulomatosis.
836. A conjugate comprising the BCMA binding molecule of any one of embodiments 1 to 716 and a moiety that extends the in vivo half life of the BCMA binding molecule.
837. The conjugate of embodiment 836, wherein the moiety is any moiety described in Section 7.8.
838. The conjugate of embodiment 836 or embodiment 837, wherein the moiety comprises polyethylene glycol, a polypeptide, a carbohydrate, a fatty acid, or any combination thereof.

839. The conjugate of embodiment 838, the moiety comprises polyethylene glycol.
840. The conjugate of embodiment 838, the moiety comprises a polypeptide.
841. The conjugate of embodiment 840, wherein the polypeptide comprises an albumin, optionally human serum albumin.
842. The conjugate of embodiment 838, the moiety comprises a carbohydrate.
843. The conjugate of embodiment 842, wherein the carbohydrate comprises polysialic acid.
844. The conjugate of embodiment 842, wherein the carbohydrate comprises a hydroxyethyl starch (HES) derivative.
845. The conjugate of embodiment 838, the moiety comprises a fatty acid.
846. A conjugate comprising the BCMA binding molecule of any one of embodiments 1 to 716, or the conjugate of any one of embodiments 836 to 845, and a diagnostic or detectable agent.
847. The conjugate of embodiment 846, wherein the diagnostic or detectable agent is any agent described in Section 7.10.
848. The conjugate of embodiment 846 or embodiment 847, wherein the diagnostic or detectable agent comprises an enzyme.
849. The conjugate of embodiment 846 or embodiment 847, wherein the diagnostic or detectable agent comprises a fluorescent dye.
850. The conjugate of embodiment 846 or embodiment 847, wherein the diagnostic or detectable agent comprises a radionuclide.
851. A conjugate comprising the BCMA binding molecule of any one of embodiments 1 to 716, or the conjugate of any one of embodiments 836 to 850, and an agent, optionally a therapeutic agent, a diagnostic agent, a masking moiety, a cleavable moiety, or any combination thereof.
852. The conjugate of embodiment 851, wherein the agent is a cytotoxic or cytostatic agent.
853. The conjugate of embodiment 852, wherein the agent is any one of the agents described in Section 7.9.
854. The conjugate of embodiment 852 or 853, wherein the agent is any one of the agents described in Section 7.9.1.
855. The conjugate of any one of embodiments 851 to 854, wherein the BCMA binding molecule is conjugated to a radionuclide.
856. The conjugate of any one of embodiments 851 to 854, wherein the BCMA binding molecule is conjugated to an alkylating agent.
857. The conjugate of any one of embodiments 851 to 854, wherein the BCMA binding molecule is conjugated to a topoisomerase inhibitor, which is optionally a topoisomerase I inhibitor or a topoisomerase II inhibitor.
858. The conjugate of any one of embodiments 851 to 854, wherein the BCMA binding molecule is conjugated to a DNA damaging agent.
859. The conjugate of any one of embodiments 851 to 854, wherein the BCMA binding molecule is conjugated to a DNA intercalating agent, optionally a groove binding agent such as a minor groove binding agent.
860. The conjugate of any one of embodiments 851 to 854, wherein the BCMA binding molecule is conjugated to a RNA/DNA antimetabolite.
861. The conjugate of any one of embodiments 851 to 854, wherein the BCMA binding molecule is conjugated to a kinase inhibitor.
862. The conjugate of any one of embodiments 851 to 854, wherein the BCMA binding molecule is conjugated to a protein synthesis inhibitor.
863. The conjugate of any one of embodiments 851 to 854, wherein the BCMA binding molecule is conjugated to a histone deacetylase (HDAC) inhibitor.
864. The conjugate of any one of embodiments 851 to 854, wherein the BCMA binding molecule is conjugated to a mitochondrial inhibitor, which is optionally an inhibitor of a phosphoryl transfer reaction in mitochondria.
865. The conjugate of any one of embodiments 851 to 854, wherein the BCMA binding molecule is conjugated to an antimitotic agent.
866. The conjugate of any one of embodiments 851 to 854, wherein the BCMA binding molecule is conjugated to a maytansinoid.
867. The conjugate of any one of embodiments 851 to 854, wherein the BCMA binding molecule is conjugated to a kinesin inhibitor.
868. The conjugate of any one of embodiments 851 to 854, wherein the BCMA binding molecule is conjugated to a kinesin-like protein KIF11 inhibitor.
869. The conjugate of any one of embodiments 851 to 854, wherein the BCMA binding molecule is conjugated to a V-ATPase (vacuolar-type H+-ATPase) inhibitor.
870. The conjugate of any one of embodiments 851 to 854, wherein the BCMA binding molecule is conjugated to a pro-apoptotic agent.
871. The conjugate of any one of embodiments 851 to 854, wherein the BCMA binding molecule is conjugated to a Bcl2 (B-cell lymphoma 2) inhibitor.
872. The conjugate of any one of embodiments 851 to 854, wherein the BCMA binding molecule is conjugated to an MCL1 (myeloid cell leukemia 1) inhibitor.
873. The conjugate of any one of embodiments 851 to 854, wherein the BCMA binding molecule is conjugated to a HSP90 (heat shock protein 90) inhibitor.
874. The conjugate of any one of embodiments 851 to 854, wherein the BCMA binding molecule is conjugated to an IAP (inhibitor of apoptosis) inhibitor.
875. The conjugate of any one of embodiments 851 to 854, wherein the BCMA binding molecule is conjugated to an mTOR (mechanistic target of rapamycin) inhibitor.
876. The conjugate of any one of embodiments 851 to 854, wherein the BCMA binding molecule is conjugated to a microtubule stabilizer.
877. The conjugate of any one of embodiments 851 to 854, wherein the BCMA binding molecule is conjugated to a microtubule destabilizer.
878. The conjugate of any one of embodiments 851 to 854, wherein the BCMA binding molecule is conjugated to an auristatin.
879. The conjugate of any one of embodiments 851 to 854, wherein the BCMA binding molecule is conjugated to a dolastatin.
880. The conjugate of any one of embodiments 851 to 854, wherein the BCMA binding molecule is conjugated to a MetAP (methionine aminopeptidase).

881. The conjugate of any one of embodiments 851 to 854, wherein the BCMA binding molecule is conjugated to a CRM1 (chromosomal maintenance 1) inhibitor.
882. The conjugate of any one of embodiments 851 to 854, wherein the BCMA binding molecule is conjugated to a DPPIV (dipeptidyl peptidase IV) inhibitor.
883. The conjugate of any one of embodiments 851 to 854, wherein the BCMA binding molecule is conjugated to a proteasome inhibitor.
884. The conjugate of any one of embodiments 851 to 854, wherein the BCMA binding molecule is conjugated to a protein synthesis inhibitor.
885. The conjugate of any one of embodiments 851 to 854, wherein the BCMA binding molecule is conjugated to a CDK2 (cyclin-dependent kinase 2) inhibitor.
886. The conjugate of any one of embodiments 851 to 854, wherein the BCMA binding molecule is conjugated to a CDK9 (cyclin-dependent kinase 9) inhibitor.
887. The conjugate of any one of embodiments 851 to 854, wherein the BCMA binding molecule is conjugated to a RNA polymerase inhibitor.
888. The conjugate of any one of embodiments 851 to 854, wherein the BCMA binding molecule is conjugated to a DHFR (dihydrofolate reductase) inhibitor.
889. The conjugate of any one of embodiments 851 to 888, wherein the agent is attached to the BCMA binding molecule with a linker, which is optionally a cleavable linker or a non-cleavable linker, e.g., a linker as described in Section 7.9.2.
890. A conjugate comprising the BCMA binding molecule of any one of embodiments 1 to 716, or the conjugate of any one of embodiments 836 to 889, and a solid support.
891. The conjugate of embodiment 890, wherein the solid support comprises glass, cellulose, polyacrylamide, nylon, polystyrene, polyvinyl chloride, polypropylene, or any combination thereof.
892. A pharmaceutical composition comprising the BCMA binding molecule of any one of embodiments 1 to 716 or the conjugate of any one of embodiments 836 to 889 and a pharmaceutically acceptable excipient.
893. A method of treating a subject having a disease or disorder associated with expression of BCMA, comprising administering to the subject an effective amount of the BCMA binding molecule of any one of embodiments 1 to 716, the conjugate of any one of embodiments 836 to 889, or the pharmaceutical composition of embodiment 892.
894. The method of embodiment 893, wherein the disease or disorder comprises a cancer.
895. The method of embodiment 894, wherein the cancer comprises a B cell malignancy.
896. The method of embodiment 895, wherein the B cell malignancy is Hodgkin's lymphoma, non-Hodgkin's lymphoma or multiple myeloma.
897. The method of embodiment 894, wherein the cancer is Hodgkin's lymphoma.
898. The method of embodiment 897, wherein the Hodgkin's lymphoma is nodular sclerosing Hodgkin's lymphoma.
899. The method of embodiment 897, wherein the Hodgkin's lymphoma is mixed-cellularity subtype Hodgkin's lymphoma.
900. The method of embodiment 897, wherein the Hodgkin's lymphoma is lymphocyte-rich or lymphocytic predominance Hodgkin's lymphoma.
901. The method of embodiment 897, wherein the Hodgkin's lymphoma is lymphocyte depleted Hodgkin's lymphoma.
902. The method of embodiment 894, wherein the cancer is non-Hodgkin's lymphoma.
903. The method of embodiment 902, wherein the non-Hodgkin's lymphoma is a B cell lymphoma or a T cell lymphoma.
904. The method of embodiment 903, wherein the non-Hodgkin's lymphoma is a B cell lymphoma.
905. The method of embodiment 904, wherein the non-Hodgkin's lymphoma is diffuse large B-cell lymphoma (DLBCL), follicular lymphoma, chronic lymphocytic leukemia (CLL)/small lymphocytic lymphoma (SLL), mantle cell lymphoma (MCL), marginal zone lymphoma, Burkitt lymphoma, lymphoplasmacytic lymphoma (Waldenstrom macroglobulinemia), hairy cell leukemia, primary central nervous system (CNS) lymphoma, primary mediastinal large B-cell lymphoma, mediastinal grey-zone lymphoma (MGZL), splenic marginal zone B-cell lymphoma, extranodal marginal zone B-cell lymphoma of MALT, nodal marginal zone B-cell lymphoma, or primary effusion lymphoma.
906. The method of embodiment 905, wherein the non-Hodgkin's lymphoma is diffuse large B-cell lymphoma (DLBCL).
907. The method of embodiment 905, wherein the non-Hodgkin's lymphoma is follicular lymphoma.
908. The method of embodiment 905, wherein the non-Hodgkin's lymphoma is chronic lymphocytic leukemia (CLL)/small lymphocytic lymphoma (SLL).
909. The method of embodiment 905, wherein the non-Hodgkin's lymphoma is mantle cell lymphoma (MCL).
910. The method of embodiment 905, wherein the non-Hodgkin's lymphoma is marginal zone lymphoma.
911. The method of embodiment 905, wherein the non-Hodgkin's lymphoma is Burkitt lymphoma.
912. The method of embodiment 905, wherein the non-Hodgkin's lymphoma is lymphoplasmacytic lymphoma (Waldenstrom macroglobulinemia).
913. The method of embodiment 905, wherein the non-Hodgkin's lymphoma is hairy cell leukemia.
914. The method of embodiment 905, wherein the non-Hodgkin's lymphoma is primary central nervous system (CNS) lymphoma.
915. The method of embodiment 905, wherein the non-Hodgkin's lymphoma is primary mediastinal large B-cell lymphoma.
916. The method of embodiment 905, wherein the non-Hodgkin's lymphoma is mediastinal grey-zone lymphoma (MGZL).
917. The method of embodiment 905, wherein the non-Hodgkin's lymphoma is splenic marginal zone B-cell lymphoma.
918. The method of embodiment 905, wherein the non-Hodgkin's lymphoma is extranodal marginal zone B-cell lymphoma of MALT.
919. The method of embodiment 905, wherein the non-Hodgkin's lymphoma is nodal marginal zone B-cell lymphoma.
920. The method of embodiment 905, wherein the non-Hodgkin's lymphoma is primary effusion lymphoma.
921. The method of embodiment 903, wherein the non-Hodgkin's lymphoma is a T cell lymphoma.
922. The method of embodiment 921, wherein the non-Hodgkin's lymphoma is anaplastic large cell lymphoma (ALCL), adult T-cell lymphoma/leukemia, angiocentric lymphoma, angioimmunoblastic T-cell lymphoma, cutaneous T-cell lymphoma, extranodal natural killer/T-cell lymphoma, enteropathy type intestinal T-cell lymphoma, precursor T-lymphoblastic lymphoma/leukemia (T-LBL/L), or unspecified peripheral T-cell lymphoma.
923. The method of embodiment 922, wherein the non-Hodgkin's lymphoma is anaplastic large cell lymphoma (ALCL).
924. The method of embodiment 922, wherein the non-Hodgkin's lymphoma is adult T-cell lymphoma/leukemia.
925. The method of embodiment 922, wherein the non-Hodgkin's lymphoma is angiocentric lymphoma.
926. The method of embodiment 922, wherein the non-Hodgkin's lymphoma is angioimmunoblastic T-cell lymphoma.
927. The method of embodiment 922, wherein the non-Hodgkin's lymphoma is cutaneous T-cell lymphoma.
928. The method of embodiment 922, wherein the non-Hodgkin's lymphoma is extranodal natural killer/T-cell lymphoma.
929. The method of embodiment 922, wherein the non-Hodgkin's lymphoma is enteropathy type intestinal T-cell lymphoma.
930. The method of embodiment 922, wherein the non-Hodgkin's lymphoma is precursor T-lymphoblastic lymphoma/leukemia (T-LBL/L).
931. The method of embodiment 922, wherein the non-Hodgkin's lymphoma is unspecified peripheral T-cell lymphoma.
932. The method of embodiment 894, wherein the cancer is multiple myeloma.
933. The method of embodiment 894, wherein the cancer is a plasmacytic dendritic cell neoplasm.
934. The method of embodiment 894, wherein the cancer comprises a leukemia.
935. The method of embodiment 934, wherein the leukemia is B-cell acute lymphoid leukemia ("BALL"), T-cell acute lymphoid leukemia ("TALL"), acute lymphoid leukemia (ALL), chronic myelogenous leukemia (CML), chronic lymphocytic leukemia (CLL), B-cell chronic lymphocytic leukemia (B-CLL), B-cell prolymphocytic leukemia (B-PLL), hair cell leukemia, plasmacytoma/myeloma, precursor B-lymphoblastic leukemia/lymphoma (PB-LBL/L), large granular lymphocyte leukemia, precursor T-lymphoblastic lymphoma/leukemia (T-LBL/L), T-cell chronic lymphocytic leukemia/prolymphocytic leukemia (T-CLL/PLL).
936. The method of embodiment 934, wherein the leukemia is B-cell acute lymphoid leukemia ("BALL").
937. The method of embodiment 934, wherein the leukemia is T-cell acute lymphoid leukemia ("TALL").
938. The method of embodiment 934, wherein the leukemia is acute lymphoid leukemia (ALL).
939. The method of embodiment 934, wherein the leukemia is chronic myelogenous leukemia (CML).
940. The method of embodiment 934, wherein the leukemia is chronic lymphocytic leukemia (CLL).
941. The method of embodiment 934, wherein the leukemia is B-cell chronic lymphocytic leukemia (B-CLL).
942. The method of embodiment 934, wherein the leukemia is B-cell prolymphocytic leukemia (B-PLL).
943. The method of embodiment 934, wherein the leukemia is hair cell leukemia.
944. The method of embodiment 934, wherein the leukemia is plasmacytoma/myeloma.
945. The method of embodiment 934, wherein the leukemia is precursor B-lymphoblastic leukemia/lymphoma (PB-LBL/L).
946. The method of embodiment 934, wherein the leukemia is large granular lymphocyte leukemia.
947. The method of embodiment 934, wherein the leukemia is precursor T-lymphoblastic lymphoma/leukemia (T-LBL/L).
948. The method of embodiment 934, wherein the leukemia is T-cell chronic lymphocytic leukemia/prolymphocytic leukemia (T-CLL/PLL).
949. The method of embodiment 894, wherein the cancer is a brain cancer.
950. The method of embodiment 949, wherein the brain cancer is astrocytoma or glioblastoma.
951. The method of embodiment 950, wherein the brain cancer is astrocytoma.
952. The method of embodiment 950, wherein the brain cancer is glioblastoma.
953. The method of embodiment 894, wherein the cancer is prostate cancer.
954. The method of embodiment 953, wherein the prostate cancer is castrate-resistant prostate cancer.
955. The method of embodiment 953, wherein the prostate cancer is therapy-resistant prostate cancer.
956. The method of embodiment 953, wherein the prostate cancer is metastatic prostate cancer.
957. The method of embodiment 894, wherein the cancer is pancreatic cancer.
958. The method of embodiment 894, wherein the cancer is lung cancer.
959. The method of embodiment 893, wherein the disease or disorder comprises a plasma cell neoplasm.
960. The method of embodiment 959, wherein plasma cell neoplasm comprises smoldering multiple myeloma (SMM) or monoclonal gammopathy of undetermined significance (MGUS).
961. The method of embodiment 960, wherein the plasma cell neoplasm comprises smoldering multiple myeloma (SMM).
962. The method of embodiment 960, wherein the plasma cell neoplasm comprises monoclonal gammopathy of undetermined significance (MGUS).
963. The method of embodiment 893, wherein the disease or disorder comprises a plasmacytoma.
964. The method of embodiment 963, wherein the plasmacytoma is plasma cell dyscrasia, solitary myeloma, solitary plasmacytoma, extramedullary plasmacytoma, or multiple plasmacytoma.
965. The method of embodiment 963, wherein the plasmacytoma is plasma cell dyscrasia.
966. The method of embodiment 963, wherein the plasmacytoma is solitary myeloma.
967. The method of embodiment 963, wherein the plasmacytoma is solitary plasmacytoma.
968. The method of embodiment 963, wherein the plasmacytoma is extramedullary plasmacytoma.
969. The method of embodiment 963, wherein the plasmacytoma is multiple plasmacytoma.
970. The method of embodiment 893, wherein the disease or disorder comprises systemic amyloid light chain amyloidosis.
971. The method of embodiment 893, wherein the disease or disorder comprises POEMS syndrome.

972. The method of any one of any one of embodiments 893 to 971, further comprising administering at least one additional agent to the subject.

973. The method of embodiment 972, wherein the additional agent is a chemotherapeutic agent.

974. The method of embodiment 972 or embodiment 973, wherein the additional agent is an anthracycline.

975. The method of embodiment 972 or embodiment 973, wherein the additional agent is a vinca alkaloid.

976. The method of embodiment 972 or embodiment 973, wherein the additional agent is an alkylating agent.

977. The method of embodiment 972 or embodiment 973, wherein the additional agent is an immune cell antibody.

978. The method of embodiment 972 or embodiment 973, wherein the additional agent is an antimetabolite.

979. The method of embodiment 972 or embodiment 973, wherein the additional agent is an adenosine deaminase inhibitor 980. The method of embodiment 972 or embodiment 973, wherein the additional agent is an mTOR inhibitor.

981. The method of embodiment 972 or embodiment 973, wherein the additional agent is a TNFR glucocorticoid induced TNFR related protein (GITR) agonist.

982. The method of embodiment 972 or embodiment 973, wherein the additional agent is a proteasome inhibitor.

983. The method of embodiment 972 or embodiment 973, wherein the additional agent is a BH3 mimetic.

984. The method of embodiment 972 or embodiment 973, wherein the additional agent is a cytokine.

985. The method of embodiment 972 or embodiment 973, wherein the additional agent prevents or slows shedding of BCMA from a cancer cell.

986. The method of embodiment 985, wherein the additional agent comprises an ADAM10 inhibitor and/or an ADAM 17 inhibitor.

987. The method of embodiment 985, wherein the additional agent comprises a phospholipase inhibitor.

988. The method of embodiment 972 or embodiment 973, wherein the additional agent is a gamma secretase inhibitor (GSI).

989. The method of embodiment 988, wherein the GSI is BMS-986115.

990. The method of embodiment 988, wherein the GSI is BMS-906024.

991. The method of embodiment 972 or embodiment 973, wherein the additional agent is an immunomodulatory.

992. The method of embodiment 972 or embodiment 973, wherein the additional agent is a thalidomide derivative.

993. The method of embodiment 972 or embodiment 973, wherein the additional agent is an EGFR inhibitor.

994. The method of embodiment 972 or embodiment 973, wherein the additional agent is an adenosine A2A receptor antagonist.

995. The method of embodiment 972 or embodiment 973, wherein the additional agent is a CD20 inhibitor.

996. The method of embodiment 972 or embodiment 973, wherein the additional agent is a CD22 inhibitor.

997. The method of embodiment 972 or embodiment 973, wherein the additional agent is a FCRL2 inhibitor.

998. The method of embodiment 972 or embodiment 973, wherein the additional agent is a FCRL5 inhibitor.

999. The method of embodiment 972 or embodiment 973, wherein the additional agent is a IL-15/IL15-Ra complex.

1000. The method of embodiment 972 or embodiment 973, wherein the additional agent is a PD-1 inhibitor.

1001. The method of embodiment 972 or embodiment 973, wherein the additional agent is a PD-L1 inhibitor.

1002. The method of embodiment 972 or embodiment 973, wherein the additional agent is a LAG-3 inhibitor.

1003. The method of embodiment 972 or embodiment 973, wherein the additional agent is a TIM-3 inhibitor.

1004. The method of embodiment 972 or embodiment 973, wherein the additional agent is a TGF-8 inhibitor.

1005. The method of embodiment 972 or embodiment 973, wherein the additional agent is a CD73 inhibitor.

1006. The method of embodiment 972 or embodiment 973, wherein the additional agent is a IL-17 inhibitor.

1007. The method of embodiment 972 or embodiment 973, wherein the additional agent is a CD32B inhibitor 1008. The method of embodiment 972 or embodiment 973, wherein the additional agent is an agent selected from those listed in Table A.

1009. The method of embodiment 972, wherein the additional agent is an agent that reduces or ameliorates a side effect associated with the administration of a BCMA binding molecule that is bispecific for BCMA and CD3.

1010. The method of embodiment 1009, wherein the additional agent comprises a steroid (e.g., corticosteroid), an inhibitor of TNFα (e.g., an anti-TNFα antibody molecule such as infliximab, adalimumab, certolizumab pegol, or golimumab, a fusion protein such as entanercept, a small molecule inhibitor of TNFα such as a xanthine derivative (e.g. pentoxifylline) or bupropion), an IL-6 inhibitor (e.g., an IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, or FM101), an IL-1R based inhibitor such as anakinra, a corticosteroid (e.g., methylprednisolone or hydrocortisone) in combination with Benadryl and Tylenol, a vasopressor (e.g., norepinephrine, dopamine, phenylephrine, epinephrine, vasopressin, or any combination thereof), an antipyretic agent, or an analgesic agent.

1011. The method of any one of embodiments 972 to 1010, wherein the additional agent is not an antibody.

1012. The method of embodiment 893, wherein the disease or disorder is an infection.

1013. The method of embodiment 1012, wherein the infection is a viral infection.

1014. The method of embodiment 1013, wherein the viral infection is an HIV infection.

1015. The method of embodiment 1012, wherein the infection is a fungal infection.

1016. The method of embodiment 1015, wherein the fungal infection is a *C. neoformans* infection.

1017. The method of embodiment 893, wherein the disease or disorder is an autoimmune disorder.

1018. The method of embodiment 1017, wherein the autoimmune disorder is systemic lupus erythematosus (SLE), Sjögren's syndrome, scleroderma, rheumatoid arthritis (RA), juvenile idiopathic arthritis, graft versus host disease, dermatomyositis, type I diabetes mellitus, Hashimoto's thyroiditis, Graves's disease, Addison's disease, celiac disease, Crohn's Disease, pernicious anaemia, pemphigus vulgaris, vitiligo, autoimmune haemolytic anaemia, idiopathic thrombocytopenic purpura, giant cell arteritis, myasthenia gravis, multiple sclerosis (MS) (e.g., relapsing-remitting MS (RRMS)), glomerulonephritis, Goodpasture's syndrome, bullous pemphigoid, colitis ulcerosa, Guillain-Barré syndrome, chronic inflammatory demyelinating polyneuropathy, anti-phospholipid syndrome, narcolepsy, sarcoidosis, or Wegener's granulomatosis.

1019. The method of embodiment 1018, wherein the autoimmune disorder is systemic lupus erythematosus (SLE).
1020. The method of embodiment 1018, wherein the autoimmune disorder is Sjögren's syndrome.
1021. The method of embodiment 1018, wherein the autoimmune disorder is scleroderma.
1022. The method of embodiment 1018, wherein the autoimmune disorder is rheumatoid arthritis (RA).
1023. The method of embodiment 1018, wherein the autoimmune disorder is juvenile idiopathic arthritis.
1024. The method of embodiment 1018, wherein the autoimmune disorder is graft versus host disease.
1025. The method of embodiment 1018, wherein the autoimmune disorder is dermatomyositis.
1026. The method of embodiment 1018, wherein the autoimmune disorder is type I diabetes mellitus.
1027. The method of embodiment 1018, wherein the autoimmune disorder is Hashimoto's thyroiditis.
1028. The method of embodiment 1018, wherein the autoimmune disorder is Graves's disease.
1029. The method of embodiment 1018, wherein the autoimmune disorder is Addison's disease.
1030. The method of embodiment 1018, wherein the autoimmune disorder is celiac disease.
1031. The method of embodiment 1018, wherein the autoimmune disorder is Crohn's Disease.
1032. The method of embodiment 1018, wherein the autoimmune disorder is pernicious anaemia.
1033. The method of embodiment 1018, wherein the autoimmune disorder is pemphigus vulgaris.
1034. The method of embodiment 1018, wherein the autoimmune disorder is vitiligo.
1035. The method of embodiment 1018, wherein the autoimmune disorder is autoimmune haemolytic anaemia.
1036. The method of embodiment 1018, wherein the autoimmune disorder is idiopathic thrombocytopenic purpura.
1037. The method of embodiment 1018, wherein the autoimmune disorder is giant cell arteritis.
1038. The method of embodiment 1018, wherein the autoimmune disorder is myasthenia gravis.
1039. The method of embodiment 1018, wherein the autoimmune disorder is multiple sclerosis (MS).
1040. The method of embodiment 1039, wherein the MS is relapsing-remitting MS (RRMS).
1041. The method of embodiment 1018, wherein the autoimmune disorder is glomerulonephritis.
1042. The method of embodiment 1018, wherein the autoimmune disorder is Goodpasture's syndrome.
1043. The method of embodiment 1018, wherein the autoimmune disorder is bullous pemphigoid.
1044. The method of embodiment 1018, wherein the autoimmune disorder is colitis ulcerosa.
1045. The method of embodiment 1018, wherein the autoimmune disorder is Guillain-Barré syndrome.
1046. The method of embodiment 1018, wherein the autoimmune disorder is chronic inflammatory demyelinating polyneuropathy.
1047. The method of embodiment 1018, wherein the autoimmune disorder is anti-phospholipid syndrome.
1048. The method of embodiment 1018, wherein the autoimmune disorder is narcolepsy.
1049. The method of embodiment 1018, wherein the autoimmune disorder is sarcoidosis.
1050. The method of embodiment 1018, wherein the autoimmune disorder is Wegener's granulomatosis.
1051. A nucleic acid or plurality of nucleic acids encoding the BCMA binding molecule of any one of embodiments 1 to 716.
1052. The nucleic acid or plurality of nucleic acids of embodiment 1051 which is/are DNA.
1053. The nucleic acid or plurality of nucleic acids of embodiment 1051 which is/are mRNA.
1054. A cell engineered to express the BCMA binding molecule of any one of embodiments 1 to 716.
1055. A cell transfected with one or more expression vectors comprising one or more nucleic acid sequences encoding the BCMA binding molecule of any one of embodiments 1 to 716 or the conjugate of any one of embodiments 717 to 889 under the control of one or more promoters.
1056. The cell of embodiment 1054 or embodiment 1055, wherein expression of the BCMA binding molecule is under the control of an inducible promoter.
1057. The cell of any one of embodiments 1054 to 1056, wherein the BCMA binding molecule is produced in secretable form.
1058. A method of producing a BCMA binding molecule, comprising:
  (a) culturing the cell of any one of embodiments 1054 to 1057 in conditions under which the BCMA binding molecule is expressed; and
  (b) recovering the BCMA binding molecule from the cell culture.

SEQUENCE LISTING

```
Sequence total quantity: 603
SEQ ID NO: 1           moltype = AA  length = 15
FEATURE                Location/Qualifiers
source                 1..15
                       mol_type = protein
                       organism = synthetic construct
                       note = Description of Artificial Sequence: Synthetic peptide
SEQUENCE: 1
GGGGSGGGGS GGGGS                                                           15

SEQ ID NO: 2           moltype = AA  length = 11
FEATURE                Location/Qualifiers
source                 1..11
                       mol_type = protein
```

```
                              organism = synthetic construct
                              note = Description of Artificial Sequence: Synthetic peptide
SEQUENCE: 2
RASQSISSYL N                                                                        11

SEQ ID NO: 3                  moltype = AA   length = 7
FEATURE                       Location/Qualifiers
source                        1..7
                              mol_type = protein
                              organism = synthetic construct
                              note = Description of Artificial Sequence: Synthetic peptide
SEQUENCE: 3
SQSISSY                                                                              7

SEQ ID NO: 4                  moltype = AA   length = 6
FEATURE                       Location/Qualifiers
source                        1..6
                              mol_type = protein
                              organism = synthetic construct
                              note = Description of Artificial Sequence: Synthetic peptide
SEQUENCE: 4
QSISSY                                                                               6

SEQ ID NO: 5                  moltype = AA   length = 7
FEATURE                       Location/Qualifiers
source                        1..7
                              mol_type = protein
                              organism = synthetic construct
                              note = Description of Artificial Sequence: Synthetic peptide
SEQUENCE: 5
AASSLQS                                                                              7

SEQ ID NO: 6                  moltype =    length =
SEQUENCE: 6
000

SEQ ID NO: 7                  moltype = AA   length = 9
FEATURE                       Location/Qualifiers
source                        1..9
                              mol_type = protein
                              organism = synthetic construct
                              note = Description of Artificial Sequence: Synthetic peptide
VARIANT                       6
                              note = MOD_RES - S or T
SEQUENCE: 7
QQSYSXPLT                                                                            9

SEQ ID NO: 8                  moltype = AA   length = 9
FEATURE                       Location/Qualifiers
source                        1..9
                              mol_type = protein
                              organism = synthetic construct
                              note = Description of Artificial Sequence: Synthetic peptide
VARIANT                       5
                              note = MOD_RES - S, G, D, Y, or A
VARIANT                       6
                              note = MOD_RES - S, T, or A
VARIANT                       8
                              note = MOD_RES - P or L
SEQUENCE: 8
QQSYXXPXT                                                                            9

SEQ ID NO: 9                  moltype = AA   length = 6
FEATURE                       Location/Qualifiers
source                        1..6
                              mol_type = protein
                              organism = synthetic construct
                              note = Description of Artificial Sequence: Synthetic peptide
VARIANT                       4
                              note = MOD_RES - S or T
SEQUENCE: 9
SYSXPL                                                                               6

SEQ ID NO: 10                 moltype =    length =
SEQUENCE: 10
000

SEQ ID NO: 11                 moltype = AA   length = 5
FEATURE                       Location/Qualifiers
```

| | |
|---|---|
| source | 1..5<br>mol_type = protein<br>organism = synthetic construct<br>note = Description of Artificial Sequence: Synthetic peptide |
| SEQUENCE: 11<br>SYAMS | 5 |
| SEQ ID NO: 12<br>FEATURE<br>source | moltype = AA  length = 7<br>Location/Qualifiers<br>1..7<br>mol_type = protein<br>organism = synthetic construct<br>note = Description of Artificial Sequence: Synthetic peptide |
| SEQUENCE: 12<br>GFTFSSY | 7 |
| SEQ ID NO: 13<br>FEATURE<br>source | moltype = AA  length = 8<br>Location/Qualifiers<br>1..8<br>mol_type = protein<br>organism = synthetic construct<br>note = Description of Artificial Sequence: Synthetic peptide |
| SEQUENCE: 13<br>GFTFSSYA | 8 |
| SEQ ID NO: 14<br>FEATURE<br>source | moltype = AA  length = 10<br>Location/Qualifiers<br>1..10<br>mol_type = protein<br>organism = synthetic construct<br>note = Description of Artificial Sequence: Synthetic peptide |
| SEQUENCE: 14<br>GFTFSSYAMS | 10 |
| SEQ ID NO: 15<br>FEATURE<br>source<br><br>VARIANT<br><br>VARIANT<br><br>VARIANT<br><br>VARIANT | moltype = AA  length = 17<br>Location/Qualifiers<br>1..17<br>mol_type = protein<br>organism = synthetic construct<br>note = Description of Artificial Sequence: Synthetic peptide<br>4<br>note = MOD_RES - G or E<br>8<br>note = MOD_RES - S or R<br>9<br>note = MOD_RES - T or A<br>10<br>note = MOD_RES - Y or A |
| SEQUENCE: 15<br>AISXSGGXXX YADSVKG | 17 |
| SEQ ID NO: 16<br>FEATURE<br>source<br><br>VARIANT<br><br>VARIANT<br><br>VARIANT<br><br>VARIANT<br><br>VARIANT<br><br>VARIANT | moltype = AA  length = 17<br>Location/Qualifiers<br>1..17<br>mol_type = protein<br>organism = synthetic construct<br>note = Description of Artificial Sequence: Synthetic peptide<br>4<br>note = MOD_RES - G, E, or A<br>5<br>note = MOD_RES - S, A, H, or E<br>7<br>note = MOD_RES - G, D, E, H, R, or A<br>8<br>note = MOD_RES - S, R, V, T, or Y<br>9<br>note = MOD_RES - T, A, E, H, or R<br>10<br>note = MOD_RES - Y, A, or S |
| SEQUENCE: 16<br>AISXXGXXXX YADSVKG | 17 |
| SEQ ID NO: 17<br>FEATURE<br>source<br><br>VARIANT | moltype = AA  length = 6<br>Location/Qualifiers<br>1..6<br>mol_type = protein<br>organism = synthetic construct<br>note = Description of Artificial Sequence: Synthetic peptide<br>2 |

```
                            note = MOD_RES - G or E
VARIANT                     6
                            note = MOD_RES - S or R
SEQUENCE: 17
SXSGGX                                                                          6

SEQ ID NO: 18               moltype =    length =
SEQUENCE: 18
000

SEQ ID NO: 19               moltype = AA  length = 8
FEATURE                     Location/Qualifiers
source                      1..8
                            mol_type = protein
                            organism = synthetic construct
                            note = Description of Artificial Sequence: Synthetic peptide
VARIANT                     3
                            note = MOD_RES - G or E
VARIANT                     7
                            note = MOD_RES - S or R
VARIANT                     8
                            note = MOD_RES - T or A
SEQUENCE: 19
ISXSGGXX                                                                        8

SEQ ID NO: 20               moltype =    length =
SEQUENCE: 20
000

SEQ ID NO: 21               moltype = AA  length = 17
FEATURE                     Location/Qualifiers
source                      1..17
                            mol_type = protein
                            organism = synthetic construct
                            note = Description of Artificial Sequence: Synthetic peptide
VARIANT                     4
                            note = MOD_RES - G, E, or A
VARIANT                     5
                            note = MOD_RES - S, A, H, or E
VARIANT                     7
                            note = MOD_RES - G, D, E, H, R, or A
VARIANT                     8
                            note = MOD_RES - S, R, V, T, or Y
VARIANT                     9
                            note = MOD_RES - T, A, E, H, or R
VARIANT                     10
                            note = MOD_RES - Y, A, or S
SEQUENCE: 21
AISXXGXXXX YADSVKG                                                             17

SEQ ID NO: 22               moltype = AA  length = 8
FEATURE                     Location/Qualifiers
source                      1..8
                            mol_type = protein
                            organism = synthetic construct
                            note = Description of Artificial Sequence: Synthetic peptide
VARIANT                     3
                            note = MOD_RES - G or E
VARIANT                     7
                            note = MOD_RES - S or R
VARIANT                     8
                            note = MOD_RES - T or A
SEQUENCE: 22
ISXSGGXX                                                                        8

SEQ ID NO: 23               moltype =    length =
SEQUENCE: 23
000

SEQ ID NO: 24               moltype = AA  length = 12
FEATURE                     Location/Qualifiers
source                      1..12
                            mol_type = protein
                            organism = synthetic construct
                            note = Description of Artificial Sequence: Synthetic peptide
SEQUENCE: 24
REWWYDDWYL DY                                                                  12

SEQ ID NO: 25               moltype = AA  length = 14
```

```
FEATURE                 Location/Qualifiers
source                  1..14
                        mol_type = protein
                        organism = synthetic construct
                        note = Description of Artificial Sequence: Synthetic peptide
SEQUENCE: 25
ARREWWYDDW YLDY                                                              14

SEQ ID NO: 26           moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 26
TGTSSDVGGY NYVS                                                              14

SEQ ID NO: 27           moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 27
TSSDVGGYNY                                                                   10

SEQ ID NO: 28           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 28
SSDVGGYNY                                                                    9

SEQ ID NO: 29           moltype = AA   length = 7
FEATURE                 Location/Qualifiers
source                  1..7
                        mol_type = protein
                        organism = synthetic construct
                        note = Description of Artificial Sequence: Synthetic peptide
VARIANT                 6
                        note = MOD_RES - L or P
VARIANT                 7
                        note = MOD_RES - R or S
SEQUENCE: 29
DVSNRXX                                                                      7

SEQ ID NO: 30           moltype = AA   length = 7
FEATURE                 Location/Qualifiers
source                  1..7
                        mol_type = protein
                        organism = synthetic construct
                        note = Description of Artificial Sequence: Synthetic peptide
VARIANT                 1
                        note = MOD_RES - D or E
VARIANT                 6
                        note = MOD_RES - L, P, or A
VARIANT                 7
                        note = MOD_RES - R, S, G, or W
SEQUENCE: 30
XVSNRXX                                                                      7

SEQ ID NO: 31           moltype =    length =
SEQUENCE: 31
000

SEQ ID NO: 32           moltype =    length =
SEQUENCE: 32
000

SEQ ID NO: 33           moltype = AA   length = 10
FEATURE                 Location/Qualifiers
source                  1..10
                        mol_type = protein
                        organism = synthetic construct
                        note = Description of Artificial Sequence: Synthetic peptide
VARIANT                 6
                        note = MOD_RES - L or P
```

```
                                    -continued

VARIANT                 7
                        note = MOD_RES - R or S
SEQUENCE: 33
DVSNRXXGVS                                                              10

SEQ ID NO: 34           moltype = AA  length = 10
FEATURE                 Location/Qualifiers
source                  1..10
                        mol_type = protein
                        organism = synthetic construct
                        note = Description of Artificial Sequence: Synthetic peptide
VARIANT                 1
                        note = MOD_RES - D or E
VARIANT                 6
                        note = MOD_RES - L, P, or A
VARIANT                 7
                        note = MOD_RES - R, S, G, or W
SEQUENCE: 34
XVSNRXXGVS                                                              10

SEQ ID NO: 35           moltype = AA  length = 10
FEATURE                 Location/Qualifiers
source                  1..10
                        mol_type = protein
                        organism = synthetic construct
                        note = Description of Artificial Sequence: Synthetic peptide
VARIANT                 6
                        note = MOD_RES - L or P
VARIANT                 7
                        note = MOD_RES - R or S
SEQUENCE: 35
DVSNRXXGVS                                                              10

SEQ ID NO: 36           moltype =     length =
SEQUENCE: 36
000

SEQ ID NO: 37           moltype = AA  length = 11
FEATURE                 Location/Qualifiers
source                  1..11
                        mol_type = protein
                        organism = synthetic construct
                        note = Description of Artificial Sequence: Synthetic peptide
VARIANT                 8
                        note = MOD_RES - A or T
SEQUENCE: 37
SSYTSSSXLY V                                                            11

SEQ ID NO: 38           moltype = AA  length = 8
FEATURE                 Location/Qualifiers
source                  1..8
                        mol_type = protein
                        organism = synthetic construct
                        note = Description of Artificial Sequence: Synthetic peptide
VARIANT                 6
                        note = MOD_RES - A or T
SEQUENCE: 38
YTSSSXLY                                                                8

SEQ ID NO: 39           moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 39
SYGMH                                                                   5

SEQ ID NO: 40           moltype = AA  length = 7
FEATURE                 Location/Qualifiers
source                  1..7
                        mol_type = protein
                        organism = synthetic construct
                        note = Description of Artificial Sequence: Synthetic peptide
VARIANT                 4
                        note = MOD_RES - V or F
SEQUENCE: 40
GFTXSSY                                                                 7
```

```
SEQ ID NO: 41              moltype = AA  length = 8
FEATURE                    Location/Qualifiers
source                     1..8
                           mol_type = protein
                           organism = synthetic construct
                           note = Description of Artificial Sequence: Synthetic peptide
VARIANT                    4
                           note = MOD_RES - V or F
SEQUENCE: 41
GFTXSSYG                                                                          8

SEQ ID NO: 42              moltype = AA  length = 10
FEATURE                    Location/Qualifiers
source                     1..10
                           mol_type = protein
                           organism = synthetic construct
                           note = Description of Artificial Sequence: Synthetic peptide
VARIANT                    4
                           note = MOD_RES - V or F
SEQUENCE: 42
GFTXSSYGMH                                                                       10

SEQ ID NO: 43              moltype = AA  length = 17
FEATURE                    Location/Qualifiers
source                     1..17
                           mol_type = protein
                           organism = synthetic construct
                           note = Description of Artificial Sequence: Synthetic peptide
VARIANT                    5
                           note = MOD_RES - T or D
SEQUENCE: 43
VISYXGSNKY YADSVKG                                                               17

SEQ ID NO: 44              moltype = AA  length = 17
FEATURE                    Location/Qualifiers
source                     1..17
                           mol_type = protein
                           organism = synthetic construct
                           note = Description of Artificial Sequence: Synthetic peptide
VARIANT                    5
                           note = MOD_RES - H, K, T, R, D, N, or S
VARIANT                    6
                           note = MOD_RES - G, D, or E
VARIANT                    7
                           note = MOD_RES - S, T, F, A, or L
VARIANT                    8
                           note = MOD_RES - H, N or K
SEQUENCE: 44
VISYXXXXKY YADSVKG                                                               17

SEQ ID NO: 45              moltype = AA  length = 6
FEATURE                    Location/Qualifiers
source                     1..6
                           mol_type = protein
                           organism = synthetic construct
                           note = Description of Artificial Sequence: Synthetic peptide
VARIANT                    3
                           note = MOD_RES - T or D
SEQUENCE: 45
SYXGSN                                                                            6

SEQ ID NO: 46              moltype = AA  length = 8
FEATURE                    Location/Qualifiers
source                     1..8
                           mol_type = protein
                           organism = synthetic construct
                           note = Description of Artificial Sequence: Synthetic peptide
VARIANT                    3
                           note = MOD_RES - H, K, T, R, D, N, or S
VARIANT                    4
                           note = MOD_RES - G, D, or E
VARIANT                    5
                           note = MOD_RES - S, T, F, A, or L
VARIANT                    6
                           note = MOD_RES - H, N, or K
SEQUENCE: 46
SYXXXXKG                                                                          8

SEQ ID NO: 47              moltype = AA  length = 8
```

```
FEATURE                     Location/Qualifiers
source                      1..8
                            mol_type = protein
                            organism = synthetic construct
                            note = Description of Artificial Sequence: Synthetic peptide
VARIANT                     4
                            note = MOD_RES - T or D
SEQUENCE: 47
ISYXGSNK                                                                            8

SEQ ID NO: 48               moltype = AA  length = 8
FEATURE                     Location/Qualifiers
source                      1..8
                            mol_type = protein
                            organism = synthetic construct
                            note = Description of Artificial Sequence: Synthetic peptide
VARIANT                     4
                            note = MOD_RES - H, K, T, R, D, N, or S
VARIANT                     5
                            note = MOD_RES - G, D, or E
VARIANT                     6
                            note = MOD_RES - S, T, F, A, or L
VARIANT                     7
                            note = MOD_RES - H, N, or K
SEQUENCE: 48
ISYXXXXK                                                                            8

SEQ ID NO: 49               moltype = AA  length = 14
FEATURE                     Location/Qualifiers
source                      1..14
                            mol_type = protein
                            organism = synthetic construct
                            note = Description of Artificial Sequence: Synthetic peptide
SEQUENCE: 49
SGYALHDDYY GLDV                                                                    14

SEQ ID NO: 50               moltype = AA  length = 14
FEATURE                     Location/Qualifiers
source                      1..14
                            mol_type = protein
                            organism = synthetic construct
                            note = Description of Artificial Sequence: Synthetic peptide
VARIANT                     4
                            note = MOD_RES - A, N, or E
VARIANT                     5
                            note = MOD_RES - L, F, V, or Y
VARIANT                     6
                            note = MOD_RES - H, Q, R, or D
VARIANT                     7
                            note = MOD_RES - D, E, G, or Q
VARIANT                     8
                            note = MOD_RES - D, Q, or F
VARIANT                     9
                            note = MOD_RES - Y or Q
VARIANT                     10
                            note = MOD_RES - Y, K, or D
VARIANT                     11
                            note = MOD_RES - G or P
VARIANT                     12
                            note = MOD_RES - L, Q, V, or T
SEQUENCE: 50
SGYXXXXXXX XXDV                                                                    14

SEQ ID NO: 51               moltype = AA  length = 16
FEATURE                     Location/Qualifiers
source                      1..16
                            mol_type = protein
                            organism = synthetic construct
                            note = Description of Artificial Sequence: Synthetic peptide
SEQUENCE: 51
GGSGYALHDD YYGLDV                                                                  16

SEQ ID NO: 52               moltype = AA  length = 16
FEATURE                     Location/Qualifiers
source                      1..16
                            mol_type = protein
                            organism = synthetic construct
                            note = Description of Artificial Sequence: Synthetic peptide
VARIANT                     6
```

| | | |
|---|---|---|
| VARIANT | 7 | note = MOD_RES - A, N, or E |
| VARIANT | 8 | note = MOD_RES - L, F, V, or Y |
| VARIANT | 9 | note = MOD_RES - H, Q, R, or D |
| VARIANT | 10 | note = MOD_RES - D, E, G, or Q |
| VARIANT | 11 | note = MOD_RES - D, Q, or F |
| VARIANT | 12 | note = MOD_RES - Y or Q |
| VARIANT | 13 | note = MOD_RES - Y, K, or D |
| VARIANT | 14 | note = MOD_RES - G or P |
| | | note = MOD_RES - L, Q, V, or T |

SEQUENCE: 52
GGSGYXXXXX XXXXDV                                                    16

SEQ ID NO: 53          moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 53
QQSYSSPLT                                                             9

SEQ ID NO: 54          moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 54
QQSYSTPLT                                                             9

SEQ ID NO: 55          moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 55
QQSYGSPPT                                                             9

SEQ ID NO: 56          moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 56
QQSYDSPLT                                                             9

SEQ ID NO: 57          moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 57
QQSYYSPLT                                                             9

SEQ ID NO: 58          moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 58
QQSYYAPLT                                                             9

SEQ ID NO: 59          moltype = AA   length = 9
FEATURE                Location/Qualifiers
source                 1..9
                       mol_type = protein
                       organism = synthetic construct

```
SEQUENCE: 59
QQSYASPLT                                                                9

SEQ ID NO: 60          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 60
QQSYGSPLT                                                                9

SEQ ID NO: 61          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 61
QQSYDAPLT                                                                9

SEQ ID NO: 62          moltype = AA  length = 17
FEATURE                Location/Qualifiers
source                 1..17
                       mol_type = protein
                       organism = synthetic construct
                       note = Description of Artificial Sequence: Synthetic peptide
SEQUENCE: 62
AISGSGGSTY YADSVKG                                                       17

SEQ ID NO: 63          moltype = AA  length = 17
FEATURE                Location/Qualifiers
source                 1..17
                       mol_type = protein
                       organism = synthetic construct
                       note = Description of Artificial Sequence: Synthetic peptide
SEQUENCE: 63
AISESGGRAA YADSVKG                                                       17

SEQ ID NO: 64          moltype = AA  length = 17
FEATURE                Location/Qualifiers
source                 1..17
                       mol_type = protein
                       organism = synthetic construct
                       note = Description of Artificial Sequence: Synthetic peptide
SEQUENCE: 64
AISGSGGRAA YADSVKG                                                       17

SEQ ID NO: 65          moltype = AA  length = 17
FEATURE                Location/Qualifiers
source                 1..17
                       mol_type = protein
                       organism = synthetic construct
                       note = Description of Artificial Sequence: Synthetic peptide
SEQUENCE: 65
AISESGDVEA YADSVKG                                                       17

SEQ ID NO: 66          moltype = AA  length = 17
FEATURE                Location/Qualifiers
source                 1..17
                       mol_type = protein
                       organism = synthetic construct
                       note = Description of Artificial Sequence: Synthetic peptide
SEQUENCE: 66
AISEAGTTS YADSVKG                                                        17

SEQ ID NO: 67          moltype = AA  length = 17
FEATURE                Location/Qualifiers
source                 1..17
                       mol_type = protein
                       organism = synthetic construct
                       note = Description of Artificial Sequence: Synthetic peptide
SEQUENCE: 67
AISEHGHYTS YADSVKG                                                       17

SEQ ID NO: 68          moltype = AA  length = 17
FEATURE                Location/Qualifiers
source                 1..17
```

```
SEQ ID NO: 68      moltype = AA   length = 17
FEATURE            Location/Qualifiers
source             1..17
                   mol_type = protein
                   organism = synthetic construct
                   note = Description of Artificial Sequence: Synthetic peptide
SEQUENCE: 68
AISGSGHTAA YADSVKG                                                    17

SEQ ID NO: 69      moltype = AA   length = 17
FEATURE            Location/Qualifiers
source             1..17
                   mol_type = protein
                   organism = synthetic construct
                   note = Description of Artificial Sequence: Synthetic peptide
SEQUENCE: 69
AISGSGRTHA YADSVKG                                                    17

SEQ ID NO: 70      moltype = AA   length = 17
FEATURE            Location/Qualifiers
source             1..17
                   mol_type = protein
                   organism = synthetic construct
                   note = Description of Artificial Sequence: Synthetic peptide
SEQUENCE: 70
AISAEGGVRA YADSVKG                                                    17

SEQ ID NO: 71      moltype = AA   length = 17
FEATURE            Location/Qualifiers
source             1..17
                   mol_type = protein
                   organism = synthetic construct
                   note = Description of Artificial Sequence: Synthetic peptide
SEQUENCE: 71
AISGSGGTTA YADSVKG                                                    17

SEQ ID NO: 72      moltype = AA   length = 17
FEATURE            Location/Qualifiers
source             1..17
                   mol_type = protein
                   organism = synthetic construct
                   note = Description of Artificial Sequence: Synthetic peptide
SEQUENCE: 72
AISGSGATTA YADSVKG                                                    17

SEQ ID NO: 73      moltype = AA   length = 6
FEATURE            Location/Qualifiers
source             1..6
                   mol_type = protein
                   organism = synthetic construct
                   note = Description of Artificial Sequence: Synthetic peptide
SEQUENCE: 73
SYSSPL                                                                 6

SEQ ID NO: 74      moltype = AA   length = 6
FEATURE            Location/Qualifiers
source             1..6
                   mol_type = protein
                   organism = synthetic construct
                   note = Description of Artificial Sequence: Synthetic peptide
SEQUENCE: 74
SYSTPL                                                                 6

SEQ ID NO: 75      moltype = AA   length = 6
FEATURE            Location/Qualifiers
source             1..6
                   mol_type = protein
                   organism = synthetic construct
                   note = Description of Artificial Sequence: Synthetic peptide
SEQUENCE: 75
SYGSPP                                                                 6

SEQ ID NO: 76      moltype = AA   length = 6
FEATURE            Location/Qualifiers
source             1..6
                   mol_type = protein
                   organism = synthetic construct
                   note = Description of Artificial Sequence: Synthetic peptide
SEQUENCE: 76
SYDSPL                                                                 6

SEQ ID NO: 77      moltype = AA   length = 6
```

```
FEATURE                 Location/Qualifiers
source                  1..6
                        mol_type = protein
                        organism = synthetic construct
                        note = Description of Artificial Sequence: Synthetic peptide
SEQUENCE: 77
SYYSPL                                                                          6

SEQ ID NO: 78           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 78
SYYAPL                                                                          6

SEQ ID NO: 79           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 79
SYASPL                                                                          6

SEQ ID NO: 80           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 80
SYGSPL                                                                          6

SEQ ID NO: 81           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 81
SYDAPL                                                                          6

SEQ ID NO: 82           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 82
SGSGGS                                                                          6

SEQ ID NO: 83           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 83
SESGGR                                                                          6

SEQ ID NO: 84           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 84
SGSGGR                                                                          6

SEQ ID NO: 85           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 85
SESGDV                                                                          6
```

```
SEQ ID NO: 86           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 86
SEHGHY                                                                      6

SEQ ID NO: 87           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 87
SGSGHT                                                                      6

SEQ ID NO: 88           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 88
SGSGRT                                                                      6

SEQ ID NO: 89           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 89
SAEGGV                                                                      6

SEQ ID NO: 90           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 90
SGSGGT                                                                      6

SEQ ID NO: 91           moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 91
SGSGAT                                                                      6

SEQ ID NO: 92           moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 92
ISGSGGST                                                                    8

SEQ ID NO: 93           moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 93
ISESGGRA                                                                    8

SEQ ID NO: 94           moltype = AA  length = 8
FEATURE                 Location/Qualifiers
source                  1..8
                        mol_type = protein
                        organism = synthetic construct
                        note = Description of Artificial Sequence: Synthetic peptide
```

```
SEQUENCE: 94
ISGSGGRA                                                                         8

SEQ ID NO: 95            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 95
ISESGDVE                                                                         8

SEQ ID NO: 96            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 96
ISEHGHYT                                                                         8

SEQ ID NO: 97            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 97
ISGSGHTA                                                                         8

SEQ ID NO: 98            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 98
ISGSGRTH                                                                         8

SEQ ID NO: 99            moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 99
ISAEGGVR                                                                         8

SEQ ID NO: 100           moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 100
ISGSGGTT                                                                         8

SEQ ID NO: 101           moltype = AA  length = 8
FEATURE                  Location/Qualifiers
source                   1..8
                         mol_type = protein
                         organism = synthetic construct
                         note = Description of Artificial Sequence: Synthetic peptide
SEQUENCE: 101
ISGSGATT                                                                         8

SEQ ID NO: 102           moltype = AA  length = 7
FEATURE                  Location/Qualifiers
source                   1..7
                         mol_type = protein
                         organism = synthetic construct
                         note = Description of Artificial Sequence: Synthetic peptide
SEQUENCE: 102
DVSNRLR                                                                          7

SEQ ID NO: 103           moltype = AA  length = 7
FEATURE                  Location/Qualifiers
source                   1..7
                         mol_type = protein
```

```
                            -continued

SEQUENCE: 103
DVSNRPS                                                             7

SEQ ID NO: 104          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 104
EVSNRLS                                                             7

SEQ ID NO: 105          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 105
EVSNRLR                                                             7

SEQ ID NO: 106          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 106
DVSNRPW                                                             7

SEQ ID NO: 107          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 107
DVSNRLS                                                             7

SEQ ID NO: 108          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 108
DVSNRAW                                                             7

SEQ ID NO: 109          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 109
EVSNRLG                                                             7

SEQ ID NO: 110          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 110
SSYTSSSALY V                                                       11

SEQ ID NO: 111          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 111
SSYTSSSTLY V                                                       11

SEQ ID NO: 112          moltype = AA   length = 17
FEATURE                 Location/Qualifiers
```

```
source                    1..17
                          mol_type = protein
                          organism = synthetic construct
                          note = Description of Artificial Sequence: Synthetic peptide
SEQUENCE: 112
VISYTGSNKY YADSVKG                                                              17

SEQ ID NO: 113            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 113
VISYDGSNKY YADSVKG                                                              17

SEQ ID NO: 114            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 114
VISYHGSNKY YADSVKG                                                              17

SEQ ID NO: 115            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 115
VISYKGSNKY YADSVKG                                                              17

SEQ ID NO: 116            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 116
VISYTGTKKY YADSVKG                                                              17

SEQ ID NO: 117            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 117
VISYRGFNKY YADSVKG                                                              17

SEQ ID NO: 118            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 118
VISYKGSHKY YADSVKG                                                              17

SEQ ID NO: 119            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 119
VISYDDAHKY YADSVKG                                                              17

SEQ ID NO: 120            moltype = AA   length = 17
FEATURE                   Location/Qualifiers
source                    1..17
                          mol_type = protein
                          organism = synthetic construct
                          note = Description of Artificial Sequence: Synthetic peptide
SEQUENCE: 120
VISYNDLNKY YADSVKG                                                              17
```

-continued

| | |
|---|---|
| SEQ ID NO: 121<br>FEATURE<br>source | moltype = AA  length = 17<br>Location/Qualifiers<br>1..17<br>mol_type = protein<br>organism = synthetic construct<br>note = Description of Artificial Sequence: Synthetic peptide |

SEQUENCE: 121
VISYSGSNKY YADSVKG                                                17

| | |
|---|---|
| SEQ ID NO: 122<br>FEATURE<br>source | moltype = AA  length = 17<br>Location/Qualifiers<br>1..17<br>mol_type = protein<br>organism = synthetic construct<br>note = Description of Artificial Sequence: Synthetic peptide |

SEQUENCE: 122
VISYTGANKY YADSVKG                                                17

| | |
|---|---|
| SEQ ID NO: 123<br>FEATURE<br>source | moltype = AA  length = 17<br>Location/Qualifiers<br>1..17<br>mol_type = protein<br>organism = synthetic construct<br>note = Description of Artificial Sequence: Synthetic peptide |

SEQUENCE: 123
VISYNDANKY YADSVKG                                                17

| | |
|---|---|
| SEQ ID NO: 124<br>FEATURE<br>source | moltype = AA  length = 17<br>Location/Qualifiers<br>1..17<br>mol_type = protein<br>organism = synthetic construct<br>note = Description of Artificial Sequence: Synthetic peptide |

SEQUENCE: 124
VISYDESNKY YADSVKG                                                17

| | |
|---|---|
| SEQ ID NO: 125<br>FEATURE<br>source | moltype = AA  length = 17<br>Location/Qualifiers<br>1..17<br>mol_type = protein<br>organism = synthetic construct<br>note = Description of Artificial Sequence: Synthetic peptide |

SEQUENCE: 125
VISYDDANKY YADSVKG                                                17

| | |
|---|---|
| SEQ ID NO: 126<br>FEATURE<br>source | moltype = AA  length = 14<br>Location/Qualifiers<br>1..14<br>mol_type = protein<br>organism = synthetic construct<br>note = Description of Artificial Sequence: Synthetic peptide |

SEQUENCE: 126
SGYALHDDYY GQDV                                                   14

| | |
|---|---|
| SEQ ID NO: 127<br>FEATURE<br>source | moltype = AA  length = 14<br>Location/Qualifiers<br>1..14<br>mol_type = protein<br>organism = synthetic construct<br>note = Description of Artificial Sequence: Synthetic peptide |

SEQUENCE: 127
SGYALHDQYK PVDV                                                   14

| | |
|---|---|
| SEQ ID NO: 128<br>FEATURE<br>source | moltype = AA  length = 14<br>Location/Qualifiers<br>1..14<br>mol_type = protein<br>organism = synthetic construct<br>note = Description of Artificial Sequence: Synthetic peptide |

SEQUENCE: 128
SGYALHDFQD PTDV                                                   14

| | |
|---|---|
| SEQ ID NO: 129<br>FEATURE<br>source | moltype = AA  length = 14<br>Location/Qualifiers<br>1..14<br>mol_type = protein<br>organism = synthetic construct<br>note = Description of Artificial Sequence: Synthetic peptide |

SEQUENCE: 129

| | | |
|---|---|---|
| SGYNLHDDYY GLDV | | 14 |
| SEQ ID NO: 130<br>FEATURE<br>source<br><br>SEQUENCE: 130 | moltype = AA  length = 14<br>Location/Qualifiers<br>1..14<br>mol_type = protein<br>organism = synthetic construct<br>note = Description of Artificial Sequence: Synthetic peptide | |
| SGYEFHEDYY GLDV | | 14 |
| SEQ ID NO: 131<br>FEATURE<br>source<br><br>SEQUENCE: 131 | moltype = AA  length = 14<br>Location/Qualifiers<br>1..14<br>mol_type = protein<br>organism = synthetic construct<br>note = Description of Artificial Sequence: Synthetic peptide | |
| SGYEFQGDYY GLDV | | 14 |
| SEQ ID NO: 132<br>FEATURE<br>source<br><br>SEQUENCE: 132 | moltype = AA  length = 14<br>Location/Qualifiers<br>1..14<br>mol_type = protein<br>organism = synthetic construct<br>note = Description of Artificial Sequence: Synthetic peptide | |
| SGYELRDDYY GLDV | | 14 |
| SEQ ID NO: 133<br>FEATURE<br>source<br><br>SEQUENCE: 133 | moltype = AA  length = 14<br>Location/Qualifiers<br>1..14<br>mol_type = protein<br>organism = synthetic construct<br>note = Description of Artificial Sequence: Synthetic peptide | |
| SGYEVDQDYY GLDV | | 14 |
| SEQ ID NO: 134<br>FEATURE<br>source<br><br>SEQUENCE: 134 | moltype = AA  length = 14<br>Location/Qualifiers<br>1..14<br>mol_type = protein<br>organism = synthetic construct<br>note = Description of Artificial Sequence: Synthetic peptide | |
| SGYAYDGDYY GLDV | | 14 |
| SEQ ID NO: 135<br>SEQUENCE: 135<br>000 | moltype =    length = | |
| SEQ ID NO: 136<br>FEATURE<br>source<br><br>SEQUENCE: 136 | moltype = AA  length = 8<br>Location/Qualifiers<br>1..8<br>mol_type = protein<br>organism = synthetic construct<br>note = Description of Artificial Sequence: Synthetic peptide | |
| YTSSSALY | | 8 |
| SEQ ID NO: 137<br>FEATURE<br>source<br><br>SEQUENCE: 137 | moltype = AA  length = 8<br>Location/Qualifiers<br>1..8<br>mol_type = protein<br>organism = synthetic construct<br>note = Description of Artificial Sequence: Synthetic peptide | |
| YTSSSTLY | | 8 |
| SEQ ID NO: 138<br>FEATURE<br>source<br><br>SEQUENCE: 138 | moltype = AA  length = 7<br>Location/Qualifiers<br>1..7<br>mol_type = protein<br>organism = synthetic construct<br>note = Description of Artificial Sequence: Synthetic peptide | |
| GFTVSSY | | 7 |
| SEQ ID NO: 139 | moltype = AA  length = 7 | |

```
FEATURE                 Location/Qualifiers
source                  1..7
                        mol_type = protein
                        organism = synthetic construct
                        note = Description of Artificial Sequence: Synthetic peptide
SEQUENCE: 139
GFTLSSY                                                                         7

SEQ ID NO: 140          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 140
SYTGSN                                                                          6

SEQ ID NO: 141          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 141
SYDGSN                                                                          6

SEQ ID NO: 142          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 142
SYHGSN                                                                          6

SEQ ID NO: 143          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 143
SYKGSN                                                                          6

SEQ ID NO: 144          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 144
SYTGTK                                                                          6

SEQ ID NO: 145          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 145
SYRGFN                                                                          6

SEQ ID NO: 146          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 146
SYKGSH                                                                          6

SEQ ID NO: 147          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 147
SYDDAH                                                                          6
```

```
SEQ ID NO: 148          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 148
SYNDLN                                                                           6

SEQ ID NO: 149          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 149
SYSGSN                                                                           6

SEQ ID NO: 150          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 150
SYTGAN                                                                           6

SEQ ID NO: 151          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 151
SYNDAN                                                                           6

SEQ ID NO: 152          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 152
SYDESN                                                                           6

SEQ ID NO: 153          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 153
SYDDAN                                                                           6

SEQ ID NO: 154          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 154
DVSNRLRGVS                                                                      10

SEQ ID NO: 155          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 155
DVSNRPSGVS                                                                      10

SEQ ID NO: 156          moltype = AA   length = 10
FEATURE                 Location/Qualifiers
source                  1..10
                        mol_type = protein
                        organism = synthetic construct
                        note = Description of Artificial Sequence: Synthetic peptide
```

```
SEQUENCE: 156
EVSNRLSGVS                                                                          10

SEQ ID NO: 157          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 157
EVSNRLRGVS                                                                          10

SEQ ID NO: 158          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 158
DVSNRPWGVS                                                                          10

SEQ ID NO: 159          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 159
DVSNRLSGVS                                                                          10

SEQ ID NO: 160          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 160
DVSNRAWGVS                                                                          10

SEQ ID NO: 161          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 161
EVSNRLGGVS                                                                          10

SEQ ID NO: 162          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 162
GFTVSSYG                                                                            8

SEQ ID NO: 163          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 163
GFTFSSYG                                                                            8

SEQ ID NO: 164          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 164
GFTLSSYG                                                                            8

SEQ ID NO: 165          moltype = AA   length = 8
FEATURE                 Location/Qualifiers
source                  1..8
                        mol_type = protein
```

```
                              organism = synthetic construct
                              note = Description of Artificial Sequence: Synthetic peptide
SEQUENCE: 165
ISYTGSNK                                                              8

SEQ ID NO: 166                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 166
ISYDGSNK                                                              8

SEQ ID NO: 167                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 167
ISYHGSNK                                                              8

SEQ ID NO: 168                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 168
ISYKGSNK                                                              8

SEQ ID NO: 169                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 169
ISYTGTKK                                                              8

SEQ ID NO: 170                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 170
ISYRGFNK                                                              8

SEQ ID NO: 171                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 171
ISYKGSHK                                                              8

SEQ ID NO: 172                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 172
ISYDDAHK                                                              8

SEQ ID NO: 173                moltype = AA  length = 8
FEATURE                       Location/Qualifiers
source                        1..8
                              mol_type = protein
                              organism = synthetic construct
                              note = Description of Artificial Sequence: Synthetic peptide
SEQUENCE: 173
ISYNDLNK                                                              8

SEQ ID NO: 174                moltype = AA  length = 8
FEATURE                       Location/Qualifiers
```

```
source                  1..8
                        mol_type = protein
                        organism = synthetic construct
                        note = Description of Artificial Sequence: Synthetic peptide
SEQUENCE: 174
ISYSGSNK                                                                          8

SEQ ID NO: 175          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 175
ISYTGANK                                                                          8

SEQ ID NO: 176          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 176
ISYNDANK                                                                          8

SEQ ID NO: 177          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 177
ISYDESNK                                                                          8

SEQ ID NO: 178          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 178
ISYDDANK                                                                          8

SEQ ID NO: 179          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 179
GGSGYALHDD YYGQDV                                                                16

SEQ ID NO: 180          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 180
GGSGYALHDQ YKPVDV                                                                16

SEQ ID NO: 181          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 181
GGSGYALHDF QDPTDV                                                                16

SEQ ID NO: 182          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 182
GGSGYNLHDD YYGLDV                                                                16
```

```
SEQ ID NO: 183          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 183
GGSGYEFHED YYGLDV                                                         16

SEQ ID NO: 184          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 184
GGSGYEFQGD YYGLDV                                                         16

SEQ ID NO: 185          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 185
GGSGYELRDD YYGLDV                                                         16

SEQ ID NO: 186          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 186
GGSGYEVDQD YYGLDV                                                         16

SEQ ID NO: 187          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 187
GGSGYAYDGD YYGLDV                                                         16

SEQ ID NO: 188          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 188
GFTVSSYGMH                                                                10

SEQ ID NO: 189          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 189
GFTFSSYGMH                                                                10

SEQ ID NO: 190          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 190
GFTLSSYGMH                                                                10

SEQ ID NO: 191          moltype = AA  length = 107
FEATURE                 Location/Qualifiers
source                  1..107
                        mol_type = protein
                        organism = synthetic construct
                        note = Description of Artificial Sequence: Synthetic
                        polypeptide
```

```
SEQUENCE: 191
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSSPLTFGQ GTKVEIK                107

SEQ ID NO: 192          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 192
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGQ GTKVEIK                107

SEQ ID NO: 193          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 193
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYGSPPTFGQ GTKVEIK                107

SEQ ID NO: 194          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 194
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYDSPLTFGQ GTKVEIK                107

SEQ ID NO: 195          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 195
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYYSPLTFGQ GTKVEIK                107

SEQ ID NO: 196          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 196
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYYAPLTFGQ GTKVEIK                107

SEQ ID NO: 197          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 197
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYASPLTFGQ GTKVEIK                107

SEQ ID NO: 198          moltype = AA  length = 107
FEATURE                 Location/Qualifiers
source                  1..107
                        mol_type = protein
                        organism = synthetic construct
                        note = Description of Artificial Sequence: Synthetic
                         polypeptide
SEQUENCE: 198
DIQMTQSPSS LSASVGDRVT ITCRASQSIS SYLNWYQQKP GKAPKLLIYA ASSLQSGVPS    60
```

```
RFSGSGSGTD FTLTISSLQP EDFATYYCQQ SYGSPLTFGQ GTKVEIK              107

SEQ ID NO: 199         moltype = AA   length = 107
FEATURE                Location/Qualifiers
source                 1..107
                       mol_type = protein
                       organism = synthetic construct
                       note = Description of Artificial Sequence: Synthetic
                       polypeptide
SEQUENCE: 199
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYDAPLTFGQ GTKVEIK              107

SEQ ID NO: 200         moltype = AA   length = 111
FEATURE                Location/Qualifiers
source                 1..111
                       mol_type = protein
                       organism = synthetic construct
                       note = Description of Artificial Sequence: Synthetic
                       polypeptide
SEQUENCE: 200
QSALTQPASV SGSPGQSITI SCTGTSSDVG GYNYVSWYQQ HPGKAPKLMI YDVSNRLRGV  60
SNRFSGSKSG NTASLTISGL QAEDEADYYC SSYTSSSALY VFGSGTKVTV L         111

SEQ ID NO: 201         moltype = AA   length = 111
FEATURE                Location/Qualifiers
source                 1..111
                       mol_type = protein
                       organism = synthetic construct
                       note = Description of Artificial Sequence: Synthetic
                       polypeptide
SEQUENCE: 201
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTLY VFGSGTKVTV L         111

SEQ ID NO: 202         moltype = AA   length = 111
FEATURE                Location/Qualifiers
source                 1..111
                       mol_type = protein
                       organism = synthetic construct
                       note = Description of Artificial Sequence: Synthetic
                       polypeptide
SEQUENCE: 202
QSALTQPASV SGSPGQSITI SCTGTSSDVG GYNYVSWYQQ HPGKAPKLMI YEVSNRLSGV  60
SNRFSGSKFG NTASLTISGL QAEDEADYYC SSYTSSSTLY VFGSGTKVTV L         111

SEQ ID NO: 203         moltype = AA   length = 111
FEATURE                Location/Qualifiers
source                 1..111
                       mol_type = protein
                       organism = synthetic construct
                       note = Description of Artificial Sequence: Synthetic
                       polypeptide
SEQUENCE: 203
QSALTQPASV SGSPGQSITI SCTGTSSDVG GYNYVSWYQQ HPGKAPKLMI YEVSNRLRGV  60
SNRFSGSKFG NTASLTISGL QAEDEADYYC SSYTSSSALY VFGSGTKVTV L         111

SEQ ID NO: 204         moltype = AA   length = 111
FEATURE                Location/Qualifiers
source                 1..111
                       mol_type = protein
                       organism = synthetic construct
                       note = Description of Artificial Sequence: Synthetic
                       polypeptide
SEQUENCE: 204
QSALTQPASV SGSPGQSITI SCTGTSSDVG GYNYVSWYQQ HPGKAPKLMI YEVSNRLRGV  60
SNRFSGSKFG NTASLTISGL QAEDEADYYC SSYTSSSTLY VFGSGTKVTV L         111

SEQ ID NO: 205         moltype = AA   length = 111
FEATURE                Location/Qualifiers
source                 1..111
                       mol_type = protein
                       organism = synthetic construct
                       note = Description of Artificial Sequence: Synthetic
                       polypeptide
SEQUENCE: 205
QSALTQPASV SGSPGQSITI SCTGTSSDVG GYNYVSWYQQ HPGKAPKLMI YDVSNRPWGV  60
SNRFSGSKFG NTASLTISGL QAEDEADYYC SSYTSSSALY VFGSGTKVTV M         111
```

```
SEQ ID NO: 206            moltype = AA  length = 111
FEATURE                   Location/Qualifiers
source                    1..111
                          mol_type = protein
                          organism = synthetic construct
                          note = Description of Artificial Sequence: Synthetic
                            polypeptide
SEQUENCE: 206
QSALTQPASV SGSPGQSITI SCTGTSSDVG GYNYVSWYQQ HPGKAPKLMI YDVSNRLSGV   60
SNRFSGSKFG NTASLTISGL QAEDEADYYC SSYTSSSTLY VFGSGTKVTV L           111

SEQ ID NO: 207            moltype = AA  length = 111
FEATURE                   Location/Qualifiers
source                    1..111
                          mol_type = protein
                          organism = synthetic construct
                          note = Description of Artificial Sequence: Synthetic
                            polypeptide
SEQUENCE: 207
QSALTQPASV SGSPGQSITI SCTGTSSDVG GYNYVSWYQQ HPGKAPKLMI YDVSNRPWGV   60
SNRFSGSKFG NTASLTISGL QAEDEADYYC SSYTSSSTLY VFGSGTKVTV L           111

SEQ ID NO: 208            moltype = AA  length = 111
FEATURE                   Location/Qualifiers
source                    1..111
                          mol_type = protein
                          organism = synthetic construct
                          note = Description of Artificial Sequence: Synthetic
                            polypeptide
SEQUENCE: 208
QSALTQPASV SGSPGQSITI SCTGTSSDVG GYNYVSWYQQ HPGKAPKLMI YDVSNRLRGV   60
SNRFSGSKFG NTASLTISGL QAEDEADYYC SSYTSSSALY VFGSGTKVTV L           111

SEQ ID NO: 209            moltype = AA  length = 111
FEATURE                   Location/Qualifiers
source                    1..111
                          mol_type = protein
                          organism = synthetic construct
                          note = Description of Artificial Sequence: Synthetic
                            polypeptide
SEQUENCE: 209
QSALTQPASV SGSPGQSITI SCTGTSSDVG GYNYVSWYQQ HPGKAPKLMI YDVSNRAWGV   60
SNRFSGSKFG NTASLTISGL QAEDEADYYC SSYTSSSALY VFGSGTKVTV L           111

SEQ ID NO: 210            moltype = AA  length = 111
FEATURE                   Location/Qualifiers
source                    1..111
                          mol_type = protein
                          organism = synthetic construct
                          note = Description of Artificial Sequence: Synthetic
                            polypeptide
SEQUENCE: 210
QSALTQPASV SGSPGQSITI SCTGTSSDVG GYNYVSWYQQ HPGKAPKLMI YEVSNRLRGV   60
SNRFSGSKFG NTASLTISGL QAEDEAYYYC SSYTSSSTLY VFGSGTKVTV L           111

SEQ ID NO: 211            moltype = AA  length = 111
FEATURE                   Location/Qualifiers
source                    1..111
                          mol_type = protein
                          organism = synthetic construct
                          note = Description of Artificial Sequence: Synthetic
                            polypeptide
SEQUENCE: 211
QSALTQPASV SGSPGQSITI SCTGTSSDVG GYNYVSWYQQ HPGKAPKLMI YEVSNRLSGV   60
SNRFSGSKFG NTASLTISGL QAEDEADYYC SSYTSSSALY VFGSGTKVTV L           111

SEQ ID NO: 212            moltype = AA  length = 111
FEATURE                   Location/Qualifiers
source                    1..111
                          mol_type = protein
                          organism = synthetic construct
                          note = Description of Artificial Sequence: Synthetic
                            polypeptide
SEQUENCE: 212
QSALTQPASV SGSPGQSITI SCTGTSSDVG GYNYVSWYQQ HPGKAPKLMI YEVSNRLGGV   60
SNRFSGSKFG NTASLTISGL QAEDEADYYC SSYTSSSALY VFGSGTKVTV L           111

SEQ ID NO: 213            moltype = AA  length = 121
FEATURE                   Location/Qualifiers
```

```
source                  1..121
                        mol_type = protein
                        organism = synthetic construct
                        note = Description of Artificial Sequence: Synthetic
                        polypeptide
SEQUENCE: 213
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARRE WWYDDWYLDY WGQGTLVTVS   120
S                                                                  121

SEQ ID NO: 214          moltype = AA  length = 121
FEATURE                 Location/Qualifiers
source                  1..121
                        mol_type = protein
                        organism = synthetic construct
                        note = Description of Artificial Sequence: Synthetic
                        polypeptide
SEQUENCE: 214
EVQLLESGGG LVQPGGSLRL SCAASGFTFS SYAMSWVRQA PGKGLEWVSA ISESGGRAAY    60
ADSVKGRFTI SRDNSKNTLY LQMNSLRAED TAVYYCARRE WWYDDWYLDY WGQGTLVTVS   120
S                                                                  121

SEQ ID NO: 215          moltype = AA  length = 121
FEATURE                 Location/Qualifiers
source                  1..121
                        mol_type = protein
                        organism = synthetic construct
                        note = Description of Artificial Sequence: Synthetic
                        polypeptide
SEQUENCE: 215
EVQLLESGGG LVQPGGSLRL SCAASGFTFS SYAMSWVRQA PGKGLEWVSA ISGSGGRAAY    60
ADSVKGRFTI SRDNSKNTLY LQMNSLRAED TAVYYCARRE WWYDDWYLDY WGQGTLVTVS   120
S                                                                  121

SEQ ID NO: 216          moltype = AA  length = 121
FEATURE                 Location/Qualifiers
source                  1..121
                        mol_type = protein
                        organism = synthetic construct
                        note = Description of Artificial Sequence: Synthetic
                        polypeptide
SEQUENCE: 216
EVQLLESGGG LVQPGGSLRL SCAASGFTFS SYAMSWVRQA PGKGLEWVSA ISESGDVEAY    60
ADSVKGRFTI SRDNSKNTLY LQMNSLRAED TAVYYCARRE WWYDDWYLDY WGQGTLVTVS   120
S                                                                  121

SEQ ID NO: 217          moltype = AA  length = 121
FEATURE                 Location/Qualifiers
source                  1..121
                        mol_type = protein
                        organism = synthetic construct
                        note = Description of Artificial Sequence: Synthetic
                        polypeptide
SEQUENCE: 217
EVQLLESGGG LVQPGGSLRL SCAASGFTFS SYAMSWVRQA PGKGLEWVSA ISEAGETTSY    60
ADSVKGRFTI SRDNSKNTLY LQMNSLRAED TAVYYCARRE WWYDDWYLDY WGQGTLVTVS   120
S                                                                  121

SEQ ID NO: 218          moltype = AA  length = 121
FEATURE                 Location/Qualifiers
source                  1..121
                        mol_type = protein
                        organism = synthetic construct
                        note = Description of Artificial Sequence: Synthetic
                        polypeptide
SEQUENCE: 218
EVQLLESGGG LVQPGGSLRL SCAASGFTFS SYAMSWVRQA PGKGLEWVSA ISEHGHYTSY    60
ADSVKGRFTI SRDNSKNTLY LQMNSLRAED TAVYYCARRE WWYDDWYLDY WGQGTLVTVS   120
S                                                                  121

SEQ ID NO: 219          moltype = AA  length = 121
FEATURE                 Location/Qualifiers
source                  1..121
                        mol_type = protein
                        organism = synthetic construct
                        note = Description of Artificial Sequence: Synthetic
                        polypeptide
SEQUENCE: 219
EVQLLESGGG LVQPGGSLRL SCAASGFTFS SYAMSWVRQA PGKGLEWVSA ISGSGHTAAY    60
```

```
ADSVKGRFTI SRDNSKNTLY LQMNSLRAED TAVYYCARRE WWYDDWYLDY WGQGTLVTVS    120
S                                                                  121

SEQ ID NO: 220          moltype = AA   length = 121
FEATURE                 Location/Qualifiers
source                  1..121
                        mol_type = protein
                        organism = synthetic construct
                        note = Description of Artificial Sequence: Synthetic
                           polypeptide
SEQUENCE: 220
EVQLLESGGG LVQPGGSLRL SCAASGFTFS SYAMSWVRQA PGKGLEWVSA ISGSGRTHAY    60
ADSVKGRFTI SRDNSKNTLY LQMNSLRAED TAVYYCARRE WWYDDWYLDY WGQGTLVTVS    120
S                                                                  121

SEQ ID NO: 221          moltype = AA   length = 121
FEATURE                 Location/Qualifiers
source                  1..121
                        mol_type = protein
                        organism = synthetic construct
                        note = Description of Artificial Sequence: Synthetic
                           polypeptide
SEQUENCE: 221
EVQLLESGGG LVQPGGSLRL SCAASGFTFS SYAMSWVRQA PGKGLEWVSA ISAEGGVRAY    60
ADSVKGRFTI SRDNSKNTLY LQMNSLRAED TAVYYCARRE WWYDDWYLDY WGQGTLVTVS    120
S                                                                  121

SEQ ID NO: 222          moltype = AA   length = 121
FEATURE                 Location/Qualifiers
source                  1..121
                        mol_type = protein
                        organism = synthetic construct
                        note = Description of Artificial Sequence: Synthetic
                           polypeptide
SEQUENCE: 222
EVQLLESGGG LVQPGGSLRL SCAASGFTFS SYAMSWVRQA PGKGLEWVSA ISGSGGTTAY    60
ADSVKGRFTI SRDNSKNTLY LQMNSLRAED TAVYYCARRE WWYDDWYLDY WGQGTLVTVS    120
S                                                                  121

SEQ ID NO: 223          moltype = AA   length = 121
FEATURE                 Location/Qualifiers
source                  1..121
                        mol_type = protein
                        organism = synthetic construct
                        note = Description of Artificial Sequence: Synthetic
                           polypeptide
SEQUENCE: 223
EVQLLESGGG LVQPGGSLRL SCAASGFTFS SYAMSWVRQA PGKGLEWVSA ISGSGATTAY    60
ADSVKGRFTI SRDNSKNTLY LQMNSLRAED TAVYYCARRE WWYDDWYLDY WGQGTLVTVS    120
S                                                                  121

SEQ ID NO: 224          moltype = AA   length = 123
FEATURE                 Location/Qualifiers
source                  1..123
                        mol_type = protein
                        organism = synthetic construct
                        note = Description of Artificial Sequence: Synthetic
                           polypeptide
SEQUENCE: 224
QVQLVESGGG VVQPGRSLRL SCAASGFTVS SYGMHWVRQA PGKGLEWVAV ISYTGSNKYY    60
ADSVKGRFTI SRDNSKNTLY LQMNSLRAED TAVYYCGGSG YALHDDYYGL DVWGQGTLVT    120
VSS                                                                123

SEQ ID NO: 225          moltype = AA   length = 123
FEATURE                 Location/Qualifiers
source                  1..123
                        mol_type = protein
                        organism = synthetic construct
                        note = Description of Artificial Sequence: Synthetic
                           polypeptide
SEQUENCE: 225
QVQLQESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCGGSG YALHDDYYGL DVWGQGTLVT    120
VSS                                                                123

SEQ ID NO: 226          moltype = AA   length = 124
FEATURE                 Location/Qualifiers
source                  1..124
                        mol_type = protein
```

```
                        organism = synthetic construct
                        note = Description of Artificial Sequence: Synthetic
                          polypeptide
SEQUENCE: 226
QAQLQSSEGG VVQPGRSLRL SCAASGFTFS SYGMHWVRQA PGKGLEWVAV ISYHGSNKYY        60
ADSVKGRFTI SRDNSKNTLY LQMNSLRAED TAVYYCGGSG YALHDDYYGL DVWGQGTLVT       120
VSSS                                                                    124

SEQ ID NO: 227          moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 227
QVQLQSSEGG VVQPGRSLRL SCAASGFTFS SYGMHWVRQA PGKGLEWVAV ISYKGSNKYY        60
ADSVKGRFTI SRDNSKNTLY LQMNSLRAED TAVYYCGGSG YALHDDYYGL DVWGQGTLVT       120
VSS                                                                     123

SEQ ID NO: 228          moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 228
QAQLQSSGGG VVQPGRSLRL SCAASGFTFS SYGMHWVRQA PGKGLEWVAV ISYKGSNKYY        60
ADSVKGRFTI SRDNSKNTLY LQMNSLRAED TAVYYCGGSG YALHDDYYGL DVWGQGTLVT       120
VSS                                                                     123

SEQ ID NO: 229          moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 229
QVQLQDSEGG VVQPGRSLRL SCAASGFTFS SYGMHWVRQA PGKGLEWVAV ISYTGTKKYY        60
ADSVKGRFTI SRDNSKNTLY LQMNSLRAED TAVYYCGGSG YALHDDYYGL DVWGQGTLVT       120
VSS                                                                     123

SEQ ID NO: 230          moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 230
QAQLQSSEGG VVQPGRSLRL SCAASGFTFS SYGMHWVRQA PGKGLEWVAV ISYRGFNKYY        60
ADSVKGRFTI SRDNSKNTLY LQMNSLRAED TAVYYCGGSG YALHDDYYGQ DVWGQGTLVT       120
VSS                                                                     123

SEQ ID NO: 231          moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 231
QAQLQGSGGG VVQPGRSLRL SCAASGFTFS SYGMHWVRQA PGKGLEWVAV ISYKGSHKYY        60
ADSVKGRFTI SRDNSKNTLY LQMNSLRAED TAVYYCGGSG YALHDDYYGL DVWGQGTLVT       120
VSS                                                                     123

SEQ ID NO: 232          moltype = AA  length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 232
QAQLQSSGGG VVQPGRSLRL SCAASGFTVS SYGMHWVRQA PGKGLEWVAV ISYTGSNKYY        60
ADSVKGRFTI SRDNSKNTLY LQMNSLRAED TAVYYCGGSG YALHDDYYGL DVWGQGTLVT       120
VSS                                                                     123
```

```
SEQ ID NO: 233          moltype = AA   length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 233
QVQLQSSGGG VVQPGRSLRL SCAASGFTFS SYGMHWVRQA PGKGLEWVAV ISYTGSNKYY    60
ADSVKGRFTI SRDNSKNTLY LQMNSLRAED TAVYYCGGSG YALHDDYYGL DVWGQGTLVT   120
VSS                                                                 123

SEQ ID NO: 234          moltype = AA   length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 234
QAQLQGSGGG VVQPGRSLRL SCAASGFTFS SYGMHWVRQA PGKGLEWVAV ISYKGSNKYY    60
ADSVKGRFTI SRDNSKNTLY LQMNSLRAED TAVYYCGGSG YALHDDYYGL DVWGQGTLVT   120
VSS                                                                 123

SEQ ID NO: 235          moltype = AA   length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 235
QVQLQGSGGG VVQPGRSLRL SCAASGFTFS SYGMHWVRQA PGKGLEWVAV ISYDDAHKYY    60
ADSVKGRFTI SRDNSKNTLY LQMNSLRAED TAVYYCGGSG YALHDQYKPV DVWGQGTLVT   120
VSS                                                                 123

SEQ ID NO: 236          moltype = AA   length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 236
QAQLQESEGG VVQPGGSLRL SCAASGFTFS SYGMHWVRQA PGKGLEWVAV ISYNDLNKYY    60
ADSVKGRFTI SRDNSKNTLY LQMNSLRAED TAVYYCGGSG YALHDFQDPT DVWGQGTLVT   120
VSS                                                                 123

SEQ ID NO: 237          moltype = AA   length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 237
QVQLQSSGGG VVQPGRSLRL SCAASGFTVS SYGMHWVRQA PGKGLEWVAV ISYSGSNKYY    60
ADSVKGRFTI SRDNSKNTLY LQMNSLRAED TAVYYCGGSG YALHDQYKPV DVWGQGTLVT   120
VSS                                                                 123

SEQ ID NO: 238          moltype = AA   length = 123
FEATURE                 Location/Qualifiers
source                  1..123
                        mol_type = protein
                        organism = synthetic construct
                        note = Description of Artificial Sequence: Synthetic
                          polypeptide
SEQUENCE: 238
QVQLQGSGGG VVQPGRSLRL SCAASGFTFS SYGMHWVRQA PGKGLEWVAV ISYTGANKYY    60
ADSVKGRFTI SRDNSKNTLY LQMNSLRAED TAVYYCGGSG YNLHDDYYGL DVWGQGTLVT   120
VSS                                                                 123

SEQ ID NO: 239          moltype = AA   length = 123
FEATURE                 Location/Qualifiers
source                  1..123
                        mol_type = protein
                        organism = synthetic construct
                        note = Description of Artificial Sequence: Synthetic
```

```
                                    polypeptide
SEQUENCE: 239
QAQLQRSGGG VVQPGRSLRL SCAASGFTFS SYGMHWVRQA PGKGLEWVAV ISYDDAHKYY   60
ADSVKGRFTI SRDNSKNTLY LQMNSLRAED TAVYYCGGSG YALHDQYKPV DVWGQGTLVT  120
VSS                                                                123

SEQ ID NO: 240          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 240
QVQLQSSEGG VVQPGRSLRL SCAASGFTLS SYGMHWVRQA PGKGLEWVAV ISYTGSNKYY   60
ADSVKGRFTI SRDNSKNTLY LQMNSLRAED TAVYYCGGSG YEFHEDYYGL DVWGQGTLVT  120
VSS                                                                123

SEQ ID NO: 241          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 241
QAQLQGSEGG VVQPGRSLRL SCAASGFTFS SYGMHWVRQA PGKGLEWVAV ISYDDAHKYY   60
ADSVKGRFTI SRDNSKNTLY LQMNSLRAED TAVYYCGGSG YALHDQYKPV DVWGQGTLVT  120
VSS                                                                123

SEQ ID NO: 242          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 242
QVQLQSSGGG VVQPGRSLRL SCAASGFTFS SYGMHWVRQA PGKGLEWVAV ISYNDLNKYY   60
ADSVKGRFTI SRDNSKNTLY LQMNSLRAED TAVYYCGGSG YEFQGDYYGL DVWGQGTLVT  120
VSS                                                                123

SEQ ID NO: 243          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 243
QVQLQSSEGG VVQPGRSLRL SCAASGFTFS SYGMHWVRQA PGKGLEWVAV ISYNDANKYY   60
ADSVKGRFTI SRDNSKNTLY LQMNSLRAED TAVYYCGGSG YELRDDYYGL DVWGQGTLVT  120
VSS                                                                123

SEQ ID NO: 244          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 244
QAQLQSSEGG VVQPGRSLRL SCAASGFTFS SYGMHWVRQA PGKGLEWVAV ISYDESNKYY   60
ADSVKGRFTI SRDNSKNTLY LQMNSLRAED TAVYYCGGSG YEVDQDYYGL DVWGQGTLVT  120
VSS                                                                123

SEQ ID NO: 245          moltype = AA  length = 123
FEATURE                 Location/Qualifiers
source                  1..123
                        mol_type = protein
                        organism = synthetic construct
                        note = Description of Artificial Sequence: Synthetic
                         polypeptide
SEQUENCE: 245
QVQLQESGGG VVQPGRSLRL SCAASGFTFS SYGMHWVRQA PGKGLEWVAV ISYDDAHKYY   60
ADSVKGRFTI SRDNSKNTLY LQMNSLRAED TAVYYCGGSG YALHDQYKPV DVWGQGTLVT  120
VSS                                                                123

SEQ ID NO: 246          moltype = AA  length = 123
```

```
FEATURE                 Location/Qualifiers
source                  1..123
                        mol_type = protein
                        organism = synthetic construct
                        note = Description of Artificial Sequence: Synthetic
                          polypeptide
SEQUENCE: 246
QVQLQGSGGG VVQPGRSLRL SCAASGFTVS SYGMHWVRQA PGKGLEWVAV ISYDDANKYY    60
ADSVKGRFTI SRDSSKNTLY LQMNSLRAED TAVYYCGGSG YAYDGDYYGL DVWGQGTLVT   120
VSS                                                                 123

SEQ ID NO: 247          moltype = AA  length = 255
FEATURE                 Location/Qualifiers
source                  1..255
                        mol_type = protein
                        organism = synthetic construct
                        note = Description of Artificial Sequence: Synthetic
                          polypeptide
SEQUENCE: 247
QVQLQSSEGG VVQPGRSLRL SCAASGFTFS SYGMHWVRQA PGKGLEWVAV ISYKGSNKYY    60
ADSVKGRFTI SRDNSKNTLY LQMNSLRAED TAVYYCGGSG YALHDDYYGL DVWGQGTLVT   120
VSSSGGGGSG GGGSGGGGSG GGGSQSALTQ PASVSGSPGQ SITISCTGTS SDVGGYNYVS   180
WYQQHPGKAP KLMIYEVSNR LRGVSNRFSG SKFGNTASLT ISGLQAEDEA DYYCSSYTSS   240
SALYVFGSGT KVTVL                                                   255

SEQ ID NO: 248          moltype = AA  length = 255
FEATURE                 Location/Qualifiers
source                  1..255
                        mol_type = protein
                        organism = synthetic construct
                        note = Description of Artificial Sequence: Synthetic
                          polypeptide
SEQUENCE: 248
QAQLQSSGGG VVQPGRSLRL SCAASGFTFS SYGMHWVRQA PGKGLEWVAV ISYKGSNKYY    60
ADSVKGRFTI SRDNSKNTLY LQMNSLRAED TAVYYCGGSG YALHDDYYGL DVWGQGTLVT   120
VSSSGGGGSG GGGSGGGGSG GGGSQSALTQ PASVSGSPGQ SITISCTGTS SDVGGYNYVS   180
WYQQHPGKAP KLMIYEVSNR LRGVSNRFSG SKFGNTASLT ISGLQAEDEA DYYCSSYTSS   240
STLYVFGSGT KVTVL                                                   255

SEQ ID NO: 249          moltype = AA  length = 255
FEATURE                 Location/Qualifiers
source                  1..255
                        mol_type = protein
                        organism = synthetic construct
                        note = Description of Artificial Sequence: Synthetic
                          polypeptide
SEQUENCE: 249
QVQLQDSEGG VVQPGRSLRL SCAASGFTFS SYGMHWVRQA PGKGLEWVAV ISYTGTKKYY    60
ADSVKGRFTI SRDNSKNTLY LQMNSLRAED TAVYYCGGSG YALHDDYYGL DVWGQGTLVT   120
VSSSGGGGSG GGGSGGGGSG GGGSQSALTQ PASVSGSPGQ SITISCTGTS SDVGGYNYVS   180
WYQQHPGKAP KLMIYDVSNR PWGVSNRFSG SKFGNTASLT ISGLQAEDEA DYYCSSYTSS   240
SALYVFGSGT KVTVM                                                   255

SEQ ID NO: 250          moltype = AA  length = 255
FEATURE                 Location/Qualifiers
source                  1..255
                        mol_type = protein
                        organism = synthetic construct
                        note = Description of Artificial Sequence: Synthetic
                          polypeptide
SEQUENCE: 250
QAQLQSSEGG VVQPGRSLRL SCAASGFTFS SYGMHWVRQA PGKGLEWVAV ISYRGFNKYY    60
ADSVKGRFTI SRDNSKNTLY LQMNSLRAED TAVYYCGGSG YALHDDYYGQ DVWGQGTLVT   120
VSSSGGGGSG GGGSGGGGSG GGGSQSALTQ PASVSGSPGQ SITISCTGTS SDVGGYNYVS   180
WYQQHPGKAP KLMIYDVSNR LSGVSNRFSG SKFGNTASLT ISGLQAEDEA DYYCSSYTSS   240
STLYVFGSGT KVTVL                                                   255

SEQ ID NO: 251          moltype = AA  length = 255
FEATURE                 Location/Qualifiers
source                  1..255
                        mol_type = protein
                        organism = synthetic construct
                        note = Description of Artificial Sequence: Synthetic
                          polypeptide
SEQUENCE: 251
QAQLQGSGGG VVQPGRSLRL SCAASGFTFS SYGMHWVRQA PGKGLEWVAV ISYKGSHKYY    60
ADSVKGRFTI SRDNSKNTLY LQMNSLRAED TAVYYCGGSG YALHDDYYGL DVWGQGTLVT   120
VSSSGGGGSG GGGSGGGGSG GGGSQSALTQ PASVSGSPGQ SITISCTGTS SDVGGYNYVS   180
WYQQHPGKAP KLMIYDVSNR PWGVSNRFSG SKFGNTASLT ISGLQAEDEA DYYCSSYTSS   240
```

```
STLYVFGSGT KVTVL                                                          255

SEQ ID NO: 252          moltype = AA   length = 255
FEATURE                 Location/Qualifiers
source                  1..255
                        mol_type = protein
                        organism = synthetic construct
                        note = Description of Artificial Sequence: Synthetic
                           polypeptide
SEQUENCE: 252
QVQLQSSEGG VVQPGRSLRL SCAASGFTFS SYGMHWVRQA PGKGLEWVAV ISYKGSNKYY          60
ADSVKGRFTI SRDNSKNTLY LQMNSLRAED TAVYYCGGSG YALHDDYYGL DVWGQGTLVT         120
VSSSGGGGSG GGGSGGGGSG GGGSQSALTQ PASVSGSPGQ SITISCTGTS SDVGGYNYVS         180
WYQQHPGKAP KLMIYDVSNR PWGVSNRFSG SKFGNTASLT ISGLQAEDEA DYYCSSYTSS         240
STLYVFGSGT KVTVL                                                         255

SEQ ID NO: 253          moltype = AA   length = 255
FEATURE                 Location/Qualifiers
source                  1..255
                        mol_type = protein
                        organism = synthetic construct
                        note = Description of Artificial Sequence: Synthetic
                           polypeptide
SEQUENCE: 253
QAQLQSSGGG VVQPGRSLRL SCAASGFTVS SYGMHWVRQA PGKGLEWVAV ISYTGSNKYY          60
ADSVKGRFTI SRDNSKNTLY LQMNSLRAED TAVYYCGGSG YALHDDYYGL DVWGQGTLVT         120
VSSSGGGGSG GGGSGGGGSG GGGSQSALTQ PASVSGSPGQ SITISCTGTS SDVGGYNYVS         180
WYQQHPGKAP KLMIYDVSNR LRGVSNRFSG SKFGNTASLT ISGLQAEDEA DYYCSSYTSS         240
SALYVFGSGT KVTVL                                                         255

SEQ ID NO: 254          moltype = AA   length = 255
FEATURE                 Location/Qualifiers
source                  1..255
                        mol_type = protein
                        organism = synthetic construct
                        note = Description of Artificial Sequence: Synthetic
                           polypeptide
SEQUENCE: 254
QVQLQSSGGG VVQPGRSLRL SCAASGFTFS SYGMHWVRQA PGKGLEWVAV ISYTGSNKYY          60
ADSVKGRFTI SRDNSKNTLY LQMNSLRAED TAVYYCGGSG YALHDDYYGL DVWGQGTLVT         120
VSSSGGGGSG GGGSGGGGSG GGGSQSALTQ PASVSGSPGQ SITISCTGTS SDVGGYNYVS         180
WYQQHPGKAP KLMIYDVSNR AWGVSNRFSG SKFGNTASLT ISGLQAEDEA DYYCSSYTSS         240
SALYVFGSGT KVTVL                                                         255

SEQ ID NO: 255          moltype = AA   length = 255
FEATURE                 Location/Qualifiers
source                  1..255
                        mol_type = protein
                        organism = synthetic construct
                        note = Description of Artificial Sequence: Synthetic
                           polypeptide
SEQUENCE: 255
QAQLQGSGGG VVQPGRSLRL SCAASGFTFS SYGMHWVRQA PGKGLEWVAV ISYKGSNKYY          60
ADSVKGRFTI SRDNSKNTLY LQMNSLRAED TAVYYCGGSG YALHDDYYGL DVWGQGTLVT         120
VSSSGGGGSG GGGSGGGGSG GGGSQSALTQ PASVSGSPGQ SITISCTGTS SDVGGYNYVS         180
WYQQHPGKAP KLMIYEVSNR LRGVSNRFSG SKFGNTASLT ISGLQAEDEA DYYCSSYTSS         240
STLYVFGSGT KVTVL                                                         255

SEQ ID NO: 256          moltype = AA   length = 119
FEATURE                 Location/Qualifiers
source                  1..119
                        mol_type = protein
                        organism = synthetic construct
                        note = Description of Artificial Sequence: Synthetic
                           polypeptide
SEQUENCE: 256
QVQLQQSGAE LARPGASVKM SCKASGYTFT RYTMHWVKQR PGQGLEWIGY INPSRGYTNY          60
NQKFKDKATL TTDKSSSTAY MQLSSLTSED SAVYYCARYY DDHYCLDYWG QGTTLTVSS          119

SEQ ID NO: 257          moltype = AA   length = 106
FEATURE                 Location/Qualifiers
source                  1..106
                        mol_type = protein
                        organism = synthetic construct
                        note = Description of Artificial Sequence: Synthetic
                           polypeptide
SEQUENCE: 257
QIVLTQSPAI MSASPGEKVT MTCSASSSVS YMNWYQQKSG TSPKRWIYDT SKLASGVPAH          60
FRGSGSGTSY SLTISGMEAE DAATYYCQQW SSNPFTFGSG TKLEIN                       106
```

```
SEQ ID NO: 258           moltype = AA   length = 125
FEATURE                  Location/Qualifiers
source                   1..125
                         mol_type = protein
                         organism = synthetic construct
                         note = Description of Artificial Sequence: Synthetic
                            polypeptide
SEQUENCE: 258
EVQLVESGGG LVQPKGSLKL SCAASGFTFN TYAMNWVRQA PGKGLEWVAR IRSKYNNYAT       60
YYADSVKDRF TISRDDSQSI LYLQMNNLKT EDTAMYYCVR HGNFGNSYVS WFAYWGQGTL      120
VTVSA                                                                  125

SEQ ID NO: 259           moltype = AA   length = 109
FEATURE                  Location/Qualifiers
source                   1..109
                         mol_type = protein
                         organism = synthetic construct
                         note = Description of Artificial Sequence: Synthetic
                            polypeptide
SEQUENCE: 259
QAVVTQESAL TTSPGETVTL TCRSSTGAVT TSNYANWVQE KPDHLFTGLI GGTNKRAPGV       60
PARFSGSLIG DKAALTITGA QTEDEAIYFC ALWYSNLWVF GGGTKLTVL                  109

SEQ ID NO: 260           moltype = AA   length = 119
FEATURE                  Location/Qualifiers
source                   1..119
                         mol_type = protein
                         organism = synthetic construct
                         note = Description of Artificial Sequence: Synthetic
                            polypeptide
SEQUENCE: 260
QVQLQQSGAE LARPGASVKM SCKASGYTFT SYTMHWVKQR PGQGLEWIGY INPSSGYTKY       60
NQKFKDKATL TADKSSSTAY MQLSSLTSED SAVYYCARWQ DYDVYFDYWG QGTTLTVSS      119

SEQ ID NO: 261           moltype = AA   length = 106
FEATURE                  Location/Qualifiers
source                   1..106
                         mol_type = protein
                         organism = synthetic construct
                         note = Description of Artificial Sequence: Synthetic
                            polypeptide
SEQUENCE: 261
QIVLSQSPAI LSASPGEKVT MTCRASSSVS YMHWYQQKPG SSPKPWIYAT SNLASGVPAR       60
FSGSGSGTSY SLTISRVEAE DAATYYCQQW SSNPPTFGGG TKLETK                    106

SEQ ID NO: 262           moltype = AA   length = 106
FEATURE                  Location/Qualifiers
source                   1..106
                         mol_type = protein
                         organism = synthetic construct
                         note = Description of Artificial Sequence: Synthetic
                            polypeptide
SEQUENCE: 262
QIVLTQSPAI MSASPGEKVT MTCRASSSVS YMNWYQQKSG TSPKRWIYDT SKVASGVPYR       60
FSGSGSGTSY SLTISSMEAE DAATYYCQQW SSNPLTFGSG TKLEIN                    106

SEQ ID NO: 263           moltype = AA   length = 119
FEATURE                  Location/Qualifiers
source                   1..119
                         mol_type = protein
                         organism = synthetic construct
                         note = Description of Artificial Sequence: Synthetic
                            polypeptide
SEQUENCE: 263
QVQLVQSGGG VVQPGRSLRL SCKASGYTFT RYTMHWVRQA PGKGLEWIGY INPSRGYTNY       60
NQKVKDRFTI SRDNSKNTAF LQMDSLRPED TGVYFCARYY DDHYCLDYWG QGTPVTVSS      119

SEQ ID NO: 264           moltype = AA   length = 106
FEATURE                  Location/Qualifiers
source                   1..106
                         mol_type = protein
                         organism = synthetic construct
                         note = Description of Artificial Sequence: Synthetic
                            polypeptide
SEQUENCE: 264
DIQMTQSPSS LSASVGDRVT ITCSASSSVS YMNWYQQTPG KAPKRWIYDT SKLASGVPSR       60
FSGSGSGTDY TFTISSLQPE DIATYYCQQW SSNPFTFGQG TKLQIT                    106
```

-continued

| | |
|---|---|
| SEQ ID NO: 265 | moltype = AA  length = 118 |
| FEATURE | Location/Qualifiers |
| source | 1..118 |
| | mol_type = protein |
| | organism = synthetic construct |
| | note = Description of Artificial Sequence: Synthetic polypeptide |

SEQUENCE: 265
QVQLVESGGG VVQPGRSLRL SCAASGFKFS GYGMHWVRQA PGKGLEWVAV IWYDGSKKYY   60
VDSVKGRFTI SRDNSKNTLY LQMNSLRAED TAVYYCARQM GYWHFDLWGR GTLVTVSS    118

| | |
|---|---|
| SEQ ID NO: 266 | moltype = AA  length = 108 |
| FEATURE | Location/Qualifiers |
| source | 1..108 |
| | mol_type = protein |
| | organism = synthetic construct |
| | note = Description of Artificial Sequence: Synthetic polypeptide |

SEQUENCE: 266
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPPLTFG GGTKVEIK                108

| | |
|---|---|
| SEQ ID NO: 267 | moltype = AA  length = 124 |
| FEATURE | Location/Qualifiers |
| source | 1..124 |
| | mol_type = protein |
| | organism = synthetic construct |
| | note = Description of Artificial Sequence: Synthetic polypeptide |

SEQUENCE: 267
EVQLVESGGG LVQPGGSLRL SCAASGFTFS TYAMNWVRQA PGKGLEWVGR IRSKYNNYAT   60
YYADSVKDRF ISRDDSKNSL YLQMNSLKTE DTAVYYCVRH GNFGNSYVSW FAYWGQGTLV  120
TVSS                                                               124

| | |
|---|---|
| SEQ ID NO: 268 | moltype = AA  length = 107 |
| FEATURE | Location/Qualifiers |
| source | 1..107 |
| | mol_type = protein |
| | organism = synthetic construct |
| | note = Description of Artificial Sequence: Synthetic polypeptide |

SEQUENCE: 268
QAVVTQEPSL TVSPGGTVTL TCRSSTGAVT TSNYANWVQQ KPGQAPRGLI GGTNKRAPWT   60
PARFSGSLLG GKAALIGAQA EDEADYYCAL WYSNLWVFGG GTKLTVL                107

| | |
|---|---|
| SEQ ID NO: 269 | moltype = AA  length = 119 |
| FEATURE | Location/Qualifiers |
| source | 1..119 |
| | mol_type = protein |
| | organism = synthetic construct |
| | note = Description of Artificial Sequence: Synthetic polypeptide |

SEQUENCE: 269
DIKLQQSGAE LARPGASVKM SCKTSGYTFT RYTMHWVKQR PGQGLEWIGY INPSRGYTNY   60
NQKFKDKATL TTDKSSSTAY MQLSSLTSED SAVYYCARYY DDHYCLDYWG QGTTLTVSS   119

| | |
|---|---|
| SEQ ID NO: 270 | moltype = AA  length = 105 |
| FEATURE | Location/Qualifiers |
| source | 1..105 |
| | mol_type = protein |
| | organism = synthetic construct |
| | note = Description of Artificial Sequence: Synthetic polypeptide |

SEQUENCE: 270
DIQLTQSPAI MSASPGEKVT MTCRASSSVS YMNWYQQKSG TSPKRWIYDT SKVASGVPYR   60
FSGSGSGTSY SLISSMEAED AATYYCQQWS SNPLTFGAGT KLELK                  105

| | |
|---|---|
| SEQ ID NO: 271 | moltype = AA  length = 124 |
| FEATURE | Location/Qualifiers |
| source | 1..124 |
| | mol_type = protein |
| | organism = synthetic construct |
| | note = Description of Artificial Sequence: Synthetic polypeptide |

SEQUENCE: 271
EVQLVESGGG LVQPGGSLRL SCAASGFTFN TYAMNWVRQA PGKGLEWVAR IRSKYNNYAT   60
YYADSVKDRF ISRDDSKNSL YLQMNSLKTE DTAVYYCVRH GNFGNSYVSW FAYWGQGTLV  120
TVSS                                                               124

```
SEQ ID NO: 272            moltype = AA  length = 125
FEATURE                   Location/Qualifiers
source                    1..125
                          mol_type = protein
                          organism = synthetic construct
                          note = Description of Artificial Sequence: Synthetic
                            polypeptide
SEQUENCE: 272
EVKLLESGGG LVQPKGSLKL SCAASGFTFN TYAMNWVRQA PGKGLEWVAR IRSKYNNYAT    60
YYADSVKDRF TISRDDSQSI LYLQMNNLKT EDTAMYYCVR HGNFGNSYVS WFAYWGQGTL   120
VTVSA                                                               125

SEQ ID NO: 273            moltype = AA  length = 125
FEATURE                   Location/Qualifiers
source                    1..125
                          mol_type = protein
                          organism = synthetic construct
                          note = Description of Artificial Sequence: Synthetic
                            polypeptide
SEQUENCE: 273
EVQLVESGGG LVQPGGSLKL SCAASGFTFN SYAMNWVRQA PGKGLEWVAR IRSKYNNYAT    60
YYADSVKGRF TISRDDSKNT AYLQMNNLKT EDTAVYYCVR HGNFGNSYVS WWAYWGQGTL   120
VTVSS                                                               125

SEQ ID NO: 274            moltype = AA  length = 109
FEATURE                   Location/Qualifiers
source                    1..109
                          mol_type = protein
                          organism = synthetic construct
                          note = Description of Artificial Sequence: Synthetic
                            polypeptide
SEQUENCE: 274
QTVVTQEPSL TVSPGGTVTL TCGSSTGAVT SGNYPNWVQQ KPGQAPRGLI GGTKFLAPGT    60
PQRFSGSLLG GKAALTLSGV QPEDEAEYYC VLWYSNRWVF GGGTKLTVL               109

SEQ ID NO: 275            moltype = AA  length = 125
FEATURE                   Location/Qualifiers
source                    1..125
                          mol_type = protein
                          organism = synthetic construct
                          note = Description of Artificial Sequence: Synthetic
                            polypeptide
SEQUENCE: 275
EVQLVESGGG LVQPGGSLKL SCAASGFTFN KYAMNWVRQA PGKGLEWVAR IRSKYNNYAT    60
YYADSVKDRF TISRDDSKNT AYLQMNNLKT EDTAVYYCVR HGNFGNSYIS YWAYWGQGTL   120
VTVSS                                                               125

SEQ ID NO: 276            moltype = AA  length = 109
FEATURE                   Location/Qualifiers
source                    1..109
                          mol_type = protein
                          organism = synthetic construct
                          note = Description of Artificial Sequence: Synthetic
                            polypeptide
SEQUENCE: 276
QTVVTQEPSL TVSPGGTVTL TCGSSTGAVT SGNYPNWVQQ KPGQAPRGLI GGTKFLAPGT    60
PARFSGSLLG GKAALTLSGV QPEDEAEYYC VLWYSNRWVF GGGTKLTVL               109

SEQ ID NO: 277            moltype = AA  length = 119
FEATURE                   Location/Qualifiers
source                    1..119
                          mol_type = protein
                          organism = synthetic construct
                          note = Description of Artificial Sequence: Synthetic
                            polypeptide
SEQUENCE: 277
QVQLVQSGAE VKKPGASVKV SCKASGYTFT RYTMHWVRQA PGQGLEWMGY INPSRGYTNY    60
NQKFKDRVTM TTDTSISTAY MELSRLRSDD TAVYYCARYY DDHYCLDYWG QGTLVTVSS    119

SEQ ID NO: 278            moltype = AA  length = 106
FEATURE                   Location/Qualifiers
source                    1..106
                          mol_type = protein
                          organism = synthetic construct
                          note = Description of Artificial Sequence: Synthetic
                            polypeptide
SEQUENCE: 278
EIVLTQSPAT LSLSPGERAT LSCSASSSVS YMNWYQQKPG QAPRLLIYDT SKLASGVPAH    60
FRGSGSGTDF TLTISSLEPE DFAVYYCQQW SSNPFTFGQG TKVEIK                  106
```

```
SEQ ID NO: 279          moltype = AA   length = 125
FEATURE                 Location/Qualifiers
source                  1..125
                        mol_type = protein
                        organism = synthetic construct
                        note = Description of Artificial Sequence: Synthetic
                         polypeptide
SEQUENCE: 279
EVQLVESGGG LVQPGGSLRL SCAASGFTFS TYAMNWVRQA PGKGLEWVSR IRSKYNNYAT    60
YYADSVKDRF TISRDDSKNT LYLQMNSLRA EDTAVYYCAR HGNFGNSYVS WFAYWGQGTM   120
VTVSS                                                               125

SEQ ID NO: 280          moltype = AA   length = 109
FEATURE                 Location/Qualifiers
source                  1..109
                        mol_type = protein
                        organism = synthetic construct
                        note = Description of Artificial Sequence: Synthetic
                         polypeptide
SEQUENCE: 280
QAVVTQEPSL TVSPGGTVTL TCRSSTGAVT TSNYANWVQQ KPGQAPRGLI GGTNKRAPGT    60
PARFSGSLLG GKAALTLSGV QPEDEAEYYC ALWYSNLWVF GGGTKLTVL               109

SEQ ID NO: 281          moltype = AA   length = 125
FEATURE                 Location/Qualifiers
source                  1..125
                        mol_type = protein
                        organism = synthetic construct
                        note = Description of Artificial Sequence: Synthetic
                         polypeptide
SEQUENCE: 281
EVQLVESGGG LVQPGGSLRL SCAASGFTFN TYAMNWVRQA PGKGLEWVGR IRSKYNNYAT    60
YYADSVKDRF TISRDDSKNS LYLQMNSLKT EDTAVYYCVR HGNFGNSYVS WFAYWGQGTL   120
VTVSS                                                               125

SEQ ID NO: 282          moltype = AA   length = 109
FEATURE                 Location/Qualifiers
source                  1..109
                        mol_type = protein
                        organism = synthetic construct
                        note = Description of Artificial Sequence: Synthetic
                         polypeptide
SEQUENCE: 282
QAVVTQEPSL TVSPGGTVTL TCRSSTGAVT TSNYANWVQE KPGQAPRGLI GGTNKRAPWT    60
PARFSGSLLG GKAALTITGA QAEDEADYYC ALWYSNLWVF GGGTKLTVL               109

SEQ ID NO: 283          moltype = AA   length = 125
FEATURE                 Location/Qualifiers
source                  1..125
                        mol_type = protein
                        organism = synthetic construct
                        note = Description of Artificial Sequence: Synthetic
                         polypeptide
SEQUENCE: 283
EVQLVESGGG LVQPGGSLRL SCAASGFTFN TYAMNWVRQA PGKGLEWVGR IRSKYNNYAT    60
YYADSVKGRF TISRDDSKNT LYLQMNSLRA EDTAVYYCVR HGNFGNSYVS WFAYWGQGTL   120
VTVSS                                                               125

SEQ ID NO: 284          moltype = AA   length = 109
FEATURE                 Location/Qualifiers
source                  1..109
                        mol_type = protein
                        organism = synthetic construct
                        note = Description of Artificial Sequence: Synthetic
                         polypeptide
SEQUENCE: 284
QAVVTQEPSL TVSPGGTVTL TCGSSTGAVT TSNYANWVQQ KPGQAPRGLI GGTNKRAPGV    60
PARFSGSLLG GKAALTLSGA QPEDEAEYYC ALWYSNLWVF GGGTKLTVL               109

SEQ ID NO: 285          moltype = AA   length = 125
FEATURE                 Location/Qualifiers
source                  1..125
                        mol_type = protein
                        organism = synthetic construct
                        note = Description of Artificial Sequence: Synthetic
                         polypeptide
SEQUENCE: 285
EVQLVESGGG LVQPGGSLRL SCAASGFTFS TYAMNWVRQA PGKGLEWVGR IRSKYNNYAT    60
```

```
YYADSVKGRF TISRDDSKNT LYLQMNSLRA EDTAVYYCVR HGNFGDSYVS WFAYWGQGTL    120
VTVSS                                                               125

SEQ ID NO: 286          moltype = AA   length = 109
FEATURE                 Location/Qualifiers
source                  1..109
                        mol_type = protein
                        organism = synthetic construct
                        note = Description of Artificial Sequence: Synthetic
                            polypeptide
SEQUENCE: 286
QAVVTQEPSL TVSPGGTVTL TCGSSTGAVT TSNYANWVQQ KPGKSPRGLI GGTNKRAPGV    60
PARFSGSLLG GKAALTISGA QPEDEADYYC ALWYSNHWVF GGGTKLTVL                109

SEQ ID NO: 287          moltype = AA   length = 101
FEATURE                 Location/Qualifiers
source                  1..101
                        mol_type = protein
                        organism = synthetic construct
                        note = Description of Artificial Sequence: Synthetic
                            polypeptide
SEQUENCE: 287
DIQMTQSPSS LSASVGDRVT ITCSASSSVS YMNWYQQTPG KAPKRWIYDT SKLASGVPSR    60
FSGSGSGTDY TFTISSLQPE DIATYYCQQW SSNPFTFGQG T                       101

SEQ ID NO: 288          moltype = AA   length = 119
FEATURE                 Location/Qualifiers
source                  1..119
                        mol_type = protein
                        organism = synthetic construct
                        note = Description of Artificial Sequence: Synthetic
                            polypeptide
SEQUENCE: 288
QVQLVQSGGG VVQPGRSLRL SCKASGYTFT RYTMHWVRQA PGKGLEWIGY INPSRGYTNY    60
NQKVKDRFTI SRDNSKNTAF LQMDSLRPED TGVYFCARYY DDHYSLDYWG QGTPVTVSS    119

SEQ ID NO: 289          moltype = AA   length = 122
FEATURE                 Location/Qualifiers
source                  1..122
                        mol_type = protein
                        organism = synthetic construct
                        note = Description of Artificial Sequence: Synthetic
                            polypeptide
SEQUENCE: 289
EVQLQQSGPE LVKPGASMKI SCKASGYSFT GYTMNWVKQS HGKNLEWMGL INPYKGVSTY    60
NQKFKDKATL TVDKSSSTAY MELLSLTSED SAVYYCARSG YYGDSDWYFD VWGQGTTLTV   120
FS                                                                  122

SEQ ID NO: 290          moltype = AA   length = 107
FEATURE                 Location/Qualifiers
source                  1..107
                        mol_type = protein
                        organism = synthetic construct
                        note = Description of Artificial Sequence: Synthetic
                            polypeptide
SEQUENCE: 290
DIQMTQTTSS LSASLGDRVT ISCRASQDIR NYLNWYQQKP DGTVKLLIYY TSRLHSGVPS    60
KFSGSGSGTD YSLTISNLEQ EDIATYFCQQ GNTLPWTFAG GTKLEIK                 107

SEQ ID NO: 291          moltype = AA   length = 257
FEATURE                 Location/Qualifiers
source                  1..257
                        mol_type = protein
                        organism = synthetic construct
                        note = Description of Artificial Sequence: Synthetic
                            polypeptide
SEQUENCE: 291
EVQLVESGGG LVQPGGSLRL SCAASGFTFN TYAMNWVRQA PGKGLEWVGR IRSKYNNYAT    60
YYADSVKGRF TISRDDSKNT LYLQMNSLRA EDTAVYYCVR HGNFGNSYVS WFAYWGQGTL   120
VTVSSGGGGS GGGGSGGGGS QAVVTQEPSL TVSPGGTVTL TCGSSTGAVT TSNYANWVQQ   180
KPGQAPRGLI GGTNKRAPGV PARFSGSLLG GKAALTLSGA QPEDEAEYYC ALWYSNLWVF   240
GGGTKLTVLG SHHHHHH                                                  257

SEQ ID NO: 292          moltype = AA   length = 254
FEATURE                 Location/Qualifiers
source                  1..254
                        mol_type = protein
                        organism = synthetic construct
                        note = Description of Artificial Sequence: Synthetic
```

```
                              polypeptide
SEQUENCE: 292
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVL                                                    254

SEQ ID NO: 293           moltype = AA  length = 125
FEATURE                  Location/Qualifiers
source                   1..125
                         mol_type = protein
                         organism = synthetic construct
                         note = Description of Artificial Sequence: Synthetic
                              polypeptide
SEQUENCE: 293
EVQLVESGGG LVQPGGSLRL SCAASGFTFS TYAMNWVRQA PGKGLEWVGR IRSKANNYAT    60
YYADSVKGRF TISRDDSKNT LYLQMNSLRA EDTAVYYCVR HGNFGDSYVS WFAYWGQGTL   120
VTVSS                                                              125

SEQ ID NO: 294           moltype = AA  length = 254
FEATURE                  Location/Qualifiers
source                   1..254
                         mol_type = protein
                         organism = synthetic construct
                         note = Description of Artificial Sequence: Synthetic
                              polypeptide
SEQUENCE: 294
EVQLVESGGG LVQPGGSLRL SCAASGFTFS TYAMNWVRQA PGKGLEWVGR IRSKANNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVL                                                    254

SEQ ID NO: 295           moltype = AA  length = 125
FEATURE                  Location/Qualifiers
source                   1..125
                         mol_type = protein
                         organism = synthetic construct
                         note = Description of Artificial Sequence: Synthetic
                              polypeptide
SEQUENCE: 295
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDEYVS WFAYWGQGTL   120
VTVSS                                                              125

SEQ ID NO: 296           moltype = AA  length = 254
FEATURE                  Location/Qualifiers
source                   1..254
                         mol_type = protein
                         organism = synthetic construct
                         note = Description of Artificial Sequence: Synthetic
                              polypeptide
SEQUENCE: 296
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDEYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVL                                                    254

SEQ ID NO: 297           moltype = AA  length = 125
FEATURE                  Location/Qualifiers
source                   1..125
                         mol_type = protein
                         organism = synthetic construct
                         note = Description of Artificial Sequence: Synthetic
                              polypeptide
SEQUENCE: 297
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDPYVS WFAYWGQGTL   120
VTVSS                                                              125

SEQ ID NO: 298           moltype = AA  length = 254
FEATURE                  Location/Qualifiers
source                   1..254
                         mol_type = protein
                         organism = synthetic construct
                         note = Description of Artificial Sequence: Synthetic
                              polypeptide
```

```
SEQUENCE: 298
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDPYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                   254

SEQ ID NO: 299          moltype = AA  length = 125
FEATURE                 Location/Qualifiers
source                  1..125
                        mol_type = protein
                        organism = synthetic construct
                        note = Description of Artificial Sequence: Synthetic
                          polypeptide
SEQUENCE: 299
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFDYWGQGTL  120
VTVSS                                                             125

SEQ ID NO: 300          moltype = AA  length = 254
FEATURE                 Location/Qualifiers
source                  1..254
                        mol_type = protein
                        organism = synthetic construct
                        note = Description of Artificial Sequence: Synthetic
                          polypeptide
SEQUENCE: 300
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFDYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                   254

SEQ ID NO: 301          moltype = AA  length = 125
FEATURE                 Location/Qualifiers
source                  1..125
                        mol_type = protein
                        organism = synthetic construct
                        note = Description of Artificial Sequence: Synthetic
                          polypeptide
SEQUENCE: 301
EVQLVESGGG LVQPGGSLRL SCAASGFTFS TYAMSWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSS                                                             125

SEQ ID NO: 302          moltype = AA  length = 254
FEATURE                 Location/Qualifiers
source                  1..254
                        mol_type = protein
                        organism = synthetic construct
                        note = Description of Artificial Sequence: Synthetic
                          polypeptide
SEQUENCE: 302
EVQLVESGGG LVQPGGSLRL SCAASGFTFS TYAMSWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                   254

SEQ ID NO: 303          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 303
RYTMH                                                               5

SEQ ID NO: 304          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 304
SASSSVSYMN                                                          10

SEQ ID NO: 305          moltype = AA  length = 5
FEATURE                 Location/Qualifiers
```

```
source                   1..5
                         mol_type = protein
                         organism = synthetic construct
                         note = Description of Artificial Sequence: Synthetic peptide
SEQUENCE: 305
TYAMN                                                                              5

SEQ ID NO: 306           moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 306
RSSTGAVTTS NYAN                                                                   14

SEQ ID NO: 307           moltype = AA  length = 5
FEATURE                  Location/Qualifiers
source                   1..5
                         mol_type = protein
                         organism = synthetic construct
                         note = Description of Artificial Sequence: Synthetic peptide
SEQUENCE: 307
SYTMH                                                                              5

SEQ ID NO: 308           moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 308
RASSSVSYMH                                                                        10

SEQ ID NO: 309           moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 309
RASSSVSYMN                                                                        10

SEQ ID NO: 310           moltype = AA  length = 5
FEATURE                  Location/Qualifiers
source                   1..5
                         mol_type = protein
                         organism = synthetic construct
                         note = Description of Artificial Sequence: Synthetic peptide
SEQUENCE: 310
GYGMH                                                                              5

SEQ ID NO: 311           moltype = AA  length = 11
FEATURE                  Location/Qualifiers
source                   1..11
                         mol_type = protein
                         organism = synthetic construct
                         note = Description of Artificial Sequence: Synthetic peptide
SEQUENCE: 311
RASQSVSSYL A                                                                      11

SEQ ID NO: 312           moltype = AA  length = 5
FEATURE                  Location/Qualifiers
source                   1..5
                         mol_type = protein
                         organism = synthetic construct
                         note = Description of Artificial Sequence: Synthetic peptide
SEQUENCE: 312
SYAMN                                                                              5

SEQ ID NO: 313           moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 313
GSSTGAVTSG NYPN                                                                   14
```

```
SEQ ID NO: 314          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 314
KYAMN                                                                   5

SEQ ID NO: 315          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 315
GSSTGAVTTS NYAN                                                         14

SEQ ID NO: 316          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 316
GYTMN                                                                   5

SEQ ID NO: 317          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 317
RASQDIRNYL N                                                            11

SEQ ID NO: 318          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 318
TYAMS                                                                   5

SEQ ID NO: 319          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 319
TYAMH                                                                   5

SEQ ID NO: 320          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 320
GSSTGAVTSS NYAN                                                         14

SEQ ID NO: 321          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 321
GSSTGAVTSG HYAN                                                         14

SEQ ID NO: 322          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 322
```

```
KSSTGAVTTS NYAN                                                            14

SEQ ID NO: 323          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 323
YINPSRGYTN YNQKFKD                                                         17

SEQ ID NO: 324          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 324
DTSKLAS                                                                    7

SEQ ID NO: 325          moltype = AA  length = 19
FEATURE                 Location/Qualifiers
source                  1..19
                        mol_type = protein
                        organism = synthetic construct
                        note = Description of Artificial Sequence: Synthetic peptide
SEQUENCE: 325
RIRSKYNNYA TYYADSVKD                                                       19

SEQ ID NO: 326          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 326
GTNKRAP                                                                    7

SEQ ID NO: 327          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 327
YINPSSGYTK YNQKFKD                                                         17

SEQ ID NO: 328          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 328
ATSNLAS                                                                    7

SEQ ID NO: 329          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 329
DTSKVAS                                                                    7

SEQ ID NO: 330          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 330
YINPSRGYTN YNQKVKD                                                         17

SEQ ID NO: 331          moltype = AA  length = 17
FEATURE                 Location/Qualifiers
source                  1..17
                        mol_type = protein
                        organism = synthetic construct
```

```
                        note = Description of Artificial Sequence: Synthetic peptide
SEQUENCE: 331
VIWYDGSKKY YVDSVKG                                                  17

SEQ ID NO: 332          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 332
DASNRAT                                                             7

SEQ ID NO: 333          moltype = AA  length = 15
FEATURE                 Location/Qualifiers
source                  1..15
                        mol_type = protein
                        organism = synthetic construct
                        note = Description of Artificial Sequence: Synthetic peptide
SEQUENCE: 333
RIRSKYNNYA TYYAD                                                    15

SEQ ID NO: 334          moltype = AA  length = 19
FEATURE                 Location/Qualifiers
source                  1..19
                        mol_type = protein
                        organism = synthetic construct
                        note = Description of Artificial Sequence: Synthetic peptide
SEQUENCE: 334
RIRSKYNNYA TYYADSVKG                                                19

SEQ ID NO: 335          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 335
GTKFLAP                                                             7

SEQ ID NO: 336          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 336
LINPYKGVST YNQKFKD                                                  17

SEQ ID NO: 337          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 337
YTSRLH                                                              6

SEQ ID NO: 338          moltype = AA  length = 19
FEATURE                 Location/Qualifiers
source                  1..19
                        mol_type = protein
                        organism = synthetic construct
                        note = Description of Artificial Sequence: Synthetic peptide
SEQUENCE: 338
RIRSKANNYA TYYADSVKG                                                19

SEQ ID NO: 339          moltype = AA  length = 20
FEATURE                 Location/Qualifiers
source                  1..20
                        mol_type = protein
                        organism = synthetic construct
                        note = Description of Artificial Sequence: Synthetic peptide
SEQUENCE: 339
RIRSKANNYY ATYYADSVKG                                               20

SEQ ID NO: 340          moltype = AA  length = 19
FEATURE                 Location/Qualifiers
source                  1..19
```

```
                        mol_type = protein
                        organism = synthetic construct
                        note = Description of Artificial Sequence: Synthetic peptide
SEQUENCE: 340
RIRSKANSYA TYYADSVKG                                                   19

SEQ ID NO: 341          moltype = AA   length = 19
FEATURE                 Location/Qualifiers
source                  1..19
                        mol_type = protein
                        organism = synthetic construct
                        note = Description of Artificial Sequence: Synthetic peptide
SEQUENCE: 341
RIRSKYNNYA TAYADSVKG                                                   19

SEQ ID NO: 342          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 342
DTNKRAP                                                                 7

SEQ ID NO: 343          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 343
GTNNRAP                                                                 7

SEQ ID NO: 344          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 344
GTNKRAS                                                                 7

SEQ ID NO: 345          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 345
GTSNKHS                                                                 7

SEQ ID NO: 346          moltype = AA   length = 18
FEATURE                 Location/Qualifiers
source                  1..18
                        mol_type = protein
                        organism = synthetic construct
                        note = Description of Artificial Sequence: Synthetic peptide
SEQUENCE: 346
RIRSNGGYST YYADSVKG                                                    18

SEQ ID NO: 347          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 347
YYDDHYCLDY                                                             10

SEQ ID NO: 348          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 348
QQWSSNPFT                                                               9

SEQ ID NO: 349          moltype = AA   length = 14
```

-continued

```
FEATURE              Location/Qualifiers
source               1..14
                     mol_type = protein
                     organism = synthetic construct
                     note = Description of Artificial Sequence: Synthetic peptide
SEQUENCE: 349
HGNFGNSYVS WFAY                                                          14

SEQ ID NO: 350       moltype = AA   length = 9
FEATURE              Location/Qualifiers
source               1..9
                     mol_type = protein
                     organism = synthetic construct
                     note = Description of Artificial Sequence: Synthetic peptide
SEQUENCE: 350
ALWYSNLWV                                                                9

SEQ ID NO: 351       moltype = AA   length = 10
FEATURE              Location/Qualifiers
source               1..10
                     mol_type = protein
                     organism = synthetic construct
                     note = Description of Artificial Sequence: Synthetic peptide
SEQUENCE: 351
WQDYDVYFDY                                                               10

SEQ ID NO: 352       moltype = AA   length = 9
FEATURE              Location/Qualifiers
source               1..9
                     mol_type = protein
                     organism = synthetic construct
                     note = Description of Artificial Sequence: Synthetic peptide
SEQUENCE: 352
QQWSSNPPT                                                                9

SEQ ID NO: 353       moltype = AA   length = 9
FEATURE              Location/Qualifiers
source               1..9
                     mol_type = protein
                     organism = synthetic construct
                     note = Description of Artificial Sequence: Synthetic peptide
SEQUENCE: 353
QQWSSNPLT                                                                9

SEQ ID NO: 354       moltype = AA   length = 9
FEATURE              Location/Qualifiers
source               1..9
                     mol_type = protein
                     organism = synthetic construct
                     note = Description of Artificial Sequence: Synthetic peptide
SEQUENCE: 354
QMGYWHFDL                                                                9

SEQ ID NO: 355       moltype = AA   length = 10
FEATURE              Location/Qualifiers
source               1..10
                     mol_type = protein
                     organism = synthetic construct
                     note = Description of Artificial Sequence: Synthetic peptide
SEQUENCE: 355
QQRSNWPPLT                                                               10

SEQ ID NO: 356       moltype = AA   length = 16
FEATURE              Location/Qualifiers
source               1..16
                     mol_type = protein
                     organism = synthetic construct
                     note = Description of Artificial Sequence: Synthetic peptide
SEQUENCE: 356
VRHGNFGNSY VSWFAY                                                        16

SEQ ID NO: 357       moltype = AA   length = 14
FEATURE              Location/Qualifiers
source               1..14
                     mol_type = protein
                     organism = synthetic construct
                     note = Description of Artificial Sequence: Synthetic peptide
SEQUENCE: 357
HGNFGNSYVS WWAY                                                          14
```

```
SEQ ID NO: 358           moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 358
VLWYSNRWV                                                              9

SEQ ID NO: 359           moltype = AA   length = 14
FEATURE                  Location/Qualifiers
source                   1..14
                         mol_type = protein
                         organism = synthetic construct
                         note = Description of Artificial Sequence: Synthetic peptide
SEQUENCE: 359
HGNFGNSYIS YWAY                                                       14

SEQ ID NO: 360           moltype = AA   length = 14
FEATURE                  Location/Qualifiers
source                   1..14
                         mol_type = protein
                         organism = synthetic construct
                         note = Description of Artificial Sequence: Synthetic peptide
SEQUENCE: 360
HGNFGDSYVS WFAY                                                       14

SEQ ID NO: 361           moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 361
ALWYSNHWV                                                              9

SEQ ID NO: 362           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 362
YYDDHYSLDY                                                            10

SEQ ID NO: 363           moltype = AA   length = 13
FEATURE                  Location/Qualifiers
source                   1..13
                         mol_type = protein
                         organism = synthetic construct
                         note = Description of Artificial Sequence: Synthetic peptide
SEQUENCE: 363
SGYYGDSDWY FDV                                                        13

SEQ ID NO: 364           moltype = AA   length = 9
FEATURE                  Location/Qualifiers
source                   1..9
                         mol_type = protein
                         organism = synthetic construct
                         note = Description of Artificial Sequence: Synthetic peptide
SEQUENCE: 364
QQGNTLPWT                                                              9

SEQ ID NO: 365           moltype = AA   length = 14
FEATURE                  Location/Qualifiers
source                   1..14
                         mol_type = protein
                         organism = synthetic construct
                         note = Description of Artificial Sequence: Synthetic peptide
SEQUENCE: 365
HGNFGDEYVS WFAY                                                       14

SEQ ID NO: 366           moltype = AA   length = 14
FEATURE                  Location/Qualifiers
source                   1..14
                         mol_type = protein
                         organism = synthetic construct
                         note = Description of Artificial Sequence: Synthetic peptide
```

```
SEQUENCE: 366
HGNFGDPYVS WFAY                                                          14

SEQ ID NO: 367           moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 367
HGNFGDSYVS WFDY                                                          14

SEQ ID NO: 368           moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 368
HGNFGQSYVS WFAY                                                          14

SEQ ID NO: 369           moltype = AA  length = 14
FEATURE                  Location/Qualifiers
source                   1..14
                         mol_type = protein
                         organism = synthetic construct
                         note = Description of Artificial Sequence: Synthetic peptide
SEQUENCE: 369
HGNFGNSYVS WFDY                                                          14

SEQ ID NO: 370           moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 370
LLWYSNLWV                                                                9

SEQ ID NO: 371           moltype = AA  length = 7
FEATURE                  Location/Qualifiers
source                   1..7
                         mol_type = protein
                         organism = synthetic construct
                         note = Description of Artificial Sequence: Synthetic peptide
SEQUENCE: 371
GYTFTRY                                                                  7

SEQ ID NO: 372           moltype = AA  length = 6
FEATURE                  Location/Qualifiers
source                   1..6
                         mol_type = protein
                         organism = synthetic construct
                         note = Description of Artificial Sequence: Synthetic peptide
SEQUENCE: 372
SSSVSY                                                                   6

SEQ ID NO: 373           moltype = AA  length = 7
FEATURE                  Location/Qualifiers
source                   1..7
                         mol_type = protein
                         organism = synthetic construct
                         note = Description of Artificial Sequence: Synthetic peptide
SEQUENCE: 373
GFTFNTY                                                                  7

SEQ ID NO: 374           moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 374
STGAVTTSNY                                                               10

SEQ ID NO: 375           moltype = AA  length = 7
FEATURE                  Location/Qualifiers
source                   1..7
                         mol_type = protein
```

```
                                 organism = synthetic construct
                                 note = Description of Artificial Sequence: Synthetic peptide
SEQUENCE: 375
GYTFTSY                                                                              7

SEQ ID NO: 376                   moltype = AA   length = 7
FEATURE                          Location/Qualifiers
source                           1..7
                                 mol_type = protein
                                 organism = synthetic construct
                                 note = Description of Artificial Sequence: Synthetic peptide
SEQUENCE: 376
GFKFSGY                                                                              7

SEQ ID NO: 377                   moltype = AA   length = 7
FEATURE                          Location/Qualifiers
source                           1..7
                                 mol_type = protein
                                 organism = synthetic construct
                                 note = Description of Artificial Sequence: Synthetic peptide
SEQUENCE: 377
SQSVSSY                                                                              7

SEQ ID NO: 378                   moltype = AA   length = 7
FEATURE                          Location/Qualifiers
source                           1..7
                                 mol_type = protein
                                 organism = synthetic construct
                                 note = Description of Artificial Sequence: Synthetic peptide
SEQUENCE: 378
GFTFSTY                                                                              7

SEQ ID NO: 379                   moltype = AA   length = 7
FEATURE                          Location/Qualifiers
source                           1..7
                                 mol_type = protein
                                 organism = synthetic construct
                                 note = Description of Artificial Sequence: Synthetic peptide
SEQUENCE: 379
GFTFNSY                                                                              7

SEQ ID NO: 380                   moltype = AA   length = 10
FEATURE                          Location/Qualifiers
source                           1..10
                                 mol_type = protein
                                 organism = synthetic construct
                                 note = Description of Artificial Sequence: Synthetic peptide
SEQUENCE: 380
STGAVTSGNY                                                                          10

SEQ ID NO: 381                   moltype = AA   length = 7
FEATURE                          Location/Qualifiers
source                           1..7
                                 mol_type = protein
                                 organism = synthetic construct
                                 note = Description of Artificial Sequence: Synthetic peptide
SEQUENCE: 381
GFTFNKY                                                                              7

SEQ ID NO: 382                   moltype = AA   length = 7
FEATURE                          Location/Qualifiers
source                           1..7
                                 mol_type = protein
                                 organism = synthetic construct
                                 note = Description of Artificial Sequence: Synthetic peptide
SEQUENCE: 382
GYSFTGY                                                                              7

SEQ ID NO: 383                   moltype = AA   length = 7
FEATURE                          Location/Qualifiers
source                           1..7
                                 mol_type = protein
                                 organism = synthetic construct
                                 note = Description of Artificial Sequence: Synthetic peptide
SEQUENCE: 383
SQDIRNY                                                                              7

SEQ ID NO: 384                   moltype = AA   length = 6
FEATURE                          Location/Qualifiers
```

```
source                  1..6
                        mol_type = protein
                        organism = synthetic construct
                        note = Description of Artificial Sequence: Synthetic peptide
SEQUENCE: 384
NPSRGY                                                                        6

SEQ ID NO: 385          moltype =    length =
SEQUENCE: 385
000

SEQ ID NO: 386          moltype = AA   length = 8
FEATURE                 Location/Qualifiers
source                  1..8
                        mol_type = protein
                        organism = synthetic construct
                        note = Description of Artificial Sequence: Synthetic peptide
SEQUENCE: 386
RSKYNNYA                                                                      8

SEQ ID NO: 387          moltype =    length =
SEQUENCE: 387
000

SEQ ID NO: 388          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 388
NPSSGY                                                                        6

SEQ ID NO: 389          moltype =    length =
SEQUENCE: 389
000

SEQ ID NO: 390          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 390
WYDGSK                                                                        6

SEQ ID NO: 391          moltype =    length =
SEQUENCE: 391
000

SEQ ID NO: 392          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 392
RSKYNNYAT                                                                     9

SEQ ID NO: 393          moltype =    length =
SEQUENCE: 393
000

SEQ ID NO: 394          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 394
NPYKGV                                                                        6

SEQ ID NO: 395          moltype =    length =
SEQUENCE: 395
000

SEQ ID NO: 396          moltype = AA   length = 6
FEATURE                 Location/Qualifiers
source                  1..6
```

```
                        mol_type = protein
                        organism = synthetic construct
                        note = Description of Artificial Sequence: Synthetic peptide
SEQUENCE: 396
WSSNPF                                                                          6

SEQ ID NO: 397          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 397
WYSNLW                                                                          6

SEQ ID NO: 398          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 398
WSSNPP                                                                          6

SEQ ID NO: 399          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 399
WSSNPL                                                                          6

SEQ ID NO: 400          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 400
RSNWPPL                                                                         7

SEQ ID NO: 401          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 401
HGNFGNSYVS WFA                                                                 13

SEQ ID NO: 402          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 402
WYSNRW                                                                          6

SEQ ID NO: 403          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 403
WYSNHW                                                                          6

SEQ ID NO: 404          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 404
GNTLPW                                                                          6

SEQ ID NO: 405          moltype = AA   length = 10
```

```
FEATURE                 Location/Qualifiers
source                  1..10
                        mol_type = protein
                        organism = synthetic construct
                        note = Description of Artificial Sequence: Synthetic peptide
SEQUENCE: 405
GYTFTRYTMH                                                            10

SEQ ID NO: 406          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 406
GFTFNTYAMN                                                            10

SEQ ID NO: 407          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 407
GYTFTSYTMH                                                            10

SEQ ID NO: 408          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 408
GFKFSGYGMH                                                            10

SEQ ID NO: 409          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 409
GFTFSTYAMN                                                            10

SEQ ID NO: 410          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 410
GFTFNSYAMN                                                            10

SEQ ID NO: 411          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 411
GFTFNKYAMN                                                            10

SEQ ID NO: 412          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 412
GYSFTGYTMN                                                            10

SEQ ID NO: 413          moltype = AA   length = 18
FEATURE                 Location/Qualifiers
source                  1..18
                        mol_type = protein
                        organism = synthetic construct
                        note = Description of Artificial Sequence: Synthetic peptide
SEQUENCE: 413
RIRSKYNNYA TYYADSVK                                                   18
```

```
SEQ ID NO: 414          moltype = AA   length = 7
FEATURE                 Location/Qualifiers
source                  1..7
                        mol_type = protein
                        organism = synthetic construct
                        note = Description of Artificial Sequence: Synthetic peptide
SEQUENCE: 414
YTSRLHS                                                                   7

SEQ ID NO: 415          moltype = AA   length = 152
FEATURE                 Location/Qualifiers
source                  1..152
                        mol_type = protein
                        organism = synthetic construct
                        note = Description of Artificial Sequence: Synthetic
                          polypeptide
SEQUENCE: 415
MQIFVKTLTG KTITLEVEPS DTIENVKAKI QDKEGIPPDQ QWLWFAGKQL EDGRTLSDYN          60
IQKESTLKLW LVDKAAMQIF VYTRTGKTIT LEVEPSDTIE NVKAKIQDKE GIPPDQQRLI         120
WAGKQLEDGR TLSDYNIALE SGLHVLRLR AA                                        152

SEQ ID NO: 416          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 416
KASGYKFTSY VMH                                                           13

SEQ ID NO: 417          moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 417
YINPYNDVTK YNEKFK                                                        16

SEQ ID NO: 418          moltype = AA   length = 11
FEATURE                 Location/Qualifiers
source                  1..11
                        mol_type = protein
                        organism = synthetic construct
                        note = Description of Artificial Sequence: Synthetic peptide
SEQUENCE: 418
GSYYDYDGFV Y                                                             11

SEQ ID NO: 419          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 419
SATSSVSYMH                                                               10

SEQ ID NO: 420          moltype = AA   length = 120
FEATURE                 Location/Qualifiers
source                  1..120
                        mol_type = protein
                        organism = synthetic construct
                        note = Description of Artificial Sequence: Synthetic
                          polypeptide
SEQUENCE: 420
EVQLQQSGPE LVKPGASVKM SCKASGYKFT SYVMHWVKQK PGQGLEWIGY INPYNDVTKY         60
NEKFKGKATL TSDKSSSTAY MELSSLTSED SAVHYCARGS YYDYDGFVYW GQGTLVTVSA        120

SEQ ID NO: 421          moltype = AA   length = 106
FEATURE                 Location/Qualifiers
source                  1..106
                        mol_type = protein
                        organism = synthetic construct
                        note = Description of Artificial Sequence: Synthetic
                          polypeptide
SEQUENCE: 421
QIVLTQSPAI MSASPGEKVT MTCSATSSVS YMHWYQQKSG TSPKRWIYDT SKLASGVPAR         60
FSGSGSGTSY SLTISSMEAE DAATYYCQQW SSNPLTFGAG TKLELK                       106
```

```
SEQ ID NO: 422          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 422
CPPC                                                                           4

SEQ ID NO: 423          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 423
SPPS                                                                           4

SEQ ID NO: 424          moltype = AA   length = 19
FEATURE                 Location/Qualifiers
source                  1..19
                        mol_type = protein
                        organism = Homo sapiens
SEQUENCE: 424
VPSTPPTPSP STPPTPSPS                                                          19

SEQ ID NO: 425          moltype = AA   length = 6
FEATURE                 Location/Qualifiers
source                  1..6
                        mol_type = protein
                        organism = Homo sapiens
SEQUENCE: 425
VPPPPP                                                                         6

SEQ ID NO: 426          moltype = AA   length = 58
FEATURE                 Location/Qualifiers
source                  1..58
                        mol_type = protein
                        organism = Homo sapiens
SEQUENCE: 426
ESPKAQASSV PTAQPQAEGS LAKATTAPAT TRNTGRGGEE KKKEKEKEEQ EERETKTP              58

SEQ ID NO: 427          moltype = AA   length = 15
FEATURE                 Location/Qualifiers
source                  1..15
                        mol_type = protein
                        organism = Homo sapiens
SEQUENCE: 427
EPKSCDKTHT CPPCP                                                              15

SEQ ID NO: 428          moltype = AA   length = 12
FEATURE                 Location/Qualifiers
source                  1..12
                        mol_type = protein
                        organism = Homo sapiens
SEQUENCE: 428
ERKCCVECPP CP                                                                 12

SEQ ID NO: 429          moltype = AA   length = 62
FEATURE                 Location/Qualifiers
source                  1..62
                        mol_type = protein
                        organism = Homo sapiens
SEQUENCE: 429
ELKTPLGDTT HTCPRCPEPK SCDTPPPCPR CPEPKSCDTP PPCPRCPEPK SCDTPPPCPR             60
CP                                                                            62

SEQ ID NO: 430          moltype = AA   length = 12
FEATURE                 Location/Qualifiers
source                  1..12
                        mol_type = protein
                        organism = Homo sapiens
SEQUENCE: 430
ESKYGPPCPS CP                                                                 12

SEQ ID NO: 431          moltype = AA   length = 12
FEATURE                 Location/Qualifiers
source                  1..12
```

```
                              mol_type = protein
                              organism = Homo sapiens
SEQUENCE: 431
ESKYGPPCPP CP                                                              12

SEQ ID NO: 432                moltype = AA   length = 4
FEATURE                       Location/Qualifiers
source                        1..4
                              mol_type = protein
                              organism = synthetic construct
                              note = Description of Artificial Sequence: Synthetic peptide
SEQUENCE: 432
CPSC                                                                       4

SEQ ID NO: 433                moltype = AA   length = 4
FEATURE                       Location/Qualifiers
source                        1..4
                              mol_type = protein
                              organism = synthetic construct
                              note = Description of Artificial Sequence: Synthetic peptide
SEQUENCE: 433
CPRC                                                                       4

SEQ ID NO: 434                moltype = AA   length = 4
FEATURE                       Location/Qualifiers
source                        1..4
                              mol_type = protein
                              organism = synthetic construct
                              note = Description of Artificial Sequence: Synthetic peptide
SEQUENCE: 434
SPPC                                                                       4

SEQ ID NO: 435                moltype = AA   length = 4
FEATURE                       Location/Qualifiers
source                        1..4
                              mol_type = protein
                              organism = synthetic construct
                              note = Description of Artificial Sequence: Synthetic peptide
SEQUENCE: 435
CPPS                                                                       4

SEQ ID NO: 436                moltype = AA   length = 8
FEATURE                       Location/Qualifiers
source                        1..8
                              mol_type = protein
                              organism = synthetic construct
                              note = Description of Artificial Sequence: Synthetic peptide
SEQUENCE: 436
DKTHTCAA                                                                   8

SEQ ID NO: 437                moltype = AA   length = 11
FEATURE                       Location/Qualifiers
source                        1..11
                              mol_type = protein
                              organism = synthetic construct
                              note = Description of Artificial Sequence: Synthetic peptide
SEQUENCE: 437
DKTHTCPPCP A                                                               11

SEQ ID NO: 438                moltype = AA   length = 18
FEATURE                       Location/Qualifiers
source                        1..18
                              mol_type = protein
                              organism = synthetic construct
                              note = Description of Artificial Sequence: Synthetic peptide
SEQUENCE: 438
DKTHTCPPCP ATCPPCPA                                                        18

SEQ ID NO: 439                moltype = AA   length = 25
FEATURE                       Location/Qualifiers
source                        1..25
                              mol_type = protein
                              organism = synthetic construct
                              note = Description of Artificial Sequence: Synthetic peptide
SEQUENCE: 439
DKTHTCPPCP ATCPPCPATC PPCPA                                                25

SEQ ID NO: 440                moltype = AA   length = 30
FEATURE                       Location/Qualifiers
```

```
                                  -continued
source              1..30
                    mol_type = protein
                    organism = synthetic construct
                    note = Description of Artificial Sequence: Synthetic
                     polypeptide
SEQUENCE: 440
DKTHTCPPCP AGKPTLYNSL VMSDTAGTCY                                        30

SEQ ID NO: 441      moltype = AA  length = 31
FEATURE             Location/Qualifiers
source              1..31
                    mol_type = protein
                    organism = synthetic construct
                    note = Description of Artificial Sequence: Synthetic
                     polypeptide
SEQUENCE: 441
DKTHTCPPCP AGKPTHVNVS VVMAEVDGTC Y                                      31

SEQ ID NO: 442      moltype = AA  length = 15
FEATURE             Location/Qualifiers
source              1..15
                    mol_type = protein
                    organism = synthetic construct
                    note = Description of Artificial Sequence: Synthetic peptide
SEQUENCE: 442
DKTHTCCVEC PPCPA                                                        15

SEQ ID NO: 443      moltype = AA  length = 26
FEATURE             Location/Qualifiers
source              1..26
                    mol_type = protein
                    organism = synthetic construct
                    note = Description of Artificial Sequence: Synthetic peptide
SEQUENCE: 443
DKTHTCPRCP EPKSCDTPPP CPRCPA                                            26

SEQ ID NO: 444      moltype = AA  length = 11
FEATURE             Location/Qualifiers
source              1..11
                    mol_type = protein
                    organism = synthetic construct
                    note = Description of Artificial Sequence: Synthetic peptide
SEQUENCE: 444
DKTHTCPSCP A                                                            11

SEQ ID NO: 445      moltype = AA  length = 50
FEATURE             Location/Qualifiers
source              1..50
                    mol_type = protein
                    organism = synthetic construct
                    note = Description of Artificial Sequence: Synthetic
                     polypeptide
VARIANT             1..50
                    note = MISC_FEATURE - This sequence may encompass 1-10 'Gly
                     Gly Gly Gly Ser' repeating units
REGION              1..50
                    note = See specification as filed for detailed description
                     of substitutions and preferred embodiments
SEQUENCE: 445
GGGGSGGGGS GGGGSGGGGS GGGGSGGGGS GGGGSGGGGS GGGGSGGGGS                  50

SEQ ID NO: 446      moltype = AA  length = 5
FEATURE             Location/Qualifiers
source              1..5
                    mol_type = protein
                    organism = synthetic construct
                    note = Description of Artificial Sequence: Synthetic peptide
SEQUENCE: 446
ADAAP                                                                    5

SEQ ID NO: 447      moltype = AA  length = 11
FEATURE             Location/Qualifiers
source              1..11
                    mol_type = protein
                    organism = synthetic construct
                    note = Description of Artificial Sequence: Synthetic peptide
SEQUENCE: 447
ADAAPTVSIF P                                                            11
```

```
SEQ ID NO: 448            moltype = AA  length = 12
FEATURE                   Location/Qualifiers
source                    1..12
                          mol_type = protein
                          organism = synthetic construct
                          note = Description of Artificial Sequence: Synthetic peptide
SEQUENCE: 448
ADAAPTVSIF PP                                                              12

SEQ ID NO: 449            moltype = AA  length = 6
FEATURE                   Location/Qualifiers
source                    1..6
                          mol_type = protein
                          organism = synthetic construct
                          note = Description of Artificial Sequence: Synthetic peptide
SEQUENCE: 449
AKTTAP                                                                      6

SEQ ID NO: 450            moltype = AA  length = 13
FEATURE                   Location/Qualifiers
source                    1..13
                          mol_type = protein
                          organism = synthetic construct
                          note = Description of Artificial Sequence: Synthetic peptide
SEQUENCE: 450
AKTTAPSVYP LAP                                                             13

SEQ ID NO: 451            moltype = AA  length = 17
FEATURE                   Location/Qualifiers
source                    1..17
                          mol_type = protein
                          organism = synthetic construct
                          note = Description of Artificial Sequence: Synthetic peptide
SEQUENCE: 451
AKTTPKLEEG EFSEARV                                                         17

SEQ ID NO: 452            moltype = AA  length = 9
FEATURE                   Location/Qualifiers
source                    1..9
                          mol_type = protein
                          organism = synthetic construct
                          note = Description of Artificial Sequence: Synthetic peptide
SEQUENCE: 452
AKTTPKLGG                                                                   9

SEQ ID NO: 453            moltype = AA  length = 6
FEATURE                   Location/Qualifiers
source                    1..6
                          mol_type = protein
                          organism = synthetic construct
                          note = Description of Artificial Sequence: Synthetic peptide
SEQUENCE: 453
AKTTPP                                                                      6

SEQ ID NO: 454            moltype = AA  length = 13
FEATURE                   Location/Qualifiers
source                    1..13
                          mol_type = protein
                          organism = synthetic construct
                          note = Description of Artificial Sequence: Synthetic peptide
SEQUENCE: 454
AKTTPPSVTP LAP                                                             13

SEQ ID NO: 455            moltype = AA  length = 6
FEATURE                   Location/Qualifiers
source                    1..6
                          mol_type = protein
                          organism = synthetic construct
                          note = Description of Artificial Sequence: Synthetic peptide
SEQUENCE: 455
ASTKGP                                                                      6

SEQ ID NO: 456            moltype = AA  length = 13
FEATURE                   Location/Qualifiers
source                    1..13
                          mol_type = protein
                          organism = synthetic construct
                          note = Description of Artificial Sequence: Synthetic peptide
SEQUENCE: 456
```

```
ASTKGPSVFP LAP                                                              13

SEQ ID NO: 457         moltype = AA  length = 26
FEATURE                Location/Qualifiers
source                 1..26
                       mol_type = protein
                       organism = synthetic construct
                       note = Description of Artificial Sequence: Synthetic peptide
SEQUENCE: 457
ASTKGPSVFP LAPASTKGPS VFPLAP                                                26

SEQ ID NO: 458         moltype = AA  length = 14
FEATURE                Location/Qualifiers
source                 1..14
                       mol_type = protein
                       organism = synthetic construct
                       note = Description of Artificial Sequence: Synthetic peptide
SEQUENCE: 458
EGKSSGSGSE SKST                                                             14

SEQ ID NO: 459         moltype = AA  length = 15
FEATURE                Location/Qualifiers
source                 1..15
                       mol_type = protein
                       organism = synthetic construct
                       note = Description of Artificial Sequence: Synthetic peptide
SEQUENCE: 459
GEGESGEGES GEGES                                                            15

SEQ ID NO: 460         moltype = AA  length = 20
FEATURE                Location/Qualifiers
source                 1..20
                       mol_type = protein
                       organism = synthetic construct
                       note = Description of Artificial Sequence: Synthetic peptide
SEQUENCE: 460
GEGESGEGES GEGESGEGES                                                       20

SEQ ID NO: 461         moltype = AA  length = 15
FEATURE                Location/Qualifiers
source                 1..15
                       mol_type = protein
                       organism = synthetic construct
                       note = Description of Artificial Sequence: Synthetic peptide
SEQUENCE: 461
GEGGSGEGGS GEGGS                                                            15

SEQ ID NO: 462         moltype = AA  length = 15
FEATURE                Location/Qualifiers
source                 1..15
                       mol_type = protein
                       organism = synthetic construct
                       note = Description of Artificial Sequence: Synthetic peptide
SEQUENCE: 462
GENKVEYAPA LMALS                                                            15

SEQ ID NO: 463         moltype = AA  length = 15
FEATURE                Location/Qualifiers
source                 1..15
                       mol_type = protein
                       organism = synthetic construct
                       note = Description of Artificial Sequence: Synthetic peptide
SEQUENCE: 463
GGEGSGGEGS GGEGS                                                            15

SEQ ID NO: 464         moltype = AA  length = 15
FEATURE                Location/Qualifiers
source                 1..15
                       mol_type = protein
                       organism = synthetic construct
                       note = Description of Artificial Sequence: Synthetic peptide
SEQUENCE: 464
GGGESGGEGS GEGGS                                                            15

SEQ ID NO: 465         moltype = AA  length = 15
FEATURE                Location/Qualifiers
source                 1..15
                       mol_type = protein
                       organism = synthetic construct
```

```
                        note = Description of Artificial Sequence: Synthetic peptide
SEQUENCE: 465
GGGESGGGES GGGES                                                    15

SEQ ID NO: 466          moltype = AA   length = 10
FEATURE                 Location/Qualifiers
source                  1..10
                        mol_type = protein
                        organism = synthetic construct
                        note = Description of Artificial Sequence: Synthetic peptide
SEQUENCE: 466
GGGGSGGGGS                                                          10

SEQ ID NO: 467          moltype = AA   length = 20
FEATURE                 Location/Qualifiers
source                  1..20
                        mol_type = protein
                        organism = synthetic construct
                        note = Description of Artificial Sequence: Synthetic peptide
SEQUENCE: 467
GGGGSGGGGS GGGGSGGGGS                                               20

SEQ ID NO: 468          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 468
GGGKSGGGKS GGGKS                                                    15

SEQ ID NO: 469          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 469
GGGKSGGKGS GKGGS                                                    15

SEQ ID NO: 470          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 470
GGKGSGGKGS GGKGS                                                    15

SEQ ID NO: 471          moltype = AA   length = 5
FEATURE                 Location/Qualifiers
source                  1..5
                        mol_type = protein
                        organism = synthetic construct
                        note = Description of Artificial Sequence: Synthetic peptide
SEQUENCE: 471
GGSGG                                                               5

SEQ ID NO: 472          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 472
GGSGGGSG                                                            9

SEQ ID NO: 473          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 473
GGSGGGGSGG GGS                                                      13

SEQ ID NO: 474          moltype = AA   length = 15
FEATURE                 Location/Qualifiers
source                  1..15
```

```
                        mol_type = protein
                        organism = synthetic construct
                        note = Description of Artificial Sequence: Synthetic peptide
SEQUENCE: 474
GHEAAAVMQV QYPAS                                                          15

SEQ ID NO: 475          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 475
GKGGSGKGGS GKGGS                                                          15

SEQ ID NO: 476          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 476
GKGKSGKGKS GKGKS                                                          15

SEQ ID NO: 477          moltype = AA   length = 20
FEATURE                 Location/Qualifiers
source                  1..20
                        mol_type = protein
                        organism = synthetic construct
                        note = Description of Artificial Sequence: Synthetic peptide
SEQUENCE: 477
GKGKSGKGKS GKGKSGKGKS                                                     20

SEQ ID NO: 478          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 478
GKPGSGKPGS GKPGS                                                          15

SEQ ID NO: 479          moltype = AA   length = 20
FEATURE                 Location/Qualifiers
source                  1..20
                        mol_type = protein
                        organism = synthetic construct
                        note = Description of Artificial Sequence: Synthetic peptide
SEQUENCE: 479
GKPGSGKPGS GKPGSGKPGS                                                     20

SEQ ID NO: 480          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 480
GPAKELTPLK EAKVS                                                          15

SEQ ID NO: 481          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 481
GSAGSAAGSG EF                                                             12

SEQ ID NO: 482          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 482
IRPRAIGGSK PRVA                                                           14

SEQ ID NO: 483          moltype = AA   length = 18
```

```
FEATURE                 Location/Qualifiers
source                  1..18
                        mol_type = protein
                        organism = synthetic construct
                        note = Description of Artificial Sequence: Synthetic peptide
SEQUENCE: 483
KESGSVSSEQ LAQFRSLD                                                      18

SEQ ID NO: 484          moltype = AA   length = 15
FEATURE                 Location/Qualifiers
source                  1..15
                        mol_type = protein
                        organism = synthetic construct
                        note = Description of Artificial Sequence: Synthetic peptide
SEQUENCE: 484
KTTPKLEEGE FSEAR                                                         15

SEQ ID NO: 485          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 485
QPKAAP                                                                    6

SEQ ID NO: 486          moltype = AA   length = 13
FEATURE                 Location/Qualifiers
source                  1..13
                        mol_type = protein
                        organism = synthetic construct
                        note = Description of Artificial Sequence: Synthetic peptide
SEQUENCE: 486
QPKAAPSVTL FPP                                                           13

SEQ ID NO: 487          moltype = AA   length = 27
FEATURE                 Location/Qualifiers
source                  1..27
                        mol_type = protein
                        organism = synthetic construct
                        note = Description of Artificial Sequence: Synthetic peptide
SEQUENCE: 487
RADAAAAGGG GSGGGGSGGG GSGGGGS                                            27

SEQ ID NO: 488          moltype = AA   length = 12
FEATURE                 Location/Qualifiers
source                  1..12
                        mol_type = protein
                        organism = synthetic construct
                        note = Description of Artificial Sequence: Synthetic peptide
SEQUENCE: 488
RADAAAAGGP GS                                                            12

SEQ ID NO: 489          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 489
RADAAP                                                                    6

SEQ ID NO: 490          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 490
RADAAPTVS                                                                 9

SEQ ID NO: 491          moltype = AA   length = 6
FEATURE                 Location/Qualifiers
source                  1..6
                        mol_type = protein
                        organism = synthetic construct
                        note = Description of Artificial Sequence: Synthetic peptide
SEQUENCE: 491
SAKTTP                                                                    6
```

```
SEQ ID NO: 492           moltype = AA   length = 18
FEATURE                  Location/Qualifiers
source                   1..18
                         mol_type = protein
                         organism = synthetic construct
                         note = Description of Artificial Sequence: Synthetic peptide
SEQUENCE: 492
SAKTTPKLEE GEFSEARV                                                  18

SEQ ID NO: 493           moltype = AA   length = 10
FEATURE                  Location/Qualifiers
source                   1..10
                         mol_type = protein
                         organism = synthetic construct
                         note = Description of Artificial Sequence: Synthetic peptide
SEQUENCE: 493
SAKTTPKLGG                                                           10

SEQ ID NO: 494           moltype = AA   length = 14
FEATURE                  Location/Qualifiers
source                   1..14
                         mol_type = protein
                         organism = synthetic construct
                         note = Description of Artificial Sequence: Synthetic peptide
SEQUENCE: 494
STAGDTHLGG EDFD                                                      14

SEQ ID NO: 495           moltype = AA   length = 5
FEATURE                  Location/Qualifiers
source                   1..5
                         mol_type = protein
                         organism = synthetic construct
                         note = Description of Artificial Sequence: Synthetic peptide
SEQUENCE: 495
TVAAP                                                                5

SEQ ID NO: 496           moltype = AA   length = 12
FEATURE                  Location/Qualifiers
source                   1..12
                         mol_type = protein
                         organism = synthetic construct
                         note = Description of Artificial Sequence: Synthetic peptide
SEQUENCE: 496
TVAAPSVFIF PP                                                        12

SEQ ID NO: 497           moltype = AA   length = 24
FEATURE                  Location/Qualifiers
source                   1..24
                         mol_type = protein
                         organism = synthetic construct
                         note = Description of Artificial Sequence: Synthetic peptide
SEQUENCE: 497
TVAAPSVFIF PPTVAAPSVF IFPP                                           24

SEQ ID NO: 498           moltype = AA   length = 18
FEATURE                  Location/Qualifiers
source                   1..18
                         mol_type = protein
                         organism = synthetic construct
                         note = Description of Artificial Sequence: Synthetic peptide
SEQUENCE: 498
GSTSGSGKPG SGEGSTKG                                                  18

SEQ ID NO: 499           moltype = AA   length = 19
FEATURE                  Location/Qualifiers
source                   1..19
                         mol_type = protein
                         organism = synthetic construct
                         note = Description of Artificial Sequence: Synthetic peptide
SEQUENCE: 499
PRGASKSGSA SQTGSAPGS                                                 19

SEQ ID NO: 500           moltype = AA   length = 19
FEATURE                  Location/Qualifiers
source                   1..19
                         mol_type = protein
                         organism = synthetic construct
                         note = Description of Artificial Sequence: Synthetic peptide
```

```
SEQUENCE: 500
GTAAAGAGAA GGAAAGAAG                                                19

SEQ ID NO: 501          moltype = AA  length = 19
FEATURE                 Location/Qualifiers
source                  1..19
                        mol_type = protein
                        organism = synthetic construct
                        note = Description of Artificial Sequence: Synthetic peptide
SEQUENCE: 501
GTSGSSGSGS GGSGSGGGG                                                19

SEQ ID NO: 502          moltype = AA  length = 450
FEATURE                 Location/Qualifiers
source                  1..450
                        mol_type = protein
                        organism = synthetic construct
                        note = Description of Artificial Sequence: Synthetic
                        polypeptide
SEQUENCE: 502
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARRE WWYDDWYLDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SDTKVDKKVE PKSCDKTHTC PPCPAPPVAG    240
PSVFLFPPKP KDTLMISRTP EVTCVVVDVK HEDPEVKFNW YVDGVEVHNA KTKPREEEYN    300
STYRVVSVLT VLHQDWLNGK EYKCKVSNKA LPAPIEKTIS KAKGQPREPQ VYTLPPSREE    360
MTKNQVSLTC DVSGFYPSDI AVEWESDGQP ENNYKTTPPV LDSDGSFFLY SKLTVDKSRW    420
EQGDVFSCSV MHEALHNHYT QKSLSLSPGK                                    450

SEQ ID NO: 503          moltype = AA  length = 214
FEATURE                 Location/Qualifiers
source                  1..214
                        mol_type = protein
                        organism = synthetic construct
                        note = Description of Artificial Sequence: Synthetic
                        polypeptide
SEQUENCE: 503
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSSPLTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 504          moltype = AA  length = 485
FEATURE                 Location/Qualifiers
source                  1..485
                        mol_type = protein
                        organism = synthetic construct
                        note = Description of Artificial Sequence: Synthetic
                        polypeptide
SEQUENCE: 504
EVQLVESGGG LVQPGGSLRL SCAASGFTFS TYAMNWVRQA PGKGLEWVGR IRSKANNYAT    60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PPVAGPSVFL FPPKPKDTLM ISRTPEVTCV    300
VVDVKHEDPE VKFNWYVDGV EVHNAKTKPR EEQYNSTYRV VSVLTVLHQD WLNGKEYKCK    360
VSNKALPAPI EKTISKAKGQ PREPQVYTLP PSREQMTKNQ VKLTCLVKGF YPSDIAVEWE    420
SNGQPENNYK TTPPVLDSDG SFFLYSKLTV DKSRWQQGNV FSCSVMHEAL HNHYTQKSLS    480
LSPGK                                                               485

SEQ ID NO: 505          moltype = AA  length = 723
FEATURE                 Location/Qualifiers
source                  1..723
                        mol_type = protein
                        organism = synthetic construct
                        note = Description of Artificial Sequence: Synthetic
                        polypeptide
SEQUENCE: 505
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARRE WWYDDWYLDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCGGGGSG GGGSEVQLVE    240
SGGGLVQPGG SLRLSCAASG FTFSTYAMNW VRQAPGKGLE WVGRIRSKAN NYATYYADSV    300
KGRFTISRDD SKNTLYLQMN SLRAEDTAVY YCVRHGNFGD SYVSWFAYWG QGTLVTVSSG    360
KPGSGKPGSG KPGSGKPGSQ AVVTQEPSLT VSPGGTVTLT CGSSTGAVTT SNYANWVQQK    420
PGKSPRGLIG GTNKRAPGVP ARFSGSLLGG KAALTISGAQ PEDEADYYCA LWYSNHWVFG    480
GGTKLTVLGG GGSGGGGSKT HTCPPCPAPP VAGPSVFLFP PKPKDTLMIS RTPEVTCVVV    540
DVKHEDPEVK FNWYVDGVEV HNAKTKPREE QYNSTYRVVS VLTVLHQDWL NGKEYKCKVS    600
NKALPAPIEK TISKAKGQPR EPQVYTLPPS REQMTKNQVK LTCLVKGFYP SDIAVEWESN    660
```

-continued

```
GQPENNYKTT PPVLDSDGSF FLYSKLTVDK SRWQQGNVFS CSVMHEALHN HYTQKSLSLS  720
PGK                                                                723

SEQ ID NO: 506          moltype = AA  length = 450
FEATURE                 Location/Qualifiers
source                  1..450
                        mol_type = protein
                        organism = synthetic construct
                        note = Description of Artificial Sequence: Synthetic
                        polypeptide
SEQUENCE: 506
EVQLLESGGG LVQPGGSLRL SCAASGFTFS SYAMSWVRQA PGKGLEWVSA ISESGGRAAY   60
ADSVKGRFTI SRDNSKNTLY LQMNSLRAED TAVYYCARRE WWYDDWYLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SDTKVDKKVE PKSCDKTHTC PPCPAPPVAG  240
PSVFLFPPKP KDTLMISRTP EVTCVVVDVK HEDPEVKFNW YVDGVEVHNA KTKPREEEYN  300
STYRVVSVLT VLHQDWLNGK EYKCKVSNKA LPAPIEKTIS KAKGQPREPQ VYTLPPSREE  360
MTKNQVSLTC DVSGFYPSDI AVEWESDGQP ENNYKTTPPV LDSDGSFFLY SKLTVDKSRW  420
EQGDVFSCSV MHEALHNHYT QKSLSLSPGK                                   450

SEQ ID NO: 507          moltype = AA  length = 214
FEATURE                 Location/Qualifiers
source                  1..214
                        mol_type = protein
                        organism = synthetic construct
                        note = Description of Artificial Sequence: Synthetic
                        polypeptide
SEQUENCE: 507
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 508          moltype = AA  length = 723
FEATURE                 Location/Qualifiers
source                  1..723
                        mol_type = protein
                        organism = synthetic construct
                        note = Description of Artificial Sequence: Synthetic
                        polypeptide
SEQUENCE: 508
EVQLLESGGG LVQPGGSLRL SCAASGFTFS SYAMSWVRQA PGKGLEWVSA ISESGGRAAY   60
ADSVKGRFTI SRDNSKNTLY LQMNSLRAED TAVYYCARRE WWYDDWYLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCGGGGSG GGGSEVQLVE  240
SGGGLVQPGG SLRLSCAASG FTFSTYAMNW VRQAPGKGLE WVGRIRSKAN NYATYYADSV  300
KGRFTISRDD SKNTLYLQMN SLRAEDTAVY YCVRHGNFGD YSVSWFAYWG QGTLVTVSSG  360
KPGSGKPGSG KPGSGKPGSQ AVVTQEPSLT VSPGGTVTLT CGSSTGAVTT SNYANWVQQK  420
PGKSPRGLIG GTNKRAPGVP ARFSGSLLGG KAALTISGAQ PEDEADYYCA LWYSNHWVFG  480
GGTKLTVLGG GGSGGGGSKT HTCPPCPAPP VAGPSVFLFP PKPKDTLMIS RTPEVTCVVV  540
DVKHEDPEVK FNWYVDGVEV HNAKTKPREE QYNSTYRVVS VLTVLHQDWL NGKEYKCKVS  600
NKALPAPIEK TISKAKGQPR EPQVYTLPPS REQMTKNQVK LTCLVKGFYP SDIAVEWESN  660
GQPENNYKTT PPVLDSDGSF FLYSKLTVDK SRWQQGNVFS CSVMHEALHN HYTQKSLSLS  720
PGK                                                                723

SEQ ID NO: 509          moltype = AA  length = 452
FEATURE                 Location/Qualifiers
source                  1..452
                        mol_type = protein
                        organism = synthetic construct
                        note = Description of Artificial Sequence: Synthetic
                        polypeptide
SEQUENCE: 509
QVQLVESGGG VVQPGRSLRL SCAASGFTVS SYGMHWVRQA PGKGLEWVAV ISYTGSNKYY   60
ADSVKGRFTI SRDNSKNTLY LQMNSLRAED TAVYYCGGSG YALHDDYYGL DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV  240
AGPSVFLFPP KPKDTLMISR TPEVTCVVVD VKHEDPEVKF NWYVDGVEVH NAKTKPREEE  300
YNSTYRVVSV LTVLHQDWLN GKEYKCKVSN KALPAPIEKT ISKAKGQPRE PQVYTLPPSR  360
EEMTKNQVSL TCDVSGFYPS DIAVEWESDG QPENNYKTTP PVLDSDGSFF LYSKLTVDKS  420
RWEQGDVFSC SVMHEALHNH YTQKSLSLSP GK                                452

SEQ ID NO: 510          moltype = AA  length = 217
FEATURE                 Location/Qualifiers
source                  1..217
                        mol_type = protein
                        organism = synthetic construct
                        note = Description of Artificial Sequence: Synthetic
                        polypeptide
```

```
SEQUENCE: 510
QSALTQPASV SGSPGQSITI SCTGTSSDVG GYNYVSWYQQ HPGKAPKLMI YDVSNRLRGV    60
SNRFSGSKSG NTASLTISGL QAEDEADYYC SSYTSSSALY VFGSGTKVTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 511          moltype = AA   length = 725
FEATURE                 Location/Qualifiers
source                  1..725
                        mol_type = protein
                        organism = synthetic construct
                        note = Description of Artificial Sequence: Synthetic
                         polypeptide
SEQUENCE: 511
QVQLVESGGG VVQPGRSLRL SCAASGFTVS SYGMHWVRQA PGKGLEWVAV ISYTGSNKYY    60
ADSVKGRFTI SRDNSKNTLY LQMNSLRAED TAVYYCGGSG YALHDDYYGL DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCGGGG SGGGGSEVQL   240
VESGGGLVQP GGSLRLSCAA SGFTFSTYAM NWVRQAPGKG LEWVGRIRSK ANNYATYYAD   300
SVKGRFTISR DDSKNTLYLQ MNSLRAEDTA VYYCVRHGNF GDSYVSWFAY WGQGTLVTVS   360
SGKPGSGKPG SGKPGSGKPG SQAVVTQEPS LTVSPGGTVT LTCGSSTGAV TTSNYANWVQ   420
QKPGKSPRGL IGGTNKRAPG VPARFSGSLL GGKAALTISG AQPEDEADYY CALWYSNHWV   480
FGGGTKLTVL GGGGSGGGGS KTHTCPPCPA PPVAGPSVFL FPPKPKDTLM ISRTPEVTCV   540
VVDVKHEDPE VKFNWYVDGV EVHNAKTKPR EEQYNSTYRV VSVLTVLHQD WLNGKEYKCK   600
VSNKALPAPI EKTISKAKGQ PREPQVYTLP PSREQMTKNQ VKLTCLVKGF YPSDIAVEWE   660
SNGQPENNYK TTPPVLDSDG SFFLYSKLTV DKSRWQQGNV FSCSVMHEAL HNHYTQKSLS   720
LSPGK                                                               725

SEQ ID NO: 512          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 512
GFLG                                                                  4

SEQ ID NO: 513          moltype = AA   length = 4
FEATURE                 Location/Qualifiers
source                  1..4
                        mol_type = protein
                        organism = synthetic construct
                        note = Description of Artificial Sequence: Synthetic peptide
SEQUENCE: 513
ALAL                                                                  4

SEQ ID NO: 514          moltype = AA   length = 4
FEATURE                 Location/Qualifiers
source                  1..4
                        mol_type = protein
                        organism = synthetic construct
                        note = Description of Artificial Sequence: Synthetic peptide
SITE                    1
                        note =
                        N2-[1,4-dioxo-4-[[4-(4-oxo-8-phenyl-4H-1-benzopyran-2-yl)mo
                         rpholinium-4-yl]methoxy]butyl]-L-arginine
SEQUENCE: 514
RGDS                                                                  4

SEQ ID NO: 515          moltype = DNA   length = 249
FEATURE                 Location/Qualifiers
source                  1..249
                        mol_type = other DNA
                        organism = synthetic construct
                        note = Description of Artificial Sequence: Synthetic
                         polynucleotide
SEQUENCE: 515
atgttgcaaa tggctgggca atgtagtcag aatgagtact tcgattctct tctccatgct    60
tgtatcccct gccagctgag gtgttcaagc aatactccgc cccttacctg tcaacgatat   120
tgtaatgcct ccgtgaccaa ttccgtgaag ggaaccaatg ctggatccca tcaccatcac   180
catcacgaat ttagacatga tagcggcctg aacgacattt tcgaggctca aaagatcgag   240
tggcacgag                                                           249

SEQ ID NO: 516          moltype = DNA   length = 369
FEATURE                 Location/Qualifiers
source                  1..369
                        mol_type = other DNA
                        organism = synthetic construct
                        note = Description of Artificial Sequence: Synthetic
```

```
                            polynucleotide
SEQUENCE: 516
caggtgcagc tgcaggagtc ggggggaggc gtggtccagc ctgggaggtc cctgagactc       60
tcctgtgcag cctctggatt caccttcagt agctatggca tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtat      240
ctgcaaatga acagcctgag agccgaggac acggccgtat attactgtgg ggggagtggt      300
tacgcccttc acgatgacta ctacggcttg gacgtctggg gccaaggcac cctggtcacc      360
gtctcctca                                                              369

SEQ ID NO: 517           moltype = DNA  length = 333
FEATURE                  Location/Qualifiers
source                   1..333
                         mol_type = other DNA
                         organism = synthetic construct
                         note = Description of Artificial Sequence: Synthetic
                            polynucleotide
SEQUENCE: 517
cagtctgccc tgactcagcc tgcctccgtg tctgggtctc ctggacagtc gatcaccatc       60
tcctgcactg gaaccagcag tgacgttggt ggttataact atgtctcctg gtaccaacag      120
cacccaggca aagcccccaa actcatgatt tatgatgtca gtaatcggcc ctcagggggtt     180
tctaatcgct tctctggctc caagtctggc aacacggcct cctgaccat ctcgggctc        240
caggctgagg acgaggctga ttattactgc agctcatata caagcagcag cacccttat       300
gtcttcggaa gtgggaccaa ggtcaccgtc cta                                   333

SEQ ID NO: 518           moltype = AA  length = 83
FEATURE                  Location/Qualifiers
source                   1..83
                         mol_type = protein
                         organism = synthetic construct
                         note = Description of Artificial Sequence: Synthetic
                            polypeptide
SEQUENCE: 518
MLQMAGQCSQ NEYFDSLLHA CIPCQLRCSS NTPPLTCQRY CNASVTNSVK GTNAGSHHHH        60
HHEFRHDSGL NDIFEAQKIE WHE                                               83

SEQ ID NO: 519           moltype = DNA  length = 246
FEATURE                  Location/Qualifiers
source                   1..246
                         mol_type = other DNA
                         organism = synthetic construct
                         note = Description of Artificial Sequence: Synthetic
                            polynucleotide
SEQUENCE: 519
atgctccaga tggcacggca atgtagtcag aacgagtatt ttgatagcct gctccacgat       60
tgcaagccct gtcagctgcg gtgtagctcc actccgccat tgacgtgtca gcggtactgc      120
aacgcaagta tgacaaactc agtcaagggc atgaacgcag gatcccatca ccatcaccat      180
cacgaattta gacatgatag cggcctgaac gacattttcg aggctcaaaa gatcgagtgg      240
cacgag                                                                 246

SEQ ID NO: 520           moltype = DNA  length = 765
FEATURE                  Location/Qualifiers
source                   1..765
                         mol_type = other DNA
                         organism = synthetic construct
                         note = Description of Artificial Sequence: Synthetic
                            polynucleotide
SEQUENCE: 520
caagtgcagc tccagagttc gaaggcgga gtggtgcagc ctggaaggag cctgcgcctg        60
tcatgcgcag cgtccgggtt cacctctca tcctacggca tgcactggggt cagacaggcc      120
ccgggaaaag gattgaatg ggtggccgtg atttcataca agggttccaa caagtactac       180
gccgattccg tgaagggacg gtttaccatc tcgcgggaca ctcgaagaa caccctgtac       240
ctccaaatga acagcctgcg cgccgaagat actgccgtgt actactgcgg cggttccggt      300
tacgcgctcc acgacgacta ttacgggctg gacgtctgga gacagggcac cctggtcact      360
gtgtcctcgt caggtggtgg tggttctggt ggtggcggct caggcggcgg cggctcaggt      420
ggtggaggat cccagtccgc tctgacccaa ccggcttccg tgagcggaag ccccggacag      480
tccattacta tcagctgtac cggcacctcc tccgacgtcg gtggatacaa ctacgtgtcc      540
tggtatcagc agcatcctgg aaaggctcca aagctcatga tctacgaggt gtcgaacaga      600
ctgagggtg tgtccaatcg ctttccgggc tccaagttcg gaaacacggc ctcactgact      660
atctcgggac tgcaggccga agatgaagcc gactactact gctcctccta cacctcgtcc       720
tccgctctgt acgtgttcgg gtccggcacc aaagtcactg tgctg                     765

SEQ ID NO: 521           moltype = DNA  length = 765
FEATURE                  Location/Qualifiers
source                   1..765
                         mol_type = other DNA
                         organism = synthetic construct
                         note = Description of Artificial Sequence: Synthetic
                            polynucleotide
```

```
SEQUENCE: 521
caagcgcagc tccagagttc cggaggcgga gtggtgcagc tggaaggag cctgcgcctg    60
tcatgcgcag cgtccgggtt caccttctca tcctacggca tgcactggt cagacaggcc   120
ccgggaaaag gattggaatg ggtggccgtg atttcctaca aggggtccaa caagtactac   180
gccgattccg tgaagggacg gtttaccatc tcgcgggaca actcgaagaa cacctgtac   240
ctccaaatga acagcctgcg cgccgaagat actgccgtgt actactgcgg cggttccggt   300
tacgcgctcc acgacgacta ttacgggctg gacgtctggg gacagggcac cctggtcact   360
gtgtcctcgt caggtggtgg tggttctggt ggtggcggct caggcggcgg cggctcaggt   420
ggtggaggat cccagtccgc tctgacccaa ccggcttccg tgagcggaag ccccggacag   480
tccattacta tcagctgtac cggcacctcc tccgacgtcg gtggatacaa ctacgtgtcc   540
tggtatcagc agcatcctgg aaaggctcca aagctcatga tctacgaagt gtcgaacaga   600
ctgagaggtg tgtccaatcg cttttcgggc tccaagttcg aaacacggc ctcactgact   660
atctcgggac tgcaggccga agatgaagcc gactactact gctcctccta cacctcgtcc   720
tccactctgt acgtgttcgg gtccggcacc aaagtcactg tgctg                   765

SEQ ID NO: 522          moltype = DNA   length = 765
FEATURE                 Location/Qualifiers
source                  1..765
                        mol_type = other DNA
                        organism = synthetic construct
                        note = Description of Artificial Sequence: Synthetic
                            polynucleotide
SEQUENCE: 522
caagtgcagc tccaggattc cgaaggcgga gtggtgcagc tggaaggag cctgcgcctg    60
tcatgcgcag cgtccgggtt caccttctca tcctacggca tgcactggt cagacaggcc   120
ccgggaaaag gattggaatg ggtggccgtg atttcctaca ctggtaccaa aaagtactac   180
gccgattccg tgaagggacg gtttaccatc tcgcgggaca actcgaagaa cacctgtac   240
ctccaaatga acagcctgcg cgccgaagat actgccgtgt actactgcgg cggttccggt   300
tacgcgctcc acgacgacta ttacgggctg gacgtctggg gacagggcac cctggtcact   360
gtgtcctcgt caggtggtgg tggttctggt ggtggcggct caggcggcgg cggctcaggt   420
ggtggaggat cccagtccgc tctgacccaa ccggcttccg tgagcggaag ccccggacag   480
tccattacta tcagctgtac cggcacctcc tccgacgtcg gtggatacaa ctacgtgtcc   540
tggtatcagc agcatcctgg aaaggctcca aagctcatga tctacgacgt gtcgaacaga   600
ccgtggggtg tgtccaatcg cttttcgggc tccaagttcg aaacacggc ctcactgact   660
atctcgggac tgcaggccga agatgaagcc gactactact gctcctccta cacctcgtcc   720
tccgctctgt acgtgttcgg gtccggcacc aaagtcactg tgatg                   765

SEQ ID NO: 523          moltype = DNA   length = 765
FEATURE                 Location/Qualifiers
source                  1..765
                        mol_type = other DNA
                        organism = synthetic construct
                        note = Description of Artificial Sequence: Synthetic
                            polynucleotide
SEQUENCE: 523
caagcgcagc tccagagttc cgaaggcgga gtggtgcagc tggaaggag cctgcgcctg    60
tcatgcgcag cgtccgggtt caccttctca tcctacggca tgcactggt cagacaggcc   120
ccggaaaag gattggaatg ggtggccgtg atttcctacc ggggttttaa caagtactac   180
gccgattccg tgaagggacg gtttaccatc tcgcgggaca actcgaagaa cacctgtac   240
ctccaaatga acagcctgcg cgccgaagat actgccgtgt actactgcgg cggttccggt   300
tacgcgctcc acgacgacta ttacgggcag gacgtctggg gacagggcac cctggtcact   360
gtgtcctcgt caggtggtgg tggttctggt ggtggcggct caggcggcgg cggctcaggt   420
ggtggaggat cccagtccgc tctgacccaa ccggcttccg tgagcggaag ccccggacag   480
tccattacta tcagctgtac cggcacctcc tccgacgtcg gtggatacaa ctacgtgtcc   540
tggtatcagc agcatcctgg aaaggctcca aagctcatga tctacgacgt gtcgaacaga   600
ctgagcggtg tgtccaatcg cttttcgggc tccaagttcg aaacacggc ctcactgact   660
atctcgggac tgcaggccga agatgaagcc gactactact gctcctccta cacatcgtcc   720
tccactctgt acgtgttcgg gtccggcacc aaagtcactg tgctg                   765

SEQ ID NO: 524          moltype = DNA   length = 765
FEATURE                 Location/Qualifiers
source                  1..765
                        mol_type = other DNA
                        organism = synthetic construct
                        note = Description of Artificial Sequence: Synthetic
                            polynucleotide
SEQUENCE: 524
caagcgcagc tccaggggtc cggaggcgga gtggtgcagc tggaaggag cctgcgcctg    60
tcatgcgcag cgtccgggtt caccttctca tcctacggca tgcactggt cagacaggcc   120
ccggaaaag gattggaatg ggtggccgtg atttcctaca aggggtccca caagtactac   180
gccgattccg tgaagggacg gtttaccatc tcgcgggaca actcgaagaa cacctgtac   240
ctccaaatga acagcctgcg cgccgaagat actgccgtgt actactgcgg cggttccggt   300
tacgcgctcc acgacgacta ttacgggctg gacgtctggg gacagggcac cctggtcact   360
gtgtcctcgt caggtggtgg tggttctggt ggtggcggct caggcggcgg cggctcaggt   420
ggtggaggat cccagtccgc tctgacccaa ccggcttccg tgagcggaag ccccggacag   480
tccattacta tcagctgtac cggcacctcc tccgacgtcg gtggatacaa ctacgtgtcc   540
tggtatcagc agcatcctgg aaaggctcca aagctcatga tctacgacgt gtcgaacaga   600
ccgtggggtg tgtccaatcg cttttcgggc tccaagttcg aaacacggc ctcactgact   660
atctcgggac tgcaggccga agatgaagcc gactactact gctcctccta cacctcgtcc   720
```

```
tccactctgt acgtgttcgg gtccggcacc aaagtcactg tgctg              765
```

SEQ ID NO: 525              moltype = DNA   length = 765
FEATURE                     Location/Qualifiers
source                      1..765
                            mol_type = other DNA
                            organism = synthetic construct
                            note = Description of Artificial Sequence: Synthetic
                                polynucleotide
SEQUENCE: 525
```
caagtgcagc tccagagttc cgaaggcgga gtggtgcagc tggaaggag cctgcgcctg   60
tcatgcgcag cgtccgggtt caccttctca tcctacggca tgcactgggt cagacaggcc  120
ccgggaaaag gattggaatg ggtggccgtg atttcctaca aggggtcgaa caagtactac  180
gccgattccg tgaagggacg gtttaccatc tcgcgggaca actcgaagaa caccctgtac  240
ctccaaatga acagcctgcg cgccgaagat actgccgtgt actactgcgg cggttccggt  300
tacgcgctcc acgacgacta ttacgggctg gacgtctggg gacagggcac cctggtcact  360
gtgtcctcgt caggtggtgg tggttctggt ggtggcggct caggcggcgg cggctcaggt  420
ggtggaggat cccagtccgc tctgacccaa ccggcttccg tgagcggaag ccccggacag  480
tccattacta tcagctgtac cggcacctcc tccgacgtcg gtggatacaa ctacgtgtcc  540
tggtatcagc agcatcctgg aaaggctcca aagctcatga tctacgacgt gtcgaacaga  600
ccgtgggtg tgtccaatcg cttttcgggc tccaagttcg gaaacacggc ctcactgact  660
atctcgggac tgcaggccga agatgaagcc gactactact gctcctccta caccctcgcc  720
tccactctgt acgtgttcgg gtccggcacc aaagtcactg tgctg              765
```

SEQ ID NO: 526              moltype = DNA   length = 765
FEATURE                     Location/Qualifiers
source                      1..765
                            mol_type = other DNA
                            organism = synthetic construct
                            note = Description of Artificial Sequence: Synthetic
                                polynucleotide
SEQUENCE: 526
```
caagcgcagc tccagagttc cggaggtgga gtggtgcagc tggaaggag cctgcgcctg   60
tcatgcgcag cgtccgggtt caccgtctca tcctacggca tgcactgggt cagacaggcc  120
ccgggaaaag gattggaatg ggtggccgtg atttcctaca ctgggtccaa caagtactac  180
gccgattccg tgaagggacg gtttaccatc tcgcgggaca actcgaagaa caccctgtac  240
ctccaaatga acagcctgcg cgccgaagat actgccgtgt actactgcgg cggttccggt  300
tacgcgctcc acgacgacta ttacgggctg gacgtctggg gacagggcac cctggtcact  360
gtgtcctcgt caggtggtgg tggttctggt ggtggcggct caggcggcgg cggctcaggt  420
ggtggaggat cccagtccgc tctgacccaa ccggcttccg tgagcggaag ccccggacag  480
tccattacta tcagctgtac cggcacctcc tccgacgtcg gtggatacaa ctacgtgtcc  540
tggtatcagc agcatcctgg aaaggctcca aagctcatga tctacgacgt gtcgaacaga  600
ctgagggtg tgtccaatcg cttttcgggc tccaagttcg gaaacacggc ctcactgact  660
atctcgggat tgcaggccga agatgaagcc gactactact gctcctccta caccctcgtca 720
tccgctctgt acgtgttcgg gtccggcacc aaagtcactg tgctg              765
```

SEQ ID NO: 527              moltype = DNA   length = 765
FEATURE                     Location/Qualifiers
source                      1..765
                            mol_type = other DNA
                            organism = synthetic construct
                            note = Description of Artificial Sequence: Synthetic
                                polynucleotide
SEQUENCE: 527
```
caagtgcagc tccagagttc cggaggcgga gtggtgcagc tggaaggag cctgcgcctg   60
tcatgcgcag cgtccgggtt caccttctca tcctacggca tgcactgggt cagacaggcc  120
ccgggaaaag gattggaatg ggtggccgtg atttcataca ctggttctaa caagtactac  180
gccgattccg tgaagggacg gtttaccatc tcgcgggaca actcgaagaa caccctgtac  240
ctccaaatga acagcctgcg cgccgaagat actgccgtgt actactgcgg cggttccggt  300
tacgcgctcc acgacgacta ttacgggctg gacgtctggg gacagggcac cctggtcact  360
gtgtcctcgt caggtggtgg tggttctggt ggtggcggct caggcggcgg cggctcaggt  420
ggtggaggat cccagtccgc tctgacccaa ccggcttccg tgagcggaag ccccggacag  480
tccattacta tcagctgtac cggcacctcc tccgacgtcg gtggatacaa ctacgtgtcc  540
tggtatcagc agcatcctgg aaaggctcca aagctcatga tctacgacgt gtcgaacaga  600
gcgtggggtg tgtccaatcg cttttcgggc tccaagttcg gaaacacggc ctcactgact  660
atctcgggac tgcaggccga agatgaagcc gactactact gctcctccta caccctcgcc  720
tccgctctgt acgtgttcgg gtccggtacc aaagtcactg tgctg              765
```

SEQ ID NO: 528              moltype = DNA   length = 765
FEATURE                     Location/Qualifiers
source                      1..765
                            mol_type = other DNA
                            organism = synthetic construct
                            note = Description of Artificial Sequence: Synthetic
                                polynucleotide
SEQUENCE: 528
```
caagcgcagc tccaggggtc cggaggcgga gtggtgcagc tggaaggag cctgcgcctg   60
tcatgcgcag cgtccgggtt caccttctca tcctacggca tgcactgggt cagacaggcc  120
ccgggaaaag gattggaatg ggtggccgtg atttcctata agggtccaa caagtactac  180
```

```
gccgattccg tgaagggacg gtttaccatc tcgcgggaca actcgaagaa cacctgtac    240
ctccaaatga acagcctgcg cgccgaagat actgccgtgt actactgcgg cggttccggt    300
tacgcgctcc acgacgacta ttacgggctg gacgtctggg gacagggcac cctggtcact    360
gtgtcctcgt caggtggtgg tggttctggt ggtggcggct caggcggcgg cggctcaggt    420
ggtggaggat cccagtccgc tctgacccaa ccggcttccg tgagcggaag ccccggacag    480
tccattacta tcagctgtac cggcaccctcc tccgacgtcg gtggatacaa ctacgtgtcc    540
tggtatcagc agcatcctgg aaaggctcca aagctcatga tctacgaagt gtcgaacaga    600
ttgagaggtg tgtccaatcg ctttcgggc tccaagttcg gaaacacggc ctcactgact    660
atctcgggac tgcaggccga agatgaagcc gactactact gctcctccta cacctcgtcc    720
tccactctgt acgtgttcgg gtccggcacc aaagtcactg tgctg                    765

SEQ ID NO: 529          moltype = AA  length = 82
FEATURE                 Location/Qualifiers
source                  1..82
                        mol_type = protein
                        organism = synthetic construct
                        note = Description of Artificial Sequence: Synthetic
                        polypeptide
SEQUENCE: 529
MLQMARQCSQ NEYFDSLLHD CKPCQLRCSS TPPLTCQRYC NASMTNSVKG MNAGSHHHHH   60
HEFRHDSGLN DIFEAQKIEW HE                                            82

SEQ ID NO: 530          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 530
SGYALHD                                                              7

SEQ ID NO: 531          moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 531
DYYGLDV                                                              7

SEQ ID NO: 532          moltype = DNA  length = 369
FEATURE                 Location/Qualifiers
source                  1..369
                        mol_type = other DNA
                        organism = synthetic construct
                        note = Description of Artificial Sequence: Synthetic
                        polynucleotide
SEQUENCE: 532
caagtgcagc tccagggggtc cggaggtgga gtggtgcagc tggaaggag cctgcgcctg    60
tcatgcgcag cgtccgggtt caccttctca tcctacggca tgcactgggt cagacaggcc   120
ccgggaaaag gattggaatg ggtggccgtg atttcctacg atgatgccca caagtactac   180
gccgattccg tgaagggacg gtttaccatc tcgcgggaca actcgaagaa cacctgtac   240
ctccaaatga acagcctgcg cgccgaagat actgccgtgt actactgcgg cggttccggt   300
tacgcgctcc acgaccagta taagccagtc gatgtctggg gacagggcac cctggtcact   360
gtgtcctcg                                                            369

SEQ ID NO: 533          moltype = DNA  length = 333
FEATURE                 Location/Qualifiers
source                  1..333
                        mol_type = other DNA
                        organism = synthetic construct
                        note = Description of Artificial Sequence: Synthetic
                        polynucleotide
SEQUENCE: 533
cagtccgctc tgacccaacc ggcttccgtg agcggaagcc ccggacagtc cattactatc    60
agctgtaccg gcacctcctc cgacgtcggt ggatacaact acgtgtcctg gtatcagcag   120
catcctggaa aggctccaaa gctcatgatc tacgaagtgt cgaacagact aagcggtgtg   180
tccaatcgct tttcgggctc caagttcgga aacacggcct cactgactat ctcgggactg   240
caggccgaag atgaagccga ctactactgc tcctcctaca cctcgtcctc cgctctgtac   300
gtgttcgggt ccggcaccaa agtcactgtg ctg                                 333

SEQ ID NO: 534          moltype = DNA  length = 369
FEATURE                 Location/Qualifiers
source                  1..369
                        mol_type = other DNA
                        organism = synthetic construct
                        note = Description of Artificial Sequence: Synthetic
                        polynucleotide
SEQUENCE: 534
```

```
caagcgcagc tccaggagtc cgaaggcgga gtggtgcagc tggaggag cctgcgcctg    60
tcatgcgcag cgtccgggtt caccttctca tcctacggca tgcactgggt cagacaggcc   120
ccggaaaag gattggaatg ggtggccgtg atttcctaca atgatttgaa caagtactac   180
gccgattccg tgaagggacg gtttaccatc tcgcggaca actcgaagaa caccctgtac   240
ctccaaatga acagcctgcg cgccgaagat actgccgtgt actactgcgg cggttccggt   300
tacgcctcc acgacttcca ggatccaaca gatgtctggg gacagggcac cctggtcact   360
gtgtcctcg                                                           369

SEQ ID NO: 535         moltype = DNA   length = 369
FEATURE                Location/Qualifiers
source                 1..369
                       mol_type = other DNA
                       organism = synthetic construct
                       note = Description of Artificial Sequence: Synthetic
                           polynucleotide
SEQUENCE: 535
caagtgcagc tccagagttc cggaggtgga gtggtgcagc tggaaggag cctgcgcctg    60
tcatgcgcag cgtccgggtt caccgtctca tcctacggca tgcactgggt cagacaggcc   120
ccggaaaag gattggaatg ggtggccgtg atttcctaca gtgggtccaa caagtactac   180
gccgattccg tgaagggacg gtttaccatc tcgcggaca actcgaagaa caccctgtac   240
ctccaaatga acagcctgcg cgccgaagat actgccgtgt actactgcgg cggttccggt   300
tacgcctcc acgaccagta taagccagtc gatgtctggg gacagggcac cctggtcact   360
gtgtcctcg                                                           369

SEQ ID NO: 536         moltype = DNA   length = 333
FEATURE                Location/Qualifiers
source                 1..333
                       mol_type = other DNA
                       organism = synthetic construct
                       note = Description of Artificial Sequence: Synthetic
                           polynucleotide
SEQUENCE: 536
cagtccgctc tgacccaacc ggcttccgtg agcggaagcc ccggacagtc cattactatc    60
agctacaccg gcacctcctc cgacgtcggt ggatacaact acgtgtcctg gtatcagcag   120
catcctggaa aggctccaaa gctcatgatc tacgaggtgt cgaacagact gagcggtctg   180
tccaatcgct tttcgggctc caagttcgga aacacggcct cactgactat ctcgggactg   240
caggccgaag atgaagccga ctactactgc tcctcctaca cctcgtcctc cgctctgtac   300
gtgttcgggt ccggcaccaa agtcactgtg ctg                                333

SEQ ID NO: 537         moltype = DNA   length = 333
FEATURE                Location/Qualifiers
source                 1..333
                       mol_type = other DNA
                       organism = synthetic construct
                       note = Description of Artificial Sequence: Synthetic
                           polynucleotide
SEQUENCE: 537
cagtccgctc tgacccaacc ggcttccgtg agcggaagcc ccggacagtc cattactatc    60
agctgtaccg gcacctcctc cgacgtcggt ggatacaact acgtgtcctg gtatcagcag   120
catcctggaa aggctccaaa gctcatgatc tacgaagtgt cgaacagact gagaggtgtg   180
tccaatcgct tttcgggctc caagttcgga aacacggcat cactgactat ctcgggactg   240
caggccgaag atgaagccta ctactactgc tcctcctaca cctcgtcctc cactctgtac   300
gtgttcgggt ccggcaccaa agtcactgtg ctg                                333

SEQ ID NO: 538         moltype = DNA   length = 369
FEATURE                Location/Qualifiers
source                 1..369
                       mol_type = other DNA
                       organism = synthetic construct
                       note = Description of Artificial Sequence: Synthetic
                           polynucleotide
SEQUENCE: 538
caagtgcagc tccagggttc cggaggcgga gtggtgcagc tggaaggag cctgcgcctg    60
tcatgcgcag cgtccgggtt caccttctca tcctacggca tgcactgggt cagacaggcc   120
ccggaaaag gattggaatg ggtggccgtg atttcctaca ctgggccaa caagtactac   180
gccgattccg tgaagggacg gtttaccatc tcgcggaca actcgaagaa caccctgtac   240
ctccaaatga acagcctgcg cgccgaagat actgccgtgt actactgcgg cggttctggt   300
tataacttgc acgatgacta ttacgggctg gacgtctggg gacagggcac cctggtcact   360
gtgtcctcg                                                           369

SEQ ID NO: 539         moltype = DNA   length = 333
FEATURE                Location/Qualifiers
source                 1..333
                       mol_type = other DNA
                       organism = synthetic construct
                       note = Description of Artificial Sequence: Synthetic
                           polynucleotide
SEQUENCE: 539
cagtccgctc tgacccaacc ggcttccgtg agcggaagcc ccggacagtc cattactatc    60
```

```
agctgtaccg gcacctcctc cgacgtcggt ggatacaact acgtgtcctg gtatcagcag    120
catcctggaa aggctccaaa gctcatgatc tacgaggtgt cgaacagact gaggggtgtg    180
tccaatcgct tttcgggctc caagttcgga aacacggcct cactgactat ctcgggactg    240
caggccgaag atgaagccga ctactactgc tcctcctaca cctcgtcctc cactctgtac    300
gtgttcgggt ccggcaccaa agtcactgtg ctg                                 333
```

```
SEQ ID NO: 540          moltype = DNA   length = 369
FEATURE                 Location/Qualifiers
source                  1..369
                        mol_type = other DNA
                        organism = synthetic construct
                        note = Description of Artificial Sequence: Synthetic
                            polynucleotide
SEQUENCE: 540
caagcgcagc tccagaggtc cggaggtgga gtggtgcagc tggaaggag cctgcgcctg      60
tcatgcgcag cgtccgggtt caccttctca tcctacggca tgcactgggt cagacaggcc   120
ccgggaaaag gattggaatg ggtggccgtg atttcctacg atgatgccca caagtactac   180
gccgattccg tgaagggacg gtttaccatc tcgcgggaca gtcgaagaa caccctgtac   240
ctccaaatga acagcctgcg cgccgaagat actgccgtgt actactgcgg cggttccggt   300
tacgcgctcc acgaccagta taagccagtc gatgtctggg gacagggcac cctggtcact   360
gtgtcctcg                                                           369

SEQ ID NO: 541          moltype = DNA   length = 369
FEATURE                 Location/Qualifiers
source                  1..369
                        mol_type = other DNA
                        organism = synthetic construct
                        note = Description of Artificial Sequence: Synthetic
                            polynucleotide
SEQUENCE: 541
caagtgcagc tccagagttc cgaaggtgga gtggtgcagc tggaaggag cctgcgcctg      60
tcatgcgcag cgtccgggtt caccttatca tcctacggca tgcactgggt cagacaggcc   120
ccgggaaaag gattggaatg ggtggccgtg atttcctaca ctgggtccaa taagtactac   180
gccgattccg tgaagggacg gtttaccatc tcgcgggaca ctcgaagaa caccctgtac   240
ctccaaatga acagcctgcg cgccgaagat actgccgtgt actactgcgg cggttctggt   300
tatgaattcc acgaagacta ttacgggctg gacgtctggg gacagggcac cctggtcact   360
gtgtcctcg                                                           369

SEQ ID NO: 542          moltype = DNA   length = 333
FEATURE                 Location/Qualifiers
source                  1..333
                        mol_type = other DNA
                        organism = synthetic construct
                        note = Description of Artificial Sequence: Synthetic
                            polynucleotide
SEQUENCE: 542
cagtccgctc tgacccaacc ggcttccgtg agcggaagcc ccggacagtc cattactatc      60
agctgtaccg gcacctcctc cgacgtcggt ggatacaact acgtgtcctg gtatcagcag   120
catcctggaa aggctccaaa gctcatgatc tacgaagtgt cgaacagact gaggggtgtg   180
tccaatcgct tttcgggctc caagttcgga aacacggcct cactgactat ctctggactg   240
caggccgaag atgaagccga ctactactgc tcctcctaca ccacgtcctc cactctgtac   300
gtgttcgggt ccggcaccaa agtcactgtg ctg                                 333

SEQ ID NO: 543          moltype = DNA   length = 369
FEATURE                 Location/Qualifiers
source                  1..369
                        mol_type = other DNA
                        organism = synthetic construct
                        note = Description of Artificial Sequence: Synthetic
                            polynucleotide
SEQUENCE: 543
caagcgcagc tccaggggtc cgaaggtgga gtggtgcagc tggaaggag cctgcgcctg      60
tcatgcgcag cgtccgggtt caccttctca tcctacggca tgcactgggt cagacaggcc   120
ccgggaaaag gattggaatg ggtggccgtg atttcctacg atgatgccca caagtactac   180
gccgattccg tgaagggacg gtttaccatc tcgcgggaca ctcgaagaa caccctgtac   240
ctccaaatga acagcctgcg cgccgaagat actgccgtgt actactgcgg cggttccggt   300
tacgcgctcc acgaccagta taagccagtc gatgtctggg gacagggcac cctggtcact   360
gtgtcctcg                                                           369

SEQ ID NO: 544          moltype = DNA   length = 333
FEATURE                 Location/Qualifiers
source                  1..333
                        mol_type = other DNA
                        organism = synthetic construct
                        note = Description of Artificial Sequence: Synthetic
                            polynucleotide
SEQUENCE: 544
cagtccgctc tgacccaacc ggcttccgtg agcggaagcc ccggacagtc cattactatc      60
agctgtaccg gcacctcctc cgacgtcggt ggatacaact acgtgtcctg gtatcagcag   120
```

```
catcctggaa aggctccaaa gctcatgatc tacgaggtgt cgaacagact gagcggtgtg    180
tccaatcgct tttcgggctc caagttcgga aacacggcct cactgactat ctcgggactg    240
caggccgaag atgaagccga ctactactgc tcctcctaca cctcgtcctc cactctgtac    300
gtgttcgggt ccggcaccaa agtcactgtg ctg                                 333

SEQ ID NO: 545           moltype = DNA  length = 369
FEATURE                  Location/Qualifiers
source                   1..369
                         mol_type = other DNA
                         organism = synthetic construct
                         note = Description of Artificial Sequence: Synthetic
                           polynucleotide
SEQUENCE: 545
caagtgcagc tccagagttc cggaggtgga gtggtgcagc tggaaggag cctgcgcctg      60
tcatgcgcag cgtccgggtt caccttctca tcctacggca tgcactgggt cagacaggcc    120
ccgggaaaag gattggaatg ggtggccgtg atttcctaca atgatttgaa caagtactac    180
gccgattccg tgaagggacg gtttaccatc tcgcgggaca actcgaagaa caccctgtac    240
ctccaaatga acagcctgcg cgccgaagat actgccgtgt actactgcgg cggttctggt    300
tatgaattcc agggtgacta ttacgggctg gacgtctggg gacagggcac cctggtcact    360
gtgtcctcg                                                            369

SEQ ID NO: 546           moltype = DNA  length = 333
FEATURE                  Location/Qualifiers
source                   1..333
                         mol_type = other DNA
                         organism = synthetic construct
                         note = Description of Artificial Sequence: Synthetic
                           polynucleotide
SEQUENCE: 546
cagtccgctc tgacccaacc ggcttccgtg agcggaagcc ccggacagtc cattactatc     60
agctgtaccg gcacctcctc cgacgtcggt ggatacaact acgtgtcctg gtatcagcag    120
catcctggaa aggctccaaa gctcatgatc tacgaagtgt cgaacagact gaggggtgtg    180
tccaatcgct tttcgggctc caagttcgga aacacggcct cactgactat ctcgggactg    240
caggccgaag atgaagccga ctactactgc tcctcctaca cctcgtcctc cactctgtac    300
gtgttcgggt ccggcaccaa agtcactgtg ctg                                 333

SEQ ID NO: 547           moltype = DNA  length = 369
FEATURE                  Location/Qualifiers
source                   1..369
                         mol_type = other DNA
                         organism = synthetic construct
                         note = Description of Artificial Sequence: Synthetic
                           polynucleotide
SEQUENCE: 547
caagtgcagc tccagagttc cgaaggtgga gtggtgcagc tggaaggag cctgcgcctg      60
tcatgcgcag cgtccgggtt caccttctca tcctacggca tgcactgggt cagacaggcc    120
ccgggaaaag gattggaatg ggtggccgtg atttcctaca atgatgccaa caagtactac    180
gccgattccg tgaagggacg gtttaccatc tcgcgggaca actcgaagaa caccctgtac    240
ctccaaatga acagcctgcg cgccgaagat actgccgtgt actactgcgg cggttctggt    300
tatgaattga gagatgacta ttacgggctg gacgtctggg gacagggcac cctggtcact    360
gtgtcctcg                                                            369

SEQ ID NO: 548           moltype = DNA  length = 333
FEATURE                  Location/Qualifiers
source                   1..333
                         mol_type = other DNA
                         organism = synthetic construct
                         note = Description of Artificial Sequence: Synthetic
                           polynucleotide
SEQUENCE: 548
cagtccgctc tgacccaacc ggcttccgtg agcggaagcc ccggacagtc cattactatc     60
agctgtaccg gcacctcctc cgacgtcggt ggatacaact acgtgtcctg gtatcagcag    120
catcctggaa aggctccaaa gctcatgatc tacgaggtgt cgaacagact gagaggtgtg    180
tccaatcgct tttcgggctc caagttcgga aacacggcct cactgactat ctcgggactg    240
caggccgaag atgaagccga ctactactgc tcctcctaca cctcgtcctc cactctgtac    300
gtgttcgggt ccggcaccaa agtcactgtg ctg                                 333

SEQ ID NO: 549           moltype = DNA  length = 369
FEATURE                  Location/Qualifiers
source                   1..369
                         mol_type = other DNA
                         organism = synthetic construct
                         note = Description of Artificial Sequence: Synthetic
                           polynucleotide
SEQUENCE: 549
caagcgcagc tccagagttc cgaaggcgga gtggtgcagc tggaaggag cctgcgtctg      60
tcatgcgcag cgtccgggtt caccttctca tcctacggca tgcactgggt cagacaggcc    120
ccgggaaaag gattggaatg ggtggccgtg atttcctacg atgagtccaa caagtactac    180
gccgattccg tgaagggacg gtttaccatc tcgcgggaca actcgaagaa caccctgtac    240
```

```
ctccaaatga acagcctgcg cgccgaagat actgccgtgt actactgcgg cggttctggt  300
tatgaagtcg atcaggacta ttacgggctg gacgtctggg gacagggcac cctggtcact  360
gtgtcctcg                                                          369

SEQ ID NO: 550         moltype = DNA    length = 333
FEATURE                Location/Qualifiers
source                 1..333
                       mol_type = other DNA
                       organism = synthetic construct
                       note = Description of Artificial Sequence: Synthetic
                         polynucleotide
SEQUENCE: 550
cagtccgctc tgacccaacc ggcttccgtg agcggaagcc ccggacagtc cattactatc  60
agctgtaccg gcacctcctc cgacgtcggt ggatacaact acgtgtcctg gtatcagcag  120
catcctggaa aggctccaaa gctcatgatc tacgaggtgt cgaacagact gcgcggtgtg  180
tccaatcgct tttcgggctc caagttcgga aacacggcct cactgactat ctcgggactg  240
caggccgaag atgaagccga ctactactgc tcctcctaca cctcgtcctc cacactgtac  300
gtgttcgggt ccggcaccaa agtcactgtg ctg                               333

SEQ ID NO: 551         moltype = DNA    length = 369
FEATURE                Location/Qualifiers
source                 1..369
                       mol_type = other DNA
                       organism = synthetic construct
                       note = Description of Artificial Sequence: Synthetic
                         polynucleotide
SEQUENCE: 551
caagtgcagc tccaggagtc cggaggtgga gtggtgcagc ctggaaggag cctgcgcctg  60
tcatgcgcag cgtccgggtt caccttctca tcctacggca tgcactgggt cagacaggcc  120
ccgggaaaag gattggaatg ggtggccgtg atttcctaca atgatgccca caagtactac  180
gccgattccg tgaagggacg gtttaccatc tcgcgggaca actcgaagaa caccctgtac  240
ctccaaatga acagcctgcg cgccgaagat actgccgtgt actactgcgg cggttccggt  300
tacgcgctcc acgaccagta taagccagtc gatgtctggg gacagggcac cctggtcact  360
gtgtcctcg                                                          369

SEQ ID NO: 552         moltype = DNA    length = 369
FEATURE                Location/Qualifiers
source                 1..369
                       mol_type = other DNA
                       organism = synthetic construct
                       note = Description of Artificial Sequence: Synthetic
                         polynucleotide
SEQUENCE: 552
caagtgcagc tccagggttc cggaggtgga gtggtgcagc ctggaaggag cctgcgcctg  60
tcatgcgcag cgtccgggtt caccgtctca tcctacggca tgcactgggt cagacaggcc  120
ccgggaaaag gattggaatg ggtggccgtg atttcatacg atgatgccaa caagtactac  180
gccgattccg tgaagggacg gtttaccatc tcgcgggaca actcgaagaa caccctgtac  240
ctccaaatga acagcctgcg cgccgaagat actgccgtgt actactgcgg cggttctggt  300
tatgcttatg atggtgacta ttacgggctg gacgtctggg gacagggcac cctggtcact  360
gtgtcctcg                                                          369

SEQ ID NO: 553         moltype = DNA    length = 333
FEATURE                Location/Qualifiers
source                 1..333
                       mol_type = other DNA
                       organism = synthetic construct
                       note = Description of Artificial Sequence: Synthetic
                         polynucleotide
SEQUENCE: 553
cagtccgctc tgacccaacc ggcttccgtg agcggaagcc ccggacagtc cattactatc  60
agctgtaccg gcacctcctc cgacgtcggt ggatacaact acgtgtcctg gtatcagcag  120
catcctggaa aggctccaaa gctcatgatc tacgaggtgt cgaacagact gcgcggtgtg  180
tccaatcgct tttcgggctc caagttcgga aacacggcct cactgactat ctcgggactg  240
caggccgaag atgaagccga ctactactgc tcctcctaca cctcgtcctc cgctctgtac  300
gtgttcgggt ccggcaccaa agtcactgtg ctg                               333

SEQ ID NO: 554         moltype = DNA    length = 363
FEATURE                Location/Qualifiers
source                 1..363
                       mol_type = other DNA
                       organism = synthetic construct
                       note = Description of Artificial Sequence: Synthetic
                         polynucleotide
SEQUENCE: 554
gaggtgcagc tgctggagag cggggggtgga ctggtgcagc cgggaggttc cctccggttc  60
tcatgtgccg catccggctt tactttctct tcctacgcca tgtcgtgggt cagacaggcc  120
ccgggaaagg gacttgagtg ggtgtcggcc atctccggtt ccgggggatc cacctactac  180
gcggactccg tgaagggccg cttcactatt tcacgggaca cagcaagaa caccctgtac  240
ctccaaatga actcgctgcg cgccgaagat accgccgtct actactgcgc gcggagggaa  300
```

```
tggtggtacg acgattggta tctggactac tggggccagg gcactctcgt gaccgtgtcc    360
agc                                                                  363

SEQ ID NO: 555          moltype = AA  length = 224
FEATURE                 Location/Qualifiers
source                  1..224
                        mol_type = protein
                        organism = synthetic construct
                        note = Description of Artificial Sequence: Synthetic
                          polypeptide
SEQUENCE: 555
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCARRE WWYDDWYLDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SDTKVDKKVE PKSC                     224

SEQ ID NO: 556          moltype = DNA  length = 672
FEATURE                 Location/Qualifiers
source                  1..672
                        mol_type = other DNA
                        organism = synthetic construct
                        note = Description of Artificial Sequence: Synthetic
                          polynucleotide
SEQUENCE: 556
gaggtgcagc tgctggagag cgggggtgga ctggtgcagc cgggaggttc cctccggttg    60
tcatgtgccg catccggctt tacttttctct tcctacgcca tgtcgtgggt cagacaggcc    120
ccggggaaagg gacttgagtg ggtgtccggc atctccggtt ccgggggatc cacctactac    180
gcggactccg tgaagggccg cttcactatt tcacgggaca cagcaagaa caccctgtac    240
ctccaaatga actcgctgcg cgccgaagat accgccgtct actactgcgc gcggagggaa    300
tggtggtacg acgattggta tctggactac tggggccagg gcactctcgt gaccgtgtcc    360
agcgctagca ccaagggccc gtcagtgttt cctctggccc caagctccaa gtccacctcc    420
ggtggtacag ccgcgttggg atgcttggtc aaggactact ttccggaacc cgtgaccgtg    480
tcctggaact ccggcgccct gactagcgga gtgcacacct ccccgctgt gctgcagtct    540
agcgggctgt attccctctc gtccgtggtc accgtgccgt cctcatccct gggaacccag    600
acctacattt gcaacgtgaa ccacaagccg tcagacacca aggtggacaa gaaggtggag    660
ccgaagtcct gc                                                        672

SEQ ID NO: 557          moltype = DNA  length = 321
FEATURE                 Location/Qualifiers
source                  1..321
                        mol_type = other DNA
                        organism = synthetic construct
                        note = Description of Artificial Sequence: Synthetic
                          polynucleotide
SEQUENCE: 557
gacattcaga tgactcagtc cccgtcctcc ttgtccgcct ccgtgggaga cagagtcacc    60
atcacttgcc gggcatcgca gagcatctct tcatacctga actggtatca gcagaagccc    120
ggaaaggccc ctaagctgct gatctacgcg gccagcagcc ttcagtccgg cgtgccatca    180
aggttcagcg gatcgggttc gggcaccgat tttactctga ccattagctc cctgcaaccc    240
gaggacttcg ctacctacta ctgtcagcag tcctactcct ccccgctgac cttcggacaa    300
gggaccaaag tcgaaatcaa g                                              321

SEQ ID NO: 558          moltype = DNA  length = 642
FEATURE                 Location/Qualifiers
source                  1..642
                        mol_type = other DNA
                        organism = synthetic construct
                        note = Description of Artificial Sequence: Synthetic
                          polynucleotide
SEQUENCE: 558
gacattcaga tgactcagtc cccgtcctcc ttgtccgcct ccgtgggaga cagagtcacc    60
atcacttgcc gggcatcgca gagcatctct tcatacctga actggtatca gcagaagccc    120
ggaaaggccc ctaagctgct gatctacgcg gccagcagcc ttcagtccgg cgtgccatca    180
aggttcagcg gatcgggttc gggcaccgat tttactctga ccattagctc cctgcaaccc    240
gaggacttcg ctacctacta ctgtcagcag tcctactcct ccccgctgac cttcggacaa    300
gggaccaaag tcgaaatcaa gcgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                       642

SEQ ID NO: 559          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 559
```

-continued

```
RSKANNYA                                                                      8

SEQ ID NO: 560          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 560
GFTFSTYA                                                                      8

SEQ ID NO: 561          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 561
IRSKANNYAT                                                                   10

SEQ ID NO: 562          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 562
VRHGNFGDSY VSWFAY                                                            16

SEQ ID NO: 563          moltype = DNA  length = 375
FEATURE                 Location/Qualifiers
source                  1..375
                        mol_type = other DNA
                        organism = synthetic construct
                        note = Description of Artificial Sequence: Synthetic
                               polynucleotide
SEQUENCE: 563
gaagtgcagc ttgtggagtc cggggggagga ttggtccaac ccggtggctc gctgaggctg            60
agttgcgccg cttcggggtt taccttcagc acctacgcta tgaactgggt cagacaggcg           120
cctggaaagg gtttggagtg ggtcggacga atccggtcca aggccaacaa ctacgcgact           180
tactatgccg actccgtcaa gggacggttc accatctccc gggacgacag caagaacacc           240
ctgtacctgc aaatgaactc ccttcgggcc gaagataccg ccgtgtacta ctgcgtgaga           300
cacggcaact tcggcgactc ctacgtgtcc tggtttgcct actggggcca gggtactctc           360
gtgaccgtgt catca                                                            375

SEQ ID NO: 564          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 564
TGAVTTSNY                                                                     9

SEQ ID NO: 565          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 565
GTNKRAPGVP                                                                   10

SEQ ID NO: 566          moltype = DNA  length = 327
FEATURE                 Location/Qualifiers
source                  1..327
                        mol_type = other DNA
                        organism = synthetic construct
                        note = Description of Artificial Sequence: Synthetic
                               polynucleotide
SEQUENCE: 566
caggctgtgg tcacccagga accctccctg actgtgtccc cgggaggaac cgtgacactg            60
acttgtggca gctccaccgg agccgtgacc acctccaact acgccaactg ggtgcagcaa           120
aagccaggaa agtccccctag ggggctgatc ggtggcacga caagcgggc acctggagtg           180
cctgccgat tctcgggtag cctgctgggg ggaaaagccg ccctgaccat ttcgggcgct            240
cagccagagg acgaagccga ctattactgc gcactcggt actccaacca ctgggtgttc            300
ggtggaggca ccaagctgac cgtgctg                                               327

SEQ ID NO: 567          moltype = DNA  length = 762
```

```
FEATURE              Location/Qualifiers
source               1..762
                     mol_type = other DNA
                     organism = synthetic construct
                     note = Description of Artificial Sequence: Synthetic
                        polynucleotide
SEQUENCE: 567
gaagtgcagc ttgtggagtc cggggagga ttggtccaac ccggtggctc gctgaggctg    60
agttgcgccg cttcggggtt taccttcagc acctacgcta tgaactgggt cagacaggcg   120
cctggaaagg gtttggagtg gtcggacgc atccggtcca aggccaacaa ctacgcgact    180
tactatgccg actccgtcaa gggacggttc accatctccc gggacgacag caagaacacc   240
ctgtacctcc aaatgaactc ccttcgggcc gaagataccg ccgtgtacta ctgcgtgaga   300
cacggcaact tcggcgactc ctacgtgtcc tggtttgcct actggggcca gggtactctc   360
gtgaccgtgt catcaggaaa gccaggctcg gggaagcctg gctccggaaa gcctgggagc   420
ggaaagccgg gatcgcaggc tgtggtcacc caggaaccct ccctgactgt gtccccggga   480
ggaaccgtga cactgacttg tggcagctcc accggagccg tgaccacctc caactacgcc   540
aactgggtgc agcaaaagcc aggaaagtcc cctaggggc tgatcggtgg cacgaacaag    600
cgggcacctg gagtgcctgc ccgattctcg ggtagcctgc tgggggaaa agccgccctg    660
accatttcgg gcgctcagcc agaggacgaa gccgactatt actgcgcact ctggtactcc   720
aaccactggg tgttcggtgg aggcaccaag ctgaccgtgc tg                      762

SEQ ID NO: 568       moltype = DNA  length = 1350
FEATURE              Location/Qualifiers
source               1..1350
                     mol_type = other DNA
                     organism = synthetic construct
                     note = Description of Artificial Sequence: Synthetic
                        polynucleotide
SEQUENCE: 568
gaggtgcagc tgctggagag cggggggtgga ctggtgcagc cgggaggttc cctccggttg    60
tcatgtgccg catccggctt tactttctct tcctacgcca tgtcgtgggt cagacaggcc   120
ccgggaaagg gacttgagtg ggtgtcggcc atctccggtt ccgggggatc cacctactac   180
gcggactccg tgaagggccg cttcactatt tcacgggaca cagcaagaa caccctgtac   240
ctccaaatga actcgctgcg cgccgaagat accgccgtct actactgcgc gcggagggaa   300
tggtggtacg acgattggta tctggactac tgggcccagg gcactctcgt gaccgtgtcc   360
agcgctagca ccaagggccc gtcagtgttt cctctggccc caagctccaa gtccacctcc   420
ggtggtacag ccgcgttggg atgcttggtc aaggactact tccggaacc cgtgaccgtg   480
tcctggaact ccggcgccct gactagcgga gtgcacacct tccccgctgt gctgcagtct   540
agcgggctgt attccctctc gtccgtggtc accgtgccgt cctcatccct gggaaccag   600
acctacattt gcaacgtgaa ccacaagccg tcagacacca aggtggacaa gaaggtggag   660
ccgaagtcct gcgacaagac ccatacttgt cctccttgcc ccgctccacc tgtggcggga   720
ccttccgtgt tcctttttcc gccgaagccg aaggacactc tgatgatctc gcggactccc   780
gaagtcacttt gcgtggtggt ggacgtcaaa cacgaagatc ccgaggtcaa gttcaattgg   840
tacgtggacg gggtggaagt ccacaacgcc aagactaagc cgcgcgagga agtacaat    900
tccacttacc gggtcgtgtc ggtgctgact gtgctgcatc aggactggct gaacggaaag   960
gagtacaagt gcaaagtgtc gaacaaggcc ctgcctgcac aatcgaaaa gaccattagc   1020
aaagccaagg gccagccgag agaaccccaa gtctacactc tgccaccatc ccgcgaagaa   1080
atgaccaaga accaagtgtc gctgacgtgc gacgtctcgg gattctaccc gtccgatatt   1140
gccgtggaat gggagagcga cggccaaccc gagaacaact acaagactac cccccccgtc   1200
ttggattccg atggttcctt cttcctgtac tccaagctga ccgtggataa gtcccgatgg   1260
gagcagggcg atgtgttctc gtgctccgtg atgcatgaag ccctgcacaa ccactatacc   1320
cagaagtcac tgtcgctgag ccctgggaag                                   1350

SEQ ID NO: 569       moltype = DNA  length = 1455
FEATURE              Location/Qualifiers
source               1..1455
                     mol_type = other DNA
                     organism = synthetic construct
                     note = Description of Artificial Sequence: Synthetic
                        polynucleotide
SEQUENCE: 569
gaagtgcagc ttgtggagtc cggggagga ttggtccaac ccggtggctc gctgaggctg     60
agttgcgccg cttcggggtt taccttcagc acctacgcta tgaactgggt cagacaggcg   120
cctggaaagg gtttggagtg gtcggacgc atccggtcca aggccaacaa ctacgcgact    180
tactatgccg actccgtcaa gggacggttc accatctccc gggacgacag caagaacacc   240
ctgtacctcc aaatgaactc ccttcgggcc gaagataccg ccgtgtacta ctgcgtgaga   300
cacggcaact tcggcgactc ctacgtgtcc tggtttgcct actggggcca gggtactctc   360
gtgaccgtgt catcaggaaa gccaggctcg gggaagcctg gctccggaaa gcctgggagc   420
ggaaagccgg gatcgcaggc tgtggtcacc caggaaccct ccctgactgt gtccccggga   480
ggaaccgtga cactgacttg tggcagctcc accggagccg tgaccacctc caactacgcc   540
aactgggtgc agcaaaagcc aggaaagtcc cctaggggc tgatcggtgg cacgaacaag    600
cgggcacctg gagtgcctgc ccgattctcg ggtagcctgc tgggggaaa agccgccctg    660
accatttcgg gcgctcagcc agaggacgaa gccgactatt actgcgcact ctggtactcc   720
aaccactggg tgttcggtgg aggcaccaag ctgaccgtgc tggagccaaa gtcaagcgac   780
aaaactcaca cttgccctcc ttgtccggct cctcctgtgg ctggtccctc cgtgttcctc   840
ttcccgccga gccgaagga caccctcatg atttcccgga cgcccgaagt cacttgtgtg   900
gtggtcgatg tgaagcatga ggaccccgaa gtgaagttca attggtacgt ggatggcgtg   960
gaggtccaca cgccaagac caagccgcgc gaagaacagt acaacagcac ctaccgtgtc  1020
gtgagcgtgc tcaccgtgct ccaccaagat tggctgaacg gaaaggagta caagtgcaaa  1080
```

```
gtgtccaaca aggcccttcc tgcacctatt gaaaagacta ttagcaaggc caagggacag   1140
ccccgcgaac ctcaagtgta cactctgccg ccgtccagag agcagatgac caaaaaccag   1200
gtcaagctca cttgtctcgt gaagggcttc tacccgtccg atatcgcggt cgaatgggag   1260
tcaaacggcc agcccgagaa caactacaag actaccccac cggtgcttga ctccgacggt   1320
tcgttctttc tgtactccaa gctgaccgtg gacaagtccc ggtggcagca agggaatgtg   1380
ttcagctgct ccgtgatgca cgaagccctg cataaccact acacccagaa gtcgctcagc   1440
ctgtcccctg gaaaa                                                    1455

SEQ ID NO: 570           moltype = DNA   length = 363
FEATURE                  Location/Qualifiers
source                   1..363
                         mol_type = other DNA
                         organism = synthetic construct
                         note = Description of Artificial Sequence: Synthetic
                             polynucleotide
SEQUENCE: 570
gaagtgcaac ttttggaaag cggaggcgga ttggtgcaac ctggcggctc actgagactg    60
agctgcgccg cctccggatt cactttctcc tcctacgcca tgtcctgggt ccgacaggcg   120
cccgggaagg gcctcgaatg ggtgtcggcc atttccggat ctggtggaag cacctactac   180
gctgatagcg tgaagggtcg cttcaccatt tcgcgcgaca attcgaagaa cacccctgtat  240
ctgcaaatga atagcttgag agccgaagat accgccgtgt actactgcgc acggcgggag   300
tggtggtacg acgattggta cctggactac tgggggcagg ggacactcgt gaccgtgtcg   360
agc                                                                 363

SEQ ID NO: 571           moltype = DNA   length = 672
FEATURE                  Location/Qualifiers
source                   1..672
                         mol_type = other DNA
                         organism = synthetic construct
                         note = Description of Artificial Sequence: Synthetic
                             polynucleotide
SEQUENCE: 571
gaagtgcaac ttttggaaag cggaggcgga ttggtgcaac ctggcggctc actgagactg    60
agctgcgccg cctccggatt cactttctcc tcctacgcca tgtcctgggt ccgacaggcg   120
cccgggaagg gcctcgaatg ggtgtcggcc atttccggat ctggtggaag cacctactac   180
gctgatagcg tgaagggtcg cttcaccatt tcgcgcgaca attcgaagaa cacccctgtat  240
ctgcaaatga atagcttgag agccgaagat accgccgtgt actactgcgc acggcgggag   300
tggtggtacg acgattggta cctggactac tgggggcagg ggacactcgt gaccgtgtcg   360
agcgcttcca ccaagggacc gagcgtgttc ccgctgcccg cgagcagcaa atcgacttct   420
gggggaaccg cagccctggg ttgcctggtc aaggactact ccccggaacc agtcactgtg   480
tcctggaaca gcggtgccct cacctcgggc gtgcacacct tcccggccgt gctgcagtct   540
agcggactct actcgctctc ctccgtggtc accgtgccct cctcatcact gggaacccag   600
acatacattt gcaacgtgaa ccacaagccc tcggacacta aggtggacaa aaaagtggaa   660
ccaaagtcct gc                                                       672

SEQ ID NO: 572           moltype = DNA   length = 321
FEATURE                  Location/Qualifiers
source                   1..321
                         mol_type = other DNA
                         organism = synthetic construct
                         note = Description of Artificial Sequence: Synthetic
                             polynucleotide
SEQUENCE: 572
gacattcaga tgacccagtc cccgagctcc ctgtcggctt ccgtgggcga cagagtgacg    60
attacttgcc gcgcgtccca aagcatctcc tcctacctga actggtacca gcagaagccg   120
ggaaaggccc caaagctgtt gatctacgcc gcctcatcgc tccaatctgg agtgccttcc   180
cggttttcgg ggtcgggcag cgggactgat ttcaccctga ccatcagcag cctgcagcct   240
gaagatttcg ccacctacta ctgccagcag tcctattcct caccccctgac tttcggacaa   300
ggcaccaagg tcgagatcaa g                                             321

SEQ ID NO: 573           moltype = DNA   length = 642
FEATURE                  Location/Qualifiers
source                   1..642
                         mol_type = other DNA
                         organism = synthetic construct
                         note = Description of Artificial Sequence: Synthetic
                             polynucleotide
SEQUENCE: 573
gacattcaga tgacccagtc cccgagctcc ctgtcggctt ccgtgggcga cagagtgacg    60
attacttgcc gcgcgtccca aagcatctcc tcctacctga actggtacca gcagaagccg   120
ggaaaggccc caaagctgtt gatctacgcc gcctcatcgc tccaatctgg agtgccttcc   180
cggttttcgg ggtcgggcag cgggactgat ttcaccctga ccatcagcag cctgcagcct   240
gaagatttcg ccacctacta ctgccagcag tcctattcct caccccctgac tttcggacaa   300
ggcaccaagg tcgagatcaa gcgtacggtg gctgcacaca tgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

| SEQ ID NO: 574 | moltype = DNA length = 375 |
|---|---|
| FEATURE | Location/Qualifiers |
| source | 1..375 |
| | mol_type = other DNA |
| | organism = synthetic construct |
| | note = Description of Artificial Sequence: Synthetic polynucleotide |

SEQUENCE: 574
```
gaggtgcagc tcgtcgaatc cggtggaggg ctggtgcaac cgggggctc gcttaggctt   60
agctgcgctg cgtcagggtt caccttctca acttacgcga tgaattgggt cagacaggca  120
cccgaaagg gactggaatg ggtcggaaga atcagatcga aggccaacaa ctacgccact   180
tactacgccg actccgtgaa gggaaggttc actatctcgc gggacgactc caagaacact  240
ctgtatctcc aaatgaactc actccgggcc gaggatactg cggtgtacta ttgcgtgcgg  300
catggaaact tcggggacag ctacgtcagc tggttcgcct actggggcca aggcactctc  360
gtcaccgtgt catcc                                                  375
```

| SEQ ID NO: 575 | moltype = DNA length = 327 |
|---|---|
| FEATURE | Location/Qualifiers |
| source | 1..327 |
| | mol_type = other DNA |
| | organism = synthetic construct |
| | note = Description of Artificial Sequence: Synthetic polynucleotide |

SEQUENCE: 575
```
caggccgtcg tgacccagga accgagcctg accgtgtccc ccggcggtac cgtgaccttg   60
acttgcggtt cctccactgg agccgtgact acctcgaact acgccaactg ggtgcagcag  120
aagccgggaa agtcgcctcg cggactgatc ggtggaacta acaaacgcgc ccgggcgtg   180
ccagccagat tcagcggtag cctgctcggc ggaaaggccg cgctgaccat ctccggggcc  240
cagccccgagg atgaggccga ctattactgc gctctgtggt actccaacca ctgggtgttt  300
ggcgggggca ctaagctgac tgtgctg                                     327
```

| SEQ ID NO: 576 | moltype = DNA length = 762 |
|---|---|
| FEATURE | Location/Qualifiers |
| source | 1..762 |
| | mol_type = other DNA |
| | organism = synthetic construct |
| | note = Description of Artificial Sequence: Synthetic polynucleotide |

SEQUENCE: 576
```
gaggtgcagc tcgtcgaatc cggtggaggg ctggtgcaac cgggggctc gcttaggctt   60
agctgcgctg cgtcagggtt caccttctca acttacgcga tgaattgggt cagacaggca  120
cccgaaagg gactggaatg ggtcggaaga atcagatcga aggccaacaa ctacgccact   180
tactacgccg actccgtgaa gggaaggttc actatctcgc gggacgactc caagaacact  240
ctgtatctcc aaatgaactc actccgggcc gaggatactg cggtgtacta ttgcgtgcgg  300
catggaaact tcggggacag ctacgtcagc tggttcgcct actggggcca aggcactctc  360
gtcaccgtgt catccgggaa gccgggttcc ggaaagccta gatcgggcaa accggggatcg  420
ggaaaacccg gaagccaggc cgtcgtgacc caggaaccga gcctgaccgt gtccccggc   480
ggtaccgtga ccttgacttg cggttcctcc actggagccg tgactacctc gaactacgcc  540
aactgggtgc agcagaagcc gggaaagtcg cctcgcggac tgatcggtgg aactaacaaa  600
cgcgtgccagc cagattcagc ggtagcctgc tcggcggaaa ggccgcgctg  660
accatctccg ggccccagcc cgaggatgag gccgactatt actgcgctct gtggtactcc  720
aaccactggg tgtttggcgg gggcactaag ctgactgtgc tg                    762
```

| SEQ ID NO: 577 | moltype = DNA length = 1350 |
|---|---|
| FEATURE | Location/Qualifiers |
| source | 1..1350 |
| | mol_type = other DNA |
| | organism = synthetic construct |
| | note = Description of Artificial Sequence: Synthetic polynucleotide |

SEQUENCE: 577
```
gaagtgcaac ttttggaaag cggaggcgga ttggtgcaac ctggcggctc actgagactg   60
agctgcgccg cctccggatt cactttctcc tcctacgcca tgtcctggt ccgacaggcg   120
cccgggaagg gcctcgaatg ggtgtcggc atttccggat ctggtggaag cacctactac   180
gctgatagcg tgaagggtcg ctttcaccatt tcgcgcgaca attcgaagaa caccctgtat  240
ctgcaaatga atagcttgag agccgaagat accgccgtgt actactgcgc acggcgggag  300
tggtggtacg acgattggta cctggactac tgggggcagg gacactcgt gaccgtgtcg   360
agcgcttcca ccaagggacc gagcgtgttc ccgctggcc cgagcagcaa atcgacttct  420
gggggaaccg cagccctggg ttgcctggtc aaggactact cccggaacc agtcactgtg   480
tcctggaaca gcggtgccct cacctcgggc gtgcacacct tccgggcgt gctgcagtct   540
agcggactct actcgctctc ctccgtggtc accgtgccct cctcatcact gggaacccag   600
acatacatt gcaacgtgaa ccacaagccc tcggacacta aggtggacaa aaagtgaa    660
ccaaagtcct gcgacaagac ccacacttgt ccgccctcc cgtggcgggc                720
ccgtcagtgt ttctgtttcc gccaaagct aaggatacc tcatgatcag ccgcactcct    780
gaagtgacct gtgtcgtggt ggacgtgaaa cacgaggacc cggaggtcaa gttaattgga   840
tacgtggatg ggtggaggt gcacaacgcc aaaactaagc cccgggaaga agagtacaat    900
tccacctacc gcgtcgtgtc agtgttgacg gtcctgcacc aagactggct gaacggaaag   960
gagtacaagt gcaaggtgtc caacaaggca ctgcccgcccc catcgaaaa gaccatttca  1020
```

```
aaagctaagg gccagccgcg ggaaccacag gtctacaccc tgcctccctc ccgggaagag  1080
atgaccaaga accaagtctc cctcacgtgt gacgtgtccg gcttctaccc ttcggacatt  1140
gctgtggaat gggagtccga cgggcagccc gaaaacaact acaagaccac tccccctgtg  1200
ctggactccg acggctcatt ctttctgtac tccaagctca ccgtcgataa gtcgagatgg  1260
gagcagggag atgtgttctc ctgctccgtg atgcacgagg ccctgcataa ccattacact  1320
cagaagtccc tctccctgtc ccctgggaag                                   1350
```

SEQ ID NO: 578          moltype = DNA   length = 2169
FEATURE                 Location/Qualifiers
source                  1..2169
                        mol_type = other DNA
                        organism = synthetic construct
                        note = Description of Artificial Sequence: Synthetic
                        polynucleotide
SEQUENCE: 578
```
gaagtgcaac ttttggaaag cggaggcgga ttggtgcaac ctggcggctc actgagactg   60
agctgcgccg cctccggatt cactttctcc tcctacgcca tgtcctgggt ccgacaggcg  120
cccgggaagg gcctcgaatg ggtgtcggcc atttccgagt ctggtggaag cacctactac  180
gctgatagcg tgaagggtcg cttcaccatt tcgcgcgaca attcgaagaa caccctgtat  240
ctgcaaatga atagcttgag agccgaagat accgccgtgt actactgcgc acggcgggag  300
tggtggtacg acgattggta cctggactac tgggggcagg gacactcgt gaccgtgtcg  360
agcgcttcca ccaagggacc gagcgtgttc ccgctgcgcc cgagcagcaa atcgacttct  420
gggggaaccg cagccctggg ttgcctggtc aaggactact ccccggaacc agtcactgtg  480
tcctggaaca gcggtgccct cacctcgggc gtgcacacct tcccggccgt gctgcagtct  540
agcggactct actcgctctc ctccgtggtc accgtgccct cctcatcact gggaacccag  600
acatacattt gcaacgtgaa ccacaagccg tccaacacca aggtcgacaa gaaagtggag  660
cctaagtcct gtggtggcgg aggctccggc ggaggaggat cggaggtgca gctcgtcgaa  720
tccggtggag ggctggtgca accgggggc tcgcttaggc ttagctgcgc tgcgtcaggg  780
ttcaccttct caacttacgc gatgaattgg gtcagacagg cacccggaaa gggactggaa  840
tgggtcggaa gaatcagatc gaaggccaac aactacgcc cttactacgc cgactcgtg  900
aagggaaggt tcactatctc gcgggacgac tccaagaaca ctctgtatct ccaaatgaac  960
tcactccggg ccgaggatac tgcggtgtac tattgcgtgc ggcatggaaa cttcgggac  1020
agctacgtca gctggttcgc ctactgggc caaggcactc tcgtcaccgt gtcatccggg  1080
aagccgggtt ccggaaagcc tggatcgggc aaaccgggat cgggaaaacc cggaagccg  1140
gccgtctga cccaggaacc gagcctgacc gtgtccccg gcggtaccgt gaccttgact  1200
tgcggttcct ccactggagc cgtgactacc tcgaactacg ccaactgggt gcagcagaag  1260
ccgggaaagt cgcctcgcgg actgatcggt ggaactaaca acgcgcccc gggcgtgcca  1320
gccagattca gcggtagcct gctcggcgga aaggccgcgc tgaccatctc cgggcccag  1380
cccgaggatg aggccgacta ttactgcgct ctgtggtact ccaaccactg ggtgtttggc  1440
gggggcacta agctgactgt gctgggcggc ggcggctccg gggggggggg ctccaagacc  1500
cacacttgtc cgccctgccc tgccctccc gtgcgggcc cgtcagtgtt tctgtttccg  1560
ccaaagccta aggataccct catgatcagc cgcactcctg aagtgacctg tgtcgtggtg  1620
gacgtgaaac acgaggaccc ggaggtcaag tttaattggt acgtggatgg ggtggaggtg  1680
cacaacgcca aaactaagcc ccgggaagaa cagtacaatt ccacctaccg cgtcgtgtca  1740
gtgttgacgg tcctgcacca agactggctg aacggaaagg agtacaagtg caaggtgtcc  1800
aacaaggcac tgcccgcccc catcgaaaag accatttcaa aagctaaggg ccagccgcgg  1860
gaaccacagg tctacaccct gcctccctcc cgggaacaga gccaagtcaag  1920
ctcacgtgtc tcgtgaaggg cttctaccct tcggacattg ctgtggaatg ggagtccaac  1980
gggcagcccg aaaacaacta caagaccact ccccctgtgc tggactccga cggctcattc  2040
tttctgtact ccaagctcac cgtcgataag tcgagatgga gcagggaaaa cgtgttctcc  2100
tgctccgtga tgcacgaggc cctgcataac cattacactc agaagtccct ctccctgtcc  2160
cctgggaag                                                          2169
```

SEQ ID NO: 579          moltype = DNA   length = 363
FEATURE                 Location/Qualifiers
source                  1..363
                        mol_type = other DNA
                        organism = synthetic construct
                        note = Description of Artificial Sequence: Synthetic
                        polynucleotide
SEQUENCE: 579
```
gaagtgcagc tgctggagag cggcggaggt ctggtgcagc caggcggatc cttgcgcctc   60
agttgtgccg cgtccggatt cactttctcg tcttacgcca tgtcctgggt cagacaggcc  120
cctgggaagg gtctggagtg ggtgtccgcg atcagcgagt caggagggag agccgcctac  180
gccgactccg tgaagggccg ctttaccatt tcgcgggaca actccaagaa cacctgtac  240
cttcaaatga acagcctgcg ggcagaggac accgccgtct actactgcgc ccggagggaa  300
tggtggtacg atgattggta tctggactac tggggccagg gaactctcgt gaccgtgtcc  360
tcg                                                                363
```

SEQ ID NO: 580          moltype = AA    length = 224
FEATURE                 Location/Qualifiers
source                  1..224
                        mol_type = protein
                        organism = synthetic construct
                        note = Description of Artificial Sequence: Synthetic
                        polypeptide
SEQUENCE: 580
```
EVQLLESGGG LVQPGGSLRL SCAASGFTFS SYAMSWVRQA PGKGLEWVSA ISESGGRAAY   60
ADSVKGRFTI SRDNSKNTLY LQMNSLRAED TAVYYCARRE WWYDDWYLDY WGQGTLVTVS  120
```

SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SDTKVDKKVE PKSC                   224

SEQ ID NO: 581          moltype = DNA   length = 672
FEATURE                 Location/Qualifiers
source                  1..672
                        mol_type = other DNA
                        organism = synthetic construct
                        note = Description of Artificial Sequence: Synthetic
                            polynucleotide
SEQUENCE: 581
gaagtgcagc tgctggagag cggcggaggt ctggtgcagc caggcggatc cttgcgcctc   60
agttgtgccg cgtccggatt cactttctcg tcttacgcca tgtcctgggt cagacaggcc  120
cctgggaagg gtctggagtg ggtgtccgcg atcagcgagt caggagggag agccgcctac  180
gccgactccg tgaagggccg ctttaccatt tcgcgggaca actccaagaa caccctgtac  240
cttcaaatga acagcctgcg ggcagaggac accgccgtct actactgcgc ccggagggaa  300
tggtggtacg atgattggta tctggactac tggggccagg gaactctcgt gaccgtgtcc  360
tcggctagca ccaagggccc gtcagtgttt cctctggccc caagctccaa gtccacctcc  420
ggtggtacag ccgcgttggg atgcttggtc aaggactact ttccggaacc cgtgaccgtg  480
tcctggaact ccggcgccct gactagcgga gtgcacacct tccccgctgt gctgcagtct  540
agcgggctgt attccctctc gtccgtggtc accgtgccgt cctcatccct gggaacccag  600
acctacattt gcaacgtgaa ccacaagccg tcagacacca aggtggacaa gaaggtggag  660
ccgaagtcct gc                                                      672

SEQ ID NO: 582          moltype = DNA   length = 321
FEATURE                 Location/Qualifiers
source                  1..321
                        mol_type = other DNA
                        organism = synthetic construct
                        note = Description of Artificial Sequence: Synthetic
                            polynucleotide
SEQUENCE: 582
gacattcaga tgacccagtc cccgtcctcg ctgagcgcat cagtcggcga tcgcgtgact   60
attacttgtc gggcgtccca gtcgatctcc tcgtacttga actggtatca gcagaagccc  120
ggaaaagccc cgaagttact gatctacgct gcctcatccc tccaatctgg ggtgccttcg  180
cggttctccg gttccggaag cggaaccgac ttcaccctga ccatcagcag cctgcagcca  240
gaggactttg ccacctacta ctgccagcag tcctactcca caccctcac tttcggacaa  300
ggcaccaagg tcgaaatcaa g                                            321

SEQ ID NO: 583          moltype = DNA   length = 642
FEATURE                 Location/Qualifiers
source                  1..642
                        mol_type = other DNA
                        organism = synthetic construct
                        note = Description of Artificial Sequence: Synthetic
                            polynucleotide
SEQUENCE: 583
gacattcaga tgacccagtc cccgtcctcg ctgagcgcat cagtcggcga tcgcgtgact   60
attacttgtc gggcgtccca gtcgatctcc tcgtacttga actggtatca gcagaagccc  120
ggaaaagccc cgaagttact gatctacgct gcctcatccc tccaatctgg ggtgccttcg  180
cggttctccg gttccggaag cggaaccgac ttcaccctga ccatcagcag cctgcagcca  240
gaggactttg ccacctacta ctgccagcag tcctactcca caccctcac tttcggacaa  300
ggcaccaagg tcgaaatcaa gcgtacggtg ccgctcccca gcgtgttcat cttccccccc  360
agcgacgagc agctgaagag cggcaccgcc agcgtggtgt gcctgctgaa caacttctac  420
ccccggggagg ccaaggtgca gtggaaggtg gacaacgcc tgcagagcgg caacagccag  480
gagagcgtca ccgagcagga cagcaaggac tccacctaca gcctgagcag cacctgacc  540
ctgagcaagg ccgactacga aagcataag gtgtacgcct gcgaggtgac ccaccagggc  600
ctgtccagcc ccgtgaccaa gagcttcaac aggggcgagt gc                    642

SEQ ID NO: 584          moltype = DNA   length = 1350
FEATURE                 Location/Qualifiers
source                  1..1350
                        mol_type = other DNA
                        organism = synthetic construct
                        note = Description of Artificial Sequence: Synthetic
                            polynucleotide
SEQUENCE: 584
gaagtgcagc tgctggagag cggcggaggt ctggtgcagc caggcggatc cttgcgcctc   60
agttgtgccg cgtccggatt cactttctcg tcttacgcca tgtcctgggt cagacaggcc  120
cctgggaagg gtctggagtg ggtgtccgcg atcagcgagt caggagggag agccgcctac  180
gccgactccg tgaagggccg ctttaccatt tcgcgggaca actccaagaa caccctgtac  240
cttcaaatga acagcctgcg ggcagaggac accgccgtct actactgcgc ccggagggaa  300
tggtggtacg atgattggta tctggactac tggggccagg gaactctcgt gaccgtgtcc  360
tcggctagca ccaagggccc gtcagtgttt cctctggccc caagctccaa gtccacctcc  420
ggtggtacag ccgcgttggg atgcttggtc aaggactact ttccggaacc cgtgaccgtg  480
tcctggaact ccggcgccct gactagcgga gtgcacacct tccccgctgt gctgcagtct  540
agcgggctgt attccctctc gtccgtggtc accgtgccgt cctcatccct gggaacccag  600
acctacattt gcaacgtgaa ccacaagccg tcagacacca aggtggacaa gaaggtggag  660
ccgaagtcct gcgacaagac ccatacttgt cctccttgcc ccgctccacc tgtggcggga  720

```
ccttccgtgt tccttttccc gccgaagccg aaggacactc tgatgatctc gcggactccc   780
gaagtcactt gcgtggtggt ggacgtcaaa cacgaagatc ccgaggtcaa gttcaattgg   840
tacgtggacg gggtggaagt ccacaacgcc aagactaagc cgcgcgagga agagtacaat   900
tccacttacc gggtcgtgtc ggtgctgact gtgctgcatc aggactggct gaacggaaag   960
gagtacaagt gcaaagtgtc gaacaaggcc ctgcctgcac caatcgaaaa gaccattagc  1020
aaagccaagg gccagccgag agaacccca  gtctacactc tgccaccatc ccgcgaagaa  1080
atgaccaaga accaagtgtc gctgacgtgc gacgtgtcgg gattctaccc gtccgatatt  1140
gccgtggaat gggagagcga cggccaaccc gagaacaact acaagactac ccccccgtc   1200
ttggattccg atggttcctt cttcctgtac tccaagctga ccgtggataa gtcccgatgg  1260
gagcagggcg atgtgttctc gtgctccgtg atgcatgaag ccctgcacaa ccactatacc  1320
cagaagtcac tgtcgctgag ccctgggaag                                   1350

SEQ ID NO: 585         moltype = DNA  length = 672
FEATURE                Location/Qualifiers
source                 1..672
                       mol_type = other DNA
                       organism = synthetic construct
                       note = Description of Artificial Sequence: Synthetic
                       polynucleotide
SEQUENCE: 585
gaagtgcagc tgctggagag cggcggaggt ctggtgcagc caggcggatc cttgcgcctc    60
agttgtgccg cgtccggatt cactttctcg tcttacgcca tgtcctgggt cagacaggcc   120
cctgggaagg gtctggagtg ggtgtccgcg atcagcgagt caggaggag  agccgcctac   180
gccgactccg tgaagggccg ctttaccatt tcgcgggaca actccaagaa caccctgtac   240
cttcaaatga acagcctgcg ggcagaggac accgccgtct actactgcgc ccggagggaa   300
tggtggtacg atgattggta tctgggactac tggggccagg gaacctctgt gaccgtgtcc   360
tcggctagca ccaagggtcc gtcagtgttt cctctggccc caagctccaa gtccacctcc   420
ggtggtacag ccgcgttggg atgcttggtc aaggactact ttccggaacc cgtgaccgtg   480
tcctggaact ccggcgccct gactagcgga gtgcacacct tccccgctgt gctgcagtct   540
agcgggctgt attccctctc gtccgtggtc accgtgccgt cctcatccct gggaacccag   600
acctacattt gcaacgtgaa ccacaagccg tcagacacca aggtggacaa gaaggtggag   660
ccgaagtcct gc                                                      672

SEQ ID NO: 586         moltype = DNA  length = 375
FEATURE                Location/Qualifiers
source                 1..375
                       mol_type = other DNA
                       organism = synthetic construct
                       note = Description of Artificial Sequence: Synthetic
                       polynucleotide
SEQUENCE: 586
gaagtccaac tggtcgagtc aggcggcgga cttgtccagc ccggaggtag cctgcgcctc    60
tcctgtgctg cctccggttt taccttctcg acctatgcca tgaactgggt gcgccaagca   120
cctgggaagg gactcgaatg ggtcggcagg attcggtcca aggccaacaa ctacgctacc   180
tactacgccg actcggtcaa ggggcggttc actatttccc gcgacgactc caagaacact   240
ctgtatcttc agatgaatag cttgagagcc gaggataccg ccgtgtacta ttgcgtgcgc   300
cacgggaact tcggcgattc ctacgtgtcc tggttcgctt actggggaca gggcaccctg   360
gtcaccgtgt caagc                                                   375

SEQ ID NO: 587         moltype = DNA  length = 326
FEATURE                Location/Qualifiers
source                 1..326
                       mol_type = other DNA
                       organism = synthetic construct
                       note = Description of Artificial Sequence: Synthetic
                       polynucleotide
SEQUENCE: 587
aggcggtggt gacccaagaa ccctcccctga ccgtgtcacc gggaggcacc gtgaccctga    60
cttgcgggag ctccactggc gcagtgacta catccaacta cgccaactgg gtgcagcaga   120
agcctggaaa gtccccgaga ggactccattg gaggaaccaa caagagagcc cctgtgtcc   180
ctgcccgctt tagcggttcg ctgttgggag gaaaggccgc tctgactatt tccggcgctc   240
agccagagga cgaggctgac tactactgcg cattgtggta ctccaatcac tgggtgttcg   300
gagggggcac taagctgacc gtgctg                                       326

SEQ ID NO: 588         moltype = DNA  length = 762
FEATURE                Location/Qualifiers
source                 1..762
                       mol_type = other DNA
                       organism = synthetic construct
                       note = Description of Artificial Sequence: Synthetic
                       polynucleotide
SEQUENCE: 588
gaagtccaac tggtcgagtc aggcggcgga cttgtccagc ccggaggtag cctgcgcctc    60
tcctgtgctg cctccggttt taccttctcg acctatgcca tgaactgggt gcgccaagca   120
cctgggaagg gactcgaatg ggtcggcagg attcggtcca aggccaacaa ctacgctacc   180
tactacgccg actcggtcaa ggggcggttc actatttccc gcgacgactc caagaacact   240
ctgtatcttc agatgaatag cttgagagcc gaggataccg ccgtgtacta ttgcgtgcgc   300
cacgggaact tcggcgattc ctacgtgtcc tggttcgctt actggggaca gggcaccctg   360
gtcaccgtgt caagcggaaa gcccgggtcc ggaaaaccgg gtcgggaaa  gccggggagc  420
```

```
ggaaagcccg gttcacaggc ggtggtgacc caagaaccct ccctgaccgt gtcaccggga   480
ggcaccgtga ccctgacttg cgggagctca actggcgcag tgactacatc aactacgcc    540
aactgggtgc agcagaagcc tggaaagtcc cgagaggac  tcattggagg aaccaacaag   600
agagcccctg tgtccctgc  ccgctttagc ggttcgctgt tgggaggaaa ggccgctctg   660
actatttccg gcgctcagcc agaggacgag gctgactact actgcgcatt gtggtactcc   720
aatcactggg tgttcgagg  gggcactaag ctgaccgtgc tg                     762
```

| SEQ ID NO: 589 | moltype = DNA   length = 1350 |
|---|---|
| FEATURE | Location/Qualifiers |
| source | 1..1350 |
| | mol_type = other DNA |
| | organism = synthetic construct |
| | note = Description of Artificial Sequence: Synthetic polynucleotide |

SEQUENCE: 589
```
gaagtgcagc tgctggagag cggcggaggt ctggtgcagc caggcggatc cttgcgcctc    60
agttgtgccg cgtccggatt cactttctcg tcttacgcca tgtcctgggt cagacaggcc   120
cctgggaagg gtctggagtg ggtgtccgcg atcagcgagt caggagggag agccgcctac   180
gccgactccg tgaagggccg ctttaccatt tcgcgggaca actccaagaa cacccctgtac  240
cttcaaatga acagcctgcg ggcagaggac accgccgtct actactcgc  ccggagggaa   300
tggtggtacg atgattggta tctggactac tggggccagg gaactctcgt gaccgtgtcc   360
tcggctagca ccaagggtcc gtcagtgttt cctctgcccc aagctccaa  gtccacctcc   420
ggtggtacag ccgcgttggg atgcttggtc aaggactact ttccggaacc cgtgaccgtg   480
tcctggaact ccggcgccct gactagcgga gtgcacacct tccccgctgt gctgcagtct   540
agcgggctgt attccctctc gtccgtggtc accgtgccgt cctcatccct gggaacccag   600
acctacattt gcaacgtgaa ccacaagccc tcagacacca aggtggacaa gaaagtggag   660
ccgaagtcct gcgacaagac ccatacttgt cctccttgcc ccgctccacc tgtggcggga   720
ccttccgtgt tcctttttccc gccgaagccg aaggacactc tgatgatctc gcggactccc   780
gaagtcactt gcgtggtggt ggacgtcaaa cacgaagatc ccgaggtcaa gttcaattgg   840
tacgtggacg gggtggaagt ccacaacgcc aagactacgc cgccgaggga agagtacaat   900
tccacttacc gggtcgtgtc ggtgctgact gtgctgcatc aggactggct gaacggaaag   960
gagtacaagt gcaaagtgtc gaacaaggcc ctgcctgcac caatcgaaaa gaccattagc  1020
aaagccaagg gccagccgag agaaccccaa gtctacactc tgccaccatc ccgcgaagaa  1080
atgaccaaga accaagtgtc gctgacgtgc gacgtgtcgg gattctaccc gtccgatatt  1140
gccgtggaat gggagagcga cggccaaccc gagaacaact acaagactac ccccccgtc   1200
ttggattccg atggttcctt cttcctgtac tccaagctga ccgtggataa gtcccgatgg  1260
gagcagggcg atgtgttctc gtgctccgtg atgcatgaag ccctgcacaa ccactatacc  1320
cagaagtcac tgtcgctgag ccctgggaag                                    1350
```

| SEQ ID NO: 590 | moltype = DNA   length = 2169 |
|---|---|
| FEATURE | Location/Qualifiers |
| source | 1..2169 |
| | mol_type = other DNA |
| | organism = synthetic construct |
| | note = Description of Artificial Sequence: Synthetic polynucleotide |

SEQUENCE: 590
```
gaagtgcagc tgctggagag cggcggaggt ctggtgcagc caggcggatc cttgcgcctc    60
agttgtgccg cgtccggatt cactttctcg tcttacgcca tgtcctgggt cagacaggcc   120
cctgggaagg gtctggagtg ggtgtccgcg atcagcgagt caggagggag agccgcctac   180
gccgactccg tgaagggccg ctttaccatt tcgcgggaca actccaagaa cacccctgtac  240
cttcaaatga acagcctgcg ggcagaggac accgccgtct actactcgc  ccggagggaa   300
tggtggtacg atgattggta tctggactac tggggccagg gaactctcgt gaccgtgtcc   360
tcggctagca ccaagggccc ttcggtgttc cccctcgccc cttcatcaaa gtccacttca   420
ggaggaaccg ccgccttggg ttgcctcgtg aaggattact ccccgaacc  agtgaccgtg   480
tcctggaact ccggagccct gaccagcgga gtgcacactt tccctgcggt gttgcagagc   540
tccggcctct acagcctgag cagcgtggtg accgtgccga gctcctccct gggcactcag   600
acctacatct gcaacgtcaa ccacaagccc tcgaatacca aggtcgacaa gaaggtggag   660
ccgaagtcct gtgcgaggg  aggatcggga gggggtggat cggaagtcca actggtcgag   720
tcaggcggcg gacttgtcca gcccggaggt agcctgcgcc tctcctgtgc tgcctccggt   780
tttaccttct cgacctatgc catgaactgg gtgcgccaag cacctgggaa gggactcgaa   840
tgggtcggca ggattcggtc caaggccaac aactacgcta cctactacgc cgactcggtc   900
aagggccggt tcactatttc ccgcgacgac tccaagaaca ctctgtatct tcagatgaat   960
agcttgagag ccgaggatac cgccgtgtac tattcgtgc  ccacgggaca cttcggcgat  1020
tcctacgtgt cctggttcgc ttactgggga cagggcaccc tggtcaccgt gtcaagcgga  1080
aagcccgggt ccggaaaacc cgggtcggga aagccgggga gcggaaagcc cggttcacag  1140
gcggtggtga cccaagaacc ctccctgacc gtgtcaccgg gaggcaccgt gaccctgact  1200
tgcgggagct ccactggcgc agtgactaca tccaactacg ccaactgggt gcagcagaag  1260
cctggaaagt ccccgagagg actcattgga gaaccaacaa agagaccctg tggtgtccctg 1320
ccccgcttta gcggttcgct gttgggagga aaggccgctc tgactatttc cggcgctcag  1380
ccagaggacg aggctgacta ctactgcgca ttgtggtact ccaatcactg ggtgttcgga  1440
ggggcacta  agctgaccgt gctggtggt  ggcggatctg tggtggcgg  ctcgaaaacc  1500
cacacctgtc caccttgtcc ggcgcctcct gtcgctggac cctccgtgtt cctcttccct  1560
cccaagccga aggatacgct gatgatcagc cgaaccccg  aagtgacttg tgtggtggtg  1620
gatgtgaagc acgaagatcc cgaagtcaag ttcaactggt acgtggacgg agtggaggtc  1680
cacaatgcca agaccaagcc gcgggaagaa cagtacaact cgacctaccg ggtggtcagc  1740
gtgctgactg tgctccacca agactggctg aacgggaagg agtacaagtg caaagtgtcg  1800
aacaaggccc ttcctgcacc tatcgaaaag accatctcca aggcgaaagg acagccgaga  1860
gagcccccagg tctacactct gccgccatcc agagagcaaa tgaccaagaa ccaagtcaag  1920
```

```
ctgacctgtc ttgtcaaggg tttctacccg tccgatatcg cggtcgaatg ggagtcaaac    1980
ggccagcccg agaacaacta caagactacc ccaccggtgc ttgactccga cggttcgttc    2040
tttctgtact ccaagctgac cgtggacaag tcccggtggc agcaagggaa tgtgttcagc    2100
tgctccgtga tgcacgaagc cctgcataac cactacaccc agaagtcgct cagcctgtcc    2160
cctggaaaa                                                            2169

SEQ ID NO: 591           moltype = DNA  length = 369
FEATURE                  Location/Qualifiers
source                   1..369
                         mol_type = other DNA
                         organism = synthetic construct
                         note = Description of Artificial Sequence: Synthetic
                         polynucleotide
SEQUENCE: 591
caagtgcagc tcgtggagtc tggagggggga gtcgtgcagc ctggacgctc cctgagactg    60
tcctgtgcgg cttcgggatt cactgtgtcc agctacggca tgcattgggt ccgccaagca    120
ccgggaaaag gcctggagtg ggtggccgtg atctcctaca ccggctcaaa caagtactac    180
gccgacagcg tgaagggccg gttcaccatt tcaaggaca actccaagaa taccctgtat    240
ctgcaaatga actcgctgcg ggcagaggac accgccgtgt actactgcgg tggctccggt    300
tacgccctgc acgatgacta ctacgggctc gatgtctggg gacaggggac gctcgtgact    360
gtgtcctcg                                                            369

SEQ ID NO: 592           moltype = AA  length = 226
FEATURE                  Location/Qualifiers
source                   1..226
                         mol_type = protein
                         organism = synthetic construct
                         note = Description of Artificial Sequence: Synthetic
                         polypeptide
SEQUENCE: 592
QVQLVESGGG VVQPGRSLRL SCAASGFTVS SYGMHWVRQA PGKGLEWVAV ISYTGSNKYY    60
ADSVKGRFTI SRDNSKNTLY LQMNSLRAED TAVYYCGGSG YALHDDYYGL DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSDTKVDKK VEPKSC                   226

SEQ ID NO: 593           moltype = DNA  length = 678
FEATURE                  Location/Qualifiers
source                   1..678
                         mol_type = other DNA
                         organism = synthetic construct
                         note = Description of Artificial Sequence: Synthetic
                         polynucleotide
SEQUENCE: 593
caagtgcagc tcgtggagtc tggagggggga gtcgtgcagc ctggacgctc cctgagactg    60
tcctgtgcgg cttcgggatt cactgtgtcc agctacggca tgcattgggt ccgccaagca    120
ccgggaaaag gcctggagtg ggtggccgtg atctcctaca ccggctcaaa caagtactac    180
gccgacagcg tgaagggccg gttcaccatt tcaaggaca actccaagaa taccctgtat    240
ctgcaaatga actcgctgcg ggcagaggac accgccgtgt actactgcgg tggctccggt    300
tacgccctgc acgatgacta ctacgggctc gatgtctggg gacaggggac gctcgtgact    360
gtgtcctcgg ctagcaccaa gggcccgtca gtgtttcctc tggccccaag ctccaagtcc    420
acctccggtg gtacagccgc gttggatgc ttggtcaagg actactttcc ggaacccgtc    480
accgtgtcct ggaactccgg cgccctgact agcggagtgc acaccttccc cgctgtgctg    540
cagtctagcg ggctgtattc cctctcgtcc gtggtcaccg tgccgtcctc atccctggga    600
acccagacct catttgcaa cgtgaaccac aagccgtcag acaccaaggt ggacaagaag    660
gtggagccga agtcctgc                                                  678

SEQ ID NO: 594           moltype = DNA  length = 333
FEATURE                  Location/Qualifiers
source                   1..333
                         mol_type = other DNA
                         organism = synthetic construct
                         note = Description of Artificial Sequence: Synthetic
                         polynucleotide
SEQUENCE: 594
cagtcggcgc tgactcagcc cgcatccgtg agcggttcac cgggacagag catcaccatt    60
tcctgcaccg gaacctcaag cgacgtgggc ggctacaact acgtgtcctg gtatcagcag    120
cacccgggaa aggcccccaa agctcatgat ctacgacgtgt ccaatagact gcggggagtg    180
tccaaccggt tctcgggaag caaatccggc aacactgctt ccctgaccat cagcggactc    240
caggccgaag atgaggccga ctactactgc tcatcctaca gtcctctctt cggcgcttac    300
gtgttcgggt cggggaccaa ggtcaccgtc ctg                                 333

SEQ ID NO: 595           moltype = DNA  length = 651
FEATURE                  Location/Qualifiers
source                   1..651
                         mol_type = other DNA
                         organism = synthetic construct
                         note = Description of Artificial Sequence: Synthetic
                         polynucleotide
SEQUENCE: 595
```

```
cagtcggcgc tgactcagcc cgcatccgtg agcggttcac cgggacagag catcaccatt    60
tcctgcaccg gaacctcaag cgacgtgggc ggctacaact acgtgtcctg gtatcagcag   120
cacccgggaa aggccccaaa gctcatgatc tacgacgtgt ccaatagact gcggggagtg   180
tccaaccggt tctcgggaag caaatccggc aacactgctt ccctgaccat cagcggactc   240
caggccgaag atgaggccga ctactactgc tcatcctaca cgtcctcttc ggcgctttac   300
gtgttcgggt cggggaccaa ggtcaccgtc ctgggccaac ctaaggcggc gccctcagtg   360
accctgttcc ctccgtcgtc tgaagaactc caggccaaca aggccaccct cgtgtgcctg   420
atttcggact tctacccggg agccgtcact gtggcctgga aggccgacag cagcccagtg   480
aaggccggcg tggaaactac caccccgtcc aagcagtcca acaataagta cgcagccagc   540
tcctacctgt ccctgacccc cgaacaatgg aagtcacaca gatcctactc ctgtcaagtc   600
acccacgagg gcagcactgt cgaaaagacc gtggcaccga ctgagtgctc g            651

SEQ ID NO: 596           moltype = DNA  length = 1356
FEATURE                  Location/Qualifiers
source                   1..1356
                         mol_type = other DNA
                         organism = synthetic construct
                         note = Description of Artificial Sequence: Synthetic
                            polynucleotide
SEQUENCE: 596
caagtgcagc tcgtggagtc tggagggggga gtcgtgcagc tggacgctc cctgagactg      60
tcctgtgcgg cttcgggatt cactgtgtcc agctacggca tgcattgggt ccgccaagca   120
ccgggaaaag gcctggagtg ggtggccgtg atctcctaca ccggctcaaa caagtactac   180
gccgacagcg tgaagggccg gttcaccatt tcaaggggaca actccaagaa tacccctgtat   240
ctgcaaatga actcgctgcg ggcagaggac accgccgtgt actactgcgg tggctccggt   300
tacccctgc acgatgacta ctacgggctc gatgtctgga gcaggggac gctcgtgact   360
gtgtcctcgg ctagcaccaa gggcccgtca gtgtttcctc tggcccccaag ctccaagtcc   420
acctccggtg gtacagccgc gttgggatgc ttggtcaagg actactttcc ggaacccgtg   480
accgtgtcct ggaactccgg cgccctgact agcggagtgc acaccttccc cgctgtgctg   540
cagtctagcg ggctgtattc cctctcgtcc gtggtcaccg tgccgtcctc atccctggga   600
acccagacct acatttgcaa cgtgaaccac aagccgtcag acaccaaggt ggacaagaag   660
gtggagccga agtcctgcga caagacccat acttgtcctc cttgccccgc tccacctgtg   720
gcgggaccttt ccgtgttcct tttcccgccg aagccgaagg acactctgat gatctcgcgg   780
actcccgaag tcacttgcgt ggtggtggac gtcaaacacg aagatcccga ggtcaagttc   840
aattggtacg tggacgggt ggaagtccaa aacgccaaga ctaagccgcg cgaggaagag   900
tacaattcca cttaccgggt cgtgtcggtg ctgactgtgc tgcatcagga ctggctgaac   960
ggaaaggagt acaagtgcaa agtgtcgaac aaggccctgc ctgcaccaat cgaaaagacc  1020
attagcaaag ccaagggcca gccgagagaa ccccaagtct cactctgcc accatcccgc  1080
gaagaaatga ccaagaacca agtgtcgctg acgtgcgaag tgtcgggatt ctacccgtcc  1140
gatattgccg tggaatggga gagcgacggc cagcccgaga caactacaa gactaccccc  1200
cccgtcttgg attccgatgg ttccttcttc ctgtactcca agctgaccgt ggataagtcc  1260
cgatgggagc agggcgatgt gttctcgtgc tccgtgatgc atgaagccct gcacaaccac  1320
tatacccaga agtcactgtc gctgagccct gggaag                              1356

SEQ ID NO: 597           moltype = DNA  length = 369
FEATURE                  Location/Qualifiers
source                   1..369
                         mol_type = other DNA
                         organism = synthetic construct
                         note = Description of Artificial Sequence: Synthetic
                            polynucleotide
SEQUENCE: 597
caagtgcagc ttgtggagtc gggaggggga gtggtgcagc ctggtcgctc actgaggctg      60
agctgtgctg cctccggctt taccgtgtcc tcctacggaa tgcattgggt cagacaggca   120
ccgggaaaag gcctggaatg ggtggccgtc atcagctaca ccggctccaa caagtactac   180
gccgactcag tgaaggggcg gttcactatt agccgcgata ctcgaagaa tacccctgtat   240
ctgcaaatga actctttgcg ggccgaagat accgccgtgt actactgcgg aggctccggt   300
tacgcgctcc acgacgacta ctacggactg gacgtgtggg gacaggggac tctcgtgacc   360
gtgtcgtcc                                                            369

SEQ ID NO: 598           moltype = DNA  length = 678
FEATURE                  Location/Qualifiers
source                   1..678
                         mol_type = other DNA
                         organism = synthetic construct
                         note = Description of Artificial Sequence: Synthetic
                            polynucleotide
SEQUENCE: 598
caagtgcagc ttgtggagtc gggaggggga gtggtgcagc ctggtcgctc actgaggctg      60
agctgtgctg cctccggctt taccgtgtcc tcctacggaa tgcattgggt cagacaggca   120
ccgggaaaag gcctggaatg ggtggccgtc atcagctaca ccggctccaa caagtactac   180
gccgactcag tgaaggggcg gttcactatt agccgcgata ctcgaagaa tacccctgtat   240
ctgcaaatga actctttgcg ggccgaagat accgccgtgt actactgcgg aggctccggt   300
tacgcgctcc acgacgacta ctacggactg gacgtgtggg gacaggggac tctcgtgacc   360
gtgtcgtccg ctagcaccaa gggaccgagc gtgttcccgc tggcgccgag cagcaaatcc   420
acttctgggg gaaccgcagc cctggttgc ctggtcaagg actactttcc ggaaccagtc   480
actgtgtcct ggaacagcgg tgccctcacc tcgggcgtgc acaccttccc ggccgtgctg   540
cagtctagcg gactctactc gctctcctcc gtggtcaccg tgccctcctc atcactggga   600
acccagacat acatttgcaa cgtgaaccac aagccctcgg acactaaggt ggacaaaaaa   660
```

```
gtggaaccaa agtcctgc                                                       678

SEQ ID NO: 599          moltype = DNA  length = 333
FEATURE                 Location/Qualifiers
source                  1..333
                        mol_type = other DNA
                        organism = synthetic construct
                        note = Description of Artificial Sequence: Synthetic
                            polynucleotide
SEQUENCE: 599
caatccgccc tgactcagcc ggccagcgtg tcaggttccc cgggccaaag cattaccatc   60
tcctgcactg ggacctcctc cgatgtcggg ggctacaact acgtgtcgtg gtatcagcag  120
caccctggaa aggcgcccaa gctgatgatc tacgacgtgt ccaaccggct gaggggagtc  180
agcaaccgct tcagcggctc caagtccgga aacaccgcat cactcacaat cagcggtctg  240
caggctgagg atgaagcgga ctactactgt tcctcctaca cctcctcctc ggcgctttac  300
gtctttgggt cgggaaccaa agtcactgtg ctg                               333

SEQ ID NO: 600          moltype = DNA  length = 651
FEATURE                 Location/Qualifiers
source                  1..651
                        mol_type = other DNA
                        organism = synthetic construct
                        note = Description of Artificial Sequence: Synthetic
                            polynucleotide
SEQUENCE: 600
caatccgccc tgactcagcc ggccagcgtg tcaggttccc cgggccaaag cattaccatc   60
tcctgcactg ggacctcctc cgatgtcggg ggctacaact acgtgtcgtg gtatcagcag  120
caccctggaa aggcgcccaa gctgatgatc tacgacgtgt ccaaccggct gaggggagtc  180
agcaaccgct tcagcggctc caagtccgga aacaccgcat cactcacaat cagcggtctg  240
caggctgagg atgaagcgga ctactactgt tcctcctaca cctcctcctc ggcgctttac  300
gtctttgggt cgggaaccaa agtcactgtg ctgggacagc cgaaggcagc cccatccgtg  360
accctgttcc ccccgtcatc cgaggaactg caggctaaca aggccaccct cgtgtgcctg  420
attagcgact ctaccctgg agccgtgacc gtggcctgga aggccgactc cagcccagtg  480
aaggccgagt ggagactac caccccgagc aaacagtcga acaataagta cgccgcgtca  540
tcgtacctgt ccctcacgcc cgaacagtgg aagtccccta gatcgtactc ctgccaagtg  600
acccagtgag gcagcactgt ggaaaagact gtgcccccta ccgagtgctc t           651

SEQ ID NO: 601          moltype = DNA  length = 1356
FEATURE                 Location/Qualifiers
source                  1..1356
                        mol_type = other DNA
                        organism = synthetic construct
                        note = Description of Artificial Sequence: Synthetic
                            polynucleotide
SEQUENCE: 601
caagtgcagc ttgtggagtc gggaggggga gtggtgcagc ctggtcgctc actgaggctg   60
agctgtgctg cctccggctt taccgtgtcc tcctacggaa tgcattgggt cagacaggca  120
ccgggaaaag gcctggaatg ggtggccgtc atcagctaca ccggctccaa caagtactac  180
gccgactcag tgaaggggcg gttcactatt agccgcgata ctcgaagaa taccctgtat  240
ctgcaaatga actctttgcg ggccgaagat accgccgtgt actactgcgg aggctccggt  300
tacgcgctcc acgacgacta ctacggactg gacgtgtggg gacaggggac tctcgtgacc  360
gtgtcgtccg ctagcaccaa gggaccgagc gtgttcccgc tggcgccgag cagcaaatcg  420
acttctgggg gaaccgcagc cctgggttgc ctggtcaagg actactcc ggaaccagtc  480
actgtgtcct ggaacagcgg tgccctcacc tcgggcgtgc acaccttccc ggccgtgctg  540
cagtctagcg gactctactc gctctcctcc gtggtcaccg tgccctcctc atcactggga  600
acccagacat acatttgcaa cgtgaaccac aagcccctcg gacactaagg tggacaaaaaa  660
gtggaaccaa agtcctgcga caagacccac acttgtccgc cctgccctgc cctcccgtg  720
gcgggcccgt cagtgttct gtttccgcca agcctaagg ataccctcat gatcagccgc  780
actcctgaag tgacctgtgt cgtggtggac gtgaaacacg aggacccgga ggtcaagttt  840
aattggtacg tggatggggt ggaggtgcac aacgccaaaa ctaagcccg ggaagaagag  900
tacaattcca cctaccgcgt cgtgtcagtg ttgacggtcc tgcaccaaga ctggctgaac  960
ggaaaggagt acaagtgcaa ggtgtccaac aaggcactgc ccgcccccat cgaaaagacc 1020
atttcaaaag ctaagggcca gccgcgggaa ccacaggtct acaccctgcc tccctccggg 1080
gaagagatga ccaagaacca agtctcccctc acgtgtgacg tgtccggctt ctaccctag 1140
gacattgctg tggaatggga gtccgacggg cagcccgaaa acaactacaa gaccactccc 1200
cctgtgctgg actccgacgg ctcattcttt ctgtactcca agctcaccgt cgataagtcg 1260
agatgggagc agggagatgt gttctcctgc tccgtgatgc acgaggccct gcataaccat 1320
tacactcaga agtccctctc cctgtcccct gggaag                           1356

SEQ ID NO: 602          moltype = DNA  length = 2175
FEATURE                 Location/Qualifiers
source                  1..2175
                        mol_type = other DNA
                        organism = synthetic construct
                        note = Description of Artificial Sequence: Synthetic
                            polynucleotide
SEQUENCE: 602
caagtgcagc ttgtggagtc gggaggggga gtggtgcagc ctggtcgctc actgaggctg   60
agctgtgctg cctccggctt taccgtgtcc tcctacggaa tgcattgggt cagacaggca  120
```

```
ccgggaaaag gcctggaatg ggtggccgtc atcagctaca ccggctccaa caagtactac  180
gccgactcag tgaaggggcg gttcactatt agccgcgata actcgaagaa taccctgtat  240
ctgcaaatga actctttgcg ggccgaagat accgccgtgt actactgcgg aggctccggt  300
tacgcgctcc acgacgacta ctacggactg gacgtgtggg gacaggggac tctcgtgacc  360
gtgtcgtccg ctagcaccaa gggaccgagc gtgttcccgc tggcgccgag cagcaaatcg  420
acttctgggg gaaccgcagc cctgggttgc ctggtcaagg actacttccc ggaaccagtc  480
actgtgtcct ggaacagcgg tgccctcacc tcgggcgtgc acaccttccc ggccgtgctg  540
cagtctagcg gactctactc gctctcctcc gtggtcaccg tgccctcctc atcactggga  600
acccagacat acatttgcaa cgtgaaccac aagccgtcca acaccaaggt cgacaagaaa  660
gtggagccta agtcctgtgg tggcggaggc tccggcggag gaggatcgga ggtgcagctc  720
gtcgaatccg gtggagggct ggtgcaaccg ggggctcgc ttaggcttag ctgcgctgcg  780
tcagggttca ccttctcaac ttacgcgatg aattgggtca gacaggcacc cggaaaggga  840
ctggaatggg tcggaagaat cagatcgaag gccaacaact acgccactta ctacgccgac  900
tccgtgaagg gaaggttcac tatctcgcgg gacgactcca agaacactct gtatctccaa  960
atgaactcac tccgggccga ggatactgcg gtgtactatt gcgtgcggca tggaaacttc 1020
ggggacagct acgtcagctg gttcgcctac tggggccaag gcactctcgt caccgtgtca 1080
tccgggaagc cgggttccgg aaagcctgga tcgggcaaac cgggatcggg aaaacccgga 1140
agccaggccg tcgtgaccca ggaaccgagc ctgaccgtgt ccccccggcgg taccgtgacc 1200
ttgacttgcg gttcctccac tggagccgtg actacctcga actacgccaa ctgggtgcag 1260
cagaagccgg gaaagtcgcc tcgcggactg atcggtggaa ctaacaaacg cgcccgggc 1320
gtgccagcca gattcagcgg tagcctgctc ggcgaaagg ccgcgctgac catctccggg 1380
gcccagcccg aggatgaggc cgactattac tgcgctctgt ggtactccaa ccactgggtg 1440
tttggcgggg gcactaagct gactgtgctg ggcggcggcg gctccggggg ggggggctcc 1500
aagacccaca cttgtccgcc ctgccctgcc cctcccgtgg cgggcccgtc agtgtttctg 1560
tttccgccaa agcctaagga taccctcatg atcagccgca ctcctgaagt gacctgtgtc 1620
gtggtggacg tgaaacacga ggacccggag gtcaagttta attggtacgt ggatggggtg 1680
gaggtgcaca acgccaaaac taagcccgg gaagaacagt acaattccac ctaccgcgtc 1740
gtgtcagtgt tgacggtcct gcaccaagac tggctgaacg gaaaggagta caagtgcaag 1800
gtgtccaaca aggcactgcc cgcccccatc gaaaagacca tttcaaaagc taagggccag 1860
ccgcgggaac cacaggtcta caccctgcct ccctcccggg aacagatgac caagaaccaa 1920
gtcaagctca cgtgtctcgt gaagggcttc tacccttcgg acattgctgt ggaatgggag 1980
tccaacgggc agcccgaaaa caactacaag accactcccc ctgtgctgga ctccgacggc 2040
tcattctttc tgtactccaa gctcaccgtc gataagtcga gatggcagca gggaaacgtg 2100
ttctcctgct ccgtgatgca cgaggccctg cataaccatt acactcagaa gtccctctcc 2160
ctgtcccctg ggaag                                                   2175

SEQ ID NO: 603        moltype = AA  length = 6
FEATURE               Location/Qualifiers
source                1..6
                      mol_type = protein
                      organism = synthetic construct
                      note = Description of Artificial Sequence: Synthetic 6xHis
                      tag
SEQUENCE: 603
HHHHHH                                                                6
```

What is claimed is:

1. A nucleic acid or plurality of nucleic acids encoding a B-cell maturation antigen (BCMA) binding molecule that specifically binds to human BCMA and comprises:
   (a) according to the combined Kabat and Chothia definitions a CDR-L1, CDR-L2 and CDR-L3 sequence of SEQ ID NOs: 26, 102, and 110, respectively, and a CDR-H1, CDR-H2 and CDR-H3 sequence of SEQ ID NOs: 188, 112, and 49, respectively;
   (b) according to the Kabat definition a CDR-L1, CDR-L2 and CDR-L3 sequence of SEQ ID NOs: 26, 102, and 110, respectively, and a CDR-H1, CDR-H2 and CDR-H3 sequence of SEQ ID NOs: 39, 112, and 49, respectively;
   (c) according to the Chothia definition a CDR-L1, CDR-L2 and CDR-L3 sequence of SEQ ID NO: 27, DVS, and SEQ ID NO: 136, respectively, and a CDR-H1, CDR-H2 and CDR-H3 sequence of SEQ ID NOs: 138, 140, and 49, respectively; or
   (d) according to the IMGT definition a CDR-L1, CDR-L2 and CDR-L3 sequence of SEQ ID NOs: 28, 154, and 110, respectively, and a CDR-H1, CDR-H2 and CDR-H3 sequence of SEQ ID NOs: 162, 165, and 51, respectively.

2. The nucleic acid or plurality of nucleic acids of claim 1, wherein the BCMA binding molecule comprises a CDR-L1, CDR-L2 and CDR-L3 sequence of SEQ ID NOs: 26, 102, and 110, respectively, and a CDR-H1, CDR-H2 and CDR-H3 sequence of SEQ ID NOs: 39, 112, and 49, respectively.

3. The nucleic acid or plurality of nucleic acids of claim 1, wherein the BCMA binding molecule comprises a light chain variable sequence comprising the amino acid sequence of SEQ ID NO:200 and a heavy chain variable sequence comprising the amino acid sequence of SEQ ID NO:224.

4. The nucleic acid or plurality of nucleic acids of claim 1, wherein the BCMA binding molecule comprises an antibody, an antibody fragment, an scFv, a dsFv, a Fv, a Fab, an scFab, a (Fab')2, or a single domain antibody (SDAB).

5. The nucleic acid or plurality of nucleic acids of claim 4, wherein the BCMA binding molecule comprises an antibody or an antibody fragment.

6. The nucleic acid or plurality of nucleic acids of claim 4, wherein the BCMA binding molecule comprises a scFv.

7. The nucleic acid or plurality of nucleic acids of claim 1, wherein the BCMA binding molecule is a multispecific binding molecule.

8. The nucleic acid or plurality of nucleic acids of claim 7, wherein the BCMA binding molecule is a bispecific binding molecule (BBM).

9. The nucleic acid or plurality of nucleic acids of claim 8, wherein the BBM comprises:

(a) an antigen-binding domain 1 (ABD1) that binds specifically to BCMA; and
(b) an antigen-binding domain 2 (ABD2) that binds specifically to a human T-cell receptor (TCR).

10. The nucleic acid or plurality of nucleic acids of claim 9, wherein ABD1 is an antibody, an antibody fragment, an scFv, a dsFv, a Fv, a Fab, an scFab, or a (Fab')2.

11. The nucleic acid or plurality of nucleic acids of claim 10, wherein ABD1 is a Fab.

12. The nucleic acid or plurality of nucleic acids of claim 10, wherein ABD1 is an anti-BCMA antibody or an antigen-binding domain thereof.

13. The nucleic acid or plurality of nucleic acids of claim 9, wherein ABD2 is an antibody, an antibody fragment, an scFv, a dsFv, a Fv, a Fab, an scFab, a (Fab')2, a single domain antibody (SDAB), a VH or VL domain, or a camelid VHH domain.

14. The nucleic acid or plurality of nucleic acids of claim 13, wherein ABD2 is an scFv.

15. The nucleic acid or plurality of nucleic acids of claim 9, wherein the TCR is CD3.

16. The nucleic acid or plurality of nucleic acids of claim 15, wherein ABD2 is an anti-CD3 antibody or an antigen-binding domain thereof.

17. The nucleic acid or plurality of nucleic acids of claim 16, wherein ABD2 comprises the CDR sequences of any one of the following:
according to the Kabat numbering scheme:
(a) a VH comprising a CDR1, CDR2, and CDR3 of SEQ ID NOs: 303, 323, and 347, respectively, and a VL comprising a CDR1, CDR2, and CDR3 of SEQ ID NOs: 304, 324, and 348, respectively;
(b) a VH comprising a CDR1, CDR2, and CDR3 of SEQ ID NOs: 305, 325, and 349, respectively, and a VL comprising a CDR1, CDR2, and CDR3 of SEQ ID NOs: 306, 326, and 350, respectively;
(c) a VH comprising a CDR1, CDR2, and CDR3 of SEQ ID NOs: 307, 327, and 351, respectively, and a VL comprising a CDR1, CDR2, and CDR3 of SEQ ID NOs: 308, 328, and 352, respectively;
(d) a VH comprising a CDR1, CDR2, and CDR3 of SEQ ID NOs: 303, 323, and 347, respectively, and a VL comprising a CDR1, CDR2, and CDR3 of SEQ ID NOs: 309, 329, and 353, respectively;
(e) a VH comprising a CDR1, CDR2, and CDR3 of SEQ ID NOs: 303, 330, and 347, respectively, and a VL comprising a CDR1, CDR2, and CDR3 of SEQ ID NOs: 304, 324, and 348, respectively;
(f) a VH comprising a CDR1, CDR2, and CDR3 of SEQ ID NOs: 310, 331, and 354, respectively, and a VL comprising a CDR1, CDR2, and CDR3 of SEQ ID NOs: 311, 332, and 355, respectively;
(g) a VH comprising a CDR1, CDR2, and CDR3 of SEQ ID NOs: 305, 333, and 356, respectively, and a VL comprising a CDR1, CDR2, and CDR3 of SEQ ID NOs: 306, 326, and 350, respectively;
(h) a VH comprising a CDR1, CDR2, and CDR3 of SEQ ID NOs: 312, 334, and 357, respectively, and a VL comprising a CDR1, CDR2, and CDR3 of SEQ ID NOs: 313, 335, and 358, respectively;
(i) a VH comprising a CDR1, CDR2, and CDR3 of SEQ ID NOs: 314, 325, and 359, respectively, and a VL comprising a CDR1, CDR2, and CDR3 of SEQ ID NOs: 313, 335, and 358, respectively;
(j) a VH comprising a CDR1, CDR2, and CDR3 of SEQ ID NOs: 303, 323, and 347, respectively, and a VL comprising a CDR1, CDR2, and CDR3 of SEQ ID NOs: 304, 324, and 348, respectively;
(k) a VH comprising a CDR1, CDR2, and CDR3 of SEQ ID NOs: 305, 334, and 349, respectively, and a VL comprising a CDR1, CDR2, and CDR3 of SEQ ID NOs: 315, 326, and 350, respectively;
(l) a VH comprising a CDR1, CDR2, and CDR3 of SEQ ID NOs: 305, 334, and 360, respectively, and a VL comprising a CDR1, CDR2, and CDR3 of SEQ ID NOs: 315, 326, and 361, respectively;
(m) a VH comprising a CDR1, CDR2, and CDR3 of SEQ ID NOs: 303, 330, and 362, respectively, and a VL comprising a CDR1, CDR2, and CDR3 of SEQ ID NOs: 304, 324, and 348, respectively;
(n) a VH comprising a CDR1, CDR2, and CDR3 of SEQ ID NOs: 316, 336, and 363, respectively, and a VL comprising a CDR1, CDR2, and CDR3 of SEQ ID NOs: 315, 326, and 350, respectively;
(o) a VH comprising a CDR1, CDR2, and CDR3 of SEQ ID NOs: 305, 334, and 349, respectively, and a VL comprising a CDR1, CDR2, and CDR3 of SEQ ID NOs: 317, 337, and 364, respectively;
(p) a VH comprising a CDR1, CDR2, and CDR3 of SEQ ID NOs: 305, 338, and 360, respectively, and a VL comprising a CDR1, CDR2, and CDR3 of SEQ ID NOs: 315, 326, and 361, respectively;
(q) a VH comprising a CDR1, CDR2, and CDR3 of SEQ ID NOs: 305, 334, and 365, respectively, and a VL comprising a CDR1, CDR2, and CDR3 of SEQ ID NOs: 315, 326, and 361, respectively;
(r) a VH comprising a CDR1, CDR2, and CDR3 of SEQ ID NOs: 305, 334, and 366, respectively, and a VL comprising a CDR1, CDR2, and CDR3 of SEQ ID NOs: 315, 326, and 361, respectively;
(s) a VH comprising a CDR1, CDR2, and CDR3 of SEQ ID NOs: 305, 334, and 367, respectively, and a VL comprising a CDR1, CDR2, and CDR3 of SEQ ID NOs: 315, 326, and 361, respectively;
(t) a VH comprising a CDR1, CDR2, and CDR3 of SEQ ID NOs: 318, 334, and 360, respectively, and a VL comprising a CDR1, CDR2, and CDR3 of SEQ ID NOs: 315, 326, and 361, respectively;
(u) a VH comprising a CDR1, CDR2, and CDR3 of SEQ ID NOs: 319, 334, and 349, respectively, and a VL comprising a CDR1, CDR2, and CDR3 of SEQ ID NOs: 315, 326, and 350, respectively;
(v) a VH comprising a CDR1, CDR2, and CDR3 of SEQ ID NOs: 318, 334, and 349, respectively, and a VL comprising a CDR1, CDR2, and CDR3 of SEQ ID NOs: 315, 326, and 350, respectively;
(w) a VH comprising a CDR1, CDR2, and CDR3 of SEQ ID NOs: 305, 339, and 349, respectively, and a VL comprising a CDR1, CDR2, and CDR3 of SEQ ID NOs: 315, 326, and 350, respectively;
(x) a VH comprising a CDR1, CDR2, and CDR3 of SEQ ID NOs: 305, 340, and 349, respectively, and a VL comprising a CDR1, CDR2, and CDR3 of SEQ ID NOs: 315, 326, and 350, respectively;
(y) a VH comprising a CDR1, CDR2, and CDR3 of SEQ ID NOs: 305, 341, and 349, respectively, and a VL comprising a CDR1, CDR2, and CDR3 of SEQ ID NOs: 315, 326, and 350, respectively;
(z) a VH comprising a CDR1, CDR2, and CDR3 of SEQ ID NOs: 305, 334, and 360, respectively, and a VL comprising a CDR1, CDR2, and CDR3 of SEQ ID NOs: 315, 326, and 350, respectively;

(aa) a VH comprising a CDR1, CDR2, and CDR3 of SEQ ID NOs: 305, 334, and 368, respectively, and a VL comprising a CDR1, CDR2, and CDR3 of SEQ ID NOs: 315, 326, and 350, respectively;

(bb) a VH comprising a CDR1, CDR2, and CDR3 of SEQ ID NOs: 305, 334, and 369, respectively, and a VL comprising a CDR1, CDR2, and CDR3 of SEQ ID NOs: 315, 326, and 350, respectively;

(cc) a VH comprising a CDR1, CDR2, and CDR3 of SEQ ID NOs: 305, 334, and 349, respectively, and a VL comprising a CDR1, CDR2, and CDR3 of SEQ ID NOs: 320, 326, and 350, respectively;

(dd) a VH comprising a CDR1, CDR2, and CDR3 of SEQ ID NOs: 305, 334, and 349, respectively, and a VL comprising a CDR1, CDR2, and CDR3 of SEQ ID NOs: 321, 326, and 350, respectively;

(ee) a VH comprising a CDR1, CDR2, and CDR3 of SEQ ID NOs: 305, 334, and 349, respectively, and a VL comprising a CDR1, CDR2, and CDR3 of SEQ ID NOs: 315, 342, and 350, respectively;

(ff) a VH comprising a CDR1, CDR2, and CDR3 of SEQ ID NOs: 305, 334, and 349, respectively, and a VL comprising a CDR1, CDR2, and CDR3 of SEQ ID NOs: 315, 343, and 350, respectively;

(gg) a VH comprising a CDR 1, CDR2, and CDR3 of SEQ ID NOs: 305, 334, and 349, respectively, and a VL comprising a CDR1, CDR2, and CDR3 of SEQ ID NOs: 315, 344, and 350, respectively;

(hh) a VH comprising a CDR 1, CDR2, and CDR3 of SEQ ID NOs: 305, 334, and 349, respectively, and a VL comprising a CDR1, CDR2, and CDR3 of SEQ ID NOs: 315, 345, and 350, respectively;

(ii) a VH comprising a CDR 1, CDR2, and CDR3 of SEQ ID NOs: 305, 334, and 349, respectively, and a VL comprising a CDR1, CDR2, and CDR3 of SEQ ID NOs: 315, 326, and 370, respectively;

(jj) a VH comprising a CDR 1, CDR2, and CDR3 of SEQ ID NOs: 305, 334, and 349, respectively, and a VL comprising a CDR1, CDR2, and CDR3 of SEQ ID NOs: 315, 326, and 361, respectively;

(kk) a VH comprising a CDR 1, CDR2, and CDR3 of SEQ ID NOs: 305, 334, and 349, respectively, and a VL comprising a CDR1, CDR2, and CDR3 of SEQ ID NOs: 306, 326, and 350, respectively;

(ll) a VH comprising a CDR 1, CDR2, and CDR3 of SEQ ID NOs: 305, 334, and 349, respectively, and a VL comprising a CDR1, CDR2, and CDR3 of SEQ ID NOs: 322, 326, and 350, respectively;

(mm) a VH comprising a CDR 1, CDR2, and CDR3 of SEQ ID NOs: 305, 338, and 360, respectively, and a VL comprising a CDR1, CDR2, and CDR3 of SEQ ID NOs: 315, 326, and 350, respectively;

(nn) a VH comprising a CDR1, CDR2, and CDR3 of SEQ ID NOs: 305, 334, and 367, respectively, and a VL comprising a CDR1, CDR2, and CDR3 of SEQ ID NOs: 315, 326, and 350, respectively;

(oo) a VH comprising a CDR1, CDR2, and CDR3 of SEQ ID NOs: 318, 338, and 367, respectively, and a VL comprising a CDR1, CDR2, and CDR3 of SEQ ID NOs: 315, 326, and 350, respectively; or (pp) a VH comprising a CDR1, CDR2, and CDR3 of SEQ ID NOs: 305, 346, and 349, respectively, and a VL comprising a CDR1, CDR2, and CDR3 of SEQ ID NOs: 315, 326, and 350, respectively.

18. The nucleic acid or plurality of nucleic acids of claim 8, wherein the BCMA binding molecule is bivalent.

19. A cell comprising the nucleic acid or plurality of nucleic acids of claim 1.

20. A cell transfected with one or more expression vectors comprising the nucleic acid or plurality of nucleic acids of claim 1 under the control of one or more promoters.

21. A method of producing a BCMA binding molecule, comprising:
(a) culturing the cell of claim 19 in conditions under which the BCMA binding molecule is expressed; and
(b) recovering the BCMA binding molecule from the cell culture.

22. A nucleic acid or plurality of nucleic acids encoding a BCMA binding molecule comprising:
(a) a first polypeptide comprising:
(i) a first heavy chain constant domain comprising a first Fc region of an IgG1;
(ii) a scFv comprising the amino acid sequence of SEQ ID NO: 294; wherein the scFv is covalently attached to the N-terminus of the first Fc region by a hinge;
(b) a second polypeptide comprising:
(i) a heavy chain variable domain;
(ii) a second heavy chain constant domain comprising a second Fc region of an IgG1; and
(c) a third polypeptide comprising a light chain constant domain and a light chain variable domain;
wherein
A. the first and second Fc regions form an Fc domain;
B. the first and second Fc regions have a set of amino acid substitutions comprising S364K/E357Q:L368D/K370S;
C. the first and/or second Fc regions comprise amino acid modifications E223P, L234V, L235A, G236del, and S267K;
D. the first and/or second Fc regions comprise amino acid substitutions N208D, Q295E, N384D, Q418E, and N421D; and
E. the light chain variable sequence comprises the amino acid sequence of SEQ ID NO:200 and the heavy chain variable sequence comprises the amino acid sequence of SEQ ID NO:224.

23. A nucleic acid or plurality of nucleic acids encoding a BCMA binding molecule comprising:
(a) a first polypeptide comprising the amino acid sequence of SEQ ID NO:509;
(b) a second polypeptide comprising the amino acid sequence of SEQ ID NO:510; and
(c) a third polypeptide comprising the amino acid sequence of SEQ ID NO:504.

* * * * *

UNITED STATES PATENT AND TRADEMARK OFFICE
CERTIFICATE OF CORRECTION

| | |
|---|---|
| PATENT NO. | : 12,275,795 B2 |
| APPLICATION NO. | : 17/934064 |
| DATED | : April 15, 2025 |
| INVENTOR(S) | : Abujoub et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 180 days.

Signed and Sealed this
Twenty-second Day of July, 2025

Coke Morgan Stewart
*Acting Director of the United States Patent and Trademark Office*